US006380241B1

(12) United States Patent
Winn et al.

(10) Patent No.: US 6,380,241 B1
(45) Date of Patent: *Apr. 30, 2002

(54) TREATMENT OF DISEASES USING ENDOTHELIN ANTAGONISTS

(75) Inventors: Martin Winn, Deerfield; Steven A. Boyd, Mundelein; Charles W. Hutchins, Gurnee; Hwan-Soo Jae, Glencoe; Andrew S. Tasker, Gurnee; Thomas W. von Geldern, Richmond; Jeffrey A. Kester, Deerfield; Bryan K. Sorensen, Waukegan; Bruce G. Szczepankiewicz, Gages Lake; Kenneth J. Henry, Waukegan; Gang Liu, Gurnee; Steven J. Wittenberger, Mundelein; Steven A. King, Gurnee, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/714,934

(22) Filed: Nov. 17, 2000

Related U.S. Application Data

(63) Continuation of application No. 08/905,913, filed on Aug. 4, 1997, now Pat. No. 6,162,927, which is a continuation-in-part of application No. 08/794,506, filed on Feb. 4, 1997, now abandoned, which is a continuation-in-part of application No. 08/600,625, filed on Feb. 13, 1996, now abandoned, which is a continuation-in-part of application No. 08/497,998, filed on Aug. 2, 1995, now abandoned, which is a continuation-in-part of application No. 08/442,575, filed on May 30, 1995, now Pat. No. 5,767,144, which is a continuation-in-part of application No. 08/334,717, filed on Nov. 4, 1994, now abandoned, which is a continuation-in-part of application No. 08/293,349, filed on Aug. 19, 1994, now abandoned.

(51) Int. Cl.[7] .................. C07D 405/02; C07D 405/06; A61K 41/30; A61N 9/06; A61N 9/10
(52) U.S. Cl. ................ 514/422; 514/423; 514/424; 514/425; 514/426; 514/428; 514/429; 548/412; 548/413; 548/517; 548/518; 548/526; 548/531; 548/544; 548/557; 548/566; 548/567; 548/570; 548/571; 548/572; 548/577
(58) Field of Search ................. 548/412, 413, 548/517, 518, 529, 531, 544, 557, 566, 567, 570, 571, 572, 577; 514/422, 423, 424, 425, 426, 428, 429

(56) References Cited

U.S. PATENT DOCUMENTS

| | | | |
|---|---|---|---|
| 3,342,833 A | 9/1967 | Fremery et al. | 548/531 |
| 4,132,709 A | 1/1979 | Santrouch et al. | 514/422 |
| 4,216,218 A | 8/1980 | Ehrogott et al. | 514/422 |
| 4,340,715 A | 7/1982 | Grounder et al. | 528/99 |
| 5,482,960 A | 1/1996 | Berryman et al. | 514/422 |
| 5,668,164 A | 9/1997 | Ma et al. | 514/376 |
| 5,767,144 A | 6/1998 | Winn et al. | 514/422 |
| 6,162,927 A | 12/2000 | Winn et al. | 548/526 |

FOREIGN PATENT DOCUMENTS

| | | |
|---|---|---|
| EP | 0439444 | 7/1991 |
| GB | 2275926 | 9/1994 |
| WO | 9308799 | 5/1993 |
| WO | 9402474 | 2/1994 |
| WO | 9414434 | 7/1994 |
| WO | 9504534 | 2/1995 |
| WO | 9505372 | 2/1995 |
| WO | 9505376 | 2/1995 |
| WO | 9533748 | 12/1995 |
| WO | 9533752 | 12/1995 |
| WO | 9535107 | 12/1995 |
| WO | 9606095 | 2/1996 |
| WO | 9730046 | 8/1997 |

OTHER PUBLICATIONS

Bhagwat, S., "Synthesis of Enantiomerically Pure Pyrrolidinones as Endothelin Receptor Antagonists", Thtrahedron Letters, 37(27), 1996, pp. 4627–4630.
R. Craig et al., "Modern Pharmacology, Third Edition", Little, Brown and Company, Boston, US, p. 33, col. 2—p. 35, col. 1.
Ge, et al. Yaoxue Xuebao, 20 427–432 (1985).
Jae, et al., "Pyrrolidine–3–carboxylic acids as Endothelin Antagonists. 2. Sulfonamide–Based ETA–ETB Mixed Antagonists." Journal of Medicinal Chemistry, vol. 40, No. 20, 1997, pp. 3217–3227.
Rahman, Indian J. Chem., Sec B 19B 828–830 (1980).
J. K. Seydal et al, "ChemiStruktur und biologische Aktivitat von Wirkstoffen." Verlag Chemi, Weinheim, DE, 1979, p. 124, paragraph 2—p. 126, paragraph 2.
Tasker, et al., "Potent and Selective Non–Benzodioxole Containing Endothelin—A Receptor Antagonists" 1997, Journal of Medicinal Chemistry.
J. G. Topliss, "Quantitiative Structure–Activity Relationships of Drugs", Academic Press, New York, p. 453, paragraph 2—p. 456, paragraph 2.
Tsuge, et al. Bull Chem. Soc. Jpn 59 2537 (1986).
Tsuge, et al. Chemistry Letters, 801–804 (1984).
Winn, et al., "2.4–Diarylpyrrolidine–3–carboxylic Acids–Potent Et$_A$ Selective Endothelin Receptor Antagonists. 1. Discovery of A–127722." Journal of Medicinal Chemistry, vol. 39, No. 5, 1996, pp. 1039–1048.

Primary Examiner—Floyd D. Higel
(74) Attorney, Agent, or Firm—Gregory Donner; Gregory Steele

(57) ABSTRACT

A compound of the formula (I):

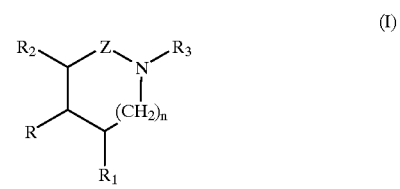

or a pharmaceutically acceptable salt thereof is disclosed, as well as processes for and intermediates in the preparation thereof, and a method of antagonizing endothelin.

6 Claims, No Drawings

TREATMENT OF DISEASES USING ENDOTHELIN ANTAGONISTS

This application is a continuation of U.S. patent application Ser. No. 08/905,913, filed Aug. 4, 1997 and issued as U.S. Pat. No. 6,162,927 on Dec. 19, 2000, which is a continuation-ivar application of U.S. patent application Ser. No. 08/794,506, filed Feb. 4, 1997, now abandoned, which is a continuation-in-part of U.S. patent application Ser. No. 08/600,625, filed Feb. 13, 1996, now abandoned which is a continuation-in-part of U.S. patent application Ser. No. 08/497,998, filed Aug. 2, 1995, now abandoned which is a continuation-in-part of U.S. patent application Ser. No. 08/442,575, filed May 30, 1995, now U.S. Pat. No. 5,767,144 which is a continuation-in-part of U.S. patent application Ser. No. 08/334,717, filed Nov. 4, 1994, now abandoned which is a continuation-in-part of U.S. patent application Ser. No. 08/293,349, filed Aug. 19, 1994, now abandoned.

TECHNICAL FIELD

The present invention relates to compounds which are endothelin antagonists, processes for making such compounds, synthetic intermediates employed in these processes and methods and compositions for antagonizing endothelin.

BACKGROUND OF THE INVENTION

Endothelin (ET) is a 21 amino acid peptide that is produced by endothelial cells. ET is produced by enzymatic cleavage of a Trp-Val bond in the precursor peptide big endothelin (Big ET). This cleavage is caused by an endothelin converting enzyme (ECE). Endothelin has been shown to constrict arteries and veins, increase mean arterial blood pressure, decrease cardiac output, increase cardiac contractibility in vitro, stimulate mitogenesis in vascular smooth muscle cells in vitro, contract non-vascular smooth muscle including guinea pig trachea, human urinary bladder strips and rat uterus in vitro, increase airway resistance in vivo, induce formation of gastric ulcers, stimulate release of atrial natriuretic factor in vitro and in vivo, increase plasma levels of vasopressin, aldosterone and catecholamines, inhibit release of renin in vitro and stimulate release of gonadotropins in vitro.

It has been shown that vasoconstriction is caused by binding of endothelin to its receptors on vascular smooth muscle (Nature 332 411 (1988), FEBS Letters 231 440 (1988) and Biochem. Biophys. Res. Commun. 154 868 (1988)). An agent which suppresses endothelin production or an agent which binds to endothelin or which inhibits the binding of endothelin to an endothelin receptor will produce beneficial effects in a variety of therapeutic areas. In fact, an anti-endothelin antibody has been shown, upon intrarenal infusion, to ameliorate the adverse effects of renal ischemia on renal vascular resistance and glomerular filtration rate (Kon, et al., J. Clin. Invest. 83 1762 (1989)). In addition, an anti-endothelin antibody attenuated the nephrotoxic effects of intravenously administered cyclosporin (Kon, et al., Kidney Int. 37 1487 (1990)) and attenuated infarct size in a coronary artery ligation-induced myocardial infarction model (Watanabe, et al., Nature 344 114 (1990)).

Clozel et al. (Nature 365: 759–761 (1993)) report that Ro 46-2005, a nonpeptide ET-A/B antagonist, prevents post-ischaemic renal vasoconstriction in rats, prevents the decrease in cerebral blood flow due to subarachnoid hemorrhage (SAH) in rats, and decreases MAP in sodium-depleted squirrel monkeys when dosed orally. A similar effect of a linear tripeptide-like ET-A antagonist, BQ-485, on arterial caliber after SAH has also been recently reported (S. Itoh, T. Sasaki, K. Ide, K. Ishikawa, M. Nishikibe, and M. Yano, Biochem. Biophys. Res. Comm., 195: 969–75 (1993). These results indicate that agents which antagonize ET/ET receptor binding will provide therapeutic benefit in the indicated disease states.

Agents with the ability to antagonize ET/ET receptor binding have been shown to be active in a number of animal models of human disease. For example, Hogaboam et al (EUR. J. Pharmacol. 1996, 309, 261–269), have shown that an endothelin receptor antagonist reduced injury in a rat model of colitis. Aktan et al (Transplant Int 1996, 9, 201–207) have demonstrated that a similar agent prevents ischemia-reperfusion injury in kidney transplantation. Similar studies have suggested the use of endothelin antagonists in the treatment of angina, pulmonary hypertension, Raynaud's disease, and migraine. (Ferro and Webb, Drugs 1996, 51, 12–27).

Abnormal levels of endothelin or endothelin receptors have also been associated with a number of disease states, including prostate cancer (Nelson et al, Nature Medicine 1995, 1, 944–949), suggesting a role of endothelin in the pathophysiology of these diseases.

Wu-Wong et al (Life Sciences 1996, 58, 1839–1847) have shown that both endothelin and endothelin antagonists bind tightly to plasma proteins, e.g., serum albumin. This plasma protein binding can decrease the effectiveness with which the antagonists inhibit endothelin's action. Thus, endothelin antagonists with reduced plasma protein binding may be more effective than highly bound congeners.

DISCLOSURE OF THE INVENTION

In accordance with the present invention there are compounds of the formula (I):

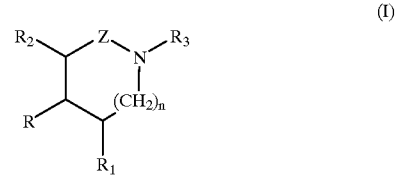

wherein

Z is —C($R_{18}$)($R_{19}$)— or —C(O)— wherein $R_{18}$ and $R_{19}$ are independently selected from hydrogen and loweralkyl;

n is 0 or 1;

R is —(CH$_2$)$_m$—W wherein m is an integer from 0 to 6 and W is
 (a) —C(O)$_2$—G wherein G is hydrogen or a carboxy protecting group,
 (b) —PO$_3$H$_2$,
 (c) —P(O)(OH)E wherein E is hydrogen, loweralkyl or arylalkyl,
 (d) —CN,
 (e) —C(O)NHR$_{17}$ wherein R$_{17}$ is loweralkyl,
 (f) alkylaminocarbonyl,
 (g) dialkylaminocarbonyl,
 (h) tetrazolyl,
 (i) hydroxy,
 (j) alkoxy,
 (k) sulfonamido,
 (l) —C(O)NHS(O)$_2$R$_{16}$ wherein R$_{16}$ is loweralkyl, haloalkyl, aryl or dialkylamino, (m) —S(O)$_2$NHC(O)R$_{16}$ wherein R$_{16}$ is defined as above, (n)
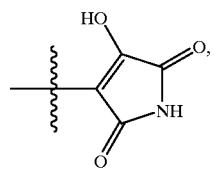

(o)
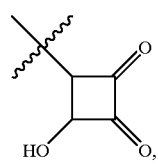

(p)
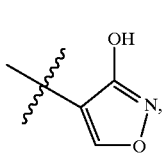

(q)
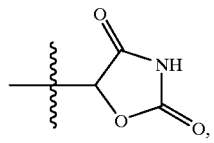

(r)
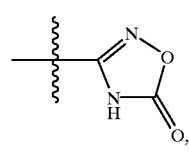

(s)
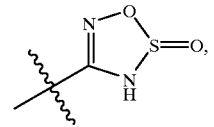

(t)
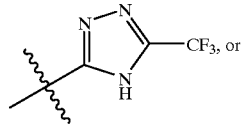

(u)
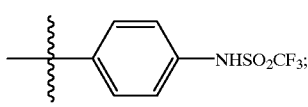

R$_1$ and R$_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl)aminoalkyl, alkylsulfonylamidoalkyl, heterocyclic, (heterocyclic)alkyl and (R$_{aa}$)(R$_{bb}$)N—R$_{cc}$— wherein R$_{aa}$ is aryl or arylalkyl, R$_{bb}$ is hydrogen or alkanoyl and R$_{cc}$ is alkylene, with the proviso that one or both of R$_1$ and R$_2$ is other than hydrogen;

R$_3$ is (a) R$_4$—C(O)—R$_5$—, R$_4$—R$_{5a}$—, R$_4$—C(O)—R$_5$—N(R$_6$)—, R$_6$—S(O)$_2$—R$_7$— or R$_{26}$—S(O)—R$_{27}$— wherein R$_5$ is (i) a covalent bond, (ii) alkylene, (iii) alkenylene, (iv) —N(R$_{20}$)—R$_8$— or —R$_{8a}$—N(R$_{20}$)—R$_8$— wherein R$_8$ and R$_{8a}$ are independently selected from the group consisting of alkylene and alkenylene and R$_{20}$ is hydrogen, loweralkyl, alkenyl, haloalkyl, alkoxyalkyl, haloalkoxyalkyl, cylcoalkyl or cycloalkylalkyl or (v) —O—R$_9$— or —R$_{9a}$—O—R$_9$— wherein R$_9$ and R$_{9a}$ are independently selected from alkylene;

R$_{5a}$ is (i) alkylene or (ii) alkenylene;

R$_7$ is (i) a covalent bond, (ii) alkylene, (iii) alkenylene or (iv) —N(R$_{21}$)—R$_{10}$— or —R$_{10a}$—N(R$_{21}$)—R$_{10}$— wherein R$_{10}$ and R$_{10a}$ are independently selected from the group consisting of alkylene and alkenylene and R$_{21}$ is hydrogen, loweralkyl, alkenyl, haloalkyl, alkoxyalkyl, haloalkoxyalkyl, aryl or arylalkyl;

R$_4$ and R$_6$ are independently selected from the group consisting of (i) (R$_{11}$)(R$_{12}$)N— wherein R$_{11}$ and R$_{12}$ are independently selected from
  (1) hydrogen,
  (2) loweralkyl,
  (3) haloalkyl,
  (4) alkoxyalkyl,
  (5) haloalkoxyalkyl,
  (6) alkenyl,
  (7) alkynyl,
  (8) cycloalkyl,
  (9) cycloalkylalkyl,
  (10) aryl,
  (11) heterocyclic,
  (12) arylalkyl,
  (13) (heterocyclic)alkyl,
  (14) hydroxyalkyl,
  (15) alkoxy,
  (16) aminoalkyl,
  (17) trialkylaminoalkyl,
  (18) alkylaminoalkyl,
  (19) dialkylaminoalkyl, and
  (20) carboxyalkyl,
(ii) loweralkyl,
(iii) alkenyl,
(iv) alkynyl,
(v) cycloalkyl,
(vi) cycloalkylalkyl,
(vii) aryl,
(viii) arylalkyl,
(ix) heterocyclic,
(x) (heterocyclic)alkyl,
(xi) alkoxyalkyl,
(xii) hydroxyalkyl,
(xiii) haloalkyl,
(xiv) haloalkenyl,
(xv) haloalkoxyalkyl,
(xvi) haloalkoxy,
(xvii) alkoxyhaloalkyl,
(xviii) alkylaminoalkyl,
(xix) dialkylaminoalkyl, (xx) alkoxy, and

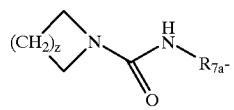

(xxi)

wherein z is 0–5 and $R_{7a}$ is alkylene;
$R_{26}$ is (i) loweralkyl, (ii) haloalkyl, (iii) alkenyl, (iv) alkynyl, (v) cycloalkyl, (vi) cycloalkylalkyl, (vii) aryl, (viii) arylalkyl, (ix) heterocyclic, (x) (heterocyclic)alkyl, (xi) alkoxyalkyl or (xii) alkoxy-substituted haloalkyl; and
$R_{27}$ is alkylene or alkenylene;
(b) $R_{22}$—O—C(O)—$R_{23}$— wherein $R_{22}$ is a carboxy protecting group or heterocyclic and $R_{23}$ is (i) a covalent bond, (ii) alkylene, (iii) alkenylene or (iv) —N($R_{24}$)—$R_{25}$— wherein $R_{25}$ is alkylene and $R_{24}$ is hydrogen or loweralkyl,
(c) loweralkyl,
(d) alkenyl,
(e) alkynyl,
(f) cycloalkyl,
(g) cycloalkylalkyl,
(h) aryl,
(i) arylalkyl,
(j) aryloxyalkyl,
(k) heterocyclic,
(l) (heterocyclic)alkyl,
(m) alkoxyalkyl,
(n) alkoxyalkoxyalkyl, or
(o) $R_{13}$—C(O)—CH($R_{14}$)—
wherein $R_{13}$ is amino, alkylamino or dialkylamino and $R_{14}$ is aryl or $R_{15}$—C(O)— wherein $R_{15}$ is amino, alkylamino or dialkylamino;
or a pharmaceutically acceptable salt thereof.

A preferred embodiment of the invention is a compound of formula (II)

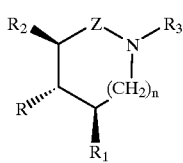

(II)

wherein the substituents —$R_2$, —R and —$R_1$ exist in a trans,trans relationship and Z, n, R, $R_1$, $R_2$, and $R_3$ are as defined above.

Another preferred embodiment of the invention is a compound of formula (I) or (II) wherein n is 0 and Z is —$CH_2$—.

Another preferred embodiment of the invention is a compound of formula (I) or (II) wherein n is 1 and Z is —$CH_2$—.

Another preferred embodiment of the invention is a compound of formula (I) or (II) wherein n is 0, Z is —$CH_2$—, and $R_3$ is $R_4$—C(O)—$R_5$—, $R_6$—S(O)$_2$—$R_7$— or $R_{26}$—S(O)—$R_{27}$— wherein $R_4$, $R_5$, $R_6$, $R_7$, $R_{26}$ and $R_{27}$ are as defined above.

Another preferred embodiment of the invention is a compound of formula (I) or (II) wherein n is 0, Z is —$CH_2$—, and $R_3$ is alkoxyalkyl or alkoxyalkoxyalkyl.

A more preferred embodiment of the invention is a compound of formula (I) or (II) wherein n is 0, Z is —$CH_2$—, and $R_3$ is $R_4$—C(O)—$R_5$— wherein $R_4$ is ($R_{11}$)($R_{12}$)N— as defined above and $R_5$ is alkylene or $R_3$ is $R_6$—S(O)$_2$—$R_7$— or $R_{26}$—S(O)—$R_{27}$— wherein $R_7$ is alkylene, $R_{27}$ is alkylene and $R_6$ and $R_{26}$ are defined as above.

Another more preferred embodiment of the invention is a compound of formula (I) or (II) wherein n is 0, Z is —$CH_2$— and $R_3$ is $R_4$—C(O)—N($R_{20}$)—$R_8$— or $R_6$—S(O)$_2$—N($R_{21}$)—$R_{10}$— wherein $R_8$ and $R_{10}$ are alkylene and $R_4$, $R_6$, $R_{20}$ and $R_{21}$ are defined as above.

An even more preferred embodiment of the invention is a compound of formula (I) or (II) wherein n is 0, R is tetrazolyl or —C(O)$_2$—G wherein G is hydrogen or a carboxy protecting group or R is tetrazolyl or R is —C(O)—NHS(O)$_2$$R_{16}$ wherein $R_{16}$ is loweralkyl, haloalkyl or aryl, Z is —$CH_2$—, $R_1$ and $R_2$ are independently selected from (i) loweralkyl, (ii) cycloalkyl, (iii) substituted aryl wherein aryl is phenyl substituted with one, two or three substituents independently selected from loweralkyl, alkoxy, halo, alkoxyalkoxy and carboxyalkoxy, (iv) substituted or unsubstituted heterocyclic, (v) alkenyl, (vi) heterocyclic (alkyl), (vii) arylalkyl, (viii) aryloxyalkyl, (ix) (N-alkanoyl-N-alkyl) aminoalkyl and (x) alkylsulfonylamidoalkyl, and $R_3$ is $R_4$—C(O)—$R_5$— wherein $R_4$ is ($R_{11}$)($R_{12}$)N— wherein $R_{11}$ and $R_{12}$ are independently selected from loweralkyl, haloalkyl, alkoxyalkyl, haloalkoxyalkyl, aryl, arylalkyl, heterocyclic, hydroxyalkyl, alkoxy, aminoalkyl, and trialkylaminoalkyl, and $R_5$ is alkylene; or $R_3$ is $R_4$—C(O)—N($R_{20}$)—$R_8$— or $R_6$—S(O)$_2$—N($R_{21}$)—$R_{10}$— wherein $R_4$ is loweralkyl, aryl, alkoxy, alkylamino, aryloxy or arylalkoxy and $R_6$ is loweralkyl, haloalkyl, alkoxyalkyl, haloalkoxyalkyl, aryl or arylalkyl, $R_8$ and $R_{10}$ are alkylene and $R_{20}$ and $R_{21}$ are loweralkyl; or $R_3$ is $R_6$—S(O)$_2$—$R_7$— or $R_{26}$—S(O)—$R_{27}$— wherein $R_6$ is loweralkyl or haloalkyl, $R_7$ is alkylene, $R_{26}$ is loweralkyl and $R_{27}$ is alkylene.

A yet more preferred embodiment of the invention is a compound of formula (I) or (II) wherein n is 0, R is —C(O)$_2$—G wherein G is hydrogen or a carboxy protecting group, tetrazolyl or —C(O)—NHS(O)$_2$$R_{16}$ wherein $R_{16}$ is loweralkyl, haloalkyl or aryl, Z is —$CH_2$—, $R_1$ is (i) loweralkyl, (ii) alkenyl, (iii) alkoxyalkyl, (iv) cycloalkyl, (v) phenyl, (vi) pyridyl, (vii) furanyl, (viii) substituted or unsubstituted 4-methoxyphenyl, 4-fluorophenyl, 3-fluorophenyl, 4-ethoxyphenyl, 4-ethylphenyl, 4-methylphenyl, 4-trifluoromethylphenyl, 4-pentafluoroethylphenyl, 3-fluoro-4-methoxyphenyl, 3-fluoro-4-ethoxyphenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from alkoxy, alkoxyalkoxy and carboxyalkoxy, (ix) heterocyclic (alkyl), (x) arylalkyl, (xi) aryloxyalkyl, (xii) (N-alkanoyl-N-alkyl)aminoalkyl, or (xiii) alkylsulfonylamidoalkyl, $R_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl and $R_3$ is $R_4$—C(O)—N($R_{20}$)—$R_8$— or $R_6$—S(O)$_2$—N($R_{21}$)—$R_{10}$ wherein $R_8$ and $R_{10}$ are alkylene, $R_{20}$ and $R_{21}$ are loweralkyl, $R_4$ is loweralkyl, aryl, alkoxy, alkylamino, aryloxy or arylalkoxy and $R_6$ is loweralkyl, haloalkyl, alkoxyalkyl, aryl or arylalkyl.

Another yet more preferred embodiment of the invention is a compound of formula (I) or (II) wherein n is 0, R is —C(O)$_2$—G wherein G is hydrogen or a carboxy protecting group, tetrazolyl or —C(O)—NHS(O)$_2$R$_{16}$ wherein R$_{16}$ is loweralkyl, haloalkyl or aryl, Z is —CH$_2$—, R$_1$ is (i) loweralkyl, (ii) alkenyl, (iii) alkoxyalkyl, (iv) cycloalkyl, (v) phenyl, (vi) pyridyl, (vii) furanyl, (viii) substituted or unsubstituted 4-methoxyphenyl, 4-fluorophenyl, 3-fluorophenyl, 4-ethoxyphenyl, 4-ethylphenyl, 4-methylphenyl, 4-trifluoromethylphenyl, 4-pentafluoroethylphenyl, 3-fluoro-4-methoxyphenyl, 3-fluoro-4-ethoxyphenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from alkoxy, alkoxyalkoxy and carboxyalkoxy, (ix) heterocyclic (alkyl), (x) arylalkyl, (xi) aryloxyalkyl, (xii) (N-alkanoyl-N-alkyl)aminoalkyl, or (xiii) alkylsulfonylamidoalkyl, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl and R$_3$ is R$_4$—C(O)—R$_5$— wherein R$_5$ is alkylene and R$_4$ is (R$_{11}$)(R$_{12}$)N— wherein R$_{11}$ and R$_{12}$ are independently selected from loweralkyl, haloalkyl, alkoxyalkyl, haloalkoxyalkyl, aryl, arylalkyl, heterocyclic, hydroxyalkyl, alkoxy, aminoalkyl, and trialkylaminoalkyl.

Another yet more preferred embodiment of the invention is a compound of formula (I) or (II) wherein n is 0, R is —C(O)$_2$—G wherein G is hydrogen or a carboxy protecting group, tetrazolyl or —C(O)—NHS(O)$_2$R$_{16}$ wherein R$_{16}$ is loweralkyl, haloalkyl or aryl, Z is —CH$_2$—, R$_1$ is (i) loweralkyl, (ii) alkenyl, (iii) heterocyclic (alkyl), (iv) aryloxyalkyl, (v) arylalkyl, (vi) aryl, (vii) (N-alkanoyl-N-alkyl)aminoalkyl, or (viii) alkylsulfonylamidoalkyl, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl wherein the substituent is selected from loweralkyl, alkoxy and halogen and R$_3$ is R$_4$—C(O)—R$_5$— wherein R$_5$ is alkylene and R$_4$ is (R$_{11}$)(R$_{12}$)N— wherein R$_{11}$ is loweralkyl and R$_{12}$ is aryl, arylalkyl, hydroxyalkyl, alkoxy, aminoalkyl, trialkylaminoalkyl, or heterocyclic.

Another yet more preferred embodiment of the invention is a compound of formula (I) or (II) wherein n is 0, R is —C(O)$_2$—G wherein G is hydrogen or a carboxy protecting group, tetrazolyl or —C(O)—NHS(O)$_2$R$_{16}$ wherein R$_{16}$ is loweralkyl, haloalkyl or aryl, Z is —CH$_2$—, R$_1$ is (i) loweralkyl, (ii) alkenyl, (iii) heterocyclic (alkyl), (iv) aryloxyalkyl, (v) arylalkyl, (vi) (N-alkanoyl-N-alkyl) aminoalkyl, or (vii) alkylsulfonylamidoalkyl, (vii) phenyl, or (ix) substituted or unsubstituted 4-methoxyphenyl, 3-fluoro-4-methoxyphenyl, 3-fluorophenyl, 3-fluoro-4-ethoxyphenyl, 2-fluorophenyl, 4-methoxymethoxyphenyl, 1,3-benzodioxolyl, 1,4-benzodioxanyl or dihydrobenzofuranyl wherein the substituent is selected from loweralkyl, haloalkyl, alkoxy, alkoxyalkoxy and carboxyalkoxy, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, 4-methoxyphenyl, dimethoxyphenyl, fluorophenyl or difluorophenyl wherein the substituent is selected from loweralkyl, alkoxy and halogen and R$_3$ is R$_6$—S(O)$_2$—N(R$_{21}$)—R$_{10}$— wherein R$_{10}$ is alkylene, R$_6$ is loweralkyl, haloalkyl, alkoxyalkyl, haloalkoxyalkyl, aryl or arylalkyl and R$_{21}$ is loweralkyl, haloalkyl, alkoxyalkyl, haloalkoxyalkyl, aryl or arylalkyl.

Another yet more preferred embodiment of the invention is a compound of formula (I) or (II) wherein n is 0, R is —C(O)$_2$—G wherein G is hydrogen or a carboxy protecting group, tetrazolyl or —C(O)—NHS(O)$_2$R$_{16}$ wherein R$_{16}$ is loweralkyl, haloalkyl or aryl, Z is —CH$_2$—, R$_1$ is (i) substituted or unsubstituted 4-methoxyphenyl, 3-fluoro-4-methoxyphenyl, 3-fluorophenyl, 3-fluoro-4-ethoxyphenyl, 4-methoxymethoxyphenyl, 1,3-benzodioxolyl or 1,4-benzodioxanyl wherein the substituent is selected from loweralkyl, haloalkyl, alkoxy and alkoxyalkoxy, (ii) loweralkyl, (iii) alkenyl, (iv) heterocyclic (alkyl), (v) aryloxyalkyl, (vi) arylalkyl, (vii) (N-alkanoyl-N-alkyl) aminoalkyl, (viii) alkylsulfonylamidoalkyl,or (ix) phenyl, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, 4-methoxyphenyl, dimethoxyphenyl, fluorophenyl or difluorophenyl wherein the substituent is selected from loweralkyl, alkoxy and halogen and R$_3$ is alkoxycarbonyl or R$_6$—S(O)$_2$—N(R$_{21}$)—R$_{10}$— wherein R$_{10}$ is alkylene, R$_6$ is loweralkyl, haloalkyl, alkoxyalkyl or haloalkoxyalkyl and R$_{21}$ is loweralkyl, haloalkyl, alkoxyalkyl or haloalkoxyalkyl.

Another yet more preferred embodiment of the invention is a=compound of formula (I) or (II) wherein n is 0, R is —C(O)$_2$—G wherein G is hydrogen or a carboxy protecting group, tetrazolyl or —C(O)—NHS(O)$_2$R$_{16}$ wherein R$_{16}$ is loweralkyl or haloalkyl, Z is —CH$_2$—, R$_1$ is loweralkyl, alkenyl, heterocyclic (alkyl), aryloxyalkyl, aryalkyl, aryl, (N-alkanoyl-N-alkyl)aminoalkyl, or alkylsulfonylamidoalkyl, and R$_3$ is R$_4$—C(O)—R$_5$— wherein R$_5$ is alkylene and R$_4$ is (R$_{11}$)(R$_{12}$)N— wherein R$_{11}$ and R$_{12}$ are independently selected from alkyl, aryl, hydroxyalkyl, alkoxy, aminoalkyl, trialkylaminoalkyl, and heterocyclic.

A still more preferred embodiment of the invention is a compound of formula (I) or (II) wherein n is 0, R is —C(O)$_2$—G wherein G is hydrogen or a carboxy protecting group, tetrazolyl or —C(O)—NHS(O)$_2$R$_{16}$ wherein R$_{16}$ is loweralkyl or haloalkyl, Z is —CH$_2$—, R$_1$ is substituted or unsubstituted 4-methoxyphenyl, 4-fluorophenyl, 2-fluorophenyl, 4-methylphenyl, 4-trifluoromethylphenyl, 4-pentafluoroethylphenyl, 4-methoxymethoxyphenyl, 4-hydroxyphenyl, 4-ethylphenyl, 1,3-benzodioxolyl, 1,4-benzodioxanyl or dihydrobenzofuranyl wherein the substituent is selected from alkoxy, alkoxyalkoxy and carboxyalkoxy, (ii) loweralkyl, (iii) alkenyl, (iv) heterocyclic (alkyl), (v) aryloxyalkyl, (vi) arylalkyl, (vii) (N-alkanoyl-N-alkyl)aminoalkyl, (viii) alkylsulfonylamidoalkyl, or (ix) phenyl, R$_2$ is 1,3-benzodioxolyl, 1,4-benzodioxanyl, dihydrobenzofuranyl, benzofuranyl, 4-methoxyphenyl, dimethoxyphenyl, fluorophenyl or difluorophenyl and R$_3$ is R$_4$—C(O)—R$_5$— wherein R$_5$ is alkylene and R$_4$ is (R$_{11}$)(R$_{12}$)N— wherein R$_{11}$ and R$_{12}$ are independently selected from loweralkyl, aryl, arylalkyl, hydroxyalkyl, alkoxy, aminoalkyl, trialkylaminoalkyl, or heterocyclic.

Another still more preferred embodiment of the invention is a compound of formula (I) or (II) wherein n is 0, R is —C(O)$_2$—G wherein G is hydrogen or a carboxy protecting group, tetrazolyl or —C(O)—NHS(O)$_2$R$_{16}$ wherein R$_{16}$ is loweralkyl or haloalkyl, Z is —CH$_2$—, R$_1$ is loweralkyl, alkenyl, heterocyclic (alkyl), aryloxyalkyl, arylalkyl, (N-alkanoyl-N-alkyl)aminoalkyl, alkylsulfonylamidoalkyl, phenyl, or alkoxyalkyl, R$_2$ is 1,3-benzodioxolyl, 1,4-benzodioxanyl, dihydrobenzofuranyl, benzofuranyl, 4-methoxyphenyl, dimethoxyphenyl, fluorophenyl or difluorophenyl and R$_3$ is R$_4$—C(O)—R$_5$— wherein R$_5$ is alkylene and R$_4$ is (R$_{11}$)(R$_{12}$)N— wherein R$_{11}$ and R$_{12}$ are independently selected from loweralkyl, aryl, arylalkyl, hydroxyalkyl, alkoxy, aminoalkyl, trialkylaminoalkyl, or heterocyclic.

A most highly preferred embodiment of the invention is a compound of formula (I) or (II) wherein n is 0, R is —C(O)$_2$—G wherein G is hydrogen or a carboxy protecting group, Z is —CH$_2$—, R$_1$ is substituted or unsubstituted 4-methoxyphenyl, 4-fluorophenyl, 2-fluorophenyl, 4-methylphenyl, 4-trifluoromethylphenyl, 4-pentafluoroethylphenyl, 4-methoxymethoxyphenyl, 4-hydroxyphenyl, 4-ethylphenyl, 1,3-benzodioxolyl, 1,4-benzodioxanyl or dihydrobenzofuranyl wherein the substituent is selected from alkoxy, alkoxyalkoxy and carboxyalkoxy, R$_2$ is 1,3-benzodioxolyl, 1,4-benzodioxanyl, dihydrobenzofuranyl, benzofuranyl, 4-methoxyphenyl, dimethoxyphenyl, fluorophenyl or difluorophenyl and R$_3$ is R$_4$—C(O)—R$_5$— wherein R$_5$ is alkylene and R$_4$ is (R$_{11}$)(R$_{12}$)N— wherein R$_{11}$ and R$_{12}$ are independently selected from loweralkyl.

Another most highly preferred embodiment of the invention is a compound of formula (I) or (II) wherein n is 0, R is —C(O)$_2$—G wherein G is hydrogen or a carboxy protecting group, Z is —CH$_2$—, R$_1$ is substituted or unsubstituted 4-methoxyphenyl, 4-fluorophenyl, 2-fluorophenyl, 4-methylphenyl, 4-trifluoromethylphenyl, 4-pentafluoroethylphenyl, 4-methoxymethoxyphenyl, 4-hydroxyphenyl, 4-ethylphenyl, 1,3-benzodioxolyl, 1,4-benzodioxanyl or dihydrobenzofuranyl wherein the substituent is selected from alkoxy, alkoxyalkoxy and carboxyalkoxy, R$_2$ is 1,3-benzodioxolyl, 1,4-benzodioxanyl, dihydrobenzofuranyl, benzofuranyl, 4-methoxyphenyl, dimethoxyphenyl, fluorophenyl or difluorophenyl and R$_3$ is R$_4$—C(O)—R$_5$— wherein R$_5$ is alkylene and R$_4$ is (R$_{11}$)(R$_{12}$)N— wherein R$_{11}$ is loweralkyl and R$_{12}$ is aryl.

Another most highly preferred embodiment of the invention is a compound of formula (I) or (II) wherein n is 0, R is —C(O)$_2$—G wherein G is hydrogen or a carboxy protecting group, Z is —CH$_2$—, R$_1$ is substituted or unsubstituted 4-methoxyphenyl, 3-fluoro-4-methoxyphenyl, 3-fluorophenyl, 2-fluorophenyl, 3-fluoro-4-ethoxyphenyl, 4-methoxymethoxyphenyl, 1,3-benzodioxolyl, 1,4-benzodioxanyl or dihydrobenzofuranyl wherein the substituent is selected from loweralkyl, haloalkyl, alkoxy, alkoxyalkoxy and carboxyalkoxy, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, 4-methoxyphenyl, dimethoxyphenyl, fluorophenyl or difluorophenyl wherein the substituent is selected from loweralkyl, alkoxy and halogen and R$_3$ is R$_6$—S(O)$_2$—N(R$_{21}$)—R$_{10}$— wherein R$_{10}$ is alkylene, R$_6$ is loweralkyl, haloalkyl, alkoxyalkyl or haloalkoxyalkyl and R$_{21}$ is loweralkyl, haloalkyl or alkoxyalkyl.

Another most highly preferred embodiment of the invention is a compound of formula (I) or (II) wherein n is 0, R is —C(O)$_2$—G wherein G is hydrogen or a carboxy protecting group, Z is —CH$_2$—, R$_1$ is substituted or unsubstituted 4-methoxyphenyl, 3-fluoro-4-methoxyphenyl, 3-fluorophenyl, 2-fluorophenyl, 3-fluoro-4-ethoxyphenyl, 4-methoxymethoxyphenyl, 1,3-benzodioxolyl, 1,4-benzodioxanyl or dihydrobenzofuranyl wherein the substituent is selected from loweralkyl, haloalkyl, alkoxy, alkoxyalkoxy and carboxyalkoxy, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, 4-methoxyphenyl, dimethoxyphenyl, fluorophenyl or difluorophenyl wherein the substituent is selected from loweralkyl, alkoxy and halogen and R$_3$ is R$_4$—C(O)—R$_5$— wherein R$_5$ is alkylene and R$_4$ is (R$_{11}$)(R$_{12}$)N— wherein R$_{11}$ is alkyl and R$_{12}$ is selected from aryl, aminoalkyl, trialkylaminoalkyl, and heterocyclic.

Another most highly preferred embodiment of the invention is a compound of formula (I) or (II) wherein n is 0, R is —C(O)$_2$—G wherein G is hydrogen or a carboxy protecting group, Z is —CH$_2$—, R$_1$ is loweralkyl,alkenyl, heterocyclic (alkyl), aryloxyalkyl, aryalkyl, aryl, (N-alkanoyl-N-alkyl)aminoalkyl, or alkylsulfonyl-amidoalkyl, and R$_3$ is R$_4$—C(O)—R$_5$— wherein R$_5$ is alkylene and R$_4$ is (R$_{11}$)(R$_{12}$)N— wherein R$_{11}$ and R$_{12}$ are independently selected from alkyl, aryl, hydroxyalkyl, alkoxy, aminoalkyl, trialkylaminoalkyl, and heterocyclic, with the proviso that one or R$_{11}$ and R$_{12}$ is alkyl.

Another most highly preferred embodiment of the invention is a compound of formula (I) or (II) wherein n is 0, Z is —CH$_2$—, and R$_3$ is R$_4$—C(O)—R$_5$— wherein R$_4$ is (R$_{11}$)(R$_{12}$)N— as defined therein and R$_5$ is alkylene.

Another most highly preferred embodiment of the invention is a compound of formula (I) or (II) wherein n is 0, Z is —CH$_2$—, R$_1$ is loweralkyl, and R$_3$ is R$_4$—C(O)—R$_5$— wherein R$_4$ is (R$_{11}$)(R$_{12}$)N— as defined therein and R$_5$ is alkylene.

Another most highly preferred embodiment of the invention is a compound of formula (I) or (II) wherein n is 0, Z is —CH$_2$—, R$_1$ is alkenyl, and R$_3$ is R$_4$—C(O)—R$_5$— wherein R$_4$ is (R$_{11}$)(R$_{12}$)N— as defined therein and R$_5$ is alkylene.

Another most highly preferred embodiment of the invention is a compound of formula (I) or (II) wherein n is 0, Z is —CH$_2$—, R$_1$ is heterocyclic (alkyl), and R$_3$ is R$_4$—C(O)—R$_5$— wherein R$_4$ is (R$_{11}$)(R$_{12}$)N— as defined therein and R$_5$ is alkylene.

Another most highly preferred embodiment of the invention is a compound of formula (I) or (II) wherein n is 0, Z is —CH$_2$—, R$_1$ is aryloxyalkyl, and R$_3$ is R$_4$—C(O)—R$_5$— wherein R$_4$ is (R$_{11}$)(R$_{12}$)N— as defined therein and R$_5$ is alkylene.

Another most highly preferred embodiment of the invention is a compound of formula (I) or (II) wherein n is 0, Z is —CH$_2$—, R$_1$ is arylalkyl, and R$_3$ is R$_4$—C(O)—R$_5$— wherein R$_4$ is (R$_{11}$)(R$_{12}$)N— as defined therein and R$_5$ is alkylene.

Another most highly preferred embodiment of the invention is a compound of formula (I) or (II) wherein n is 0, Z is —CH$_2$—, R$_1$ is aryl, and R$_3$ is R$_4$—C(O)—R$_5$— wherein R$_4$ is (R$_{11}$)(R$_{12}$)N— as defined therein and R$_5$ is alkylene.

Another most highly preferred embodiment of the invention is a compound of formula (I) or (II) wherein n is 0, Z is —CH$_2$—, R$_1$ is (N-alkanoyl-N-alkyl)aminoalkyl, and R$_3$ is R$_4$—C(O)—R$_5$— wherein R$_4$ is (R$_{11}$)(R$_{12}$)N— as defined therein and R$_5$ is alkylene.

Another most highly preferred embodiment of the invention is a compound of formula (I) or (II) wherein n is 0, Z is —CH$_2$—, R$_1$ is alkylsulfonylamidoalkyl, and R$_3$ is R$_4$—C(O)—R$_5$— wherein R$_4$ is (R$_{11}$)(R$_{12}$)N— as defined therein and R$_5$ is alkylene.

The present invention also relates to processes for preparing the compounds of formula (I) and (II) and to the synthetic intermediates employed in these processes.

The present invention also relates to a method of antagonizing endothelin in a mammal (preferably, a human) in need of such treatment, comprising administering to the mammal a therapeutically effective amount of a compound of formula (I) or (II).

The invention further relates to endothelin antagonizing compositions comprising a pharmaceutical carrier and a therapeutically effective amount of a compound of formula (I) or (II).

The compounds of the invention comprise two or more asymmetrically substituted carbon atoms. As a result, racemic mixtures, mixtures of diastereomers, as well as single diastereomers of the compounds of the invention are included in the present invention. The terms "S" and "R" configuration are as defined by the IUPAC 1974 Recommendations for Section E, Fundamental Stereochemistry, Pure Appl. Chem. (1976) 45, 13–30.

The term "carboxy protecting group" as used herein refers to a carboxylic acid protecting ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields, as described in U.S. Pat. No. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ alkyl (e.g., methyl, ethyl or tertiary butyl and the like); haloalkyl; alkenyl; cycloalkyl and substituted derivatives thereof such as cyclohexyl, cylcopentyl and the like; cycloalkylalkyl and substituted derivatives thereof such as cyclohexylmethyl, cylcopentylmethyl and the like; arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen4-yl)alkyl, such as (5-phenyl-2-oxo-1,3-dioxolen-4-yl)methyl and the like.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "alkanoyl" as used herein refers to an alkyl group as previously defined appended to the parent molecular moiety through a carbonyl (—C(O)—) group. Examples of alkanoyl include acetyl, propionyl and the like.

The term "alkanoylamino" as used herein refers to an alkanoyl group as previously defined appended to an amino group. Examples alkanoylamino include acetamido, propionylamido and the like.

The term "alkanoylaminoalkyl" as used herein refers to $R_{43}$—NH—$R_4$— wherein $R_{43}$ is an alkanoyl group and $R_{44}$ is an alkylene group.

The term "alkanoyloxyalkyl" as used herein refers to $R_{30}$—O—$R_{31}$— wherein $R_{30}$ is an alkanoyl group and $R_{31}$ is an alkylene group. Examples of alkanoyloxyalkyl include acetoxymethyl, acetoxyethyl and the like.

The term "alkenyl" as used herein refers to a straight or branched chain hydrocarbon radical containing from 2 to 15 carbon atoms and also containing at least one carbon-carbon double bond. Alkenyl groups include, for example, vinyl (ethenyl), allyl (propenyl), butenyl, 1-methyl-2-buten-1-yl and the like.

The term "alkenylene" denotes a divalent group derived from a straight or branched chain hydrocarbon containing from 2 to 15 carbon atoms and also containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkenyloxy" as used herein refers to an alkenyl group, as previously defined, connected to the parent molecular moiety through an oxygen (—O—) linkage. Examples of alkenyloxy include allyloxy, butenyloxy and the like.

The term "alkoxy" as used herein refers to $R_{41}O$— wherein $R_{41}$ is a loweralkyl group, as defined herein. Examples of alkoxy include, but are not limited to, ethoxy, tert-butoxy, and the like.

The term "alkoxyalkoxy" as used herein refers to $R_{80}O$—$R_{81}O$— wherein $R_{80}$ is loweralkyl as defined above and $R_{81}$ is alkylene. Representative examples of alkoxyalkoxy groups include methoxymethoxy, ethoxymethoxy, t-butoxymethoxy and the like.

The term "alkoxyalkoxyalkyl" as used herein refers to an alkoxyalkoxy group as previously defined appended to an alkyl radical. Representative examples of alkoxyalkoxyalkyl groups include methoxyethoxyethyl, methoxymethoxymethyl, and the like.

The term "alkoxyalkyl" as used herein refers to an alkoxy group as previously defined appended to an alkyl radical as previously defined. Examples of alkoxyalkyl include, but are not limited to, methoxymethyl, methoxyethyl, isopropoxymethyl and the like.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, isopropoxycarbonyl and the like.

The term "alkoxycarbonylalkenyl" as used herein refers to an alkoxycarbonyl group as previously defined appended to an alkenyl radical. Examples of alkoxycarbonylalkenyl include methoxycarbonylethenyl, ethoxycarbonylethenyl and the like.

The term "alkoxycarbonylalkyl" as used herein refers to $R_{34}$—C(O)—$R_{35}$— wherein $R_{34}$ is an alkoxy group and $R_{35}$ is an alkylene group. Examples of alkoxycarbonylalkyl include methoxycarbonylmethyl, methoxcarbonylethyl, ethoxycarbonylmethyl and the like.

The term "alkoxycarbonylaminoalkyl" as used herein refers to $R_{38}$—C(O)—NH—$R_{39}$— wherein $R_{38}$ is an alkoxy group and $R_{39}$ is an alkylene group.

The term "alkoxycarbonyloxyalkyl" as used herein refers to $R_{36}$—C(O)—O—$R_{37}$— wherein $R_{36}$ is an alkoxy group and $R_{37}$ is an alkylene group.

The term "(alkoxycarbonyl)thioalkoxy" as used herein refers to an alkoxycarbonyl group as previously defined appended to a thioalkoxy radical. Examples of (alkoxycarbonyl)thioalkoxy include methoxycarbonylthiomethoxy, ethoxycarbonylthiomethoxy and the like.

The term "alkoxyhaloalkyl" as used herein refers to a haloalkyl radical to which is appended an alkoxy group.

The terms "alkyl" and "loweralkyl" as used herein refer to straight or branched chain alkyl radicals containing from 1 to 15 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "(N-alkanoyl-N-alkyl)aminoalkyl" as used herein refers to $R_{85}C(O)N(R_{86})R_{87}$— wherein $R_{85}$ is an alkanoyl as previously defined, $R_{86}$ is loweralkyl, and $R_{87}$ is alkylene.

The term "alkylamino" as used herein refers to $R_{51}NH$— wherein $R_{51}$ is a loweralkyl group, for example, ethylamino, butylamino, and the like.

The term "alkylaminoalkyl" as used herein refers to a loweralkyl radical to which is appended an alkylamino group.

The term "alkylaminocarbonyl" as used herein refers to an alkylamino group, as previously defined, appended to the parent molecular moiety through a carbonyl (—C(O)—) linkage. Examples of alkylaminocarbonyl include methylaminocarbonyl, ethylaminocarbonyl, isopropylaminocarbonyl and the like.

The term "alkylaminocarbonylalkenyl" as used herein refers to an alkenyl radical to which is appended an alkylaminocarbonyl group.

The term "alkylaminocarbonylalkyl" as used herein refers to a loweralkyl radical to which is appended an alkylaminocarbonyl group.

The term "alkylaminocarbonylaminoalkyl" as used herein refers to $R_{40}$—C(O)—NH—$R_{41}$— wherein $R_{40}$ is an alkylamino group and $R_{41}$ is an alkylene group.

The term "alkylene" denotes a divalent group derived from a straight or branched chain saturated hydrocarbon having from 1 to 15 carbon atoms by the removal of two hydrogen atoms, for example —$CH_2$—, —$CH_2CH_2$—, —$CH(CH_3)$—, —$CH_2CH_2CH_2$—, —$CH_2C(CH_3)_2CH_2$— and the like.

The term "alkylsulfonylamidoalkyl" as used herein refers $R_{88}S(O)_2NHR_{89}$— wherein $R_{88}$ is loweralkyl and $R_{89}$ is alkylene.

The term "alkylsulfonylamino" as used herein refers to an alkyl group as previously defined appended to the parent molecular moiety through a sulfonylamino (—$S(O)_2$—NH—) group. Examples of alkylsulfonylamino include methylsulfonylamino, ethylsulfonylamino, isopropylsulfonylamino and the like.

The term "alkynyl" as used herein refers to a straight or branched chain hydrocarbon radical containing from 2 to 15 carbon atoms and also containing at least one carbon-carbon triple bond. Examples of alkynyl include —C≡C—H, H—C—C— $CH_2$—, H—C≡C—$CH(CH_3)$— and the like.

The term "alkynylene" refers to a divalent group derived by the removal of two hydrogen atoms from a straight or branched chain acyclic hydrocarbon group containing from 2 to 15 carbon atoms and also containing a carbon-carbon triple bond. Examples of alkynylene include —C≡C—, —C≡C—$CH_2$—, —C≡C—$CH(CH_3)$— and the like.

The term "aminoalkyl" as used herein refers to a —$NH_2$, alkylamino, or dialkylamino group appended to the parent molecular moiety through an alkylene.

The term "aminocarbonyl" as used herein refers to $H_2N$—C(O)—.

The term "aminocarbonylalkenyl" as used herein refers to an alkenyl radical to which is appended an aminocarbonyl ($NH_2C(O)$—) group.

The term "aminocarbonylalkoxy" as used herein refers to $H_2N$—C(O)— appended to an alkoxy group as previously defined. Examples of aminocarbonylalkoxy include aminocarbonylmethoxy, aminocarbonylethoxy and the like.

The term "aminocarbonylalkyl" as used herein refers to a loweralkyl radical to which is appended an aminocarbonyl ($NH_2C(O)$—) group.

The term "trialkylaminoalkyl" as used herein refers to $(R_{90})(R_{91})(R_{92})N(R_{93})$— wherein $R_{90}$, $R_{91}$, and $R_{92}$ are independently selected from loweralkyl and $R_{93}$ is alkylene.

The term "aroyloxyalkyl" as used herein refers to $R_{32}$—C(O)—O—$R_{33}$— wherein $R_{32}$ is an aryl group and $R_{33}$ is an alkylene group. Examples of aroyloxyalkyl include benzoyloxymethyl, benzoyloxyethyl and the like.

The term "aryl"0 as used herin refers to a mono- or bicycilc carbocyclic ring system having one or two aromatic rings including, but not limited to, phenyl, naphthyl, tetrahydronaphthyl, indanyl, indenyl and the like. Aryl groups can be unsubstituted or substituted with one, two or three substituents independently selected from loweralkyl, halo, haloalkyl, haloalkoxy, hydroxyalkyl, alkenyloxy, alkoxy, alkoxyalkoxy, alkoxycarbonyl, alkoxycarbonylalkenyl, (alkoxycarbonyl)thioalkoxy, thioalkoxy, amino, alkylamino, dialkylamino, aminoalkyl, trialkylaminoalkyl, aminocarbonyl, aminocarbonylalkoxy, alkanoylamino, arylalkoxy, aryloxy, mercapto, cyano, nitro, carboxaldehyde, carboxy, carboxyalkenyl, carboxyalkoxy, alkylsulfonylamino, cyanoalkoxy, (heterocyclic)alkoxy, hydroxy, hydroxalkoxy, phenyl and tetrazolylalkoxy. In addition, substituted aryl groups include tetrafluorophenyl and pentafluorophenyl.

The term "arylalkenyl" as used herein refers to an alkenyl radical to which is appended an aryl group, for example, phenylethenyl and the like.

The term "arylalkoxy" as used herein refers to $R_{42}O$— wherein $R_{42}$ is an arylalkyl group, for example, benzyloxy, and the like.

The term "arylalkoxyalkyl" as used herein refers to a loweralkyl radical to which is appended an arylalkoxy group, for example, benzyloxymethyl and the like.

The term "arylalkyl" as used herein refers to an aryl group as previously defined, appended to a loweralkyl radical, for example, benzyl and the like.

The term "aryloxy" as used herein refers to $R_{45}O$— wherein $R_{45}$ is an aryl group, for example, phenoxy, and the like.

The term "arylalkylcarbonyloxyalkyl" as used herein refers to a loweralkyl radical to which is appended an arylalkylcarbonyloxy group (i.e., $R_{62}C(O)$— wherein $R_{62}$ is an arylalkyl group).

The term "aryloxyalkyl" refers to an aryloxy group as previously defined appended to an alkyl radical. Examples of aryloxyalkyl include phenoxymethyl, 2-phenoxyethyl and the like.

The term "carboxaldehyde" as used herein refers to a formaldehyde radical, —C(O)H.

The term "carboxy" as used herein refers to a carboxylic acid radical, —C(O)OH.

The term "carboxyalkenyl" as used herein refers to a carboxy group as previously defined appended to an alkenyl radical as previously defined. Examples of carboxyalkenyl include 2-carboxyethenyl, 3-carboxy-1-ethenyl and the like.

The term "carboxyalkoxy" as used herein refers to a carboxy group as previously defined appended to an alkoxy radical as previously defined. Examples of carboxyalkoxy include carboxymethoxy, carboxyethoxy and the like.

The term "cyanoalkoxy" as used herein refers to an alkoxy radical as previously defined to which is appended a cyano (—CN) group. Examples of cyanoalkoxy include 3-cyanopropoxy, 4-cyanobutoxy and the like.

The term "cycloalkanoyloxyalkyl" as used herein refers to a loweralkyl radical to which is appended a cycloalkanoyloxy group (i.e., $R_{60}$—C(O)—O— wherein $R_{60}$ is a cycloalkyl group).

The term "cycloalkyl" as used herein refers to an aliphatic ring system having 3 to 10 carbon atoms and 1 to 3 rings including, but not limited to, cyclopropyl, cyclopentyl, cyclohexyl, norbornyl, adamantyl, and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkylalkyl" as used herein refers to a cycloalkyl group appended to a loweralkyl radical, including but not limited to cyclohexylmethyl.

The term "dialkylamino" as used herein refers to $R_{56}R_{57}N$— wherein $R_{56}$ and $R_{57}$ are independently selected from loweralkyl, for example diethylamino, methyl propylamino, and the like.

The term "dialkylaminoalkyl" as used herein refers to a loweralkyl radical to which is appended a dialkylamino group.

The term "dialkylaminocarbonyl" as used herein refers to a dialkylamino group, as previously defined, appended to the parent molecular moiety through a carbonyl (—C(O)—) linkage. Examples of dialkylaminocarbonyl include dimethylaminocarbonyl, diethylaminocarbonyl and the like.

The term "dialkylaminocarbonylalkenyl" as used herein refers to an alkenyl radical to which is appended a dialkylaminocarbonyl group.

The term "dialkylaminocarbonylalkyl" as used herein refers to $R_{50}$—C(O)—$R_{51}$— wherein $R_{50}$ is a dialkylamino group and $R_{51}$ is an alkylene group.

The term "halo" or "halogen" as used herein refers to I, Br, Cl or F.

The term "haloalkenyl" as used herein refers to an alkenyl radical to which is appended at least one halogen substituent.

The term "haloalkoxy" as used herein refers to an alkoxy radical as defined above, bearing at least one halogen substituent, for example, 2-fluoroethoxy, 2,2,2-trifluoroethoxy, trifluoromethoxy, 2,2,3,3,3-pentafluoropropoxy and the like.

The term "haloalkoxyalkyl" as used herein refers to a loweralkyl radical to which is appended a haloalkoxy group.

The term "haloalkyl" as used herein refers to a lower alkyl radical, as defined above, to which is appended at least one halogen substituent, for example, chloromethyl, fluoroethyl, trifluoromethyl or pentafluoroethyl and the like.

The term "heterocyclic ring" or "heterocyclic" or "heterocycle" as used herein refers to any 3— or 4-membered ring containing a heteroatom selected from oxygen, nitrogen and sulfur; or a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; or two sulfur atoms in non-adjacent positions. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, dihydroindolyl, quinolyl, isoquinolyl, tetrahydroquinolyl, tetrahydroisoquinolyl, decahydroquinolyl, decahydroisoquinolyl, benzofuryl, dihydrobenzofuryl or benzothienyl and the like). Heterocyclics include: aziridinyl, azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, oxetanyl, furyl, tetrahydrofuranyl, thienyl, thiazolidinyl, isothiazolyl, triazolyl, tetrazolyl, isoxazolyl, oxadiazolyl, thiadiazolyl, pyrrolyl, pyrimidyl and benzothienyl. Heterocyclics also include compounds of the formula

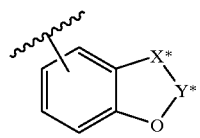

where X* is —CH$_2$— or —O— and Y* is —C(O)— or [—C(R")$_2$—]$_v$ where R" is hydrogen or C$_1$–C$_4$-alkyl and v is 1, 2 or 3 such as 1,3-benzodioxolyl, 1,4-benzodioxanyl and the like. Heterocyclics also include bicyclic rings such as quinuclidinyl and the like.

Heterocyclics can be unsubstituted or monosubstituted or disubstituted with substituents independently selected from hydroxy, halo, oxo (═O), alkylimino (R*N═ wherein R* is a loweralkyl group), amino, alkylamino, dialkylamino, alkoxy, alkoxyalkoxy, aminoalkyl, trialkylaminoalkyl, haloalkyl, cycloalkyl, aryl, arylalkyl, —COOH, —SO$_3$H, alkoxycarbonyl, nitro, cyano and loweralkyl. In addition, nitrogen containing heterocycles can be N-protected.

The term "(heterocyclic)alkoxy" as used herein refers to a heterocyclic group as defined above appended to an alkoxy radical as defined above. Examples of (heterocyclic)alkoxy include 4-pyridylmethoxy, 2-pyridylmethoxy and the like.

The term "(heterocyclic)alkyl" as used herein refers to a heterocyclic group as defined above appended to a loweralkyl radical as defined above.

The term "heterocycliccarbonyloxyalkyl" as used herein refers to R$_{46}$—C(O)—O—R$_{47}$— wherein R$_{46}$ is a heterocyclic group and R$_{47}$ is an alkylene group.

The term "hydroxy" as used herein refers to —OH.

The term "hydroxyalkenyl" as used herein refers to an alkenyl radical to which is appended a hydroxy group.

The term "hydroxyalkoxy" as used herein refers to an alkoxy radical as previously defined to which is appended a hydroxy (—OH) group. Examples of hydroxyalkoxy include 3-hydroxypropoxy, 4-hydroxybutoxy and the like.

The term "hydroxyalkyl" as used herein refers to a loweralkyl radical to which is appended a hydroxy group.

The term "leaving group" as used herein refers to a halide (for example, Cl, Br or I) or a sulfonate (for example, mesylate, tosylate, triflate and the like).

The term "mercapto" as used herein refers to —SH.

The terms "methylenedioxy" and "ethylenedioxy" refer to one or two carbon chains attached to the parent molecular moiety through two oxygen atoms. In the case of methylenedioxy, a fused 5 membered ring is formed. In the case of ethylenedioxy, a fused 6 membered ring is formed. Methylenedixoy substituted on a

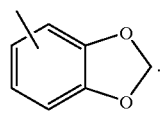

phenyl ring results in the formation of a benzodioxolyl radical. Ethylenedioxy substituted on a phenyl ring results in the formation of a

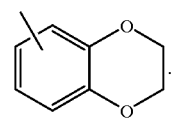

benzodioxanyl radical.

The term "substantially pure" as used herein means 95% or more of the specified compound.

The term "tetrazolyl" as used herein refers to a radical of the formula

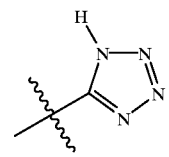

or a tautomer thereof.

The term "tetrazolylalkoxy" as used herein refers to a tetrazolyl radical as defined above appended to an alkoxy group as defined above. Examples of tetrazolylalkoxy include tetrazolylmethoxy, tetrazolylethoxy and the like.

The term "thioalkoxy" as used herein refers to R$_{70}$S— wherein R$_{70}$ is loweralkyl. Examples of thioalkoxy include, but are not limited to, methylthio, ethylthio and the like.

The term "thioalkoxyalkoxy" as used herein refers to R$_{80}$S—R$_{81}$O— wherein R$_{80}$ is loweralkyl as defined above and R$_{81}$ is alkylene. Representative examples of alkoxyalkoxy groups include CH$_3$SCH$_2$O—, EtSCH$_2$O—, t-BuSCH$_2$O— and the like.

The term "thioalkoxyalkoxyalkyl" as used herein refers to a thioalkoxyalkoxy group appended to an alkyl radical. Representative examples of alkoxyalkoxyalkyl groups include CH$_3$SCH$_2$CH$_2$OCH$_2$CH$_2$—, CH$_3$SCH$_2$OCH$_2$—, and the like.

The term "trans,trans" as used herein refers to the orientation of substituents

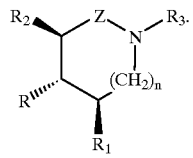

(R$_1$ and R$_2$) relative to the central substituent R as shown

The term "trans,cis" as used herein refers to the orientation of substituents

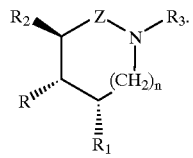

($R_1$ and $R_2$) relative to the central substituent R as shown

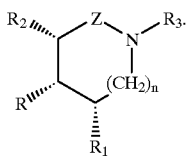

This definition encompasses both the case where R and $R_2$ are cis and R and $R_1$ are trans and the case where $R_2$ and R are trans and R and $R_1$ are cis.

The term "cis,cis" as used herein refers to the orientation of substituents ($R_1$ and $R_2$) relative to the central substituent R as shown

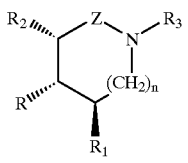

Preferred compounds of the invention are selected from the group consisting of:

trans-trans-2-(4-Methoxyphenyl)-4-(1,3-benzodioxol-5-yl)-1-[3-(N-propyl-N-n-pentanesulfonylamino)propyl]-pyrrolidine-3-carboxylic acid;

trans,trans-2-(4-Methoxymethoxyphenyl)-4-(1,3-benzodioxol-5-yl)-(2-(N-propyl-N-n-pentanesulfonylamino)ethyl]pyrrolidine-3-carboxylic acid;

trans,trans-2-(3,4-Dimethoxyphenyl)-4-(1,3-benzodioxol-5-yl)-1-[2-(N-propyl-N-n-pentanesulfonylamino)ethyl]pyrrolidine-3-carboxylic acid;

trans,trans-2-(3,4-Dimethoxyphenyl)-4-(1,3-benzodioxol-5-yl)-1-[2-(N-propyl-N-n-hexanesulfonylamino)ethyl]pyrrolidine-3-carboxylic acid;

trans,trans-2-(4-Propoxyphenyl)-4-(1,3-benzodioxol-5-yl)-1-[2-(N-propyl-N-n-pentanesulfonylamino)ethyl]pyrrolidine-3-carboxylic acid;

trans,trans-2-(3,4-Difluorophenyl)-4-(1,3-benzodioxol-5-yl)-1-(N,N-di(n-butyl)aminocarbonylmethyl)-pyrrolidine-3-carboxylic acid;

trans,trans-2-(3,4-Difluorophenyl)-4-(1,3-benzodioxol-5-yl)-1-[2-(N-propyl-N-n-pentanesulfonylamino)ethyl]pyrrolidine-3-carboxylic acid;

trans,trans-2-(3-Fluoro-4-methoxyphenyl)-4-(1,3-benzodioxol-5-yl)-1-[2-(N-propyl-N-n-hexanesulfonylamino)ethyl]pyrrolidine-3-carboxylic acid;

trans,trans-2-(3-Fluoro-4-methoxyphenyl)-4-(1,3-benzodioxol-5-yl)-1-(2-(N-propyl-N-(3-chloropropanesulfonyl)amino)ethyl)-pyrrolidine-3-carboxylic acid;

trans,trans-2-(3-Fluoro-4-methoxyphenyl)-4-(1,3-benzodioxol-5-yl)-1-(2-(N-isobutyl-N-(3-chloropropanesulfonyl)amino)ethyl)pyrrolidine-3-carboxylic acid;

trans,trans-2-(3-Fluoro-4-methoxyphenyl)-4-(1,3-benzodioxol-5-yl)-1-[2-(N-propyl-N-(4-methylbutanesulfonyl)amino)ethyl]pyrrolidine-3-carboxylic acid;

trans,trans-2-(4-Methoxy-3-fluorophenyl)-4-(7-methoxy-1,3-benzodioxol-5-yl)-1-[2-(N-propyl-N-(n-pentanesulfonyl)amino)ethyl]pyrrolidine-3-carboxylic acid;

trans,trans-2-(3-Fluoro-4-methoxyphenyl)-4-(1,3-benzodioxol-5-yl)-1-[2-(N-propyl-N-(2,2,3,3,3-pentafluoropropoxyethanesulfonyl)-amino)ethyl]pyrrolidine-3-carboxylic acid;

trans,trans-2-(1,4-Benzodioxan-6-yl)-4-(7-methoxy-1,3-benzodioxol-5-yl)-1-[2-(N-propyl-N-(n-pentanesulfonyl)amino)ethyl]pyrrolidine-3-carboxylic acid;

trans,trans-2-(3-Fluoro-4-methoxyphenyl)-4-(1,3-benzodioxol-5-yl)-1-(2-(N-isobutyl-N-(pentanesulfonylamino)ethyl)pyrrolidine-3-carboxylic acid;

trans,trans-2-(3-Fluoro-4-methoxyphenyl)-4-(1,3-benzodioxol-5-yl)-1-(2-(N-(2-methoxyethyl)-N-(3-chloropropanesulfonyl)amino)-ethyl)pyrrolidine-3-carboxylic acid;

trans,trans-2-(3-Fluoro-4-methoxyphenyl)-4-(1,3-benzodioxol-5-yl)-1-(2-(N-(2-methoxyethyl)-N-(pentanesulfonyl)amino)ethyl)pyrrolidine-3-carboxylic acid;

trans,trans-2-(3-Fluoro-4-methoxyphenyl)-4-(1,3-benzodioxol-5-yl)-1-[2-(N-propyl-N-((2,2,2-trifluoroethoxyethane)sulfonyl)amino)-ethyl]pyrrolidine-3-carboxylicacid;

trans,trans-2-(3-Fluoro-4-methoxyphenyl)-4-(1,3-benzodioxol-5-yl)-1-(2-(N-(2-methoxyethyl)-N-(butanesulfonylamino)ethyl)-pyrrolidine-3-carboxylic acid;

trans,trans-2-(3-Fluoro-4-methoxyphenyl)-4-(1,3-benzodioxol-5-yl)-1-[2-(N-propyl-N-(2-methylpropanesulfonyl)amino)ethyl]pyrrolidine-3-carboxylic acid;

trans,trans-2-(3-Fluoro-4-methoxyphenyl)-4-(1,3-benzodioxol-5-yl)-1-(2-(N-isobutyl-N-(butanesulfonylamino))ethyl)pyrrolidine-3-carboxylic acid;

trans,trans-2-(2-Methylpentyl)-4-(1,3-benzodioxol-5-yl)-1-(N,N-di(n-butyl)aminocarbonylmethyl)-pyrrolidine-3-carboxylic acid;

trans,trans-2-(2,2-Dimethylpentyl)-4-(1,3-benzodioxol-5-yl)-1-(N,N-di(n-butyl)aminocarbonylmethyl)-pyrrolidine-3-carboxylic acid;

trans,trans-2-(2-(1,3-Dioxo-2-yl)ethyl)-4-(1,3-benzodioxol-5-yl)-1-(N,N-di(n-butyl)aminocarbonylmethyl)-pyrrolidine-3-carboxylic acid;

trans,trans-2-(2-(2-Tetrahydro-2H-pyran)ethyl)-4-(1,3-benzodioxol-5-yl)-1-(N,N-di(n-butyl)aminocarbonylmethyl)-pyrrolidine-3-carboxylic acid;

trans,trans-2-(2,2,4-Trimethyl-3-pentenyl)-4-(1,3-benzodioxol-5-yl)-1-(N,N-di(n-butyl)aminocarbonylmethyl)-pyrrolidine-3-carboxylic acid;

trans,trans-2-(2,2-Dimethyl-2-(1,3-dioxolan-2-yl)ethyl)-4-(1,3-benzodioxol-5-yl)-1-(N,N-di(n-butyl)aminocarbonylmethyl)-pyrrolidine-3-carboxylic acid;

trans,trans-2-(2-(1,3-Dioxo-2-yl)ethyl)-4-(1,3-benzodioxol-5-yl)-1-[[N-4-heptyl-N(2-methyl-3-fluorophenyl)] amino carbonylmethyl]-pyrrolidine-3-carboxylic acid;

trans,trans-2-((2-Methoxyphenoxy)-methyl)-4-(1,3-benzodioxol-5-yl)-1-(N,N-di(n-butyl)aminocarbonylmethyl)-pyrrolidine-3-carboxylic acid;

(2S,3R,4S)-2-(2,2-Dimethylpentyl)-4-(1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2-(2-Oxopyrrolidin-1-yl)ethyl)-4-(1,3-benzodioxol-5-yl)-1-(N,N-di(n-butyl)aminocarbonylmethyl)-pyrrolidine-3-carboxylic acid;

trans,trans-2-(2-(1,3-Dioxol-2-yl)ethyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethylpentyl)-4-(7-methoxy-1,3-benzodioxol-5-yl)-1-(N,N-di(n-butyl)aminocarbonylmethyl)-pyrrolidine-3-carboxylic acid;

trans,trans-2-(2,2-dimethylpentyl)-4-(2,3-dihydrobenzofuran-5-yl)-1-(N,N-di(n-butyl)aminocarbonylmethyl)-pyrrolidine-3-carboxylic acid;

trans,trans-2-(2,2,-Dimethyl-2-(1,3-dioxolan-2-yl)ethyl)-4-(7-methoxy-1,3-benzodioxol-5-yl)-1-(N,N-di(n-butyl)aminocarbonylmethyl)-pyrrolidine-3-carboxylic acid;

trans,trans-2-(2-(2-Methoxyphenyl)-ethyl)-4-(1,3-benzodioxol-5-yl)-1-(N,N-di(n-butyl)aminocarbonylmethyl)-pyrrolidine-3-carboxylic acid;

trans,trans-2-(2,2-Dimethyl-3-(E)-pentenyl)-4-(7-methoxy-1,3-benzodioxol-5-yl)-1-(N,N-di(n-butyl)aminocarbonylmethyl)-pyrrolidine-3-carboxylic acid;

trans,trans-2-(2-(2-pyridyl)ethyl)-4-(1,3-benzodioxol-5-yl)-1-(N,N-di(n-butyl)aminocarbonylmethyl)-pyrrolidine-3-carboxylic acid;

(2S, 3R, 4S)-2-(2-(2-oxopyrrolidin-1-yl)ethyl)-4-(1,3-benzodioxol-5-yl)-1-(N,butyl)aminocarbonylmethyl)-pyrrolidine-3-carboxylic acid;

(2S, 3R, 4S)-2-(2-(2-oxopyrrolidin-1-yl)ethyl)-4-(1,3-benzodioxol-5-yl)-1-N-(4-fluoro-3-methylphenyl))aminocarbonylmethyl)-pyrrolidine-3-carboxylic acid;

trans,trans-2-(2-(I-pyrazolyl)ethyl)-4-(1,3-benzodioxol-5-yl)-1-(N,N-di(n-butyl)aminocarbonylmethyl)-pyrrolidine-3-carboxylic acid;

trans,trans-2-(4-Methoxyphenyl)-4-(1,3-benzodioxol-5-yl)-1-[(N-butyl-N-(4-dimethylaminobutyl)amino)carbonylmethyl]-pyrrolidine-3-carboxylic acid;

(2R,3R,4S)-2-(3-Fluoro-4-methoxyphenyl)-4-(1,3-benzodioxol-5-yl)1-(2-(N-propyl-N-pentanesulfonylamino)ethyl)-pyrrolidine-3-carboxylic acid;

trans,trans-2-(2,2-Dimethylpentyl)-4-(1,3-benzodioxol-5-yl)-1-((N-butyl-N-(4-dimethylamino)butyl)aminocarbonylmethyl)-pyrrolidine-3-carboxylic acid;

trans,trans-2-(2,2-Dimethylpentyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethylpentyl)-4-(7-methoxy-1,3-benzodioxol-5-yl)-1-((N-butyl-N-(4-dimethylamino)butyl)aminocarbonylmethyl)-pyrrolidine-3-carboxylic acid;

trans,trans-2-(2,2-Dimethylpent-3-enyl)-4-(1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethylpent-3-enyl)-4-(1,3-benzodioxol-5-yl)-1-((N-butyl-N-(4-dimethylamino)butyl)aminocarbonylmethyl)-pyrrolidine-3-carboxylic acid;

trans,trans-2-(2,2-Dimethylpent-3-enyl)-4-(7-methoxy-1,3-benzodioxol-5-yl)-1-(N,N-di(n-butyl)aminocarbonylmethyl)-pyrrolidine-3-carboxylic acid;

trans,trans-2-(2,2-Dimethylpent-3-enyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethylpent-3-enyl)-4-(7-methoxy-1,3-benzodioxol-5-yl)-1-((N-butyl-N-(4-dimethylamino)butyl)aminocarbonylmethyl)-pyrrolidine-3-carboxylic acid;

trans,trans-2-(2,2,4-Trimethylpent-3-enyl)-4-(1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2,4-Trimethylpent-3-enyl)-4-(1,3-benzodioxol-5-yl)-1-((N-butyl-N-(4-dimethylamino)butyl)aminocarbonylmethyl)-pyrrolidine-3-carboxylic acid;

trans,trans-2-(2,2,4-Trimethylpent-3-enyl)-4-(7-methoxy-1,3-benzodioxol-5-yl)-1-(N,N-di(n-butyl)aminocarbonylmethyl)-pyrrolidine-3-carboxylic acid;

trans,trans-2-(2,2,4-Trimethylpent-3-enyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2,4-Trimethylpent-3-enyl)-4-(7-methoxy-1,3-benzodioxol-5-yl)-1-((N-t-butyl-N-(4-dimethylamino)butyl)aminocarbonylmethyl)-pyrrolidine-3-carboxylic acid;

trans,trans-2-(2-(1,3-Dioxol-2-yl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(1,3-Dioxol-2-yl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2,2,-Dimethyl-2-(1,3-Dioxol-2-yl)ethyl)-4-(1,3-benzodioxol-5-yl)-1-heptyl-N-(4-fluoro-3-methylphenyl))aminocarbonylmethyl)-pyrrolidine-3-carboxylic acid;

trans,trans-2-(2,2-Dimethyl-2-(1,3-dioxolan-2-yl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2,2,-Dimethyl-2-(1,3-Dioxol-2-yl)ethyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethyl-2-(1,3-dioxolan-2-yl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(2-Methoxyphenyl)-ethyl)-4-(1,3-benzodioxol-5-yl)-1-(N-4-heptyl-N-(4-fluoro-3-methylphenyl))amino)carbonylmethyl]-pyrrolidine-3-carboxylic acid;

trans,trans-2-(2-(2-Methoxyphenyl)-ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(2-Methoxyphenyl)-ethyl)-4-(7-methoxy-1,3-benzodioxol-5-yl)-1-(N,N-di(n-butyl)aminocarbonylmethyl)-pyrrolidine-3-carboxylic acid;

trans,trans-2-(2-(2-Methoxyphenyl)-ethyl)-4-(7-methoxy-1,3-benzodioxol-5-yl)-1-(N-4-heptyl-N-(4-fluoro-3-methylphenyl))amino)carbonylmethyl]-pyrrolidine-3-carboxylic acid;

trans,trans-2-(2-(2-Methoxyphenyl)-ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-((2-Methoxyphenoxy)-methyl)-4-(1,3-benzodioxol-5-yl)-1-(N-4-heptyl-N-(4-fluoro-3-methylphenyl))amino)carbonylmethyl-pyrrolidine-3-carboxylic acid;

trans,trans-2-((2-Methoxyphenoxy)-methyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-((2-Methoxyphenoxy)-methyl)-4-(7-methoxy-1,3-benzodioxol-5-yl)-1-(N,N-di(n-butyl)aminocarbonylmethyl)-pyrrolidine-3-carboxylic acid;

trans,trans-2-((2-Methoxyphenoxy)-methyl)-4-(7-methoxy-1,3-benzodioxol-5-yl)-1-(N-4-heptyl-N-(4-fluoro-3-methylphenyl))amino)carbonylmethyl-pyrrolidine-3-carboxylic acid;

trans,trans-2-((2-Methoxyphenoxy)-methyl)-4-(7-methoxy-1,3-benzodioxol-5-yl)-1-(N-butyl-N-(4-dimethylaminobutyl)amino)carbonylmethyl]-pyrrolidine-3-carboxylic acid;

trans,trans-2-(2-(2-Oxo-1,2-dihydro pyridin-1-yl)-ethyl)-4-(1,3-benzodioxol-5-(N,N-di(n-butyl)aminocarbonyl-methyl)-pyrrolidine-3-carboxylic acid;

trans,trans-2-(2-(2-Oxopyridin-1-yl)-ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(2-Oxopyridin-1-yl)-ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(2-Oxopyridin-1-yl)-ethyl)-4-(7-methoxy-1,3-benzodioxol-5-yl)-1-(N,N-di(N-butyl)aminocarbonylmethyl)-pyrrolidine-3-carboxylic acid;

trans,trans-2-(2-(2-Oxopyridin-1-yl)-ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(2-Oxopyridin-1-yl)-ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2(-2-Oxopiperidin-1-yl)-ethyl)-4-(1,3-benzodioxol-5-yl)-1-(N,N-di(N-butyl)aminocarbonyl-methyl)-pyrrolidine-3-carboxylic acid;

trans,trans-2-(2-(2-Oxopiperidin-1-yl)-ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(2-Oxopiperidin-1-yl)-ethyl)-4-(7-methoxy-1,3-benzodioxol-5-yl)-1-(N,N-di(N-butyl)aminocarbonylmethyl)-pyrrolidine-3-carboxylic acid;

trans,trans-2-(2-(2-Oxopiperidin-1-yl)-ethyl)-4-(7-methoxy-1,3-benzodioxol-5-yl)-1-(N,N-di(N-butyl)aminocarbonylmethyl)-pyrrolidine-3-carboxylic acid;

trans,trans-2-(2-(2-Oxopiperidin-1-yl)-ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(2-Oxopiperidin-1-yl)-ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(2-Oxopyrrolidin-1-yl)ethyl)-4-(1,3-benzodioxol-5-yl)-1-[(N-butyl-N-(3-hydroxypropyl)amino)carbonylmethyl]-pyrrolidine-3-carboxylic acid;

trans,trans-2-(2-(2-Oxopyrrolidin-1-yl)ethyl)-4-(1,3-benzodioxol-5-yl)-1-[(N-butyl-N-(propoxy)amino)carbonylmethyl]-pyrrolidine-3-carboxylic acid;

trans,trans-2-(2-(2-Oxopyrrolidin-1-yl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(2-Oxopyrrolidin-1-yl)ethyl)-4-(1,3-benzodioxol-5-yl)-1-[(N-butyl-N-(4-trimethylammoniobutyl)amino)carbonylmethyl]-pyrrolidine-3-carboxylic acid;

trans,trans-2-(2-(2-Oxopyrrolidin-1-yl)ethyl)-4-(7-methoxy-1,3-benzodioxol-5-yl)-1-(N,N-di(N-butyl)aminocarbonylmethyl)-pyrrolidine-3-carboxylic acid;

trans,trans-2-(2-(2-Oxopyrrolidin-1-yl)ethyl)-4-(7-methoxy-1,3-benzodioxol-5-yl)-1-[(N-butyl-N-(3-hydroxypropyl)amino)carbonylmethyl]-pyrrolidine-3-carboxylic acid;

trans,trans-2-(2-(2-Oxopyrrolidin-1-yl)ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(2-Oxopyrrolidin-1-yl)ethyl)-4-(7-methoxy-1,3-benzodioxol-5-yl)-1-[(N-butyl-N-(propoxy)amino)carbonylmethyl]-pyrrolidine-3-carboxylic acid;

trans,trans-2-(2-(2-Oxopyrrolidin-1-yl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(2-Oxopyrrolidin-1-yl)ethyl)-4-(7-methoxy-1,3-benzodioxol-5-yl)-1-[N-butyl-N-(4-trimethylammoniobutyl)amino)carbonylmethyl]-pyrrolidine-3-carboxylic acid;

trans,trans-2-(2-(2-Oxopyrrolidin-1-yl)ethyl)-4-(2,3-dihydro-benzofuran-5-yl)-1-(N,N-di(N-butyl)aminocarbonylmethyl)-pyrrolidine-3-carboxylic acid;

trans,trans-2-(2-(2-Oxopyrrolidin-1-yl)ethyl)-4-(2,3-dihydro-benzofuran-5-yl)-1-[(N4-heptyl-N-(4-fluoro-3-methylphenyl)amino)carbonylmethyl]-pyrrolidine-3-carboxylic acid;

trans,trans-2-(2-(2-Oxopyrrolidin-1-yl)ethyl)-4-(2,3-dihydro-benzofuran-5-yl)-1-[(N-butyl-N-(4-dimethylaminobutyl)amino)carbonylmethyl]-pyrrolidine-3-carboxylic acid;

trans,trans-2-(2-(3,3-Dimethyl-2-oxopyrrolidin-1-yl)ethyl)-4-(1,3-benzodioxol-5-yl)-1-(N,N-di(N-butyl)aminocarbonylmethyl)-pyrrolidine-3-carboxylic acid;

trans,trans-2-(2-(3,3-Dimethyl-2-oxopyrrolidin-1-yl)ethyl)-4-(1,3-benzodioxol-5-yl)-1-[(N4-heptyl-N-(4-fluoro-3-methylphenyl)amino)carbonylmethyl]-pyrrolidine-3-carboxylic acid;

trans,trans-2-(2-(3,3-Dimethyl-2-oxopyrrolidin-1-yl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(4,4-Dimethyl-2-oxopyrrolidin-1-yl)ethyl)-4-(1,3-benzodioxol-5-yl)-1-(N,N-di(N-butyl)aminocarbonylmethyl)-pyrrolidine-3-carboxylic acid;

trans,trans-2-(2-(4,4-Dimethyl-2-oxopyrrolidin-1-yl) ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(4,4-Dimethyl-2-oxopyrrolidin-1-yl) ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(1-propanesultamyl)ethyl)-4-(1,3-benzodioxol-5-yl)-1-(N,N-dibutylaminocarbonyl-methyl)-pyrrolidine-3-carboxylic acid;

trans,trans-2-(2-(1-propanesultamyl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(1-propanesultamyl)ethyl)-4-(1,3-benzodioxol-5-yl)-1-[(N-butyl-N-(3-hydroxypropyl) amino)carbonylmethyl]-pyrrolidine-3-carboxylic acid;

trans,trans-2-(2-(1-propanesultamyl)ethyl)-4-(1,3-benzodioxol-5-yl)-1-[(N-butyl-N-(propoxy)amino) carbonylmethyl]-pyrrolidine-3-carboxylic acid;

trans,trans-2-(2-(1-propanesultamyl)ethyl)-4-(1,3-benzodioxol-5-yl)-1-[(N-butyl-N-(4 dimethylamino-butyl)amino)carbonylmethyl]-pyrrolidine-3-carboxylic acid;

trans,trans-2-(2-(1-propanesultamyl)ethyl)-4-(7-methoxy-1,3-benzodioxol-5-yl)-1-(N,N-di(n-butyl) aminocarbonylmethyl)-pyrrolidine-3-carboxylic acid;

trans,trans-2-(2-(1-propanesultamyl)ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(1-propanesultamyl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(1-propanesultamyl)ethyl)-4-(2,3-dihydro-benzofuran-5-yl)-1-(N,N-di(n-butyl) aminocarbonylmethyl)-pyrrolidine-3-carboxylic acid;

trans,trans-2-(2-(1-propanesultamyl)ethyl)-4-(2,3-dihydro-benzofuran-5-yl)-1-[(N4-heptyl-N-(4-fluoro-3-methylphenyl)amino)carbonylmethyl]-pyrrolidine-3-carboxylic acid;

trans,trans-2-(2-(1-propanesultamyl)ethyl)-4-(2,3-dihydro-benzofuran-5-yl)-1-[(N-butyl-N-(4-dimethylaminobutyl)amino)carbonylmethyl]-pyrrolidine-3-carboxylic acid;

trans,trans-2-(2-(1-pyrazolyl)ethyl)-4-(1,3-benzodioxol-5-yl)-1-[(N4-heptyl-N-(4-fluoro-3-methylphenyl) amino)carbonylmethyl]-pyrrolidine-3-carboxylic acid;

trans,trans-2-(2-(1-pyrazolyl)ethyl)-4-(1,3-benzodioxol-5-yl)-1-[(N-butyl-N-(3-hydroxypropyl)amino) carbonylmethyl]-pyrrolidine-3-carboxylic acid;

trans,trans-2-(2-(1-pyrazolyl)ethyl)-4-(1,3-benzodioxol-5-yl)-1-(N-butyl-N-(propoxy)amino)carbonylmethyl]-pyrrolidine-3-carboxylic acid;

trans,trans-2-(2-(1-pyrazolyl)ethyl)-4-(1,3-benzodioxol-5-yl)-1-[(N-butyl-N-(4-dimethylaminobutyl)amino) carbonylmethyl]-pyrrolidine-3-carboxylic acid;

trans,trans-2-(2-(1-pyrazolyl)ethyl)-4-(7-methoxy-1,3-benzodioxol-5-yl)-1-(N,N-dibutylamino-carbonylmethyl)-pyrrolidine-3-carboxylic acid;

trans,trans-2-(2-(1-pyrazolyl)ethyl)-4-(7-methoxy-1,3-benzodioxol-5-yl)-1-[(N4-heptyl-N-(4-fluoro-3-methylphenyl)amino)carbonylmethyl]-pyrrolidine-3-carboxylic acid;

trans,trans-2-(2-(1-pyrazolyl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(1-pyrazolyl)ethyl)-4-(2,3-dihydro-benzofuran-5-yl)-1-(N,N-dibutylaminocarbonylmethyl)-pyrrolidine-3-carboxylic acid;

trans,trans-2-(2-(1-pyrazolyl)ethyl)-4-(2,3-dihydro-benzofuran-5-yl)-1-[(N4-heptyl-N-(4-fluoro-3-methylphenyl)amino)carbonylmethyl]-pyrrolidine-3-carboxylic acid;

trans,trans-2-(2-(1-pyrazolyl)ethyl)-4-(2,3-dihydro-benzofuran-5-yl)-1-[(N-butyl-N-(4-dimethylaminobutyl)amino)carbonylmethyl]-pyrrolidine-3-carboxylic acid;

trans,trans-2-(2-(2-oxazolyl)ethyl)-4-(1,3-benzodioxol-5-yl)-1-(N,N-di(n-butyl)aminocarbonylmethyl)-pyrrolidine-3-carboxylic acid;

trans,trans-2-(2-(Oxazol-2-yl)ethyl)-4-(1,3-benzodioxol-5-yl)-1-[(N-4-heptyl-N-(4-fluoro-3-methylphenyl) amino)carbonylmethyl]-pyrrolidine-3-carboxylic acid;

trans,trans-2-(2-(Oxazol-2-yl)ethyl)-4-(1,3-benzodioxol-5-yl)-1-[(N-butyl-N-(3-hydroxypropyl)amino) carbonylmethyl]-pyrrolidine-3-carboxylic acid;

trans,trans-2-(2-(Oxazol-2-yl)ethyl)-4-(1,3-benzodioxol-5-yl)-1-[(N-butyl-N-(propoxy)carbonyl-methyl]-pyrrolidine-3-carboxylic acid;

trans,trans-2-(2-(Oxazol-2-yl)ethyl)-4-(1,3-benzodioxol-5-yl)-1-[(N-butyl-N-(4-dimethylaminobutyl)amino) carbonylmethyl]-pyrrolidine-3-carboxylic acid;

trans,trans-2-(2-(Oxazol-2-yl)ethyl)-4-(7-methoxy-1,3-benzodioxol-5-yl)-1-(N,N-di(n-butyl)aminocar-bonylmethyl)-pyrrolidine-3-carboxylic acid;

trans,trans-2-(2-(Oxazol-2-yl)ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(Oxazol-2-yl)ethyl)-4-(7-methoxy-1,3-benzodioxol-5-yl)-1-[(N-butyl-N-(4-dimethylamino-butyl)amino)carbonylmethyl]-pyrrolidine-3-carboxylic acid;

trans,trans-2-(2-(5-Methyloxazol-2-yl)ethyl)-4-(1,3-benzodioxol-5-yl)-1-(N,N-di(n-butyl)aminocar-bonylmethyl)-pyrrolidine-3-carboxylic acid;

trans,trans-2-(2-(5-Methyloxazol-2-yl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(5-Methyloxazol-2-yl)ethyl)-4-(1,3-benzodioxol-5-yl)-1-[(N-butyl-N-(4-dimethylamino-butyl)amino)carbonylmethyl]-pyrrolidine-3-carboxylic acid;

trans,trans-2-(2-(2,5-Dioxopyrrolidin-1-yl)ethyl)-4-(1,3-benzodioxol-5-yl)-1-(N,N-di(n-butyl)aminocar-bonylmethyl)-pyrrolidine-3-carboxylic acid;

trans,trans-2-(2-(2,5-Dioxopyrrolidin-1-yl)ethyl)-4-(1,3-benzodioxol-5-yl)-1-[(N4-heptyl-N-(4-fluoro-3-methylphenyl)amino)carbonylmethyl]-pyrrolidine-3-carboxylic acid;

trans,trans-2-(2-(2,5-Dioxopyrrolidin-1-yl)ethyl)-4-(1,3-benzodioxol-5-yl)-1-[(N-butyl-N-(3-hydroxypropyl) amino)carbonylmethyl]-pyrrolidine-3-carboxylic acid;

trans,trans-2-(2-(2,5-Dioxopyrrolid in-1-yl)ethyl)-4-(1,3-benzodioxol-5-yl)-1-[(N-butyl-N-(propoxy)amino) carbonylmethyl]-pyrrolidine-3-carboxylic acid;

trans,trans-2-(2-(2,5-Dioxopyrrolidin-1-yl)ethyl)-4-(1,3-benzodioxol-5-yl)-1-[(N-butyl-N-(4-dimethylamino-butyl) amino)carbonylmethyl]-pyrrolidine-3-carboxylic acid;

trans,trans-2-(2-(2,5-Dioxopyrrolidin-1-yl)ethyl)-4-(7-methoxy-1,3-benzodioxol-5-yl)-1-(N,N-di(n-butyl) aminocarbonylmethyl)-pyrrolidine-3-carboxylic acid;

trans,trans-2-(2-(2,5-Dioxopyrrolidin-1-yl)ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(Pyridin-2-yl)ethyl)-4-(1,3-benzodioxol-5-yl)-1-[(N-4-heptyl-N-(4-fluoro-3-methylphenyl) amino)carbonylmethyl]-pyrrolidine-3-carboxylic acid;

trans,trans-2-(2-(Pyridin-2-yl)ethyl)-4-(1,3-benzodioxol-5-yl)-1-[(N-butyl-N-(3-hydroxypropyl)amino) carbonylmethyl]-pyrrolidine-3-carboxylic acid;

trans,trans-2-(2-(Pyridin-2-yl)ethyl)-4-(1,3-benzodioxol-5-yl)-1-[(N-butyl-N-(propoxy)amino)carbonyl-methyl]-pyrrolidine-3-carboxylic acid;

trans,trans-2-(2-(Pyridin-2-yl)ethyl)-4-(1,3-benzodioxol-5-yl)-1-[(N-butyl-N-(4-dimethylaminobutyl)amino) carbonylmethyl]-pyrrolidine-3-carboxylic acid;

trans,trans-2-(2-(Pyridin-2-yl)ethyl)-4-(7-methoxy-1,3-benzodioxol-5-yl)-1-(N,N-di(n-butyl)aminocar-bonylmethyl)-pyrrolidine-3-carboxylic acid;

trans,trans-2-(2-(Pyridin-2-yl)ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(Pyridin-2-yl)ethyl)-4-(7-methoxy-1,3-benzodioxol-5-yl)-1-[(N-butyl-N-(4-dimethylamino-butyl)amino)carbonylmethyl]-pyrrolidine-3-carboxylic acid;

trans,trans-2-(2-(Pyrimidin-2-yl)ethyl)-4-(1,3-benzodioxol-5-yl)-1-(N,N-di(n-butyl)aminocar-bonylmethyl)-pyrrolidine-3-carboxylic acid;

trans,trans-2-(2-(Pyrimidin-2-yl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(Pyrimidin-2-yl)ethyl)-4-(1,3-benzodioxol-5-yl)-1-[(N-butyl-N-(4-dimethylamino-butyl)amino)carbonylmethyl]-pyrrolidine-3-carboxylic acid;

trans,trans-2-(2-(1,3-benzodioxol-4-yl)ethyl)-4-(1,3-benzodioxol-5-yl)-1-(N,N-di(n-butyl)aminocar-bonylmethyl)-pyrrolidine-3-carboxylic acid;

trans,trans-2-(2-(1,3-benzodioxol-4-yl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid; and trans,trans-2-(2-(1,3-benzodioxol-4-yl)ethyl)-4-(1,3-benzodioxol-5-yl)-1-[(N-butyl-N-(4 dimethylamino-butyl)amino)carbonylmethyl]-pyrrolidine-3-carboxylic acid;

(2S,3R,4S)-2-(2,2-Dimethylpentyl)-4-(1,3-benzodioxol-5-yl)-1-(N,N-di(n-butyl)aminocarbonylmethyl)-pyrrolidine-3-carboxylic acid;

(2S,3R,4S)-2-(2,2-Dimethylpent-(E)-3-enyl)-4-(1,3-benzodioxol-5-yl)-1-(N,N-di(n-butyl)aminocarbonylmethyl)-pyrrolidine-3-carboxylic acid;

(2S,3R,4S)-2-(2,2-Dimethylpent-(E)-3-enyl)-4-(7-methoxy-1,3-benzodioxol-5-yl)-1-(N,N-d i(n-butyl) aminocarbonylmethyl)-pyrrolidine-3-carboxylic acid;

(2S,3R,4S)-2-((2-Methoxyphenoxy)-methyl)-4-(1,3-benzodioxol-5-yl)-1-(N,N-di(n-butyl)aminocar-bonylmethyl)-pyrrolidine-3-carboxylic acid;

(2S,3R,4S)-2-(2-(2-Methoxyphenyl)ethyl)-4-(1,3-benzodioxol-5-yl)-1-(N,N-di(n-butyl)aminocar-bonylmethyl)-pyrrolidine-3-carboxylic acid;

or a pharmaceutically acceptable salt.

Most preferred compounds of the invention are selected from the group consisting of:

trans,trans-2-(2-(1,3-Dioxol-2-yl)ethyl)-4-(1,3-benzodioxol-5-yl)-1-(N,N-di(n-butyl)aminocar-bonylmethyl)-pyrrolidine-3-carboxylic acid;

trans,trans-2-(2,2,-Dimethyl-2-(1,3-dioxolan-2-yl)ethyl)-4-(1,3-benzodioxol-5-yl)-1-(N,N-di(n-butyl) aminocarbonylmethyl)-pyrrolidine-3-carboxylic acid;

trans,trans-2-(2-(1,3-Dioxol-2-yl)ethyl)-4-(1,3-benzodioxol-5-yl)-1-[[N-4-heptyl-N-(2-methyl-3-fluorophenyl)] aminocarbonylmethyl]-pyrrolidine-3-carboxylic acid;

trans,trans-2-(2-(1,3-Dioxol-2-yl)ethyl)-4-(7-methoxy-1,3-benzodioxol-5-yl)-1-(N,N-di(n-butyl)aminocar-bonylmethyl)-pyrrolidine-3-carboxylic acid;

trans,trans-2-((2-Methoxyphenoxy)-methyl)-4-(1,3-benzodioxol-5-yl)-1-(N,N-di(n-butyl)aminocar-bonylmethyl)-pyrrolidine-3-carboxylic acid;

trans,trans-2-(2-(2-Oxopyrrolidin-1-yl)ethyl)-4-(1,3-benzodioxol-5-yl)-1-(N,N-di(n-butyl)aminocar-bonylmethyl)-pyrrolidine-3-carboxylic acid;

trans,trans-2-(2-(1,3-Dioxol-2-yl)ethyl)-4-(7-methoxy-1,3-benzodioxol-5-yl)-1-(N4-heptyl-N-(4-fluoro-3-methylphenyl))aminocarbonylmethyl)-pyrrolidine-3-carboxylic acid;

trans,trans-2-(2,2-Dimethylpentyl)-4-(7-methoxy-1,3-benzodioxol-5-yl)-1-(N,N-di(n-butyl)aminocar-bonylmethyl)-pyrrolidine-3-carboxylic acid;

trans,trans-2-(2,2,-Dimethyl-2-(1,3-dioxolan-2-yl)ethyl)-4-(7-methoxy-1,3-benzodioxol-5-yl)-1-(N,N-di(n-butyl)aminocarbonylmethyl)-pyrrolidine-3-carboxylic acid;

trans,trans-2-(2-(2-Methoxyphenyl)-ethyl)-4-(1,3-benzodioxol-5-yl)-1-(N,N-di(n-butyl)aminocar-bonylmethyl)-pyrrolidine-3-carboxylic acid;

trans,trans-2-(2,2-Dimethyl-3-(E)-pentenyl)-4-(7-methoxy-1,3-benzodioxol-5-yl)-1-(N,N-di(n-butyl) aminocarbonylmethyl)-pyrrolidine-3-carboxylic acid;

trans,trans-2-(2-(2-pyridyl)ethyl)-4-(1,3-benzodioxol-5-yl)-1-(N,N-di(n-butyl)aminocarbonylmethyl)-pyrrolidine-3-carboxylic acid;

(2S, 3R, 4S)-2-(2-(2-oxopyrrolidin-1-yl)ethyl)-4-(1,3-benzodioxol-5-yl)-1-(N,N-di(n-butyl)aminocar-bonylmethyl)-pyrrolidine-3-carboxylic acid;

(2S, 3R, 4S)-2-(2,2 Dimethylpentyl)-4-(7-methoxy-1,3-benzodioxol-5-yl)-1-(N,N-di(n-butyl)aminocar-bonylmethyl)-pyrrolidine-3-carboxylic acid;

(2S, 3R, 4S)-2-(2-(2-oxopyrrolidin-1-yl)ethyl)-4-(1,3-benzodioxol-5-yl)-1-(N-4-N-(4-fluoro-3-methyl-phenyl))aminocarbonylmethyl)-pyrrolidine-3-carboxylic acid;

trans,trans-2-(2-(1-pyrazolyl)ethyl)-4-(1,3-benzodioxol-5-yl)-1-(N,N-di(n-butyl)aminocarbonylmethyl)-pyrrolidine-3-carboxylic acid;

(2R, 3R, 4S)-2-(3-Fluoro-4-methoxyphenyl)-4-(1,3-benzodioxol-5-yl)-1-[((N-propyl-N-pentanesulfonyl)amino)ethyl]-pyrrolidine-3-carboxylic acid;

(2S,3R,4S)-2-(2,2-Dimethylpentyl)-4-(1,3-benzodioxol-5-yl)-1-(N,N-di(n-butyl)aminocarbonylmethyl)-pyrrolidine-3-carboxylic acid;

(2S,3R,4S)-2-(2,2-Dimethylpent-(E)-3-enyl)-4-(1,3-benzodioxol-5-yl)-1-(N,N-di(n-butyl)aminocarbonylmethyl)-pyrrolidine-3-carboxylic acid;

(2S,3R,4S)-2-(2,2-Dimethylpent-(E)-3-enyl)-4-(7-methoxy-1,3-benzodioxol-5-yl)-1-(N,N-di(n-butyl)aminocarbonylmethyl)-pyrrolidine-3-carboxylic acid;

(2S,3R,4S)-2-((2-Methoxyphenoxy)-methyl)-4-(1,3-benzodioxol-5-yl)-1-(N,N-di(n-butyl)aminocarbonylmethyl)-pyrrolidine-3-carboxylic acid; and (2S,3R,4S)-2-(2-(2-Methoxyphenyl)ethyl)-4-(1,3-benzodioxol-5-yl)-1-(N,N-di(n-butyl)aminocarbonylmethyl)-pyrrolidine-3-carboxylic acid;

or a pharmaceutically acceptable salt thereof.

Methods for preparing the compounds of the invention are shown in Schemes I–XV.

Scheme I illustrates the general procedure for preparing the compounds of the invention when n and m are 0, Z is —$CH_2$— and W is —$CO_2H$. A β-ketoester 1, where E is loweralkyl or a carboxy protecting group is reacted with a nitro vinyl compound 2, in the presence of a base (for example, 1,8-diazabicyclo[5.4.0]undec-7-ene (DBU) or sodium ethoxide or sodium hydride and the like) in an inert solvent such as toluene, benzene, tetrahydrofuran or ethanol and the like. The condensation product 3 is reduced (for example, hydrogenation using a Raney nickel or platinum catalyst). The resulting amine cyclizes to give the dihydro pyrrole 4. Reduction of 4 (for example, sodium cyanoborohydride or catalytic hydrogenation and the like) in a protic solvent such as ethanol or methanol and the like gives the pyrrolidine compound 5 as a mixture of cis-cis, trans,trans and cis,trans products. Chromatographic separation removes the cis-cis isomer leaving a mixture of the trans,trans and cis,trans isomers which is further elaborated. The cis-cis isomer can be epimerized (for example, using sodium ethoxide in ethanol) to give the trans,trans isomer and then carried on as described below. The pyrrolidine nitrogen is (1) acylated or sulfonylated with $R_3$—X ($R_3$ is $R_4$—C(O)— or $R_6$—S(O)$_2$— and X is a leaving group such as a halide (Cl is preferred) or X taken together with $R_4$—C(O)— or $R_6$—S(O)$_2$— forms an activated ester including esters or anhydrides derived from formic acid, acetic acid and the like, alkoxycarbonyl halides, N-hydroxysuccinimide, N-hydroxyphthalimide, N-hydroxybenzotriazole, N-hydroxy-5-norbornene-2,3-dicarboxamide, 2,4,5-trichlorophenol and the like) or (2) alkylated with $R_3$—X where X is a leaving group (for example, X is a halide (for example, Cl, Br or I) or X is a leaving group such as a sulfonate (for example, mesylate, tosylate, triflate and the like)) in the presence of a base such as diisopropyl ethylamine or triethylamine and the like to give the N-derivatized pyrrolidine 6 which is still a mixture of trans,trans and cis,trans isomers. Hydrolysis of the ester 6 (for example, using a base such a sodium hydroxide in EtOH/$H_2O$) selectively hydrolyzes the trans,trans ester to give a mixture of 7 and 8, which are readily separated.

Scheme II illustrates a general procedure for preparing the compounds of the invention when n is 1, m is 0, Z is —$CH_2$— and W is —$CO_2H$. A substituted benzyl chloride 9 is reacted with a lithio dithiane 10 in an inert solvent such as THF or dimethoxyethane to give the alkylated adduct 11. The anion of compound 11 is formed using a base such as n-butyllithium and then reacted with $R_1$—$CH_2$—X' wherein X' is a leaving group such as a halide or sulfonate to give compound 12. The dithiane protecting group is cleaved (for example, using a mercuric salt in water) to give the keto compound 13. Reaction of ketone 13 with benzyl amine and formaldehyde gives the keto piperidine compound 14. Treatment of compound 14 with an activated nitrile such as trimethylsilyl cyanide followed by a dehydrating agent such as phosphorous oxychloride provides the isomeric ene nitriles 15. Reduction of the double bond (for example, using sodium borohydride) affords the piperidinyl nitrile 16. Hydrolysis of the nitrile using hydrochloric acid in the presence of a carboxy protecting reagent (for example, an alkyl alcohol) affords ester 17 (where E is a carboxy protecting group). Debenzylation by catalytic hydrogenation under acidic conditions affords the free piperidine compound 18. Compound 18 is further elaborated by the procedures described in Scheme I for compound 5 to give the final product compound 19.

Scheme III illustrates a general procedure for preparing the compounds of the invention when m and n are 0, Z is —C(O)— and W is —$CO_2H$. β-Keto ester 20 (wherein E is loweralkyl or a carboxy protecting group) is reacted with an α-haloester 21 (where J is lower alkyl or a carboxy protecting group and the halogen is bromine, iodine or chlorine) in the presence of a base such as NaH or potassium tert-butoxide or lithium diisopropylamide in an inert solvent such as THF or dimethoxyethane to give diester 22. Treating compound 22 with $R_3$—$NH_2$ and heating in acetic acid gives the cyclic compound 23. The double bond is reduced (for example, by catalytic hydrogenation using a palladium on carbon catalyst or sodium cyanoborohydride reduction) to give pyrrolidone 24. Epimerization with sodium ethoxide in ethanol to give the desired trans,trans configuration, followed by sodium hydroxide hydrolysis of the ester, affords the desired trans,trans carboxylic acid 25.

Scheme IV illustrates a general procedure for preparing the compounds of the invention when n is 0, m is 1, Z is —$CH_2$— and W is —$CO_2H$. The trans,trans compound Z, prepared in Scheme I, is homologated by the Arndt-Eistert synthesis. The carboxy terminus is activated (for example, by making the acid chloride using thionyl chloride) to give compound 52, where L is a leaving group (in the case of an acid chloride, L is Cl). Compound 52 is treated with diazomethane to give the diazo ketone 53. Rearrangement of compound 53 (for example, using water or an alcohol and silver oxide or silver benzoate and triethylamine, or heating or photolysis in the presence of water or an alcohol) affords the acetic acid compound 54 or an ester which may be hydrolyzed. Compounds where m is from 2 to 6 can be obtained by repetition of the above described process.

A preferred embodiment is shown in Schemes V and VI. A benzoyl acetate 26 is reacted with a nitro vinyl benzodioxolyl compound 27 using 1,8-diazabicyclo[5.4.0]undec-7-ene (DBU) as the base in toluene to give compound 28. Catalytic hydrogenation using Raney nickel leads to reduction of the nitro group to an amine and subsequent cyclization to give the dihydropyrrole 29. The double bond is reduced with sodium cyanoborohydride to give the pyrrolidine compound 30 as a mixture of cis-cis, trans,trans and cis,trans isomers. Chromatography separates out the cis-cis isomer, leaving a mixture of the trans,trans and cis,trans isomers (31).

Scheme VI illustrates the further elaboration of the trans,trans isomer. The mixture (31) of trans,trans and cis,trans pyrrolidines described in Scheme IV is reacted with N-propyl bromoacetamide in acetonitrile in the presence of ethyldiisopropylamine to give the alkylated pyrrolidine compound 32, still as a mixture of trans,trans and cis,trans isomers. Sodium hydroxide in ethanol-water hydrolyzes the ethyl ester of the trans,trans compound but leaves the ethyl ester of the cis,trans compound untouched, thus allowing separation of the trans,trans carboxylic acid 33 from the cis,trans ester 34.

Scheme VII illustrates the preparation of a specific piperidinyl compound. Benzodioxolyl methyl choloride 35 is reacted with lithio dithiane 36 to give the alkylated compound 37. Treatment of compound 37 with 4-methoxybenzyl chloride in the presence of lithium diisopropylamide gives compound 38. Cleavage of the dithiane protecting group using a mercuric salt in aqueous solution gives ketone 39. Treatment of 39 with benzylamine and formaldehyde gives the keto piperidine 40. Treatment of compound 40 with trimethylsilyl cyanide followed by phosphorous oxychloride gives the ene nitrile as a mixture of isomers 41. Sodium borohydride reduction of the double bond gives the piperidinyl nitrile 42. Hydrochloric acid hydrolysis in the presence of ethanol gives ethyl ester 43. The N-benzyl protecting group is removed by catalytic hydrogenation to give the free piperidine compound 44. Compound 44 is further elaborated by the procedures described in Scheme V for compound 31 resulting in the formation of the N-derivatized carboxylic acid 45.

A preferred embodiment of the process shown in Scheme III is shown in Scheme VII. 4-Methoxybenzoylacetate 46 (wherein E is loweralkyl or a carboxy protecting group) is reacted with an benzodioxolyl a-bromoacetate 47 (wherein E is lower alkyl or a carboxy protecting group) in the presence of NaH in THF to give diester 48. Treating compound 48 with ethoxypropylamine and heating in acetic acid gives the cyclic compound 49. The double bond is reduced by catalytic hydrogenation using a palladium on carbon catalyst to give pyrrolidone 50. Epimerization with sodium ethoxide in ethanol to give the desired trans,trans configuration is followed by sodium hydroxide hydrolysis of the ester to afford the desired trans,trans carboxylic acid 51.

Scheme IX illustrates the preparation of compounds where n is 0, Z is —$CH_2$—, and W is other than carboxylic acid. Compound 55, which can be prepared by the procedures described in Scheme IV, is converted (for example, using peptide coupling condition, e.g. N-methylmorpholine, EDCl and HOBt, in the presence of ammonia or other amide forming reactions) to give carboxamide 56. The carboxamide is dehydrated (for example, using phosphorus oxychloride in pyridine) to give nitrile 57. Nitrile 57 under standard tetrazole forming conditions (sodium azide and triethylamine hydrochloride or trimethylsilylazide and tin oxide) is reacted to give tetrazole 58. Alternatively nitrile 57 is reacted with hydroxylamine hydrochloride in the presence of a base (for example, potassium carbonate, sodium carbonate, sodium hydroxide, triethylamine, sodium methoxide or NaH) in a solvent such as DMF, DMSO, or dimethylacetamide to give amidoxime 59. The amidoxime 59 is allowed to react with a methyl or ethyl chloroformate in a conventional organic solvent (such as, chloroform, methylene chloride, dioxane, THF, acetonitrile or pyridine) in the presence of a base (for example, triethylamine, pyridine, potassium carbonate and sodium carbonate) to give an O-acyl compound. Heating of the O-acyl amidoxime in an inert solvent (such as benzene, toluene, xylene, dioxane, THF, dichloroethane, or chloroform and the like) results in cyclization to compound 60. Alternatively reacting the amidoxime 59 with thionyl chloride in an inert solvent (for example, chloroform, dichloromethane, dixoane and THF and the like) affords the oxathiadiazole 61.

Scheme X illustrates the preparation of compounds in which $R_3$ is an acylmethylene group. A carboxylic acid 62 (where $R_4$ is as previously defined herein) is treated with oxalyl chloride in a solution of methylene chloride containing a catalytic amount of N,N-dimethylformamide to give the acid chloride. Treatment of the acid chloride with excess ethereal diazomethane affords a diazoketone, and then treatment with anhydrous HCl in dioxane gives the α-chloroketone 63. Pyrrolidine ester 5 where E is lower alkyl or a carboxy protecting group, prepared in Scheme I, is alkylated with the α-chloroketone 63 to provide alkylated pyrrolidine 64. Carboxy deprotection (for example, hydrolysis of an alkyl ester using lithium or sodium hydroxide in ethanol-water) gives the alkylated pyrrolidine acid 65.

Scheme XI illustrates the preparation of "reverse amides and sulfonamides". The carboxy protected pyrrolidine 5, prepared in Scheme I, is reacted with a difunctionalized compound X—$R_8$—X where $R_8$ is alkylene and X is a leaving group (for example a halide where Br is preferred) to give N-alkylated compound 66. Treatment of 66 with an amine ($R_{20}NH_2$) affords secondary amine 67. This amine (67) can be reacted with an activated acyl compound (for example, $R_4$—C(O)—Cl) and then carboxy deprotected (for example, hydrolysis of an ester or hydrogenation of a benzyl moiety) to afford amide 68. Alternatively amine 67 can be reacted with an activated sulfonyl compound (for example, $R_6$—$S(O)_2$—Cl) and then carboxy deprotected (for example, hydrolysis of an ester or hydrogenation of a benzyl moiety) to afford sulfonamide 69.

Scheme XII illustrates a method for synthesizing pyrrolidines by an azomethineylide type [3+2]-cycloaddition to an acrylate. General structures such as compound 70 are known to add to unsaturated esters such as 71 to provide pyrrolidines such as compound 72 (O. Tsuge, S. Kanemasa, K. Matsuda, Chem. Lett. 1131–4 (1983), O. Tsuge, S. Kanemasa, T. Yamada, K. Matsuda, J. Org. Chem. 52 2523–30 (1987), and S. Kanemasa, K. Skamoto, O. Tsuge, Bull. Chem. Soc. Jpn. 62 1960–68 (1989)). A specific example is also shown in Scheme XII. Silylimine 73 is reacted with acrylate 74 in the presence of trimethylsilyl triflate and tetrabutylammonium fluoride to give the desired pyrrolidine 75 as a mixture of isomers. This method can be modified to provide the N-acetamido derivatives directly by reacting 73 and 74 with the appropriate bromoacetamide (for example, dibutyl bromoacetamide) in the presence of tetrabutylammonium iodide and cesium fluoride to give compound 76.

Scheme XII illustrates a method for producing an enantiomerically pure pyrrolidine 80, which can be further elaborated on the pyrrolidine nitrogen. Intermediate racemic pyrrolidine ester 77 (for example, prepared by the procedure described in Scheme V) is Boc-nitrogen protected (for example, by treatment with $Boc_2O$) and then the ester is hydrolyzed (for example, using sodium or lithium hydroxide in ethanol and water) to give t-butyl carbamoyl pyrrolidine carboxylic acid 78. The carboxylic acid is converted to its (+)-cinchonine salt, which can be recrystallized (for example from ethyl acetate and hexane or chloroform and hexane) to afford the diastereomerically pure salt. This diastereomerically pure salt can be neutralized (for example, with sodium carbonate or citric acid) to afford enantiomerically pure carboxylic acid 79. The pyrrolidine nitrogen can be deprotected (for example, using trifluoroacetic acid) and the ester reformed by the use of ethanolic hydrochloric acid to give salt 80. Alternatively one can use ethanol HCl to cleave the protecting group and form the ester in one step. The pyrrolidine nitrogen can be further elaborated (for example, by treatment with the dibutyl amide of bromoacetamide in acetonitrile in the presence of diisopropylethylamine) to give optically active compound 81. The use of (–)-cinchonine will give the opposite enantiomer.

Scheme XIV describes another procedure for preparation of pyrrolidines. Pyrrolidines may be synthesized by the use of an azomethine ylide cycloaddition to an acrylate derivative as described by Cottrell, I. F., et.al., J. Chem. Soc., Perkin Trans. 1, 5: 1091–97 (1991). Thus, the azomethine ylide precursor 82 (where $R_{55}$ is hydrogen or methyl) is condensed with a substituted acrylate 83 (wherein $R_2$ is as described herein and $R_{56}$ is loweralkyl) under acidic conditions to afford the substituted pyrrolidine 84. The N-protecting group can be removed (for example, by hydrogenolysis of an N-benzyl group) to give 85, which can be alkylated under the conditions described above to provide the N-substituted pyrrolidine 86. Standard ester hydrolysis of 86 produces the desired pyrrolidine carboxylic acid 87.

A preferred process is shown in Scheme XV. Nitro vinyl compound (88) is reacted with beta-keto ester 89 in the presence of a base such as sodium ethoxide and the like or a trialkylamine such as triethylamine or diisopropylethylamine and the like or an amidine such as DBU and the like in an inert solvent such as THF, toluene, DMF, acetonitrile, ethyl acetate, isopropyl acetate or methylene chloride and the like at a temperature of from about 0° C. to about 100° C. for a period of time from about at a temperature of from about 0° C. to about 100° C. for a period of time from about by cyclization was effected for example by catalytic hydrogenation with a hydrogen pressure of from about atmospheric pressure to 300 p.s.i. over from about 1 hour to about 1 day of compound 90 in an inert solvent such as THF, ethyl acetate, toluene, ethanol, isopropanol, DMF or acetonitrile and the like, using a hydrogenation catalyst such as Raney nickel, palladium on carbon, a platinum catalyst, such as platinum oxide, platinum on carbon or platinum on alumina and the like, or a rhodium catalyst, such as rhodium on carbon or rhodium on alumina and the like, and the like affords intermediate nitrone 91a or a mixture of nitrone 91a and imine 91b. The reaction mixture comprising the nitrone or nitrone/imine mixture is treated with an acid such as trifluoroacetic acid or acetic acid or sulfuric acid or phosphoric acid or methanesulfonic acid and the like, and the hydrogenation is continued to give pyrrolidine compound 92 as the cis,cis-isomer. Epimerization at C-3 is effected by treatment of compound 92 with a base such as sodium ethoxide, potassium t-butoxide, lithium t-butoxide or potassium t-amyloxide and the like or a trialkylamine such as triethylamine or diisopropylethylamine and the like or an amidine such as DBU and the like in an inert solvent such as ethanol, ethyl acetate, isopropyl acetate, THF, toluene or DMF and the like at a temperature of from about −20° C. to about 120° C. to give the trans,trans compound 93. Compound 93 itself can optionally be resolved into enantiomers prior to reacting with X-R$_3$. The substantially pure (i.e., at least 95% of the desired isomer) optically active (+)-isomer of compound 93 is obtained by treatment of a mixture of the (+)-isomer and the (−)-isomer of 93 with S-(+)-mandelic acid, D-tartaric acid or D-dibenzoyl tartaric acid and the like in a solvent such as acetonitrile, ethyl acetate, isopropyl acetate, ethanol or isopropanol and the like. The (+)-isomer of 93 selectively crystallizes as the salt, leaving the (−)-isomer of 93 in solution. Alternatively, the substantially pure (i.e., at least 95% of the desired isomer) optically active (−)-isomer of compound 93 can be selectively crystallized by reaction of a mixture of the (+)-isomer and the (−)-isomer of 93 with L-tartaric acid, L-dibenzoyl tartaric acid or L-pyroglutamic acid and the like, leaving the desired (+)-isomer of compound 93 in solution.

Compound 93 (racemic or optically active) is reacted with X—R$_3$ (where X is a leaving group (for example, a halide or a sulfonate) and R$_3$ is as previously defined) using a base such as diisopropylethylamine, triethylamine, sodium bicarbonate or potassium carbonate and the like in an inert solvent such as acetonitrile, THF, toluene, DMF or ethanol and the like at a temperature of from about 0° C. to about 100° C. to give the intermediate ester 94. The ester can be isolated or converted in situ to the carboxylic acid (95) using hydrolysis conditions such as a base such as sodium hydroxide or lithium hydroxide or potassium hydroxide and the like in a solvent such as ethanol-water or THF-ethanol and the like.

A more detailed description of the preparation of some specific analogs is provided in Schemes XVI–XXI. Aliphatic β-ketoesters (Scheme XVI) may be prepared by copper-catalyzed addition of a Grignard reagent (for example, propylmagnesium bromide) to an unsaturated ester, for example, ethyl 3,3-dimethylacrylate. The resultant ester is hydrolyzed, for example with sodium hydroxide in aqueous alcohol, and is homologated in stepwise fashion to the corresponding β-ketoester, for example by activation using carbonyldiimidazole and condensation with magnesio-ethoxymalonate. Alternatively, olefinic β-ketoesters may be prepared by Claisen rearrangement of the corresponding allylic alcohols; hydrolysis and homologation as described above produce the desired β-ketoester.

N-alkyl,O-alkyl bromohydroxamates are prepared according to Scheme XVII. N-Boc-O-allyl hydroxylamine is alkylated with and alkyl halide, for example using sodium hydride as base; the double bond is selectively reduced, for example using hydrogen and a palladium catalyst. After removal of the Boc protecting group, for example with TFA, the resultant amine is acylated, for example using bromoacetyl bromide.

The β-ketoesters described in Scheme XVI may be converted to pyrrolidine derivatives as described in Scheme XVIII. Michael addition onto a nitrostyrene derivative can be catalyzed with base, for example DBU or potassium t-butoxide; the resultant adduct is hydrogenated, for example using Raney Nickel as catalyst, to give an imine, which is reduced further, for example using sodium cyanoborohydride under controlled pH. A mixture of isomers are generated, in which the trans-trans is generally preferred.

Scheme XIX describes several strategies for resolving the racemic pyrrolidines described above. Treatment with a chiral acid, for example (S)-(+)-mandelic acid, may provide a crystalline derivative, which can be further enriched through recrystallization. The salt may be washed with base to extract the resolving agent and return the optically active pyrrolidine product. Alternatively, the amino ester can be N-protected (for example with Boc-anhydride) and hydrolyzed (for example with sodium hydroxide) to give the corresponding N-protected amino acid. Activation of the acid, for example as the pentafluorophenyl ester, followed by coupling with a chiral nonracemic oxazolidinone anion, provides the corresponding acyloxazolidinone diastereomers, which may be separated chromatographically. Alcoholysis of one acyloxazolidinone diastereomer, followed by cleavage of the N-protecting group, returns an optically enriched amino ester. A similar transformation may be accomplished through coupling of the protected amino acid with a chiral nonracemic amino alcohol. After chromatographic separation of the resultant diastereomers, the amide is cleaved and the protecting group is removed to provide optically enriched product.

Optically active amino esters prepared as described above may be alkylated (Scheme XX) with a variety of electrophiles, for example dibutyl bromoacetamide, N-butyl,N-alkoxy bromoacetamide, N-(4-heptyl)-N-(3-methyl-4-fluorophenyl) bromoacetamide, or N-(Ω-hydroxyalkyl)-N-alkyl haloacetamide. Hydrolysis of the resultant ester, for example using sodium hydroxide in aqueous alcohol, provides the product.

For one particular class of electrophile, N-(Ω-hydroxyalkyl)-N-alkyl haloacetamides, further transformations of the alkylation product are possible (Scheme XXI). Activation (for example using methanesulfonyl chloride) of the alcohol, followed by displacement with halogen (for example, using lithium bromide) provides the corresponding halide. Displacement of halide with an amine, for example dimethylamine, provides the corresponding amino ester, which may be hydrolyzed as previously described to provide product.

Scheme I
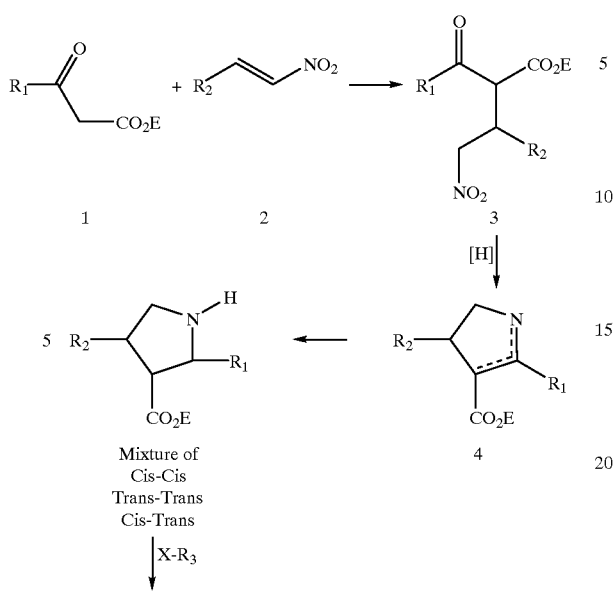
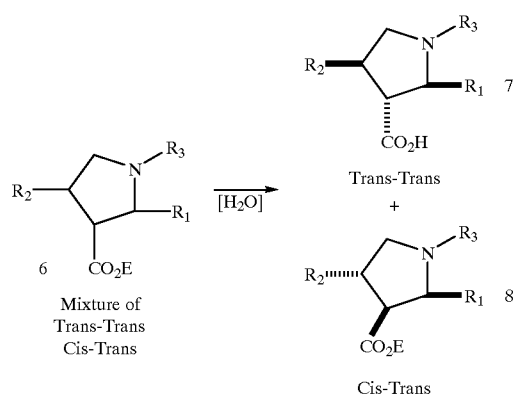
Scheme II
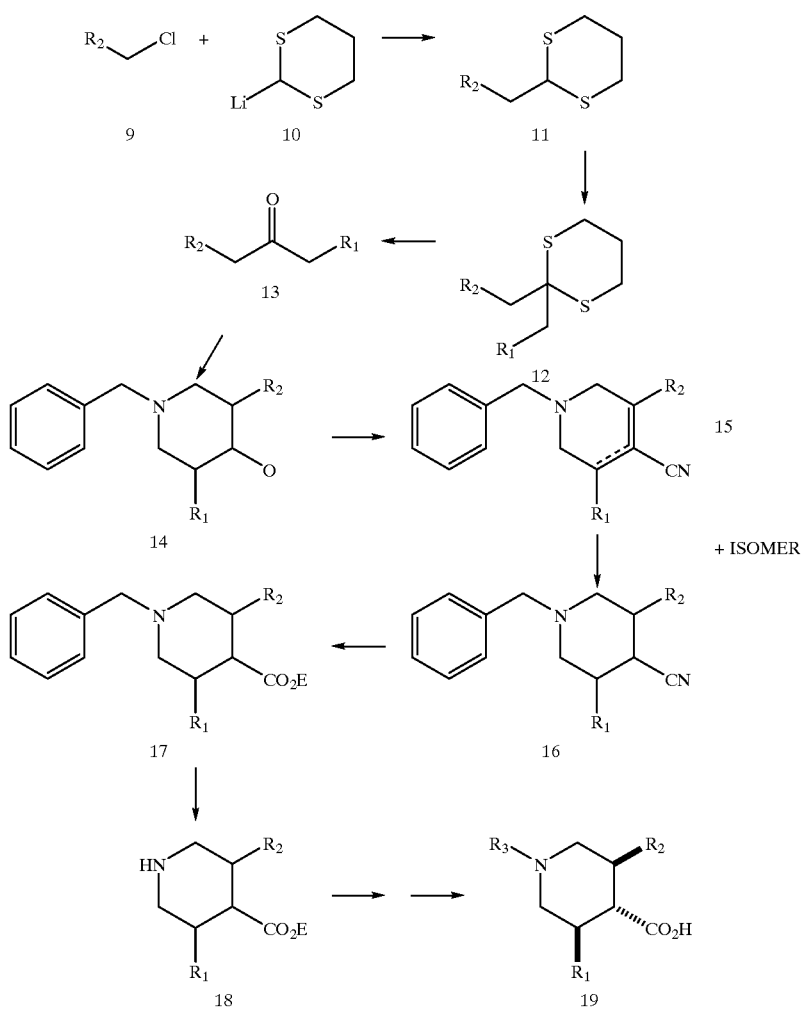

Scheme III
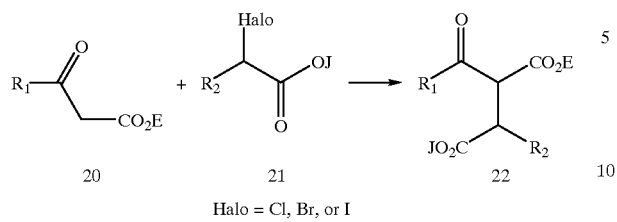
Halo = Cl, Br, or I
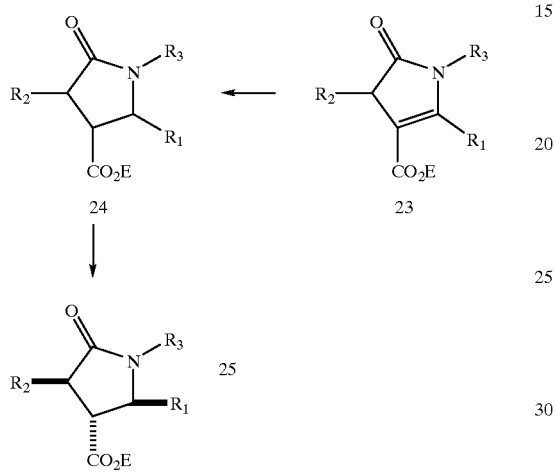
Trans-Trans
Scheme IV
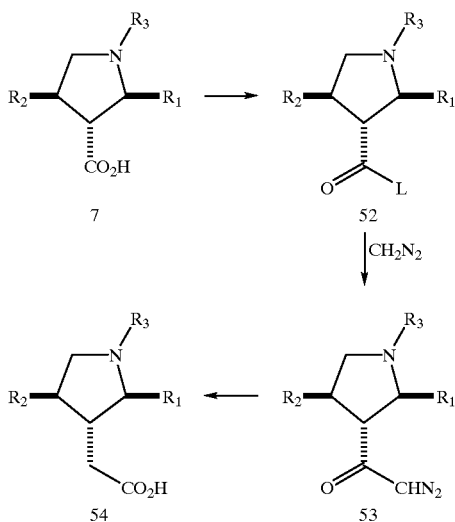
Scheme V
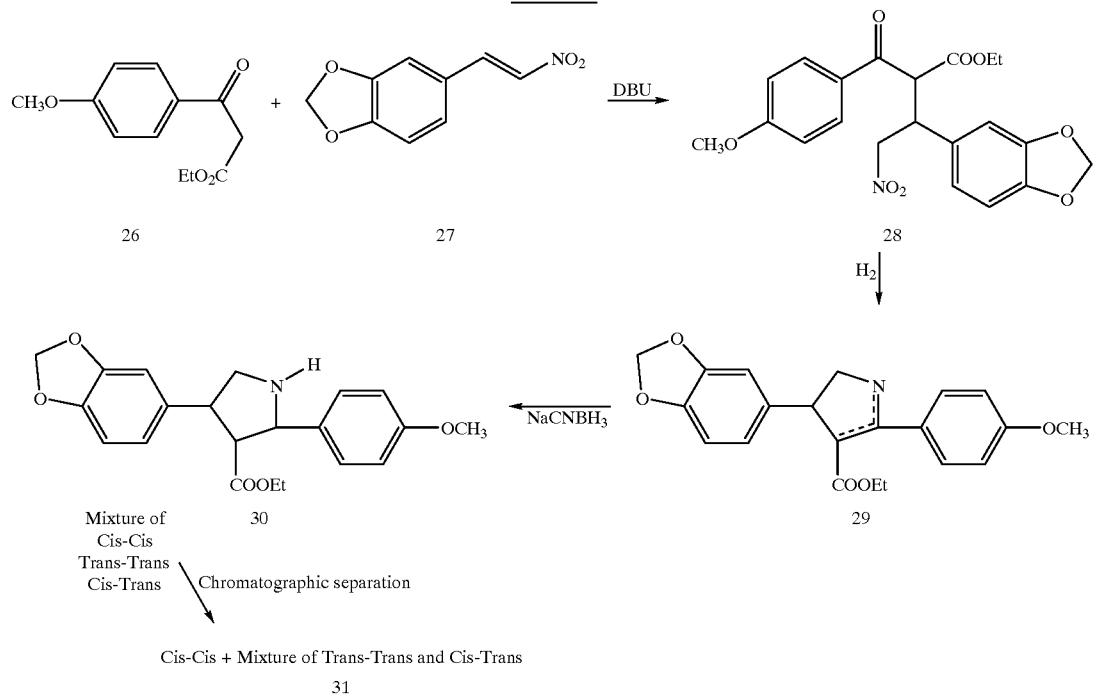

Scheme V
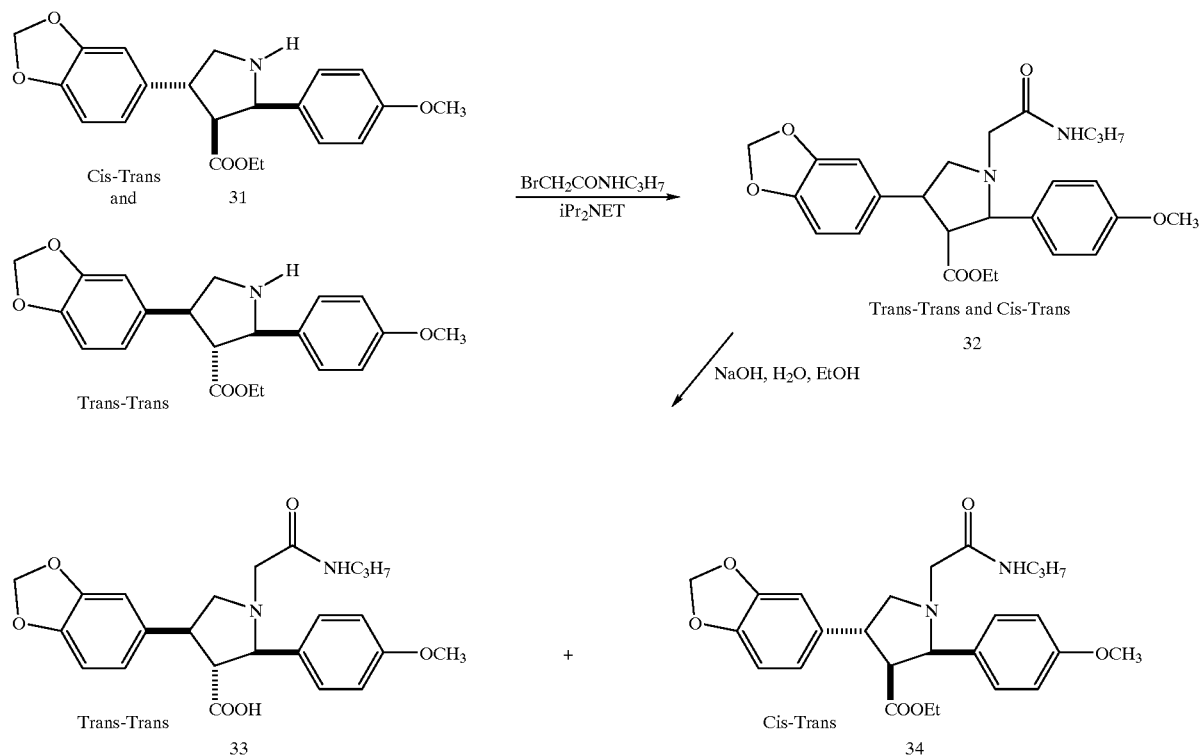
Scheme VII
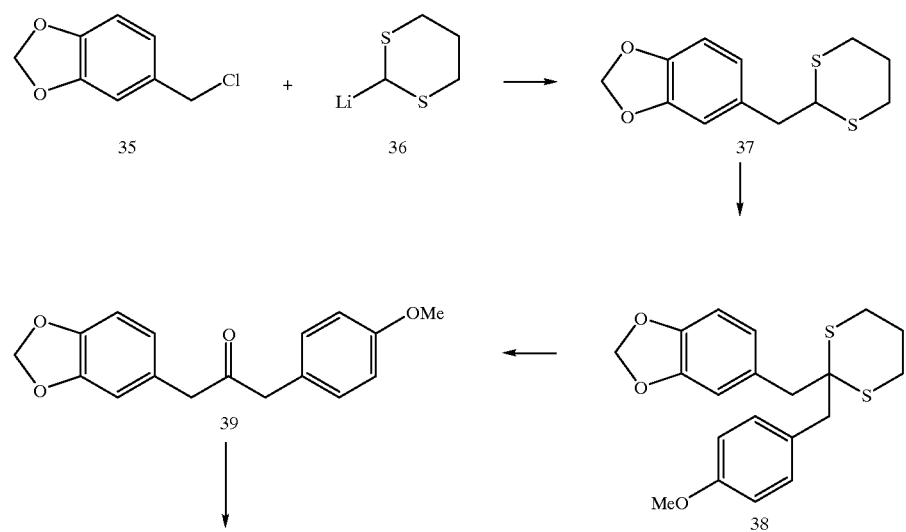

41                                          42
-continued
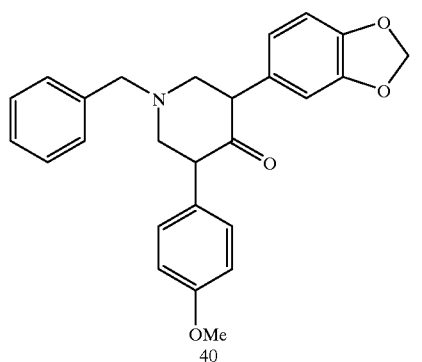  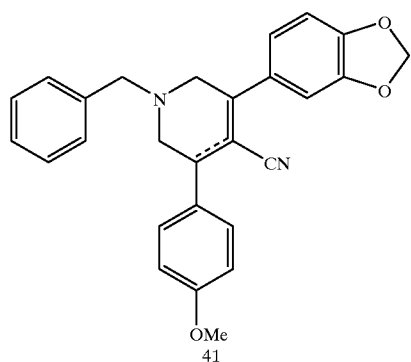 + ISOMER
40                                              41
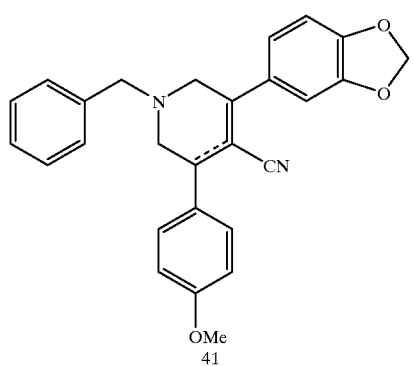  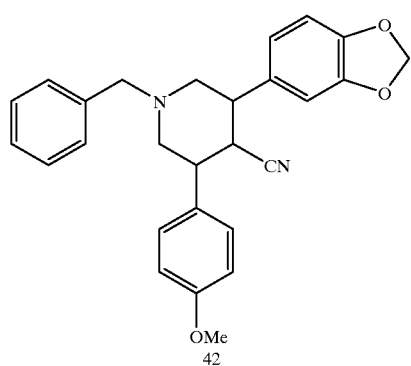
41                                              42
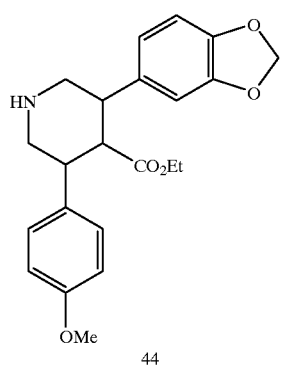  
44                                              43
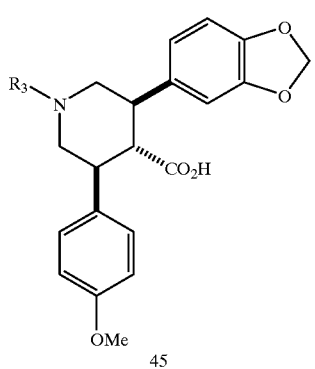
45

Scheme VIII
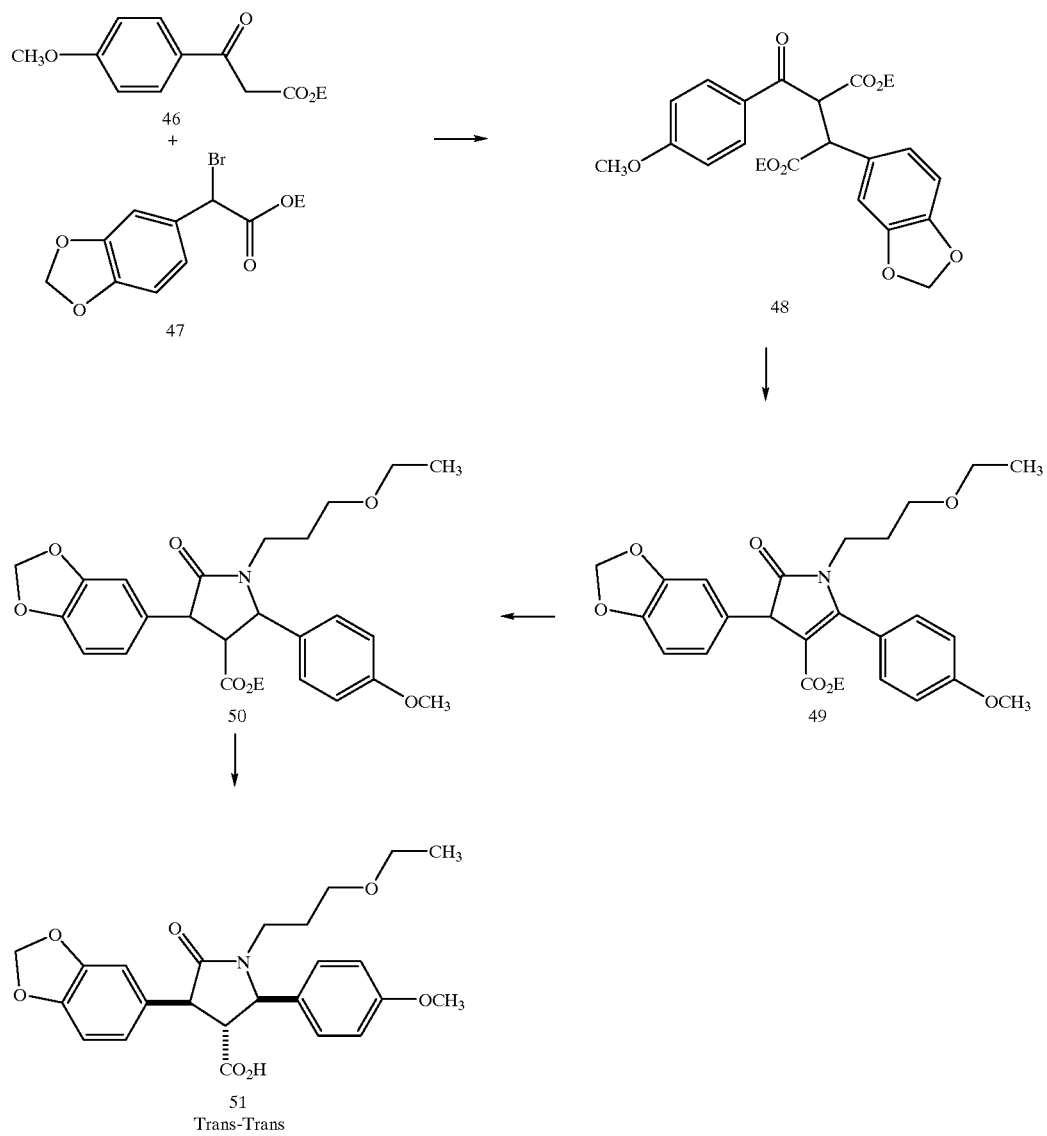
Scheme IX
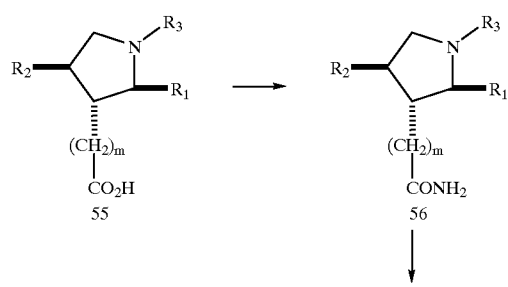

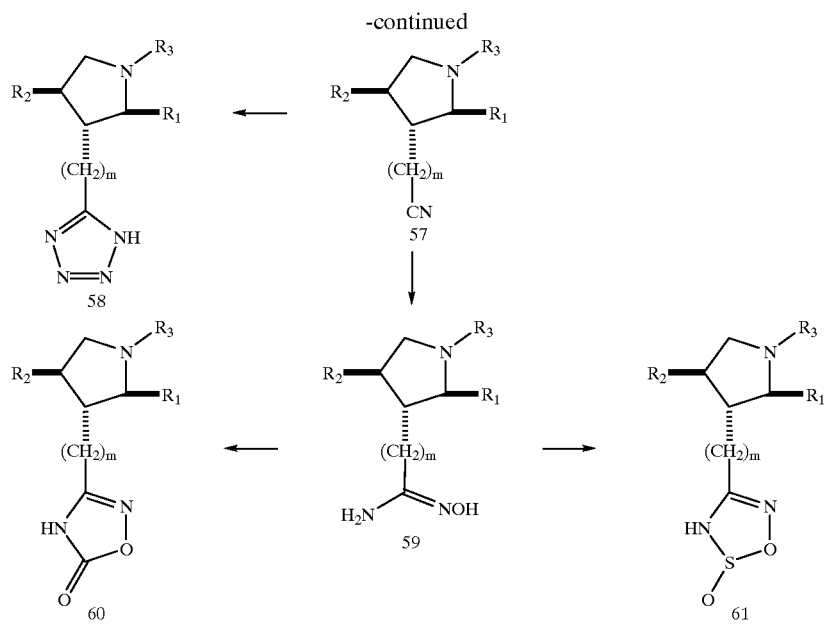
Scheme X
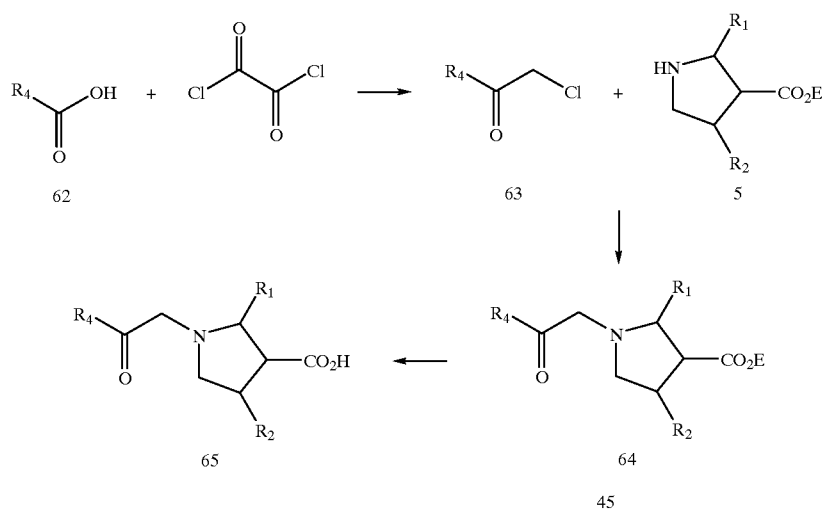
Scheme XI
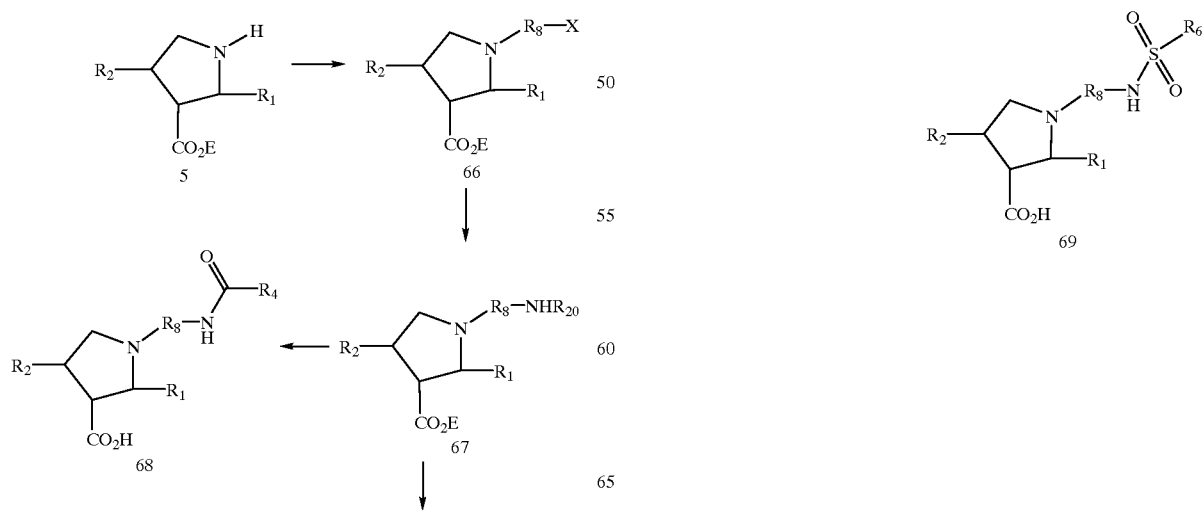

Scheme XII
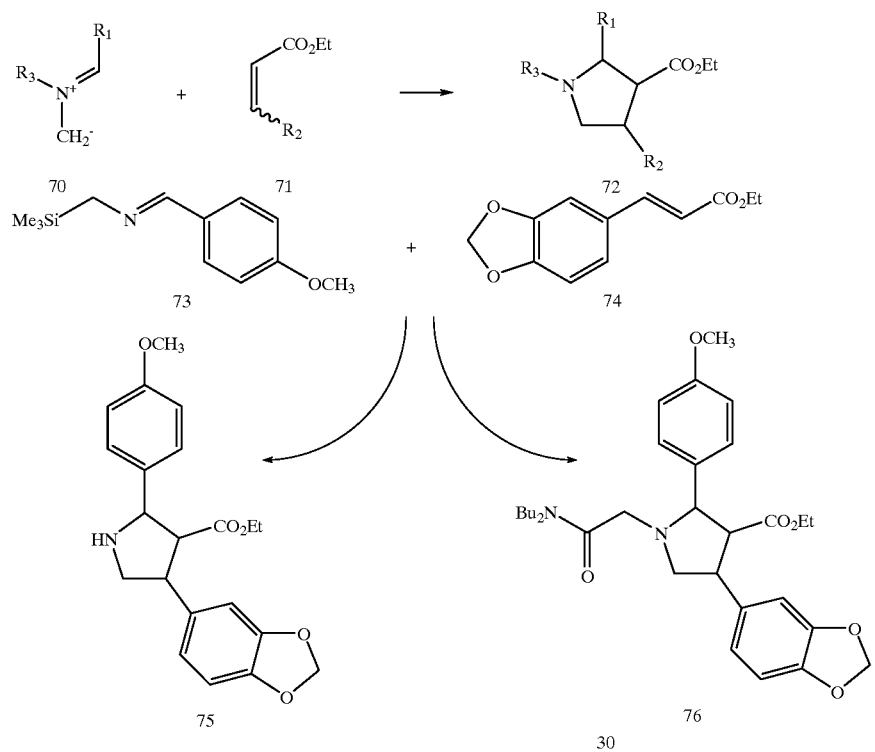
Scheme XIII
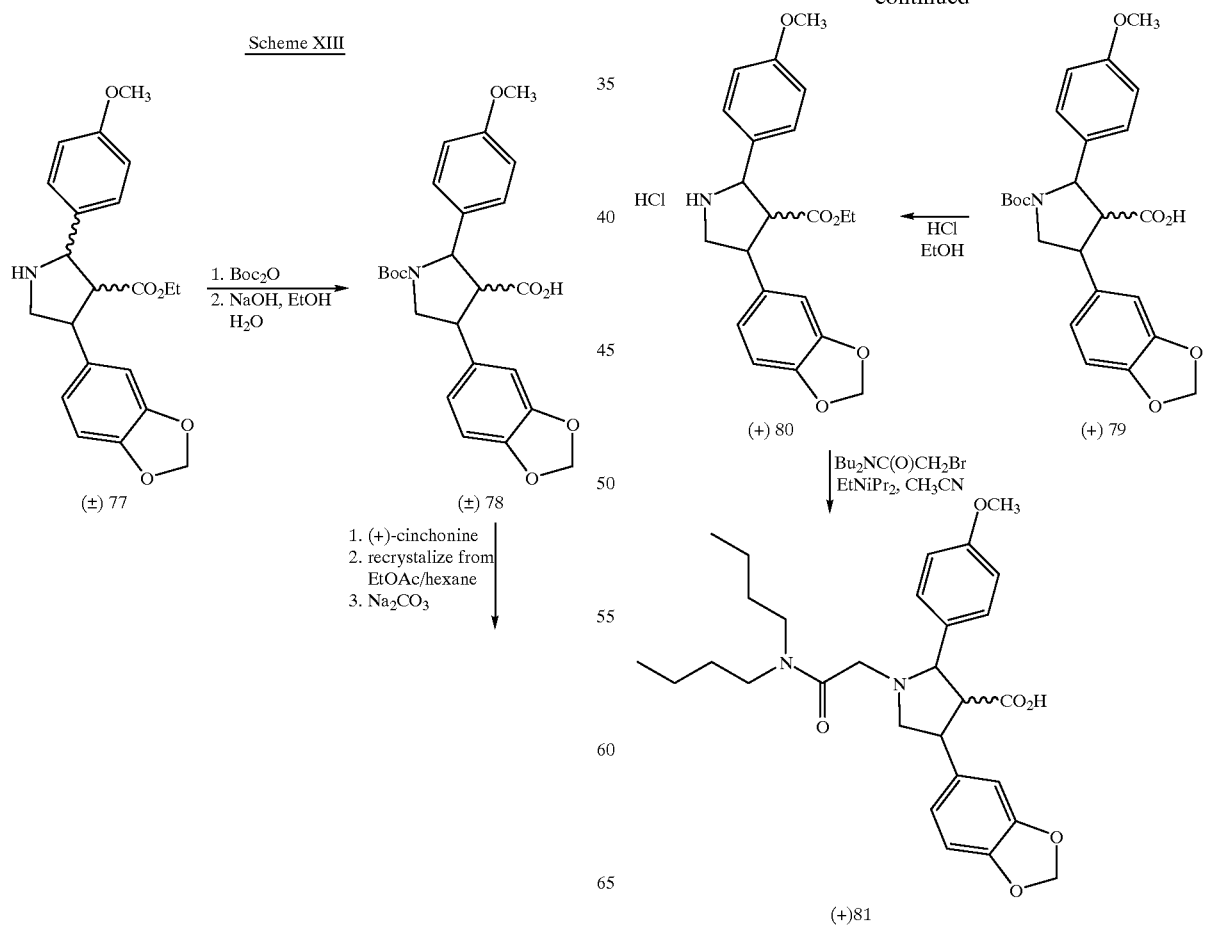

Scheme XIV
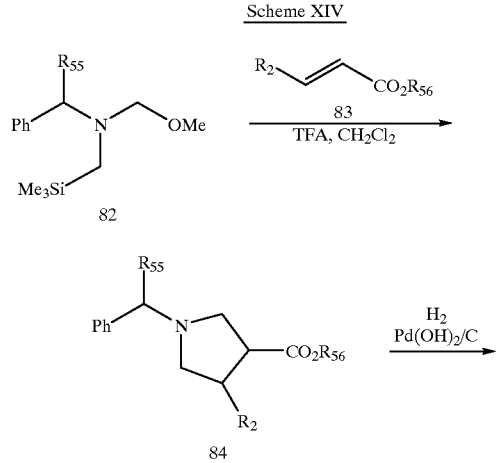
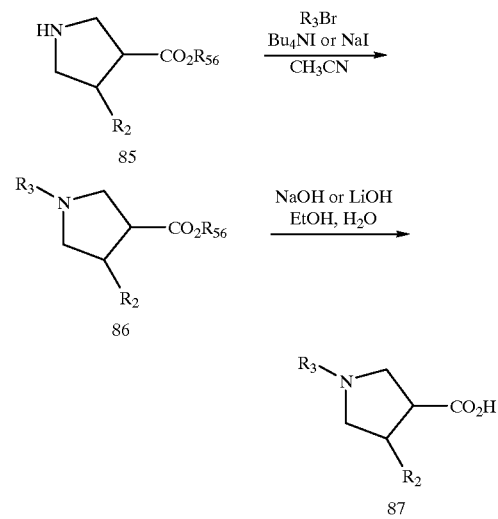
Scheme XV
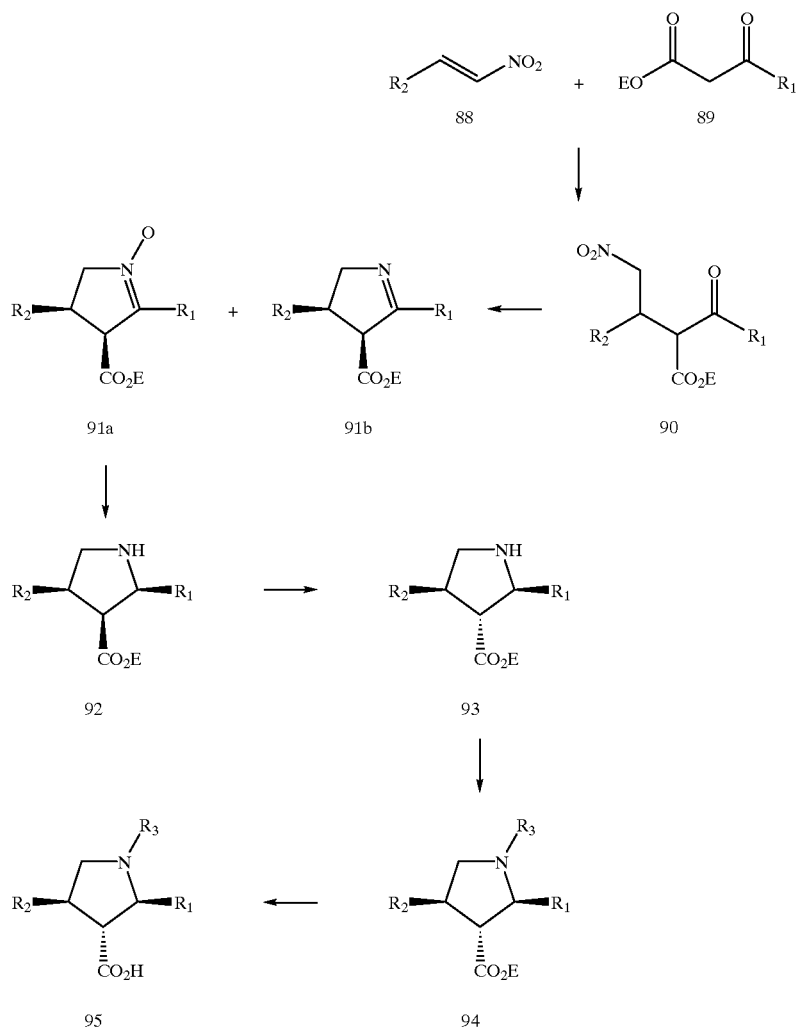

SCHEME XVI
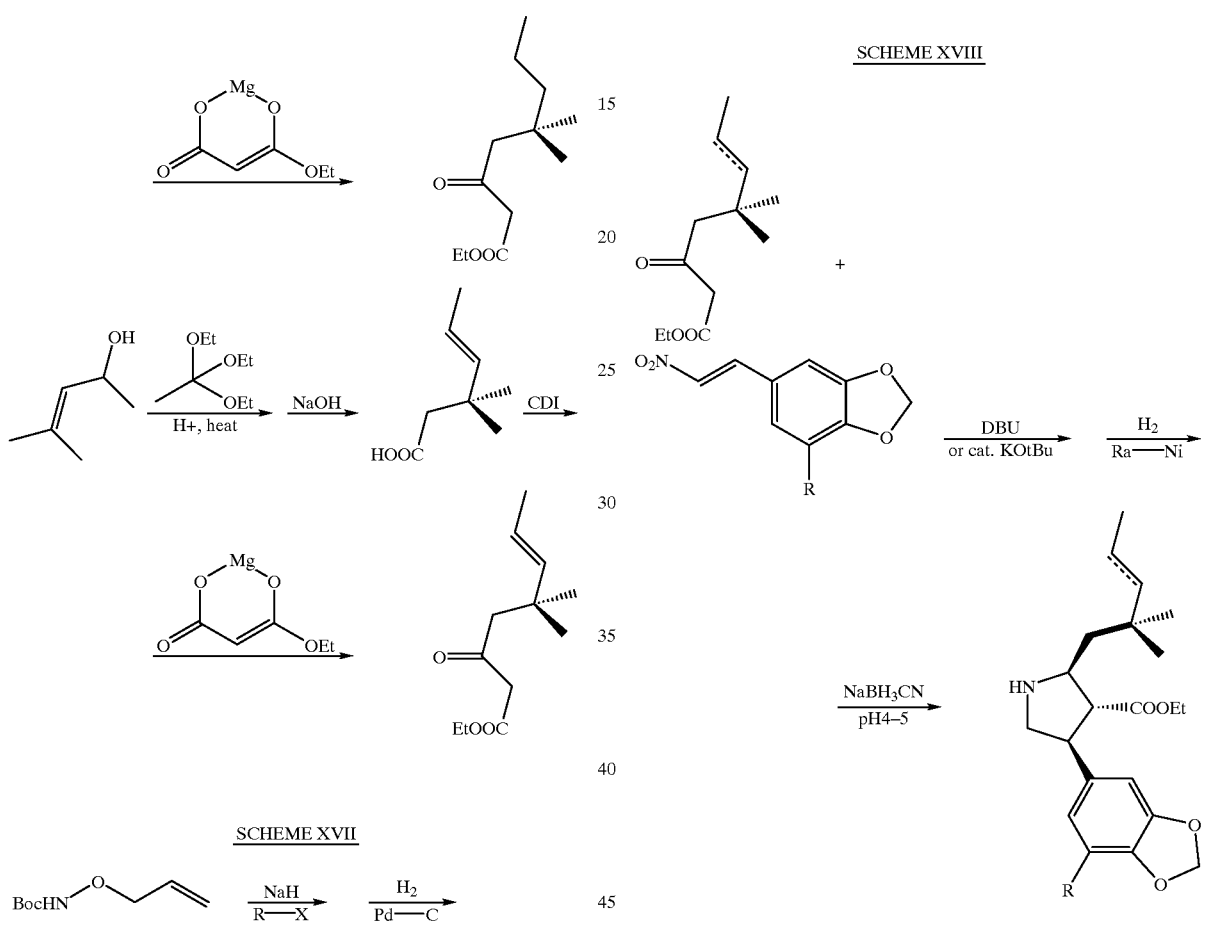
SCHEME XVII
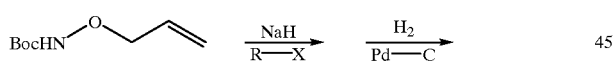
SCHEME XVIII
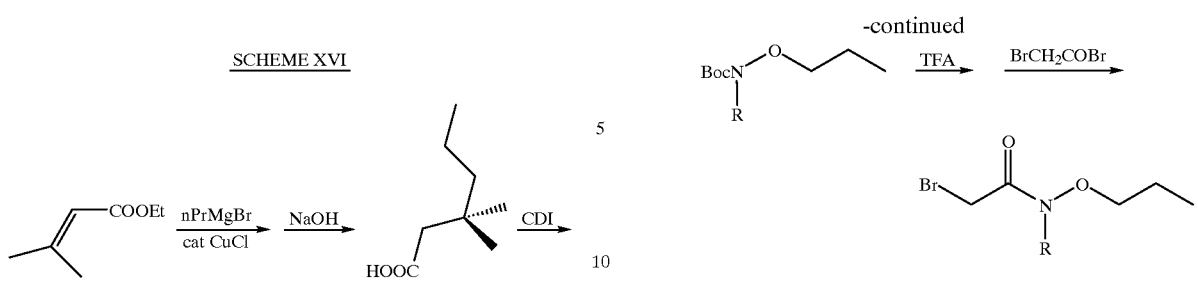
SCHEME XIX
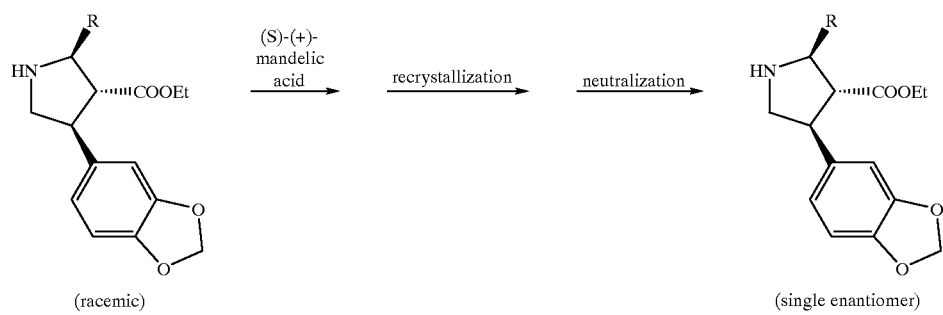

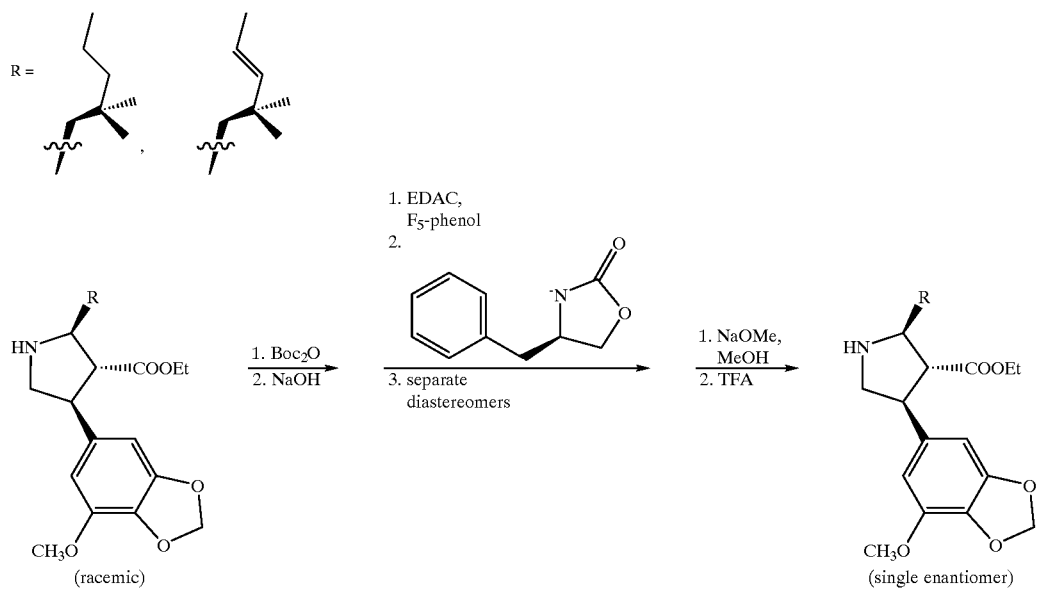
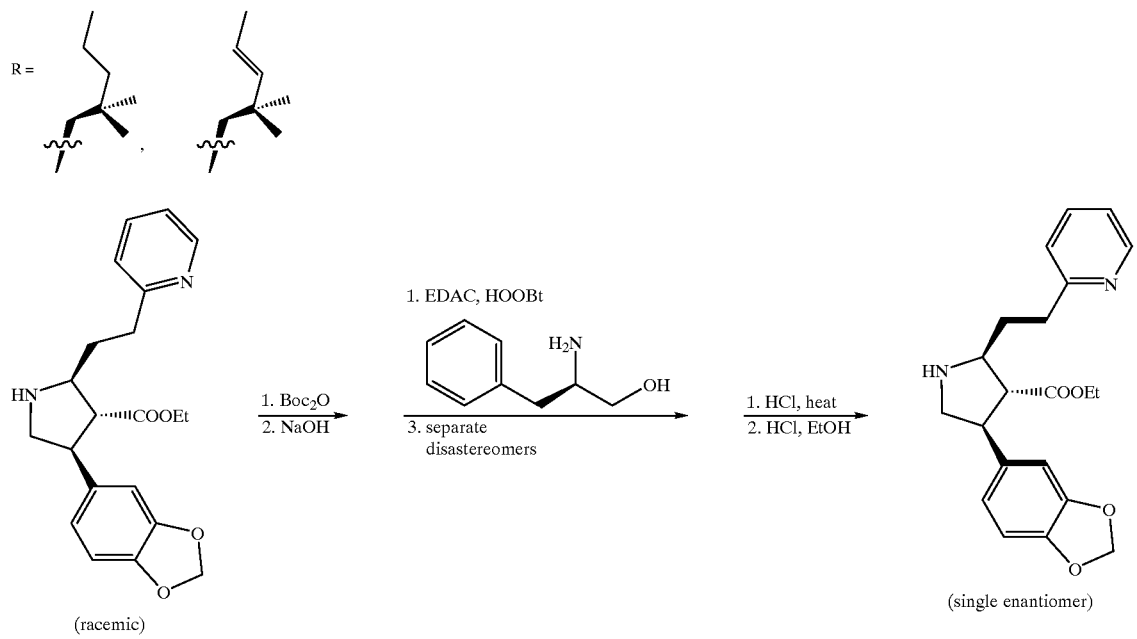
SCHEME XX
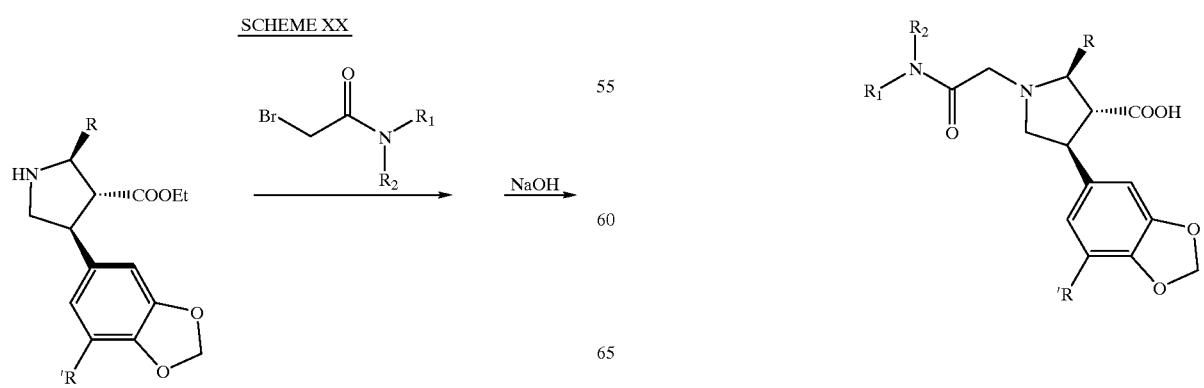

-continued

NR₁R₂ =

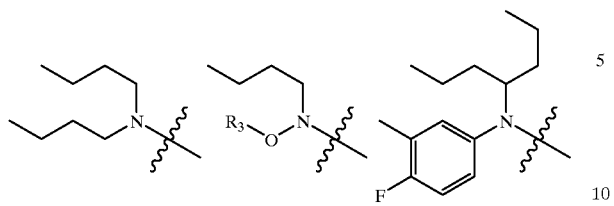

SCHEME XXI

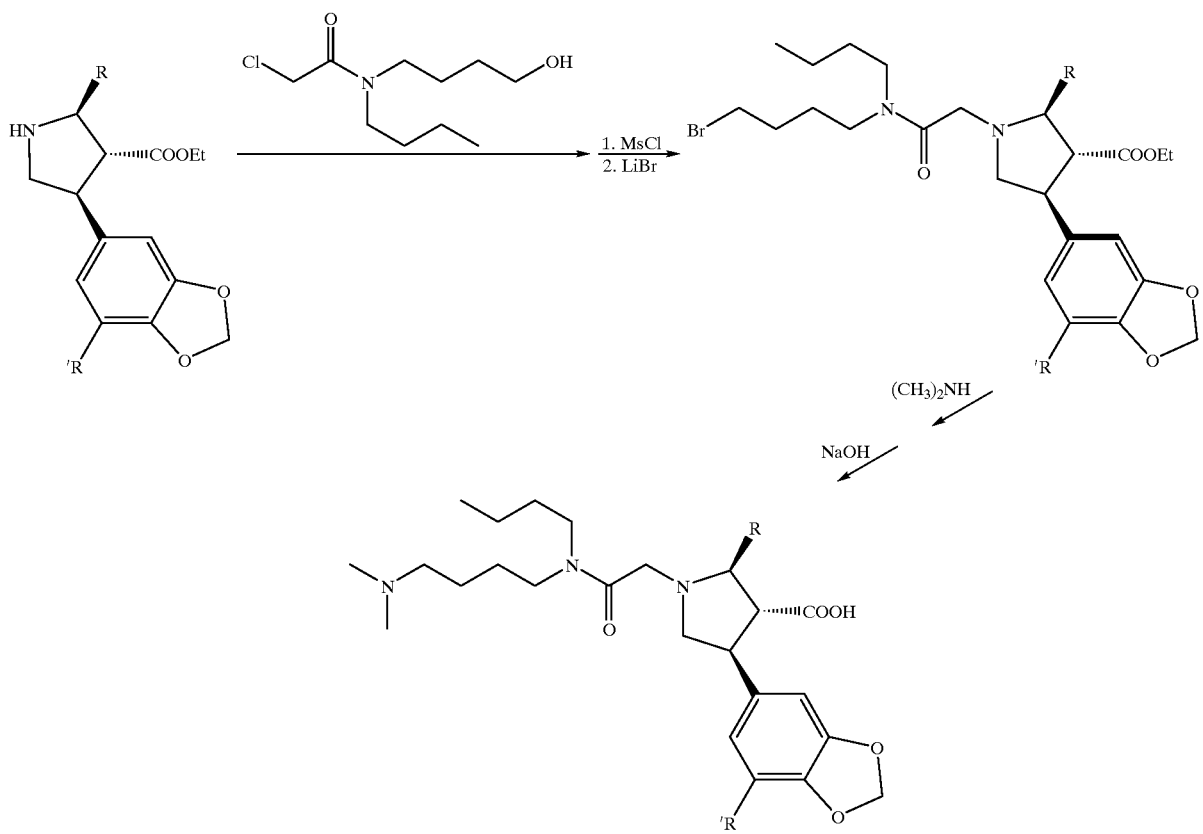

Compounds which are useful as intermediates for the preparation of compounds of the invention are:

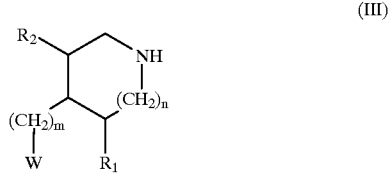
(III)

wherein n is 0 or 1;
m is 0 to 6;
W is (a) —C(O)₂—G where G is hydrogen or a carboxy protecting group, (b) —PO₃H₂,
(c) —P(O)(OH)E where E is hydrogen, loweralkyl or arylalkyl,
(d) —CN,
(e) —C(O)NHR₁₇ where R₁₇ is loweralkyl,
(f) alkylaminocarbonyl,
(g) dialkylaminocarbonyl,
(h) tetrazolyl,
(i) hydroxy,
(j) alkoxy,
(k) sulfonamido,
(l) —C(O)NHS(O)₂R₁₆ where R₁₆ is loweralkyl, haloalkyl, phenyl or dialkylamino,
(m) —S(O)₂NHC(O)R₁₆,

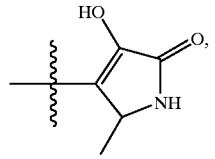
(n)

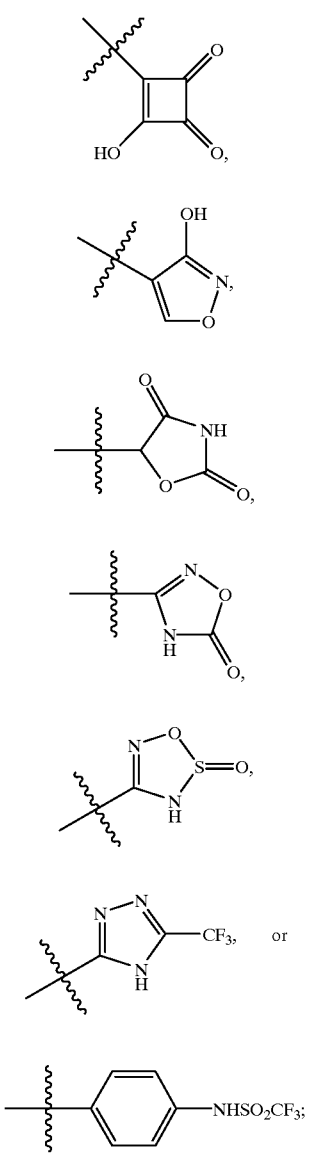

(o)

(p)

(q)

(r)

(s)

(t) CF₃, or (u)

and

R₁ and R₂ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl) aminoalkyl, alkylsulfonylamidoalkyl, heterocyclic, (heterocyclic)alkyl and $(R_{aa})(R_{bb})N\!-\!R_{cc}\!-\!$ wherein $R_{aa}$ is aryl or arylalkyl, $R_{bb}$ is hydrogen or alkanoyl and $R_{cc}$ is alkylene, with the proviso that one or both of $R_1$ and $R_2$ is other than hydrogen;

or a salt thereof;

or a compound of the formula:

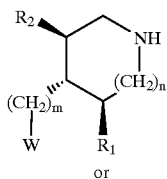
(IV)

or

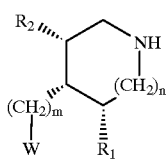
(V)

wherein n is 0 or 1;

m is 0 to 6;

W is (a) $-C(O)_2-G$ where G is hydrogen or a carboxy protecting group, (b) $-PO_3H_2$,
(c) $-P(O)(OH)E$ where E is hydrogen, loweralkyl or arylalkyl,
(d) $-CN$,
(e) $-C(O)NHR_{17}$ where $R_{17}$ is loweralkyl,
(f) alkylaminocarbonyl,
(g) dialkylaminocarbonyl,
(h) tetrazolyl,
(i) hydroxy,
(j) alkoxy,
(k) sulfonamido,
(l) $-C(O)NHS(O)_2R_{16}$ where $R_{16}$ is loweralkyl, haloalkyl, phenyl or dialkylamino,
(m) $-S(O)_2NHC(O)R_{16}$, (n)
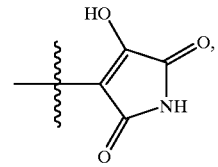

(o)
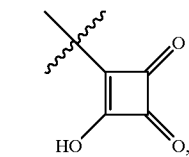

(p)
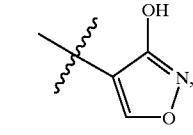

(q)
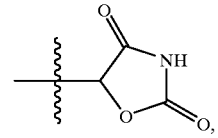

(r) 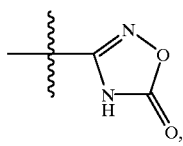

(s) 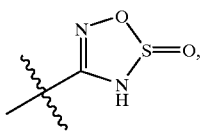

(t) 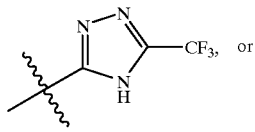

(u) 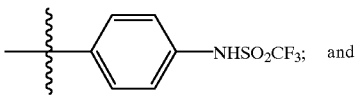

$R_1$ and $R_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl)aminoalkyl, alkylsulfonylamidoalkyl, heterocyclic, (heterocyclic)alkyl and $(R_{aa})(R_{bb})N—R_{cc}$— wherein $R_{aa}$ is aryl or arylalkyl, $R_{bb}$ is hydrogen or alkanoyl and $R_{cc}$ is alkylene, with the proviso that one or both of $R_1$ and $R_2$ is other than hydrogen;

or a salt thereof.

Preferred intermediates include compounds of formula (III), (IV) and (V) wherein
m is zero or 1;
W is —$CO_2$—G wherein G is hydrogen or a carboxy protecting group, and $R_1$ and $R_2$ are as defined above;
or
the substantially pure (+)- or (−)-isomer thereof.

Particularly preferred intermediates are compounds of formula (III), (IV) and (V) wherein
n and m are both 0;
W is —$CO_2$—G wherein G is hydrogen or a carboxy protecting group;
and $R_1$ is (i) loweralkyl, (ii) alkenyl, (iii) alkoxyalkyl, (iv) cycloalkyl, (v) phenyl, (vi) pyridyl, (vii) furanyl or (viii) substituted or unsubstituted 4-methoxyphenyl, 4-fluorophenyl, 3-fluorophenyl, 4-ethoxyphenyl, 4-ethylphenyl, 4-methylphenyl, 4-trifluoromethylphenyl, 4-pentafluoroethylphenyl, 3-fluoro-4-methoxyphenyl, 3-fluoro-4-ethoxyphenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from loweralkyl, haloalkyl, alkoxy, alkoxyalkoxy and carboxyalkoxy (ix) arylalkyl, (x) aryloxyalkyl, (xi) heterocyclic (alkyl), (xii) (N-alkanoyl-N-alkyl)aminoalkyl, and (xiii) alkylsulfonylamidoalkyl, and $R_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl wherein the substituent is selected from loweralkyl, alkoxy and halogen; or the substantially pure (+)- or (−)-isomer thereof.

Other compounds which are useful as intermediates for the preparation of compounds of the invention are:

(VI)

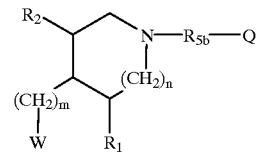

wherein n is 0 or 1;
m is 0 to 6;
$R_{5b}$ is alkylene;
Q is a leaving group;
W is (a) —$C(O)_2$—G where G is hydrogen or a carboxy protecting group, (b) —$PO_3H_2$,
(c) —P(O)(OH)E where E is hydrogen, loweralkyl or arylalkyl,
(d) —CN,
(e) —$C(O)NHR_{17}$ where $R_{17}$ is loweralkyl,
(f) alkylaminocarbonyl,
(g) dialkylaminocarbonyl,
(h) tetrazolyl,
(i) hydroxy,
(j) alkoxy,
(k) sulfonamido,
(l) —$C(O)NHS(O)_2R_{16}$ where $R_{16}$ is loweralkyl, haloalkyl, phenyl or dialkylamino,
(m) —$S(O)_2NHC(O)R_{16}$, (n) 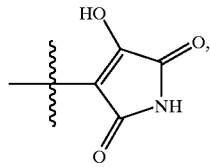

(o) 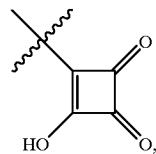

(p) 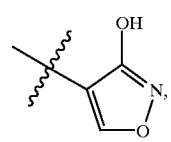

(q) 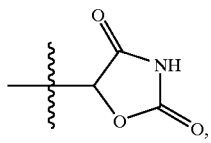

(r) 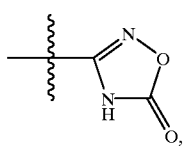

(s) 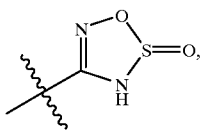

(t) 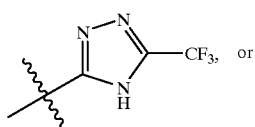

(u) 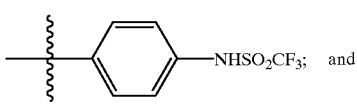

$R_1$ and $R_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl)aminoalkyl, alkylsulfonylamidoalkyl, heterocyclic, (heterocyclic)alkyl and $(R_{aa})(R_{bb})N-R_{cc}-$ wherein $R_{aa}$ is aryl or arylalkyl, $R_{bb}$ is hydrogen or alkanoyl and $R_{cc}$ is alkylene, with the proviso that one or both of $R_1$ and $R_2$ is other than hydrogen;

or a salt thereof;

or a compound of the formula:

(VII) 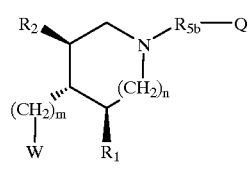

or (VIII) 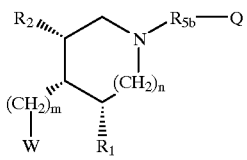

wherein n is 0 or 1;

m is 0 to 6;

$R_{5b}$ is alkylene;

Q is a leaving group;

W is (a) —C(O)$_2$—G where G is hydrogen or a carboxy protecting group, (b) —PO$_3$H$_2$,
  (c) —P(O)(OH)E where E is hydrogen, loweralkyl or arylalkyl,
  (d) —CN,
  (e) —C(O)NHR$_{17}$ where $R_{17}$ is loweralkyl,
  (f) alkylaminocarbonyl,
  (g) dialkylaminocarbonyl,
  (h) tetrazolyl,
  (i) hydroxy,
  (j) alkoxy,
  (k) sulfonamido,
  (l) —C(O)NHS(O)$_2$R$_{16}$ where $R_{16}$ is loweralkyl, haloalkyl, phenyl or dialkylamino,
  (m) —S(O)$_2$NHC(O)R$_{16}$, (n) 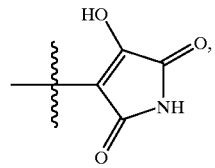

(o) 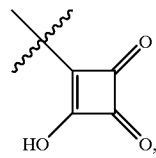

(p) 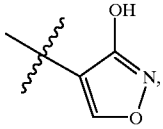

(q) 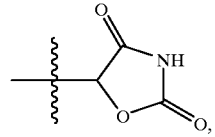

(r) 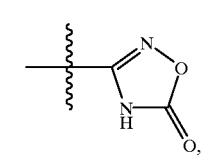

(s) 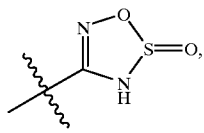

(t) 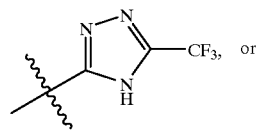

(u) 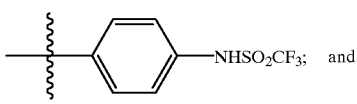

$R_1$ and $R_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl) aminoalkyl, alkylsulfonylamidoalkyl, heterocyclic, (heterocyclic)alkyl and $(R_{aa})(R_{bb})N—R_{cc}$— wherein $R_{aa}$ is aryl or arylalkyl, $R_{bb}$ is hydrogen or alkanoyl and $R_{cc}$ is alkylene, with the proviso that one or both of $R_1$ and $R_2$ is other than hydrogen;

or a salt thereof.

Preferred intermediates include compounds of formula (VI), (VII) and (VIII) wherein m is zero or 1;

$R_{5b}$ is alkylene;

Q is a leaving group;

W is —$CO_2$—G wherein G is hydrogen or a carboxy protecting group, and $R_1$ and $R_2$ are as defined above; or the substantially pure (+)- or (−)-isomer thereof.

Particularly preferred intermediates are compounds of formula (VI), (VII) and (VIII) wherein n and m are both 0;

$R_{5b}$ is alkylene;

Q is a leaving group;

W is —$CO_2$—G wherein G is hydrogen or a carboxy protecting group;

and $R_1$ is (i) loweralkyl, (ii) alkenyl, (iii) alkoxyalkyl, (iv) cycloalkyl, (v) phenyl, (vi) pyridyl, (vii) furanyl or (viii) substituted or unsubstituted 4-methoxyphenyl, 4-fluorophenyl, 3-fluorophenyl, 4-ethoxyphenyl, 4-ethylphenyl, 4-methylphenyl, 4-trifluoromethylphenyl, 4-pentafluoroethylphenyl, 3-fluoro-4-methoxyphenyl, 3-fluoro-4-ethoxyphenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from loweralkyl, haloalkyl, alkoxy, alkoxyalkoxy and carboxyalkoxy, (ix) arylalkyl, (x) aryloxyalkyl, (xi) heterocyclic (alkyl), (xii) (N-alkanoyl-N-alkyl)aminoalkyl, and (xiii) alkylsulfonylamidoalkyl, and $R_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl wherein the substituent is selected from loweralkyl, alkoxy and halogen; or the substantially pure (+)- or (−)-isomer thereof.

Other compounds which are useful as intermediates for the preparation of compounds of the invention are:

(IX)

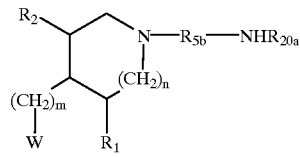

wherein n is 0 or 1;

m is 0 to 6;

$R_{5b}$ is alkylene;

$R_{20a}$ is hydrogen, loweralkyl, alkenyl, haloalkyl, alkoxyalkyl, haloalkoxyalkyl, cycloalkyl, cycloalkylalkyl, aryl or arylalkyl;

W is (a) —$C(O)_2$—G where G is hydrogen or a carboxy protecting group, (b) —$PO_3H_2$, (c) —P(O)(OH)E where E is hydrogen, loweralkyl or arylalkyl, (d) —CN, (e) —$C(O)NHR_{17}$ where $R_{17}$ is loweralkyl, (f) alkylaminocarbonyl, (g) dialkylaminocarbonyl, (h) tetrazolyl, (i) hydroxy, (j) alkoxy, (k) sulfonamido, (l) —$C(O)NHS(O)_2R_{16}$ where $R_{16}$ is loweralkyl, haloalkyl, phenyl or dialkylamino, (m) —$S(O)_2NHC(O)R_{16}$, (n) 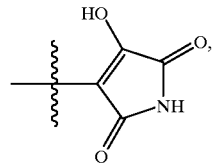

(o) 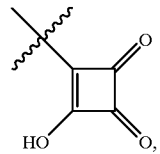

(p) 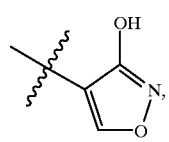

(q) 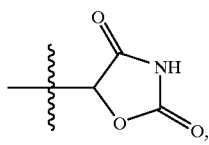

(r) 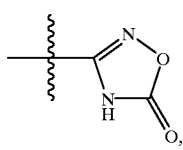

(s) 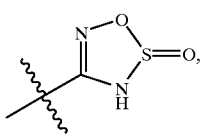

(t) 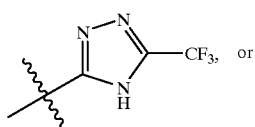

(u) 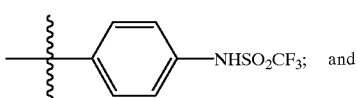

$R_1$ and $R_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxy-alkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl)aminoalkyl, alkylsulfonylamidoalkyl, heterocyclic, (heterocyclic)alkyl and $(R_{aa})(R_{bb})N—R_{cc}$— wherein $R_{aa}$ is aryl or arylalkyl, $R_{bb}$ is hydrogen or alkanoyl and $R_{cc}$ is alkylene, with the proviso that one or both of $R_1$ and $R_2$ is other than hydrogen;

or a salt thereof;

or a compound of the formula:

(X) 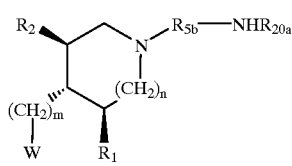

or

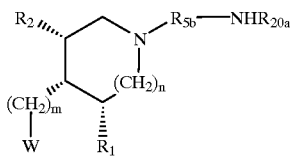

(XI)

wherein n is 0 or 1;
m is 0 to 6;
$R_{5b}$ is alkylene;
$R_{20a}$ is hydrogen, loweralkyl, alkenyl, haloalkyl, alkoxyalkyl, haloalkoxyalkyl, cycloalkyl, cycloalkylalkyl, aryl or arylalkyl;
W is (a) —C(O)$_2$—G where G is hydrogen or a carboxy protecting group, (b) —PO$_3$H$_2$,
(c) —P(O)(OH)E where E is hydrogen, loweralkyl or arylalkyl,
(d) —CN,
(e) —C(O)NHR$_{17}$ where R$_{17}$ is loweralkyl,
(f) alkylaminocarbonyl,
(g) dialkylaminocarbonyl,
(h) tetrazolyl,
(i) hydroxy,
(j) alkoxy,
(k) sulfonamido,
(l) —C(O)NHS(O)$_2$R$_{16}$ where R$_{16}$ is loweralkyl, haloalkyl, phenyl or dialkylamino,
(m) —S(O)$_2$NHC(O)R$_{16}$, (n) 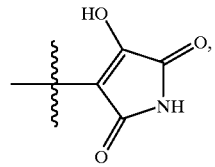

(o) 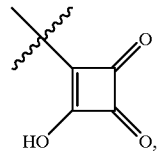

(p) 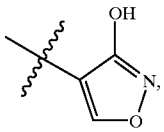

(q) 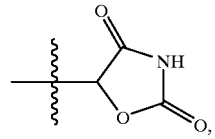

(r) 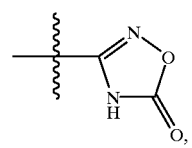

(s) 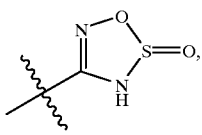

(t) 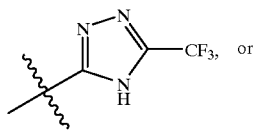

(u) 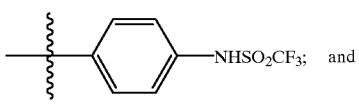

R₁ and R₂ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl) aminoalkyl, alkylsulfonylamidoalkyl, heterocyclic, (heterocyclic)alkyl and $(R_{aa})(R_{bb})N-R_{cc}-$ wherein $R_{aa}$ is aryl or arylalkyl, $R_{bb}$ is hydrogen or alkanoyl and $R_{cc}$ is alkylene, with the proviso that one or both of R₁ and R₂ is other than hydrogen;

or a salt thereof.

Preferred intermediates include compounds of formula (IX), (X) and (XI) wherein m is zero or 1;

$R_{5b}$ is alkylene;

$R_{20a}$ is hydrogen, loweralkyl, alkenyl, haloalkyl, alkoxyalkyl, haloalkoxyalkyl, cycloalkyl, cycloalkylalkyl, aryl or arylalkyl;

W is —CO₂—G wherein G is hydrogen or a carboxy protecting group, and R₁ and R₂ are as defined above; or the substantially pure (+)- or (−)-isomer thereof.

Particularly preferred intermediates are compounds of formula (IX), (X) and (XI) wherein n and m are both 0;

$R_{5b}$ is alkylene;

$R_{20a}$ is hydrogen, loweralkyl, alkenyl, haloalkyl, alkoxyalkyl, haloalkoxyalkyl, cycloalkyl, cycloalkylalkyl, aryl or arylalkyl;

W is —CO₂—G wherein G is hydrogen or a carboxy protecting group; and R₁ is (i) loweralkyl, (ii) alkenyl, (iii) alkoxyalkyl, (iv) cycloalkyl, (v) phenyl, (vi) pyridyl, (vii) furanyl or (viii) substituted or unsubstituted 4-methoxyphenyl, 4-fluorophenyl, 3-fluorophenyl, 4-ethoxyphenyl, 4-ethylphenyl, 4-methylphenyl, 4-trifluoromethylphenyl, 4-pentafluoroethylphenyl, 3-fluoro-4-methoxyphenyl, 3-fluoro-4-ethoxyphenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from loweralkyl, haloalkyl, alkoxy, alkoxy- alkoxy and carboxyalkoxy, (ix) aryalkyl, (x) aryloxyalkyl, (xi) heterocyclic (alkyl), (xii) (N-alkanoyl-N-alkyl)aminoalkyl, and (xiii) alkylsulfonylamidoalkyl, and R₂ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl wherein the substituent is selected from loweralkyl, alkoxy and halogen; or the substantially pure (+)- or (−)-isomer thereof.

The foregoing may be better understood by reference to the following examples which are provided for illustration and not intended to limit the scope of the inventive concept. The following abbreviations are used: Boc for tert-butyloxycarbonyl, Cbz for benzyloxycarbonyl, DBU for 1,8-diazabicyclo[5.4.0]undec-7-ene, EDCl for 1-(3-dimethylaminopropyl-3-ethylcarbodiimide hydrochloride, EtOAc for ethyl acetate, EtOH for ethanol, HOBt for 1-hydroxybenzotriazole, Et₃N for triethylamine, TFA for trifluoroacetic acid and THF for tetrahydrofuran.

EXAMPLE 1 trans,trans-2-(4-Methoxyphenyl)-4-(1,3-benzodioxol-5-yl)-1-(propylaminocarbonylmethyl)-pyrrolidine-3-carboxylic Acid

EXAMPLE 1A

Ethyl 2-(4-methoxybenzoyl)-4-nitromethyl-3-(1,3-benzodioxole-5-yl)butyrate

To ethyl (4-methoxybenzoyl)acetate (23.0 g, 0.104 mol), prepared by the method of Krapcho et al., Org. Syn. 47, 20 (1967), and 5-(2-nitrovinyl)-1,3-benzodioxole (17.0 g, 0.088 mol) dissolved in 180 mL of toluene and heated to 80° C. was added 1,8-diazabicyclo[5,4,0] undec-7-ene (DBU, 0.65 g) with stirring. The mixture was heated until all the nitro startin material dissolved. The solution was stirred without heating for 30 minutes (min) and then an additional 0.65 g of DBU was added. After stirring an additional 45 minutes, thin layer chromatography (5% ethyl acetate in methylene chloride) indicated the absence of nitro starting material. Toluene (200 mL) was added, and the organic phase was washed with dilute hydrochloric acid and NaCl solution. The organic phase was dried over sodium sulfate and then concentrated under reduced pressure. The residue obtained was chromatographed on silica gel eluting with 3:1 hexane-ethyl acetate to give 21.22 g of the desired product as a mixture of isomers and 9.98 g. of recovered ethyl (4-methoxybenzoyl)acetate.

EXAMPLE 1B

Ethyl 2-(4-methoxyphenyl)-4-(1,3-benzodioxol-5-yl)-4,5-dihydro-3H-pyrrole-3-carboxylate The compound resulting from Example 1A (21 g) in 500 mL of ethanol was hydrogenated under 4 atmospheres of hydrogen pressure using a Raney nickel 2800 catalyst (51 g). (The Raney nickel was washed with ethanol three times before use.) The catalyst was removed by filtration, and the solution was concentrated under reduced pressure. The residue obtained was chromatographed on silica gel eluting with 8.5% ethyl acetate in methylene chloride to give 12.34 g of the desired product.

EXAMPLE 1C

Ethyl 2-(4-methoxyphenyl-4-(1,3-benzodioxol-5-yl)-pyrrolidine-3-carboxylate) as a Mixture of cis-cis; trans,trans: and cis trans-isomers The compound resulting from Example 1B (11.89 g, 0.324 mol) was dissolved in 27 mL of tetrahydrofuran and 54 mL of ethanol. Sodium cyanoborohydride (2.35 g, 0.374 mol) and 5 mg bromocresol green were added. To this blue solution was added dropwise a solution of 1:2 concentrated HCl in ethanol at such a rate that the color was kept at light yellow-green. After the yellow color persisted without additional HCl, the solution was stirred an additional 20 minutes. The solution was concentrated in vacuo and then partitioned between chloroform and an aqueous potassium bicarbonate solution. The organic phase was separated, dried over sodium sulfate, and concentrated under reduced pressure. The residue was chromatographed on silica gel eluting with 85:15 ethyl acetate-hexane to give 5.96 g. of a mixture of 64% trans,trans-compound and 34% cis,trans-compound. Further elution with pure ethyl acetate gave 0.505 g of an unknown solid followed by 3.044 g of pure cis,cis-compound.

EXAMPLE 1D trans,trans-2-(4-Methoxyphenyl)-4-(1,3-benzodioxol-5-yl)-1-(propylaminocarbonylmethyl)-pyrrolidine-3-carboxylic Acid The mixture of 64% trans,trans- and 34% cis,trans-pyrrolidines (the mixture resulting from Example 1C) (5.72 g, 15.50 mmol), ethyldiisopropylamine (4.20 g, 32.56 mmol), and N-propyl bromoacetamide (3.42 g, 19.0 mmol), prepared by the method of Weaver, W. E. and Whaley, W. M., J. Amer. Chem. Soc., 69: 515 (1947), in 30 mL of acetonitrile was heated at 50° C. for 1 hour. The solution was concentrated in vacuo. The residue was dissolved in toluene, shaken with potassium bicarbonate solution, dried over sodium sulfate and concentrated in vacuo to give 7.16 g of product as a mixture of trans,trans- and cis,trans- ethyl esters.

This mixture was dissolved in a solution of 50 mL of ethanol and 15 mL of water containing 5.00 g of sodium hydroxide and stirred for 3 hours at room temperature. The solution was concentrated in vacuo and 60 mL of water added. The mixture was extracted with ether to remove the unreacted cis,trans- ethyl ester. The aqueous phase was treated with hydrochloric acid until slightly cloudy. It was then further neutralized with acetic acid to give the crude acid product. The crude product was filtered and purified by dissolving it in tetrahydrofuran, drying over sodium sulfate, concentrating in vacuo, and crystallizing from ether to give 3.230 g of the title compound. m.p. 151–153° C. $^1$H NMR (CD$_3$OD, 300 MHz) δ 0.87 (t, J=7 Hz, 3H), 1.49 (sextet, J=7 Hz, 2H), 2.84 (d, J=16 Hz, 1H), 2.95–3.20 (m, 4H), 3.20 (d, J=16 Hz, 1H), 3.34–3.42 (m, 1H), 3.58–3.66 (m, 1H), 3.78 (s, 3H), 3.88 (d, J=10 Hz, 1H), 5.92 (s, 2H), 6.75 (d, J=8 Hz, 1H), 6.86 (dd, J=8 Hz, J=1 Hz, 1H), 6.90 (d, J=9 Hz, 2H), 7.02 (d, J=1 Hz,1H), 7.40 (d, J=9 Hz, 2H).

EXAMPLE 2 trans,trans-2-(4-Methoxyphenyl)-4-(1,3-benzodioxol-5-yl)-1-(aminocarbonylmethyl)-pyrrolidine-3-carboxylic Acid Using the method described in Example 1D, 300 mg of the mixture of 64% trans,trans- and 34% cis,trans-pyrrolidines (the mixture resulting from Example 1C), 220 mg of diisopropylethylamine and 184 mg iodoacetamide were reacted at 45° C. in 1 mL acetonitrile to give 291 mg of a mixture of trans,trans- and cis,trans- N-alkylated esters. A portion (270 mg.) was hydrolyzed with 200 mg NaOH in 1 mL of water and 3 mL of ethanol; a chloroform extraction was used to remove the unreacted cis,trans- ethyl ester. The isolation and purification procedures described in Example 1D were used to give 134 mg of the title compound. m.p. 246–248° C. $^1$H NMR (DMSO-d$_6$, 300 MHz) δ 2.61 (d, J=16 Hz, 1H), 2.71 (t, J=9 Hz, 1H), 2.90 (t, J=9 Hz, 1H), 2.98 (d, J=16 Hz, 1H),3.25–3.35 (m, 1H), 3.45–3.55 (m, 1H), 3.71 (s, 3H), 3.75 (d, J=10 Hz, 1H), 6.00 (s, 2H), 6.81 (s, 2H), 6.90 (d, J=8 Hz, 2H), 7.10 (s, 1H), 7.17 (s, 1H), 7.34 (s, 1H), 7.38 (d, J=8 Hz, 2H).

EXAMPLE 3 trans,trans-2-(4-Methoxyphenyl)-4-(1,3-benzodioxol-5-yl)-1-(4-fluorobenzyl)-Pyrrolidine-3-carboxylic Acid Using the method described in Example 1D, 300 mg of the mixture of 64% trans,trans- and 34% cis,trans- pyrrolidines (the mixture resulting from Example 1C), 220 mg of diisopropylethylamine and 185 mg of 4-fluorobenzyl bromide were reacted at room temperature for 3 hours in 1 mL of acetonitrile to give 387 mg of a mixture of trans,trans- and cis,trans-N-alkylated esters. A portion (360 mg) was hydrolyzed with 250 mg NaOH in 1 mL of water and 4 mL of ethanol to give 160 mg of the title compound as an amorphous powder. $^1$H NMR (CDCl$_3$, 300 MHz) δ 2.74 (t, J=9 Hz, 1H), 2.95 (t, J=7 Hz, 1H), 2.98 (d, J=14, 1H), 3.07 (dd, J=9 Hz, 1 Hz, 1H), 3.42–3.53 (m, 1H), 3.70 (d, J=9 Hz, 1H), 3.78 (d, J=14, 1H), 3.81 (s, 3H), 5.92 (s, 2H), 6.70 (d, J=8 Hz, 1H), 6.77 (dd, J=8 Hz, 1 Hz,1H), 6.91 (d, J=9 Hz, 2H), 6.94–7.00 (m, 3H), 7.20–7.25 (M, 1H), 7.44 (d, J=9 Hz, 2H).

EXAMPLE 4 trans,trans-2-(4-Methoxyphenyl)-4-(1,3-benzodioxol-5-yl)-1-(2-ethoxyethyl)-pyrrolidine-3-carboxylic Acid Using the method described in Example 1D, 300 mg. of the mixture of 64% trans,trans- and 34% cis,trans- pyrrolidines (the mixture resulting from Example 1C), 220 mg of diisopropylethylamine and 152 mg of 2-bromoethyl ethyl ether were refluxed in 1.5 mL acetonitrile for 3 hours (bath temperature at 95° C.) to give 346 mg of a mixture of trans,trans- and cis,trans-esters. Hydrolysis with 250 mg NaOH in 1 mL of water and 3 mL of ethanol afforded 140 mg of the title compound. m.p. 88–90° C. $^1$H NMR (CDCl$_3$, 300 MHz) δ 1.25 (t, J=7 Hz, 3H), 2.21–2.32 (m, 1H), 2.70–2.80 (m, 1H), 2.85–2,94 (m, 2H), 3.38–3.55 (m, 6H), 3.67 (d, J=10 Hz, 1H), 3.79 (s, 3H), 5.94 (s, 2H), 6.72 (d, J=8 Hz, 1H), 6,84 (m, 1H), 6.84 (d, J=9 Hz, 2H), 7.08 (d, J=1 Hz, 1H), 7.33 (d, J=9 Hz, 2H).

EXAMPLE 5 trans,trans-2-(4-Methoxyphenyl)-4-(1,3-benzodioxol-5-yl)-1-(2-propoxy ethyl)-pyrrolidine-3-carboxylic Acid Using the method described in Example 1D, 520 mg of the mixture resulting from Example 1C, 364 mg of diisopropylethylamine, 50 mg potassium iodide and 350 mg 2-chloroethyl propyl ether were reacted at 125° C. in 0.5 mL acetonitrile for 4 hours to give 517 mg of a mixture of trans,trans- and cis,trans-esters. A portion (500 mg) was hydrolyzed with 315 mg NaOH in 1 mL of water and 4 mL of ethanol to give 225 mg of the title compound as an amorphous powder. $^1$H NMR (CDCl$_3$, 300 MHz) δ 0.87 (t, J=7 Hz, 3H), 1.53 (sextet, J=7 Hz, 2H), 2.28–2.41 (m, 1H), 2.71–2.83 (m, 1H), 2.92–3.08 (m, 2H), 3.30 (t, J=7 Hz, 2H), 3.40–3.60 (m, 4H), 3.72–3.83 (m, 1H), 3.76 (s, 3H), 5.92 (s, 2H), 6.71 (d, J=8 Hz, 2H), 6.74 (dd, J=8 Hz, 1 Hz), 6.71 (d, J=9 Hz, 2H), 7.07 (d, J=9 Hz, 2H), 7.73 (d, J=9 Hz, 2).

EXAMPLE 6 trans,trans-2-(4-Methoxyphenyl)-4-(1,3-benzodioxol-5-yl)-1-[2-(2-methoxyethyl)ethyl]-pyrrolidine-3-carboxylic Acid

EXAMPLE 6A

Ethyl trans,trans-2-(4-methoxyphenyl)-4-(1,3-benzodioxol-5-yl) pyrrolidine-3-carboxylate To the pure cis,cis-compound resulting from Example 1C (3.02 g) dissolved in 10 mL of ethanol was added 20 drops of a solution of 21% sodium ethoxide in ethanol. The reaction mixture was refluxed overnight, at which time thin layer chromatography in ethyl acetate indicated the absence of starting material. The NaOEt was neutralized with HCl in ethanol, and the solution was concentrated in vacuo. The residue was taken up in toluene and extracted with potassium bicarbonate in water. The toluene was dried over sodium sulfate and concentrated under reduced pressure to give 2.775 of the title compound which was pure by TLC (ethyl acetate).

EXAMPLE 6B trans,trans-2-(4-Methoxyphenyl)-4-(1,3-benzodioxol-5-yl)-1-[2-(2-methoxyethoxy)ethyl]-pyrrolidine-3-carboxylic Acid Using the method described in Example 1D, 250 mg of the compound resulting from Example 6A, 150 mg of 2-(2-methoxyethoxy)ethyl bromide and 175 mg diisopropyl-ethylamine in 1 mL acetonitrile were heated at 100° C. for 3 hours to give 229 mg of the trans,trans-ester. A portion (200 mg) was hydrolyzed with 125 mg NaOH in 1 mL of water and 2 mL of ethanol to give 151 mg of the title compound as an amorphous powder. $^1$H NMR (CD$_3$OD, 300 MHz) δ 2.9–3.9 (m, 13H), 3.81 (s, 3H), 4.49 (d, J=10 Hz, 1H), 5.94 (s, 2H), 6.79 (d, J=8 Hz, 1H), 6.89 (dd, J=8 Hz, 1 Hz, 1H), 7.00 (d, J=9 Hz, 2H), 7.05 (d, J=1 Hz, 1H), 7.49 (d, J=9 Hz, 2H).

EXAMPLE 7 trans,trans-2-(4-Methoxyphenyl)-4-(1,3-benzodioxol-5-yl)-1-[2-(2-Dyidyl)ethyl]-Pyrrolidine-3-carboxylic Acid The compound resulting from Example 6A (250 mg), 2-vinyl pyridine (355 mg) and one drop of acetic acid were dissolved in 2-methoxyethanol, and stirred at 100° C. for 2.5 hours. Toluene was added, and the solution was washed with potassium bicarbonate solution. The solution was dried over potassium bicarbonate and concentrated in vacuo. Toluene was added and the solution re-concentrated. This was done until the odor of 2-vinylpyridine was gone. The residue was taken up in hot heptane, filtered to remove a small amount of insoluble impurity, and concentrated in vacuo to give 225 mg of intermediate ester. The ester was hydrolyzed by the method described in Example 1D to give 202 mg of the title compound as the dihydrate. m.p. 77–80° C. $^1$H NMR (CD$_3$OD, 300 MHz) δ 2.8–3.3 (m, 6H), 3.55–3.70 (m, 2H), 3.76 (s, 3H), 3.99 (d, J=10 Hz, 1H), 5.92 (d, J=1 Hz, 2H), 6.72 (d, J=8 Hz, 1H), 6.80 (dd, J=8 Hz, 1 Hz), 6.85 (d, J=9 Hz, 2H), 6.92 (d, J=1 Hz, 1H), 7.20 (d, J=9 Hz, 2H), 7.20–7.32 (m, 2H), 7.70–7.80 (m, 2H), 8.40 (d, J=4Hz, 1H).

EXAMPLE 8 trans,trans-2-(4-Methoxyphenyl)-4-(1,3-benzodioxol-5-yl)-1-(mornholin-4-ylcarbonyl)-pyrrolidine-3-carboxylic Acid To the compound resulting from Example 6A (300 mg) and 164 mg triethylamine dissolved in 2 mL of methylene chloride and cooled in an ice bath was added 146 mg 1-morpholinocarbonyl chloride. The mixture was stirred 3 hours at room temperature. Toluene was added and the solution was washed with potassium bicarbonate solution, dried over sodium sulfate and concentrated in vacuo to give the intermediate ester. The ester was hydrolyzed by the method described in Example 1D to give 288 mg of the title compound. m.p. 244–246° C. $^1$H NMR (DMSO-d$_6$, 300 MHz) δ 2.96 (dd, J=12 Hz, 13 Hz, 1H), 3.03–3.13 (m, 2H), 3.20–3.30 (m, 2H), 3.40–3.60 (m, 5H), 3.74 (s, 3H), 3.70–3.85 (m, 3H), 5.10 (d, J=10 Hz, 1H), 5.99 (d, J=1 Hz, 2H), 6.80–6.90 (m, 2H), 6.87 (d, J=9 Hz, 2H), 7.07 (s, 1H), 7.25 (d, J=9 Hz, 2H).

EXAMPLE 9 trans,trans-2-(4-Methoxyphenyl)-4-(1,3-benzodioxole-5-yl)-1-(butylaminocarbonyl)-Pyrrolidine-3-carboxylic Acid To the compound resulting from Example 6A (300 mg) dissolved in 2 mL tetrahydrofuran and cooled in an ice bath was added 88 mg of butyl isocyanate. After 40 minutes at room temperature, toluene was added, and the solution was concentrated in vacuo to give the intermediate ester. The ester was hydrolyzed by the method described in Example 1D to give 232 mg of the title compound. m.p. 220–221° C. $^1$H NMR (DMSO-d$_6$, 300 MHz) δ 0.78 (t, J=7 Hz, 3H), 1.10 (sextet, J=7 Hz, 2H), 1.22 (quintet, J=7 Hz, 2H), 2.78–3.05 (m, 3H), 3.40–3.56 (m, 2H), 3.74 (s, 3H), 3.95–4.05 (m, 1H), 4.93 (d, J=9 Hz, 1H), 5.80 (t, broad, J=7 Hz, 1H), 5.99 (s, 2H), 6.78–6.86 (m, 2H), 6.88 (d, J=9 Hz, 2H), 7.00 (d, J=1 Hz, 1H), 7.12 (d, J=9 Hz, 2H).

EXAMPLE 10 trans,trans-2-(4-Methoxyphenyl)-4-(1,3-benzodioxol-5-yl)-1-(4-methoxyphenylaminocarbonyl)-3-pyrrolidine-3-carboxylic Acid The compound resulting from Example 6A (300 mg) was treated with 133 mg of 4-methoxyphenyl isocyanate by the procedure described in Example 9. The resulting ester was hydrolyzed with NaOH using the method described in Example 1D to give 279 mg of the title compound. m.p. 185–187° C. $^1$H NMR (CDCl$_3$, 300 MHz) δ 3.23 (dd, J=12 Hz, 13 Hz, 1H), 3.55–3.68 (m, 2H), 3.72 (s, 3H), 3.83 (s, 3H), 4.50–4.65 (m, 1H), 5.06 (d, J=10 Hz, 1H), 5.90 (s, 1H), 5.95 (s, 1H), 6.72 (d, J=9 Hz, 2H), 6.7–6.8 (m, 3H), 6.92 (d, J=9 Hz, 2H), 6.97 (d, J=9 Hz, (d, J=9 Hz, 2H), 7.37 (d, J=9 Hz, 2H).

EXAMPLE 11 trans,trans-2-(4-Methoxyphenyl)-4-(1,3-benzodioxol-5-yl)-1-acetylpyrrolidine-3-carboxylic Acid The compound resulting from Example 6A (250 mg) in 0.5 mL of toluene was treated with 200 mg of acetic anhydride. After stirring 2 hours at room temperature, water was added and the acetic acid neutralized with potassium bicarbonate. The mixture was extracted with toluene to give 273 mg of the intermediate ester. A portion of the ester (200 mg) was hydrolyzed using the method of Example 1D to give 211 mg of the title compound. m.p. 248–250° C. Rotational isomers are seen in the NMR. $^1$H NMR (DMSO-$d_6$, 300 MHz) δ 1.55 and 2.00 (s, 3H), 2.94 and 3.03 (dd, J=12 Hz, 13 Hz, 1H), 3.3–3.6 (m, 2H), 3.72 and 3.76 (s, 3H), 4.12 and 4.28 (dd, J=12 Hz, 7 Hz, 1H), 4.95 and 5.04 (d, J=10 Hz, 1H), 6.00 (s, 2H), 6.75–6.87 (m, 3H), 6.95 and 7.04 (d, J=9 Hz, 2H), 7.18 and 7.32 (d, J=9 Hz, 2H).

EXAMPLE 12 trans,trans-2-(4-Methoxyphenyl)-4-(1,3-benzodioxol-5-yl)-1-(2-furoyl)-pyrrolidine-3-carboxylic Acid To the compound resulting from Example 6A (300 mg) and 164 mg triethylamine dissolved in 2 mL methylene chloride and cooled in an ice bath was added 138 mg of 2-furoyl chloride. The mixture was stirred 30 minutes at room temperature and then worked up by the procedures described in Example 8 to give the intermediare ester. The ester was hydrolyzed by the procedure described in Example 1D to give 269 mg of the title compound as an amorphous powder. $^1$H NMR (DMSO-$d_6$, 300 MHz) δ 3.06 (dd, J=12 Hz, 13 Hz, 1H), 3.3–3.6 (m, 2H), 4.25 (m, 1H), 5.19 (d, J=10 Hz, 1H), 6.67.4 (m, 8H), 7.8–7.9 (m, 1H).

EXAMPLE 13 trans,trans-2-(4-Methoxnphenyl)-4-(1,3-benzodioxol-5-yl)-1-(phenylaminocarbonyl)-pyrrolidine-3-carboxylic Acid Starting with the compound resulting from Example 6A, phenyl isocyanate and the procedures described in Example 9, the title compound was prepared. m.p. 209–211° C. $^1$H NMR (DMSO-$d_6$, 300 MHz) δ 3.03 (dd, 1H), 3.55 (m, 1H), 3.70 (m, 1H), 3.72 (s, 3H), 4.15 (m, 1H), 5.13 (d, 1H), 6.00 (s, 2H), 6.88 (m, 5H), 7.07–7.20 (m, 3H), 7.30 (d, 2H), 7.38 (d, 2H), 8.20 (bs, 1H).

EXAMPLE 14 trans,trans-2-(4-Methoxyphenyl)-4-(1,3-benzodioxol-5-yl)-1-(allylaminocarbonylmethyl)-pyrrolidine-3-carboxylic Acid Using the procedures described in Example 1 the title compound was prepared. m.p. 138–140° C. $^1$H NMR (CDCl$_3$, 300 MHz) δ 2.84 (d, 1H), 2.90–3.10 (dt, 2H), 3.28 (d, 1H), 3.35 (dd, 1H), 3.62 (m, 1H), 3.72–3.97 (m, 3H), 3.80 (s, 3H), 5.13 (bd, 2H), 5.80 (m, 1H), 5.97 (s, 2H), 6.74–6.97 (m, 5H), 7.38 (d, 2H).

EXAMPLE 15 trans,trans-2-(4-Methoxyphenyl)-4-(1,3-benzodioxol-5-yl)-1-(n-butylaminocarbonylmethyl)-pyrrolidine-3-carboxylic Acid Using the procedures described in Example 1 the title compound was prepared. m.p. 105–107° C. $^1$H NMR (CDCl$_3$, 300 MHz) δ 0.90 (t, 3H), 1.30 (m, 2H), 1.45 (m, 2H), 2.80 (d, 1H), 2.87–3.35 (m, 6H), 3.62 (m, 1H), 3.80 (s, 3H), 5.97 (s, 2H), 6.75–6.92 (m, 5H), 7.28 (d, 2H).

EXAMPLE 16 trans,trans-2-(4-Methoxyphenyl)-4-(1,3-benzodioxol-5-yl)-1-(N-(n-propyl)-N-methylaminocarbonylmethyl)-pyrrolidine-3-carboxylic Acid Using the procedures described in Example 1 the title compound was prepared as an amorphous solid. Rotational isomers are seen in the NMR. $^1$H NMR (CDCl$_3$, 300 MHz) δ 0.73, 0.84 (2t, 3H), 1.49 (m, 2H), 2.80 (dd, 1H), 2.85 (2s, 3H), 2.95–3.20 (m, 3H), 3.20–3.40 (m, 1H), 3.40 (d, 1H), 3.60 (m, 1H), 3.79 (s, 3H), 5.93 (s, 2H), 6.73 (d, 1H), 6.86 (m, 2H), 7.03 (m, 1H), 7.32 (d, 2H).

EXAMPLE 17 trans,trans-2-(4-Methoxyphenyl)-4-(1,3-benzodioxol-5-yl)-1-(pyrrolidin-1-ylcarbonylmethyl)-pyrrolidine-3-carboxylic Acid Using the procedures described in Example 1 the title compound was prepared as an amorphous solid. $^1$H NMR (CDCl$_3$, 300 MHz) δ 1.40–1.70 (m, 6H), 2.80 (d, 1H), 3.00 (m, 2H), 3.24–3.43 (m, 5H), 3.60 (m, 2H), 3.73 (d, 1H), 3.80 (s, 3H), 5.95 (s, 2H), 6.74 (d, 1H), 6.80–6.90 (m, 3H), 7.04 (d, 1H), 7.30 (d, 2H).

EXAMPLE 18 trans,trans-2-(4-Methoxyphenyl)-4-(1,3-benzodioxol-5-yl)-1-(isobutylaminocarbonylmethyl)-pyrrolidine-3-carboxylic Acid Using the procedures described in Example 1 the title compound was prepared. m.p. 175–177° C. $^1$H NMR (CD$_3$OD, 300 MHz) δ 0.87 (dd, 6H), 1.75 (septet, 1H), 2.85 (d, 1H), 2.90–3.10 (m, 4H), 3.23 (d, 1H), 3.40 (m, 1H), 3.58–3.67 (m, 1H), 3.78 (s, 3H), 3.89 (d, 1H), 5.92 (s, 2H), 6.76 (d, 1H), 6.86 (dd, 1H), 6.91 (d, 2H), 7.02 (d, 1H), 7.40 (d, 2H).

EXAMPLE 19 trans,trans-2-(4-Methoxyphenyl)-4-(1,3-benzodioxol-5-yl)-1-(cyclopentylaminocarbonylmethyl)-pyrrolidine-3-carboxylic Acid Using the procedures described in Example 1 the title compound was prepared. m.p. 137–139° C. $^1$H NMR (CDCl$_3$, 300 MHz) δ 1.34 (m, 2H), 1.62 (m, 4H), 1.90 (m, 2H), 2.76 (d, 1H), 2.90 (t, 1H), 3.04 (dd, 1H), 3.22 (d, 1H), 3.28 (dd, 1H), 3.40 (m, 1H), 3.80 (s, 3H), 4.15 (m, 1H), 5.97 (d, 2H), 6.75–6.95 (m, 5H), 7.27 (m, 2H).

EXAMPLE 20 trans,trans-2-(4-Methoxyphenyl)-4-(1,3-benzodioxol-5-yl)-1-(morpholin-4-ylaminocarbonylmethyl)-pyrrolidine-3-carboxylic Acid Using the procedures described in Example 1 the title compound was prepared as an amorphous solid. $^1$H NMR (CDCl$_3$, 300 MHz) δ 2.82 (d, 1H), 3.00 (m, 2H), 3.24 (m, 1H), 3.30–3.52 (m, 4H), 3.52–3.75 (m, 8H), 3.80 (s, 3H), 5.95 (s, 2H), 6.75 (d, 1H), 6.84 (d, 3H), 7.00 (s, 1H), 7.28 (d, 2H).

EXAMPLE 21 trans,trans-2-(4-Methoxyphenyl)-4-(1,3-benzodioxol-5-yl)-1-(2-phenoxyethyl)-pyrrolidine-3-carboxylic Acid Using the procedures described in Example 4 the title compound was prepared as an amorphous solid. $^1$H NMR (CD₃OD, 300 MHz) δ 2.82 (m, 1H), 2.96 (dd, 1H), 3.13 (m, 1H), 3.32 (m, 1H), 3.51–3.70 (m, 2H), 3.77 (s, 3H), 4.00 (d, 1H), 4.07 (m, 2H), 5.91 (s, 2H), 6.72 (d, 1H), 6.80–6.95 (m, 6H), 7.03 (d, 1H), 7.22 (dd, 2H), 7.39 (d, 2H).

EXAMPLE 22 trans,trans-2-(4-Methoxyphenyl)-4-(1,3-benzodioxol-5-yl)-1-(2-methoxyethylaminocarbonylmethyl)-pyrrolidine-3-carboxylic Acid Using the procedures described in Example 1 the title compound was prepared. m.p. 107–109° C. $^1$H NMR (CD₃OD, 300 MHz) δ 2.82 (d, 1H), 2.97 (q, 2H), 3.21 (d, 1H), 3.38 (m, 1H), 3.32 (s, 3H), 3.44 (m, 4H), 3.62 (m, 1H), 3.79 (s, 3H), 3.86 (d, 1H), 5.93 (s, 2H), 6.76 (d, 1H), 6.85 (dd, 1H), 6.91 (d, 2H), 7.01 (d, 1H), 7.38 (d, 2H).

EXAMPLE 23 trans,trans-2-(4-Methoxyphenyl)-4-(1,3-benzodioxol-5-yl)-1-(2-butoxyethyl)-pyrrolidine-3-carboxylic Acid Using the procedures described in Example 4 the title compound was prepared. m.p. 53–55° C. $^1$H NMR (CDCl₃, 300 MHz) δ 0.88 (t, J=7 Hz, 3H), 1.32 (sextet, J=7 Hz, 2H), 1.50 (pentet, J=7 Hz, 2H), 2.27 (tt, J=6 Hz, 6 Hz, 1H), 2.92 (q, J=10 Hz, 2H), 3.35 (t, J=7 Hz, 2H), 3.42–3.56 (m, 4H), 3.68 (d, J=10 Hz, 1H), 3.78 (s, 3H), 5.94 (s, 2H), 6.73 (d, J=8 Hz, 1H), 6.83 (d, J=9 Hz, 2H), 6.82–6.87 (m, 1), 7.06 (d, J=2 Hz, 1H), 7.32 (d, J=9 Hz, 2H). MS m/e 442 (M+H)⁺.

EXAMPLE 24 trans,trans-2-(1,3-Benzodioxol-5-yl)-4-(4-methoxyphenyl)-1-(propylaminocarbonylmethyl)-pyrrolidine-3-carboxylic Acid Using the procedures described in Example 1 and substituting ethyl (1,3-benzodioxol-5-ylcarbonyl)acetate for ethyl (4-methoxybenzoyl)acetate and 4-(2-nitrovinyl)anisole for 5-(2-nitrovinyl)-1,3-benzodioxol-5yl afforded the title compound. m.p. 97–99° C. $^1$H NMR (CDCl₃, 300 MHz) δ 0.78 (t, J=7 Hz, 3H), 1.39 (sextet, J=7 Hz, 2H), 2.72 (d, J=16 Hz, 1H), 2.74 (t, J=10 Hz, 1H), 2.80–3.10 (m, 4H), 3.26–3.38 (m, 1H), 3.53 (m, 1H), 3.73 (s, 3H), 3.80 (d, J=10 Hz, 2H), 7.80 (t, J=6 Hz, 1H). MS (DCl/NH₃) m/e 441 (M+H)⁺.

EXAMPLE 25 trans,trans-2-(1,3-Benzodioxol-5-yl)-4-(4-methoxyphenyl)-1-(2-propoxyethyl)-pyrrolidine-3-carboxylic Acid Using the procedures described in Example 5 and substituting ethyl (1,3-benzodioxol-5-ylcarbonyl)acetate for ethyl (4-methoxybenzoyl)acetate and 4-(2-nitrovinyl)anisole for 5-(2-nitrovinyl)-1,3-benzodioxol-5yl afforded the title compound. m.p. 67–69° C. $^1$H NMR (CDCl₃, 300 MHz) δ0.89 (t, J=7 Hz, 3H),1.56 (sextet, J=7 Hz, 2H), 2.33 (m, 1H), 2.78–3.00 (m, 3H), 3.32 (t, J=7 Hz, 2H), 3.45–3.57 (m, 4H), 3.73 (m, 1H), 3.79 (s, 3H), 5.93 (s, 2H), 6.22 (d, J=8 Hz, 1H), 6.85 (d, J=8 Hz, 3H), 6.98 (s, 1H), 7.37 (d, J=8 Hz, 2H). MS (DCl/NH₃) m/e 428 (M+H)⁺.

EXAMPLE 26 trans,trans-2-(1,3-Benzodioxol-5-yl)-4-(4-methoxyphenyl)-1-[2-(2-methoxyethoxy)ethyl)]-pyrrolidine-3-carboxylic Acid Using the procedures described in Example 4 and substituting the starting materials described in Example 25 and using 2-(2-methoxyethoxy)ethylbromide to alkylate the pyrrolidine nitrogen afforded the title compound. m.p. 85–86° C. $^1$H NMR (CD₃OD, 300 MHz) δ 3.18–3.90 (m, 15H), 3.79 (s, 3H), 4.57 (d, J=10 Hz, 1H), 6.02 (s, 2H), 6.91 (d, J=8 Hz, 1H), 6.95 (d, J=9 Hz, 2H), 7.06 (dd, J=8 Hz, 1H), 7.12 (dd, J=1 Hz, 1H), 7.37 (d, J=9 Hz, 2H). MS (DCl/NH₃) m/e 444 (M+H)⁺.

EXAMPLE 27 trans,trans-2-(1,3-Benzodioxol-5-yl)-4-(4-methoxyphenyl)-1-(butoxyethyl)-pyrrolidine-3-carboxylic Acid Using the procedures described in Example 4, substituting the starting materials described in Example 25 and using 2-ethoxyethylbromide to alkylate the pyrrolidine nitrogen afforded the title compound. m.p. 54–56° C. $^1$H NMR (CDCl₃, 300 MHz) δ 0.89 (t, J-7 Hz, 3H), 1.44 (sextet, J=7 Hz, 2H), 1.52 (pentet, J=7 Hz, 2H), 2.40 (m, 1H), 2.74–2.98 (m, 3H), 3.46 (t, J=7 Hz, 2H), 3.42–3.56 (m, 4H), 3.68 (d, J=10 Hz, 1H), 3.80 (s, 3H), 5.93 (dd, J=6 Hz, 1 Hz, 2H), 6.72 (d, J=8 Hz, 1H), 6.74 (dd, J=9 Hz, 3H), 6.96 (s, 1H), 7.36 (d, J=9 Hz, 2H).

EXAMPLE 28 trans,trans-2-(4-Methoxyphenyl)-4-(1,4-benzodioxan-6-yl)-1-(propylaminocarbonylmethyl)-pyrrolidine-3-carboxylic Acid Using the procedures described in Example 1 and substituting 6-(2-nitrovinyl)-1,4-benzodioxane for 5-(2-nitrovinyl)-1,3-benzodioxole afforded the title compound. m.p. 80–81° C. $^1$H NMR (CDCl₃, 300 MHz) δ 0.89 (t, J-7 Hz, 3H), 1.49 (sextet, J=7 Hz, 2H), 2.78 (d, J=16 Hz, 1H), 2.92 (t, J=10 Hz, 1H), 3.05–3.43 (m, 5H), 3.24 (d, J=16 Hz, 1H), 3.52–3.62 (m, 1H), 3.80 (s, 3H), 3.80 (t, J=10 Hz, 1H), 4.27 (s, 4H), 6.74–6.93 (m, 5H), 7.29 (d, J=9 Hz, 2H). MS (DCl/NH₃) m/e 455 (M+H)⁺.

EXAMPLE 29 trans,trans-2-(4-Methoxyphenyl)-4-(1,4-benzodioxan-6-yl)-1-(N-methyl-N-propylaminocarbonylmethyl)-pyrrolidine-3-carboxylic Acid Using the procedures described in Example 1, substituting 6-(2-nitrovinyl)-1,4-benzodioxane for 5-(2-nitrovinyl)-1,3-benzodioxole and alkylating the pyrrolidine nitrogen with N-methyl-N-propyl bromoacetamide afforded the title compound. m.p. 74–76° C. Rotational isomers are seen in the NMR. $^1$H NMR (CDCl₃, 300 MHz) δ 0.73, 0.83 (2t, J=7 Hz, 3H), 1.48 (m, 2H), 2.78 (dd, 1H), 2.85 (2s, 3H), 2.96–3.15 (m, 3H), 3.27–3.42 (m, 3H), 3.52–3.60 (m, 1H), 3.75 (d, 1H), 3.78 (s, 3H), 4.22 (s, 4H), 6.80–6.98 (m, 5H), 7.32 (d, 2H). MS (DCl/NH₃) m/e 469 (M+H)⁺.

EXAMPLE 30 trans,trans-2-(4-Methoxyphenyl)-4-(1,3-benzodioxol-5-yl)-1-(N-methyl-N-butylaminocarbonylmethyl)-pyrrolidine-3-carboxylic Acid Using the procedures described in Example 1, the title compound was prepared. Rotational isomers are seen in the NMR. $^1$H NMR (CD₃OD, 300 MHz) δ 0.86 (2t, 3H), 1.04–1.50 (m, 4H), 2.85 (2s, 3H), 2.93–3.20 (m, 4H), 3.40

(m, 2H), 3.52 (dd, 1H), 3.60 (m, 1H), 3.80 (s, 3H), 3.85 (m, 1H), 5.91 (s, 2H), 6.74 (d, 1H), 6.83–6.95 (m, 3H), 7.03 (dd,1H), 7.35 (dd, 2H).

EXAMPLE 31 trans,trans-2-(4-Methoxy-2-methoxymethoxyphenyl)-4-(1,3-benzodioxol-5-yl)-1-(N-methyl-N-butylaminocarbonylmethyl)-pyrrolidine-3-carboxylic Acid

EXAMPLE 31A

Ethyl 2-(4-methoxy-2-methoxymethoxyphenyl4-(1,3-benzodioxol-5-yl)-pyrrolidine-3-carboxylate)

Using the procedures described in Examples 1A and 1B and substituting ethyl (4-methoxy-2-methoxymethoxybenzoyl)acetate for ethyl (4-methoxybenzoyl)acetate afforded ethyl 2-(4-methoxy-2-methoxymethoxyphenyl)-4-(1,3-benzodioxol-5-yl)-4,5-dihydro-3H-pyrrole-3-carboxylate.

The above dihydro pyrrole carboxylate (3.0 g, 7.0 mmol) was dissolved in 20 mL of methanol, treated with 500 mg of 10% Pd/C and placed under hydrogen atmosphere for 32 hours. The catalyst was removed by filtration and the filtrate was concentrated under reduced pressure and chromatographed on silica gel eluting with ethyl acetate to afford the title compound (1.9 g, 63%) as the cis-cis isomer.

EXAMPLE 31B trans,trans-2-(4-Methoxy-2-methoxymethoxyphenyl)-4-(1,3-benzodioxol-5-yl)-1-(N-methyl-N-butylaminocarbonylmethyl)-pyrrolidine-3-carboxylic Acid The compound resulting from Example 31A was epimerized by the procedure described in Example 6A. The resulting trans,trans compound (100 mg, 0.23 mmol) was then reacted by the procedures described in Example 1D substituting N-methyl-N-butyl bromoacetamide for N-propyl bromoacetamide to give the title compound (75 mg, 62%). m.p. 65–67° C. Rotational isomers are seen in the NMR. $^1$H NMR (CDCl$_3$, 300 MHz) δ 0.64, 0.68 (2t, J=7 Hz, 3H), 1.14,1.12 (2 sextet, J=7 Hz 2H), 1.40–1.48 (m, 2H), 2.86, 2.89 (2s, 3H), 2.95–3.42 (m, 6H), 3.50 (s, 3H), 3.43–3.65 (m, 2H), 3.78 (s, 3H), 4.30 (t, J=7 Hz, 1H), 5.09 (q, J=7 Hz, 2H), 5.92 (s, 2H), 6.55 (dd, J=3 Hz, 1H), 6.68 (s, 1H), 6.72 (s, 1H), 6.85 (2t, J=1 Hz, 1H), 7.04 (t, J1 Hz, 1H), 7.42 (dd, J=3 Hz, 1H).

EXAMPLE 32 trans,trans-2-(4-Methoxyphenyl)-4-(1,3-benzodioxol-5-yl)-1-(3-ethoxypropyl)-pyrrolidin-5-one-3-carboxylic Acid

EXAMPLE 32A

Ethyl 2-(4-methoxybenzoyl)-3-carbomethoxy-1,3-benzodioxole-5-propionate

To ethyl (4-methoxybenzoyl)acetate (4.44 g, 0.02 mmol) dissolved in 20 mL of anhydrous THF was added in portions 480 mg of NaH. The mixture was stirred for 30 minutes under nitrogen at ambient temperature. Methyl (1,3-benzodioxol-5-yl) bromoacetate (5.46 g, 0.02 mol) in 5 mL of THF was added. The mixture was stirred overnight at ambient temperature, diluted with 200 mL of EtOAc, and washed with water and brine. The organic phase was dried over sodium sulfate and concentrated in vacuo to afford the title compound (7.67 g, 92%) which was used without further purification.

EXAMPLE 32B

Ethyl 1-(3-ethoxypropyl)-2-(4-methoxyphenyl)-4-(1,3-benzodioxol-5-yl)-4,5-dihydro-5-oxo-1H-pyrrole-3-carboxylate A mixture of the compound resulting from Example 32A (700 mg, 1.69 mmol), 3-ethoxypropylamine (348 mg, 3.38 mmol) and 1 mL of acetic acid in a sealed tube was heated for 18 hours at 125° C. After cooling the contents of the tube to ambient temperature, 5 mL of water was added and the mixture extracted with ethyl acetate (2×100 mL). The combined organic extracts were washed with saturated sodium bicarbonate solution, water and brine, dried over sodium sulfate and concentrated under reduced pressure. The residue obtained was chromatographed on silica gel eluting with 3:2 hexane-ethyl acetate to give 330 mg (42%) of the title compound.

EXAMPLE 32C

Ethyl 1-(3-ethoxypropyl)-2-(4-methoxyphenyl)-4-(1,3-benzodioxol-5-yl)-pyrrolidin-5-one-3-carboxylate The compound resulting from Example 32B (300 mg, 0.64 mmol) in 15 mL of methanol was reduced with 100 mg of 10% Pd/C under hydrogen for 3 hours at ambient temperature. The catalyst was removed by filtration and the filtrate was concentrated under reduced pressure to give the title compound.

EXAMPLE 32D trans,trans-2-(4-Methoxyphenyl)-4-(1,3-benzodioxol-5-yl)-1-(3-ethoxypropyl)-pyrrolidin-5-one-3-carboxylic Acid To the compound resulting from Example 32C (100 mg, 0.21 mmol) dissolved in 1 mL of ethanol was added 3 drops of a solution of 21% sodium ethoxide in ethanol. The mixture was heated to 70–80° C. for 3 hours, and then a solution of sodium hydroxide (100 mg) in 1 mL of water was added and heating was continued for 1 additional hour. The reaction mixture was cooled to ambient temperature, the ethanol was removed under reduced pressure, and water was added to the residue which was washed with ether. The aqueous layer was neutralized with 3 M HCl and allowed to stand overnight. The white crystalline solid was collected by filtration to give the title compound (60 mg, 64%). m.p. 134–140° C. $^1$H NMR (DMSO-d$_6$, 300 MHz) δ 1.04 (t, J=7 Hz, 3H), 1.55 (sextet, J=7 Hz, 2H), 2.48–2.56 (m, 1H), 2.93 (dd, J=9 Hz, 1H), 3.25 (t, J=7 Hz, 2H), 3.28–3.40 (m, 2H), 3.48–3.57 (m, 1H), 3.78 (s, 3H), 3.88 (d, J=10 Hz, 1H), 4.72 (d, J=10 Hz, 1H), 6.02 (s, 2H), 6.74 (dd, J=8 Hz, 1 Hz, 1H), 6.87 (d, J=8 Hz, 2H), 6.98 (d, J=8 Hz, 2H), 7.38 (d, J=8 Hz, 2H). MS (DCl/NH$_3$) m/e 442 (M+H)$^+$.

EXAMPLE 33 trans,trans-2-(4-Methoxyphenyl)-4-(1,3-benzodioxol-5-yl)-1-(3-methoxybenzyl)-pyrrolidin-5-one-3-carboxylic Acid Following the procedures described in Example 32 and substituting 3-methoxybenzylamine for 3-ethoxypropylamine afforded the title compound (123 mg, 65%). m.p. 150–152° C. ¹H NMR (CD₃OD, 300 MHz) δ 2.96 (dd, J=8 Hz, 10 Hz, 1H), 3.72 (s, 3H), 3.80 (s, 3H), 4.06 (d, J=10 Hz, 1H), 4.58 (d, J=8 Hz, 1H), 4.92 (q, J=16 Hz, 2H), 5.92 (s, 2H), 6.55–6.63 (m, 2H), 6.82 (d, J=8 Hz, 4H), 6.94 (d, J=8 Hz, 2H), 7.15–7.22 (m, 3H). MS (DCl/NH₃) m/e 475 (M+H)⁺.

EXAMPLE 34 trans,trans-2-(4-Methoxyphenyl)-4-(1,3-benzodioxol-5-yl)-1-(N,N-diisoamylaminocarbonylmethyl)-pyrrolidine-3carboxylic Acid The title compound was prepared as an amorphous solid using the procedures described in Example 1. ¹H NMR (CDCl₃, 300 MHz) δ 0.70–0.90 (m, 12H), 1.10–1.60 (m, 10H), 2.75 (d, J=13 Hz, 1H), 2.90–3.10 (m, 4H), 3.15–3.3 (m, 2H), 3.40 (d, J=10 Hz, 1H), 3.40–3.52 (m, 2H), 3.55–3.62 (m, 1H), 3.75 (d, J=12 Hz, 1H), 3.79 (s, 3H), 5.93 (dd, J=1 Hz, 3 Hz, 2H), 6.72 (d, J=8 Hz, 1H), 6.82–6.90 (m, 3H), 7.03 (d, J=2 Hz, 1H), 7.30 (d, J=9 Hz, 2H).

EXAMPLE 35 trans,trans-2-(4-Methoxyphenyl)-4-(1,3-benzodioxol-5-yl)-1-(N,N-dipentylaminocarbonylmethyl)-pyrrolidine-3-carboxylic Acid The title compound was prepared as an amorphous solid using the procedures described in Example 1. ¹H NMR (CDCl₃, 300 MHz) δ 0.82 (t, J 7 Hz, 6H), 0.95–1.03 (m, 2H), 1.10–1.30 (m, 8H), 1.40–1.51 (m, 2H), 2.72 (d, J=13 Hz, 1H), 2.90–3.08 (m, 4H), 3.25–3.50 (m, 3H), 3.37 (d, J=13 Hz, 1H), 3.52–3,60 (m, 1H, 3.70 (J=10 Hz, 1H), 3.75 (s, 3H), 5.92 (dd, J=2 Hz, 5 Hz, 2H), 6.72 (d, J=8 Hz, 1H), 6.80–6.88 (m, 3H), 7.03 (d, J=2 Hz, 1H), 7.30 (d, J=9 Hz, 2H).

EXAMPLE 36 trans,trans-2-(4-Methoxyphenyl)-4-(1,3-benzodioxol-5-yl)-1-(N,N-di(2-methoxyethyl)aminocarbonylmethyl)-pyrrolidine-3-carboxylic Acid The title compound was prepared using the procedures described in Example 1. m.p. 120–122° C. ¹H NMR (CDCl₃, 300 MHz) δ 2.82 (d, J=13, 1H), 2.94–3.08 (m, 2H), 3.12 (s, 3H), 3.23 (s, 3H), 3.20–3.70 (m, 11H), 3.73 (d, J=10 Hz, 1H), 3.79 (s, 3H), 5.92 (dd, J=2 Hz, 2 Hz, 2H), 6.72 (d, J=8 Hz, 1H), 6.80–6.90 (m, 3H), 7.04 (d, J=2 Hz, 1H), 7.30 (d, J=9 Hz, 2H).

EXAMPLE 37 trans,trans-2-(4-Methoxyphenyl)-4-(1,3-benzodioxol-5-yl)-1-(2-hexenyl)-pyrrolidine-3-carboxylic Acid Using the procedures described in Example 4, 200 mg. of the pure trans,trans isomer, the compound resulting from Example 6A was reacted with 109 mg of 1-bromo-2-hexyne, prepared by the method described in Perkin I, 2004 (1987), for 1 hour at 55° C., to give 226 mg of the intermediate ester. The ester was hydrolyzed using NaOH in ethanol-water for 3 hours at room temperature to give 175 mg of the title compound. ¹H NMR (CDCl₃, 300 MHz) δ 1.00 (t, J=7 Hz, 3H), 1.54 (m, 2H), 2.14–2.22 (m, 2H), 2.96 (dd, J=7 Hz, 13 Hz, 1H), 3.07 (dd, J=18 Hz, 2 Hz, 1H), 3.15 (dd, J=9 Hz, 2 Hz, 1H), 3.26 (t, J=9 Hz, 1H), 3.36 (dd, J=18 Hz, 2 Hz, 1H), 3.47–3.55 (m, 1H), 3.79 (s, 3H), 3.88 (d, J=9 Hz, 1H), 5.95 (s, 2H), 6.72 (d, J=8 Hz, 1 Hz, 1H), 6.80–6.88 (m, 3H), 7.03 (d, J=2 Hz, 1H), 7.22 (d, J=9 Hz, 2H).

EXAMPLE 38 trans,trans-2-(4-Methoxyphenyl)-4-(1,3-benzodioxol-5-yl)-1-(N-cyclopropylmethyl-N-propylaminocarbonylmethyl)-pyrrolidine-3-carboxylic Acid The title compound was prepared using the procedures described in Example 1. m.p. 167–169° C. Rotational isomers were seen in the NMR. ¹H NMR (CDCl₃, 300 MHz) δ −0.1 (m), 0.05 (m), 0.12–0.25 (m), 0.32–0.51 (m), 0.67 and 0.74 (2 triplets, 3H), 0.90–1.00 (m), 1.20–1.55 (m), 2.72 (d, J=13 Hz, 1H), 2.85–3.29 (m, 4H), 3.30–3.50 (m, 3H), 3.52–3.62 (m, 1H), 3.65–3.73 (2 doublets, J=10 Hz, 2 Hz, 1H), 3.78 (s, 3H), 5.95 (2 singlets, 2H), 6.72 (2 doublets, 2H), 6.80–6.90 (m, 3H), 7.00 and 7.05 (2 doublets, J=9 Hz, 2H).

EXAMPLE 39 trans,trans-2-(4-Methoxyphenyl)-4-(1,3-benzodioxol-5-yl)-1-(N-methyl-N-pentylaminocarbonylmethyl)-pyrrolidine-3-carboxylic Acid The title compound was prepared as an amorphous solid using the procedures described in Example 1. Rotational isomers were seen in the NMR. ¹H NMR (CDCl₃, 300 MHz) δ 0.85 (t, J=7 Hz, 3H), 1.00–1.08 (m), 1.13–1.32 (m), 1.35–1,50 (m), 2.72–2.82 (2 doublets, J=13 Hz, 1H), 2.83 and 2.86 (2 singlets, 3H), 2.92–3.20 (m, 3H), 3.22–3.45 (m, 3H), 3.52–3.62 (m, 1H), 3.72 (2 doublets, 1H), 3.75 and 3.76 (2 singlets, 3H), 5.92 (2 singlets, 2H), 6.72 (d, J=8 Hz, 1H), 6.80–6.87 (m, 3H), 7.03 (2 doublets, J=2 Hz, 1H), 7.30 (d, J=9 Hz, 2H).

EXAMPLE 40 trans,trans-2-(4-Methoxyphenyl)-4-(1,3-benzodioxol-5-yl)-1-(N,N-d-usobutylaminocarbonylmethyl)-pyrrolidine-3-carboxylic Acid The title compound was prepared using the procedures described in Example 1. m.p. 141–143° C. ¹H NMR (CDCl₃, 300 MHz) δ 0.54 (d, J=7 Hz, 3H), 0.70–0.90 (3 doublets, J=7 Hz, 9H), 1.60–1.75 (m, 1H), 1.90–2.02 (m, 1H), 2.67 (d, J=13 Hz, 1H), 2.70 (d, J=13 Hz, 1H), 2.84 (dd, J=6 Hz, 15 Hz, 1H), 2.96–3.06 (m, 2H), 3.20 (dd, J=9 Hz, 15 Hz, 1H), 3.35 (dd, J=2 Hz, 10 Hz, 1H), 3.44–3.60 (m, 4H), 3.70 (d, J=9 Hz, 1H), 3.79 (s, 3H), 5.94 (dd, J=2 Hz, 2 Hz, 2H), 6.72 (d, J=9 Hz, 1H), 6.82–6.90 (m, 3H), 7.03 (d, J=2 Hz, 1H), 7.31 (d, J=9 Hz, 2H).

EXAMPLE 41 trans,trans-2-(4-Methoxyphenyl)-4-(1,3-benzodioxol-5-yl)-1-(N-methyl-N-(2-propynyl)aminocarbonylmethyl)-pyrrolidine-3-carboxylic Acid The title compound was prepared as an amorphous solid using the procedures described in Example 1. Rotational isomers were seen in the NMR. $^1$H NMR (CDCl$_3$, 300 MHz) 62.09 and 2.32 (2 triplets, J=2 Hz, 1H), 2.80–3.10 (m, 3H), 2.90 and 2.99 (2 singlets, 3H), 3.35–3.50 (m, 2H), 3.52–3.62 (m, 1H), 3.78 (s, 3H), 4.03 (d, J=13 Hz, 3H), 4.00–4.30 (m, 3H), 5.93 (s, 2H), 6.72 (2 doublets, J=8 Hz, 1H), 6.80–6.90 (m, 3H), 7.02 and 7.11(2 doublets, J 2 Hz, 1H), 7.30 (2 doublets, J9 Hz, 2H).

EXAMPLE 42 trans,trans-2-(4-Methoxyphenyl)-4-(1,3-benzodioxol-5-yl)-1-(N-methyl-N-(n-hexyl) aminocarbonylmethyl)-pyrrolidine-3-carboxylic Acid The title compound was prepared as an amorphous solid using the procedures described in Example 1. $^1$H NMR (CDCl$_3$, 300 MHz) δ 0.85 (2 triplets, J=7 Hz, 3H), 1.00–1.50 (m, 8H), 2.72–2.82(2 doublets, J=13 Hz, 1H), 2.81 and 2.86 (2 singlets, 3H), 2.92–3.20 (m, 3H), 3.22–3.45 (m, 3H), 3.52–3.62 (m, 1H), 3.72 (2 doublets, 1H), 3.7 5 and 3.76 (2 singlets 3H), 5.94 (2 singlets, 2H), 6.72 (d, J=8 Hz, 1H), 6.80–6.87 (m, 3H), 7.03 (2 doublets, J=2 Hz, 1H), 7.30 (d, J=9 Hz, 1H).

EXAMPLE 43 trans,trans-2-(4-Methoxyphenyl)-4-(1,3-benzodioxol-5-yl)-1-(N,N-di(n-butyl) aminocarbonylmethyl)-pyrrolidine-3-carboxylic Acid The title compound was prepared using the procedures described in Example 1. m.p. 123–125° C. $_1$H NMR (CDCl$_3$, 300 MHz) δ 0.79 (t, J=7 Hz, 3H), 0.85 (t, J=7 Hz, 3H), 1.00–1.50 (m, 8H), 2.74 (d, J=13 Hz, 1H), 2.90–3.09 (m, 4H), 3.23–3.50 (m, 3H), 3.38 (d, J=13 Hz, 1H), 3.52–3.62 (m, 1H), 3.75 (d, J=10 Hz, 1H), 3.78 (s, 3H), 5.93 (dd, J=2 Hz, 4 Hz), 6.71 (d, J=8 Hz, 1H), 6.81–6.89 (m, 3H), 7.03 (d, J=2 Hz, 1H), 7.30 (d, J=9 Hz, 2H). MS (DCl/NH$_3$) m/e 511 (M+H)$^+$. Anal calcd for C$_{29}$H$_{38}$N$_2$O$_6$: C, 68.21; H, 7.50; N, 5.49. Found: C, 68.07; H, 7.47; N, 5.40.

EXAMPLE 44 trans,trans-2-(4-Methoxyphenyl)-4-(1,3-benzodioxol-5-yl)-1-(N,N-diethylaminocarbonylmethyl)-pyrrolidine-3-carboxylic Acid The title compound was prepared using the procedures described in Example 1. m.p. 132–134° C. $^1$H NMR (CDCl$_3$, 300 MHz) δ 0.98 (t, J=7 Hz, 3H), 1.06 (t, J=7 Hz, 3H), 2.78 (d, J=113 Hz, 1H), 2.95–3.20 (m, 4H), 3.30–3.50 (m, 4H), 3.55–3.65 (m, 1H), 3.76 (d, J=12 Hz, 1H), 3.79 (s, 3H), 5.93 (s, 2H), 6.72 (d, J=8 Hz, 1H), 6.80–6.90 (m, 3H), 7.02 (d, J=2 Hz, 1H), 7.32 (d, J=9 Hz, 2H).

EXAMPLE 45 trans,trans-2-(4-Methoxyphenyl)-4-(1,3-benzodioxol-5-yl)-1-(N-methyl-N-Phenylaminocarbonylmethyl)-pyrrolidine-3-carboxylic Acid The title compound was prepared as an amorphous solid using the procedures described in Example 1. $^1$H NMR (CD$_3$OD, 300 MHz) δ 2.75–2.85 (m, 2H), 3.05–3.13 (m, 1H), 3.18 (s, 3H), 3.40–3.58 (m, 2H), 3.78 (s, 3H), 3.88 (d, J=12 Hz, 1H), 5.92 (s, 2H), 6.72 (d, J=8 Hz, 1H), 6.75–6.85 (m, 3H), 7.00–7.12 (m, 5H), 7.82–7.92 (m, 3H).

EXAMPLE 46 trans,trans-2-(4-Methoxyphenyl)-4-(1,3-benzodioxol-5-yl)-1-(N-methyl-N-cyclohexylaminocarbonylmethyl)-pyrrolidine-3-carboxylic Acid The title compound was prepared as an amorphous solid using the procedures described in Example 1. Rotational isomers were seen in the NMR. $^1$H NMR (CD$_3$OD, 300 MHz) δ 1.00–1.85 (m, 10H), 2.72 and 2.78 (2 singlets, 3H), 2.75–2.82 (2 doublets, J=12 Hz, 1H), 2.96–3.22 (m, 3H), 3.40–3.65 (m, 3H), 3.68 and 3.82 (2 doublets, J=10 Hz, 1H), 3.77 and 3.78 (2 singlets, 3H), 5.92 (s, 2H), 6.72 (2 doublets, J=8 Hz, 1H), 6.82–6.88 (m, 3H), 7.02 (2 doublets, J=2 Hz, 1H), 7.30–7.40 2 doublets, J=9 Hz, 2H).

EXAMPLE 47 trans,trans-2-(4-Methoxyphenyl)-4-(1,3-benzodioxol-5-yl)-1-(N,N-di(n-propyl) aminocarbonylmethyl)-pyrrolidine-3-carboxylic Acid The title compound was propared using the procdures described Example 1. m.p. 170–172° C. $^1$H NMR (CDCl$_3$, 300 MHz) δ 0.69 (t, J=7 Hz, 3H), 0.85 (t, J=7 Hz, 3H), 1.20–1.55 (m, 4H), 2.72 (d, J=13 Hz, 1), 2.90–3.10 (m, 4H), 3.25–3.47 (m, 4), 3.35–3.62 (m, 1), 3.72 (d, J=9 Hz, 1H), 3.79 (s, 3H), 5.94 (s, 2H), 6.72 (d, d, J=8 Hz, 1H), 6.80–6.90 (m, 3H), 7.02 (d, J=2 Hz, 1H), 7.30 (d, J=9 Hz, 2H).

EXAMPLE 48 trans,trans-2-(4-Methoxyphenyl)-4-(1,3-benzodioxol-5-yl)-1-(N-methyl-N-isobutylaminocarbonylmethyl)-pyrrolidine-3-carboxylic Acid The title compound was prepared as an amorphous solid using the procedures described in Example 1. Rotational isomers were seen in the NMR. $^1$H NMR (CD$_3$OD, 300 MHz) δ 0.65–0.85 (4 doublets, J=7 Hz, 6H), 1.75–1.95 (m, 1H), 2.80 and 2.90 singlets, 3H), 2.90–3.10 (m, 4), 3.10–3.65 (m, 4H), 3.74 9S, 3H), 3.81 and 3.88 (2 doublets, J=10 Hz, 1H), 5.93 (s, 2H), 6.72 (d, J=8 Hz, 1H), 6.80–6.90 (m, 3H), 7.02 (2 doublets, J=2 Hz, 1H), 7.80–7.90 (2 doublets, J=9 Hz, 2H).

EXAMPLE 49

Alternate Prepration of

Ethyl 2-(4-methoxybenzoyl)-4-nitromethyl-3-(1,3-benzodioxole-5-yl)butyrate

EXAMPLE 49A

E-2-(3,4-Methylenedioxyphenyl)-1-nitroethene

To a stirred solution of piperonal (75 g, 500 mmol) in methanol (120 mL) at 10° C. was added nitromethane (27.1 mL, 500 mmol, 1 eq)followed by the dropwise addition of sodium hydroxide (21 g, 525 mmol, 1 eq) in sufficient water to achieve a total volume of 50 mL while maintaining the temperature between 10–15° C. The reaction mixture became cloudy, turning to a thick paste. The mixture was stirred for 30 minutes upon complention of the addition, and the mixture was then diluted with ice-water (~350 mL) maintaining the temperature below 5° C. until solution was achieved. The resultant solution was poured in a narrow stream (such that it just failed to break into drops (into a rapidly stirred solution of 36% hydrochoric acid (100 mL) in water (150 mL). A yellow solid preciptated (nitrostyrene), and this was collected by filtration, washed with water (1.5 L) until the filrate was neutral. The filter cake was air dried and then recrystallized from hot ethanol (3 L) to yield E-2-(3,4-methylenedioxy)-nitrostyrene as yellow needles (53 g, 55%). $^1$H NMR (300 MHz, CDCl$_3$) δ 7.94 (1H, d, J=13.5 Hz), 7.47 (1H, d, J=13.5 Hz), 7.09 (1H, dd, J=7.5 & 2 Hz), 7.01 (1H, d, J=2 Hz), 6.87 (1H, d, J=7.5 Hz), 6.06 (2H, s). MS (DCl/NH$_3$) m/e 194 (M+H)$^+$, 211 (M+H+NH$_3$)$^+$.

EXAMPLE 49B

Ethyl 2-(4-methoxyphenyl)oxo-4-nitro-3-(3,4-methylenedioxyphenyl)butyrate

To a stirred solution of the nitrostyrene resulting from Example 49A (14.17 g, 73.34 mmol, 1.2 eq) in a mixture of propan-2-ol (75 mL) and tetrahydrofuran (175 mL) at room temperature was added successively a solution of ethyl (4-methoxybenzoyl)acetate (11.5 g, 51.7 mmol) in THF (50 mL) followed by 1,8-diazabicyclo[5,4,0]undec-7-ene (DBU) (0.45 mL, 3.0 mmol, 0.05 eq). The resultant mixture was stirred at room temperature for 1 hour, then additional DBU (0.45 mL, 3.0 mmol, 0.05 eq) was added. The mixture was stirred a further 1 hour, then the volatiles were removed in vacuo and the residue purified by flash chromatography on 500 g silica gel, eluting with 20% ethyl acetate-hexanes changing to 25% ethyl acetate-hexanes as the product eluted. The solvents were removed in vacuo to yield the nitroketoester (19.36 g, 76%) as a viscous oil. Diastereomers were seen in the NMR. $^1$H NMR (300 MHz, CDCl$_3$) δ 8.06 (2H, d, J=9 Hz), 7.89 (2H, d, J=9 Hz), 6.96 (2H, d, J=9 Hz), 6.91 (2H, d, J=9 Hz), 6.77 (1H, dd, J=9 Hz, 3 Hz), 6.73 (1H, d, J=9 Hz), 6.65 (1H, d, J=3 Hz), 5.95 (2H, s), 5.89 (1H, d, J=4 Hz), 5.88 (1H, d, J=4 Hz), 4.90–4.60 (3H, m), 4.39 (1H, m), 4.18 (2H, q, J=7 Hz), 3.94 (2H, m), 3.80 (3H, s), 3.78 (3H, s), 1.19 (3H, t, J=7 Hz), 0.99 (3H, t, J=7 Hz), MS (DCl/NH$_3$) m/e 416 (M+H)$^+$, 433 (M+H+NH$_3$)$^+$.

EXAMPLE 50 trans,trans-2-(4-Methoxyphenyl)-4-(1,3-benzodioxol-5-yl)-1-(t-butyloxycarbonylmethyl)-pyrrolidine-3-carboxylic Acid To a stirred solution of the compound resulting from Example 1C (100 mg, 0.27 mmol) in acetonitrile (2 mL) was added successively diisopropylethylamine (70 μL, 0.40 mmol, 1.5 eq) and t-butyl bromoacetate (48 μL, 0.29 mmol, 1.1 eq). The mixture was stirred 2 hours, then the solvent was removed in vacuo to yield the crude diester. To a stirred solution of the diester in ethanol (1 mL) at room temperature was added 50% w/w sodium hydroxide (300 mg, 3.75 mmol) in water. The mixture was stirred 2 hours, then the volatiles were removed in vacuo. The residue was dissolved in water (5 mL), and the solution was washed with ether. The aqueous phase was acidified with acetic acid (300 EL), and then extracted with ethyl acetate (2×). The combined organic extracts were dried (Na$_2$SO$_4$), filtered, and concentrated to yield the title compound (74 mg, 60%) as a white solid. $^1$H NMR (300 MHz, CDCl$_3$) δ 7.36 (2H, d, J=8 Hz), 7.13 (1H, d, J=3 Hz), 6.90 (1H, dt, J=3 Hz, 8 Hz), 6.88 (2H, d, J=8 Hz), 6.76 (1H, d, J=8 Hz), 5.96 (2H, s), 3.96 (1H, J=9 Hz), 3.81 (3H, s), 3.58 (1H, ddd, J=12, 10 Hz, 3 Hz), 3.52 (1H, dd, J=9 Hz, 3 Hz), 3.32 (1H, d, J=17 Hz), 3.08 (1H, t, J=10 Hz), 2.92 (1H, dd, J=9 Hz, 7 Hz), 2.83 (1H, d, J=17 Hz). MS (DCl/NH$_3$) m/e 456 (M+H)$^+$. Anal calcd for C$_{29}$H$_{29}$NO$_7$.0.3 H$_2$O: C, 65.07; H, 6.48; N, 3.04. Found: C, 65.02; H 6.42; N, 2.93.

EXAMPLE 51 trans,trans-2-(4-Methoxyphenyl)-4-(1-naphthyl)-1-(N-methyl-N-propyl)aminocarbonylmethyl)-pyrrolidine-3-carboxylic Acid The title compound was prepared by the procedures described in Examples 1 and 49 substituting naphthalene-1-carboxaldehyde for piperonyl in Example 49A. Rotational isomers are seen in the NMR. $^1$H NMR (300 MHz, CDCl$_3$) 68.29 (1H, bd, J=8 Hz), 7.86 (2H, d, J=8 Hz),7.75 (1H, d, J=8 Hz), 7.49 (3H, m), 7.34 (2H, dd, J=3 Hz, 9 Hz), 6.83 (2H, dd, J=9 Hz, 2 Hz), 4.50 (1H, m), 3.94 (1H, dd, J=9 Hz, 2 Hz,), 3.78 (3H, s), 3.65 (1H, m), 3.49 (1H, d, J=14 Hz), 3.40–2.93 (5H, m), 2.91, 2.83 (3, s), 1.48 (2H, sept, J=7 Hz), 0.83, 0.77 (3H, t, J=7 Hz). MS (DCl/NH$_3$) m/e 461 (M+H)$^+$. Anal calcd for C$_{29}$H$_{29}$NO$_7$.0.5 HOAc: C, 71.00; H, 6.99; N, 5.71. Found: C, 70.95; H, 7.00; N, 5.46.

EXAMPLE 52 trans,trans-2-(4-Methoxyphenyl)-4-(2,3-dihydrobenzofuran-5-yl)-1-(N-methyl-N-propyl)aminocarbonylmethyl)-pyrrolidine-3-carboxylic Acid

EXAMPLE 52A 2,3-Dihydrobenzofuran-5-carboxaldehyde

To a stirred solution of α,α-dichloromethyl methyl ether (2.15 g, 19 mmol, 1.35 eq) in methylene chloride (30 mL) at −40° C. was added successively stannic chloride (1.65 g, 17 mmol, 1.2 eq) and 15 minutes later, a solution of 2,3-dihydrobenzofuran (1.68 g, 14 mmol) in CH$_2$Cl$_2$ (5 mL) maintaining the temperature at or below −35° C. The mixture was warmed to 0° C., stirred 1 hour, then poured into ice-water, and stirred a further 30 minutes. The mixture was diluted with ether, and the phases separated. The organic phase was concentrated in vacuo, and the residue purified by vacuum distillation to yield the title compound (1.25 g, 60%) as a colorless liquid. b.p. 119–121° C. at 0.3 mm Hg.

EXAMPLE 52B trans,trans-2-(4-Methoxyphenyl)-4-(2,3-dihydrobenzofuran-5-yl)-1-(N-methyl-N-propyl)aminocarbonylmethyl)-pyrrolidine-3-carboxylic Acid The title compound was prepared by the procedures described in Examples 1 and 49 substituting the compound resulting from Example 52A for piperonal in Example 49A. Rotational isomers are seen in the NMR. $^1$H NMR (300 MHz, CDCl$_3$) δ 7.33 (1H, d, J=8 Hz), 7.28 (1H, m), 7.19 (1H, m), 6.87 (1H, d, J=8 Hz), 6.73 (1H, d, J=8 Hz), 4.56 (1H, t, J=8 Hz), 3.83 (1H, d, J=10 Hz), 3.80 (3H, s), 3.63 (1H, m), 3.4–3.0 (9H, m), 2.87, 2.84 (3H, s), 1.51 (2H, septet, J=7 Hz), 0.88, 0.78 (3H, t, J=7 Hz). MS (DCl/NH$_3$) m/e 453 (M+H)$^+$. Anal calcd for C$_{26}$H$_{32}$N$_2$O$_5$.0.25 H$_2$O: C, 68.33; H, 7.17; N, 6.13. Found: C, 68.60; H, 6.88; N, 5.80.

EXAMPLE 53 trans,trans-2,4-Bis(4-methoxyphenyl)-1-(N-methyl-N-propyl)aminocarbonylmethyl)-pyrrolidine-3-carboxylic Acid The title compound was prepared by the procedures described in Examples 1 and 49 substituting 4-methoxybenzaldehyde for piperonal in Example 49A. Rotational isomers are seen in the NMR. $^1$H NMR (300 MHz, CDCl$_3$) δ 7.37 (2H, d, J=7.5 Hz), 7.32 (2H, d, J=7.5 Hz), 6.86 (4H, m), 3.83 (1H, m), 3.81 (3H, s), 3.79 (3H, s), 3.64 (1H, m), 3.48–2.97 (6H, m), 2.87, 2.83 (3H, s), 2.85 (1H, m), 1.45 (2H, m), 0.84, 0.74 (3H, t, J=7.5 Hz). MS (DCl/NH$_3$) m/e 441 (M+H)$^+$. Anal calcd for C$_{25}$H$_{32}$N$_2$O$_5$.0.5 H$_2$O: C, 66.80; H, 7.40; N, 6.23. Found: C, 67.15; H, 7.32; N, 6.00.

EXAMPLE 54 trans,trans-2-(4-Methoxyphenyl)-4-(3,4-dimethoxyphenyl)-1-(N-methyl-N-propyl) aminocarbonylmethyl)-pyrrolidine-3-carboxylic Acid The title compound was prepared by the procedures described in Examples 1 and 49 substituting 3,4-dimethoxybenzaldehyde for piperonal in Example 49A. Rotational isomers are seen in the NMR. $^1$H NMR (300 MHz, CDCl$_3$) δ 7.33 (2H, d, J=7.5 Hz), 7.07 (1H, d, J=2.0 Hz), 6.98 (1H, m), 6.85 (1H, d, 7.5 Hz), 6.82 (2H, d, 7.5 Hz), 3.91 (3H, s), 3.86 (3H, s), 3.83 (1H, m), 3.79 (3H, s), 3.64 (1H, m), 3.50–2.95 (6H, m), 2.87 (1H, m), 2.85, 2.83 (3H, s), 1.45 (2H, m), 0.84, 0.74 (3H, t, J=7.5 Hz), MS (DCl/NH$_3$) m/e 471 (M+H)$^+$. Anal calcd for C$_{26}$H$_{34}$N$_2$O$_6$.0.5 H$_2$O: C, 65.12; H, 7.36; N, 5.84. Found: C, 65.22; H, 7.27; N, 5.59.

EXAMPLE 55 trans,trans-2-(4-Methoxyphenyl)-4-(3-methoxyphenyl)-1-(N-methyl-N-propyl) aminocarbonylmethyl)-pyrrolidine-3-carboxylic Acid The title compound was prepared by the procedures described in Examples 1 and 49 substituting 3-methoxybenzaldehyde for piperonal in Example 49A. Rotational isomers are seen in the NMR. $^1$H NMR (300 MHz, CDCl$_3$) δ 7.33 (2H, d, J=7.5 Hz), 7.24 (1H, t, J=7.5 Hz), 7.05 (2H, m), 6.85 (2H, dd, J=7.5&2 Hz), 6.76 (1H, m), 3.83 (1H, m), 3.81 (3H, s), 3.79 (3H, s), 3.64 (1H, m), 3.48–2.97 (6H, m), 2.87, 2.83 (3H, s), 2.85 (1H, m), 1.45 (2H, m), 0.84, 0.74 (3H, t, J=7.5 Hz). MS (DCl/NH$_3$) m/e 441 (M+H)$^+$. Anal calcd for C$_{25}$H$_{32}$N$_2$O$_5$.0.5 H$_2$O: C, 66.80; H, 7.40; N, 6.23. Found: C, 66.76; H, 7.36; N, 6.05.

EXAMPLE 56 trans,trans-2-(4-Methoxyphenyl)-4-(2-naphthyl)-1-(N-methyl-N-propyl)aminocarbonylmethyl)-pyrrolidine-3-carboxylic Acid The title compound was prepared by the procedures described in Examples 1 and 49 substituting naphthylene-2-carboxaldehyde for piperonal in Example 49A. Rotational isomers are seen in the NMR. $^1$H NMR (300 MHz, CDCl$_3$) δ 7.82 (4H, m), 7.69 (1H, m), 7.47 (2H, m), 7.37 (2H, dd, J=7.5&2 Hz), 6.85 (2H, dd, J=7.5&2 Hz), 3.90 (1H, d, J=8 Hz), 3.78 (3H, s), 3.57 (1H, m), 3.52–2.97 (6H, m), 2.93, 2.85 (3H, s), 2.90 (1H, m), 1.52 (2H, m), 0.86, 0.76 (3H, t, J=7.5 Hz). MS (DCl/NH$_3$) m/e 461 (M+H)$^+$. Anal calcd for C$_{28}$H$_{32}$N$_2$O$_4$.0.5 H$_2$O: C, 71.62; H, 7.08; N, 5.97. Found: C, 71.58; H, 7.11; N, 6.01.

EXAMPLE 57 trans,trans-2-(4-Methoxyphenyl)-4-(1,3-benzodioxol-5-yl)-1-(2-(ethylsulfinyl)ethyl)-pyrrolidine-3-carboxylic Acid To the compound resulting from Example 1C (100 mg, 0.27 mmol) and 2-chloroethyl ethyl sulfide (67.5 mg, 0.5 mmol, 2 equivalents) dissolved in 6 mL of acetonitrile was added 10 mg of Kl and 0.5 mL of diisopropylethylamine. The mixture was refluxed for 4 hours and then concentrated in vacuo. The residue obtained was purified by flash chromatography on silica gel eluting with 4:1 hexane-ethyl acetate to afford 93 mg (75%) of the ethylthioethyl compound.

To the sulfide (90 mg, 0.2 mmol) dissolved in 5 mL of CH$_2$Cl$_2$ in an ice bath was added 68 mg of 3-chloroperoxybenzoic acid. The mixture was stirred for 40 minutes in the ice bath and for 3 hours at room temperature. A 10% solution of sodium hydroxide (2 mL) was added, and the mixture was extracted with EtOAc (2×50 mL). The combined organic extracts were washed with water and brine, dried over sodium sulfate and concentrated in vacuo. The residue obtained was chromatographed on silica gel eluting with EtOAc and 10% MeOH in CH$_2$Cl$_2$ to afford the sulfoxide (62 mg, 65%).

The ethyl ester was hydrolyzed by the procedure described in Example 1D to afford the title compound as a diastereomeric mixture. m.p. 61–63° C. MS (DCl/NH$_3$) m/e 446 (M+H)$^+$. $^1$H NMR (CDCl$_3$, 300 MHz) δ 1.25, 1.32 (t, J=9 Hz, 3H), 2.45–2.75 (m, 4H), 2.84–2.96 (m, 3H), 3.02–3.08 (m, 1H), 3.32, 3.36 (d, J=3 Hz, 1H), 3.47–3.58 (m, 2H), 3.65, 3.68 (d, J=7.5 Hz, 1H), 3.76, 3.80 (s, 3H), 5.94 (s, 2H), 6.72 (d, J=7.5 Hz, 1H), 3.84–3.89 (m, 3H), 7.02 (d, J=6 Hz, 1H), 7.30, 7.34 (d, J=7.5 Hz, 2H).

EXAMPLE 58 trans,trans-2-(4-Methoxyphenyl)-4-(1,3-benzodioxol-5-yl)-1-(2-(isopropylsulfonylamino) ethyl)-pyrrolidine-3-carboxylic Acid To 2-bromoethylamine hydrobromide (1 mmol) suspended in anhydrous CH$_3$CN was added 1 equivalent of Et$_3$N. The mixture was stirred for 30 minutes and then 1 equivalent of isopropyl sulfonyl chloride and 1 equivalent of Et$_3$N were added. The resulting mixture was stirred for 2 hours at room temperature and then added to a solution of the compound resulting from Example 1C (185 mg, 0.5 mmol) in 3 mL of CH$_3$CN. The mixture was warmed at 50–60° C. for 2 hours, cooled to room temperature, treated with water and extracted with EtOAc. The combined organic extracts were washed with water and brine, dried and concentrated in vacuo. The residue obtained was chromatographed on silica gel eluting with 3:2 hexane-EtOAc to give 195 mg (75%) of the ethyl ester. The ethyl ester (160 mg, 0.31 mmol) was hydrolyzed by the procedure described in Example 1D to afford the title compound (133 mg, 88%). m.p. 94–96° C. $^1$H NMR (CD$_3$OD, 300 MHz) δ 1.26 (d, J=6 Hz, 6H), 1.97 (s, 1H), 2.38 (m, 1H), 2.77 (m, 1H), 2.88 (t, J=9 Hz, 1H), 3.04 (m, 1H), 3.14 (t, J=7.5 Hz, 2H), 3.35 (m, 2H), 3.46 (m, 1H), 3.58 (m, 1H), 3.78 (s, 3H), 5.92 (s, 2H), 6.74 (d, J=9 Hz, 1H), 6.86 (dd, J=9 Hz, 3 Hz, 1H), 6.92 (d, J=9 Hz, 2H), 7.00 (d, J=3 Hz, 1H), 7.36 (d, J=9 Hz, 2H). MS (DCl/NH$_3$) m/e (M+H)$^+$.

EXAMPLE 59 trans,trans-2-(4-Methoxyphenyl)-4-(1,3-benzodioxol-5-yl)-1-(2-(isobutoxy)ethyl)-pyrrolidine-3-carboxylic Acid The title compound was prepared by the procedures described in Example 1D from the compound resulting from Example 1C and 2-(isobutoxy)ethyl bromide. m.p. 68–70° C. $^1$H NMR (CDCl$_3$, 300 MHz) δ 0.88 (d, J=6 Hz, 6H), 1.82

(quintet, J=6 Hz, 1H), 2.22 (m, 2H), 2.72–2.79 (m, 1H), 2.86–2.95 (m, 2H), 3.13 (d, J=6 Hz, 2H), 3.45–3.56 (m, 4H), 3.68 (d, J=9 Hz, 1H), 3.79 (s, 3H), 5.94 (s, 2H), 6.72 (d, J=7.5 Hz, 1H), 6.85 (dd, J=9 Hz, 7.5 Hz, 3H), 7.08 (s,1H), 7.34 (d, J=9 Hz, 2H). MS (DCl/NH$_3$) m/e 442 (M+H)$^+$.

EXAMPLE 60 trans,trans-2-(4-Methoxyphenyl)-4-(1,3-benzodioxol-5-yl)-1-(butylsulfonyl)-pyrrolidine-3-carboxylic Acid To 100 mg (0.271 mmol) of the compound resulting from Example 1C dissolved in 10 mL of THF was added 1-butanesulfonyl chloride (46.7 mg, 1.1 equivalents) and diisopropylethylamine (53 mg, 1.5 equivalents). The resulting mixture was stirred for 2.5 hours at room temperature and then the solvent evaporated. The crude product was purified by flash chromatography on silica gel eluting with 3:2 hexane-EtOAc to afford 120 mg (90%) of the ethyl ester.

The ester (120 mg, 0.244 mmol) was dissolved in 1 mL of EtOH, and a solution of 100 mg of NaOH in 1 mL of water was added. The mixture was stirred for 3 hours at room temperature and then concentrated under reduced pressure. Water (5 mL) was added and the solution was washed with ether to remove any unhydrolyzed trans-cis isomer. The aqueous solution was acidified to pH~6 with acetic acid and then extracted with EtOAc (2×50 mL). The combined organic extracts were washed with brine, dried over sodium sulfate and concentrated under reduced pressure to afford the pure title compound (60 mg, 53%) as a white solid. m.p. 67–69° C. $^1$H NMR (CDCl$_3$, 300 MHz) δ 0.82 (t, J=7.5 Hz, 3H), 1.20–1.33 (m, 2H), 1.58–1.68 (m, 2H), 2.48–2.69 (m, 2H), 3.28 (dd, J=9 Hz, 1H), 3.49 (t, J=12 Hz, 1H), 3.65 (dd, J=12 Hz, 1H), 3.82 (s, 3H), 4.32 (dd, J=12 Hz, 1H), 5.17 (d, J=9 Hz, 2H), 5.95 (s, 2H), 6.70–6.78 (m, 3H), 6.92 (d, J=9 Hz, 2H), 7.35 (d, J=9 Hz, 2H). MS (DCl/NH$_3$) m/e 462 (M+H)$^+$.

EXAMPLE 61 trans,trans-2-(4-Methoxyphenyl)-4-(1, 3-benzodioxol-5-yl)-1-(2-(N-methyl-N-isopropylcarbonylamino)ethyl)-pyrrolidine-3-carboxylic Acid

EXAMPLE 61A trans,trans-2-(4-Methoxyphenyl)-4-(1,3-benzodioxol-5-yl)-1-(2-bromoethyl)-pyrrolidine-3-carboxylic Acid Ethyl Ester To the mixture of cis,trans and trans,trans pyrrolidines resulting from Example 1C (400 mg) dissolved in 9 mL of 1,2-dibromoethane was added 0.7 mL of diisopropylethylamine and 30 mg of sodium iodide. The resultant mixture was heated at 100° C. for 1 hour, and then the solvents were removed in vacuo. The residue was taken up in EtOAc and washed sequentially with water and brine, dried and concentrated under reduced pressure. The crude product was purified by flash chromatography on silica gel eluting with 4:1 hexane-EtOAc to give 470 mg of the title product.

EXAMPLE 61B trans,trans-2-(4-Methoxyphenyl)-4-(1,3-benzodioxol-5-yl)-1-(2-(methylamino)ethyl)-pyrrolidine-3-carboxylic Acid ethyl ester To the compound resulting from Example 61A (450 mg) dissolved in 10 mL of EtOH was added 0.5 mL of 40% aqueous methylamine and 50 mg of sodium iodide. The mixture was heated at 80° C. for 1 hour, and then the solvents were removed in vacuo. The residue was taken up in EtOAc and washed sequentially with water and brine, dried and concentrated in vacuo. The resultant product was carried on without further purification.

EXAMPLE 61C trans,trans-2-(4-Methoxyphenyl)-4-(1,3-benzodioxol-5-yl)-1-(2-(N-methyl-N-isobutyrylamino)ethyl)-pyrrolidine-3-carboxylic Acid To the compound resulting from Example 61B (~150 mg) dissolved in 5 mL of 1,2-dichloroethane was added 0.3 mL of diisopropylethylamine. The solution was cooled to −40° C., isobutyryl chloride (0.17 mL) was added, the bath was removed, and the solution was allowed to warm to ambient temperature and stirred for 15 hours. The solvent was removed in vacuo; the residue was taken up in EtOAc and washed sequentially with 1:1 sodium bicarbonate solution/ water and brine, dried and concentrated in vacuo. The product was purified by flash chromatography on silica gel eluting with a gradient 1:1 EtOAc-hexanes going to EtOAc and finally using 10% MeOH-EtOAc.

The ester was dissolved in 1.5 mL of EtOH; 0.75 mL of a 17% aqueous NaOH solution was added, and the resultant mixture was stirred at ambient temperature for 3 hours. The solvents were removed in vacuo; the residue was taken up in water and washed with ether. The aqueous phase was acidified with 1 N H$_3$PO$_4$ to pH 3 and extracted twice with ether. The combined organic extracts were washed with brine and dried over Na$_2$SO$_4$. The solvents were removed in vacuo to provide 82 mg of the title compound as a white foam. Rotamers were seen in the NMR. $^1$H NMR (CDCl$_3$, 300 MHz) δ of the major rotamer δ 1.06 (d, 3H, J=10 Hz), 1.12 (d, 3H, J=10 Hz), 2.15 (m, 1H), 2.5–3.0 (m, 3H), 2.91 (s, 3H), 3.32 (m, 2H), 3.50 (m, 2H), 3.65 (m, 2H), 3.77 (s, 3H), 5.92 (s, 2H), 6.73 (d, 1H, J=8 Hz), 6.75–6.9 (m, 4H), 6.96 (d, 1H, J=2 Hz), 7.29 (m, 1H). MS (DCl/NH$_3$) m/z 469 (M+H)$^+$. Analysis calcd for C$_{26}$H$_{32}$N$_2$O$_6$.0.3 TFA: C, 63.55; H, 6.48; N, 5.57. Found: C, 63.44; H, 6.71; N, 5.24.

EXAMPLE 62 trans,trans-2-(4-Methoxyphenyl)-4-(1,3-benzodioxol-5-yl)-1-(2-(N-methyl-N-propionylamino)ethyl)-pyrrolidine-3-carboxylic Acid The title compound was prepared by the procedures described in Example 61 substituting propionyl chloride for isobutyryl chloride in Example 61C. $^1$H NMR (CDCl$_3$, 300 MHz) of the major rotamer δ 1.13 (t, 3H, J=8 Hz), 2.19 (m, 1H), 2.30 (m, 2H), 2.65–3.0 (m, 3H), 2.85 (s, 3H), 3.25–3.4 (m, 2H), 3.5–3.7 (m, 3H), 3.79 (s, 3H), 5.92 (s, 2H), 6.74 (d, 1H, J=8 Hz), 6.75–6.9 (m, 4H), 7.00 (bd s, 1H), 7.29 (bd s, 1H). MS (DCl/NH$_3$) m/z 455 (M+H)$^+$. Analysis calcd for C$_{25}$H$_{30}$N$_2$O$_6$.1.0 H$_2$O: C, 63.55; H, 6.83; N, 5.93. Found: C, 63.55; H, 6.52; N, 5.73.

EXAMPLE 63 trans,trans-2-(4-Methoxyphenyl)-4-(1,3-benzodioxol-5-yl)-1-(N-methyl-N-benzylaminocarbonylmethyl)-pyrrolidine-3-carboxylic Acid Using the procedures described in Example 1 the title compound was prepared. $^1$H NMR (CDCl$_3$, 300 MHz) of the major rotamer δ 2.79 (s, 3H), 2.8–3.2 (m, 2H), 3.48 (m, 2H), 3.61 (m, 2H), 3.77 (s, 3H), 3.78 (m, 1H), 4.3–4.5 (m, 2H), 5.95 (d, 2H, J=2 Hz), 6.7–6.9 (m, 4H), 7.00 (m, 1H), 7.15–7.35 (m, 7H). MS (FAB/NBA) m/z 503 (M+H)$^+$. Anal calcd for $C_{29}H_{30}N_2O_6 \cdot 0.5\ H_2O$: C, 68.36; H,5.74; N, 5.50. Found: C,68.41; H, 5.74; N, 5.36.

EXAMPLE 64 trans,trans-2-(4-Methoxyphenyl)-4-(1,3-benzodioxol-5-yl)-1-(N-ethyl-N-butylaminocarbonylmethyl)-pyrrolidine-3-carboxylic Acid Using the procedures described in Example 1 the title compound was prepared. $^1$H NMR (CDCl$_3$, 300 MHz) of the major rotamer δ 0.88 (t, 3H, J=7 Hz), 1.06 (t, 3H, J=7 Hz), 1.27 (m, 2H), 1.45 (m, 2H), 2.8–3.6 (m, 11 H), 3.79 (s, 3H), 3.80 (m, 1H), 5.92 (bd s, 2H), 6.75 (d, 1H, J=8 Hz), 6.85 (d, 1H, J=8 Hz), 6.92 (d, 2H, J=8 Hz), 7.03 (s, 1H), 7.33 (d, 1H, J=8 Hz). MS (DCl/NH$_3$) m/z 483 (M+H)$^+$. Anal calcd for $C_{27}H_{34}N_2O_6 \cdot 0.5$ HOAc: C, 65.61; H,7.08; N, 5.46. Found: C,65.51; H, 6.70; N, 5.66.

EXAMPLE 65 trans,trans-2-(4-Methoxyphenyl)-4-(1,3-benzodioxol-5-yl)-1-(N-methyl-N-(2,2-dimethylpropyl)aminocarbonylmethyl)-pyrrolidine-3-carboxylic Acid Using the procedures described in Example 1 the title compound was prepared. $^1$H NMR (CDCl$_3$, 300 MHz) of the major rotamer6 0.90 (s, 9H), 2.8–3.1 (m, 4H), 2.94 (s, 3H), 3.3–3.5 (m, 3H), 3.61 (m, 1H), 3.80 (s, 3H), 3.82 (m, 1H), 5.94 (bd s, 2H), 6.74 (d, 1H, J=8 Hz), 6.86 (d, 2H, J=8 Hz), 6.87 (m, 1H), 7.03 (d, 1H, J=2 Hz), 7.33 (d, 2H, J=8 Hz). MS (DCl/NH$_3$) m/z 483 (M+H)$^+$.

EXAMPLE 66 trans,trans-2-(4-Methoxyphenyl)-4-(1,3-benzodioxol-5-yl)-1-(2-(N-methyl-N-butylsulfonylamino)ethyl)-pyrrolidine-3-carboxylic Acid To the compound resulting from Example 61B (60 mg, 0.13 mmol) dissolved in 5 mL of CH$_3$CN was added 0.2 mL of Et$_3$N and 22 mg (0.143 mmol, 1.1 equivalents) of 1-butanesulfonyl chloride. The mixture was stirred for 1 hour at room temperature and then concentrated in vacuo. The crude product was purified by column chromatography on silica gel eluting with 1:1 EtOAc-hexane to yield 64 mg (90%) of the ester. Ester hydrolysis by the procedure described in Example 1D afforded the title compound. m.p. 64–66° C. $^1$H NMR (CDCl$_3$, 300 MHz) δ 0.92 (t, J=7.5 Hz, 3H), 1.39 (hexad, J=7.5 Hz, 2H), 1.68–1.76 (m, 2H), 2.16–2.25 (m, 1H), 2.27 (s, 3H), 2.75–2.92 (m, 5H), 3.12–3.20 (m, 1H), 3.25–3.34 (m, 1H), 3.46–3.5 (m, 2H), 3.65 (d, J=9 Hz, 1H), 3.78 (s, 3H), 5.53 (s, 2H), 6.72 (d, J=7.5 Hz, 1H), 6.82 (dd, J=7.5 Hz, 3 Hz, 1H), 6.86 (d, J=9 Hz, 2H), 7.02 (d, J=3 Hz, 1H), 7.34 (d, J=9 Hz, 2H). MS (DCl/NH$_3$) m/e 519 (M+H)$^+$.

EXAMPLE 67 trans,trans-2-(4-Methoxyphenyl)-4-(1,3-benzodioxol-5-yl)-1-(2-(N-methyl-N-propylsulfonylamino)ethyl)-pyrrolidine-3-carboxylic Acid The title compound was prepared by the procedures described in Example 66 substituting 1-propanesulfonyl chloride for 1-butanesulfonyl chloride. m.p. 69–70° C. $^1$H NMR (CDCl$_3$, 300 MHz) δ 1.02 (t, J=7.5 Hz, 3H), 1.78 (hexad, J=7.5 Hz, 2H), 2.18–2.26 (m, 1H), 2.72 (s, 3H), 2.75–2.95 (m, 6H), 3.13–3.22 (m, 1H), 3.25–3.35 (m, 1H), 3.47–3.58 (m, 2H), 3.66 (d, J=9 Hz, 1H), 3.80 (s, 3H), 5.96 (s, 2H), 6.74 (d, J=7.5 Hz, 1H), 6.84 (d,d, J=7.5 Hz, 3 Hz, 1H), 6.87 (d, J=9 Hz, 2H), 7.04 (d, J=3 Hz, 1H), 7.43 (d, J=9 Hz, 2H). MS (DCl/NH$_3$) m/e 505 (M+H)$^+$.

EXAMPLE 68 trans,trans-2-(4-Methoxyphenyl)-4-(1,3-benzodioxol-5-yl)-1-(2-(propylsulfonyl)ethyl)-pyrrolidine-3-carboxylic Acid To 1-propanethiol (3.5 g, 46.05 mmol) dissolved in 10 mL of anhydrous THF was added 632 mg (26.32 mmol) of NaH in portions under a nitrogen atmosphere. The mixture was heated at 60–70° C. for 1 hours. To this mixture was added the compound resulting from Example 61A (180 mg, 0.38 mmol) in 2 mL THF. Heating was continued at 60–70° C. for an additional 2 hours, and then the volatiles were removed under reduced pressure. The crude propylthioethyl adduct was purified by flash chromatography on silica gel eluting with 3:2 hexane-EtOAc to give 170 mg (95%).

To a solution of 170 mg (0.36 mmol) of the sulfide and 93 mg (0.8 mmol) of N-methylmorpholine N-oxide (NMO) in a mixture of 20 mL of acetone and 5 mL of H$_2$O was added a solution of osmium tetroxide (10 mg) in 0.3 mL of t-butanol. The resulting mixture was stirred overnight at room temperature and then concentrated under reduced pressure. The residue was partitioned between EtOAc and H$_2$O. The organic phase was washed with brine, dried over Na$_2$SO$_4$ and concentrated in vacuo. Flash chromatography afforded 177 mg (98%) of the ethyl ester which was hydrolyzed by the procedures described in Example 1D to afford the title compound. m.p. 73–75° C. $^1$H NMR (CDCl$_3$, 300 MHz) δ 1.04 (t, J=7.5 Hz, 3H), 1.78 (hexad, J=7.5 Hz, 2H), 2.59–2.66 (m, 1H), 2.84–3.08 (m, 7H), 3.43 (dd, J=9 Hz, 1H), 3.53–3.60 (m, 1H), 3.68 (d, J=9 Hz, 1H), 3.82 (s, 3H), 5.96 (s, 2H), 6.75 (d, J=7.5 Hz, 1H), 6.82 (dd, J=7.5 Hz, 3 Hz, 1H), 6.88 (d, J=9 Hz, 2H), 6.99 (d, J=3 Hz, 1H), 7.32 (d, J=9 Hz, 2H). MS (DCl/NH$_3$) m/e 476 (M+H)$^+$.

EXAMPLE 69 trans,trans-2-(4-Methoxyphenyl)-4-(1,3-benzodioxol-5-yl)-1—N-(trans-5-methylhex-2-enyl)-pyrrolidine-3-carboxylic Acid

EXAMPLE 69A trans-5-Methylhex-2-enoic Acid Ethyl Ester

Oil dispersion sodium hydride (0.85 g) was washed with hexanes and suspended in THF (20 mL), and the mixture was cooled in an ice bath to 0° C. Diisopropyl (ethoxycarbonylmethyl) phosphonate (5.0 mL) was added slowly and the mixture stirred for 20 minutes at 0° C. Isovaleraldehyde (2.0 mL) in THF (5 mL) was added dropwise over five minutes. The ice bath was removed and the mixture stirred for 18 hours at ambient temperature. Saturated ammonium chloride solution (50 mL) was added and the mixture extracted with diethyl ether (3×50 mL). The ether extracts were combined, dried with Na$_2$SO$_4$, and evaporated to give a colorless oil which was purified by flash chromatography on silica gel eluting with hexanes. The title compound was isolated as a colorless oil (2.1 g).

EXAMPLE 69B trans-5-Methylhex-2-en-1-ol

The compound resulting from Example 69A (2.0 g) was dissolved in toluene and cooled to 0° C. in an ice bath.

Diisobutylaluminum hydride (1.5 N in toluene, 20 mL) was added dropwise and the solution stirred at 0° C. for two hours. Citric acid solution (25 mL) was added very slowly to the cooled solution. The resulting mixture was stirred for 18 hours at ambient temperature. Diethyl ether (50 mL) was added, the solids removed by filtration and washed with additional ether (2×25 mL). The filtrate was extracted with ether (2×25 mL). The ether extractions and washings were combined, dried, and evaporated to give a colorless oil which was purified by flash chromatography on silica gel eluting with 25% EtOAc-hexanes. The title compound was isolated as a colorless oil (1.25 g).

EXAMPLE 69C trans-1-Bromo-5-methylhex-2-ene

The compound resulting from Example 69B (1.0 g) was dissolved in diethyl ether and cooled to 0° C. in an ice bath. Phosphorus tribromide (2.5 g, 0.87 mL) was added dropwise and the solution stirred at 0° C. for two hours. The solution was poured onto ice, the layers separated, and the aqueous layer extracted with additional ether (3×25 mL). The ether layers were combined, dried, and evaporated to give a colorless oil which was used without further purification (0.95 g).

EXAMPLE 69D trans,trans-2-(4-Methoxyphenyl)-4-(1,3-benzodioxol-5-yl)-1—N-(trans-5-methylhex-2-enyl)-pyrrolidine-3-carboxylic Acid The title compound was synthesized using the methods detailed in Example 1D but substituting the compound resulting from Example 69C for N-propyl bromoacetamide. $^1$H NMR (CDCl$_3$, 300 MHz) δ 0.84 (d, 6H, J=8 Hz), 1.57 (heptet, 1H, J=8 Hz), 1.87 (t, 2H, J=6 Hz), 2.60 (dd, 1H, J=8 Hz, 14 Hz), 2.86 (t, 1H, J=10 Hz), 2.96 (dd, 1H, J=8 Hz, 10 Hz), 3.20 (dd, 1H, J=5 Hz, 14 Hz), 3.29 (dd, 1H, J=3 Hz, 10 Hz), 3.50 (m, 1), 3.70 (d, 1H, J=10 Hz), 3.78 (s, 3H), 5.47 (m, 2H), 5.93 (s, 2H), 6.71 (d, 1H, J=8 Hz), 6.83 (d, 3H, J=9 Hz), 7.05 (s, 1H), 7.32 (d, 2H, J=9 Hz). MS (DCl/NH$_3$) m/e 438 (M+H)$^+$. Anal calcd for C$_{26}$H$_{31}$NO$_5$: C, 71.37; H, 7.14; N, 3.20. Found: C, 71.16; H, 7.24; N, 3.17.

EXAMPLE 70 trans,trans-2-(4-Methoxyphenyl)-4-(1,3-benzodioxol-5-yl)-1-N-(trans-3,5-dimethylhex-2-enyl)-pyrrolidine-3-carboxylic Acid The title compound was prepared by the procedures described in Example 69 but substituting 4-methyl-2-pentanone for isovaleraldehyde in Example 69A, which gave ~7:1 mixture of trans/cis olefins. The crude product was purified by preparative HPLC (Vydac μC18) eluting with a 10–70% gradient of CH$_3$CN in 0.1% TFA. The desired fractions were lyophilized to give the product (and its diastereomer) as a white solid. $^1$H NMR of the major (trans) isomer: (CDCl$_3$, 300 MHz) δ 0.83 (d, 6H, J=8 Hz), 1.56 (s,3H), 1.74 (m, 1H), 1.92 (d, 2H, J=6 Hz), 3.3–3.5 (m, 3H), 3.6–3.8 (m, 4H), 3.78 (s, 3H), 3.94.0 (m, 1H), 5.22 (m, 1H), 5.90 (d, 2H, J=12 Hz), 6.63 (m, 1H), 6.78 (m, 3H), 6.95 (s, 1H), 7.45 (d, 3H, J=8 Hz). MS (DCl/NH$_3$) m/e 438 (M+H)$^+$. Anal calcd for C$_{27}$H$_{33}$NO$_5$.1.0 TFA: C, 61.59; H, 6.06; N, 2.48. Found: C, 61.36; H, 6.1 0; N, 2.34.

EXAMPLE 71 trans,trans-2-(4-Methoxyphenyl)-4-(1,3-benzodioxol-5-yl)-1-(4-heptylcarbonylmethyl)-pyrrolidine-3-carboxylic Acid

EXAMPLE 71A

1-Chloro-3-propyl-2-hexanone

To 2-propylpentanoic acid (156.6 μl, 1.00 mmol) dissolved in anhydrous dichloromethane (2 mL) was added DMF (3 μL, 4 mole %), and the solution was cooled to 0° C. under a nitrogen atmosphere. To the solution was added oxalyl chloride (94.3 μL, 1.08 mmol) dropwise over a few minutes. The reaction was stirred 18 hours while warming to ambient temperature. The mixture was cooled to 0° C. and excess ~0.3 M ethereal diazomethane solution was added. The reaction mixture was stirred 18 hours while warming to ambient temperature. The reaction mixture was washed with 1 M aqueous sodium carbonate solution (30 mL), dried over anhydrous sodium sulfate, filtered and concentrated under reduced pressure. The residue was dissolved in ether (2 mL) and cooled to 0° C. under a nitrogen atmosphere. Hydrogen chloride as a 4 N solution in dioxane (275 μL, 1.10 mmol) was added dropwise over a few minutes. The reaction was stirred 18 hours while warming to ambient temperature. The reaction mixture was concentrated under reduced pressure and the residual oil was used in the next step without further purification.

EXAMPLE 71B trans,trans-Ethyl 2-(4-methoxyphenyl)-4-(1,3-benzodioxol-5-yl)-1-(4-heptylcarbonylmethyl)-pyrrolidine-3-carboxylate To the compound resulting from Example 71A (1.00 mmol, maximum theoretical yield) was added a solution of the trans,trans ethyl carboxylate from Example 1C (295 mg, 0.80 mmol as a 50% solution in toluene), diisopropylethylamine (700 μL, 4.00 mmol) and acetonitrile (4 mL). To the resulting solution was added sodium iodide (12 mg, 10 mole %), and the reaction mixture was stirred 18 hours under a nitrogen atmosphere at ambient temperature. Additional sodium iodide (24 mg, 20 mole %) and acetonitrile (4 mL) were added, and the reaction mixture was heated at 45–50° C. with stirring for 18 hours. The reaction mixture was concentrated under reduced pressure, and the residue was chromatographed on silica gel eluting with 1:9 ethyl acetate-hexane to give 237 mg (46%) of the title compound as a yellow oil.

EXAMPLE 71C trans,trans-2-(4-Methoxyphenyl)-4-(1,3-benzodioxol-5-yl)-1-(4-heptylcarbonylmethyl)-pyrrolidine-3-carboxylic Acid To the compound resulting from Example 71B (231 mg, 0.4532 mmol) dissolved in ethanol (10 mL) was added a solution of lithium hydroxide (38 mg, 0.9065 mmol) in water (2.5 mL). The solution was stirred for 18 hours under a nitrogen atmosphere, additional lithium hydroxide (19 mg, 0.4532 mmol) in water (0.5 mL) was added, and stirring was continued 24 hours. The reaction mixture was concentrated under reduced pressure to remove the ethanol, and the aqueous residue was diluted with water (45 mL) and washed with ether (50 mL). The aqueous layer was neutralized with 1 N hydrochloric acid to cloudiness and then 10% aqueous citric acid was added to adjust the pH to ~5. This solution was then extracted with 10% ethanol in chloroform (4×25 mL). The combined organic extracts were dried over anhydrous sodium sulfate, filtered and concentrated under reduced pressure. The residue was purified by preparative TLC on silica gel eluted with 1:1 ethyl acetate-hexane to give 86 mg (39%) of the title compound as an off white powder. $^1$H NMR (CDCl$_3$, 300 MHz) δ 0.73–0.97 (m, 6H), 1.03–1.33 (m, 6H), 1.36–1.58 (m, 2H), 2.46 (m, 1H), 2.80–2.98 (m, 3H), 3.38–3.64 (m, 3H), 3.75–3.90 (m, 1H), 3.79 (s, 3H), 5.94 (s, 2H), 6.75 (d, 1H), 6.86 (d, 2H), 6.92

(d, 1H), 7.12 (s, 1H), 7.32 (d, 2H). MS (FAB) m/e 482 (M+H)$^+$. Anal calcd for $C_{28}H_{35}NO_6$: C, 69.83; H, 7.32; N, 2.91. Found: C, 69.57; H, 7.41; N, 2.73.

EXAMPLE 72 trans,trans-2-(4-Methoxyphenyl)-4-(1,3-benzodioxol-5-yl)-1-(valeryimethyl)-pyrrolidine-3-carboxylic Acid

EXAMPLE 72A

1-Chloro-2-hexanone

Using the procedure described in Example 71A and substituting pentanoic acid for 2-propylpentanoic acid afforded the title compound as an oil which was used in the next step without further purification.

EXAMPLE 72B trans,trans-Ethyl 2-(4-methoxyphenyl)-4-(1,3-benzodioxole-5-yl)-1-(valerylmethyl)-pyrrolidine-3-carboxylate Substituting the compound resulting from Example 72A for 1-chloro-3-propyl-2-hexanone and using the procedure described in Example 71B, except deleting the first addition of sodium iodide, stirring 18 hours at ambient temperature and purifying by silica gel chromatography eluting with 3:17 ethyl acetate-hexane, the title compound 305 mg (65%) was obtained as a yellow oil.

EXAMPLE 72C trans,trans-2-(4-Methoxyphenyl)-4-(1,3-benzodioxol-5-yl)-1-(valerylmethyl)-pyrrolidine-3-carboxylic Acid By substituting the compound resulting from Example 72B for trans,trans-Ethyl 2-(4-methoxyphenyl)-4-(1,3-benzodioxol-5-yl)-1-(4-heptylcarbonylmethyl)-pyrrolidine-3-carboxylate and using the procedure described in Example 71C, except only one solution of lithium hydroxide (81.5 mg, 1.942 mmol) in water (3.5 mL) was added followed by stirring for 18 hours, the title compound 130 mg (46%) was obtained as an off white powder. $^1$H NMR (CDCl$_3$, 300 MHz) δ 0.87 (t, 3H), 1.26 (m, 2H), 1.49 (m, 2H), 2.37 (m, 2H), 2.79–2.98 (m, 3H), 3.31–3.49 (m, 2H), 3.56 (m, 1H), 3.77, 3.79 (d,s, 4H), 5.94 (s, 2H), 6.75 (d, 1H), 6.81–6.93 (m, 3H), 7.09 (d, 1H), 7.33 (d, 2H). MS (FAB) m/e 440 (M+H)$^+$. Anal. calcd for $C_{25}H_{29}NO_6$: C, 68.32; H, 6.65; N, 3.19. Found: C, 67.95; H, 6.64; N, 3.05.

EXAMPLE 73 trans,trans-2-(4-Methoxyphenyl)-4-(1, 3-benzodioxol-5-yl)-1-(N-(3,4-dimethoxybenzyl)-N-methylaminocarbonylmethyl)pyrrolidine-3-carboxylic Acid

EXAMPLE 73A trans,trans- and cis,trans-2-(4-Methoxyphenyl)-4-(1, 3-benzodioxol-5-yl)-1-((3,4-dimethoxybenzyl) aminocarbonylmethyl)pyrrolidine-3-carboxylic Acid Ethyl Ester Using the procedure of Example 1D, paragraph 1, substituting 3,4-dimethoxybenzyl bromoacetamide for dipropyl bromoacetamide, the desired product mixture was obtained as a white foam in 81% yield.

EXAMPLE 73B trans,trans- and cis,trans-2-(4-Methoxyphenyl)-4-(1, 3-benzodioxol-5-yl)-1-(N-(3,4-dimethoxybenzyl)-N-methylaminocarbonylmethyl)pyrrolidine-3-carboxylic Acid Ethyl ester The resultant product from Example 73A (220 mg, 0.404 mmol) was dissolved in 2 mL dry THF and added dropwise to a stirred, cooled (0° C.) suspension of sodium hydride (23 mg of a 60% by weight mineral oil suspension, 16.5 mg, 0.69 mmol) in 0.2 mL THF, under an argon atmosphere. The resulting mixture was stirred at 0° C. for 1 hour, then methyl iodide (28 μL, 64 mg, 0.45 mmol) was added. The reaction mixture was stirred at 0° C. for 45 minutes. TLC (Et$_2$O) indicated incomplete reaction. An additional portion of methyl iodide (28 μL, 64 mg, 0.45 mmol) and dry 1,3-dimethyl-3,4,5,6-tetrahydro-2(1H)pyrimidinone (50 μL, 0.41 mmol) were added. The reaction mixture was stirred at ambient temperature for 2 days. The reaction was poured into 25 mL of 0.5 M aqueous citric acid and extracted with 2×25 mL EtOAc. The combined organic extracts were washed sequentially with 30 mL water and 30 mL brine, then dried (Na$_2$SO$_4$), filtered and concentrated under reduced pressure to produce 270 mg of crude material. Flash chromatography on silica gel eluting with Et$_2$O gave the title compounds as an inseparable mixture in 43% yield. $^1$H NMR (CDCl$_3$, 300 MHz) δ 2.79 (s) and 2.81 (s), for the N-CH$_3$ signals. MS m/z 591 (M+H)$^+$.

EXAMPLE 73C trans,trans-2-(4-Methoxyphenyl)-4-(1,3-benzodioxol-5-yl)-1-(N-(3,4-dimethoxybenzyl)-N-methylaminocarbonylmethyl)pyrrolidine-3-carboxylic Acid To the resultant compound from Example 73B (98 mg, 0.17 mmol) dissolved in 1 mL EtOH and cooled to 0° C. was added a solution of lithium hydroxide monohydroxide (17 mg, 0.41 mmol) in 0.5 mL H$_2$O. The resulting solution was stirred under a nitrogen atmosphere for 16 hours. The solution was concentrated in vacuo, and the residue was partitioned between 15 mL H$_2$0 and 15 mL Et$_2$O. The aqueous phase was extracted with 5 mL Et$_2$O, then the aqueous phase was acidified with 10% aqueous citric acid. The acidic aqueous phase was saturated with NaCl and extracted with 3×15 mL EtOAc. The EtOAc extracts were combined, dried (Na$_2$SO$_4$), then filtered and concentrated in vacuo to give 40 mg (42%) of the title compound as a white foam. $^1$H NMR (CD$_3$OD, 300 MHz, two rotameric forms) δ 2.85 (s, 3H), 2.94–3.25 (br m, 3H), 3.35–3.70 (br m) and 3.64 (s, 4H total), 3.70–3.97 (br m), 3.74 (s), 3.76 (s), 3.78 (s), 3.79 (s), 3.81 (s), and 4.03 (br d, J=14 Hz, 8H total), 4.43 (AB, 1H), 5.91 (s) and 5.93 (s, 2H total), 6.50–6.60 (m, 1H), 6.67–7.02 (br m, 6H), 7.29 (br d) and 7.35 (br d, 2H total). HRMS calcd for $C_{31}H_{35}N_2O_8$ (M+H)$^+$: 563.2393. Found: 563.2385.

EXAMPLE 74 trans,trans-2-(4-Methoxyphenyl)-4-(1,3-benzodioxol-5-yl)-1-(N-(3,4-dimethoxybenzyl) aminocarbonylmethyl)pyrrolidine-3-carboxylic Acid The procedure of Example 73C was used, with the substitution of the resultant compound from Example 73A for the resultant compound from Example 73B, to provide the title compound. $^{1}$H NMR (CD$_{3}$OD, 300 MHz) δ 2.85 (d, J=16 Hz, 1H), 2.92 (br t, J=9 Hz, 1H), 2.98 (br t, J=10 Hz, 1H), 3.32–3.39 (br m, 2H), 3.54–6.95 (m, 7H), 1H), 3.67 (s, 3H), 3.78 (s, 3H), 3.80 (s, 3H), 3.85 (d, J=10 Hz, 1H), 4.21 (d, J=15 Hz, 1H), 4.41 (d, J=15 Hz, 1H), 5.91 (s, 2H), 6.67 (d, J=8 Hz, 1H), 6.75–6.95 (m, 7H), 7.33–7.40 (m, 2H). HRMS calcd for C$_{30}$H$_{32}$N$_{2}$O$_{8}$ (M+H$^{+}$: 549.2237. Found: 549.2224.

EXAMPLE 75

(2R,3R,4R)-2-(4-Methoxyphenyl)-4-(1,3-benzodioxol-5-yl)-1-((1R)-1-(N,N-dipropylaminocarbonyl)-1-butyl)pyrrolidine-3-carboxylic Acid

EXAMPLE 75A trans,trans-2-(4-Methoxyphenyl)-4-(1,3-benzodioxol-5-yl)-1-((1R)-1-(benzyloxycarbonyl) butyl)pyrrolidine-3-carboxylic Acid Ethyl Ester The procedure of Fung, et. al., J. Med. Chem., 35(10): 1722–34 (1992) was 35 adapted. The resultant compound from Example 6A (103 mg, 0.279 mmol) was dissolved in 0.7 mL of nitromethane and 0.7 mL of H$_{2}$O, and ammonium carbonate (34 mg, 0.35 mmol) and (2S)-benzyl 2-bromopentanoate (78 mg, 0.30 mmol) were added. The reaction was refluxed for 24 hours. The reaction was partitioned between 15 mL of 1 M aqueous Na$_{2}$CO$_{3}$ and 25 mL of CH$_{2}$Cl$_{2}$. The aqueous phase as extracted with 2×10 mL CH$_{2}$Cl$_{2}$, and the combined organic phases were ashed with 15 mL brine, dried (Na$_{2}$SO$_{4}$), then filtered and concentrated under reduced pressure to a brown oil (169 mg). The crude product was purified by silica gel chromatography eluting with 3:1 CH$_{2}$Cl$_{2}$-hexane to produce 106 mg (68%) of the title compound as a waxy solid. $^{1}$H NMR indicated the presence of two diastereomeric products.

EXAMPLE 75B trans,trans-2-(4-Methoxyphenyl)-4-(1,3-benzodioxol-5-yl)-1-((1R)-1-(N,N-dipropylaminocarbonyl)-1-butyl)pyrrolidine-3-carboxylic Acid Ethyl Ester The resultant compound from Example 75A (101 mg, 0.180 mmol) and 30 mg of 10% palladium on charcoal were stirred in 2 mL EtOAc under 1 atmosphere of H$_{2}$ for 4 hours. The reaction mixture was filtered through a plug of Celite, using 15 mL MeOH to wash the catalyst. The combined filtrate and wash were concentrated in vacuo to give 81.4 mg (96%) of the crude acid as a white solid.

The above crude acid was combined with HOBt hydrate (41 mg, 0.27 mmol), dipropylamine (26 mg, 0.26 mmol), and 4-methylmorpholine (37 mg, 0.37 mmol) in 2 mL dry DMF. The solution was cooled to −15° C., then 1-ethyl-3-(3-dimethylaminopropyl)carbodiimide hydrochloride (44 mg, 0.23 mmol) was added. The mixture was stirred at −15° C. and allowed to warm slowly to room temperature overnight. The solvent was removed by distillation under reduced pressure, and the residue was partitioned between 20 mL EtOAc and 10 mL of 1 M aqueous Na$_{2}$CO$_{3}$. The organic phase was washed with 10 mL of brine, dried (Na$_{2}$SO$_{4}$), then filtered and concentrated in vacuo. The crude product was purified by flash chromatography on silica gel, eluting with 1:2 Et$_{2}$O-hexane. Further purification of overlap fractions by preparative TLC eluting with 1:2 Et$_{2}$O-hexane yielded 32 mg (34%) of a less polar product, and 44 mg (46%) of a more polar product.

EXAMPLE 75C (2R,3R,4R)-2-(4-Methoxyphenyl)-4-(1,3-benzodioxol-5-yl)-1-((1R-1-(N,N-dipropylaminocarbonyl)-1-butyl)pyrrolidine-3-carboxylic Acid The procedure of Example 73C was followed, with the substitution of the less polar isomer from Example 75B for the resultant product from Example 73B, to provide the title compound in 94% yield. [α]$_{D}$=−52° (c=0.235, CH$_{3}$OH). $^{1}$H NMR (CD$_{3}$OD, 300 MHz) δ 0.55 (t, J=7 Hz, 3H), 0.87 (t, J=7 Hz) and 0.87–0.94 (m, 6H total), 1.03–1.25 (br m, 2H), 1.25–1.68 (br m, 4H), 1.90–2.07 (br m, 1H), 2.75–2.94 (br, m, 2H), 2.94–3.02 (br m, 2H), 3.20–3.40 (m, overlapping with CD$_{2}$HOD signal), 3.40–3.60 (br m, 2H), 3.79 (s, 3H), 4.04 (br d, J=9 Hz, 1H), 5.92 (dd, J=3,5 Hz, 2H), 6.72 (d, J=8 Hz, 1H), 6.79 (dd, J=1.5,8 Hz, 1H), 6.92–6.98 (br m, 3H), 7.29–7.39 (m, 2H). MS m/z 525 (M+H)$^{+}$.

EXAMPLE 76

(2S,3S,4S)-2-(4-Methoxyphenyl)-4-(1,3-benzodioxol-5-yl)-1-((1R)-1-(N,N-dipropylaminocarbonyl)-1-butyl)pyrrolidine-3-carboxylic Acid The procedure of Example 73C was followed, with the substitution of the more polar isomer from Example 75B for the resultant product from Example 73B, to provide the title compound in 88% yield. [α]$_{D}$=+58° (c=0.37, CH$_{3}$OH). $^{1}$H NMR (CD$_{3}$OD, 300 MHz) δ 0.57 (br t, J=7 Hz, 3H), 0.88–0.98 (m, 6H) 1.08–1.35 (br m, 2H), 1.35–1.68 (br m, 4H), 1.75–1.90 (br m, 1H), 2.75–2.86 (br m, 2H), 3.10–3.30 (br m, 2H), 3.51–3.65 (br m, 2 H), 3.69 (s, 3H), 4.03–4.16 (br m, 2H), 5.91 (s, 2H), 6.71–6.83 (m, 2H), 6.86–6.97 (m, 3H), 7.32 (br d, J=9 Hz, 2H). MS m/z 525 (M+H)$^{+}$.

EXAMPLE 77

(2S,3S,4S)-2-(4-Methoxyphenyl)-4-(1,3-benzodioxol-5-yl)-1-((1S)-1-(N,N-dipropylaminocarbonyl)-1-butyl)pyrrolidine-3-carboxylic Acid

EXAMPLE 77A trans,trans-2-(4-Methoxyphenyl)-4-(1,3-benzodioxol-5-yl)-1-((1 S)-1-(N,N-dipropylaminocarbonyl)-1-butyl)pyrrolidine-3-carboxylic Acid Ethyl Ester (2R)-N,N-dipropyl 2-hydroxypentanamide (106 mg, 0.528 mmol, made by standard procedure) was dissolved in 2 mL THF under an argon atmosphere, diisopropylethylamine (75 mg, 0.58 mmol) was added, then the solution was cooled to −20° C. Trifluoromethanesulfonic anhydride (95 μL, 159 mg, 0.565 mmol) was added to the cooled solution over 1 minute, and the reaction mixture was stirred at −20° C. for 1 hour, and at room temperature for an additional 1 hour. The resulting slurry was recooled to 0° C., and a solution of the resultant compound from Example 6A (195 mg, 0.528 mmol) and diisopropylethylamine (101 μL, 75 mg, 0.58 mmol) in 3 mL of CH$_{2}$Cl$_{2}$ was added. The reaction was stirred at 0° C. for 3 hours and for an additional 2 days at room temperature. TLC (Et$_{2}$O-hexane 1:2) indicated starting materials remained, so the mixture was warmed to reflux for 4 hours. The reaction was cooled, then partitioned between 30 mL EtOAc and 15 mL of 1 M aqueous $Na_2CO_3$. The aqueous phase was extracted with 15 mL EtOAc, then the combined organic phases were washed with 20 mL brine, dried ($Na_2SO_4$), filtered and concentrated in vacuo to a yellowish oil. Purification by flash chromatography on silica gel eluting with 1:2 $Et_2O$-hexane gave 19.9 mg (7%) of a less polar product and 20.1 mg (7%) of a more polar product. $^1$H NMR spectra and MS were the same as those of Example 76B.

EXAMPLE 77B (2S,3S,4S)-2-(4-Methoxyphenyl)-4-(1,3-benzodioxol-5-yl)-1-((1 S)-1-(N,N-dipropylaminocarbonyl)-1-butyl)pyrrolidine-3-carboxylic Acid The procedure of Example 73C was followed, with the substitution of the less polar isomer from Example 77A for the resultant product from Example 73B, to provide the title compound in 100% yield. $^1$H NMR ($CD_3OD$, 300 MHz) and MS identical to those of Example 75C.

EXAMPLE 78

(2R,3R,4R)-2-(4-Methoxyphenyl)-4-(1,3-benzodioxol-5-yl)-1-((1 S)-1-(N,N-dipropylaminocarbonyl)-1-butyl)pyrrolidine-3-carboxylic Acid The procedure of Example 73C was followed, with the substitution of the more polar isomer from Example 77A for the resultant product from Example 73B, to provide the title compound in 88% yield. $^1$H NMR ($CD_3OD$, 300 MHz) and MS identical to those of Example 76.

EXAMPLE 79 trans,trans-2-(4-Methoxyphenyl)-4-(1,3-benzodioxol-5-yl)-1-(N,N-di(n-butyl) aminocarbonylmethyl)-3-(5-tetrazolyl)pyrrolidine Carbonyidiimidazole (510 mg, 3.148 mmol) was added to 1.020 g (2.00 mmol) of the compound resulting from Example 43 in 2.7 mL THF, and the mixture was heated for 40 minutes at 50° C. The reaction mixture was cooled in an ice bath, and 25% solution of ammonia in methanol was added. After 30 minutes, the solid which had formed was filtered, washed with ethanol and finally with ether to yield 850 mg (83%) of the 3-carboxamide compound. m.p. 194–196° C.

Phosphorus oxychloride (1.06 g) was added to this amide in 7 mL of pyridine, and the mixture was stirred 1 hour at room temperature. Dichloromethane was added, and the solution was washed with potassium bicarbonate solution, dried over sodium sulfate, and concentrated. The residue was chromatographed on silica gel eluting with 2:1 hexane-ethyl acetate to give 790 mg (96%) of the 3-carbonitrile compound.

To this nitrile in 5 mL toluene was added 385 mg of trimethyl tin chloride and 126 mg sodium azide. The mixture was heated 20 hours at 125° C. (bath temp). After cooling, methanol (5 mL) was added, and the solution was concentrated in vacuo. To the resulting residue was added 6 mL of methanol and 6 mL of water containing 0.2 g phosphoric acid. After stirring 1 hour at room temperature, water was added and the mixture extracted with dichloromethane. The combined organic extracts were dried and concentrated, and the resulting residue was crystallized from ether to give a solid. The solid was dissolved in sodium hydroxide solution, filtered from insoluble material and acidified with acetic acid to get 532 mg (62%) of the title compound. m.p. 165–167° C. $^1$H NMR ($CDCl_3$, 300 MHz) δ 0.85 (t, J=7 Hz, 3H), 0.87 (t, J=7 Hz, 3H), 1.10–1.50 (m, 8H), 3.0–3.6 (m, 8H), 3.70 (s, 3H), 3.7–3.8 (m, 1H), 3.90 (t, J=9 Hz, 1H), 4.37 (d, J=9 Hz, 1H), 5.86 (s, 2H), 6.62 (d, J=8 Hz, 1H), 6.65–6.73 (m, 3H), 6.95 (d, J=2 Hz, 1H), 7.11 (d, J=9 Hz, 2H).

EXAMPLE 80 trans,trans-2-(4-Fluorophenyl)-4-(1,3-benzodioxol-5-yl)-1-(N,N-di(n-butyl)aminocarbonylmethyl) pyrrolidine-3-carboxylic Acid The title compound was prepared as an amorphous solid from methyl (4-flourobenzoyl) acetate and 5-(2-nitrovinyl)-1,3-benzodioxole using the procedures described in Examples 1 and 43. $^1$H NMR ($CDCl_3$, 300 MHz) δ 0.81 (t, J=7 Hz, 3H), 0.90 (t, J=7 Hz, 3H), 1.0–1.55 (m, 8H), 2.81 (d, J=13 Hz, 1H), 2.90–3.10 (m, 4H), 3.15–3.30 (m, 1H), 3.32–3.45 (m, 3H), 3.55–3.65 (m, 1H), 3.86 (d, J=10 Hz, 1H), 5.94 (dd, J=2 Hz, 4 Hz, 2H), 6.72 (d, J=8 Hz, 1H), 6.86 (d, J=8 Hz, 1H), 6.95–7.07 (m, 3H), 7.32–7.45 (m, 2H).

EXAMPLE 81 trans,trans-2-(4-Methoxyphenyl)-4-(1,3-benzodioxol-5-yl)-1-(N,N-di(n-butyl) aminocarbonylmethyl)pyrrolidine-3-carboxylic Acid N,N-Dibutyl glycine (1 50 mg, 0.813 mmol), prepared by the method of Bowman, R. E., J. Chem. Soc. 1346 (1950), in 0.7 mL of THF was treated with 138 mg (0.852 mmol) carbonyidlimidazole and heated for 30 minutes at 50° C. After cooling to room temperature, 250 mg (0.678 mmol) of ethyl trans,trans-2-(4-methoxyphenyl)-4-(1,3-benzodioxol-5-yl)-pyrrolidine-3-carboxylate, the compound resulting from Example 6A, was added, and the mixture was heated at 45° C. for 30 minutes. The product was chromatographed on silica gel, eluting with 1:1 hexane-ethyl acetate to give 306 mg of the intermediate ethyl ester.

The ester was hydrolyzed with sodium hydroxide in water and ethanol to give 265 mg of the title compound as a white powder. $^1$H NMR ($CDCl_3$, 300 MHz) δ rotational isomers –0.75 and 0.85 (2 t, J=7 Hz, 3H), 1.05–1.5 (m, 8H), 2.65–3.20 (m, 6H) 3.43–3.70 (m, 3H), 3.72 (s, 3H), 3.87 (d, J=I 5 Hz, 1H), 4.49 (dd, J=12 Hz, 6 Hz) and 5.23 (dd, J=12 Hz, 8 Hz) 2H, 5.90 (dd, J=2 Hz, 4 Hz, 2H), 6.63–6.78 (m, 3H), 6.86 and 7.04 (d, J=9 Hz, 2H), 7.22 (d, J=9 Hz, 2H).

EXAMPLE 82 trans,trans-2-(4-Methoxyphenyl)-4-(1,3-benzodioxol-5-yl)-1-(N-n-butyl)-N-(n-propyl) aminocarbonylmethyl)pyrrolidine-3-carboxylic Acid The title compound was prepared using the procedures described in Example 1. m.p. 160–162° C. $^1$H NMR ($CDCl_3$, 300 MHz) rotational isomers δ 0.69, 0.80, 0.84, 0.87 (four triplets, J=7 Hz, 6H), 1.00–1.52 (m, 6H), 2.63 and 2.66 (two doublets, J=13 Hz, 1H), 2.90–3.10 (m, 4H), 3.23–3.61 (m, 5H), 3.71 and 3.75 (two doublets, J=10 Hz, 1H), 3.78 (s, 3H), 5.92–5.96 (m, 2H), 6.72 (d, J=8 Hz, 1H), 6.83–6.89 (m, 3H), 7.03 (d, J=2 Hz, 1H), 7.81 (d, J=9 Hz, 2H).

EXAMPLE 83 trans,trans-2-(4-Methoxyphenyl)-4-(1,3-benzodioxol-5-yl)-1-[2-(N,N-di(n-propyl) aminocarbonyl)ethyl]pyrrolidine-3-carboxylic Acid The compound resulting from Example 6A (250 mg, 0.677 mmol), 205 mg (1,36 mmol) diallyl acrylamide (Polysciences, Inc.), and 10 mg acetic acid were heated at 85° C. in 0.75 mL of methoxyethanol for one hour. Toluene was added, and the solution was washed with bicarbonate solution, dried, and concentrated. Chromatography on silica gel eluting with 3:1 hexane-ethyl acetate gave 283 mg (80%) of the diallyl compound.

The diallyl compound was hydrogenated using 10% Pd/C catalyst (27 mg) in ethyl acetate (25 mL) under a hydrogen atmosphere. The catalyst was removed by filtration, and the filtrate was concentrated to afford the dipropyl amide ethyl ester in 100% yield.

The ester was hydrolyzed to the title compound by the method of Example 1D in 83% yield. $^1$H NMR (CDCl$_3$, 300 MHz) δ 0.82 and 0.83 (two triplets, J=7 Hz, 6H), 1.39–1.54 (m, 4H), 2.35–2.60 (m, 3H), 2.80–3.07 (m, 5H), 3.14–3.21 (m, 2H), 3.31–3.38 (m, 1H), 3.51–3.61 (m, 1H), 3.73 (d, J=12H, 1H), 3.75 (s, 3H), 5.94 (s, 2H), 6.71 (d, J=9 Hz, 1H), 6.79–6.85 (m, 3H), 7.04 (d, J=2 Hz, 1H)<7.32 (d, J=9 Hz, 2H).

EXAMPLE 84 trans,trans-2-(4-Methoxyphenyl)-4-(1,3-benzodioxol-5-yl)-1-(N,N-di(n-butyl)aminocarbonyl)pyrrolidine-3-carboxylic Acid The title compound was prepared by the procedures described in Example 8 using dibutyl carbamoyl chloride, prepared by the method of Hoshino et al., Syn. Comm., 17: 1887–1892 (1987), as a starting material. $^1$H NMR (CDCl$_3$, 300 MHz) δ 0.86 (t, J=7 Hz, 6H), 1.14–1.28 (m, 4H), 1.35–1.48 (m, 4H), 2.81–2.94 (m, 2H), 3.11 (t, J=12 Hz, 1H), 3.30–3.41 (m, 2H), 3.59–3.68 (m, 2H), 3.76 (s, 3H), 3.78–3.85 (m, 1H), 5.81 (d, J=9 Hz, $_1$ H), 5.94 (s, 2H), 6.73–6.86 (m, 5H), 7.24 (d, J=9 Hz, 2H).

EXAMPLE 85 trans,trans-2-(4-Methoxyphenyl)-4-(1,3-benzodioxol-5-yl)-1-(N,N-di(n-butyl)aminocarbonylmethyl)pyrrolidine-3-carboxylic Acid sodium salt Sodium hydroxide (48.2 mg of 98.3% pure, 1.184 mmol) in 2 mL of MeOH was added to the compound resulting from Example 43 (610 mg, 1.196 mmol.) in 5 mL MeOH. The solution was concentrated to dryness, and the resulting powder was stirred with heptane. The heptane was removed in vacuo to give a powder which was dried in the vacuum oven for 2 hours at 60° C. to yield 627.5 mg of the title compound.

EXAMPLE 86 trans,trans-2-(4-Methoxyphenyl)-4-(1,3-benzodioxol-5-yl)-1-[2-(N,N-di(n-butyl)amino)ethyl]pyrrolidine-3-carboxylic Acid A solution of the bromoethyl compound resulting from Example 61A (150 mg), dibutylamine (150 mg) and sodium iodide (18 mg) in 0.75 mL ethanol was heated at 80° C. for 1 hour. After cooling, toluene was added, and the solution was washed with potassium bicarbonate solution, dried over Na$_2$SO$_4$ and concentrated. More toluene was added, and the solution was again concentrated to get rid of excess dibutylamine. The residue was dissolved in warm heptane and filtered from a small amount of insoluble material. The hepane was removed in vacuo to give 143 mg (87%) of the intermediate ethyl ester.

The ester was hydrolyzed by the method of Example 1D to give the title compound as a white powder. $^1$H NMR (CD$_3$OD, 300 MHz) δ 0.89 (t, J=7 Hz, 6H), 1.16–1.30 (m, 4H), 1.44–1.56 (m, 4H), 2.48–2.57 (m, 1H), 2.80–3.08 (m, 8H), 3.14–3.25 (m, 1H), 3.31–3.38 (m, 1H), 3.59–3.60 (m, 1H), 3.74 (s, 3H), 3.75 (d, J=10 Hz, 1H), 5.89 (s, 2H), 6.71 (d, J=9 Hz, 1H), 6.81 (dd, J=9 Hz, 2 Hz, 1H), 6.90 (d, J=10 Hz, 2H), 6.96 (d, J=2 Hz, 1H), 7.37 (d, J=10 Hz, 2H).

EXAMPLE 87 trans,trans-2-(4-Methoxyphenyl)-4-(1,3-benzodioxol-5-yl)-1-{2-[N-(N,N-di(n-butyl)aminocarbonyl)-N-methylamino]ethyl}pyrrolidine-3-carboxylic Acid Dibutyl carbamoyl chloride (135 mg) was added to the compound resulting from Example 61B (250 mg) and 150 mg triethylamine in 1 mL dichloromethane. After stirring 1 hour at room temperature, toluene was added, and the solution was washed with potassium bicarbonate solution, dried over Na$_2$SO$_4$ and concentrated. The residue was chromatographed on silica gel, eluting with a mixture of 38% EtOAc and 62% hexane to give 194 mg of the ethyl ester intermediate.

The ester was hydrolyzed by the method of Example 1D to afford 141 mg of the title compound. $^1$H NMR (CD$_3$OD, 300 MHz) δ 0.92 (t, J=7 Hz, 6H), 1.21–1.32 (m, 4H), 1.42–1.53 (m, 4H), 2.62 (s, 3H), 2.65–2.76 (m, 1H), 3.00–3.20 (m, 8H), 3.44–3.55 (m, 1H), 3.62–3.78 (m, 2H), 3.80 (s, 3H), 4.07 (d, J=12 Hz, 1H), 5.93 (s, 2H), 6.75 (d, J=9 Hz, 1H), 6.87 (dd, J=9 Hz, 2 Hz, 1H), 6.94 (d, J=10 Hz, 2H), 7.04 (d, J=2 Hz, 1H), 7.40 (d, J=10 Hz, 2H).

EXAMPLE 88 trans,trans-2-(4-Methoxyphenyl)-4-(1,3-benzodioxol-5-yl)-1-(N,N-di(n-butyl)aminocarbonylmethyl)pyrrolidine-3-(N-methanesulfonyl)carboxamide Carbonyldiimidazole (75 mg, 0.463 mmol) was added to 150 mg (0.294 mmol) of the compound resulting from Example 43 in 0.4 mL of tetrahydrofuran, and the solution was stirred at 60° C. for 2 hours. After cooling, 50 mg (0.526 mmol) of methanesulfonamide and 68 mg (0.447 mmol) of DBU in 0.3 mL of THF were added. The mixture was stirred at 45° C. for 2 hours. The solvents were removed in vacuo, and the residue was dissolved in water. A few drops of acetic acid were added, and the solution was lyophilized to give 121 mg (70%) of the title compound. m.p. 170–173° C. $^1$H NMR (CDCl$_3$, 300 MHz) δ 0.82 (t, J=7 Hz, 3H), 0.88 (t, J=7 Hz, 3H), 1.05–1.51 (m, 8H), 2.75–2.86 (m, 2H), 2.83–3.25 (m, 4H), 3.17 (s, 3H), 3.32–3.50 (m, 3H), 3.70–3.78 (m, 1H), 3.80 (s, 3H), 3.87 (d, J=10 Hz, 1H), 5.96 (dd, J=2 Hz, 4 Hz, 2H), 6.74 (d, J=9 Hz, 1H), 6.84 (dd, J=9 Hz, 2 Hz, 1H), 6.90 (d, J=10 Hz, 2H), 7.01 (d, J=2 Hz, 1H), 7.34 (d, J=10 Hz, 2H).

EXAMPLE 89 trans,trans-2-(4-Methoxyphenyl)-4-(1,3-benzodioxol-5-yl)-1-(N,N-di(n-butyl)aminocarbonylmethyl)pyrrolidine-3-(N-benzenesulfonyl)carboxamide The compound resulting from Example 43 was converted to the title compound by the method of Example 88 substituting benzenesulfonamide for methanesulfonamide. m.p. 169–171° C. for a sample recrystallized from acetonitrile. $^1$H NMR (CDCl$_3$, 300 MHz) δ 0.81(t, J=7 Hz, 3H), 0.89 (t, J=7 Hz, 3H), 1.02–1.50 (m, 8H), 2.65–2.80 (m, 2H), 2.90–3.25 (m, 4H), 3.80–3.95 (m, 3H), 3.50–3.60 (m 1H), 3.65 (d, J=10 Hz, 1H), 3.81 (s, 3H), 5.94 (s, 2H), 6.70 (s, 2H), 6.81–6.90 (m, 3H), 7.17 (d, J=10 Hz, 2H), 7.55 (t, J=7 Hz, 2H), 7.66 (t, J=7 Hz, 1H), 8.95 (d, J=7 Hz, 2H).

EXAMPLE 90 trans,trans-2-(4-Methoxyphenyl)-4-(1,3-benzodioxol-5-yl)-1-[N,N-di(n-butyl)aminosulfonylmethyl]-pyrrolidine-3-carboxylic Acid Chloromethyl sulfenyl chloride, prepared by the method of Brintzinger et. al., Chem. Ber. 85: 455–457 (1952), is reacted with dibutylamine by the method of E. Vilsmaier described in Liebigs Ann. Chem. 1055–1063 (1980) to give N,N-dibutyl chloromethyl sulfenyl chloride. Alternatively dimethyl(methylthio)sulfonium tetraflouroborate is reacted with dibutylamine to give N,N-dibutyl methylsulfenyl chloride which is chlorinated with N-chlorosuccinimide to give chloromethyl sulfenyl chloride by the method of E. Vilsmaier, described in the above reference.

The N,N-dibutyl chloromethyl sulfenyl chloride is reacted with the compound resulting from Example 6A to give ethyl trans,trans-2-(4-Methoxyphenyl)-4-(1,3-benzodioxol-5-yl)-1-[N,N-di(n-butyl)aminosulfenylmethyl]-pyrrolidine-3-carboxylate.

This is oxidized with osmium tetroxide and N-methyl morpholine N-oxide by the method of S. Kaldor and M. Hammond, Tet. Lett. 32: 5043–5045 (1991) to give the title compound after hydrolysis of the ethyl ester.

EXAMPLE 91 trans,trans-2-(4-Methoxyphenyl)-4-(1,3-benzodioxol-5-yl)-1-[(N,N-di(n-butyl)aminocarbonyl-1-(RS)-ethyl]pyrrolidine-3-carboxylic Acid

EXAMPLE 91A (±)-Dibutyl 2-bromopropanamide

2-Bromopropanoic acid (510 mg, 3.33 mmol) and 4-methylmorpholine (0.74 mL, 6.73 mmol) were dissolved in 10 mL of $CH_2Cl_2$, the solution was cooled to 0° C. under a $N_2$ atmosphere, and then treated dropwise with isobutyl chloroformate (0.45 mL, 3.5 mmol). After 10 minutes at 0° C., dibutylamine (0.57 mL, 3.4 mmol) was added. The reaction was stirred at 0° C. for 1 hour and for an additional 16 hours at room temperature. The mixture was partitioned with 25 mL of 1.0 M aqueous $Na_2CO_3$ solution, then the organic phase was washed sequentially with 25 mL of 1 M aqueous $NaHSO_4$ and 25 mL brine, dried ($Na_2SO_4$), filtered, and concentrated under reduced pressure to afford 698 mg (2.64 mmol, 79%) of the crude bromoamide as a colorless oil. $^1$H NMR ($CDCl_3$, 300 MHz) δ 0.93 (t, J=7 Hz) and 0.97 (t, J=7.5 Hz, 6H total), 1.26–1.60 (m, 7H), 1.60–1.78 (m, 1H), 1.82 (d, J=6 Hz, 3H), 3.04–3.27 (m, 2H), 3.42–3.64 (m, 2H), 4.54 (q, J=7H, 1 H). MS ($DCl/NH_3$) m/e 264 and 266 $(M+H)^+$.

EXAMPLE 91B trans,trans- and cis,trans-2-(4-Methoxyphenyl)-4-(1,3-benzodioxol-5-yl)-1-((N,N-di(n-butyl)amino)carbonyl-1-(RS)-ethyl)pyrrolidine-3-carboxylic Acid Ethyl Ester A solution of the resultant mixture of trans,trans and cis,trans compounds from Example 1C (232 mg, 0.628 mmol) and the resultant compound from Example 91A (183 mg, 0.693 mmol) in 2 mL of $CH_3CN$ was treated with diisopropylethylamine (0.22 mL, 1.3 mmol). The solution was stirred at 60–80° C. under a $N_2$ atmosphere for 16 hours. The reaction was concentrated under reduced pressure, then the residue was partitioned between 30 mL Et2O and 10 mL of 1 M aqueous $Na_2CO_3$ solution. The organic phase was washed with 20 mL water and 20 mL brine, dried over $Na_2SO_4$, filtered and concentrated under reduced pressure to afford the crude amino amide as a brown oil (339 mg, 98% crude). The product was obtained by flash chromatography on silica gel eluting with 20% EtOAc-hexane to provide 224 mg (70%) of the title compounds as a mixture of 4 diastereomers. $^1$H NMR ($CDCl_3$, 300 MHz) δ 0.66–1.55 (several m, 19H), 2.63–3.00 (m, 3H), 3.05–3.39 (m, 2H), 3.40–3.76 (m, 4H), 3.78–3.80 (4s, 3H), 3.84–4.25 (m, 2.6H), 4.38 (d, J=10.5 Hz, 0.2H) and 4.58 (d, J=10.5 Hz, 0.2H), 5.90–5.97 (m, 2H), 6.68–6.96 (m, 5H), 7.38–7.43 (m, 2H). MS ($DCl/NH_3$) m/e 553 $(M+H)^+$.

EXAMPLE 91C trans,trans-2-(4-Methoxyphenyl)-4-(1,3-benzodioxol-5-yl)-1-((N,N-dibutylamino)carbonyl-1-(RS)-ethyl)pyrrolidine-3-carboxylic Acid The procedure of Example 73C was used, substituting the resultant compound from Example 91B for the resultant compound from Example 73B to give the title compound in 61% yield. $^1$H NMR ($CD_3OD$, 300 MHz) δ 0.70–1.05 (several m, 8H), 1.14 (d, J=6 Hz, 2H), 1.17–1.55 (m, 6H), 2.79–3.03 (m, 3.5H), 3.20–3.65 (br m, 4.6H plus $CD_2HOD$), 3.70–3.78 (m, 0.4H), 3.79 (s, 3H), 3.98 (d, J=8 Hz, 0.6H), 4.06 (t, J=7.5 Hz, 0.4H), 4.25 (d, J=8 Hz, 0.4H), 5.92 (s) and 5.94 (s, 2H total 6H), 6.73 (d, J=2.5 Hz) and 6.75 (d, J=3 Hz, 1H total), 6.78–6.85 (m, 1H), 6.91–7.00 (m, 3H), 7.30–7.38 (m, 2H). MS ($DCl/NH_3$) m/e 525 $(M+H)^+$. Anal calcd for $C_{30}H_{40}N_2O_6 \cdot 0.5H_2O$ C, 67.52; H, 7.74; N, 5.25. Found: C, 67.63; H, 7.65; N, 5.21.

EXAMPLE 92 trans,trans-2-(Pentyl)-4-(1,3-benzodioxol-5-yl)-1-(N,N-di(n-butyl)aminocarbonylmethyl)pyrrolidine-3-carboxylic Acid

EXAMPLE 92A

Methyl 2-(4-hexenoyl)-4-nitro-3-(1,3-benzodioxole-5-yl)butyrate

A solution of methyl 3-oxo-6-octenoate (502 mg, 2.95 mmol) in 10 mL of isopropanol was added to a solution of 5-(2-nitrovinyl)-1,3-benzodioxole (712 mg, 3.69 mmol) in 10 mL THF, then DBU (22 μL, 0.15 mmol) was added. The resulting reddish solution was stirred at room temperature for 20 minutes. TLC (ethyl acetate-hexane, 1:3) indicated complete consumption of ketoester. The solution was concentrated in vacuo and flash chromatographed on silica gel eluting with 18% ethyl acetate in hexane to produce 879 mg (2.42 mmol, 82%) of the title compound as a mixture of diastereomers in a 1:1 ratio. $^1$H NMR ($CDCl_3$, 300 MHz) 61.55–1.66 (m, 3H), 2.02–2.17 (br m, 1H), 2.20–2.37 (m, 1.5H), 2.49–2.76 (m, 1.5H), 3.57 (s, 1.5H), 3.74 (s, 1.5H), 3.97 (d, J=7.5H, 0.5H) and 4.05 (d, J=8 Hz, 0.5H), 4.10–4.20 (m, 1H), 4.68–4.82 (m, 2H), 5.06–5.52 (m, 2H), 5.95 (2s, 2H), 6.65 (m, 1H), 6.68 (dr s, 1H), 6.75 (d, 7.5 Hz, 1H). MS ($DCl/NH_3$) m/e 381 $(M+NH_4)^+$. Anal calcd for $C_{18}H_{21}NO_7$: C, 59.50; H, 5.82; N, 3.85. Found: C, 59.32; H, 5.71; N, 3.72.

EXAMPLE 92B

Methyl trans,trans-2-(pentyl)-4-(1,3-benzodioxol-5-yl)pyrrolidine-3-carboxylate

The procedures of Example 1B and Example 1C were followed, with the substitution of the resultant compound from Example 92A for the resultant compound from Example 1A, and the substitution of the this resultant compound for the resultant compound from Example 1B, to provide the title compound in crude form as a yellow oil. This crude compound was epimerized under the following conditions. A solution of the crude compound (660 mg, 2.07 mmol) in 3 mL methanol was treated with a solution of sodium methoxide (made by the addition of sodium metal (14 mg, 0.61 mmol) to 1 mL of methanol). The resultant solution was heated at reflux for 18 hours. The reaction was concentrated under reduced pressure, and the residue was partitioned between 25 mL saturated $NaHCO_3$ diluted with 10 mL water and 30 mL of $CH_2Cl_2$. The aqueous phase was extracted (2×30 mL $CH_2Cl_2$), then the combined organic phases were washed with 20 mL brine, dried over $Na_2SO_4$, filtered and the filtrate concentrated under reduced pressure to afford the crude product. Purification by flash chromatography on silica gel eluting with 3.5% methanol in $CH_2Cl_2$ gave 336 mg (57%) the title compound as a yellow oil. $^1H$ NMR ($CDCl_3$, 300 MHz) δ 0.90 (br t, 3H), 1.25–1.70 (br m, 8H), 1.83–2.02 (br s, 2H), 2.58 (dd, J=8,9 Hz, 1H), 2.99 (dd, J=8,14 Hz, 1H), 3.34–3.45 (m, 2H), 3.53 (q, J=9 Hz, 1H), 3.66 (s, 3H), 5.94 (s, 2H), 6.65–6.75 (m, 3H). MS (DCl/$NH_3$) m/e 320 (M+H)$^+$. Anal calcd for $C_{18}H_{25}NO_4$: C, 67.69; H, 7.89; N, 4.39. Found: C, 67.39; H, 7.84; N, 4.37.

EXAMPLE 92C trans,trans-2-(Pentyl)-4-(1,3-benzodioxol-5-yl)-1-(N,N-di(n-butyl)aminocarbonylmethyl)pyrrolidine-3-carboxylic Acid The procedures of Example 1B–1D were used, with the substitution of the resultant compound from Example 92A for the resultant compound from Example 1B, to provide the title compound as a white foam. $^1H$ NMR ($CDCl_3$, 300 MHz) δ 0.87 (br t) and 0.89 (br t, 6H total), 0.97 (t, J=7.5 Hz, 3H), 1.21–1.42 (br m, 10), 1.43–1.78 (br m, 6H), 2.76 (t, J=7 Hz, 1H), 3.02–3.30 (br m, 6H), 3.40–3.60 (m, 3H), 3.73 (d, J=14 Hz, 1H), 5.98 (AB, 2H), 6.70 (d, J=7 Hz, 1H), 6.77 (dd, J=1.5,7 Hz, 1H), 6.89 (d, J=1.5 Hz, 1 H). MS (DCl/$NH_3$) m/e 475 (M+H)$^+$. Anal calcd for $C_{27}H_{42}N_2O_5$·0.5$H_2O$ C, 67.05; H, 8.96; N, 5.79. Found: C, 67.30; H, 8.77; N, 5.68.

EXAMPLE 93 trans,trans-2-(Pentyl)-4-(1,3-benzodioxol-5-yl)-1-[2-(N-propyl-N-propylsulfonylamino)ethyl]pyrrolidine-3-carboxylic Acid

EXAMPLE 93A

Methyl trans,trans-2-(pentyl)-4-(1,3-benzodioxol-5-yl)-1-(2-bromoethyl)pyrrolidine-3-carboxylate The procedure of Example 61A was used, with the substitution of the resultant compound from Example 92B for the resultant compound from Example 1C, to provide the title compound as a yellow oil. $^1H$ NMR ($CDCl_3$, 300 MHz) δ 0.89 (br t, J=7 Hz, 3H), 1.24–1.40 (br m, 6H), 1.60–1.80 (br m, 2H), 2.61–2.75 (m, 2H), 2.76–6.77 (m, 2H), 3.10–3.22 (m, 2H), 3.36–3.47 (m, 2H), 3.68 (s, 3H), 5.92 (s, 2H), 6.69–6.77 (m, 2H), 6.90–6.94 (m, 1 H). MS (DCl/$NH_3$) m/e 426, 428 (M+H)$^+$.

EXAMPLE 93B

Methyl trans,trans-2-(Pentyl)-4-(1,3-benzodioxol-5-yl)-1-[2-(N-propyl-N-propylsulfonylamino)ethyl]pyrrolidine-3-carboxylate A solution of the resultant compound from Example 93A (102 mg, 0.24 mmol) and tetrabutylammonium iodide (6 mg, 16 μmol) in 1 mL EtOH was treated with propylamine (60 μL, 0.73 mmol). The solution was warmed to 80° C. for 4 hours. The reaction was concentrated under reduced pressure, then the residue was dissolved in 35 mL ethyl acetate and extracted with 2×15 mL of 1 M aqueous $Na_2CO_3$. The organic phase was washed with 15 mL brine, then dried over $Na2SO_4$, filtered and concentrated under reduced pressure to provide the crude secondary amine as a yellow oil (94.2 mg). The crude amine was dissolved in 1 mL of $CH_2Cl_2$, diiosopropylethylamine (65 μL, 0.373 mmol) was added, followed by propylsulfonyl chloride (29 μL, 0.26 mmol). The solution was stirred at room temperature for 4 hours. The reaction was quenched with 10% aqueous citric acid (to pH 4), and the mixture was extracted with 2×3 mL $CH_2Cl_2$. The combined organic extracts were washed with 2 mL brine, then dried over $Na_2SO_4$, filtered, concentrated in vacuo. Purification by flash chromatography eluting with 20% ethyl acetate in hexane provided 65.0 mg (53%) of the title compound as a waxy solid. $R_f$=0.17 (20% EtOAc-hexane). MS (DCl/$NH_3$) m/e 511 (M+H)$^+$.

EXAMPLE 93C trans,trans-2-(Pentyl)-4-(1,3-benzodioxol-5-yl)-1-[2-(N-propyl-N-propylsulfonylamino)ethyl]pyrrolidine-3-carboxylic Acid The procedure of Example 71C was followed, with the substitution of the resultant compound from Example 93B for the resultant compound from Example 71B, to provide the title compound as a white foam (47 mg, 80%), $R_f$=0.14 (5% MeOH-$CH_2Cl_2$). $^1H$ NMR ($CDCl_3$, 300 MHz) δ 0.88 (br t, and 0.92 (t, J=7 Hz, 6H total), 1.22–1.52 (br m, 6H), 1.63 (sextet, J=8 Hz, 2H), 1.75–2.10 (br m, 4H), 2.89–2.98 (m, 2H), 3.05 (br t, J=9 Hz, 1H), 3.10–3.30 (m, 3H), 3.30–3.80 (br m, 7H), 5.94 (s, 2H), 6.71 (t, J=8 Hz, 1H), 6.77 (dd, J=1.5,8 Hz, 1H), 6.89 (d, J=1.5 Hz, 1H). MS (DCl/$NH_3$) m/e 497 (M+H)$^+$.

EXAMPLE 94 trans,trans-2-(Propyl)-4-(1,3-benzodioxol-5-yl)-1-(N,N-di(n-butyl)aminocarbonylmethyl)pyrrolidine-3-carboxylic Acid

EXAMPLE 94A

Ethyl 2-(4-butanoyl)-4-nitro-3-(1,3-benzodioxole-5-yl)butyrate

The procedure of Example 92A was followed, with the substitution of ethyl butyryl acetate for methyl 3-oxo-6-octenoate, to provide the title compound as a mixture of trans and cis isomers (47 mg, 80%), $R_f$=0.28 (25% EtOAc-hexane). $^1H$ NMR ($CDCl_3$, 300 MHz) δ 0.74 (t, J=7.5 Hz) and 0.91 (t, J=7.5 Hz, 3H total), 1.08 (t, J=7 Hz) and 1.28 (t, J=7 Hz, 3H total), 1.45 (sextet, J=7 Hz, 1.5H), 1.63 (sextet, J=7 Hz, approx. 1.5H), 2.17 (t, J=7 Hz) and 2.24 (t, J=7 Hz, 0.5H total) 2.40–2.54 (m, 1H), 2.60 (t, J=7.5 Hz) and 2.67 (t, J=7.5 Hz, 0.5H total), 3.93–4.09 (m, 2H), 4.10–4.20 (br m, 1H), 4.23 (q, J=7 Hz, 1H), 4.67–4.85 9m, 2H), 5.94 (s, 2H), 6.62–6.75 (m, 3H). MS (DCl/NH$_3$) m/e 369 (M+NH$_4$)$^+$. Anal calcd for C$_{17}$H$_{21}$NO$_7$: C, 58.11; H, 6.02; N, 3.99. Found: C, 58.21; H, 5.98; N, 3.81.

EXAMPLE 94B

Ethyl trans,trans-2-(Propyl)-4-(1,3-benzodioxol-5-yl)pyrrolidine-3-carboxylate

The procedure of Example 92B was followed, with the substitution of the resultant compound from Example 94A for the resultant compound from Example 92A, to afford the title compound. MS (DCl/NH$_3$) m/e 306 (M+H)$^+$.

EXAMPLE 94C trans,trans-2-(Propyl)-4-(1,3-benzodioxol-5-yl)-1-((N,N-di(n-butyl)aminocarbonylmethyl)-pyrrolidine-3-carboxylic Acid The procedure of Example 92C was followed, with the substitution of the resultant product from Example 94B for the resultant product from Example 92B, to give the title compound. $^1$H NMR (CDCl$_3$, 300 MHz) δ 0.89 (t, J=7.5 Hz), 0.92 (t, J=7.5 Hz), and 0.97 (t, J=7.5H, 9H total), 1.22–1.80 (br m, 12H), 2.83 (t, J=7.5 Hz, 1H), 3.40–3.55 (br m, 2H), 3.55–3.68 (m, 1H), 3.78 (d, J=15 Hz, 1H), 5.92 (q, J=1 Hz, 2H), 6.70 (d, J=8 Hz, 1H), 6.79 (dd, J=1 Hz, 8 Hz, 1H), 6.90 (d, J=1 Hz, H). MS (DCl/NH$_3$) m/e 447 (M+H)$^+$. Anal calcd for C$_{25}$H$_{38}$N$_2$O$_5$.0.5 H$_2$O: C, 65.91; H, 8.63; N, 6.15. Found: C, 65.91; H, 8.68; N, 5.94.

EXAMPLE 95

(2R,3R,4S)-(+)-2-(4-Methoxyphenyl)-4-(1,3-benzodioxol-5-yl)-1-(tert-butyloxycarbonyl-aminocarbonylmethyl)-pyrrolidine-3-carboxylic Acid

EXAMPLE 95A trans,trans-2-(4-Methoxyphenyl)-4-(1,3-benzodioxol-5-yl)-1-([tert-butyloxycarbonylaminocarbonylmethyl]pyrrolidine-3-carboxylic Acid The resulting mixture of 64% trans,trans- and cis,trans-pyrrolidines resulting from Example 1C (3.01 g, 8.15 mmol) was dissolved in 50 mL of methylene chloride. To this was added dropwise a solution of di-tert-butyl dicarbonate (1.96 g, 8.97 mmol) in 20 mL methylene chloride under a nitrogen atmosphere, and the resulting solution was stirred 30 minutes at which point TLC (ethyl acetate:hexane, 1:1) indicated that all of the starting material was consumed. The reaction mixture was concentrated and dried under high vacuum to give 3.94 g of the ethyl ester as a yellow-brown oil. $^1$H NMR (CDCl$_3$, 300 MHz) δ 0.99, 1.07 (br t, br t, J=7 Hz, 3H), 1.11–1.62 (several br m, 9H), 3.05 (br m, 1H), 3.44–3.95 (m, 3H), 3.81 (s, 3H), 4.04 (q, J=7 Hz, 1H), 4.14–4.28 (br m, 1H), 4.89–5.24 (br m, 1H), 5.94 (d, J=3 Hz, 2H), 6.69–6.90 (m, 5H), 7.06–7.20 (m, 2H). MS (DCl/NH$_3$) m/e 470 (M+H)$^+$.

To the ethyl ester dissolved in 170 mL of ethanol was added a solution of lithium hydroxide (1.06 g, 25.17 mmol) in 60 mL of water. The reaction mixture was vigorously stirred for 18 hours under a nitrogen atmosphere. The reaction mixture was concentrated to remove ethanol, diluted with 250 mL of water and extracted three times with 250 mL of ether. The organic phase acidified to slight cloudiness (pH ~7) with 1 N hydrochloric acid, then to pH 4 with 10% citric acid and extracted with 5% ethanol in methylene chloride (3×100 mL). The combined organic layers dried (Na$_2$SO$_4$), filtered, concentrated and dried on high vacuum to give the title compound as a white foam (2.19 g, 60%). $^1$H NMR (CDCl$_3$, 300 MHz) δ 1.16 (v br s, 9H), 3.11 (br m, 1H), 3.50–3.64 (m, 2H), 3.81 (s, 3H), 4.24 (br m, 1H), 4.96 (br m, 1H), 5.94 (s, 2H), 6.71–6.79 (m, 3H), 6.84–6.91 (m, 2H), 7.19 (d, J=9 Hz, 2H). MS (DCl/NH$_3$) m/e 442 (M+H)$^+$.

EXAMPLE 95B (2R,3R,4S)-(+)-2-(4-Methoxyphenyl)-4-(1,3-benzodioxol-5-yl)-1-(tert-butyloxycarbonylaminocarbonylmethyl)-pyrrolidine-3-carboxylic Acid The compound resulting from Example 95A (2.15 g, 4.86 mmol) and (+)-cinchonine (1.43 g, 4.86 mmol) were added to 100 mL of methylene chloride; this suspension was swirled with warming as necessary to get all solids to dissolve. The solution was then concentrated and dried on high vacuum to a white foam. This material was crystallized from a mixture of refluxing chloroform (64 mL) and hexane (360 mL). The resulting crystals were isolated by filtration and recrystallized under the same conditions seven additional times. Each time the resulting crystals and filtrate were monitored by $^1$H NMR and chiral HPLC. The amount of (2S,3S,4R)-(−)-enantiomer decreased first in the crystals and then in the filtrate with the predetermined endpoint achieved when the (2S,3S,4R)-(−)-enantiomer could no longer be detected in the filtrate. The pure (2R,3R,4S)-(+)-enantiomer thus obtained was partitioned between 100 mL of 10% citric acid and 100 mL of ether. The aqueaous layer was further extracted twice with 100 mL of ether. The combined ether layers were washed with brine, dried (Na$_2$SO$_4$), filtered, concentrated and dried on high vacuum to a white powder (550 mg, 55% of theoretical 50% maximum, >99.5 ee). $^1$H NMR (CDCl$_3$, 300 MHz) δ 1.05–1.50 (br m, 9H), 3.12 (br m, 1H), 3.50–3.65 (m, 2H), 3.81 (s, 3H), 4.24 (m, 1H), 4.96 (br m, 1H), 5.95 (s, 2H), 6.70–6.79 (m, 3H). 6.86 (d, J=9 Hz, 2H), 7.19 (d, J=9 Hz, 2H). MS (DCl/NH$_3$) m/e 442 (M+H)$^+$.

EXAMPLE 95C (2R,3R,4S)-(+)-Ethyl 2-(4-methoxyphenyl)-4-(1,3-benzodioxol-5-yl)-pyrrolidine-3-carboxylate The compound resulting from Example 95B (251 mg, 0.568 mmol) was dissolved in 20 mL of a saturated solution of anhydrous HCl(g) in anhydrous ethanol. The resulting solution was heated at 50° C. with stirring for 18 hours at which point all of the precipitated solid had dissolved. The reaction mixture was concentrated to a solid which was partitioned between 0.8 M aqueous sodium carbonate (50 mL) and methylene chloride (50 mL). The aqueous layer was further extracted with methylene chloride (2×50 mL). The combined organic layers were dried (Na$_2$SO$_4$), filtered, concentrated and dried under high vacuum to give the title compound as an almost colorless oil (158 mg, 69%). $^1$H NMR (CDCl$_3$, 300 MHz) δ 1.11 (t, J=7 Hz, 3H), 2.18 (v br s, 1H), 2.93 (t, J=9 Hz, 1H), 3.19,3.22 (dd, J=7 Hz, 1H), 3.50–3.69 (m, 2H), 3.80 (s, 3H), 4.07 (q, J=9 Hz, 1H), 3.19, 3.22 (dd, J=7 Hz, 1H), 3.50–3.69 (m, J=2 Hz, 2H), 6.81–6.92 (m, 3H), 7.34–7.41 (m, 2H). MS (DCl/NH$_3$) m/e 370 (M+H)$^+$.

EXAMPLE 95D (2R, 3R,4S)-(+)-2-(4-Methoxyphenyl)-4-(1,3-benzodioxol-5-yl)-1-(tert-butyloxycarbonyl-aminocarbonylmethyl)-pyrrolidine-3-carboxylic Acid To the resulting compound from Example 95C (131 mg, 0.355 mmol) was added, diisopropylethylamine (137 mg, 185 µL, 1.06 mmol), acetonitrile (2 mL), N,N-di-(n-butyl) bromoacetamide (133 mg, 0.531 mmol), and the mixture was heated at 50° C. for 1.5 hours. The reaction mixture was concentrated to a solid, dried under high vacuum, and purified by chromatography on silica gel eluting with 1:3 ethyl acetate-hexane to give pure ester as a colorless oil. $^1$H NMR (CDCl$_3$, 300 MHz) δ 0.81 (t, J=7 Hz, 3H), 0.88 (t, J=7 Hz, 3H), 1.10 (t, J=7 Hz, 3H), 1.00–1.52 (m, 8H), 2.78 (d, J=14 Hz, 1H), 2.89–3.10 (m, 4H), 3.23–3.61 (m, 5H), 3.71 (d, J=9 Hz, 1H), 3.80 (s, 3H), 4.04 (q, J=7 Hz, 2H), 5.94 (dd, J=1.5 Hz, 2H), 6.74 (d, J=9 Hz, 1H), 6.83–6.90 (m, 3H), 7.03 (d, J=2 Hz, 1H), 7.30 (d, J=9 Hz, 2H). MS (DCl/NH$_3$) m/e 539 (M+H)$^+$.

To the ethyl ester dissolved in 7 mL of ethanol was added a solution of lithium hydroxide (45 mg, 1.06 mmol) in water (2.5 mL). The mixture was stirred for 1 hour at ambient temperature and then warmed slowly to 40° C. over 2.5 hours at which point all of the starting material had been consumed. The reaction mixture was concentrated to remove the ethanol, diluted with 60 mL water and extracted with ether (3×40 mL). The aqueous solution was treated with 1 N aqueous hydrochloric acid until cloudy, and the pH was then adjusted to ~4–5 with 10% aqueous citric acid. This mixture was extracted with 1:19 ethanol-methylene chloride (3×50 mL). The combined extracts were dried (Na$_2$SO$_4$), filtered, concentrated and dried under high vacuum to give the title compound as a white foam (150 mg, 83%). $^1$H NMR (CDCl$_3$, 300 MHz) δ 0.80 (t, J=7 Hz, 3H), 0.88 (t, J=7 Hz, 3H), 1.08 (m, 2H), 1.28 (m, 3H), 1.44 (m, 3H), 2.70–3.77 (svr br m, 12H), 3.79 (s, 3H), 5.95 (m, 2H), 6.75 (d, J=8 Hz, 1H), 6.87 (br d, J=8 Hz, 3H), 7.05 (br s,1H), 7.33 (v br s, 2H). MS (DCl/NH$_3$) m/e 511 (M+H)$^+$. [α]$^{22}$=+74.42°. Anal calcd for C$_{29}$H$_{38}$N$_2$O$_6$·0.5 H$_2$O: C, 67.03; H, 7.56; N, 5.39. Found: C, 67.03; H, 7.59; N, 5.33.

EXAMPLE 95E

Alternate Preparation of (2R,3R,4S)-(+)-2-(4-Methoxyphenyl)-4-(1,3-benzodioxol-5-yl)-1-(tert-butyloxycarbonylaminocarbonylmethyl)-pyrrolidine-3-carboxylic Acid The product of Example 95A (2.858 g) was suspended in 10 mL of EtOAc. 0.7833 g of R (+) alpha methyl benzylamine in 3 mL ethyl acetate was added. On swirling all of the solids were dissolved. The ethyl acetate was removed in vacuum. Ether (13 ml) was added to the residue. When all of the residue had dissolved, 5 mg of seed crystals were added and these crystals were crushed with a metal spatula while cooling in ice. The product crystallized very slowly. After 1 hour the solid was filtered and washed with ether giving 1.4213 g, m.p. 163–167°. The filtrate was concentrated, cooled and scratched with a spatula to give a second crop 0.1313 g, m.p. 164–1680. The filtrate was concentrated again and put in the refrigerator and let stand overnight giving 1.6906 g, m.p. 102–1100. (HPLC of this showed 20% of the desired enantiomer and 80% of the unwanted enantiomer.)

The first two batches of crystallized material were combined and suspended in 20 mL dichloromethane (Note: the unwanted isomer is more soluble in dichloromethane) and stirred for 2 minutes. The mixture was concentrated, but not to dryness, and ether (10 mL) was added. After stirring for a few minutes the crystals were filtered. Yield: 1.401 g, m.p. 164–172°.

Treatment of the crystalline product with 10% citric acid and ether according the method described in Example 95B provided the title compound.

EXAMPLE 96 trans,trans-2-(4-Methoxyphenyl)-4-(1, 3-benzodioxol-5-yl)-1-[2-(N-propyl-N-butyrylamino) ethyl]pyrrolidine-3-carboxylic Acid The title compound was prepared by the methods described in Example 61, but substituting propylamine for methylamine in Example 61B and butyryl chloride for isobutyryl chloride in Example 61C. The product was purified by preparative HPLC (Vydac µC18) eluting with a 10–70% gradient of CH$_3$CN in 0.1% TFA. The desired fractions were lyophilized to give the product as a white solid. $^1$H NMR (CDCl$_3$, 300 MHz) δ 0.80 (m, 3H), 0.90 (t, 3H, J=8 Hz), 1.42 (m, 2H), 1.58 (heptet, 2H, J=8 Hz), 2.20 (t, 3H, J=8 Hz), 2.94 (br m, 2H), 3.10 (br m, 2H), 3.48 (br m, 4H), 3.76 (br m, 2H), 3.78 (s, 3H), 4.30 (br s, 1H), 5.95 (s, 2H), 6.75 (d, 1H, J=8 Hz), 6.84 (m, 1H), 6.85 (d, 2H, J=8 Hz), 7.04 (d, 1H, J=1 Hz), 7.40 (d, 2H, J=8 Hz). MS (DCl/NH$_3$) m/e 497 (M+H)$^+$. Anal calcd for C$_{28}$H$_{36}$N$_2$O$_6$·1.0 TFA: C, 58.82; H, 6.42; N, 4.57. Found: C, 58.77; H, 6.30; N, 4.42.

EXAMPLE 97 trans,trans-2-(4-Methoxyphenyl)-4-(1,3-benzodioxol-5-yl)-1-[2-(N-propyl-N-(ethylaminocarbonyl)amino)ethylipyrrolidine-3-carboxylic Acid The title compound was prepared by the methods described in Example 61, but substituting propylamine for methylamine in Example 61B and ethyl isocyanate for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CDCl$_3$, 300 MHz) mixture of rotamers δ 0.80 (t, J=8 Hz) and 1.05 (t, J=8 Hz) and 1.20 (m) and 1.42 (m) total of 8H for the four peaks, 2.35 (br s, 1H), 2.70 (m, 1H), 3.0 (m, 3H), 3.2 (m, 3H), 3.25 (dq, 1H, J=1,8 Hz), 3.42 (m, 1H), 3.6 (m, 1H), 3.75 (m, 1H), 3.78 (s, 3H), 4.8 (br s, 1H), 5.95 (s, 2H), 6.74 (d, 1H, J=8 Hz), 6.85 (m, 3H), 7.00 (s, 1H), 7.30 (d, 2H, J=8 Hz). MS (DCl/NH$_3$) m/e 498 (M+H)$^+$. Anal calcd for C$_{27}$H$_{35}$N$_3$O$_6$·0.75 H$_2$O: C, 63.45; H, 7.20; N, 8.22. Found: C, 63.38; H, 7.29; N, 8.44.

EXAMPLE 98 trans,trans-2-(4-Methoxyphenyl)-4-(1,3-benzodioxol-5-yl)-1-[2-(N-butyl-N-butyrylamino) ethyl]pyrrolidine-3-carboxylic Acid The title compound was prepared by the methods described in Example 61, but substituting butylamine for methylamine in Example 61B and butyryl chloride for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CDCl$_3$, 300 MHz) δ 0.80 (m, 3H), 0.90 (t, 3H, J=8 Hz), 1.45 (m, 4H), 1.6 (m, 2H), 2.20 (t, 3H, J=8 Hz), 2.94 (br m, 2H), 3.10 (br m, 2H), 3.5 (br m, 4H), 3.80 (br m, 2H), 3.82 (s, 3H), 4.30 (br s, 1H), 5.95 (s, 2H), 6.75 (d, 1H, J=8 Hz), 6.84 (m, 1H), 6.85 (d, 2H, J=8 Hz), 7.04 (d, 1H, J=1 Hz), 7.40 (d, 2H, J=8 Hz). MS (DCl/NH$_3$) m/e 511 (M+H)$^+$. HRMS calcd for C$_{29}$H$_{38}$N$_2$O$_6$: 511.2808. Found: 511.2809

EXAMPLE 99 trans,trans-2-(4-Methoxyphenyl)-4-(1,3-benzodioxol-5-yl)-1-[2-(N-propyl-N-ethoxycarbonylamino)ethyl]pyrrolidine-3-carboxylic Acid The title compound was prepared by the methods described in Example 61, but substituting propylamine for methylamine in Example 61B and ethyl chloroformate for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CDCl$_3$, 300 MHz) δ 0.80 (t, 3H, J=8 Hz), 1.05 (m, 2H), 1.22 (m, 3H), 1.45 (m, 3H), 2.08 (br s, 1H), 2.75 (m, 1H), 2.88 (br q, 2H, J=8 Hz), 3.08 (br m, 2H), 3.27 (br m, 2H), 3.44 (m, 1H), 3.54 (dt, 1H, J=1,8 Hz), 3.63 (d, 1H, J=8 Hz), 3.78 (s, 3H), 4.02 (br d, 2H), 5.93 (s, 2H), 6.72 (d, 1H, J=8 Hz), 6.81 (dd, 1H, J=1,8 Hz), 6.85 (d, 2H, J=8 Hz), 7.00 (s, 1H), 7.30 (d, 2H, J=8 Hz). MS (DCl/NH$_3$) m/e499 (M+H)$^+$. Anal calcd for C$_{27}$H$_{34}$N$_2$O$_7$·0.5 H$_2$O: C, 63.89; H, 6.95; N, 5.52. Found: C, 64.03; H, 6.71; N, 5.30.

EXAMPLE 100 trans,trans-2-(4-Methoxyphenyl)-4-(1,3-benzodioxol-5-yl)-1-[2-(N-methyl-N-(2-ethylbutyryl)amino)ethyl]pyrrolidine-3-carboxylic Acid To the compound resulting from Example 61B (190 mg) dissolved in THF (2 mL) was added HOBt (60 mg), EDCI (85 mg), N-methylmorpholine (50 μL), and DMF (2 mL). 2-Ethylbutyric acid was added and the solution stirred overnight at ambient temperature. Water (10 mL) was added, and the mixture was extracted with EtOAc (2×25 mL). The combined organic extracts were washed with saturated sodium bicarbonate solution, 1 N H$_3$PO$_4$, and brine, dried with Na$_2$SO$_4$, and evaporated to give an oil which was purified by flash chromatography on silica gel eluting with 1:3 EtOAc-hexane. The resulting ethyl ester was saponified by the procedure described in Example 61C. The crude product was dissolved in CH$_3$CN and water and lyophilized to give the product as a white solid. $^1$H NMR (CDCl$_3$, 300 MHz) (mixture of rotamers) δ 0.66, 0.74, 0.80, 0.88 (all triplets, total of 6H, J=8 Hz), 1.05 (m, 2H), 1.25–1.75 (m, 5H), 2.16 (m, 1H), 2.32 (m, 1H), 2.45 (m, 1H), 2.70 (m, 1H), 2.86, 2.94 (s, total 3H), 2.95 (m, 1H), 3.35 (m, 1H), 3.52 (m, 2H), 3.65 (m, 1H), 3.80 (s, 3H), 5.94, 5.96 (s, total 2H), 6.73 (m, 1H), 6.84 (m, 3H), 6.97 (m, 1H), 7.30 (m, 2H). MS (DCl/NH$_3$) m/e 497 (M+H)$^+$. Anal calcd for C$_{28}$H$_{36}$N$_2$O$_6$·0.25 H$_2$O: C, 67.1 1; H, 7.34; N, 5.59. Found: C, 67.13; H, 7.24; N, 5.56.

EXAMPLE 101 trans,trans-2-(4-Methoxyphenyl)-4-(1,3-benzodioxol-5-yl)-1-[2-(N-methyl-N-(2-propylvaleryl)amino)ethyl]pyrrolidine-3-carboxylic Acid The title compound was prepared by the procedure described in Example 100, but substituting 2-propylpentanoic acid for 2-ethylbutyric acid. The crude product was purified by preparative HPLC (Vydac μC18) eluting with a 10–70% gradient of CH$_3$CN in 0.1% TFA. The desired fractions were lyophilized to give the product as a white solid. $^1$H NMR (CDCl$_3$, 300 MHz) δ 0.79 (t, 3H, J=8 Hz), 0.82 (t, 3H, J=8 Hz), 1.10 (m, 4H), 1.2–1.5 (m, 4H), 2.55 (m, 1H), 2.96 (s, 3H), 3.15 (br m, 1H), 3.32 (br m, 1H), 3.56 (m, 2H), 3.68 (m, 1 H) 3.68 (s, 3H), 3.70 (m, 1H), 3.80 (m, 2H), 4.65 (br d, 1H), 5.92 (s, 2H), 6.75 (d, 1H, J=8 Hz), 6.84 (m, 1H), 6.85 (d, 2H, J=8 Hz), 7.05 (s, 1H), 7.42 (d, 2H, J=8 Hz). MS (DCl/NH$_3$) m/e 525 (M+H)$^+$. Anal calcd for C$_{30}$H$_{40}$N$_2$O$_6$·1.25 TFA: C, 58.51; H, 6.23; N, 4.20. Found: C, 58.52; H, 6.28; N, 4.33.

EXAMPLE 102 trans,trans-2-(4-Methoxaphenyl)-4-(1,3-benzodioxol-5-yl)-1-[2-(N-propyl-N-(tert-butoxycarbonylmethyl)amino)ethyl]pyrrolidine-3-carboxylic Acid The title compound was prepared by the methods described in Example 61, but substituting propylamine for methylamine in Example 61B and t-butyl bromoacetate for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CDCl$_3$, 300 MHz) δ 0.82 (t, 3H, J=8 Hz), 1.18 (m, 2H), 1.19 (s, 9H), 2.12 (m, 1H), 2.46 (m, 2H), 2.70 (m, 3H), 2.85 (m, 2H), 3.20 (s, 2H), 3.40 (dd,1H, J=2,8 Hz), 3.50 (dt, 1H, J=2,8 Hz), 3.62 (d, 1H, J=8 Hz), 3.78 (s, 3H), 5.95 (s, 2H), 6.72 (d, 1H, J=8 Hz), 6.84 (m, 1H), 6.85 (d, 2H, J=8 Hz), 7.05 (s, 1H), 7.16 (d, 2H, J=8 Hz). MS (DCl/NH$_3$) m/e 541 (M+H)$^+$. Anal calcd for C$_{30}$H$_{40}$N$_2$O$_7$·1.0 H$_2$O: C, 64.50; H, 7.58; N, 5.01. Found: C, 64.75; H, 7.35; N, 4.86.

EXAMPLE 103 trans,trans-2-(4-Methoxyphenyl)-4-(1,3-benzodioxol-5-yl)-1-[2-(N-propyl-N-(n-propylaminocarbonylmethyl)amino)ethyl] pyrrolidine-3-carboxylic Acid The title compound was prepared by the methods described in Example 61, but substituting propylamine for methylamine in Example 61B and N-propyl bromoacetamide for isobutyryl chloride in Example 61C. The crude product was purified by preparative HPLC (Vydac μC18) eluting with a 10–70% gradient of CH$_3$CN in 0.1% TFA. The desired fractions were lyophilized to give the product as a white solid. $^1$H NMR (CDCl$_3$, 300 MHz) δ 0.78 (t, 3H, J=8 Hz), 0.88 (t, 3H, J=8 Hz), 1.45 (m, 2H), 1.48 (m, 3H, J=8 Hz), 2.55–2.7 (m, 2H), 2.90 (m, 1H), 3.04 (m, 1H), 3.15 (m, 3H), 3.28 (t, 1H, J=8 Hz), 3.45 (t, 1H, J=8 Hz), 3.60 (m, 2H), 3.70 (d, 2H, J=8 Hz), 3.75 (m, 1H), 3.80 (s, 3H), 4.25 (d, 1H, J=8 Hz), 5.95 (s, 2H), 6.75(d, 1H, J=8 Hz), 6.86 (dt, 1H, J=1,8 Hz), 6.88 (d, 2H, J=8 Hz), 7.04 (d, 1H, J=1 Hz), 7.40 (d, 2H, J=8 Hz). MS (DCl/NH$_3$) m/e 526 (M+H)$^+$. Anal calcd for C$_{29}$H$_{39}$N$_3$O$_6$·1.85 TFA: C, 53.32; H, 5.59; N, 5.70. Found: C, 53.45; H, 5.62; N, 5.63.

EXAMPLE 104 trans,trans-2-(4-Methoxyphenyl)-4-(1I3-benzodioxol-5-yl)-1-[2-(N-propyl-N-(4-methoxyphenoxycarbonyl)amino)ethyl]pyrrolidine-3-carboxylic Acid The title compound was prepared by the methods described in Example 61, but substituting propylamine for methylamine in Example 61B and 4-methoxyphenylchloroformate for isobutyryl chloride in Example 61C. The crude product was purified by trituration with 1:1 diethyl ether-hexane. The resulting solid was dissolved in $CH_3CN$ and water and lyophilized to give the product as a white solid. $^1H$ NMR ($CD_3OD$, 300 MHz) mixture of rotamers δ 0.88 (m, 3H), 1.57 (m, 2H), 2.45 (brs) and 2.60 (brs, total of 1H), 2.90–3.15 (m, 4H), 3.42–3.7 (m, 5H), 3.78 (s, 3H), 3.80 (s, 3H), 3.85 (m) and 4.0 (m, total of 1H), 5.95 (s) and 5.98 (s, total of 2H), 6.63(m, 1H), 6.72 (d, 1H, J=8 Hz), 6.81 (m, 2H), 6.93 (m, 5H), 7.40 (m, 2H), ($DCl/NH_3$) m/e 577 (M+H)$^+$. Anal calcd for $C_{32}H_{36}N_2O_8 \cdot 1.0$ $H_2O$: C, 64.63; H, 6.44; N, 4.71. Found: C, 64.70; H, 6.38; N, 4.63.

EXAMPLE 105 trans,trans-2-(4-Methoxyphenyl)-4-(1,3-benzodioxol-5-yl)-1-[2-(N-propyl-N-(4-methoxybenzoyl)amino)ethyl]pyrrolidine-3-carboxylic Acid The title compound was prepared by the methods described in Example 61, but substituting propylamine for methylamine in Example 61B and anisoyl chloride for isobutyryl chloride in Example 61C. The crude product was purified by trituration with 1:1 diethyl ether-hexane. The resulting solid was dissolved in $CH_3CN$ and water and lyophilized to give the product as a white solid. $^1H$ NMR ($CDCl_3$, 300 MHz) mixture of rotamers δ 0.78 (m) and 0.98 (t, J=8 Hz) total of 3H, 1.47 (m) and 1.52 (q, J=8 Hz) total of 2H, 2.25 (br s,1H), 2.78 (br s,1H), 2.90 (br t, 2H), 3.12–3.68 (m, 7H), 3.80 (s, 3H), 3.82 (s, 3H), 5.94 (s, 2H), 6.75(d, 1H, J=8 Hz), 6.83 (m, 5H), 6.94 (m, 1H), 7.22 (m, 4H). MS (FAB) m/e 561 (M+H)$^+$. Anal calcd for $C_{32}H_{36}N_2O_7 \cdot 0.75$ $H_2O$: C, 66.94; H, 6.58; N, 4.88. Found: C, 67.00; H, 6.38; N, 4.59.

EXAMPLE 106 trans,trans-2-(4-Methoxyphenyl)-4-(1,3-benzodioxol-5-yl)-1-[2-(N-propyl-N-benzoylamino)ethyl]pyrrolidine-3-carboxylic Acid The title compound was prepared by the methods described in Example 61, but substituting propylamine for methylamine in Example 61B and benzoyl chloride for isobutyryl chloride in Example 61C. The crude product was purified by trituration with 1:1 diethyl ether-hexane. The resulting solid was dissolved in $CH_3CN$ and water and lyophilized to give the product as a white solid. $^1H$ NMR ($CDCl_3$, 300 MHz) mixture of rotamers δ 0.65 and 0.9 (m, total of 3H), 1.4 and 1.55 (m, total of 2H), 2.05 and 2.15 (m, total of 1H), 2.6–3.6 (m, 8H), 5.92 (s, 2H), 6.70 (d, 1H, J=8 Hz), 6.82 (m, 4H), 7.2–7.4 (m, 6H). MS ($DCl/NH_3$) m/e 531 (M+H)$^+$. Anal calcd for $C_{31}H_{34}N_2O_6 \cdot 0.3$ $H_2O$: C, 69.46; H, 6.51; N, 5.23. Found: C, 69.48; H, 6.19; N, 4.84.

EXAMPLE 107 trans,trans-2-(4-Methoxyphenyl)-4-(1,3-benzodioxol-5-yl)-1-[2-(N-propyl-N-benzyloxycarbonylamino)ethyl]pyrrolidine-3-carboxylic Acid The title compound was prepared by the methods described in Example 61, but substituting propylamine for methylamine in Example 61B and benzyl chloroformate for isobutyryl chloride in Example 61C. The crude product was purified by preparative HPLC (Vydac µC18) eluting with a 10–70% gradient of $CH_3CN$ in 0.1% TFA. The desired fractions were lyophilized to give the product as a white solid. $^1H$ NMR ($CDCl_3$, 300 MHz) δ 0.8 (m, 3H) 1.45 (m, 2H), 2.20 (br m, 1H), 2.75 (m, 1H), 2.93 (m, 1H), 3.15 (m, 2H), 3.32 (m, 3H), 3.52 (m, 2H), 3.66 (m, 1H), 3.78 (s, 3H), 5.00 (m, 2H), 5.94 (s, 2H), 6.72(d, 1H, J=8 Hz), 6.82 (m, 3H), 7.0 (br d, 1H, J=15 Hz), 7.2 (s, 4H), 7.30 (m, 3H). MS (FAB) m/e 561 (M+H)$^+$. Anal calcd for $C_{32}H_{36}N_2O_7 \cdot 1.0$ TFA; C, 60.53; H, 5.53; N, 4.15. Found: c, 60.66; H, 5.34; N, 4.28.

EXAMPLE 108 trans,trans-2-(4-Methoxyphenyl)-4-(1,3-benzodioxol-5-yl)-1-[2-(N-propyl-N-(4-methoxybenzyloxycarbonyl)amino)ethyl]pyrrolidine-3-carboxylic Acid The title compound is prepared by the methods described in Example 61, substituting propylamine for methylamine in Example 61B and 4-methoxybenzyl chloroformate for isobutyryl chloride in Example 61C.

EXAMPLE 109 trans,trans-2-(4-Methoxyphenyl)-4-(1,3-benzodioxol-5-yl)-1-[2-(N-butyl-N-ethoxycarbonylamino)ethyl]pyrrolidine-3-carboxylic Acid The title compound was prepared by the methods described in Example 61, but substituting butylamine for methylamine in Example 61B and ethyl chloroformate for isobutyryl chloride in Example 61C. The crude product was purified by preparative HPLC (Vydac µC18) eluting with a 10–70% gradient of $CH_3CN$ in 0.1% TFA. The desired fractions were lyophilized to give the product as a white solid. $^1H$ NMR ($CDCl_3$, 300 MHz) δ 0.82 (t, 3H, J=8 Hz), 1.20 (m, 5H), 1.34 (m, 2H), 3.08 (m, 2H), 3.17 (m, 2H), 3.52 (m, 2H), 3.75 (m, 2H), 3.78 (s, 3H), 4.06 (q, 2H, J=8 Hz), 4.35 (br s, 1H), 5.94 (s, 2H), 6.76 (d, 1H, J=8 Hz), 6.92 (d, 2H, J=8 Hz), 7.03 (br s, 1H), 7.17 (br s, 1H), 7.7 (br s, 2H). MS (FAB) m/e 513 (M+H)$^+$. Anal calcd for $C_{28}H_{36}N_2O_7 \cdot 0.5$ TFA: C, 61.15; H, 6.46; N, 4.92. Found: C, 60.99; H, 6.80; N, 4.93.

EXAMPLE 110 trans,trans-2-(4-Methoxyphenyl)-4-(1,3-benzodioxol-5-yl)-1-[2-(N-butyl-N-propoxycarbonylamino)ethyl]pyrrolidine-3-carboxylic Acid The title compound was prepared by the methods described in Example 61, but substituting butylamine for methylamine in Example 61B and propyl chloroformate for isobutyryl chloride in Example 61C. The crude product was purified by trituration with 1:1 diethyl ether-hexane. The resulting solid was dissolved in $CH_3CN$ and water and lyophilized to give the product as a white solid. $^1H$ NMR ($CDCl_3$, 300 MHz) δ 0.80 (br s, 1H), 0.85 (t, 3H, J=8 Hz), 0.92 (br s, 1H), 1.22 (m, 3H), 1.40 (m, 3H), 1.62 (brm, 1H), 2.15 (brs, 1H), 2.72 (m, 1H), 2.87 (m, 1H), 3.1–3.45 (m, 5H), 3.55 (m, 1H), 3.64 (d, 1H, J=8 Hz), 3.79 (s, 3H), 3.88 (br s, 1H), 3.97 (br s, 1H), 5.95 (s, 2H), 6.73(d, 1H, J=8 Hz), 6.85 (m, 3H, 7.0 (s, 1H), 7.30 (d, 2H, J=8 Hz). MS (FAB) m/e 527 (M+H)$^+$. Anal calcd for $C_{29}H_{38}N_2O_7 \cdot 0.15$ $H_2O$: C, 65.80; H, 7.29; N, 5.29. Found: C, 65.79; H, 7.30; N, 5.2.

EXAMPLE 111 trans,trans-2-(4-Methoxyphenyl)-4-(1,3-benzodioxol-5-yl)-1-[2-(N-propyl-N-propoxycarbonylamino)ethyl]pyrrolidine-3-carboxylic Acid The title compound was prepared by the methods described in Example 61, but substituting propylamine for methylamine in Example 61B and propyl chloroformate for isobutyryl chloride in Example 61C. The crude product was purified by trituration with 1:1 diethyl ether-hexane. The resulting solid was dissolved in $CH_3CN$ and water and lyophilized to give the product as a white solid. $^1H$ NMR ($CDCl_3$, 300 MHz) δ 0.80 (t, 3H, J=8 Hz), 093 (m, 3H), 1.43 (m, 3H), 1.62 (m, 1H), 2.15 (brs, 1H), 2.68–3.45 (m, 8H), 3.54 (m, 1H), 3.66 (m, 1H), 3.78 (s, 3H), 3.94 (m, 2H), 5.94 (s, 2H), 6.72 (d, 1H, J=8 Hz), 6.82 (m, 1H), 6.84 (d, 2H, J=8 Hz), 7.00 (br s, 1H), 7.33 (m, 2H). MS ($DCl/NH_3$) m/e 513 $(M+H)^+$. Anal calcd for $C_{28}H_{36}N_2O_7$. 0.15 $H_2O$: C, 65.26; H, 7.10; N, 5.44. Found: C, 65.22; H, 6.74; N, 5.06.

EXAMPLE 112 trans,trans-1-(N,N-Di(n-butyl)aminocarbonylmethyl)-2,4-di(1,3-benzodioxol-5-yl)pyrrolidine-3-carboxylic Acid Ethyl (3,4-methylenedioxybenzoyl)acetate, prepared by the method of Krapcho et al., Org. Syn. 47, 20 (1967) starting with 3,4-methylenedioxyacetophenone instead of 4-methoxyacetophenone, was reacted by the procedures described in Example 1 to give the title compound as a white solid. m.p. 58–60°. $^1H$ NMR ($CDCl_3$, 300 MHz) δ 0.87 (quintet, J=6 Hz, 6H), 1.12 (sextet, J=6 Hz, 2H), 1.24–1.51 (m, 6H), 2.80 (d, J=13 Hz, 1H), 2.94–3.12 (m, 4H), 3.28–3.50 (m, 4H), 3.58–3.62 (m, 1H), 3.78 (d, J=9 Hz, 1H), 5.95 (s, 4H), 6.73 (dd, J=8 Hz, 3 Hz, 2H), 6.84–6.89 (m, 2H), 6.92 (d, J=Hz, 1H), 7.01 (d, H=1 Hz, 1H). MS ($DCl/NH_3$) m/e 525 $(M+H)^+$.

EXAMPLE 113 trans,trans-1-(2-(N-(n-Butyl)-N-propylsulfonylamino)ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 64–65° C. $^1H$ NMR ($CDCl_3$, 300 MHz) δ 0.83 (t, J=7 Hz, 3H), 0.98 (t, J=7 Hz, 3H), 1.12–1.25 (m, 2H), 1.32–1.41 (m, 2H), 1.75 (sextet, J=7 Hz, 2H), 2.23–2.31 (m, 2H), 2.72–3.32 (m, 8H), 3.43 (dd, J=9 Hz, 3 Hz, 1H), 3.53–3.59 (m, 1H), 3.65 (d, J=9 Hz, 1H), 3.80 (s, 3H), 5.95 (s, 2H), 6.73 (d, J=8 Hz, 1H), 6.83 (dd, J=8 Hz, 1 Hz, 1H), 6.88 (d, J=9 Hz, 2H), 7.02 (d, J=1 Hz, 1H), 7.33 (d, J=9 Hz, 2H). MS ($DCl/NH_3$) m/e 547 $(M+H)^+$.

EXAMPLE 114 trans,trans-1-(N,N-Di(n-butyl)aminocarbonylmethyl)-2-(4-methoxyphenyl)-4-(1,3-benzodioxol-5-yl)pyrrolidine-3-carboxylic Acid Using the procedures described in Examples 28 and 43, the title compound was prepared as a white solid. m.p. 74–76° C. $^1H$ NMR ($CDCl_3$, 300 MHz) δ 0.80 (t, J=6 Hz, 3H), 0.88 (t, J=8 Hz, 3H), 1.08 (sextet, J=8 Hz, 2H), 1.21–1.48 (m, 6H), 2.75 (d, J=12 Hz, 1H), 2.95–3.09 (m, 4H), 3.26–3.59 (m, 5H), 3.75 (d, J=9 Hz, 1H), 3.79 (s, 3H), 4.28 (s, 4H), 6.78 (d, J=9 Hz, 1H), 6.85 (d, J=9 Hz, 2H), 6.91 (d,d, J=3 Hz, 9 Hz, 1H), 6.98 (d, J=3 Hz, 1H), 7.32 (d, J=9 Hz, 2H). MS ($DCl/NH_3$) m/e 525 $(M+H)^+$.

EXAMPLE 115 trans,trans-1-(2-(N-Propyl-N-propylsulfonylamino)ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 72–73° C. $^1H$ NMR ($CDCl_3$, 300 MHz) δ 0.79 (t, J=8 Hz, 3H), 0.98 (t, J=8 Hz, 3H), 1.43 (sextet, J=8 Hz, 2H), 1.75 (sextet, J=8 Hz, 2H), 2.22–2.32 (m, 1H), 2.69–3.32 (m, 9H), 3.42 (dd, J=3 Hz, 12 Hz, 1H), 3.52–3.58 (m, 1H), 3.64 (d, J=12 Hz, 1H), 3.80 (s, 3H), 5.95 (s, 2H), 6.73 (d, J=11 Hz, 1H), 6.83 (dd, J=1 Hz, 11 Hz, 1H), 6.87 (d, J=11 Hz, 2H), 7.0 (d, J=2 Hz 1H), 7.32 (d, J=11 Hz, 2H), MS ($DCl/NH_3$) m/e 533 $(M+H)^+$.

EXAMPLE 116 trans,trans-1-(2-(N-Butyl-N-butylsulfonylamino)ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 62–63° C. $^1H$ NMR ($CDCl_3$, 300 MHz) δ 0.82 (t, J=6 Hz, 3H), 0.91)t, J=6 Hz, 3H), 1.20 (sextet, J=6 Hz, 2H), 1.33–1.42 (m, 4H), 1.68 (quintet, J=6 Hz, 3H), 2.23–2.32 (m, 1H), 2.70–3.28 (m, 9H), 3.41 (d, J=8 Hz, 1H), 3.52–3.58 (m, 1H), 3.65 (d, J=8 Hz, 1H), 3.79 (s, 3H), 5.95 (s, 2H), 6.72 (d, J=8 Hz, 1H), 6.82 (d, J=8 Hz, 1H), 6.87 (d, J=8 Hz, 2H), 7.01 (s, 1H), 7.32 (d, J=8 Hz, 2H). MS ($DCl/NH_3$) m/e 561 $(M+H)^+$.

EXAMPLE 117 trans,trans-1-(2-(N,N-Di(n-butyl)aminocarbonylmethyl)-2-(4-methoxymethoxyphenyl)-4-(1,3-benzodioxol-5-yl)pyrrodlidine-3-carboxylic Acid 4-Hydroxyacetophenone was treated with chloromethyl methyl ether and triethylamine in THF at room temperature to give ethyl 4-methoxymethoxybenzoylacetate which was treated by the procedures described in Example 1 to afford the title compound as a white solid. m.p. 4849° C. $^1H$ NMR ($CDCl_3$, 300 MHz) δ 0.81 (t, J=7 Hz, 3H), 0.88 (t, J=7 Hz, 3H), 1.06 (sextet, J=7 Hz, 2H), 1.20–1.35 (m, 4H), 1.44 (quintet, J=7 Hz, 2H), 2.75 (d, J=12 Hz, 1H), 2.94–3.10 (m, 4H), 3.25–3.35 (m, 1H), 3.40 (d, J=12 Hz, 1H), 3.43–3.52 (m, 2H), 3.47 (s, 3), 3.55–3.62 (m, 1H), 3.77 (d, J=9 Hz, 1H), 5.15 (s, 2H), 5.94 (m, 2H), 6.73 (d, J=8 Hz, 1H), 6.86 (dd, J=1 Hz, 8 Hz, 1H), 7.0 (d, J=8 Hz, 2H), 7.04 (d, J=1 Hz, 1H), 7.32 (d, J=8 Hz, 2H). MS ($DCl/NH_3$) m/e 541 $(M+H)^+$.

EXAMPLE 118 trans,trans-1-(2-(N,N-Di(n-butyl)aminocarbonylmethyl)-2-(4-hydroxyphenyl)-4-(1,3-benzodioxol-5-yl)pyrrolidine-3-carboxylic Acid Hydrochloride Salt The compound resulting from Example 116 was treated with concentrated HCl in 1:1 THF-isopropanol to give the title compound as a white solid. m.p. 211–212° C. $^1H$ NMR ($CD_3OD$, 300 MHz) δ 0.90 (t, J=8 Hz, 6H), 1.12–1.27 (m, 6H), 1.36–1.45 (m, 2H), 3.04 (bs, 1H), 3.14–3.35 (t, J=9 Hz, 1H), 3.90 (bs, 3H), 4.17 (d, J=15 Hz, 1H), 5.96 (s, 2H), 6.82–6.93 (m, 4H), 7.03 (d, J=1 Hz, 1H), 7.42 (bs, 2H). MS (DCl/NH$_3$) m/e 497 (M+H)$^+$.

EXAMPLE 119 trans,trans-1-(2-(N-isobutyl-N-propylsulfonylamino) ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 73–74° C. $^1$H NMR (CDCl$_3$, 300 MHz) δ 0.80 (d, J=6 Hz, 6H), 0.98 (t, J=8 Hz, 3H), 1.62 (sextet, J=6 Hz, 1H), 1.74 (sextet, J=8 Hz, 2H), 2.23–2.34 (m, 1H), 2.68–2.98 (m, 7H), 3.08–3.18 (m, 1H), 3.26–3.42 (m, 2H), 3.52–3.58 (m, 1H), 3.65 (d, J=9 Hz, 1H), 3.80 (s, 3H), 5.90 (s, 2H), 6.74 (d, J=8 Hz, 1H), 6.82 (d, J=8 Hz, 1H), 6.86 (d, J=8 Hz, 2H), 6.98 (d, J=1 Hz, 1H), 7.33 (d, 8 Hz, 2H). MS (DCl/NH$_3$) m/e 547 (M+H)$^+$.

EXAMPLE 120 trans,trans-1-(2-(N-Benzenesulfonyl-N-propylamino)ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 89–91° C. $^1$H NMR (CDCl$_3$, 300 MHz) δ 0.74 (t, J=6 Hz, 3H), 1.33 (sextet, J=6 Hz, 2H), 2.20–2.30 (m, 1H), 2.62–2.72 (m, 1H), 2.85–3.05 (m, 4H), 3.12–3.22 (m, 1H), 3.38 (dd, J=3 Hz, 9 Hz, 1H), 3.49–3.57 (m, 1H), 3.62 (d, J=9 Hz, 1H), 3.82 (s, 3H), 5.96 (s, 2H), 6.73 (d, J=8 Hz, 1H), 6.84 (dd, J=1 Hz, 8 Hz, 1H), 6.85 (d, J=9 Hz, 2H), 7.02 (d, J=1 Hz, 1H), 7.28 (d, J=9 Hz, 2H), 7.39–7.45 (m, 3H), 7.70 (d, J=7 Hz, 2H). MS (DCl/NH$_3$) m/e 567 (M+H)$^+$.

EXAMPLE 121 trans,trans-1-(2-(N-(4-Methoxybenzenesulfonic)-N-propylamino)ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 96–97° C. $^1$H NMR (CDCl$_3$, 300 MHz) δ 0.73 (t, J=7 Hz, 3H), 1.34 (sextet, J=7 Hz, 2H), 2.20–2.30 (m, 1H), 2.62–2.71 (m, 1), 2.82–3.03 (m, 4H), 3.08–3.18 (m, 2H), 3.38 (dd, J=3 Hz, 9 Hz, 1H), 3.48–3.56 (m, 1H), 3.62 (d, J=9 Hz, 1H), 3.81 (s, 3H), 3.86 (s, 3H), 5.95 (s, 2H), 6.73 (d, J=8 Hz, 1H), 6.81–6.89 (m, SH), 7.01 (d, J=1 Hz, 1H), 7.28 (d, J=8 Hz, 2H), 7.62 (d, J=8 Hz, 2H). MS (DCl/NH$_3$) m/e 597 (M+H)$^+$.

EXAMPLE 122 trans,trans-1-(N,N-Di(n-butyl) aminocarbonylmethyl)-2-(2-methylethoxy-4-methoxyphenyl)-4-(1,3-benzodioxol-5-yl) pyrrolidine-3-carboxylic Acid 2-Hydroxy-5-methoxyacetophenone was treated with sodium hydride and bromoethyl methyl ether in THF at 70° C. to provide ethyl 2-methoxyethoxy-4-methoxybenzoylacetate which was treated by the procedures described in Example 1 to provide the title compound as a white solid. m.p. 63–65° C. $^1$H NMR (CDCl$_3$, 300 MHz) δ 0.84 (t, J=7 Hz, 3H), 0.89 (t, J=7 Hz, 3H), 1.16 (sextet, J=7 Hz, 2H), 1.28 (sextet, J=7 Hz, 2H), 1.45–1.52 (m, 4H), 2.87–2.94 (m, 2H), 3.00–3.16 (m, 3H), 3.26–3.36 (m, 2H), 3.43 (s, 3H), 3.47–3.54 (m, 3H), 3.66–3.72 (m, 2H), 3.78 (s, 3H), 3.76–3.84 (m, 1H), 4.02–4.10 (m, 2H), 4.25 (d, J=9 Hz, 1H), 5.92 (s, 2H), 6.40 (d, J=2 Hz, 1H), 6.52 (dd, J=2 Hz, 9 Hz, 1H), 6.70 (d, J=8 Hz, 1H), 6.83 (dd, J=1 Hz, 8 Hz, 1H), 5.98 (d, J=2 Hz, 1H), 7.53 (d, J=9 Hz, 1 H). MS (DCl/NH$_3$) m/e 585 (M+H)$^+$.

EXAMPLE 123 trans,trans-1-(2-(N-Propyl-N-(2,4-dimethylbenzenesulfonyl)amino)ethyl)-2-(4-methoxyphenyl)-4-(1,3-benzodioxol-5-yl) pyrrolidine-3-carboxylic Acid Using the procedures described in Example 66, the title compound was prepared as a white solid. m.p. 88–90° C. $^1$H NMR (CDCl$_3$, 300 MHz) δ 0.69 (t, J=7 Hz, 3H), 1.32 (sextet, J=7 Hz, 2H), 2.12–2.20 (m, 1H), 2.32 (s, 3H), 2.47 (s, 3H), 2.62–2.69 (m, 1H), 2.78 (t, J=9 Hz, 1H), 2.89 (dd, J=8 Hz, 1H), 3.02 (sextet, J=9 Hz, 2H), 3.15–3.32 (m, 3H), 3.46–3.55 (m, 1H), 3.60 (d, J=9 Hz, 1H), 3.82 (s, 3H), 5.96 (s, 2H), 6.72 (d, J=7 Hz, 1H), 6.80 (dd, J=1 Hz, 9 Hz, 1H), 6.86 (d, J=9 Hz, 2H), 6.97 (d, J=1 Hz, 1H), 7.03 (bs, 2H), 7.29 (d, J=9 Hz, 1 H). MS (DCl/NH$_3$) m/e 595 (M+H)$^+$.

EXAMPLE 124 trans,trans-1-(2-(N-Propyl-N-(3-chloropropylsulfonyl)amino)ethyl)-2-(4-methoxyphenyl)-4-(1,3-benzodioxoxl-5-yl) pyrrolidine-3-carboxylic Acid Using the procedures described in Example 66, the title compound was prepared as a white solid. m.p. 75–76° C. $^1$H NMR (CDCl$_3$, 300 MHz) δ 0.80 (t, J=7 Hz, 3H), 1.45 (sextet, J=7 Hz, 2H), 2.15–2.31 (m, 3H), 2.70–2.80 (m, 1H), 2.85–3.10 (m, 6H), 3.23–3.31 (m, 2H), 3.43 (bd, J=9 Hz, 1H), 3.55–3.66 (m, 4H), 3.81 (s, 3H), 5.94 (s, 2H), 6.73 (d, J=8 Hz, 1H), 6.82 (d, J=8 Hz, 1H), 6.86 (d, J=8 Hz, 2H), 7.00 (s, 1H), 7.33 (d, J=8 Hz, 2H). MS (DCl/NH$_3$) m/e 567 (M+H)$^+$.

EXAMPLE 125 trans,trans-1-(2-(N-Propyl-N-(3-chloropropylsulfonyl)amino)ethyl)-2-(4-methoxyphenyl)-4-(1,3-benzodioxol-5-yl) pyrrolidine-3-carboxylic Acid Using the procedures described in Example 66, trans, trans-1-(2-(N-Propyl-N-(vinylsulfonyl)amino)ethyl)-2-(4-methoxyphenyl)-4-(1,3-benzodioxol-5-yl)pyrrolidine-3-carboxylic Acid was prepared. Ester hydrolysis using aqueous sodium hydroxide in methanol afforded the title compound as a white solid. m.p. 62–64° C. $^1$H NMR (CDCl$_3$, 300 MHz) δ 0.78 (t, J=7 Hz, 3H), 1.42 (sextet, J=7 Hz, 2H), 2.23–2.32 (m, 1H), 2.72–2.79 (m, 1H), 2.86–3.05 (m, 4H), 3.10–3.27 (m, 4H), 3.32 (s, 3H), 3.43 (dd, J=3 Hz, 9 Hz, 1H), 3.53–3.58 (m, 1H), 3.65 (d, J=9 Hz, 1H), 3.69 (t, J=6 Hz, 2H), 3.80 (s, 3H), 5.94 (s, 2H), 6.73 (d, J=8 Hz, 1H), 6.82 (dd, J=1 Hz, 8 Hz, 1H), 6.87 (d, J=8 Hz, 2H), 7.02 (d, J=1 Hz, 1H), 7.33 (d, J=8 Hz, 2H). MS (DCl/NH$_3$) m/e 549 (M+H)$^+$.

EXAMPLE 126 trans,trans-1-(2-(N-Propyl-N-(2-ethoxvethylsulfonyl)amino)ethyl)-2-(4-methoxyphenyl)-4-(1,3-benzodioxol-5-yl) pyrrolidine-3-carboxylic Acid Using the procedures described in Example 66, the title compound was prepared as a white solid. m.p. 58–60° C. $^1$H NMR (CDCl₃, 300 MHz) δ 0.78 (t, J=7 Hz, 3H), 1.18 (t, J=7 Hz, 3H), 1.43 (sextet, J=7 Hz, 2H), 2.24–2.33 (m, 1H), 2.70–2.80 (m, 1H), 2.87–3.05 (m, 4H), 3.13–3.20 (m, 2H), 3.22–3.32 (m, 2H), 3.42 (dd, J=2 Hz, 9 Hz, 1H), 3.46 (q, J=7 Hz, 2H), 3.52–3.58 (m, 1H), 3.65 (d J=9 Hz, 1H), 3.72 (t, J=6 Hz, 2H), 3.80 (s, 3H), 5.95 (s, 2H), 6.73 (d, J=7 Hz, 1H), 6.83 (dd, J=1 Hz, 7 Hz), 1H), 6.87 (d, J=8 Hz, 2H), 7.00 (d, J=Hz, 1H), 7.32 (d, J=8 Hz, 2H). MS (DCI/NH₃) m/e 563 (M+H)⁺.

EXAMPLE 127 trans,trans-1-(2-(N-Propyl-N-(5-dimethylamino-1-naphthylsulfonyl)amino)ethyl)-2-(4-methoxyphenyl)-4-(1,3-benzodioxol-5-yl)pyrrolidine-3-carboxylic Acid Using the procedures described in Example 66, the title compound was prepared as a yellow solid. m.p. 102–104° C. ¹H NMR (CDCl₃, 300 MHz) δ 0.62 (t, J=7 Hz, 3H), 1.28 (sextet, J=7 Hz, 2H), 2.12–2.20 (m, 1H), 2.78 (t, J=9 Hz, 1H), 2.88 (s, 6H), 2.72–2.89 (m, 1H), 3.05–3.12 (m, 2H), 3.26–3.45 (m, 3H), 3.45–3.52 (m, 1H), 3.58 (d, J=9 Hz, 1H), 6.97 (d, J=1 Hz, 1H), 7.13 (d, J=7 Hz, 1H), 7.26 (d, J=8 Hz, 1H), 7.42–7.50 (m, 2H), 8.08 (dd, J=1 Hz, 7 Hz, 1H), 8.20 (d, J=8 Hz, 1H), 8.48 (d, J=8 Hz, 1 H). MS (DCI/NH₃) m/e 660 (M+H)⁺.

EXAMPLE 128 trans,trans-1-(2-(N-Propyl-N-(ethylsulfonyl)amino)ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 70–72° C. ¹H NMR (CDCl₃, 300 MHz) δ 0.79 (t, J=8 Hz, 3H), 1.28 (t, J=7 Hz, 3H), 1.43 (q, J=8 Hz, 2H), 2.22–2.30 (m, 1H), 2.71–2,80 (m, 1H), 2.82–3.10 (m, 6H), 3.18–3.32 (m, 2H), 3.43 (dd, J=3 Hz, 9 Hz, 1H), 3.53–3.60 (m, 1H), 3.65 (d, J=9 Hz, 1H), 3.80 (s, 3H), 5.96 (s, 2H), 6.73 (d, J=7 Hz, 1 H), 6.82 (dd, J=1 Hz, 7 Hz, 1H), 6.88 (d, J=8 Hz, 2H), 7.00 (d, J=1 Hz, 1H),. 7.32 (d, J=8 Hz, 2H). MS (DCI/NH₃) m/e 519 (M+H)⁺.

EXAMPLE 129 trans,trans-1-(2-(N-Propyl-N-(4-methylbenzenesulfonyl)amino)ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 78–79° C. ¹H NMR (CDCl₃, 300 MHz) δ 0.73 (t, J=7 Hz, 3H), 1.33 (sextet, J=7 Hz, 2H), 2.20–2.30 (m, 1H), 2.40 (s, 3H), 2.61–2.72 (m, 1H), 2.83–3.05 (m, 4H), 3.08–3.19 (m, 2H), 3.48 (dd, J=3 Hz, 9 Hz, 1H), 3.49–3.57 (m, 1H), 3.62 (d, J=9 Hz, 1H), 3.81 (s, 3H), 5.95 (s, 2H), 6.73 (d, J=8 Hz, 1H), 6.82 (d, J=8 Hz, 1H), 6.87 (d, J=8 Hz, 2H), 7.00 (s,1H), 7.21 (d, J=8 Hz, 2H), 7.29 (d, J=8 Hz, 2H), 7.57 (d, J=8 Hz, 2H). MS (DCI/NH₃) m/e 581 (M+H)⁺.

EXAMPLE 130 trans,trans-1-(N,N-Di(n-butyl)aminocarbonylmethyl)-2-(3-pyridyl)-4-(1,3-benzodioxol-5-yl)pyrrolidine-3-carboxylic Acid Methyl nicotinoyl acetate was prepared by the method of Wenkert, et al., J. Org. Chem. 48: 5006 (1983) and treated by the procedures described in Example 1 to provide the title compound as a white solid. m.p. 167–168° C. ¹H NMR (CDCl₃, 300 MHz) δ 0.82 (t, J-7 Hz, 3H), 0.89 (t, J=7 Hz, 3H), 1.14 (sextet, J=7 Hz, 2H), 1.23–1.48 (m, 6H), 2.86–3.20 (m, 6H), 3.34–3.43 (m, 2H), 3.57 (dd, J=3 Hz, 9 Hz, 1H), 3.75–3.83 (m, 1H), 4.08 (d, J=9 Hz, 1H), 5.93 (s, 2H), 6.73 (d, J=8 Hz, 1H), 6.90 (dd, J=2 Hz, 8 Hz, 1H), 7.03 (d, J=2 Hz, 1H), 7.38 (dd, J=4 Hz, 8 Hz, 1H), 8.04 (d, J=8 Hz, 1H), 8.48 (dd, J=2 Hz, 4 Hz, 2H). MS (DCI/NH₃) m/e 482 (M+H)⁺.

EXAMPLE 131 trans,trans-1-(2-(N-Propyl-N-(n-butylsulfonyl)amino)ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 65–66° C. ¹H NMR (CDCl₃, 300 MHz) δ 0.78 (t, J=7 Hz, 3H), 0.92 (t, J=7 Hz, 3H), 1.31–1.46 (m, 4H), 1.68 (quintet, J=7 Hz, 2H), 2.21–2.32 (m, 1H), 2.70–3.08 (m, 7H), 3.12–3.23 (m, 2H), 3.42 (dd, J=2 Hz, 9 Hz, 1H), 3.52–3.58 (m, 1H), 3.64 (d, J=9 Hz, 1H), 3.80 (s, 3H), 5.96 (s, 2H), 6.72 (d, J=7 Hz, 1H), 6.83 (dd, J=1 Hz, 7 Hz, 1H), 6.86 (d, J=8 Hz, 2H), 7.00 (d, J=1 Hz, 1H), 7.32 (d, J=8 Hz, 2H). MS (DCI/NH₃) m/e 547 (M+H)⁺.

EXAMPLE 132 trans,trans-1-(2-(N-Propyl-N-(4-chlorobenzenesulfonyl)amino)ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 105–106° C. ¹H NMR (CDCl₃, 300 MHz) δ 0.72 (t, J=7 Hz, 3H), 1.34 (sextet, J=7 Hz, m, 2H), 2.56–2.62 (m, 1H), 2.78–2.86 (m, 1H), 2.96–3.03 (m, 3H), 3.13–3.26 (m, 3H), 3.51 (dd, J=5 Hz, 9 Hz, 1H), 3.62–3.68 (m, 1H), 3.80 (s, 3H), 3.94 (d, J=9 Hz, 1H), 5.92 (s, 2H), 6.75 (d, J=8 Hz, 1H), 6.84 (dd, J=2 Hz, 8 Hz, 1H), 6.94 (d, J=8 Hz, 2H), 6.98 (d, J=2 Hz, 1H), 7.36 (d, J=8 Hz, 1H), 7.49 (d, J=8 Hz, 1H), 7.68 (d, J=8 Hz, 1H). MS (DCI/NH₃) m/e 601 (M+H)⁺.

EXAMPLE 133 trans,trans-1-(2-(N-Propyl-N-(benzylsulfonyl)amino)ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 88–89° C. ¹H NMR (CDCl₃, 300 MHz) δ 0.72 (t, J=7 Hz, 3H), 1.32 (sextet, J=7 Hz, 2H), 2.06–2.16 (m, 1H), 2.56–2.67 (m, 1H), 2.75–3.10 (m, 6H), 3.30 (dd, J=2 Hz, 9 Hz, 1H), 5.95 (s, 2H), 6.73 (d, J=7 Hz, 1H), 6.80 (dd, J=1 Hz, 7 Hz, 1H), 6.86 (d, J=8 Hz, 2H), 6.97 (d, J=1 Hz, 1H), 7.27–7.35 (m, 7H). MS (DCI/NH₃) m/e 581 (M+H)⁺.

EXAMPLE 134 trans,trans-1-(2-(N-Propyl-N-(4-fluorobenzenesulfonyl)amino)ethyl)-2-(4-methoxyphenyl)-4-(1,3-benzodioxol-5-yl)pyrrolidine-3-carboxylic Acid Using the procedures described in Example 66, the title compound was prepared as a white solid. m.p. 91–93° C. ¹H NMR (CDCl$_3$, 300 MHz) δ 0.73 (t, J=7 Hz, 3H), 1.44 (sextet, J=7 Hz, 2H), 2.18–2.27 (m, 1H), 2.56–2.67 (m, 1H), 2.78–2.87 (m, 2H), 2.97 (septet, J=8 Hz, 2H), 3.11–3.16 (m, 2H), 3.33 (dd, J=2 Hz, 9 Hz, 1H), 3.43–3.50 (m, 1H), 3.57 (d, J=9 Hz, 1H), 3.78 (s, 3H), 7.08 (t, J=8 Hz, 2H), 7.24 (d, J=8 Hz, 2H), 7.69 (dd, J=5 Hz, 8 Hz, 2H). MS (DCl/NH$_3$) m/e 585 (M+H)$^+$.

EXAMPLE 135 trans,trans-1-(N-Methyl-N-propylaminocarbonylmethyl)-2-(4-methoxyphenyl)-4-(4-benzofuranyl)pyrrolidine-3-carboxylic Acid

EXAMPLE 135A

Benzofuran-4-carboxaldehyde

To a suspension of 60% sodium hydride in mineral oil (4.00 g, 100 mmol, 1.25 eq) in DMF (60 mL) at 0° C. was added a solution of 3-bromophenol (13.8 g, 80 mmol) in DMF (5 mL). After 10 minutes, bromoacetaldehyde diethyl acetal (14.9 mL, 96.6 mmol, 1.24 eq) was added, and the resultant mixture then heated at 120° C. for 2.5 hours. The mixture was cooled to room temperature and was poured into water, and extracted once with ether. The organic solution was dried over MgSO$_4$, filtered, evaporated and vacuum distilled to yield a colorless liquid (17.1 g, 74%). b.p. 160–163° C. at 0.4 mm Hg.

To warm polyphosphoric acid (15.3 g) was added a solution of the above compound (17.1 g, 59.3 mmol) in benzene (50 mL). The resultant mixture was heated under reflux with vigorous stirring for 4 hours, after which time the benzene layer was carefully decanted off, and the lower layer washed once with hexanes. The combined organic solutions were concentrated in vacuo, and then vacuum distilled to yield a colorless liquid (8.13 g, 70%). b.p. 62–72° C. at 0.6 mm Hg.

To a solution of the above compounds (8.11 g, 41.5 mmol) in ether (80 mL) at −78° C. was added 1.7 M t-butyllithium (48.8 mL, 83 mmol, 2 eq) such that the temperature did not exceed −70° C. After stirring for 15 minutes, a solution of DMF (6.5 mL, 83 mmol, 2 eq) in ether (20 mL) was added, and the mixture allowed to warm to room temperature over 2 hours. The mixture was poured into water and the phases separated. The organic solution was dried over MgSO$_4$ and concentrated in vacuo. The residue was purified by flash chromatography on silica gel eluting with 10% ether in hexanes to yield benzofuran-6-carboxaldehyde (1.22 g) and benzofuran-4-carboxaldehyde (1.86 g), both as colorless oils.

EXAMPLE 135B trans,trans-1-(N-Methyl-N-propylaminocarbonylmethyl)-2-(4-methoxyphenyl)-4-(4-benzofuranyl)pyrrolidine-3-carboxylic Acid The title compound was prepared using the procedures described in Examples 1 and 49 substituting the compound resulting from Example 135A in Example 49A for piperonal. $^1$H NMR (300 MHz, CDCl$_3$) (minor rotamer) δ 7.59 (1H, t, J=3 Hz), 7.4–7.2 (6H, m), 6.8 (2H, d, J=8 Hz), 4.03 (1H, m), 3.94 (1H, dd, J=8 Hz, 3 Hz), 3.77 (3H, s), 3.61 (1H, dd, J=8 Hz, 7 3 Hz), 3.42 (1H, dd, J=11 Hz, 5 Hz, 3.40–2.90 (5H, m), 2.82 (2.81) (3H, s), 1.50 (2H, septet, J=7 Hz), 0.82 (0.75) (3H, t, J=7 Hz). MS (DCl/NH$_3$) m/e 451 (M+H)$^+$. Anal.calc. for C$_{26}$H$_{30}$N$_2$O$_5$.AcOH: C, 65.87; H, 6.71; N, 5.49. Found: C, 66.04; H, 6.42; N, 5.60.

EXAMPLE 136 trans,trans-1-(N-Methyl-N-propylaminocarbonylmethyl)-2-(4-methoxyphenyl)-4-(6-benzofuranyl)pyrrolidine-3-carboxylic Acid The title compound was prepared using the procedures described in Examples 1 and 49 substituting benzofuran-6-carboxaldehyde, prepared as described in Example 135A, in Example 49A for piperonal. $^1$H NMR (300 MHz, CDCl$_3$) (minor rotamer) δ 7.65 (1H, bd), 7.60 (1H, d, J=2 Hz), 7.55 (1H, d, J=8 Hz), 7.35 (3H, m), 6.85 (2H, dd, J=8 Hz, 3 Hz), 6.75 (1H, dd, J=3 Hz, 2 Hz), 3.83 (2H, m), 3.79 (3H, s), 3.60–3.0 (7H, m), 2.91 (2.83) (s, 3H), 1.51 (2H, septet, J=7 Hz), 0.83 (0.78) (3H, t, J=7 Hz). MS (DCl/NH$_3$) m/e 451 (M+H)$^+$. Anal.calc. for C$_{26}$H$_{30}$N$_2$O$_5$.0.5 H$_2$O: C, 67.96; H, 6.80; N, 6.10. Found: C, 67.90; H, 6.71; N, 6.07.

EXAMPLE 137 trans,trans-1-(N-Methyl-N-propylaminocarbonylmethyl)-2-(4-methoxyphenyl)-4-(6-benzo-2,3-dihydrofuranyl)pyrrolidine-3-carboxylic Acid The title compound was prepared by catalytic hydrogenation (4 atmospheres of H$_2$ in AcOH, followed by preparative hplc) of the compound resulting from Example 136 $^1$H NMR (300 MHz, CDCl$_3$) (minor rotamer) δ 7.49 (7.47) (2H, d, J=8 Hz), 7.19 (1H, d, J=8 Hz), 7.00 (1H, m), 7.82 (3H, m), 5.40 (1H, dd, J=11 Hz, 7 Hz), 4.58 (2H, t, J=8 Hz), 4.18 (1H, m), 4.10 (1H, m), 3.88 (1H, m), 3.79 (3H, s), 3.60 (1H, m), 3.35 (1H, m), 3.19 (2H, t, J=8 Hz), 3.00 (4H, m), 2.91 (2.78) (s, 3H), 1.53 (1.40) (2H, septet, J=7 Hz), 0.88 (0.78) (3H, t, J=7 Hz). MS (DCl/NH$_3$) m/e 453 (M+H)$^+$. Anal.calc. for C$_{26}$H$_{32}$N$_2$O$_5$.1.25 TFA: C, 57.53; H, 5.63; N, 4.71. Found: C, 57.68; H, 5.68; N, 4.70.

EXAMPLE 138 trans,trans-1-(N,N-Di(n-butyl)aminocarbonylmethyl)-2-(4-methoxyphenyl)-4-(4-benzofuranyl)pyrrolidine-3-carboxylic Acid The title compound was prepared by the procedures described in Examples 1 and 49 substituting benzofuran-4-carboxaldehyde in Example 49A for piperonal and substituting N,N-dibutyl bromoacetamide for N-methyl-N-propyl bromoacetamide. $^1$H NMR (300 MHz, CDCl$_3$) δ 7.62 (1H, d, J=3 Hz), 7.39 (1H, dt, J=8 Hz, 2 Hz), 7.34 (3H, m), 7.26 (1H, d, J=2 Hz), 7.23 (1H, d, J=8 Hz), 6.84 (2H, d, J=8 Hz), 4.02 (1H, ddd, J=8, 6 Hz, 4 Hz), 3.89 (1H, d, J=9 Hz) 3.79 (3H, s), 3.67 (1H, dd, J=10 Hz, 3 Hz), 3.44 (2H, m), 3.35–3.15 (3H, m), 3.00 (2H, m), 2.84 (1H, d, J=14 Hz), 1.43 (3H, m), 1.23 (3H, m), 1.08 (2H, m), 0.87 (3H, t, J=7 Hz), 0.82 (3H, t, J=7 Hz). MS (DCl/NH$_3$) m/e 507 (M+H)$^+$. Anal.calc. for C$_{30}$H$_{38}$N$_2$O$_5$: C, 71.12; H, 7.56; N, 5.53. Found: C, 70.86; H, 7.45; N, 5.24.

EXAMPLE 139 trans,trans-1-(N,N-Di(n-butyl)aminocarbonylmethyl)-2-(4-methoxyphenyl)-4-(4-benzofuranyl)pyrrolidine-3-carboxylic Acid The title compound was prepared by the procedures described in Examples 1 and 49 substituting benzofuran-5-carboxaldehyde, prepared by the procedures described in Example 135A substituted 4-bromophenol for 3-bromophenol, in Example 49A for piperonal and substituting N,N-dibutyl bromoacetamide for N-methyl-N-propyl bromoacetamide. $^1$H NMR (300 MHz, CDCl$_3$) δ 7.64 (1H, bd), 7.59 (1H, d, J=2 Hz), 7.43 (2H, m), 7.33 (2H, d, J=8 Hz), 6.85 (2H, d, J=8 Hz), 6.73 (1H, dd, J=3 Hz, 1 Hz), 3.82 (1H, d, J=11 Hz), 3.89 (1H, d, J=9 Hz) 3.79 (3H, s), 3.53 (1H, dd, J=10 Hz, 3 Hz), 3.44 (2H, m), 3.30 (1H, m), 3.20–2.95 (5H, m), 2.82 (1H, d, J=14 Hz), 1.43 (3H, m), 1.23 (3H, m), 1.08 (2H, m), 0.87 (3H, t, J=7 Hz), 0.82 (3H, t, J=7 Hz). MS (DCl/NH$_3$) m/e 507 (M+H)$^+$. Anal.calc. for C$_{30}$H$_{38}$N$_2$O$_5$: C, 71.12; H, 7.56; N, 5.53. Found: C, 70.73; H, 7.45; N, 5.29.

EXAMPLE 140 trans,trans-1-(N N-Di(n-butyl) aminocarbonylmethyl)-2-(4-methoxyphenyl)-4-(6-benzofuranyl)pyrrolidine-3-carboxylic Acid The title compound was prepared by the procedures described in Examples 1 and 49 substituting benzofuran-6-carboxaldehyde in Example 49A for piperonal and substituting N,N-dibutyl bromoacetamide for N-methyl-N-propyl bromoacetamide. $^1$H NMR (300 MHz, CDCl$_3$) δ 7.63 (1H, bd), 7.59 (1H, d, J=2 Hz), 7.53 (1H, d, J=8 Hz), 7.36 (3H, m), 6.85 (2H, d, J=8 Hz), 6.73 (1H, dd, J=3 Hz, 1 Hz), 3.82 (1H, d, J=11 Hz), 3.89 (1H, d, J=9 Hz) 3.79 (3H, s), 3.53 (1H, dd, J=10 Hz, 3 Hz), 3.44 (2H, m), 3.30 (1H, m), 3.20–2.95 (5H, m), 2.80 (1H, d, J=14 Hz), 1.43 (3H, m), 1.23 (3H, m), 1.08 (2H, m), 0.87 (3H, t, J=7 Hz), 0.82 (3H, t, J=7 Hz). MS (DCl/NH$_3$) m/e507 (M+H)$^+$. Anal.calc. for C$_{30}$H$_{38}$N$_2$O$_5$.0.75 H$_2$O: C, 69.28; H, 7.65; N, 5.39. Found: C, 69.11; H, 7.33; N, 5.32.

EXAMPLE 141 trans,trans-1-(N,N-Di(n-butyl) aminocarbonylmethyl)-2-(4-methoxyphenyl)-4-(6-benzo-2,3-dihydrofuranyl)pyrrolidine-3-carboxylic Acid The title compound was prepared by catalytic hydrogenation of the compound resulting from Example 140 (4 atmospheres of H$_2$ in AcOH, followed by preparative hplc). $^1$H NMR (300 MHz, CDCl$_3$) δ 7.40 (2H, d, J=8 Hz), 7.16 (1H, d, J=8 Hz), 6.97 (1H, dd, J=8 Hz, 2 Hz), 6.89 (3H, m), 5.90 (1H, bs) 4.57 (2H, t, J=9 Hz), 4.93 (2H, m), 3.80 (3H, s), 3.70–3.58 (2H, m), 3.40 (1H, m), 3.30–2.90 (8H, m), 1.40 (2H, m), 1.29 (3H, m), 1.08 (2H, m), 0.92 (3H, t, J=7 Hz), 0.82 (3H, t, J=7 Hz). MS (DCl/NH$_3$) m/e 509 (M+H)$^+$. Anal.calc. for C$_{30}$H$_{40}$N$_2$O$_5$.0.85 TFA: C, 62.88; H, 6.80; N, 4.63. Found: C, 63.04; H, 6.66; N, 4.60.

EXAMPLE 142 trans,trans-1-(N-Methyl-N-propylaminocarbonylmethyl)-2-(4-methoxyphenyl)-4-(5-indanyl)pyrrolidine-3-carboxylic Acid

EXAMPLE 142A

Indane-5-carboxaldehyde

Indane-5-carboxaldehyde was prepared by formylation of indane under the conditions described for 2,3-dihydrobenzofuran in Example 52A. The resultant mixture of 4- and 5-carboxaldehydes was purified as follows: to a 6:1 mixture of indane-4-carboxaldehyde and indane-5-carboxaldehyde (3.46 g, 23 mmol) was added aniline (2.20 g, 23 mmol, 1 eq). The resultant solution slowly solidfied to a mixture of imines which was recrystallized from hot acetonitrile to yield the 5-aldimine as a white solid. The aldimine (2.65 g) was suspended in water (6 mL), and treated with 4 N hydrochloric dioxane (10 mL). The mixture was boiled for 1 hour, cooled to room temperature, and poured into ether. The organic solution was dried over MgSO$_4$, filtered, and concentrated in vacuo. Vacuum distillation of the residue afforded indane-5-carboxaldehyde (1.54 g, 88%) as a colorless liquid. b.p. 88–90° C. at 0.9 mm Hg.

EXAMPLE 142B trans,trans-1-(N-Methyl-N-proppylaminocarbonylmethyl)-2-(4-methoxyphenyl)-4-(5-indanyl)pyrrolidine-3-carboxylic Acid The title compound was prepared by the procedures described in Examples 1 and 49 substituting indane-5-carboxaldehyde for piperonal in Example 49A. $^1$H NMR (300 MHz, CDCl$_3$) (minor rotamer) δ 7.25–7.1 (5H, m), 6.78 (2H, d, J=8 Hz), 3.89 (1 H, d, J=8 Hz), 3.75 (3H, s), 3.50–2.90 (6H, m), 2.88 (6H, t, J=6 Hz), 2.82 (2.80) (3H, s), 2.04 (2H, t, J=8 Hz), 1.48 (2H, septet, J=7 Hz), 0.83 (0.73) (3H, t, J=7 Hz). MS (DCl/NH$_3$) m/e 451 (M+H)$^+$, 473 (M+Na)$^+$. Anal.calc. for C$_{27}$H$_{34}$N$_2$O$_4$.2.5 H$_2$O: C, 65.44; H, 7.93; N, 5.65. Found: C, 65.36; H, 7.45; N, 5.53.

EXAMPLE 143 trans,trans-1-(N-Methyl-N-propylaminocarbonylmethyl)-2-(4-methoxyphenyl)-4-(6-indolyl)pyrrolidine-3-carboxylic Acid The title compound was prepared by the procedures described in Examples 1 and 49 substituting indole-6-carboxaldehyde, prepared by the method of Rapoport, J. Org. Chem. 51: 5106 (1986), for piperonal in Example 49A. $^1$H NMR (300 MHz, CDCl$_3$) (minor rotamer) δ 8.43 (1H, brs), 7.57 (1H, d, J=8 Hz), 7.43 (1H, s), 7.31 (2H, dd, J=6 Hz, 3 Hz), 7.22 (1H, d, J=8 Hz), 7.1 (1H, t, J=3 Hz), 6.78 (2H, dd, J=6 Hz, 3 Hz), 6.45 (1H, m), 3.93 (1H, dd, J=6 Hz, 3 Hz), 3.80 (1H, m), 3.73 (3H, s), 3.60–2.90 (6H, m), 2.86 (2.82) (3H, s), 1.47 (2H, septet, J=7 Hz), 0.83 (0.73) (3H, t, J=7 Hz). MS (DCl/NH$_3$) m/e 450 (M+H)$^+$. Anal.calc. for C$_{26}$H$_{31}$N$_3$O$_4$.0.75 H$_2$O: C, 67.44; H, 7.07; N, 9.07. Found: C, 67.42; H, 7.09; N, 8.91.

EXAMPLE 144 trans,trans-1-(N-Methyl-N-propylaminocarbonylmethyl)-2-(4-methoxyphenyl)-4-(3,4-difluorophenyl)pyrrolidine-3-carboxylic Acid The title compound was prepared by the procedures described in Examples 1 and 49 substituting 3,4-difluorobenzaldehyde for piperonal in Example 49A. $^1$H NMR (300 MHz, CDCl$_3$) (minor rotamer) δ 7.60–7.3 (4H, m), 7.13 (1H, q, J=9 Hz), 6.90 (2H, d, J=8 Hz), 3.90 (1H, m), 3.79 (3H, s), 3.60–2.95 (6H, m), 2.92 (2.78) (3H, d), 1.55 (2H, septet, J=7 Hz), 0.88 (0.73) (3H, t, J=7 Hz). MS (DCl/NH$_3$) m/e 447 (M+H)$^+$. Anal.calc. for C$_{24}$H$_{28}$F$_2$N$_2$O$_4$.1.80 H$_2$O: C, 60.19; H, 6.65; N, 5.85. Found: C, 60.13; H, 6.34; N, 5.84.

EXAMPLE 145 trans,trans-1-(N-Methyl-N-propylaminocarbonylmethyl)-2-(4-methoxyphenyl)-4-(phenyl)pyrrolidine-3-carboxylic Acid The title compound was prepared by the procedures described in Examples 1 and 49 substituting benzaldehyde for piperonal in Example 49A. ¹H NMR (300 MHz, CDCl₃) (minor rotamer) δ 7.53 (4H, d, J=6 Hz), 7.40–7.20 (3H, m), 6.88 (2H, d, J=8 Hz), 3.90 (1H, m), 3.79 (3H, s), 3.70–2.95 (8H, m), 2.90 (2.79) (3H, s), 1.50 (2H, sept, J=7 Hz), 0.87 (0.72) (3H, t, J=7 Hz). MS (DCl/NH₃) m/e 411 (M+H)⁺. Anal.calc. for $C_{24}H_{30}N_2O_4 \cdot 2.00 H_2O$: C, 64.55; H, 7.67; N, 6.27. Found: C, 64.37; H, 7.43; N, 6.29.

EXAMPLE 146 trans,trans-1-(N-Methyl-N-propylaminocarbonylmethyl)-2-(4-methoxyphenyl)-4-(4-hydroxyphenyl)pyrrolidine-3-carboxylic Acid The title compound was prepared by the procedures described in Examples 1 and 49 substituting 4-hydroxybenzaldehyde for piperonal in Example 49A. ¹H NMR (300 MHz, CDCl₃-CD₃OD) (minor rotamer) δ 7.35 (2H, d, J=8 Hz), 7.28 (2H, dd, J=7 Hz, 3 Hz), 6.90 (2H, dd, J=7 Hz, 3 Hz), 6.89 (2H, d, J=8 Hz), 3.81 (3H, s), 3.65 (1H, d, J=8 Hz), 3.70–3.00 (8H, m), 2.92 (2.83) (3H, s), 1.50 (2H, septet, J=7 Hz), 0.87 (0.77) (3H, t, J=7 Hz). MS (DCl/NH₃) m/e 427 (M+H)⁺. Anal.calc. for $C_{24}H_{30}N_2O_5 \cdot 1.00 H_2O$: C, 64.85; H, 7.26; N, 6.30. Found: C, 64.82; H, 7.39; N, 6.46.

EXAMPLE 147 trans,trans-1-(N-Methyl-N-propylaminocarbonylmethyl)-2-(4-methoxyphenyl)-4-(2,4-dimethoxyphenyl)pyrrolidine-3-carboxylic Acid The title compound was prepared by the procedures described in Examples 1 and 49 substituting 2,4-dimethoxybenzaldehyde for piperonal in Example 49A. ¹H NMR (300 MHz, CDCl₃-CD₃OD) (minor rotamer) δ 7.61 (1H, d, J=8 Hz), 7.30 (2H, d, J=8 Hz), 6.82 (2H, d, J=8 Hz), 6.55 (1H, d, J=8 Hz), 6.45 (1H, d, J=3 Hz), 3.90 (1H, m), 3.81 (3H, s), 3.79 (3H, s), 3.77 (3H, s), 3.70–2.90 (8H, m), 2.85 (3H, s), 1.50 (2H, m), sept, J=7 Hz), 0.87 (0.77) (3H, t, J=7 Hz). MS (DCl/NH₃) m/e 471 (M+H)⁺. Anal.calc. for $C_{26}H_{34}N_2O_6 \cdot 0.75 H_2O$: C, 64.51; H, 7.39; N, 5.79. Found: C, 64.65; H, 7.07; N, 5.75.

EXAMPLE 148 trans,trans-1-(N,N-Di(n-butyl)aminocarbonylmethyl)-2-(4-methoxyphenyl)-4-(5-benzo-2,3-dihydrofuranyl)pyrrolidine-3-carboxylic Acid The title compound was prepared by the procedures described in Examples 1 and 49 substituting 2,3-dihydrobenzofuran-5-carboxaldehyde for piperonal in Example 49A. ¹H NMR (300 MHz, CDCl₃) δ 7.31 (2H, d, J=8 Hz), 7.27 (1H, d, J=2 Hz), 7.18 (1H, dd, J=7 Hz, 3 Hz), 6.86 (2H, d, J=8 Hz), 6.72 (1H, d, J=8 Hz), 4.56 (2H, t, J=7 Hz), 3.78 (3H, s), 3.62 (1H, m), 3.50–3.25 (4H, m), 3.17 (2H, t, J=7 Hz), 3.15–2.90 (5H, m), 2.79 (1H, d, J=14 Hz), 1.43 (3H, m), 1.26 (3H, m), 1.08 (2H, m), 0.87 (3H, t, J=7 Hz), 0.81 (3H, t, J=7 Hz). MS (DCl/NH₃) m/e 509 (M+H)⁺. Anal.calc. for $C_{30}H_4CN_2O_5 \cdot 0.25 H_2O$: C, 70.22; H, 7.95; N, 5.46. Found: C, 70.21; H, 7.92; N, 5.36.

EXAMPLE 149 trans,trans-1-(N,N-Di(n-butyl)aminocarbonylmethyl)-2-(4-methoxyphenyl)-4-(4-methoxyphenyl)pyrrolidine-3-carboxylic Acid The title compound was prepared by the procedures described in Examples 1 and 49 substituting 4-methoxybenzaldehyde for piperonal in Example 49A. ¹H NMR (300 MHz, CDCl₃) δ 7.38 (2H, d, J=8 Hz), 7.30 (2H, d, J=8 Hz), 6.87 (4H, dd, J=7 Hz, 3 Hz), 3.78 (3H, s), 3.76 (3H, s), 3.63 (1H, m), 3.50–3.20 (4H, m), 3.15–2.90 (5H, m), 2.78 (1H, d, J=14 Hz), 1.43 (3H, m), 1.27 (3H, m), 1.09 (2H, m), 0.87 (3H, t, J=7 Hz), 0.81 (3H, t, J=7 Hz). MS (DCl/NH₃) m/e 497 (M+H)⁺. Anal.calc. for $C_{29}H_{40}N_2O_5$: C, 70.13; H, 8.12; N, 5.64. Found: C, 69.78; H, 8.10; N, 5.54.

EXAMPLE 150 trans,trans-1-(N,N-Di(n-butyl)aminocarbonylmethyl)-2-(4-methoxyphenyl)-4-(3,4-difluorophenyl)pyrrolidine-3-carboxylic Acid The title compound was prepared by the procedures described in Examples 1 and 49 substituting 3,4-difluorobenzaldehyde for piperonal in Example 49A. ¹H NMR (300 MHz, CDCl₃) δ 7.35 (1H, m), 7.30 (2H, d, J=8 Hz), 7.20–7.00 (2H, m), 6.87 (2H, d, J=8 Hz), 3.78 (3H, s), 3.79 (1H, m), 3.62 (1H, m), 3.50–3.30 (3H, m), 3.23 (1H, m), 3.15–2.90 (4H, m), 2.78 (1H, d, J=14 Hz), 1.43 (2H, m), 1.27 (4H, m), 1.08 (2H, m), 0.85 (3H, t, J=7 Hz), 0.80 (3H, t, J=7 Hz). MS (DCl/NH₃) m/e 503 (M+H)⁺. Anal.calc. for $C_{28}H_{36}F_2N_2O_4 \cdot 1 H_2O$: C, 64.60; H, 7.36; N, 5.38. Found: C, 64.59; H, 7.20; N, 5.35.

EXAMPLE 151 trans,trans-1-(N,N-Di(n-butyl)aminocarbonylmethyl)-2-(4-methoxyphenyl)A-(2,4-dimethoxyphenyl)pyrrolidine-3-carboxylic Acid The title compound was prepared by the procedures described in Examples 1 and 49 substituting 2,4-dimethoxybenzaldehyde for piperonal in Example 49A. ¹H NMR (300 MHz, CDCl₃) δ 7.37 (2H, d, J=8 Hz), 7.20 (1H, d, J=8 Hz), 6.92 (2H, d, J=8 Hz), 6.60 (1H, d, J=3 Hz), 6.49 (1H, dd, J=6 Hz, 2 Hz), 5.35 (1H, d, J=8 Hz), 4.20 (3H, m), 4.10 (3H, s), 3.83 (3H, s), 3.81 (3H, s), 3.75 (3H, m), 3.17 (2H, hep, J=7 Hz), 3.05 (2H, t, J=7 Hz), 1.30 (4H, m), 1.07 (4H, m), 0.87 (3H, t, J=7 Hz), 0.80 (3H, t, J=7 Hz). MS (DCl/NH₃) m/e 527 (M+H)⁺. Anal.calc. for $C_{30}H_{42}N_2O_6 \cdot 1.30$ TFA: C, 58.02; H, 6.47; N, 4.15. Found: C, 57.92; H, 6.43; N, 4.07.

EXAMPLE 152 trans,trans-1-(N,N-Di(n-butyl)aminocarbonylmethyl)-2-phenyl-4-(1,3-benzodioxol-5-yl)pyrrolidine-3-carboxylic Acid The title compound was prepared by the procedures described in Examples 1 and 49 substituting ethyl benzoylacetate in Example 49B. ¹H NMR (300 MHz, CDCl₃) δ 7.50–7.25 (5H, m), 7.04 (1H, d, J=3 Hz), 6.87 (1H, dd, J=7 Hz, 3 Hz), 6.74 (1H, d, J=8 Hz), 5.94 (1H, d, J=4 Hz), 5.92 (1H, d, J=4 Hz), 3.85 (1H, d, J=8 Hz), 3.64 (1H, m), 3.42 (3H, m), 3.27 (2H, m), 3.20–2.90 (5H, m), 2.81 (1H, d, J=14 Hz), 1.43 (2H, m), 1.27 (4H, m), 1.05 (2H, m), 0.85 (3H, t, J=7 Hz), 0.80 (3H, t, J=7 Hz). MS (DCl/NH₃) m/e 481 (M+H)⁺. Anal.calc. for $C_{28}H_{36}N_2O_5$: C, 69.98; H, 7.55; N, 5.83. Found: C, 69.69; H, 7.63; N, 5.71.

EXAMPLE 153 trans,trans-1-(N,N-Di(n-butyl)aminocarbonylmethyl)-2-phenyl4-(5-benzo-2,3-dihydrofuranyl)pyrrolidine-3-carboxylic Acid The title compound was prepared by the procedures described in Examples 1 and 49 substituting ethyl benzoylacetate in Example 49B and 2,3-dihydrobenzofuran-5-carboxaldehyde for piperonal in Example 49A. $^1$H NMR (300 MHz, CDCl$_3$) δ 7.53 (2H, m), 7.40 (4H, m), 7.13 (1H, dd, J=7 Hz, 3 Hz), 6.72 (1H, d, J=8 Hz), 5.40 (1H, d, J=10 Hz), 4.56 (2H, t, J=8 Hz), 4.18 (1H, d, J=14 Hz), 4.07 (2H, m), 3.79 (2H, m), 3.48 (1H, d, J=14 Hz), 3.35 (1H, m), 3.28 (3H, m), 2.95 (2H, m), 1.47 (2H, m), 1.28 (4H, m), 1.10 (2H, m), 0.93 (3H, t, J=7 Hz), 0.78 (3H, t, J=7 Hz). MS (DCl/NH$_3$) m/e 479 (M+H)$^+$. Anal.calc. for C$_{29}$H$_{38}$N$_2$O$_4$.1.10 TFA: C, 62.04; H, 6.52; N, 4.64. Found: C, 61.89; H, 6.44; N, 4.57.

EXAMPLE 154 trans,trans-1-(N,N-Di(n-butyl)
aminocarbonylmethyl)-2-(4-t-butylphenyl)-4-(5-benzo-2,3-dihydrofuranyl)pyrrolidine-3-carboxylic Acid The title compound was prepared by the procedures described in Examples 1 and 49 substituting t-butyl benzoylacetate, prepared by the method of Krapcho et al., Org. Syn. 47:20 (1967) starting from 4-t-butylacetophenone, in Example 49B and 2,3-dihydrobenzofuran-5-carboxaldehyde for piperonal in Example 49A. $^1$H NMR (300 MHz, CDCl$_3$) δ 7.60–7.30 (6H, m), 6.90 (1H, m), 4.50 (2H, m), 3.95 (1H, m), 3.85–2.95 (11H, m), 2.90 (1H, d, J=14 Hz), 1.58 (2H, m), 1.50 (7H, m), 1.41 (6H, s), 1.10 (2H, m), 1.00 (3H, t, J=7 Hz), 0.90 (3H, t, J=7 Hz). MS (DCl/NH$_3$) m/e 535 (M+H)$^+$. Anal.calc. for C$_{33}$H$_{46}$N$_2$O$_4$.0.25 H$_2$O: C, 73.50; H, 8.69; N, 5.19. Found: C, 73.57; H, 8.58; N, 5.14.

EXAMPLE 155 trans,trans-2-(N,N-Di(n-butyl)
aminocarbonylmethyl)-2-(4-methoxyphenyl)-4-(4-fluorophenyl)pyrrolidine-3-carboxylic Acid The title compound was prepared by the procedures described in Examples 1 and 49 substituting 4-fluorobenzaldehyde for piperonal in Example 49A. $^1$H NMR (300 MHz, CDCl$_3$) δ 7.50 (1H, m), 7.42 (1H, dd, J=7 Hz, 3 Hz), 7.36 (2H, d, J=8 Hz), 7.01 (3H, t, J=8 Hz), 6.87 (1H, d, J=8 Hz), 3.83 (1H, m), 3.8 (3H, s), 3.67 (1H, m), 3.47 (3H, m), 3.30–2.90 (5H, m), 2.82 (1H, d, J=14 Hz), 1.43 (2H, m), 1.28 (4H, m), 1.08 (2H, m), 0.90 (3H, t, J=7 Hz), 0.82 (3H, t, J=7 Hz). MS (DCl/NH$_3$) m/e 485 (M+H)$^+$. Anal.calc. for C$_{28}$H$_{37}$FN$_2$O$_4$: C, 69.40; H, 7.70; N, 5.78. Found: C, 69.03; H, 8.00; N, 5.74.

EXAMPLE 156 trans,trans-1-(N,N-Di(n-butyl)
aminocarbonylmethyl)-2-(3-furyl)-4-(1, 3-benzodioxol-5-yl)pyrrolidine-3-carboxylic Acid The title compound was prepared by the procedures described in Examples 1 and 49 substituting β-oxo-3-furanpropionate in Example 49B. $^1$H NMR (300 MHz, CDCl$_3$) δ 7.41 (2H, m), 6.97 (1H, d, J=3 Hz), 6.85 (1H, dd, J=7 Hz, 3 Hz), 6.72 (1H, d, J=8 Hz), 6.42 (1H, s), 5.94 (1H, d, J=4 Hz), 5.92 (1H, d, J=4 Hz), 3.90 (1H, m), 3.70–3.25 (5H, m), 3.20–2.90 (4H, m), 2.85 (1H, d, J=14 Hz), 1.43 (2H, m), 1.40–1.05 (6H, m), 0.90 (6H, m). MS (DCl/NH$_3$) m/e 471 (M+H)$^+$. Anal.calc. for C$_{26}$H$_{34}$N$_2$O$_6$: C, 66.36; H, 7.28; N, 5.95. Found: C, 66.09; H, 7.24; N, 5.87.

EXAMPLE 157 trans,trans-1-(N,N-Di(n-butyl)
aminocarbonylmethyl)-2-(isopropyl)-4-(1,3-benzodioxol-5-yl)pyrrolidine-3-carboxylic Acid The title compound was prepared by the procedures described in Examples 1 and 49 substituting ethyl isobutyrylacetate in Example 49B. $^1$H NMR (300 MHz, CDCl$_3$) δ 6.85 (1H, d, J=2 Hz), 6.76 (1H, dd, J=6 Hz, 2 Hz), 6.71 (1H, d, J=8 Hz), 5.92 (2H, s), 3.75 (1H, d, J=14 Hz), 3.66 (1H, q, J=7 Hz), 3.42 (3H, m), 3.25 (3H, m), 3.11 (2H,m), 2.83 (1H, t, J=7 Hz), 1.88 (1H, m), 1.55 (4H, m), 1.32 (4H, m), 0.92 (12H, m), MS (DCl/NH$_3$) m/e 447 (M+H)$^+$. Anal.calc. for C$_{25}$H$_{38}$N$_2$O$_5$.0.50 H$_2$O: C, 65.91; H, 8.63; N, 6.15. Found: C, 66.07; H, 8.10; N, 6.03.

EXAMPLE 158 trans,trans-1-(N,N-Di(n-butyl)
aminocarbonylmethyl)-2-(4-t-butylphenyl)-4-(1,3-benzodioxol-5-yl)pyrrolidine-3-carboxylic Acid The title compound was prepared by the procedures described in Examples 1 and 49 substituting ethyl 4-t-butylbenzoylacetate, prepared by the method of Krapcho et al., Org. Syn. 47: 20 (1967) starting with 4-t-butylacetophenone), in Example 49B. $^1$H NMR (300 MHz, CDCl$_3$) δ 7.32 (4H, d, J=3 Hz), 7.04 (1H, d, J=2 Hz), 6.87 (1H, dd, J=8 Hz, 3 Hz), 6.74 (1H, d, J=9 Hz), 5.94 (1H, d, J=4 Hz), 5.92 (1H, d, J=4 Hz), 3.77 (1H, d, J=14 Hz), 3.65–3.25 (5H, m), 3.15–2.85 (4H, m), 2.73 (1H, d, J=14 Hz), 1.45 (2H, m), 1.29 (13H, s), 1.00 (2H, m), 0.86 (3H, t, J=7 Hz), 0.76 (3H, t, J=7 Hz). MS (DCl/NH$_3$) m/e 537 (M+H)$^+$. Anal.calc. for C$_{32}$H$_{44}$N$_2$O$_5$: C, 71.61; H, 8.26; N, 5.22. Found: C, 71.43; H, 8.09; N, 5.11.

EXAMPLE 159 trans,trans-1-(N,N-Di(n-butyl)
aminocarbonylmethyl)-2-(4-t-butylphenyl)-4-(5-benzo-2,3-dihydrofuranyl)pyrrolidine-3-carboxylic Acid The title compound was prepared by the procedures described in Examples 1 and 49 substituting ethyl isobutyrylacetate in Example 49B and 2,3-dihydrobenzofuran-5-carboxaldehyde for piperonal in Example 49A. $^1$H NMR (300 MHz, CDCl$_3$) δ 7.30 (1H, s), 7.13 (1H, dd, J=7 Hz, 2 Hz), 6.82 (1H, d, J=8 Hz), 4.68 (2H, t, J=8 Hz), 4.48 (1H, s), 3.19 (3H, m), 3.80 (3H, m), 3.48 (2H, m), 3.3 (5H, m), 2.41 (1H, m), 1.65 (4H, m), 1.44 (4H, m), 1.21 (3H, d, J=5 Hz), 1.17 (3H, d, J=5 Hz), 1.05 (6H, m). MS (DCl/NH$_3$) m/e 445 (M+H)$^+$. Anal.calc. for C$_{26}$H$_{40}$N$_2$O$_4$.1.2 TFA: C, 58.67; H, 7.14; N, 4.8.2 Found: C, 58.54; H, 7.25; N, 4.74.

EXAMPLE 160 trans,trans-1-(N,N-Di(n-butyl)
aminocarbonylmethyl)-2-(anti4-methoxycyclohexyl)-4-(1,3-benzodioxol-5-yl)
pyrrolidine-3-carboxylic Acid

EXAMPLE 160A syn and anti Ethyl 4-methoxycyclohexanoylacetate

Syn, Anti-4-Methoxycyclohexane carboxylic Acid (5.00 g, 31.6 mmol) and carbonyldiimidazole (6.15 g, 37.9 mmol, 1.2 eq) were stirred in anhydrous tetrahydrofuran (50 mL) for 6 hours at room temperature. At the same time, magnesium chloride (3.01 g, 31.6 mmol) and ethyl malonate potassium salt (7.52 g, 44.2 mmol, 1.4 equivalents) were stirred in anhydrous tetrahydrofuran (75 mL) for 6 hours at 50° C. The mixture was cooled to room temperature, and the imidazole-acid mixture added to it. The reaction stirred overnight at room temerature. The solvents were removed under reduced pressure, and the residue was taken up in chloroform/water. The organic phase washed with 5% potassium bisulfate, water, and brine, dried with magnesium sulfate, filtered, and concentrated under reduced pressure. The residue was purified by flash chromatography on 175 g silica gel, eluting with 20% ethyl acetate in hexanes. Pure fractions of the syn and anti methoxycyclohexyl 0-keto esters were obtained. The solvents were removed under reduced pressure to yield the trans-4-methoxycyclohexyl β-keto ester (914 mg) as a colorless oil and the cis 4-methoxycyclohexyl β-keto ester (1.07 g) as a colorless oil.

EXAMPLE 160B trans,trans-1-(N,N-Di(n-butyl) aminocarbonylmethyl)-2-(anti4-methoxycyclohexyl)-4-(1,3-benzodioxol-5-yl) pyrrolidine-3-carboxylic Acid The title compound was prepared by the procedures described in Examples 1 and 49 substituting the anti-compound resulting from Example 160A in Example 49B. $^1$H NMR (300 MHz, CDCl$_3$) δ 6.84 (1H, d, J=2 Hz), 6.76 (1H, dd, J=7 Hz, 2 Hz), 6.61 (1H, d, J=8 Hz), 5.92 (2H, s), 3.69 (2H, m), 3.50–3.27 (5H, m), 3.26 (3H, s), 3,25–3.00 (3H, m), 2.88 (1H, m), 1.95 (2H, m), 1.62 (7H, m), 1.33 (9H, m), 0.97 (3H, t, J=7 Hz), 0.92 (3H, t, J=7 Hz). MS (DCl/NH$_3$) m/e 517 (M+H)$^+$. Anal.calc. for C$_{29}$H$_{44}$N$_2$O$_6$.0.50 H$_2$O: C, 66.26; H, 8.63; N, 5.33. Found: C, 66.27; H, 8.50; N, 5.13.

EXAMPLE 161 trans,trans-1-(N,N-Di(n-butyl) aminocarbonylmethyl)-2-(syn-4-methoxycyclohexyl)-4-(1,3-benzodioxol-5-yl) pyrrolidine-3-carboxylic Acid The title compound was prepared by the procedures described in Examples 1 and 49 substituting the syn-compound resulting from Example 160A in Example 49B. $^1$H NMR (300 MHz, CDCl$_3$) δ 6.84 (1H, d, J=2 Hz), 6.77 (1H, dd, J=6 Hz, 2 Hz), 6.61 (1H, d, J=8 Hz), 5.92 (2H, s), 3.65 (2H, m), 3.42 (2H, m), 3.32 (3H, s), 3.30–3.00 (6H, m), 2.82 (1H, m), 2.10 (2H, m), 1.83 (2H, m), 1.52 (6H, m), 1.33 (4H, m), 1.20–1.00 (4H, m), 0.96 (3H, t, J=7 Hz), 0.91 (3H, t, J=7 Hz). MS (DCl/NH$_3$) m/e 517 (M+H)$^+$. Anal.calc. for C$_{29}$H$_{44}$N$_2$O$_6$.0.30 H$_2$O: C, 66.72; H, 8.61; N, 5.37. Found: C, 66.76; H, 8.65; N, 5.28.

EXAMPLE 162 trans,trans-1-(N,N-Di(n-butyl) aminocarbonylmethyl)-2,4-di(5-benzo-2,3-dihydrofuranyl)pyrrolidine-3-carboxylic Acid

EXAMPLE 162A

5-Acetyl-2, 3-dihydrobenzofuran

To a 0° C. solution of acetyl chloride (1.64 mL, 23.0 mmol, 1.3 equivalents) in methylene chloride (30 mL) was added stannic chloride (2.49 mL, 21.3 mmol, 1.2 equivalents), maintaining the temperature below 5° C. The solution was stirred 15 minutes at 0° C., and then a solution of 2,3-dihydrofuran (2.00 mL, 17.7 mmol) in methylene chloride (5 mL) was added dropwise while maintaining the temperature below 8° C. The dark red solution was stirred 1 hour at 2° C. and then poured into 50 mL of ice water. The reaction was stirred an additional 30 minutes, and the layers were separated. The organic layer was washed with water and aqueous sodium bicarbonate, dried over magnesium sulfate, filtered, and concentrated under reduced pressure. The residue was purified by flash chromatography on 150 g silica gel, eluting with 18% ethyl acetate in hexanes. The solvents were removed under reduced pressure to yield the title compound (2.68 g, 93%) as a yellow solid.

EXAMPLE 162B trans,trans-1-(N,N-Di(n-butyl) aminocarbonylmethyl)-2.4-di(5-benzo-2,3-dihydrofuranyl)pyrrolidine-3-carboxylic Acid The title compound was prepared by the procedures described in Examples 1 and 49 substituting the compound resulting from Example 162A in Example 49B and 2,3-dihydrobenzofuran-5-carboxaldehyde for piperonal in Example 49A. $^1$H NMR (300 MHz, CDCl$_3$) δ 7.43 (1H, s), 7.38 (1H, s), 7.06 (2H, m), 6.75 (1H, d, J=6 Hz), 6.70 (1H, d, J=6 Hz), 5.40 (1H, d, J=9 Hz), 4.58 (4H, q, J=7 Hz), 4.16 (1H, d, J=14 Hz), 4.09 (2H, m), 3.82 (2H, m), 3.57 (1H, d, J=14 Hz), 3.38 (1H, m), 3.30–3.05 (6H, m), 2.95 (2H, q, J=6 Hz), 1.50 (2H, m), 1.30 (4H, m), 1.15 (2H, m), 0.94 (3H, t, J=7 Hz), 0.83 (3H, t, J=7 Hz). MS (DCl/NH$_3$) m/e 521 (M+H)$^+$. Anal.calc. for C$_{31}$H$_{40}$N$_2$O$_5$. 1.25 TFA: C, 60.67; H, 6.27; N, 4.22. Found: C, 60.49; H, 6.18; N, 4.13.

EXAMPLE 163 trans,trans-1-(N,N-Di(n-butyl) aminocarbonylmethyl)-2-(3-furyl)-4-(5-benzo-2,3-dihydrofuranyl)pyrrolidine-3-carboxylic Acid The title compound was prepared by the procedures described in Examples 1 and 49 substituting ethyl β-oxo-3-furanpropionate in Example 49B and 2,3-dihydrobenzofuran-5-carboxaldehyde for piperonal in Example 49A. $^1$H NMR (300 MHz, CDCl$_3$) δ 7.42 (1H, m), 7.38 (1H, m), 7.13 (1H, s), 7.16 (1H, dd, J=7 Hz, 3 Hz), 6.70 (1H, d, J=8 Hz), 6.41 (1H, m), 4.57 (2H, t, J=7 Hz), 3.95 (1H, d, J=8 Hz), 3.63 (1H, m), 3.55 (1H, d, J=14), 3.50–3.25 (4H, m), 3.18 (2H, t, J=6 Hz), 3.15–2.95 (3H, m), 2.87 (1H, d, J=14 Hz), 1.45 (4H, m), 1.35–1.10 (4H, m), 0.85 (6H, m). MS (DCl/NH$_3$) m/e 469 (M+H)$^+$. Anal.calc. for C$_{27}$H$_{36}$N$_2$O$_5$.0.25 H$_2$O: C, 68.55; H, 7.78; N, 5.92. Found: C, 68.62; H, 7.68; N, 5.82.

EXAMPLE 164 trans,trans-1-(N,N-Di(n-butyl) aminocarbonylmethyl)-2-(4-methoxyphenyl)-4-(3-fluorophenyl)pyrrolidine-3-carboxalic acid The title compound was prepared by the procedures described in Examples 1 and 49 substituting 3-fluorobenzenecarboxaldehyde for piperonal in Example 49A. $^1$H NMR (300 MHz, CDCl$_3$) δ 7.30 (2H, d, J=8 Hz), 7.22 (2H, m), 6.91 (1H, m), 6.86 (2H, d, J=8 Hz), 3.79 (1H, m), 3.78 (3H, s), 3.68 (1H, m), 3.55–3.37 (3H, m), 3.29 (1H, m), 3.15–2.90 (5H, m), 2.78 (1H, d, J=14 Hz), 1.43 (2H, m), 1.25 (4H, m), 1.07 (2H, m), 0.87 (3H, t, J=7 Hz), 0.80 (3H, t, J=7 Hz). MS (DCl/NH$_3$) m/e 485 (M+H)$^+$. Anal.calc. for C$_{28}$H$_{37}$FN$_2$O$_4$.0.25 H$_2$O: C, 68.76; H, 7.73; N, 5.73. Found: C, 68.87; H, 7.69; N, 5.67.

EXAMPLE 165 trans,trans-1-(N,N-Di(n-butyl) aminocarbonylmethyl)-2-(4-methoxyphenyl)-4-(3-pyridyl)pyrrolidine-3-carboxylic Acid The title compound was prepared by the procedures described in Examples 1 and 49 substituting 3-pyridinecarboxaldehyde for piperonal in Example 49A. The nitro styrene was prepared by the method of Bourguignon, et al., Can. J. Chem. 63: 2354 (1985). $^1$H NMR (300 MHz, CDCl$_3$) δ 8.82 (1H, bs), 8.73 (1H, bd, J=9 Hz), 8.62 (1H, bd, J=7 Hz), 7.78 (1H, bdd, J=9 Hz, 3 Hz), 7.38 (2H, d, J=10 Hz), 6.90 (2H, d, J=10 Hz), 4.39 (1H, d, J=12 Hz), 3.95 (1H, m), 3.80 (3H, s), 3.79 (1H, m), 3.68 (1H, d, J=18 Hz), 3.50–3.30 (3H, m), 3.25–2.90 (6H, m), 1.47 (2H, m), 1.31 (4H, m), 1.20 (2H, m), 0.92 (3H, t, J=7 Hz), 0.83 (3H, t, J=7 Hz). MS (DCl/NH$_3$) m/e468 (M+H)$^+$. Anal.calc. for C$_{27}$H$_{37}$N$_3$O$_4$. 1.65 TFA: C, 55.50; H, 5.94; N, 6.41. Found: C, 55.53; H, 5.90; N, 6.27.

EXAMPLE 166 trans,trans-1-(N,N-Di(n-butyl) aminocarbonylmethyl)-2-(2-fluorophenyl)-4-(1,3-benzodioxol-5-yl)pyrrolidine-3-carboxylic Acid The title compound was prepared by the procedures described in Examples 1 and 49 substituting ethyl 2-fluorobenzoylacetate in Example 49B. $^1$H NMR (300 MHz, CDCl$_3$) δ 7.52 (1H, dt, J=7 Hz, 3 Hz), 7.25 (1H, m), 7.13 (1H, dt, J=7 Hz, 3 Hz), 7.02 (2H, m), 6.88 (1H, dd, J=7 Hz, 3 Hz), 6.73 (1H, d, J=8 Hz), 5.93 (1H, d, J=4 Hz), 5.92 (1H, d, J=4 Hz), 4.25 (1H, d, J=9 Hz), 3.68 (1H, m), 3.42 (3H, m), 3.39 (1H, m), 3.20–2.95 (4H, m), 2.91 (1H, d, J=14 Hz), 1.45 (3H, m), 1.26 (3H, m), 1.08 (2H, m), 0.87 (3H, t, J=7 Hz), 0.81 (3H, t, J=7 Hz). MS (DCl/NH$_3$) m/e 499 (M+H)$^+$. Anal.calc. for C$_{28}$H$_{35}$FN$_2$O$_5$.0.25 H$_2$O: C, 66.85; H, 7.11; N, 5.57. Found: C, 66.51; H, 6.67; N, 5.18.

EXAMPLE 167 trans,trans-1-(N,N-Di(n-butyl) aminocarbonylmethyl)-2-(3-fluorophenyl)-4-(1,3-benzodioxol-5-yl)pyrrolidine-3-carboxylic Acid The title compound was prepared by the procedures described in Examples 1 and 49 substituting ethyl 3-fluorobenzoylacetate in Example 49B. $^1$H NMR (300 MHz, CDCl$_3$) δ 7.38 (1H, m), 7.18 (1H, d, J=7 Hz), 7.15 (1H, m), 7.00 (1H, d, J=2 Hz), 6.95 (1H, m), 6.86 (1H, dd, J=7 Hz, 2 Hz), 6.75 (1H, d, J=8 Hz), 5.93 (1H, d, J=4 Hz), 5.92 (1H, d, J=4 Hz), 3.94 (1H, d, J=14 Hz), 3.63 (1H, m), 3.42 (3H, m), 3.35–2.95 (5H, m), 2.87 (1H, d, J=14 Hz), 1.44 (3H, m), 1.27 (3H, m), 1.10 (2H, m), 0.88 (3H, t, J=7 Hz), 0.81 (3H, t, J=7 Hz). MS (DCl/NH$_3$) m/e 499 (M+H)$^+$. Anal.calc. for C$_{28}$H$_{35}$FN$_2$O$_5$: C, 67.45; H, 7.08; N, 5.62. Found: C, 67.32; H, 7.05; N, 5.40.

EXAMPLE 168 trans,trans-1-(4—N,N-Di(n-butyl)aminophenyl)-2-(4-methoxyphenyl)-4-(1,3-benzodioxol-5-yl) pyrrolidine-3-carboxylic Acid 4-Nitro-1-fluorobenzene, ethyl trans,trans-2-(4-methoxyphenyl)-4-(1,3-benzodioxol-5-yl)-pyrrolidine-3-carboxylate (the compound resulting from Example 6A), and diisopropylethylamine are heated in dioxane to give ethyl trans,trans-2-(4-methoxyphenyl)-4-(1,3-benzodioxol-5-yl)-1-(4-nitrophenyl)-pyrrolidine-3-carboxylate. The nitro compound is hydrogenated to give the corresponding aminophenyl compound. The aminophenyl compound is reacted with butyraldehyde and sodium cyanoborohydride according to the method of Borch, J. Am Chem. Soc. 93: 2897 (1971) to give the corresponding N,N-dibutylaminophenyl compound. Hydrolysis with sodium hydroxide using the method of Example 1D affords the title compound.

EXAMPLE 169 trans-1-(2-N,N-Dibutylaminopyrimidin-4-yl)-2-(4-methoxyphenyl)-4-(1,3-benzodioxol-5-yl) pyrrolidine-3-carboxylic Acid 2-(Dibutylamino)-4-chloropyrimidine is prepared from 2,4-dichloropyrimidine according to the method of Gershon, J. Heterocyclic Chem. 24: 205 (1987) and reacted with ethyl trans,trans-2-(4-methoxyphenyl)-4-(1,3-benzodioxol-5-yl)-pyrrolidine-3-carboxylate (the compound resulting from Example 6A) and diisoproplyethlamine in dioxane with heating to give the intermediate ethyl ester, which is hydrolyzed with sodium hydroxide using the method of Example 1D to the title compound.

EXAMPLES 170–266

Using the procedures described in Examples 1, 4, 5, 7, 8 and 9 and Scheme X, the following compounds can be prepared.

Ex. No.—Name
- 170 trans,trans-2-(4-Methoxyphenyl)-4-(1,3-benzodioxol-5-yl)-1-(isopropylaminocarbonylmethyl)-pyrrolidine-3-carboxylic acid;
- 171 trans,trans-2-(4-Methoxyphenyl)-4-(1,3-benzodioxol-5-yl)-1-(ethylaminocarbonylmethyl)-pyrrolidine-3-carboxylic Acid;
- 172 trans,trans-2-(4-Methoxyphenyl)-4-(1,3-benzodioxol-5-yl)-1-(1-methylpropylaminocarbonylmethyl)-pyrrolidine-3-carboxylic Acid;
- 173 trans,trans-2-(4-Methoxyphenyl)-4-(1,3-benzodioxol-5-yl)-1-(phenylaminocarbonylmethyl)-pyrrolidine-3-carboxylic Acid;
- 174 trans,trans-2-(4-Methoxyphenyl)-4-(1,3-benzodioxol-5-yl)-1-(piperidinylcarbonylmethyl)-pyrrolidine-3-carboxylic Acid;
- 175 trans,trans-2-(4-Methoxyphenyl)-4-(1,3-benzodioxol-5-yl)-1-(1-(propylaminocarbonyl)ethyl)-pyrrolidine-3-carboxylic Acid;
- 176 trans,trans-2-(4-Methoxyphenyl)-4-(1,3-benzodioxol-5-yl)-1-(α-(propylaminocarbonyl) benzyl)-pyrrolidine-3-carboxylic acid;
- 177 trans,trans-2-(4-Methoxyphenyl)-4-(1,3-benzodioxol-5-yl)-1-(bis-(propylaminocarbonyl) methyl)-pyrrolidine-3-carboxylic acid;
- 178 trans,trans-2-(4-Methoxyphenyl)-4-(1,3-benzodioxol-5-yl)-1-(2-(propylaminocarbonyl)ethyl)-pyrrolidine-3-carboxylic Acid;
- 179 trans,trans-2-(4-Methoxyphenyl)-4-(1,3-benzodioxol-5-yl)-1-(propylaminosulfonylmethyl)-pyrrolidine-3-carboxylic Acid;
- 180 trans$_1$trans-2-(4-Methoxyphenyl)-4-(1,3-benzodioxol-5-yl)-1-(2-phenethyl)-pyrrolidine-3-carboxylic Acid;
- 181 trans,trans-2-(4-Methoxyphenyl)-4-(1,3-benzodioxol-5-yl)-1-(pentanoylmethyl)-pyrrolidine-3-carboxylic Acid;
- 182 trans,trans-2-(4-Methoxyphenyl)-4-(1,3-benzodioxol-5-yl)-1-(benzoylmethyl)-pyrrolidine-3-carboxylic Acid;
- 183 trans,trans-2-(4-Methoxyphenyl)-4-(1,3-benzodioxol-5-yl)-1-(hexyl)-pyrrolidine-3-carboxylic Acid;
- 184 trans,trans-2-(4-Methoxyphenyl)-4-(1,3-benzodioxol-5-yl)-1-(2-hexynyl)-pyrrolidine-3-carboxylic Acid;

185 trans,trans-2-(4-Methoxyphenyl)-4-(1,3-benzodioxol-5-yl)-1-(propoxymethylcarbonyl-pyrrolidine-3-carboxylic Acid;

186 trans,trans-2-(4-Methoxyphenyl)-4-(1,3-benzodioxol-5-yl)-1-(phenylacetyl)-pyrrolidine-3-carboxylic Acid;

187 trans,trans-2-(4-Methoxyphenyl)-4-(1,3-benzodioxol-5-yl)-1-(anilinylcarbonyl)-pyrrolidine-3-carboxylic Acid;

188 trans,trans-2-(4-Methoxyphenyl)-4-(1,3-benzodioxol-5-yl)-1-(2-acetylaminoethyl)-pyrrolidine-3-carboxylic Acid;

189 trans,trans-2-(4-Methoxyphenyl)-4-(1,3-benzodioxol-5-yl)-1-(2-phenoxyethyl)-pyrrolidine-3-carboxylic Acid;

190 trans,trans-2-(4-Methoxyphenyl)-4-(1,3-benzodioxol-5-yl)-1-(2-benzodioxanylmethyl)-pyrrolidine-3-carboxylic Acid;

191 trans,trans-2-(4-Methoxyphenyl)-4-(1,3-benzodioxol-5-yl)-1-(2-tetrahydrofuranylmethyl)-pyrrolidine-3-carboxylic Acid;

192 trans,trans-2-(4-Methoxyphenyl)-4-(1,3-benzodioxol-5-yl)-1-(2-(propylaminocarbonylamino)ethenyl)-pyrrolidine-3-carboxylic Acid;

193 trans,trans-2-(4-Methoxyphenyl)-4-(1,3-benzodioxol-5-yl)-1-(2-(propylaminocarbonylamino)ethyl)-pyrrolidine-3-carboxylic acid;

194 trans,trans-2-(4-Methoxyphenyl)-4-(1,3-benzodioxol-5-yl)-1-(3-oxohex-1-enyl)-pyrrolidine-3-carboxylic Acid;

195 trans,trans-2-(2,4-Dimethoxyphenyl)-4-(1,3-benzodioxol-5-yl)-1-(propylaminocarbonylmethyl)-pyrrolidine-3-carboxylic acid;

196 trans,trans-2-(2-Carboxy-4-methoxyphenyl)-4-(1,3-benzodioxol-5-yl)-1-(propylaminocarbonylmethyl)-pyrrolidine-3-carboxylic Acid;

197 trans,trans-2-(2-Aminocarbonyl-4-methoxyphenyl)-4-(1,3-benzodioxol-5-yl)-1-(propylaminocarbonylmethyl)-pyrrolidine-3-carboxylic Acid;

198 trans,trans-2-(2-Methanesulfonamido-4-methoxyphenyl)-4-(1,3-benzodioxol-5-yl)-1-(propylaminocarbonylmethyl)-pyrrolidine-3-carboxylic Acid;

199 trans,trans-2-(2-Aminocarbonylmethoxy-4-methoxyphenyl)-4-(1,3-benzodioxol-5-yl)-1-(propylaminocarbonylmethyl)-pyrrolidine-3-carboxylic Acid;

200 trans,trans-2-(2-Methoxyethoxy-4-methoxyphenyl)-4-(1,3-benzodioxol-5-yl)-1-(propylaminocarbonylmethyl)-pyrrolidine-3-carboxylic Acid;

201 trans,trans-2-(2-Caroxymethoxy-4-methoxyphenyl)-4-(1,3-benzodioxol-5-yl)-1-(propylaminocarbonylmethyl)-pyrrolidine-3-carboxylic Acid;

202 trans,trans-2-(4-Methoxy-2-tetrazolylmethoxyphenyl)-4-(1,3-benzodioxol-5-yl)-1-(propylaminocarbonylmethyl)-pyrrolidine-3-carboxylic Acid;

203 trans,trans-2-(2-Allyloxy-4-methoxyphenyl)-4-(1,3-benzodioxol-5-yl)-1-(propylaminocarbonylmethyl)-pyrrolidine-3-carboxylic Acid;

204 trans,trans 2,4-Bis(4-methoxyphenyl)-1-(propylaminocarbonylmethyl)-pyrrolidine-3-carboxylic Acid;

205 trans,trans 2,4-Bis(1,3-benzodioxol-5-yl)-1-(propylaminocarbonylmethyl)-pyrrolidine-3-carboxylic Acid;

206 trans,trans-2-(4-Methoxyphenyl)-4-(1,3-benzodioxol-5-yl)-1-(N-methyl-N-propylaminocarbonylmethyl)-pyrrolidine-3-carboxylic Acid;

207 trans,trans-2-(4-Methoxyphenyl)-4-(1,3-benzodioxole-5-yl)-1-(N-methyl-N-butylaminocarbonyl)-pyrrolidine-3-carboxylic acid;

208 trans,trans-2-(4-Methoxyphenyl)-4-(1,3-benzodioxol-5-yl)-1-(N-methyl-N-(4-methoxyphenyl)aminocarbonyl)-3-pyrrolidine-3-carboxylic Acid;

209 trans,trans-2-(4-Methoxyphenyl)-4-(1,3-benzodioxol-5-yl)-1-(N-methyl-N-phenylaminocarbonyl)-pyrrolidine-3-carboxylic acid;

210 trans,trans-2-(4-Methoxyphenyl)-4-(1,3-benzodioxol-5-yl)-1-(N-methyl-N-allylaminocarbonylmethyl)-pyrrolidine-3-carboxylic Acid;

211 trans,trans-2-(4-Methoxyphenyl)-4-(1,3-benzodioxol-5-yl)-1-(N-methyl-N-(n-butyl)aminocarbonylmethyl)-pyrrolidine-3-carboxylic Acid;

212 trans,trans-2-(4-Methoxyphenyl)-4-(1,3-benzodioxol-5-yl)-1-(N-methyl-N-isobutylaminocarbonylmethyl)-pyrrolidine-3-carboxylic Acid;

213 trans,trans-2-(4-Methoxyphenyl)-4-(1,3-benzodioxol-5-yl)-1-(N-methyl-N-cyclopentylaminocarbonylmethyl)-pyrrolidine-3-carboxylic Acid;

214 trans,trans-2-(4-Methoxyphenyl)-4-(1,3-benzodioxol-5-yl)-1-(N-methyl-N-(2-methoxyethyl)aminocarbonyl)-pyrrolidine-3-carboxylic Acid;

215 trans,trans-2-(4-Methoxyphenyl)-4-(1,3-benzodioxol-5-yl)-1-(N-methyl-N-butoxyethylaminocarbonyl)-pyrrolidine-3-carboxylic Acid;

216 trans,trans-2-(1,3-Benzodioxol-5-yl)-4-(4-methoxyphenyl)-1-(N-methyl-N-propylaminocarbonylmethyl)-pyrrolidine-3-carboxylic Acid;

217 trans,trans-2-(4-Methoxyphenyl)-4-(1,4-benzodioxan-6-yl)-1-(N-methyl-N-propylaminocarbonylmethyl)-pyrrolidine-3-carboxylic Acid;

218 trans,trans-2-(4-Methoxyphenyl)-4-(1,3-benzodioxol-5-yl)-1-(N-methyl-N-isopropylaminocarbonylmethyl)-pyrrolidine-3-carboxylic Acid;

219 trans,trans-2-(4-Methoxyphenyl)-4-(1,3-benzodioxol-5-yl)-1-(N-methyl-N-ethylaminocarbonylmethyl)-pyrrolidine-3-carboxylic Acid;

220 trans,trans-2-(4-Methoxyphenyl)-4-(1,3-benzodioxol-5-yl)-1-(N-methyl-N-(1-methylpropyl)aminocarbonylmethyl)-pyrrolidine-3-carboxylic Acid;

221 trans,trans-2-(4-Methoxyphenyl)-4-(1,3-benzodioxol-5-yl)-1-(N-methyl-N-phenylaminocarbonylmethyl)-pyrrolidine-3-carboxylic Acid;

222 trans,trans-2-(4-Methoxyphenyl)-4-(1,3-benzodioxol-5-yl)-1-(1-(N-methyl-N-propylaminocarbonyl)ethyl)-pyrrolidine-3-carboxylic Acid;

223 trans,trans-2-(4-Methoxyphenyl)-4-(1,3-benzodioxol-5-yl)-1-(α-(N-methyl-N-propylaminocarbonyl)benzyl)-pyrrolidine-3-carboxylic Acid;

224 trans,trans-2-(4-Methoxyphenyl)-4-(1,3-benzodioxol-5-yl)-1-(N-ethyl-N-propylaminocarbonylmethyl)-pyrrolidine-3-carboxylic Acid;

225 trans,trans-2-(4-Methoxyphenyl)-4-(1,3-benzodioxole-5-yl)-1-(N-ethyl-N-butylaminocarbonyl)-pyrrolidine-3-carboxylic Acid;

226 trans,trans-2-(4-Methoxyphenyl)-4-(1,3-benzodioxol-5-yl)-1-(N-ethyl-N-(4-methoxyphenyl)aminocarbonyl)-3-pyrrolidine-3-carboxylic Acid;

227 trans,trans-2-(4-Methoxyphenyl)-4-(1,3-benzodioxol-5-yl)-1-(N-ethyl-N-phenylaminocarbonyl)-pyrrolidine-3-carboxylic acid;

228 trans,trans-2-(4-Methoxyphenyl)-4-(1,3-benzodioxol-5-yl)-1-(N-ethyl-N-allylaminocarbonylmethyl)-pyrrolidine-3-carboxylic acid;

229 trans,trans-2-(4-Methoxyphenyl)-4-(1,3-benzodioxol-5-yl)-1-(N-ethyl-N-isobutylaminocarbonylmethyl)-pyrrolidine-3-carboxylic Acid;

230 trans,trans-2-(4-Methoxyphenyl)-4-(1,3-benzodioxol-5-yl)-1-(N-ethyl-N-cyclopentylaminocarbonylmethyl)-pyrrolidine-3-carboxylic Acid;

231 trans,trans-2-(4-Methoxyphenyl)-4-(1,3-benzodioxol-5-yl)-1-(N-ethyl-N-methoxyethylaminocarbonyl)-pyrrolidine-3-carboxylic Acid;

232 trans,trans-2-(4-Methoxyphenyl)-4-(1,3-benzodioxol-5-yl)-1-(N-ethyl-N-butoxyethylaminocarbonyl)-pyrrolidine-3-carboxylic Acid;

233 trans,trans-2-(1,3-Benzodioxol-5-yl)-4-(4-methoxyphenyl)-1-(N-ethyl-N-propylaminocarbonylmethyl)-pyrrolidine-3-carboxylic Acid;

234 trans,trans-2-(4-Methoxyphenyl)-4-(1,4-benzodioxan-6-yl)-1-(N-ethyl-N-propylaminocarbonylmethyl)-pyrrolidine-3-carboxylic Acid;

235 trans,trans-2-(4-Methoxyphenyl)-4-(1,3-benzodioxol-5-yl)-1-(N-ethyl-N-isopropylaminocarbonylmethyl)-pyrrolidine-3-carboxylic Acid;

236 trans,trans-2-(4-Methoxyphenyl)-4-(1,3-benzodioxol-5-yl)-1-(N,N-diethylaminocarbonylmethyl)-pyrrolidine-3-carboxylic acid;

237 trans,trans-2-(4-Methoxyphenyl)-4-(1,3-benzodioxol-5-yl)-1-(N-ethyl-N-(1-methylpropyl)aminocarbonylmethyl)-pyrrolidine-3-carboxylic Acid;

238 trans,trans-2-(4-Methoxyphenyl)-4-(1,3-benzodioxol-5-yl)-1-(N-ethyl-N-phenylaminocarbonylmethyl)-pyrrolidine-3-carboxylic Acid;

239 trans,trans-2-(4-Methoxyphenyl)-4-(1,3-benzodioxol-5-yl)-1-(1-(N-ethyl-N-propylaminocarbonyl)ethyl)-pyrrolidine-3-carboxylic Acid;

240 trans,trans-2-(4-Methoxyphenyl)-4-(1,3-benzodioxol-5-yl)-1-(α-(N-ethyl-N-propylaminocarbonyl)benzyl)-pyrrolidine-3-carboxylic Acid;

241 trans,trans-2-(4-Methoxyphenyl)-4-(1,3-benzodioxol-5-yl)-1-(N-methyl-N-isobutylaminocarbonylmethyl)-pyrrolidine-3-carboxylic Acid;

242 trans,trans-2-(4-Methoxyphenyl)-4-(1,3-benzodioxol-5-yl)-1-(N-methyl-N-cyclohexylaminocarbonylmethyl)-pyrrolidine-3-carboxylic Acid;

243 trans,trans-2-(4-Methoxyphenyl)-4-(1,3-benzodioxol-5-yl)-1-(N,N-dipropylaminocarbonylmethyl)-pyrrolidine-3-carboxylic acid;

244 trans,trans-2-(4-Methoxyphenyl)-4-(1,3-benzodioxol-5-yl)-1-(isobutyloxyethyl)-pyrrolidine-3-carboxylic Acid;

245 trans,trans-2-(4-Methoxyphenyl)-4-(1,3-benzodioxol-5-yl)-1-(butylsulfonyl)-pyrrolidine-3-carboxylic Acid;

246 trans,trans-2-(4-Methoxyphenyl)-4-(1,3-benzodioxol-5-yl)-1-(isopropylsulfonylaminoethyl)-pyrrolidine-3-carboxylic Acid;

247 trans,trans-2-(4-Methoxyphenyl)-4-(1,3-benzodioxol-5-yl)-1-(ethoxymethylcarbonylmethyl)-pyrrolidine-3-carboxylic Acid;

248 trans,trans-2-(4-Methoxyphenyl)-4-(1,3-benzodioxol-5-yl)-1-(2-ethylbutyrylmethyl)-pyrrolidine-3-carboxylic Acid;

249 trans,trans-2-(4-Methoxyphenyl)-4-(1,3-benzodioxol-5-yl)-1-(N-methyl-N-(3,4-dimethoxybenzyl)aminocarbonylmethyl)-pyrrolidine-3-carboxylic Acid;

250 trans,trans-2-(4-Methoxyphenyl)-4-(1,3-benzodioxol-5-yl)-1-[(1R)-1-(N-methyl-N-propylaminocarbonyl)butyl]-pyrrolidine-3-carboxylic Acid;

251 trans,trans-2-(4-Methoxyphenyl)-4-(1,3-benzodioxol-5-yl)-1-[(1S)-1-(N-methyl-N-propylaminocarbonyl)butyl]-pyrrolidine-3-carboxylic Acid;

252 trans,trans-2-(4-Methoxyphenyl)-4-(1,3-benzodioxol-5-yl)-1-(3-isopropoxypropyl)-pyrrolidine-3-carboxylic Acid;

253 trans,trans-2-(4-Methoxyphenyl)-4-(1,3-benzodioxol-5-yl)-1-(5-methylhexyl)-pyrrolidine-3-carboxylic Acid;

254 trans,trans-2-(4-Methoxyphenyl)-4-(1,3-benzodioxol-5-yl)-1-(5-methyl-2-hexenyl)-pyrrolidine-3-carboxylic Acid;

255 trans,trans-2-(4-Methoxyphenyl)-4-(1,3-benzodioxol-5-yl)-1-(5-methyl-4-hexenyl)-pyrrolidine-3-carboxylic Acid;

256 trans,trans-2-(4-Methoxyphenyl)-4-(1,3-benzodioxol-5-yl)-1-(3,5-dimethyl-2-hexenyl)-pyrrolidine-3-carboxylic Acid;

257 trans,trans-2-(4-Methoxyphenyl)-4-(1,3-benzodioxol-5-yl)-1-(2-(N-methyl-N-isobutyrylamino)ethyl)-pyrrolidine-3-carboxylic Acid;

258 trans,trans-2-(4-Methoxyphenyl)-4-(1,3-benzodioxol-5-yl)-1-(N-methyl-N-(2,2-dimethylpropyl)aminocarbonylmethyl)-pyrrolidine-3-carboxylic Acid;

259 trans,trans-2-(4-Methoxyphenyl)-4-(1,3-benzodioxol-5-yl)-1-(N-ethyl-N-butylaminocarbonylmethyl)-pyrrolidine-3-carboxylic Acid;

260 trans,trans-2-(4-Methoxyphenyl)-4-(1,3-benzodioxol-5-yl)-1-(N-methyl-N-benzylaminocarbonylmethyl)-pyrrolidine-3-carboxylic Acid;

261 trans,trans-2-(4-Methoxyphenyl)-4-(5-indanyl)-1-(N-methyl-N-propylaminocarbonylmethyl)-pyrrolidine-3-carboxylic Acid;

262 trans,trans-2-(4-Methoxyphenyl)-4-(2,3-dihydrobenzofuran-5-yl)-1-(N-methyl-N-propylaminocarbonylmethyl)-pyrrolidine-3-carboxylic Acid;

263 trans,trans-2-(4-Methoxyphenyl)-4-(1-methylindol-5-yl)-1-(N-methyl-N-propylaminocarbonylmethyl)-pyrrolidine-3-carboxylic Acid;

264 trans,trans-2-(4-Methoxyphenyl)-4-(2-naphthyl)-1-(N-methyl-N-propylaminocarbonylmethyl)-pyrrolidine-3-carboxylic Acid;

265 trans,trans-2-(4-Methoxyphenyl)-4-(1,2-dimethoxy-4-phenyl)-1-(N-methyl-N-propylaminocarbonylmethyl)-pyrrolidine-3-carboxylic Acid;

266 trans,trans-2-(4-Methoxyphenyl)-4-(1-methoxy-3-phenyl)-1-(N-methyl-N-propylaminocarbonylmethyl)-pyrrolidine-3-carboxylic Acid;

EXAMPLES 267–288

Following the procedures described in Example 1 and Scheme II, the following compounds can be prepared.

267 trans,trans-3-(4-Methoxyphenyl)-5-(1,3-benzodioxol-5-yl)-1-(propylaminocarbonylmethyl)-piperidine-4-carboxylic Acid;

268 trans,trans-3-(4-Methoxyphenyl)-5-(1,3-benzodioxol-5-yl)-1-(aminocarbonylmethyl)-piperidine-4-carboxylic Acid;

269 trans,trans-3-(4-Methoxyphenyl)-5-(1,3-benzodioxol-5-yl)-1-(4-fluorobenzyl)-piperidine4-carboxylic Acid;

270 trans,trans-3-(4-Methoxyphenyl)-5-(1,3-benzodioxol-5-yl)-1-(2-ethoxyethyl)-piperidine4-carboxylic Acid;

271 trans,trans-3-(4-Methoxyphenyl)-5-(1,3-benzodioxol-5-yl)-1-(2-propoxyphenyl)-piperidine-4-carboxylic Acid;

272 trans,trans-3-(4-Methoxyphenyl)-5-(1,3-benzodioxol-5-yl)-1-[2-(2-methoxyethoxy)ethyl]-piperidine-4-carboxylic Acid;

273 trans,trans-3-(4-Methoxyphenyl)-5-(1,3-benzodioxol-5-yl)-1-[2-(2-pyridyl)ethyl]-piperidine-4-carboxylic Acid;

274 trans,trans-3-(4-Methoxyphenyl)-5-(1,3-benzodioxol-5-yl)-1-(morpholin-4-ylcarbonyl)-piperidine-4-carboxylic Acid;

275 trans,trans-3-(4-Methoxyphenyl)-5-(1,3-benzodioxole-5-yl)-1-(butylaminocarbonyl)-piperidine-4-carboxylic Acid;

276 trans,trans-3-(4-Methoxyphenyl)-5-(1,3-benzodioxol-5-yl)-1-(4-methoxyphenylamino-carbonyl)-3-piperidine-4-carboxylic acid;

277 trans,trans-3-(4-Methoxyphenyl)-5-(1,3-benzodioxol-5-yl)-1-acetylpiperidine-3-carboxylic Acid;

278 trans,trans-3-(4-Methoxyphenyl)-5-(1,3-benzodioxol-5-yl)-1-(2-furoyl)-piperidine-3-carboxylic Acid;

279 trans,trans-3-(4-Methoxyphenyl)-5-(1,3-benzodioxol-5-yl)-1-(phenylaminocarbonyl)-piperidine-4-carboxylic Acid;

280 trans,trans-3-(4-Methoxyphenyl)-5-(1,3-benzodioxol-5-yl)-1-(allylaminocarbonylmethyl-piperidine4-carboxylic Acid;

281 trans,trans-3-(4-Methoxyphenyl)-5-(1,3-benzodioxol-5-yl)-1-(n-butylaminocarbonylmethyl)-piperidine-4-carboxylic Acid;

282 trans,trans-3-(4-Methoxyphenyl)-5-(1,3-benzodioxol-5-yl)-1-(N-n-butyl-N-methylaminocarbonylmethyl)-piperidine-4-carboxylic Acid;

283 trans,trans-3-(4-Methoxyphenyl)-5-(1,3-benzodioxol-5-yl)-1-(pyrrolid in-1-ylcarbonylmethyl)-piperidine-4-carboxylic Acid;

284 trans,trans-3-(4-Methoxyphenyl)-5-(1,3-benzodioxol-5-yl)-1-(isobutylaminocarbonylmethyl)-piperidine-4-carboxylic Acid;

285 trans,trans-3-(4-Methoxyphenyl)-5-(1,3-benzodioxol-5-yl)-1-(cyclopentylaminocarbonylmethyl)-piperidine-4-carboxylic acid;

286 trans,trans-3-(4-Methoxyphenyl)-5-(1,3-benzodioxol-5-yl)-1-(morpholin-4-ylaminocarbonylmethyl)-piperidine-4-carboxylic acid;

287 trans,trans-3-(4-Methoxyphenyl)-5-(1,3-benzodioxol-5-yl)-1-(2-phenoxyethyl)-piperidine4-carboxylic Acid;

288 trans,trans-3-(4-Methoxyphenyl)-5-(1,3-benzodioxol-5-yl)-1-(methoxyethylaminocarbonyl)-piperidine-4-carboxylic Acid.

EXAMPLE 289 trans,trans-2-(4-Methoxyphenyl)-4-(1,3-benzodioxol-5-yl)-1-(4-dibutylaminophenyl)-pyrrolidine-3-carboxylic Acid 4-Nitro-fluorobenzene, ethyl trans,trans-2-(4-methoxyphenyl)-4-(1,3-benzodioxol-5-yl)-pyrrolidine-3-carboxylate (example 6A) and di-isopropyl ethylamine are heated in dioxane to give ethyl trans,trans-2-(4-methoxyphenyl)-4-(1,3-benzodioxol-5-yl)-1-(4-nitrophenyl)-pyrrolidine-3-carboxylate. The nitro compound is hydrogenated to the corresponding aminophenyl compound. This is reacted with butyraldehyde and sodium cyanoborohydride according to the method of Borch (J. Am Chem. Soc., 93, 2897, 1971) to give the corresponding N,N-dibutylaminophenyl compound, which is hydrolyzed with sodium hydroxide using the method of example 1D to give the title compound.

EXAMPLE 290 trans,trans-2-(4-Methoxyphenyl)-4-(1,3-benzodioxol-5-yl)-1-(2-dibutylamino-pyrimidine-4-yl)-pyrrolidine-3-carboxylic Acid 2-(Dibutylamino) 4-chloropyrimidine is prepared from 2-4-dichloropyrimidine according to the method of Gershon (J. Heterocyclic Chem. 24, 205, 1987). This compound, ethyl trans,trans-2-(4-methoxyphenyl)-4-(1,3-benzodioxol-5-yl)-pyrrolidine-3-carboxylate (example 6A), and di-isopropyl ethylamine are heated in dioxane to give the intermediate ethyl ester, which is hydrolyzed with sodium hydroxide using the method of example 1D to give the title compound.

EXAMPLE 291 trans,trans-2-(4-Methoxyphenyl)-4-(1,3-benzodioxol-5-yl)-1-(N-butyl-N-phenylaminocarbonylmethyl)-pyrrolidine-3-carboxylic Acid The title compound was prepared according to the general procedure of Example 1. $^1$H NMR (CD$_3$OD): δ 0.87 (t,3H, J=8); 1.2–1.35 (m, 2H); 1.35–1.5 (m, 2H); 2.78 (m, 2H); 3.10 (t,1H, J=9); 3.26 (d, 1H, J=15); 3.44 (dd,1H,J=5,10); 3.5–3.7 (m, 3H); 3.77 (m, 1H); 3.78 (s,3H); 5.93 (s,2H); 6.7–6.9 (m, 4H); 7.0–7.2 (m, 5H); 7.4 (m, 3H). MS (DCl/NH$_3$): m/e 531 (M+H)$^+$. Anal calcd for C$_{31}$H$_{34}$N$_2$O$_6$: C, 70.17; H, 6.46; N, 5.28. Found: C,70.36; H, 6.52; N, 4.99.

EXAMPLE 292

Sodium trans,trans-2-(4-Methoxyphenyl)-4-(1,3-benzodioxol-5-yl)-1-(N,N-di(n-butyl) aminocarbonylmethyl)-pyrrolidine-3-carboxylate

EXAMPLE 292A

Ethyl 3-(4-methoxyphenyl)-3-oxopropionate

Simultaneous reactions were run in both a 65-L reactor and a 35-L reactor that share the same reflux system. A nitrogen atmosphere was maintained in both. 4.0 kg (100 moles) of 60% sodium hydride in mineral oil and 32 L toluene were charged into the ambient temperature reactors. The mixture was agitated for 5 minutes and allowed to settle. 20 L of the toluene solution was aspirated. 28 L of toluene was added, agitated for 5 minutes, allowed to settle and 28 L of the toluene solution was aspirated. 68 L of toluene and 8.4 L (69.7 moles) diethyl carbonate were added. The agitation was begun and the flow of Syltherm (Note 4) in reactor jackets was initiated. A solution of 5.0 kg (33.3 moles) 4-methoxyacetophenone in 12 L toluene was added over 20 minutes. When additions were complete, the jacket temperature was reduced to 10° C. and stirring continued for 16 hours. A solution of 6.7 L (117 moles) glacial acetic acid in 23 L deionized water was fed at the same rate that was previously used for the acetophenone solution. When addition was complete, agitation was stopped and the layers separated. The aqueous layer was washed once with 13 L toluene. The combined organic layers were washed twice with 6.7 L portions of 7% (w:w) aqueous sodium bicarbonate. The toluene solution was washed once with 6.7 L of 23% (w:w) aqueous sodium chloride. The organic solution was dried over 10 kg sodium sulfate, filtered, and the solvent removed on the rotary evaporator to provide the desired product.

EXAMPLE 292B 3,4-Methylenedioxy-1-(2-nitroethenyl)-benzene

In a 45-L cryogenic reactor with a contoured, anchor stirrer was dissolved 5.537 kg (36.9 moles) piperonal in 9 L methanol and 2.252 kg (36.9 moles) nitromethane at 150–200° C. The jacket temperature was set to −5° C. and the reaction solution cooled to a temperature of ±3.5° C. A 21° C. solution of 3.10 kg (38.8 moles) 50% (w:w) aqueous sodium hydroxide diluted with 3.7 L water was pumped in. The reaction temperature was maintained between 10°–15° C. When addition was complete, the jacket temperature was reset to 1° C. and stirring continued for 30 minutes. A mixture of 7 kg ice in 19 L water was added to dissolve most of the solid. The reaction mixture was filtered through canvas and then a $27R_{10}SV$ Honeycomb filter. The filtered solution was metered into a 21° C. mixture of 7.4 L concentrated hydrochloric acid in 11.1 L deionized water. The final reaction temperature was 26° C. The resulting product was centrifuged and washed until the wash pH rose to least 6 (by pH indication paper). The crude was dissolved in 92 L dichloromethane and the layers separated. The aqueous layer was washed once with 8 L dichloromethane. The combined organics were dried over 1.32 kg magnesium sulfate and filtered through Whatman #1 paper. The volume was reduced to 20% and the solution cooled to 4° C. Filtration through Whatman #1 paper, followed by ambient temperature drying in vacuo with an air leak afforded 1.584 kg (22%) of a first crop Concentration of the MLS to 25% followed by similar cooling, filtration, and drying afforded 0.262 kg (4%) of a second crop. The yellow product darkened on standing in light and air.

EXAMPLE 292C

Ethyl 2-(4-methoxybenzoyl)-3-(1,3-benzodioxol-5-yl)-4-nitro-butanoate

Into a 45-L stirred reactor at ambient temperature were charged 5.819 kg (30.1 moles) 3,4-methylenedioxy-1-(2-nitroethenyl)-benzene and 24 L ethyl acetate. A solution of 5.355 kg (24.1 moles) ethyl 3-(4-methoxyphenyl)-3-oxopropionate in 16 L ethyl acetate was added. 280 g (275 ml, 1.84 moles) of 1,8-diazabicyclo[5.4.0]undec-7-ene in four equal portions was added over a 2.5 hour period. The reaction mixture was filtered through dicalite and the resulting filtered solution was used in the next step without any further purification.

EXAMPLE 292D

Ethyl 2-(4-methoxyphenyl)-4-(1,3-benzodioxol-5-yl)-4,5-dihydro-3H-pyrrol-3-carboxylate The product of Example 292C (1316 ml solution consisting of 300 g Ethyl 2-(4-methoxybenzoyl)-3-(3,4-methylenedioxyphenyl)-4 nitrobutanoate in ethyl acetate) was added to a glass reactor containing RaNi #28 (300 g). The reaction mixture was shaken under a hydrogen environment of 4 atm at room temperature for 18 hours and filtered through a nylon 0.20 micron 47 mm millipore.

The filtrate was concentrated to 1.4 kg of dark solution and purified by normal phase silica gel chromatography eluting with 85:15, hexanes:ethyl acetate. The pure fractions were combined and concentrated (as above) until crystals formed. The solution was cooled to 0° C. and filtered. The solid was washed with 2 L of 85:15, hexane:ethyl acetate (0° C.). The solids were dried in vacuo at 50° C. to a constant weight of 193.4 g (21% yield, melting point 80–81° C.) of the title compound. A further 200 g (23% yield) of product was obtained from the mother liquors.

EXAMPLE 292E

Ethyl 2-(4-methoxyphenyl)-4-(1,3-benzodioxol-5-yl)-pyrrolidine 3-carboxylate

Into a 12-L flask equipped with magnetic stirring, addition funnel, temperature probe, and nitrogen inlet was charged 0.460 kg ethyl 2-(4-methoxyphenyl)-4-(3,4-methylenedioxyphenyl)-4,5-dihydro-3H-pyrrole-3-carboxylate (1.25 mol). The reaction vessel was degassed with nitrogen. Absolute 3.7 L ethanol and 1.12 L of THF were added. 31 mg bromocresol green and 94.26 g sodium cyanoborohydride (1.5 mol) were added. A solution containing 400 mL absolute ethanol and 200 mL of 12 M HCl was then added. The reaction mixture was stirred for 30 minutes after addition was complete. After the starting material was consumed, 0.5 L of 7% aq. NaHCO3 was added. The reaction mixture was concentrated and diluted with 5 L ethyl acetate. The organic layer was washed twice with 2 L of 7% aq. $NaHCO_3$ and once with 2.5 L of 23% aq. NaCl, the dried over 190 g $MgSO_4$, filtered, and concentrated to give 447 g of the title compound as a thick yellow oil.

EXAMPLE 292F

Ethyl 2-(4-methoxypheny)-4-(1,3-benzodioxol-5-yl)-1-(N,N-di(n-butyl)aminocarbonylmethyl) pyrrolidine 3-carboxylate Into a 22-L flask equipped with overhead stirring, nitrogen inlet, and condenser was charged ethyl 2-(4-methoxyphenyl)-4-(3,4-methylenedioxyphenyl)-pyrrolidine-3-carboxylate (2.223 kg, 6.02 mol). The reaction vessel was degassed with nitrogen. 13.2 L of acetonitrile, 3.66 L diisopropylethylamine (2.71 kg, 20.9 mol), and 1.567 kg dibutylamidomethyl bromide (6.26 mol) were added. The mixture was refluxed at 78° C. for 17 hrs. After the disappearance of starting material, the mixture was concentrated until crystals formed. The solid was fitered and washed with 4 L ethyl acetate (0° C.). Concentrating of the filtrate was continued as above until all volatiles were removed. The residue was diluted with 40 L ethyl acetate and washed with 20 L deionized water. The organic layer was washed with 8 L of 23% aq. NaCl nad dried over 0.399 kg $MgSO_4$ and filtered. Concentration as above provided 3.112 kg (96% yield) of the title compound as a dark oil.

EXAMPLE 292G trans,trans-2-(4-Methoxyphenyl)-4-(1,3-benzodioxol-5-yl)-pyrrolidine 3-carboxylate and preparation of trans,trans 2-(4-methoxyphenyl)-4-(3,4-dioxyphenyl)-pyrrolidine-3-carboxylic Acid Ethyl Ester Into a 35-L reactor equipped with overhead stirring, nitrogen inlet, and condenser was charged 3.112 kg ethyl 2-(4-methoxyphenyl)-4-(3,4-methylenedioxyphenyl)-pyrrolidine 3-carboxylate (5.78 mol). 16.4 L of absolute ethanol was added and the reaction vessel was degassed with nitrogen. 0.115 kg of sodium ethoxide (1.69 mol) was added and the mixture was refluxed at 79° C. for 1 hr. The mixture was cooled to 15° C. and 5 L of 7.6 M NaOH solution (38.1 mol) was added. The mixture was stirred at 15° C. for 18 hrs. The solvent was evaporated and The ether solution was washed with 9.5 L deionized water. The aqueous wash was extracted with 3 L ether. 0.340 L of 12 M HCl was added to the aqueous layer. The aqueous layer was extracted with 24 L of ethyl acetate. The organic layer was washed with 9 L of 23% aq. NaCl, dried with 0.298 kg $MgSO_4$, filtered, and concentrated to give 2.132 kg of a dark oil. The oil was triturated with 18 L ether. The undesired solids were filtered and saved for later use. The mother liquors were concentrated to obtain 1.102 kg of light foam. The foam was dissolved in 5.5 L ethyl acetate with heating to 65° C. 14 L hexane was added slowly enough to keep the solution refluxing. The reaction mixture was cooled to 10° C. and filtered. The crystals were washed with 2 L ether (0° C.) and dried to constant weight in vacuo at 50° C. to give 0.846 kg (43% yield, melting point 119–120) of crude product, which was further purified by normal phase silica gel chromatography.

EXAMPLE 292H

Sodium trans,trans-2-(4-methoxyphenyl)-4-(1,3-benzodioxol-5-yl)-1-(N,N-di(n-butyl) aminocarbonylmethyl) Pyrrolidine 3-carboxylate Into a 20-L flask was charged trans,trans 2-(4-methoxyphenyl)-4-(3,4-methyledioxyphenyl)-1-(N,N-dibutylamino-carbonyl methyl) pyrrolidine 3-carboxylic acid (0.927 kg, 1.819 mol). A solution of 0.0720 kg NaOH (1.80 mol) dissolved in 4.65 L methanol was added. The reaction mixture was concentrated to an oil. Pentane (4 L) was added and the solution concentrated again. Pentane (4 L) was added again and concentration of this solution gave a light tan foam. The foam was dried in vacuo at 50° C. to a constant weight of 0.937 kg (97% yield) of the title compound.

EXAMPLE 293 trans-trans-2-(4-Methoxyphenyl)-4-(1 3-benzodioxol-5-yl)-1-[decahydroisoguinolin-2-carbonylmethyl]-pyrrolidine-3-carboxylic Acid The title compound was prepared using the procedures described in example 1. NMR ($CD_3OD$, 300 MHz) shows a mixture of isomers. MS ($DCl/NH_3$) m/z 521. Anal calcd for $C_{30}H_{36}N_2O_6$.1.3 TFA: C, 58.54; H, 6.62; N, 4.19. Found: C, 58.34; H, 5.58; N, 4.00.

EXAMPLE 294 trans-trans-2-(4-Methoxyphenyl)-4-(1,3-benzodioxol-5-yl)-1-[3,3-dimethylpiperidinyl-carbonylmethyl]-pyrrolidine-3-carboxylic Acid The title compound was prepared using the procedures described in example 1. NMR ($CD_3OD$, 300 MHz) indicates presence of rotamers. δ 0.84 (s, 3H), 0.86 (s, 3H), 1.35–1.6 (m, 4H), 3.83 (s, 3H), 5.96 (s, 2H), 6.81 (d, 1H, J=8), 6.90 (dd, 1H, J=1, 8), 7.01 (d, 2H, J=9), 7.03 (s, 1H), 7.47 (d, 2H, J=9). MS ($DCl/NH_3$) m/z 495. Anal calcd for $C_{28}H_{34}N_2O_6$.1.4 TFA: C, 56.55; H, 5.45; N, 4.28. Found: C, 56.52; H, 5.83; N, 4.26.

EXAMPLE 295 trans-trans-2-(4-Methoxyphenyl)-4-(1,3-benzodioxol-5-yl)-1-[2-(N-propyl-N-iso-butoxycarbonylamino)ethyl]-pyrrolidine-3-carboxylic Acid The title compound was prepared by the methods detailed in Example 61, but substituting propylamine for methylamine in Example 61B and isobutyl chloroformate for isobutyryl chloride in Example 61C. The crude product was purified by trituration with 1:1 diethyl ether/hexane. The resulting solid was dissolved in $CH_3CN$ and water and lyophilized to give the product as a white solid. $^1H$ NMR ($CDCl_3$, 300 MHz) δ 0.80 (t, 3H, J=7), 0.92 (m, 3H), 1.43 (h, 2H, J=7 Hz), 1.7–1.9 (m, 1H), 2.72 (m, 1H), 2.90 (m, 2H), 3.10 (m, 2H), 3.25 (m, 2H), 3.40 (m, 1H), 3.55 (m, 1H), 3.62 (m, 1H), 3.7–3.9 (m, 2H) 3.78 (s, 3H), 5.95 (s, 2H), 6.72 (d, 1H, J=8 Hz), 6.82 (m, 3H), 7.00 (s, 1H), 7.30 (d, 2H). MS ($DDCl/NH_3$) m/e 527 $(M+H)^+$. Anal clacd for $C_{29}H_{38}N_2O_6$.0.5 $H_2O$: C, 65.03; H, 7.34; N, 5.23. Found: C, 65.13; H, 6.96; N, 4.95.

EXAMPLE 296 trans-trans-2-(4-Methoxyphenyl)-4-(1,3-benzodioxol-5-yl)-1-[1,2,3,4-tetrahydroisoguinolin-2-carbonylmethyl]-pyrrolidine-3-carboxylic Acid The title compound was prepared using the procedures described in example 1. NMR ($CD_3OD$, 300 MHz) indicates presence of rotamers. δ 2.97 (m, 2H), 4.68 (s, 3H), 5.97 (s, 2H), 6.83 (d, 1H, J=8), 6.9–7.0 (m, 3H), 7.03 (d, 1H, J=2), 7.1–7.3 (m, 4H), 7.4–7.5 (m, 2H). MS ($DCl/NH_3$) m/z 515.

EXAMPLE 297 trans-trans-2-(4-Methoxyphenyl)-4-(1,3-benzodioxol-5-yl)-1-[2-(N-propyl-N-dimethylaminocarbonylamino)ethyl]-pyrrolidine-3-carboxylic Acid The title compound was prepared by the methods detailed in Example 61, but substituting propylamine for methylamine in Example 61B and dimethylcarbamyl chloride for isobutyryl chloride in Example 61C. The crude product was purified by preparative HPLC (Vydac μC18) eluting with a 10–70% gradient of $CH_3CN$ in 0.1% TFA. The desired fractions were lyophilized to give the product as a white solid. $^1H$ NMR ($CDCl_3$, 300 MHz) δ 0.70 (t, 3H, J=7), 1.28 (m, 2H), 2.75 (s, 3H), 2.82 (m, 2H), 3.1–3.45 (m, 4H), 3.70

(m, 1H), 3.80 (s, 3H), 3.90 (m, 3H), 4.72 (m, 1H), 5.95 (s, 2H), 6.75 (d, 1H, J=8 Hz), 6.87 (m, 3H), 7.05 (s, 1H), 7.40 (d, 2H, J=8 Hz). MS (DCl/NH$_3$) m/e 498 (M+H)$^+$. Anal calcd for $C_{27}H_{35}N_3O_6 \cdot 1.25$ TFA: C, 55.36 H, 5.71; N, 6.56. Found: C, 55.41; H, 5.71; N, 6.41.

EXAMPLE 298 trans,trans-2-(4-Methoxyphenyl)-4-(1,3-benzodioxol-5-yl)-1-(2-(N-propyl-N-(4-nitrobenzenesulfonyl)amino)ethyl)-pyrrolidine-3-carboxylic Acid Using the procedures described in Example 66, the title compound was prepared as a yellow solid. m.p. 85–87° C. $^1$H NMR (CDCl3, 300 MHz) δ 0.77 (t, J=7.5 Hz, 3H), 1.38 (sextet, J=7.5 Hz, 2H), 2.20–2.29 (m, 1H), 2.57–2.66 (m, 1H), 2.82–3.15 (m, 4H), 3.22 (t, J=7.5 Hz, 2H) 3.38 (dd, J=3 Hz, J=9 Hz, 1H), 3.49–3.57 (m, 1H), 3.59 (d, J=9 Hz, 1H), 3.83 (s, 3H), 5.96 (s, 2H), 6.73 (d, J=8 Hz, 1H), 6.82 (dd, J=1 Hz, J=8 Hz, 1H), 6.87 (d, J=9 Hz, 2H), 6.98 (d, J=Hz, 1 H), 7.27 (d, J=9 Hz, 2H), 7.82 (d, J=9 Hz, 2H), 8.23 (d, J=9 Hz, 2H). MS (DCl/NH$_3$) m/e 612 (M+H)$^+$.

EXAMPLE 299 trans,trans-2-(4-Methoxyphenyl)-4-(1,3-benzodioxol-5-yl)-1-(2-(N-propyl-N-n-Pentanesulfonylamino)ethyl)-pyrrolidine-3-carboxylic Acid Using the procedures described in Example 66, the title compound was prepared as a white solid. m.p. 59–61° C. $^1$H NMR (CDCl$_3$, 300 MHz) δ 0.79 (t, J=7.5 Hz, 3H), 0.90 (t, J=6 Hz, 3H), 1.26–1.32 (m, 4H), 1.43 (sextet, J=7.5 Hz, 2H), 1.67–1.76 (m, 2H), 2.23–2.32 (m, 1H), 2.70–3.08 (m, 7H), 3.15–3.32 (m, 2H), 3.43 (dd, J=3 Hz, J=9 Hz, 1H), 3.52–3.57 (m, 1H), 3.63 (d, J=9 Hz, 1H), 3.80 (s, 3H), 5.95 (s, 2H), 6.73 (d, J=7.5 Hz, 1H), 6.83 (dd, J=1 Hz,J=7.5 Hz, 1H), 6.87(d, J=8 Hz, 2H), 7.00 (d, J=1 Hz, 1H), 7.32 (d, J=8 Hz, 2H). MS (DCl/NH$_3$) m/e 561 (M+H)$^+$.

EXAMPLE 300 trans,trans-2-(4-Methoxyphenyl)-4-(1,3-benzodioxol-5-yl)-1-(2-(N-propyl-N-(4-trifluoromethoxybenzenesulfonyl)amino)ethyl)-pyrrolidine-3-carboxylic Acid Using the procedures described in Example 66, the title compound was prepared as a white solid. m.p.122–124° C. $^1$H NMR (CD3OD, 300 MHz) δ 0.75 (t, J=7.5 Hz, 3H), 1.26–1.45 (m, 2H), 2.96–3.08 (m, 2H), 3.23 (bs, 2H), 3.35–3.45 (m, 2H), 3.52 (t, J=10 Hz, 1H), 3.81 (d, J=9 Hz, 2H), 3.86 (s, 3H), 3.92 (t, J=9 Hz, 1H), 4.36 (d, J=10 Hz, 1H), 5.97 (s, 2H), 6.82 (d, J=9 Hz, 1H), 6.93 (dd, J=3 Hz, J=9 Hz, 1H), 7.06–7.08 (m, 3H), 7.46 (d, J=9 Hz, 2H), 7.56 (d, J=9 Hz, 2H), 7.89 (d, J=9 Hz, 2H). MS (DCl/NH$_3$), m/e 651 (M+H)$^+$.

EXAMPLE 301 trans,trans-2-(4-Methoxyphenyl)-4-(1,3-benzodioxol-5-yl)-1-(2-(N-propyl-N-(2-methyl-2-propenesulfonyl)amino)ethyl)-pyrrolidine-3-carboxylic Acid Using the procedures described in Example 66, the title compound was prepared as a white solid. m.p. 69–71° C. $^1$H NMR (CDCl3, 300 MHz) δ 0.79 (t, J=7.5 Hz, 3H), 1.93 (sextet, J+7.5 Hz, 2H), 1.92 (s, 3H), 2.25–2.35 (m, 1H), 2.68–2.77 (m, 1H), 2.85–3.28 (m, 7H), 3.40 (d, J=9 Hz, 1H), 3.52–3.68 (m, 2H), 3.66 (d, J=9 Hz, 1H), 3.80 (s, 3H), 4.92 (s, 1H), 5.07 (s, 1H), 5.97 (s, 2H), 6.74 (d, J=7 Hz, 1H), 6.82–6.89 (m, 3H), 7.01 (s,1H), 7.33 (d, J=9 Hz, 2H). MS (DCl/NH$_3$), m/e 545 (M+H)$^+$.

EXAMPLE 302 trans-trans-2-(4-Methoxyphenyl)-4-(1,3-benzodioxol-5-yl)-1-[2-ethylpiperidinyl-carbonylmethyl]-pyrrolidine-3-carboxylic Acid The title compound was prepared using the procedures described in example 1. NMR (CD$_3$OD, 300 MHz) shows a mixture of isomers. δ 0.75 (t, 3H, J=7), 1.4–1.7 (m, 8H), 3.84 (s, 3H), 5.96 (s, 2H), 6.83 (d, 1H, J=8), 6.91 (d, 1H, J=8), 7.0–7.1 (m, 3H), 7.52 (d, 2H, J=9). MS (DCl/NH$_3$) m/z 495. Anal calcd for $C_{28}H_{34}N_2O_6 \cdot 1.6$ TFA: C, 55.35; H. 5.30; N, 4.14. Found: C, 55.26; H, 5.37; N, 4.01.

EXAMPLE 303 trans,trans-2-(4-Methoxyphenyl)-4-(1,3-benzodioxol-5-yl)-1-(2-(N-propyl-N-(2-methylpropanesulfonyl)amino)ethyl)-pyrrolidine-3-carboxylic Acid Using the procedures described in Example 66, the title compound was prepared as a white solid. m.p. 72–73° C. $^1$H NMR (CDCl3, 300 MHz) δ 0.82 (t, J=7.5 Hz, 3H),1.04 (d, J=6 Hz, 6H), 1.44(q, J=7.5 Hz, 2H), 2.15–2.33 (m, 2H), 2.57–2.75 (m, 2H), 2.84–3.08 (m, 3H), 3.12–3.21 (m, 1H), 3.23–3.45 (m, 1H), 3.43 (d, J=11 Hz, 1H), 3.55–3.62 (m, 1H), 3.66 (d, J=9 Hz, 1H), 3.80 (s, 3H), 5.95 (s, 2H), 6.75 (d, J=9 Hz, 1H), 6.83 (dd, J=1 Hz, J=9 Hz, 1H), 6.87 (d, J=9 Hz, 2H), 7.02 (d, J=1 Hz, 1H), 7.33 (d, J=9 Hz, 2H). MS (DCl/NH$_3$) m/e 547 M+H)$^+$.

EXAMPLE 304 trans,trans-2-(4-Methoxyphenyl)-4-(1,3-benzodioxol-5-yl)-1-(2-(N-propyl-N-heptanesulfonylamino)ethyl)-pyrrolidine-3-carboxylic Acid Using the procedures described in Example 66, the title compound was prepared as a white solid. m.p.58–59° C. $^1$H NMR (CDCl3, 300 MHz) δ 0.80(t, J=7.5 Hz, 3H), 0.88 (t, J=7 Hz, 3H), 1.23–1.36 (m, 8H), 1.94 (q, J=7.5 Hz, 2H), 1.71(quintet, J=7 Hz, 2H), 2.23–2.32 (m, 1H), 2.70–3.09 (m, 7H), 3.13–3.32 (m, 2H), 3.43(dd, J=3 Hz, J=9 Hz, 1H), 3.52–3.58(m, 1H), 3.65(d, J=9 Hz, 1H), 3.80 (s, 3H), 5.96(s, 2H), 6.73 (d, J=7 Hz, 1H), 6.83 (dd, J=1 Hz, J=7 Hz, 1H), 6.87(d, 9 Hz, 2H), 7.01(d, J=1 Hz, 1H), 7.32(d, J=9 Hz, 2H). MS (DCl/NH$_3$) m/e 589 M+H)$^+$.

EXAMPLE 305 trans-trans-2-(4-Methoxyphenyl)-4-(1,3-benzodioxol-5-yl)-1-[2-(N-ethyl-N-ethoxycarbonylamino)ethyl]-pyrrolidine-3-carboxylic Acid Prepared by the methods detailed in Example 61, but substituting ethylamine for methylamine in Example 61B and ethyl chloroformate for isobutyryl chloride in Example 61C. The crude product was purified by preparative HPLC (Vydac μC18) eluting with a 10–70% gradient of CH$_3$CN in 0.1% TFA. The desired fractions were lyophilized to give the product as a white solid. ¹H NMR (CDCl₃, 300 MHz) δ 0.90 (t, 3H, J=7), 1.22 (m, 3H), 3.0–3.2 (m, 4H), 3.42 (m, 2H), 3.78 (s, 3H), 3.82 (m, 4H), 4.10 (q, 2H, J=7 Hz), 3.5 (brs, 1H), 5.97 (dd, 2H, J=1,7 Hz), 6.72 (d, 1H, J=8 Hz), 6.84 (m, 3H), 7.00 (s, 1H), 7.42 (d, 2H, J=8 Hz). MS (DCl/NH₃) m/e 485 (M+H)⁺. Anal calcd for $C_{26}H_{32}N_2O_7 \cdot 1.2$ TFA: C, 54.90; H, 5.39; N, 4.51. Found: C, 55.01; H, 5.36; N, 4.56.

EXAMPLE 306 trans,trans-2-(4-Methoxyphenyl)-4-(1,3-benzodioxol-5-yl)-1-(2-(N-Propyl-N-hexanesulfonylamino)ethyl)-pyrrolidine-3-carboxylic Acid Using the procedures described in Example 66, the title compound was prepared as a white solid. m.p.59–60° C. ¹H NMR (CDCl3, 300 MHz) δ 0.80(t, J=7.5 Hz, 3H), 0.89(t, J=7 Hz, 3H), 1.25–1.36(m, 6H), 1.53 (sextet, J=7.5 Hz, 2H), 1.72(quintet, J=7 Hz, 2H), 2.23–2.32(m, 1H), 2.72–3.08(m, 7H), 3.15–3.32(m, 2H), 3.43(d, J=9 Hz, 1H), 3.55–3.62(m, 1H), 3.65 (d, J=10 Hz, 1H), 3.80(s, 3H), 5.96 (s, 2H), 6.74(d, J=7.5 Hz, 1H), 6.82(d, J=7.5 Hz, 1H), 6.87(d, J=9 Hz, 2H), 7.01(s, 1H), 7.32 (d, J=9 Hz, 2H). MS (DCl/NH₃), m/e 575 (M+H)⁺.

EXAMPLE 307 trans-trans-2-(4-Ethylphenyl)-4-(1,3-benzodioxol-5-yl)-1-[N,N-di(n-butyl)aminocarbonylmethyl]-pyrrolidine-3-carboxylic Acid The title compound was prepared using the procedures described in examples 1 and 49, substituting ethyl 4-ethylbenzoylacetate (prepared by the method of Krapcho et al., Org. Syn. 47, 20 (1967) starting with 4'-ethylacetophenone) in procedure 49B. NMR (CDCl₃, 300 MHz) δ 7.31 (2H, d, J=8 Hz), 7.16 (2H, d, J=8 Hz), 7.03 (1H, d, J=3 Hz), 6.86 (1H, dd, J=8&3 Hz), 6.73 (1H, d, J=9 Hz), 5.94 (1H, d, J=4 Hz), 5.92 (1H, d, J=4 Hz), 3.77 (1H, d, J=9 Hz), 3.60 (1H, m), 3.53–3.23 (5H, m), 3.13–2.90 (4H, m), 2.73 (1H, d, J=14 Hz), 2.62 (2H, q, J=9 Hz), 1.45 (2H, m), 1.40–1.10 (6H, m), 1.02 (2H, m), 0.87 (3H, t, J=7 Hz), 0.78 (3H, t, J=7 Hz). m/e (DCI, NH₃) 509 (MH⁺) Anal.calc. for $C_{30}H_{40}N_2O_5$ C 70.84, H 7.93, N 5.51. Found C 70.80, H 7.85, N 5.25.

EXAMPLE 308 trans-trans-2-(4-Methoxyphenyl)-4-(1,3-benzodioxol-5-yl)-1-[2-(N-propyl-N-(2-chloroethoxy)carbonylamino)ethyl]-pyrrolidine-3-carboxylic Acid Prepared by the methods detailed in Example 61, but substituting propylamine for methylamine in Example 61B and 2-chloroethyl chloroformate for isobutyryl chloride in Example 61C. The crude product was purified by trituration with 1:1 diethyl ether/hexane. The resulting solid was dissolved in CH₃CN and water and lyophilized to give the product as a white solid. ¹H NMR (CDCl₃, 300 MHz) δ 0.80 (t, 3H, J=7), 1.22 (m, 3H), 2.15 (m, 1H), 2.75 (m, 1H), 2.85 (m, 1H), 3.1 (m, 2), 3.25 (m, 2H), 3.5 (m, 3H), 3.65 (m, 2H), 3.80 (s, 3H), 4.18 (m, 1H), 4.30 (m, 1H), 5.98 (s, 2H), 6.72 (m, 1H), 6.82 (m, 3H), 7.00 (m, 1H), 7.30(m, 2H). MS (DCl/NH₃) m/e 533 (M+H)⁺. Anal calcd for $C_{27}H_{33}N_2O_7Cl$: C, 60.84; H, 6.24; N, 5.26. Found: C, 60.48; H, 6.04; N, 5.10.

EXAMPLE 309 trans-trans-2-(2-Methoxyethyl)-4-(1,3-benzodioxol-5-yl)-1-[N,N-di(n-butyl)aminocarbonylmethyl]-pyrrolidine-3-carboxylic Acid The title compound was prepared using the procedures described in example 1, substituting ethyl 5-methoxy-3-oxopentanoate for ethyl 4-methoxybenzoylacetate in Example 1A. The title compound is a yellow foam. ¹H NMR (CDCl₃, 300 MHz) δ 0.91 (t, J=7 Hz) and 0.95 (t, J=7 Hz, 6H total), 1.28–1.41 (br m, 4H), 1.45–1.63 (br m, 4H), 2.00–2.20 (br m, 2H), 3.06 (br t, J=9 Hz, 1H), 3.30 (s) and 3.20–3.68 (br m, 11H total), 3.72–4.10 (br m, 4H), 5.92 (s, 2H), 6.72 (d, J=8.5 Hz, 1H), 6.82 (dd, J=1.5, 8.5 Hz, 1H), 6.91 (d, J=1.5 Hz, 1H); MS (FAB) m/e 463 (M+H)⁺. Anal calcd for $C_{25}H_{38}N_2O_5 \cdot H_2O$: C, 62.48; H, 8.39; N, 5.83. Found: C, 62.13; H, 8.15; N, 5.69.

EXAMPLE 310 trans,trans-2-(4-Methoxyphenyl)-4-(1,3-benzodioxol-5-yl)-1-(2-(N-ethyl-N-n-pentanesulfonylamino)ethyl)-pyrrolidine-3-carboxylic Acid Using the procedures described in Example 66, the title compound was prepared as a white solid. m.p.57–58° C. H NMR (CDCl3, 300 MHz) δ 0.89(t, J=7 Hz, 3H), 1.06(t, J=7.5 Hz, 3H), 1.26–1.37(m, 4H), 1.72(quintet, J=7.5 Hz, 2H), 2.22–2.32(m, 1H), 2.71–2.96 (m, 5H), 3.08–3.30(m, 4H), 3.95(d, J=9 Hz, 1H), 3.53–3.60 (m, 1H), 3.67(d, J=9 Hz, 1H), 3.80(s, 1H), 5.97(s, 2H), 6.73(d, J=9 Hz, 1H), 6.82 (d, J=9 Hz, 1H), 6.88(d, J=9 Hz, 2H),7.02(s,1H), 7.33(d, J=9 Hz, 2H). MS (CDI/NH₃) m/e 547 (M+H)⁺.

EXAMPLE 311 trans-trans-2-(4-Methoxyphenyl)-4-(1,3-benzodioxol-5-yl)-1-[N,N-dicyclohexylamino carbonylmethyl]-pyrrolidine-3-carboxylic Acid The title compound was prepared using the procedures described in example 1. NMR (CD₃OD, 300 MHz) δ 1.0–2.0 (m, 20H), 3.0–3.1 (m, 2H), 3.80 (s, 3H), 5.95 (s, 2H), 6.75 (d, 1H, J=8), 6.86 (dd,1H, J=2,8), 6.95 (d, 2H, J=9), 7.04 (d, 1H, J=2), 7.38 (d, 2H, J=9). MS (DCl/NH₃) m/z 563. Anal calcd for $C_{33}H_{42}N_2O_6 \cdot 0.5\ H_2O$; C, 69.33; H, 7.58; N, 4.90. Found: C, 69.42; H, 7.29; N, 4.78.

EXAMPLE 312 trans-trans-2-(4-Methoxyphenyl)-4-(1,3-benzodioxol-5-yl)-1-[2-(N-propyl-N-tert-butoxycarbonylamino)ethyl]-pyrrolidine-3-carboxylic Acid The title compound was prepared using the procedures described in example 61, substituting propylamine for aqueous methylamine in Example 61B and di-tert-butyidicarbonate for isobutyryl chloride in Example 61C. NMR (CD₃OD, 300 MHz) suggests presence of rotamers 6 0.81 (t, 3H, J=7), 1.2–1.5 (m, 11 H), 3.78 (s, 3H), 5.92 (dd, 2H, J=1,2), 6.74 (d, 1H, J=8), 6.84 (dd, 1H, J=2,8), 6.92 (d, 2H, J=9), 6.99 (bd s, 1H), 7.35 (d, 2H, J=9). MS (DCl/NH₃) m/z 527. Anal calcd for $C_{29}H_{38}N_2O_7$: C, 66.14; H, 7.27; N, 5.32. Found: C, 66.,05; H, 7.36; N, 5.15.

EXAMPLE 313 trans-trans-2-(4-Methoxy-3-fluorophenyl)-4-(1,3-benzodioxol-5-yl)-1-[N,N-di(n-butyl)aminocarbonylmethyl]-pyrrolidine-3-carboxylic Acid The title compound was prepared using the methods described in examples 1 and 43, using 4-methoxy-3-fluoro acetophenone in place of 4-methoxy acetophenone. m.p.

142–143° C. NMR (CDCl$_3$, 300 MHz) δ 0.82 (t, J=7 Hz, 3H), 0.88 (t, J=7 Hz, 3H), 1.03–1.50 (m, 8H), 2.82 (d, J=13 Hz, 1H), 2.90–3.13 (m, 3H), 3.20–3.50 (m, 3H), 3.39 (d, J=13H, 1H), 3.55–3.65 (m, 1H), 3.82 (d, J=10 Hz, 1H)), 3.87 (s, 3H), 5.91 (dd, J=2 Hz, 4 Hz, 2H), 6.72 (d, J=8 Hz, 1H), 6.83–6.91 (m, 2H), 6.99 (d, J=2 Hz, 1H), 7.06 (m, 2H). Anal calcd for C$_{29}$H$_{37}$N$_2$O$_6$F: C, 65.89; H, 7.06; N, 5.30. Found: C, 65.82; H, 7.13; N, 5.29.

EXAMPLE 314 trans,trans-2-(Propyl)-4-(1,3-benzodioxol-5-yl)-1-(2-(N-propyl-pentanesulfonylamino)ethyl)pyrrolidine-3-carboxylic Acid

EXAMPLE 314A

Propyl pentanesulfonamide

Pentane sulfonyl chloride (687 mg, 4.03 mmol) was dissolved in 5 mL CH$_2$Cl$_2$ and added to an ice-cooled solution of n-propylamine (0.40 mL, 4.82 mmol) and ethyldiisopropylamine (0.85 mL, 4.88 mmol) in 5 mL CH$_2$Cl$_2$ under a nitrogen atmosphere. The reaction was stirred at 0° C. for 30 min, then at 25° C. for 4 h. The solution was partitioned between 20 mL of 1.0 M aqeous NaHSO$_4$ and 25 mL CH$_2$Cl$_2$. The organic phase was washed sequentially with 25 mL H$_2$O and 25 mL brine, then dried (Na$_2$SO$_4$), filtered, and concentrated in vacuo to provide 739 mg (3.83 mmol, 95%) of the title compound as a white solid. TLC (25% EtOAc-hexane) Rf 0.23; $^1$H NMR (CDCl$_3$, 300 MHz) δ 0.92 (t, J=7 Hz, 3H), 0.97 (t, J=7 Hz, 3H), 1.28–1.50 (br m, 4H), 1.52–1.68 (m, 2H), 1.75–1.90 (br m, 2H), 2.98–3.06 (m, 2H), 3.08 (q, J=6 Hz, 2H), 4.10–4.23 (br m, 1H); MS (DCl/NH$_3$) m/e 211 (M+NH$_4$)$^+$.

EXAMPLE 3149B

Ethyl trans,trans-4-(1,3-benzodioxol-5-yl)-1-(2-bromoethyl)-2-propylpyrrolidine-3-carboxylate The title compound was prepared according the procedure of Example 61A, substituting the compound of Example 94B for the pyrrolidine mixture.

EXAMPLE 314C

Ethyltrans,trans-2-(Propyl)-4-(1,3-benzodioxol-5-yl)-1-(2-(N-propyl-pentanesulfonylamino)ethyl) pyrrolidine-3-carboxylate A solution of the compound of Example 314A (6.6 mg, 34 μmol) in 0.1 mL DMF was treated with sodium hydride (2 mg, 60% oil dispersion, 1.2 mg NaH, 50 μmol). The resulting mixture was stirred at room temperature for 15 min, then a solution of the compound of Example 189B (9.0 mg, 22 μmol) in 0.1 mL DMF was added, followed by 0.5 mg of tetra-n-butylammonium iodide. The reaction was sealed under argon and stirred at 60° C. overnight. The reaction was concentrated under high vacuum, and the residue was partitioned between 2 mL of saturated aqueous NaHCO$_3$, 1 mL water and 5 mL EtOAc. The organic phase was washed with 1 mL brine, dried by passing through a plug of Na$_2$SO$_4$, and the filtrate concentrated in vacuo to an oil. The crude product was purified by preparative TLC (silica gel, 8×20 cm, 0.25 mm thickness, eluting with 20% EtOAc-hexane, providing 8.4 mg (73%) of the title compound as a wax.

EXAMPLE 314D trans,trans-4-(1,3-benzodioxol-5-yl)-2-(Propyl)-1-(2-(N-propyl-pentanesulfonylamino)ethyl)pyrrolidine-3-carboxylic Acid The title compound was prepared according to the procedure of Example 71C. $^1$H NMR (CDCl$_3$, 300 MHz) δ 0.88–1.00 (m, 9H), 1.20–1.55 (br m, 6H), 1.55–1.68 (m, 3H), 1.70–1.85 (br m, 2H), 1.90–2.16 (br m, 2H), 2.84–3.26 (br m, 6H), 3.26–3.90 (br m, 6H), 5.95 (s, 2H), 6.76 (d, J=8 Hz, 1H), 6.79 (m, 1H), 6.93 (br s, 1); HRMS (FAB) calcd for C$_{25}$H$_{41}$N$_2$O$_6$S (M+H)$^+$497.2685, found 497.2679.

EXAMPLE 315 trans,trans-4-(1,3-benzodioxol-5-yl)-2-(Propyl)-1-(2-(N-propyl-dimethylsulfamoylamino)ethyl)-pyrrolidine-3-carboxylic Acid Using the procedures described in Example 66, the title compound was preapred as a white solid. m.p.59–61° C. $^1$H NMR (CDCl$_3$, 300 MHz) δ 0.79 (t, J=7.5 Hz, 3H), 1.45 (sextet, J=7.5 Hz, 2H), 2.22–2.31(m, 1H), 2.65(s, 6H), 2.70–2.79 (m, 1H), 2.85–3.04 (m, 4H), 3.09–3.32 (m, 2H), 3.40(d, J=9 Hz, 1H), 3.55 (t, J=9 Hz, 1H), 3.65(d, J=9 Hz, 1H), 3.81(s, 3H), 5.96(s,2H), 6.75(d, J=9 Hz, 1H), 6.83(d, J=9 Hz, 1H), 6.88(d, J=9 Hz, 2H), 7.02(s, 1H), 7.34(d, J=9 Hz, 2H). MS (DCl/NH$_3$) m/e 534 (M+H)$^+$.

EXAMPLE 316 trans-trans-2-(4-Methoxphenyl)-4-(1,3-benzodioxol-5-yl)-1-[2-(N-propyl-N-[4-methoxyphenyl] sulfonylamino)propyl]-pyrrolidine-3-carboxylic Acid

EXAMPLE 316A

Ethyl trans-trans and cis-trans 2-(4-Methoxyphenyl)-4-(1,3-benzodiox-5-yl)-1-(3-bromopropyl) pyrrolidine-3-carboxylate A 2:1 mixture of trans-trans and cis-trans ethyl 2-(4-methoxyphenyl)-4-(1,3-benzodiox-5-yl)-pyrrolidine-3-carboxylate (4.00 g; prepared according to example 1C), 32 ml dibromopropane, and 200 mg sodium iodide, were heated at 100° for 1.25 hrs. The excess dibromopropane was removed in vacuo and the residue was dissolved in toluene. After shaking with potassium bicarbonate, the solution was dried (Na$_2$SO$_4$) and the solution concentrated. The residue was chromatographed on silica gel eluting with 5:1 hexane:EtOAc. yielding 5.22 (98%) of the title compound.

EXAMPLE 316B

Ethyl trans-trans and cis-trans 2-(4-Methoxyphenyl)-4-(1,3-benzodiox-5-yl)-1-(3-propylaminopropyl) Pyrrolidine-3-carboxylate The compound described in Example 316A (5.22 g) was heated at 80° for 2 hrs. with 35 ml ethanol, 2.5 g. propyamine and 35 mg. sodium iodide. The solvents were removed in vacuo. The residue was dissolved in toluene, shaken with potassium bicarbonate solution and dried (Na$_2$SO$_4$). The solution was concentated in vacuum to give 4.96 g of the title compound as an orange oil. This was used in the next step without purification.

EXAMPLE 316C trans-trans-2-(4-Methoxphenyl)-4-(1,3-benzodioxol-5-yl)-1-[2-(N-propyl-N-[4-methoxyphenyl] sulfonylamino)propyl]-pyrrolidine-3-carboxylic Acid Using the method described in example 66, the compound prepared in Example 316B was reacted with 4-methoxybenzenesulfonyl chloride in acetonitrile containing diisopropylethylamine. The resulting product was chromatographed on silica gel (30% EtOAc in hexane), and hydrolyzed to the title compound by the method of example 1D. NMR (CDCl$_3$, 300 MHz) δ 0.83 (t, J=7 Hz, 3H), 1.40–1.52 (m, 2H), 1.56–1.70 (m, 2H), 2.00–2.11 (m, 1H), 2.40–2.51 (m, 1H), 2.69–2.78 (m, 1H), 2.84–3.03 (m, 4H), 3.19–3.34 (m, 2H), 3.48–3.59 (m, 2H), 3.80 (s, 3H), 3.86 (s, 3H), 5.95 (s, 2H), 6.74 (d, J=8 Hz, 1H), 6.85 (d, J=8 Hz, 3H), 6.93 (d, J=8 Hz, 2H), 7.02 (d, J=2 Hz, 1H), 7.29 (d, J=8 Hz, 2H), 7.69 (d, J=8 Hz, 2H). Anal calcd for C$_{32}$H$_{38}$N$_2$O$_8$S: C, 62.93; H, 6.27; N, 4.59. Found: C, 62.97; H, 6.39; N, 4.45.

EXAMPLE 317 trans-trans-2-(4-Methoxphenyl)-4-(1,3-benzodioxol-5-yl)-1-[2-(N-propyl-N-propylsulfonylamino) propyl]-pyrrolidine-3-carboxylic Acid Using the method described in example 66, the propylamino compound prepared in Example 316B was reacted with propanesulfonyl chloride in acetonitrile containing diisopropylethylamine. The resuling product was chromatographed on silica gel (30% EtOAc in hexane) and hydrolyzed to the title compound by the method of example 1D. NMR (CDCl$_3$, 300 MHz) δ 0.85 (t, J=7 Hz, 3H), 1.02 (t, J=7 Hz, 3H), 1.47–1.60 (m, 2H), 1.65–1.85 (m, 4H), 2.04–2.16 (m, 1H), 2.42–2.57 (m, 1H), 2.72–3.11 (m, 5H), 3.25–3.41 (m, 2H), 3.50–3.62 (m, 2H), 3.80 (s, 3H), 5.84 (s, 2H), 6.72 (d, J=8 Hz, 1H), 6.80–6.90 (m, 3H), 7.02 (d, J=2 Hz, 1H), 7.30 (d, J=9 Hz, 2H). Anal calcd for C$_{28}$H$_{38}$N$_2$O$_7$S: C, 61.52; H, 7.01; N, 5.12. Found: C, 61.32; H, 7.01; N, 5.01.

EXAMPLE 318 trans,trans-2-(3-Fluoro-4-methoxyphenyl)-4-(1,3-benzodioxol-5-yl)1-(2-(N-propyl-N-pentanesulfonylamino)ethyl)-pyrrolidine-3-carboxylic Acid Using the procedures described in Example 313 and Example 66, the title compound was prepared as a white solid. m.p.66–68° C. $^1$H NMR (CDCl$_3$, 300 MHz) δ 0.81 (t, J=7.5 Hz, 3H), 0.89(t, J=7 Hz, 3H), 1.26–1.35(m, 4H), 1.45(sextet, J=7.5 Hz, 2H), 1.68–1.76 (m, 2H), 2.25–2.33(m, 1H), 2.72–2.92(m, 5H), 2.97–3.12(m, 2H), 3.16–3.33(m, 2H), 3.43 (dd, J=3 Hz, J=9 Hz, 1H), 3.53–3.60(m, 1H), 3.66(d, J=10 Hz, 1H), 3.88(s, 3H), 5.95(s, 2H), 6.74(d, J=8 Hz, 1H), 6.82(dd, J=1 Hz, J=8 Hz, 1H), 6.29 (t, J=8 Hz, 1H), 6.97(d, J=1 Hz, 1H), 7.12(d, J=8 Hz, 1H), 7.18(dd, J=1 Hz, J=12 Hz, 1H) MS (DCl/NH$_3$) m/e 579 (M+H)$^+$.

EXAMPLE 319 trans-trans-2-(4-Pyridinyl)-4-(1,3-benzodioxol-5-yl)-1-[N,N-di(n-butyl)aminocarbonylmethyl]-pyrrolidine-3-carboxylic Acid The title compound was prepared using the methods described in examples 1 and 43, using methyl 3-oxo-3-(4-pyridyl)propanoate (J. Am. Chem. Soc. 1993, 115, 11705) in place of ethyl (4-methoxybenzoyl)acetate. m.p. 131–132° C. NMR (CDCl$_3$, 300 MHz) δ 0.82 (t, J+7 Hz, 3H), 0.88 (t, J=7 Hz, 3H), 1.05–1.50 (m, 8H), 2.90 (dd, J=7 Hz, 9 Hz, 1H), 2.97 (d, J=13 Hz, 1H), 3.00–3.25 (m, 4H), 3.32 (m, 1H), 3.39 (d, J=13 Hz, 1H), 3.45–3.52 (m, 1H), 3.67–3.78 (m, 1H), 4.10 (d, J=9 Hz, 1H), 5.92 (dd, J=2 Hz, 4 Hz, 2H), 6.75 (d, J=9 Hz, 1H), 6.90 (dd, J=9 Hz, 2 Hz, 1H), 7.02 (d, J=2 Hz, 1H), 7.45 (d, J=8 Hz, 2H), 8.50 (d, J=8 Hz, 2H). Anal calcd for C$_{27}$H$_{35}$N$_3$O$_5$; C, 67.34; H, 7.33; N, 8.73. Found: C, 67.39; H, 7.45; N, 8.61.

EXAMPLE 320 trans-trans-2-(4-Methoxyphenyl)-4-(1,3-benzodioxol-5-yl)-1-[2-(N-propyl-N-diethylaminocarbonylamino)ethyl]-pyrrolidine-3-carboxylic Acid The title compound was prepared using the procedures described in example 61, substituting propylamine for aqueous methylamine in Example 61B and diethylcarbamyl chloride for isobutyryl chloride in Example 61C. NMR (CD$_3$OD, 300 MHz) δ 0.74 (t, 3H, J=7), 1.09 (t, 6H, J=7), 1.33 (m, 2H), 3.17 (q, 4H, J=7), 3,78 (s, 3H), 4.04 (m, 1H), 5.93 (s, 2H), 6.86 (d, 1H, J=8), 7.06 (dd, 1H, J=2,8), 6.94 (d, 2H, J=9), 7.04 (d, 1H, J=2), 7.40 (d, 2H, J=9). MS (DCl/NH$_3$) m/z 526. Anal calcd for C$_{29}$H$_{39}$N$_3$O$_6$.0.1 TFA: C, 65.31; H, 7.34; N, 7.82. Found: C, 65.33; H, 7.43; N, 8.14.

EXAMPLE 321 trans-trans-2-(4-Methoxyphenyl)-4-(1,3-benzodioxol-5-yl)-1-[3,5-dimethylpiperidinyl-carbonylmethyl]-pyrrolidine-3-carboxylic Acid The title compound was prepared using the procedures described in example 1. NMR (CD$_3$OD, 300 MHz) shows mixture of isomers. δ 0.88 (d, 3H, J=7), 0.93 (d, 3H, J=7), 3.82 (s, 3H), 5.95 (s, 2H), 6.82 (d, 1H, J=8), 6.89 (dd, 1H, J=1,8), 7.00 d, 2H, J=9), 7.03 (m, 1H), 7.47 (d, 2H, J=9). MS (DCl/NH$_3$) m/z 495.

EXAMPLE 322 trans-trans-2-(4-Methoxyphenyl)-4-(1,3-benzodioxol-5-yl)-1-[N,N-di(s-butyl)aminocarbonylmethyl]-pyrrolidine-3-carboxylic Acid The title compound was prepared using the procedures described in example 1. NMR (CD$_3$OD, 300 MHz) suggests a mixture of isomers. δ 0.83 (t, 6H, J=8), 1.27 (d, 6H, J=7), 1.6 (m, 2H), 3.79 (s, 3H), 5.93 (s, 2H), 6.75 (d, 1H, J=8), 6.86 (d, 1H, J=8), 6.94 (d, 2H, J=9), 7.03 (d, 1H, J=2), 7.35 (d, 2H, J=9). MS (DCl/NH$_3$) m/z 511.

EXAMPLE 323 trans-trans-2-(4-Methoxyphenyl)-4-(1,3-benzodioxol-5-yl)-1-[N-(2-Methylphenyl)-N-butylamino carbonylmethyl]-pyrrolidine-3-carboxylic Acid The title compound was prepared using the procedures described in example 1. MS (DCl/NH$_3$) m/z 545. Anal calcd for C$_{32}$H$_{36}$N$_2$O$_6$. 0.9 H$_2$O: C, 68.53; H, N, 4.99. Found: C, 68.56; H, 6.62; N, 4.71.

EXAMPLE 324 trans-trans-2-(4-Methoxyphenyl)-4-(1,3-benzodioxol-5-yl)-1-[N-(3-Methylphenyl)-N-butylamino carbonylmethyl]-pyrrolidine-3-carboxylic Acid The title compound was prepared using the procedures described in example 1. NMR (CD$_3$OD, 300 MHz) d 0.88 (t, 3H, J=7), 1.2–1.5 (m, 4H), 2.31 (s, 3H), 2.8 (m, 2H), 3.14

(t, 1H, J=10), 3.3 (m, 1H), 3.44 (dd, 1H, J=5,10), 3.53 (m, 1H), 3.60 (t, 2H), J=7), 3.79 (s, 3H), 3.82 (m, 1H), 5.93 (s, 2H), 6.74 (d, 1H, J=8), 6.8–6.9 (m, 5H), 7.06 (d, 1H, J=2), 7.09 (d, 2H, J=9), 7.18 (d, 1H, J=7), 7.27 (t, 1H, J=7). MS (DCl/NH$_3$) m/z 545. Anal calcd for C$_{32}$H$_{36}$N$_2$O$_6$. 0.8 H$_2$O: C, 68.75; H, 6.78; N, 5.01. Found: C, 68.70; H, 6.67; N, 4.85.

EXAMPLE 325 trans,trans-4-(1,3-Benzodioxol-5-yl)-2-(benzyloxymethyl)-1-((N,N-dibutylaminocarbonylmethyl)pyrrolidine-3-carboxylic Acid

EXAMPLE 325A

Ethyl trans,trans-4-(1,3-Benzodioxol-5-yl)-2-(benzyloxymethyl)-1-((N,N-di(n-butyl)aminocarbonylmethyl)pyrrolidine-3-carboxylate The procedures of Example 1A-1D were followed, substituting ethyl 4-benzyloxy-3-oxobutyrate for 4-methoxybenzoylacetate in Example 1A, to afford the title compound as a colorless oil. TLC (30% EtOAc-hexane) Rf 0.18; $^1$H NMR (CDCl$_3$, 300 MHz) δ 0.88 (t, J=7 Hz, 6H), 1.17 (t, J=7 Hz, 3H), 1.20–1.34 (br m, 4H), 1.40–1.56 (br m, 3H), 2.85 (t, J=8 Hz, 1H), 2.98–3.30 (m, 5H), 3.39–3.60 (m, 3H), 3.64–3.75 (m, 2H), 3.92 (d, J-14 Hz, 1H), 4.10 (two overlapping q, J=6.5 Hz, 2H), 4.53 (s, 2H), 5.91 (m, 2H), 6.69 (d, J=9 Hz, 1H), 6.77 (dd, J=1.5, 9 Hz, 1H), 6.91 (d, J=1.5 Hz, 1H); MS (DCl/NH$_3$) m/e 553 (M+H)$^+$.

EXAMPLE 325B trans,trans-4-(1,3-Benzodioxol-5-yl)-2-(benzyloxymethyl)-1-((N,N-di(n-butyl)aminocarbonylmethyl)pyrrolidine-3-carboxylic Acid The title compound was prepared according to the procedure of Example 71C, as a colorless glass. TLC (5% MeOH-CH$_2$Cl$_2$) Rf 0.13; $^1$H NMR (CDCl$_3$, 300 MHz) δ 0.86 (t, J=7 Hz), and 0.90 (t, J=7 Hz, 6H total), 1.15–1.52 (br m, 8H), 2.96–3.35 (br m, 5H), 3.50–3.75 (br m, 2H), 3.80 (dd, J=3, 13 Hz, 1H), 3.8–84.40 (br m, 6H), 4.45 (AB, 2H), 5.90 (s, 2H), 6.70 (d, J=8 Hz, 1H), 6.84 (dd, J=1,8 Hz, 1H), 6.93 (d, J=1 Hz, 1H), 7.28–7.39 (m, 5H); MS (DCl/NH$_3$) m/e 524 (M+H)$^+$.

EXAMPLE 326 trans,trans-4-(1,3-Benzodioxol-5-yl)-2-(hydroxymethyl)-1-((N,N-di(n-butyl)aminocarbonylmethyl)pyrrolidine-3-carboxylate

EXAMPLE 326A trans,trans-4-(1,3-Benzodioxol-5-yl)-2-(hydroxymethyl)-1-((N,N-di(n-butyl)aminocarbonylmethyl)pyrrolidine-3-carboxylate Acid The resultant product from Example 325A (128 mg, 0.232 mmol) and 25 mg of 20% Pd(OH)$_2$ on charcoal in 7 mL EtOH was stirred under 1 atm hydrogen for 48 h. The mixture was filtered through a plug of celite, and the catalyst was washed with 2×10 mL EtOH, then the combined filtrate and washes were concentrated under reduced pressure to afford the crude product. Purification by flash chromatography (40% EtOAc-hexane) provided the title compound.

EXAMPLE 326B trans,trans-4-(1,3-Benzodioxol-5-yl)-2-(hydroxymethyl)-1-((N,N-di(n-di(butyl)aminocarbonylmethyl)pyrrolidine-3-carboxylic Acid The title compound was prepared according to the procedure of Example 71C.

EXAMPLE 327 trans,trans-4-(1,3-Benzodioxol-5-yl)-2-(N-methylpropenamid-3-yl)-1-((N,N-di(n-butyl)aminocarbonylmethyl)pyrrolidine-3-carboxylic Acid

EXAMPLE 327A

Ethyl trans,trans-4-(1,3-Benzodioxol-5-yl)-2-(formyl)-1-((N,N-di(n-butyl)aminocarbonylmethyl)pyrrolidine-3-carboxylate The title compound is made by selective oxidation (e.g. using the Swern oxidation with DMSO, oxalyl chloride, ethyldiisopropylamine or using the Dess-Martin periodinane) of the compound of Example 326A.

EXAMPLE 327B

Ethyl trans,trans-4-(1,3-Benzodioxol-5-yl)-2-(O-tert-butylpropenoat-3-yl)-1-((N,N-di(n-butyl)aminocarbonylmethyl)pyrrolidine-3-carboxylate The title compound is produced by condensing the compound of Example 327A with tert-butyl triphenylphosphoranylidine acetate in CH$_2$Cl$_2$ solution.

EXAMPLE 327C

Ethyl trans,trans-4-(1,3-Benzodioxol-5-yl)-2-(propenoic acid-3-yl)-1-(N,N-di(n-butyl)aminocarbonylmethyl)pyrrolidine-3-carboxylate The title compound is produced by reacting the compound of Example 327B with trifluoacetic acid in CH$_2$Cl$_2$ (1:1).

EXAMPLE 327D

Ethyl trans,trans-4-(1,3-Benzodioxol-5-yl)-2-(N-methylpropenamid-3-yl)-1-(N,N-di(n-butyl)aminocarbonylmethyl)pyrrolidine-3-carboxylate The title compound is produced by condensing the compound of Example 327C with methylamine hydrochloride in the presence of a carbodiimide (e.g. N-ethyl-N-(3-dimethylamino)propylcarbodiimide, DCC).

EXAMPLE 327E trans,trans-4-(1,3-Benzodioxol-5-yl)-2-(N-methylpropenamid-3-yl)-1-(N,N-di(n-butyl)aminocarbonylmethyl)pyrrolidine-3-carboxylic Acid The title compound is produced by reacting the compound of Example 327D with lithium hydroxide according to the procedure of Example 71C.

EXAMPLE 328 trans,trans-4-(1,3-Benzodioxol-5-yl)-2-(1-hydroxy-2-propen-3-yl)-1-(N,N-di(n-butyl)aminocarbonylmethyl)pyrrolidine-3-carboxylic Acid

EXAMPLE 328A

Ethyl trans,trans-4-(1,3-Benzodioxol-5-yl)-2-(1-hydroxy-2-propen-3-yl)-1-(N,N-di(n-butyl)aminocarbonylmethyl)pyrrolidine-3-carboxylate The title compound is produced by reacting the compound of Example 327C with borane methyl sulfide complex.

EXAMPLE 328B trans,trans-4-(1,3-Benzodioxol-5-yl)-2-(1-hydrox-2-propen-3-yl)-1-(N,N-di(n-butyl)aminocarbonylmethyl)pyrrolidine-3-carboxylic Acid The title compound is produced by condensing the compound of Example 328A with lithium hydroxide according to the procedure of Example 71C.

EXAMPLE 329 trans,trans-4-(1,3-Benzodioxol-5-yl)-2-(N-benzylaminomethyl)-1-(N,N-di(n-butyl)aminocarbonylmethyl)pyrrolidine-3-carboxylic Acid

EXAMPLE 329A

Ethyl trans,trans-4-(1,3-Benzodioxol-5-yl)-2-(N-benzylaminomethyl)-1-(N,N-di(n-butyl)aminocarbonylmethyl)pyrrolidine-3-carboxylate The title compound is produced by condensing the compound of Example 327A with benzylamine in the presence of sodium cyanoborohydride in ethanol.

EXAMPLE 329B trans,trans-4-(1,3-Benzodioxol-5-yl)-2-(N-benzylaminomethyl)-1-(N,N-di(n-butyl)aminocarbonylmethyl)pyrrolidine-3-carboxylic Acid The title compound is produced by reacting the compound of Example 329A with lithium hydroxide according to the procedure of Example 71C.

EXAMPLE 330 trans,trans-4-(1,3-Benzodioxol-5-yl)-2-(N-acetyl-N-benzylaminomethyl)-1-(N,N-di(n-butyl)aminocarbonylmethyl)pyrrolidine-3-carboxylic Acid

EXAMPLE 330A

Ethyl trans,trans-4-(1, 3-Benzodioxol-5-yl)-2-(N-acetyl-N-benzylaminomethyl)-1-(N,N-di(n-butyl)aminocarbonylmethyl)pyrrolidine-3-carboxylate The title compound is produced by reacting the compound of Example 3294A with acetic anhydride in the presence of pyridine or triethylamine.

EXAMPLE 330B trans,trans-4-(1,3-Benzodioxol-5-yl)-2-(N-acetyl-N-benzylaminomethyl)-1-(N,N-di(n-butyl)aminocarbonylmethyl)pyrrolidine-3-carboxylic Acid The title compound is produced by reacting the compound of Example 330A with lithium hydroxide according to the procedure of Example 71C.

EXAMPLE 331 trans,trans-4-(1,3-Benzodioxol-5-yl)-2-(ethynyl)-1-(N,N-di(n-butyl)aminocarbonylmethyl)pyrrolidine-3-carboxylic Acid

EXAMPLE 331A

Ethyl trans,trans-4-(1,3-Benzodioxol-5-yl)-2-(ethynyl)-1-(N,N-di(n-butyl)aminocarbonylmethyl)pyrrolidine-3-carboxylate The title compound is made by employing the procedure of Corey and Fuchs (Tetrahedron Left. 1972, 3769–72), using the compound of Example 327A.

EXAMPLE 331B trans,trans-4-(1,3-Benzodioxol-5-yl)-2-(ethynyl)-1-(N,N-di(n-butyl)aminocarbonylmethyl)pyrrolidine-3-carboxylic Acid The title compound is produced by reacting the compound of Example 331A with lithium hydroxide according to the procedure of Example 71C.

EXAMPLE 332 trans,trans-4-(1,3-Benzodioxol-5-yl)-2-(1-pentynyl)-1-(N,N-di(n-butyl)aminocarbonylmethyl)pyrrolidine-3-carboxylate

EXAMPLE 332A

Ethyl trans,trans-4-(1,3-Benzodioxol-5-yl)-2-(pentynyl)-1-(N,N-di(n-butyl)aminocarbonylmethyl)pyrrolidine-3-carboxylate The title compound is made by palladium-catalyzed coupling of the compound of Example 206A and propyl iodide, employing the procedure of Taylor, et. al. (J. Org. Chem. 1989, 54(15), 361–24).

EXAMPLE 332B trans,trans-4-(1,3-Benzodioxol-5-yl)-2-(1-pentynyl)-1-(N,N-di(n-butyl)aminocarbonylmethyl)pyrrolidine-3-carboxylic Acid The title compound is produced by reaction the compound of Example 332A with lithium hydroxide according to the procedure of Example 71C.

EXAMPLE 333 trans-trans-2-(4-Methoxphenyl)-4-(1,3-benzodioxol-5-yl)-1-[2-(2,6-dioxopiperidinyl) ethyl}-pyrrolidine-3-carboxylic Acid The compound of example 61A is added to a solution of the sodium salt of glutarimide in dimethylformamide. After stirring 24 hours, water is added and the mixture is extracted with ether. The resultant glutarimide is hydrolyzed to the title compound by the method of example 1D.

EXAMPLE 334 trans-trans-2-(4-Methoxyphenyl)-4-(1 3-benzodioxol-5-yl)-1-[N,N-diphenylaminocarbonylmethyl]-pyrrolidine-3-carboxylic Acid.

The title compound was prepared according to the procedures described in Example 1. $^1$H NMR (300 MHz, CD$_3$OD) δ 2.83 (dd, 1, J=8.1, 9.7), 2.99 (d, 1, J=15.4), 3.19 (t, 1, J=9.5), 3.49 (d, 1, J=15.3), (dd, 1, J=4.6, 95.), 3.57 (m, 1), 3.79 (s, 3), 3.85 (d, 1, J=9.5), 5.90 (s, 2), 6.71 (d, 1, J=8.0), 6.84 (m, 3), 7.04 (d, 1, J=1.6), 7.14–7.16 (m, 6), 7.19–7.34 (m, 6); MS (DCl/NH$_3$) m/z 551; Anal Calcd for C$_{33}$H$_{30}$N$_6$.0.65H$_2$O.0.35C$_2$H$_5$OCOCH$_3$: C, 69.77, H, 5.77, N, 4.76. Found: C, 69.75, H, 5.55, N, 4.64.

EXAMPLE 335 trans-trans-2-(4-Methoxyphenyl)-4-(1,3-benzodioxol-5-yl)-1-[N,N-diisopropylaminocarbonvimethyl]-pyrrolidine-3-carboxylic Acid The title compound was prepared according to the procedures described in Example 1. $^1$H NMR (300 MHz, CD$_3$OD) δ 0.95 (d, 3, J=6.5), 1.24 (d, 3, J=6.4), 1.30 (d, 6, J=6.8), 2.85 (d, 1, J=12.5), 3.04 (dd, 1, J=8.1, 9.8), 3.14 (t, 1, J=9.7), 3.32–3.55 (m, 3), 3.63 (m, 1H), 5.92 (s, 2), 6.75 (d, 1, J=8.1), 6.85 9 dd, 1, J=1.7, 8.1), 6.93 (m, 2), 7.02 (d, 1, J=1.7), 7.35 (m, 2). MS (DCl/NH$_3$) m/z 483. Anal Calcd for C$_{27}$H$_{34}$N$_2$O$_6$.0.65 EtOAc: C, 65.86, H, 7.32, N, 5.19. Found: C, 5.74, H, 7.26, N, 5.52.

EXAMPLE 336 trans,trans-2-(3-Fluoro-4-methoxyphenyl)-4-(1,3-benzodioxol-5-yl)-1-1-(2-N-propyl-N-butanesulfonylamino)ethyl)-pyrrolidine-3-carboxylic Acid Using the procedures described in Example 313 and Example 66, the title compound was prepared as a white solid. m.p.65–66° C.1 H NMR (CDCl3, 300 MHz) δ 0.82(t, J=7.5 Hz, 3H), 0.92(t, J=7.5 Hz, 3H), 1.34–1.52(m, 4H), 1.72(quintet, J=7.5 Hz, 2H), 2.25–2.35(m, 1H), 2.72–2.94 (m, 5H), 2.97–3.12(m, 2H), 3.19–3.46 (m, 2H), 3.44(d, J=9 Hz, 1H), 3.53–3.60(m, 1H), 3.67(d, J=9 Hz, 1H), 3.89(s, 3H), 5.95 (s, 2H), 6.74(d, J=8 Hz, 1H), 6.82(d, J=8 Hz, 1H), 6.92(t, J=9 Hz, 1H), 6.97(s, 1H), 7.2(d, J=9 Hz, 1H), 7.18(d, J=12 Hz, 1H). MS (DCl/NH$_3$) m/e 565 (M+H)$^+$.

EXAMPLE 337

Using methods described in the above examples, the compounds disclosed in Table 1 can be prepared.

TABLE 1

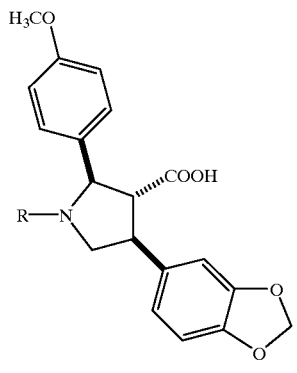

| | R |
|---|---|
| 1. | 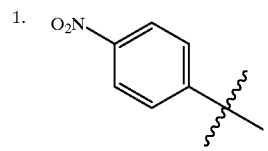 |
| 2. | 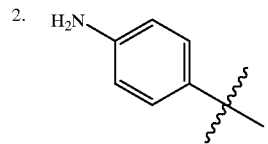 |

TABLE 1-continued

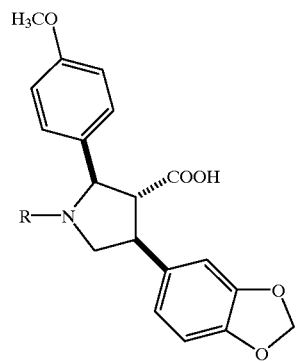

| | R |
|---|---|
| 3. | 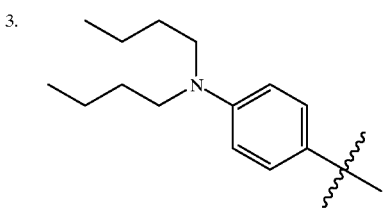 |
| 4. | 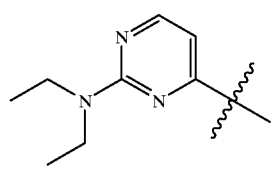 |
| 5. | 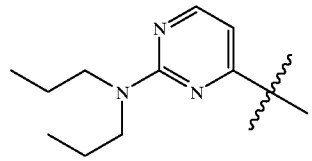 |
| 6. | 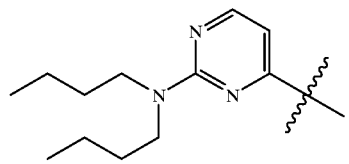 |
| 7. | 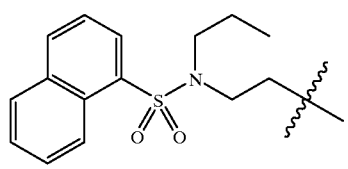 |
| 8. | 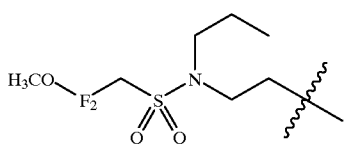 |

TABLE 1-continued
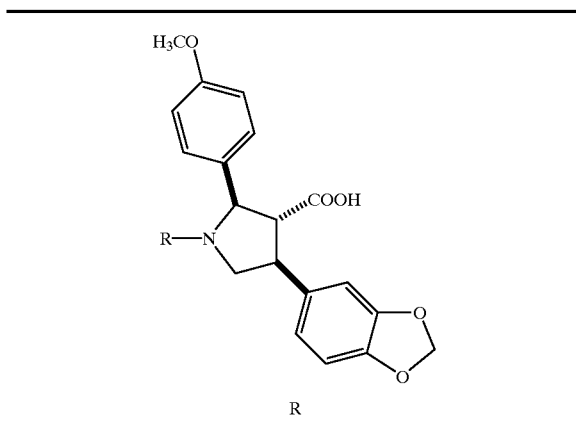
R
| | R |
|---|---|
| 9. | 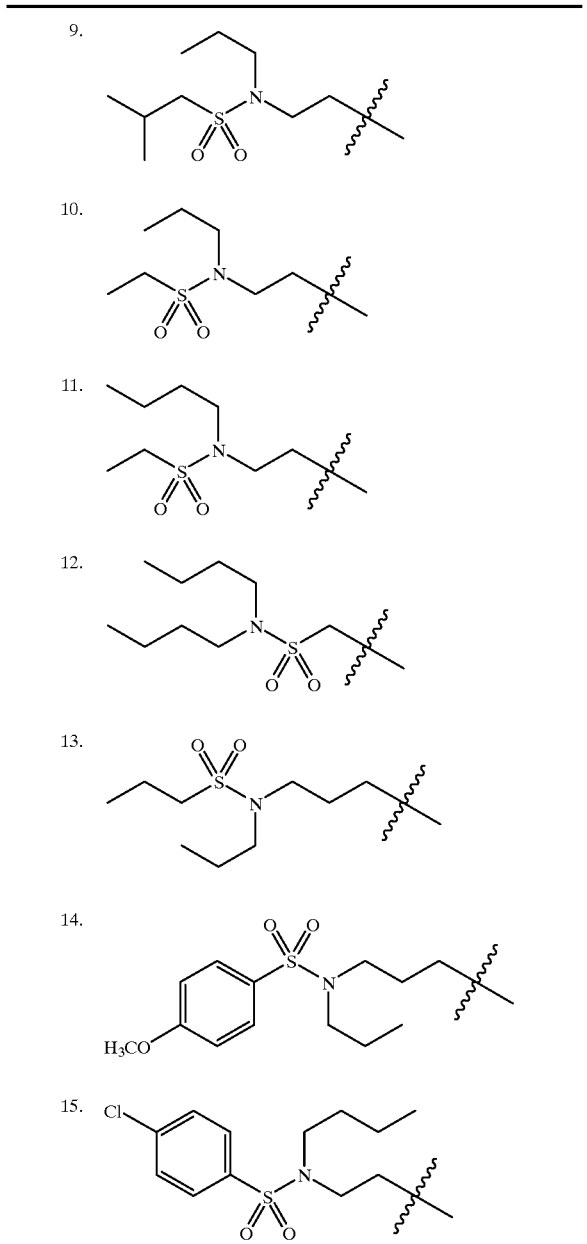 |
| 10. | |
| 11. | |
| 12. | |
| 13. | |
| 14. | |
| 15. | |
TABLE 1-continued
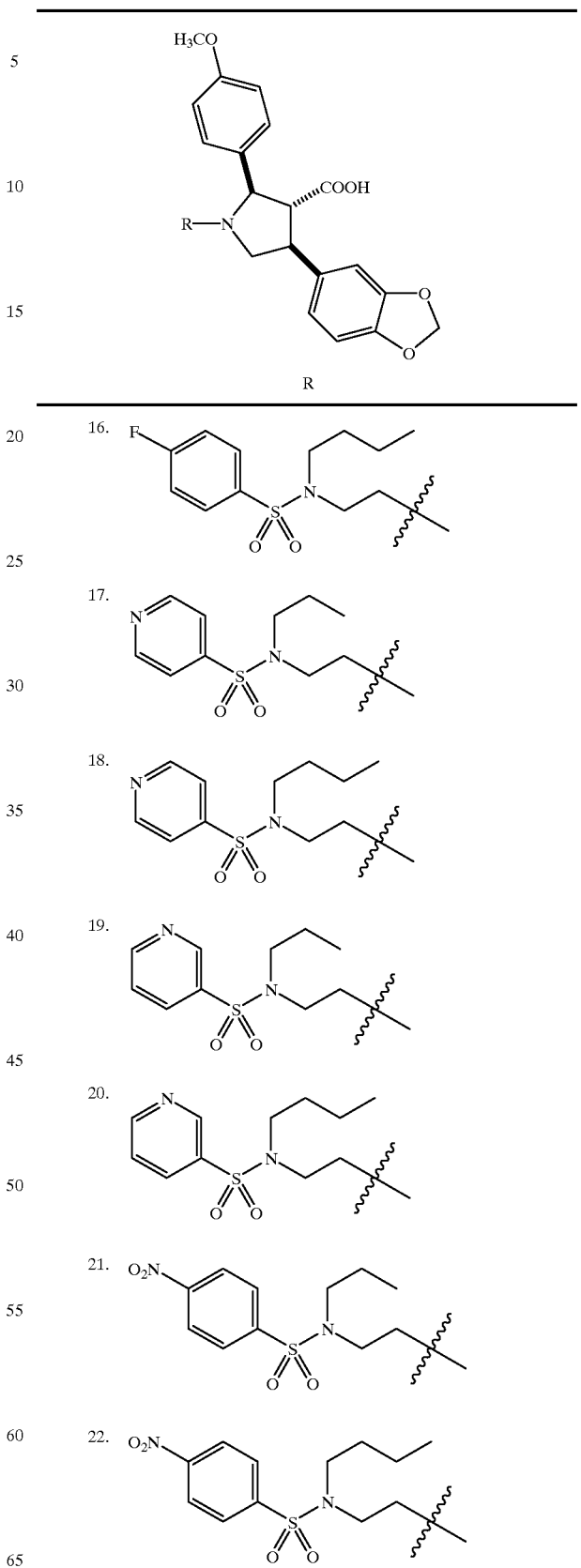
| | R |
|---|---|
| 16. | |
| 17. | |
| 18. | |
| 19. | |
| 20. | |
| 21. | |
| 22. | |

TABLE 1-continued

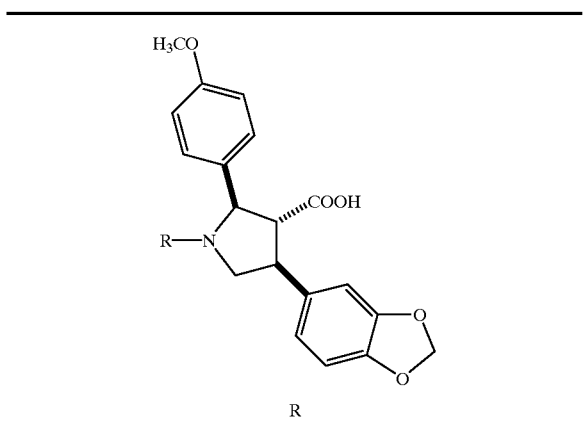

R

| | R |
|---|---|
| 23. | butyl, propylsulfonyl on N, with tether |
| 24. | butyl, 3-chloropropylsulfonyl on N, with tether |
| 25. | butyl, 4-methoxyphenylsulfonyl on N, with tether |
| 26. | butyl, methoxyethylsulfonyl on N, with tether |
| 27. | butyl, 3,3,3-trifluoropropylsulfonyl on N, with tether |
| 28. | propyl, 3,3,3-trifluoropropylsulfonyl on N, with tether |
| 29. | butyl, 3-fluoropropylsulfonyl on N, with tether |

TABLE 1-continued

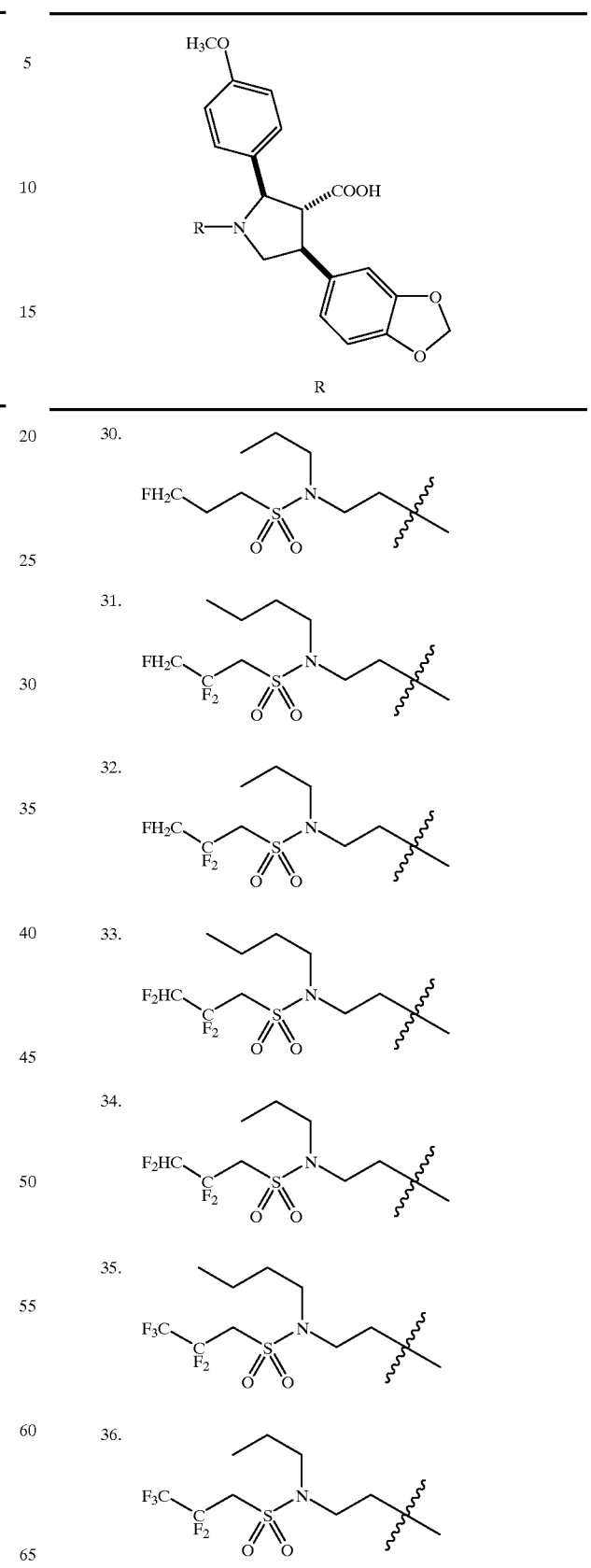

R

| | R |
|---|---|
| 30. | propyl, 3-fluoropropylsulfonyl on N, with tether |
| 31. | butyl, 3-fluoro-2,2-difluoroethyl-sulfonyl on N, with tether |
| 32. | propyl, 3-fluoro-2,2-difluoroethyl-sulfonyl on N, with tether |
| 33. | butyl, 3,3-difluoro-2,2-difluoropropylsulfonyl on N, with tether |
| 34. | propyl, 3,3-difluoro-2,2-difluoropropylsulfonyl on N, with tether |
| 35. | butyl, 3,3,3-trifluoro-2,2-difluoropropylsulfonyl on N, with tether |
| 36. | propyl, 3,3,3-trifluoro-2,2-difluoropropylsulfonyl on N, with tether |

TABLE 1-continued
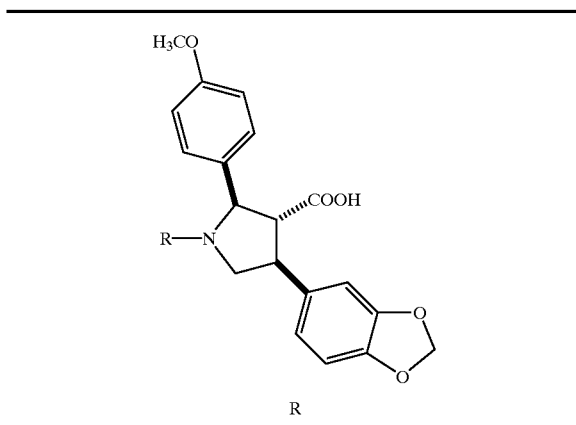
R
| | |
|---|---|
| 37. | 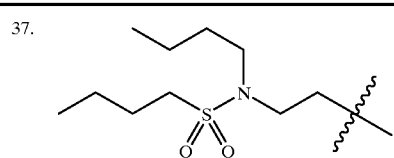 |
| 38. | 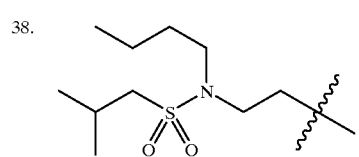 |
| 39. | 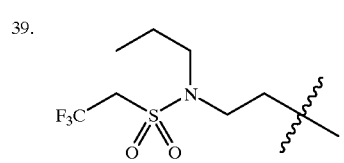 |
| 40. | 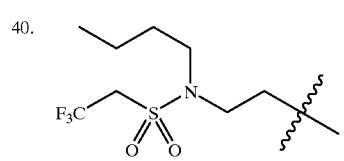 |
| 41. | 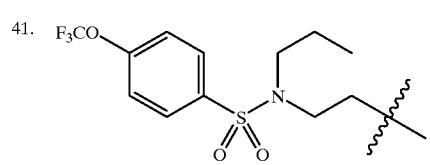 |
| 42. | 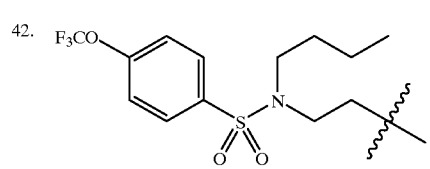 |
| 43. | 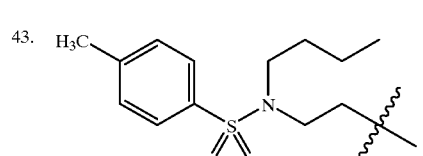 |
TABLE 1-continued
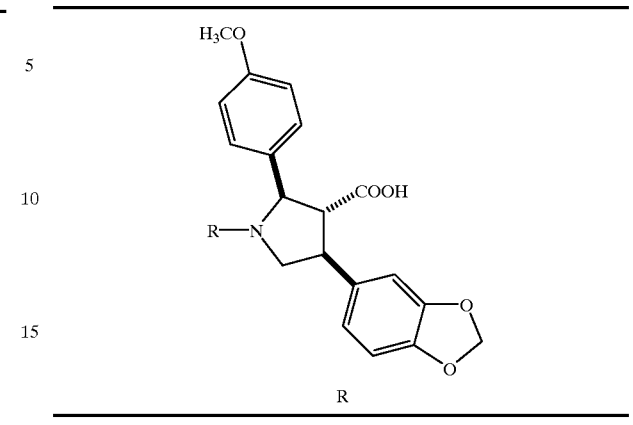
R
| | |
|---|---|
| 44. | 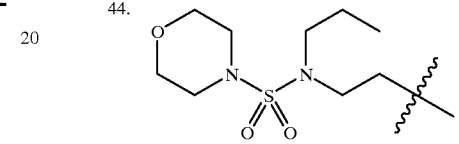 |
| 45. | 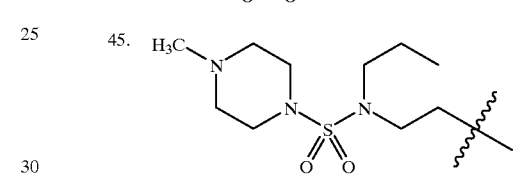 |
| 46. | 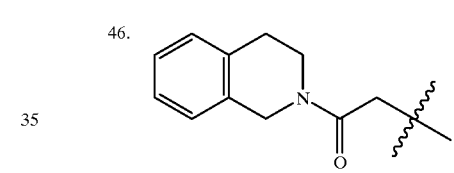 |
| 47. | 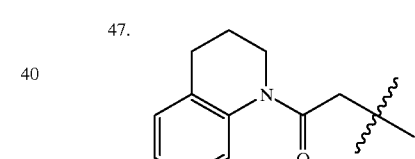 |
| 48. | 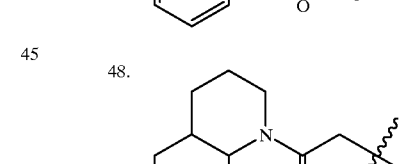 |
| 49. | 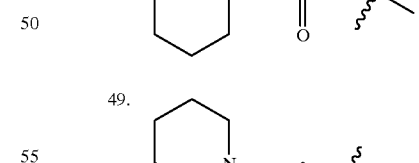 |
| 50. | 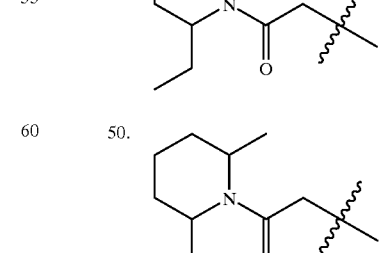 |

TABLE 1-continued
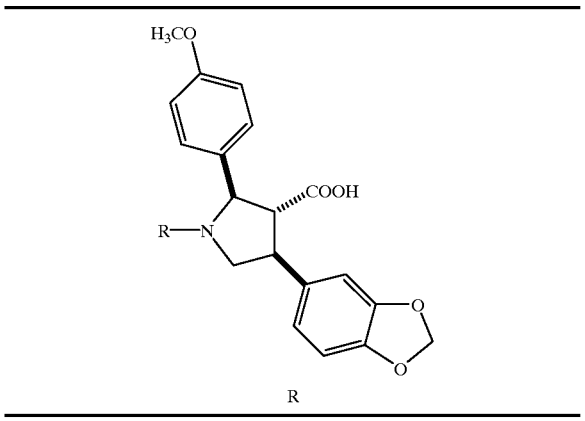
| R |
|---|
| 51. 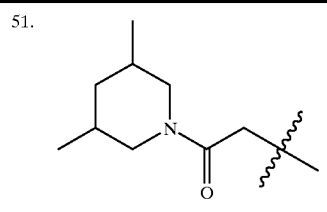 |
| 52. 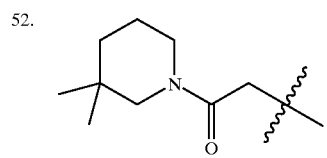 |
| 53. 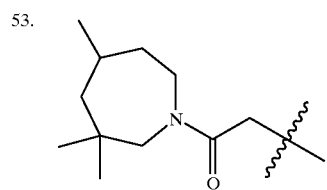 |
| 54. 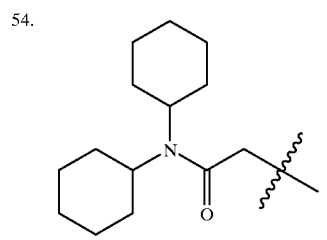 |
| 55. 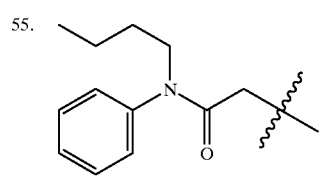 |
| 56. 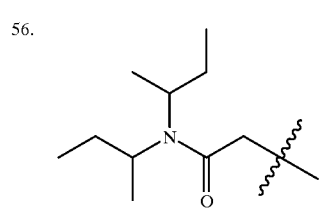 |
TABLE 1-continued
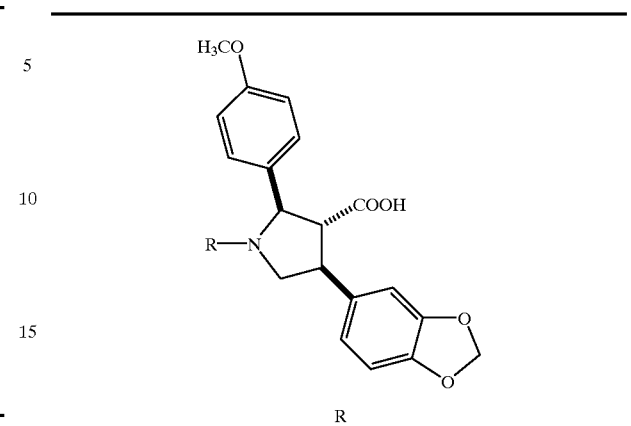
| R |
|---|
| 57. 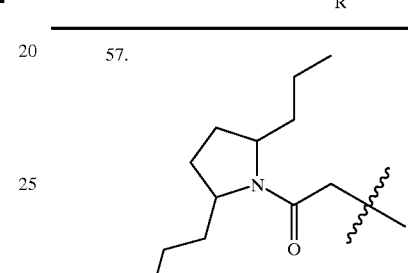 |
| 58. 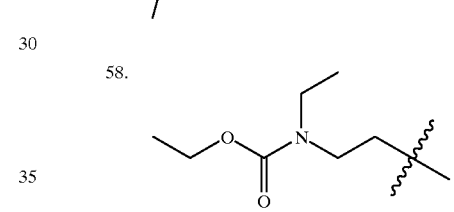 |
| 59. 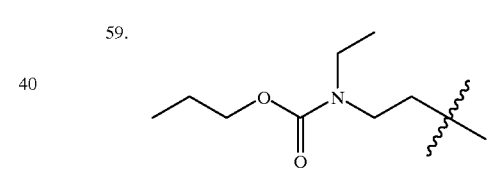 |
| 60. 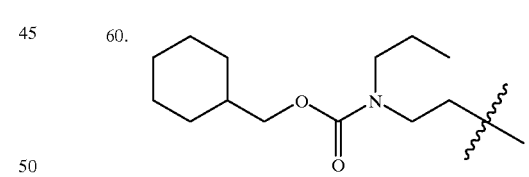 |
| 61. 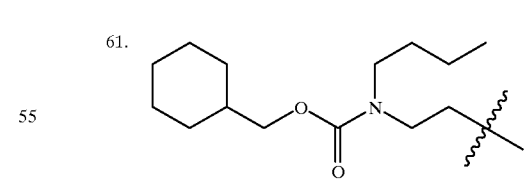 |
| 62. 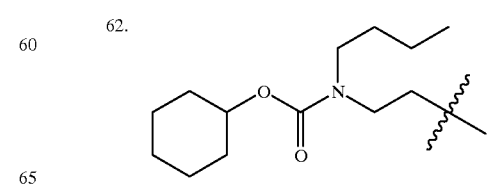 |

TABLE 1-continued
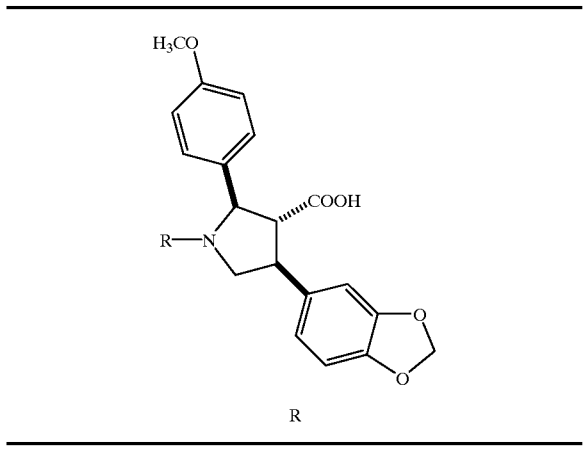
R
63.
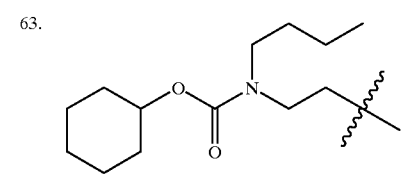
64.
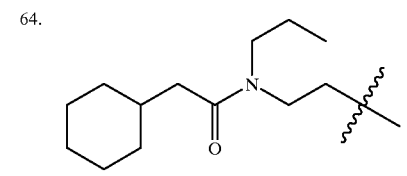
65.
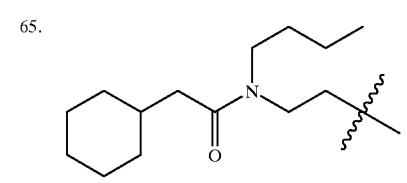
66.
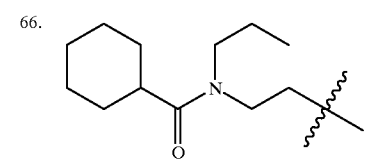
67.
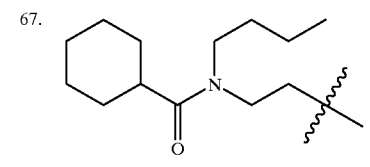
68.
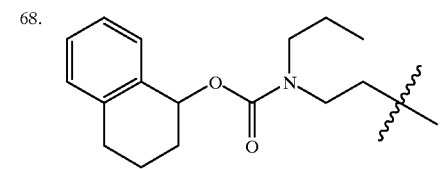
TABLE 1-continued
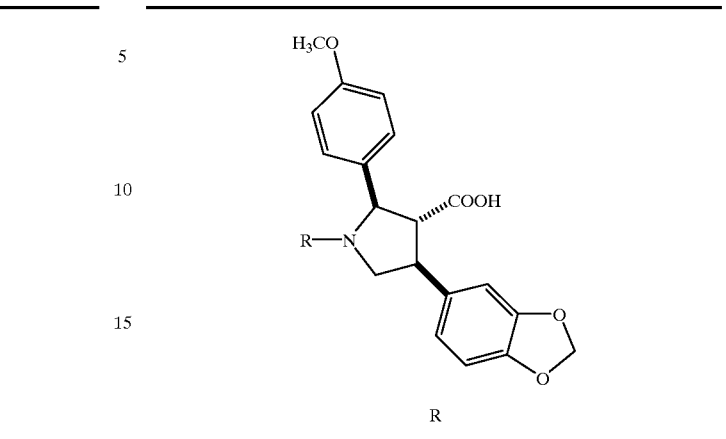
R
69.
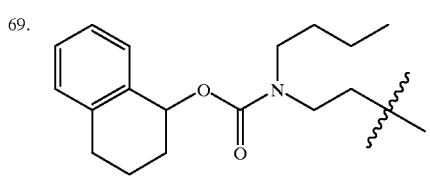
70.
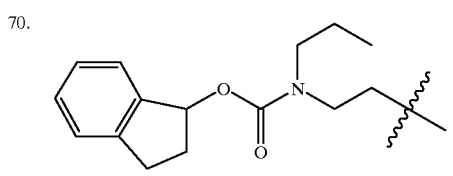
71.
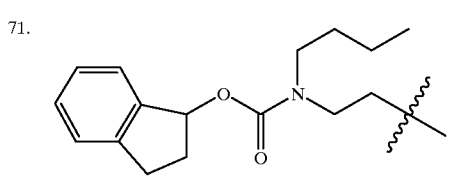
72.
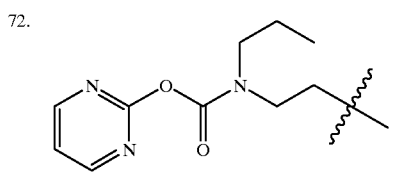
73.
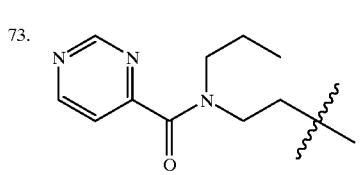
74.
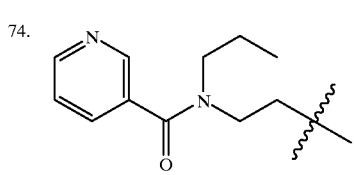

TABLE 1-continued
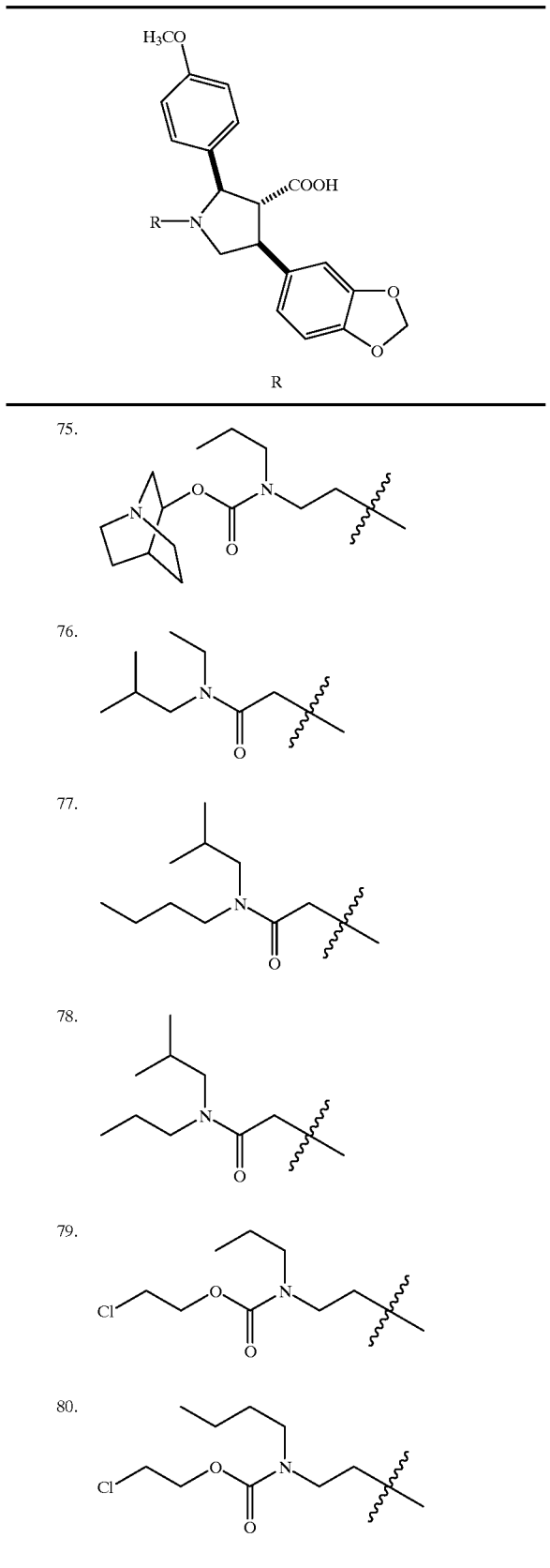
TABLE 1-continued
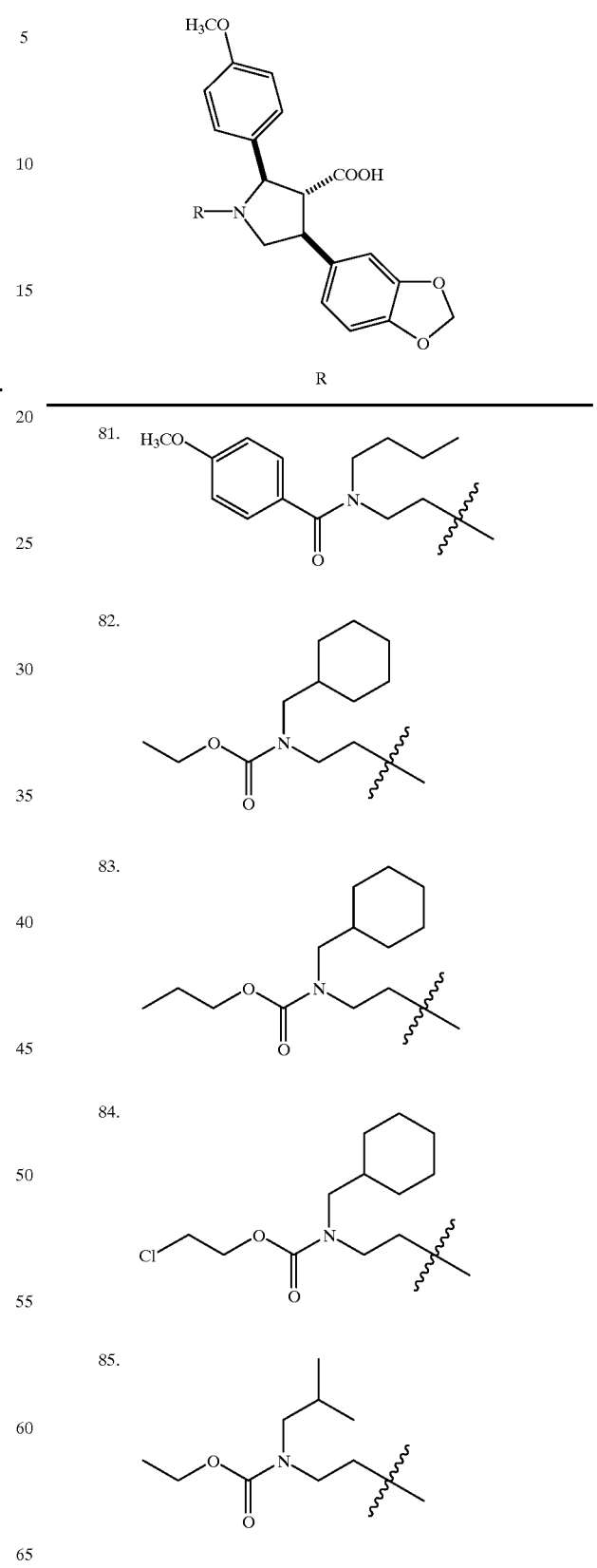

TABLE 1-continued

| # | R |
|---|---|
| 86. | propyl O-C(=O)-N(isobutyl)- CH2C(CH3)2-~ |
| 87. | 2-chloroethyl O-C(=O)-N(isobutyl)- CH2C(CH3)2-~ |
| 88. | ethyl O-C(=O)-N(neopentyl)- CH2C(CH3)2-~ |
| 89. | propyl O-C(=O)-N(neopentyl)- CH2C(CH3)2-~ |
| 90. | 2-chloroethyl O-C(=O)-N(neopentyl)- CH2C(CH3)2-~ |
| 91. | ethyl O-C(=O)-N(3-methyl-2-butenyl)- CH2C(CH3)2-~ |
| 92. | propyl O-C(=O)-N(3-methyl-2-butenyl)- CH2C(CH3)2-~ |
| 93. | 2-chloroethyl O-C(=O)-N(3-methyl-2-butenyl)- CH2C(CH3)2-~ |
| 94. | ethyl O-C(=O)-N(isopentyl)- CH2C(CH3)2-~ |
| 95. | propyl O-C(=O)-N(isopentyl)- CH2C(CH3)2-~ |

TABLE 1-continued
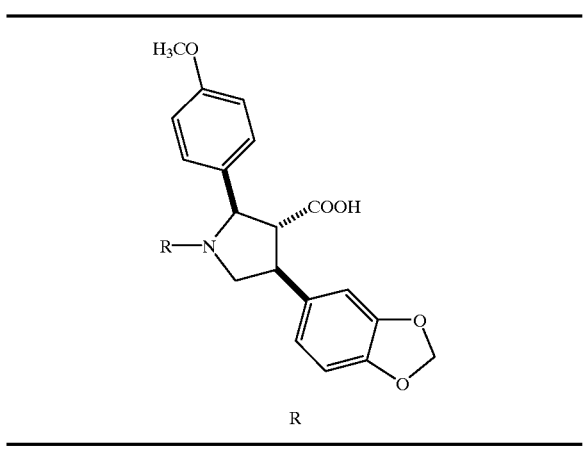
R
| | |
|---|---|
| 96. | 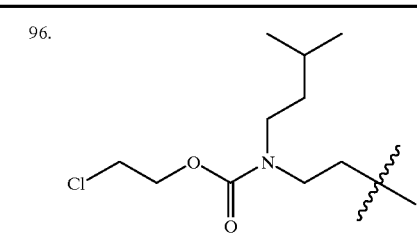 |
| 97. | |
| 98. | 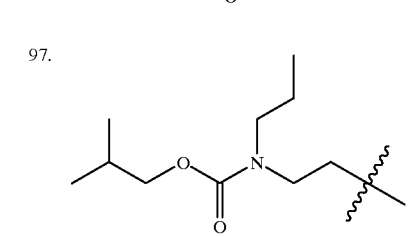 |
| 99. | |
| 100. | 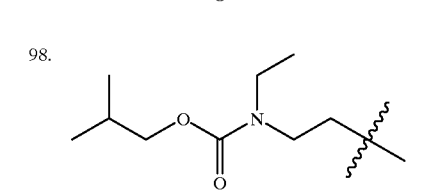 |
| 101. | 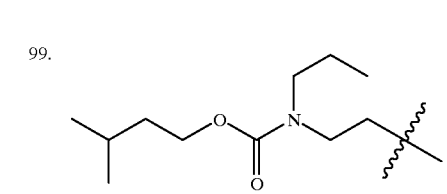 |
TABLE 1-continued
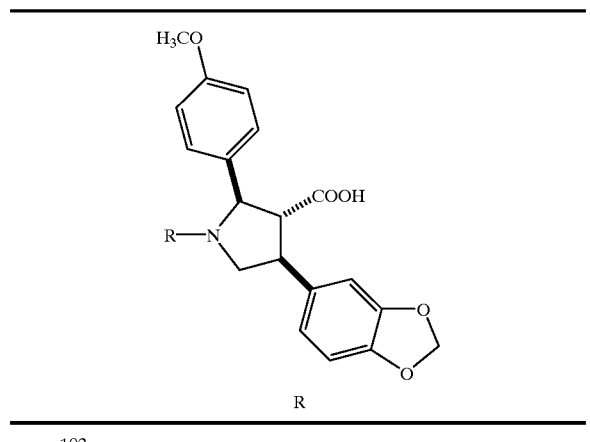
R
| | |
|---|---|
| 102. | |
| 103. | |
| 104. | |
| 105. | |
| 106. | |
| 107. | |
| 108. | |

TABLE 1-continued
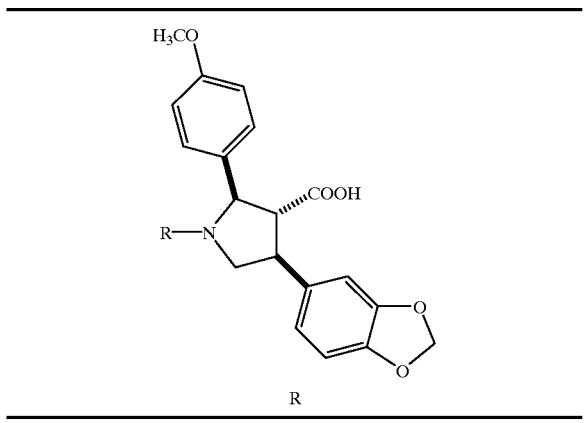
| R |
|---|
| 109. 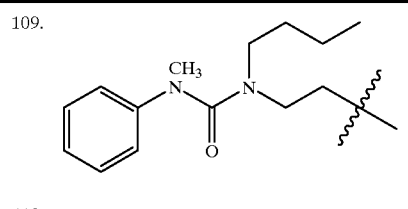 |
| 110. 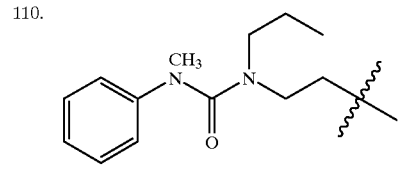 |
| 111. 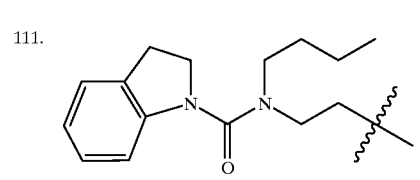 |
| 112. 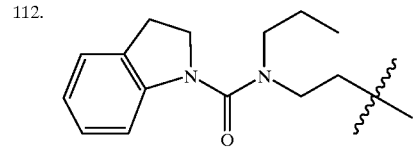 |
| 113. 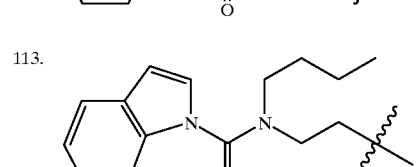 |
| 114. 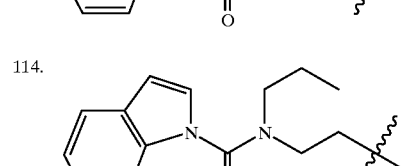 |
| 115. 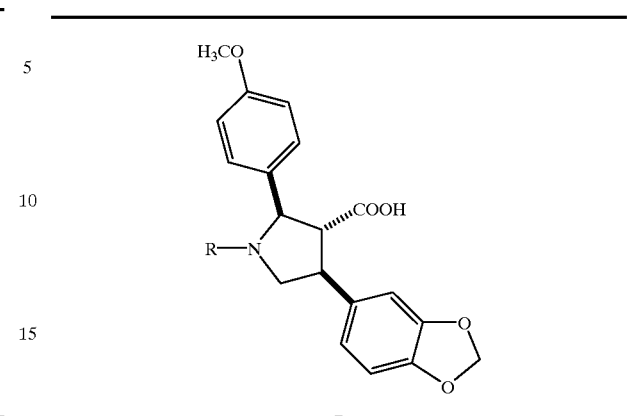 |
TABLE 1-continued
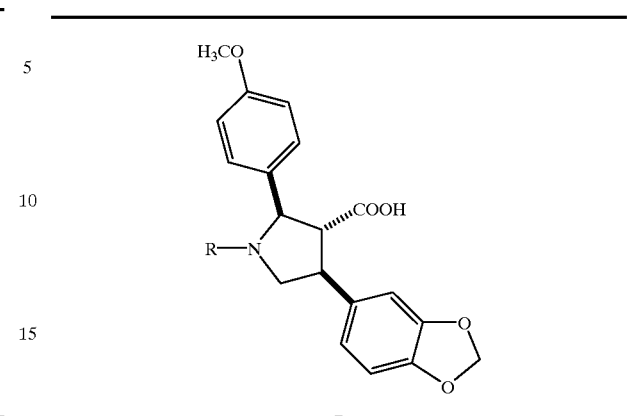
| R |
|---|
| 116. 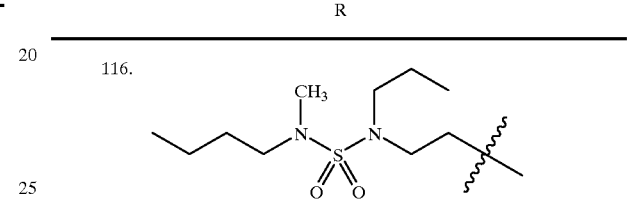 |
| 117. 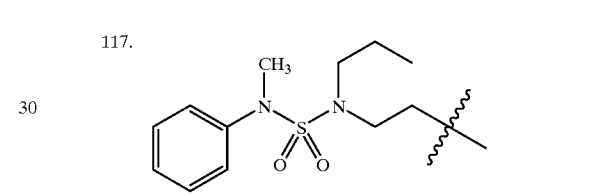 |
| 118. 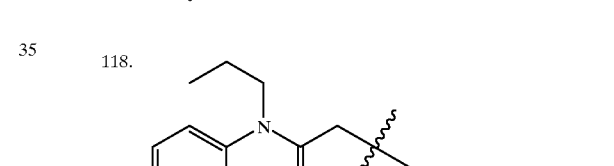 |
| 119. 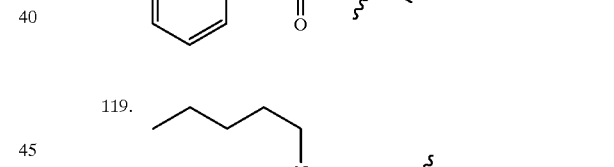 |
| 120. 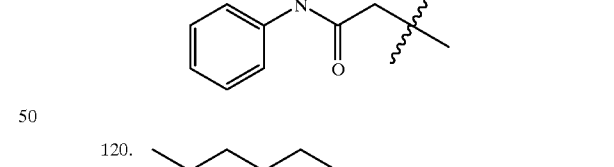 |
| 121. |

TABLE 1-continued

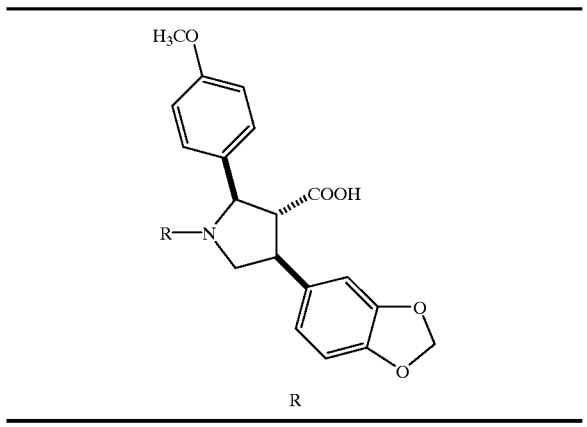

| | R |
|---|---|
| 122. | n-butyl-N-(3-methylphenyl)acetamide linker |
| 123. | n-butyl-N-(4-methylphenyl)acetamide linker |
| 124. | n-butyl-N-(2-fluorophenyl)acetamide linker |
| 125. | n-butyl-N-(3-fluorophenyl)acetamide linker |
| 126. | n-butyl-N-(4-fluorophenyl)acetamide linker |
| 127. | n-butyl-N-(2-chlorophenyl)acetamide linker |

TABLE 1-continued

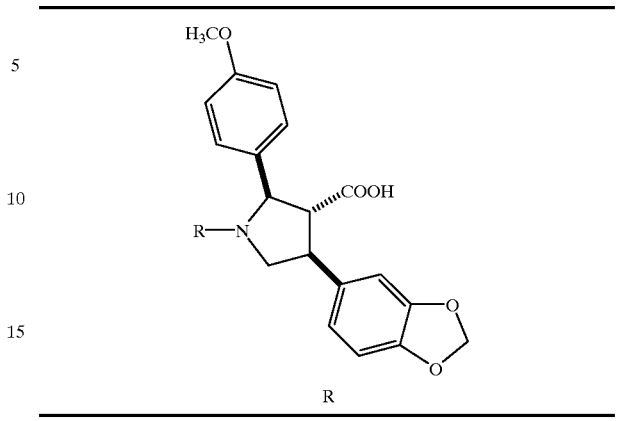

| | R |
|---|---|
| 128. | n-butyl-N-(3-chlorophenyl)acetamide linker |
| 129. | n-butyl-N-(4-chlorophenyl)acetamide linker |
| 130. | n-butyl-N-(2-methoxyphenyl)acetamide linker |
| 131. | n-butyl-N-(3-methoxyphenyl)acetamide linker |
| 132. | n-butyl-N-(4-methoxyphenyl)acetamide linker |
| 133. | n-butyl-N-(2-naphthyl)acetamide linker |

TABLE 1-continued
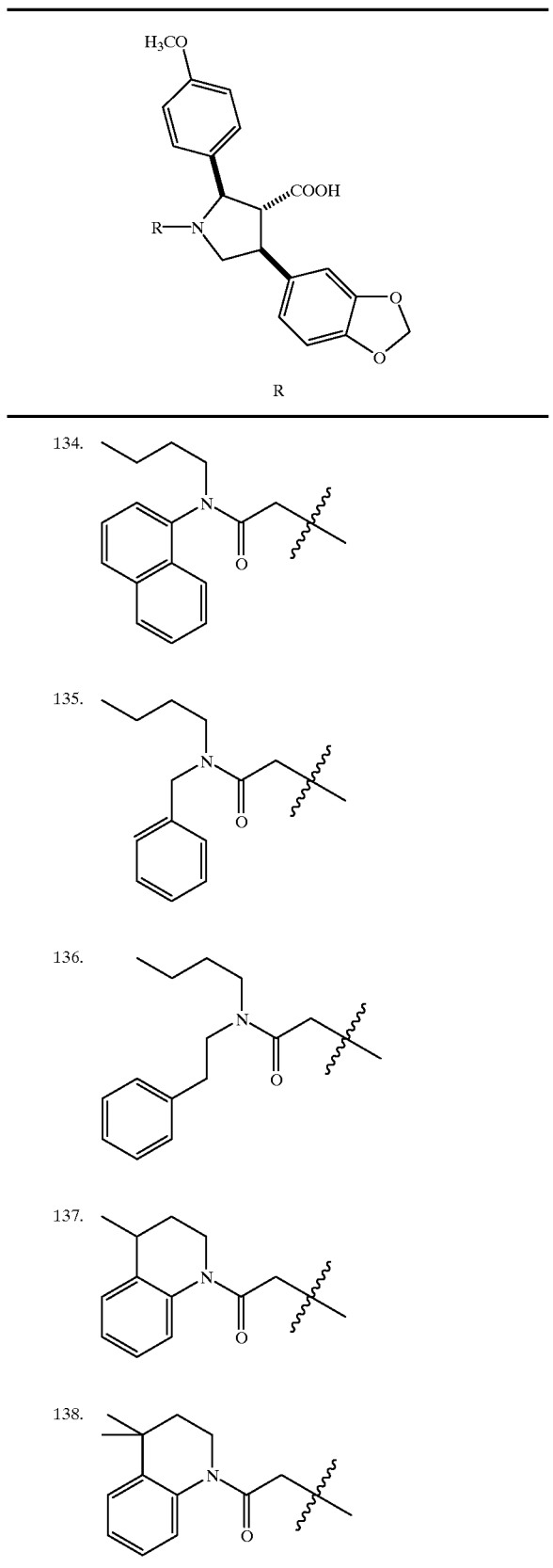
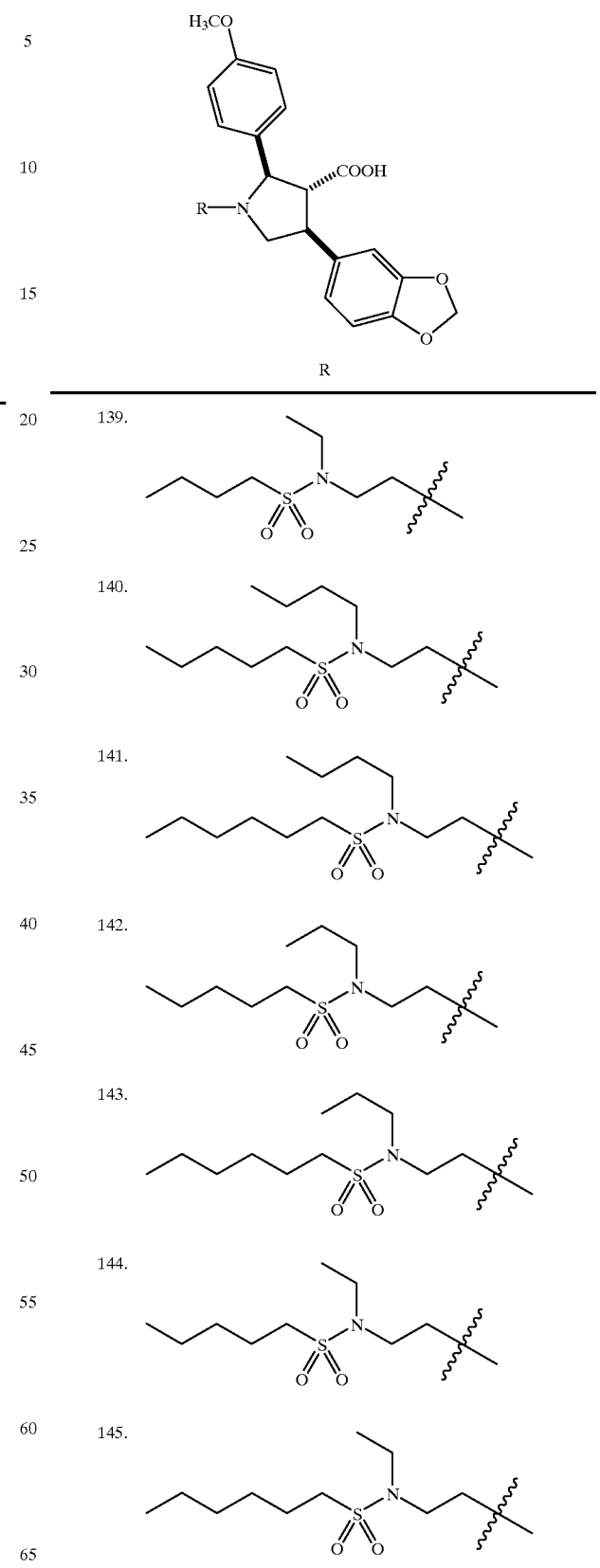

TABLE 1-continued
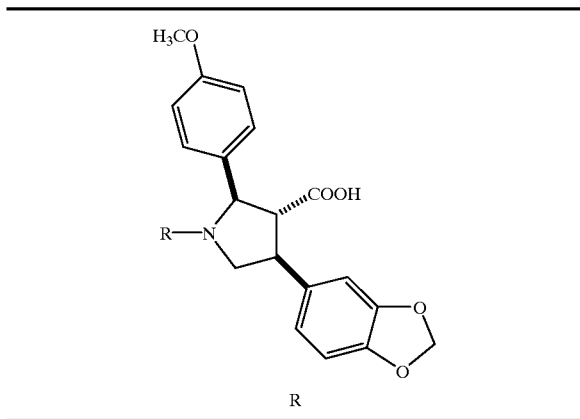
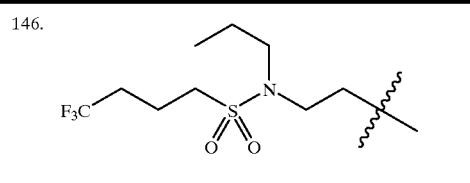
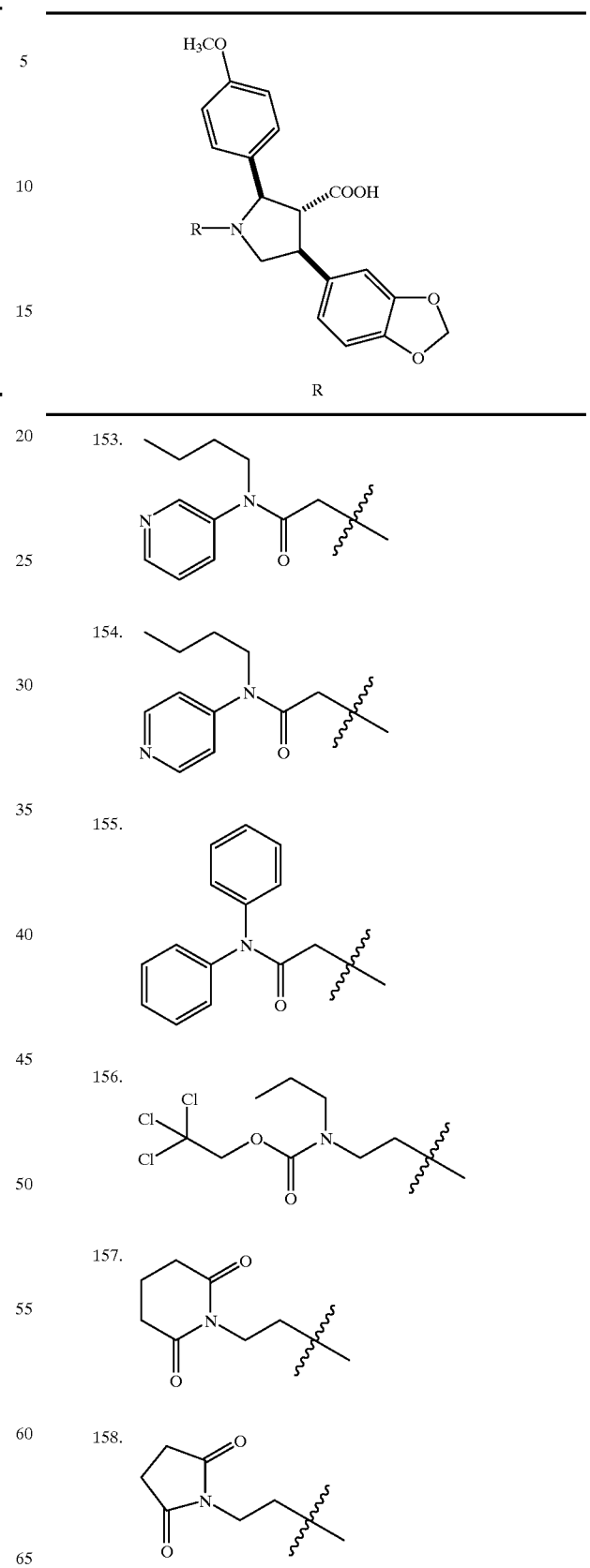

TABLE 1-continued
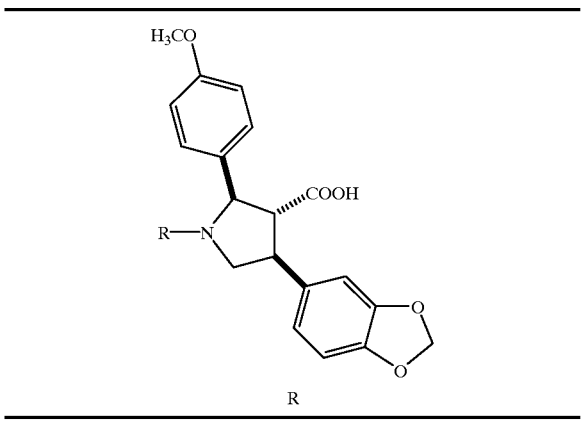
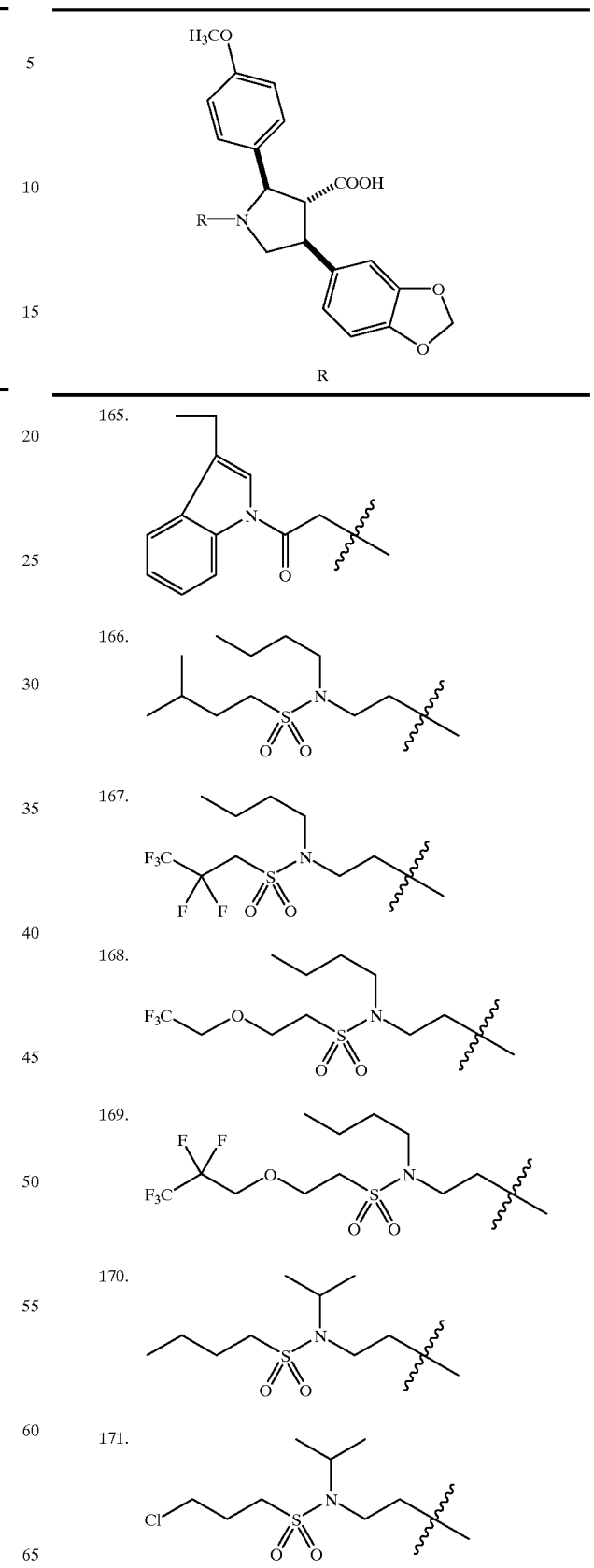

TABLE 1-continued
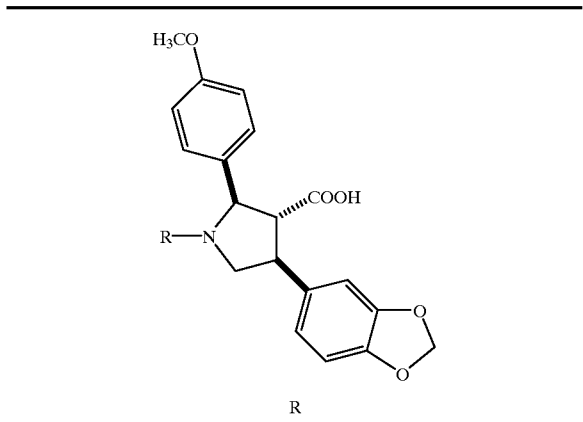
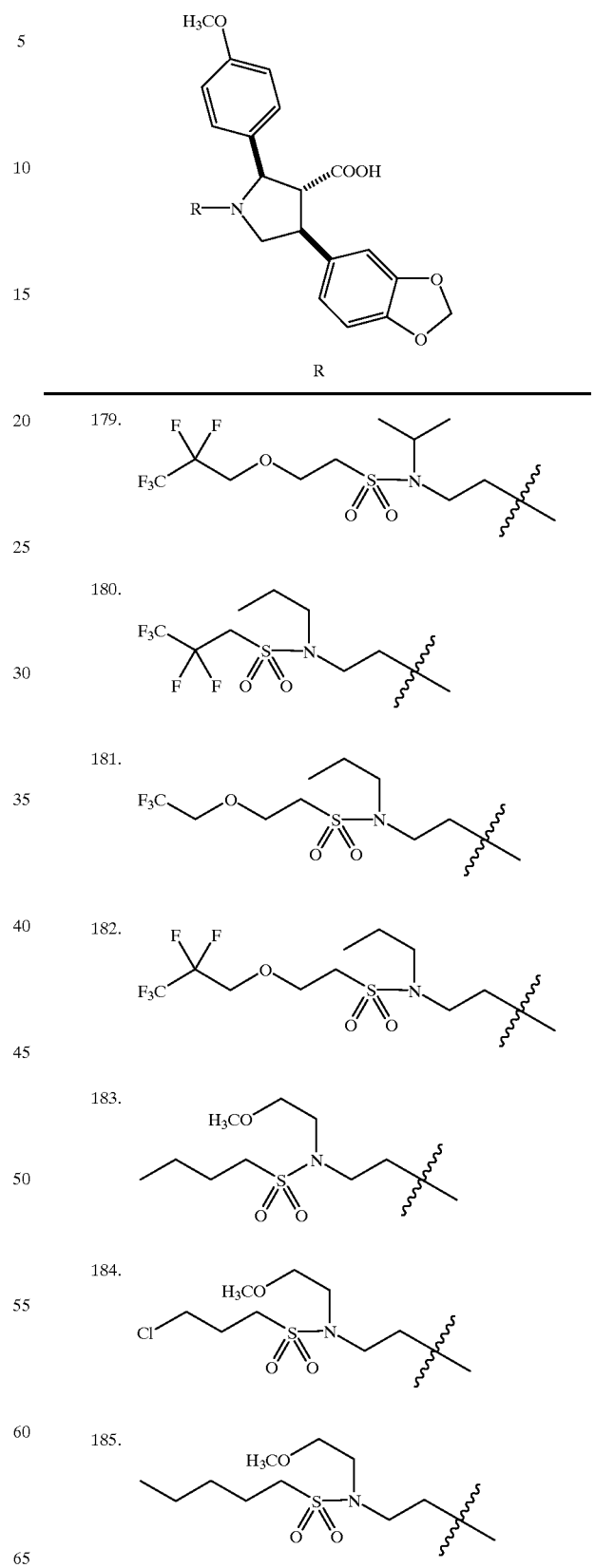

TABLE 1-continued
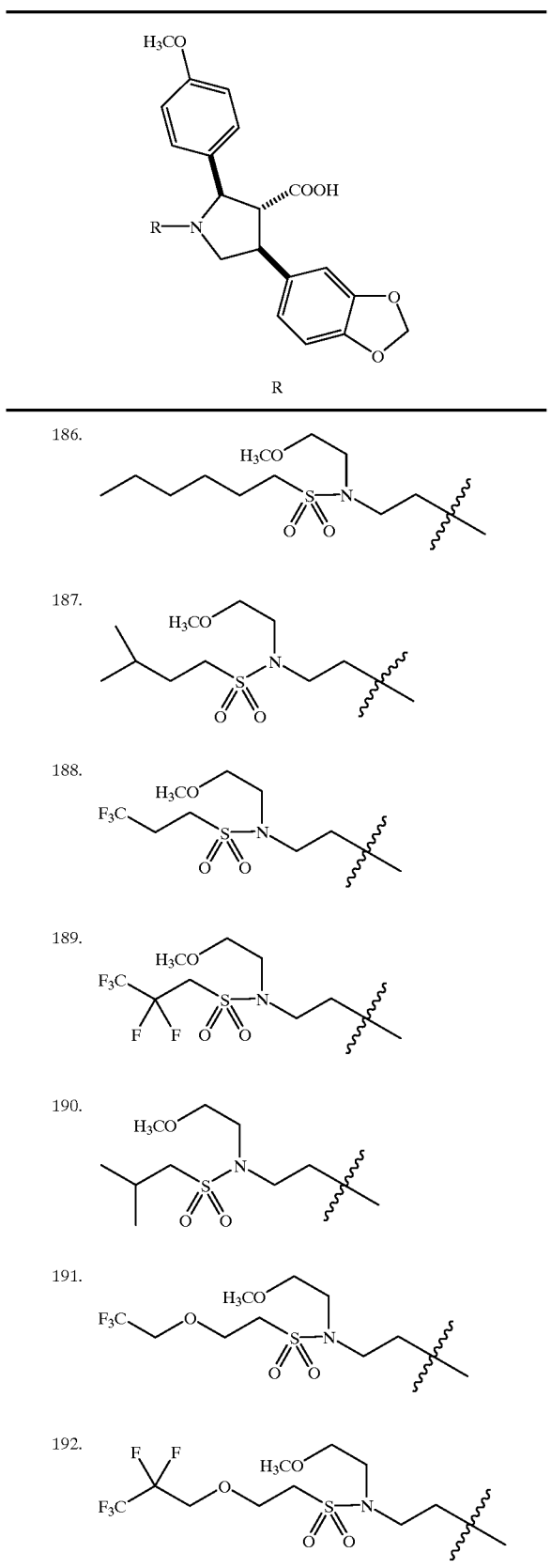
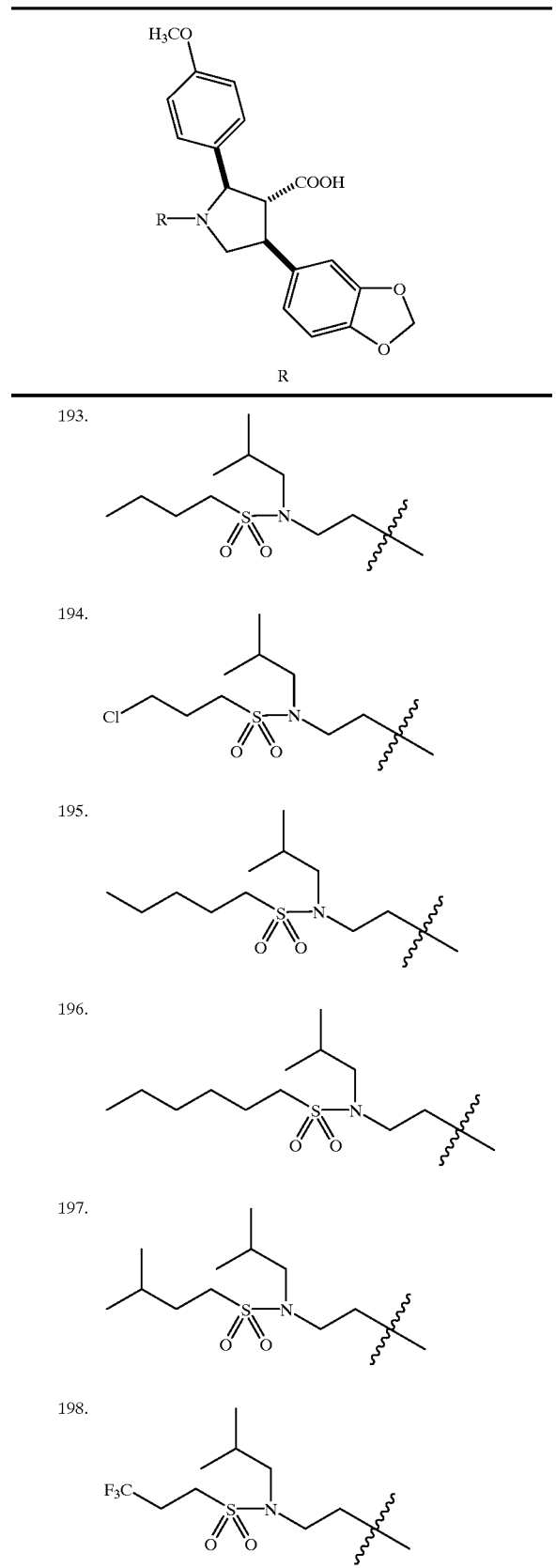

TABLE 1-continued
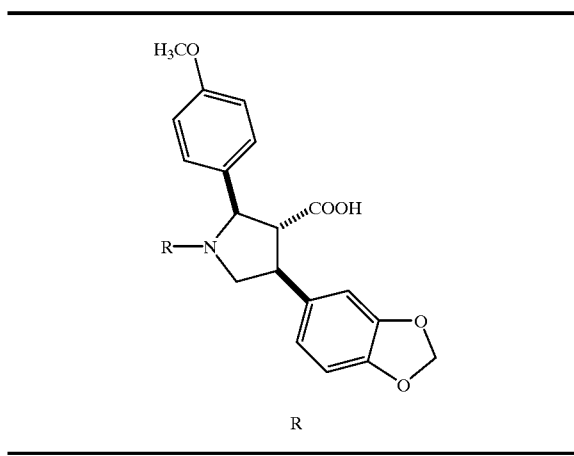
R
| 199. | 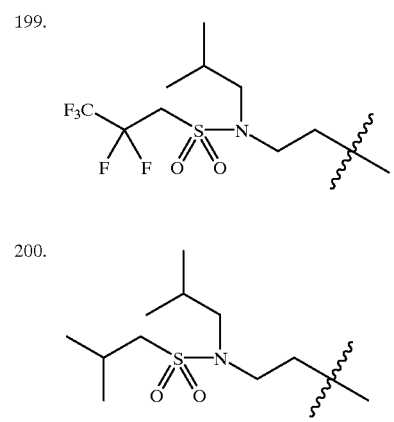 |
|---|---|
| 200. | |
| 201. | |
| 202. | |
| 203. | 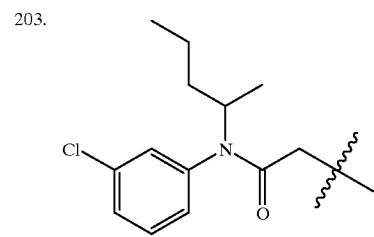 |
TABLE 1-continued
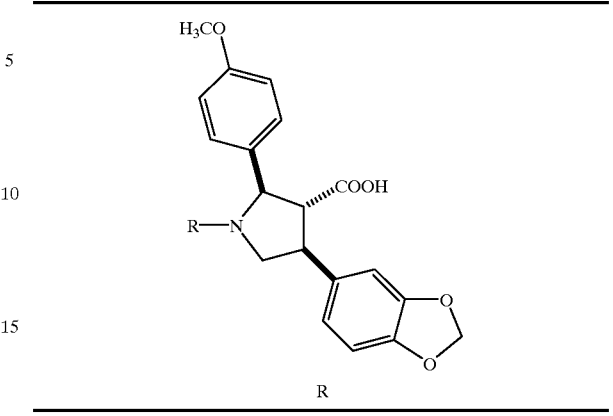
| 204. | 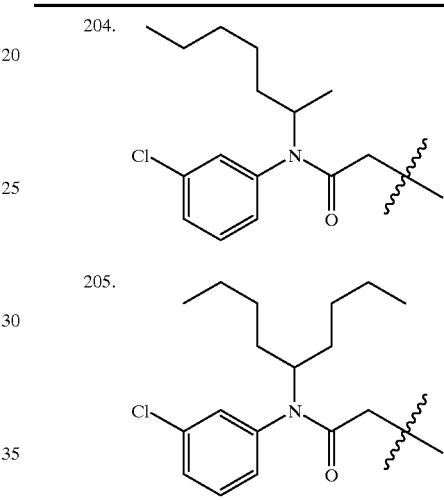 |
|---|---|
| 205. | |
| 206. | |
| 207. | |
| 208. | |

TABLE 1-continued
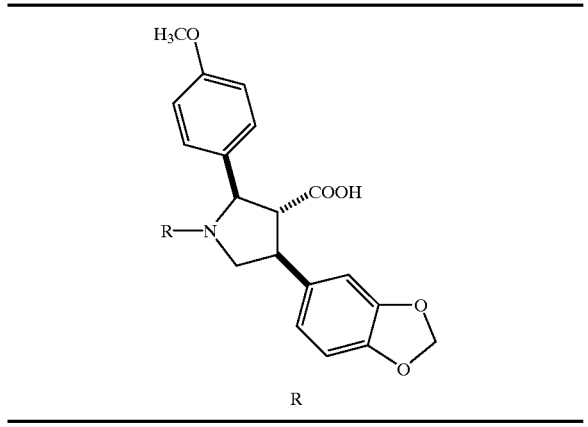
R
| 209. | 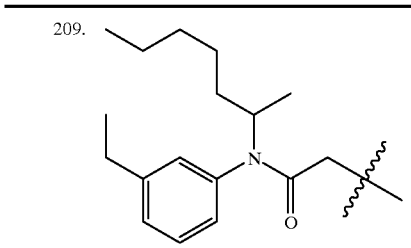 |
|---|---|
| 210. | 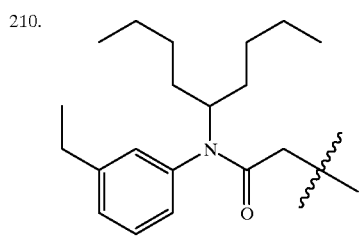 |
| 211. | 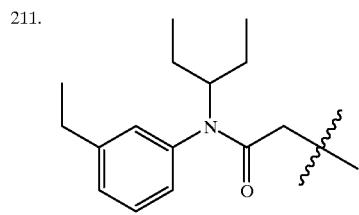 |
| 212. | 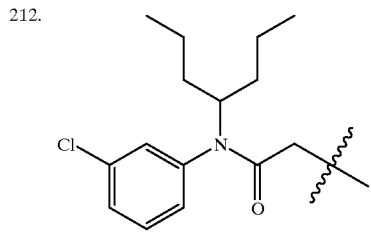 |
| 213. | 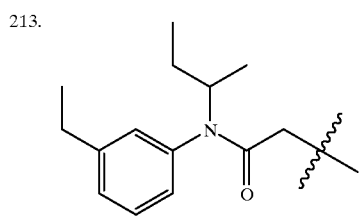 |
TABLE 1-continued
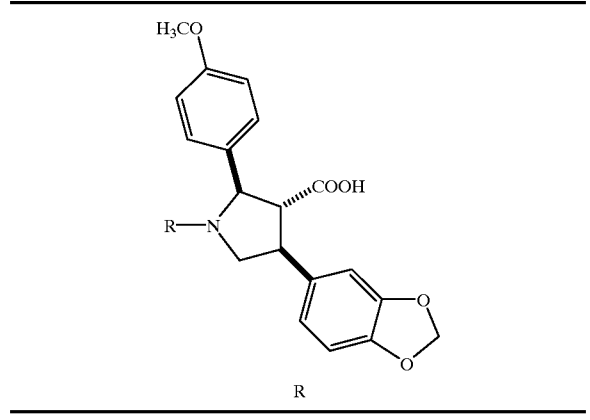
R
| 214. |  |
|---|---|
| 215. |  |
| 216. | 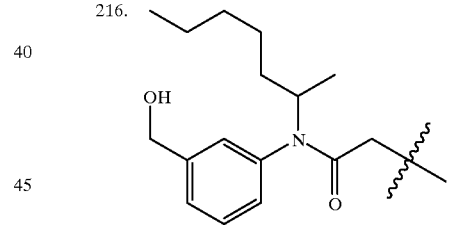 |
| 217. | 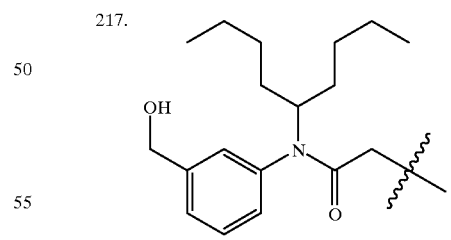 |
| 218. | 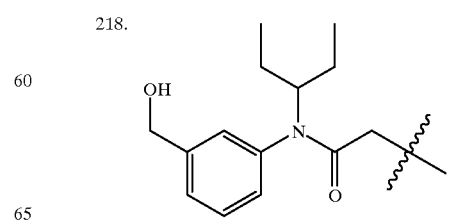 |

TABLE 1-continued
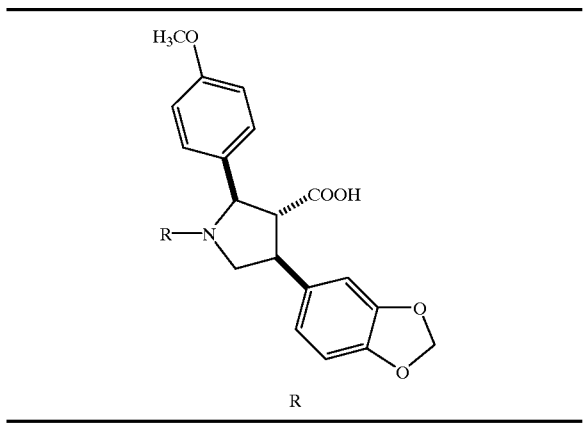
R
219. 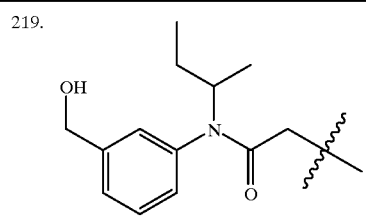
220. 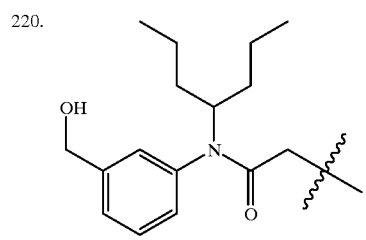
221. 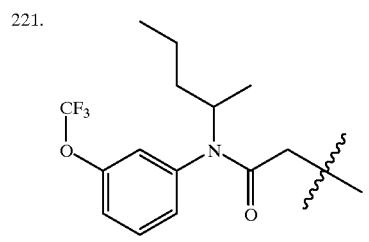
222. 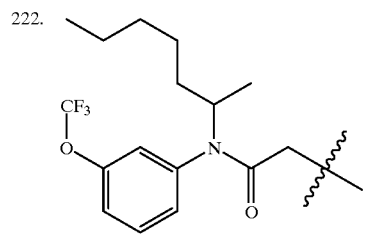
223. 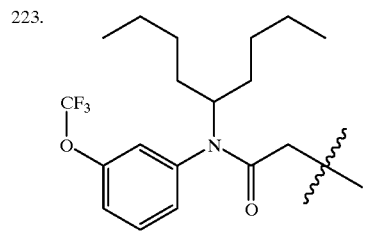
TABLE 1-continued
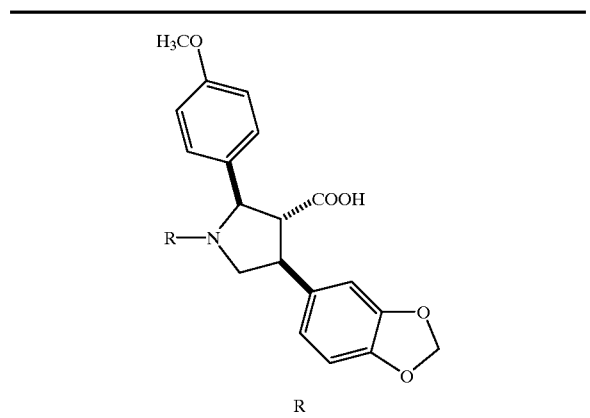
R
224. 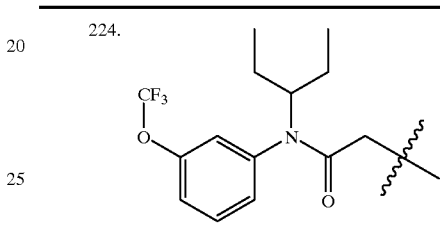
225. 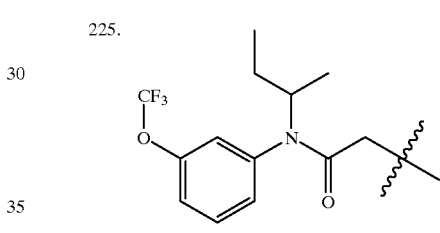
226. 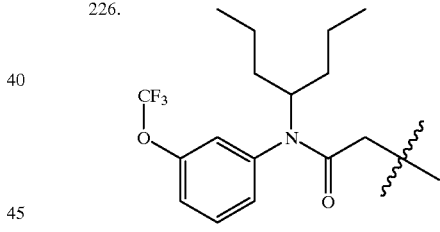
227. 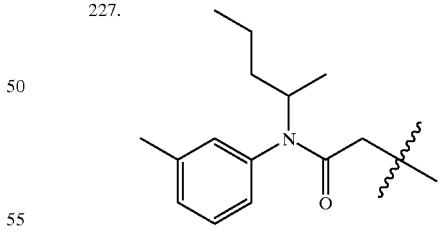
228. 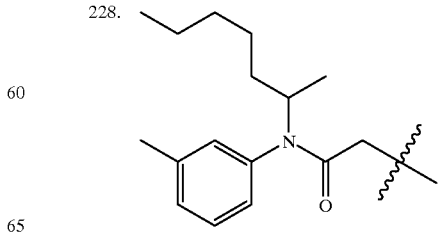

TABLE 1-continued
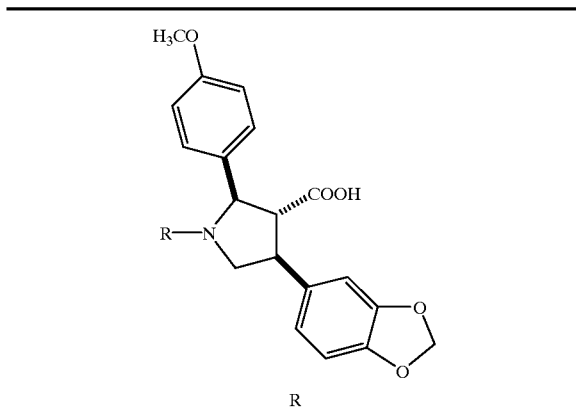
| | R |
|---|---|
| 229. | 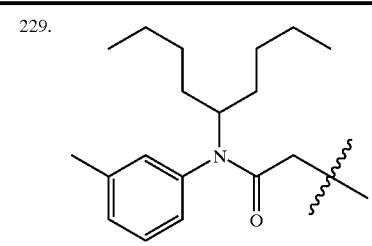 |
| 230. | 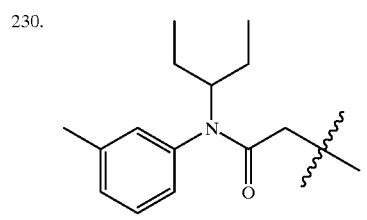 |
| 231. | 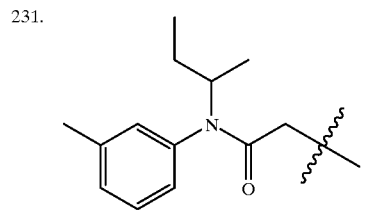 |
| 232. | 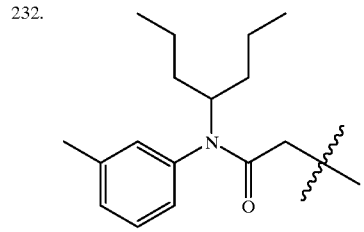 |
| 233. | 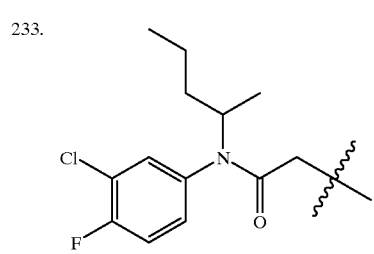 |
TABLE 1-continued
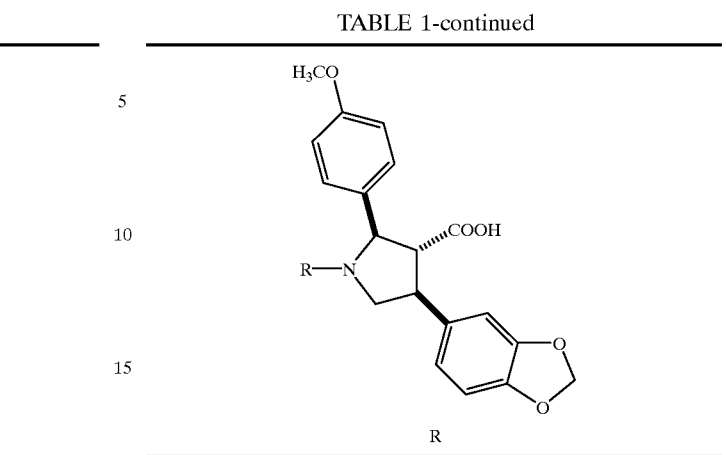
| | R |
|---|---|
| 234. | 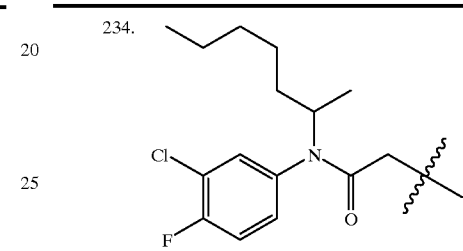 |
| 235. |  |
| 236. | 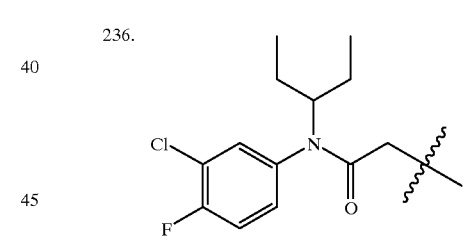 |
| 237. | 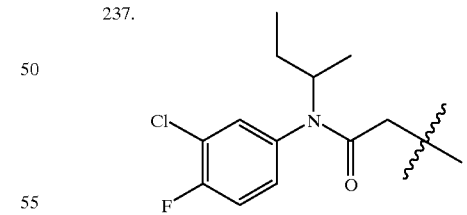 |
| 238. | 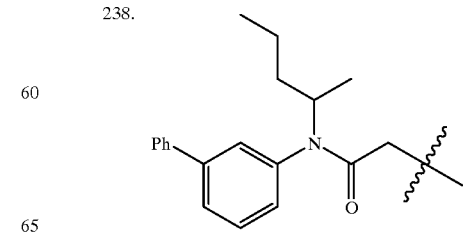 |

TABLE 1-continued
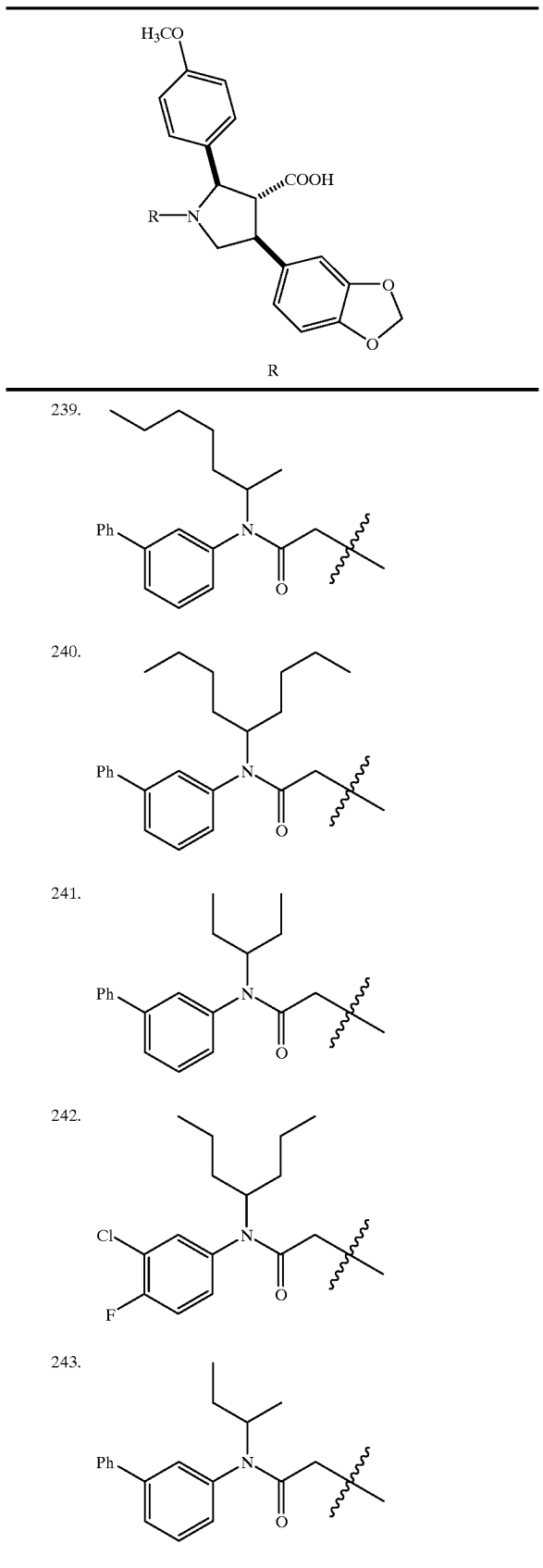
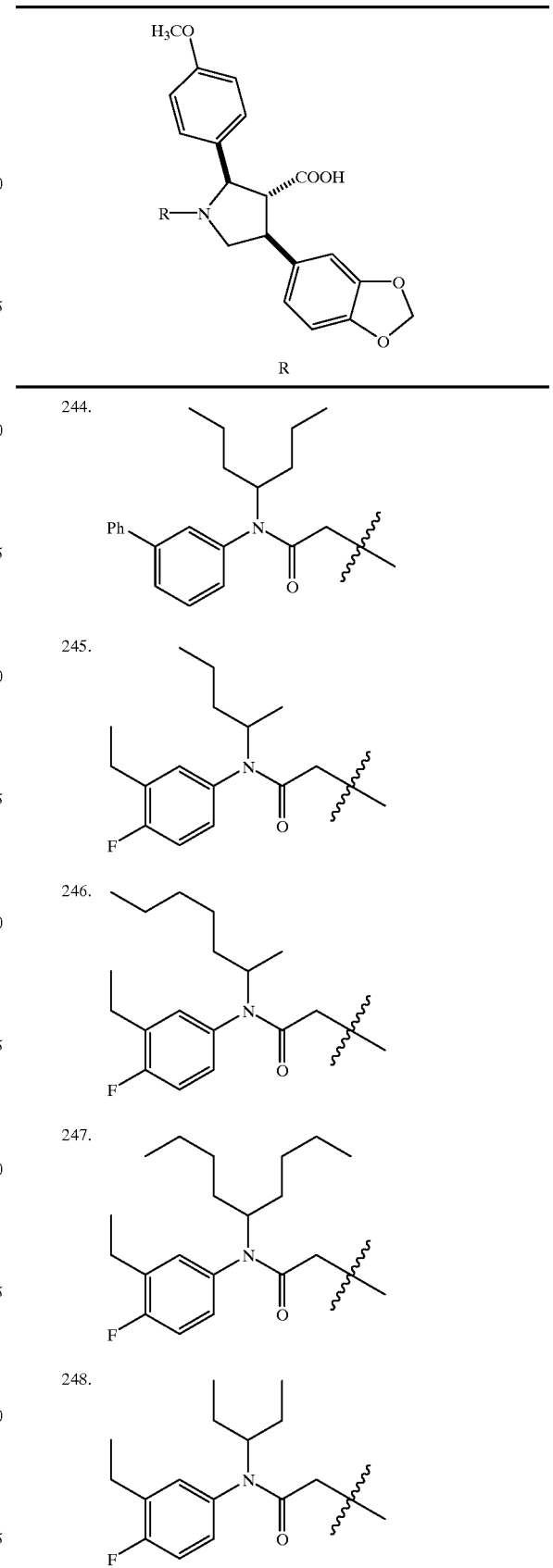

TABLE 1-continued
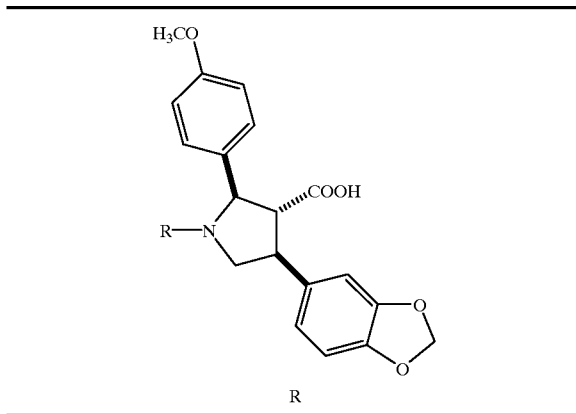
R
| | |
|---|---|
| 249. | 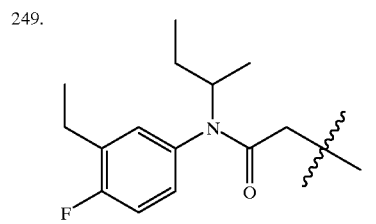 |
| 250. | 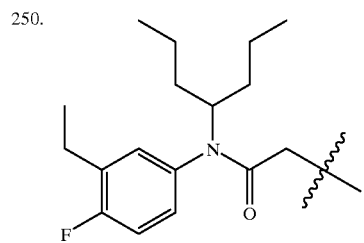 |
| 251. | 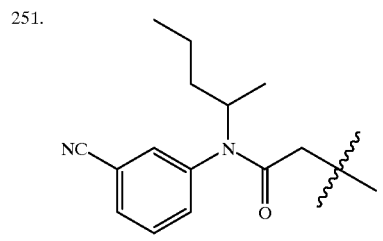 |
| 252. | 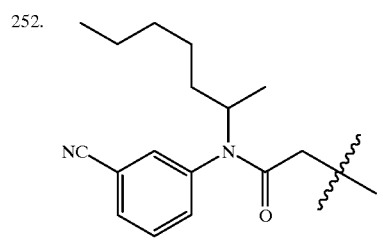 |
| 253. | 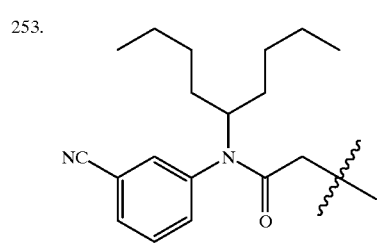 |
TABLE 1-continued
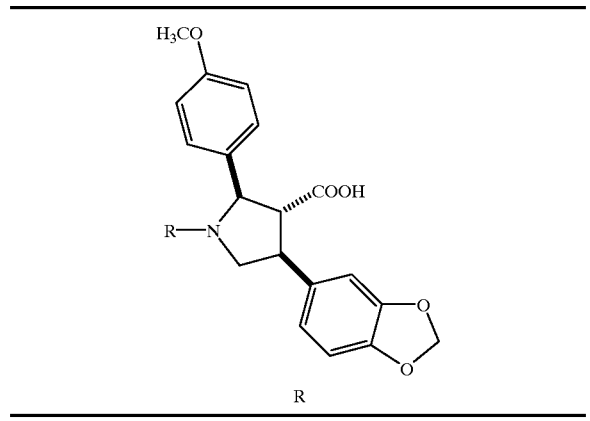
R
| | |
|---|---|
| 254. | 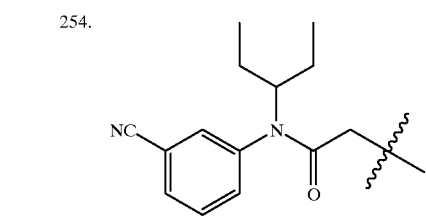 |
| 255. | 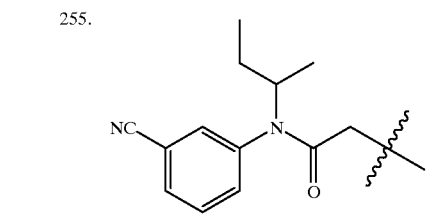 |
| 256. | 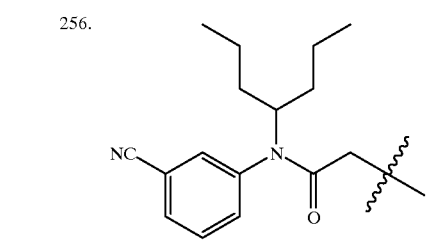 |
| 257. | 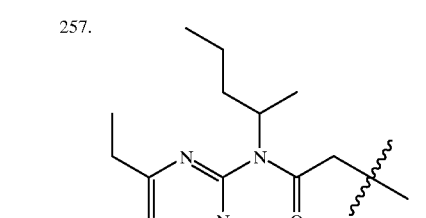 |
| 258. | 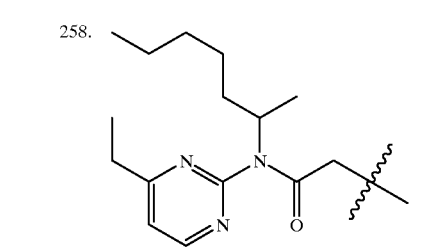 |

TABLE 1-continued
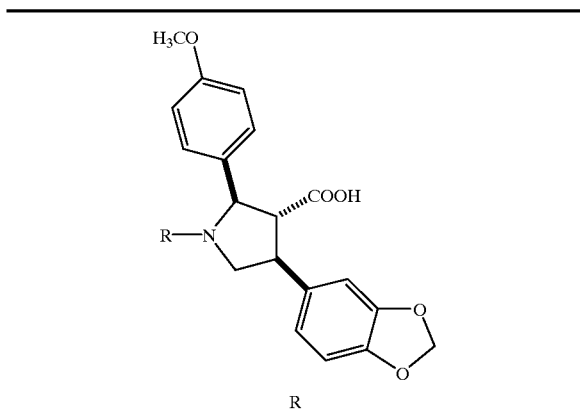
| | R |
|---|---|
| 259. | 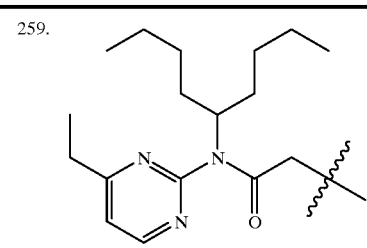 |
| 260. | 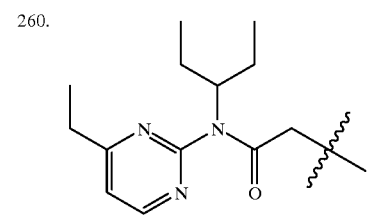 |
| 261. | 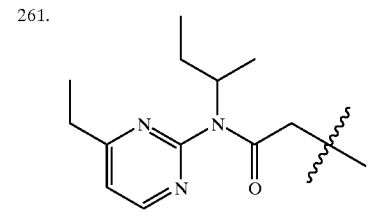 |
| 262. | 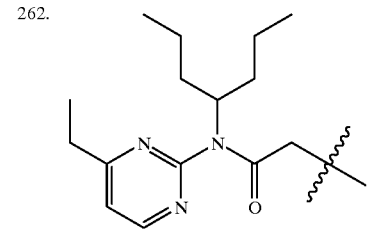 |
| 263. | 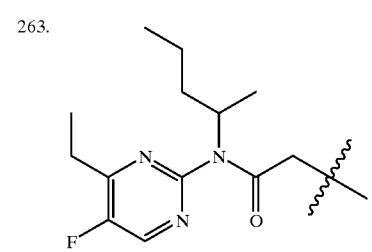 |
TABLE 1-continued
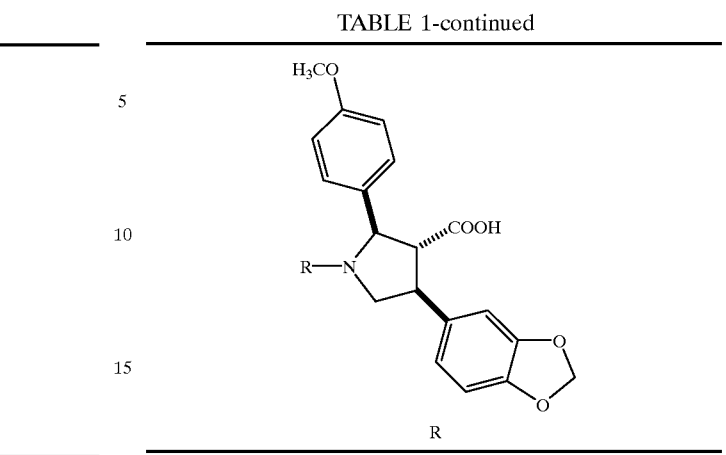
| | R |
|---|---|
| 264. | 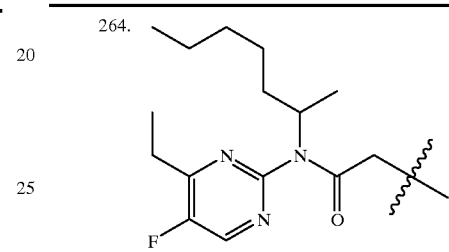 |
| 265. | 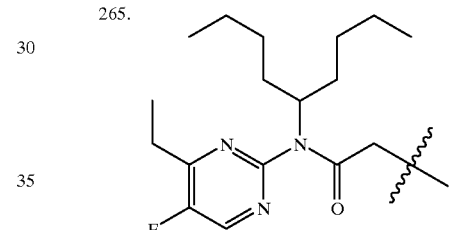 |
| 266. | 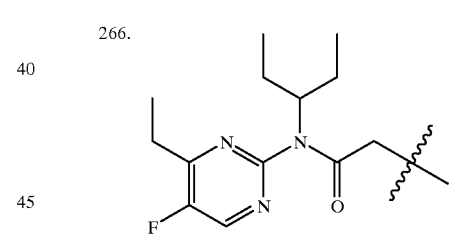 |
| 267. | 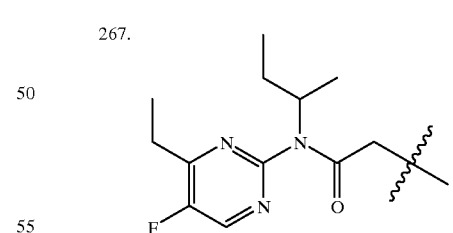 |
| 268. | 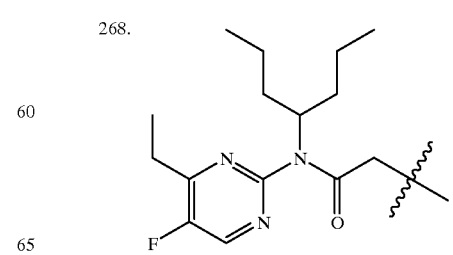 |

TABLE 1-continued
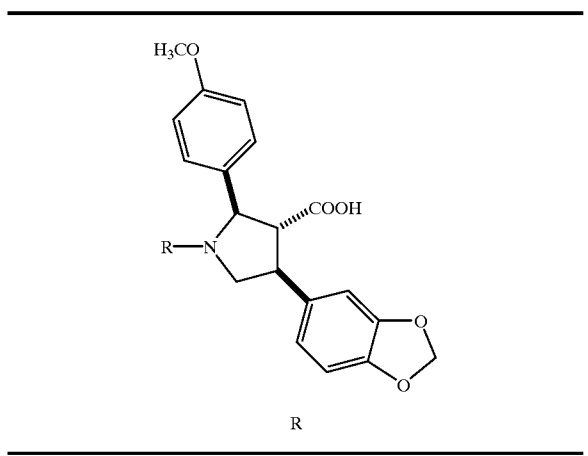
| | R |
|---|---|
| 269. | 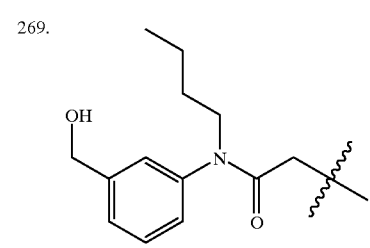 |
| 270. | 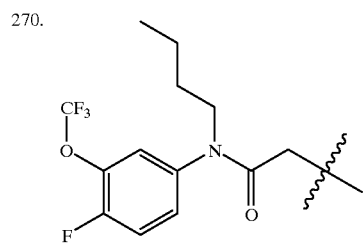 |
| 271. | 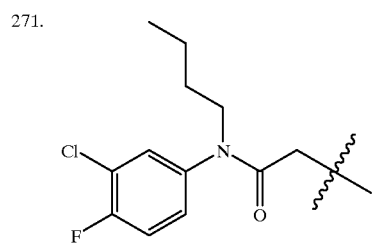 |
| 272. | 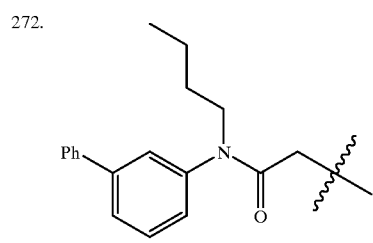 |
TABLE 1-continued
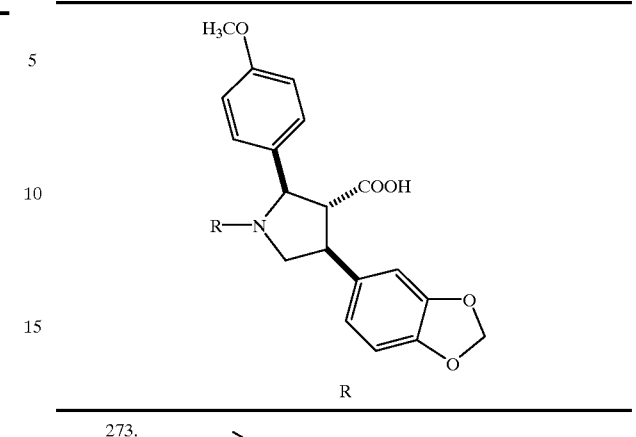
| | R |
|---|---|
| 273. | 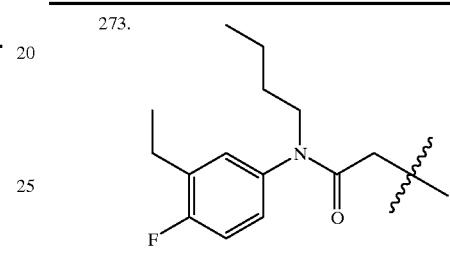 |
| 274. | 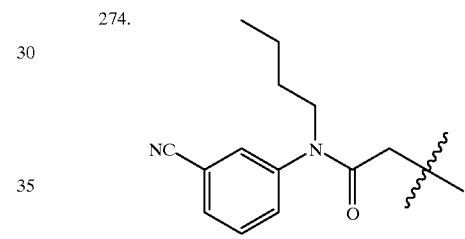 |
| 275. | 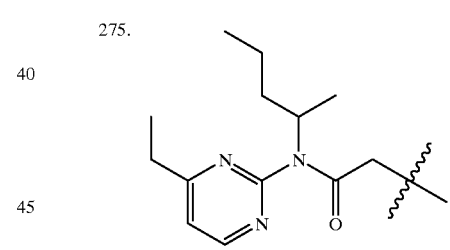 |
| 276. | 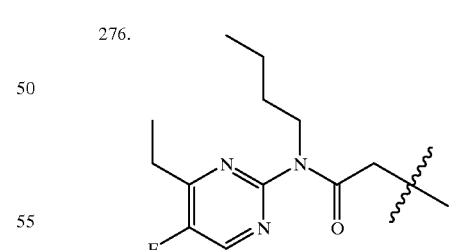 |
| 277. | 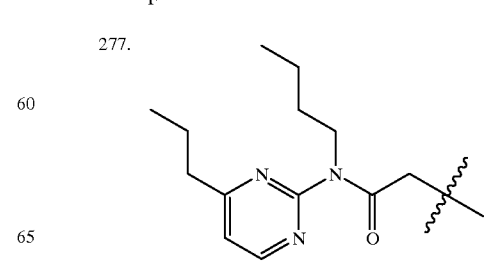 |

TABLE 1-continued
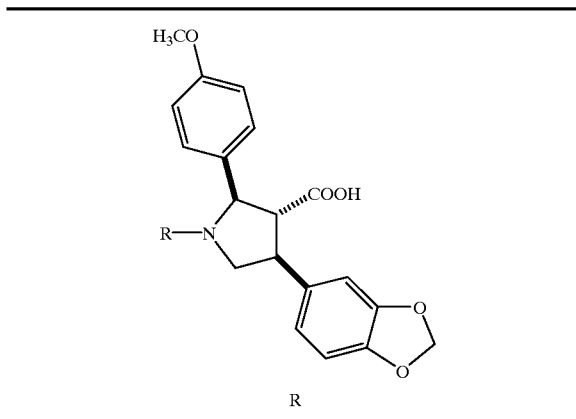
R
278. 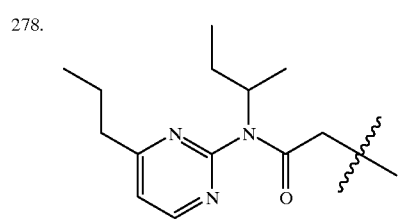
279. 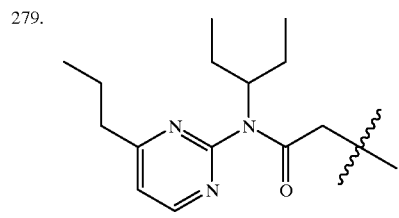
280. 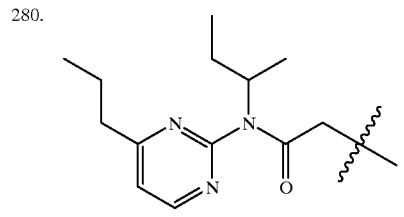
281. 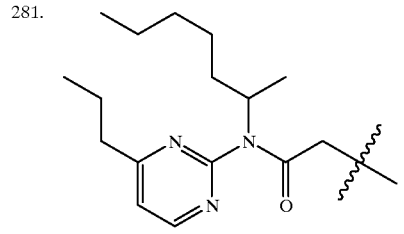
282. 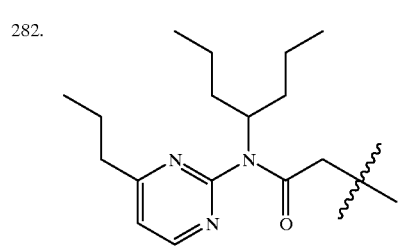
TABLE 1-continued
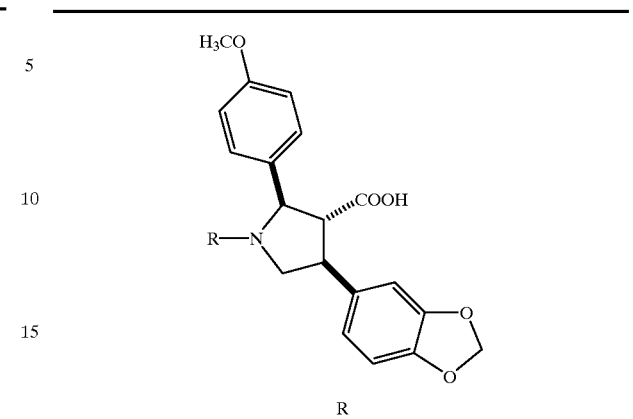
R
283. 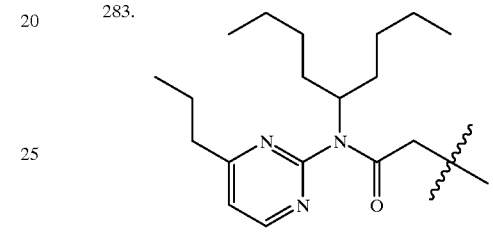
284. 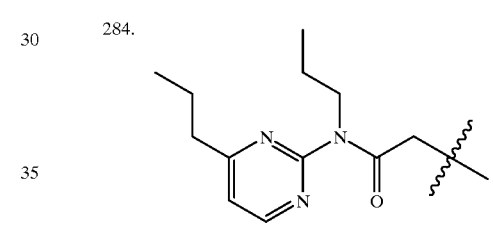
285. 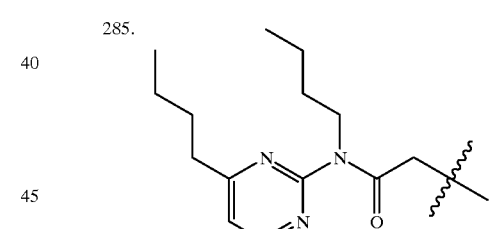
286. 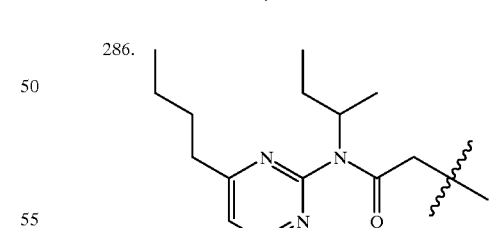
287. 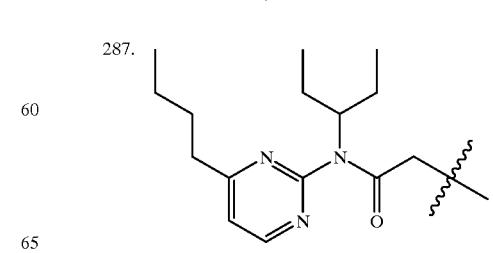

TABLE 1-continued
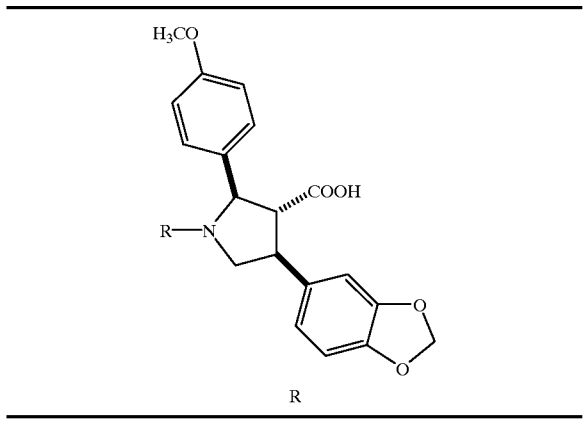
| | R |
|---|---|
| 288. | 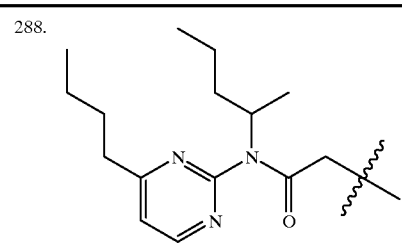 |
| 289. | 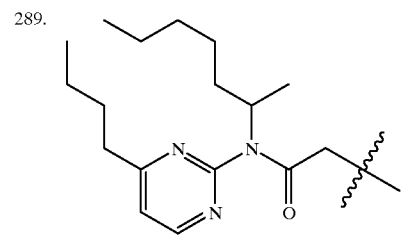 |
| 290. | 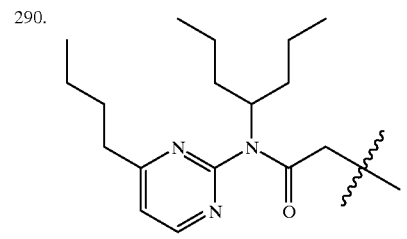 |
| 291. | 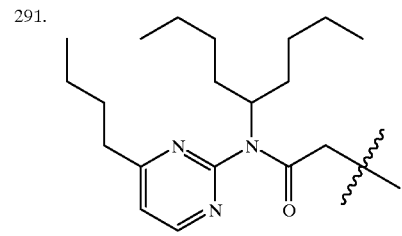 |
| 292. | 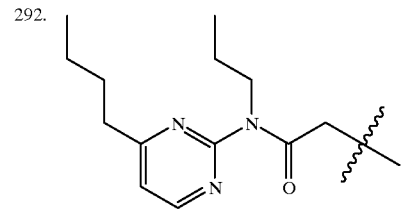 |
TABLE 1-continued
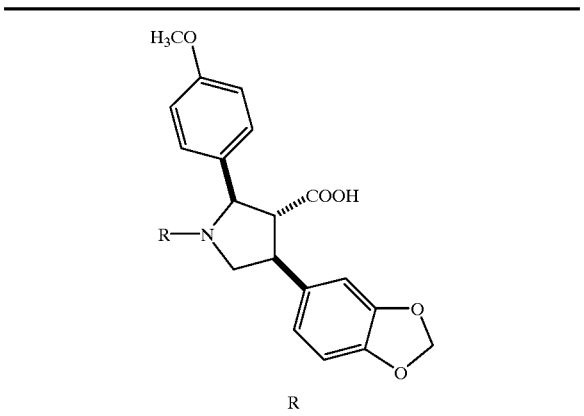
| | R |
|---|---|
| 293. | 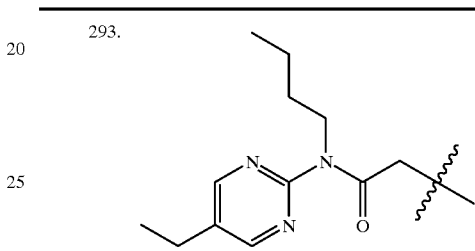 |
| 294. | 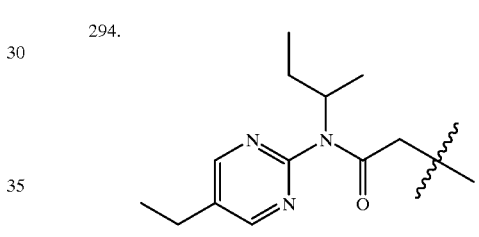 |
| 295. | 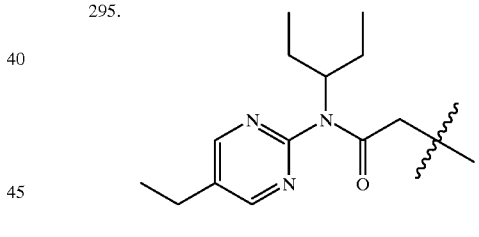 |
| 296. | 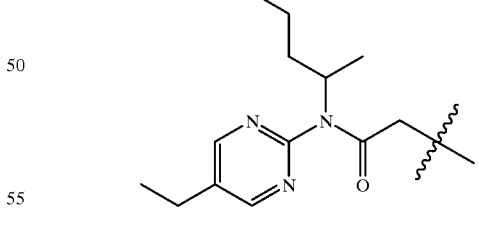 |
| 297. | 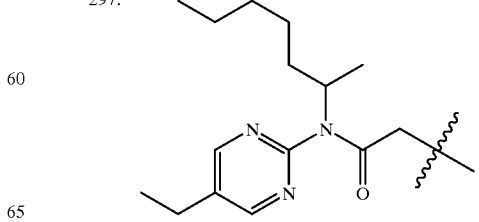 |

TABLE 1-continued
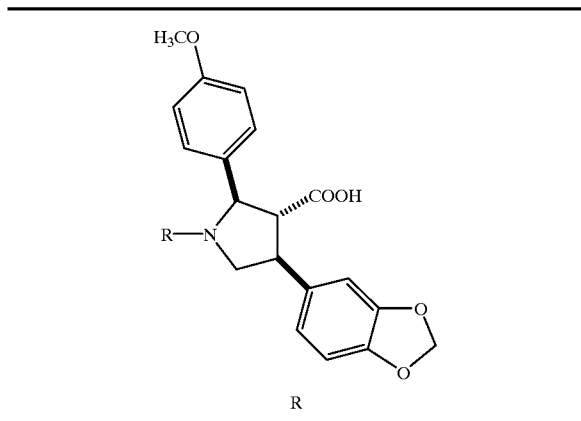
R
298. 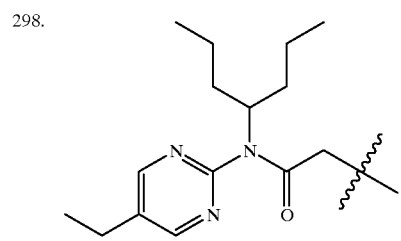
299. 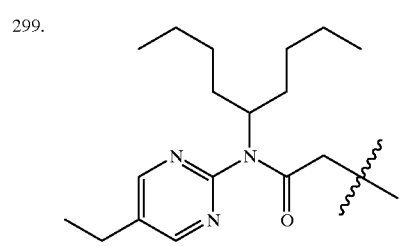
300. 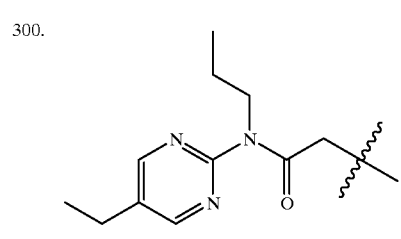
301. 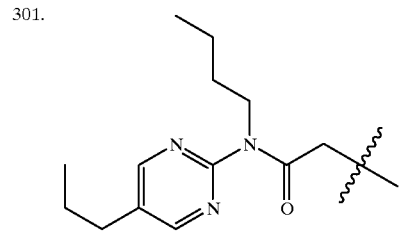
302. 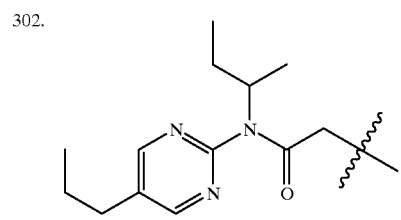
TABLE 1-continued
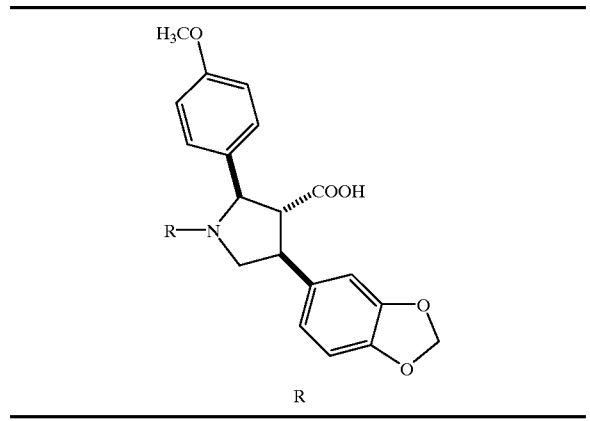
R
303. 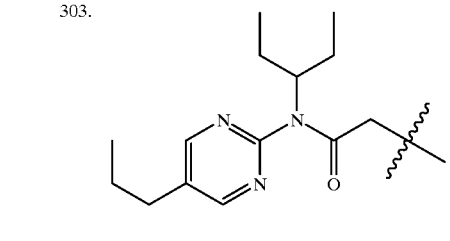
304. 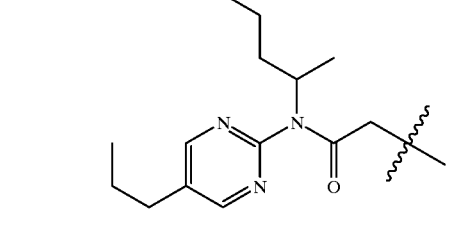
305. 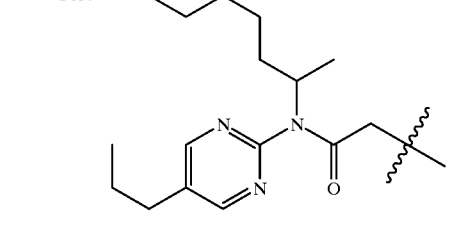
306. 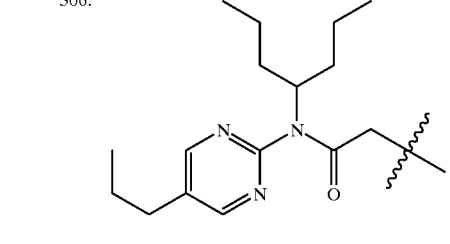
307.

TABLE 1-continued
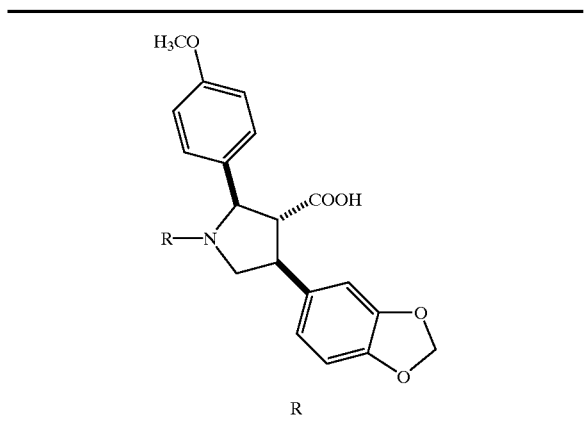
R
| | |
|---|---|
| 308. | 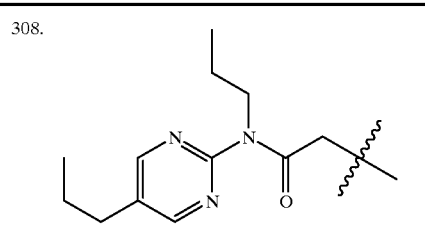 |
| 309. | 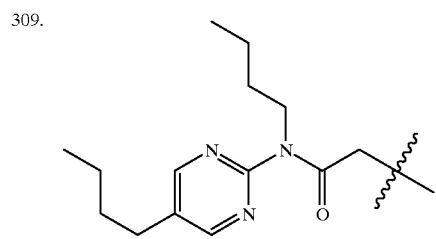 |
| 310. | 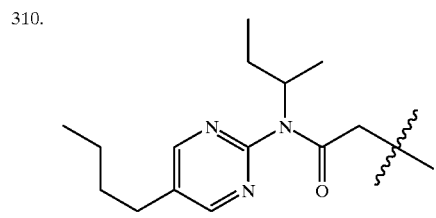 |
| 311. | 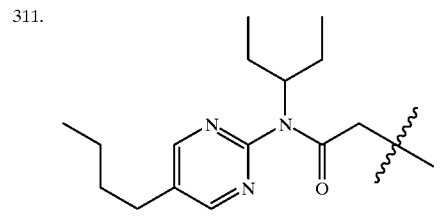 |
| 312. | 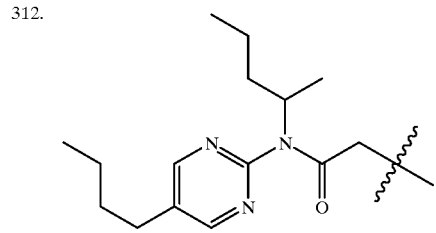 |
TABLE 1-continued
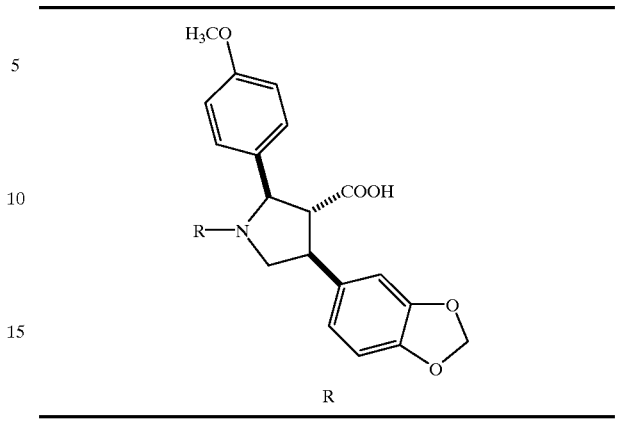
R
| | |
|---|---|
| 313. | 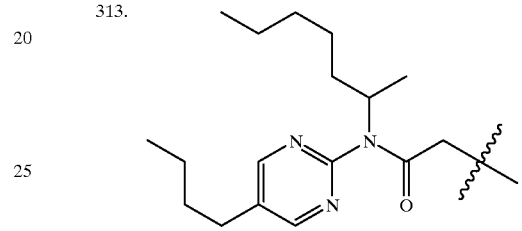 |
| 314. | 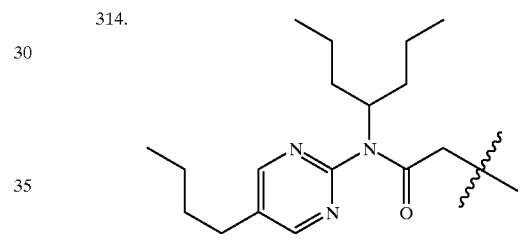 |
| 315. | 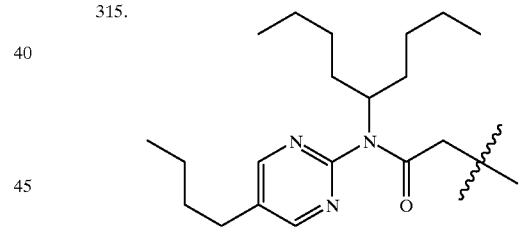 |
| 316. | 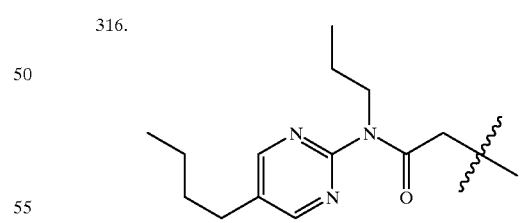 |
| 317. | 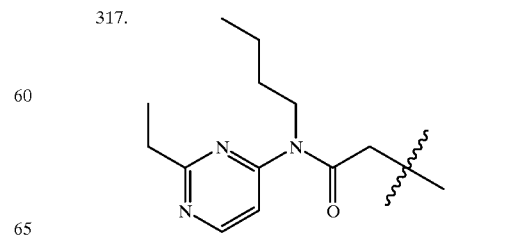 |

TABLE 1-continued
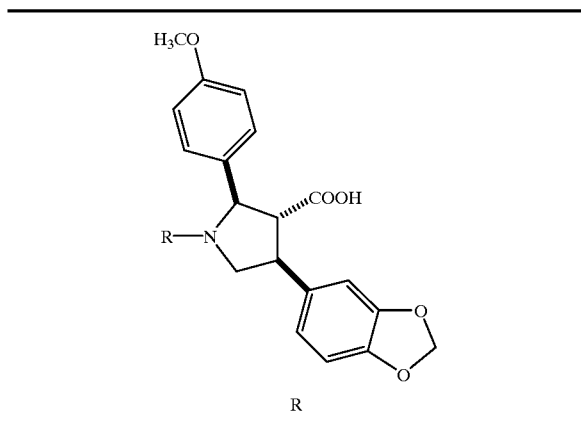
| R |
|---|
| 318. 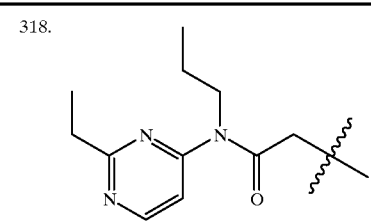 |
| 319. 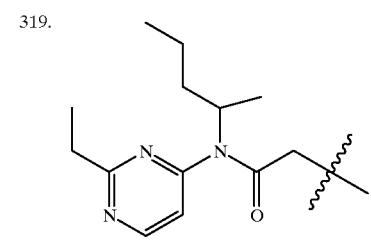 |
| 320. 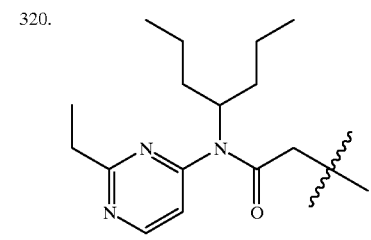 |
| 321. 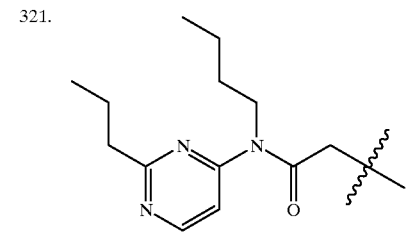 |
| 322. 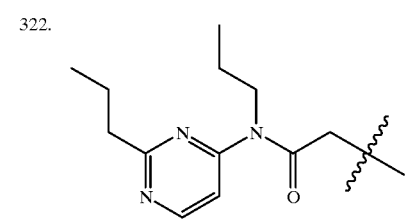 |
TABLE 1-continued
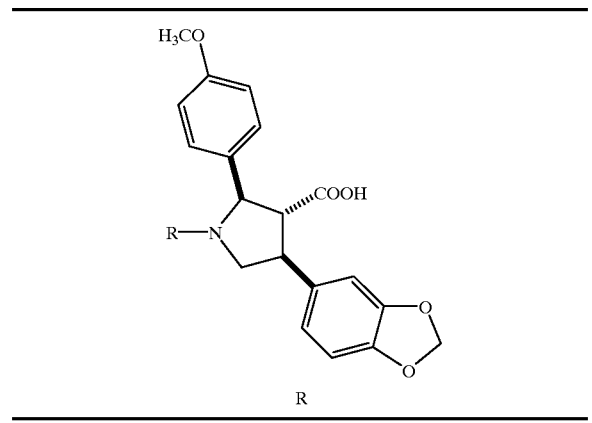
| R |
|---|
| 323. 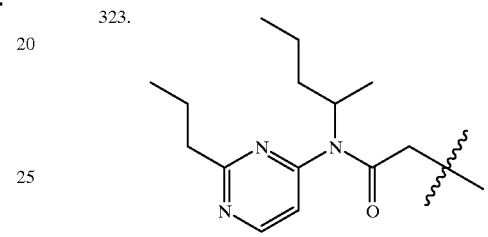 |
| 324. 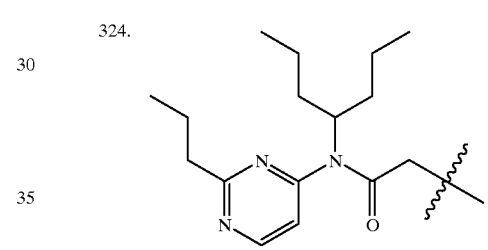 |
| 325. 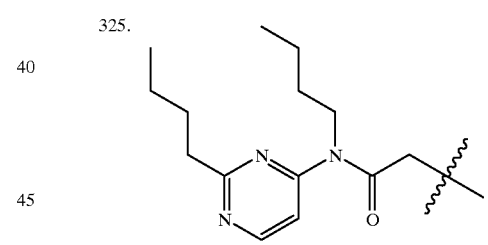 |
| 326. 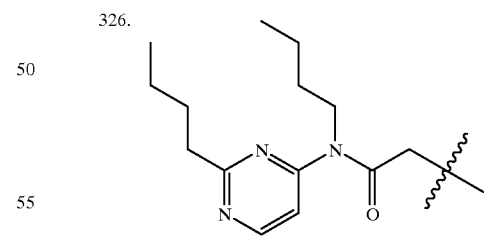 |
| 327. 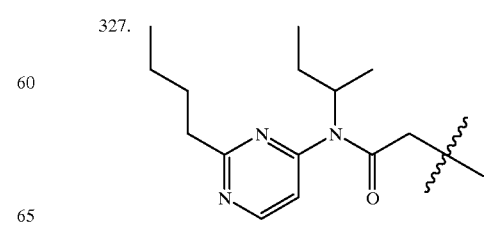 |

TABLE 1-continued
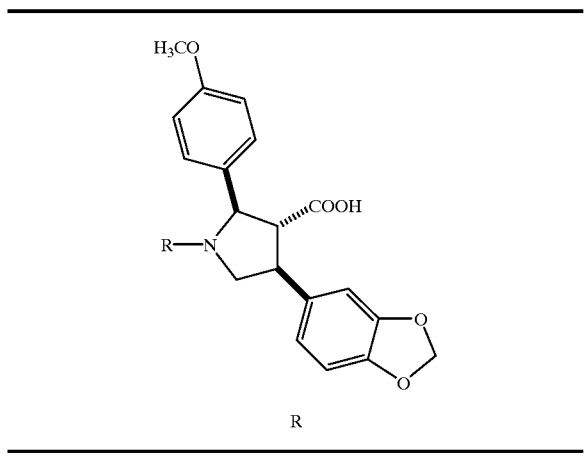
R
328.
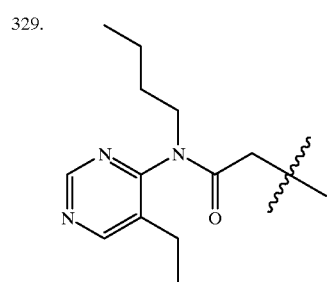
329.
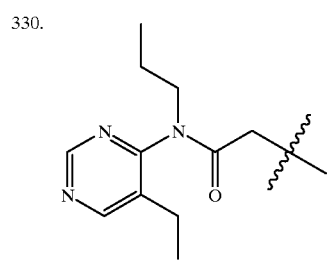
330.
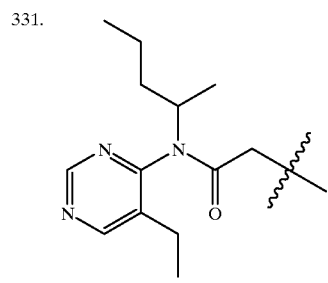
331.
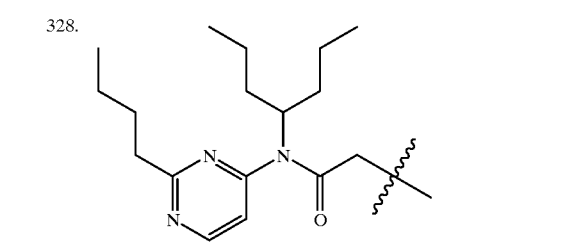
TABLE 1-continued
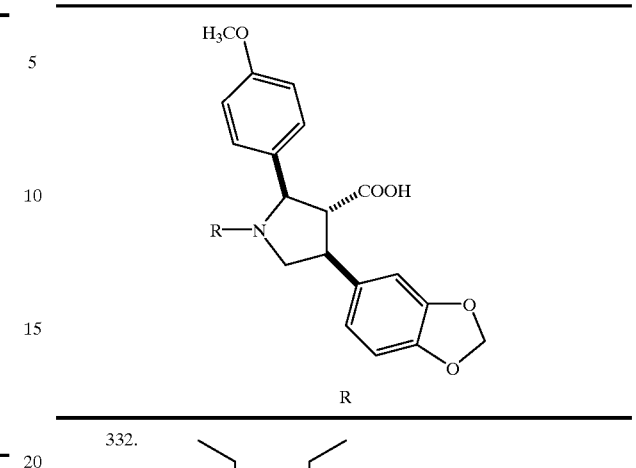
R
332.
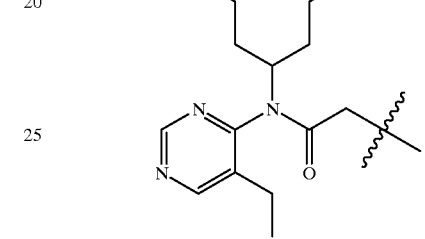
333.
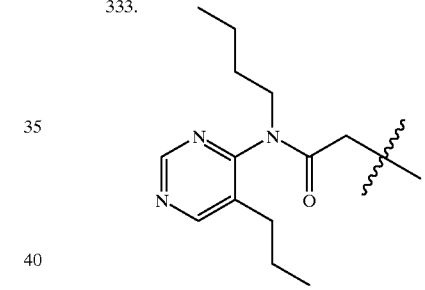
334.
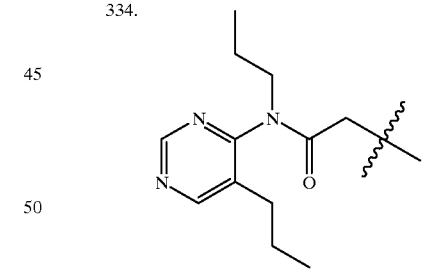
335.
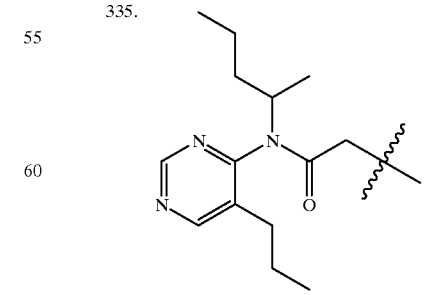

TABLE 1-continued
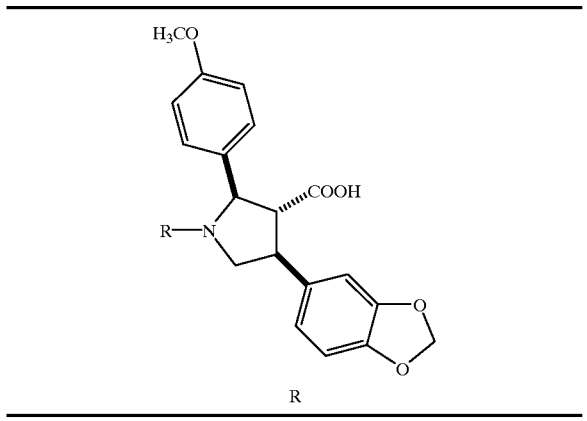
| | R |
|---|---|
| 336. | 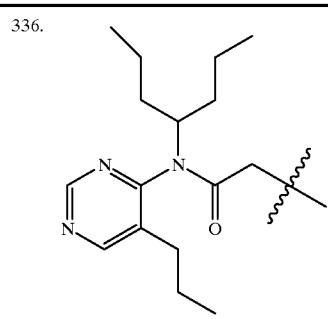 |
| 337. | 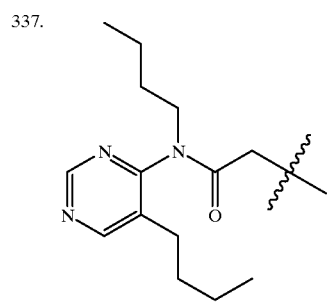 |
| 338. | 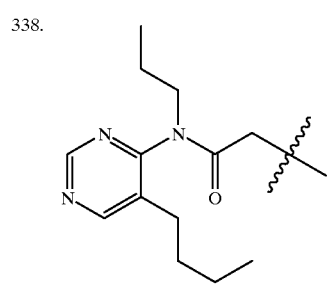 |
| 339. | 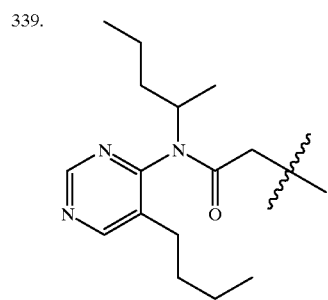 |
TABLE 1-continued
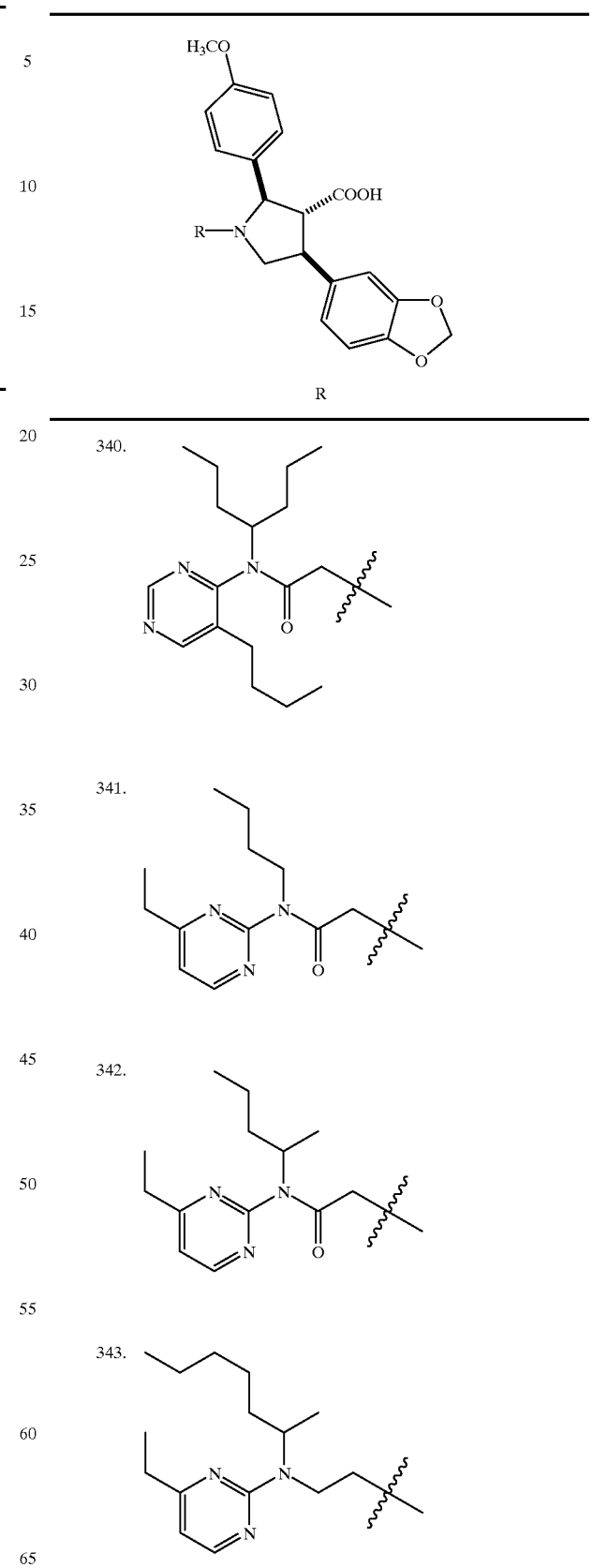

TABLE 1-continued
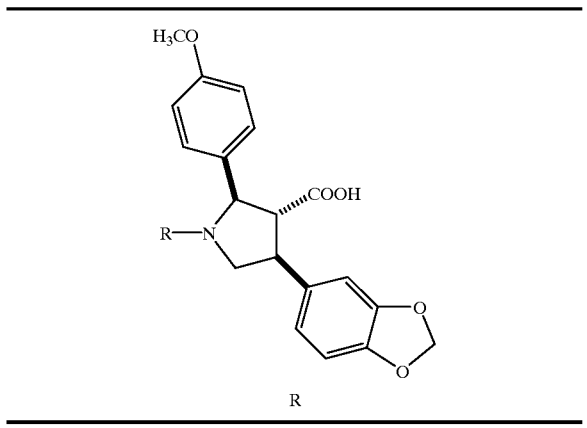
R
| 344. | 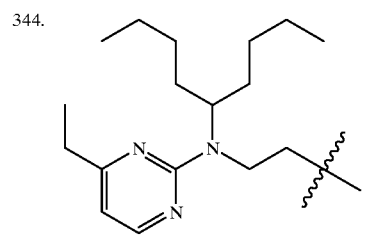 |
| 345. | 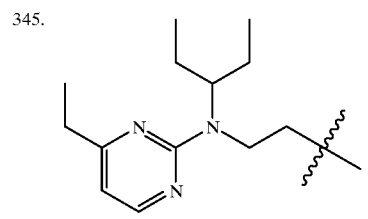 |
| 346. | 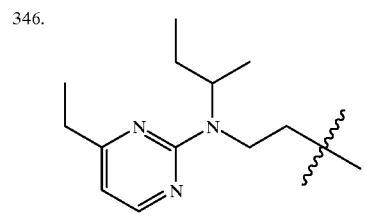 |
| 347. | 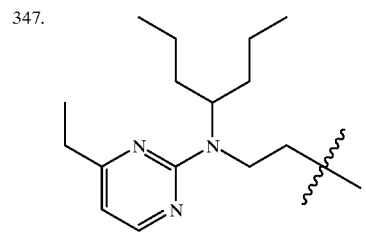 |
| 348. | 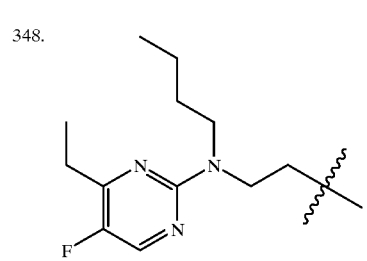 |
TABLE 1-continued
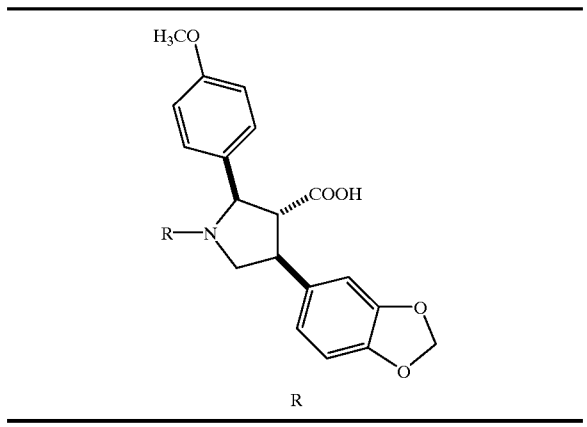
R
| 349. | 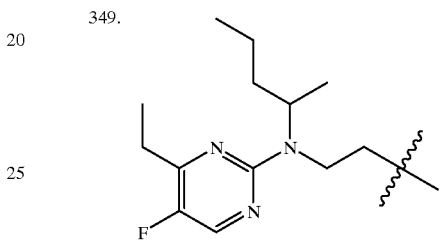 |
| 350. |  |
| 351. | 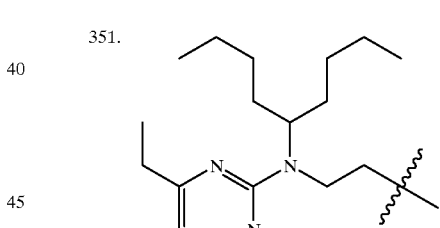 |
| 352. | 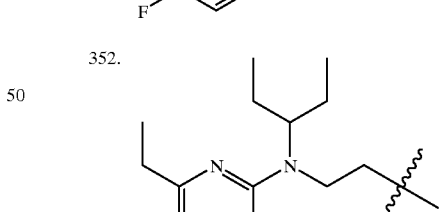 |
| 353. | 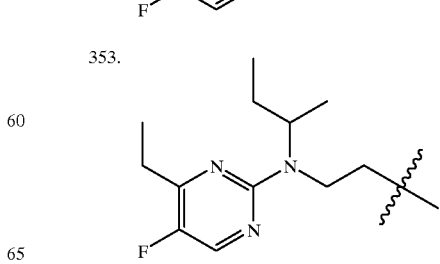 |

TABLE 1-continued
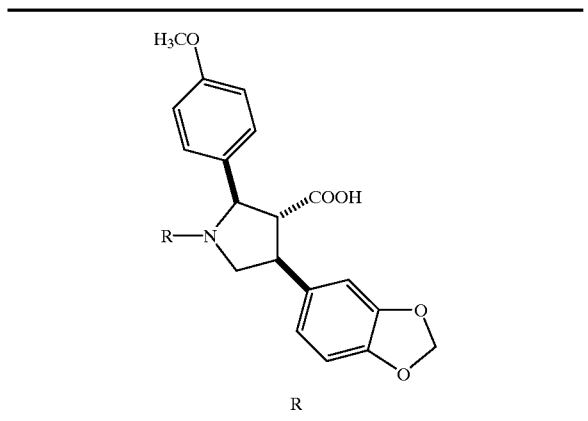
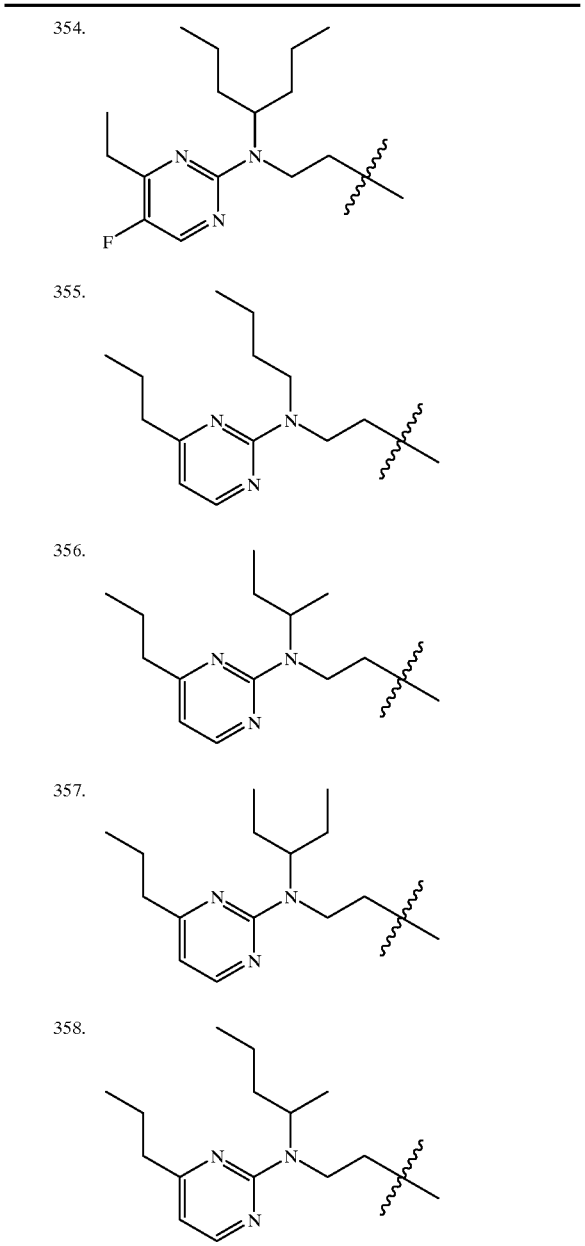
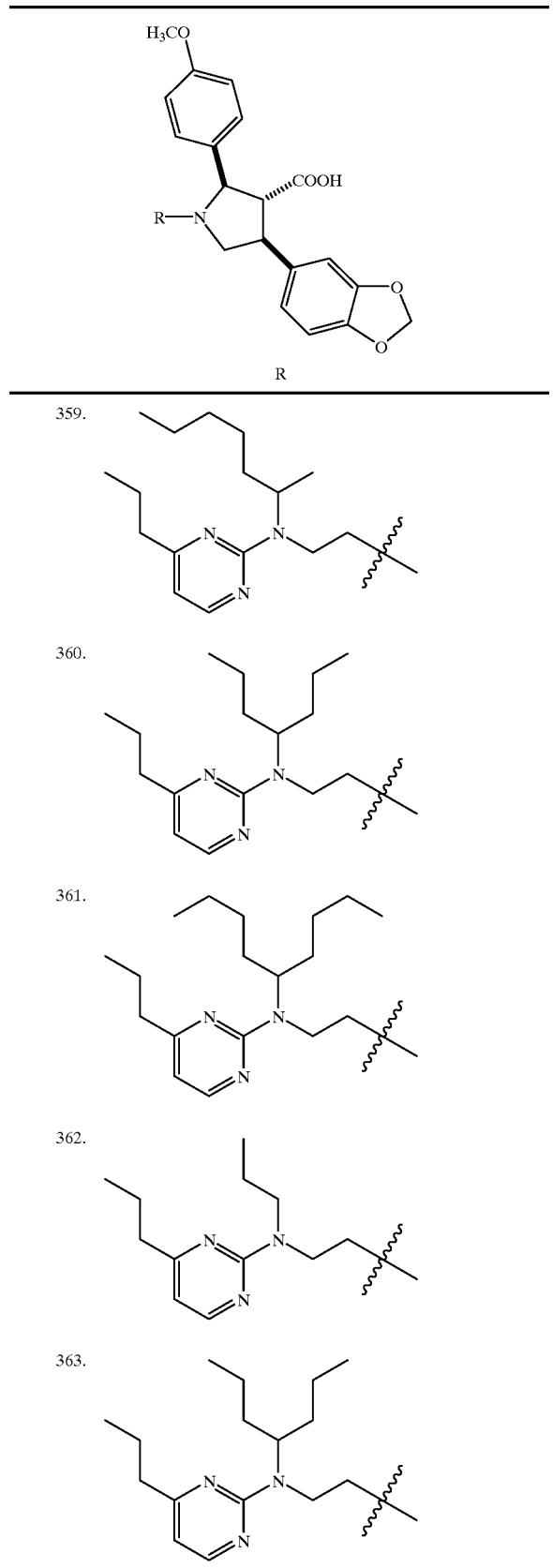

TABLE 1-continued
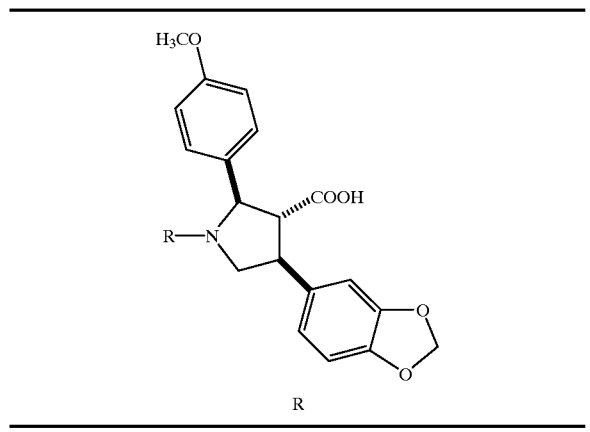
R
| 364. | 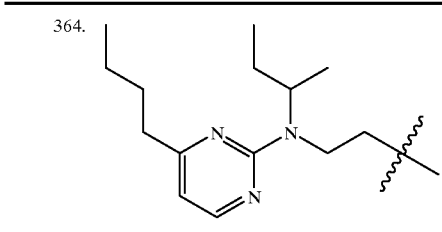 |
| --- | --- |
| 365. | 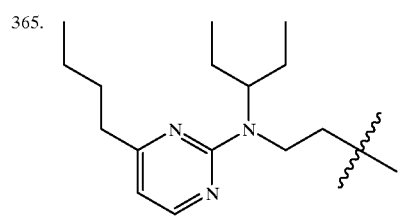 |
| 366. | 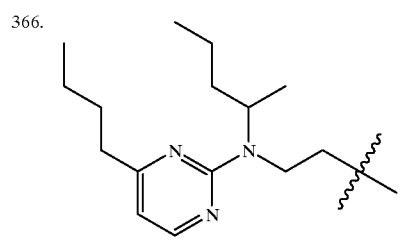 |
| 367. | 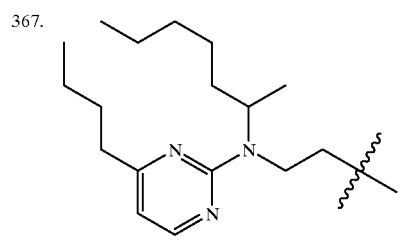 |
| 368. | 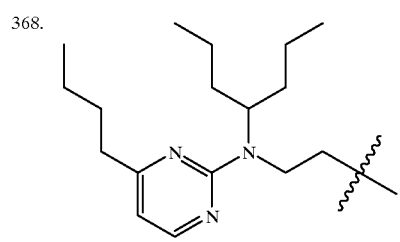 |
TABLE 1-continued
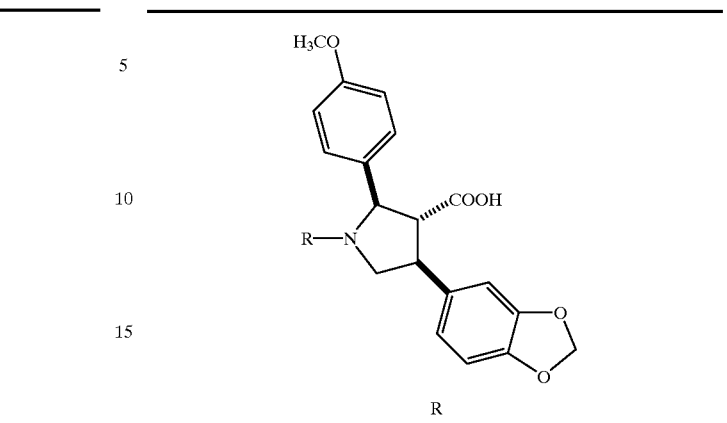
R
| 369. | 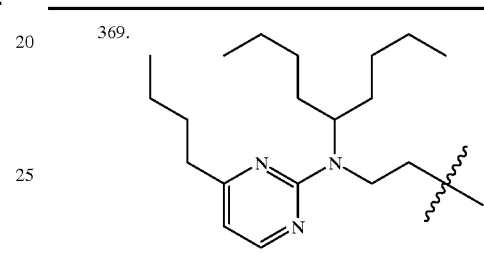 |
| --- | --- |
| 370. | 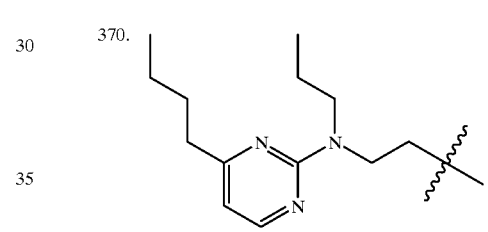 |
| 371. | 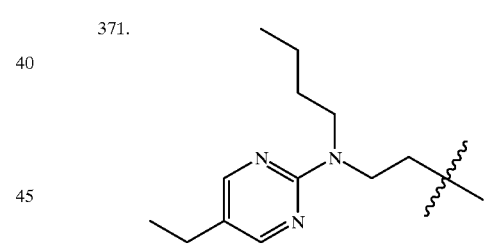 |
| 372. | 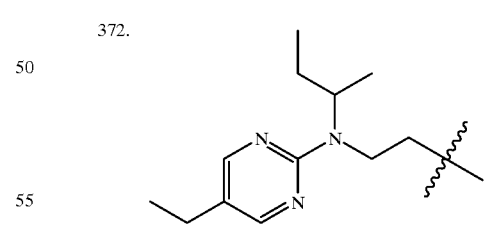 |
| 373. | 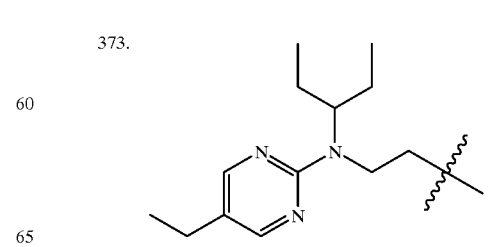 |

TABLE 1-continued
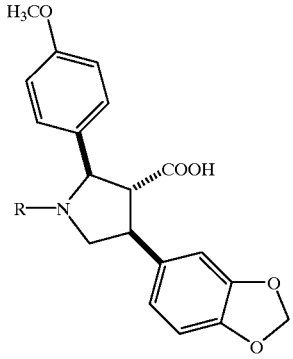
| | R |
|---|---|
| 374. | 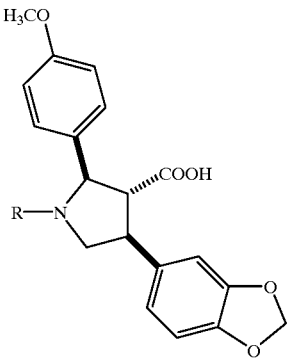 |
| 375. | 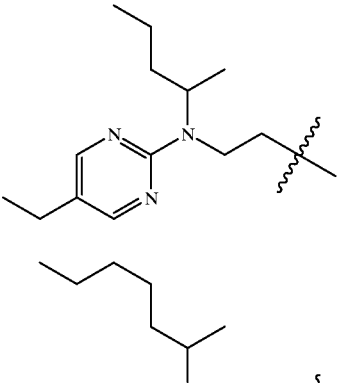 |
| 376. | 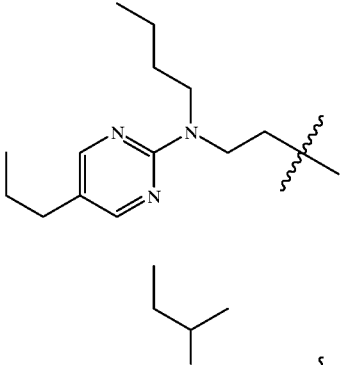 |
| 377. | 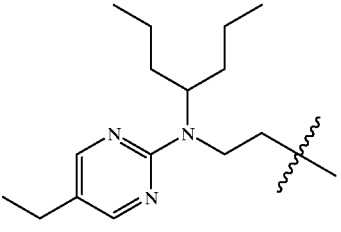 |
| 378. | 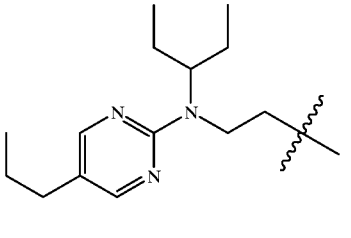 |
TABLE 1-continued
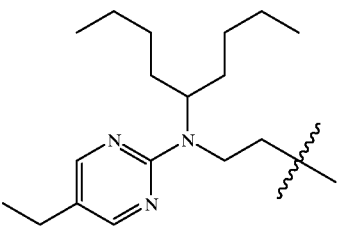
| | R |
|---|---|
| 379. | 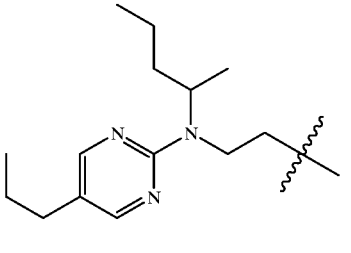 |
| 380. | 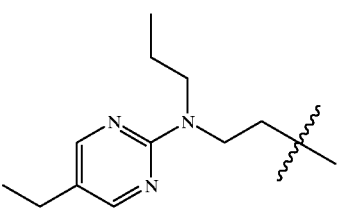 |
| 381. | 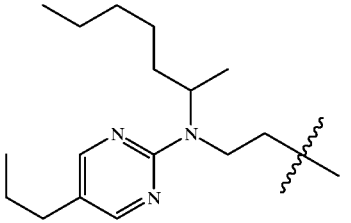 |
| 382. | |
| 383. | |

TABLE 1-continued
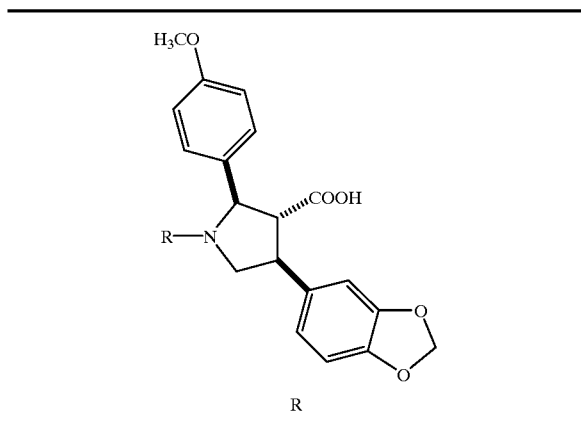
R
384. 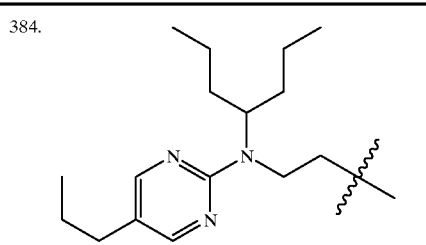
385. 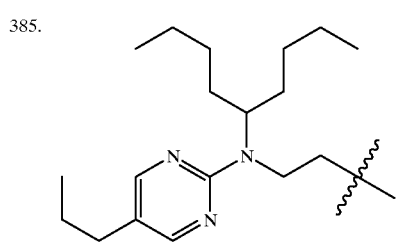
386. 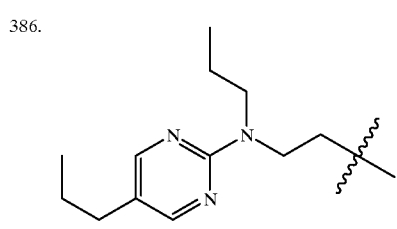
387. 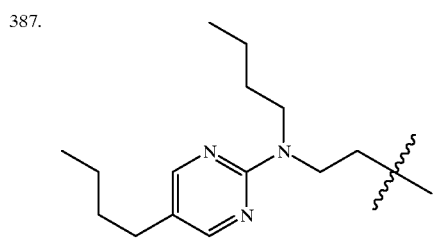
388. 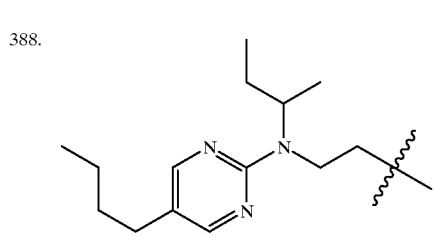
TABLE 1-continued
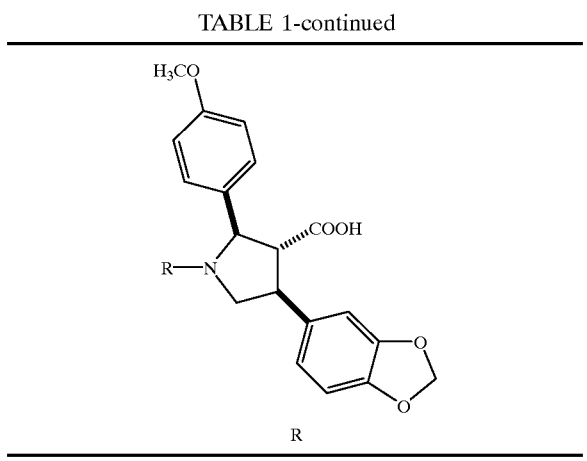
R
389. 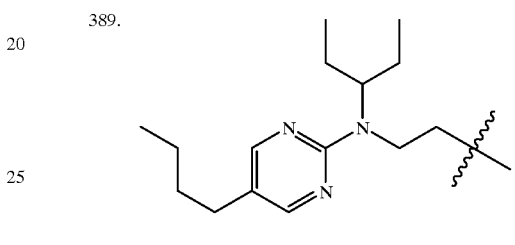
390. 
391. 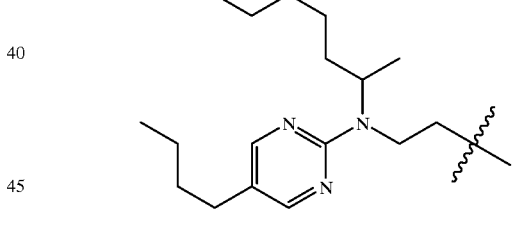
392. 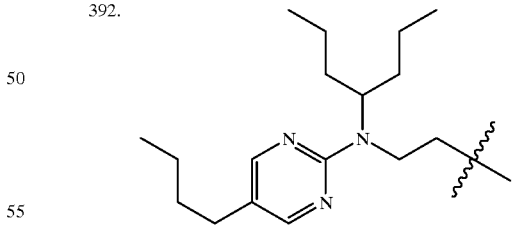
393. 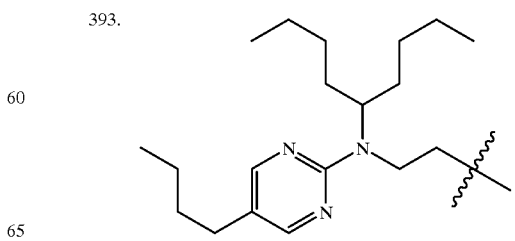

TABLE 1-continued
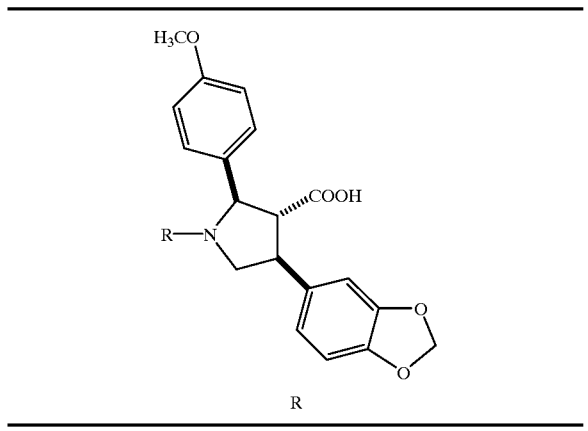
R
| | R |
|---|---|
| 394. | 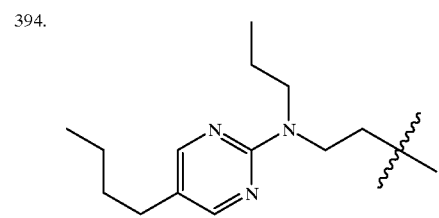 |
| 395. | 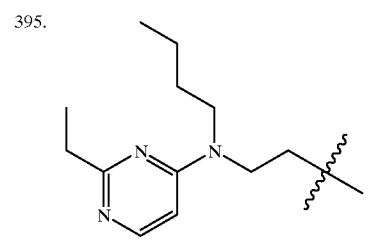 |
| 396. | 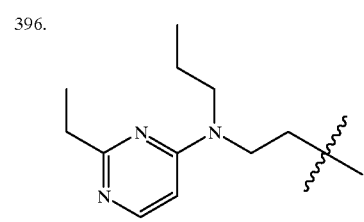 |
| 397. | 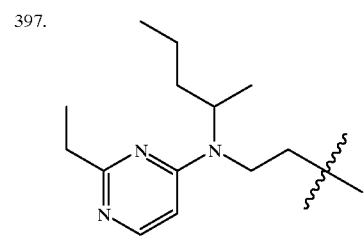 |
| 398. | |
TABLE 1-continued
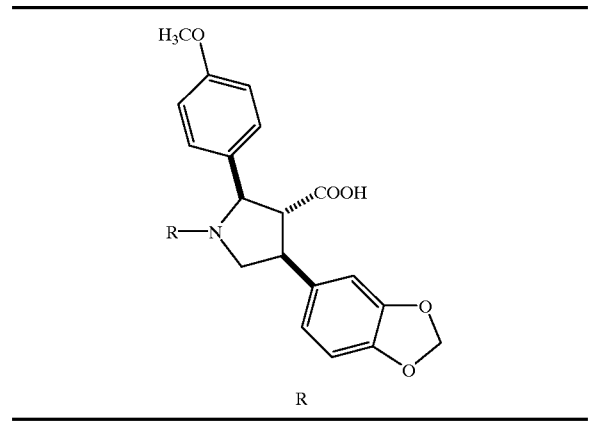
R
| | R |
|---|---|
| 399. | 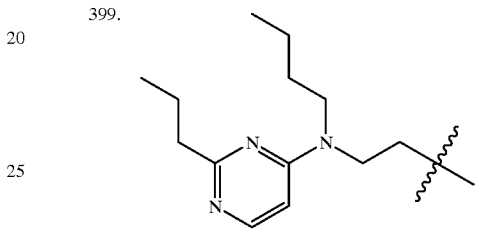 |
| 400. | 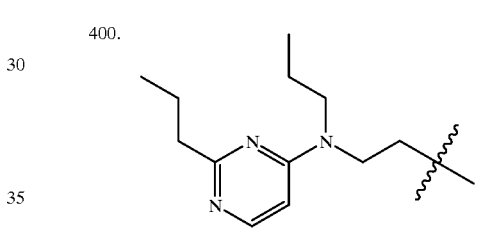 |
| 401. | 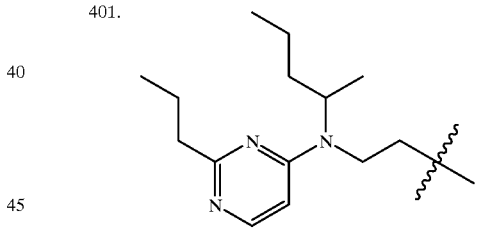 |
| 402. | 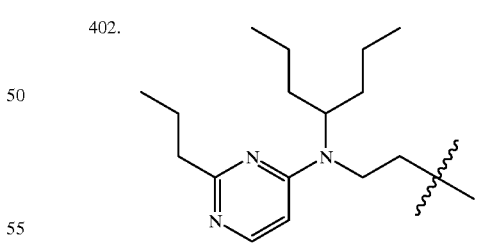 |
| 403. | |

TABLE 1-continued
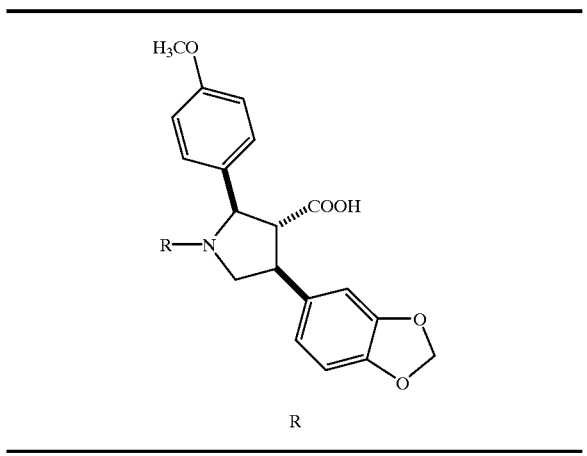
R
| 404. | 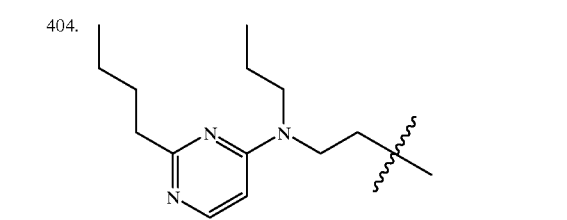 |
|---|---|
| 405. | 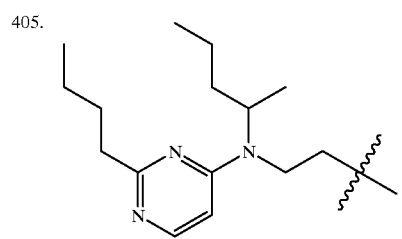 |
| 406. | 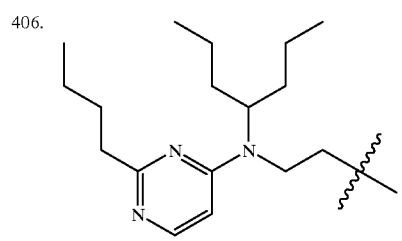 |
| 407. | 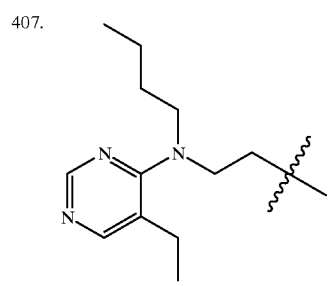 |
TABLE 1-continued
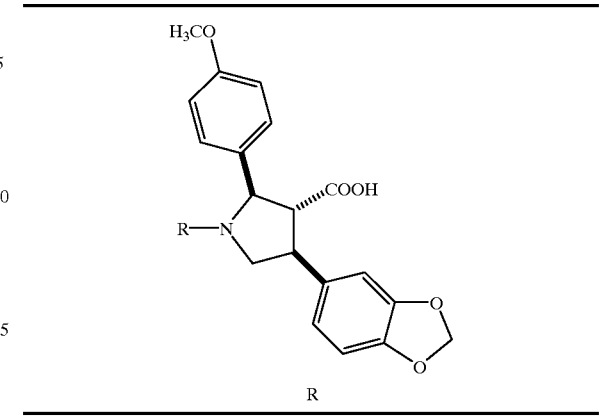
| 408. | 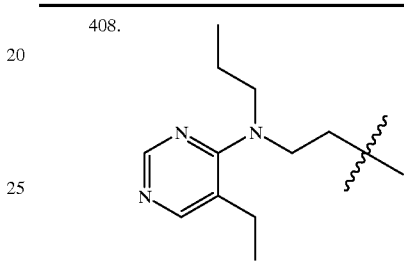 |
|---|---|
| 409. | 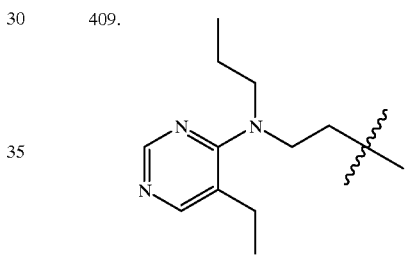 |
| 410. | 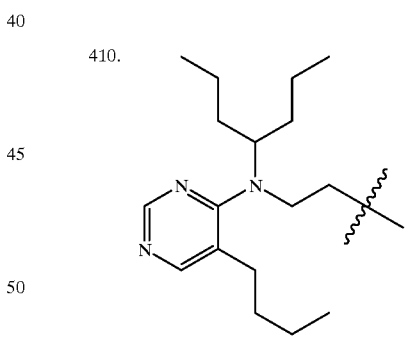 |
| 411. | 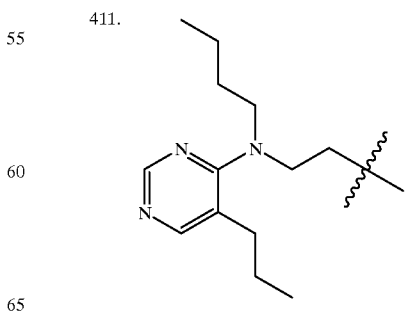 |

TABLE 1-continued
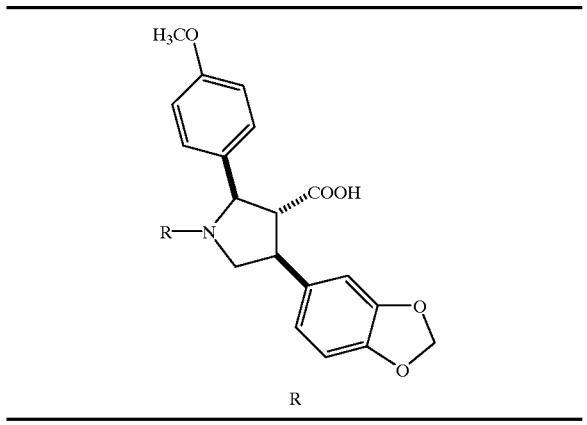
| | R |
|---|---|
| 412. | |
| 413. | |
| 414. | |
| 415. | |
TABLE 1-continued
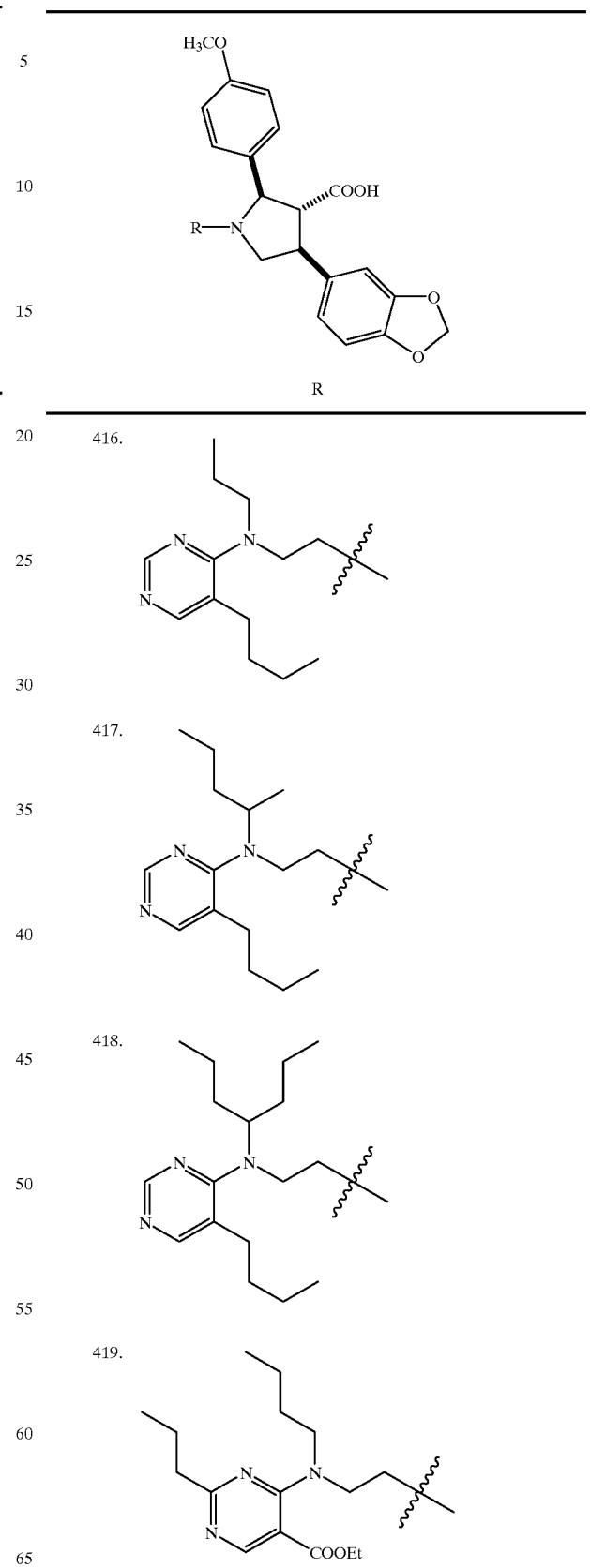

TABLE 1-continued
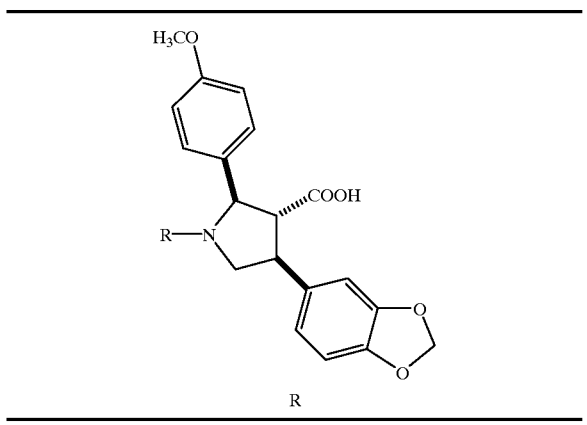
R
| | R |
|---|---|
| 420. | 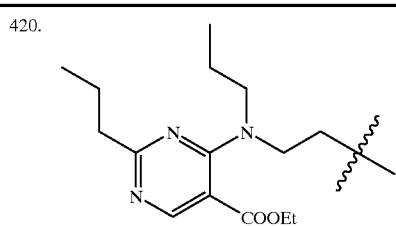 |
| 421. | 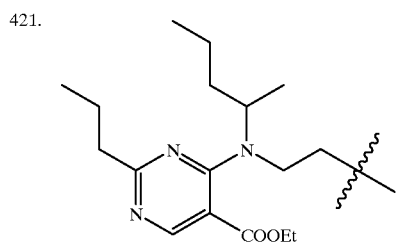 |
| 422. | 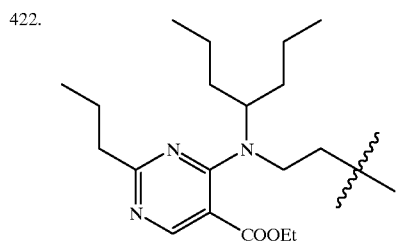 |
| 423. | 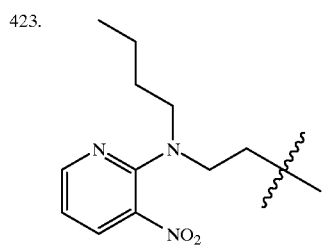 |
| 424. | 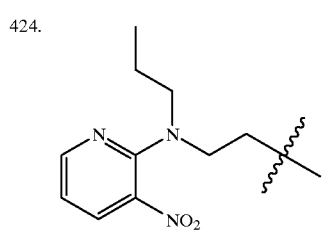 |
TABLE 1-continued
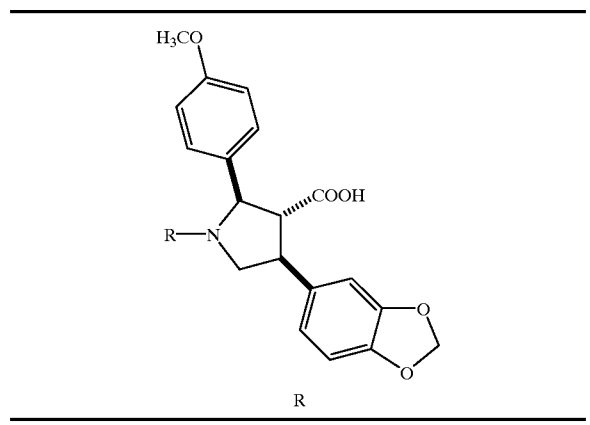
R
| | R |
|---|---|
| 425. | 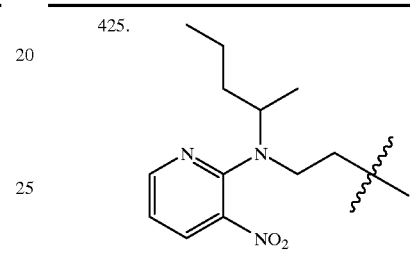 |
| 426. | 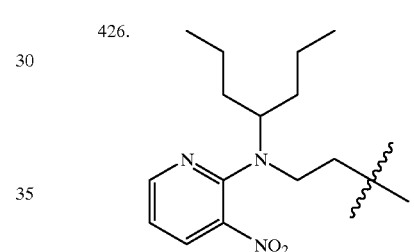 |
| 427. | 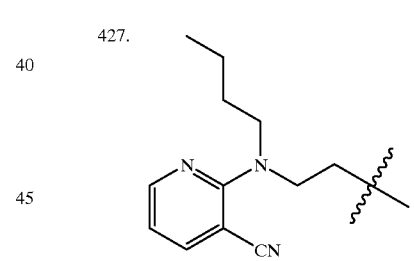 |
| 428. | 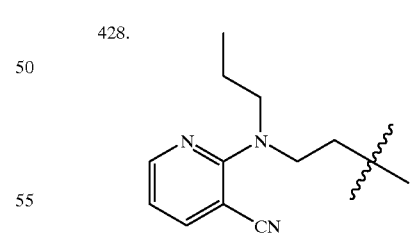 |
| 429. | 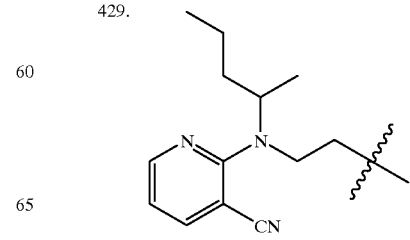 |

TABLE 1-continued
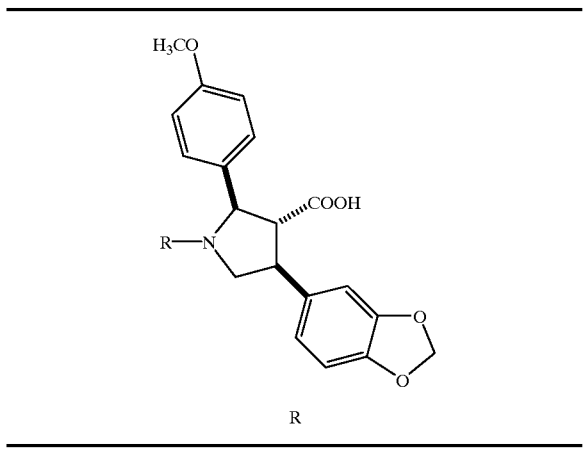
R
430.
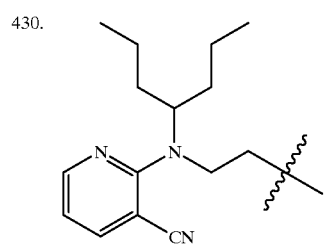
431.
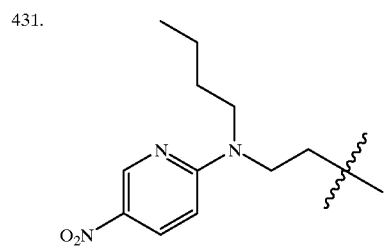
432.
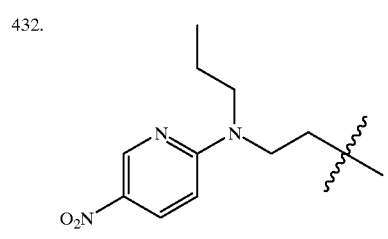
433.
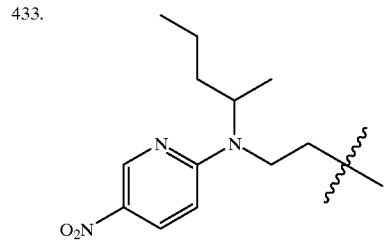
TABLE 1-continued
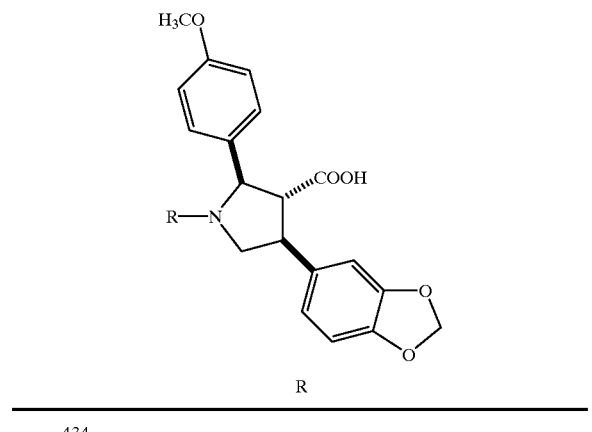
R
434.
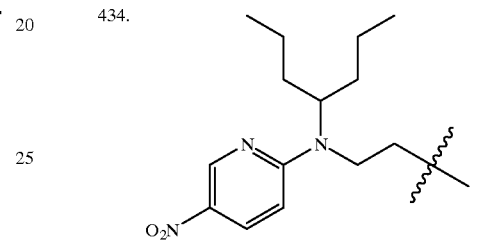
435.
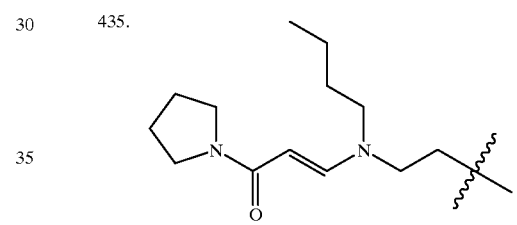
436.
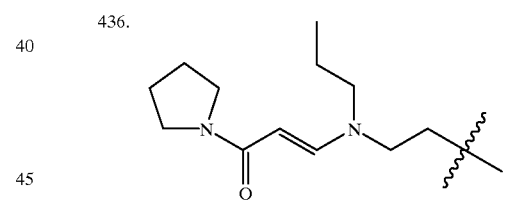
437.

438.

TABLE 1-continued
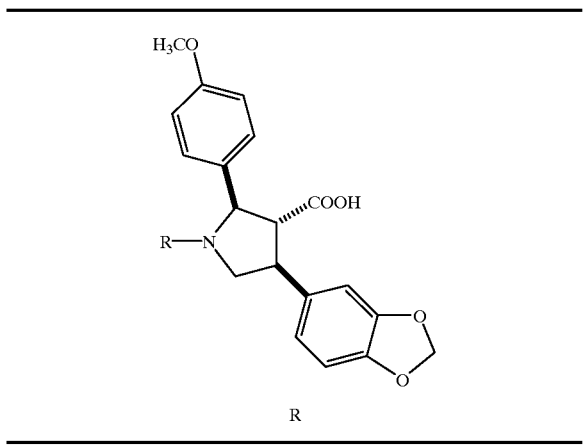
R
| 439. | 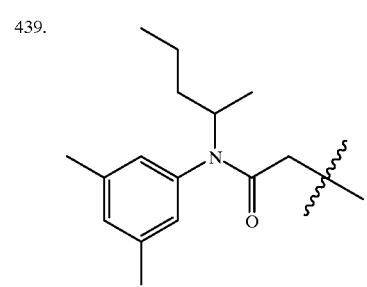 |
| --- | --- |
| 440. | 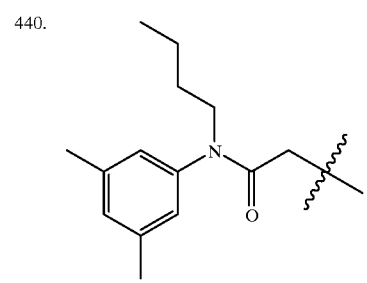 |
| 441. | 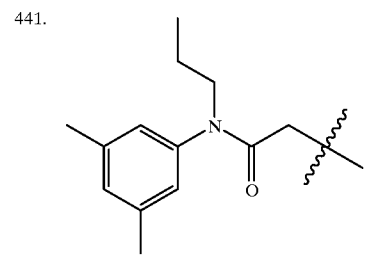 |
| 442. | 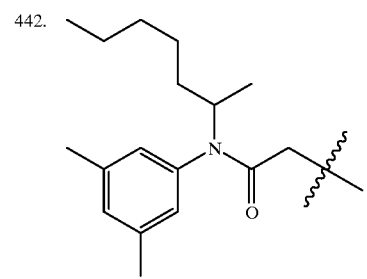 |
TABLE 1-continued
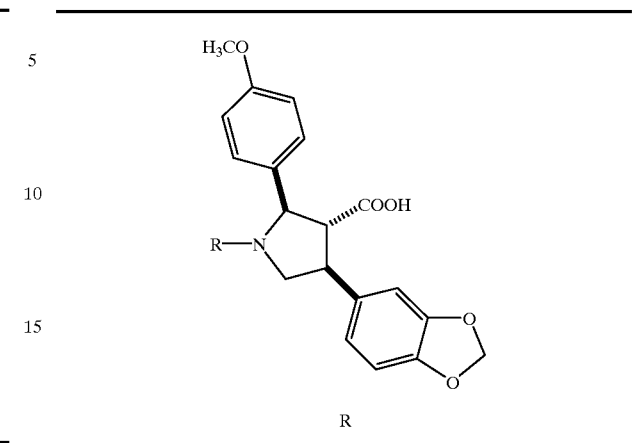
R
| 443. | 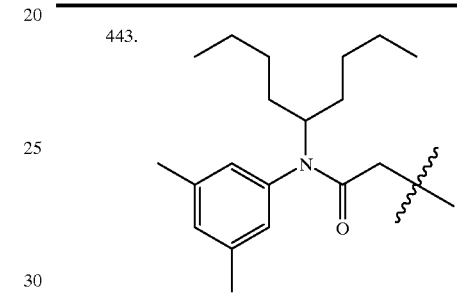 |
| --- | --- |
| 444. | 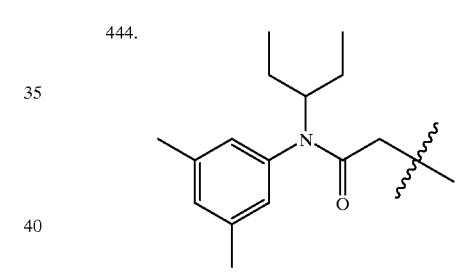 |
| 445. |  |
| 446. | 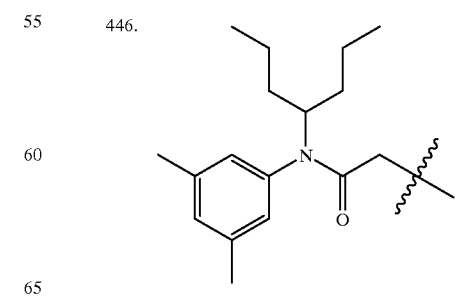 |

TABLE 1-continued
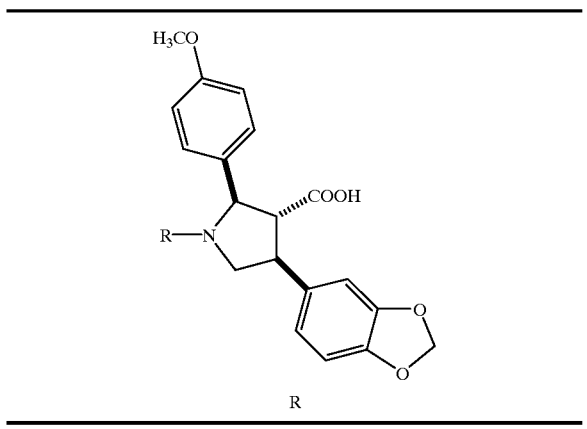
R
| | |
|---|---|
| 447. | 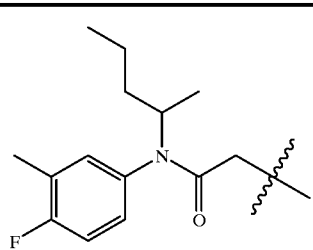 |
| 448. | 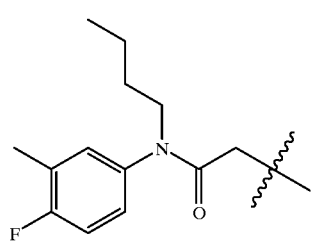 |
| 449. | 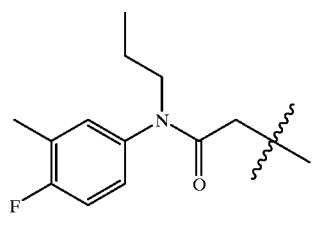 |
| 450. | 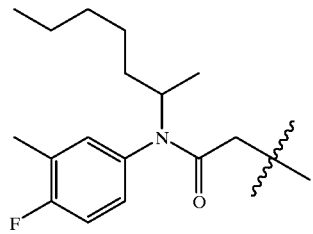 |
| 451. | 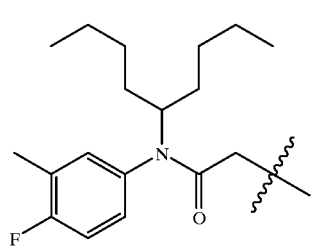 |
TABLE 1-continued
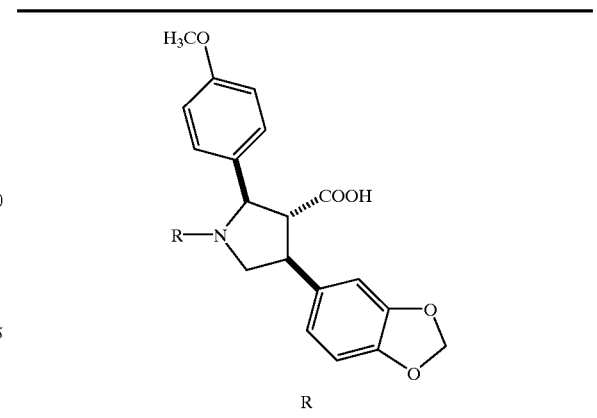
R
| | |
|---|---|
| 452. | 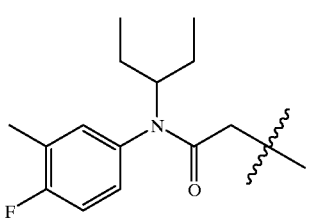 |
| 453. | 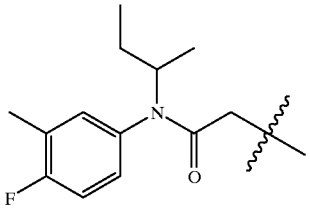 |
| 454. | 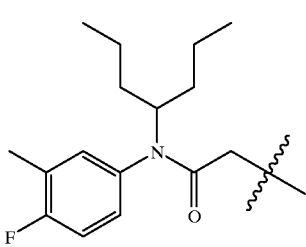 |
| 455. | 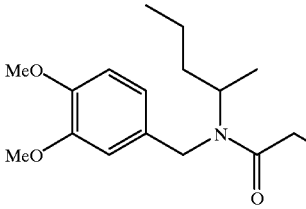 |
| 456. | 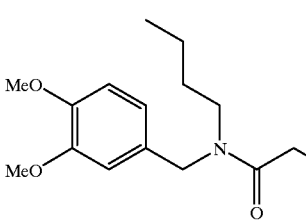 |

TABLE 1-continued
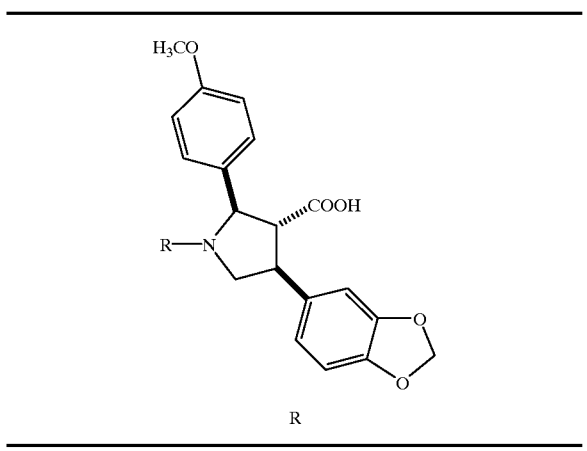
R
| | |
|---|---|
| 457. | 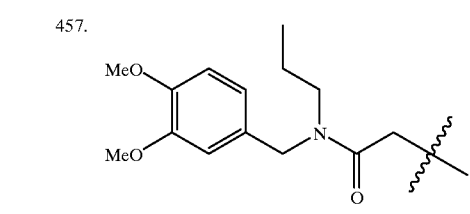 |
| 458. | 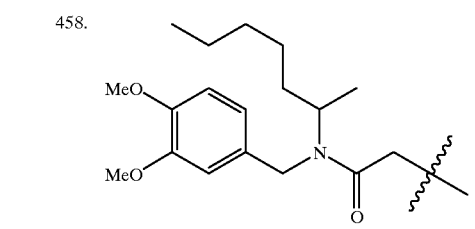 |
| 459. | 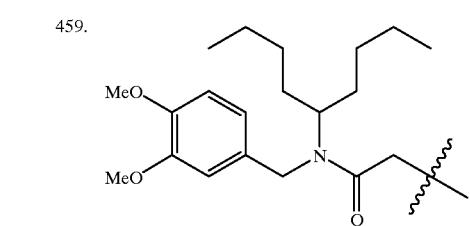 |
| 460. | 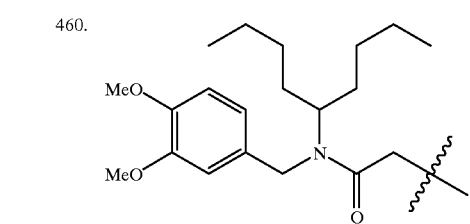 |
| 461. | 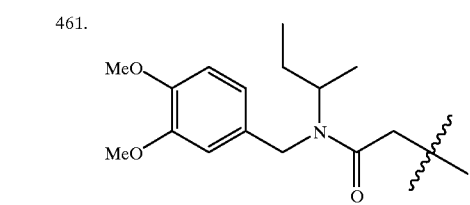 |
TABLE 1-continued
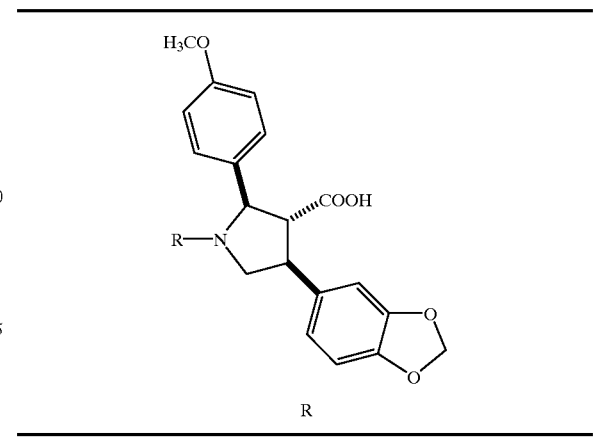
R
| | |
|---|---|
| 462. | 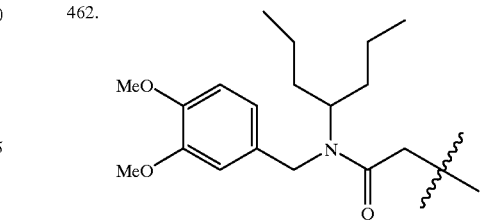 |
| 463. | 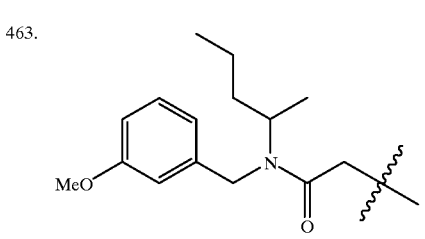 |
| 464. | 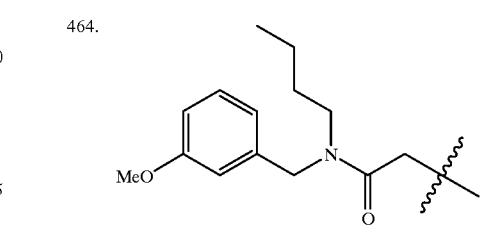 |
| 465. | 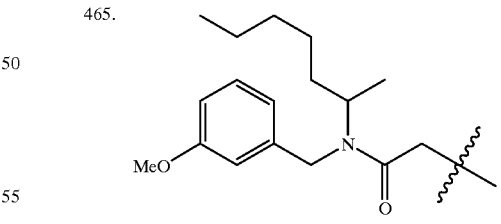 |
| 466. | 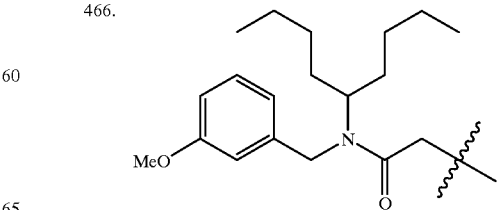 |

TABLE 1-continued
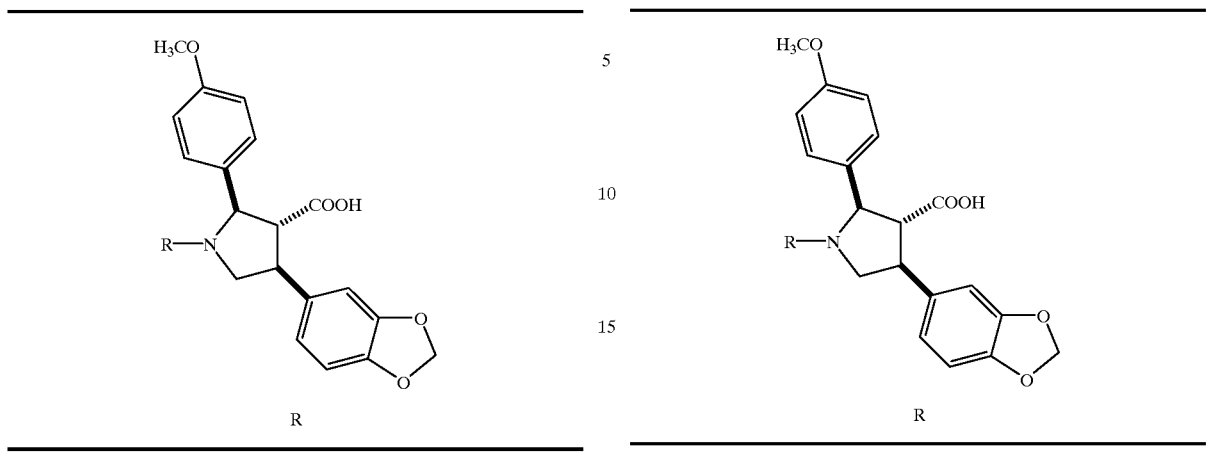
R
| 467. | 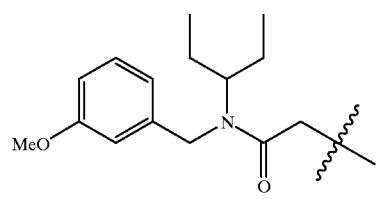 |
| --- | --- |
| 468. | 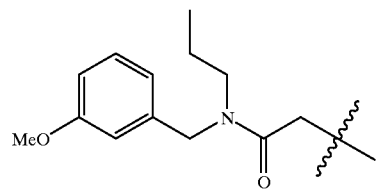 |
| 469. | 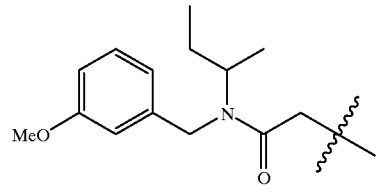 |
| 470. | 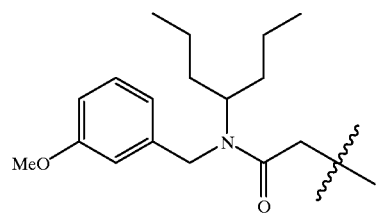 |
| 471. | 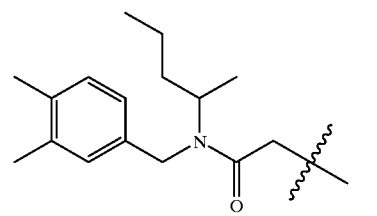 |
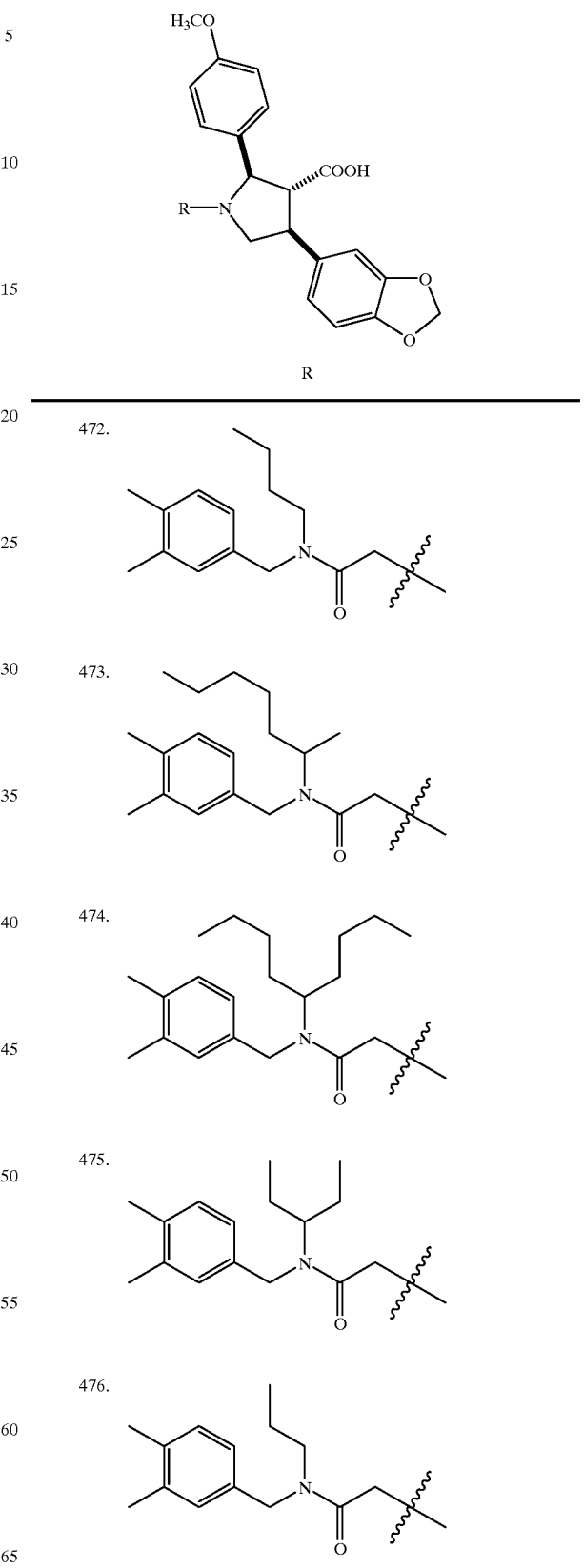

TABLE 1-continued
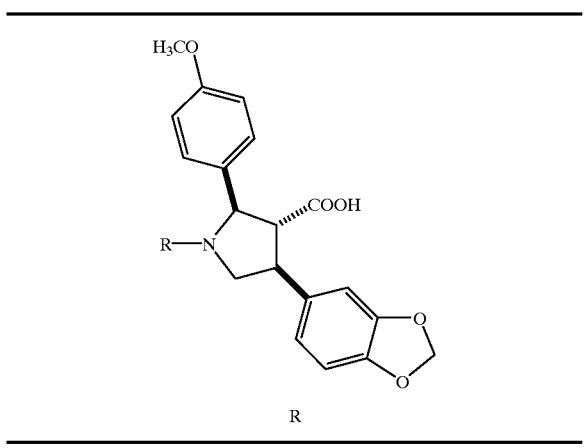
| | R |
|---|---|
| 477. | 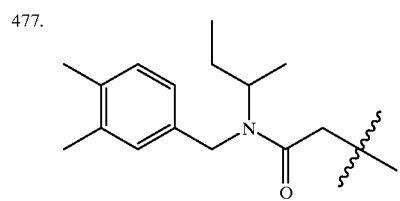 |
| 478. | 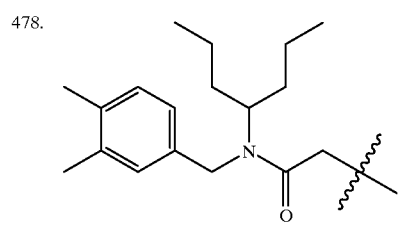 |
| 479. | 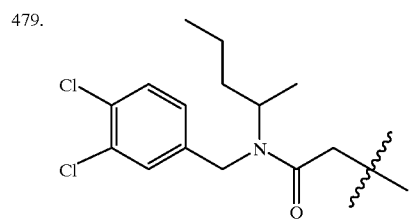 |
| 480. | 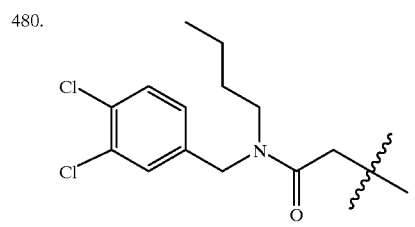 |
| 481. | 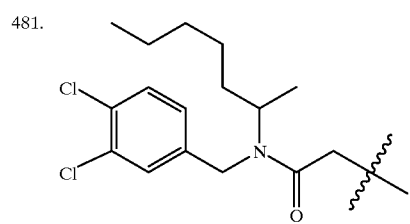 |
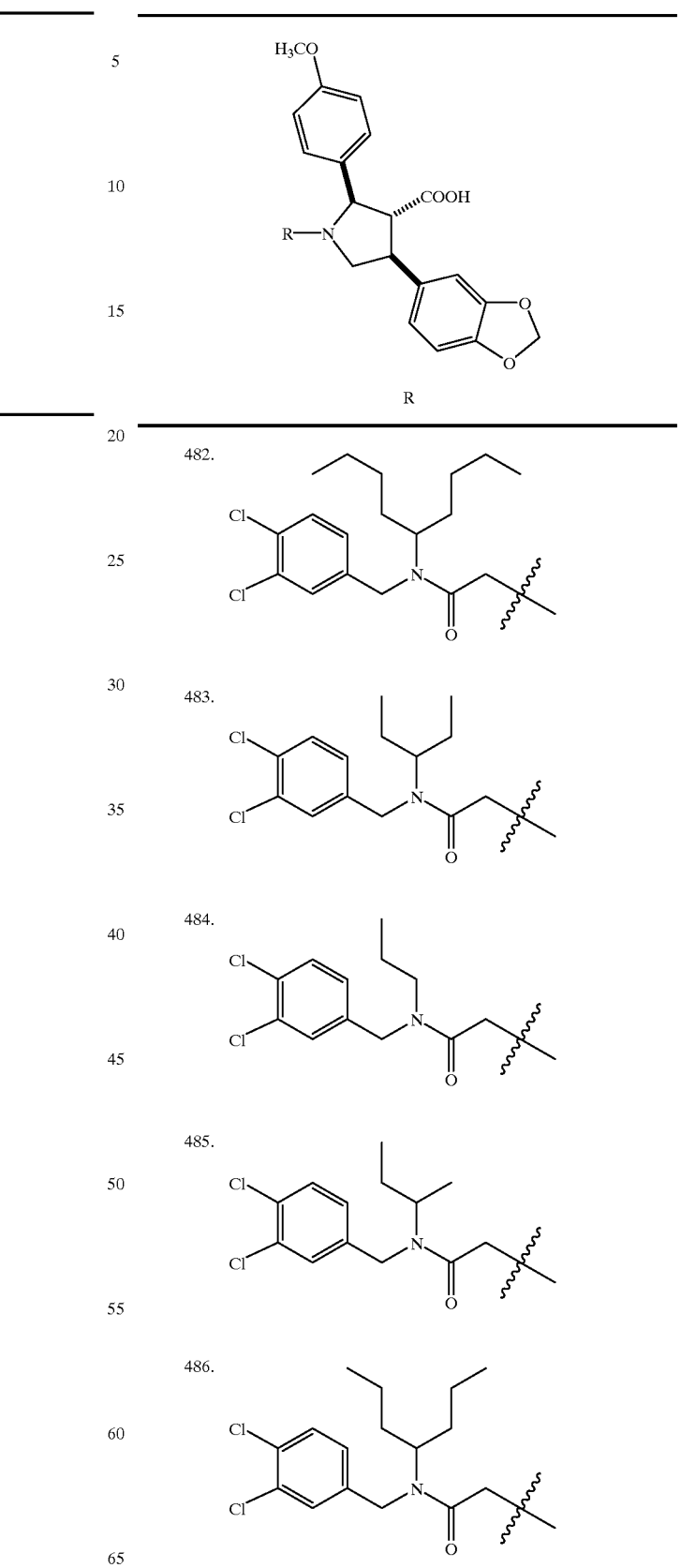

TABLE 1-continued
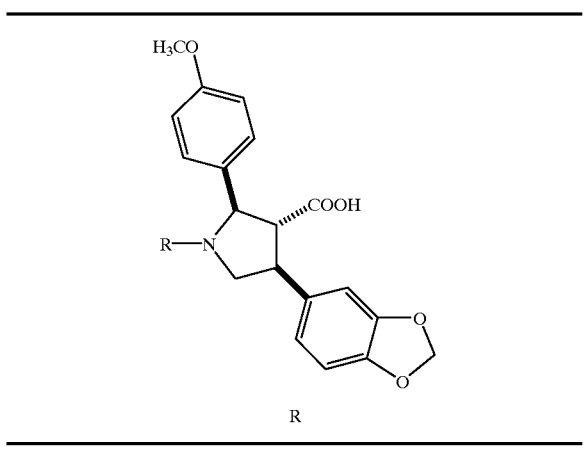
R
| 487. | 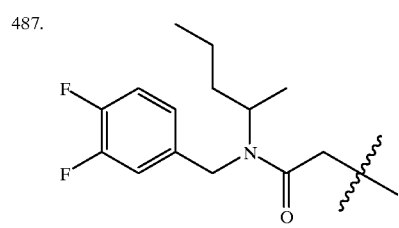 |
| --- | --- |
| 488. | 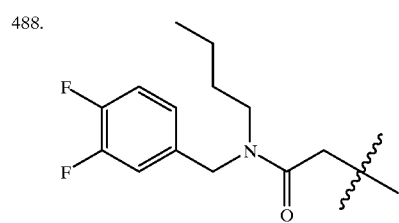 |
| 489. | 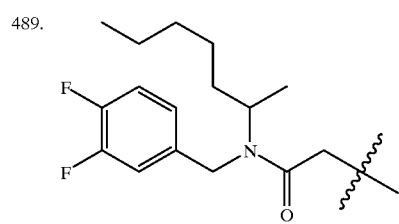 |
| 490. | 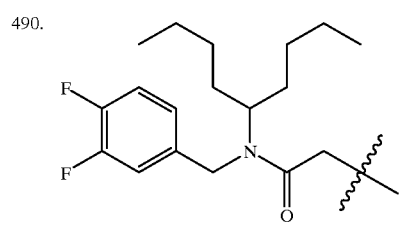 |
| 491. | 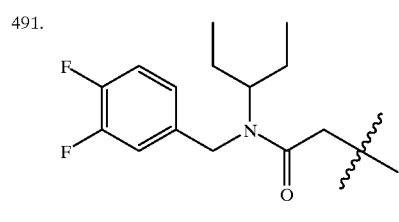 |
TABLE 1-continued
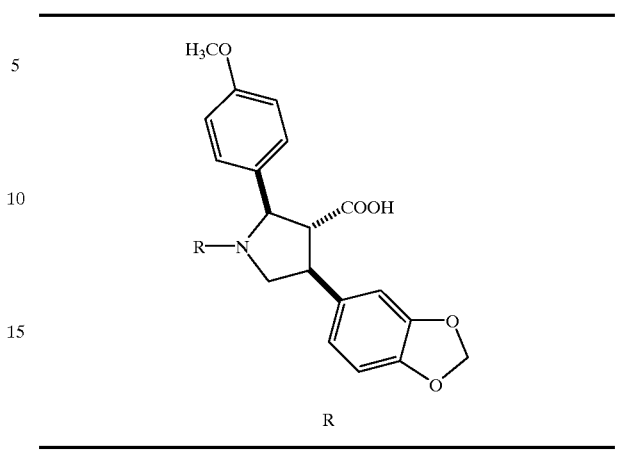
R
| 492. | 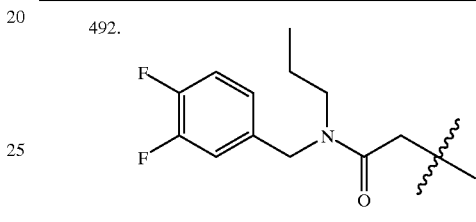 |
| --- | --- |
| 493. | 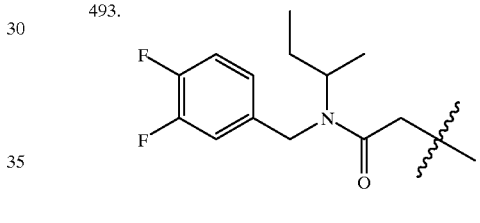 |
| 494. | 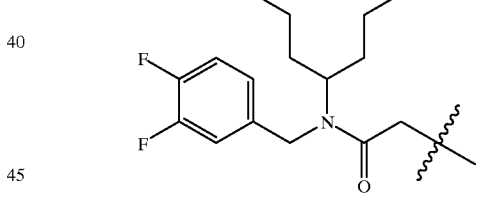 |
| 495. | 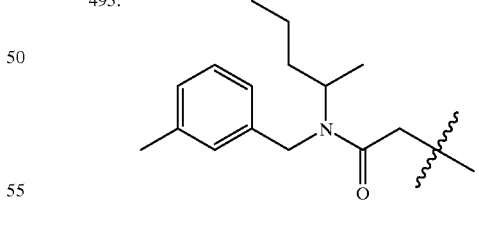 |
| 496. | 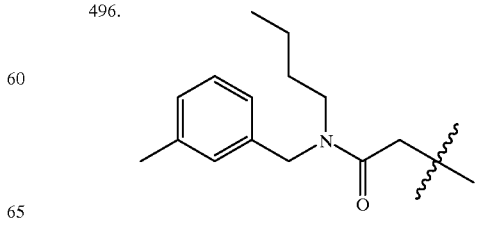 |

TABLE 1-continued
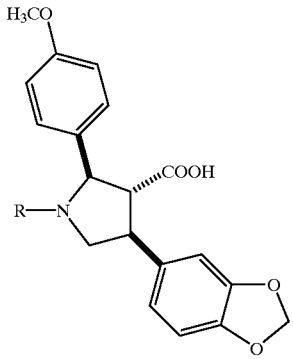
R
| | |
|---|---|
| 497. | 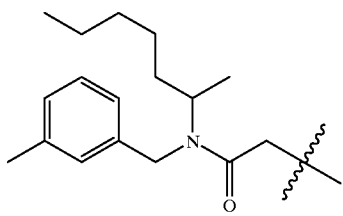 |
| 498. | 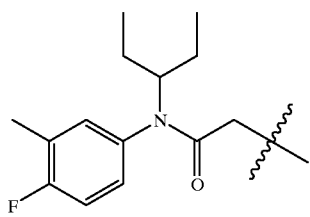 |
| 499. | 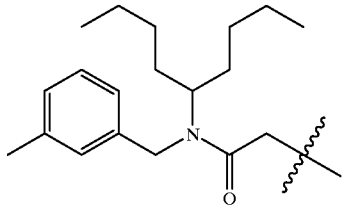 |
| 450. | 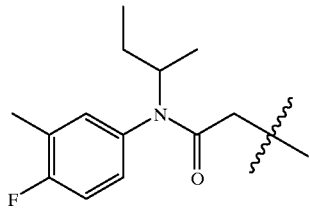 |
| 451. | 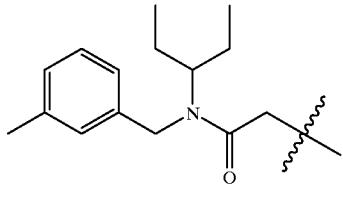 |
TABLE 1-continued
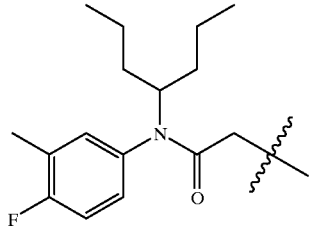
R
| | |
|---|---|
| 452. | 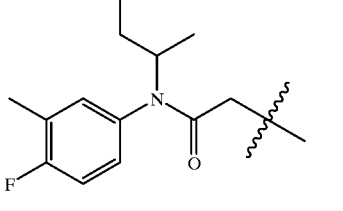 |
| 453. | 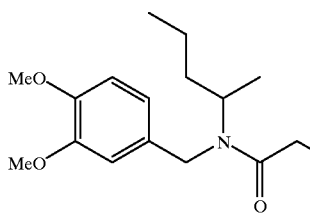 |
| 454. | 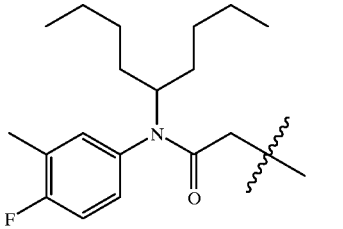 |
| 455. | 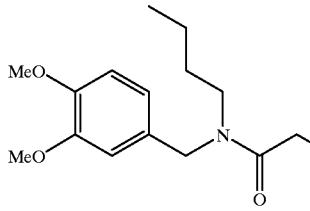 |
| 456. | 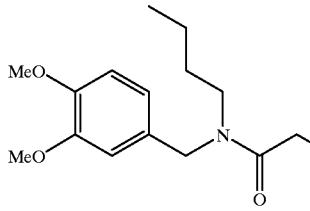 |

TABLE 1-continued
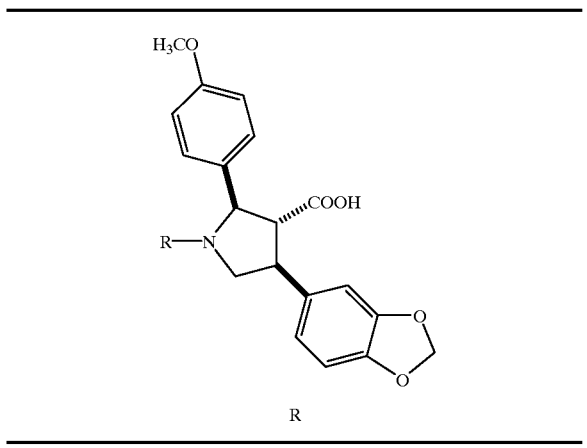
R
| | |
|---|---|
| 457. | 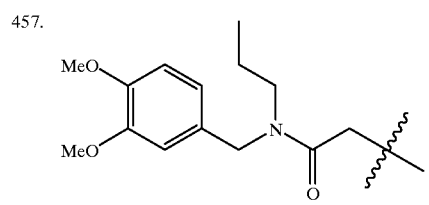 |
| 458. | 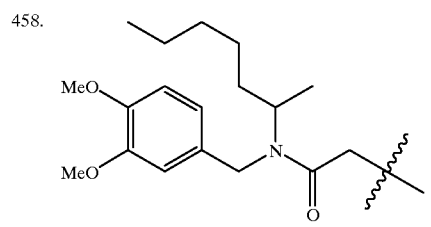 |
| 459. | 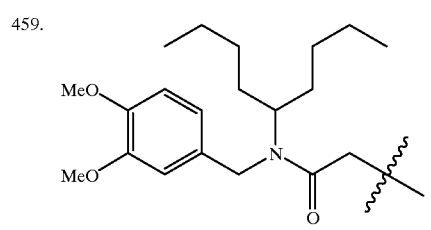 |
| 460. | 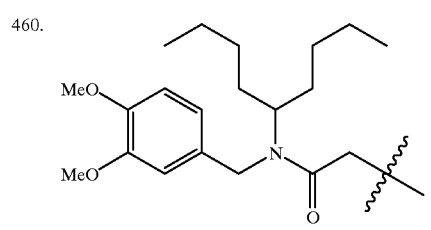 |
| 461. | 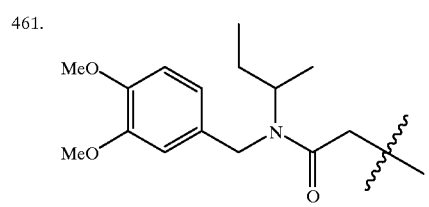 |
TABLE 1-continued
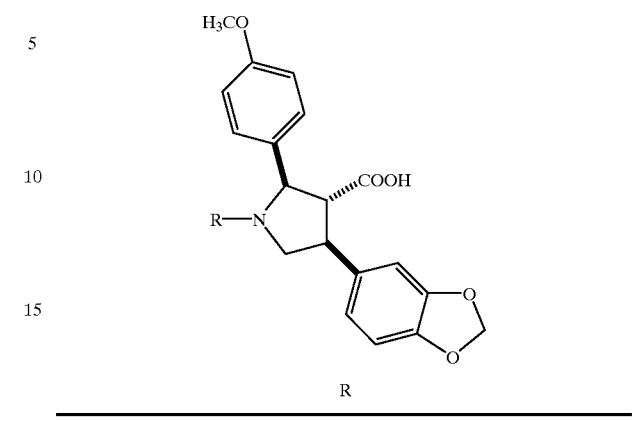
R
| | |
|---|---|
| 462. | 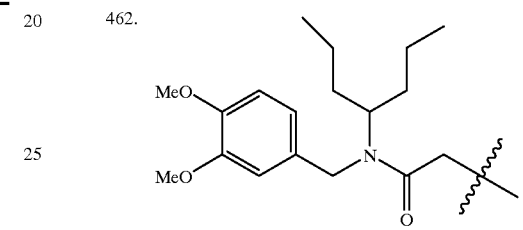 |
| 463. |  |
| 464. |  |
| 465. |  |
| 466. | 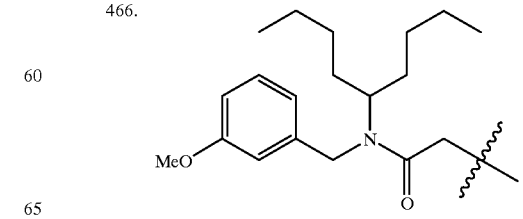 |

TABLE 1-continued
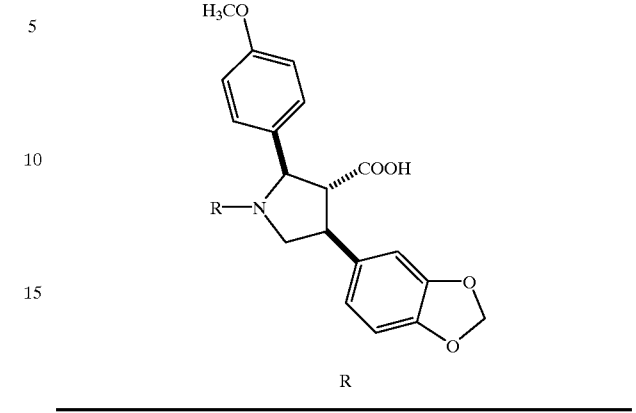
| R |
|---|
| 372. | 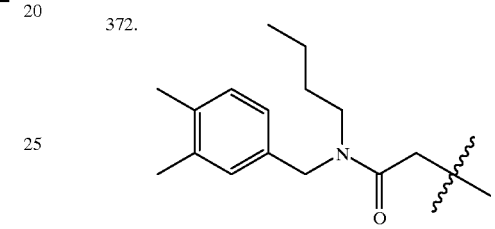 |
|---|---|
| 473. | 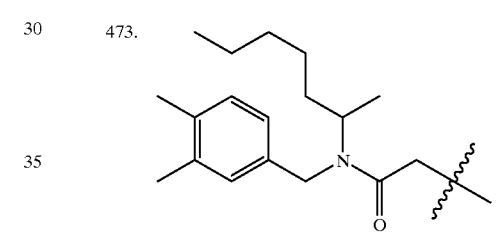 |
| 474. |  |
| 475. | 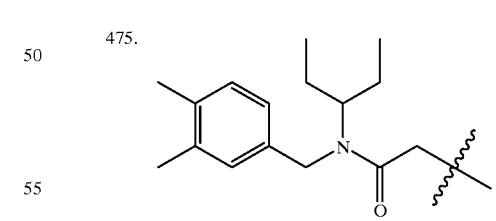 |
| 476. | 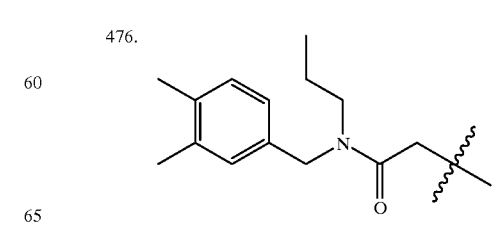 |
TABLE 1-continued
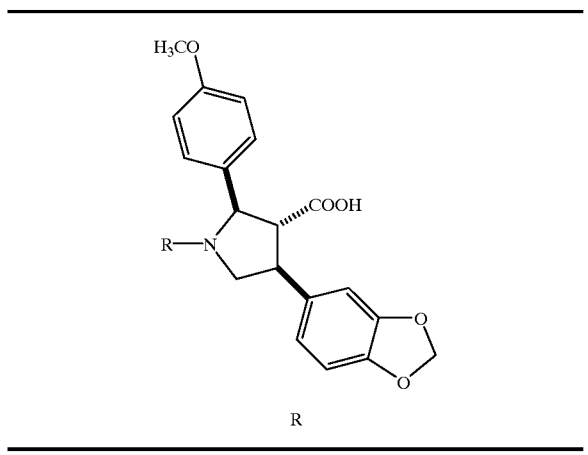
| R |
|---|
| 467. | 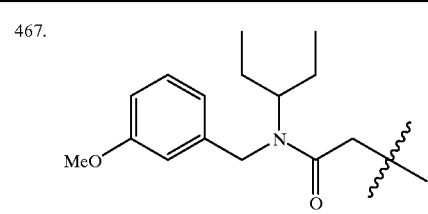 |
|---|---|
| 468. | 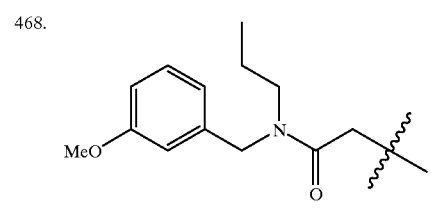 |
| 469. | 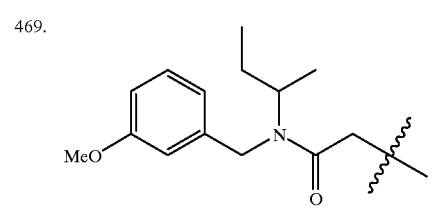 |
| 470. | 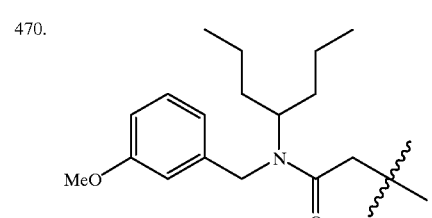 |
| 471. | 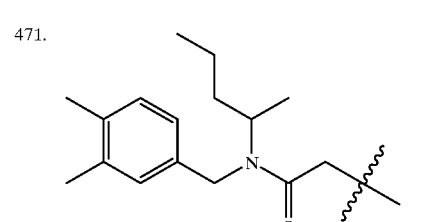 |

TABLE 1-continued
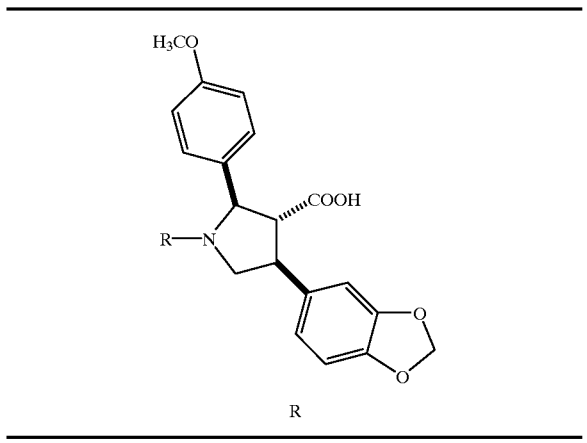
| | R |
|---|---|
| 477. | 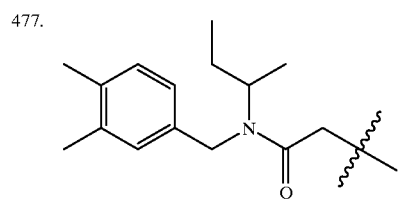 |
| 478. | 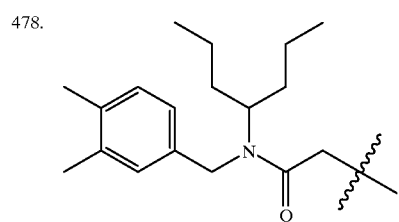 |
| 479. | 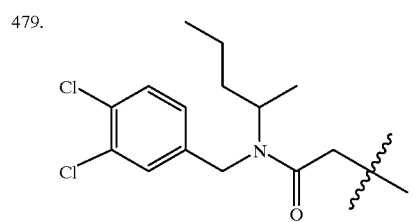 |
| 480. | 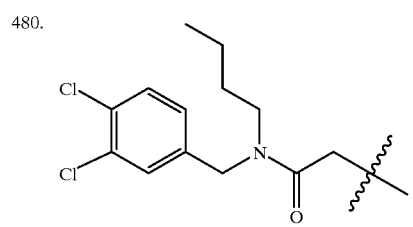 |
| 481. | 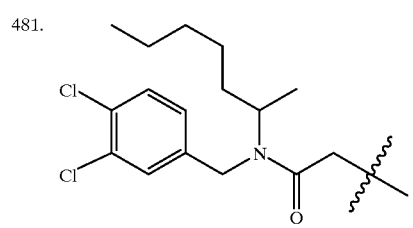 |
TABLE 1-continued
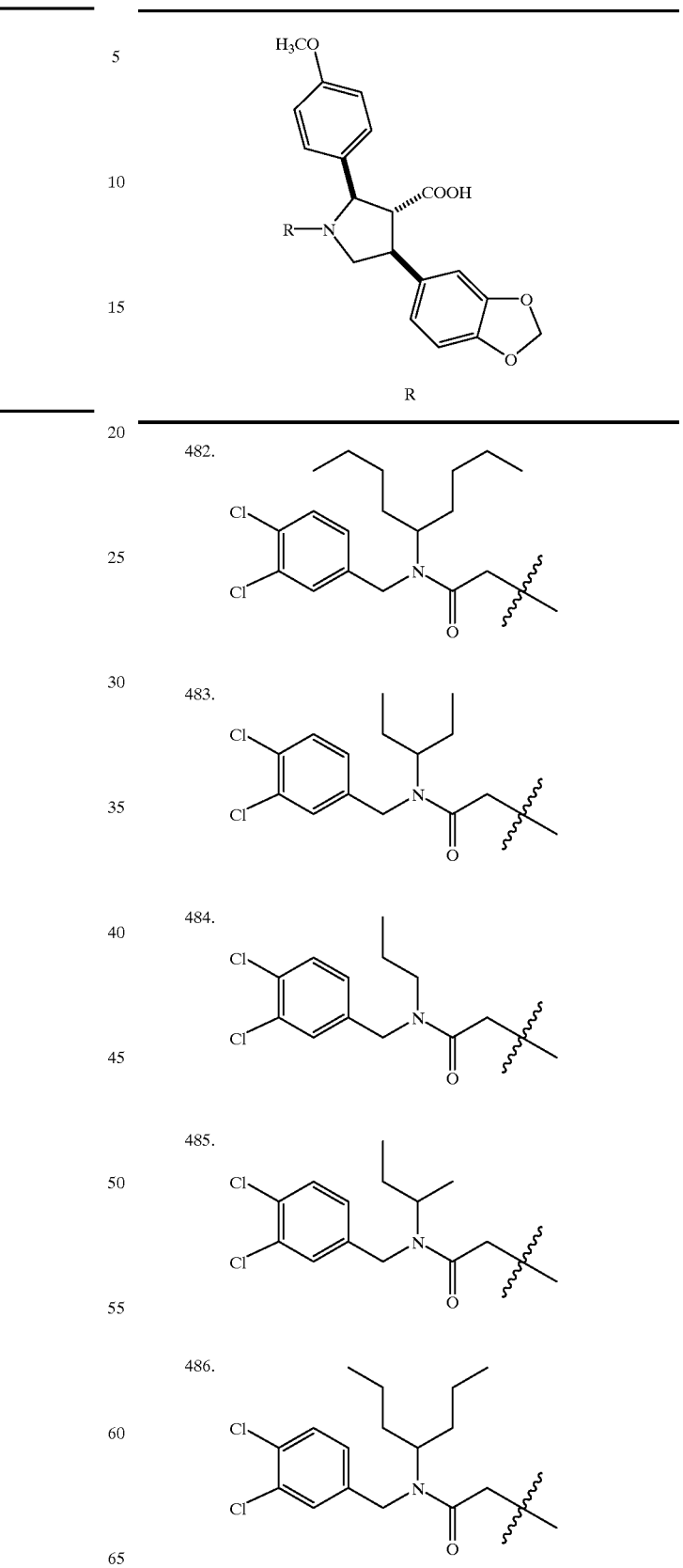

TABLE 1-continued
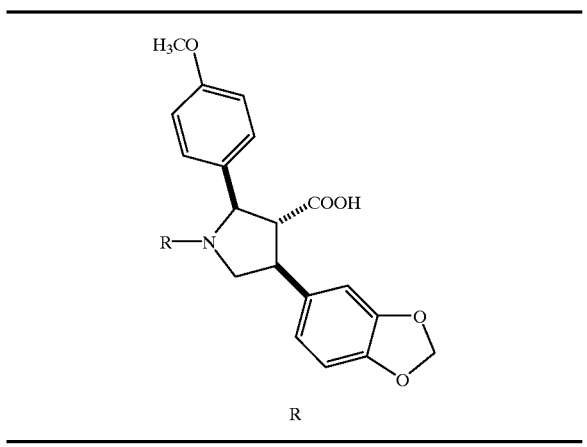
R
| | |
|---|---|
| 487. | 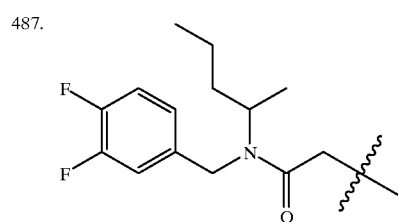 |
| 488. | 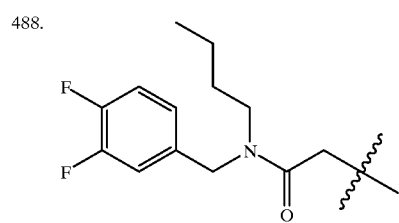 |
| 489. | 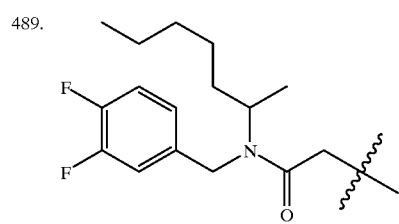 |
| 490. | 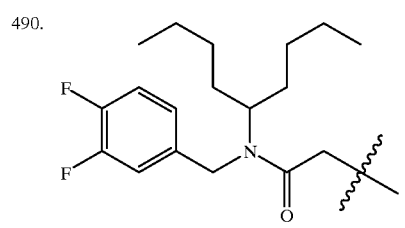 |
| 491. | 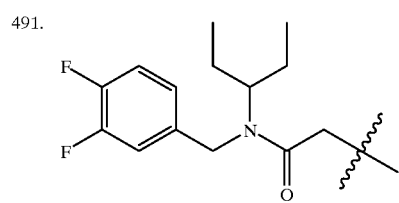 |
TABLE 1-continued
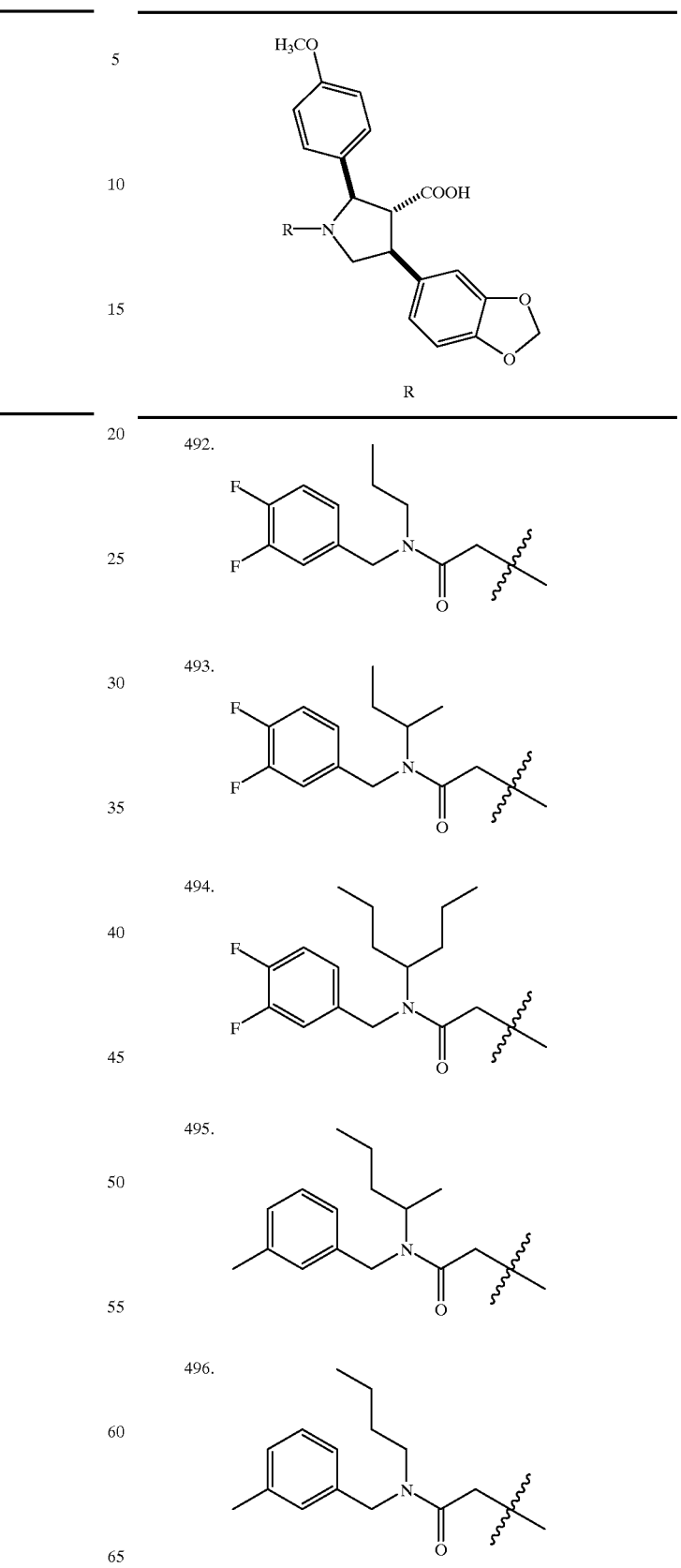

TABLE 1-continued
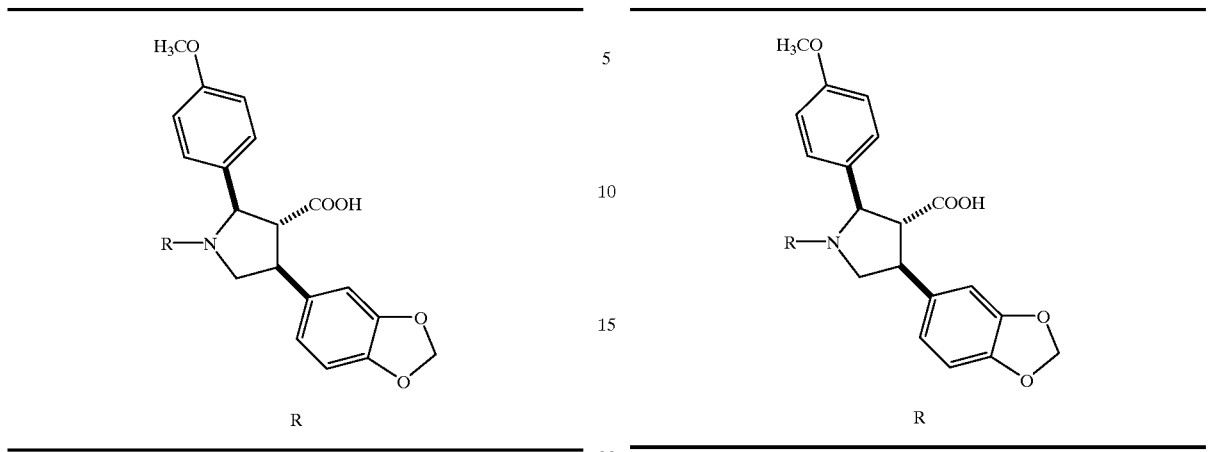

TABLE 1-continued

| No. | R |
|---|---|
| 507. | (structure) |
| 508. | (structure) |
| 509. | (structure) |
| 510. | (structure) |
| 511. | (structure) |
| 512. | (structure) |
| 513. | (structure) |
| 514. | (structure) |
| 515. | (structure) |
| 516. | (structure) |

TABLE 1-continued
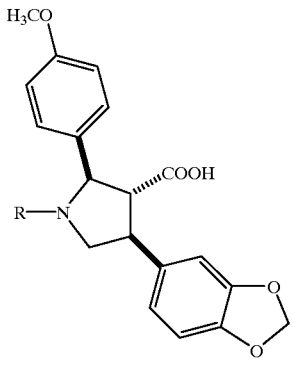
R
| 517. | 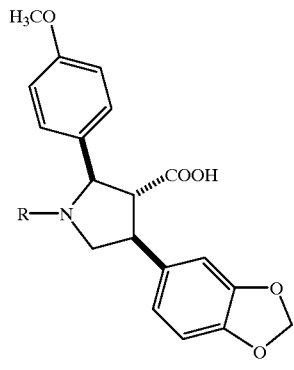 |
| 518. | 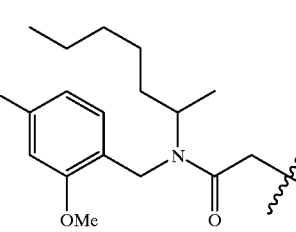 |
| 519. | 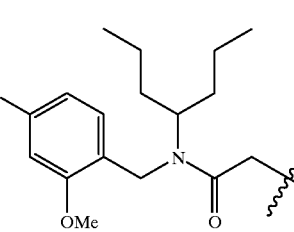 |
| 520. | 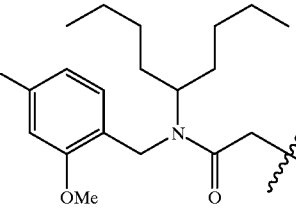 |
| 521. | 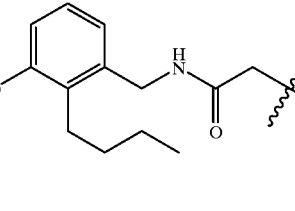 |
TABLE 1-continued
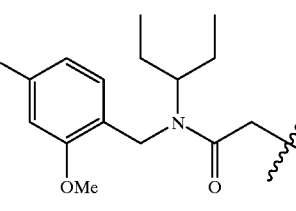
R
| 522. | 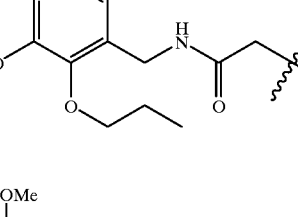 |
| 523. | 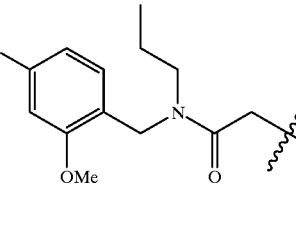 |
| 524. | 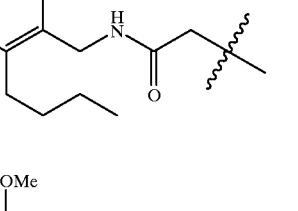 |
| 525. | 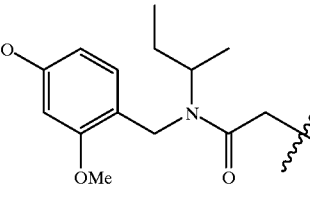 |
| 526. | 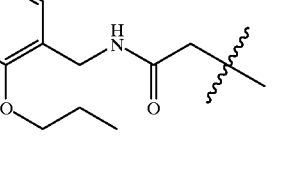 |

TABLE 1-continued
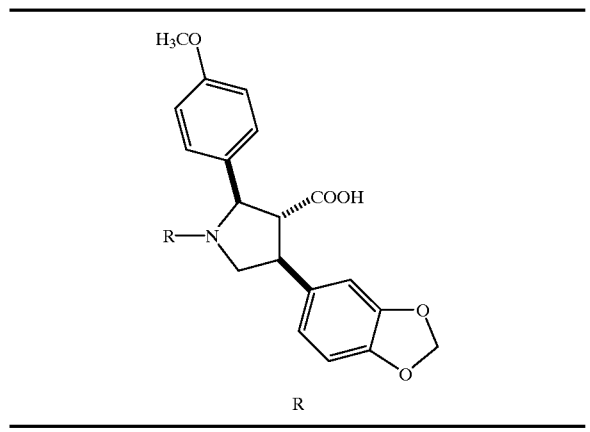
R
| 527. | 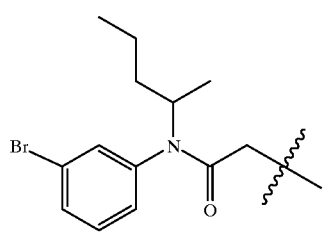 |
| --- | --- |
| 528. | 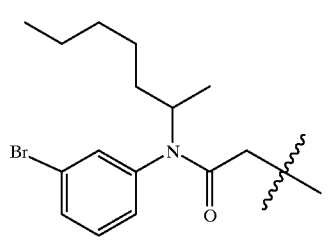 |
| 529. | 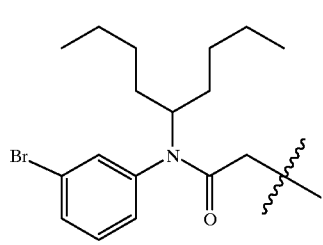 |
| 530. | 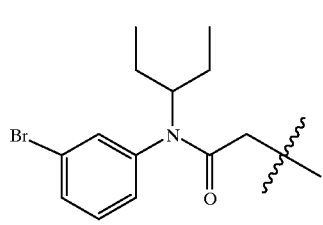 |
| 531. | 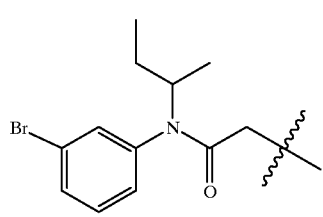 |
TABLE 1-continued
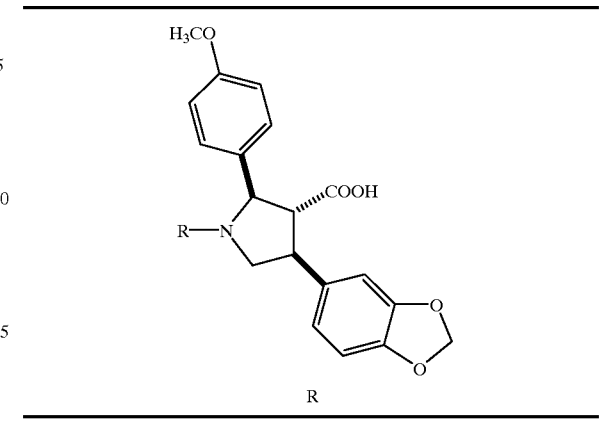
R
| 532. | 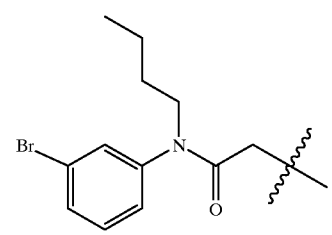 |
| --- | --- |
| 533. | 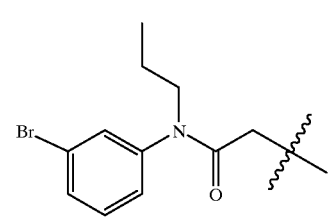 |
| 534. | 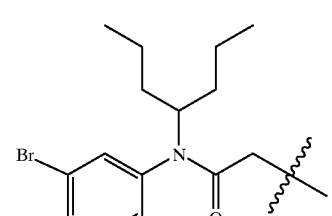 |
| 535. | 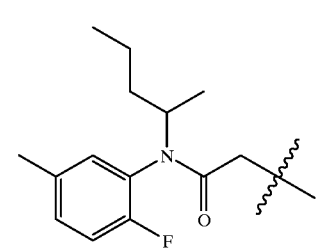 |
| 536. | 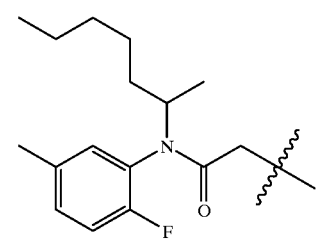 |

TABLE 1-continued
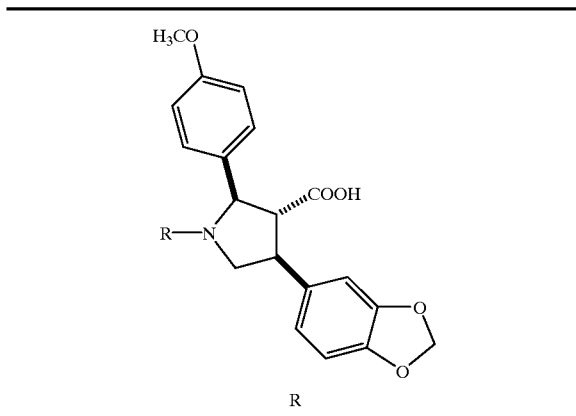
R
| 537. | 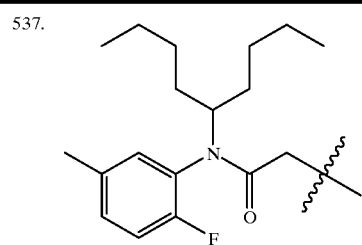 |
| --- | --- |
| 538. | 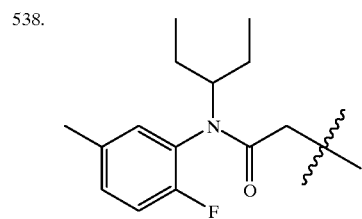 |
| 539. | 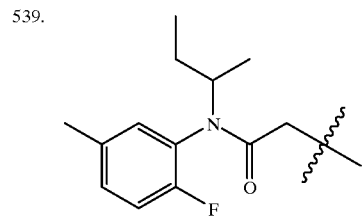 |
| 540. | 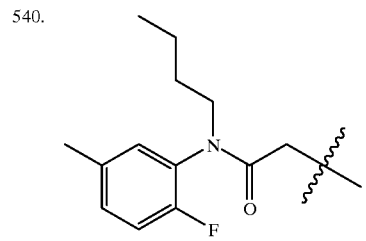 |
| 541. | 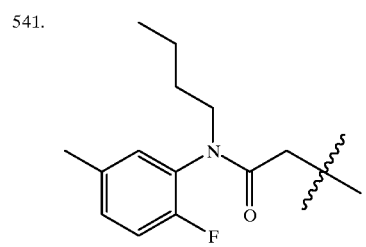 |
TABLE 1-continued
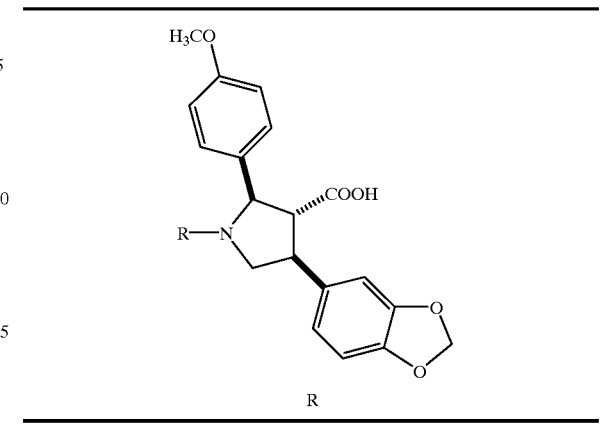
R
| 542. | 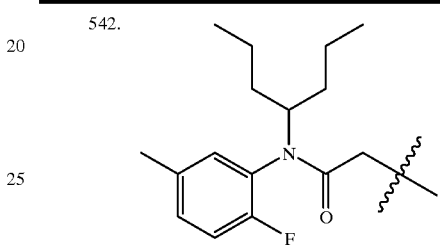 |
| --- | --- |
| 543. | 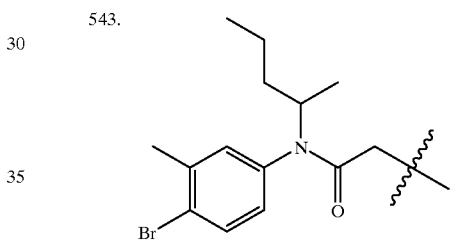 |
| 544. | 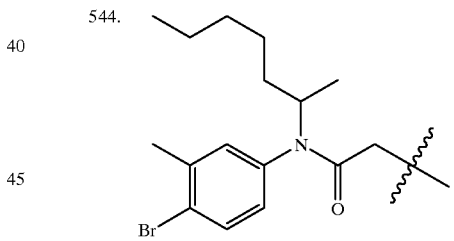 |
| 545. | 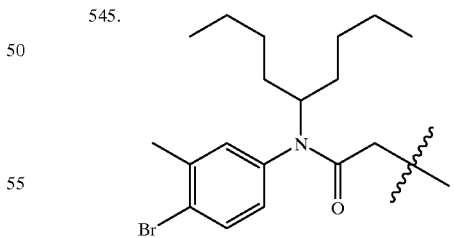 |
| 546. | 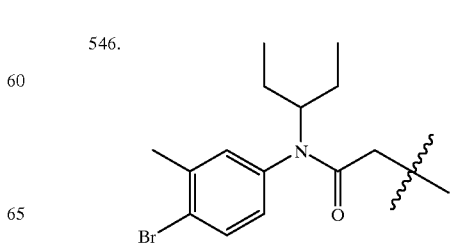 |

TABLE 1-continued
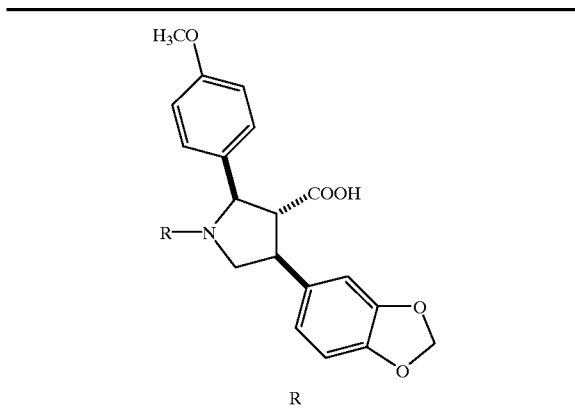
| | R |
|---|---|
| 547. | 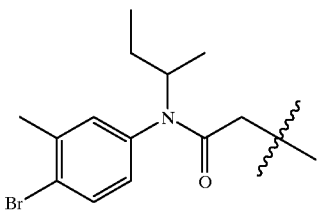 |
| 548. | 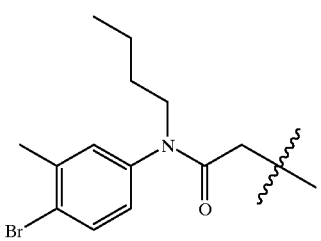 |
| 549. | 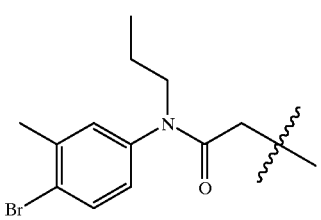 |
| 550. | 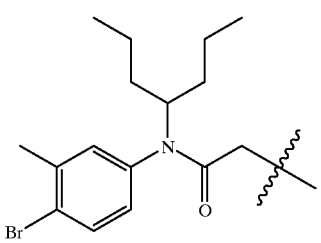 |
| 551. | 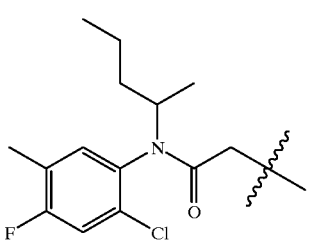 |
TABLE 1-continued
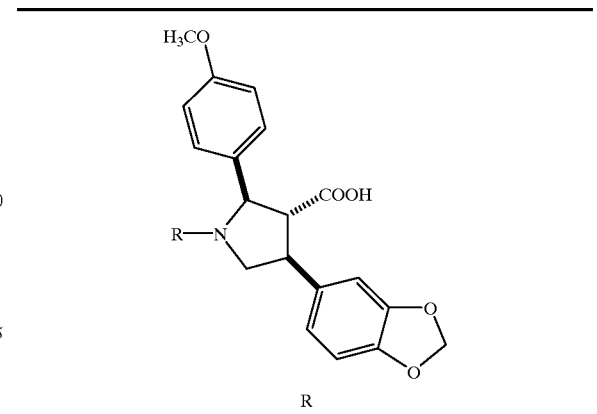
| | R |
|---|---|
| 552. | 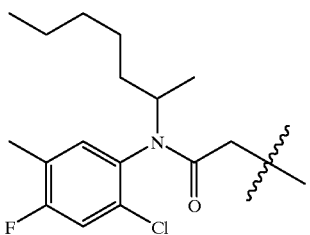 |
| 553. | |
| 554. | 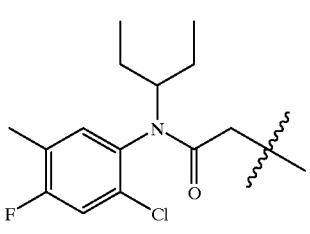 |
| 555. | 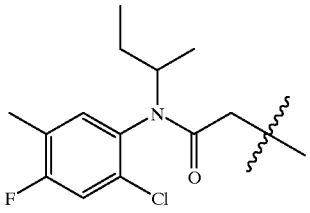 |
| 556. | 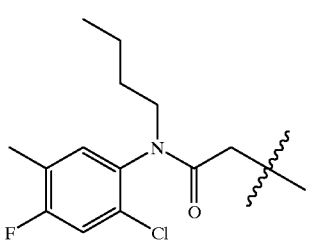 |

TABLE 1-continued
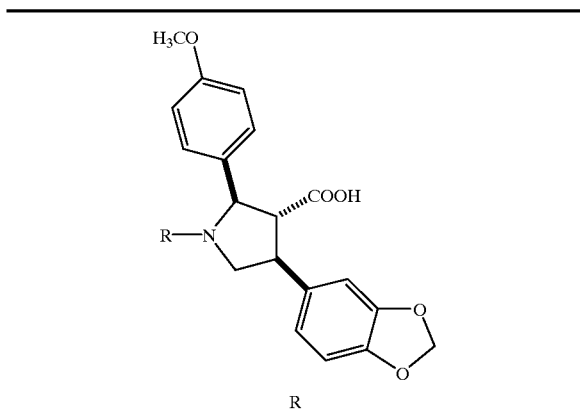
R
| | R |
|---|---|
| 557. | 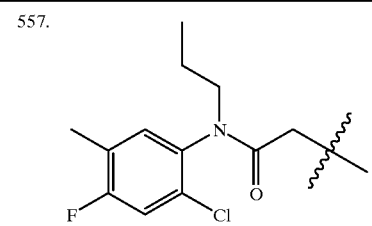 |
| 558. | 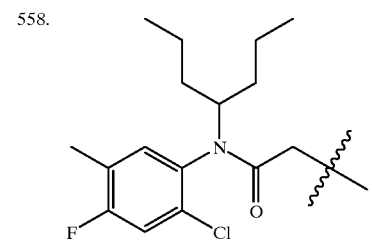 |
| 559. | 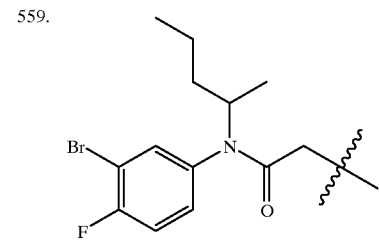 |
| 560. | 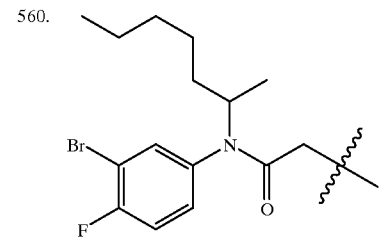 |
| 561. | 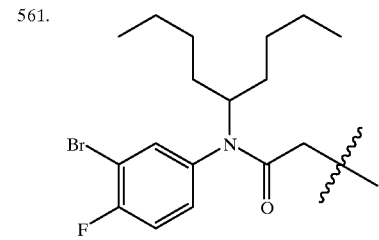 |
TABLE 1-continued
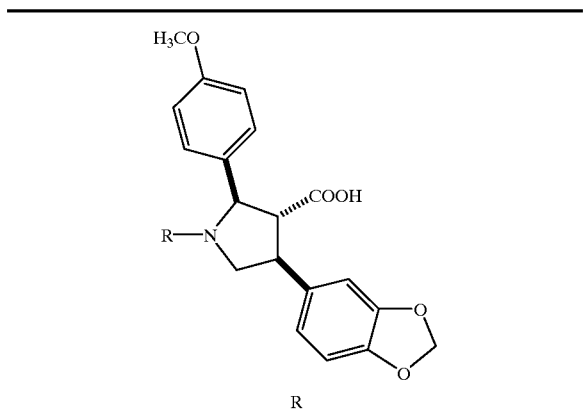
R
| | R |
|---|---|
| 562. | 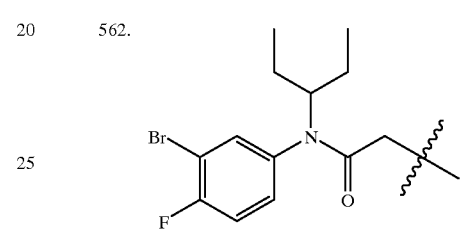 |
| 563. |  |
| 564. | 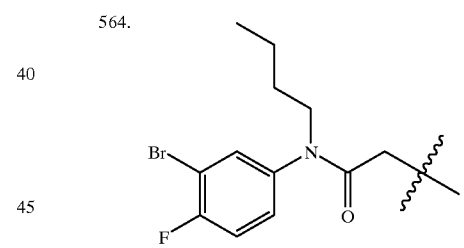 |
| 565. | 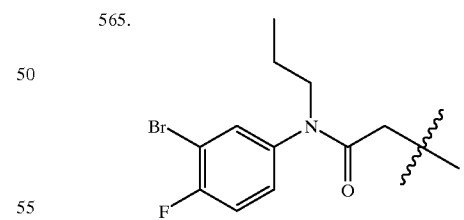 |
| 566. | 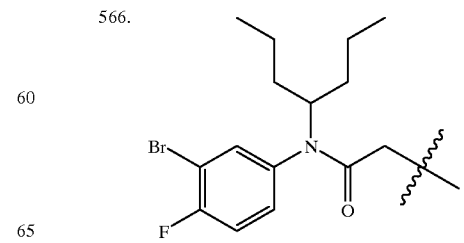 |

TABLE 1-continued
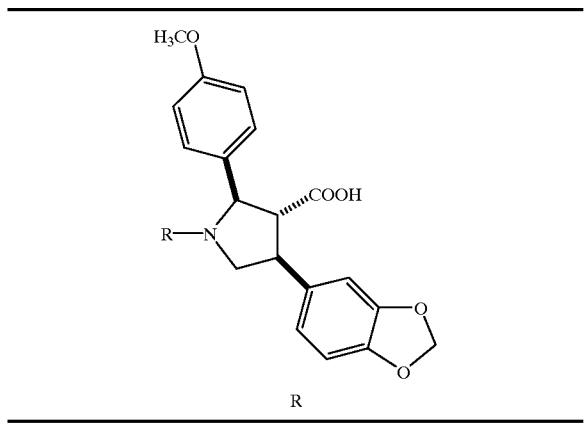
R
| | |
|---|---|
| 567. | 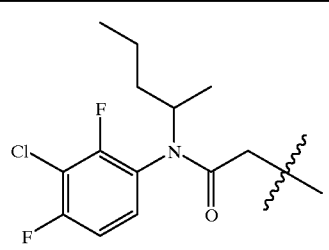 |
| 568. | 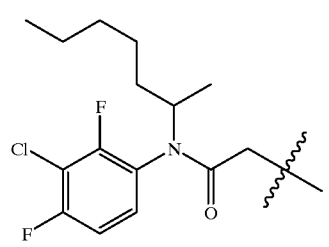 |
| 569. | 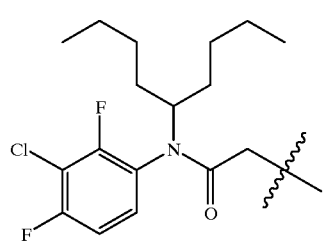 |
| 570. | 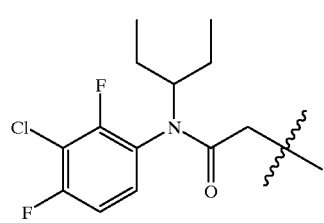 |
| 571. | 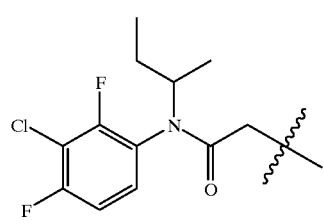 |
TABLE 1-continued
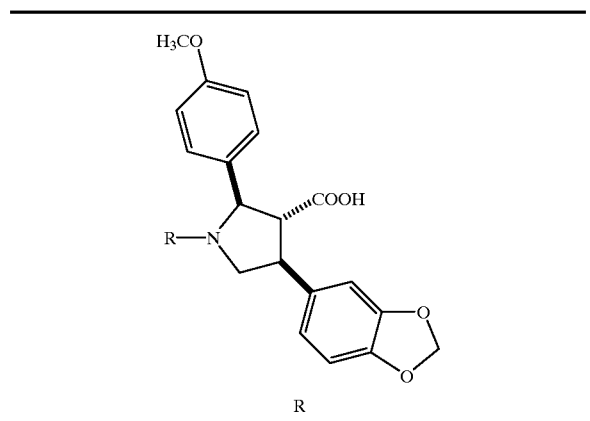
R
| | |
|---|---|
| 572. | 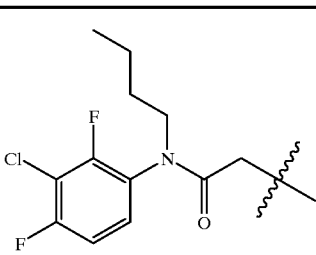 |
| 573. | 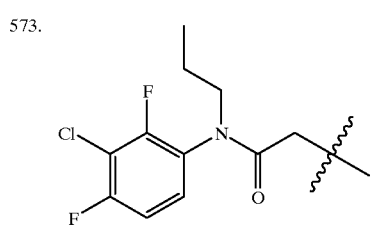 |
| 574. | 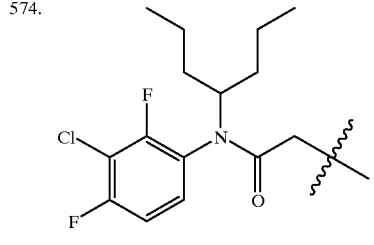 |
| 575. | 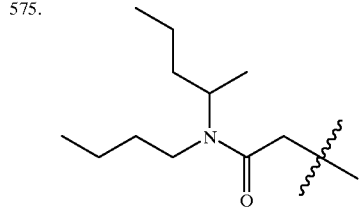 |
| 576. | 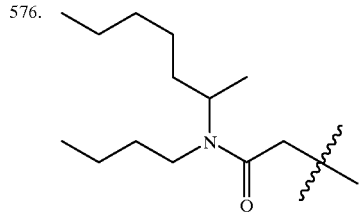 |

TABLE 1-continued
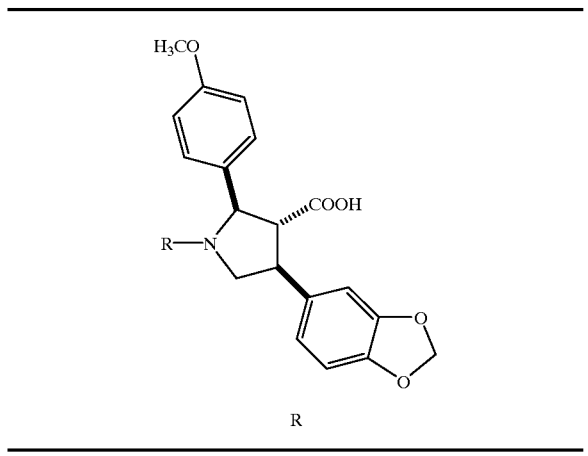
R
| | |
|---|---|
| 577. | 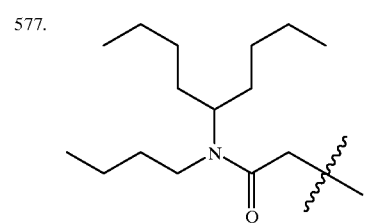 |
| 578. | 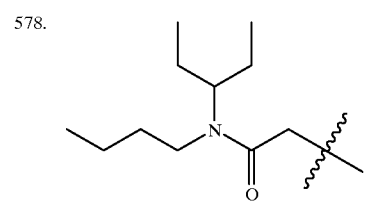 |
| 579. | 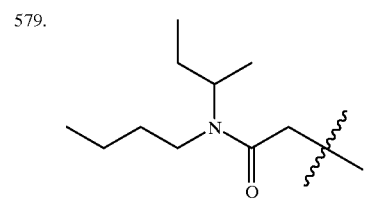 |
| 580. | 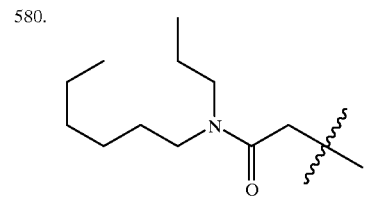 |
| 581. | 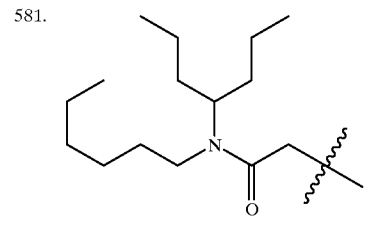 |
TABLE 1-continued
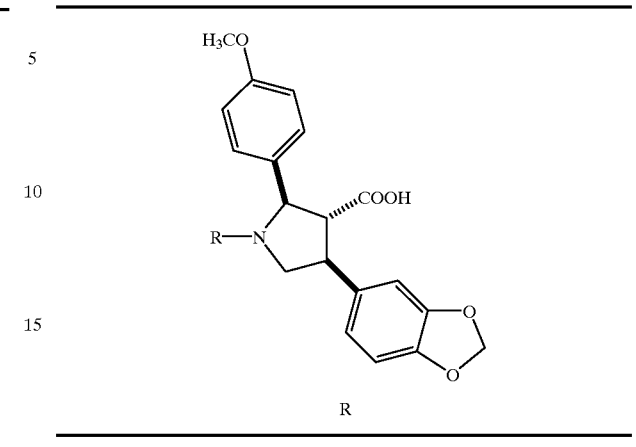
R
| | |
|---|---|
| 582. | 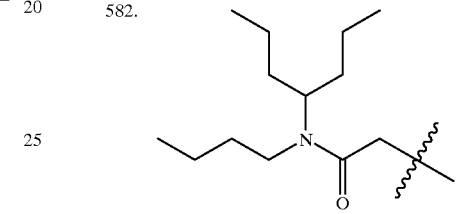 |
| 583. |  |
| 584. | 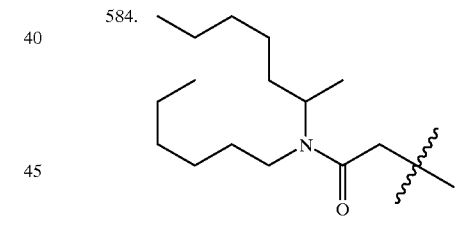 |
| 585. | 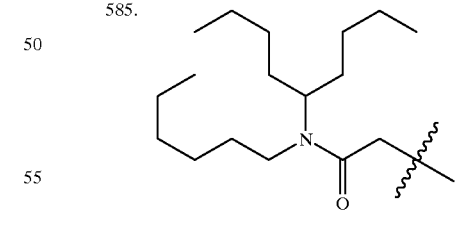 |
| 586. | 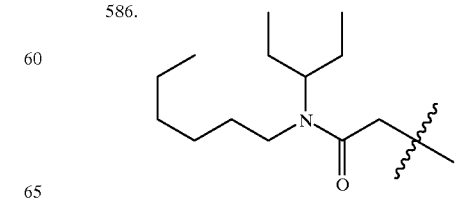 |

TABLE 1-continued
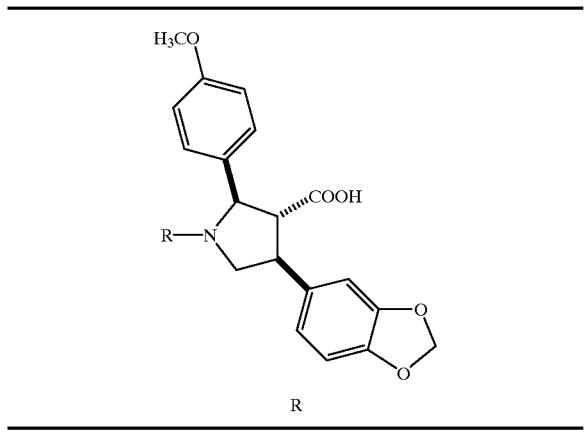
R
| | |
|---|---|
| 587. | 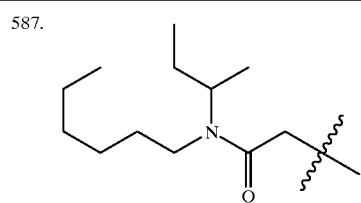 |
| 588. | 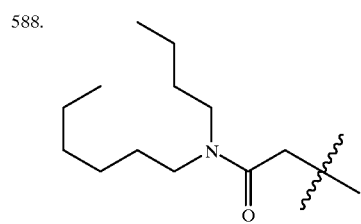 |
| 589. | 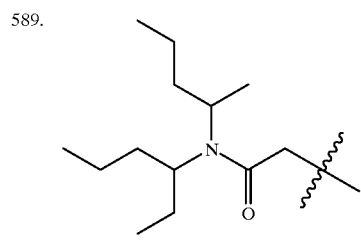 |
| 590. | 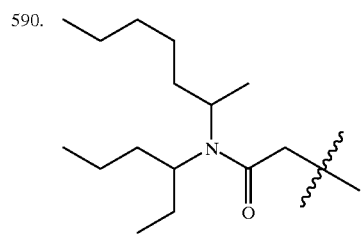 |
| 591. | 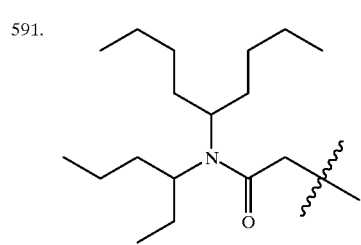 |
TABLE 1-continued
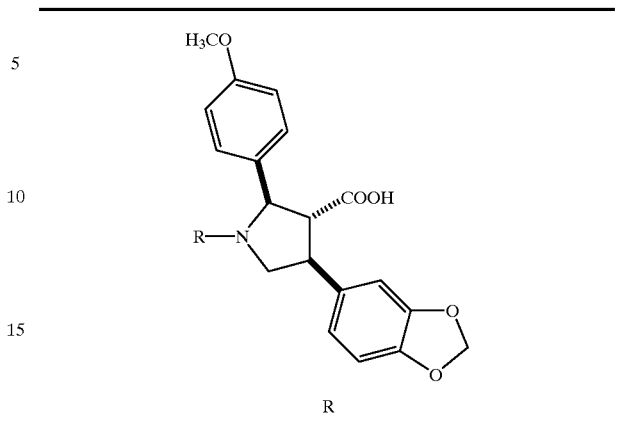
R
| | |
|---|---|
| 592. | 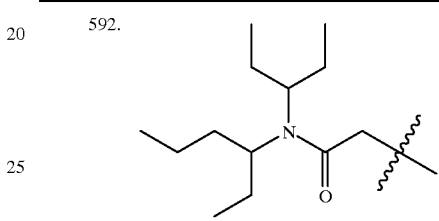 |
| 593. | 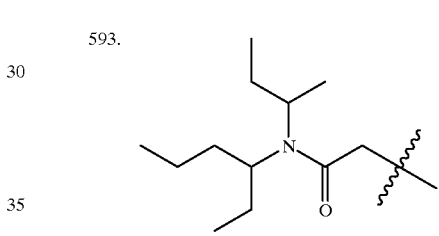 |
| 594. | 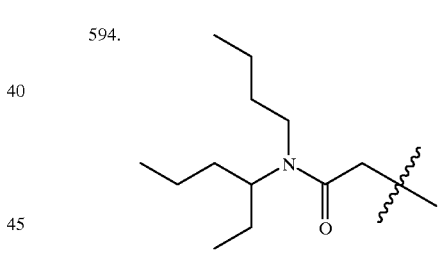 |
| 595. | 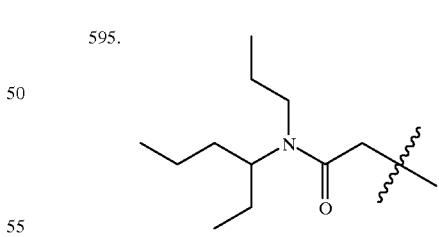 |
| 596. | 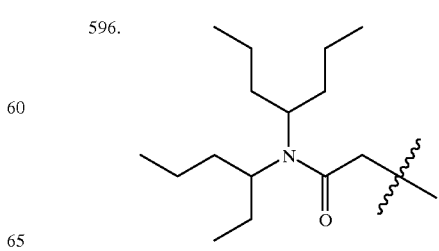 |

TABLE 1-continued
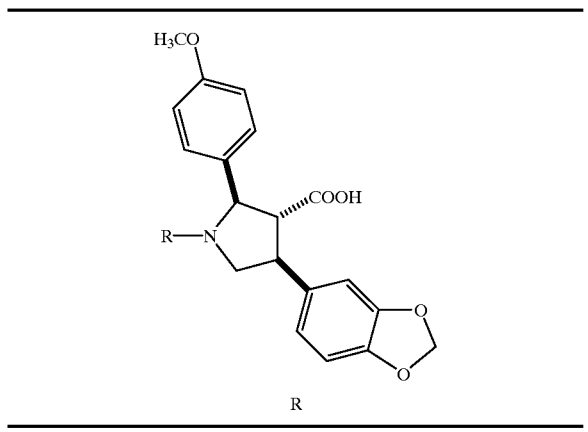
R
| 597. | 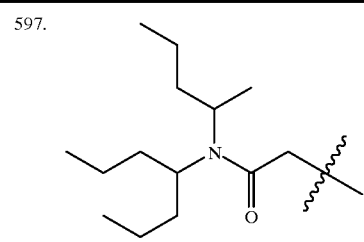 |
| --- | --- |
| 598. | 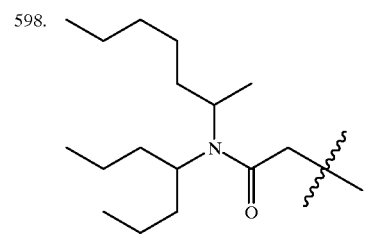 |
| 599. | 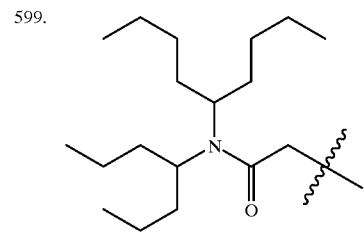 |
| 600. | 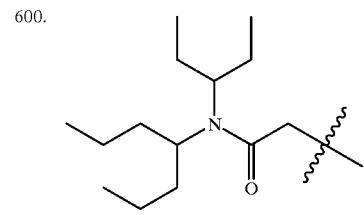 |
| 601. | 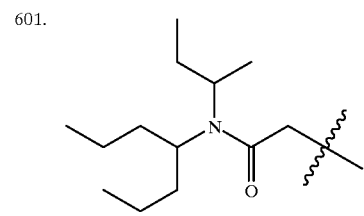 |
TABLE 1-continued
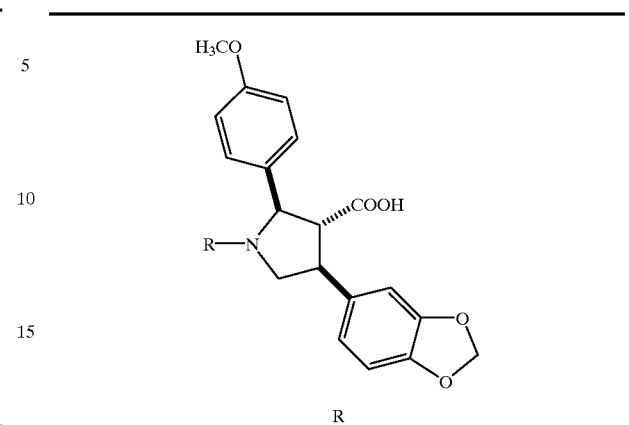
R
| 602. | 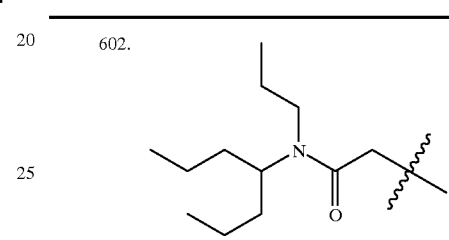 |
| --- | --- |
| 603. | 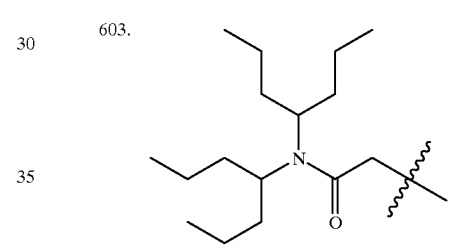 |
| 604. | 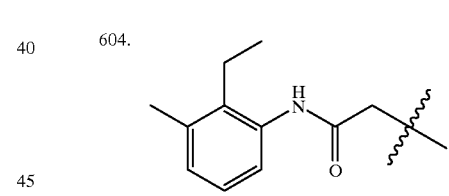 |
| 605. | 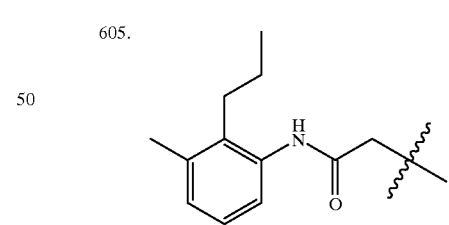 |
| 606. | 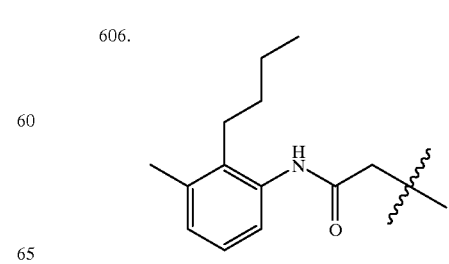 |

TABLE 1-continued
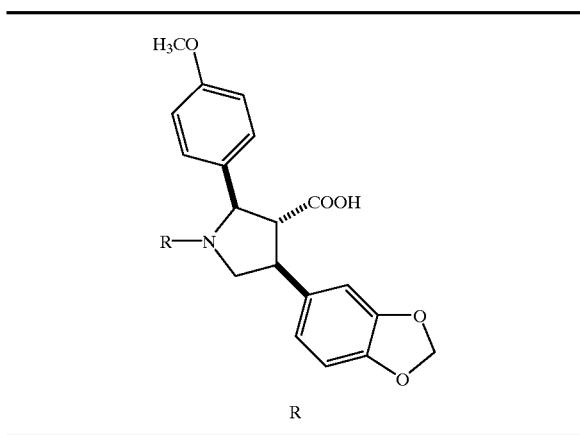
R
| | |
|---|---|
| 607. | 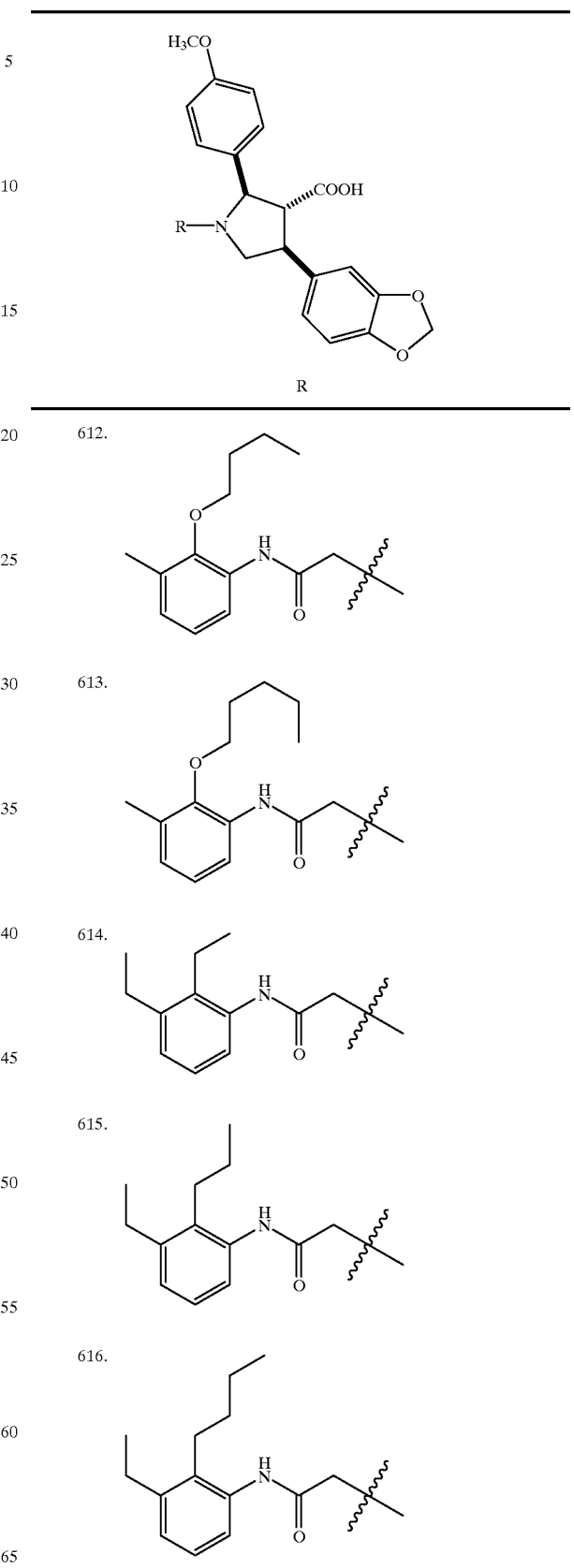 |
| 608. | |
| 609. | |
| 610. | |
| 611. | |
| 612. | |
| 613. | |
| 614. | |
| 615. | |
| 616. | |

TABLE 1-continued
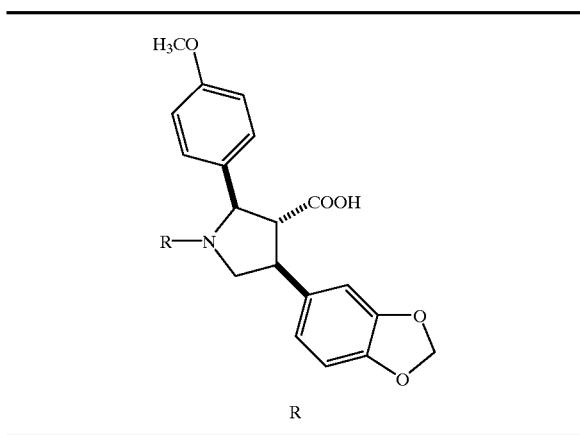
R
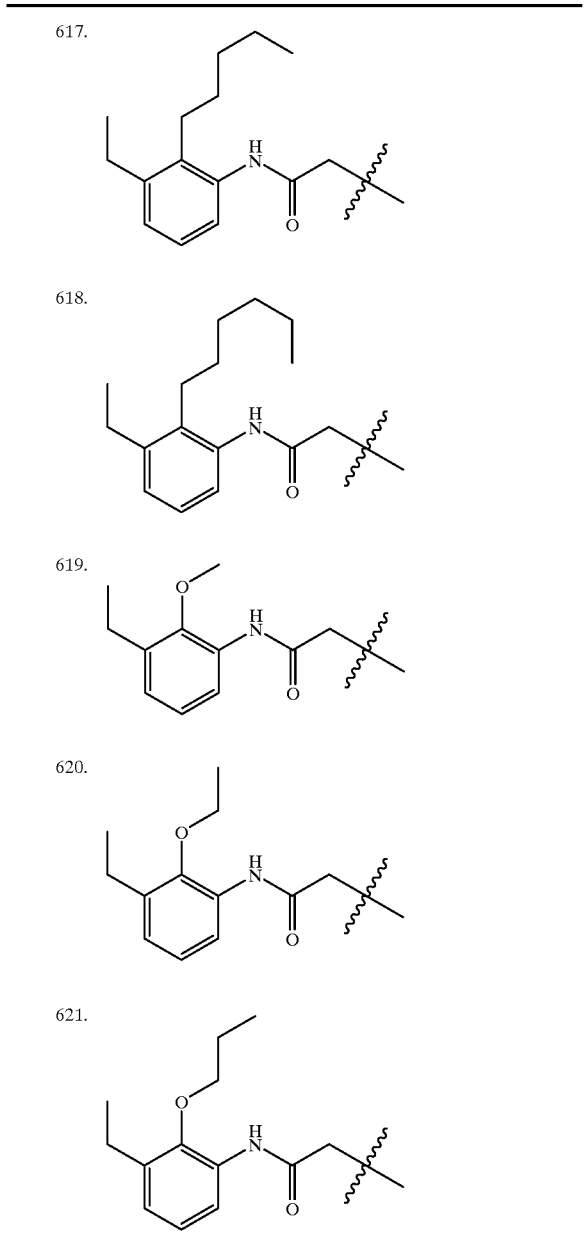
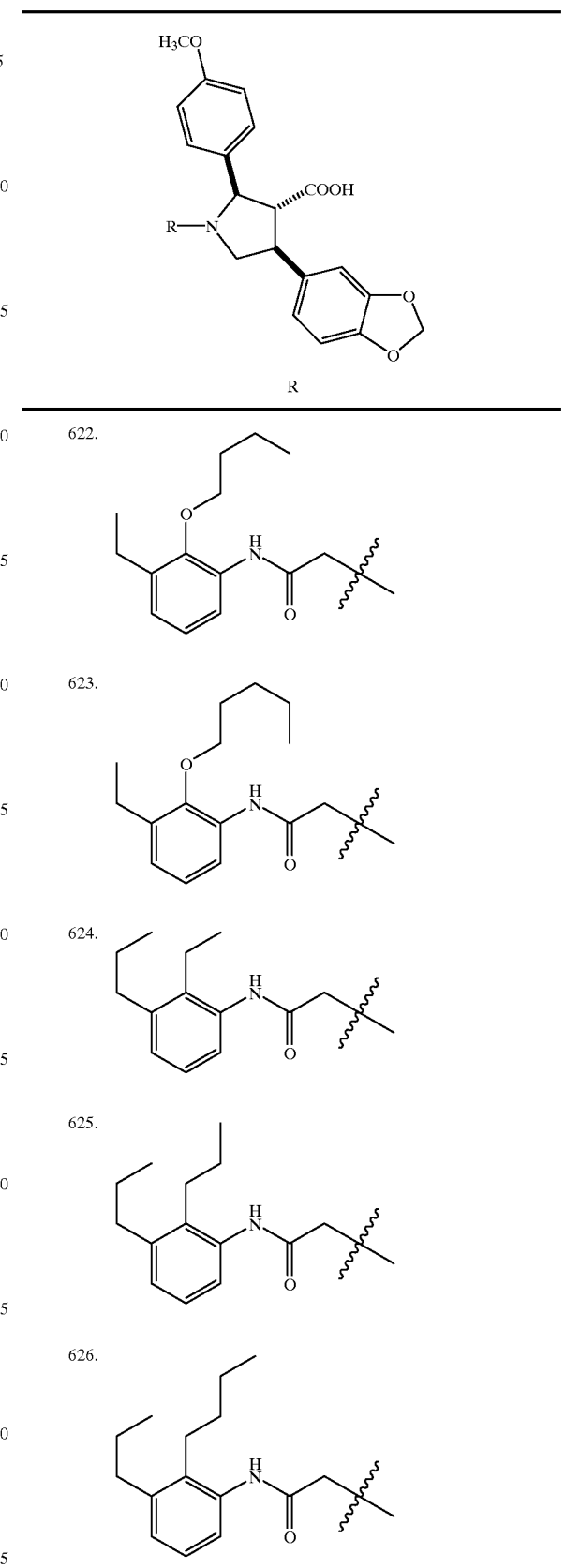

TABLE 1-continued
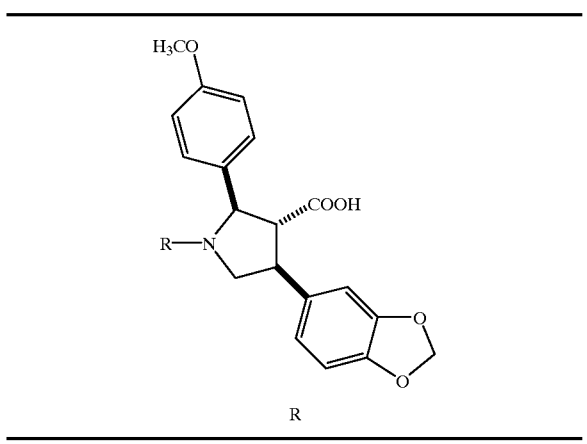
R
| | |
|---|---|
| 627. | 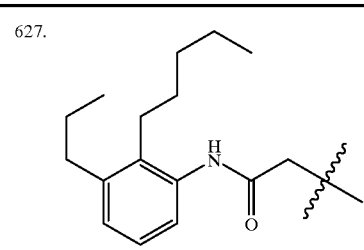 |
| 628. | 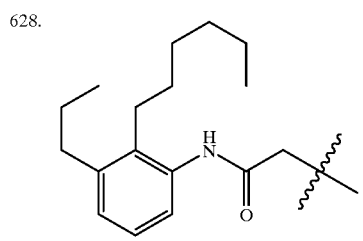 |
| 629. | 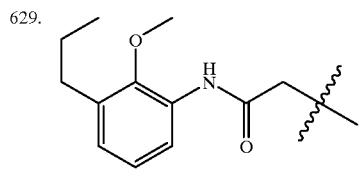 |
| 630. | 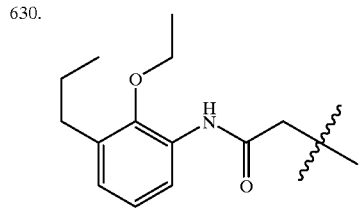 |
| 631. | 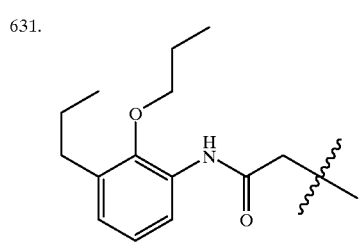 |
TABLE 1-continued
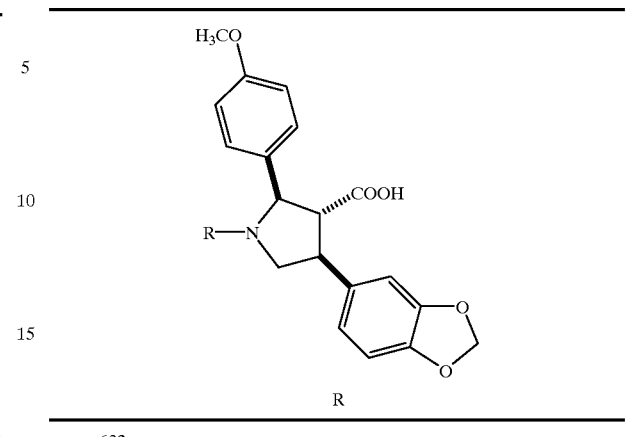
R
| | |
|---|---|
| 632. | 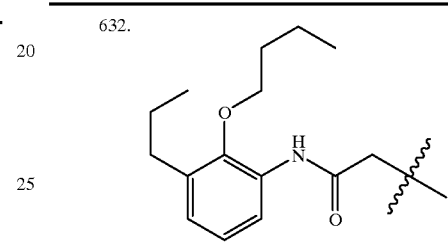 |
| 633. |  |
| 634. | 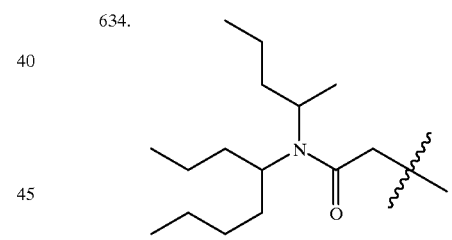 |
| 635. |  |
| 636. | 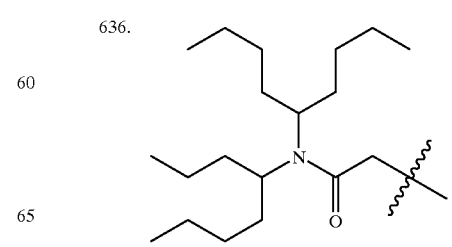 |

TABLE 1-continued
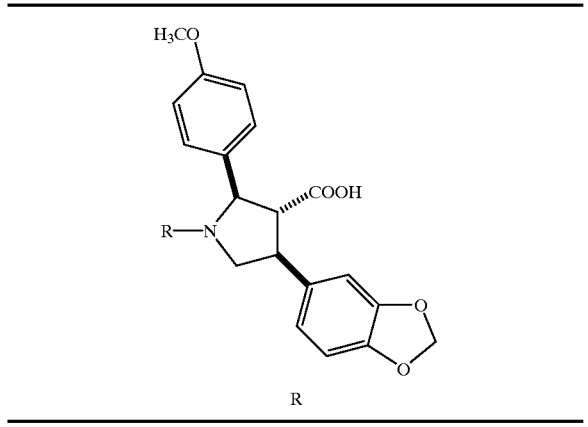
| | R |
|---|---|
| 637. | 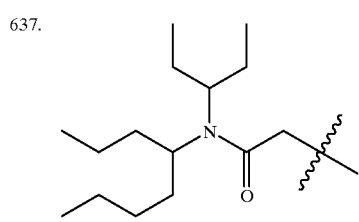 |
| 638. | 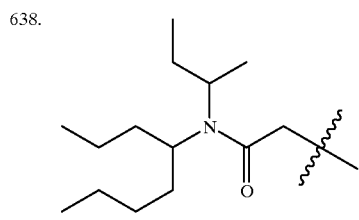 |
| 639. | 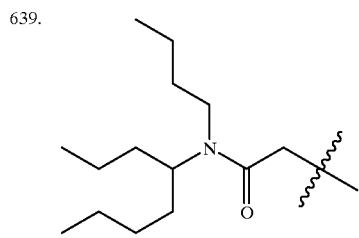 |
| 640. | 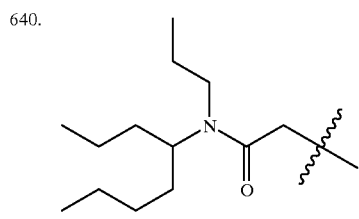 |
| 641. | 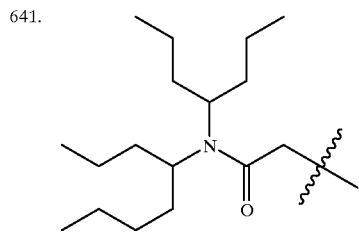 |
TABLE 1-continued
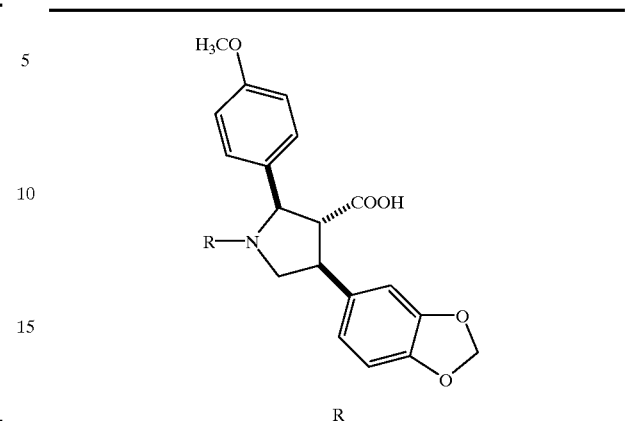
| | R |
|---|---|
| 642. | 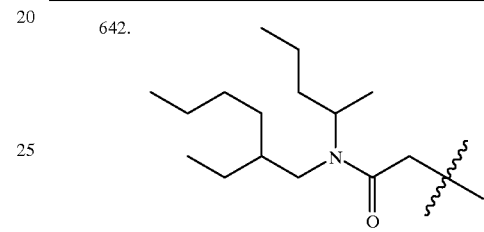 |
| 643. |  |
| 644. | 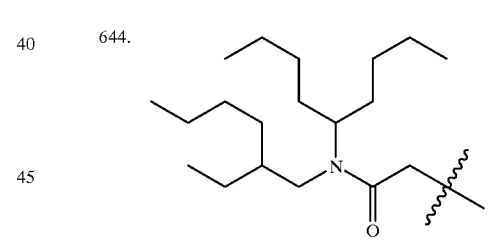 |
| 645. | 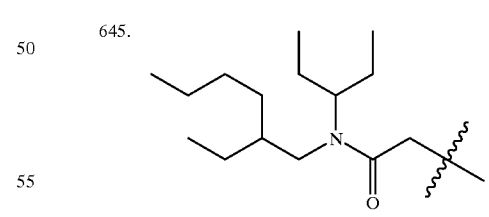 |
| 646. | 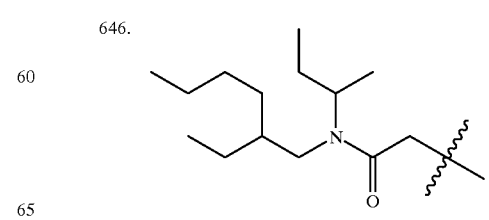 |

TABLE 1-continued
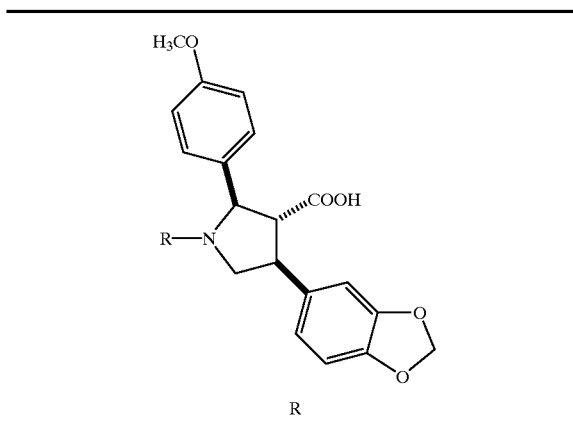
| | R |
|---|---|
| 647. | 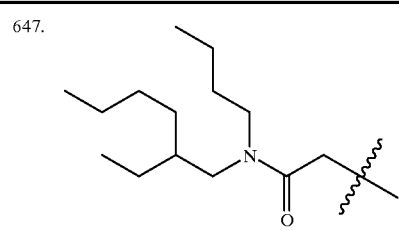 |
| 648. | 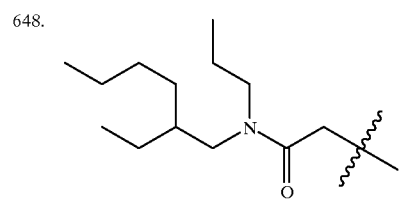 |
| 649. | 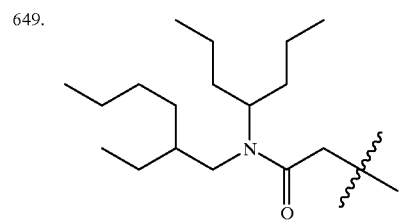 |
| 650. | 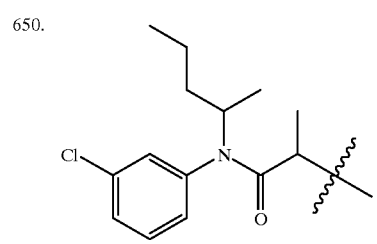 |
| 651. | 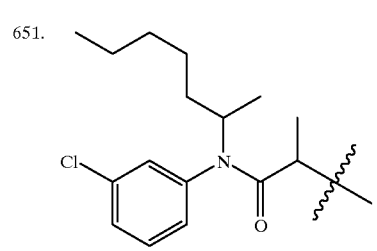 |
TABLE 1-continued
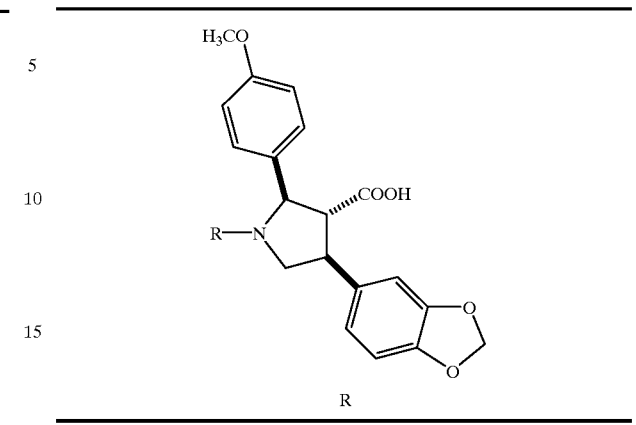
| | R |
|---|---|
| 652. | 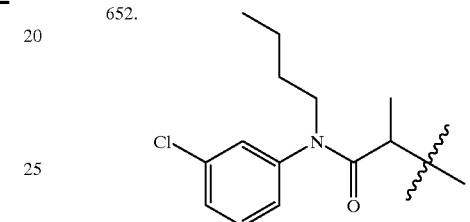 |
| 653. | 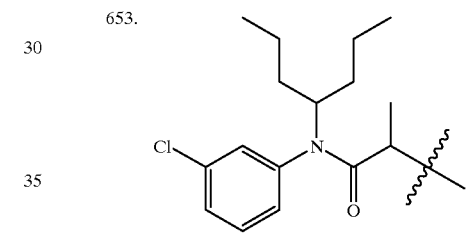 |
| 654. | 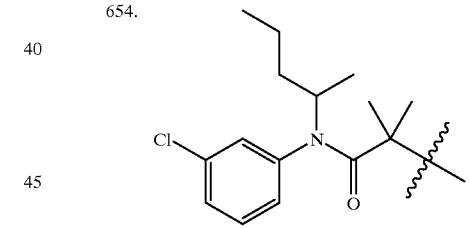 |
| 655. | 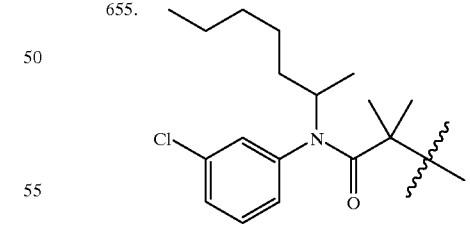 |
| 656. | 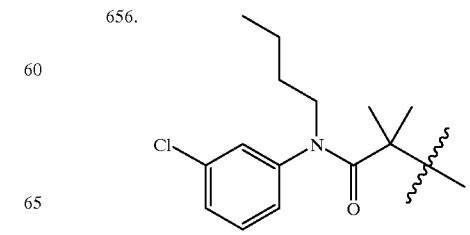 |

TABLE 1-continued
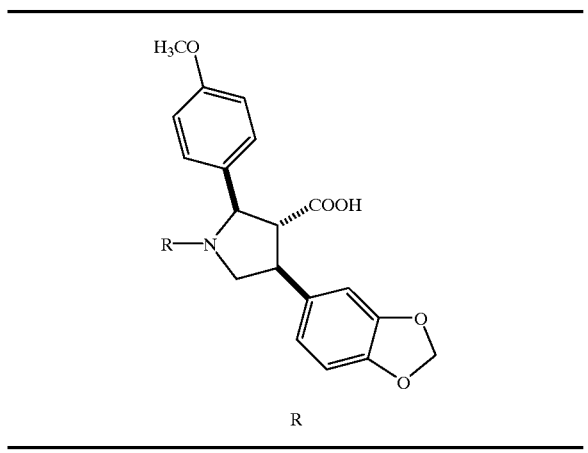
R
657. 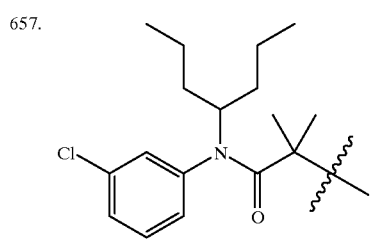
658. 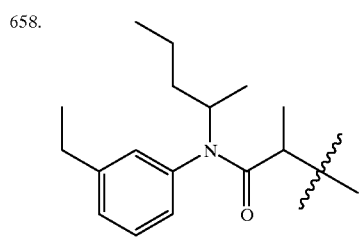
659. 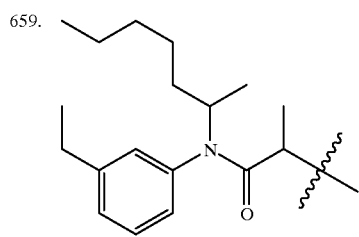
660. 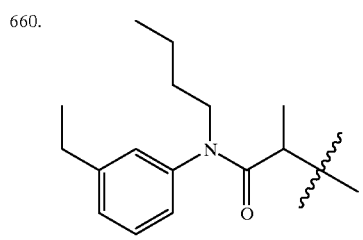
TABLE 1-continued
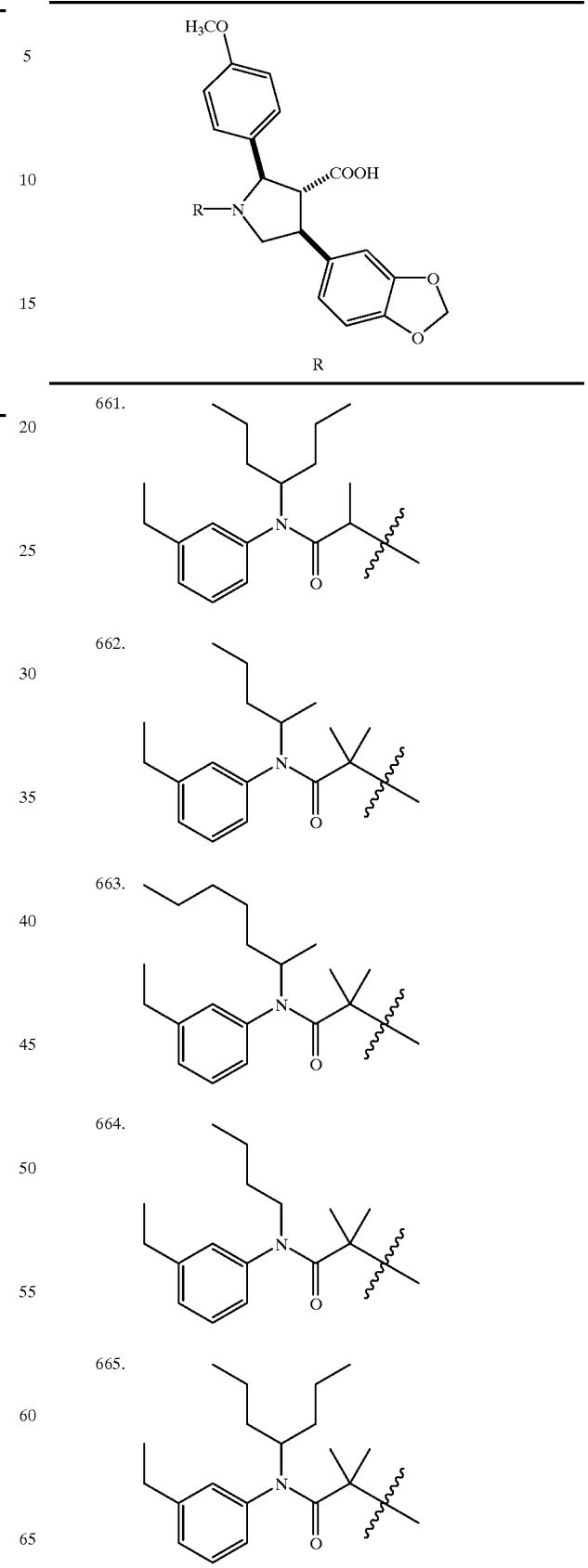

TABLE 1-continued
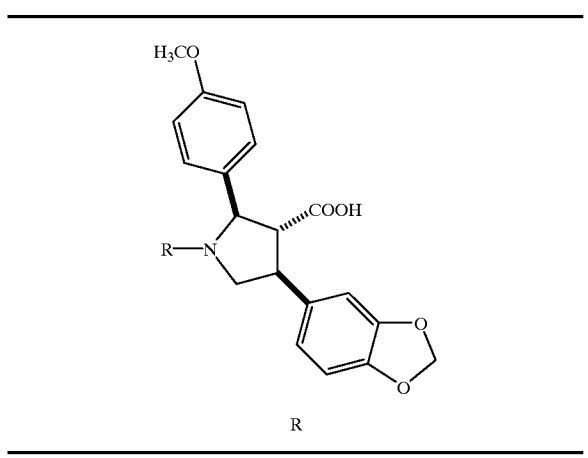
R
| 666. | 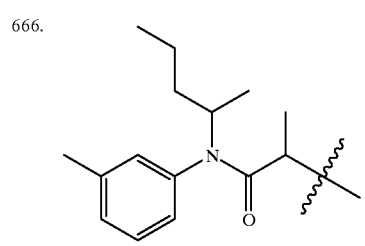 |
| --- | --- |
| 667. | 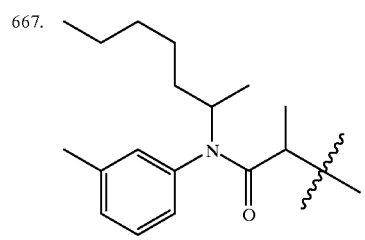 |
| 668. | 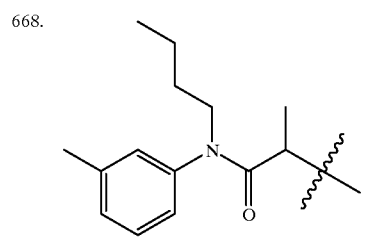 |
| 669. | 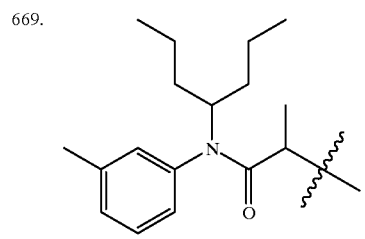 |
TABLE 1-continued
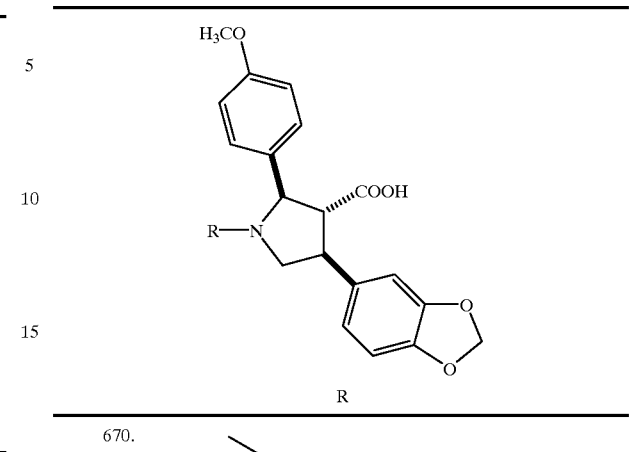
R
| 670. | 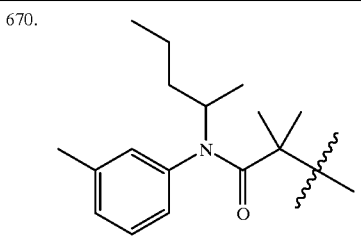 |
| --- | --- |
| 671. | 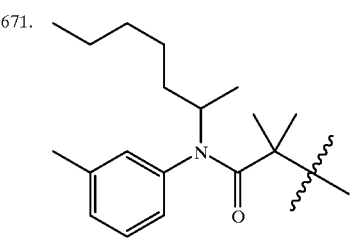 |
| 672. | 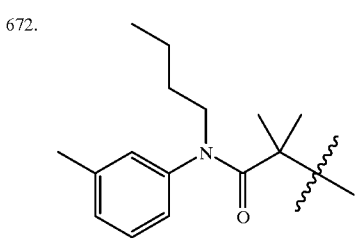 |
| 673. | 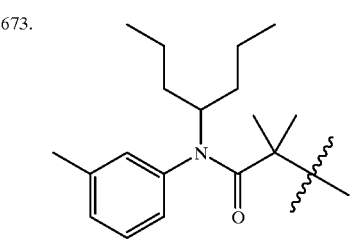 |
| 674. | |

TABLE 1-continued
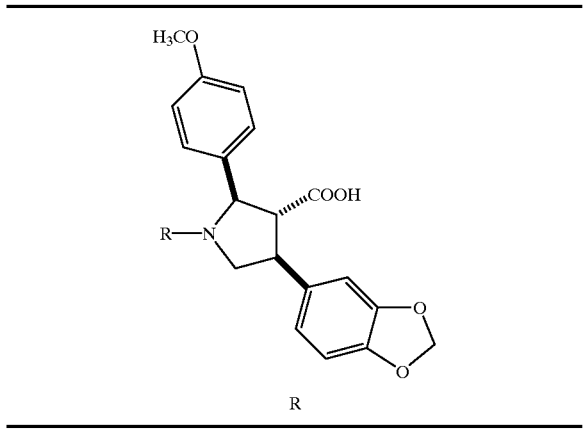
R
675. 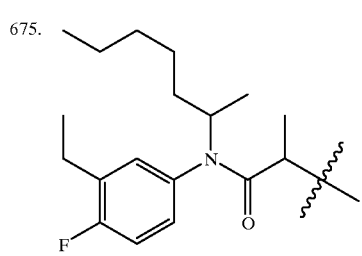
676. 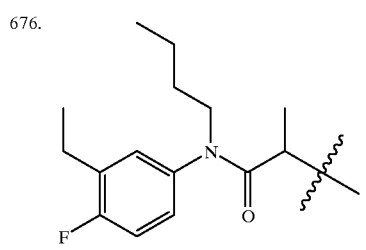
677. 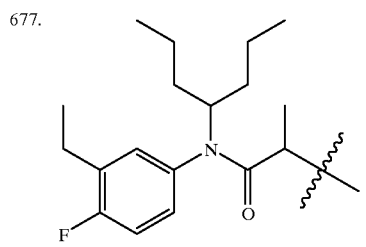
678. 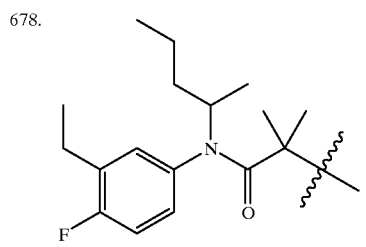
TABLE 1-continued
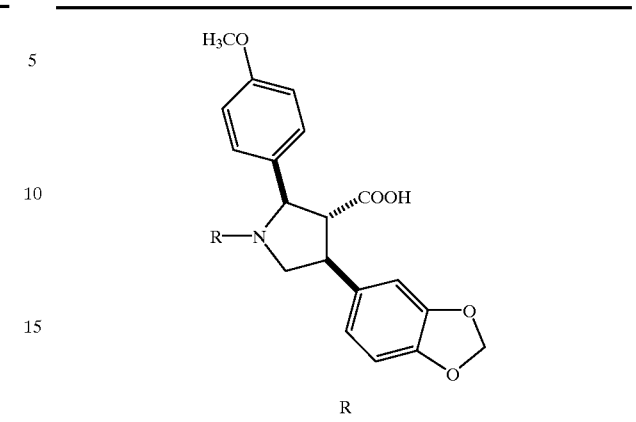
R
679. 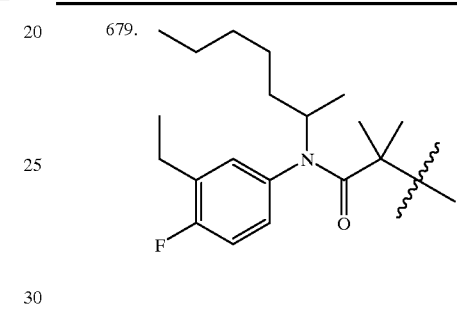
680. 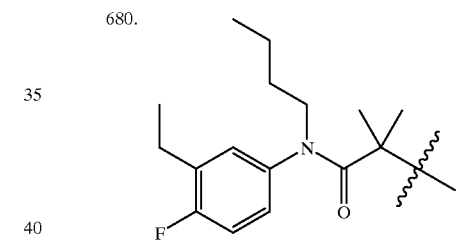
681. 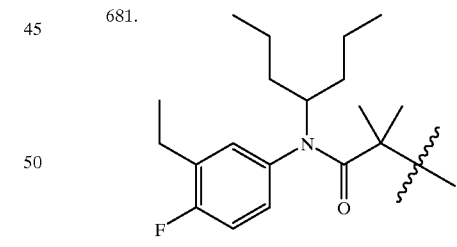
682. 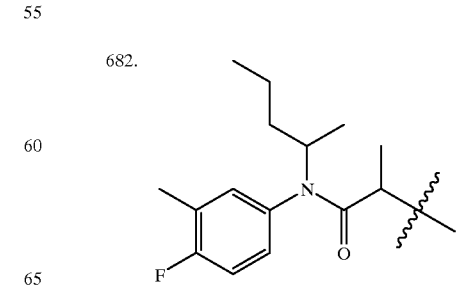

TABLE 1-continued
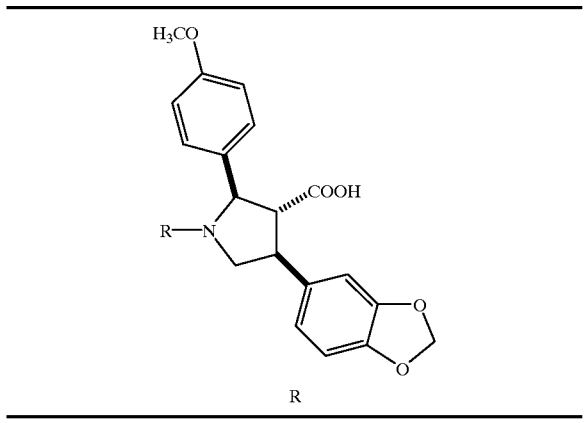
| R |
|---|
| 683. 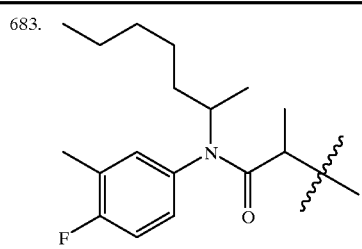 |
| 684. 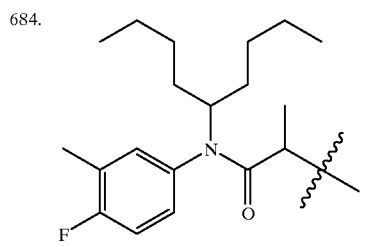 |
| 685. 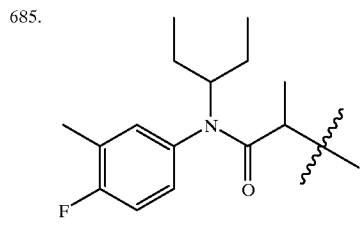 |
| 686. 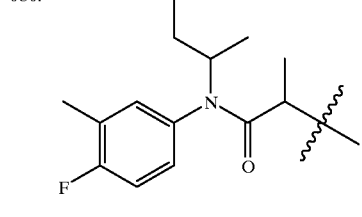 |
| 687. |
TABLE 1-continued
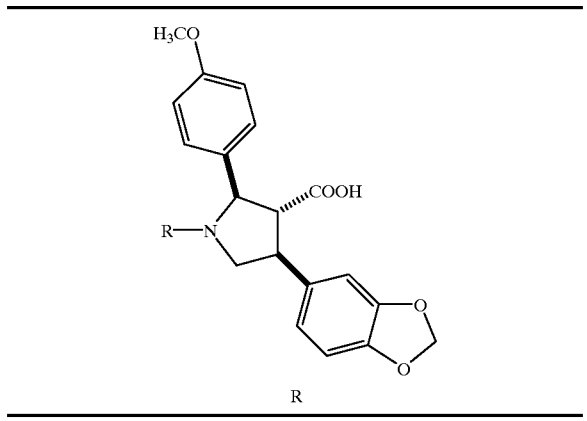
| R |
|---|
| 688.  |
| 689. 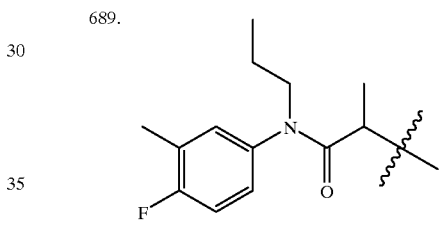 |
| 690. 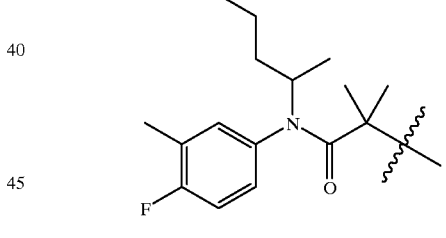 |
| 691. 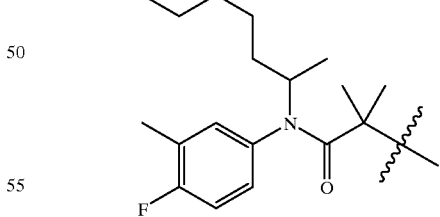 |
| 692. |

TABLE 1-continued
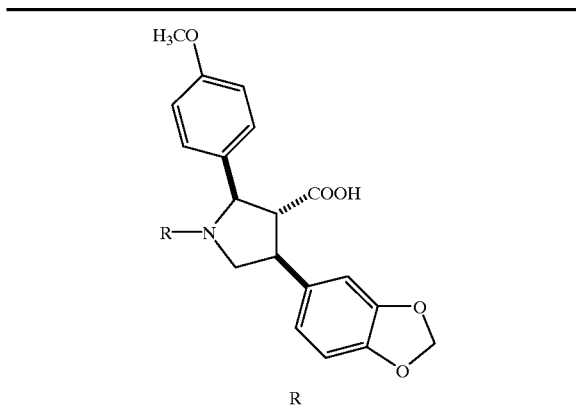
| R |
|---|
| 693. |
| 694. |
| 695. |
| 696. |
| 697. |
TABLE 1-continued
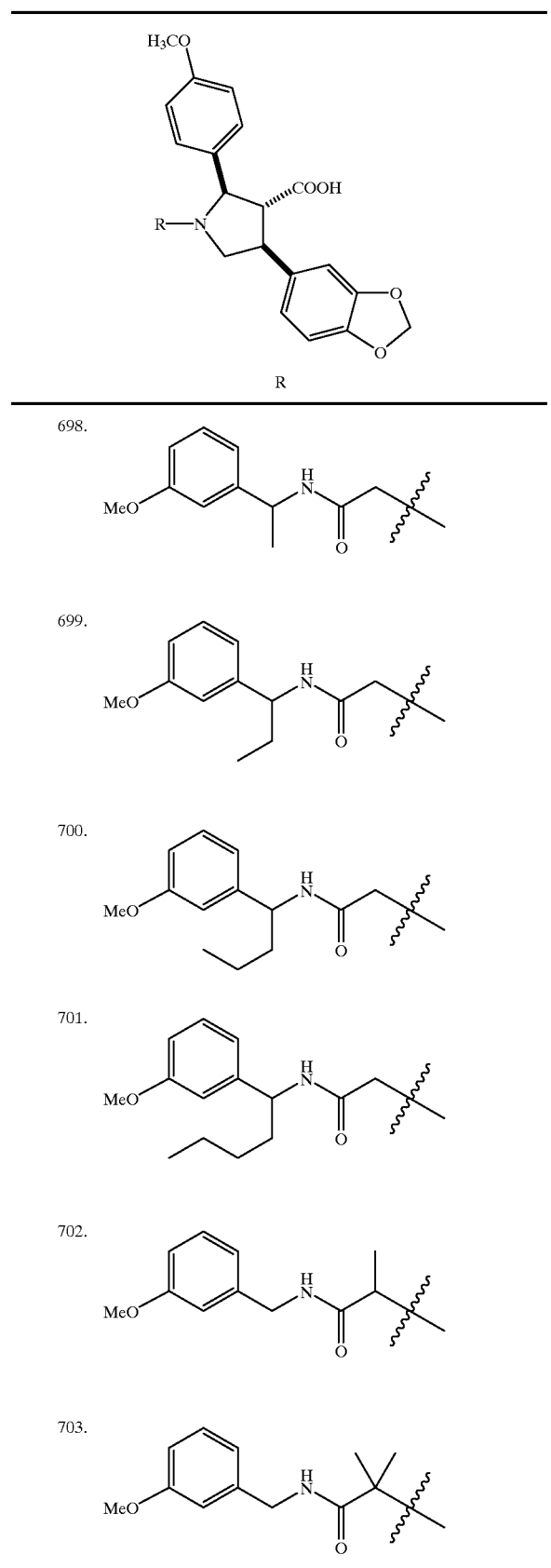
| R |
|---|
| 698. |
| 699. |
| 700. |
| 701. |
| 702. |
| 703. |

TABLE 1-continued
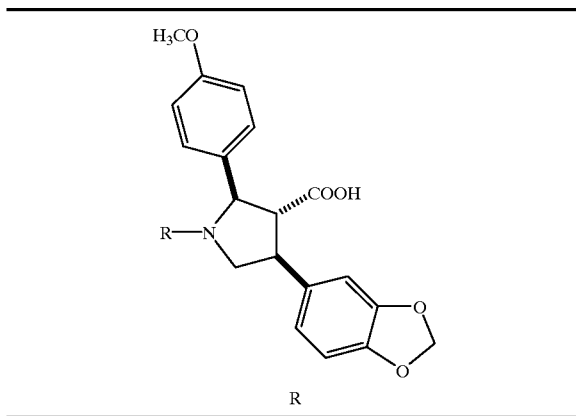
R
| | |
|---|---|
| 704. | 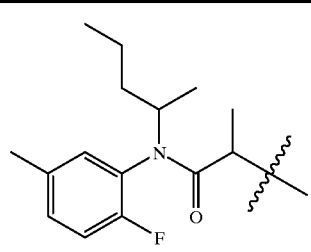 |
| 705. | 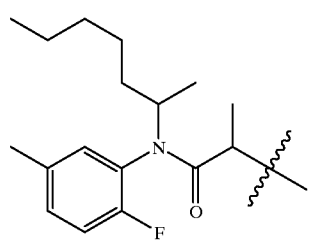 |
| 706. | 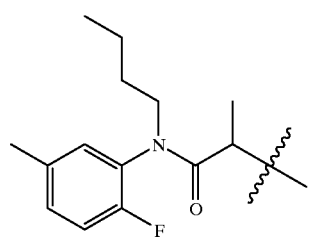 |
| 707. | 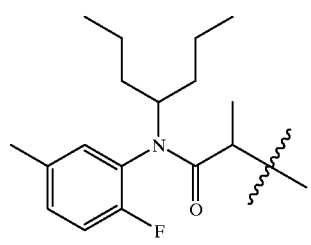 |
| 708. | 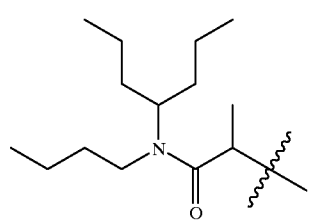 |
TABLE 1-continued
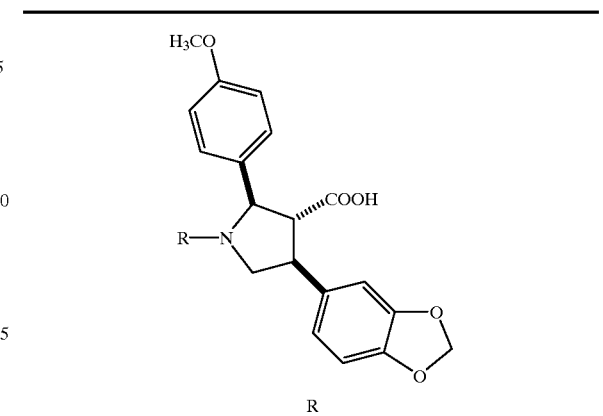
R
| | |
|---|---|
| 709. | 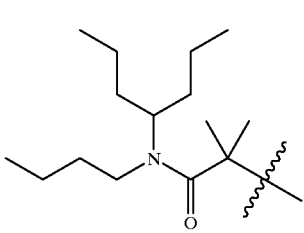 |
| 710. | 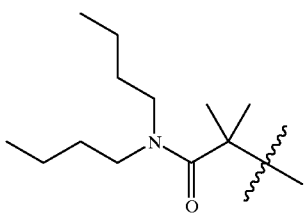 |
| 711. | 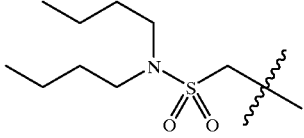 |
| 712. | 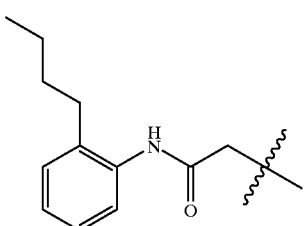 |
| 713. | 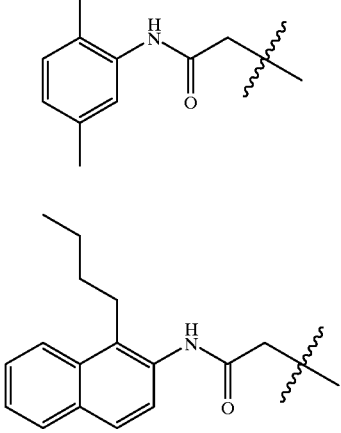 |

TABLE 1-continued
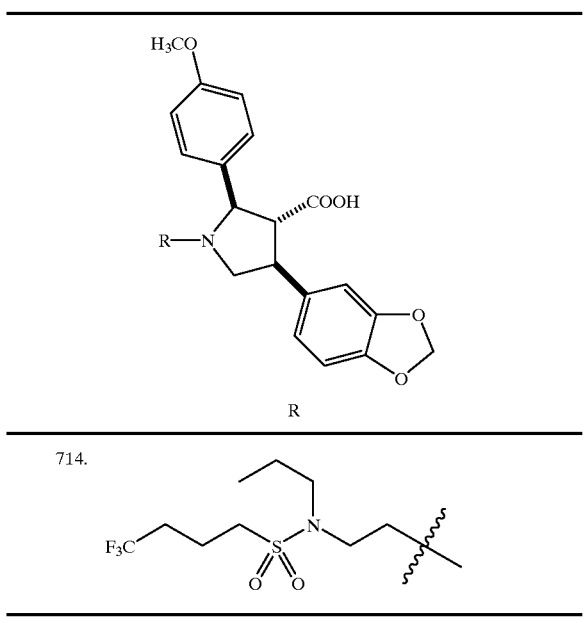
| 714. | R |
|---|---|
EXAMPLE 338
Using methods described in the above examples, compounds comprising a parent structure selected from those disclosed in Table 2A and an R substituent selected from those disclosed in Table 2B can be prepared.
TABLE 2A
1.
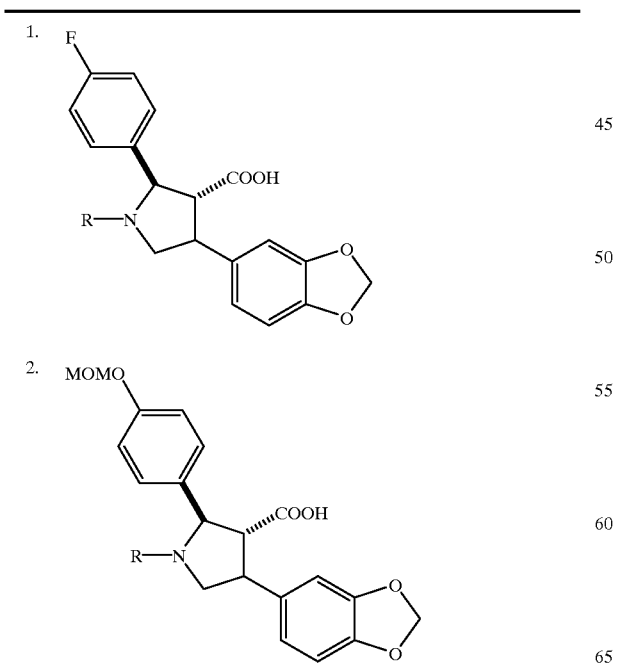
2.
TABLE 2A-continued
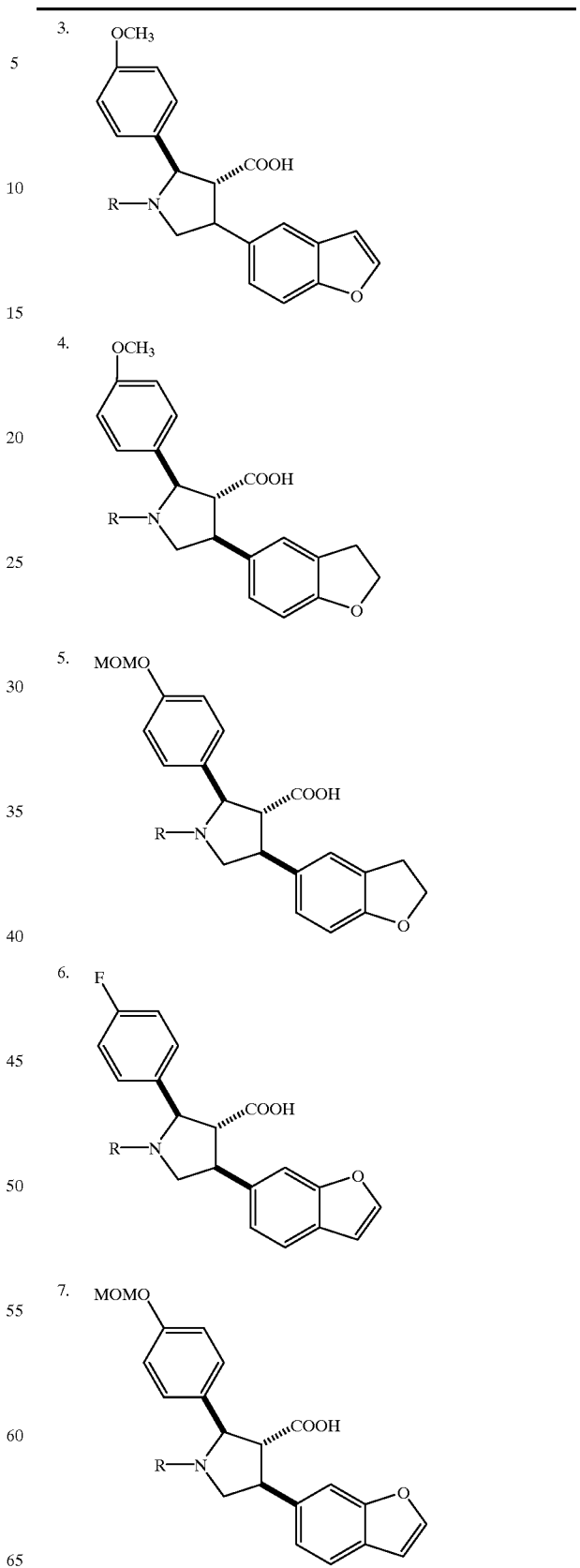
3.
4.
5.
6.
7.

TABLE 2A-continued
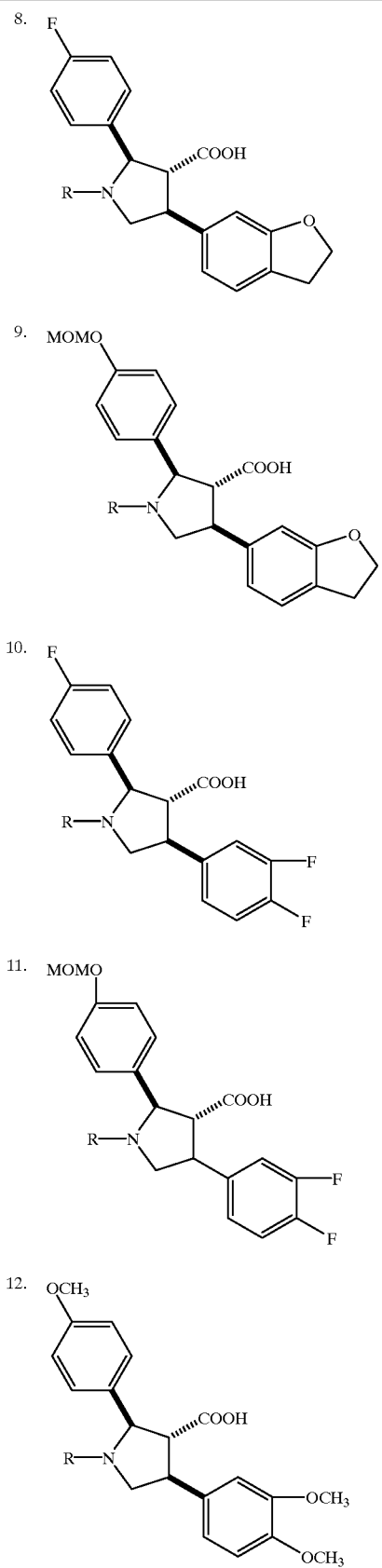
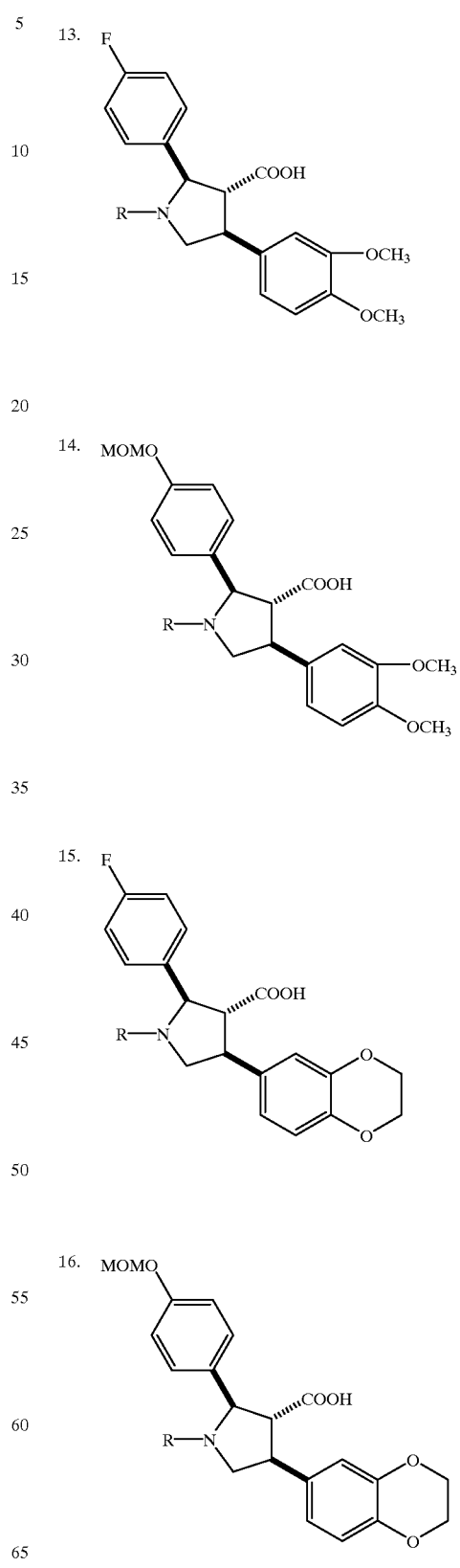

TABLE 2A-continued
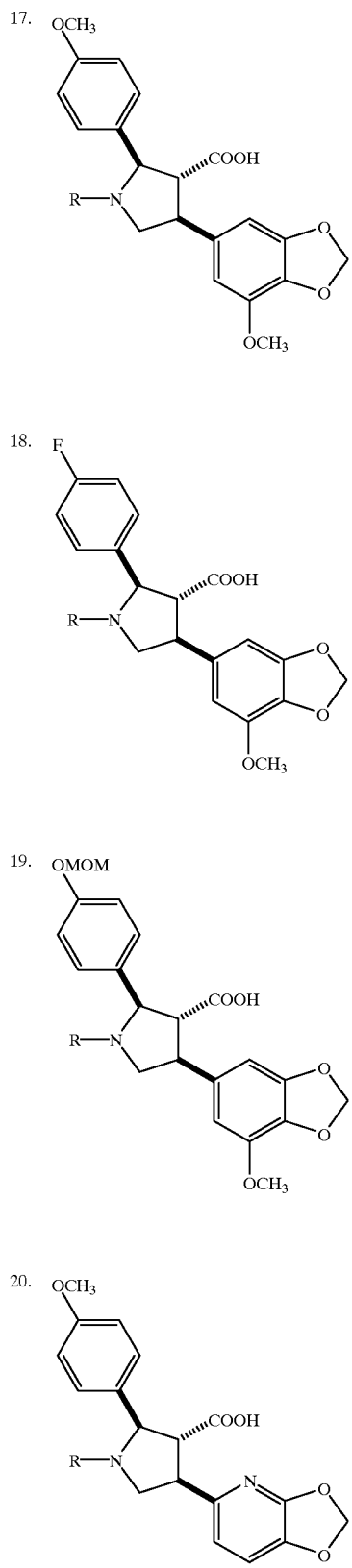
TABLE 2A-continued
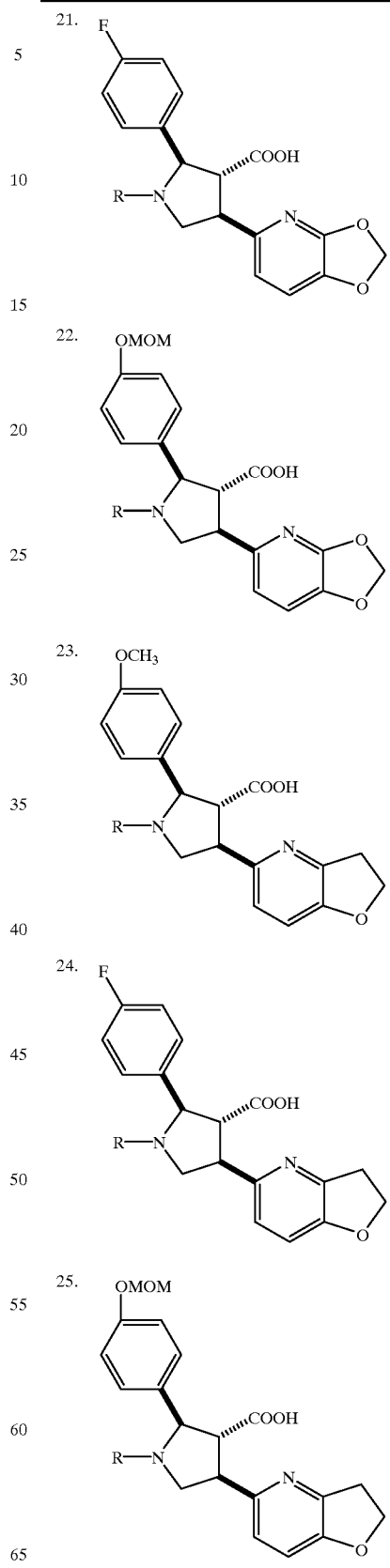

TABLE 2A-continued
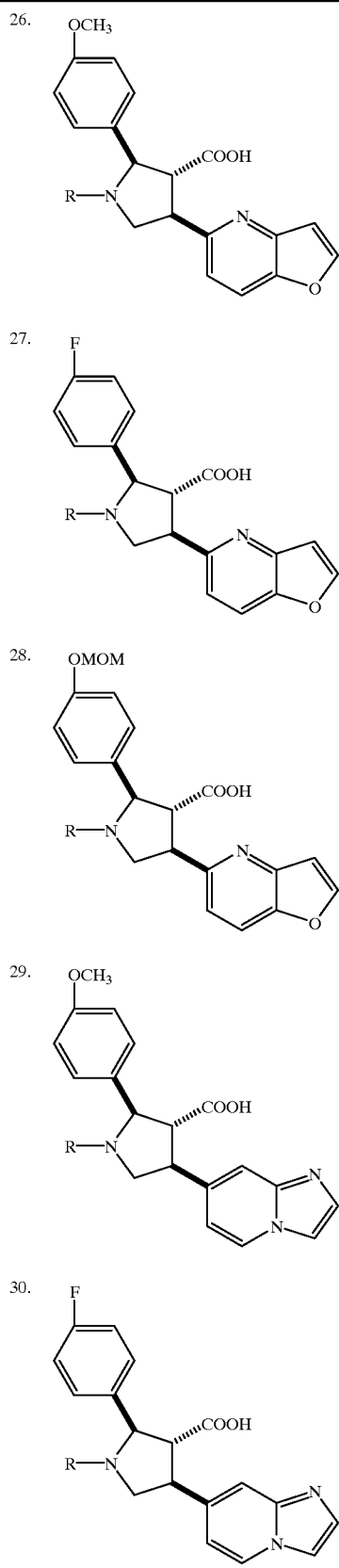
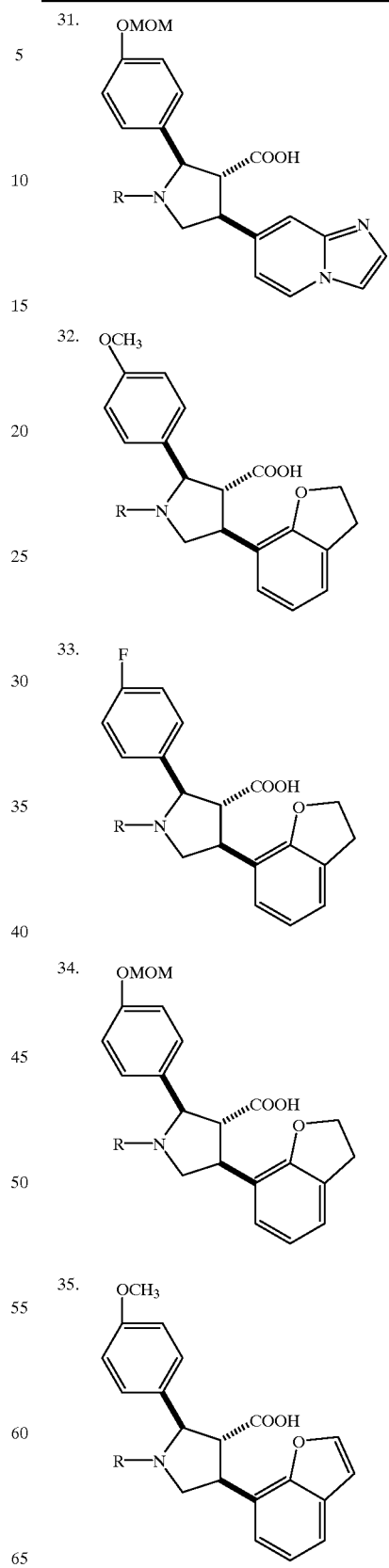

TABLE 2A-continued
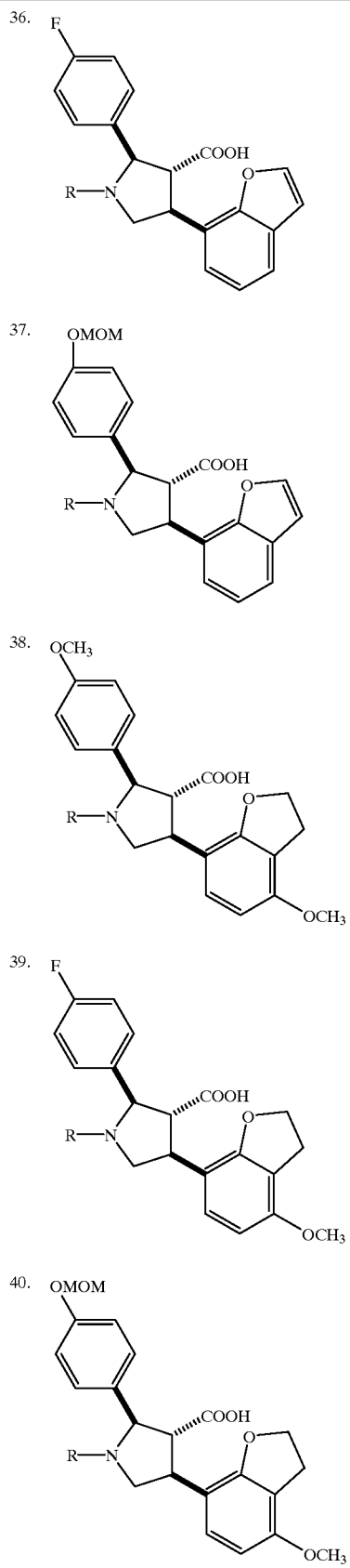
TABLE 2A-continued
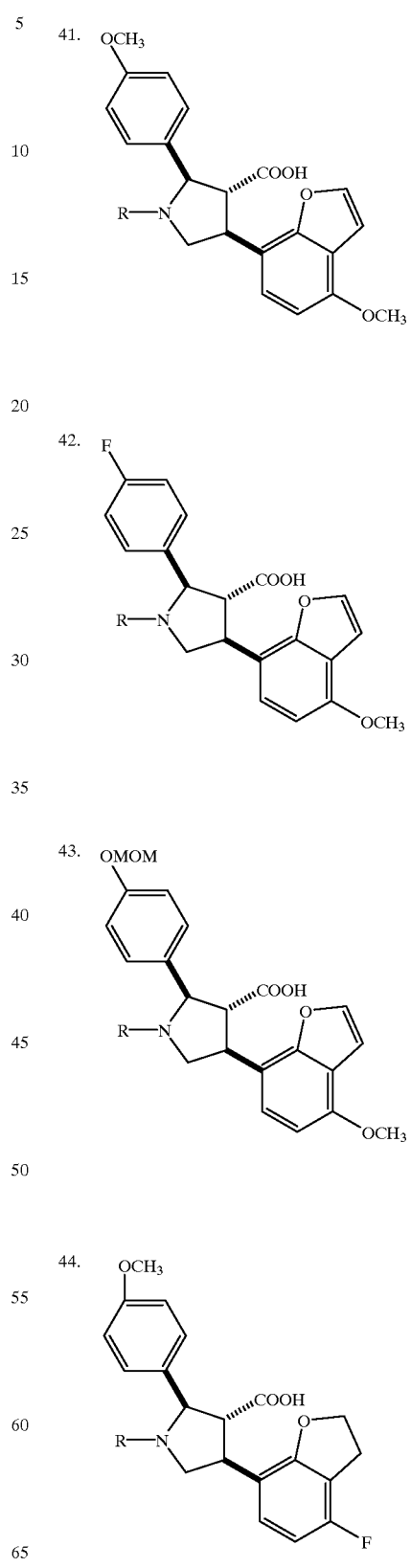

TABLE 2A-continued
45. 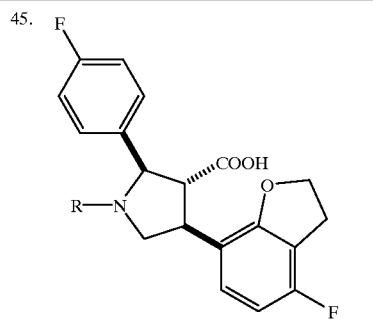
46. 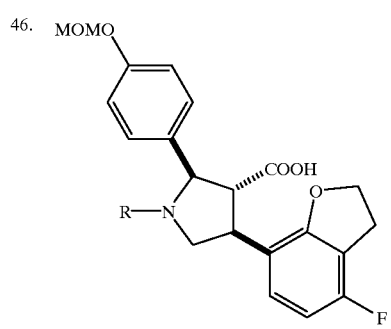
47. 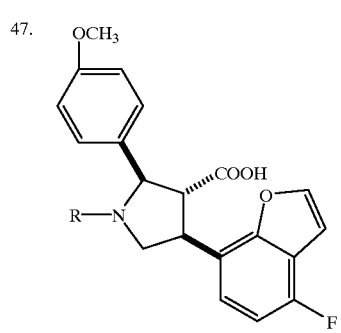
48. 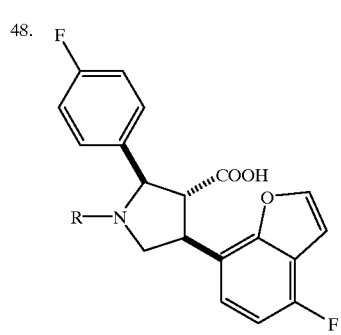
49. 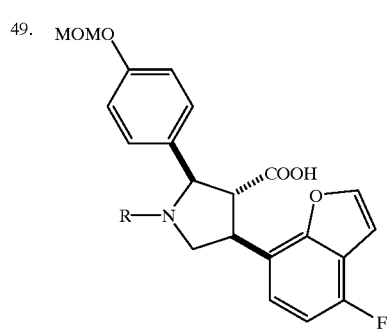
TABLE 2A-continued
50. 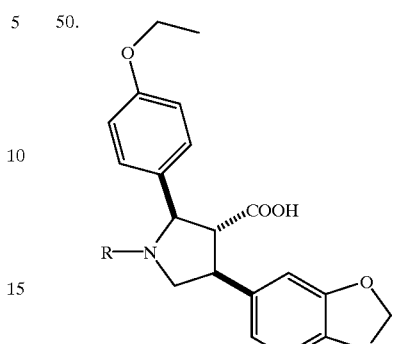
51. 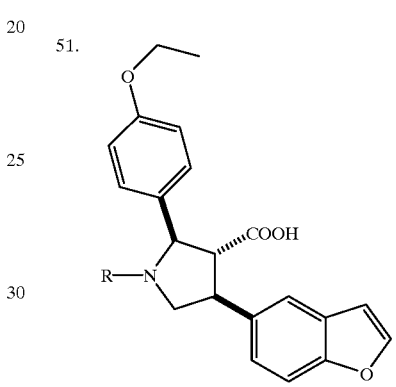
52. 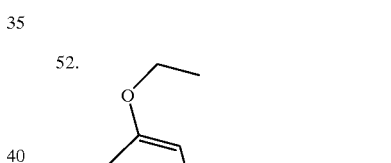
53. 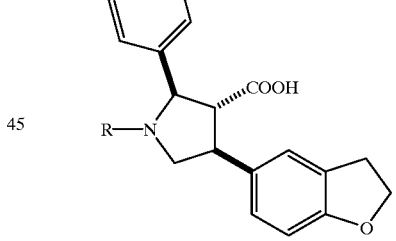
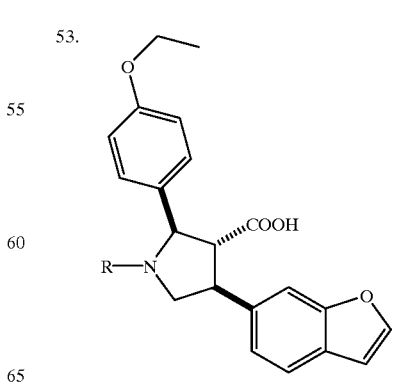

TABLE 2A-continued
54.
55.
56.
57.
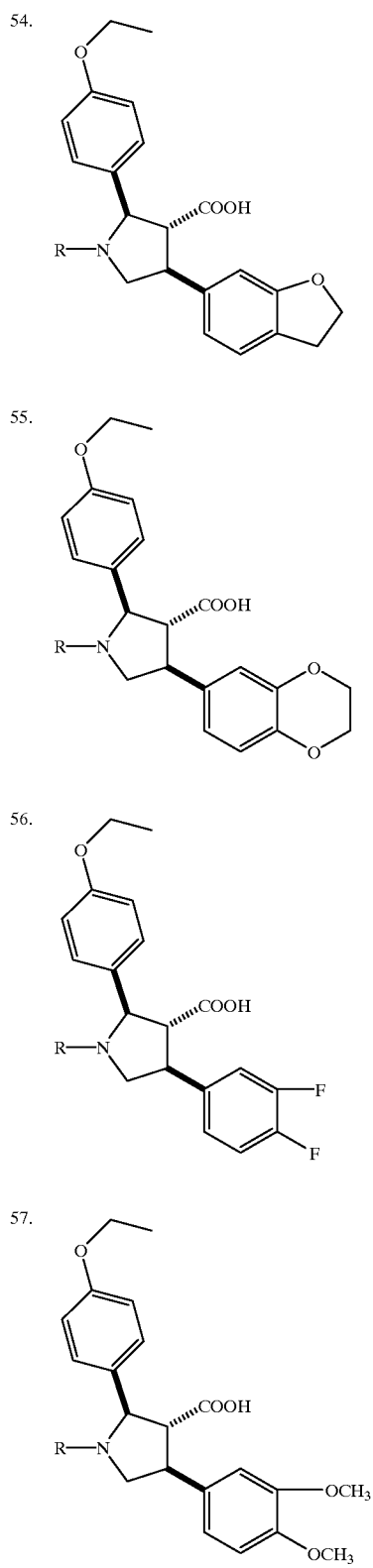
TABLE 2A-continued
58.
59.
60.
61.
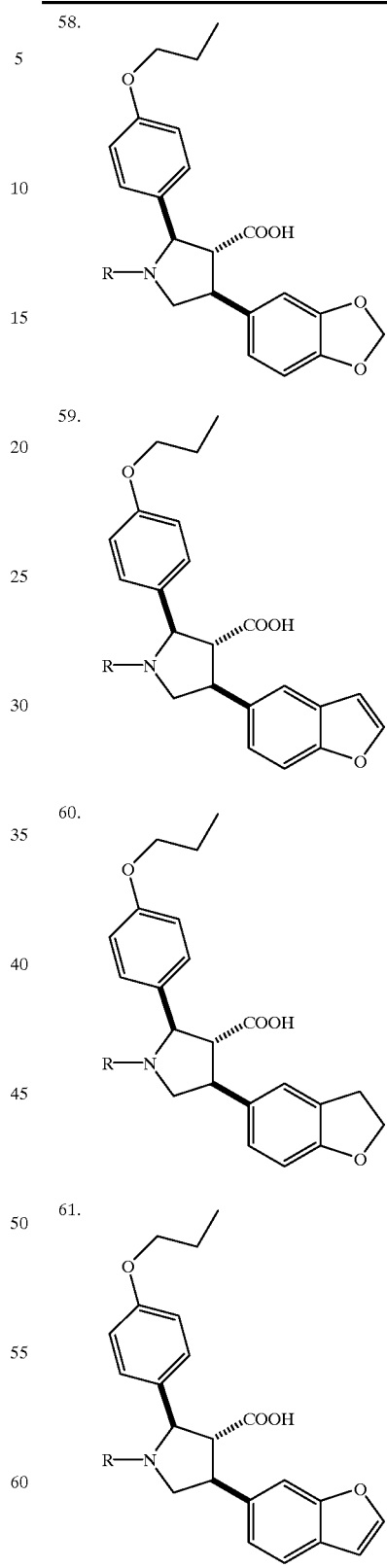

TABLE 2A-continued
62. 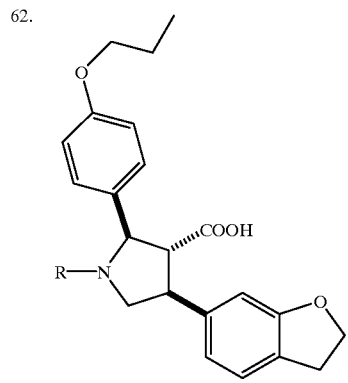
63. 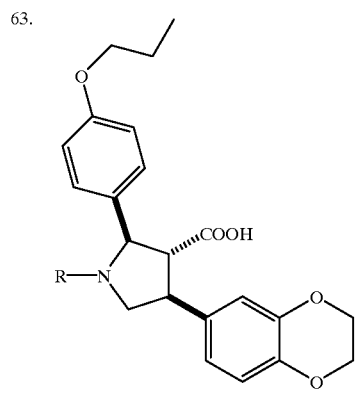
64. 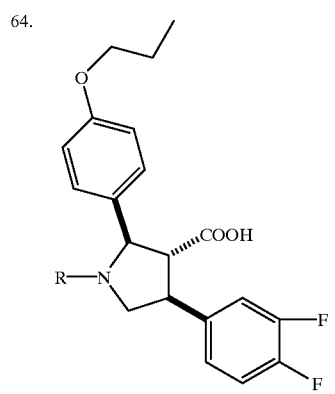
65. 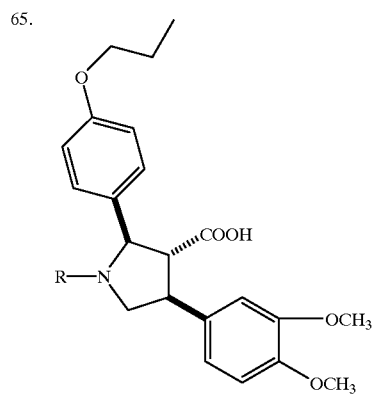
TABLE 2A-continued
66. 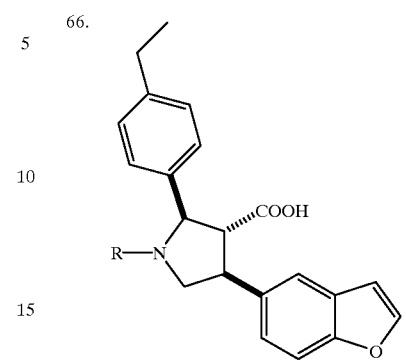
67. 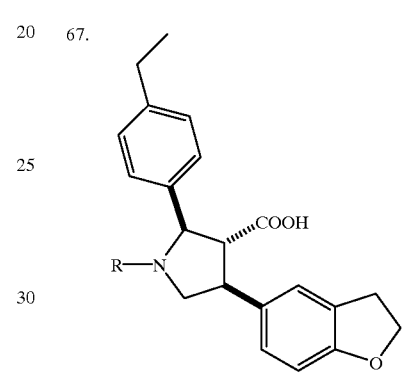
68. 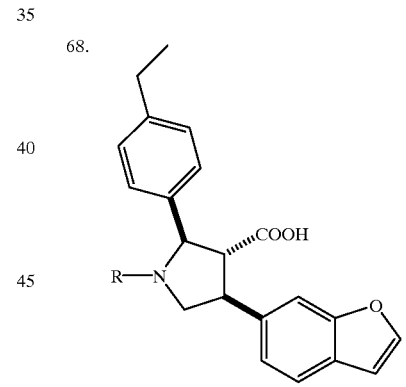
69. 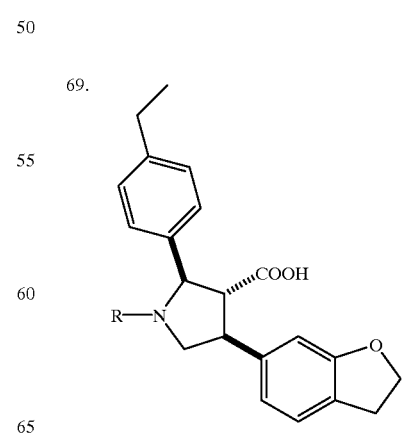

TABLE 2A-continued
70. 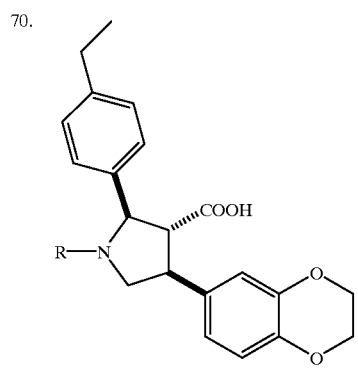
71. 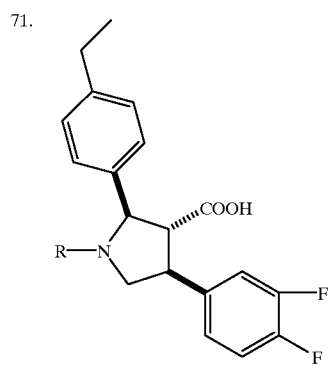
72. 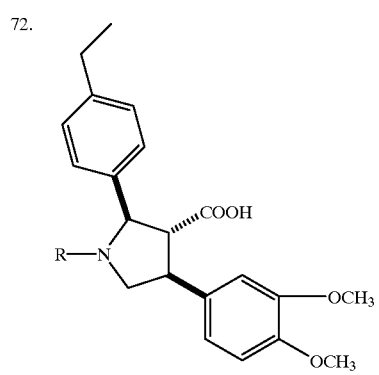
73. 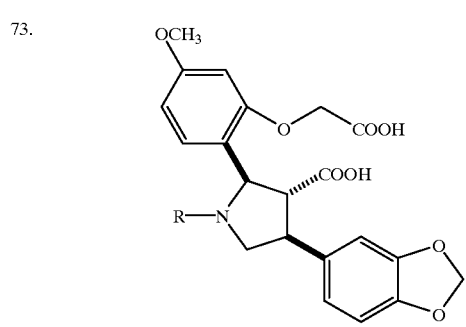
TABLE 2A-continued
74. 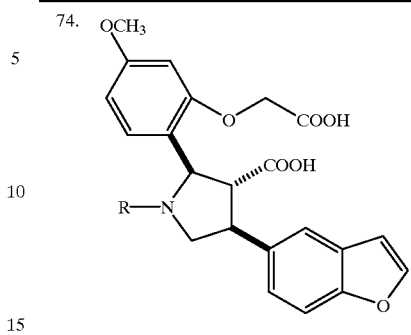
75. 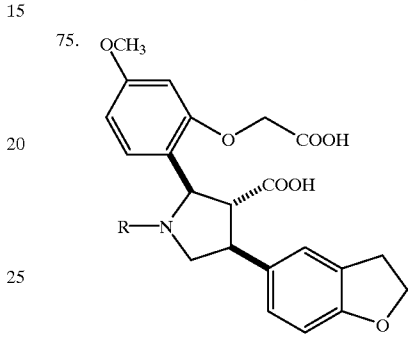
76. 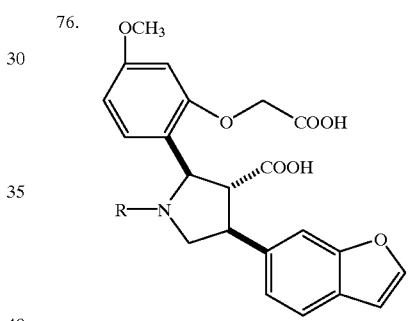
77. 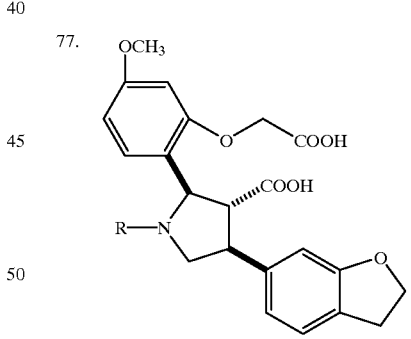
78. 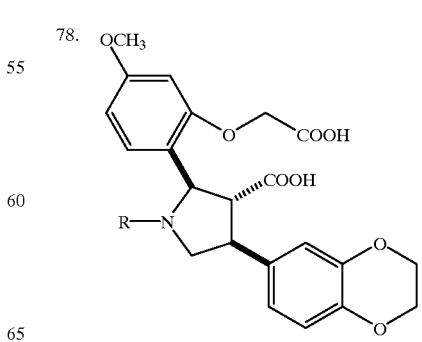

TABLE 2A-continued
79. 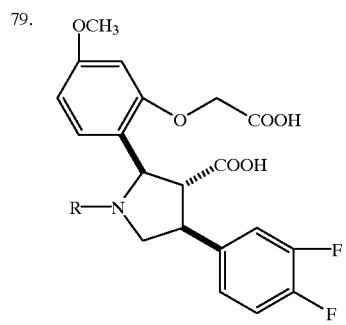
80. 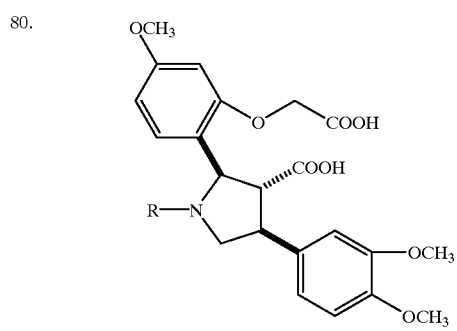
81. 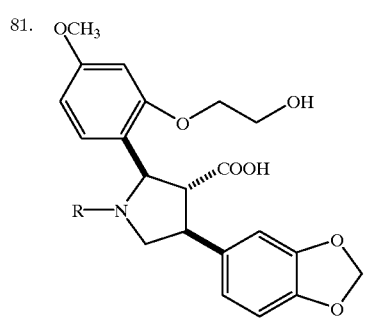
82. 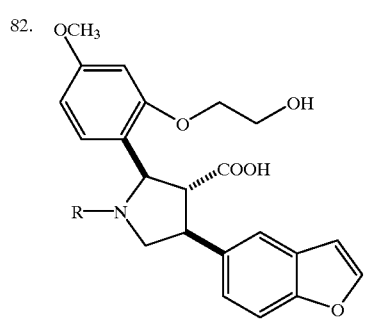
83. 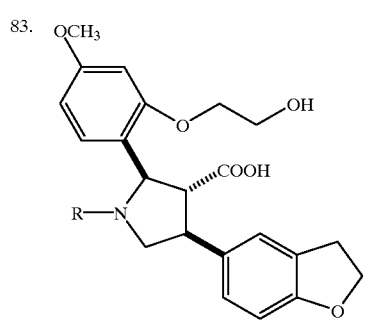
TABLE 2A-continued
84. 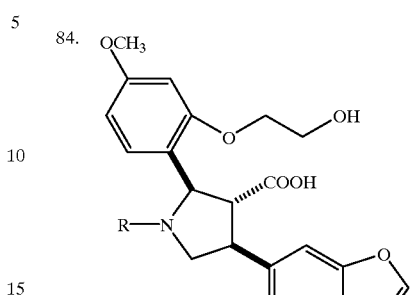
85. 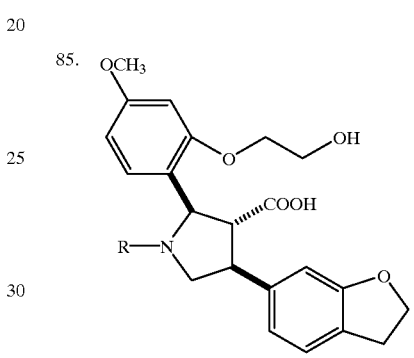
86. 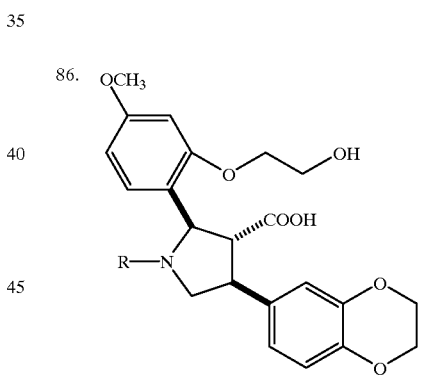
87. 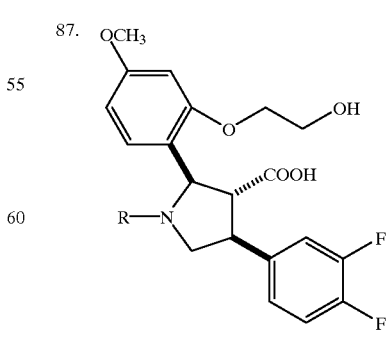

TABLE 2A-continued
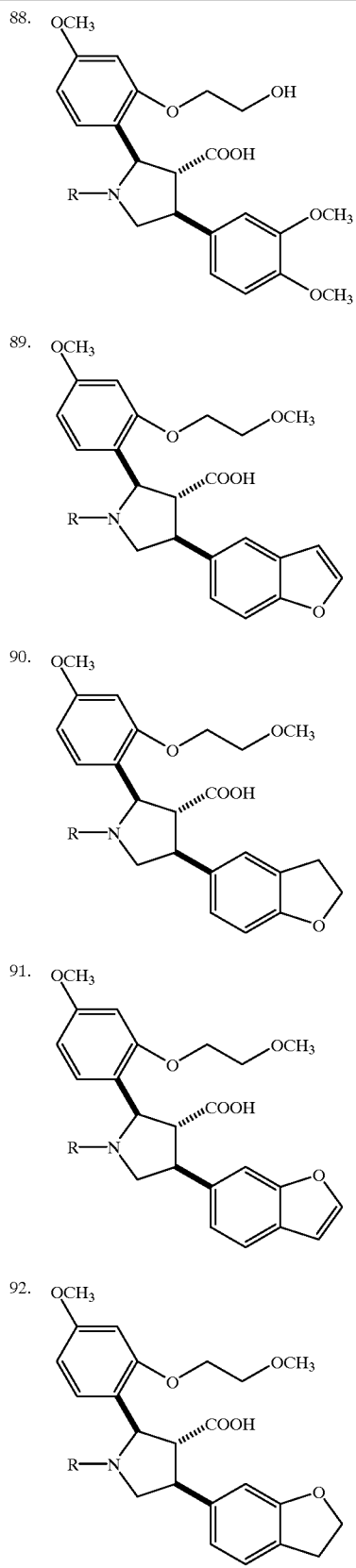
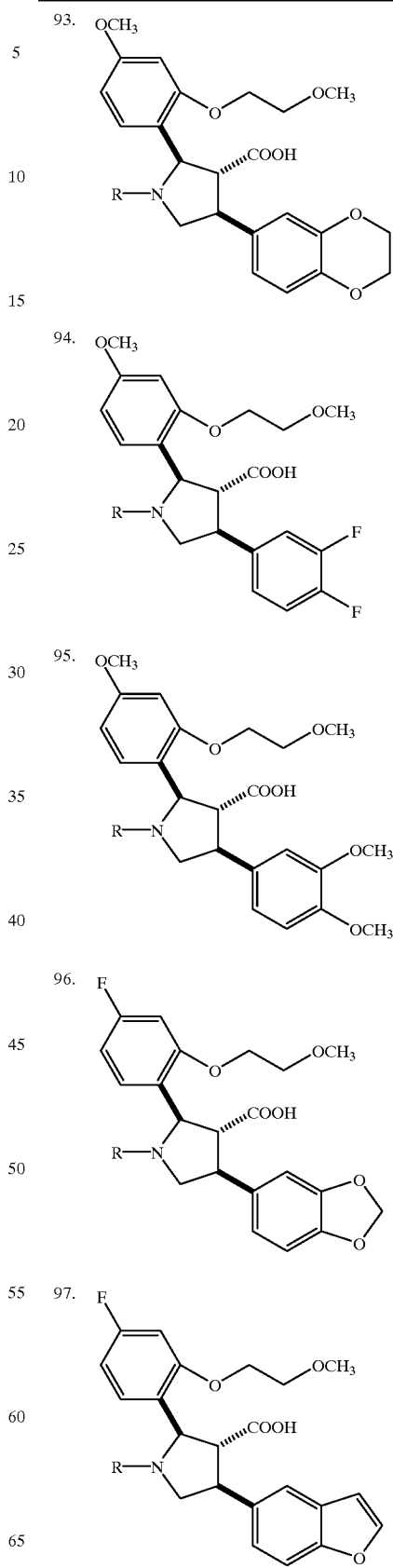

TABLE 2A-continued
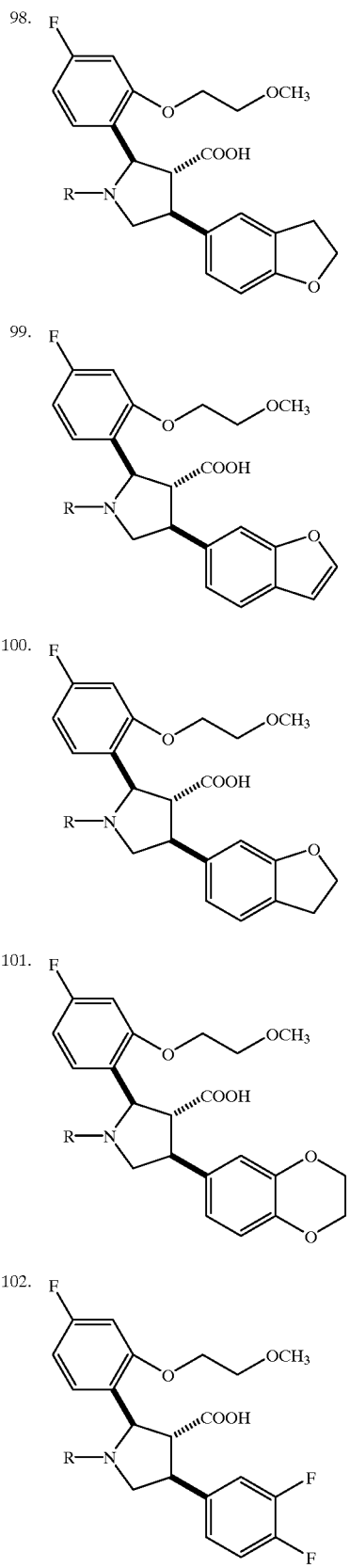
TABLE 2A-continued
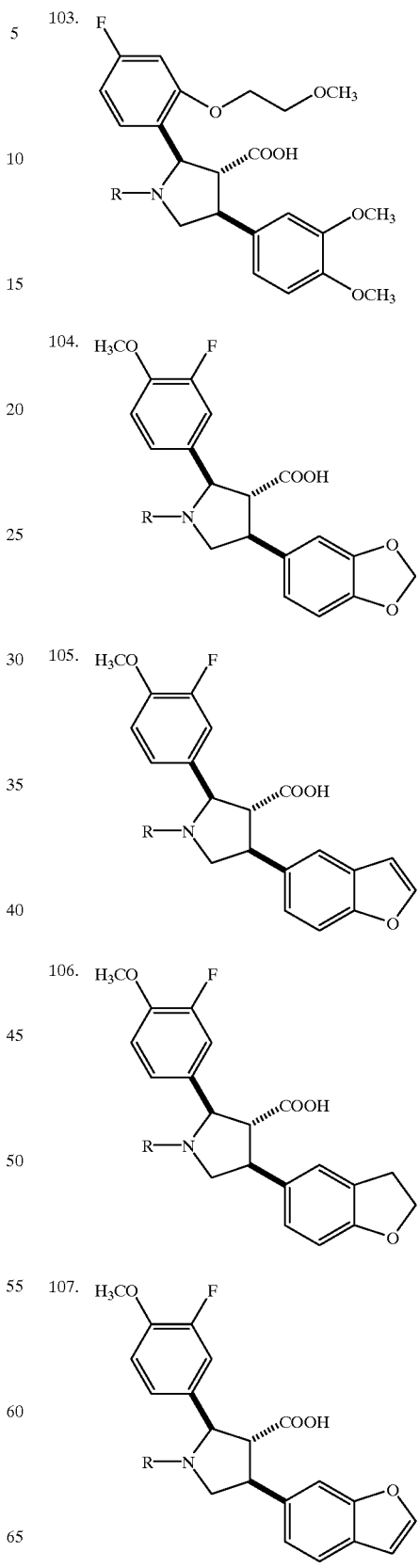

TABLE 2A-continued
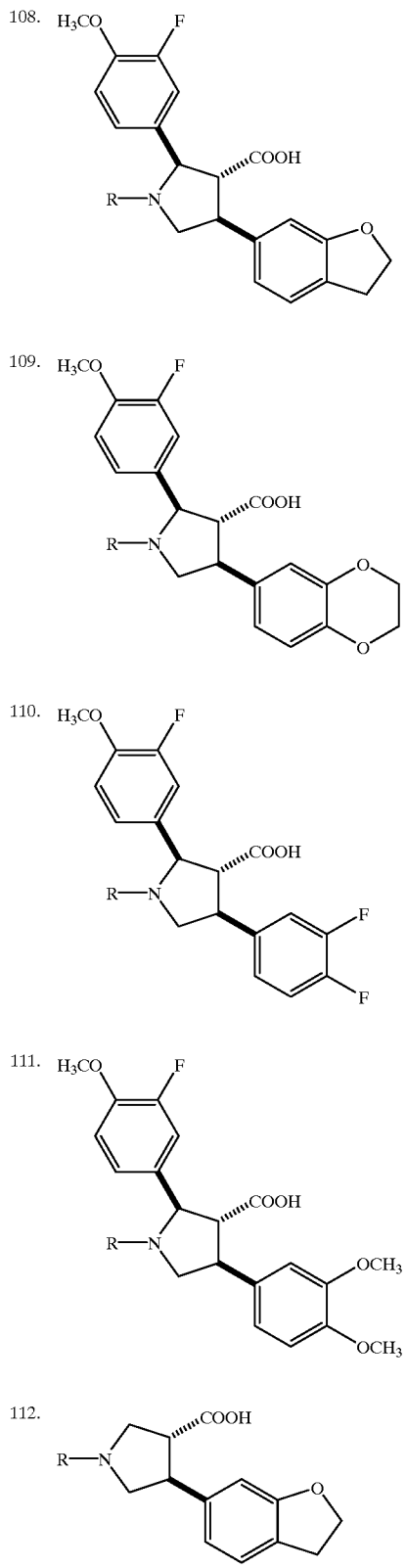
TABLE 2A-continued
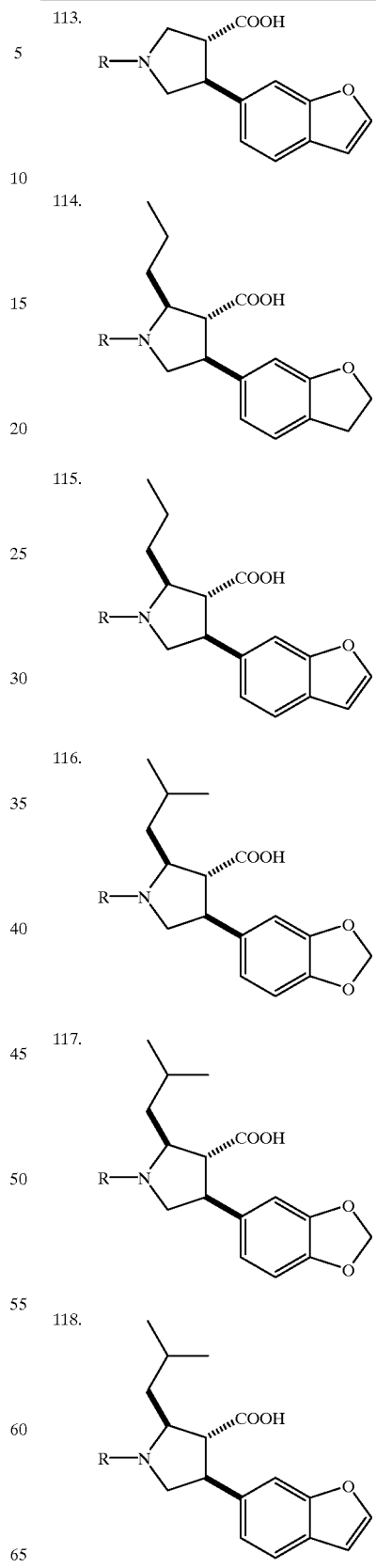

TABLE 2A-continued
119. 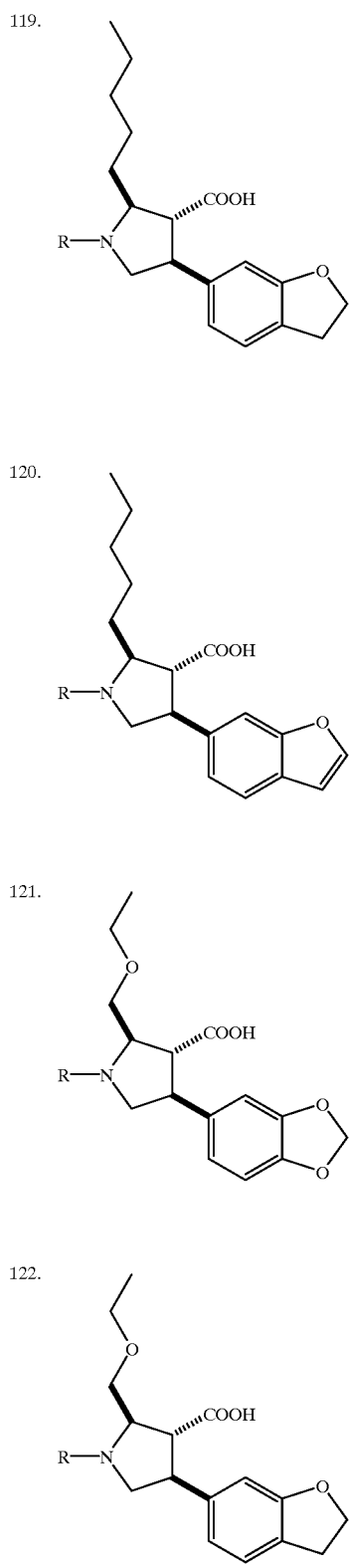
120.
121.
122.
TABLE 2A-continued
123. 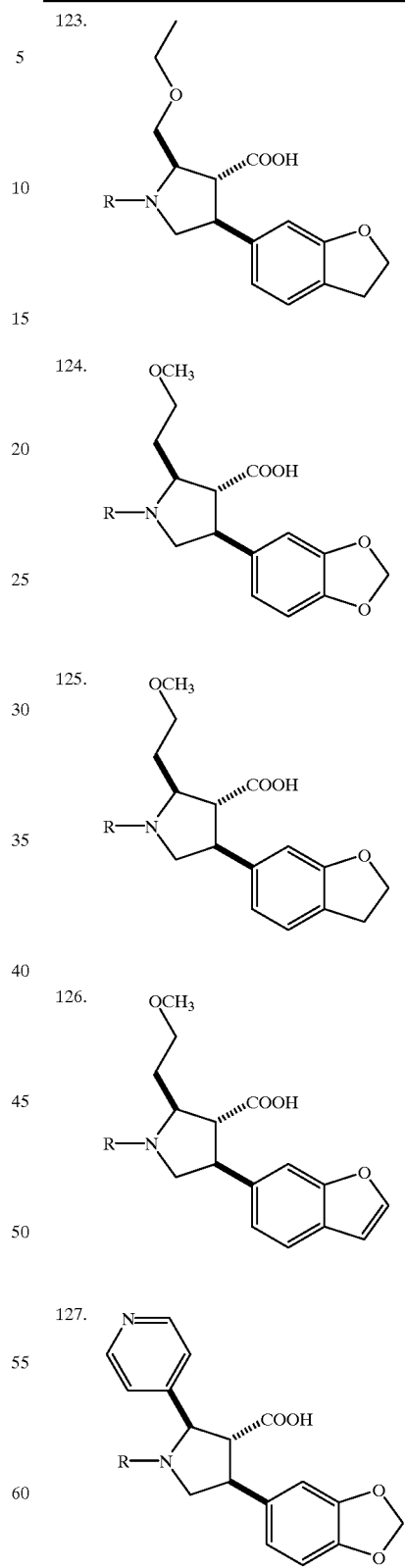
124.
125.
126.
127.

TABLE 2A-continued
| | |
|---|---|
| 128. | 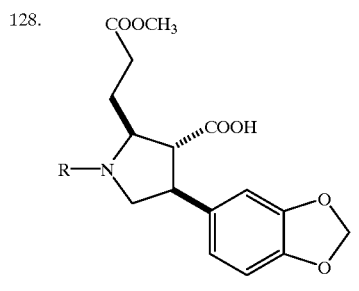 |
| 129. | 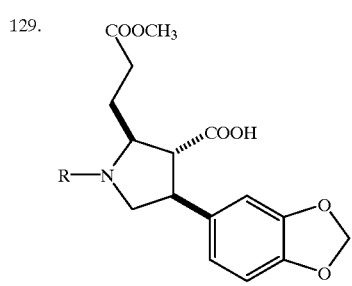 |
| 130. | 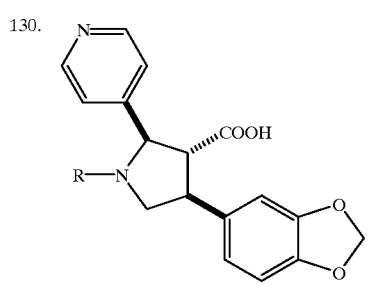 |
| 131. | 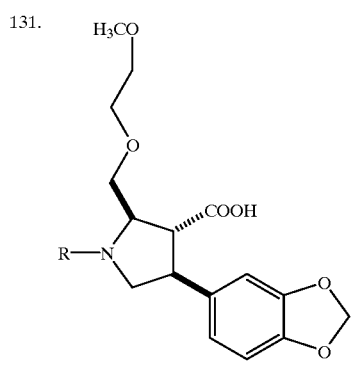 |
| 132. | 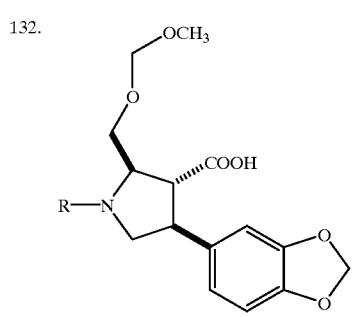 |
TABLE 2A-continued
| | |
|---|---|
| 133. | 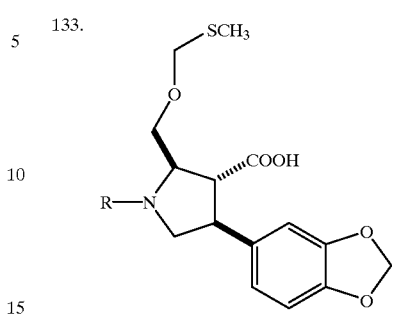 |
| 134. | 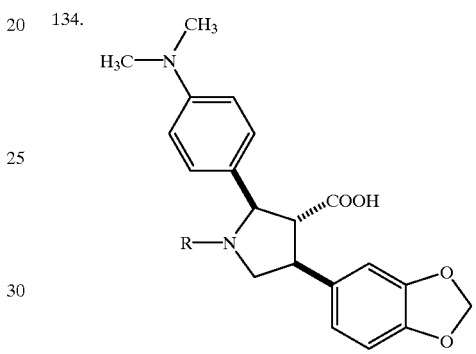 |
| 135. | 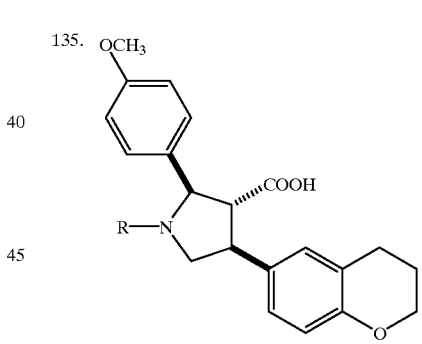 |
| 136. | 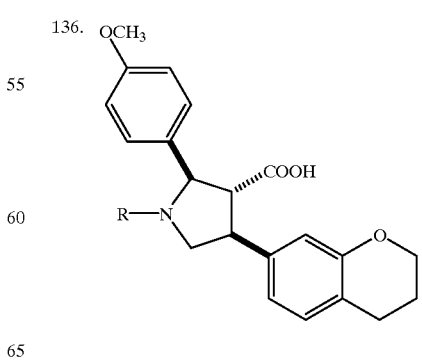 |

TABLE 2A-continued
137. 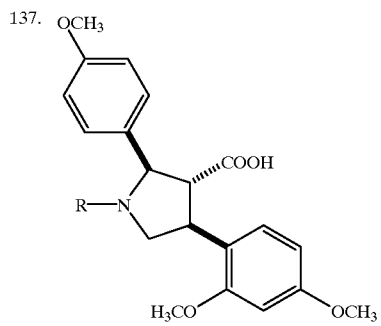
138. 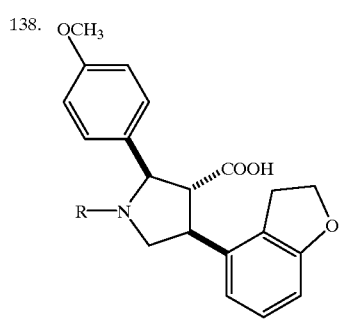
139. 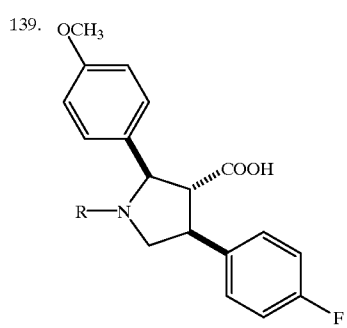
140. 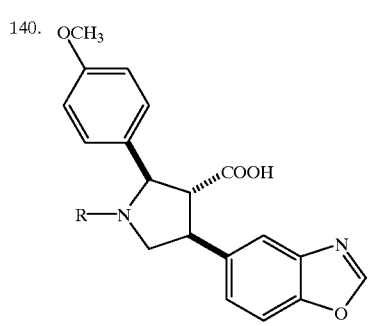
141. 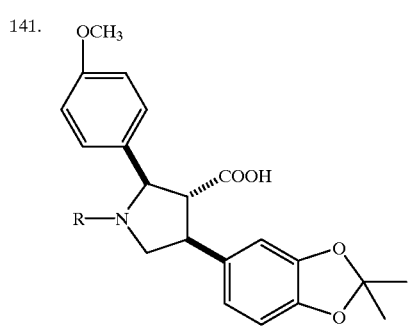
TABLE 2A-continued
142. 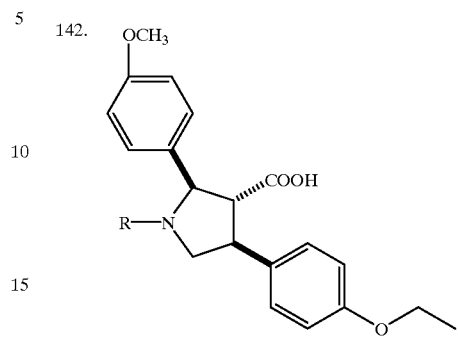
143. 
144. 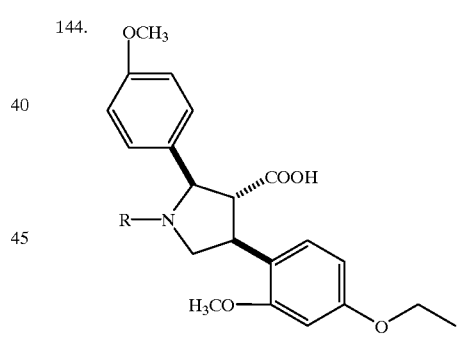
145. 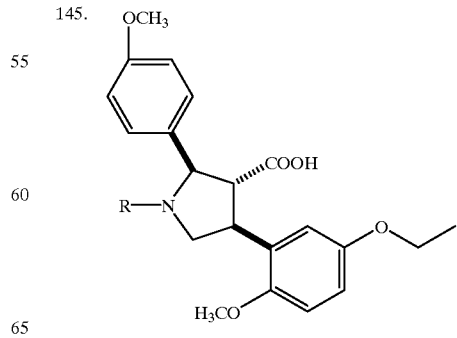

TABLE 2A-continued
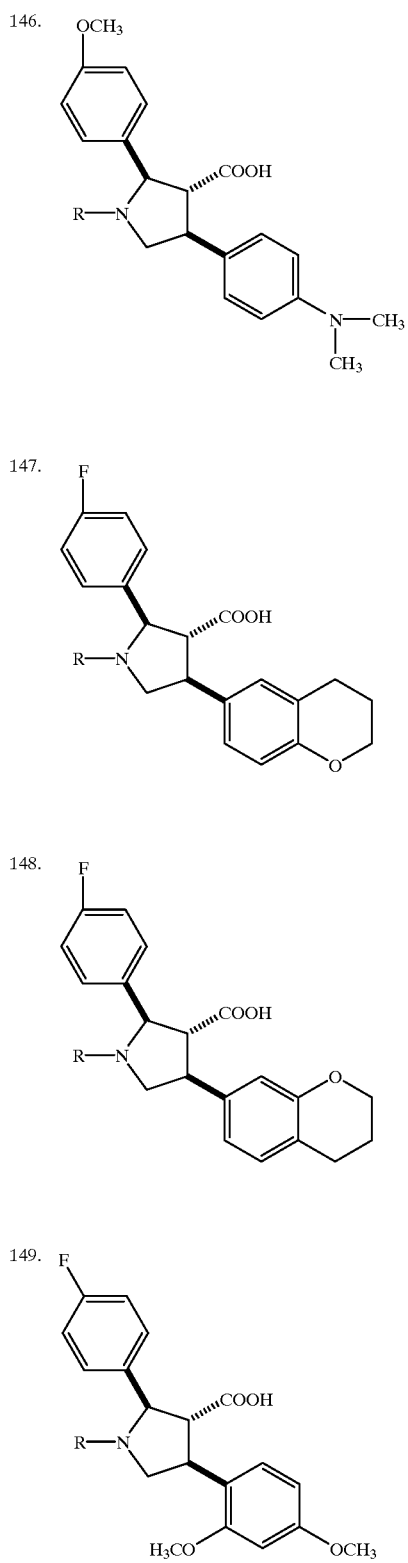
146.
147.
148.
149.
TABLE 2A-continued
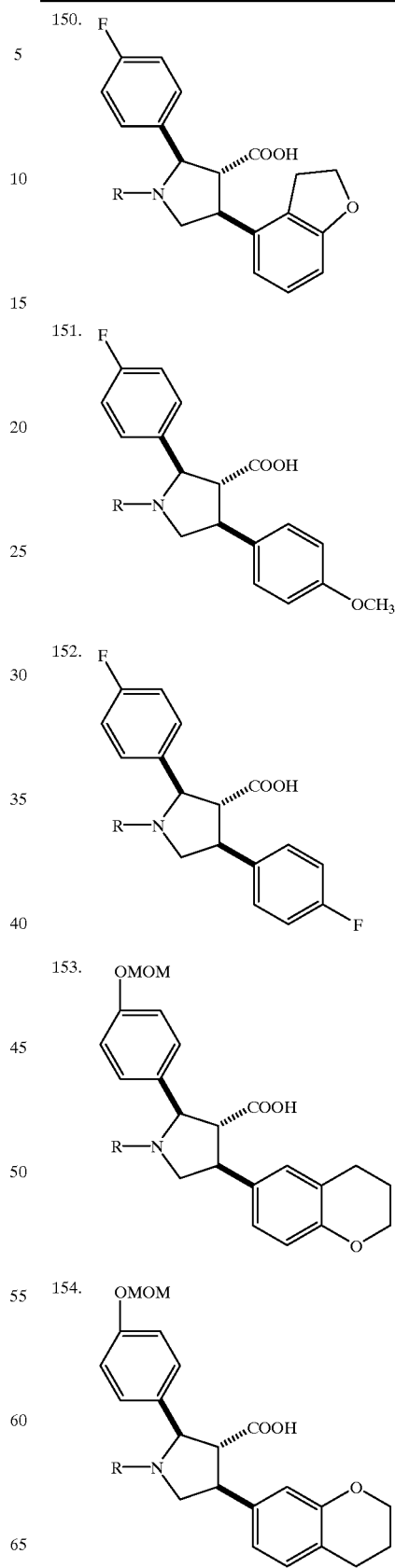
150.
151.
152.
153.
154.

TABLE 2A-continued
155. 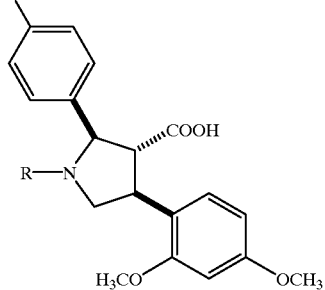
156. 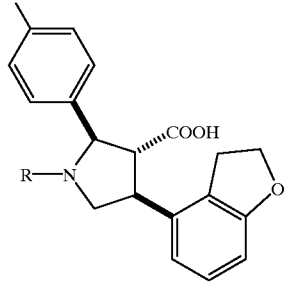
157. 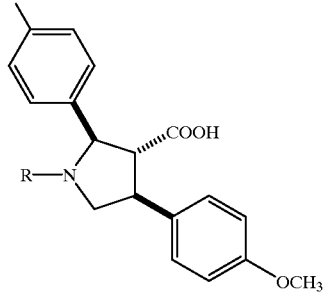
158. 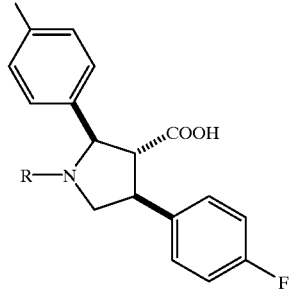
TABLE 2A-continued
159. 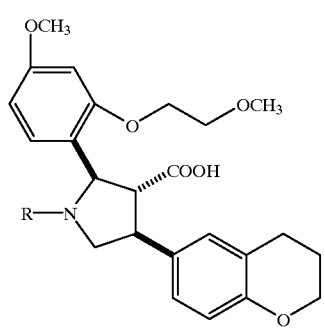
160. 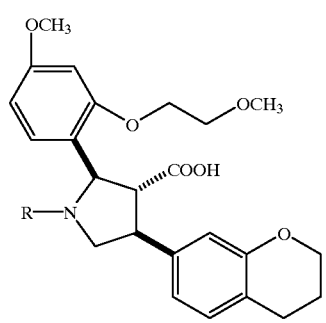
161. 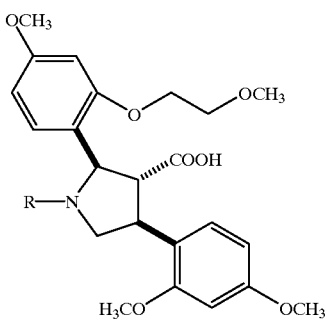
162. 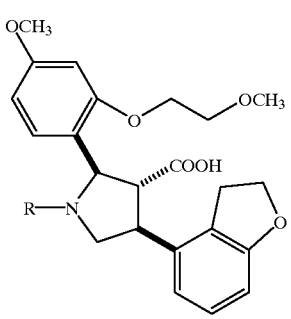

TABLE 2A-continued
163. 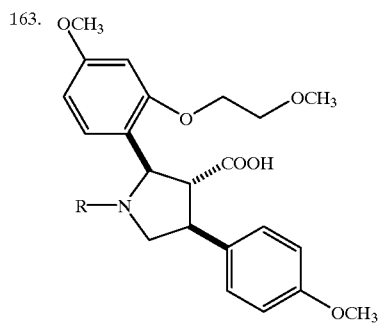
164. 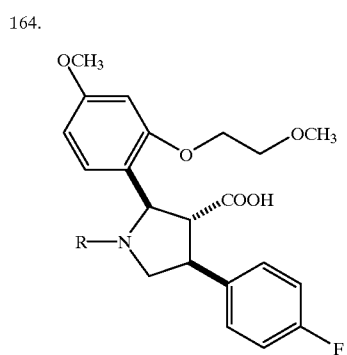
165. 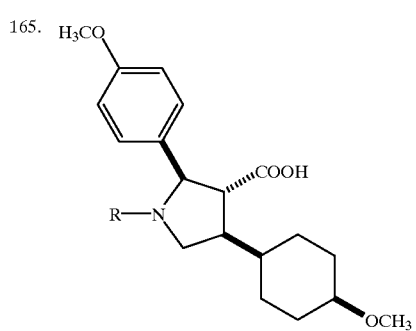
166. 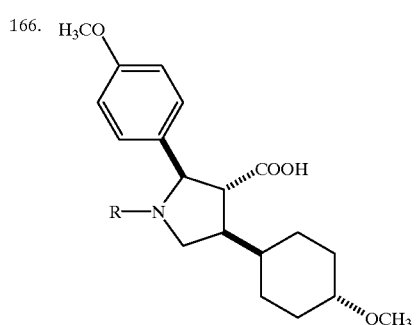
TABLE 2A-continued
167. 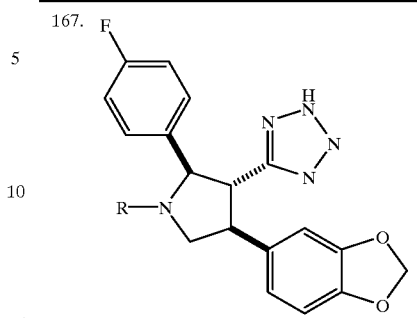
168. 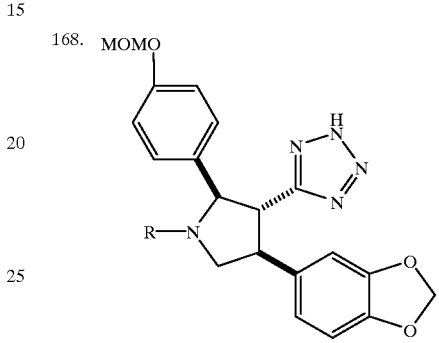
169. 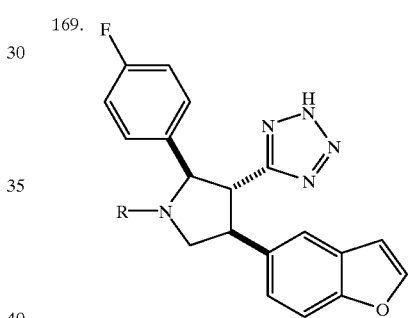
170. 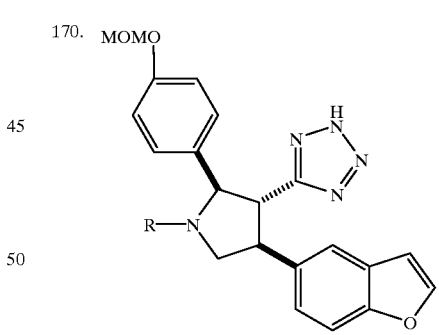
171. 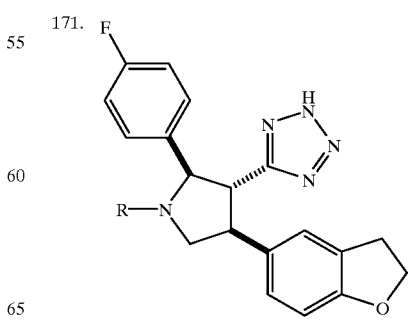

TABLE 2A-continued
172. 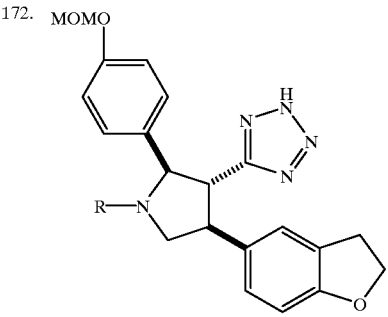
173. 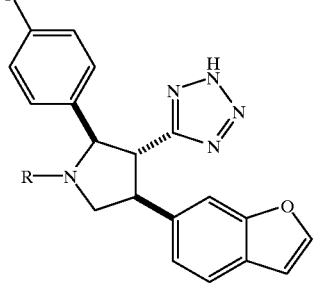
174. 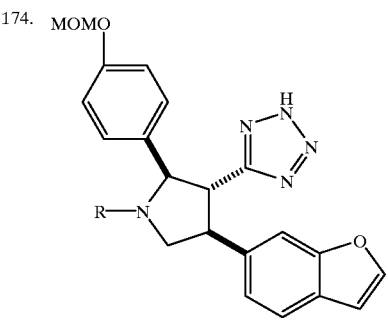
175. 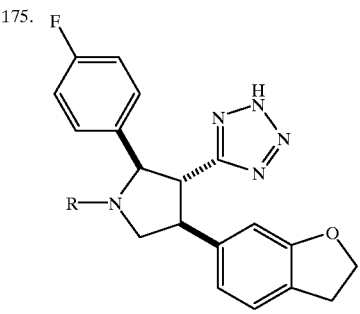
TABLE 2A-continued
176. 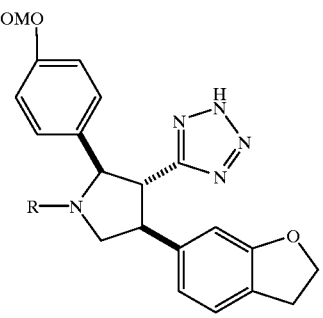
177. 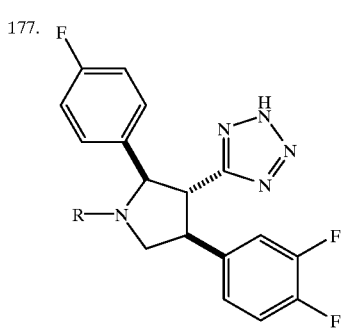
178. 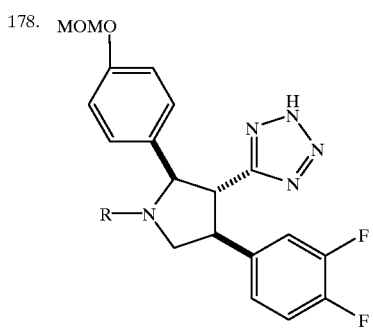
179. 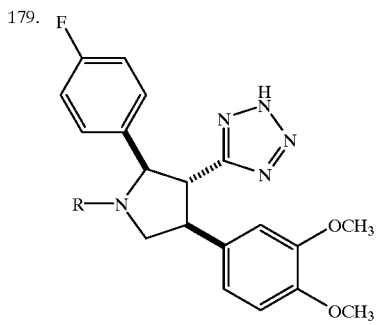

TABLE 2A-continued
180. 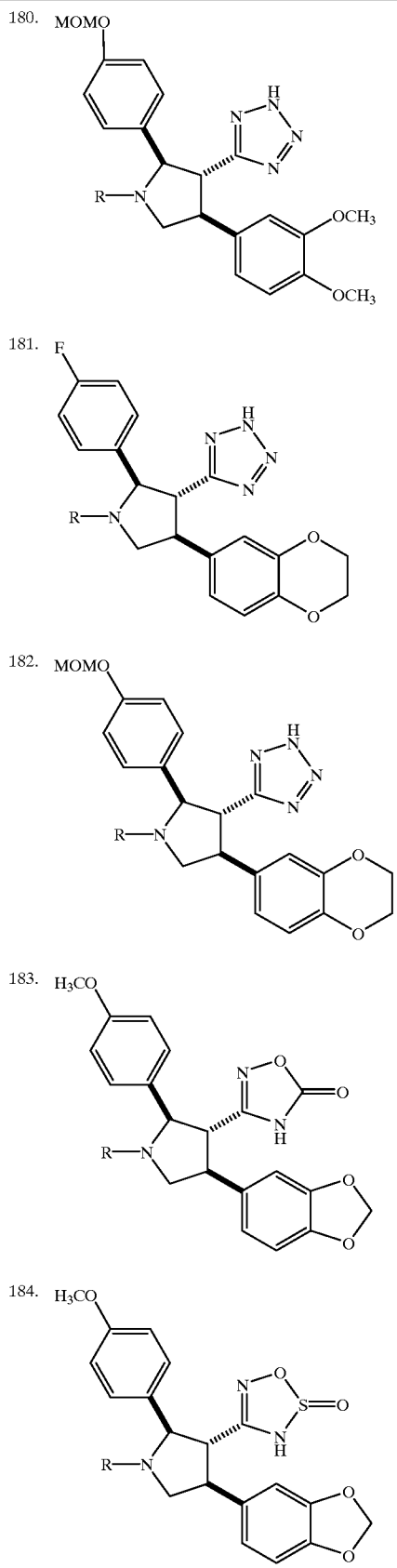
181.
182.
183.
184.
TABLE 2A-continued
185. 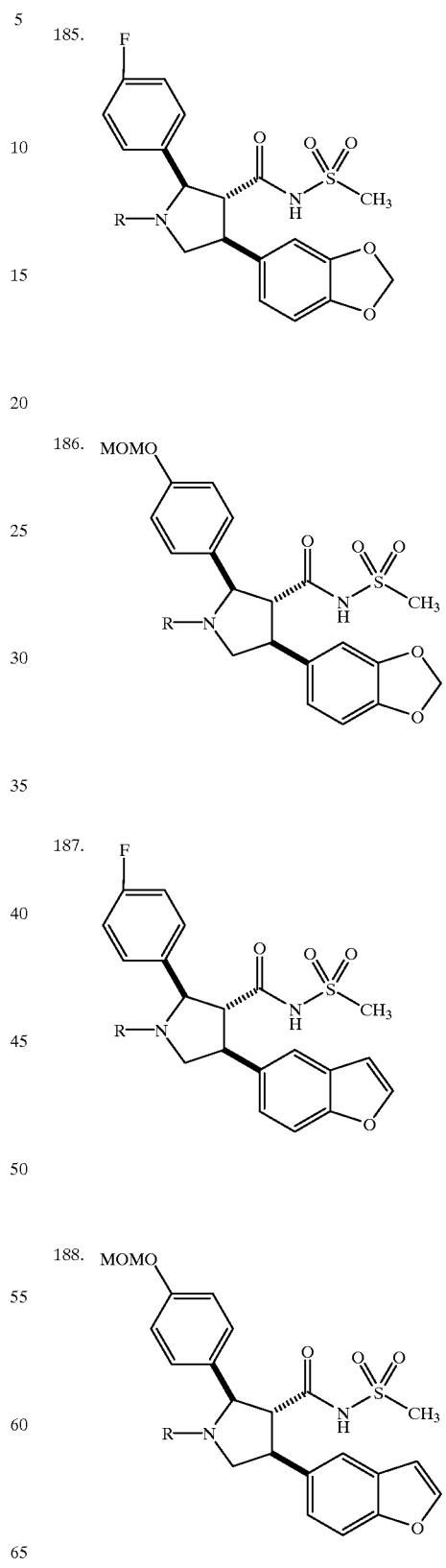
186.
187.
188.

TABLE 2A-continued
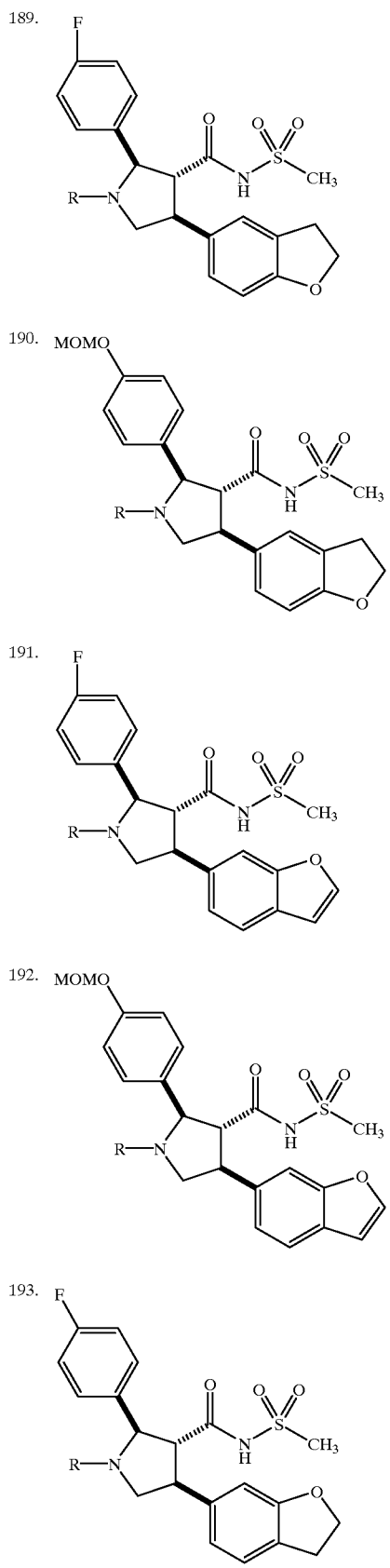
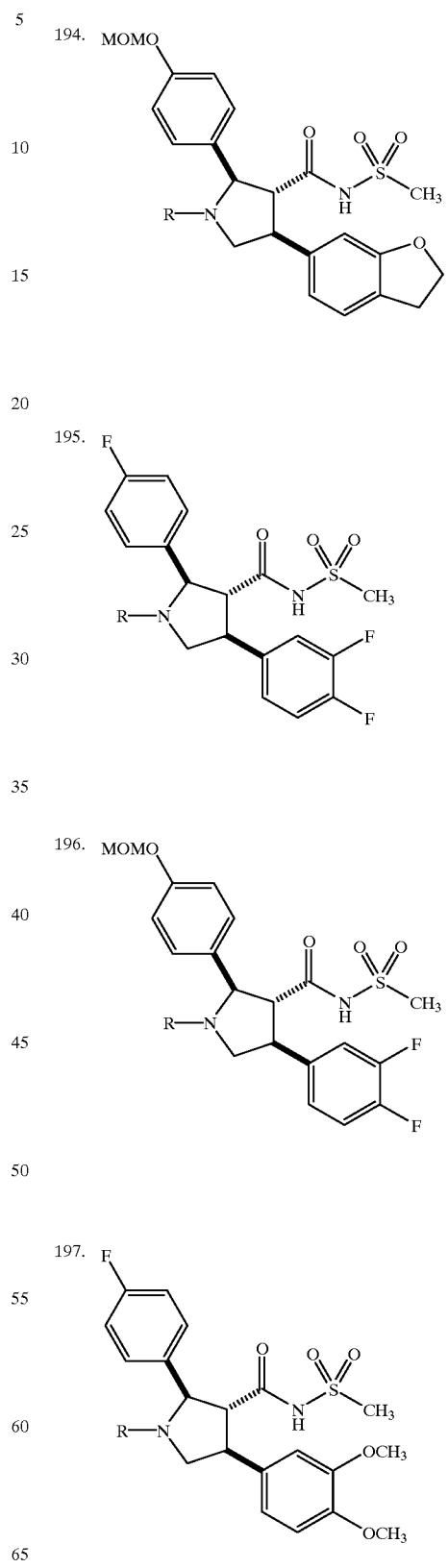

TABLE 2A-continued
198. 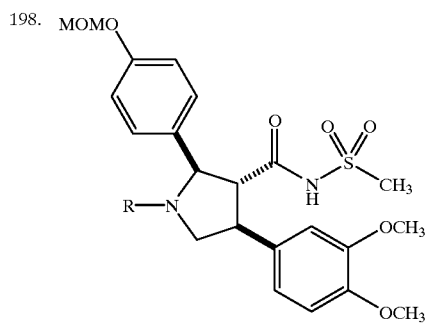
199. 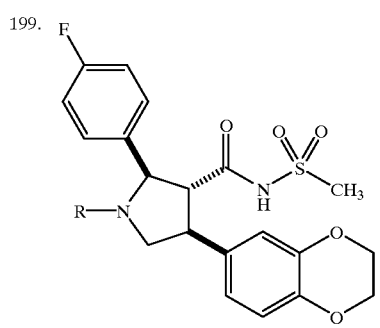
200. 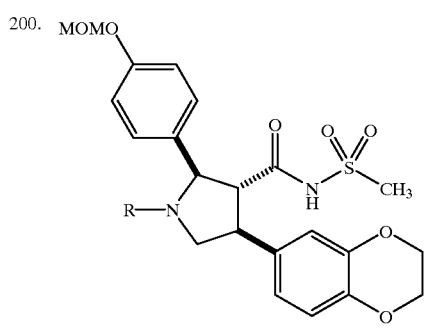
201. 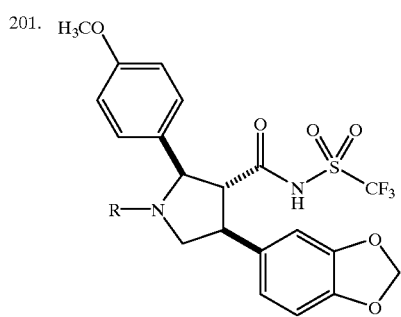
202. 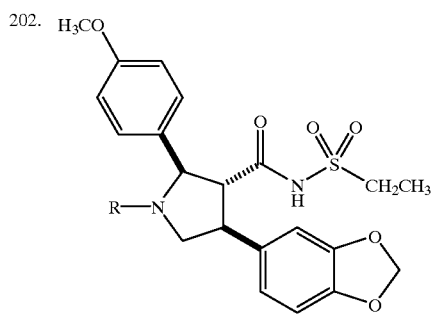
TABLE 2A-continued
203. 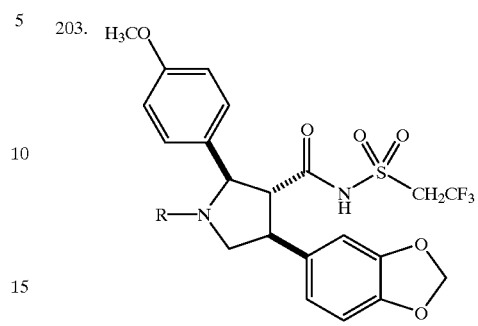
204. 
205. 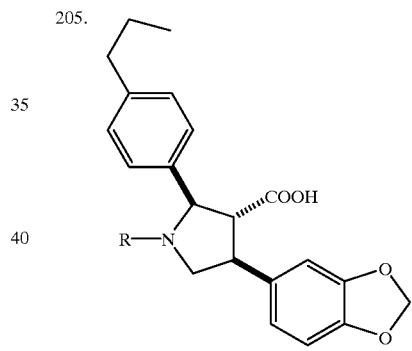
206. 
207. 

TABLE 2A-continued
208. 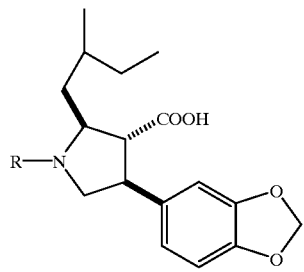
209. 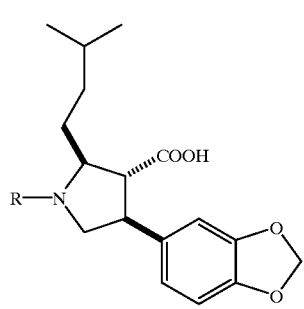
210. 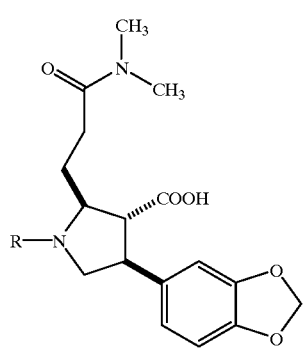
211. 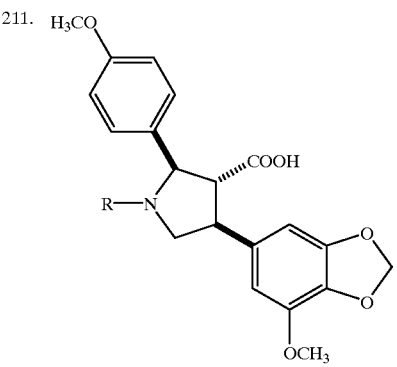
TABLE 2A-continued
212. 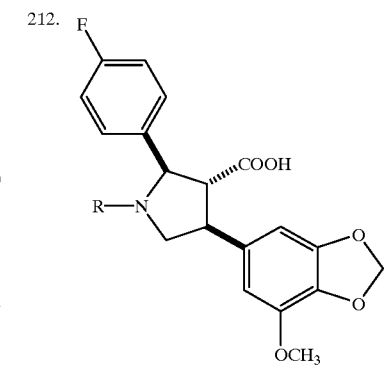
213. 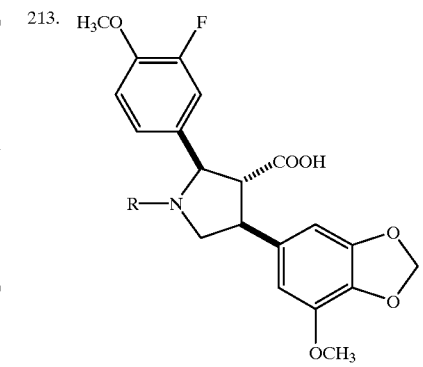
214. 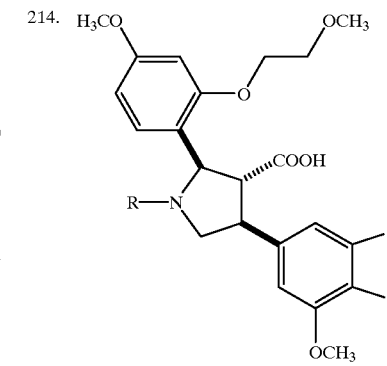
215. 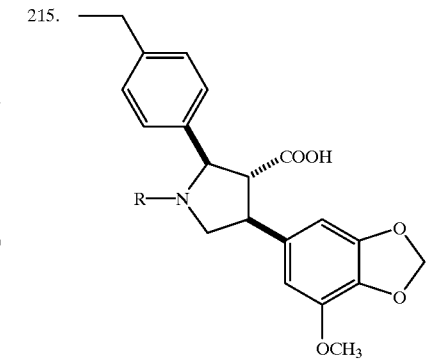

TABLE 2A-continued
216. 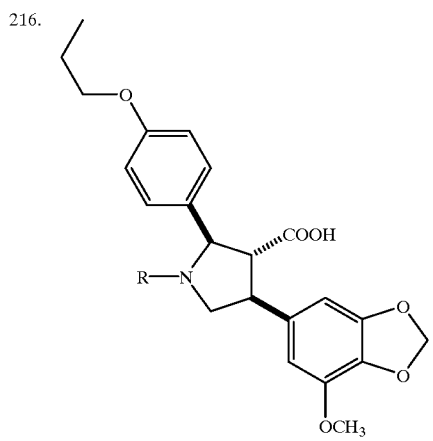
217. 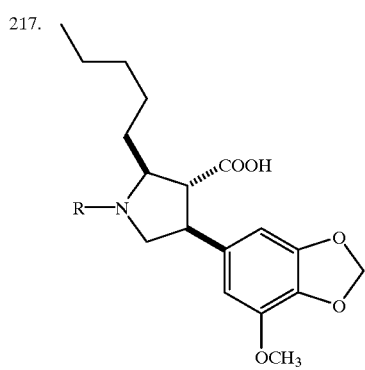
218. 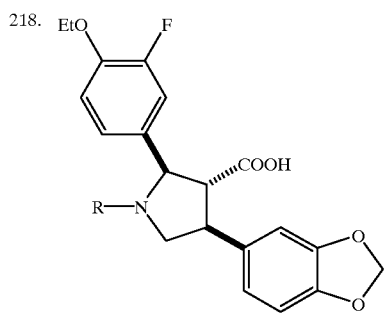
219. 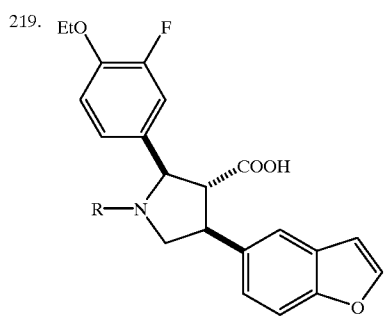
TABLE 2A-continued
220. 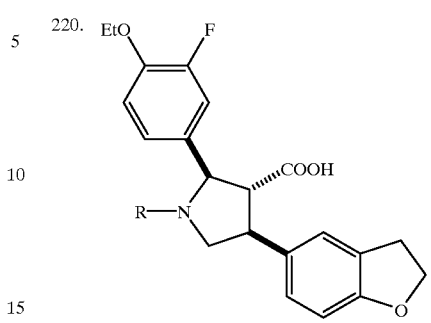
221. 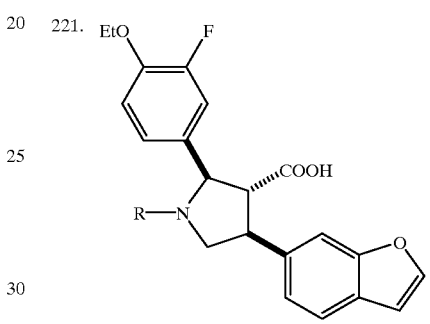
222. 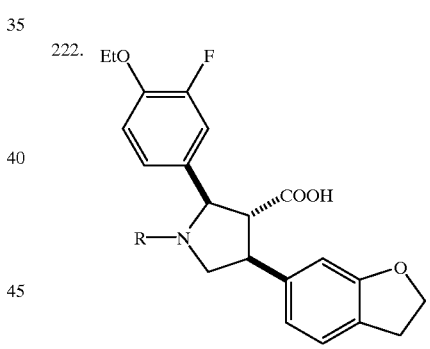
223. 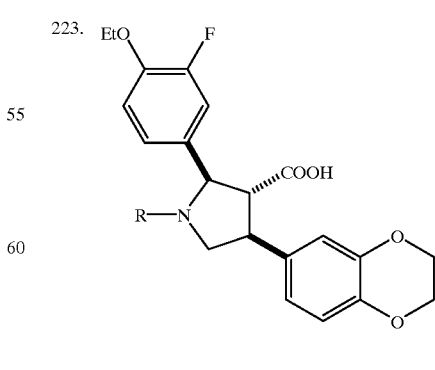

TABLE 2A-continued
224. 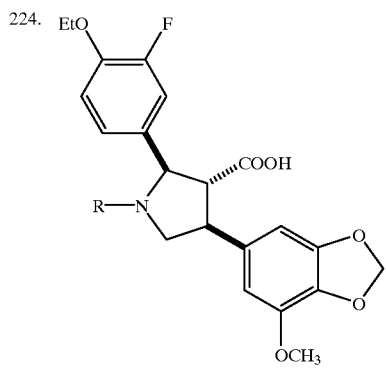
225. 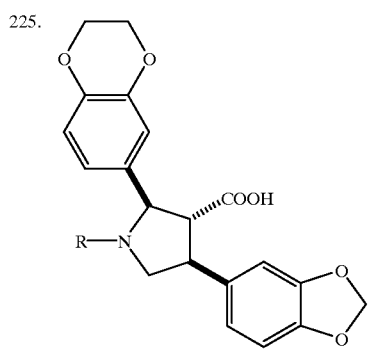
226. 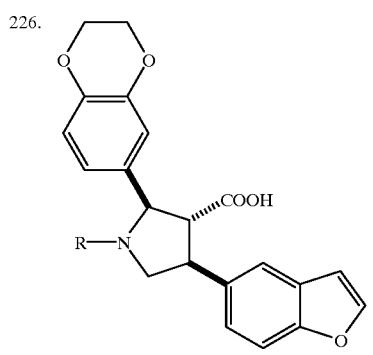
227. 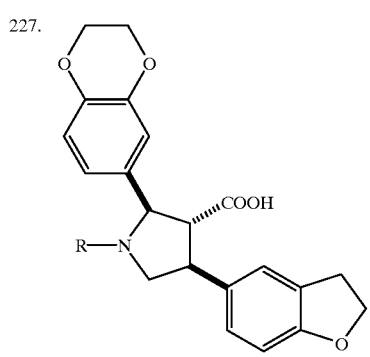
TABLE 2A-continued
228. 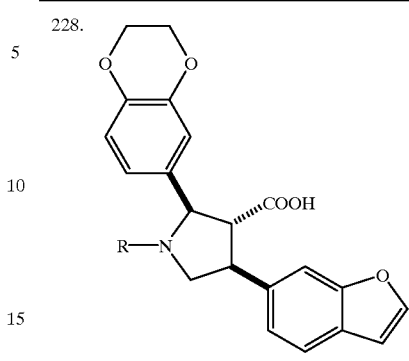
229. 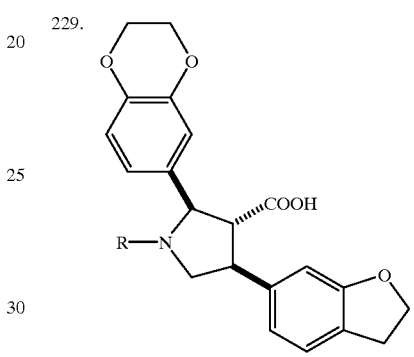
230. 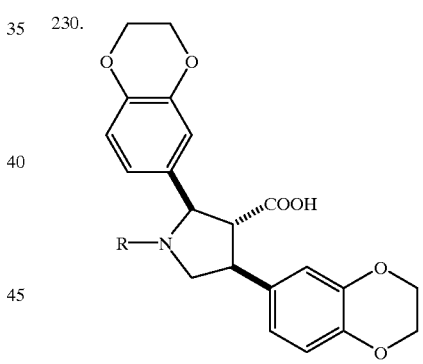
231. 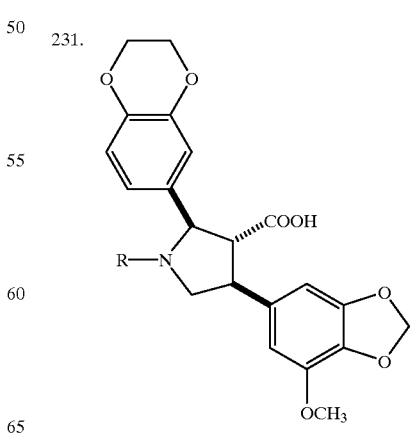

TABLE 2A-continued
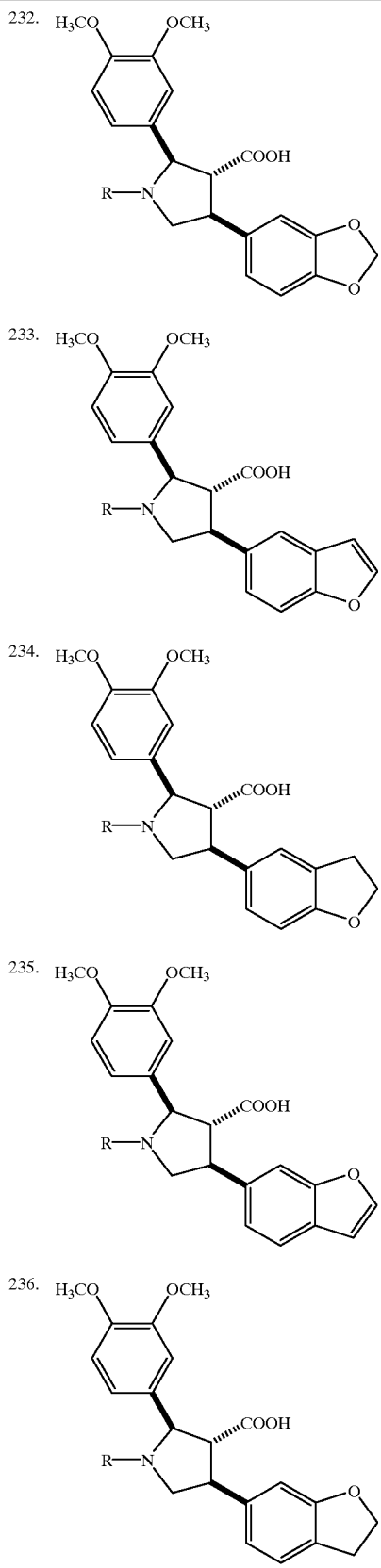
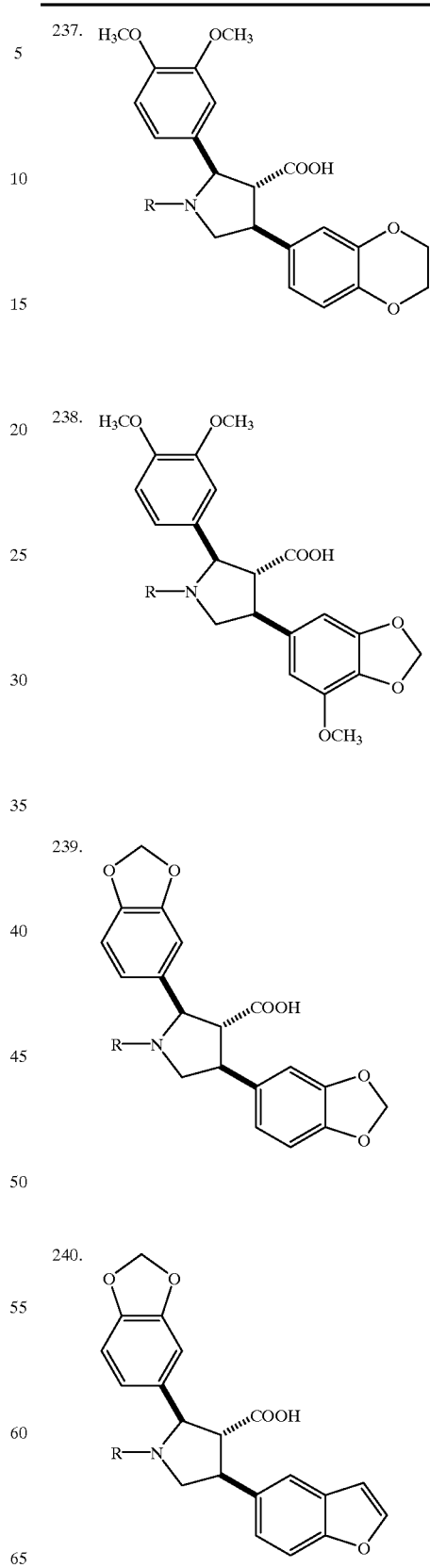

TABLE 2A-continued
241.
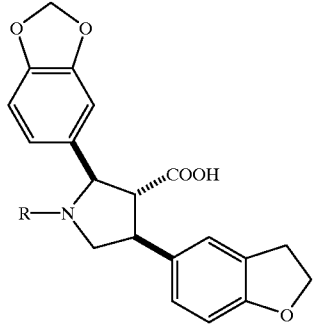
242.
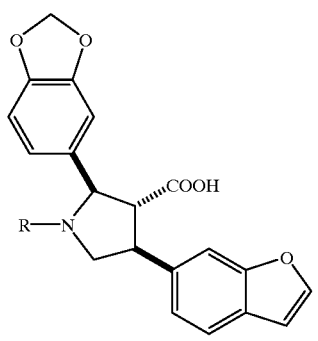
243.
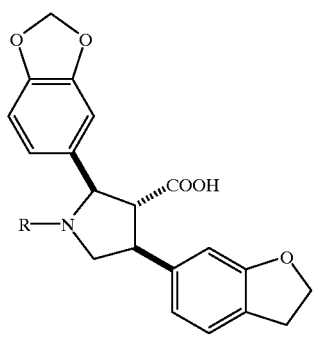
244.
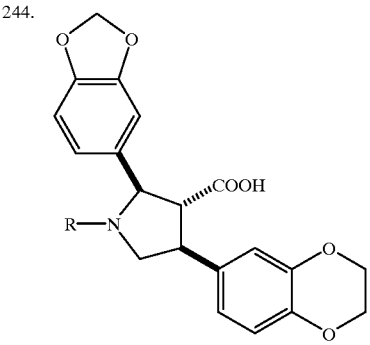
TABLE 2A-continued
245.
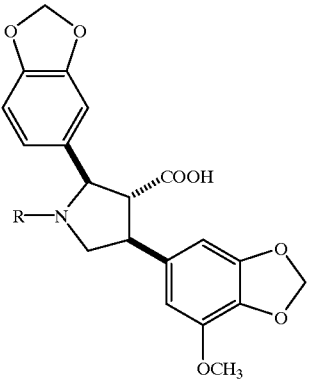
246.
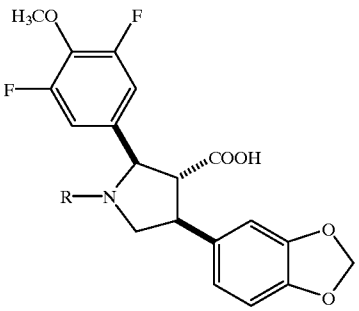
247.
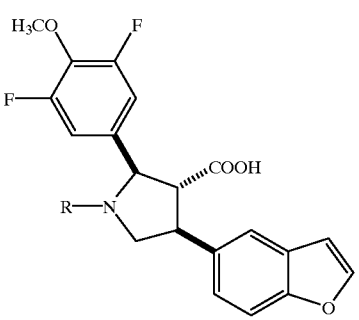
248.
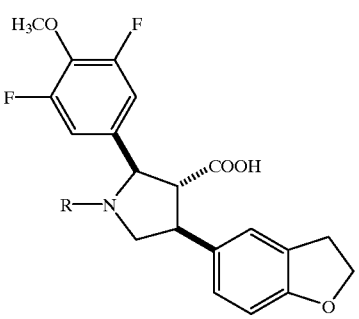

TABLE 2A-continued
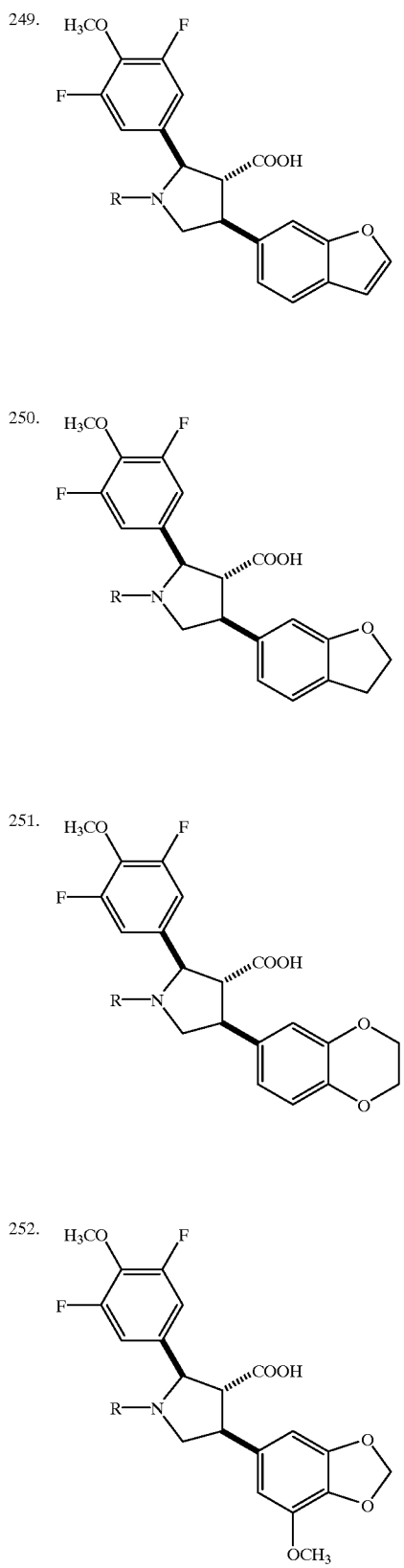
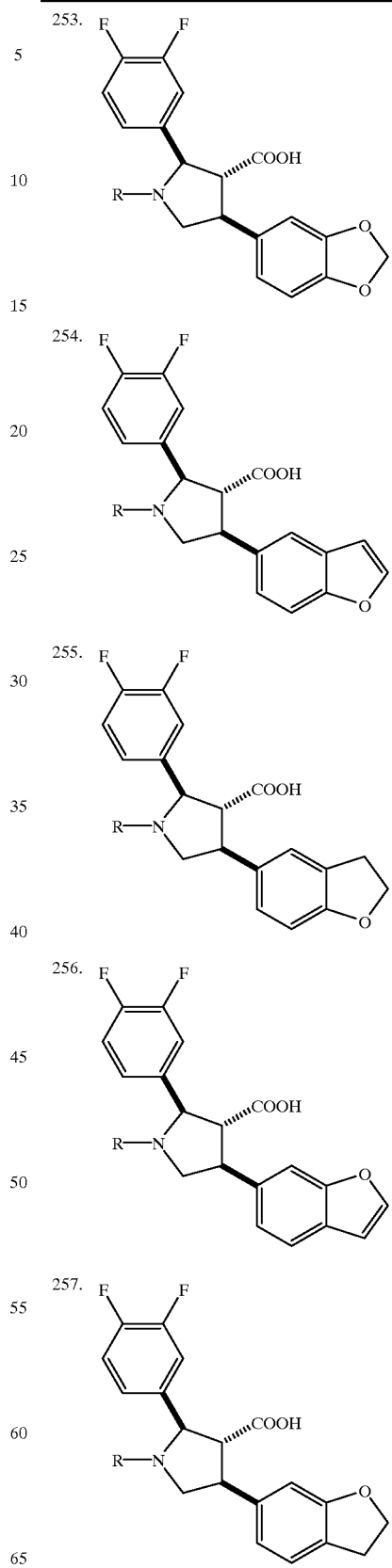

TABLE 2A-continued
258. 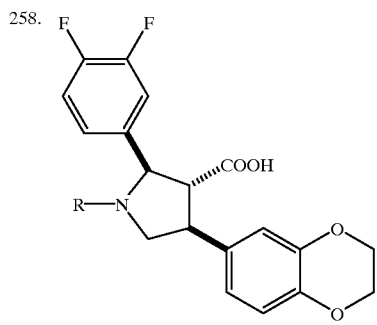
259. 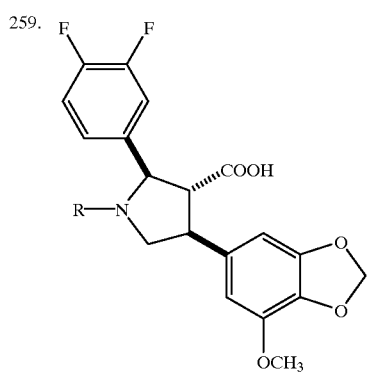
260. 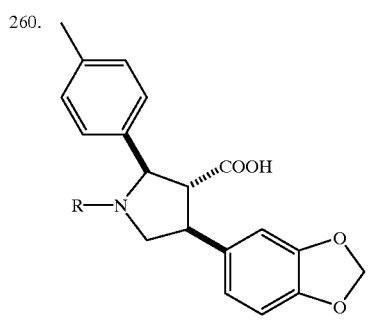
261. 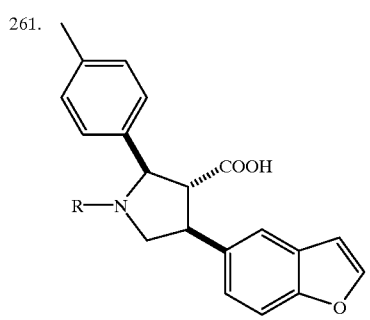
TABLE 2A-continued
262. 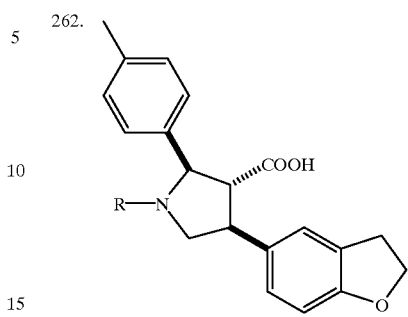
263. 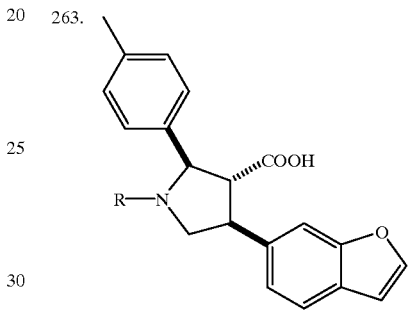
264. 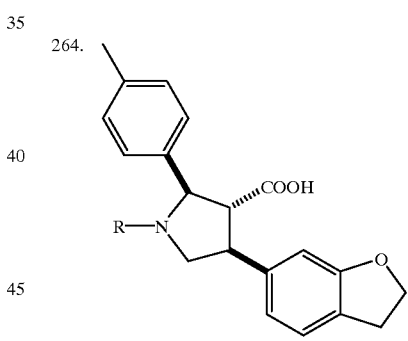
265. 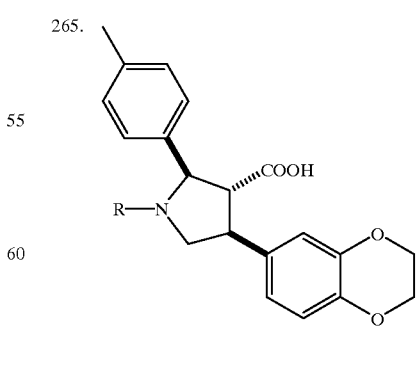

TABLE 2A-continued
266. 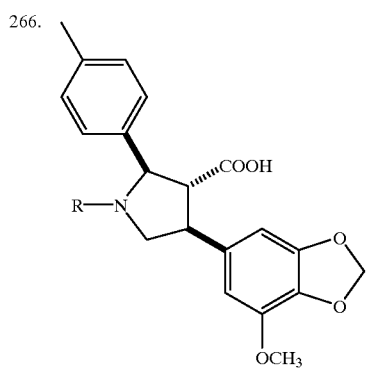
267. 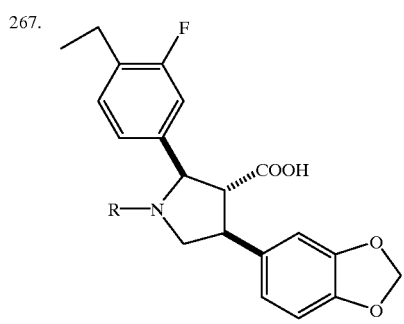
268. 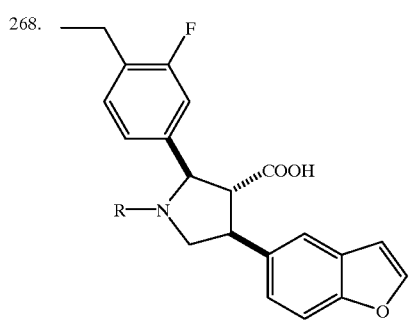
269. 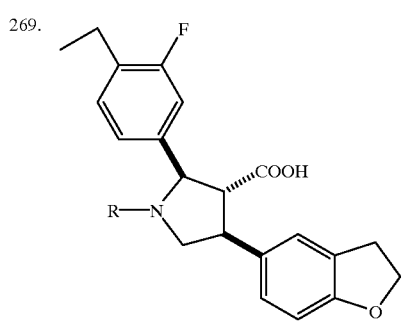
TABLE 2A-continued
270. 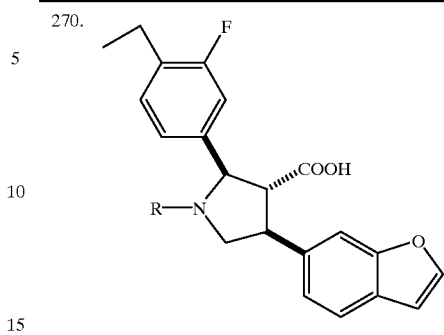
271. 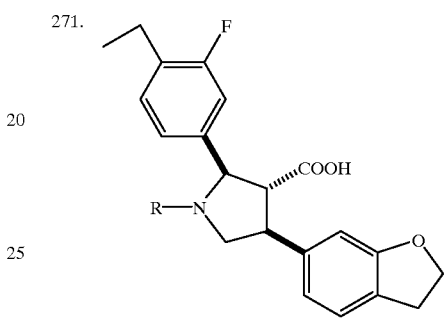
272. 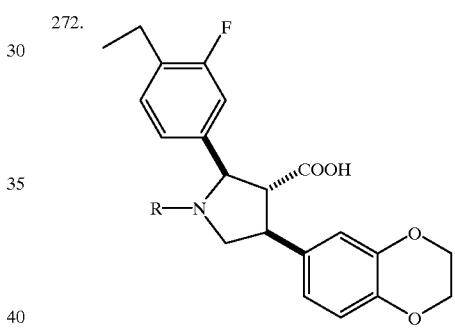
273. 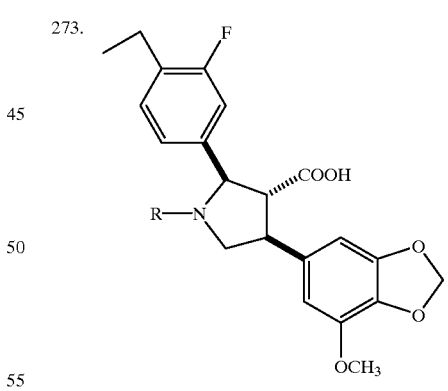
274. 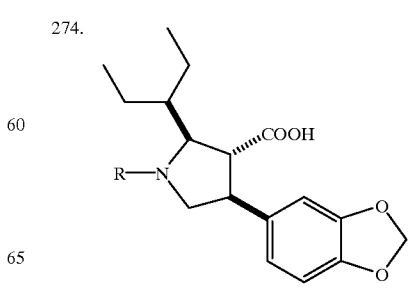

TABLE 2A-continued
275. 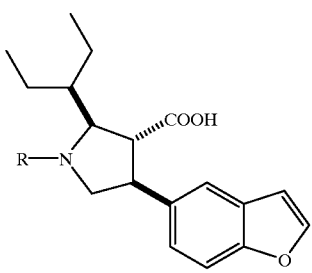
276. 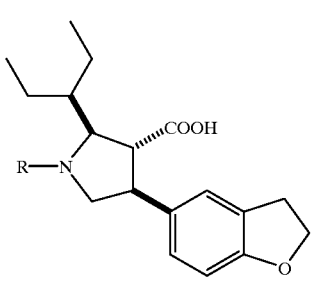
277. 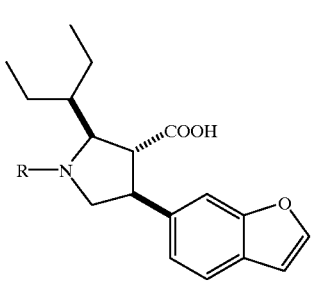
278. 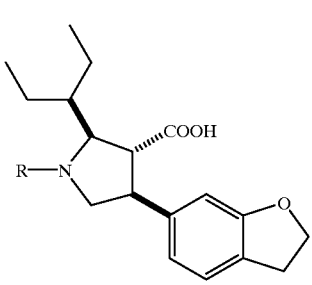
279. 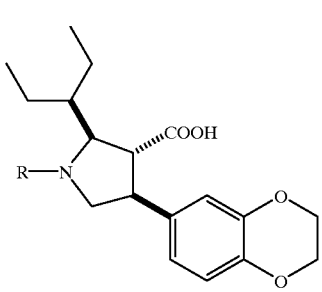
TABLE 2A-continued
280. 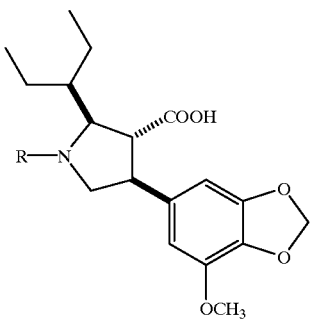
281. 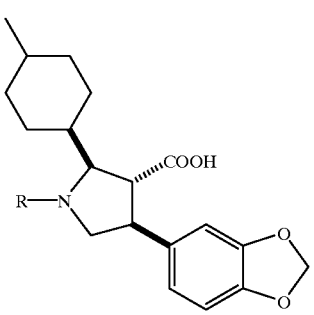
282. 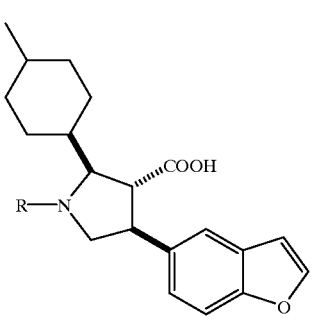
283. 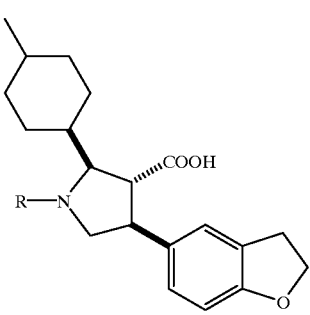
284. 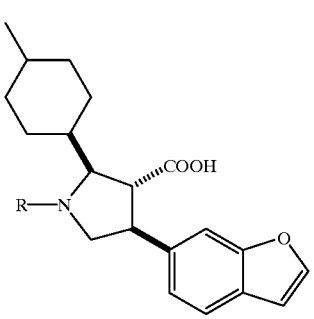

TABLE 2A-continued
285. 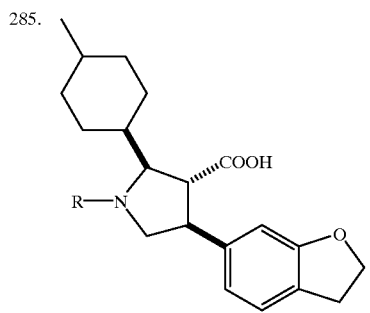
286. 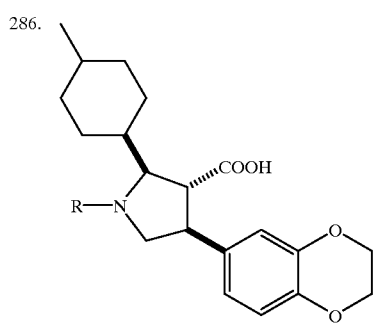
287. 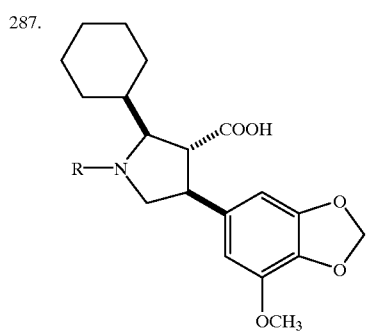
288. 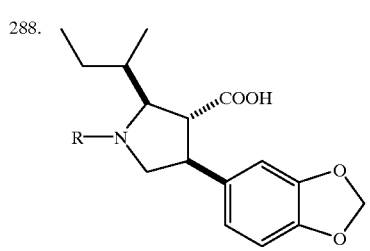
289. 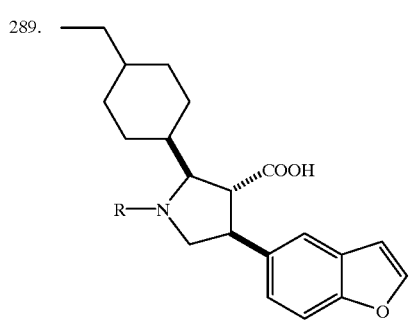
TABLE 2A-continued
290. 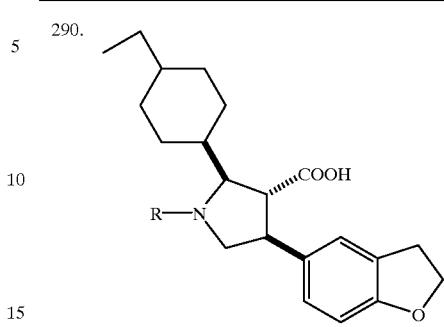
291. 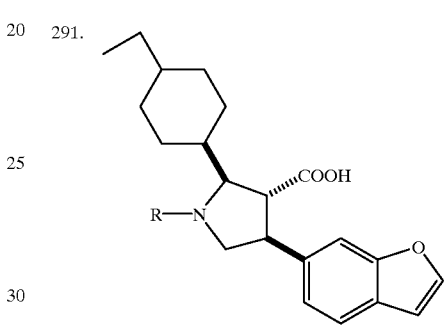
292. 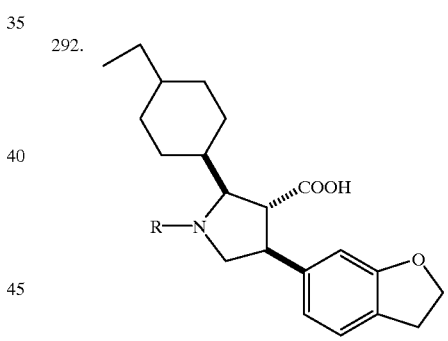
293. 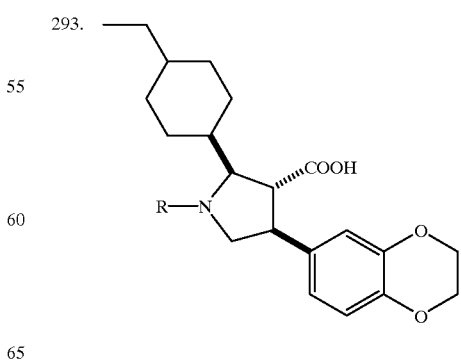

TABLE 2A-continued
294.
295.
296.
297.
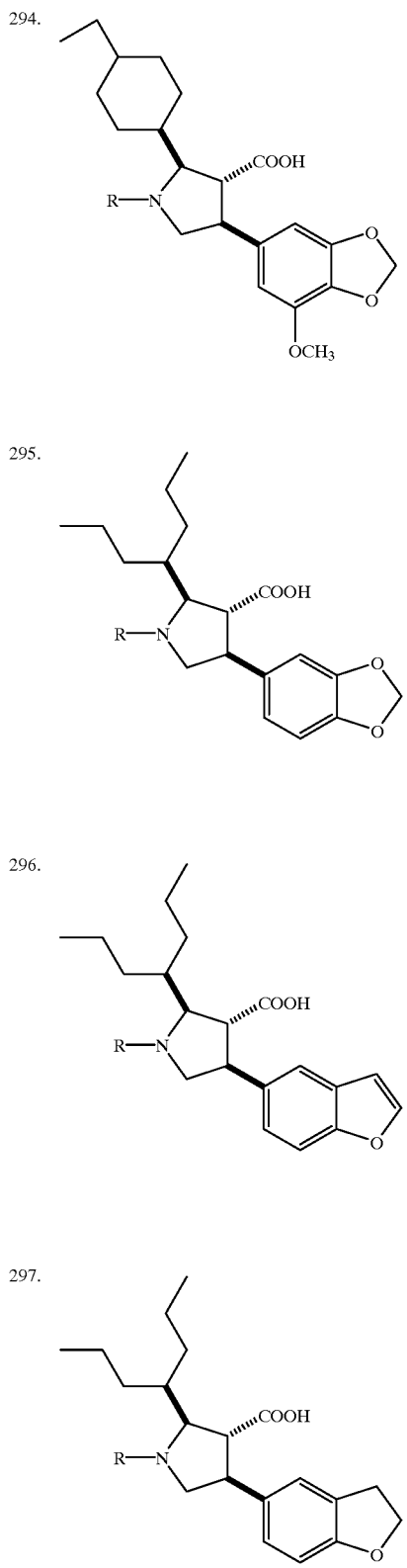
TABLE 2A-continued
298.
299.
300.
301.
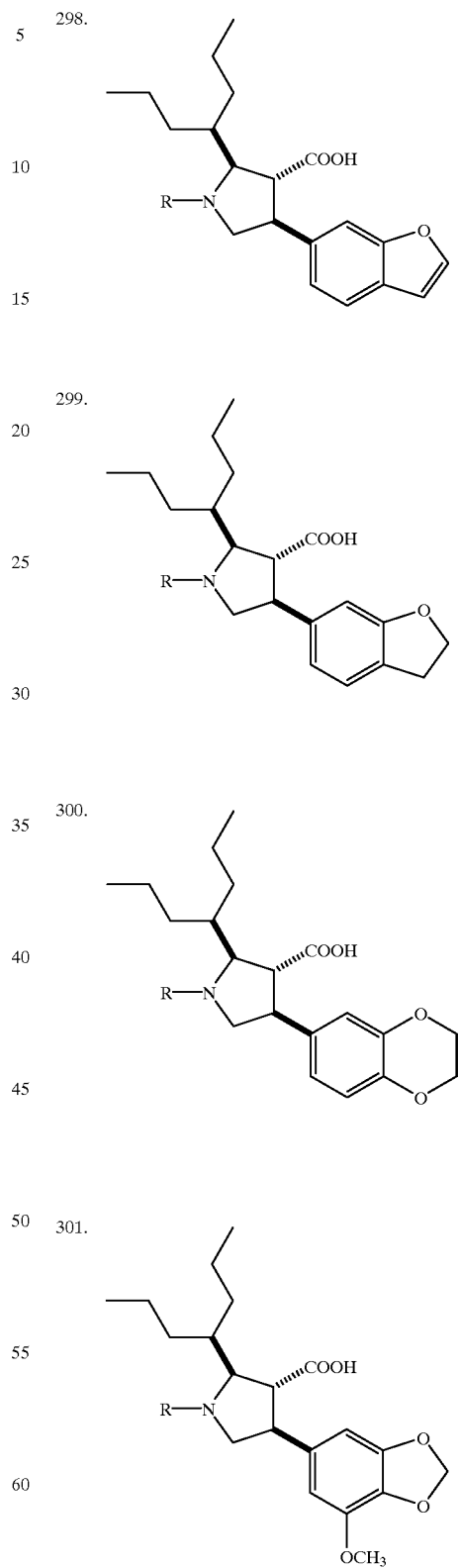

TABLE 2A-continued
302. 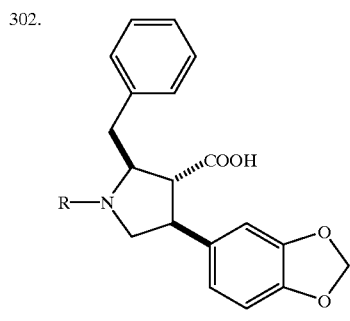
303. 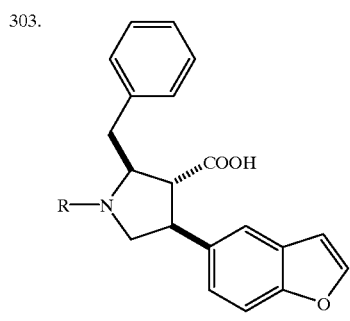
304. 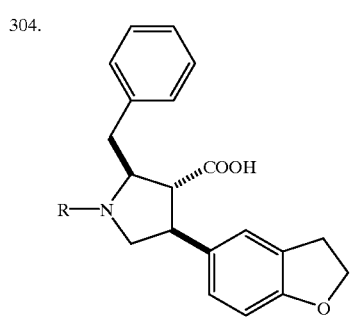
305. 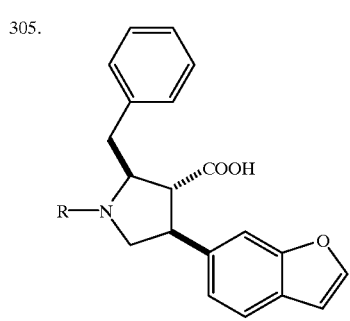
306. 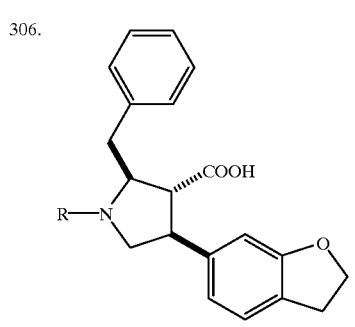
TABLE 2A-continued
307. 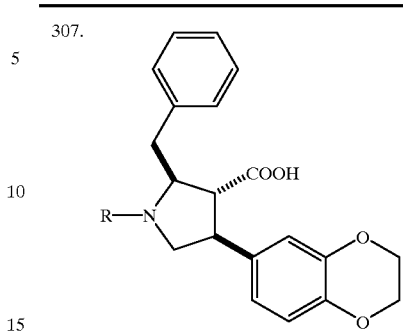
308. 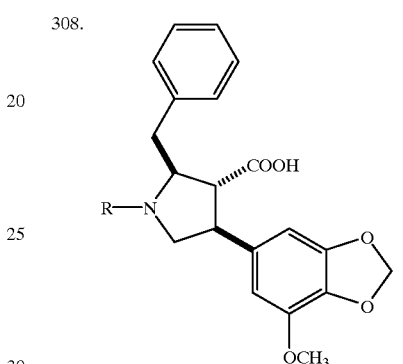
309. 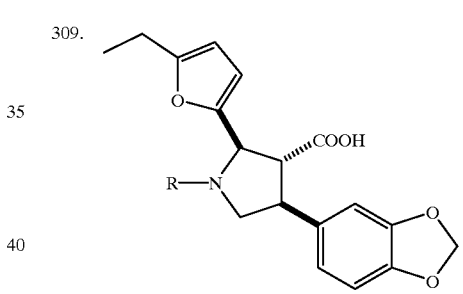
310. 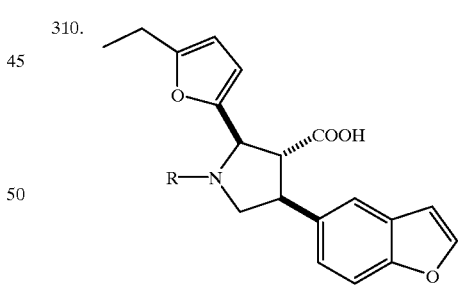
311. 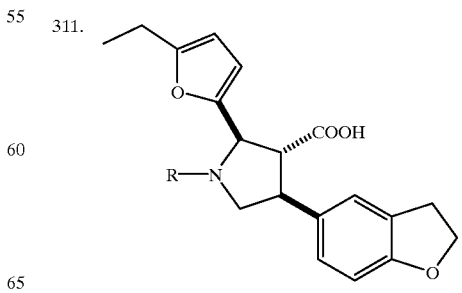

TABLE 2A-continued
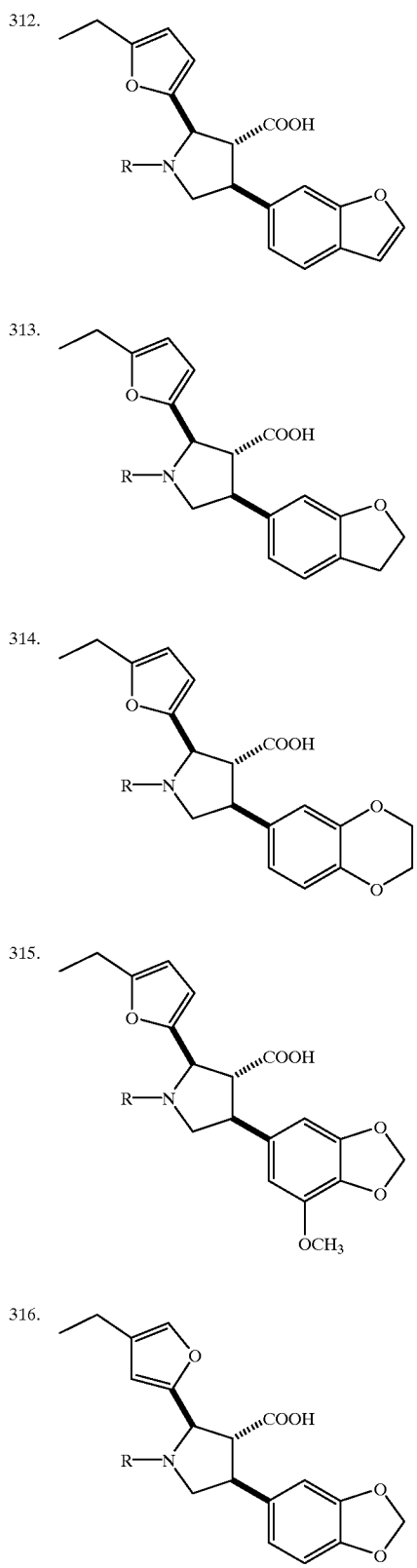
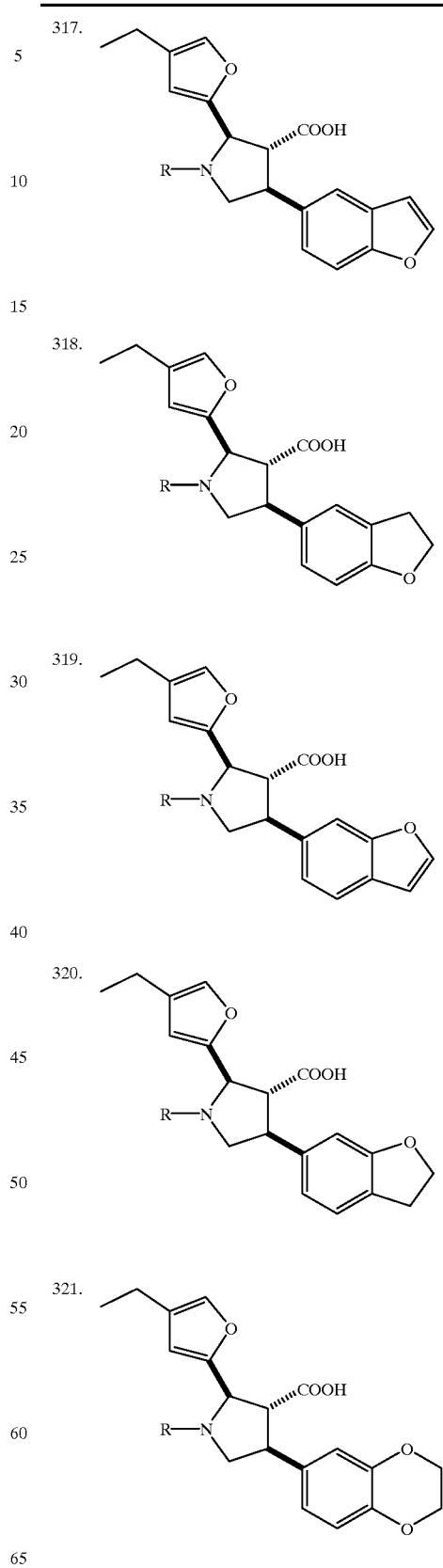

TABLE 2A-continued
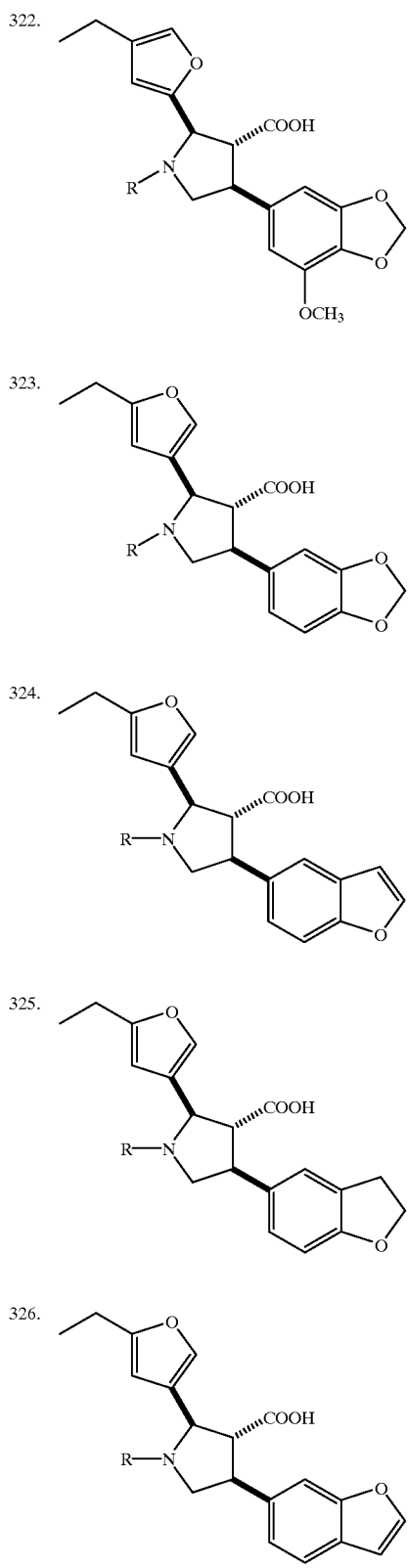
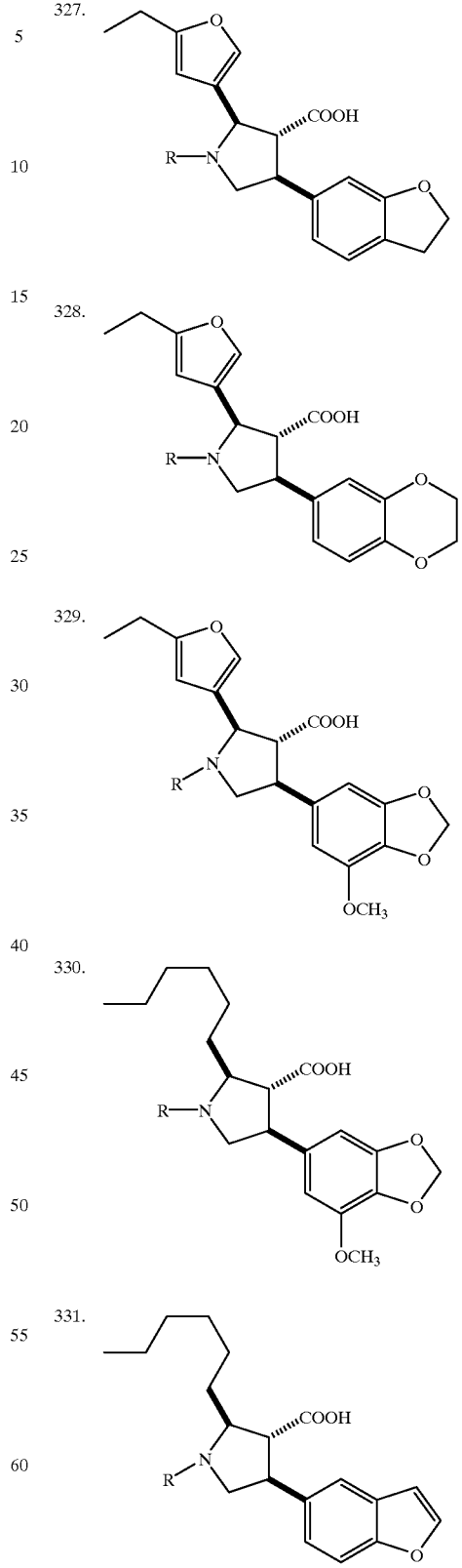

TABLE 2A-continued
332. 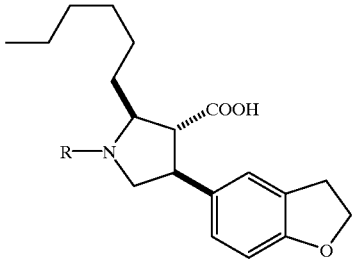
333. 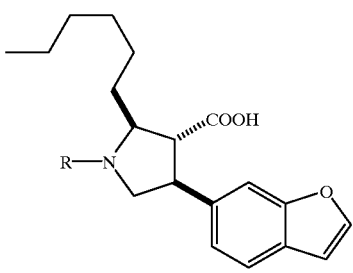
334. 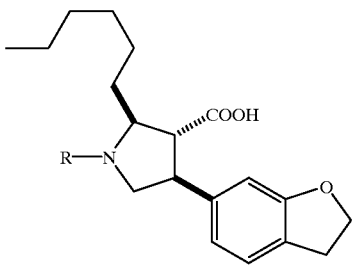
335. 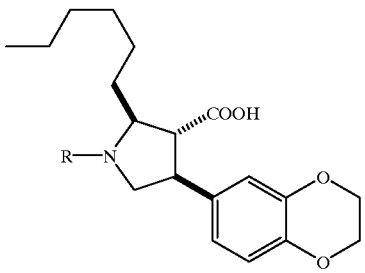
336. 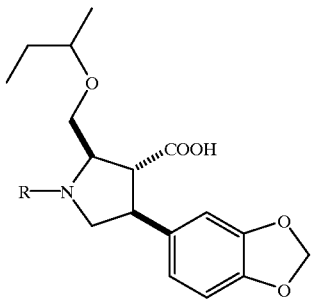
TABLE 2A-continued
337. 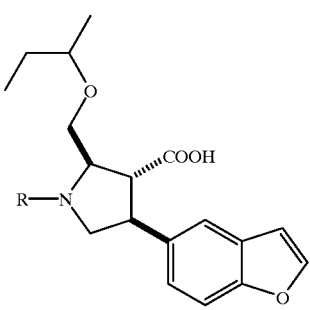
338. 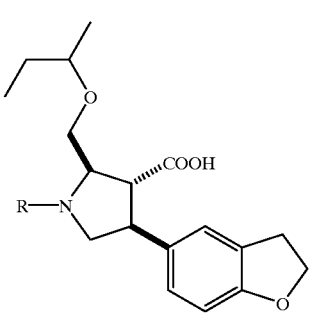
339. 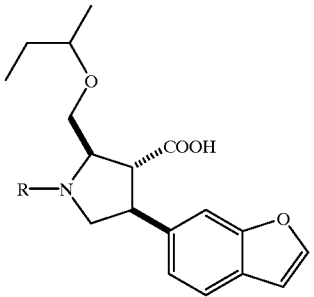
340. 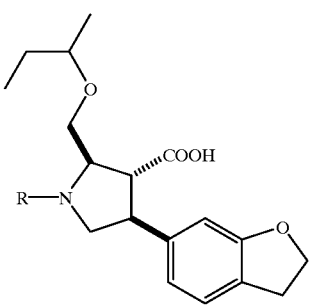
341. 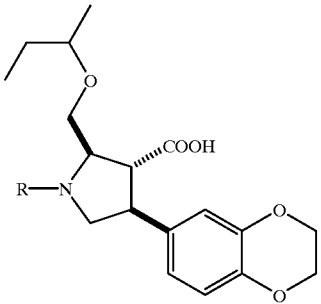

TABLE 2A-continued
342.
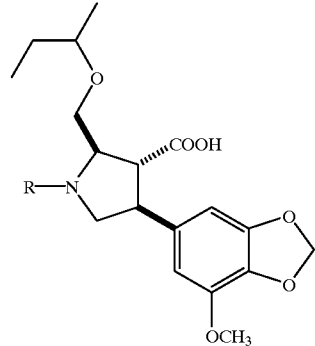
343.
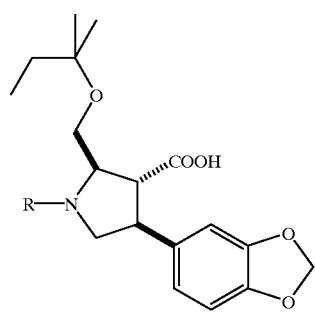
344.
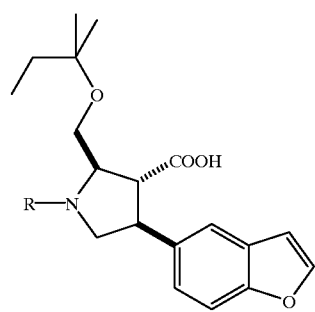
345.
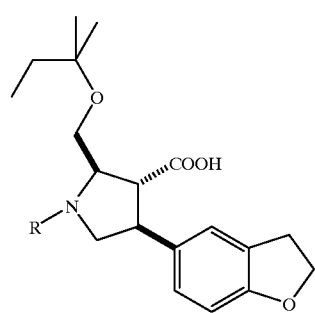
TABLE 2A-continued
346.
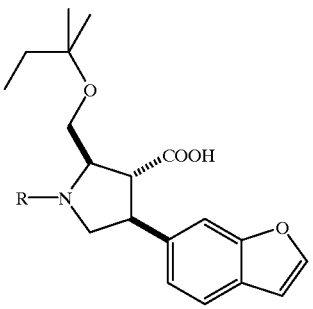
347.
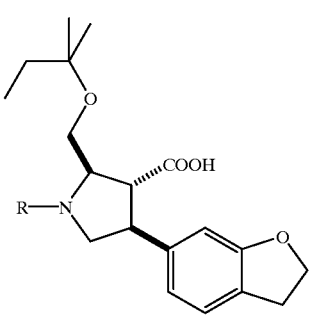
348.
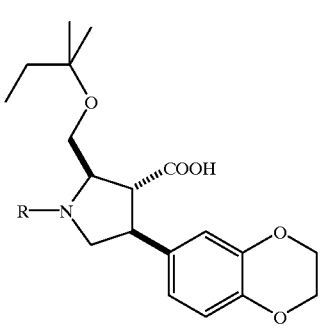
349.
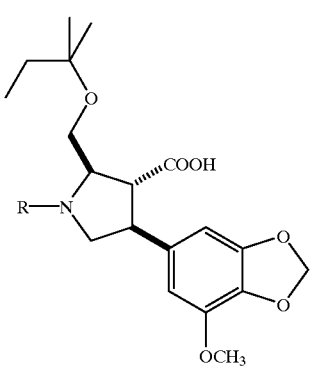

TABLE 2A-continued
350. 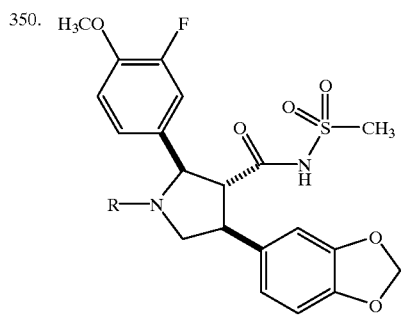
351. 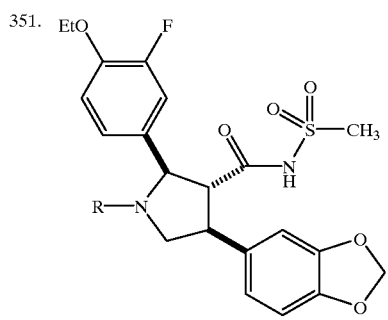
352. 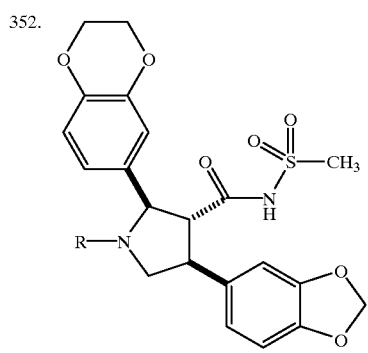
353. 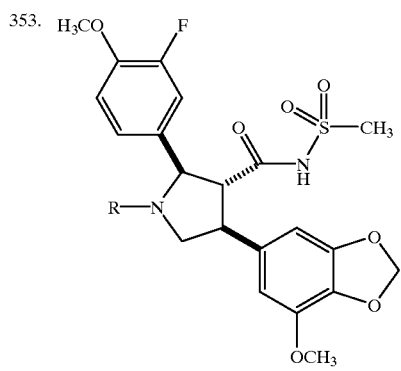
TABLE 2A-continued
354. 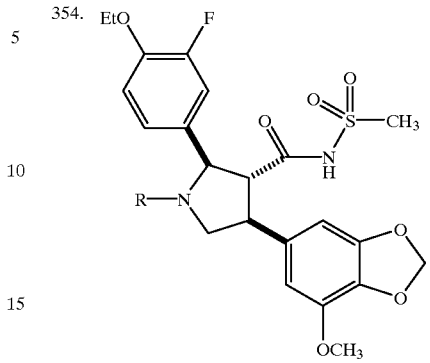
355. 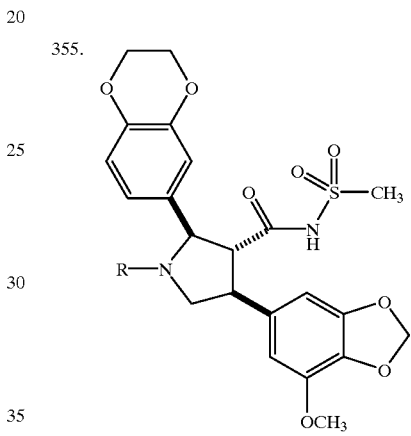
356. 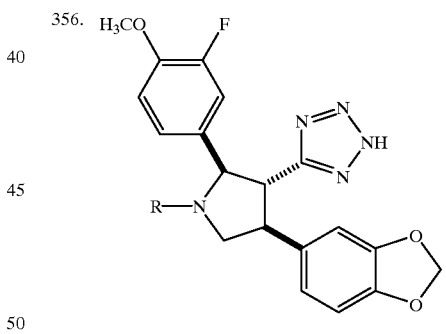
357. 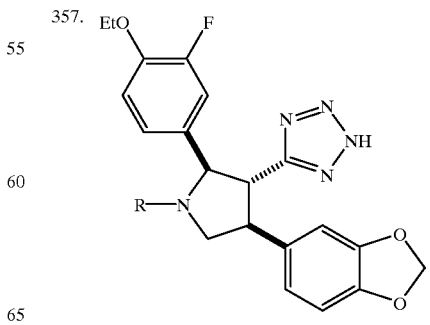

TABLE 2A-continued
358. 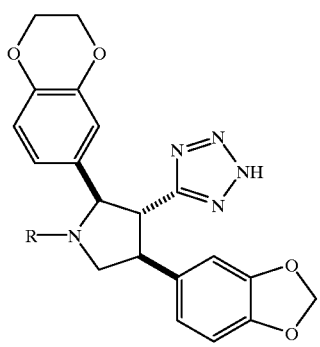
359. 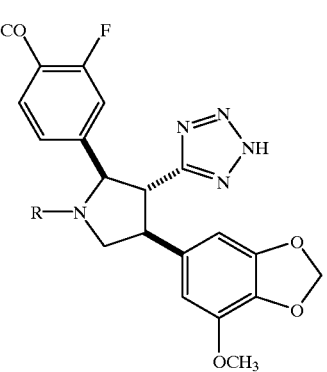
360. 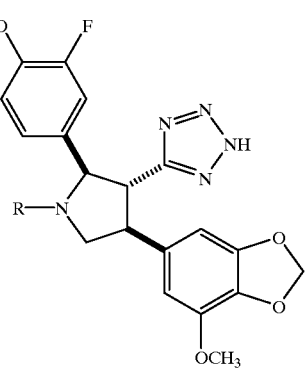
361. 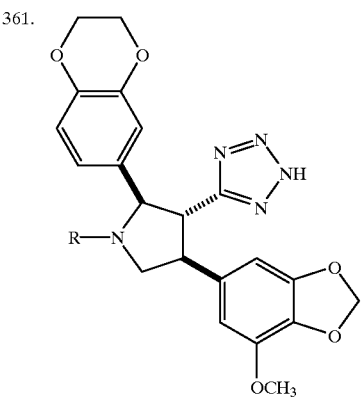
TABLE 2A-continued
362. 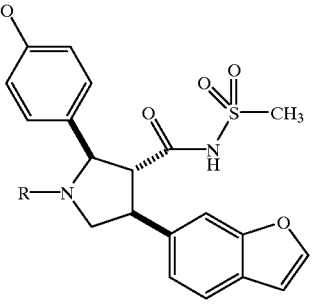
363. 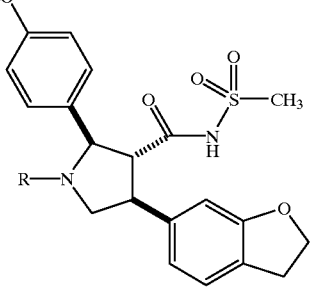
364. 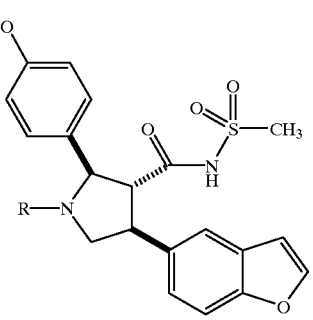
365. 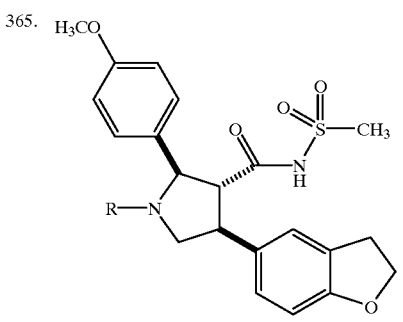
366. 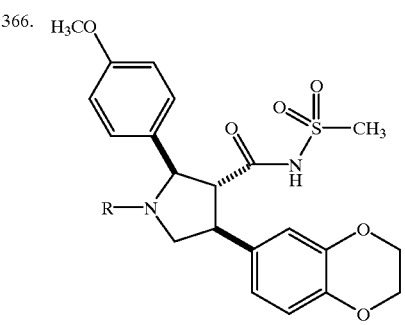

TABLE 2A-continued
367. 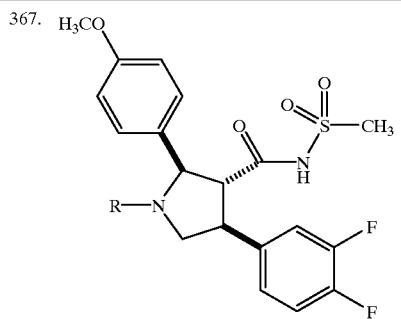
368. 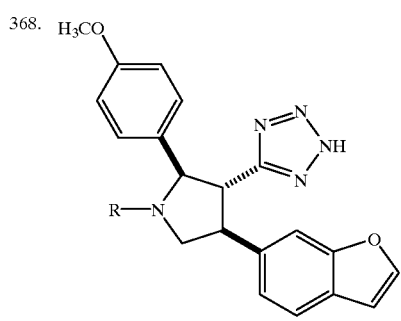
369. 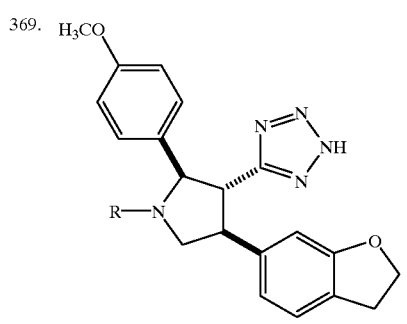
370. 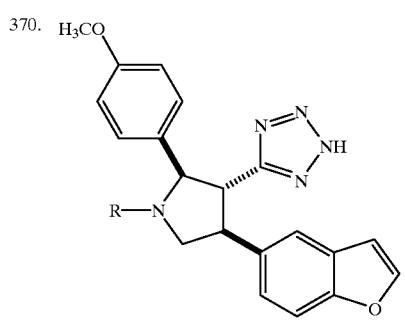
371. 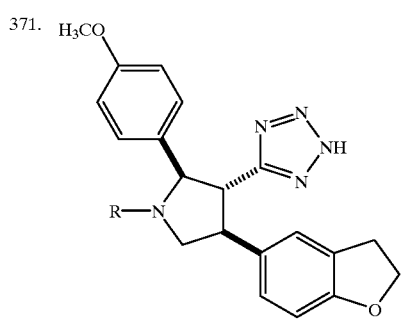
TABLE 2A-continued
372. 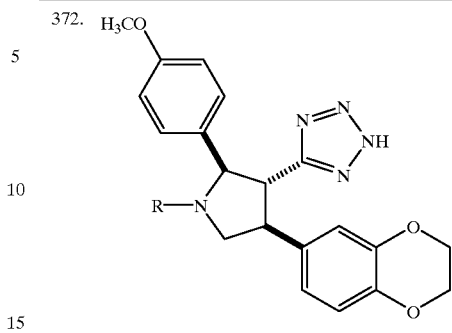
373. 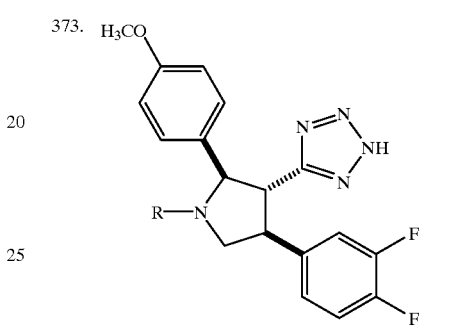
374. 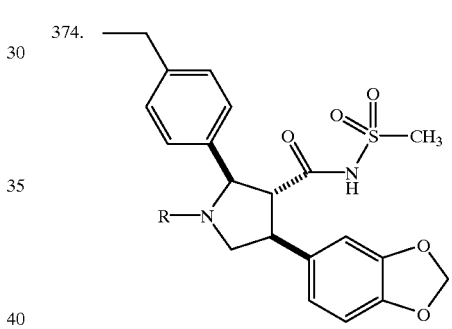
375. 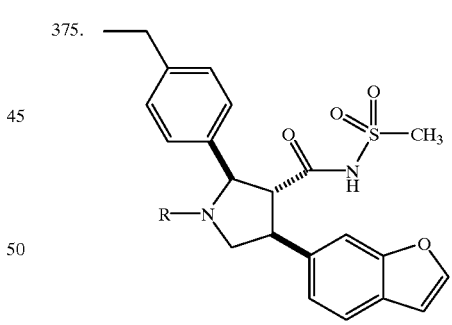
376. 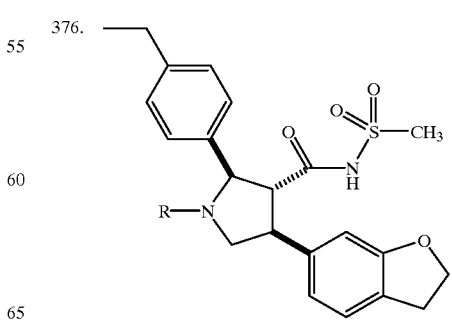

TABLE 2A-continued
377. 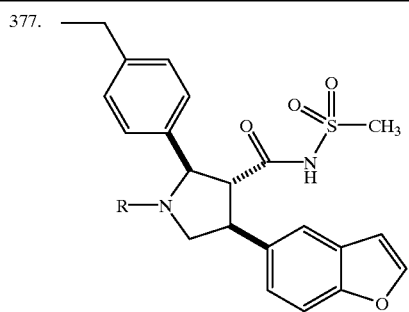
378. 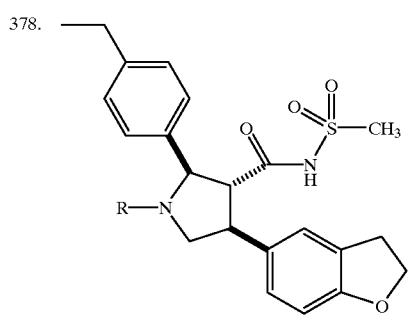
379. 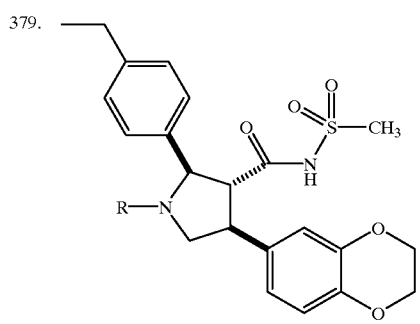
380. 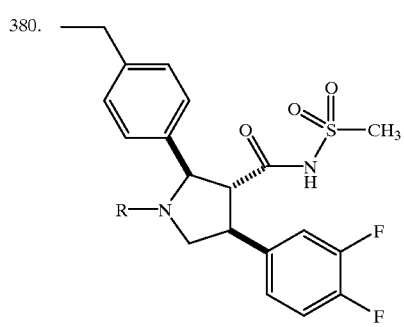
381. 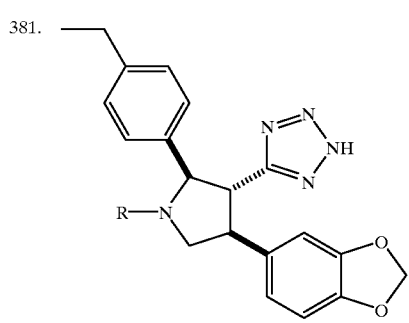
TABLE 2A-continued
382. 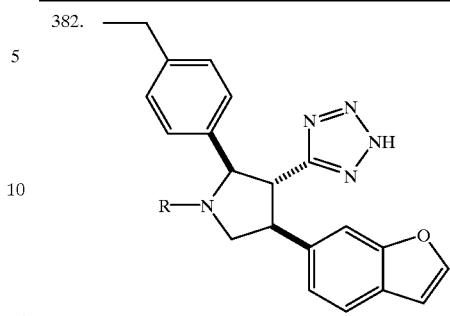
383. 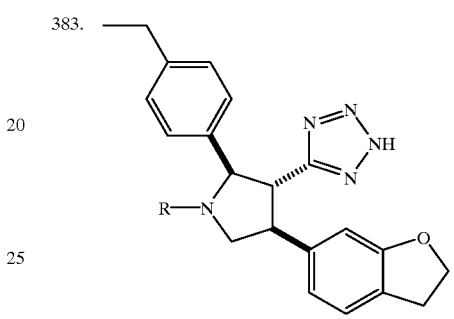
384. 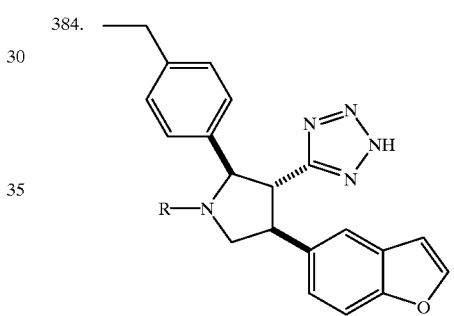
385. 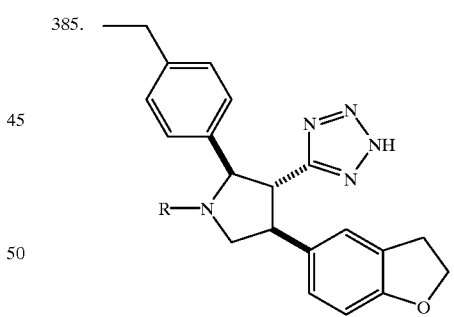
386. 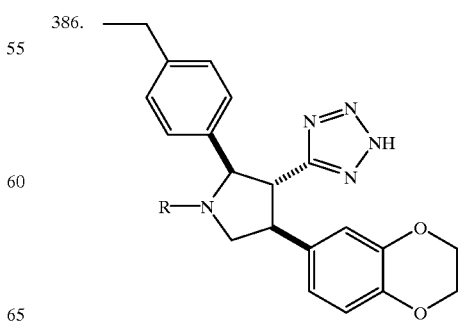

TABLE 2A-continued
387. 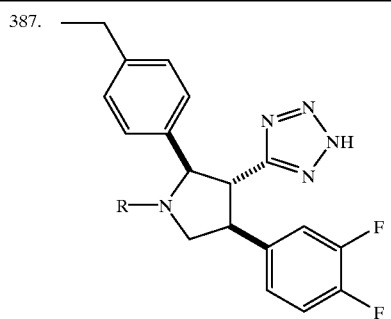
388. 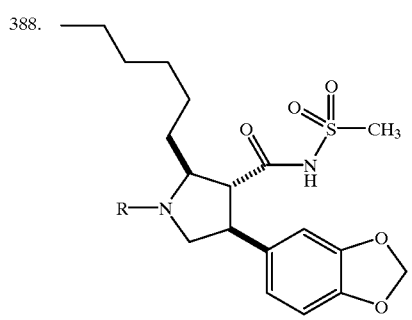
389. 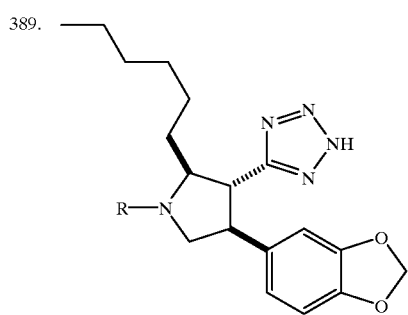
390. 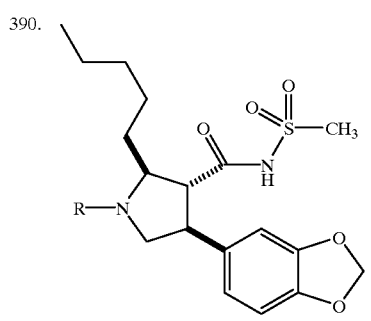
391. 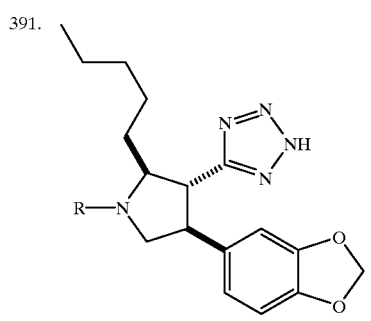
TABLE 2A-continued
392. 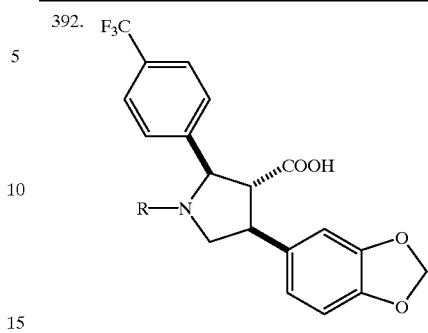
393. 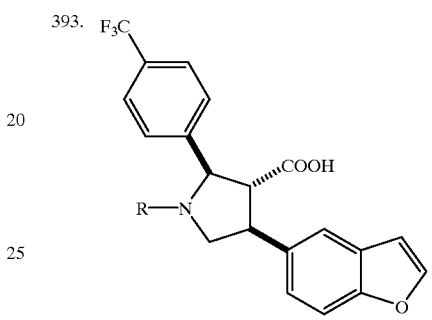
394. 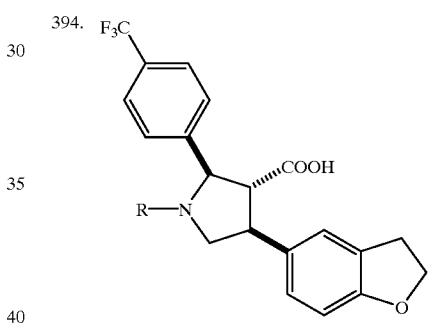
395. 
396. 

TABLE 2A-continued
397. 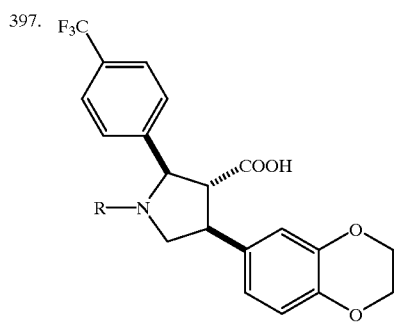
398. 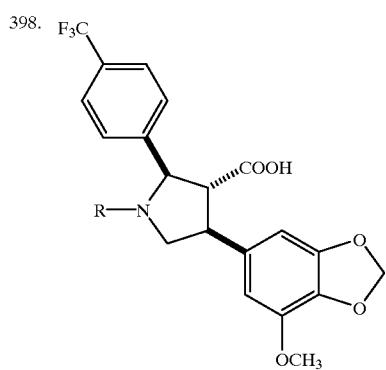
399. 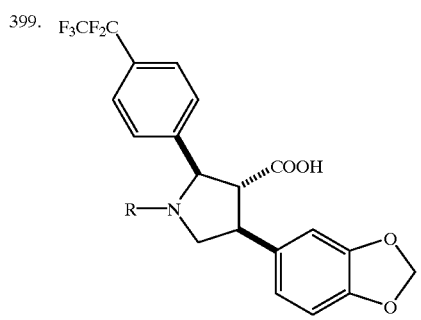
400. 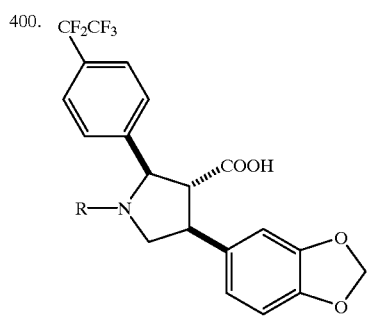
TABLE 2A-continued
401. 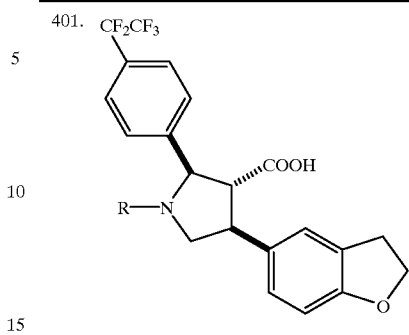
402. 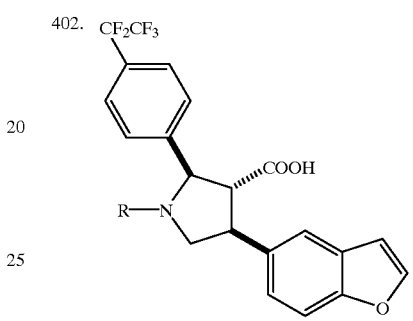
403. 
404. 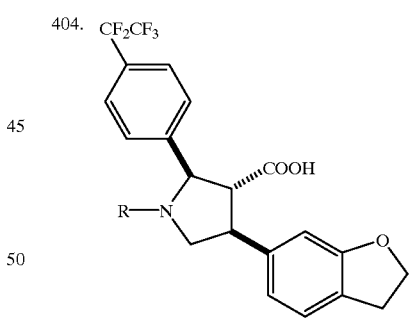
405. 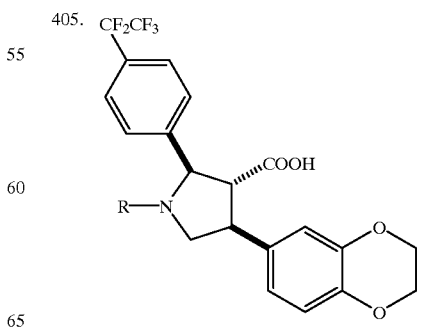

TABLE 2A-continued
406. 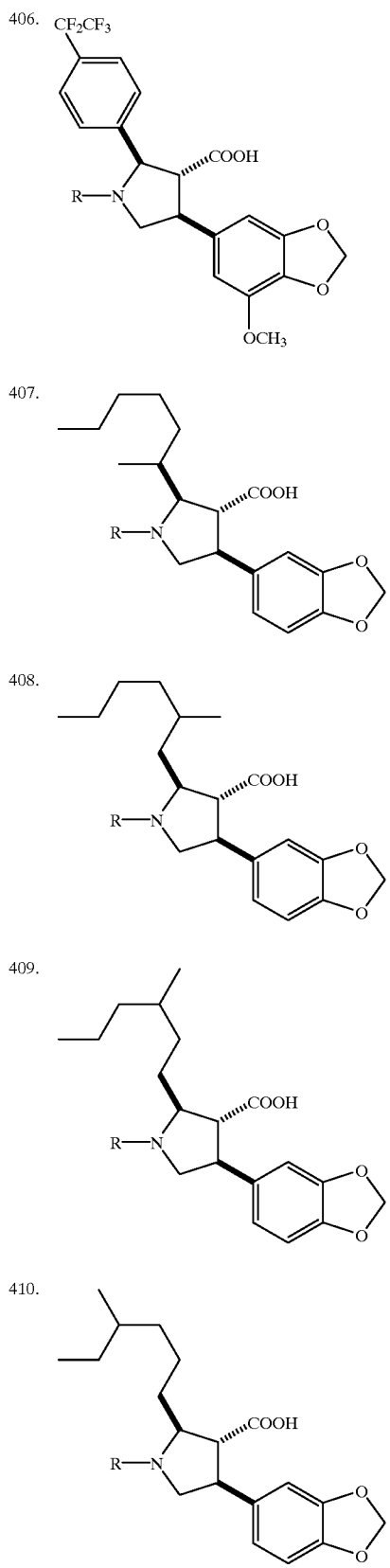
407.
408.
409.
410.
TABLE 2A-continued
411. 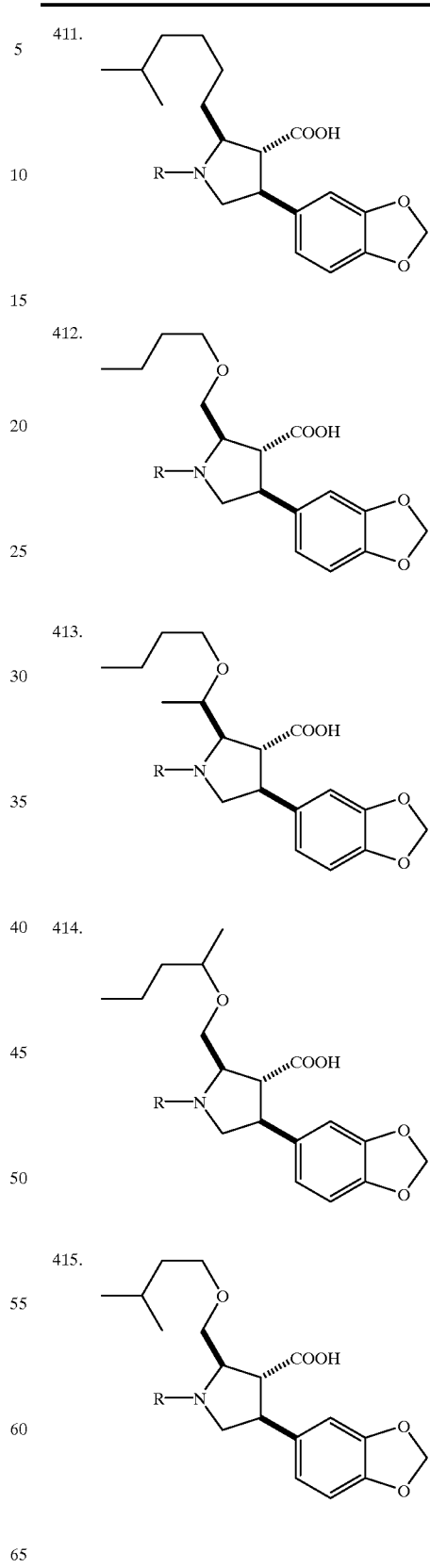
412.
413.
414.
415.

TABLE 2A-continued
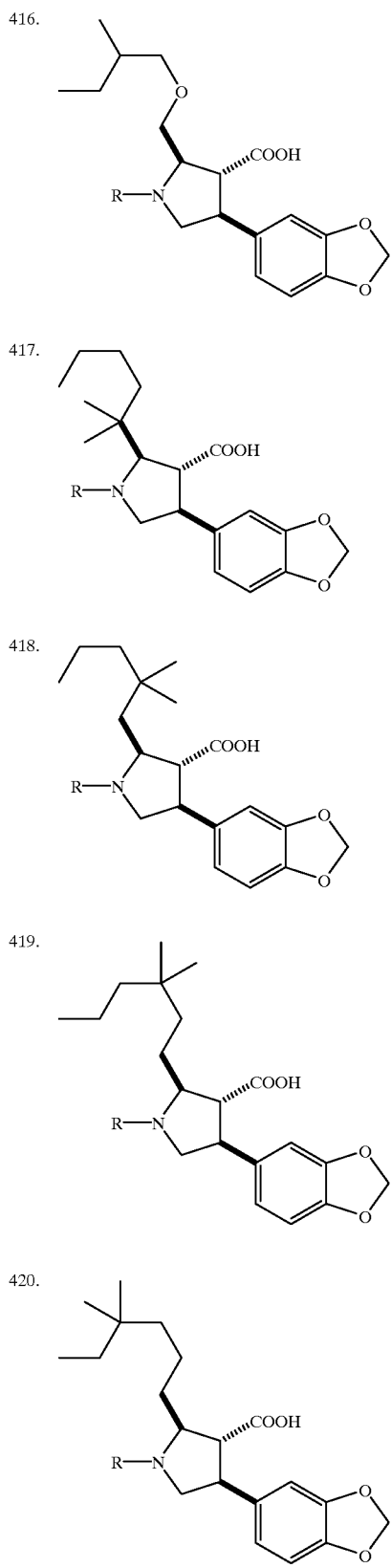
416.
417.
418.
419.
420.
TABLE 2A-continued
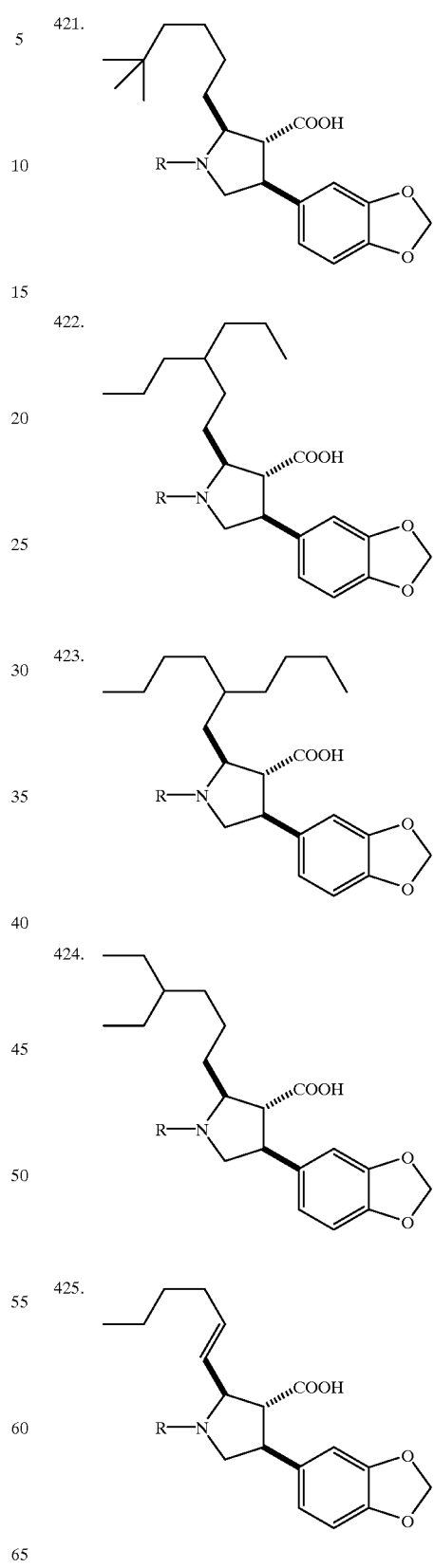
421.
422.
423.
424.
425.

TABLE 2A-continued
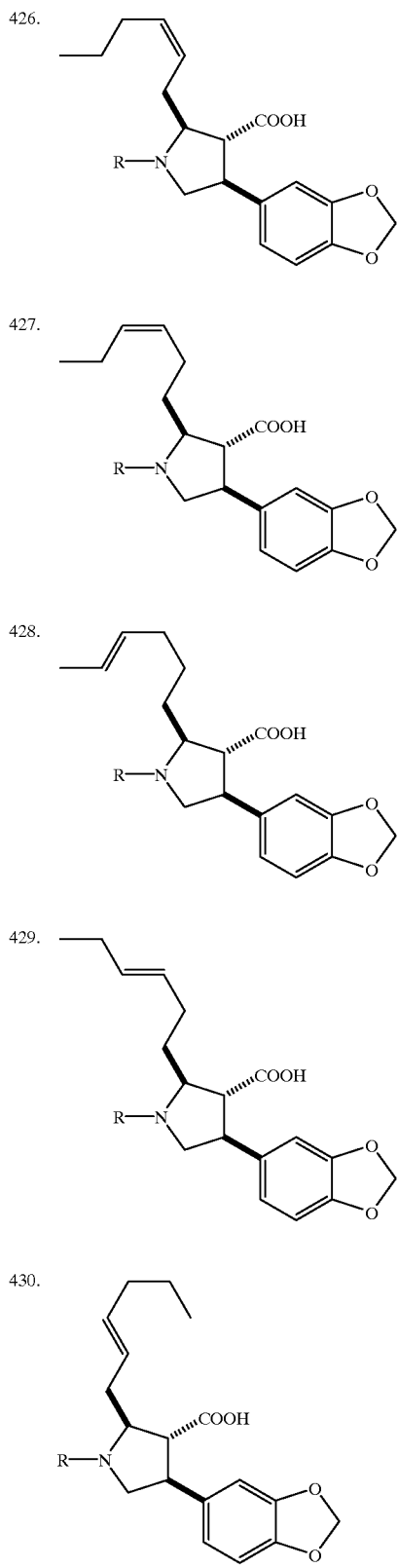
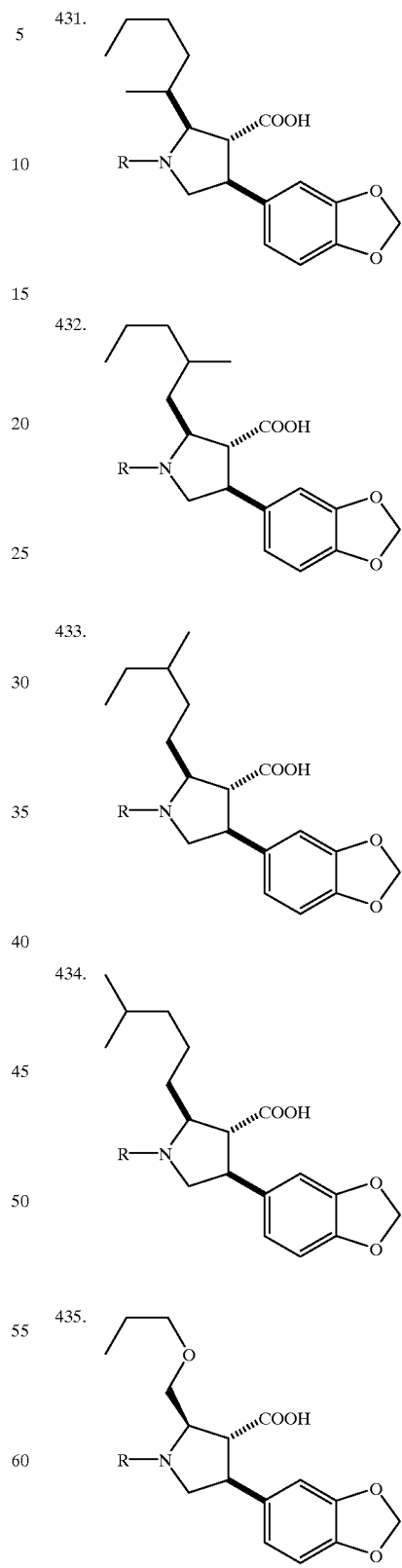

TABLE 2A-continued
436. 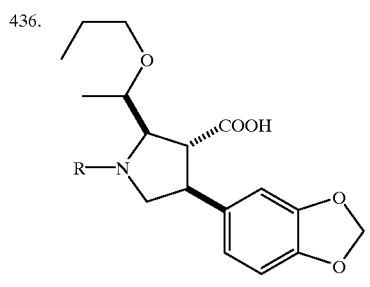
437. 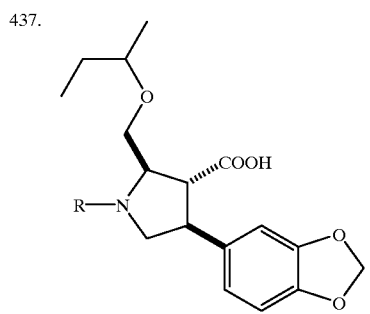
438. 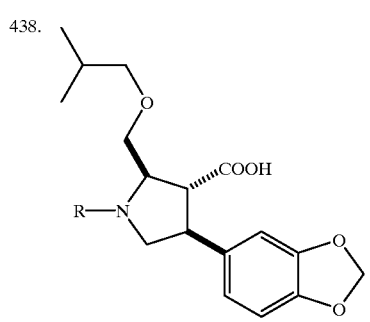
439. 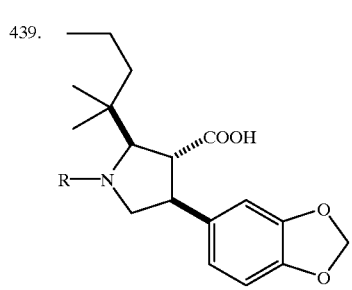
440. 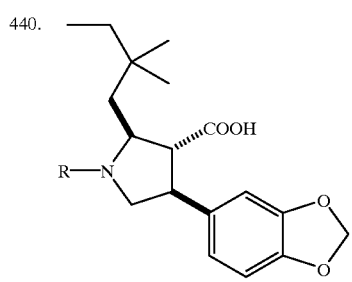
TABLE 2A-continued
441. 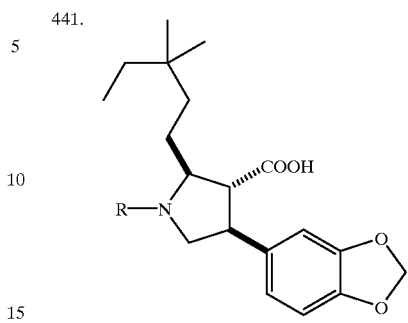
442. 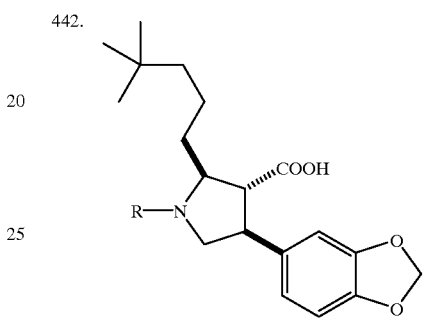
443. 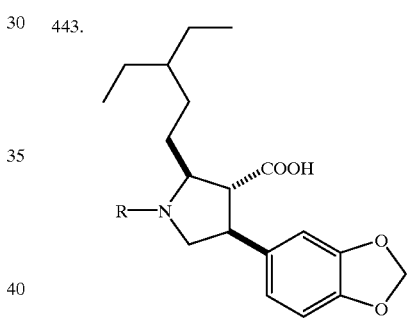
444. 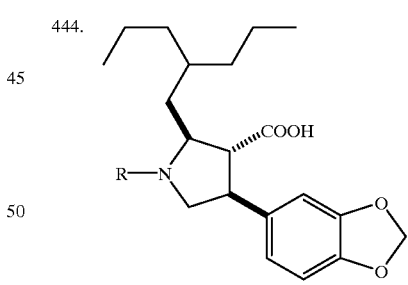
445. 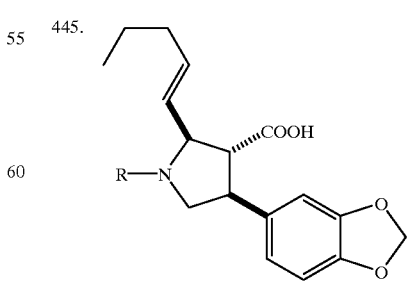

TABLE 2A-continued
446.
447.
448.
449.
450.
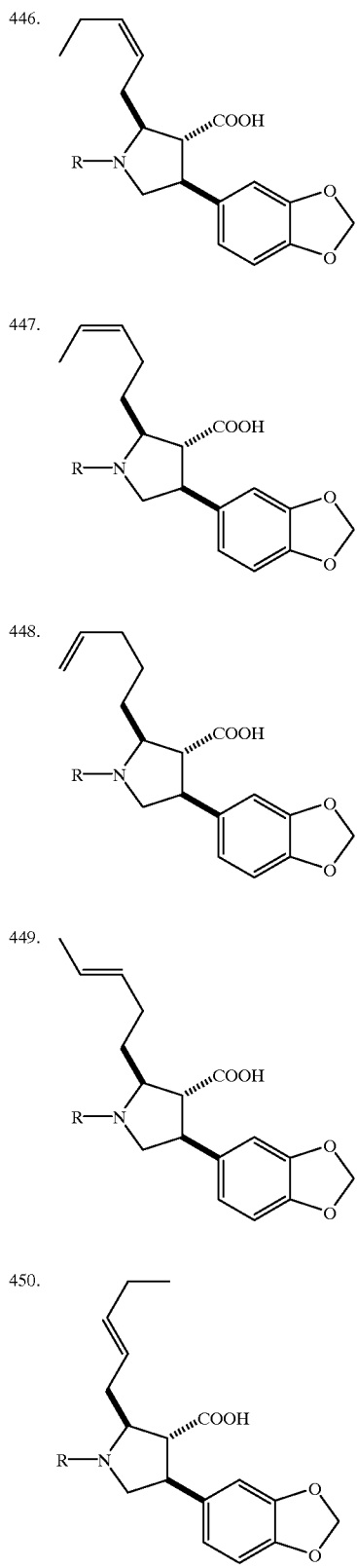
TABLE 2A-continued
451.
452.
453.
454.
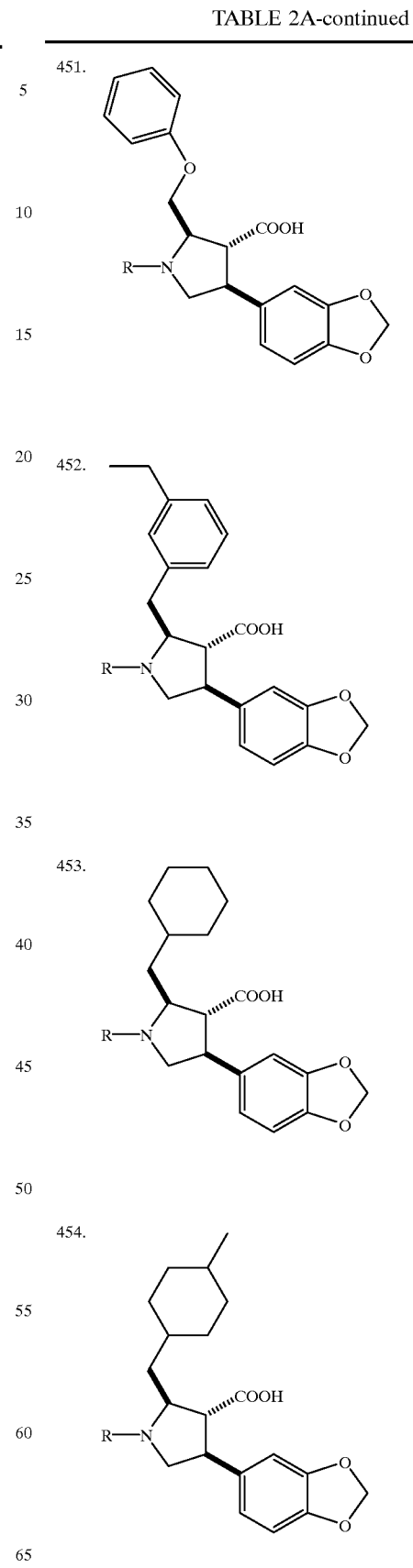

TABLE 2A-continued
| | |
|---|---|
| 455. | 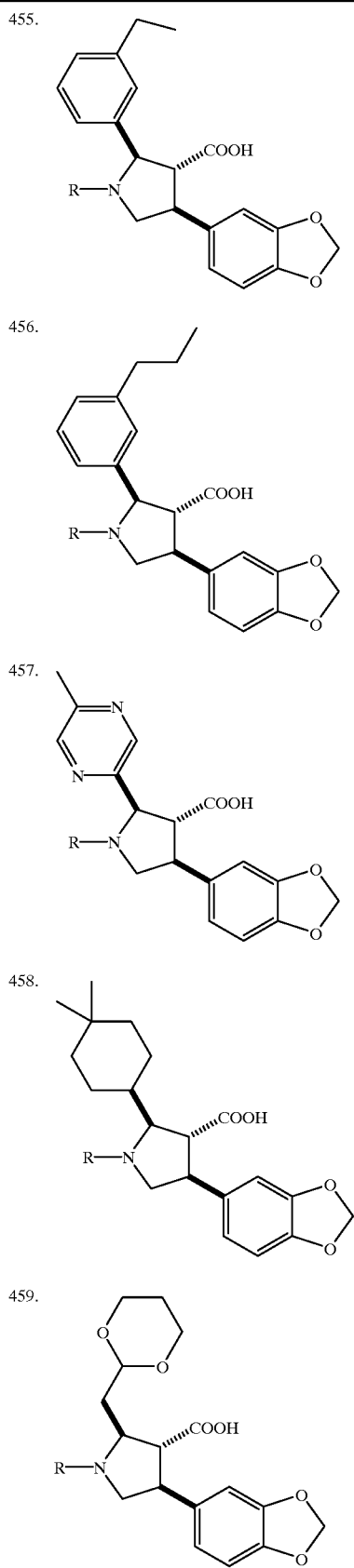 |
| 456. | |
| 457. | |
| 458. | |
| 459. | |
TABLE 2A-continued
| | |
|---|---|
| 460. | 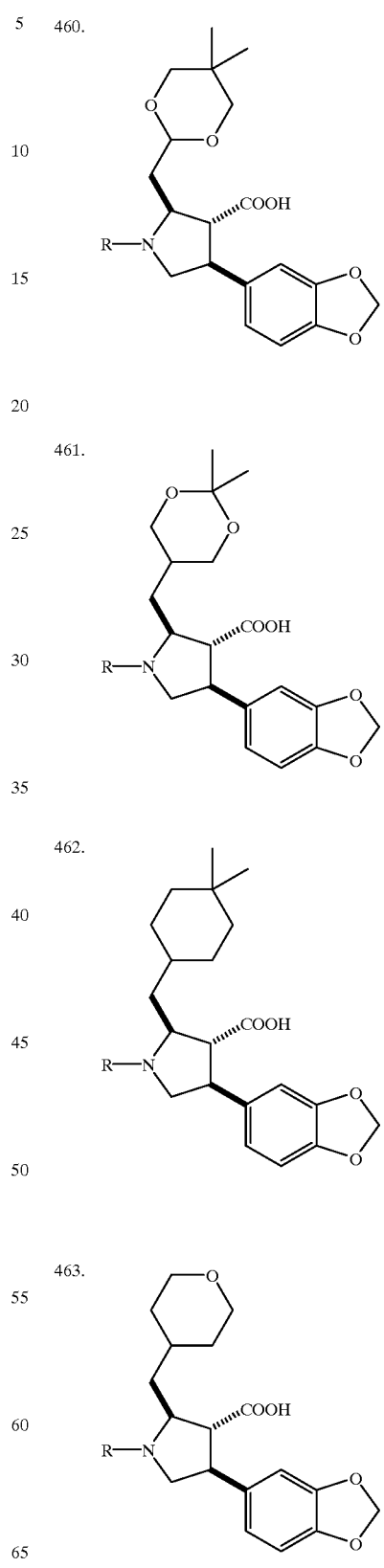 |
| 461. | |
| 462. | |
| 463. | |

TABLE 2A-continued
464.
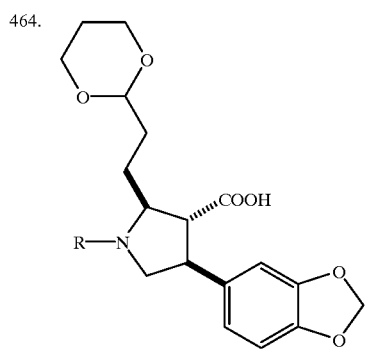
465.
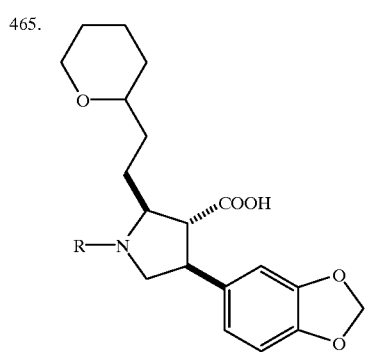
TABLE 2B
R
1. 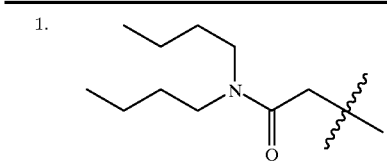
2. 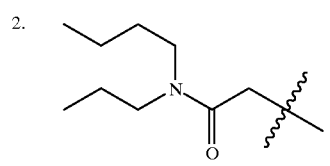
3. 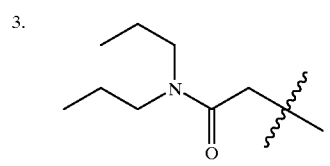
4. 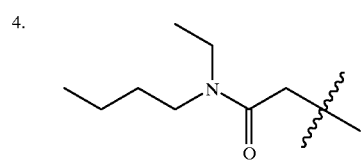
TABLE 2B-continued
R
5. 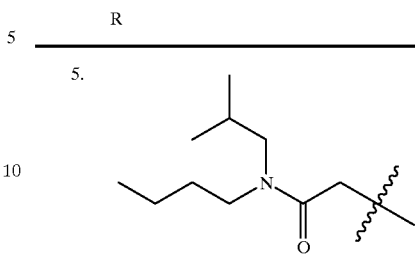
6. 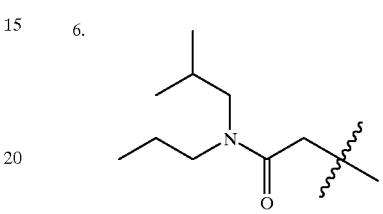
7. 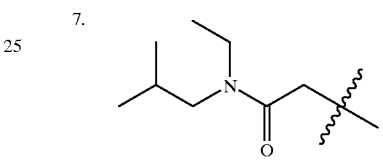
8. 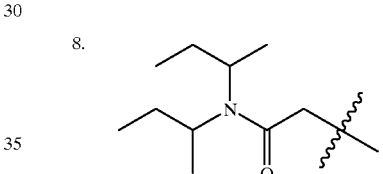
9. 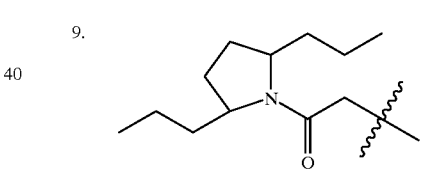
10. 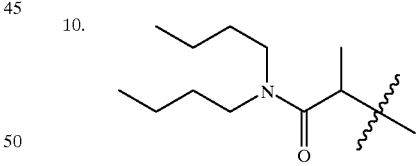
11. 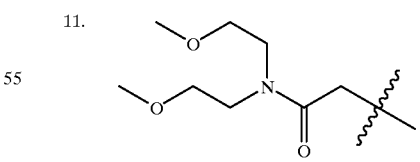
12. 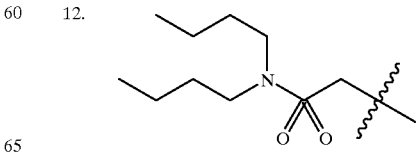

TABLE 2B-continued

| | R |
|---|---|
| 13. | (ethyl carbamate with N-propyl, N-propyl linker) |
| 14. | (ethyl carbamate with N-butyl, N-propyl linker) |
| 15. | (2-chloroethyl carbamate with N-propyl, N-propyl linker) |
| 16. | (2-chloroethyl carbamate with N-butyl, N-propyl linker) |
| 17. | (4-methoxybenzamide with N-propyl, N-propyl linker) |
| 18. | (4-methoxybenzamide with N-butyl, N-propyl linker) |
| 19. | (propylsulfonamide with N-propyl, N-propyl linker) |
| 20. | (propylsulfonamide with N-butyl, N-propyl linker) |
| 21. | (3-chloropropylsulfonamide with N-propyl, N-propyl linker) |
| 22. | (3-chloropropylsulfonamide with N-butyl, N-propyl linker) |
| 23. | (4-methoxybenzenesulfonamide with N-propyl, N-propyl linker) |
| 24. | (4-methoxybenzenesulfonamide with N-butyl, N-propyl linker) |
| 25. | (2-methoxyethylsulfonamide with N-butyl, N-propyl linker) |
| 26. | (2-methoxyethylsulfonamide with N-propyl, N-propyl linker) |
| 27. | (3,3,3-trifluoropropylsulfonamide with N-butyl, N-propyl linker) |
| 28. | (3,3,3-trifluoropropylsulfonamide with N-propyl, N-propyl linker) |
| 29. | (3-fluoropropylsulfonamide with N-butyl, N-propyl linker) |
| 30. | (3-fluoropropylsulfonamide with N-propyl, N-propyl linker) |

TABLE 2B-continued

| | R |
|---|---|
| 31. | (structure) |
| 32. | (structure) |
| 33. | (structure) |
| 34. | (structure) |
| 35. | (structure) |
| 36. | (structure) |
| 37. | (structure) |
| 38. | (structure) |
| 39. | (structure) |
| 40. | (structure) |
| 41. | (structure) |
| 42. | (structure) |
| 43. | (structure) |
| 44. | (structure) |
| 45. | (structure) |
| 46. | (structure) |
| 47. | (structure) |
| 48. | (structure) |

TABLE 2B-continued

| | R |
|---|---|
| 49. | N-propyl-N-phenyl acetamide derivative |
| 50. | N-pentyl-N-phenyl acetamide derivative |
| 51. | N-hexyl-N-phenyl acetamide derivative |
| 52. | N-butyl-N-(2-methylphenyl) acetamide derivative |
| 53. | N-butyl-N-(3-methylphenyl) acetamide derivative |
| 54. | N-butyl-N-(4-methylphenyl) acetamide derivative |
| 55. | N-butyl-N-(2-fluorophenyl) acetamide derivative |
| 56. | N-butyl-N-(3-fluorophenyl) acetamide derivative |
| 57. | N-butyl-N-(4-fluorophenyl) acetamide derivative |
| 58. | N-butyl-N-(2-chlorophenyl) acetamide derivative |
| 59. | N-butyl-N-(3-chlorophenyl) acetamide derivative |
| 60. | N-butyl-N-(4-chlorophenyl) acetamide derivative |
| 61. | N-butyl-N-(2-methoxyphenyl) acetamide derivative |
| 62. | N-butyl-N-(3-methoxyphenyl) acetamide derivative |
| 63. | N-butyl-N-(4-methoxyphenyl) acetamide derivative |

TABLE 2B-continued

| | R |
|---|---|
| 64. | (structure) |
| 65. | (structure) |
| 66. | (structure) |
| 67. | (structure) |
| 68. | (structure) |
| 69. | (structure) |
| 70. | (structure) |
| 71. | (structure) |
| 72. | (structure) |
| 73. | (structure) |
| 74. | (structure) |
| 75. | (structure) |
| 76. | (structure) |
| 77. | (structure) |
| 78. | (structure) |
| 79. | (structure) |

TABLE 2B-continued

| | R |
|---|---|
| 80. | (structure) |
| 81. | (structure) |
| 82. | (structure) |
| 83. | (structure) |
| 84. | (structure) |
| 85. | (structure) |
| 86. | (structure) |
| 87. | (structure) |
| 88. | (structure) |
| 89. | (structure) |
| 90. | (structure) |
| 91. | (structure) |
| 92. | (structure) |
| 93. | (structure) |
| 94. | (structure) |
| 95. | (structure) |
| 96. | (structure) |
| 97. | (structure) |

TABLE 2B-continued

| | R |
|---|---|
| 98. | (structure) |
| 99. | (structure) |
| 100. | (structure) |
| 101. | (structure) |
| 102. | (structure) |
| 103. | (structure) |
| 104. | (structure) |
| 105. | (structure) |
| 106. | (structure) |
| 107. | (structure) |
| 108. | (structure) |
| 109. | (structure) |
| 110. | (structure) |
| 111. | (structure) |
| 112. | (structure) |
| 113. | (structure) |
| 114. | (structure) |

TABLE 2B-continued

| R | |
|---|---|
| 115. | [structure] |
| 116. | [structure] |
| 117. | [structure] |
| 118. | [structure] |
| 119. | [structure] |
| 120. | [structure] |
| 121. | [structure] |
| 122. | [structure] |
| 123. | [structure] |
| 124. | [structure] |
| 125. | [structure] |
| 126. | [structure] |
| 127. | [structure] |

TABLE 2B-continued
R
128. 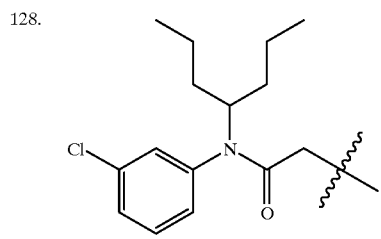
129. 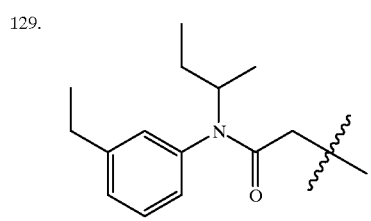
130. 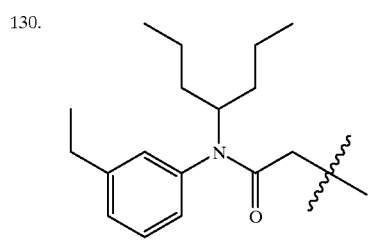
131. 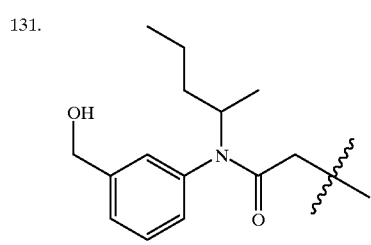
132. 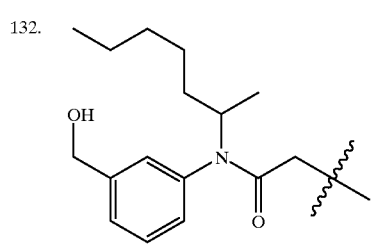
133. 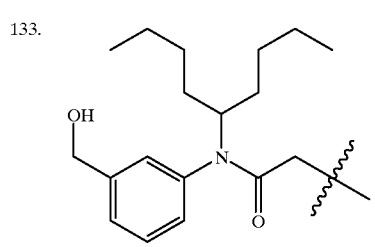
TABLE 2B-continued
R
134. 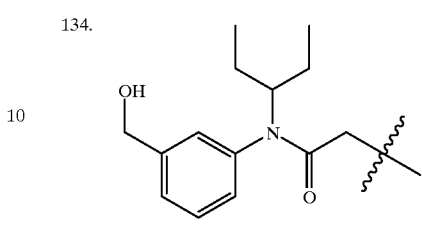
135. 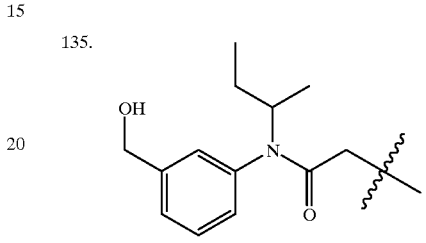
136. 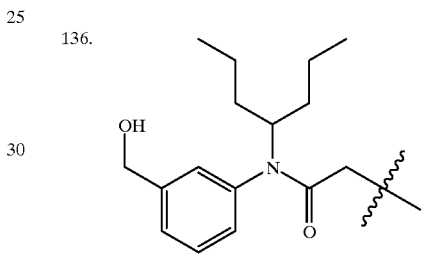
137. 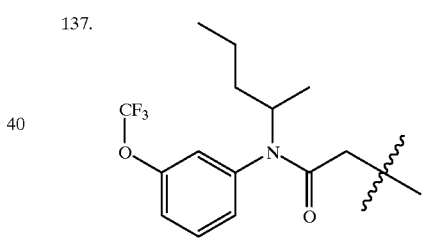
138. 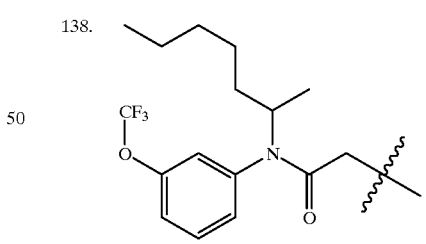
139. 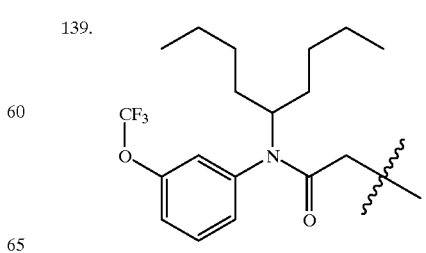

TABLE 2B-continued
| R | |
|---|---|
| 140. | 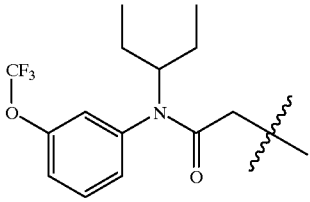 |
| 141. | 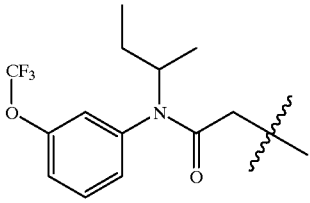 |
| 142. | 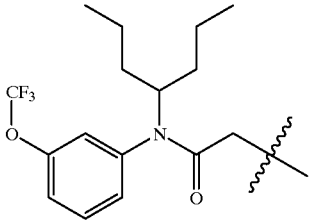 |
| 143. | 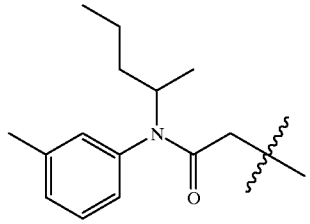 |
| 144. | 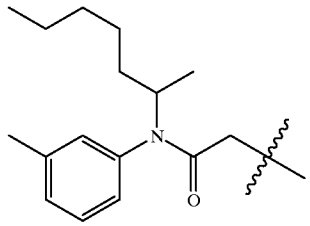 |
| 145. | 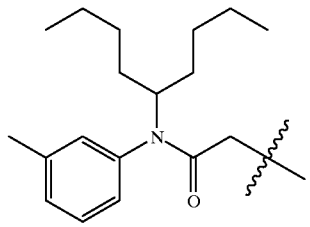 |
| 146. | 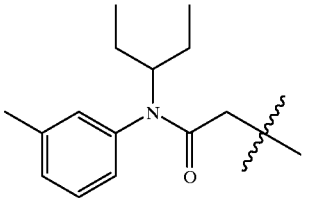 |
| 147. | 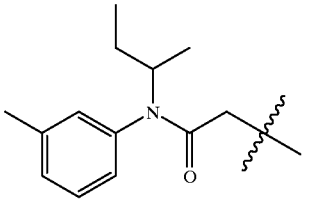 |
| 148. | 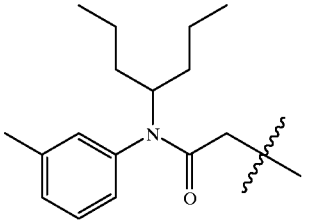 |
| 149. | 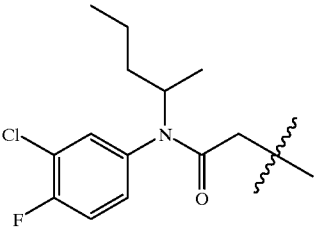 |
| 150. | 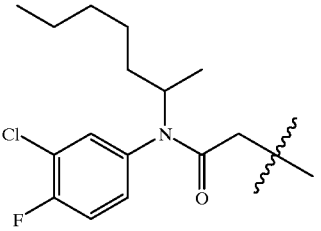 |
| 151. | 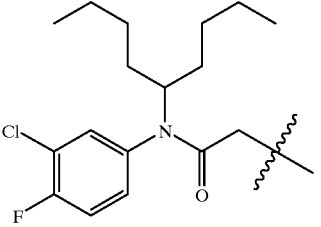 |

TABLE 2B-continued
| | R |
|---|---|
| 152. | 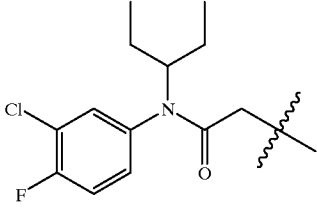 |
| 153. | 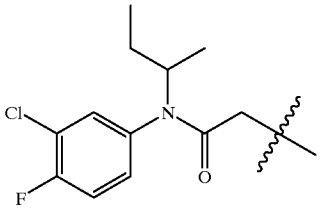 |
| 154. | 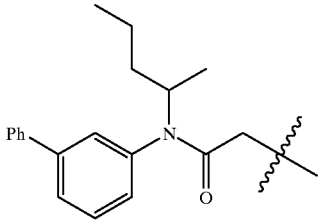 |
| 155. | 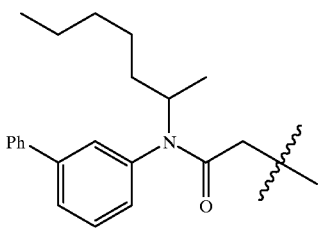 |
| 156. | 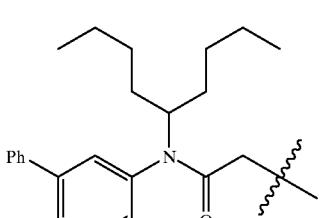 |
| 157. | 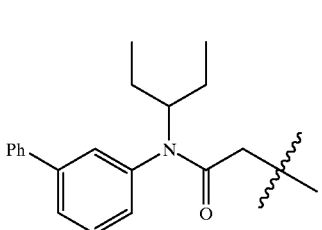 |
| 158. | 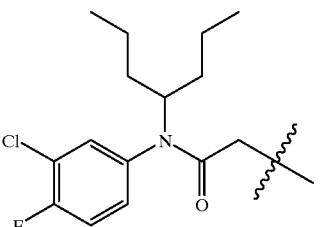 |
| 159. | 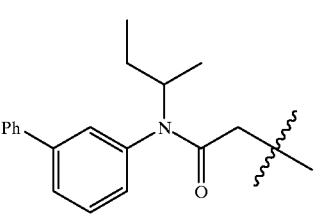 |
| 160. | 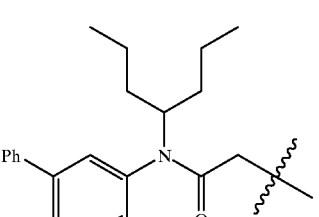 |
| 161. | 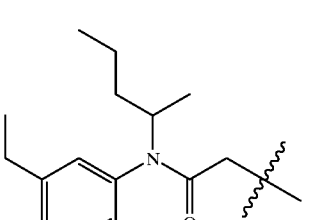 |
| 162. | 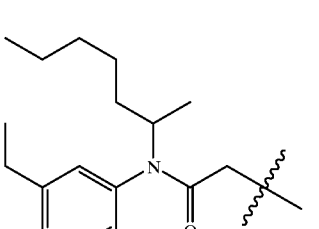 |
| 163. | 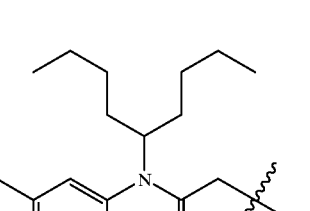 |

TABLE 2B-continued
| | R |
|---|---|
| 164. | 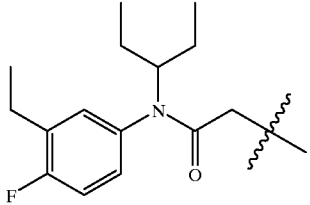 |
| 165. | 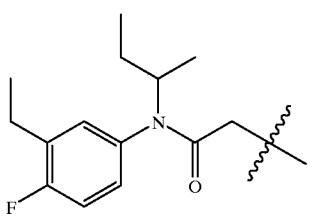 |
| 166. | 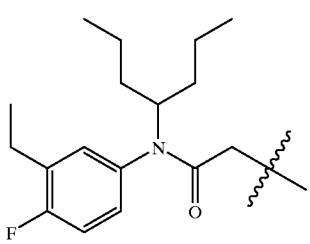 |
| 167. | 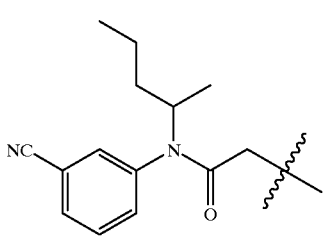 |
| 168. | 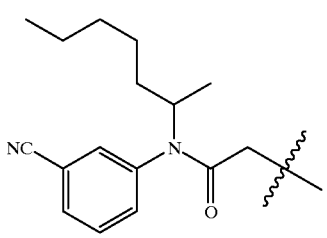 |
| 169. | 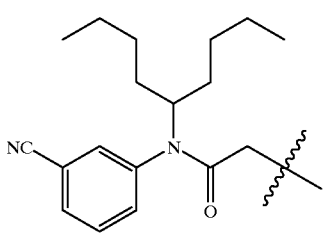 |
| 170. | 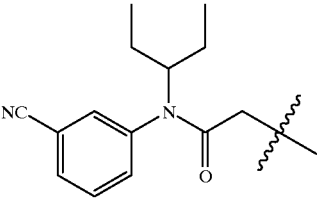 |
| 171. | 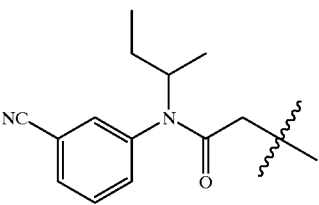 |
| 172. | 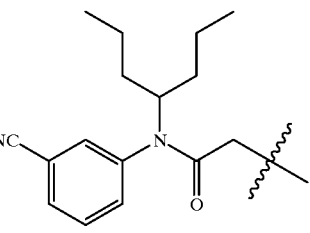 |
| 173. | 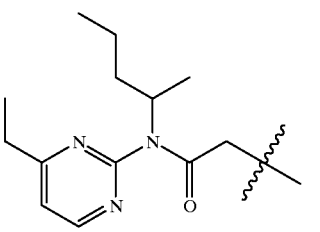 |
| 174. | 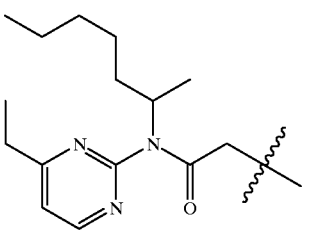 |
| 175. | 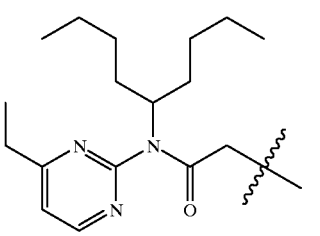 |

TABLE 2B-continued
| | R |
|---|---|
| 176. | 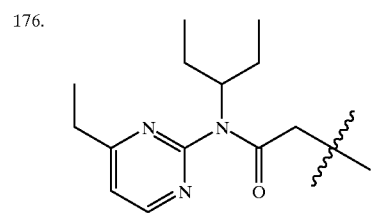 |
| 177. | 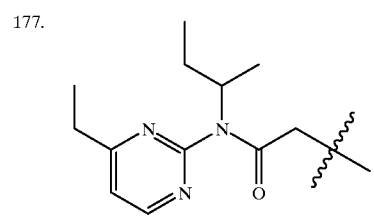 |
| 178. | 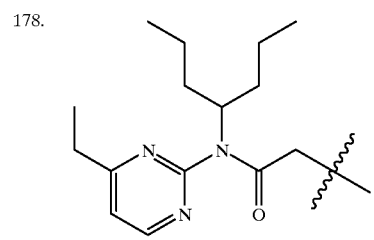 |
| 179. | 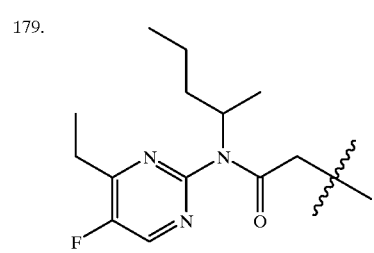 |
| 180. | 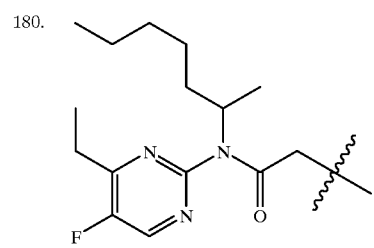 |
| 181. | 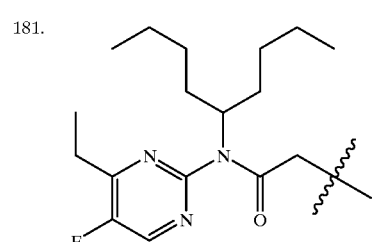 |
| 182. | 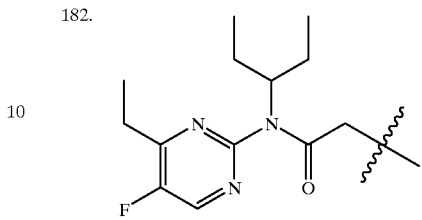 |
| 183. | 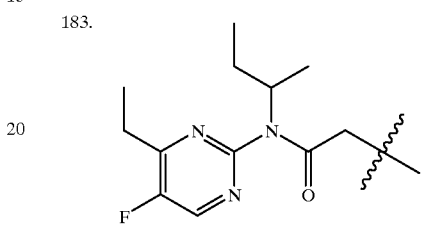 |
| 184. | 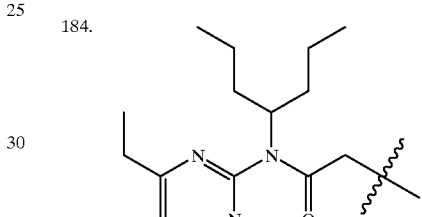 |
| 185. | 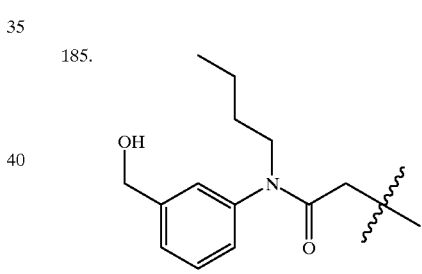 |
| 186. | 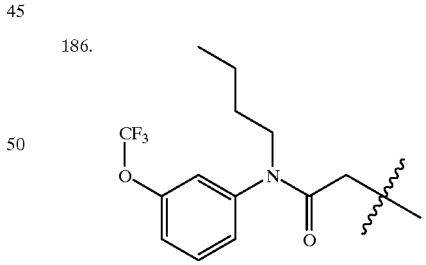 |
| 187. | 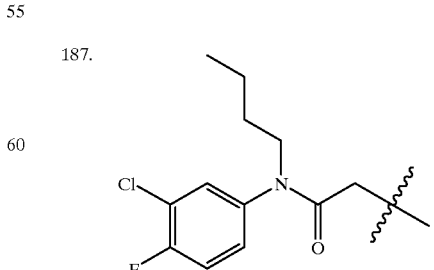 |

TABLE 2B-continued
| R |
|---|
| 188. 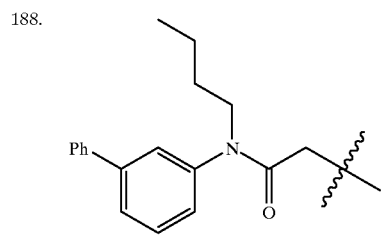 |
| 189. 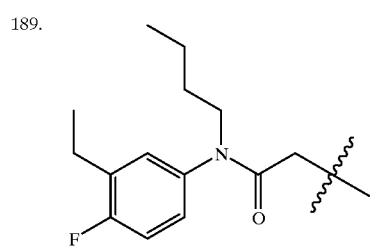 |
| 190. 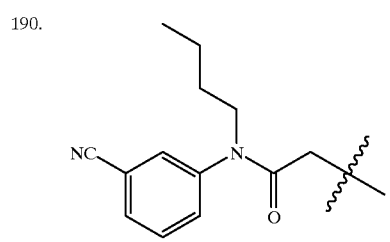 |
| 191. 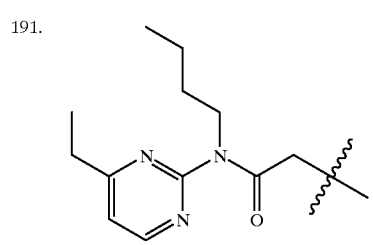 |
| 192. 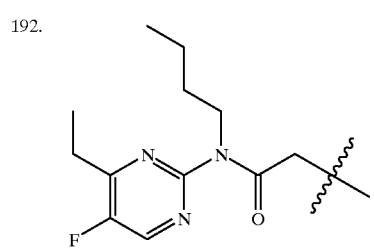 |
| 193. 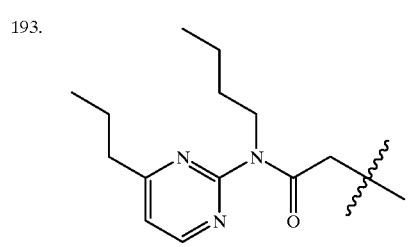 |
TABLE 2B-continued
| R |
|---|
| 194. 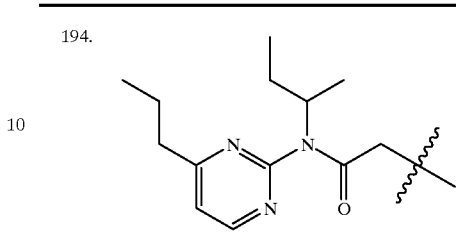 |
| 195. 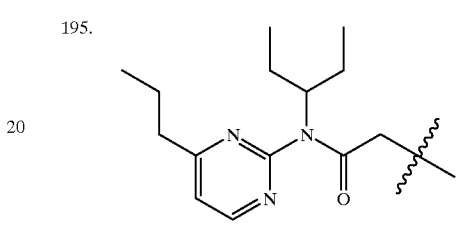 |
| 196. 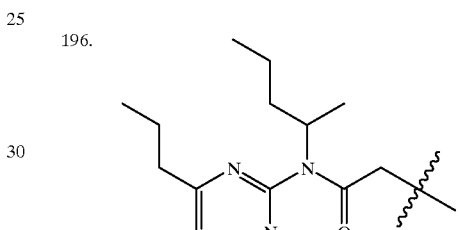 |
| 197. 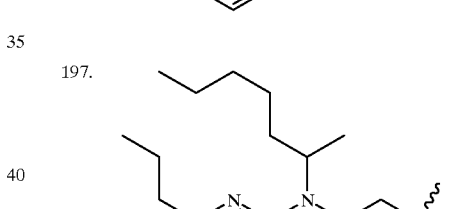 |
| 198. 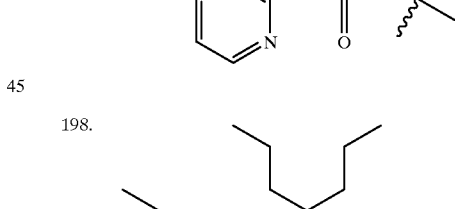 |
| 199. 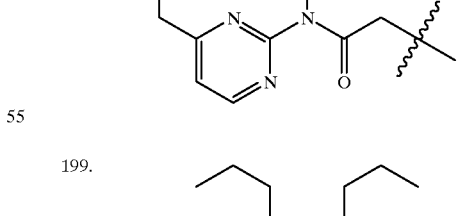 |

TABLE 2B-continued
| R |
|---|
| 200. 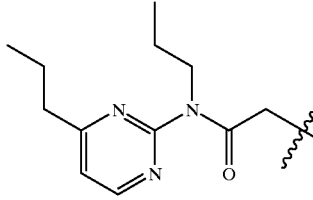 |
| 201. |
| 202. |
| 203. |
| 204. |
| 205. |
| 206. 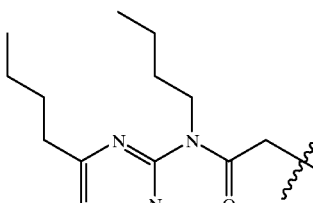 |
| 207. |
| 208. |
| 209. |
| 210. |
| 211. |

TABLE 2B-continued
| R |
|---|
| 212. 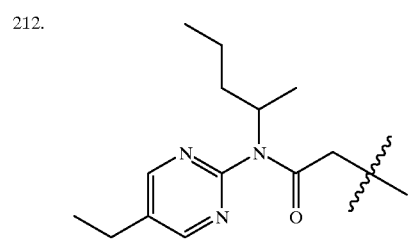 |
| 213. 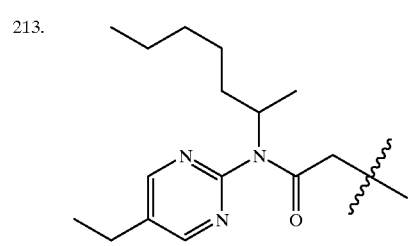 |
| 214. 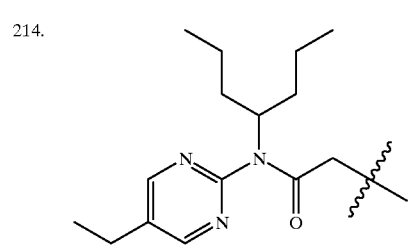 |
| 215. 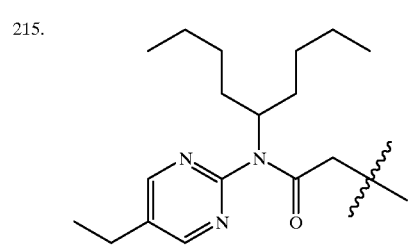 |
| 216. 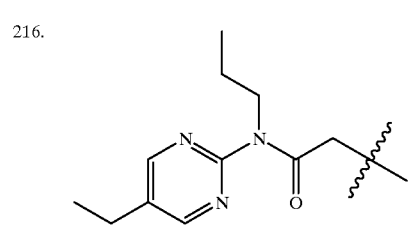 |
| 217. 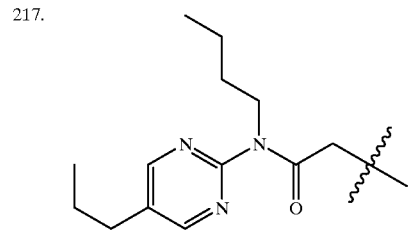 |
| 218. 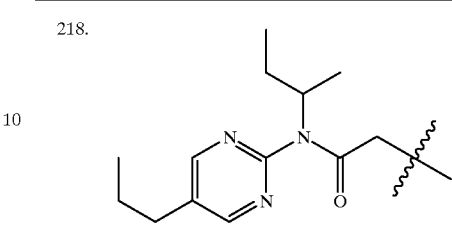 |
| 219. 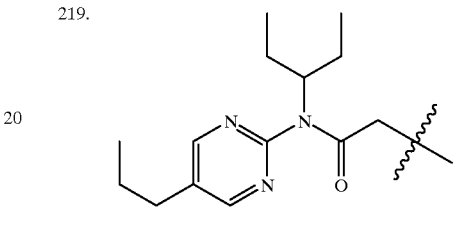 |
| 220. 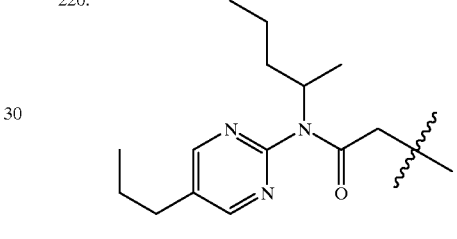 |
| 221. 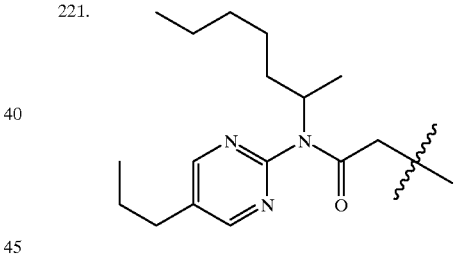 |
| 222. 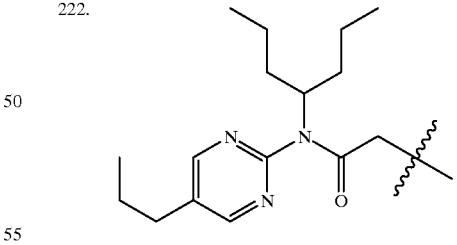 |
| 223. 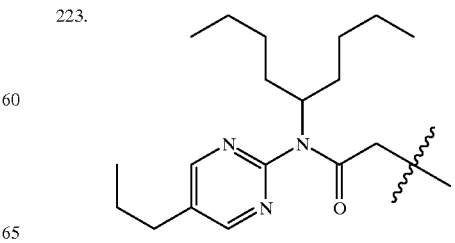 |

TABLE 2B-continued
| | R |
|---|---|
| 224. | 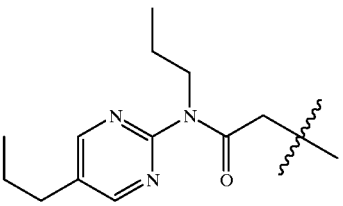 |
| 225. | 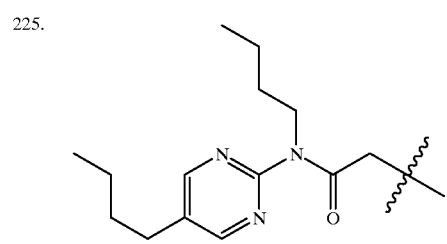 |
| 226. | 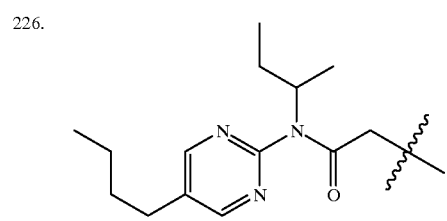 |
| 227. | 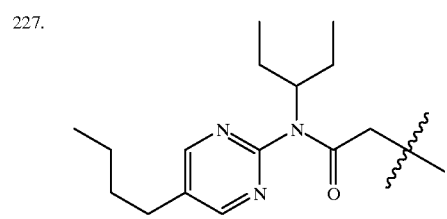 |
| 228. | 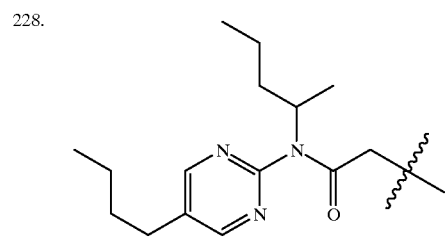 |
| 229. | 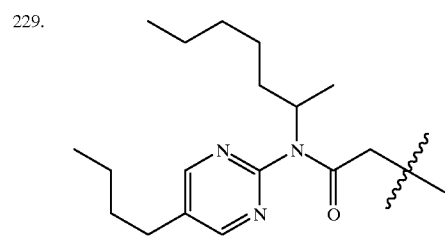 |
| 230. | 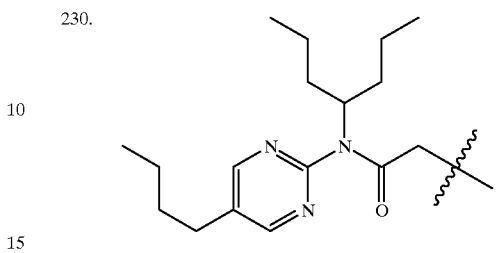 |
| 231. | 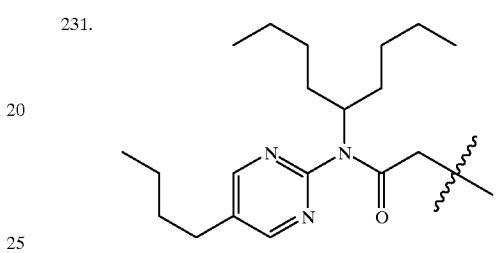 |
| 232. | 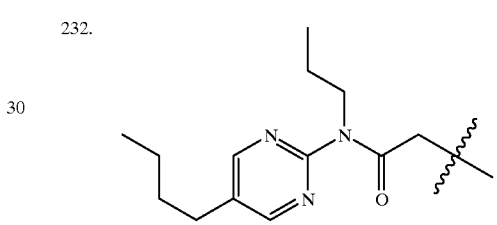 |
| 233. | 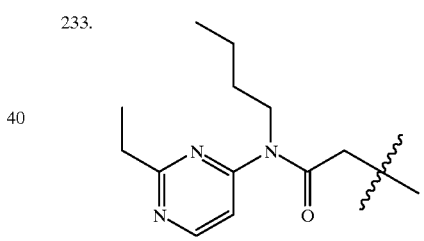 |
| 234. | 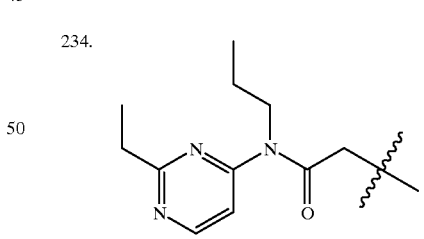 |
| 235. | 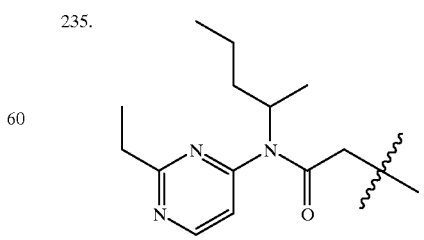 |

TABLE 2B-continued

| | R |
|---|---|
| 236. | |
| 237. | |
| 238. | |
| 239. | |
| 240. | |
| 241. | |
| 242. | |
| 243. | |
| 244. | |
| 245. | |
| 246. | |
| 247. | |

TABLE 2B-continued
| R |
|---|
| 248. 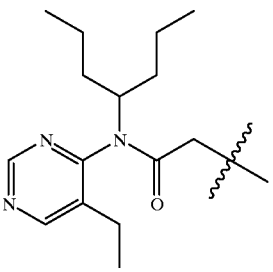 |
| 249. 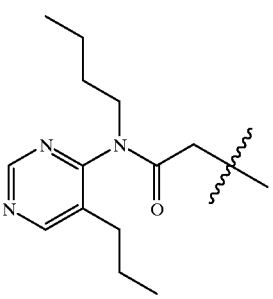 |
| 250. 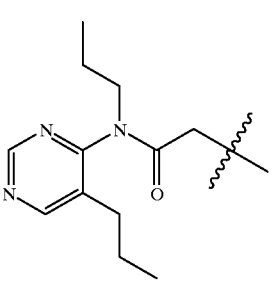 |
| 251. 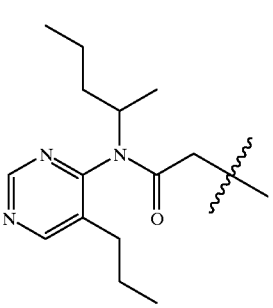 |
| 252. 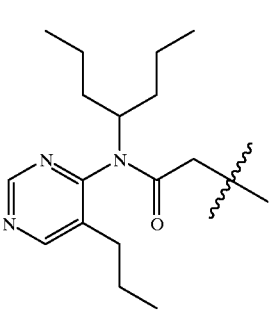 |
TABLE 2B-continued
| R |
|---|
| 253. 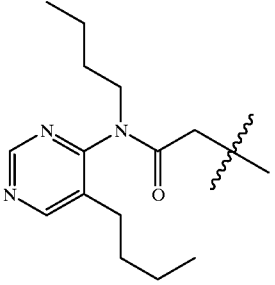 |
| 254. 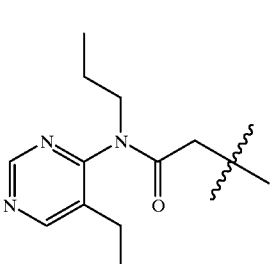 |
| 255. 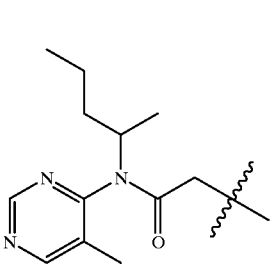 |
| 256. 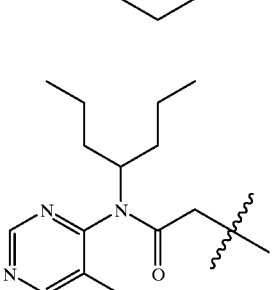 |
| 257. 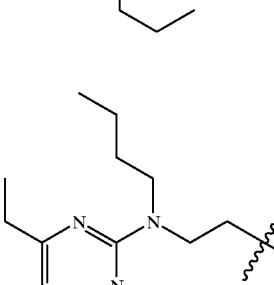 |

TABLE 2B-continued
| | R |
|---|---|
| 258. | 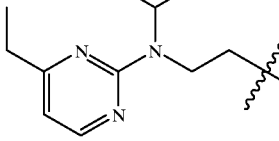 |
| 259. | 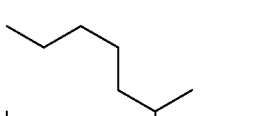 |
| 260. | 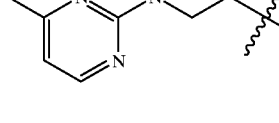 |
| 261. | 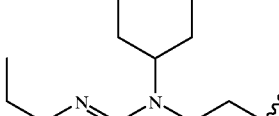 |
| 262. | 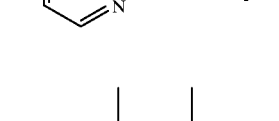 |
| 263. | 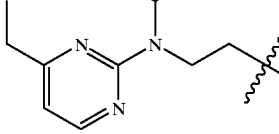 |
| 264. | 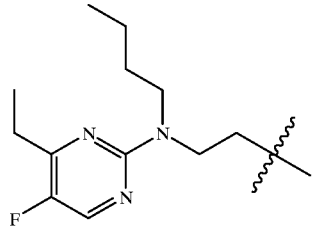 |
| 265. | 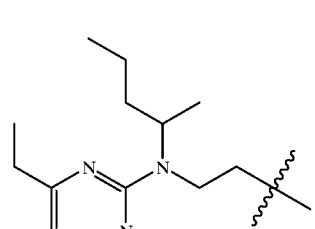 |
| 266. | 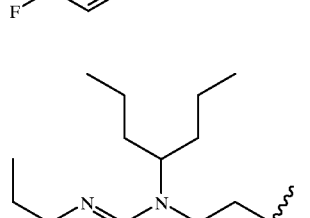 |
| 267. | 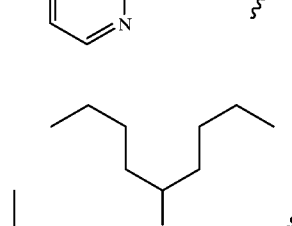 |
| 268. | 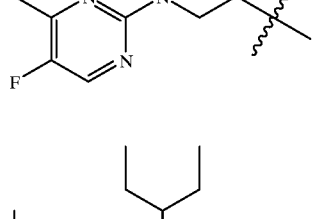 |
| 269. | 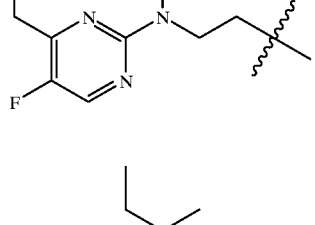 |

TABLE 2B-continued

| R |
|---|
| 270. (structure) |
| 271. (structure) |
| 272. (structure) |
| 273. (structure) |
| 274. (structure) |
| 275. (structure) |
| 276. (structure) |
| 277. (structure) |
| 278. (structure) |
| 279. (structure) |
| 280. (structure) |
| 281. (structure) |

US 6,380,241 B1
447
TABLE 2B-continued
| R |
|---|
| 282. 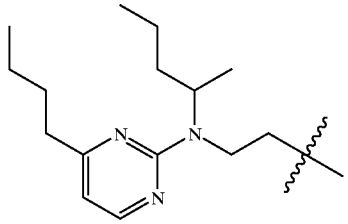 |
| 283. 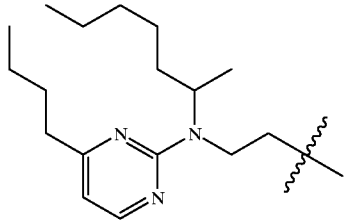 |
| 284. 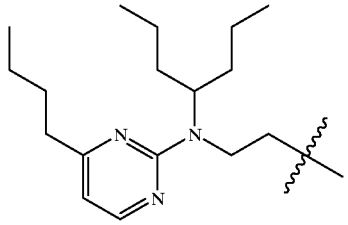 |
| 285. 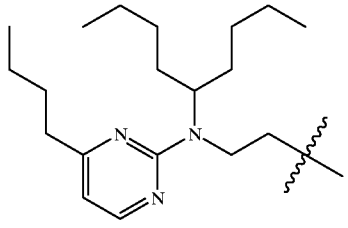 |
| 286. 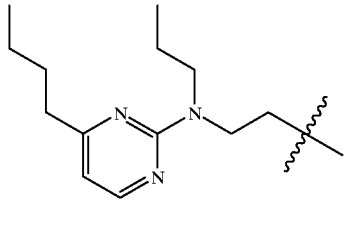 |
| 287. 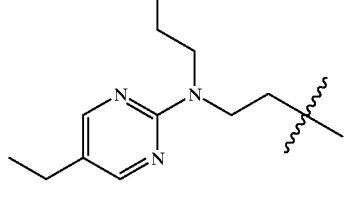 |
448
TABLE 2B-continued
| R |
|---|
| 288. 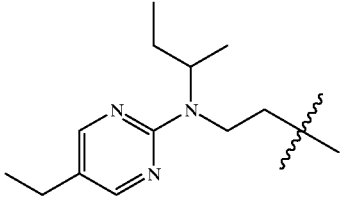 |
| 289. 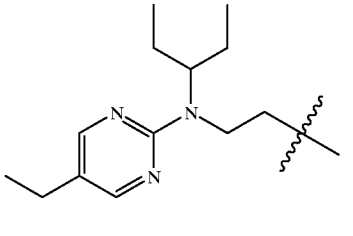 |
| 290. 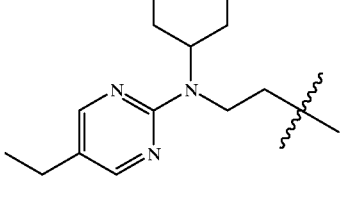 |
| 291. 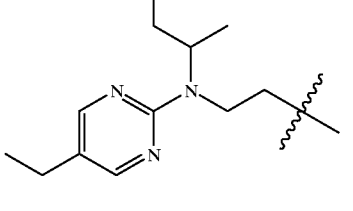 |
| 292. 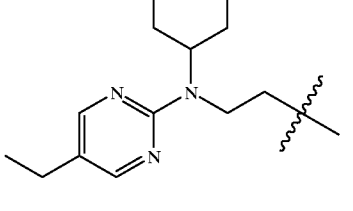 |
| 293. 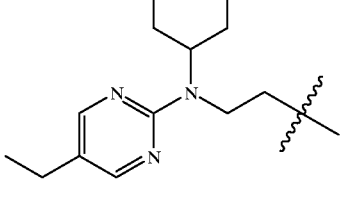 |

TABLE 2B-continued
| R |
|---|
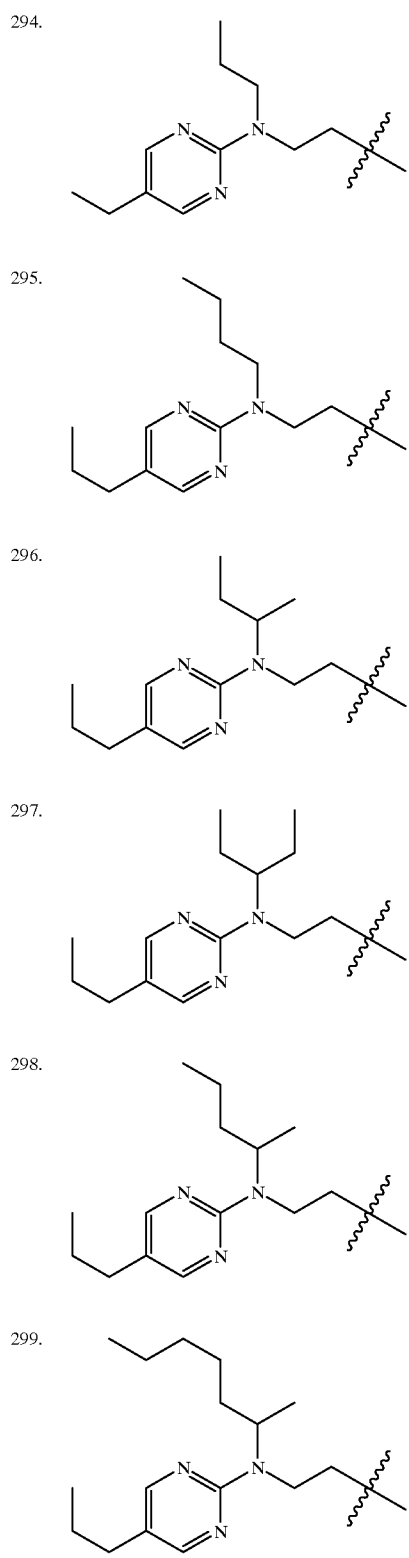
294.
295.
296.
297.
298.
299.
TABLE 2B-continued
| R |
|---|
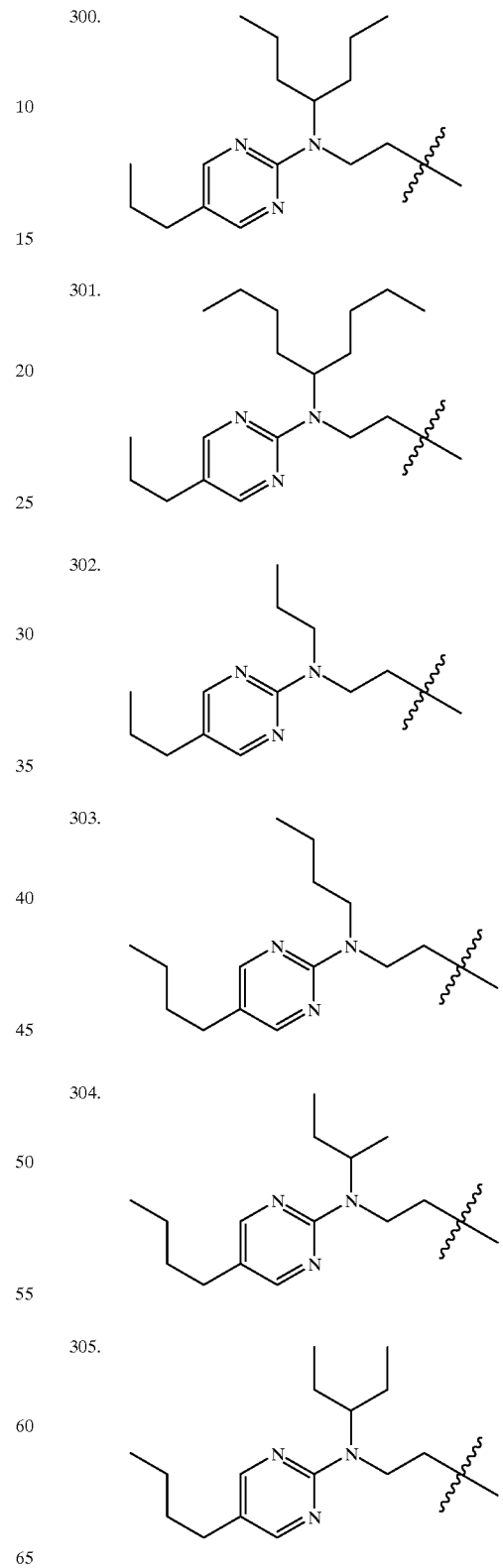
300.
301.
302.
303.
304.
305.

TABLE 2B-continued
R
306. 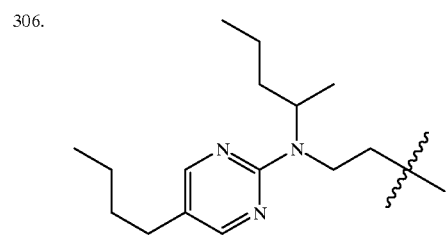
307. 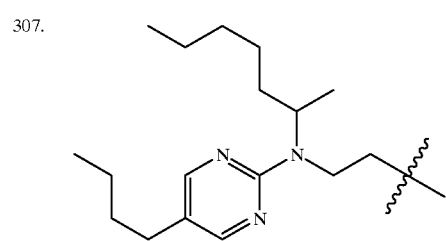
308. 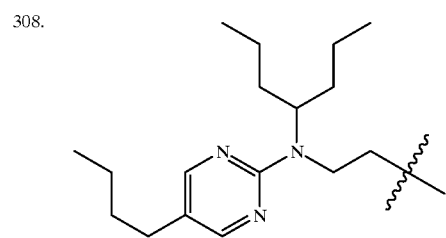
309. 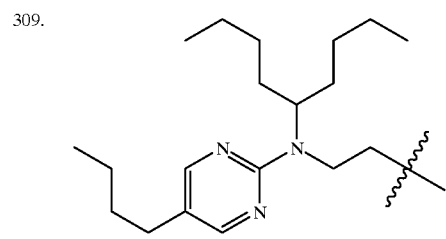
310. 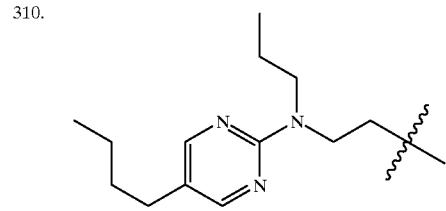
311. 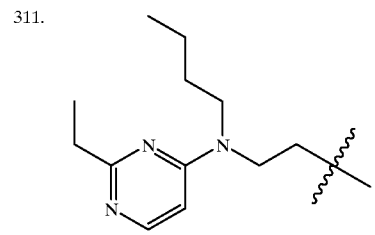
TABLE 2B-continued
R
312. 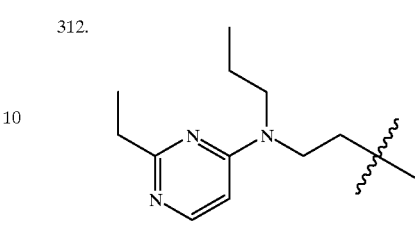
313. 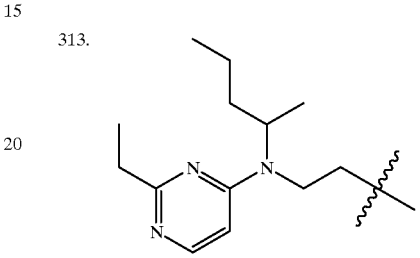
314. 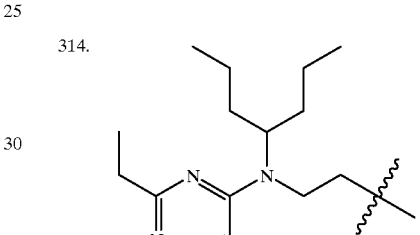
315. 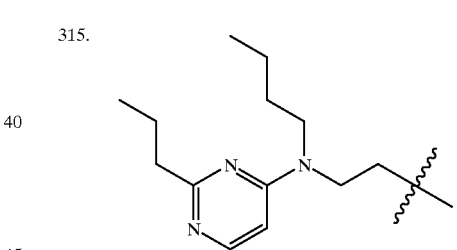
316. 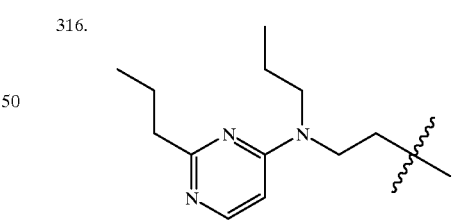
317. 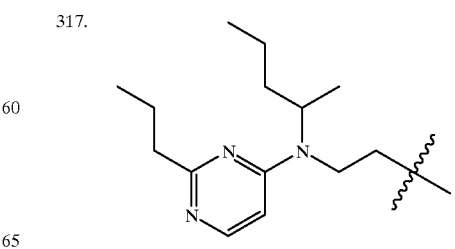

TABLE 2B-continued
R
318. 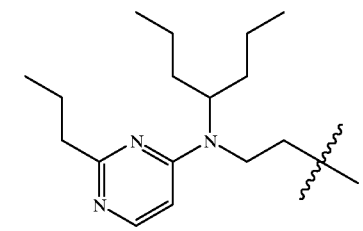
319. 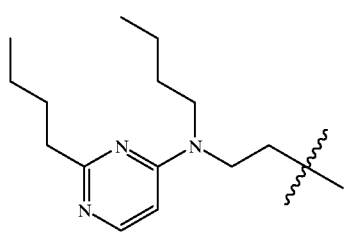
320. 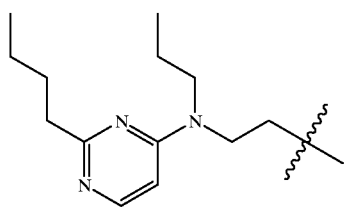
321. 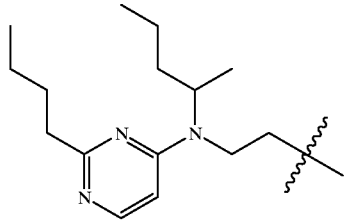
322. 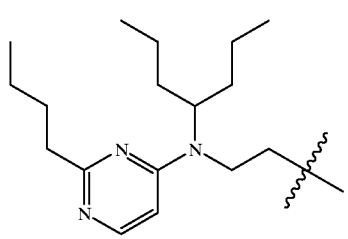
323. 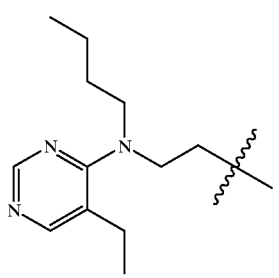
TABLE 2B-continued
R
324. 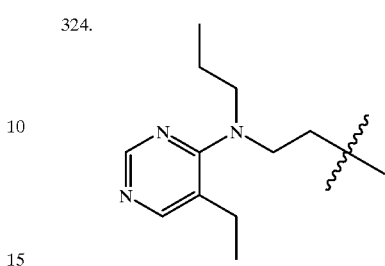
325. 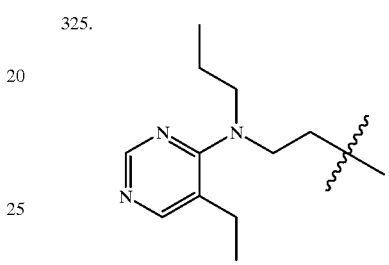
326. 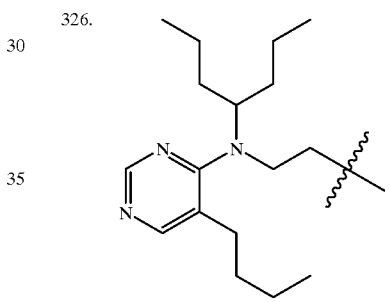
327. 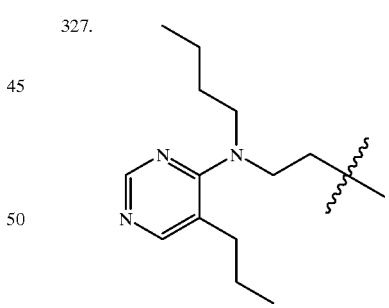
328. 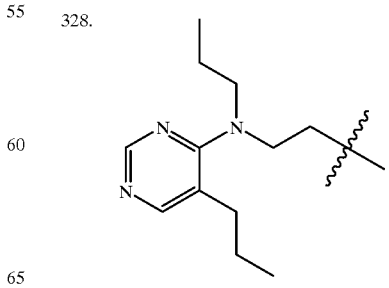

TABLE 2B-continued
R
329. 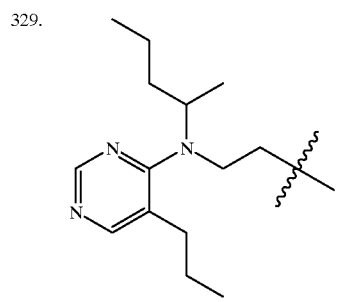
330. 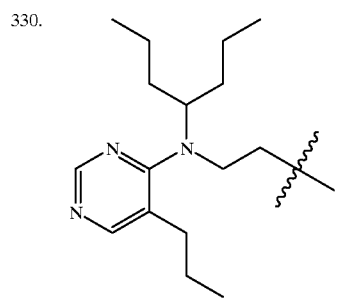
331. 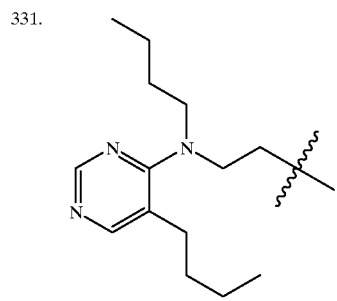
332. 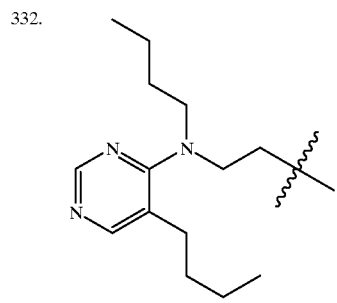
333. 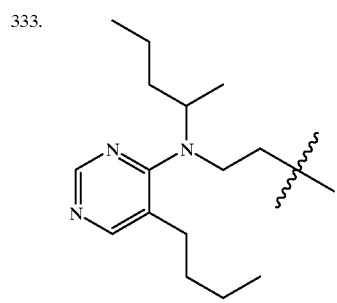
TABLE 2B-continued
R
334. 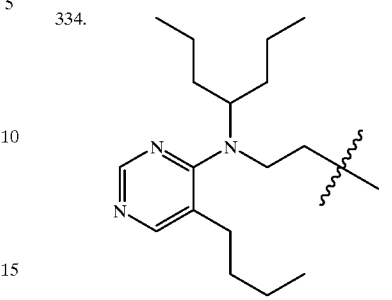
335. 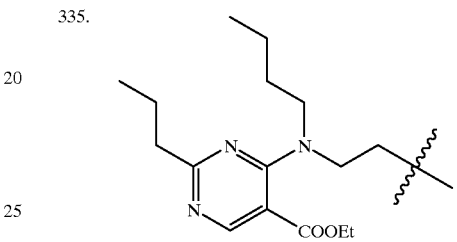
336. 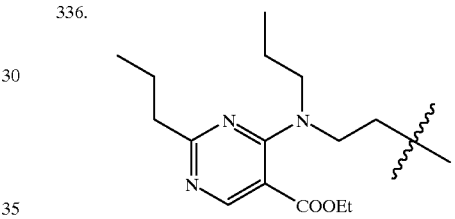
337. 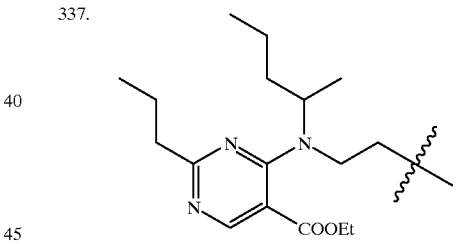
338. 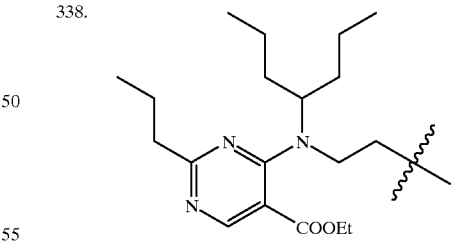
339. 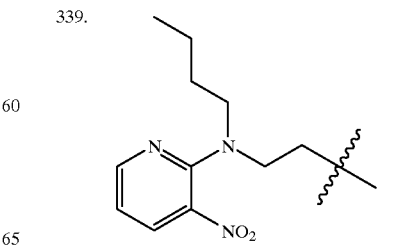

TABLE 2B-continued

| R |
|---|
| 340. (N-propyl, 3-NO2-pyridin-2-yl)-N-alkyl |
| 341. (N-(pentan-2-yl), 3-NO2-pyridin-2-yl)-N-alkyl |
| 342. (N-(heptan-4-yl), 3-NO2-pyridin-2-yl)-N-alkyl |
| 343. (N-butyl, 3-CN-pyridin-2-yl)-N-alkyl |
| 344. (N-propyl, 3-CN-pyridin-2-yl)-N-alkyl |
| 345. (N-(pentan-2-yl), 3-CN-pyridin-2-yl)-N-alkyl |
| 346. (N-(heptan-4-yl), 3-CN-pyridin-2-yl)-N-alkyl |
| 347. (N-butyl, 5-NO2-pyridin-2-yl)-N-alkyl |
| 348. (N-propyl, 5-NO2-pyridin-2-yl)-N-alkyl |
| 349. (N-(pentan-2-yl), 5-NO2-pyridin-2-yl)-N-alkyl |
| 350. (N-(heptan-4-yl), 5-NO2-pyridin-2-yl)-N-alkyl |
| 351. pyrrolidinyl-C(O)-CH=CH-N(butyl)-alkyl |

TABLE 2B-continued
| R |
|---|
| 352. 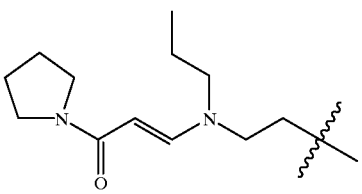 |
| 353. 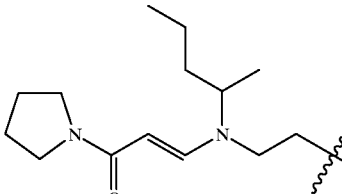 |
| 354. 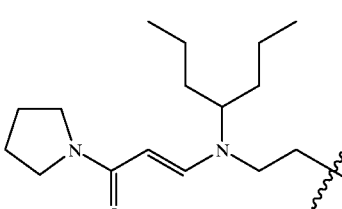 |
| 355. 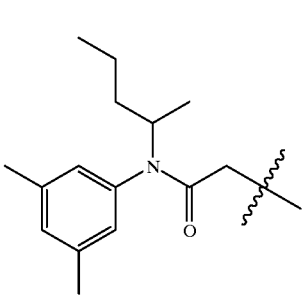 |
| 356. 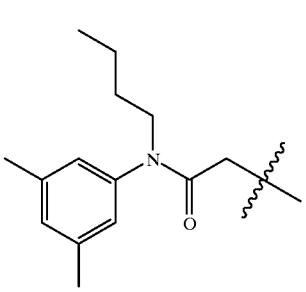 |
| 357. 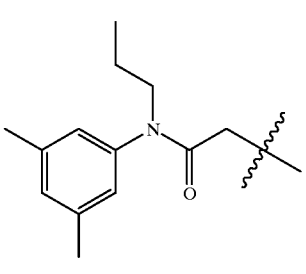 |
| 358. 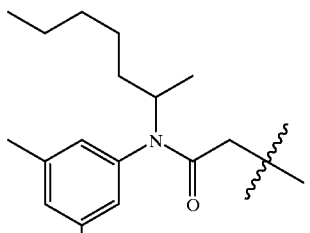 |
| 359. 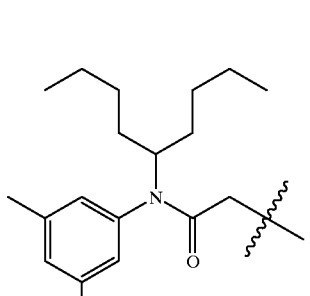 |
| 360. 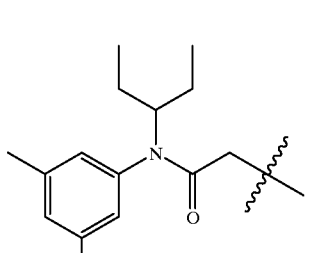 |
| 361. 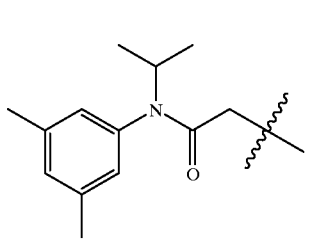 |
| 362. 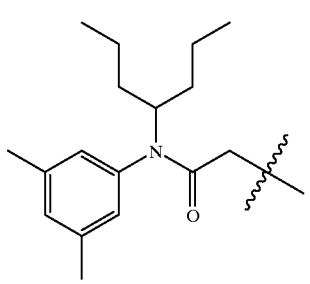 |

TABLE 2B-continued
| R |
|---|
| 363. 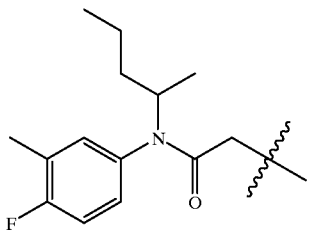 |
| 364. 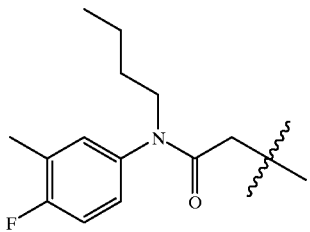 |
| 365. 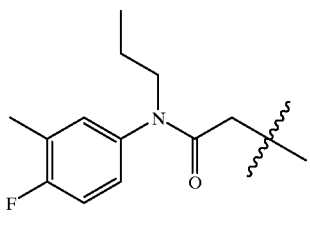 |
| 366. 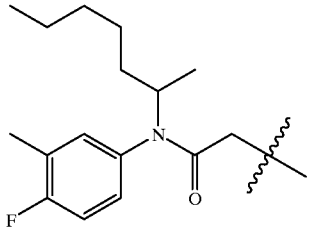 |
| 367. 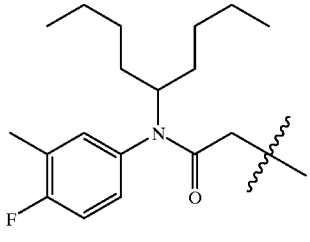 |
| 368. 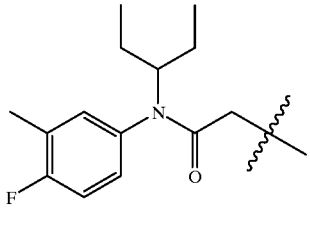 |
TABLE 2B-continued
| R |
|---|
| 369. 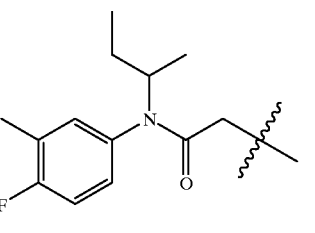 |
| 370. 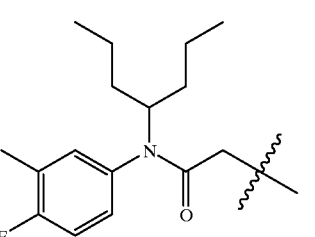 |
| 371. 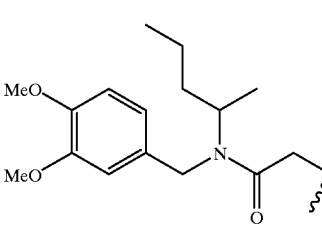 |
| 372. 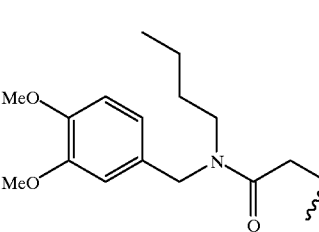 |
| 373. 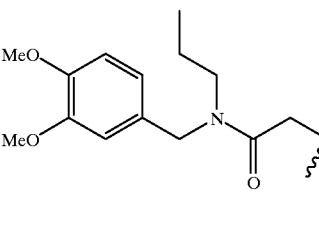 |
| 374. 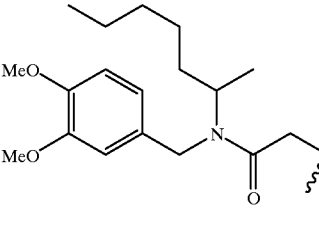 |

TABLE 2B-continued

TABLE 2B-continued

| | R |
|---|---|
| 389. | |
| 390. | |
| 391. | |
| 392. | |
| 393. | |
| 394. | |
| 395. | |
| 396. | |
| 397. | |
| 398. | |
| 399. | |
| 400. | |
| 401. | |
| 402. | |

TABLE 2B-continued

| R |
|---|
| 403. (structure) |
| 404. (structure) |
| 405. (structure) |
| 406. (structure) |
| 407. (structure) |
| 408. (structure) |
| 409. (structure) |
| 410. (structure) |
| 411. (structure) |
| 412. (structure) |
| 413. (structure) |
| 414. (structure) |
| 415. (structure) |
| 416. (structure) |

TABLE 2B-continued

| R |
|---|
| 417. |
| 418. |
| 419. |
| 420. |
| 421. |
| 422. |
| 423. |
| 424. |
| 425. |
| 426. |
| 427. |
| 428. |
| 429. |
| 430. |

TABLE 2B-continued
| | R |
|---|---|
| 431. | 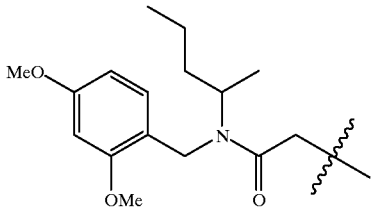 |
| 432. | 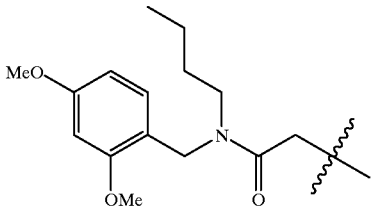 |
| 433. | 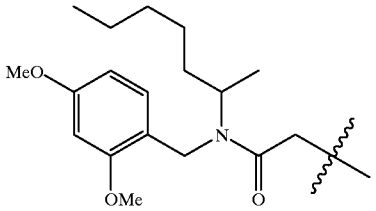 |
| 434. | 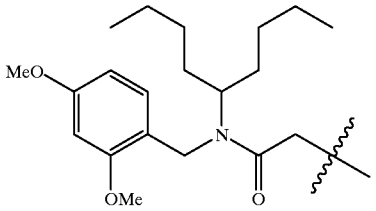 |
| 435. | 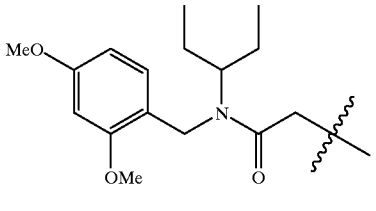 |
| 436. | 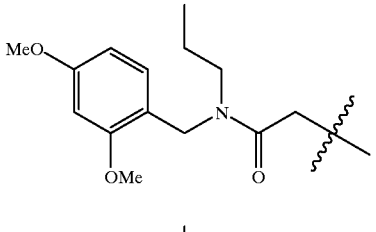 |
| 437. | 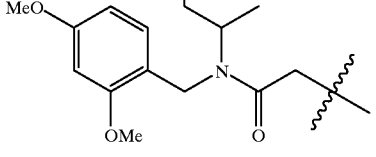 |
| 438. | 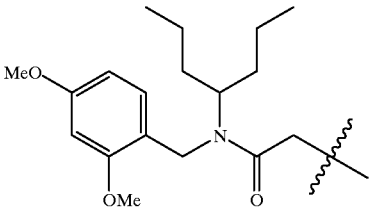 |
| 439. | 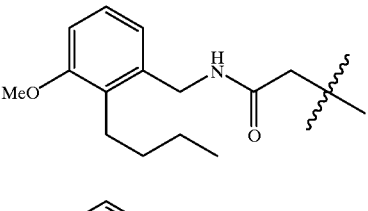 |
| 440. | 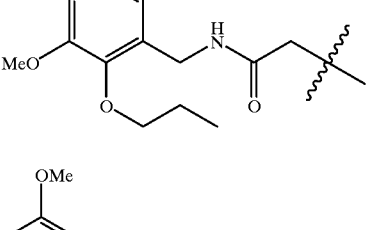 |
| 441. | 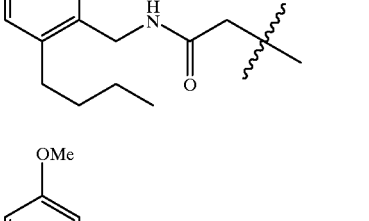 |
| 442. | 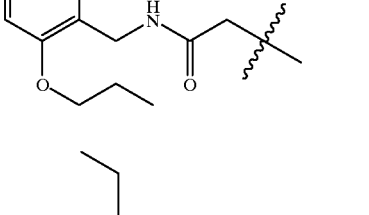 |
| 443. | 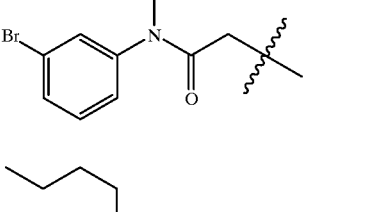 |
| 444. | 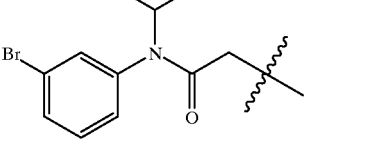 |

TABLE 2B-continued

| | R |
|---|---|
| 445. | |
| 446. | |
| 447. | |
| 448. | |
| 449. | |
| 450. | |
| 451. | |
| 452. | |
| 453. | |
| 454. | |
| 455. | |
| 456. | |

TABLE 2B-continued
| | R |
|---|---|
| 457. | 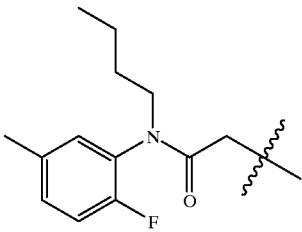 |
| 458. | 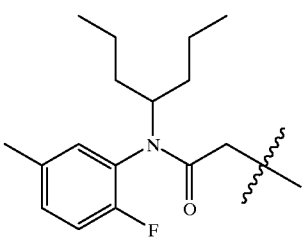 |
| 459. | 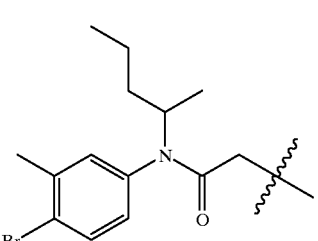 |
| 460. | 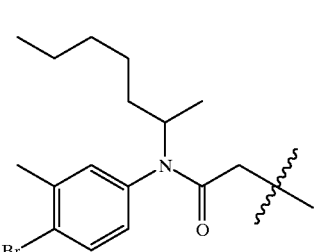 |
| 461. | 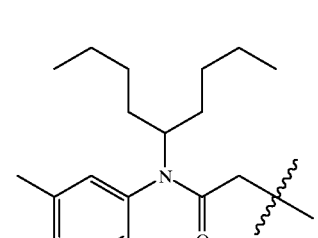 |
| 462. | 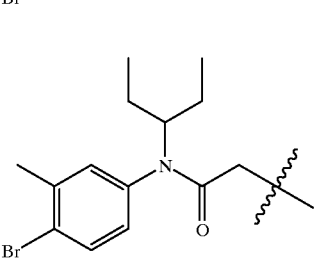 |
| 463. | 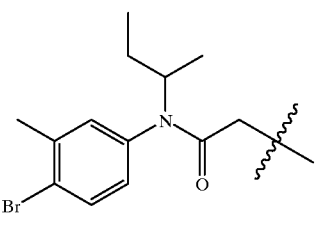 |
| 464. | 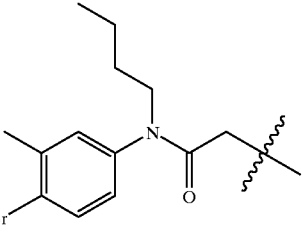 |
| 465. | 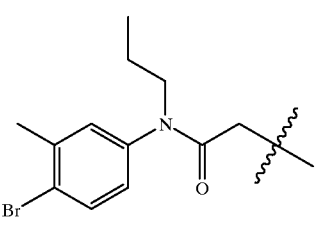 |
| 466. | 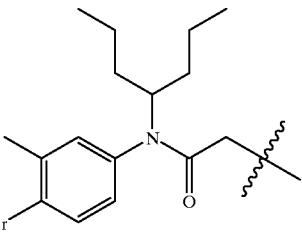 |
| 467. | 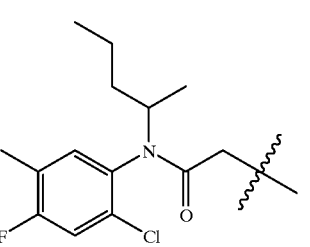 |
| 468. | 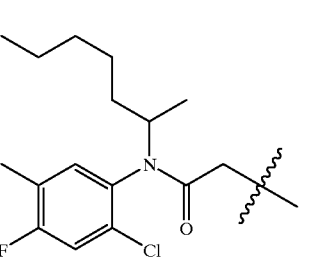 |

TABLE 2B-continued
| | R |
|---|---|
| 469. | 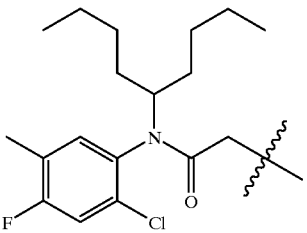 |
| 470. | 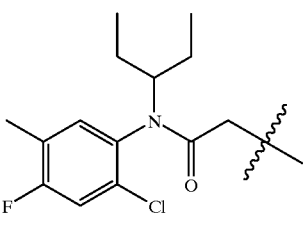 |
| 471. | 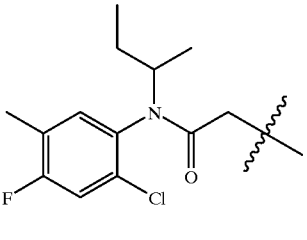 |
| 472. | 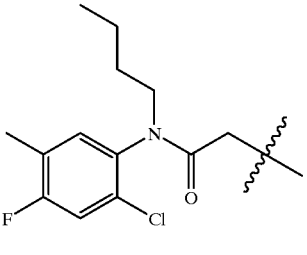 |
| 473. | 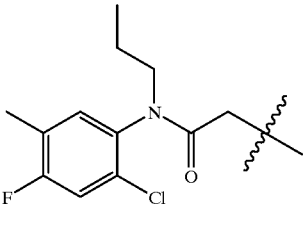 |
| 474. | 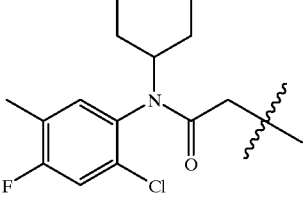 |
TABLE 2B-continued
| | R |
|---|---|
| 475. | 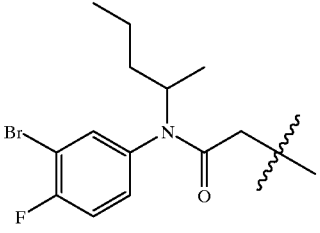 |
| 476. | 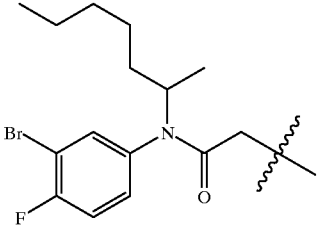 |
| 477. | 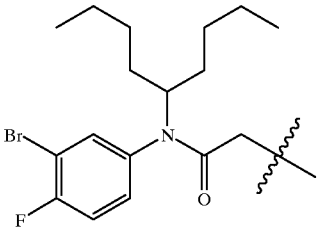 |
| 478. | 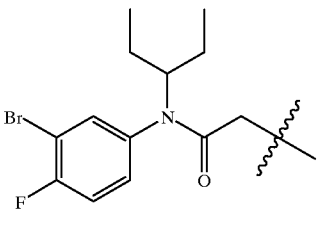 |
| 479. | 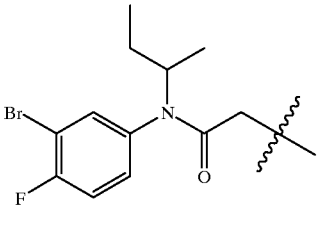 |
| 480. | 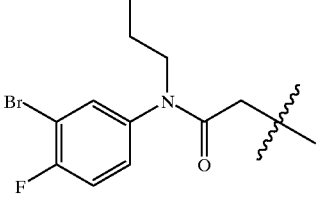 |

TABLE 2B-continued
| | R |
|---|---|
| 481. | 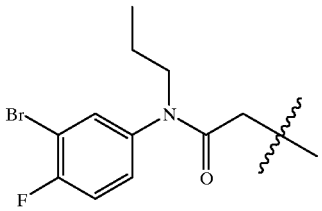 |
| 482. | 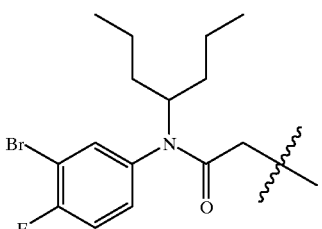 |
| 483. | 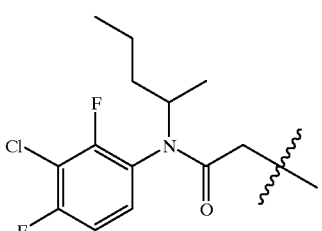 |
| 484. | 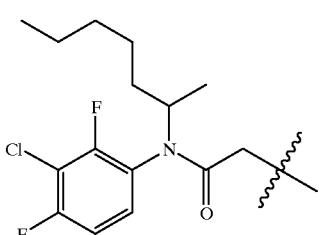 |
| 485. | 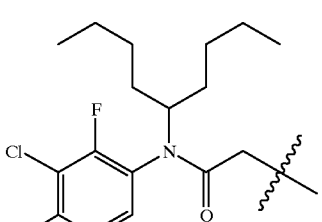 |
| 486. | 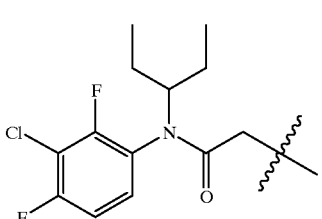 |
TABLE 2B-continued
| | R |
|---|---|
| 487. | 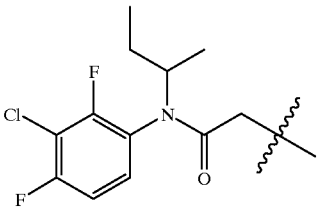 |
| 488. | 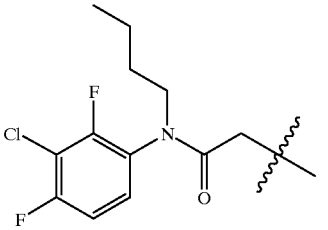 |
| 489. | 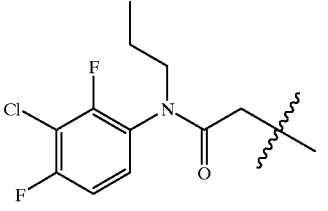 |
| 490. | 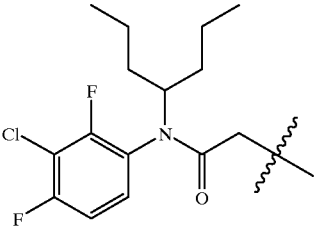 |
| 491. | 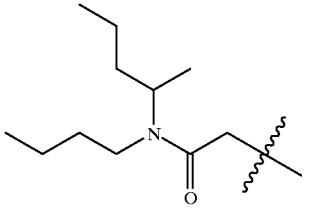 |
| 492. | 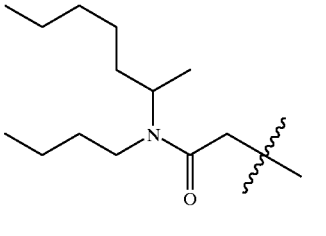 |

TABLE 2B-continued

| | R |
|---|---|
| 493. | (structure) |
| 494. | (structure) |
| 495. | (structure) |
| 496. | (structure) |
| 497. | (structure) |
| 498. | (structure) |
| 499. | (structure) |
| 500. | (structure) |
| 501. | (structure) |
| 502. | (structure) |
| 503. | (structure) |
| 504. | (structure) |
| 505. | (structure) |

TABLE 2B-continued
| | R |
|---|---|
| 506. | 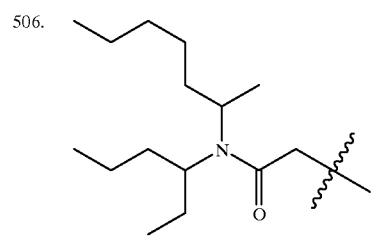 |
| 507. | 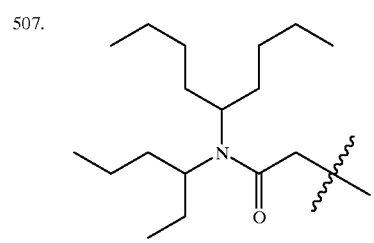 |
| 508. | 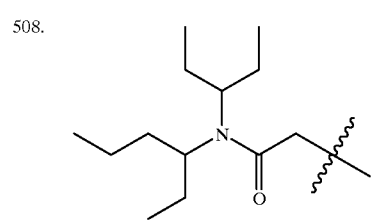 |
| 509. | 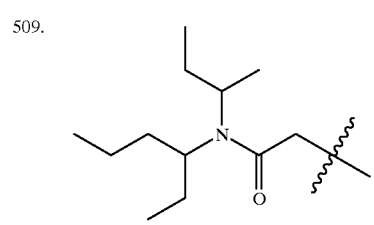 |
| 510. | 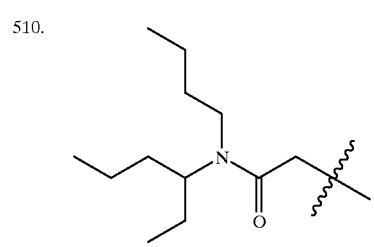 |
| 511. | 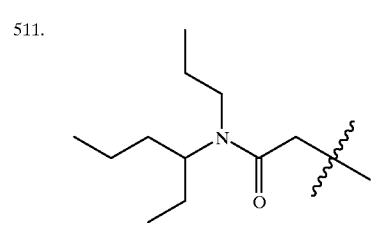 |
| 512. | 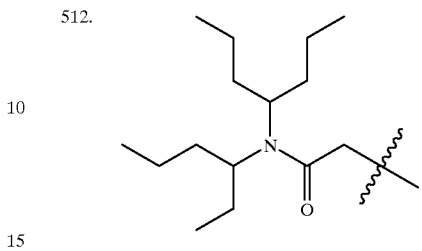 |
| 513. | 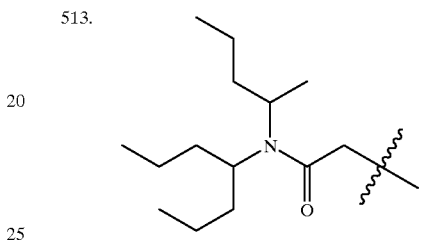 |
| 514. | 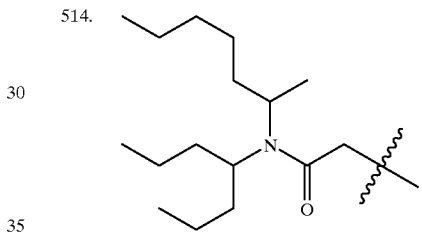 |
| 515. | 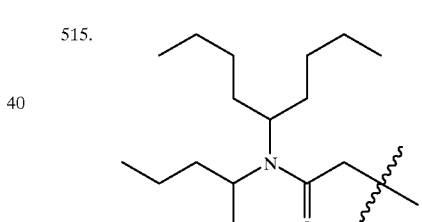 |
| 516. | 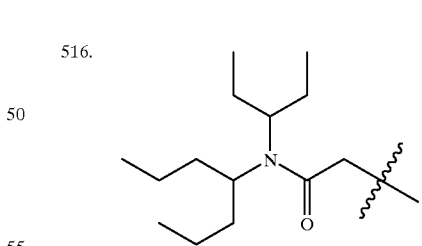 |
| 517. | 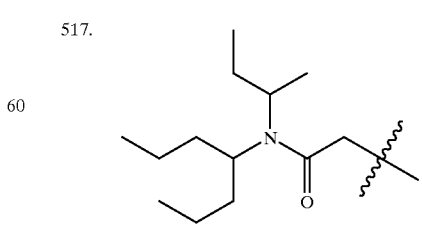 |

TABLE 2B-continued
| R |
|---|
| 518. 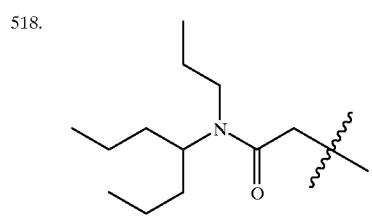 |
| 519. 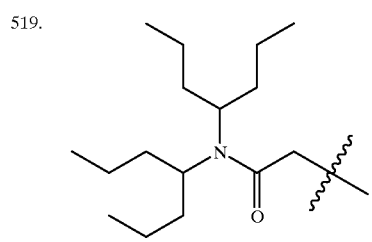 |
| 520. 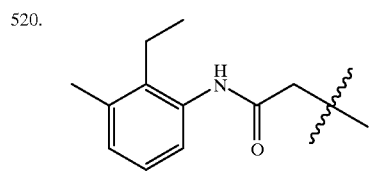 |
| 521. 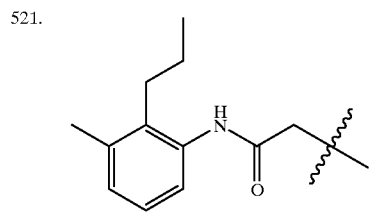 |
| 522. 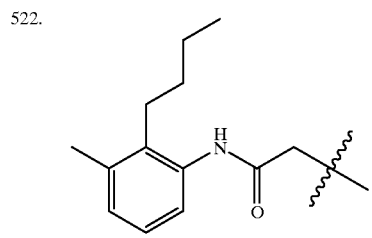 |
| 523. 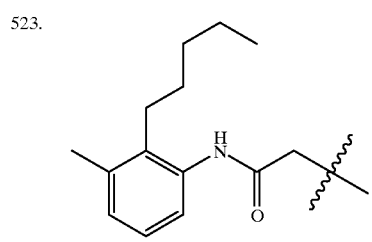 |
| 524. 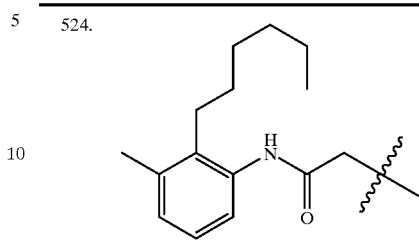 |
| 525. 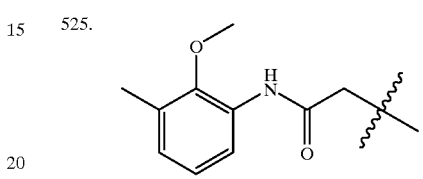 |
| 526. 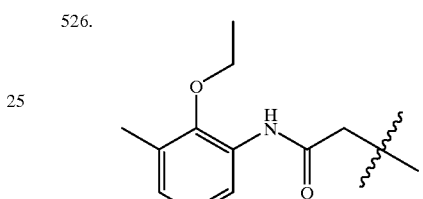 |
| 527. 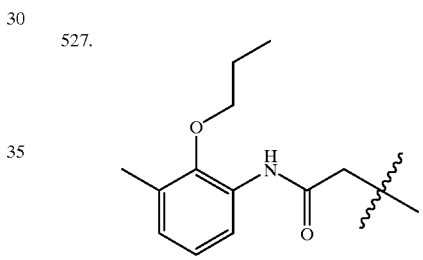 |
| 528. 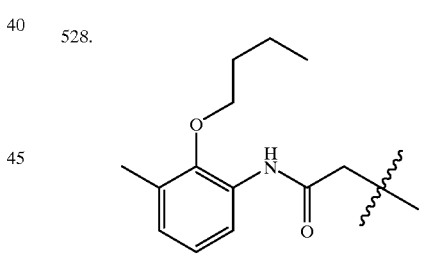 |
| 529. 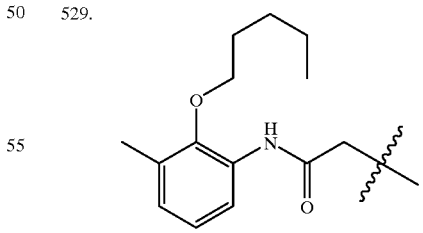 |
| 530. 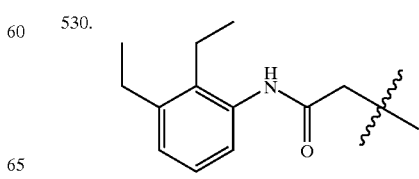 |

TABLE 2B-continued
R
531. 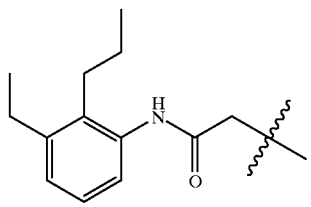
532. 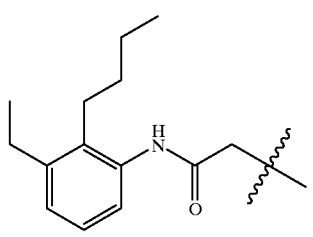
533. 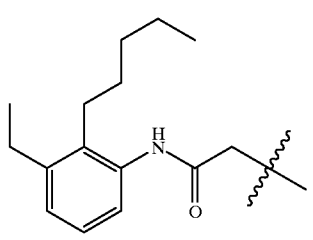
534. 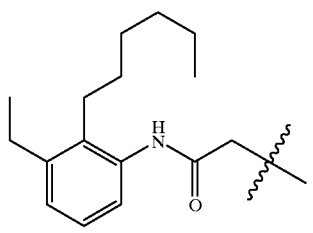
535. 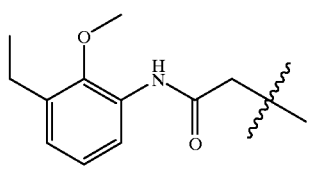
536. 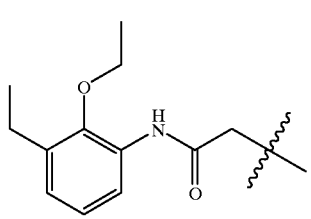
TABLE 2B-continued
R
537. 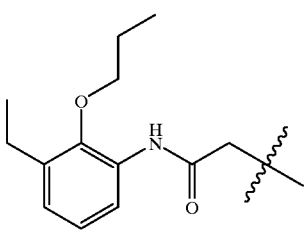
538. 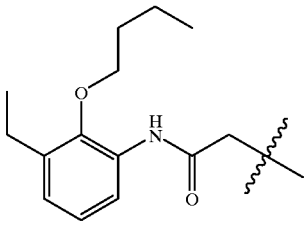
539. 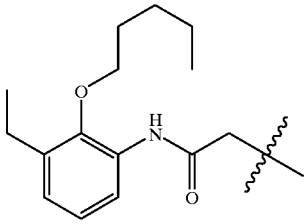
540. 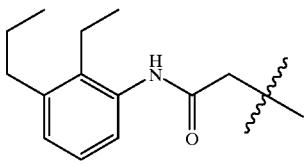
541. 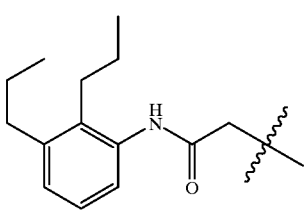
542. 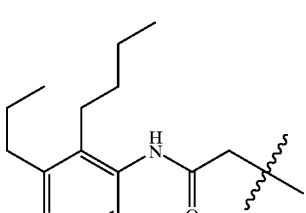

TABLE 2B-continued
| | R |
|---|---|
| 543. | 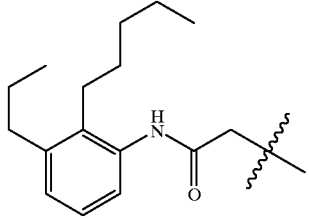 |
| 544. | 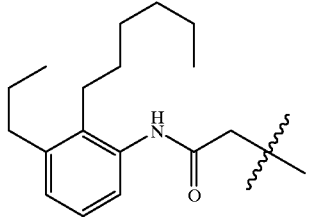 |
| 545. | 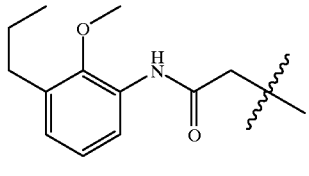 |
| 546. | 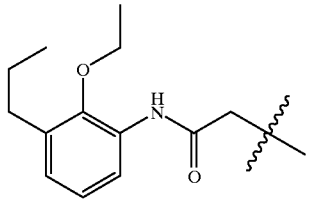 |
| 547. | 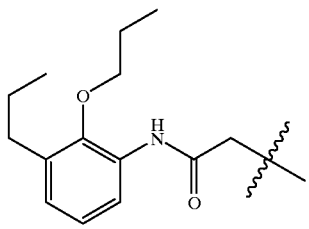 |
| 548. | 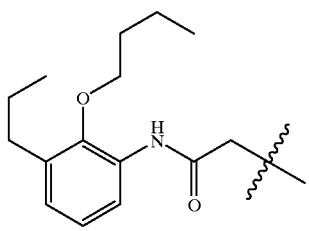 |
| 549. | 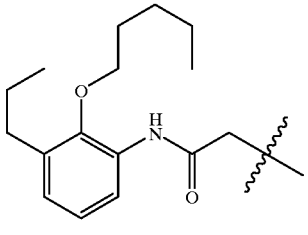 |
| 550. | 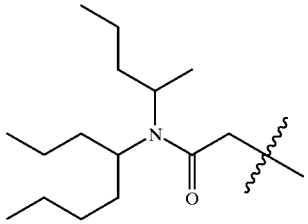 |
| 551. | 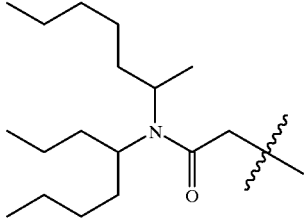 |
| 552. | 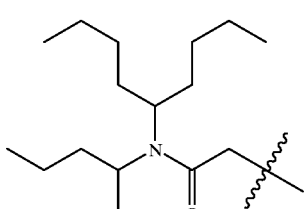 |
| 553. | 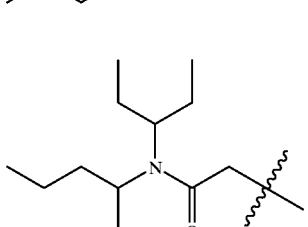 |
| 554. | 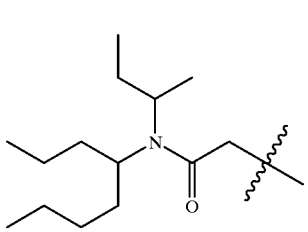 |

TABLE 2B-continued
| | R |
|---|---|
| 555. | 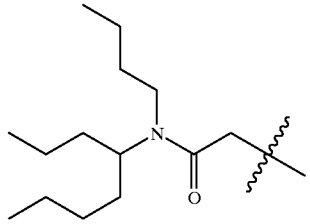 |
| 556. | 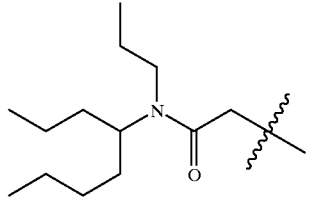 |
| 557. | 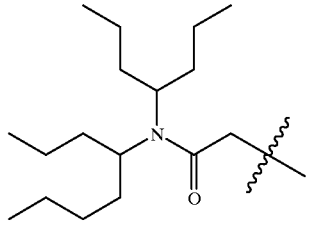 |
| 558. | 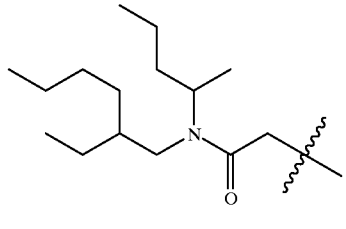 |
| 559. | 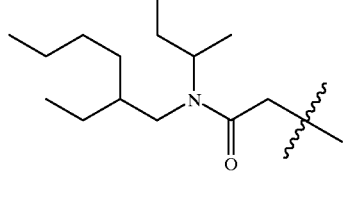 |
| 560. | 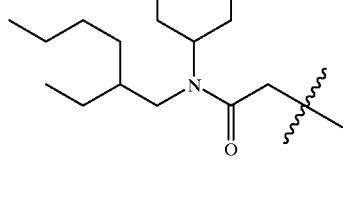 |
TABLE 2B-continued
| | R |
|---|---|
| 561. | 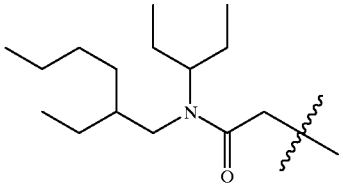 |
| 562. | 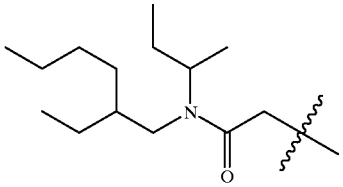 |
| 563. | 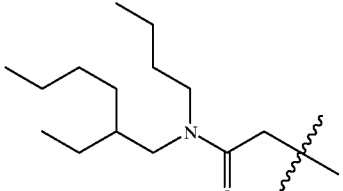 |
| 564. | 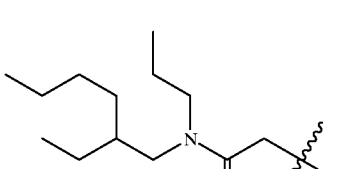 |
| 565. | 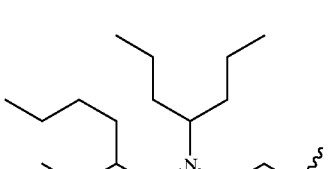 |
| 566. | 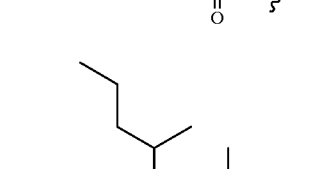 |
| 567. | 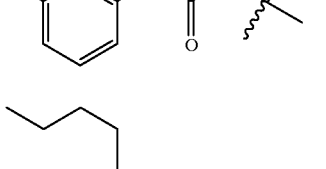 |

TABLE 2B-continued
| R |
|---|
| 568. 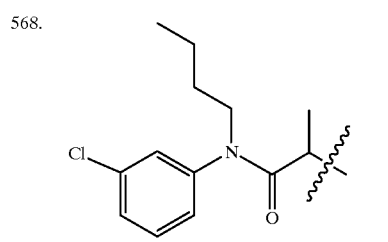 |
| 569. 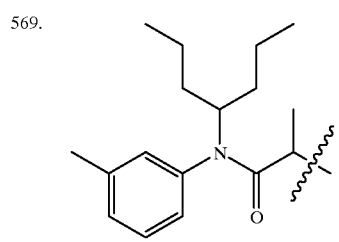 |
| 570. 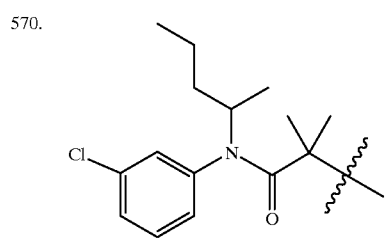 |
| 571. 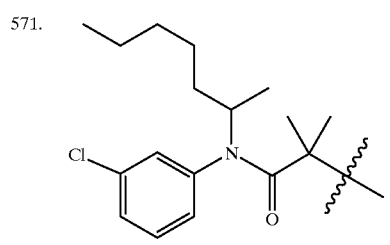 |
| 572. 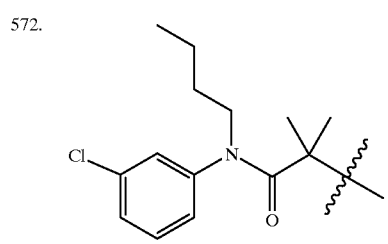 |
| 573. 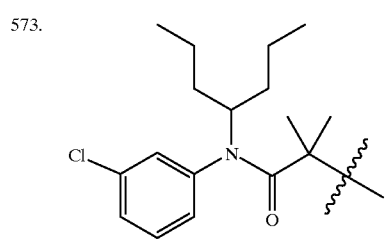 |
TABLE 2B-continued
| R |
|---|
| 574. 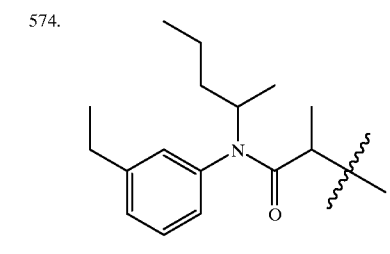 |
| 575. 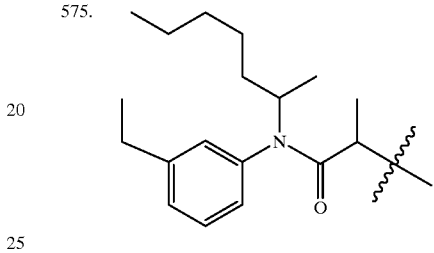 |
| 576. 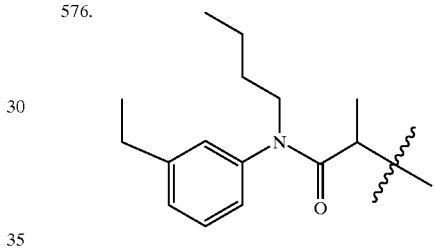 |
| 577. 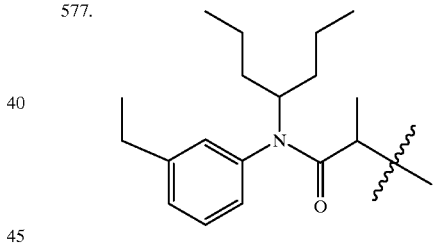 |
| 578. 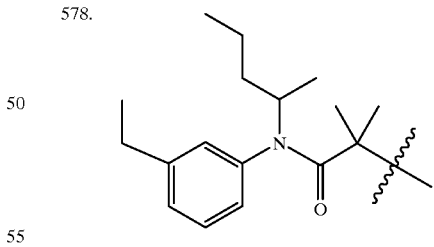 |
| 579. 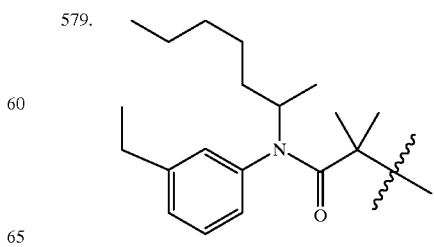 |

TABLE 2B-continued
| | R |
|---|---|
| 580. | 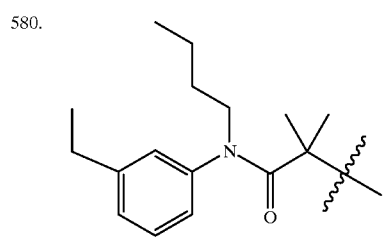 |
| 581. | 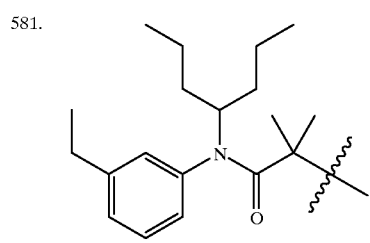 |
| 582. | 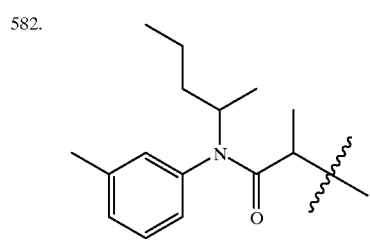 |
| 583. | 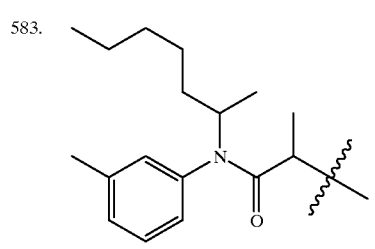 |
| 584. | 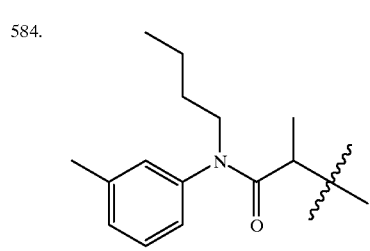 |
| 585. | 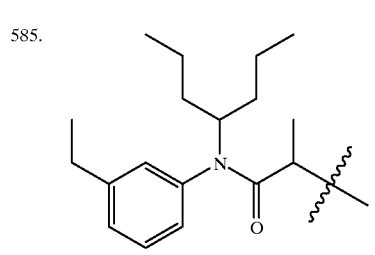 |
| 586. | 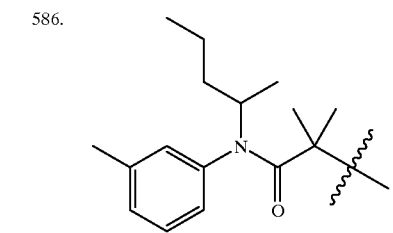 |
| 587. | 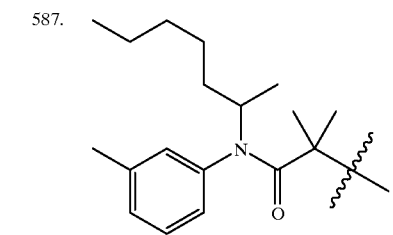 |
| 588. | 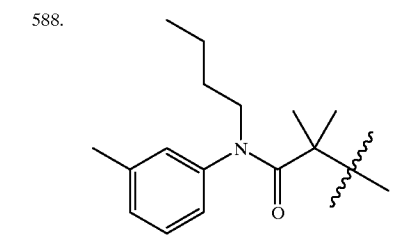 |
| 589. | 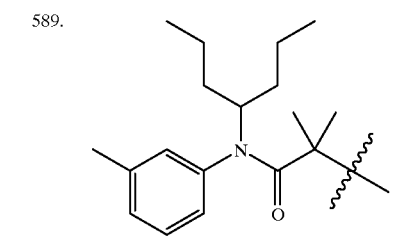 |
| 590. | 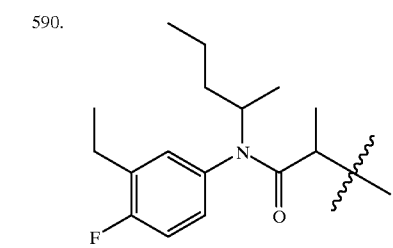 |
| 591. | 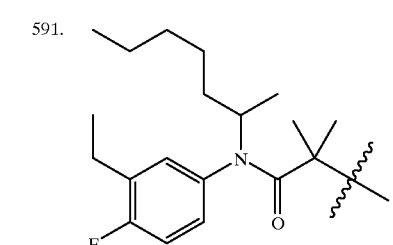 |

TABLE 2B-continued

TABLE 2B-continued

| R |
|---|
| 604. (structure) |
| 605. (structure) |
| 606. (structure) |
| 607. (structure) |
| 608. (structure) |
| 609. (structure) |
| 610. (structure) |
| 611. (structure) |
| 612. (structure) |
| 613. (structure) |
| 614. (structure) |
| 615. (structure) |
| 616. (structure) |

TABLE 2B-continued
| R | |
|---|---|
| 617. | 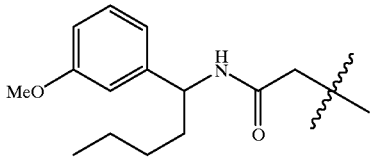 |
| 618. | 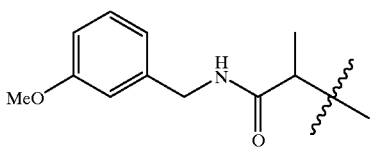 |
| 619. | 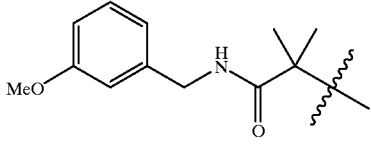 |
| 620. | 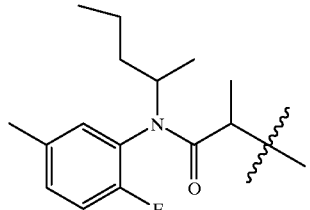 |
| 621. | 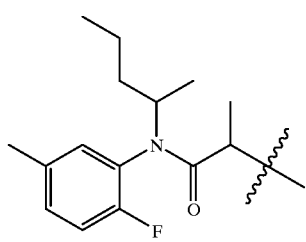 |
| 622. | 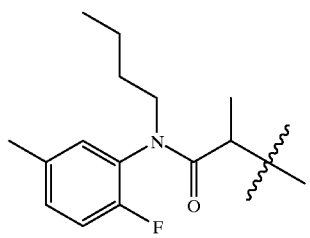 |
| 623. | 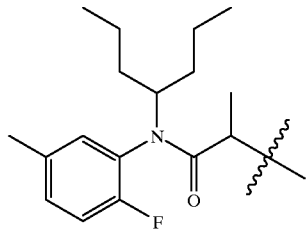 |
| 624. | 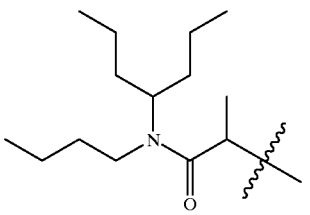 |
| 625. | 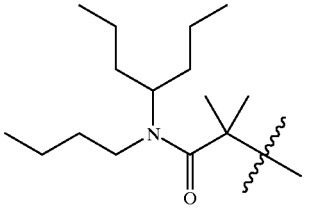 |
| 626. | 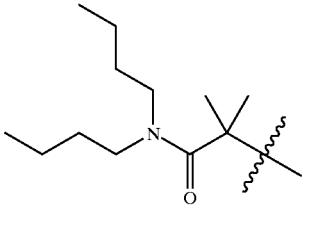 |
| 627. | 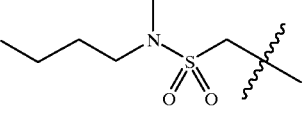 |
| 628. | 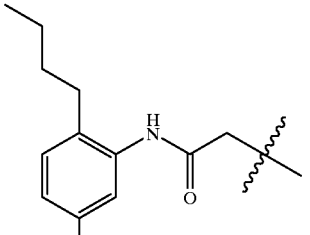 |
| 629. | 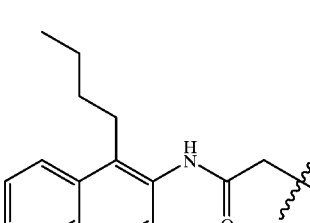 |
| 630. | 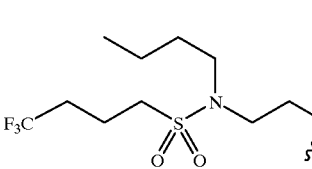 |

TABLE 2B-continued

R

631. [structure: F₃C-propyl-S(O)₂-N(isobutyl)-CH₂-C(CH₃)(~)]

632. [structure: F₃C-propyl-S(O)₂-N(propyl)-CH₂-C(CH₃)(~)]

EXAMPLE 339

Using methods described in the above examples, compounds comprising a parent structure selected from those disclosed in Table 3A and an R substituent selected from those disclosed in Table 3B can be prepared.

TABLE 3A

1. [pyrrolidine with 4-F-phenyl, COOH, and benzofuran-5-yl substituents, R-N]

2. [pyrrolidine with 4-MOMO-phenyl, COOH, and benzofuran-5-yl substituents, R-N]

TABLE 3A-continued

3. [pyrrolidine with 4-F-phenyl, COOH, and 2,3-dihydrobenzofuran-5-yl substituents, R-N]

4. [pyrrolidine with 4-OCH₃-phenyl, COOH, and benzofuran-6-yl substituents, R-N]

5. [pyrrolidine with 4-OCH₃-phenyl, COOH, and 2,3-dihydrobenzofuran-6-yl substituents, R-N]

6. [pyrrolidine with 4-OCH₃-phenyl, COOH, and 3,4-difluorophenyl substituents, R-N]

TABLE 3A-continued
7. 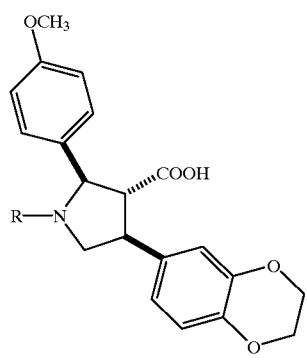
8. 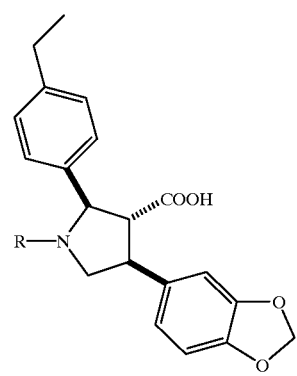
9. 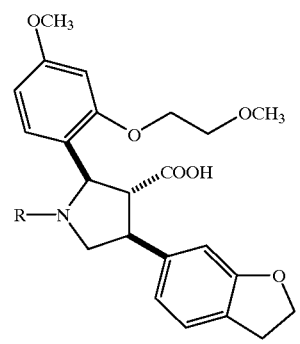
10. 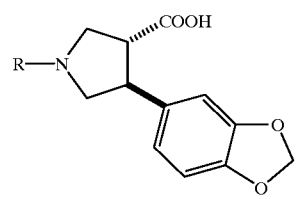
11. 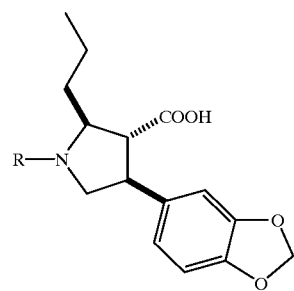
TABLE 3A-continued
12. 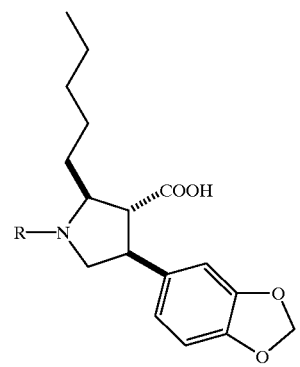
13. 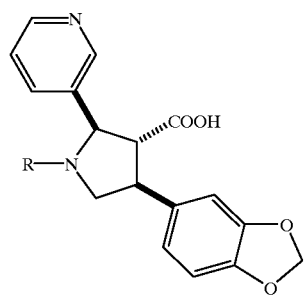
14. 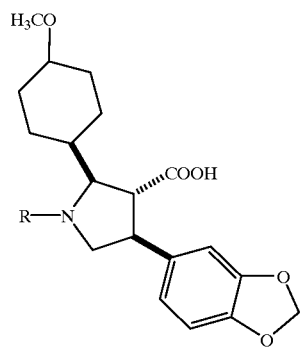
15. 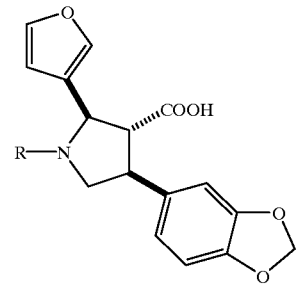

TABLE 3A-continued
16. 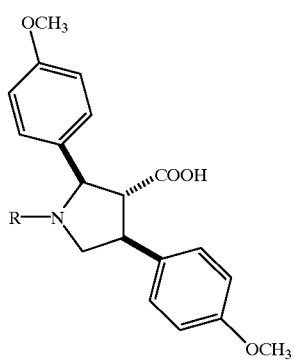
17. 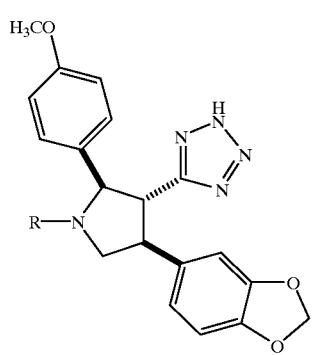
18. 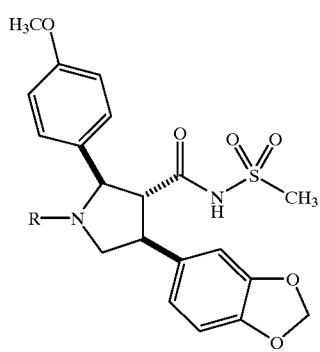
19. 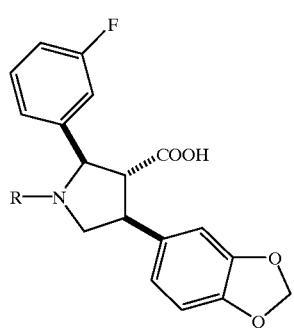
TABLE 3A-continued
20. 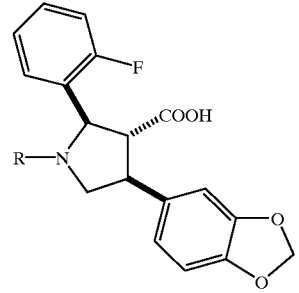
21. 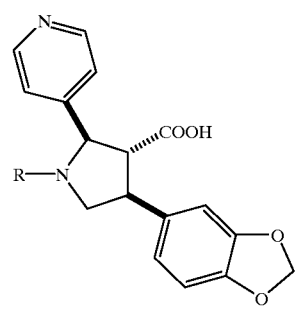
TABLE 3B
R
1. 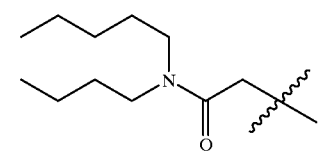
2. 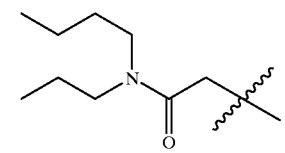
3. 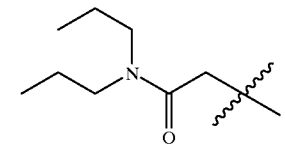
4. 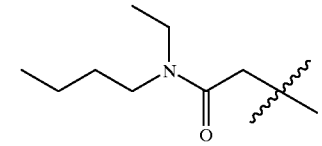
5. 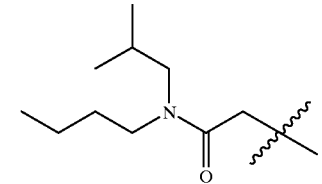

TABLE 3B-continued
| | R |
|---|---|
| 6. | 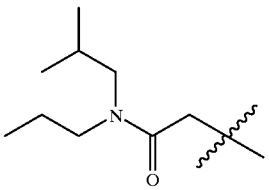 |
| 7. | 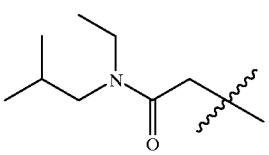 |
| 8. | 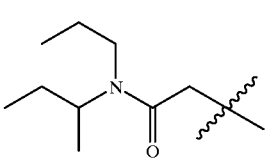 |
| 9. | 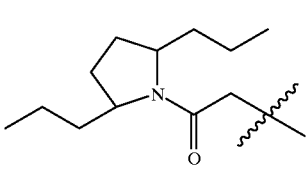 |
| 10. | 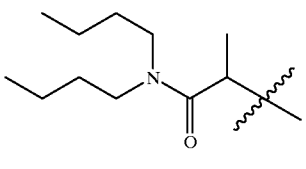 |
| 11. | 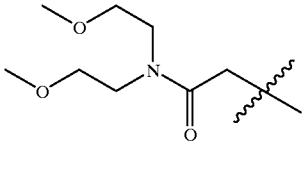 |
| 12. | 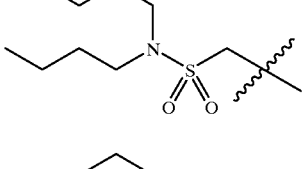 |
| 13. | 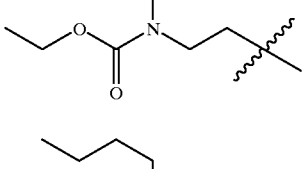 |
| 14. | 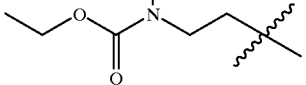 |
| 15. | 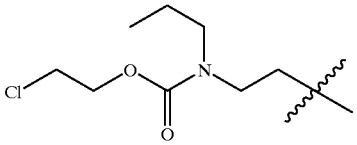 |
| 16. | 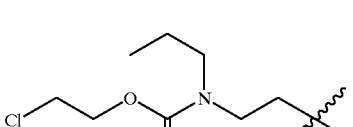 |
| 17. | 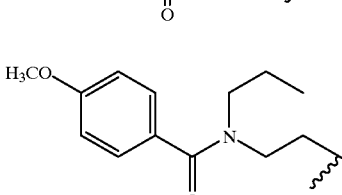 |
| 18. | 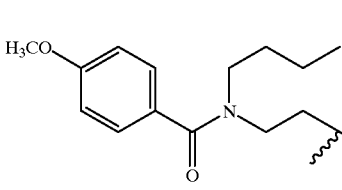 |
| 19. | 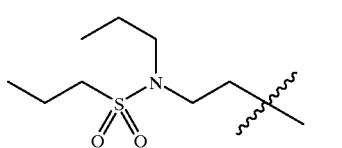 |
| 20. | 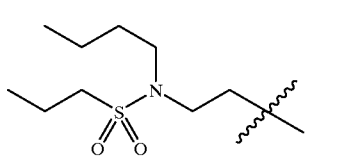 |
| 21. | 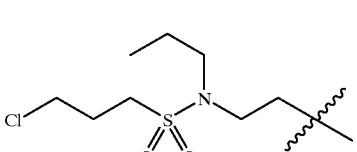 |
| 22. | 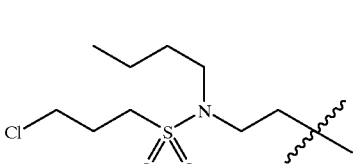 |
| 23. | 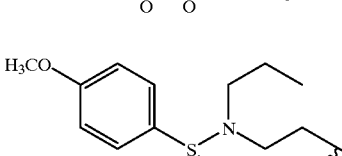 |

TABLE 3B-continued

R

24. [structure: 4-methoxyphenyl-SO2-N(butyl)-CH2CH2-]

25. [structure: H3CO-CH2CH2-SO2-N(butyl)-]

26. [structure: H3CO-CH2CH2-SO2-N(propyl)-]

27. [structure: F3C-CH2CH2-SO2-N(butyl)-]

28. [structure: F3C-CH2CH2-SO2-N(propyl)-]

29. [structure: FH2C-CH2CH2-SO2-N(butyl)-]

30. [structure: FH2C-CH2CH2-SO2-N(propyl)-]

31. [structure: FH2C-CF2-CH2-SO2-N(butyl)-]

32. [structure: FH2C-CF2-CH2-SO2-N(propyl)-]

TABLE 3B-continued

R

33. [structure: F2HC-CF2-CH2-SO2-N(butyl)-]

34. [structure: F2HC-CF2-CH2-SO2-N(propyl)-]

35. [structure: F3C-CF2-CH2-SO2-N(butyl)-]

36. [structure: F3C-CF2-CH2-SO2-N(propyl)-]

37. [structure: butyl-SO2-N(butyl)-]

38. [structure: butyl-SO2-N(propyl)-]

39. [structure: isobutyl-SO2-N(butyl)-]

40. [structure: isobutyl-SO2-N(propyl)-]

41. [structure: ethyl-SO2-N(butyl)-]

TABLE 3B-continued
| R | |
|---|---|
| 42. | 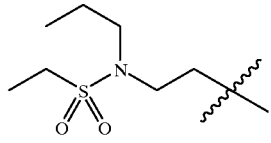 |
| 43. | 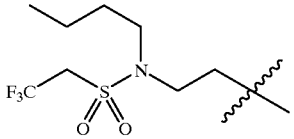 |
| 44. | 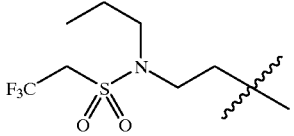 |
| 45. | 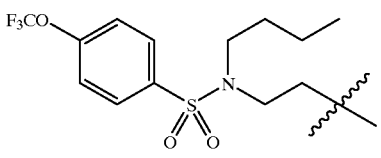 |
| 46. | 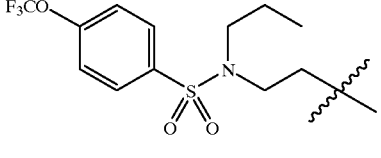 |
| 47. | 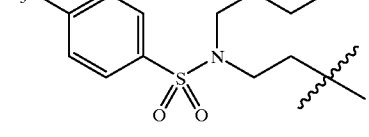 |
| 48. | 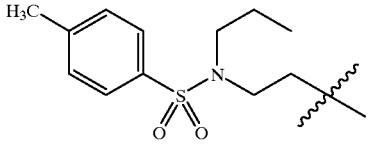 |
| 49. | 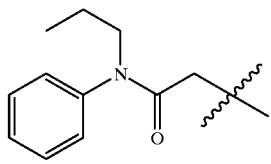 |
| 50. | 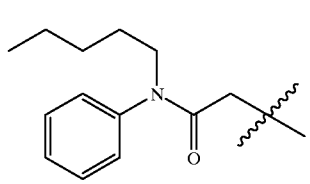 |
| 51. | 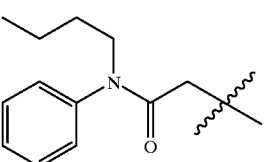 |
| 52. | 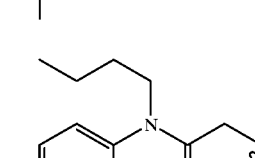 |
| 53. | 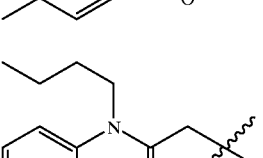 |
| 54. | 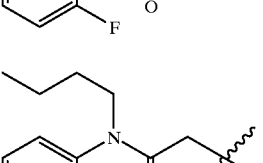 |
| 55. | 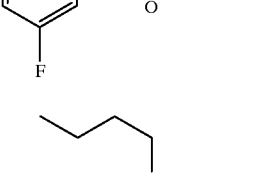 |
| 56. | 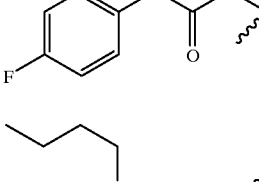 |
| 57. | 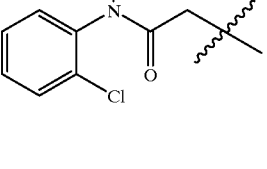 |
| 58. |  |

TABLE 3B-continued
| | R |
|---|---|
| 59. | 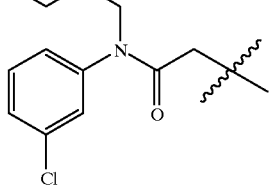 |
| 60. | 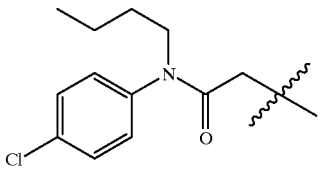 |
| 61. | 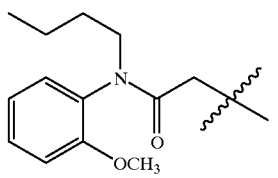 |
| 62. | 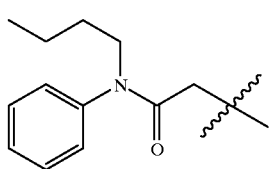 |
| 63. | 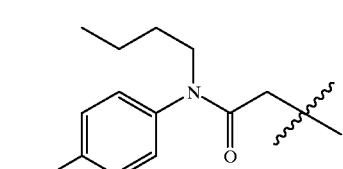 |
| 64. | 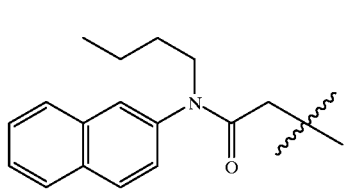 |
| 65. | 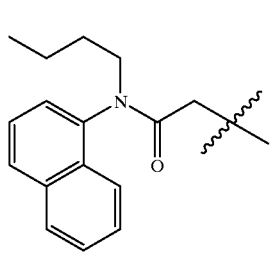 |
| 66. | 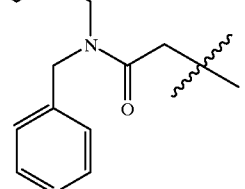 |
| 67. | 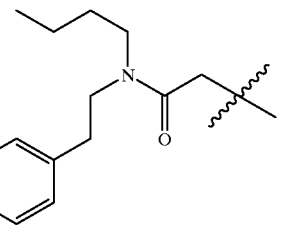 |
| 68. | 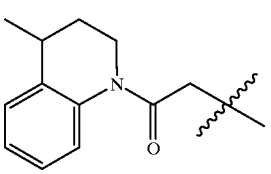 |
| 69. | 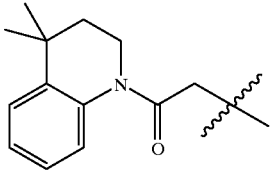 |
| 70. | 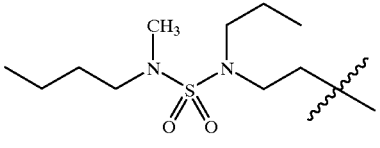 |
| 71. | 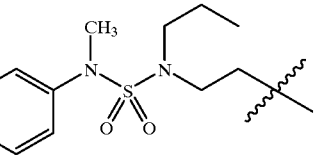 |
| 72. | 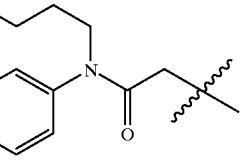 |
| 73. | 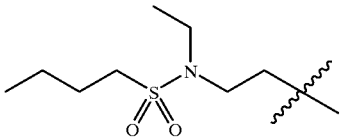 |

TABLE 3B-continued

| | R |
|---|---|
| 74. | (structure) |
| 75. | (structure) |
| 76. | (structure) |
| 77. | (structure) |
| 78. | (structure) |
| 79. | (structure) |
| 80. | (structure) |
| 81. | (structure) |
| 82. | (structure) |
| 83. | (structure) |
| 84. | (structure) |
| 85. | (structure) |
| 86. | (structure) |
| 87. | (structure) |
| 88. | (structure) |
| 89. | (structure) |
| 90. | (structure) |
| 91. | (structure) |

TABLE 3B-continued

| | R |
|---|---|
| 92. | (structure) |
| 93. | (structure) |
| 94. | (structure) |
| 95. | (structure) |
| 96. | (structure) |
| 97. | (structure) |
| 98. | (structure) |
| 99. | (structure) |
| 100. | (structure) |
| 101. | (structure) |
| 102. | (structure) |
| 103. | (structure) |
| 104. | (structure) |
| 105. | (structure) |
| 106. | (structure) |
| 107. | (structure) |
| 108. | (structure) |
| 109. | (structure) |

TABLE 3B-continued

| R |
|---|
| 110. (chemical structure) |
| 111. (chemical structure) |
| 112. (chemical structure) |
| 113. (chemical structure) |
| 114. (chemical structure) |
| 115. (chemical structure) |
| 116. (chemical structure) |

TABLE 3B-continued

| R |
|---|
| 117. (chemical structure) |
| 118. (chemical structure) |
| 119. (chemical structure) |
| 120. (chemical structure) |
| 121. (chemical structure) |
| 122. (chemical structure) |

TABLE 3B-continued
| | R |
|---|---|
| 123. | 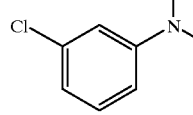 |
| 124. | 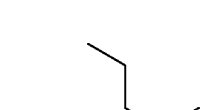 |
| 125. | 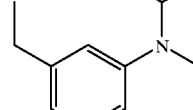 |
| 126. | 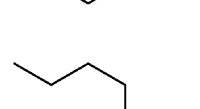 |
| 127. | 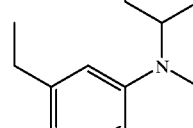 |
| 128. | 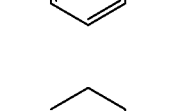 |
TABLE 3B-continued
| | R |
|---|---|
| 129. | 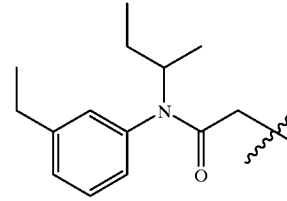 |
| 130. | 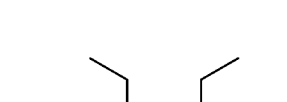 |
| 131. | 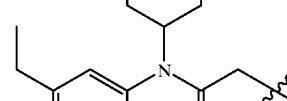 |
| 132. | 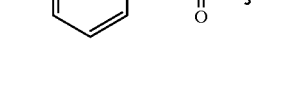 |
| 133. | 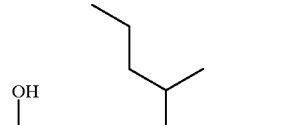 |
| 134. | 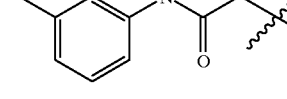 |

TABLE 3B-continued
| R | |
|---|---|
| 135. | 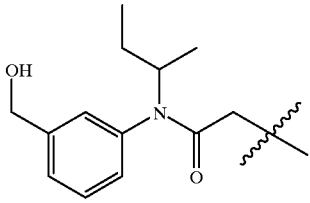 |
| 136. | 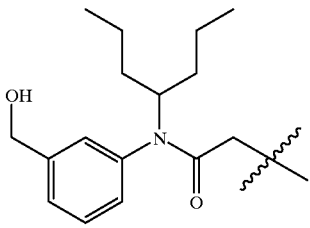 |
| 137. | 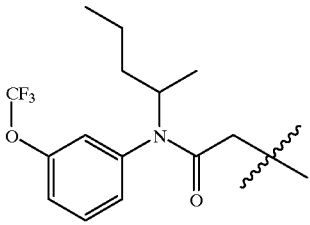 |
| 138. | 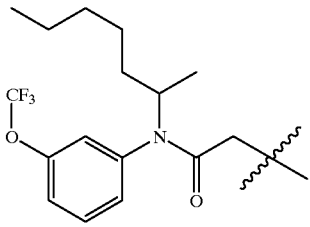 |
| 139. | 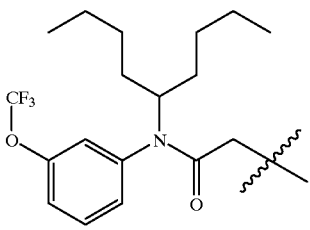 |
| 140. | 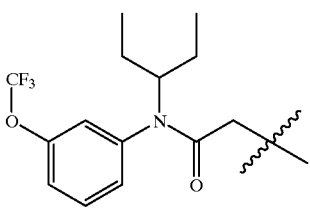 |
| 141. | 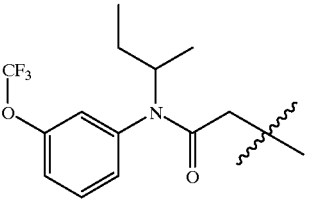 |
| 142. | 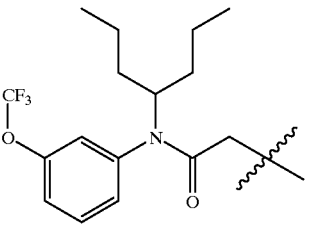 |
| 143. | 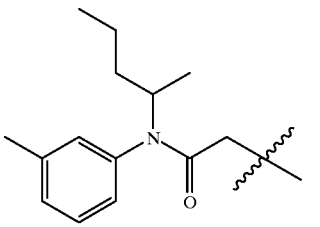 |
| 144. | 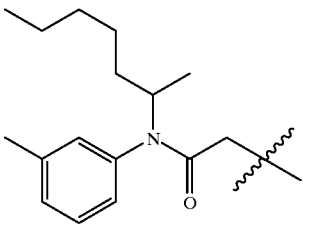 |
| 145. | 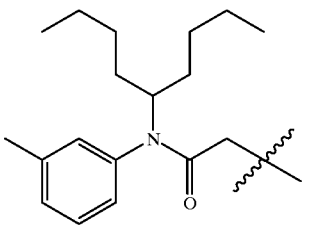 |
| 146. | 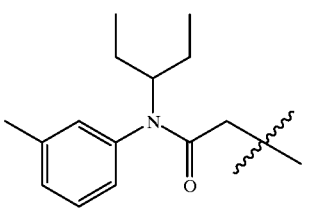 |

TABLE 3B-continued
| R | | R | |
|---|---|---|---|
| 147. | 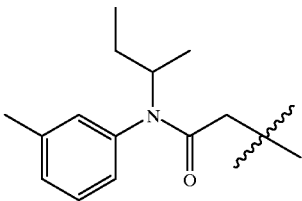 | 153. | 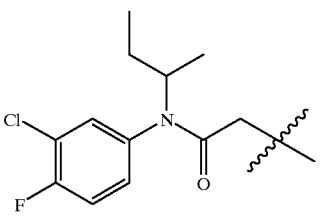 |
| 148. | 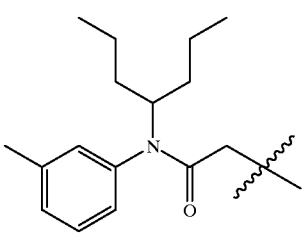 | 154. | 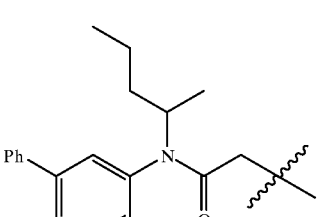 |
| 149. | 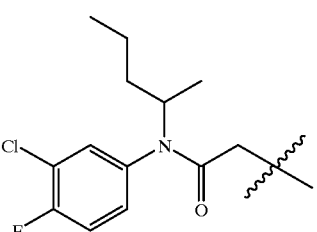 | 155. | 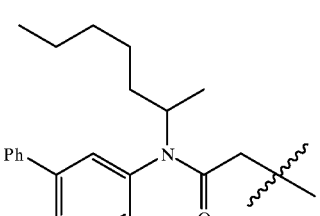 |
| 150. | 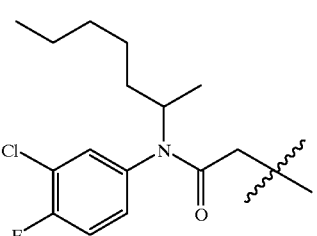 | 156. | 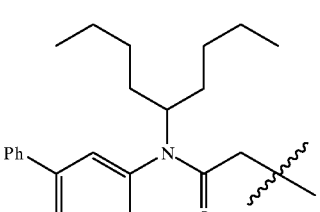 |
| 151. | 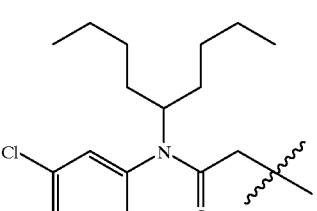 | 157. | 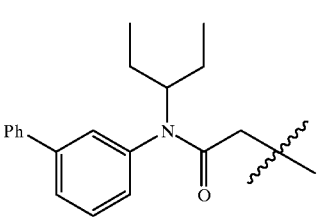 |
| 152. | 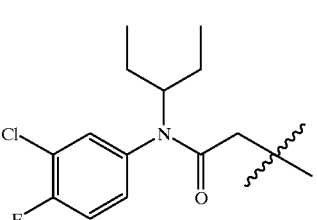 | 158. | 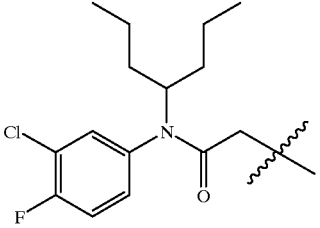 |

TABLE 3B-continued
| R | |
|---|---|
| 159. | 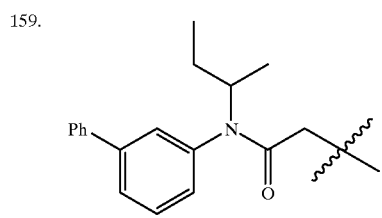 |
| 160. | 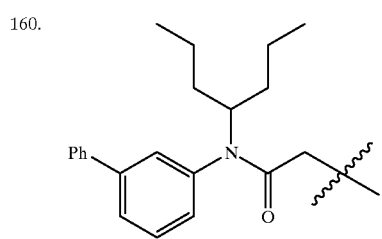 |
| 161. | 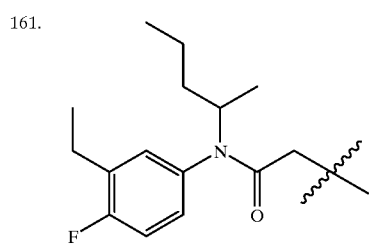 |
| 162. | 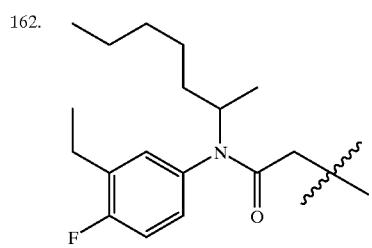 |
| 163. | 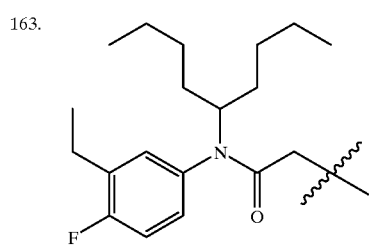 |
| 164. | 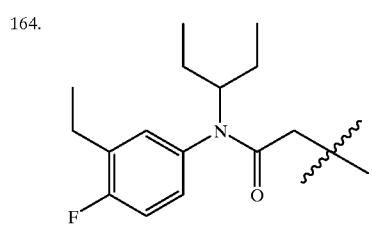 |
| 165. | 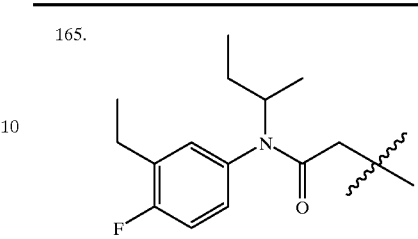 |
| 166. | 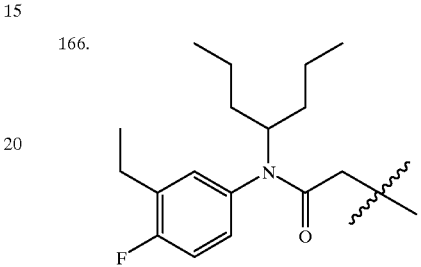 |
| 167. | 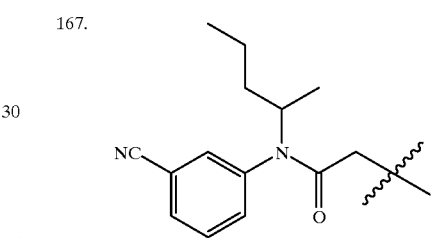 |
| 168. | 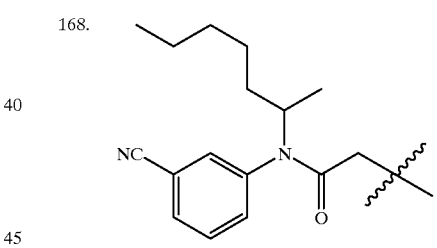 |
| 169. | 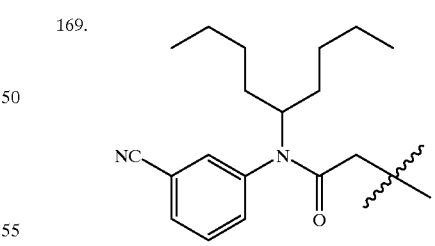 |
| 170. | 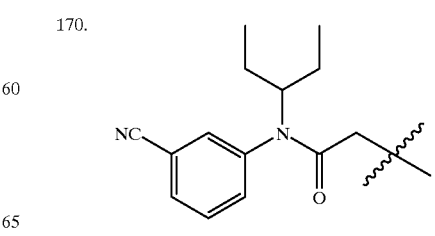 |

TABLE 3B-continued
| R |
|---|
| 171. 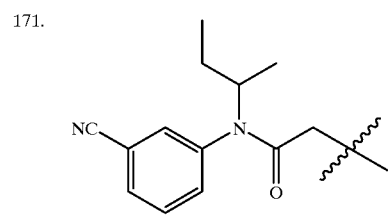 |
| 172. 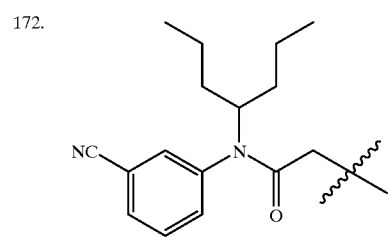 |
| 173. 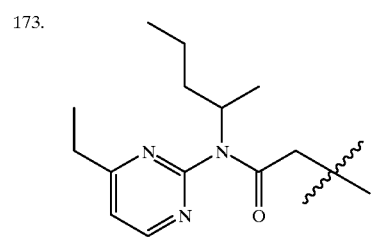 |
| 174. 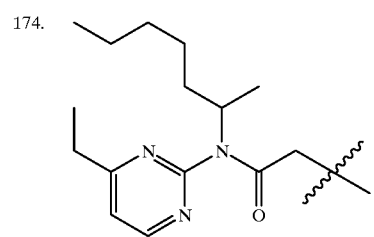 |
| 175. 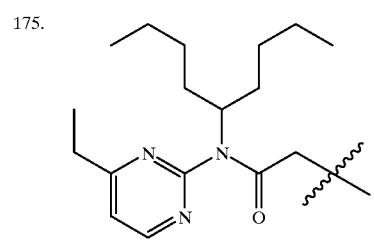 |
| 176. 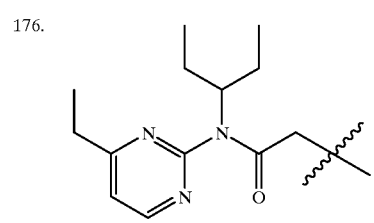 |
| 177. 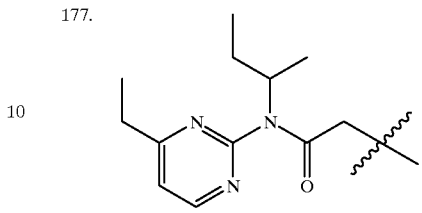 |
| 178. 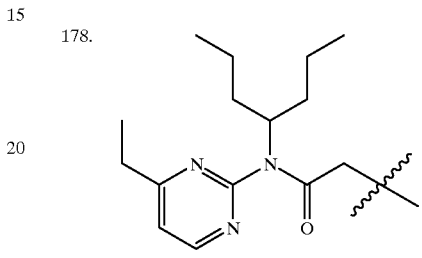 |
| 179. 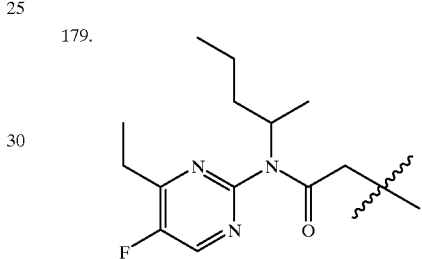 |
| 180. 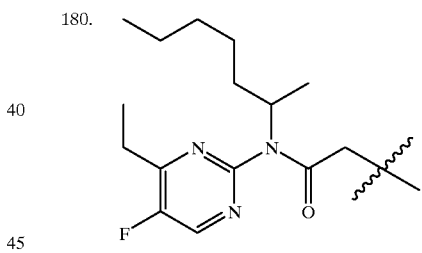 |
| 181. 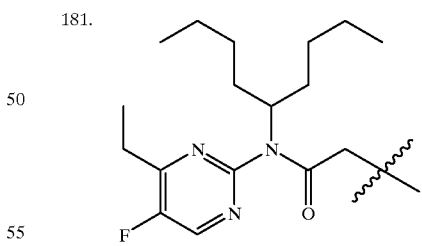 |
| 182. 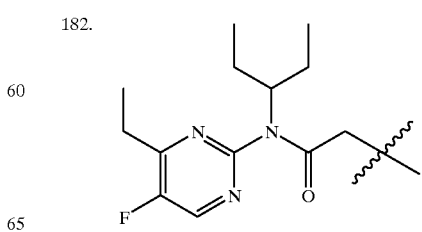 |

TABLE 3B-continued
| | R |
|---|---|
| 183. | 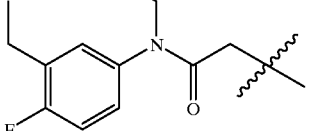 |
| 184. |  |
| 185. | 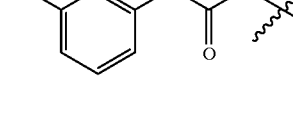 |
| 186. | 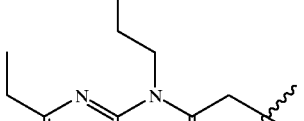 |
| 187. | 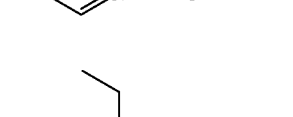 |
| 188. | 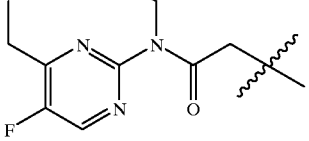 |
| 189. |  |
| 190. | 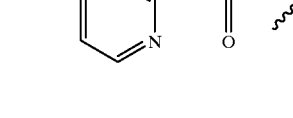 |
| 191. | 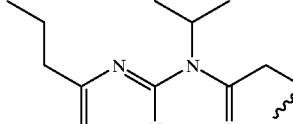 |
| 192. |  |
| 193. |  |
| 194. | |

TABLE 3B-continued
| R |
|---|
| 195. 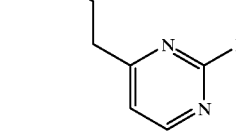 |
| 196. |
| 197. |
| 198. |
| 199. |
| 200. |
| 201. 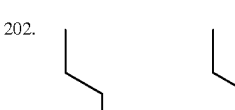 |
| 202. |
| 203. |
| 204. |
| 205. |
| 206. |

TABLE 3B-continued
| | R |
|---|---|
| 207. | 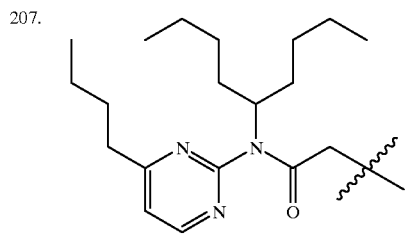 |
| 208. | 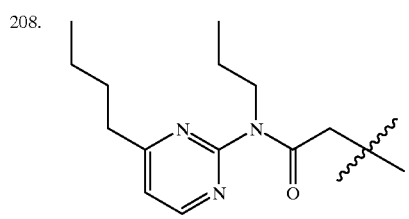 |
| 209. | 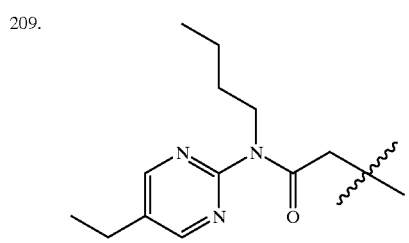 |
| 210. | 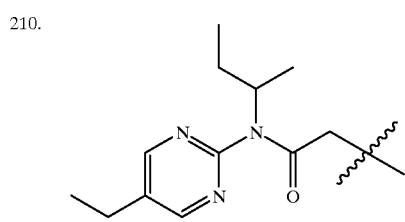 |
| 211. | 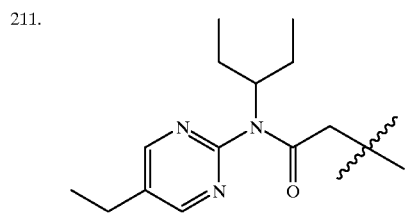 |
| 212. | 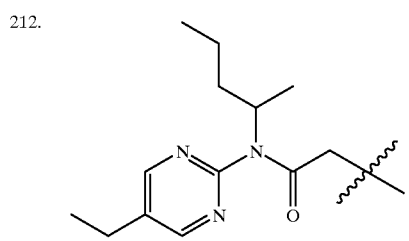 |
| 213. | 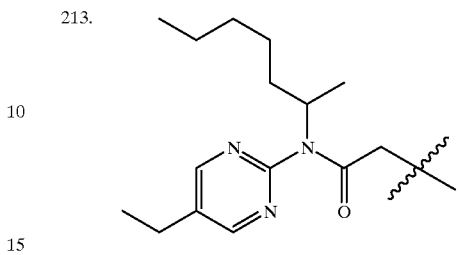 |
| 214. | 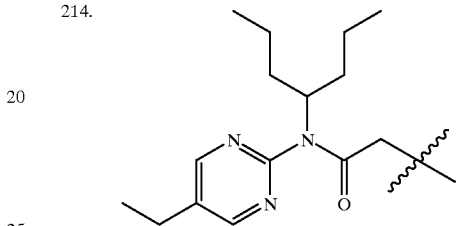 |
| 215. | 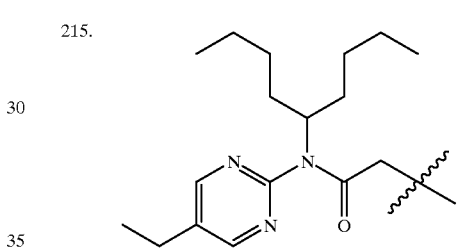 |
| 216. | 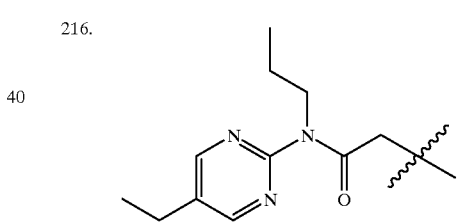 |
| 217. | 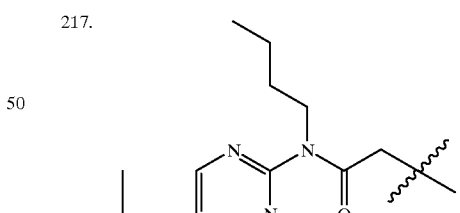 |
| 218. | 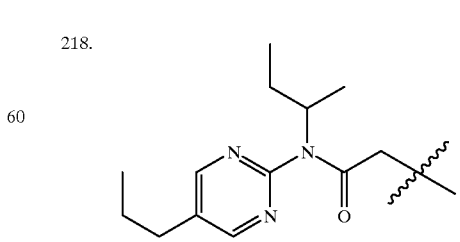 |

TABLE 3B-continued

| R |
|---|
| 219. (structure) |
| 220. (structure) |
| 221. (structure) |
| 222. (structure) |
| 223. (structure) |
| 224. (structure) |
| 225. (structure) |
| 226. (structure) |
| 227. (structure) |
| 228. (structure) |
| 229. (structure) |
| 230. (structure) |

TABLE 3B-continued
| | R |
|---|---|
| 231. | 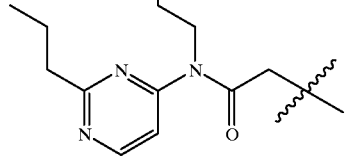 |
| 232. | 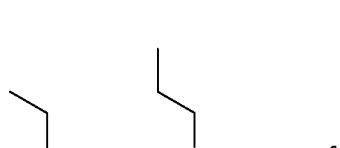 |
| 233. | |
| 234. | |
| 235. | |
| 236. | |
| 237. | |
| 238. | |
| 239. | |
| 240. | |
| 241. | |
| 242. | |

TABLE 3B-continued

| R |
|---|
| 243. |
| 244. |
| 245. |
| 246. |
| 247. |
| 248. |
| 249. |
| 250. |
| 251. |
| 252. |

TABLE 3B-continued
| R |
|---|
| 253. 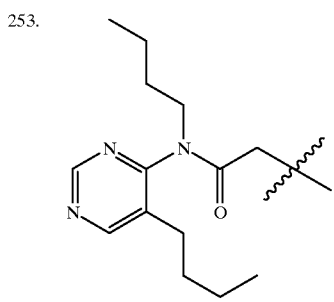 |
| 254. 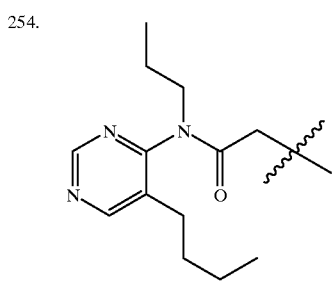 |
| 255. 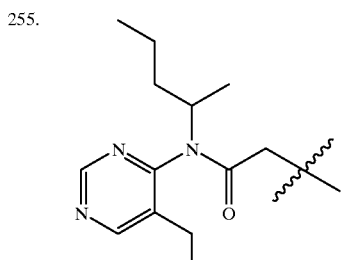 |
| 256. 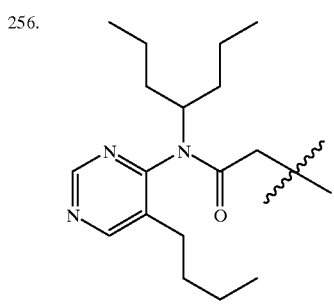 |
| 257. 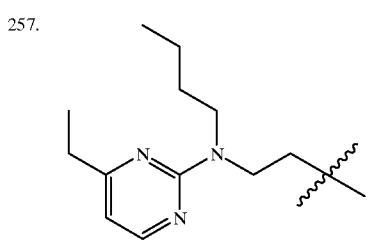 |
TABLE 3B-continued
| R |
|---|
| 258. 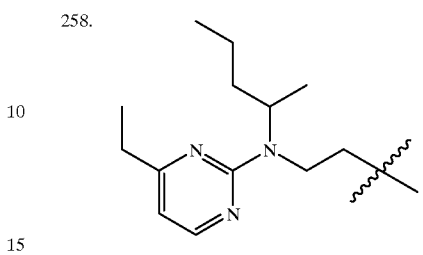 |
| 259. 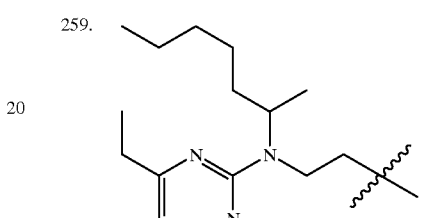 |
| 260. 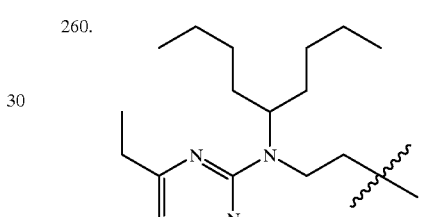 |
| 261. 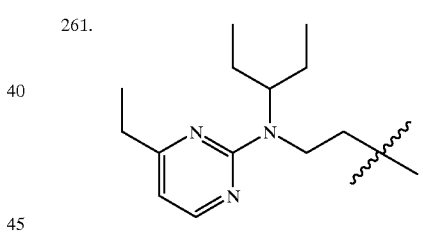 |
| 262. 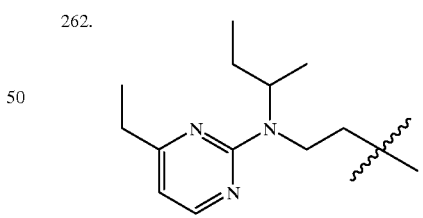 |
| 263. 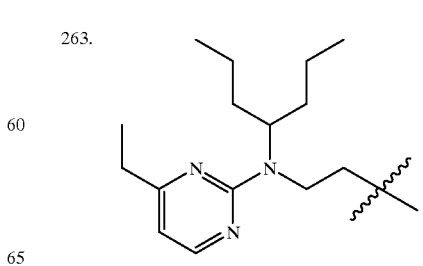 |

TABLE 3B-continued
| | R |
|---|---|
| 264. | 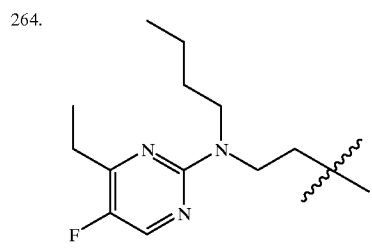 |
| 265. | 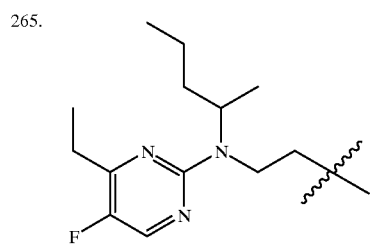 |
| 266. | 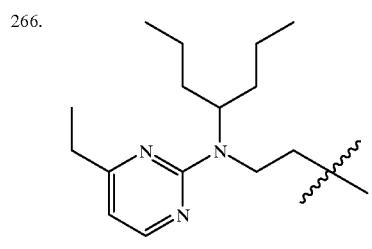 |
| 267. | 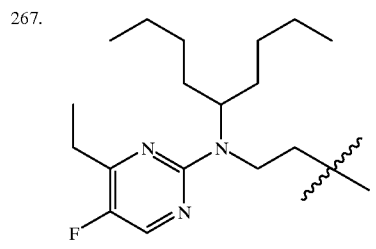 |
| 268. | 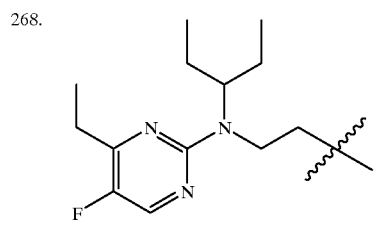 |
| 269. | 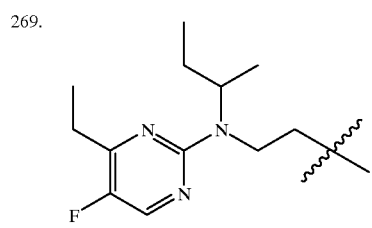 |
TABLE 3B-continued
| | R |
|---|---|
| 270. | 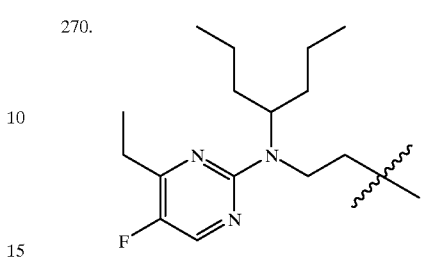 |
| 271. | 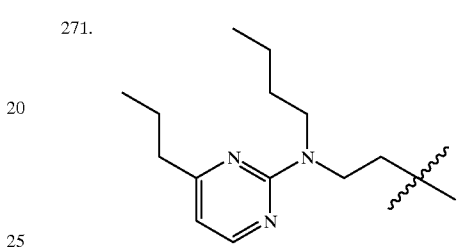 |
| 272. | 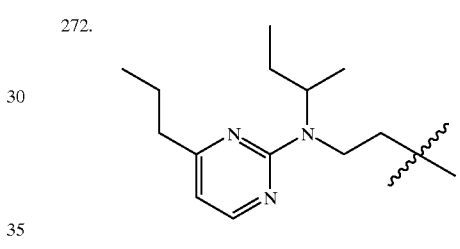 |
| 273. | 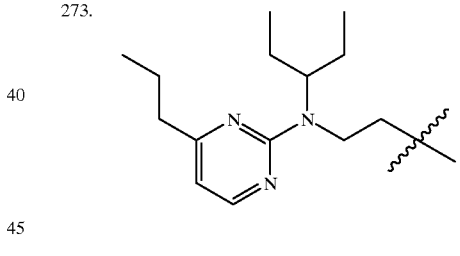 |
| 274. | 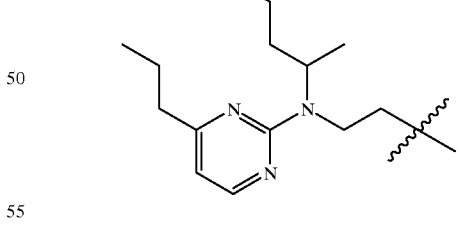 |
| 275. | 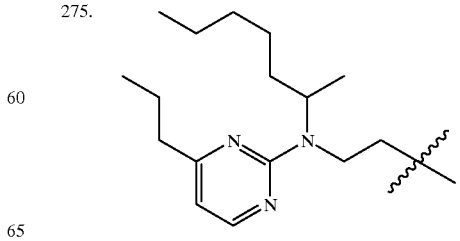 |

TABLE 3B-continued

| | R |
|---|---|
| 276. | (structure) |
| 277. | (structure) |
| 278. | (structure) |
| 279. | (structure) |
| 280. | (structure) |
| 281. | (structure) |
| 282. | (structure) |
| 283. | (structure) |
| 284. | (structure) |
| 285. | (structure) |
| 286. | (structure) |
| 287. | (structure) |

TABLE 3B-continued

| | R |
|---|---|
| 288. | (structure) |
| 289. | (structure) |
| 290. | (structure) |
| 291. | (structure) |
| 292. | (structure) |
| 293. | (structure) |
| 294. | (structure) |
| 295. | (structure) |
| 296. | (structure) |
| 297. | (structure) |
| 298. | (structure) |
| 299. | (structure) |

TABLE 3B-continued
| R |
|---|
| 300. 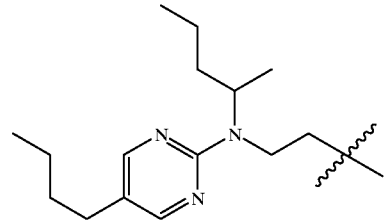 |
| 301. |
| 302. |
| 303. |
| 304. |
| 305. |
| 306. 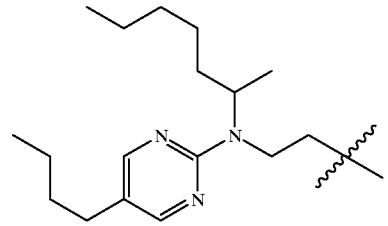 |
| 307. |
| 308. |
| 309. |
| 310. |
| 311. |

TABLE 3B-continued
R
312. 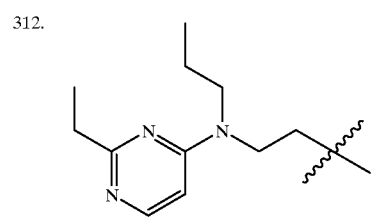
313. 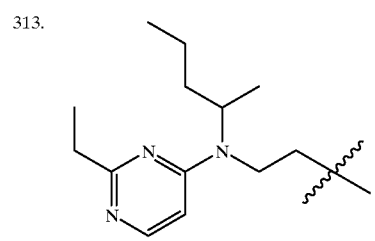
314. 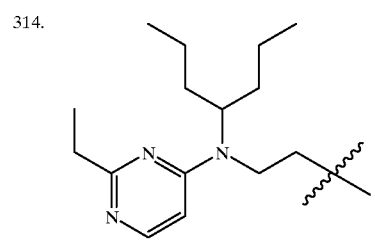
315. 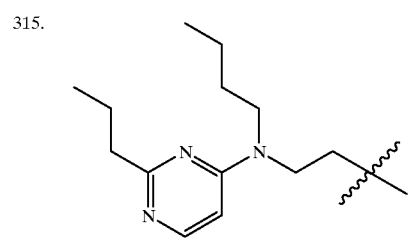
316. 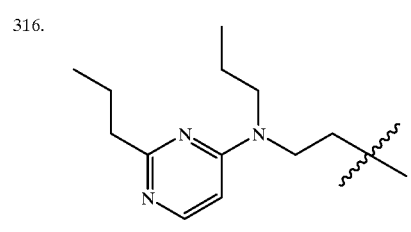
317. 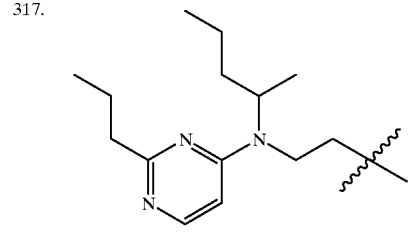
TABLE 3B-continued
R
318. 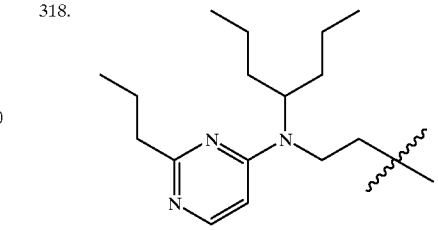
319. 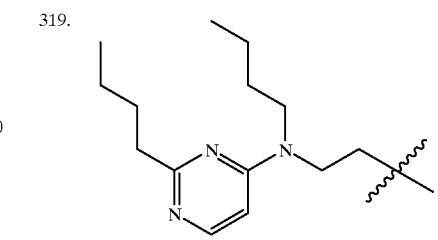
320. 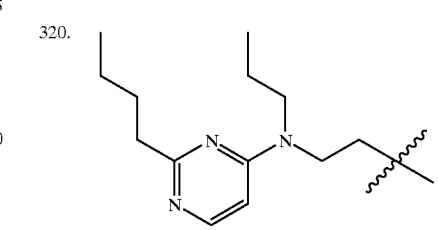
321. 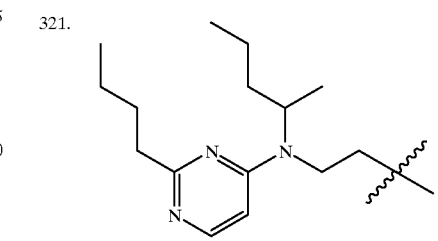
322. 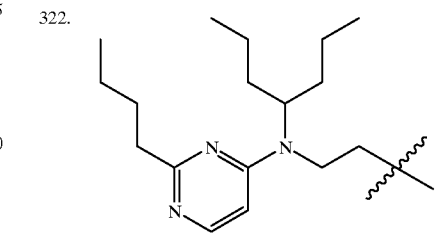
323. 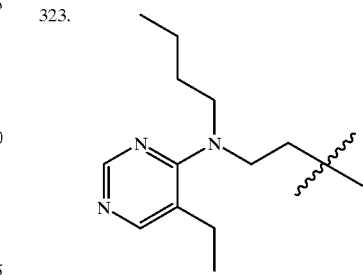

TABLE 3B-continued
| R | |
|---|---|
| 324. | 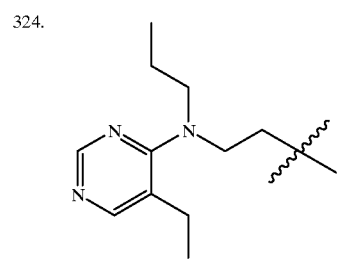 |
| 325. | 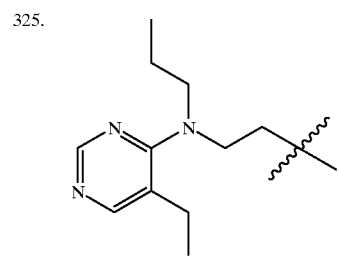 |
| 326. | 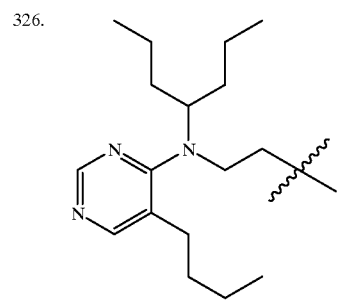 |
| 327. | 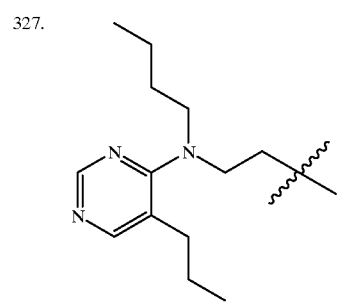 |
| 328. | 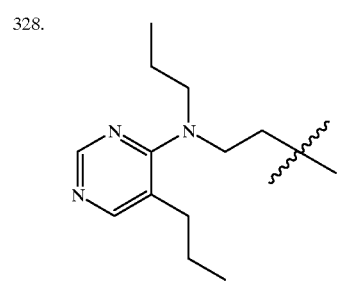 |
| 329. | 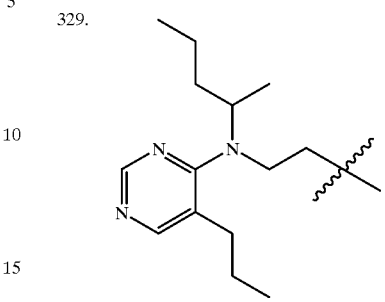 |
| 330. | 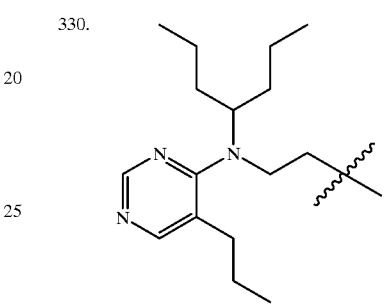 |
| 331. | 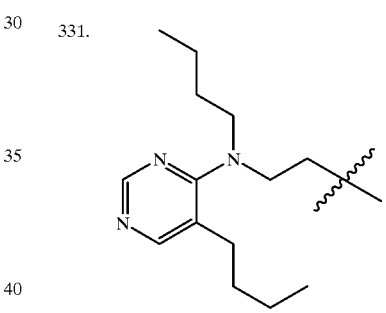 |
| 332. | 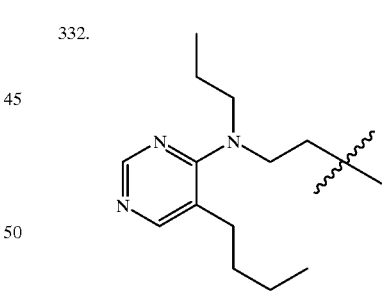 |
| 333. | 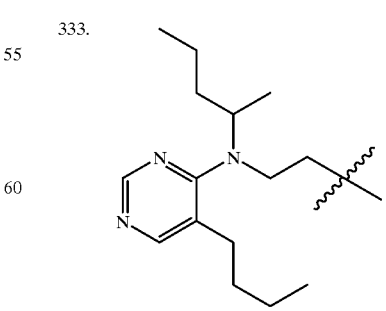 |

TABLE 3B-continued
R
334. 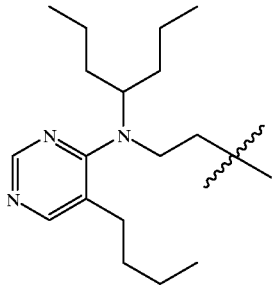
335. 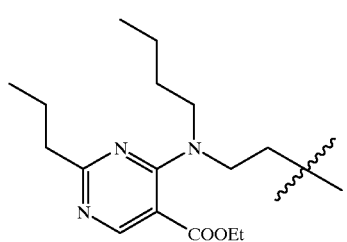
336. 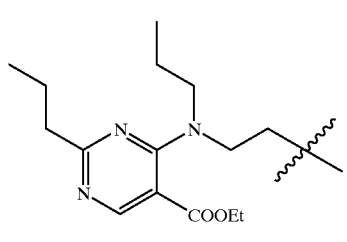
337. 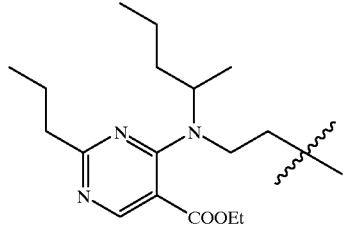
338. 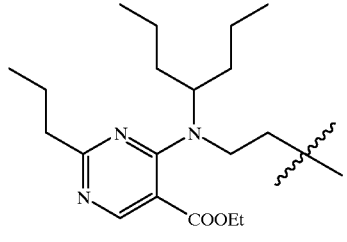
339. 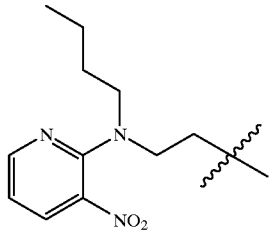
340. 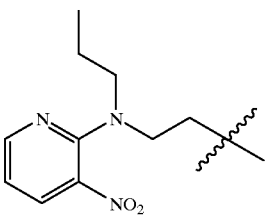
341. 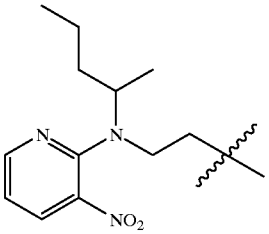
342. 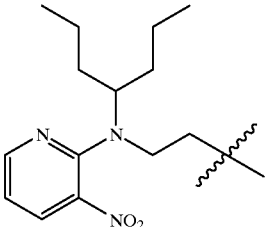
343. 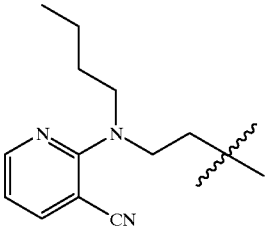
344. 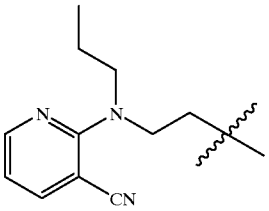
345. 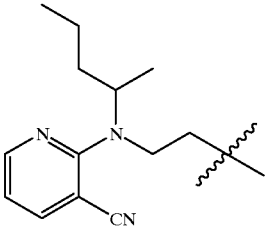

TABLE 3B-continued

| | R |
|---|---|
| 346. | (structure) |
| 347. | (structure) |
| 348. | (structure) |
| 349. | (structure) |
| 350. | (structure) |
| 351. | (structure) |
| 352. | (structure) |
| 353. | (structure) |
| 354. | (structure) |
| 355. | (structure) |
| 356. | (structure) |
| 357. | (structure) |

TABLE 3B-continued
| | R |
|---|---|
| 358. | 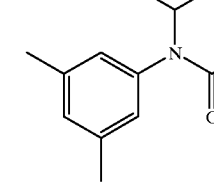 |
| 359. | 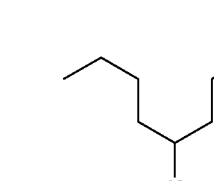 |
| 360. | 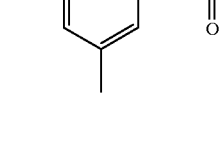 |
| 361. | 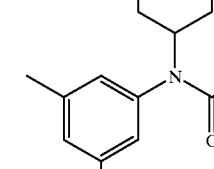 |
| 362. | 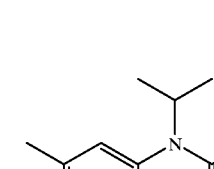 |
| 363. | 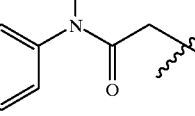 |
| 364. | 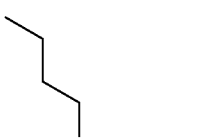 |
| 365. | 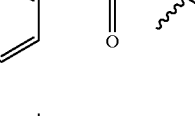 |
| 366. | 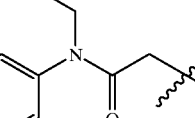 |
| 367. | 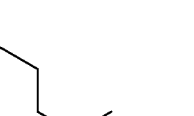 |
| 368. | 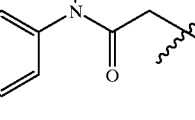 |

TABLE 3B-continued
| | R |
|---|---|
| 369. | 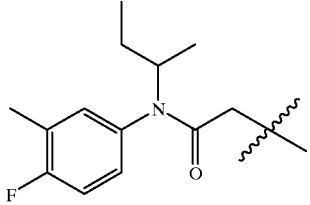 |
| 370. | 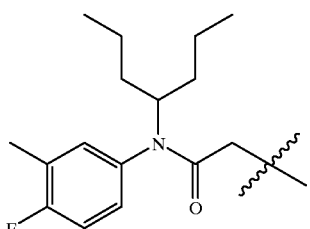 |
| 371. | 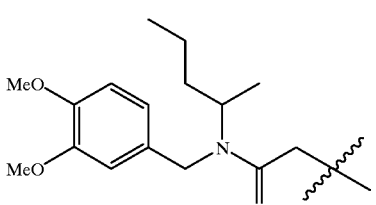 |
| 372. | 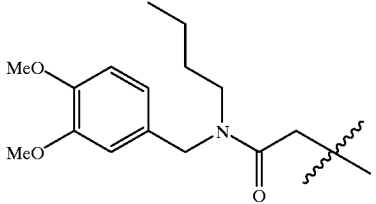 |
| 373. | 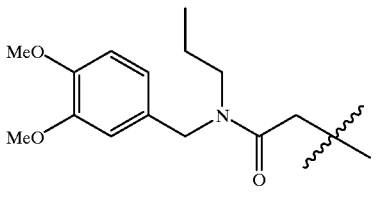 |
| 374. | 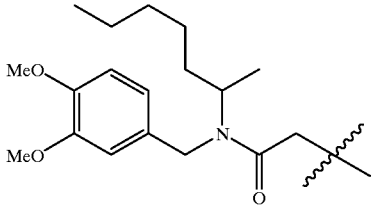 |
| 375. | 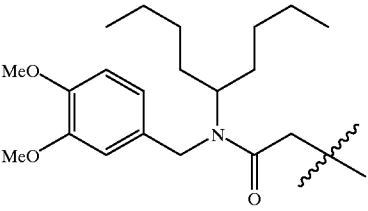 |
| 376. | 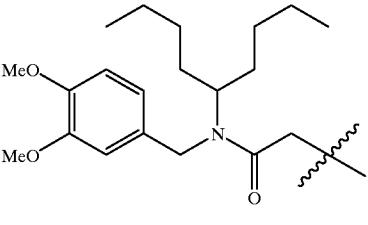 |
| 377. | 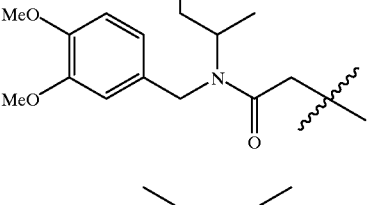 |
| 378. | 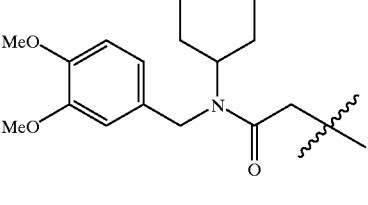 |
| 379. | 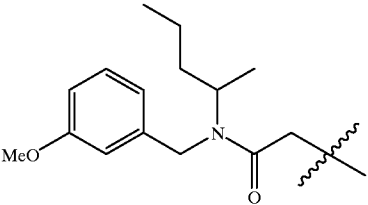 |
| 380. | 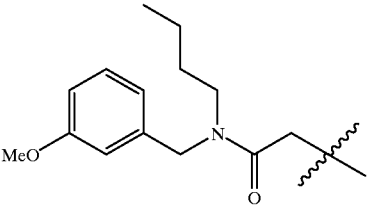 |
| 381. | 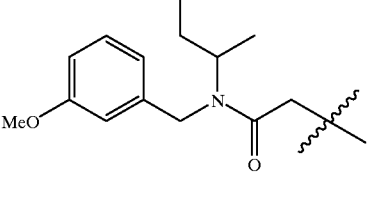 |

TABLE 3B-continued
| R | |
|---|---|
| 382. | 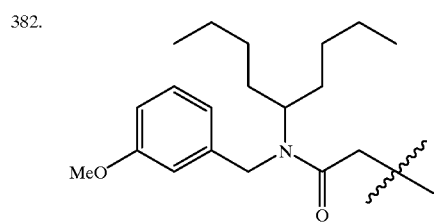 |
| 383. | 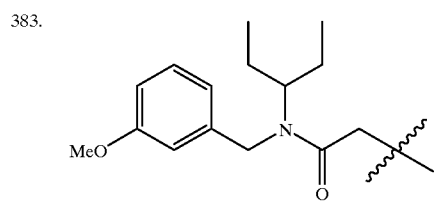 |
| 384. | 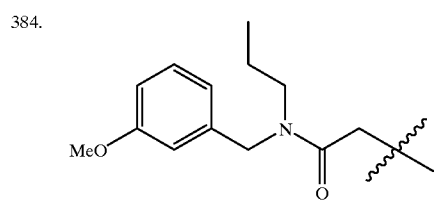 |
| 385. | 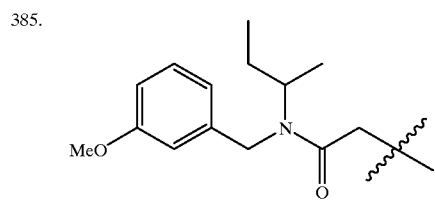 |
| 386. | 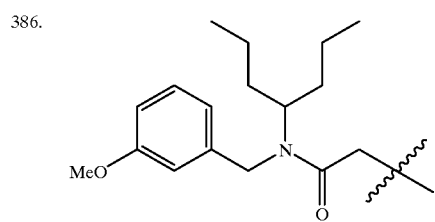 |
| 387. | 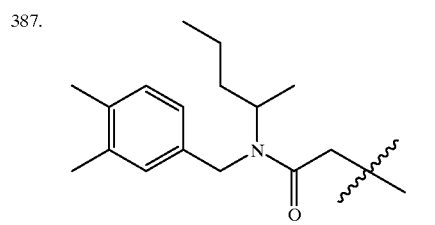 |
| 388. | 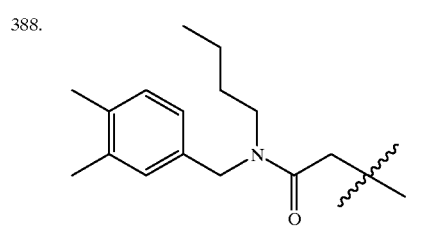 |
| 389. | 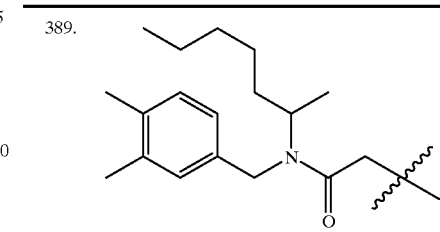 |
| 390. | 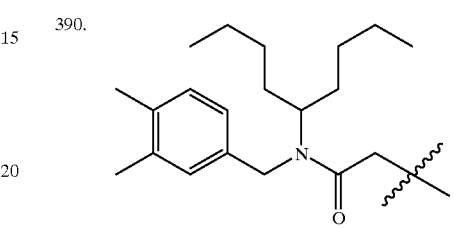 |
| 391. | 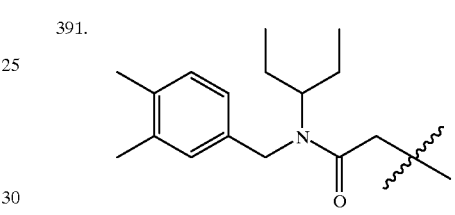 |
| 392. | 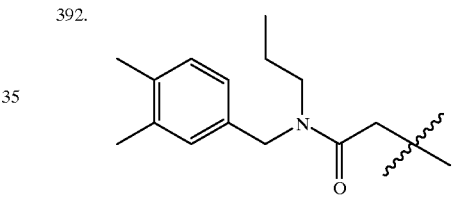 |
| 393. | 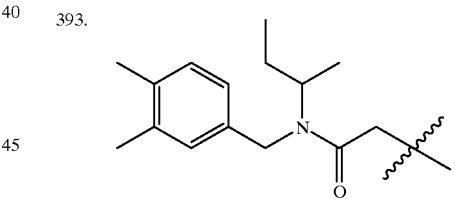 |
| 394. | 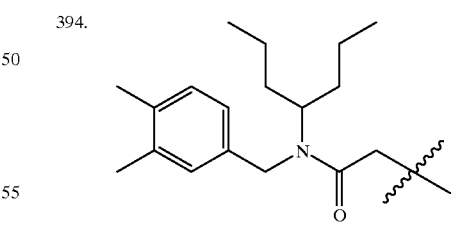 |
| 395. | 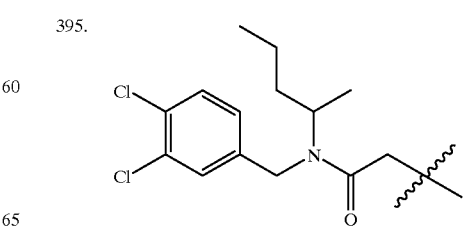 |

TABLE 3B-continued
| | R |
|---|---|
| 396. | 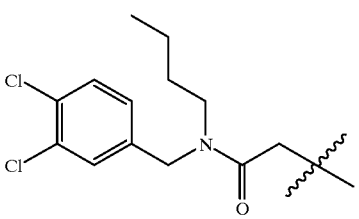 |
| 397. | 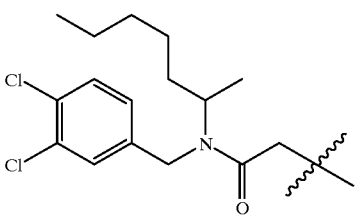 |
| 398. | 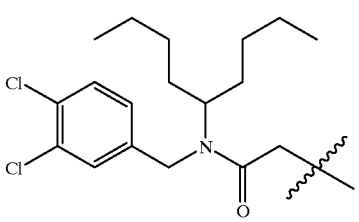 |
| 399. | 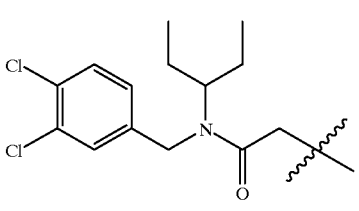 |
| 400. | 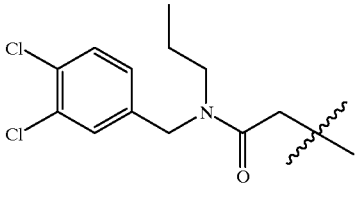 |
| 401. | 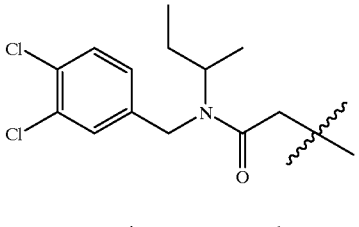 |
| 402. | 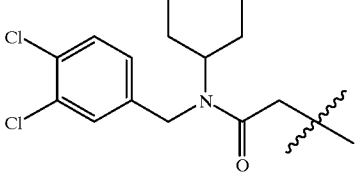 |
| 403. | 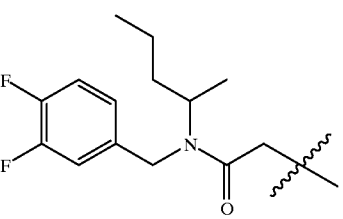 |
| 404. | 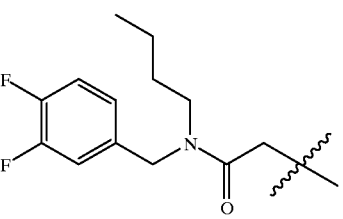 |
| 405. | 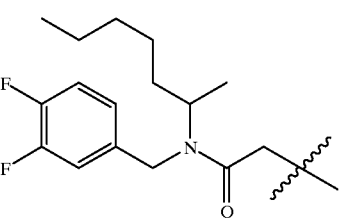 |
| 406. | 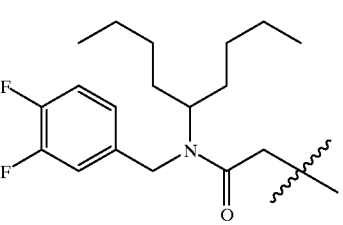 |
| 407. | 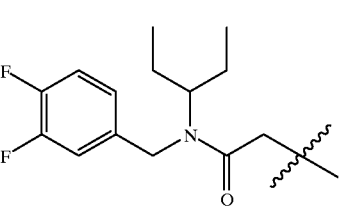 |
| 408. | 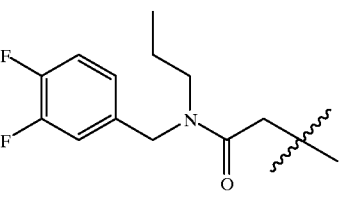 |
| 409. | 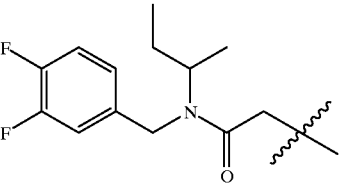 |

TABLE 3B-continued

| | R |
|---|---|
| 410. | (3,4-difluorobenzyl)(hexan-3-yl)amide |
| 411. | (3-methylbenzyl)(pentan-2-yl)amide |
| 412. | (3-methylbenzyl)(butyl)amide |
| 413. | (3-methylbenzyl)(heptan-2-yl)amide |
| 414. | (3-methylbenzyl)(nonan-5-yl)amide |
| 415. | (3-methylbenzyl)(pentan-3-yl)amide |
| 416. | (3-methylbenzyl)(propyl)amide |
| 417. | (3-methylbenzyl)(butan-2-yl)amide |
| 418. | (3-methylbenzyl)(heptan-4-yl)amide |
| 419. | (3-methylbenzyl)(pentan-3-yl)amide |
| 420. | (3-methylbenzyl)(propyl)amide |
| 421. | (3-methylbenzyl)(butan-2-yl)amide |
| 422. | (3-methylbenzyl)(heptan-4-yl)amide |
| 423. | (2,3-dimethoxybenzyl)(hexan-2-yl)amide |

TABLE 3B-continued

| R |
|---|
| 424. (structure) |
| 425. (structure) |
| 426. (structure) |
| 427. (structure) |
| 428. (structure) |
| 429. (structure) |
| 430. (structure) |
| 431. (structure) |
| 432. (structure) |
| 433. (structure) |
| 434. (structure) |
| 435. (structure) |
| 436. (structure) |
| 437. (structure) |

TABLE 3B-continued

| | R |
|---|---|
| 438. | (structure) |
| 439. | (structure) |
| 440. | (structure) |
| 441. | (structure) |
| 442. | (structure) |
| 443. | (structure) |
| 444. | (structure) |
| 445. | (structure) |
| 446. | (structure) |
| 447. | (structure) |
| 448. | (structure) |
| 449. | (structure) |
| 450. | (structure) |

TABLE 3B-continued
| R | | R | |
|---|---|---|---|
| 451. | 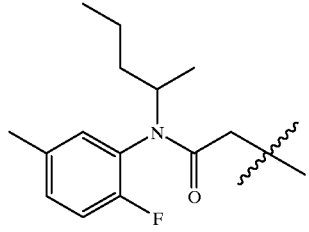 | 457. | 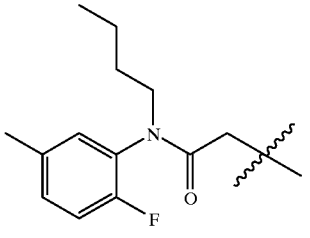 |
| 452. | 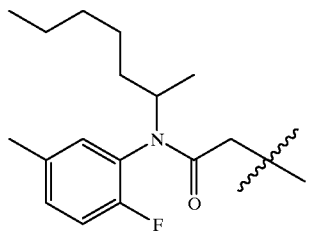 | 458. | 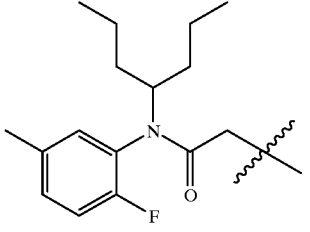 |
| 453. | 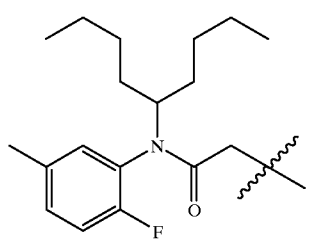 | 459. | 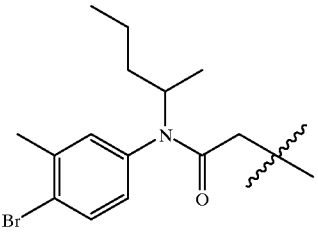 |
| 454. | 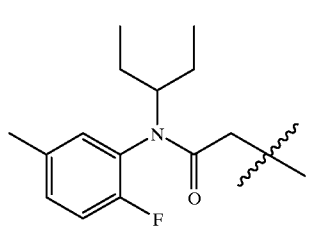 | 460. | 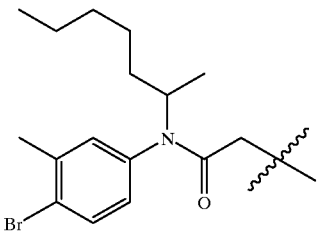 |
| 455. | 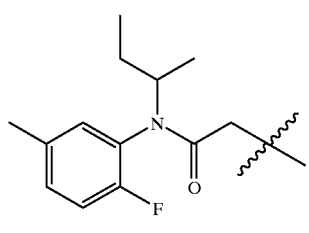 | 461. | 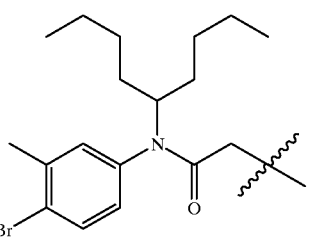 |
| 456. | 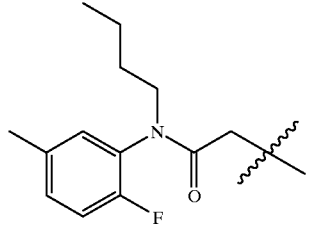 | 462. | 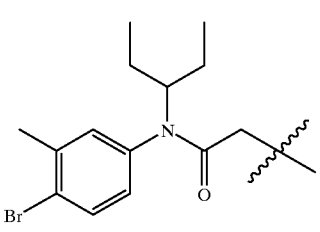 |

TABLE 3B-continued

| R | |
|---|---|
| 463. | *(structure)* |
| 464. | *(structure)* |
| 465. | *(structure)* |
| 466. | *(structure)* |
| 467. | *(structure)* |
| 468. | *(structure)* |
| 469. | *(structure)* |
| 470. | *(structure)* |
| 471. | *(structure)* |
| 472. | *(structure)* |
| 473. | *(structure)* |
| 474. | *(structure)* |

TABLE 3B-continued

| | R |
|---|---|
| 475. | 3-Br-4-F-C6H3-N(CH(CH3)CH2CH2CH3)-C(O)-CH2- |
| 476. | 3-Br-4-F-C6H3-N(CH(CH3)(CH2)3CH3)-C(O)-CH2- |
| 477. | 3-Br-4-F-C6H3-N(CH((CH2)3CH3)2)-C(O)-CH2- |
| 478. | 3-Br-4-F-C6H3-N(CH(CH2CH3)2)-C(O)-CH2- |
| 479. | 3-Br-4-F-C6H3-N(CH(CH3)CH2CH3)-C(O)-CH2- |
| 480. | 3-Br-4-F-C6H3-N(CH2CH2CH2CH3)-C(O)-CH2- |
| 481. | 3-Br-4-F-C6H3-N(CH2CH2CH3)-C(O)-CH2- |
| 482. | 3-Br-4-F-C6H3-N(CH((CH2)2CH3)2)-C(O)-CH2- |
| 483. | 3-Cl-2,4-F2-C6H2-N(CH(CH3)CH2CH2CH3)-C(O)-CH2- |
| 484. | 3-Cl-2,4-F2-C6H2-N(CH(CH3)(CH2)3CH3)-C(O)-CH2- |
| 485. | 3-Cl-2,4-F2-C6H2-N(CH((CH2)3CH3)2)-C(O)-CH2- |
| 486. | 3-Cl-2,4-F2-C6H2-N(CH(CH2CH3)2)-C(O)-CH2- |

TABLE 3B-continued
R
487. 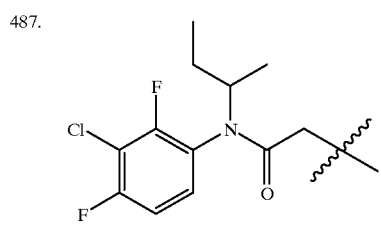
488. 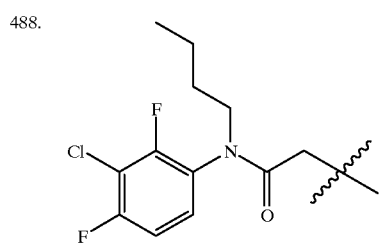
489. 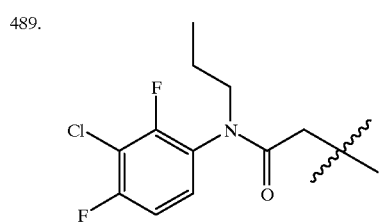
490. 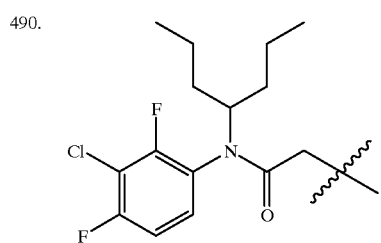
491. 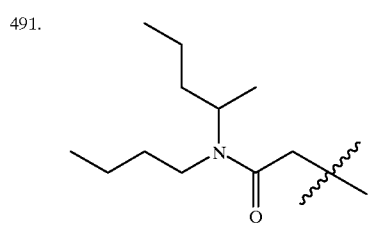
492. 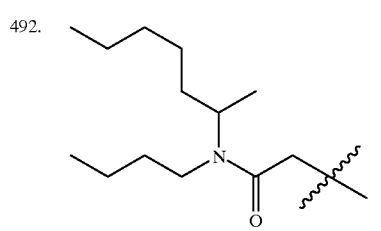
TABLE 3B-continued
R
493. 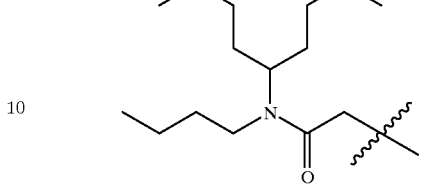
494. 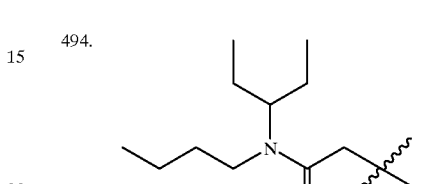
495. 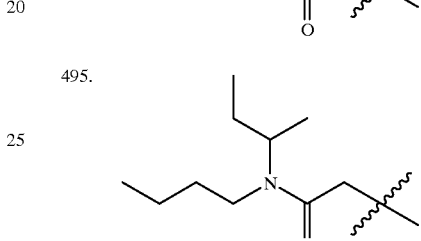
496. 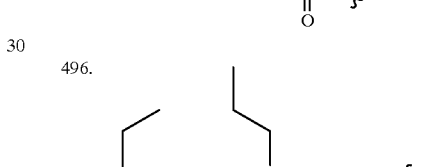
497. 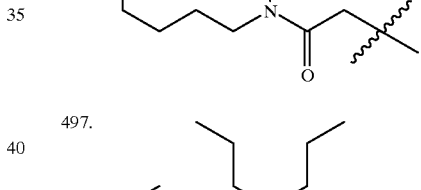
498. 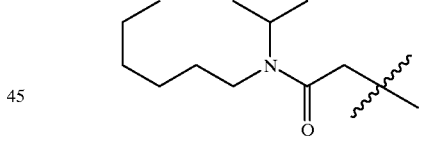
499. 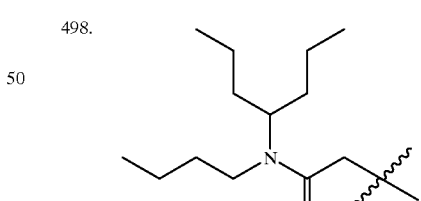
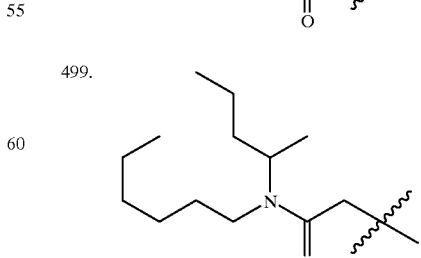

TABLE 3B-continued

| R |
|---|
| 500. (structure) |
| 501. (structure) |
| 502. (structure) |
| 503. (structure) |
| 504. (structure) |
| 505. (structure) |
| 506. (structure) |
| 507. (structure) |
| 508. (structure) |
| 509. (structure) |
| 510. (structure) |
| 511. (structure) |
| 512. (structure) |

TABLE 3B-continued

| R |
|---|
| 513. (structure) |
| 514. (structure) |
| 515. (structure) |
| 516. (structure) |
| 517. (structure) |
| 518. (structure) |
| 519. (structure) |
| 520. (structure) |
| 521. (structure) |
| 522. (structure) |
| 523. (structure) |
| 524. (structure) |
| 525. (structure) |

TABLE 3B-continued
R
526. 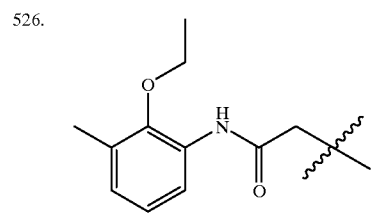
527. 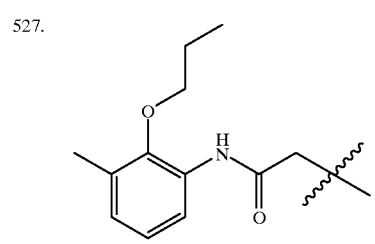
528. 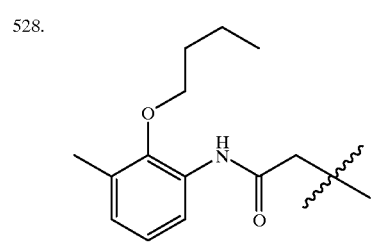
529. 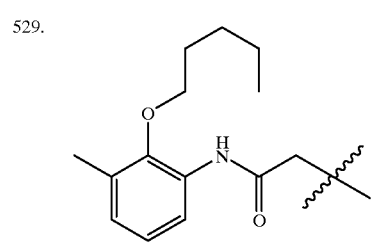
530. 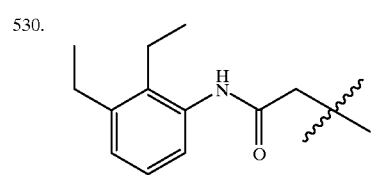
531. 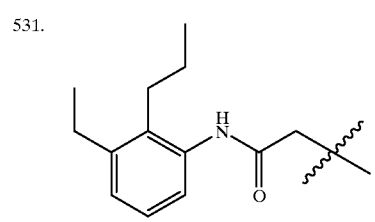
TABLE 3B-continued
R
532. 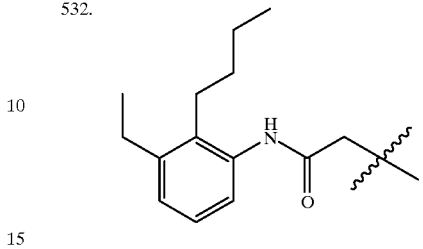
533. 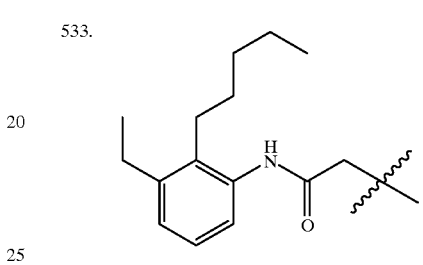
534. 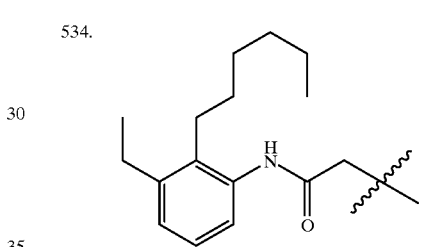
535. 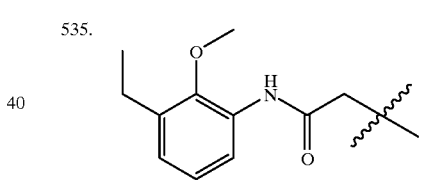
536. 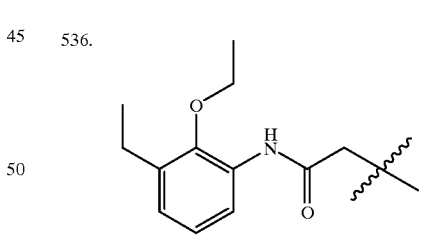
537. 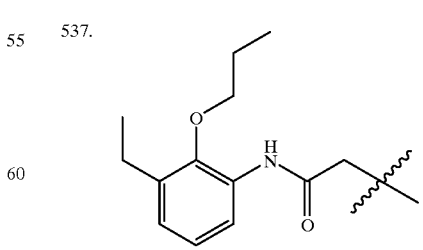

TABLE 3B-continued
| R |
|---|
| 538. 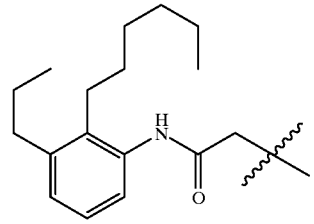 |
| 539. 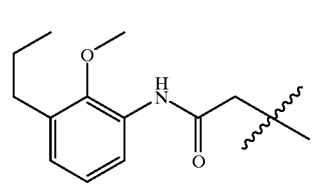 |
| 540. 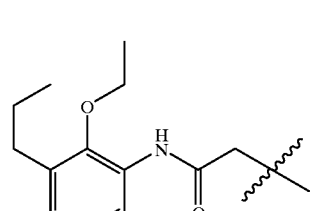 |
| 541. 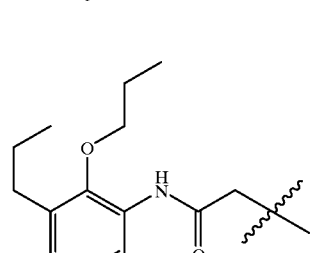 |
| 542. 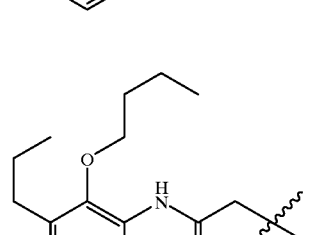 |
| 543. 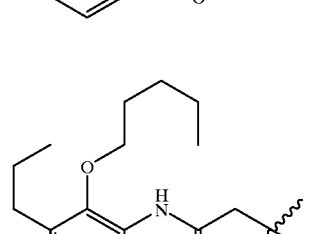 |
| 544. |
| 545. |
| 546. |
| 547. |
| 548. |
| 549. |

TABLE 3B-continued
| R |
|---|
| 550. 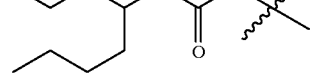 |
| 551.  |
| 552. 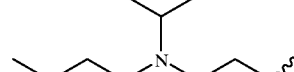 |
| 553. 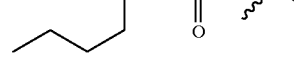 |
| 554.  |
| 555. 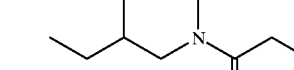 |
| 556. |
| 557. |
| 558. |
| 559. |
| 560. |
| 561. |
| 562. 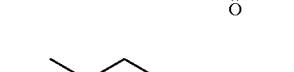 |

TABLE 3B-continued
R
563. 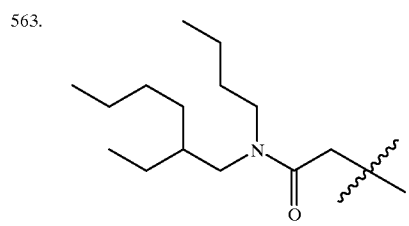
564. 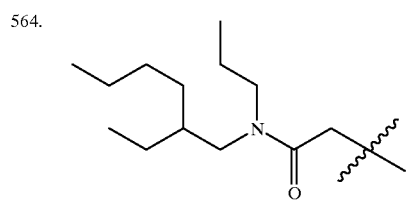
565. 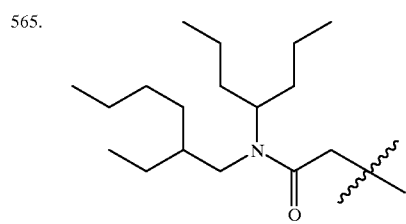
566. 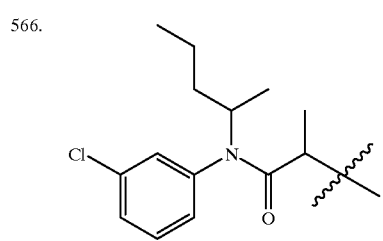
567. 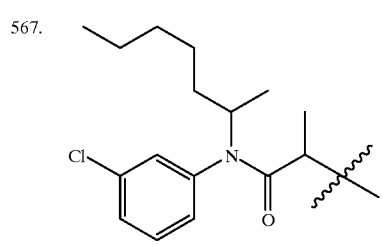
568. 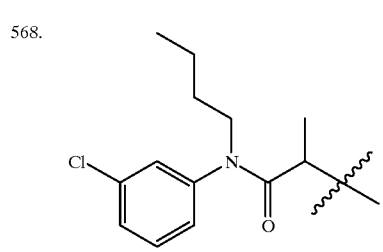
569. 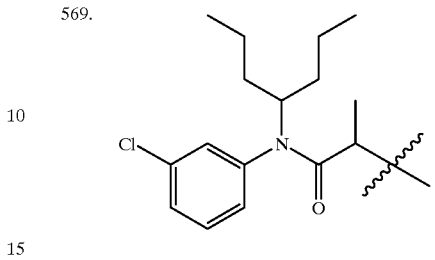
570. 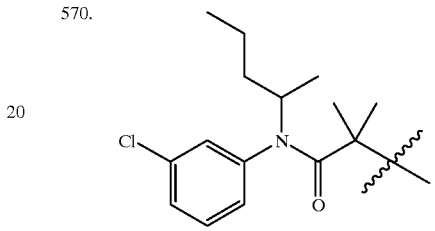
571. 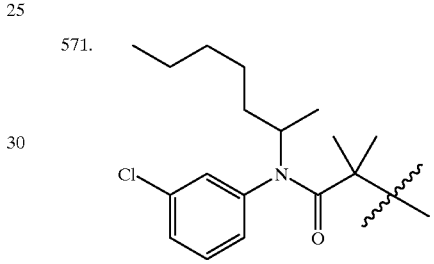
572. 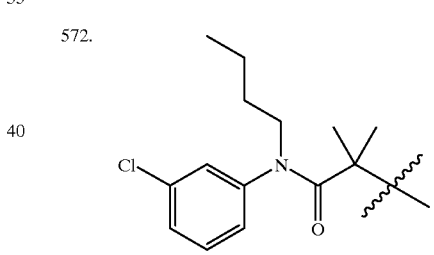
573. 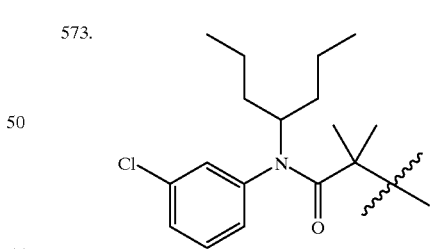
574. 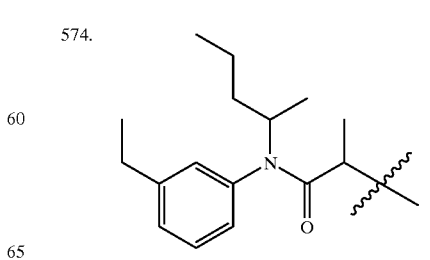

TABLE 3B-continued

| R | |
|---|---|
| 575. | (structure) |
| 576. | (structure) |
| 577. | (structure) |
| 578. | (structure) |
| 579. | (structure) |
| 580. | (structure) |
| 581. | (structure) |
| 582. | (structure) |
| 583. | (structure) |
| 584. | (structure) |
| 585. | (structure) |
| 586. | (structure) |

TABLE 3B-continued
R
587. 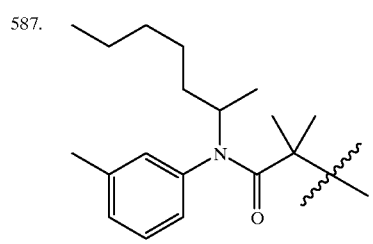
588. 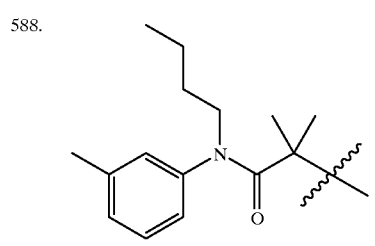
589. 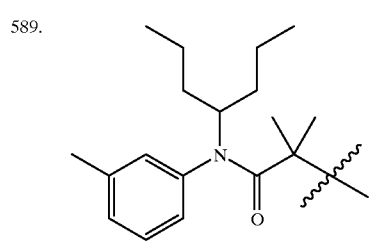
590. 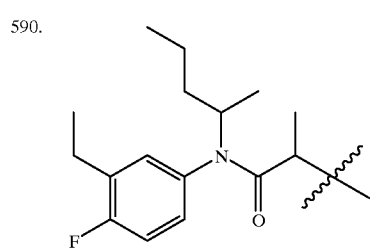
591. 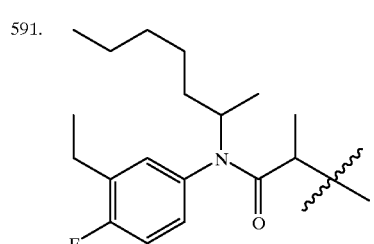
592. 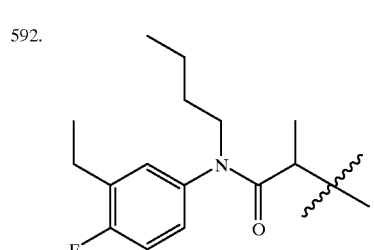
TABLE 3B-continued
R
593. 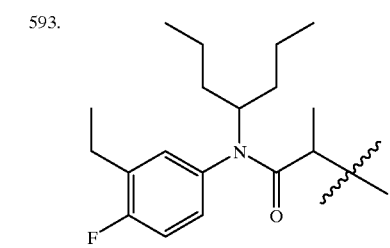
594. 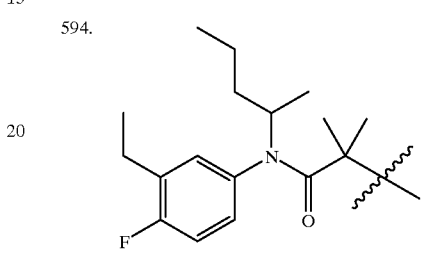
595. 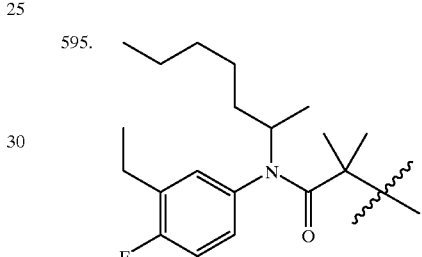
596. 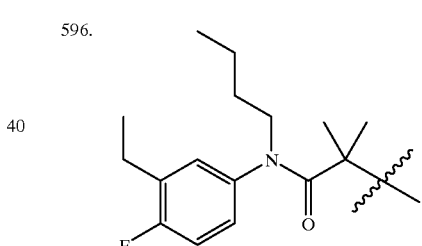
597. 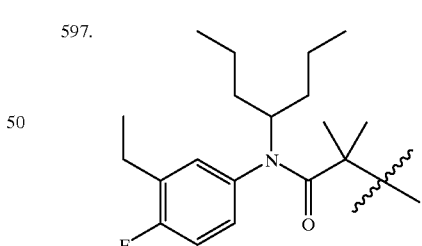
598. 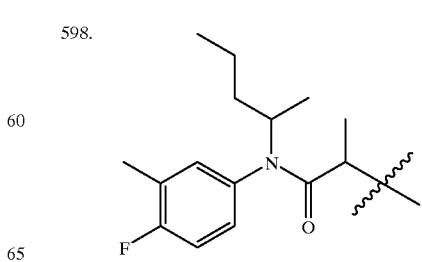

TABLE 3B-continued

| | R |
|---|---|
| 599. | |
| 600. | |
| 601. | |
| 602. | |
| 603. | |
| 604. | |

TABLE 3B-continued

| | R |
|---|---|
| 605. | |
| 606. | |
| 607. | |
| 608. | |
| 609. | |
| 610. | |

TABLE 3B-continued

| R |
|---|
| 611. |
| 612. |
| 613. |
| 614. |
| 615. |
| 616. |
| 617. |
| 618. |
| 619. |
| 620. |
| 621. |
| 622. |
| 623. |
| 624. |

TABLE 3B-continued

| R |
|---|
| 625. 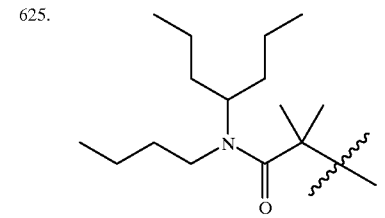 |
| 626. 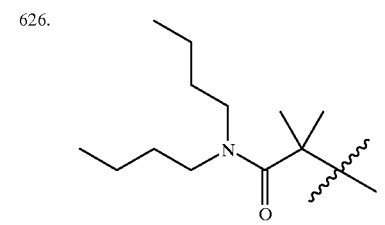 |
| 627. 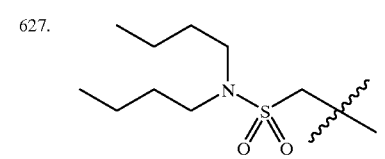 |
| 628. 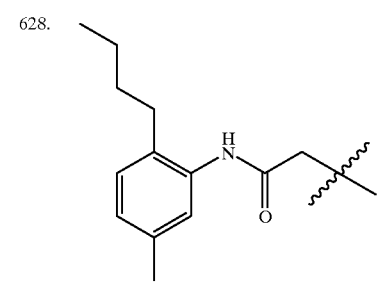 |
| 629. 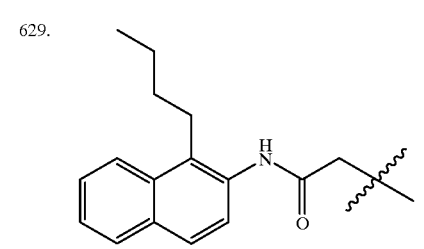 |
| 630. 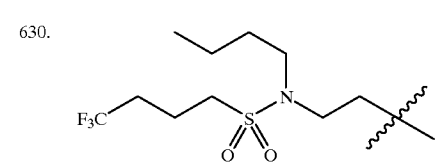 |
| 631. 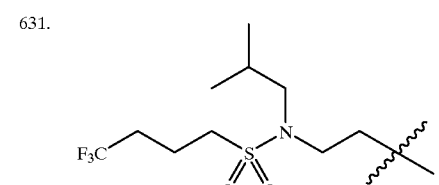 |
| 632.  |

EXAMPLE 340 trans,trans-4-(1,3-Benzodioxol-5-yl)-2-(4-methoxyphenyl)-1-(N-(3-methylbutyl-1-yl)-N-phenyl)aminocarbonylmethyl)-pyrrolidine-3-carboxylic Acid Using the procedures described in Example 1, the title compound was prepared. $^1$H NMR (300 MHz, CD$_3$OD) δ 0.85 (d, J=6 Hz, 6H), 1.25 (q, J=7 Hz, 2H), 1.42–1.56 (m, 1H), 3.43–3.85 (m, 9H), 3.88s (3), 5.95 (s, 2H), 6.80 (d, J=7 Hz), 1H), 6.86 (dd, J=9 Hz, 1H), 6.89–7.00 (m, 2H), 6.97 (d, J=1 Hz, 1H), 7.04 (d, J=9 Hz, 2H), 7.37 (d, J=9 Hz, 2H), 7.40–7.47 (m, 3H). MS (C.I.) m/e C (53.12, 53.11), H (4.63, 4.80), N (3.33, 3.28).

EXAMPLE 341 trans,trans-4-(1,3-Benzodioxol-5-yl)-2-(4-methoxyphenyl)-1-(N-butyl-N-(4-methylphenylaminocarbonylmethyl)-pyrrolidine-3-carboxylic Acid Using the procedures described in Example 1, the title compound was prepared. $^1$H NMR (300 MHz, CD$_3$OD) δ 0.87 (t, J=7 Hz, 3H), 1.20–1.47 (m, 4H), 2.37 (s, 3H), 2.83 (q, J=7 Hz, 2H), 3.06–3.25 (m, 2H), 3.40–3.50 (m, 1H), 3.51–3.63 (m, 3H), 3.80 (s, 3H), 3.87 (d, J=9 Hz, 1H), 5.92 (s, 2H), 6.74 (d, J=8 Hz, 1H), 6.80–6.86 (m, 3H), 6.89 (d, J=8 Hz, 2H), 7.04 (d, J=2 Hz, 1H), 7.12 (d, J=8 Hz, 2H), 7.19 (d, J=8 Hz, 2H). MS (DCl) m/e 545 (M+H)$^+$. Analysis calcd for C$_{32}$H$_{36}$H$_2$O$_6$: C, 70.57; H, 6.66; N, 5.14. Found: C, 70.20; H, 6.81; N, 5.03.

EXAMPLE 342 trans,trans-4-(1,3-Benzodioxol-5-yl)-2-(4-propoxyphenyl)-1-(N,N-di(n-butyl)amino)carbonyl)methyl)-pyrrolidine-3-carboxylic Acid Using the procedures described in Example 1, the title compound was prepared. $^1$H (300 MHz, CDCl$_3$) δ 7.30 (2H, d, J=9), 7.03 (1H, d, J=2), 6.83 (3H, m), 6.72 (1H, d, J=9), 5.95 (1H, d, J=2), 5.93 (1H, d, J=2), 3.88 (2H, t, J=7), 3.73 (1H, d, J=12), 3.58 (1H, m), 3.53–3.20 (4H, m), 3.10–2.90 (4H, m), 2.72 (1H, d, J=15), 1.79 (2H, q, J=8), 1.50–1.05 (8H, m), 1.02 (3H, t, J=7), 0.87 (3H, t, J=7), 0.80 (3H, t, J=7). MS (DCl/NH$_3$) m/e 539 (M+H)$^+$. Anal calcd for C$_{31}$H$_{42}$N$_2$O$_6$·0.5H$_2$O: C, 67.98; H, 7.91; N, 5.11. Found: C, 68.24; H, 7.70; N, 5.03.

EXAMPLE 343 trans,trans-4-(1,3-Benzodioxol-5-yl)-2-(4-propylphenyl)-1-(N,N-di(n-butyl)aminocarbonylmethyl)pyrrolidine-3-carboxylic Acid Using the procedures described in Example 1, the title compound was prepared. $^1$H (300 MHz, CDCl$_3$) δ 7.31(2H, d, J=9), 7.13 (2H, d, J=9), 7.03 (1H, d, J=2), 6.84 (1H, dd, J=6, 2), 6.73 (1H, d, J=9), 5.95 (1H, d, J=2), 5.93 (1H, d, J=2), 3.76 (1H, d, J=10), 3.60 (1H, m), 3.55–3.20 (4H, m), 3.13–2.88 (4H, m), 2.75 (1H, d, J=15), 2.55 (2H, t, J=8),1.62 (2H, q, J=8), 1.50–1.00 (8H, m), 0.92 (3H, t, J=7), 0.85 (3H, t, J=7), 0.78 (3H, t, J=7). MS (DCl/NH$_3$) m/e 523 (MH$^+$). Anal calcd for $C_{31}H_{42}N_2O_5 \cdot 0.25\ H_2O$: C, 70.63; H, 8.13; N, 5.31. Found: C, 70.55; H, 8.08; N, 5.18.

EXAMPLE 344 trans-trans-2-(4-Methoxyphenyl)-4-(1,3-benzodioxol-5-yl)-1-[3-(N-propyl-N-n-pentanesulfonylamino)propyl]pyrrolidine-3-carboxylic Acid Using the procedures described in Example 316, the title compound was prepared. $^1$H NMR (300 MHz, CDCl$_3$) δ 0.85 (t, J=7Hz, 3H), 0.90 (t, J=7Hz, 3H), 1.3–1.4 (m, 4H), 1.5–1.6 (sextet, J=7, 2H), 1.65–1.8 (m, 4H), 2.05–2.15 (m, 1H), 2.43–2.56 (m, 1H), 2.72–3.1 (m, 7H), 3.27–3.4 (m, 2H), 3.5–3.6 (m, 2H), 3.80 (s, 3H), 5.95 (s, 2H), 6.73 (d, J=8 Hz, 1H), 6.8–6.9 (m, 1H), 6.85 (d, J=9 Hz, 2H), 7.02 (d, J=2 Hz, 1H), 7.80 (d, J=9 Hz, 2H).

EXAMPLE 345 trans,trans-4-(1,2-Dihydrobenzofuran-5-yl)-2-(4-ethylphenyl)-1-(N,N-di(n-butyl)aminocarbonylmethyl)-pyrrolidine-3-carboxylic Acid Using the procedures described in Example 1, the title compound was prepared. $^1$H (300 MHz, CDCl$_3$) δ 7.40 (3H, m), 7.22 (2H, d, J=8), 7.13 (1H, dd, J=8, 3), 6.72 (1H, d, J=9), 5.28 (1H, d, J=12), 4.55 (2H, t, J=9), 4.15 (1H, d, J=18), 4.03 (2H, m), 3.75 (2H, m), 3.40 (2H, m), 3.20 (2H, t, J=9), 3.15 (1H, m), 3.10–2.90 (2H, m), 2.63 (2H, q, J=9), 1.47 (2H, m), 1.31 (4H, m), 1.12 (3H, t, J=8), 1.10 (2H,m), 0.92 (3H, t, J=9), 0.80 (3H, t, J=9). MS (DCl/NH$_3$) m/e 507 (M+H$^+$). Anal calcd for $C_{31}H_{42}N_2O_4 \cdot 1.0\ TFA$: C, 63.86; H, 6.98; N, 4.51. Found: C, 63.95; H, 7.12; N, 4.43.

EXAMPLE 346 trans,trans-4-(1,3-Benzodioxol-5-yl)-2-(4-methoxyphenyl)-1-(((N-(3-pentyl)-N-phenylamino)carbonyl)methyl)pyrrolidine-3-carboxylic Acid Using the procedures described in Example 1, the title compound was prepared. $^1$H NMR (300 MHz, CD$_3$OD) δ 0.93 (t, J=7.3 Hz, 3H), 0.94 (t, J=7.3 Hz, 3H), 1.33 (m, 4H), 2.72 (d, J=15.2 Hz, 1H), 2.81 (m, 1H), 3.11–3.23 (m, 2H), 3.45–3.57 (m, 2H), 3.79 (s, 3H), 3.83 (d, J=9.8 Hz, 1H), 4.54 (m, 1H), 5.92 (s, 2H), 6.73 (d, J=7.8 Hz, 1H), 6.83 (m, 3H), 6.98 (bs, 2H), 7.04 (d, J=1.7 Hz, 1H), 7.07 (2), 7.37 (m, 3H). MS (DCl) m/e 545 (M+H$^+$). Anal calcd for $C_{32}H_{33}N_2O_6 \cdot 0.35H_2O$: C, 69.76; H, 6.71; N, 5.08. Found: C, 69.72; H, 6.66; N, 4.94.

EXAMPLE 347 trans,trans-4-(1,3-Benzodioxol-5-yl)-2-(4-methoxyphenyl)-1-(((N-butyl)-N-(3-trifluoromethylphenyl)amino)carbonyl)methyl)pyrrolidine-3-carboxylic Acid Using the procedures described in Example 1, the title compound was prepared. $^1$H NMR (300 MHz, CD$_3$OD) δ 0.87 (t, J=6.6 Hz, 3H), 1.17–1.45 (m, 4H), 2.65 (d, J=16.5 Hz, 1H), 2.72 (m, 1H), 3.10 (t, J=9.5 Hz, 1H), 3.21–3.27 (m, 1H), 3.40 (dd, J=4.1, 9.9 Hz, 1H), 3.54 (m, 1H), 3.61–3.74 (m, 3H), 3.77 (s, 3H), 5.93 (s, 2H), 6.73–6.85 (m, 4H), 7.02 (m, 3H), 7.33 (d, J=7.5 Hz, 1H), 7.40 (s, 1H), 7.58 (t, J=7.8 Hz, 1H), 7.69 (d, J=7.5 Hz, 1H). MS (DCl) m/e 599 (M+H$^+$). Anal calcd for $C_{32}H_{33}F_3N_2O_6$: C, 64.21; H, 5.56; N, 4.68. Found: C, 64.09; H, 5.63; N, 4.57.

EXAMPLE 348 trans,trans-4-(1,3-Benzodioxol-5-yl)-2-(4-methoxyphenyl)-1-(N-propyl-N-(4-morpholinylcarbonyl)aminocarbonylmethyl)-pyrrolidine-3-carboxylic Acid Using the procedures described in Example 1, the title compound was prepared. $^1$H NMR (300 MHz, CD$_3$OD) δ 0.78 (t, J=7 Hz, 3H), 1.43 (q, J=7 Hz, 2H), 2.07–3.01 (m, 1H), 2.76 (dd, J=7, 9 Hz, 2H), 2.77–3.00 (m, 5H), 3.05 (3.70, J=m Hz, 11H), 3.76 (s, 3H), 5.88 (s, 2H), 6.67 (d, J=8 Hz, 1H), 6.80 (dd, J=7 Hz, 1H, 6.83–6.90 (m, 2H), 6.98 (d, J=2 Hz, 1H), 7.32–7.39 (m, 2H). MS m/e calc'd for (M+H) $C_{29}H_{39}N_3O_7$: (M+H) 540.2710. Found (M+H) 540.2713.

EXAMPLE 349 trans,trans-4-(1,3-Benzodioxol-5-yl)-2-(4-methoxyphenyl)-1-(cis-2,6-dimethylpiperidin-1-yl)carbonylmethyl)-pyrrolidine-3-carboxylic Acid Using the procedures described in Example 1, the title compound was prepared. $^1$H NMR (300 MHz, CD$_3$OD) δ 0.94 (d, J=7 Hz, 3H), 1.15d (7, 3H), 1.10–1.70 (m, 6H), 1.70–1.90 (m, 1H), 2.9. (d, J=13 Hz, 1H), 3.00–3.20 (m, 2H), 3.50 (3.70, J=m Hz, 2H), 3.79 (s, 3H), 3.80–4.00 (m, 1H), 4.10–4.65 (m, 2H), 5.95 (s, 2H), 6.70 (7.10, J=m Hz, 5H), 7.35 (m, 2H). MS m/e calc'd for (M+H)$^+$ $C_{28}H_{35}N_2O_6$: (M+H) 495.2495. Found (M+H) 495.2493.

EXAMPLE 350 trans,trans-2-(4-Methoxymethoxyphenyl)-4-(1,3-benzodioxol-5-yl)-1-(2-(N-propyl-N-n-pentanesulfonylamino)ethyl]pyrrolidine-3-carboxylic Acid Using the procedures described in Example 1, the title compound was prepared and isolated as a white solid. m.p. 57–59° C. $^1$H NMR (CDCl$_3$, 300 MHz) δ 0.78 (t, J=7 Hz, 3H), 0.90 (t, J=7 Hz, 3H), 1.28–1.36 (m, 4H), 1.93 (sextet, J=7 Hz, 2H), 1.72 (t, J=7 Hz, 2H), 2.20–2.32 (m, 1H), 2.72–3.10 (m, 7H), 3.18–3.41 (m, 2H), 3.43 (dd, J=3 Hz, J=9 Hz, 1H), 3.48 (s, 3H), 3.52–3.59 (m, 1H), 3.68 (d, J=9 Hz, 1H), 5.15 (s, 2H), 5.94 (s, 2H), 6.73 (d, J=8 Hz, 1H), 6.82 (dd, J=1 Hz, J=8 Hz, 1H), 6.98–7.02 (m, 3H), 7.32 (d, J=9 Hz, 2H). MS (DCl/NH$_3$) m/e 591 (M+H)$^+$.

EXAMPLE 351 trans,trans-4-(1,3-Benzodioxol-5-yl)-2-(4-methoxyphenyl)-1-(((N-(2-butyl)-N-phenylamino)carbonyl)methyl)pyrrolidine-3-carboxylic Acid Using the procedures described in Example 1, the title compound was prepared. $^1$H NMR (300 MHz, CD$_3$OD) δ 0.79–0.89 (m, 6H), 1.14–1.21 (m, 1H), 1.25–1.40 (m, 1H), 2.64 (dd, J=4.6, 15.4 Hz, 1H), 2.76 (t, J=9.0 Hz, 1H), 3.05–3.13 (m, 2H), 3.37–3.49 (m, 2H), 3.70 (s, 3H), 3.80 (d, J=9.8 Hz, 1H), 4.53 (m, 1H), 5.83 (m, 2H), 6.65 (d, J=8.1 Hz, 1H), 6.72 (–6.76, J=m Hz, 3H), 6.87 (m, 2H), 6.95 (d, J=1.7 Hz, 1H), 7.03 (m, 2H), 7.29 (m, 3H). MS (DCl) m/e 531 (M+H⁺). Anal calcd for $C_{31}H_{34}N_2O_6 \cdot 0.4H_2O$: C, 69.23; H, 6.52; N, 5.21. Found: C, 69.19; H, 6.52; N, 5.03.

EXAMPLE 352 trans,trans-4-(1,3-Benzodioxol-5-yl)-2-(4-methoxyphenyl)-1-(((N-(2-propyl)-N-phenylamino)carbonyl)methyl)pyrrolidine-3-carboxylic Acid Using the procedures described in Example 1, the title compound was prepared. ¹H NMR (300 MHz, CD₃OD) δ 0.99 (d, J=6.8 Hz, 6H), 2.71 (d, J=15.6 Hz, 1H), 2.84 (m, 1H), 3.13–3.18 (m, 2H), 3.45–3.58 (m, 2H), 3.79 (s, 3H), 3.88 (d, J=9.8 Hz, 1H), 4.80 (m, 1H), 5.92 (s, 2H), 6.74 (d, J=8.1 Hz, 1H), 6.83 (m, 3H), 6.96 (br s, 2H), 7.04 (d, J=1.7 Hz, 1H), 7.13 (m, 2H), 7.38 (m, 3H). MS (DCl) m/e 517 (M+H⁺). Anal calcd for $C_{30}H_{32}N_2O_6 \cdot 0.4H_2O \cdot 0.08CH_3CO_2C_2H_5$: C, 68.65; H, 6.28; N, 5.28. Found: C, 68.64; H, 6.35; N, 5.14.

EXAMPLE 353 trans,trans-4-(4-Propoxyphenyl)-2-(4-methoxyphenyl)-1-(N,N-di(n-butyl)aminocarbonylmethyl)-pyrrolidine-3-carboxylic Acid Using the procedures described in Example 1, the title compound was prepared. ¹H (300 MHz, CDCl₃) δ 7.42 (2H, d, J=10 Hz), 7.38 (2H, d, J=10 Hz), 6.92 (2H, d, J=10 Hz), 6.88 (2H, d, J=10 Hz), 5.13 (1H, bd, J=12 Hz), 4.02 (2H, m), 3.90 (2H, t, J=8 Hz), 3.80 (3H, s), 3.71 (3H, m), 3.40 (2H, m), 3.19 (1H, m), 3.10–2.90 (2H, m), 1.80 (2H, m), 1.48 (2H, m), 1.29 (4H, m), 1.13 (2H, m), 1.03 (3H, t, J=8 Hz), 0.92 (3H, t, J=9 Hz), 0.82 (3H, t, J=9 Hz). MS (DCl/NH₃) m/e 525 (MH⁺). Anal calcd for $C_{31}H_{44}N_2O_5 \cdot 1$ TFA: C, 62.06 H 7.10; N, 4.39. Found: C, 62.43; H, 7.28; N, 4.39.

EXAMPLE 354 trans,trans-4-(1,3-Benzodioxol-5-yl)-2-(4-methoxyphenyl)-1-((1,2,3,4-tetrahydroquinolin-1-yl)carbonyl)methyl)pyrrolidine-3-carboxylic Acid Using the procedures described in Example 1, the title compound was prepared. ¹H NMR (300 MHz, CD₃OD) δ 1.88 (quintet, J=6.5 Hz, 2H), 2.67 (t, J=6.4 Hz, 2H), 2.87 (t, J=8.6 Hz, 1H), 3.14 (m, 2H), 3.42 (dd, J=4.6, 9.7 Hz, 1H), 3.53–3.70 (m, 3H), 3.72–3.78 (m, 1H), 3.77 (s, 3H), 3.86 (d, J=9.6 Hz, 1H), 5.91 (s, 2H), 6.73 (d, J=8.1 Hz, 1H), 6.83 (m, 3H), 6.98 (d, J=1.1 Hz, 1H), 7.02–7.23 (m, 6H). MS (DCl) m/e 515 (M+H⁺). Anal calcd for $C_{30}H_{30}N_2O_6 \cdot 0.3H_2O \cdot 0.15 CH_3CO_2C_2H_5$: C, 68.93; H, 6.01; N, 5.25. Found: C, 68.91; H, 5.86; N, 5.19.

EXAMPLE 355 trans,trans-2-(3,4-Dimethoxyphenyl)-4-(1,3-benzodioxol-5-yl)-1-(N,N-di(n-butyl)aminocarbonylmethyl)-pyrrolidine-3-carboxylic Acid Using the procedures described in Example 1, the title compound was prepared and isolated as a white solid. m.p. 64–65° C. ¹H NMR (CDCl₃, 300 MHz) δ 0.79 (t, J=7 Hz, 3H), 0.88 (t, J=7 Hz, 3H), 1.07 (sextet, J=7 Hz, 2H), 1.20–1.35 (m, 4H), 1.43 (sextet, J=7 Hz, 2H), 2.83 (d, J=13.5 Hz, 1H), 2.94–3.17 (m, 4H), 3.22–3.42 (m, 1H), 3.40–3.48 (m, 3H), 3.58–3.65 (m, 1H), 3.82 (s, 3H), 3.85 (s, 4H), 5.92 (s, 2H), 6.73 (d, J=8 Hz, 1H), 6.81 (d, J=8 Hz, 1H), 6.86–6.96 (m, 3H), 7.07 (d, J=3 Hz, 1H). MS (DCl/NH₃) m/e 541 (M+H)⁺.

EXAMPLE 356 trans,trans-2-(3,4-Dimethoxyphenyl)-4-(1,3-benzodioxol-5-yl)-1-[2-(N-propyl-N-n-pentanesulfonylamino)ethyl]pyrrolidine-3-carboxylic Acid Using the procedures described in Example 1, the title compound was prepared and isolated as a white solid. m.p. 75–86° C. ¹H NMR (CD₃OD, 300 MHz) δ 0.75 (t, J=7 Hz, 3H), 0.82 (t, J=7 Hz, 3H), 1.32–1.43 (m, 6H), 1.65–1.77 (m, 2H), 3.0–3.09 (m, 4H), 3.23–3.27 (m, 2H), 3.44 (t, J=6 Hz, 1H), 3.47–3.56 (m, 2H), 3.78 (d, J=9 Hz, 1H), 3.83–3.93 (m, 2H), 3.87 (s, 3H), 3.92 (s, 3H), 4.63 (d, J=13 Hz, 1H), 5.97 (s, 2H), 6.82 (d, J=7 Hz, 1H), 6.93 (d, J=7 Hz, 1H), 7.06 (d, J=7 Hz, 1H), 7.08 (d, J=3 Hz, 1H), 7.16 (dd, J=3 Hz, J=7 Hz, 1H), 7.27 (d, J=3 Hz, 1H). MS (DCl/NH₃) m/e 591 (M+H)⁺.

EXAMPLE 357 trans,trans-2-(3,4-Dimethoxyphenyl)-4-(1,3-benzodioxol-5-yl)-1-[2-(N-propyl-N-n-hexanesulfonylamino)ethyl]pyrrolidine-3-carboxylic Acid Using the procedures described in Example 1, the title compound was prepared and isolated as a white solid. m.p. 65–66° C. ¹H NMR (CDCl₃, 300 MHz) δ 0.80 (t, J=7 Hz, 3H), 0.89 (t, J=7 Hz, 3H), 1.23–1.48 (m, 6H), 1.43 (sextet, J=7 Hz, 2H), 1.72 (sextet, J=7 Hz, 2H), 2.25–2.35 (m, 1H), 2.73–3.10 (m, 7H), 3.19–3.32 (m, 2H), 3.45 (dd, J=3 Hz, J=9 Hz, 1H), 3.53–3.59 (m, 1H), 3.68 (d, J=9 Hz, 1H), 3.87 (s, 6H), 5.95 (s, 2H), 6.74 (d, J=8 Hz, 1H), 6.79–6.86 (m, 2H), 6.92–6.97 (m, 2H), 7.02 (s, 1H). MS (DCl/NH₃) m/e 605 (M+H)⁺.

EXAMPLE 358 trans,trans-2-(4-Methoxyphenyl)-4-(1,3-benzodioxol-5-yl)-1-[2-(phthalimido)ethyl]-pyrrolidine-3-carboxylic Acid The compound of Example 1C (250 mg), N-bromoethylphthalimide (206 mg), and diisopropylethylamine (175 mg) were dissolved in 1 mL of acetonitrile and heated for 2.5 hours at 95° C. Toluene was added, and the mixture was washed with KHCO₃ solution. The solution was dried (Na₂SO₄) and concentrated. The crude product was purified by chromatography on silica gel eluting with 3:1 EtOAc-hexane to give 216 mg of an intermediate ethyl ester which was hydrolyzed by the method of Example 1D to give 130 mg of the title compound as a white powder. ¹H NMR (300 MHz, CDCl₃) δ 3.12–3.26 (m, 2H), 3.60–3.75 (m, 2H), 3.70 (s, 3H), 3.98–4.12 (m, 2H), 4.45–4.55 (m, 1H), 4.69 (d, J=9 Hz, 1H), 4.76–4.88 (m, 1H), 5.96 (s, 2H), 6.55 (d, J=8 Hz, 1H), 6.60–6.70 (m, 3H), 6.79 (d, J=8 Hz, 1H), 7.05–7.45 (m, 5H), 7.75 (d, J=7 Hz, 1H).

EXAMPLE 359 trans,trans-4-(1,3-Benzodioxol-5-yl)-2-(4-methoxyphenyl)-1-(((N-(2-pentyl)-N-phenylamino)carbonyl)methyl)pyrrolidine-3-carboxylic Acid Using the procedures described in Example 1, the title compound was prepared. ¹H NMR (300 MHz, CD₃OD) δ

0.86–0.98 (m, 6H), 1.17–1.22 (m, 1H), 1.23–1.41 (m, 3H), 2.70 (dd, J=11.2, 15.3 Hz, 1H), 2.83 (m, 1H), 3.10–3.21 (m, 2H), 3.45–3.60 (m, 2H), 3.79 (s, 3H), 3.86 (m, 1H), 4.74 (m, 1H), 5.91 (m, 2H), 6.73 (dd, J=1.1, 7.7 Hz, 3H), 6.82 (m, 2H), 7.04–7.14 (m, 3H), 7.36 (m, 3H). MS (DCl) m/e 545 (M+H$^+$). Anal calcd for $C_{32}H_{36}N_2O_6 \cdot 0.25\ CH_3CO_2C_2H_5$: C, 69.95; H, 6.76; N, 4.94. Found: C, 70.03; H, 6.54; N, 4.78.

EXAMPLE 360 trans,trans-4-(1,3-Benzodioxol-5-yl)-2-(4-methoxyphenyl)-1-(N-butyl-N-(2-naphthyl)aminocarbonylmethyl)-pyrrolidine-3-carboxylic Acid Using the procedures described in Example 1, the title compound was prepared. $^1$H NMR (300 MHz, CD$_3$OD) δ 0.83 (t, J=7 Hz, 3H), 1.23–1.39 (m, 4H), 1.40–1.55 (m, 3H), 2.60–2.72 (m, 2H), 3.00–3.80 (m, 5H), 3.66 (s, 3H), 5.87 (s, 2H), 6.39 (d, J=9 Hz, 2H), 6.74–6.85 (m, 3H), 7.17 (d, J=2 Hz, 1H), 7.40 (dd, J=8 Hz, 1H), 7.52–7.62 (m, 3H), 7.80–7.90 (m, 1H), 7.90–8.00 (m, 2H). MS (DCl) m/e 581 (M+H)$^+$. Analysis calcd for $C_{35}H_{36}N_2O_6 \cdot 0.3\ H_2O$: C, 71.73; H, 6.29; N, 4.78. Found: C, 71.74; H, 6.26; N, 4.72.

EXAMPLE 361 trans,trans-2-(4-Propoxyphenyl)-4-(1,3-benzodioxol-5-yl)-1-[2-(N-propyl-N-n-pentanesulfonylamino)ethyl]pyrrolidine-3-carboxylic Acid Using the procedures described in Example 66, the title compound was prepared and isolated as a white solid. m.p. 53–54° C. $^1$H NMR (CDCl$_3$, 300 MHz) δ 0.79 (t, J=7 Hz, 3H), 0.89 (t, J=7 Hz, 3H), 1.03 (t, J=7 Hz, 3H), 1.24–1.34 (m, 4H), 1.43 (sextet, J=7 Hz, 2H), 1.67–1.75 (m, 2H), 1.80 (sextet, 2H), 2.23–2.33 (m, 1H), 2.72–2.93 (m, 5H), 3.05 (septet, J=7 Hz, 2H), 3.15–3.35 (m, 2H), 3.42 (d, J=9 Hz, 1H), 3.54–3.62 (m, 1H), 3.67 (d, J=9 Hz, 1H), 4.90 (t, J=7 Hz, 2H), 5.95 (s, 2H), 6.73 (d, J=8 Hz, 1H), 6.85 (d, J=8 Hz, 2H), 7.02 (s, 1H), 7.32 (d, J=8 Hz, 2H). MS (DCl/NH$_3$) m/e 589 (M+H)$^+$.

EXAMPLE 362 trans,trans-4-(1,3-Benzodioxol-5-yl)-2-(4-methoxyphenyl)-1-((2-methylindolin-1-yl)carbonyl)methyl)pyrrolidine-3-carboxylic Acid Using the procedures described in Example 1, the title compound was prepared. $^1$H NMR (300 MHz, CD$_3$OD) δ mixture of indole $C_2$ diastereomers, 0.95 (m, 1.5 (CH$_3$)), 1.05 (d, 6.3H, 1.5 (CH$_3$)), 2.62 (m, 1H), 3.01 (m, 2H), 3.14–3.25 (m, 1H), 3.37–3.52 (m, 1.5H), 3.56–3.80 (m, 2H), 3.65 (s, 1.5 (CH$_3$O)), 3.76 (s, 1.5 (CH$_3$O)), 3.93 (m, 0.5H), 4.05–4.13 (m, 0.5H,), 4.42 (m, 0.5H), 4.65–4.74 (m, 1H), 5.91 (m, 2H), 6.72 (d, J=8.1 Hz, 0.5H), 6.75 (m, 0.5H), 6.85 (m, 2H), 6.92 (d, J=8.5 Hz, 1H), 7.00–7.06 (m, 2H), 7.14 (t, J=7.7 Hz, 1H), 7.21 (t, J=6.6 Hz, 1H), 7.38 (m, 2H), 7.99 (m, 1H). MS (DCl) m/e 515 (M+H$^+$). Anal calcd for $C_{30}H_{30}N_2O_6 \cdot 0.35H_2O \cdot 0.3\ CH_3CO_2C_2H_5$: C, 68.47; H, 6.10; N, 5.12. Found: C, 68.46; H, 5.97; N, 5.07.

EXAMPLE 363 trans,trans-4-(1,3-Benzodioxol-5-yl)-2-(4-methoxyphenyl)-1-(2-hydroxy-3-propylhex-1-yl)pyrrolidine-3-carboxylic Acid Using the procedures described in Example 1, the title compound was prepared. $^1$H NMR (300 MHz, CD$_3$OD) δ 1.06 (m, 6H), 1.26–1.60 (m, 9H), 3.16 (dd, J=10.9, 12.6 Hz, 1H), 3.18 (d, J=11 Hz, 1H), 3.44 (d, J=2.0 Hz, 1H), 3.61 (t, J=11 Hz, 1H), 3.73 (t, J=11.0 Hz, 1H), 3.85 (m, 1H), 3.96–4.17 (m, 2H), 4.02 (s, 1.5 (CH$_3$O diastereomer)), 4.03 (s, 1.5 (CH$_3$O diastereomer)), 6.15 (s, 2H), 7.01 (d, J=8.1 Hz, 0.5H), 7.00 (d, J=8.1 Hz, 0.5H), 7.10 (m, 1H), 7.23 (m, 3H), 7.77 (m, 2H). MS (DCl.) m/e 484 (M+H$^+$). Anal calcd for $C_{28}H_{37}NO_6 \cdot 0.33\ H_3PO_4$: C, 65.34; H, 7.44; N, 2.72. Found: C, 65.30; H, 7.40; N, 2.60.

EXAMPLE 364 trans,trans-4-(1,3-Benzodioxol-5-yl)-2-(4-methoxyphenyl)-1-(((N-(4-heptyl)-N-(3,4-dimethoxybenzyl)amino)carbonyl)methyl)pyrrolidine-3-carboxylic Acid Using the procedures described in Example 1, the title compound was prepared. $^1$H NMR (300 MHz, CD$_3$OD) δ1:1 mixture of rotamers, 0.61 (t, J=7.1 Hz, 1.5H), 0.72 (7.3, 1.5H), 0.76 (t, J=7.1, 1.5, 0.83, t, 7.3 Hz, 1.5H), 1.05–1.60 (m, 8H), 2.84–3.10 (m, J=2.5, 3.18, t, 9.7 Hz, 0.5H), 3.41–3.52 (m, 2H), 3.47–3.69 (m, 2H), 3.66 (s, 1.5H), 3.73 (s, 1.5H), 3.77 (s, 1.5H), 3.78 (s, 1.5H), 3.79 (s, 1.5H), 3.86 (d, J=9.8 Hz, 0.5H), 4.19 (d, J=17.7 Hz, 0.5H), 4.29 (d, J=15.2 Hz, 0.5H), 4.40–4.49 (m, 0.5H), 4.47 (d, J=15.3 Hz, 0.5H), 4.60 (d, J=17.6 Hz, 0.5H), 5.93 (m, 2H), 6.46 (dd, J=1.7, 8.2 Hz, 0.5H), 6.52 (d, J=2.0 Hz, 0.5H), 6.74 (m, 2.5H), 6.80 (s, 1H), 6.83–6.88 (m, 1H), 6.92 (m, 1.5H), 7.03 (dd, J=1.7, 6.8 Hz, 1H), 7.19 (m, 1H), 7.36 (m, 1H). MS (DCl) m/e 647 (M+H$^+$). Anal calcd for $C_{37}H_{46}N_2O_8$: C, 68.71; H, 7.17; N, 4.33. Found: C, 68.41; H, 7.26; N, 4.11.

EXAMPLE 365 trans,trans-4-(1,3-Benzodioxol-5-yl)-2-(4-methoxyphenyl)-1-((indolin-1-yl)carbonyl)methyl)pyrrolidine-3-carboxylic Acid Using the procedures described in Example 1, the title compound was prepared. $^1$H NMR (300 MHz, CD$_3$OD) δ 2.97 (dd, J=8.1, 9.5 Hz, 1H), 3.10 (t, J=8.1 Hz, 2H), 3.16–3.22 (m, 2H), 3.51–3.68 (m, 3H), 3.73 (m, 3H), 3.83–4.05 (m, 3H, 5.90 (m, 2H), 6.73 (d, J=8.1 Hz, 1H), 6.86 (m, 3H), 6.99 (dt, J=1.1, 7.4 Hz, 1H), 7.08 (d, J=0.7 Hz, 1H), 7.11 (m, 1H), 7.18 (d, J=7.1 Hz, 1H), 7.38 (d, J=8.5 Hz, 2H), 8.02 (8.1, 1H). MS (C.l.) m/e 501 (M+H$^+$). Anal calcd for $C_{29}H_{28}N_2O_6 \cdot 0.5\ H_2O \cdot 0.15\ CH_3CO_2C_2H_5$: C, 68.01; H, 5.82; N, 5.36. Found: C, 68.03; H, 5.65; N, 5.25.

EXAMPLE 366 trans,trans-4-(1,3-Benzodioxol-5-yl)-2-(4-methoxyphenol)-1-(N-butyl-N-(2-chlorophenyl)aminocarbonylmethyl)pyrrolidine-3-carboxylic Acid Using the procedures described in Example 1, the title compound was prepared. $^1$H NMR (300 MHz, CD$_3$OD) δ0.89 (dt, J=7 Hz, 3H), 1.23–1.51 (m, 4H), 2.52–4.00 (m, 8H), 3.78 (d, J=6 Hz, 3H), 5.92 (d, J=6 Hz, 2H), 6.70–6.87 (m, 4H), 7.02–7.21 (m, 4H), 7.27–7.52 (m, 3H). MS (DCl) m/e 565 (M+H)$^+$. Analysis calcd for $C_{31}H_{32}N_2O_6Cl \cdot 0.6H_2O$: C, 64.66; H, 5.99; N, 4.86. Found: C, 64.59; H, 6.00; N, 4.64.

EXAMPLE 367 trans,trans-2-(4-Methoxphenyl)-4-(1,3-benzodioxol-5-yl)-1-(3,4,5-trimethoxybenzyl)pyrrolidine-3-carboxylic Acid The compound resulting from Example 1C (0.25 g) was reacted with 0.169 g of 3,4,5-trimethoxybenzyl chloride and 0.175 g of diisopropylethylamine in 1 mL of acetonitrile for 2 hours at room temperature. The resulting ester was isolated and then hydrolyzed by the method of Example 1D to give 0.193 g of the title compound. m.p. 108–110° C. $^1$H NMR (300 MHz, CDCl$_3$) δ 2.75 (t, J=9 Hz, 1H), 2.95–3.05 (m, 2H), 3.20 (d, J=11 Hz, 1H), 3.45–3.55 (m, 1H), 3.7–3.8 (m, 2H), 3.84 (s, 3H), 5.95 (dd, J=2 Hz, 6 Hz, 2H), 6.55 (s, 2H), 6.70 (d, J=8 Hz, 1H), 6.30–6.35 (m, 1H), 6.90 (d, J=9 Hz, 2H), 7.13 (d, J=2 Hz, 1H), 7.43 (d, J=9 Hz, 2H).

EXAMPLE 368 trans,trans-4-(1,3-Benzodioxol-5-yl)-2-(4-methoxyphenyl)-1-(N-butyl-N-(3-chlorophenyl) aminocarbonylmethyl)-pyrrolidine-3-carboxylic Acid Using the procedures described in Example 1, the title compound was prepared. $^1$H NMR (300 MHz, CD$_3$OD) δ 0.89 (t, J=7 Hz, 3H), 1.20–1.42 (m, 4H), 3.42–3.87 (m, 9H), 3.9 (s, 3H), 5.96 (s, 2H), 6.75 (7.10, J=m Hz, 7H), 7.33–7.50 (m, 4H). MS (C.l.) m/e 565(M+H). Analysis calcd for C$_{31}$H$_{33}$N$_2$O$_6$Cl.1.0CF$_3$COOH: C, 58.37; H, 5.05; N, 4.13. Found: C, 58.41; H, 4.99; N, 4.08.

EXAMPLE 369 trans,trans-2-(4-Methoxphenyl)-4-(1,3-benzodioxol-5-yl)-1-[2-(di-n-butylamino)pyrimidin-4-yl] pyrrolidine-3-carboxylic Acid The compound resulting from Example 1C (0.25 g) was reacted with 0.11 g of 2,4-dichloropyrimidine and 0.175 g of diisopropylethylamine in 1 mL of acetonitrile for 2 hours at room temperature to give 0.218 g of ethyl 2-(4-methoxphenyl)-4-(1,3-benzodioxol-5-yl)-1-(2-chloro-4-pyrimidyl)-pyrrolidine-3-carboxylate. This compound was reacted with 1 mL of dibutylamine in 2 mL of toluene at 125° C. for 17 hours. The resulting ethyl ester was hydrolyzed by the method of Example 1D to give 0.142 g of the title compound as a white powder. $^1$H NMR (300 MHz, CDCl$_3$) δ0.75–0.90 (broad, 6H), 1.1–1.3 (br, 4H), 1.35–1.55 (br, 4H), 3.05 (m, 1H), 3.3–3.5 (br, 2H), 3.55–3.67 (m, 2H), 3.75 (s, 3H), 4.6 (br, 1H), 5.2 (br, 1H), 5.45 (br, 1H), 5.87 (s, 2H), 6.3 (br, 1H), 6.67 (d, J=8 Hz, 1H), 6.7–6.85 (m, 4H), 7.10 (d, J=9 Hz, 2H).

EXAMPLE 370 trans,trans-4-(1,3-Benzodioxol-5-yl)-2-(4-methoxyphenyl)-1-(((N-(2-methylbutyl-2-yl)-N-phenylamino)carbonyl)methyl)pyrrolidine-3-carboxylic Acid Using the procedures described in Example 1, the title compound was prepared. $^1$H NMR (300 MHz, CD$_3$OD) δ 0.90 (t, J=7.5 Hz, 3H), 1.12 (s, 3H), 1.14 (s, 3H), 2.06 (q, J=7.5 Hz, 2H), 2.73 (d, J=15.3 Hz, 1H), 2.91 (t, J=9.5 Hz, 1H), 3.11 (d, J=15.6 Hz, 1H), 3.21 (t, J=8.8 Hz, 1H), 3.50–3.61 (m, 2H), 3.80 (s, 3H), 4.00 (d, J=10.2 Hz, 1H), 5.91 (s, 2H), 6.74 (d, J=7.8 Hz, 1H), 6.85 (m, 3H), 6.93 (m, 1H), 6.98 (m, 1H), 7.03 (d, J=1.7 Hz, 1H), 7.17 (m, 2H), 7.36 (m, 3H). MS (DCl) m/e 545 (M+H$^+$). Anal calcd for C$_{32}$H$_{36}$N$_2$O$_6$: C, 70.57; H, 6.66; N, 5.14. Found: C, 70.17; H, 6.53; N, 4.97.

EXAMPLE 371 trans,trans-2-(4-Ethylphenyl)-4-(5-indanyl)-1-(N,N-di(n-butyl)aminocarbonylmethyl)pyrrolidine-3-carboxylic Acid Using the procedures described in Example 1, the title compound was prepared. $^1$H (300 MHz, CDCl$_3$) δ 7.25 (3H, m), 7.21 (1H, d, 3 Hz), 7.17 (3H, m), 3.80 (1H, d, 10 Hz), 3.65 (1H, ddd, 6, 5, 3 Hz), 3.4 (4H, m), 3.10 (2H, m), 2.98 (2H, m), 2.88 (5H, m), 2.79 (1H, d, 16 Hz), 2.62 (2H, q, 7 Hz), 2.05 (2H, m), 1.42 (2H, m), 1.32 (1H, m), 1.21 (3H, t, 7 Hz), 1.05 (2H, sext, 7 Hz), 0.87 (3H, t, 7 Hz). 0.79 (3H, t, 7 Hz). MS (DCl, NH$_3$) m/e 505 (M+H$^+$). Anal calcd for C$_{32}$H$_{44}$N$_2$O$_3$: C, 76.15; H, 8.79; N 5.55. Found: C, 75.96; H, 8.75; N, 5.36.

EXAMPLE 372 trans,trans-2-(3,4-Difluorophenyl)-4-(1,3-benzodioxol-5-yl)-1-(N,N-di(n-butyl) aminocarbonylmethyl)-pyrrolidine-3-carboxylic Acid Using the procedures described in Example 1, the title compound was prepared and isolated as a white solid. m.p. 62–63° C. $^1$H NMR (CDCl$_3$, 300 MHz), δ 0.83 (t, J=7 Hz, 3H), 0.88 (t, J=7 Hz, 3H), 1.13 (sextet, J=7 Hz, 2H), 1.20–1.32 (m, 3H), 1.36–1.49 (m, 3H), 2.85–2.93 (m, 2H), 2.98–3.23 (m, 4H), 3.36–3.45 (m, 3H), 3.58–3.66 (m 1H), 3.94 (d, J=8 Hz, 1H), 5.93 (s, 2H), 6.72 (d, J=7.5 Hz, 1H), 6.84 (dd, J=1 Hz, J=7.5 Hz, 1H), 6.98 (d, J=7.5 Hz, 1H), 7.08–7.15 (m, 2H), 7.22–7.28 (m, 1H). MS (CDl/NH$_3$) m/e 517 (M+H)$^+$.

EXAMPLE 373 trans,trans-2-(3,4-Difluorophenyl)-4-(1,3-benzodioxol-5-yl)-1-[2-(N-propyl-N-n-pentanesulfonylamino)ethyl]pyrrolidine-3-carboxylic Acid Using the procedures described in Example 1, the title compound was prepared and isolated as a white solid. m.p. 71–72° C. $^1$H NMR (CDCl$_3$, 300 MHz) δ 0.82 (t, J=7 Hz, 3H), 0.90 (t, J=7 Hz, 3H), 1.25–1.38 (m, 4H), 1.46 (sextet, J=7 Hz, 2H), 1.74 (quintett, J=7 Hz, 2H), 2.26–2.36 (m, 1H), 2.72–2.95 (m, 5H), 2.98–3.12 (m, 2H), 3.15–3.34 (m, 2H), 3.45 (dd, J=3 Hz, J=9 Hz, 1H), 3.53–3.60 (m, 1H), 3.71 (d, J=9 Hz, 1H), 5.96 (s, 2H), 6.75 (d, J=9 Hz, 1H), 3.82 (dd, J=2 Hz, J=9 Hz, 1H), 5.96 (d, J=2 Hz, 1H), 7.09–7.18 (m, 2H), 7.23–7.34 (m, 1H). MS (CDl/NH$_3$) m/e 567 (M+H)$^+$.

EXAMPLE 374 trans,trans-4-(1,3-Benzodioxol-5-yl)-2-(ethoxymethyl)-1-(((N,N-di(n-butyl) aminocarbonylmethyl)-pyrrolidine-3-carboxylic Acid Using the procedures described in Example 1, the title compound was prepared. TLC (10% MeOH—CH$_2$Cl$_2$) R$_f$=0.53. $^1$H NMR (CDCl$_3$, 300 MHz, rotameric forms) δ 0.70 (t, J=7 Hz), 0.80 (t, J=7 Hz) and 0.96–1.04 (m, 6H total), 1.04–1.75 (m, 11H), 1.34–1.53 (br m, 4H), 2.65 (AB) and 2.80–3.08 (m, 2H total), 3.10–3.82 (br m, 12H), 4.03 (m) and 4.22–4.45 (br m, 2H total), 5.90 (s) and 5.91 (s, 2H total), 6.65–6.84 (m) and 6.93 (m) and 6.99 (m, 3H total). MS (FAB) m/e 463 (M+H)$^+$. Anal calcd for C$_{25}$H$_{38}$N$_2$O$_6$.1.5 H$_2$O: C, 61.33; H, 8.44; N, 5.72. Found: C, 61.28; H, 7.78; N, 5.62.

EXAMPLE 375 trans,trans-4-(1,3-Benzodioxol-5-yl)-2-(n-butyl)-1-(N,N-di(n-butyl)aminocarbonylmethyl)-pyrrolidine-3-carboxylic Acid Using the procedures described in Example 1, the title compound was prepared and isolated as a colorless wax.

TLC (10% MeOH—CH$_2$Cl$_2$) R$_f$=0.37. $^1$H NMR (CDCl$_3$, 300 MHz, rotameric forms) δ 0.71 (t, J=7 Hz) and 0.77–1.05 (m, 9H total), 1.05–1.20 (m, 2H), 1.20–1.72 (br m, 13H), 2.48–2.52 (m, 1H), 2.87–3.00 (m, 1H), 3.05–3.60 (m, 5H), 3.60–3.80 (br m, 2H), 3.88–4.05 (br m, 1H), 4.28 (br d, J=15 Hz, 1H total), 5.90 (s) and 5.92 (s, 2H total), 6.67–6.82 (m, 3H total). MS (FAB) m/e 461 (M+H)$^+$. Anal calcd for C$_{26}$H$_{40}$N$_2$O$_5$.1.75 H$_2$O: C, 63.45; H, 8.90; N, 5.69. Found: C, 63.18; H, 8.22; N, 5.60.

EXAMPLE 376 trans,trans-4-(1,3-Benzodioxol-5-yl)-2-(2-methylbutyl)-1-(N,N-di(n-butyl) aminocarbonylmethyl)-pyrrolidine-3-carboxylic Acid Using the procedures described in Example 1, the title compound was prepared and isolated as a colorless glass. TLC (10% MeOH—CH$_2$Cl$_2$) R$_f$=0.49. $^1$H NMR (CDCl$_3$, 300 MHz, rotameric forms and mixture of diastereomers) δ 0.69 (br t, J=7 Hz) and 0.75–2.15 (several br m, approx. 26H total), 2.48–2.65 (br m, 1H), 2.87–3.01 (br m, 1H), 3.06–3.82 (br m, 7H), 3.90–4.40 (br m, 2H), 5.90 (s) and 5.92 (s, 2H total), 6.67–6.90 (m, 3H total). MS (FAB) m/e 475 (M+H)$^+$.

EXAMPLE 377 trans,trans-4-(1,3-Benzodioxol-5-yl)-2-(3-methylbutyl)-1-(N,N-di(n-butyl) aminocarbonylmethyl)-pyrrolidine-3-carboxylic Acid Using the procedures described in Example 1, the title compound was prepared. TLC (10% MeOH—CH$_2$Cl$_2$) R$_f$=0.41. $^1$H NMR (CDCl$_3$, 300 MHz, rotameric forms) δ 0.73 (t, J=7 Hz) and 0.77–1.05 (m, 12H total), 1.07–1.75 (m, approx. 14H plus H$_2$O), 2.48–2.63 (m, 1H), 2.87–3.05 (m, 1H), 3.05–3.60 (several br m, 5H), 3.62–4.02 (br m, 2H), 4.29 (br d, J=15 Hz, 1H), 5.89 (s) and 5.93 (s, 2total), 6.65–6.90 (m, 3H total). MS (FAB) m/e 475 (M+H)$^+$.

EXAMPLE 378 trans,trans-2-(4-Methoxyphenyl)-4-(1,3-benzodioxol-5-yl)-1-[2-(N-propyl-N-((N-methyl-N-propylamino)sulfonyl)amino)ethyl]pyrrolidine-3-carboxylic Acid Using the procedures described in Example 66, the title compound was prepared and isolated as a white solid. m.p. 58–59° C. $^1$H NMR (CDCl$_3$, 300 MHz) δ 0.78 (t, J=7 Hz, 3H), 0.90 (t, J=7 Hz, 3H), 1.27 (sextet, J=7 Hz, 2H), 1.48 (m, 4H), 2.22–2.30 (m, 1H), 2.62 (s, 3H), 2.68–2.78 (m, 1H), 2.84–3.03 (m, 5H), 3.08–3.31 (m, 3H), 3.39 (dd, J=3 Hz, J=9 Hz, 1H), 3.50–3.58 (m, 1H), 3.63 (d, J=9 Hz, 1H), 3.79 (s, 3H), 5.95 (s, 2H), 3.73 (d, J=8 Hz, 1H), 6.83 (dd, J=2 Hz, J=8 Hz, 1H), 3.87 (d, J=9 Hz, 2H), 7.01 (d, J=2 Hz, 1H), 7.33 (d, J=9 Hz, 2H). MS (DCl/NH$_3$) m/e 576 (M+H)$^+$.

EXAMPLE 379 trans,trans-2,4-Di(3,4-difluorophenyl)-1-(N,N-di(n-butyl)aminocarbonylmethyl)-pyrrolidine-3-carboxylic Acid Using the procedures described in Example 1, the title compound was prepared. $^1$H NMR (300 MHz, CDCl$_3$) δ 7.35 (2H, m), 7.18 (4H, m), 4.87 (1H, d, J=12), 4.00–3.60 (5H, m), 3.60–3.10 (3H, m), 3.10–2.90 (2H, m), 1.45 (2H, m), 1.29 (4H, m), 1.15 (2H, m), 0.91 (3H, t, J=9), 0.83 (3H, t, J=9). MS (DCl/NH$_3$) m/e 509 (M+H$^+$). Anal calcd for C$_{27}$H$_{32}$F$_4$N$_2$O$_3$.0.75 TFA: C, 57.62; H, 5.56; N, 4.72. Found: C, 57.72; H, 5.67; N, 4.66.

EXAMPLE 380 trans,trans-4-(3,4-Dimethylphenyl)-2-(4-methoxyphenyl)-1-(N,N-di(n-butyl) aminocarbonylmethyl)-pyrrolidine-3-carboxylic Acid Using the procedures described in Example 1, the title compound was prepared. $^1$H NMR (300 MHz, CDCl$_3$) δ 7.43 (2H, d, J=9), 7.25 (1H, bs), 7.18 (1H, dd, J=8, 3), 7.11 (1H, d, J=9), 6.90 (2H, d, J=10), 5.48 (1H, d, J=12), 4.26 (1H, d, J=18), 4.16 (2H, m), 3.83 (2H, m), 3.81 (3H, s), 3.56 (1H, bd, J=18), 3.37 (1H, m), 3.20 (1H, m), 2.96 (2H, m), 2.24 (3H, s), 2.22 (3H, s), 1.47 (2H, m), 1.27 (4H, m), 1.10 (2H, m), 0.93 (3H, t, J=9), 0.81 (3H, t, J=9). MS (DCl/NH$_3$) m/e 495 (M+H$^+$). Anal calcd for C$_{30}$H$_{42}$N$_2$O$_4$.1.25 TFA: C, 61.26; H, 6.84; N, 4.40. Found: C, 61.16; H, 7.05; N, 4.38.

EXAMPLE 381 trans,trans-2,4-Di(3-fluoro-4-methoxyphenyl)-1-(N,N-di(n-butyl)aminocarbony)methyl)-pyrrolidine-3-carboxylic Acid Using the procedures described in Example 1, the title compound was prepared. $^1$H NMR (300 MHz, CDCl$_3$) δ 7.20 (2H, m), 7.17 (2H, m), 6.93 (2H, m), 5.48 (1H, m), 4.26 (1H, m), 4.16 (2H, m), 3.83 (2H, m), 3.87 (6H, s), 3.56 (1H, m), 3.37 (1H, m), 3.20 (1H, m), 2.96 (2H, m), 1.47 (2H, m), 1.27 (4H, m), 1.10 (2H, m), 0.93 (3H, t, J=9), 0.81 (3H, t, J=9). MS (DCl/NH$_3$) m/e 533 (M+H$^+$). Anal calcd for C$_{29}$H$_{38}$F$_2$N$_2$O$_5$.0.75 H$_2$O: C, 63.78; H, 7.29; N, 5.13. Found: C, 63.77; H, 7.08; N, 4.99.

EXAMPLE 382 trans,trans-4-(1,3-Benzodioxol-5-yl)-2-(4-methoxyphenyl)-1-(((N-(2-pentyl),N-(3-methylphenyl)amino)carbonyl)methyl)pyrrolidine-3-carboxylic Acid Using the procedures described in Example 1, the title compound was prepared. $^1$H NMR (300 MHz, CD$_3$OD) δ 0.90 (m, 3H), 0.95 (t, J=7.3 Hz, 3H), 1.13–1.37 (m, 4H), 2.30 (s, 3H), 2.34 (s (CH$_3$ rotamer)), 2.73–2.91 (m, 2H), 3.17–3.26 (m, 2H), 3.32–3.62 (m, 2H), 3.77–4.08 (m, 1H), 3.80 (s, 3H), 4.71 (m, 1H), 5.92 (m, 2H), 6.61–6.84 (m, 6H), 7.04–7.16 (m, 3H), 7.23–7.29 (m, 2H). MS (DCl) m/e 559 (M+H$^+$). Anal calcd for C$_{33}$H$_{38}$N$_2$O$_6$.0.35 H$_2$O.0.05 CH$_3$CO$_2$C$_2$H$_5$: C, 70.03; H, 6.92; N, 4.92. Found: C, 70.08; H, 6.82; N, 4.95.

EXAMPLE 383 trans,trans-4-(1,3-Benzodioxol-5-yl)-2-(4-methoxyphenyl)-1-(N-butyl-N-(1-naphthyl) aminocarbonylmethyl)pyrrolidine-3-carboxylic Acid Using the procedures described in Example 1, the title compound was prepared. $^1$H NMR (300 MHz, CD$_3$OD) δ 0.87 (t, J=7 Hz, 3H), 1.20–1.40 (m, 2H), 1.40–1.60 (m, 2H), 2.42–2.80 (m, 2H), 2.85–4.00 (m, 6H), 3.77 (d, J=1.5 Hz, 3H), 4.05–4.20 (m, 1H), 5.94 (d, J=2 Hz, 2H), 6.6 (dd, J=9, 10 Hz, 1H), 6.70–6.85 (m, 4H), 6.95–7.02 (m, 2H), 7.17 (dd, 8H, ½), 7.25 (dd, 8H, ½), 7.38–7.60 (m, 4H), 7.87–8.00 (m, 2H). MS (E.S.I.) m/e (M+H) 581. Analysis calcd for $C_{35}H_{36}N_2O_6 \cdot 1.4\ H_2O$: C, 69.38; H, 6.45; N, 4.62. Found: C, 69.36; H, 6.07; N, 4.41.

EXAMPLE 384 trans,trans-2-(4-Methoxyphenyl)-4-(1,3-benzodioxol-5-yl)-1-[2-(N-phenyl-N-n-hexanesulfonylamino)ethyl]pyrrolidine-3-carboxylic Acid Using the procedures described in Example 66, the title compound was prepared and isolated as a tan solid. m.p. 67–68° C. $^1$H NMR (CD$_3$OD, 300 MHz) δ 0.88 (t, J=7 Hz, 3H), 1.25–1.40 (m, 6H), 1.73 (quintet, J=7 Hz, 2H), 2.13–2.23 (m, 1H), 2.64–2.88 (m, 3H), 3.02 (sextet, J=8 Hz, 2H), 3.44–3.53 (m, 2H), 3.58 (d, J=9 Hz, 1H), 3.56–3.75 (m, 1H), 3.78 (s, 3H), 3.88–3.98 (m, 1H), 5.93 (s, 2H), 6.72 (d, J=9 Hz, 1H), 5.78–5.84 (m, 3H), 6.96 (d, J=2 Hz, 1H), 7.20 (d, J=9 Hz, 2H), 7.27–7.36 (m, 5H). MS (DCl/NH$_3$) m/e 609 (M+H)$^+$.

EXAMPLE 385 trans,trans-4-(1,3-Benzodioxol-5-yl)-2-(4-methoxyphenyl)-1-(2-methyl-1,2,3,4-tetrahydroquinolin-1-yl)carbonylmethyl)pyrrolidine-3-carboxylic Acid Using the procedures described in Example 1, the title compound was prepared. $^1$H NMR (300 MHz, CD$_3$OD) δ 1.03 (m, 3H),1.10–1.45 (m,1H), 2.10–2.85 (m, 4H), 2.90–4.00 (m, 7H), 3.76 (s, 1.5H), 3.77 (s, 1.5H, isomer), 5.90 (m, 2H), 6.70–7.40 (m, 11H). MS (DCl) m/e 529 (M+H)$^+$. Analysis calcd for $C_{31}H_{32}N_2O_6 \cdot 0.3\ H_2O$: C, 69.73; H, 6.15; N, 5.25. Found: C, 69.74; H, 6.10; N, 5.01.

EXAMPLE 386 trans,trans-4-(1,3-Benzodioxol-5-yl)-2-(4-methoxyphenyl)-1-(3-butyl-hept-2-en-1-yl)pyrrolidine-3-carboxylic Acid Using the procedures described in Example 1, the title compound was prepared. $^1$H NMR (300 MHz, CD$_3$OD) δ 0.86 (t, J=7.0 Hz, 3H), 0.90 (t, J=7.0 Hz, 3H), 1.20–1.41 (m, 8H), 1.95–2.06 (m, 4H), 3.24 (d, J=11.0 Hz, 1H), 3.51–3.59 )m, 3H), 3.60–3.71 (m, 1H), 3.77–3.84 (m, 1H), 3.81 (s, 3H), 4.45 (d, J=11.0 Hz, 1H), 5.52 (t, J=7.4 Hz, 1H), 5.93 (s, 2H), 6.77 (d, J=8.1 Hz, 1H), 6.87 (dd, J=1.8, 8.1 Hz, 1H), 6.99 (m, 3H), 7.46 (m, 2H). MS (DCl) m/e 494 (M+H$^+$). Anal calcd for $C_{30}H_{39}NO_5$: C, 72.99; H, 7.96; N, 2.84. Found: C, 72.73; H, 7.89; N, 2.64.

EXAMPLE 387 trans,trans-2-(3-Fluoro4-methoxyphenyl)-4-(1,3-benzodioxol-5-yl)-1-[2-(N-propyl-N-n-hexanesulfonylamino)ethyl]pyrrolidine-3-carboxylic Acid Using the procedures described in Example 66, the title compound was prepared and isolated as a white solid. m.p. 63–65° C. $^1$H NMR (CDCl$_3$, 300 MHz) δ 0.82 (t, J=7 Hz, 3H), 0.88 (t, J=6 Hz, 3H), 1.23–1.47 (m, 6H), 1.44 (sextet, J=7 Hz, 2H), 1.71 (quintet, J=6 Hz, 2H), 2.24–2.34 (m, 1H), 2.70–2.93 (m, 5H), 2.96–3.12 (m, 2H), 3.15–3.35 (m, 2H), 3.43 (dd, J=3 Hz, J=9 Hz, 1H), 3.52–3.59 (m, 1H), 3.66 (d, J=9 Hz, 1H), 3.87 (s, 3H), 5.95 (s, 2H), 6.74 (d, J=8 Hz, 1H), 6.82 (d, J=6.42 (t, J=8 Hz, 1H), 6.96 (s, 1H), 7.12 (d, J=9 Hz, 1H), 7.17 (d, J=12 Hz, 1H). MS (DCl/NH$_3$) m/e 593 (M+H)$^+$.

EXAMPLE 388 trans,trans-4-(1,3-Benzodioxol-5-yl)-2-(4-methoxyphenyl)-1-((3-pyridyl)methyl)pyrrolidine-3-carboxylic Acid Using the procedures described in Example 1, the title compound was prepared. $^1$H NMR (300 MHz, CD$_3$OD) δ 2.87 (m, 2H), 3.04 (dd, J=3.2, 9.7 Hz, 1H), 3.21 (d, J=13.7 Hz, 1H), 3.51 (m, 1H), 3.76–3.85 (m, 2H), 3.79 (s, 3H), 5.90 (m, 2H), 6.71 (m, 1H), 6.79 (dd, J=1.7 Hz, 7.8H), 6.94 (m, 3H), 7.36–7.45 (m, 3H), 7.81 (m, 1H), 8.39 (m, 1H), 8.46 (dd, J=1.4 Hz, 1H). Anal calcd for $C_{25}H_{24}N_2O_5 \cdot 0.70\ H_2O \cdot 0.05\ CH_3CO_2C_2H_5$: C, 67.34; H, 5.79; N, 6.23. Found: C, 67.31; H, 5.63; N, 5.90.

EXAMPLE 389 trans,trans-2-(n-Hexyl)-4-(1,3-benzodioxol-5-yl)-1-(N,N-di(n-butyl)aminocarbonylmethyl)-pyrrolidine-3-carboxylic Acid Using the procedures described in Example 1, the title compound was prepared. $^1$H NMR (CDCl$_3$, 300 MHz) δ 0.82–1.00 (m, 9H), 1.20–1.40 (m, 12H), 1.45–1.60 (m, 4H), 1.70–1.90 (br m, 2H), 3.10–3.46 (m, 6H), 3.65 (t, J=10.8 Hz, 1H), 3.76 (t, J=11.0 Hz, 1H), 3.92–4.06 (m, 2H), 4.14–4.34 (m, 2H), 5.94 (s, 2H), 6.73 (d, J=8.1 Hz, 1H), 6.79 (dd, J=8.1, 1.8 Hz, 1H), 6.87 (d, J=1.8 Hz, 1H). MS(DCl/NH$_3$) m/e 489 (M+H)$^+$. Anal calcd for $C_{28}H_{44}N_2O_5 \cdot 0.9$ TFA: C, 60.53; H, 7.65; N, 4.74. Found: C, 60.62; H, 7.69; N, 4.61.

EXAMPLE 390 trans,trans-4-(1,3-Benzodioxol-5-yl)-2-(4-methoxyphenyl)-1-(((N-(2-pentyl)-N-(4-fluoro-3-methylphenyl)amino)carbonyl)methyl)pyrrolidine-3-carboxylic Acid Using the procedures described in Example 1, the title compound was prepared. $^1$H NMR (300 MHz, CD$_3$OD) δ 0.92 (m, 3H), 0.97 (t, J=7.1 Hz, 3H), 1.13–1.40 (m, 4H), 2.22 (m, 3H), 2.58–2.74 (m, 1H), 2.78–2.87 (m, 1H), 3.09–3.25 (m, 2H), 3.39–3.60 (m, 2H), 3.70–3.90 (m, 1H), 3.80 (s, 3H), 4.70 (m, 1H), 5.93 (m, 2H), 6.70–6.76 (m, 1H), 6.75 (dd, J=1.4, 8.1 Hz, 1H), 6.80–6.94 (m, 4H), 6.96–7.13 (m, 4H). MS (DCl.) m/e 577 (M+H$^+$). Anal calcd for $C_{33}H_{37}FN_2O_6 \cdot 0.25\ H_2O$: C, 68.20; H, 6.50; N, 4.82. Found: C, 68.21; H, 6.46; N, 4.74.

EXAMPLE 391 trans,trans-4-(1,3-Benzodioxol-5-yl)-2-(4-methoxyphenyl)-1-((2-pyridyl)methyl)pyrrolidine-3-carboxylic Acid Using the procedures described in Example 1, the title compound was prepared. $^1$H NMR (300 MHz, CD$_3$OD) δ 2.97 (dd, J=7.9, 9.7 Hz, 1H), 3.04 (t, J=9.6 Hz, 1H), 3.18 (dd, J=4.4 Hz, 9.9H), 3.47 (d, J=14.0 Hz, 1H), 3.59 (m, 1H), 3.78 (s, 3H), 3.96 (d, J=9.9 Hz, 1H), 3.97 (d, J=13.6 Hz, 1H), 5.90 (m, 2H), 6.73 (d, J=8.1 Hz, 1H), 6.83 (dd, J=1.7, 7.9 Hz, 1H), 6.92 (m, 2H), 6.96 (d, J=1.8 Hz, 1H), 7.28 (m, 1H), 7.44 (m, 2H), 7.53 (d, J=8.1 Hz, 1H), 7.80 (dt, J=1.8, 7.7 Hz, 1H), 8.42 (m, 1H). MS (DCl) m/e 433 (M+H$^+$). Anal calcd for $C_{25}H_{24}N_2O_5 \cdot 0.35\ H_2O$: C, 68.43; H, 5.67; N, 6.38. Found: C, 68.44; H, 5.61; N, 6.24.

EXAMPLE 392 trans,trans-2-(3-Phenylpropyl)-4-(1,3-benzodioxol-5-yl)-1-(N,N-di(n-butyl)aminocarbonylmethyl)-pyrrolidine-3-carboxylic Acid Using the procedures described in Example 1, the title compound was prepared. $^1$H NMR (CDCl$_3$, 300 MHz) δ 0.89–0.97 (m, 6H), 1.22–1.36 (m,4H), 1.41–1.55 (m, 4H), 1.63–1.95 (m, 4H), 2.62 (dt, J=7.2, 2.1 Hz, 2H), 3.05–3.44 (m, 7H), 3.53–3.60 (m, 2H), 3.65–3.76 (m, 1H), 3.82–3.90 (m, 1H), 3.96–4.10 (m, 1H), 5.92 (s, 2H), 6.71 (d, J=8.1 Hz, 1H), 6.77 (dd, J=8.1, 1.5 Hz, 1H), 6.86(d, J=1.2 Hz, 1H), 7.10–7.28 (m, 5H). MS(DCl/NH$_3$) m/e 523 (M+H)$^+$. Anal calcd for C$_{31}$H$_{42}$N$_2$O$_5$.0.6 TFA: C, 65.43; H, 7.26; N, 4.74. Found: C, 65.28; H, 7.29; N, 4.50.

EXAMPLE 393 trans-trans-2-(4-Methoxy-3-fluorophenyl)-4-(7-methoxy-1,3-benzodioxol-5-yl)-1-(N,N-di(n-butyl) aminocarbonylmethyl)-pyrrolidine-3-carboxylic Acid Using the procedures described in Example 1, the title compound was prepared and isolated as a white solid. m.p. 115–117° C. $^1$H NMR (300 MHz, CDCl$_3$) δ 0.82 (t, J=7 Hz, 3H), 0.88 (t, J=7 Hz, 3H), 1.05–1.5 (m, 8H), 2.85 (d, J=13 Hz, 1H), 2.90–3.17 (m, 5H), 3.20–3.35 (m, 1H), 3.35–3.50 (m, 3H), 3.55–3.65 (m, 1H), 3.84 (d, J=10 Hz, 1H), 3.87 (s, 3H), 3.92 (s, 3H), 5.94 (dd, J=4 Hz, 2 Hz, 2H), 6.62 (s, 1H), 6.70 (s, 1H), 6.90 (t, J=8 Hz, 1H), 7.05–7.20 (m, 2H).

EXAMPLE 394 trans-trans-2-(1,4-Benzodioxan-6-yl)-4-(7-methoxy-1,3-benzodioxol-5-yl)-1-(N,N-di(n-butyl) aminocarbonylmethyl)-pyrrolidine-3-carboxylic Acid Using the procedures described in Example 1, the title compound was prepared and isolated as a white solid. m.p. 107–110° C. $^1$H NMR (300 MHz, CDCl$_3$) δ 0.82 (t, J=7 Hz, 3H), 0.88 (t, J=7 Hz, 3H), 1.05–1.50 (m, 8H), 2.75 (d, J=13 Hz, 1H), 2.90–3.12 (m, 4H), 3.32–3.60 (m, 5H), 3.69 (d, J=8 Hz, 1H), 3.90 (s, 3H), 4.23 (s, 4H), 5.95 (dd, J=4 Hz, 2 Hz, 2H), 6.62 (s, 1H), 6.70 (s, 1H), 6.78–6.93 (m, 3H).

EXAMPLE 395 trans,trans-4-(1,3-Benzodioxol-5-yl)-2-(4-methoxyphenyl)-1-(3-butyl-2-fluoro-hept-2-en-1-yl) pyrrolidine-3-carboxylic Acid Using the procedures described in Example 1, the title compound was prepared. $^1$H NMR (300 MHz, CD$_3$OD) δ 0.84 (t, J=7.0 Hz, 3H), 0.88 (t, J=7.0 Hz, 3H), 1.16–1.37 (m, 8H), 1.83 (t, J=8.5 Hz, 2H), 2.03–2.08 (m, 2H), 2.76–2.92 (m, 2H), 3.02 (t, J=9.3 Hz, 1H), 3.32–3.42 (m, 2H), 3.50 (m, 1H), 3.71 (d, J=9.2 Hz, 1H), 3.78 (s, 3H), 5.91 (m, 2H), 6.72 (d, J=7.8 Hz, 1H), 6.83 (dd, J=1.7, 8.1 Hz, 1H), 6.90 (m, 2H), 7.02 (d, J=1.7 Hz, 1H), 7.34 (m, 2H). MS (DCl) m/e 512 (M+H$^+$). Anal calcd for C$_{30}$H$_{38}$FNO$_5$: C, 70.43; H, 7.49; N, 2.74. Found: C, 70.58; H, 7.54; N, 2.66.

EXAMPLE 396 trans,trans-2-(3-Fluoro-4-ethoxyphenyl)-4-(1,3-benzodioxol-5-yl)-1-[2-(N-propyl-N-n-pentanesulfonylamino)ethyl]pyrrolidine-3-carboxylic Acid Using the procedures described in Example 66, the title compound was prepared and isolated as a white solid. m.p. 65–66° C. $^1$H NMR (CDCl$_3$, 300 MHz) δ 0.82 (t, J=7 Hz, 3H), 0.90 (t, J=7 Hz, 3H), 1.26–1.36 (m, 4H), 1.41–1.52 (m, 5H), 1.73 (quintet, J=7 Hz, 2H), 2.23–2.33 (m, 1H), 2.69–2.96 (m, 5H), 2.97–3.12 (m, 2H), 3.16–3.37 (m, 2H), 3.43 (d, J=9 Hz, 1H), 3.52–3.59 (m, 1H), 3.66 (d, J=9 Hz, 1H), 4.08 (q, J=7 Hz, 2H), 5.95 (s, 2H), 6.74 (d, J=8 Hz, 1H), 6.82 (d, J=8 Hz, 1H), 6.92 (t, J=8 Hz, 1H), 6.97 (s, 1H), 7.07 (d, J=8 Hz, 1H), 7.15 (d, J=12 Hz, 1H). MS (DCl/NH$_3$) m/e 593 (M+H)$^+$.

EXAMPLE 397 trans,trans-2-(4-Methoxy-3-fluorophenyl)-4-(7-methoxy-1,3-benzodioxol-5-yl)-1-[(N-butyl-N-propylamino)carbonylmethyl]pyrrolidine-3-carboxylic Acid Using the procedures described in Example 1, the title compound was prepared and isolated as a white solid. m.p. 118–120° C. $^1$H NMR (300 MHz, CDCl$_3$) δ 0.70–0.90 (4 triplets, J=7 Hz), 1.05–1.55 (m, 8H), 2.80–3.50 (m, 9H), 3.55–3.65 (m, 1H), 3.82 (d, J=10 Hz, 1H), 3.85 (s, 3H), 3.92 (s, 3H), 5.96 (s, 2H), 6.62 (s, 1H), 6.70 (s, 1H), 6.90 (t, J=8 Hz, 1H), 7.08–7.22 (m, 2H).

EXAMPLE 398 trans,trans-4-(1,3-benzodioxol-5-yl)-2-(4-methoxyphenyl)-1-(N-butyl-N-(4-chlorophenyl) aminocarbonylmethyl)pyrrolidine-3-carboxylic Acid Using the procedures described in Example 1, the title compound was prepared. $^1$H NMR (300 MHz, CD$_3$OD) δ 0.87 (t, J=7 Hz, 3H), 1.20–1.50 (m, 4H), 2.66–4.00 (m, 9H), 3.81 (s, 3H), 5.95 (s, 2H), 6.77 (d, J=7 Hz, 1H), 6.85 (d, J=8 Hz, 3H), 7.05 (m, 5H), 7.33–7.42 (m, 2H). MS (C.l,) m/e 565 (M+H). Analysis calcd for C$_{31}$H$_{33}$N$_2$O$_6$Cl.0.25 H$_3$PO$_4$: C, 63.16; H, 5.77; N, 4.75. Found: C, 63.14; H, 5.59; N, 4.53.

EXAMPLE 399 trans,trans-4-(1,3-Benzodioxol-5-yl)-2-(4-methoxyphenyl)-1-(4-methyl-1,2,3,4-tetrahydroquinolin-1-yl)carbonylmethyl)pyrrolidine-3-carboxylic Acid Using the procedures described in Example 1, the title compound was prepared. $^1$H NMR (300 MHz, CD$_3$OD) δ 1.27 (d, J=7 Hz, 1.5H), 1.28 (d, 7H, 1.5-diastereomer), 1.39–1.55 (m, 1H), 2.02–2.15 (m, 1H), 2.60–3.25 (m, 5H), 3.33–4.00 (m, 5H), 3.78 (s, 3H), 5.92 (d, J=3 Hz, 2H), 6.73 (dd, J=8 Hz, 1H), 6.75–6.90 (m, 3H), 6.91–7.35 (m, 7H). MS (DCl) m/e 529 (M+H)$^+$. Analysis calcd for C$_{31}$H$_{32}$N$_2$O$_6$: C, 70.44; H, 6.10; N, 5.30. Found: C, 70.16; H, 6.04; N, 5.04.

EXAMPLE 400 trans,trans-2-(3-Fluoro-4-methoxyphenyl)-4-(1,3-benzodioxol-5-yl)-1-[2-(N-propyl-N-(2-(piperidin-1-yl)ethanesulfonylamino)ethyl]pyrrolidine-3-carboxylic Acid Using the procedures described in Example 66, the title compound was prepared and isolated as a white solid. m.p. 95–96° C. $^1$H NMR (CDCl$_3$, 300 MHz) δ 0.82 (t, J=7 Hz, 3H), 1.43–1.55 (m, 4H), 1.63–1.72 (m, 4H), 2.29–2.38 (m, 1H), 2.64 –2.78 (m, 5H), 2.87 (t, J=8 Hz, 1H), 2.95–3.04 (m, 5H), 3.20–3.30 (m, 1H), 3.23–3.43 (m, 4H), 3.54–3.63 (m, 1H), 3.78 (d, J=8 Hz, 1H), 3.87 (s, 3H), 5.92 (s, 2H), 6.72 (d, J=8 Hz, 1H), 6.78 (dd, J=2 Hz, J=8 Hz, 1H), 6.88 (t, J=8 Hz, 1H), 6.94 (d, J=2 Hz, 1H), 7.08–7.20 (m, 2H). MS (DCl/NH$_3$) m/e 620 (M+H)$^+$.

EXAMPLE 401 trans,trans-2-(n-Heptyl)-4-(1,3-benzodioxol-5-yl)-1-(N,N-di(n-butyl)aminocarbonylmethyl)-pyrrolidine-3-carboxylic Acid Using the procedures described in Example 1, the title compound was prepared. $^1$H NMR (CDCl$_3$, 300 MHz) δ 0.83–0.98 (s, 9H), 1.18–1.40 (m, 14H), 1.44–1.60 (m, 4H), 1.72–1.96 (br m, 2H), 3.12–3.45 (m, 6H), 3.65 (t, J=10.5 Hz, 1H), 3.76 (t, J=11.2 1H), 3.90–4.06 (m, 2H), 4.13–4.33 (m, 2H), 5.93(s, 2H), 6.73 (d, J=7.8 Hz, 1H), 6.79 (dd, J=7.8, 1.7 Hz, 1H), 6.87 (d, J=1.7 Hz, 1H). MS(DCl/NH$_3$) m/e 503 (M+H)$^+$. Anal calcd for C$_{29}$H$_{46}$N$_2$O$_5$.0.75 TFA: C, 62.28; H, 8.01; N, 4.76. Found: C, 62.20; H, 7.99; N, 4.50.

EXAMPLE 402 trans,trans-4-(1,3-Benzodioxol-5-yl)-2-(4-methoxyphenyl)-1-(3-methyl-1,2,3,4-tetrahydroquinolin-1-yl)carbonylmethyl)pyrrolidine-3-carboxylic Acid Using the procedures described in Example 1, the title compound was prepared. $^1$H NMR (300 MHz, CD$_3$OD) δ 0.99 (d, 1.5H), 1.03 (d, J=6 Hz, 1.5H, second diastereomer), 2.60–4.00m (12), 3.78 (s, 1.5H), 3.79 (s, 1.5H, second diastereomer), 5.92 (s, 1H), 5.93 (s, 1H, diastereomer), 6.65–7.40 (m, 11H). MS (DCl) m/e 529 (M+H)$^+$. Analysis calcd for C$_{31}$H$_{32}$N$_2$O$_6$.0.8 H$_2$O: C, 68.57; H, 6.24; N, 5.16. Found: C, 70.44; H, 6.10; N, 5.30.

EXAMPLE 403 trans,trans-4-(1,3-Benzodioxol-5-yl)-2-(4-methoxyphenyl)-1-(N-butyl-N-(4-fluorophenyl)aminocarbonylmethyl)pyrrolidine-3-carboxylic Acid Using the procedures described in Example 1, the title compound was prepared. $^1$H NMR (300 MHz, CD$_3$OD) δ 0.87 (t, J=7 Hz, 3H), 1.2–1.47 (m, 4H), 2.7 (d, J=12 Hz, 1H), 2.80 (t, J=9 Hz, 1H), 3.09 (t, J=9 Hz, 1H), 3.25 (d, J=15 Hz, 1H), 3.40–3.47 (m, 1H), 3.49–3.65 (m, 3H), 3.75 (d, J=12 Hz, 1H), 3.80 (s, 3H), 5.94 (s, 2H), 6.72–6.86 (m, 4H), 7.00–7.15 (m, 7H). MS (DCl) m/e 549 (M+H)$^+$. Analysis calcd for C$_{31}$H$_{33}$N$_2$O$_6$F.0.4 H$_2$O: C, 66.99; H, 6.13; N, 5.04. Found: C, 66.99; H, 5.94; N, 4.99.

EXAMPLE 404 trans,trans-1-(N-Butyl-N-(3-methylphenyl)aminocarbonylmethyl)-2-(4-methoxyphenyl)-4-(5-benzofuranyl)pyrrolidine-3-carboxylic Acid Using the procedures described in Example 1, the title compound was prepared. $^1$H NMR (300 MHz, CDCl$_3$) δ 7.66 (1H, bs), 7.60 (1H, d, J=3 Hz), 7.45 (2H, s), 7.15 (4H, m), 6.75 (5H, m), 3.96 (1H, d, J=10 Hz), 3.78 (3H, s), 3.74 (1H, m), 3.59 (3H, m), 3.21 (1H, t, J=9 Hz), 3.19 (1H, d, J=16 Hz), 2.92 (1H, t, J=9 Hz), 2.70 (1H, d, J=16 Hz), 2.29 (3H, s), 1.41 (2H, m), 1.24 (2H, m), 0.85 (3H, t, J=7 Hz). MS (DCl, NH$_3$) m/e 541 (M+H$^+$). Anal. calcd for C$_{33}$H$_{34}$N$_2$O.1 H$_2$O: C, 71.21; H, 6.52; N 5.03. Found: C, 71.31; H, 6.30; N, 4.98.

EXAMPLE 405 trans,trans-1-(N-Butyl-N-(3-methylphenyl)aminocarbonylmethyl)-2-(4-fluorophenyl)-4-(5-benzofuranyl)pyrrolidine-3-carboxylic Acid Using the procedures described in Example 1, the title compound was prepared. $^1$H NMR (300 MHz, CDCl$_3$) δ 7.67 (1H, bs), 7.60 (1H, d, J=3 Hz), 7.45 (2H, m), 7.18 (3H, m), 7.12 (1H, d, J=7 Hz), 6.93 (2H, m), 6.76 (1H, d, J=3 Hz), 6.70 (2H, bd), 4.02 (1H, m), 3.77 (1H, m), 3.59 (3H, m), 3.29 (1H, m), 3.19 (1H, m), 2.94 (1H, m), 2.71 (1H, m), 2.30 (3H, s), 1.45 (2H, m), 1.26 (2H, sext, J=7 Hz), 0.84 (3H, t, J=7 Hz). MS (DCl, NH$_3$) m/e 529 (M+H$^+$). Anal. calcd for C$_{33}$H$_{34}$N$_2$O$_5$.0.2 HOAc: C, 71.98; H, 6.30; N 5.18. Found: C, 71.68; H, 5.89; N, 5.25.

EXAMPLE 406 trans,trans-4-(1,3-Benzodioxol-5-yl)-2-(4-methoxyphenyl)-1-((N,N-(di-(3-methylphenyl)amino)carbonyl)methyl)pyrrolidine-3-carboxylic Acid Using the procedures described in Example 1, the title compound was prepared. $^1$H NMR (300 MHz, CD$_3$OD) δ 2.27 (s, 6H), 2.81 (dd, J=8.1, 9.5 Hz, 1H), 2.98 (d, J=15.3 Hz, 1H), 3.20 (t, J=16.6 Hz, 1H), 3.47–3.60 (m, 3H), 3.80 (s, 3H), 3.85 (d, J=9.5 Hz, 1H), 5.91 (s, 2H), 6.73 (d, J=7.8 Hz, 1H), 6.85 (m, 3H), 6.95 m, 4H), 7.05 (d, J=1.7 Hz, 1H), 7.06–7.24 (m, 6H). MS (DCl) m/e 579 (M+H$^+$). Anal calcd for C$_{35}$H$_{34}$N$_2$O$_6$.0.15 H$_2$O.0.20 CH$_3$CO$_2$C$_2$H$_5$: C, 71.79; H, 6.04; N, 4.68. Found: C, 71.81; H, 5.79; N, 4.51.

EXAMPLE 407 trans,trans-4-(1,2-Dihydrobenzofuran-5-yl)-2-(4-methoxyphenyl)-1-(((N-butyl-N-(3-methylphenyl)amino)carbonyl)methyl)pyrrolidine-3-carboxylic Acid Using the procedures described in Example 1, the title compound was prepared. $^1$H (300 MHz, CDCl$_3$) δ 7.73 (2H, m), 7.40–7.10 (4H, m), 6.92 (2H, m), 6.72 (2H, d, J=9), 6.63 (1H, m), 5.40 (1H, m), 4.55 (2H, t, J=9), 4.30–4.10 (3H, m), 3.84 (3H, s), 3.82 (1H, m), 3.65 (1H, m), 3.39 (1H, m), 3.21 (2H, t, J=9), 3.10–2.90 (2H, m), 2.26 (3H, s), 1.55 (2H, m), 1.45 (2H, m), 0.92 (3H, t, J=9). MS (DCl/NH$_3$) m/e 543 (M+H$^+$). Anal calcd for C$_{33}$H$_{38}$N$_2$O$_5$.0.65 H$_2$O: C, 71.50; H, 7.15; N, 5.05. Found: C, 71.47; H, 6.96; N, 4.83.

EXAMPLE 408 trans,trans-2-(3-Fluoro-4-methoxyphenyl)-4-(1,3-benzodioxol-5-yl)-1-{2-(N-propyl-N-[2-(N,N-dimethylamino)]ethanesulfonylamino)ethyl}pyrrolidine-3-carboxylic Acid Using the procedures described in Example 66, the title compound was prepared and isolated as a white solid. m.p. 81–82° C. $^1$H NMR (CDCl$_3$, 300 MHz) δ 0.80 (t, J=7 Hz, 3H), 1.43 (sextet, J=7 Hz, 2H), 2.15–2.24 (m, 1H), 2.36 (s, 6H), 2.66–2.76 (m, 1H), 2.83–3.04 (m, 6H), 3.18–3.41 (m, 5H), 3.55–3.63 (m, 1H), 3.72 (d, J=8 Hz, 1H), 3.85 (s, 3H), 5.90 (d, J=6 Hz, 2H), 6.67 (d, J=8 Hz, 1H), 6.78 (dd, J=2 Hz, J=8 Hz, 1H), 6.84 (t, J=8 Hz, 1H), 7.94 (d, J=2 Hz, 1H), 7.09 (d, J=8 Hz, 1H), 7.20 (dd, J=2 Hz, J=12 Hz, 1H). MS (DCl/NH$_3$) m/e 580 (M+H)$^+$.

EXAMPLE 409 trans,trans-1-(N,N-Dibutylaminocarbonylmethyl)-2-(4-fluorophenyl)-4-(5-benzofuranyl)pyrrolidine-3-carboxylic Acid Using the procedures described in Example 1, the title compound was prepared. $^1$H NMR (300 MHz, CDCl$_3$) δ 7.88 (1H, bs), 7.80 (2H, m), 7.61 (1H, d, J=3 Hz), 7.55 (1H, bd, J=8 Hz), 7.46 (1H, d, J=8 Hz), 7.07 (2H, t, J=8 Hz), 6.76 (1H, d, J=3 Hz), 5.53 (1H, bd, J=11 Hz), 4.18 (2H, m), 3.91 (3H, m), 3.55 (1H, d, J=16 Hz), 3.30 (3H, m), 3.12 (1H, dd, J=10&9 Hz), 2.95 (1H, m), 1.51 (2H, m), 1.31 (4H, m), 1.12 (2H, m), 0.92 (3H, m), 0.83 (3H, t, J=7 Hz). MS m/e (DCl, $NH_3$) 595 ($M+H^+$).

EXAMPLE 410 trans,trans-4-(1,2-Dihydrobenzofuran-5-yl)-2-(4-ethylphenyl)-1-(((N-butyl-N-(3-methylphenyl)amino)carbonyl)methyl)pyrrolidine-3-carboxylic Acid Using the procedures described in Example 1, the title compound was prepared. $^1$H NMR (300 MHz, $CDCl_3$) δ 7.35 (2H, m), 7.20–7.00 (7H, m), 6.70 (2H, d, J=9), 5.38 (1H, m), 4.55 (2H, t, J=9), 4.05 (1H, m), 3.64 (2H, m), 3.45 (1H, m), 3.21 (2H, t, J=9), 2.95 (1H, m), 2.75 (1H, m), 2.63 (2H, q, J=8), 2.38 (2H, m), 2.27 (3H, s), 1.43 (2H, m), 1.30 (2H, m), 1.22 (3H, t, J=9), 0.89 (3H, t, J=9). MS (DCl/$NH_3$) m/e 541 ($M+H^+$). Anal calcd for $C_{34}H_{40}N_2O_4 \cdot 1.6$ AcOH: C, 70.17; H, 7.34; N, 4.40. Found: C, 70.11; H, 7.06; N, 4.80.

EXAMPLE 411 trans,trans-4-(1,2-Dihydrobenzofuran-5-yl)-2-(4-fluorophenyl)-1-(N,N-di(n-butyl)aminocarbonylmethyl)-pyrrolidine-3-carboxylic Acid Using the procedures described in Example 1, the title compound was prepared. $^1$H NMR (300 MHz, $CDCl_3$) δ 7.40 (2H, m), 7.28 (1H, bs), 7.18 (1H, dd, J=8, 3), 7.00 (2H, t, J=9), 6.72 (1H, d, J=9), 4.53 (2H, t, J=9), 3.92 (1H, m), 3.65 (1H, m), 3.42 (3H, m), 3.19 (2H, t, J=9), 3.15–2.90 (6H, m), 1.43 (3H, m), 1.25 (3H, m), 1.10 (2H, m), 0.90 (3H, t, J=8), 0.83 (3H, t, J=8). MS (DCl/$NH_3$) m/e 497 ($M+H^+$). Anal calcd for $C_{29}H_{37}FN_2O_4 \cdot 0.25 H_2O$: C, 69.51; H, 7.54; N, 5.59. Found: C, 69.45; H, 7.60; N, 5.44.

EXAMPLE 412 trans,trans-4-(1,2-Dihydrobenzofuran-5-yl)-2-(4-fluorophenyl)-1-(((N-butyl-N-(3-methylphenyl)amino)carbonyl)methyl)pyrrolidine-3-carboxylic Acid Using the procedures described in Example 1, the title compound was prepared. $^1$H NMR (300 MHz, $CDCl_3$) δ 7.28 (1H, bs), 7.25–7.00 (5H, m), 6.91 (2H, m), 6.72 (3H, d, J=9), 4.54 (2H, t, J=9), 4.00 (1H, m), 3.60 (3H, m), 3.45 (1H, m), 3.19 (2H, t, J=9), 3.11 (2H, m), 2.84 (1H, m), 2.67 (1H, bd, J=18), 2.26 (3H, s), 1.42 (2H, m), 1.25 (2H, m), 0.88 (3H, t, J=8). MS (DCl/$NH_3$) m/e 531 ($M+H^+$). Anal calcd for $C_{32}H_{35}FN_2O_4 \cdot 0.25 H_2O$: C, 71.82; H, 6.69; N, 5.23. Found: C, 71.66; H, 6.55; N, 5.03.

EXAMPLE 413 trans,trans-4-(Indan-5-yl)-2-(4-methoxyphenyl)-1-(N,N-di(n-butyl)aminocarbonylmethyl)-pyrrolidine-3-carboxylic Acid Using the procedures described in Example 1, the title compound was prepared. $^1$H NMR (300 MHz, $CDCl_3$) δ 7.32 (3H, m), 7.18 (2H, m), 6.85 (2H, d, J=9), 3.83 (1H, m), 3.79 (3H, s), 3.67 (1H, m), 3.50–3.20 (4H, m), 3.20–2.92 (4H, m), 2.87 (5H, m), 2.79 (1H, bd, J=15), 2.06 (2H, m), 1.43 (2H, m), 1.27 (4H, m), 1.08 (2H, m), 0.88 (3H, t, J=8), 0.82 (3H, t, J=8). MS (DCl/$NH_3$) m/e 507 ($M+H^+$). Anal calcd for $C_{31}H_{42}N_2O_4$: C, 73.49; H, 8.36; N, 5.53. Found: C, 73.18; H, 8.29; N, 5.17.

EXAMPLE 414 trans,trans-2-(4-Methoxyphenyl)-4-(3,4-difluorophenyl)-1-[(N-butyl-N-(3-methylphenyl)amino)carbonylmethyl]pyrrolidine-3-carboxylic Acid Using the procedures described in Example 1, the title compound was prepared. $^1$H NMR (300 MHz, $CDCl_3$) δ 0.86 (t, J=7 Hz, 3H), 1.10–1.35 (m, 2H), 1.35–1.52 (m, 2H), 2.29 (s, 3H), 2.63 (d, J=13 Hz, 1H), 2.76 (t, J=7 Hz, 1H), 3.06–3.20 (m, 2H), 3.42–3.53 (m, 1H), 3.50–3.64 (m, 3H), 3.80 (s, 3H), 3.86 (d, J=9 Hz, 1H), 6.66–6.82 (m, 4H), 7.02–7.22 (m, 6H), 7.30–7.40 (m, 1H).

EXAMPLE 415 trans,trans-1-(N-Butyl-N-(3-chlorophenyl)aminocarbonylmethyl)-2-(4-fluorophenyl)-4-(5-benzofuranyl)pyrrolidine-3-carboxylic Acid Using the procedures described in Example 1, the title compound was prepared. $^1$H NMR (300 MHz, $CDCl_3$) δ 7.64 (1H, d, J=2 Hz), 7.61 (1H, d, J=3 Hz), 7.47 (1H, d, J=8 Hz), 7.41 (1H, dd, J=8&3 Hz), 7.30 (1H, dt, J=8&2 Hz), 7.21 (1H, d, J=8 Hz), 7.19 (2H, m), 7.00 (1H, bs), 6.94 (2H, t, J=8 Hz), 6.83 (1H, bd, J=8 Hz), 6.74 (1H, dd, J=2&1 Hz), 3.96 (1H, d, J=10 Hz), 3.75 (1H, ddd, 6, 5&3 Hz), 3.59 (3H, m), 3.23 (1H, t, J=10 Hz), 3.18 (1H, d, J=16 Hz), 2.92 (1H, dd, J=10&9 Hz), 2.69 (1H, d, J=16 Hz), 1.41 (2H, m), 1.23 (2H, m), 0.87 (3H, t, J=7 Hz). MS (DCl, $NH_3$) 549, 551 ($M+H^+$). Anal. calcd for $C_{31}H_{30}ClFN_2O$: C, 67.82; H, 5.51; N, 5.10. Found: C, 67.43; H, 5.33; N, 4.78.

EXAMPLE 416 trans,trans-4-(1,3-Benzodioxol-5-yl)-2-(4-methoxyphenyl)-1-(((N-propyl-N-(4-phenoxybenzyl)amino)carbonyl)methyl)pyrrolidine-3-carboxylic Acid Using the procedures described in Example 1, the title compound was prepared. $^1$H NMR (300 MHz, $CDCl_3$) δ (rotamer) 7.40–7.20 (5H, m), 7.13 (2H, m), 6.98 (2H, m), 6.93–6.60 (7H, m), 5.93 (1H, d, J=2), 5.88 (5.85) (1H, d, J=2), 4.90 (4.50) (1H, d, J=15), 4.10 (4.25) (1H, d, J=15), 3.77 (3.73) (3H, s), 3.72 (1H, m), 3.60 (1H, m), 3.53–3.20 (3H, m), 3.15–2.75 (4H, m), 1.60–1.20 (2H, m), 0.83 (0.64) (3H, t, J=8). MS (DCl/$NH_3$) m/e 623 ($M+H^+$). Anal calcd for $C_{37}H_{38}N_2O_7 \cdot 0.25 H_2O$: C, 70.85; H, 6.19; N, 4.47. Found: C, 70.68; H, 6.10; N, 4.42.

EXAMPLE 417 trans,trans-4-(1,2-Dihydrobenzofuran-5-yl)-2-(4-ethylphenyl)-1-(((N-(2-pentyl)-N-(4-fluoro-3-methylphenyl)amino)carbonyl)methyl)pyrrolidine-3-carboxylic Acid Using the procedures described in Example 1, the title compound was prepared. $^1$H NMR (300 MHz, $CDCl_3$) δ 7.30 (1H, bs), 7.20–7.00 (5H, m), 6.87 (1H, m), 6.73 (2H, d, J=9), 6.57 (1H, m), 4.81 (1H, m), 4.55 (2H, t, J=9), 3.92 (1H, bd, J=11), 3.60 (1H, m), 3.43 (1H, m), 3.18 (2H, t, J=9), 3.17 (1H, m), 3.06 (1H, dd, J=15, 6), 2.88 (1H, dd, J=11, 9), 2.61

(2H, q, J=8), 2.59 (1H, m), 2.18 (3H, m), 1.40–1.10 (4H, m), 1.22 (3H, t, J=9), 1.00–0.80 (6H, m). MS (DCl/NH$_3$) m/e 573 (M+H$^+$). Anal calcd for C$_{35}$H$_{41}$FN$_2$O$_4$.0.75 H$_2$O: C, 71.71; H, 7.31; N, 4.78. Found: C, 71.56; H, 7.33; N, 4.56.

EXAMPLE 418 trans,trans-2-(4-Methoxphenyl)-4-(1,3-benzodioxol-5-yl)-1-[2-(N-propyl-N-[2-pyrimidinyl]amino)ethyl] pyrrolidine-3-carboxylic Acid Ethyl 2-(4-methoxyphenyl)-4-(1,3-benzodioxol-5-yl)-1-[2-(N-propylamino)propyl]pyrrolidine-3-carboxylate, prepared by the procedures of Example 61B (300 mg), 138 mg of 2-bromopyrimidine, and 150 mg of diisopropylethylamine were heated at 95° C. for 15 hours in 2 mL of acetonitrile. The resulting intermediate trans-trans ethyl ester was isolated by chromatography on silica gel eluting with 5–10% ETOAc in CH$_2$Cl$_2$ and hydrolyzed with NaOH in ethanol/water to give 95 mg of the title compound. $^1$H NMR (300 MHz, CDCl$_3$) δ 0.82 (t, J=7 Hz, 3H), 1.50 (sextet, J=7 Hz, 2H), 2.15–2.30 (m, 1H), 2.75–2.97 (m, 3H), 3.40–3.55 (m, 4H), 3.60–3.70 (m, 3H), 3.75 (s, 3H), 5.95 (s, 2H), 6.34 (t, J=4 Hz, 1H), 6.65 (d, J=8 Hz, 1H), 6.75–6.82 (m, 1H), 6.78 (d, J=9 Hz, 2H), 6.96 (d, J=2 Hz, 1H), 7.27 (d, J=9 Hz, 2H), 8.20 (d, J=4 Hz, 2H).

EXAMPLE 419 trans,trans-4-(1,3-Benzodioxol-5-yl)-2-(4-methoxyphenyl)-1-(3-butyl-2-chloro-hept-2-en-1-yl) pyrrolidine-3-carboxylic Acid Using the procedures described in Example 1, the title compound was prepared. $^1$H NMR (300 MHz, CD$_3$OD) δ 0.84 (t, J=6.8 Hz, 3H), 0.88 (t, J=6.7 Hz, 3H), 1.19–1.39 (m, 8H), 2.05–2.09 (m, 2H), 2.17–2.23 (m, 2H), 2.78 (dd, J=6.6, 9.2 Hz, 1H), 2.95 (t, J=9.2 Hz, 1H), 3.32–3.37 (m, 2H), 3.49 (m, 1H), 3.70 (d, J=9.2 Hz, 1H), 3.77 (s, 3H), 5.91 (m, 2H), 6.72 (d, J=8.1 Hz, 1H), 6.85 (dd, J=1.9, 8.1 Hz, 1H), 6.89 (m, 2H), 7.08 (d, J=1.5 Hz, 1H), 7.36 (m, 2H). MS (DCl) m/e 528 (M+H$^+$). Anal calcd for C$_{30}$H$_{38}$ClNO$_5$.0.25 H$_2$O: C, 67.66; H, 7.29; N, 2.63. Found: C, 67.62; H, 7.18; N, 2.40.

EXAMPLE 420 trans,trans-4-(1,2-Dihydrobenzofuran-5-yl)-2-(4-methoxyphenyl)-1-(((N-(2-pentyl)-N-(4-fluoro-3-methylphenyl)amino)carbonyl)methyl)pyrrolidine-3-carboxylic Acid Using the procedures described in Example 1, the title compound was prepared. $^1$H NMR (300 MHz, CDCl$_3$) δ 7.28 (1H, bs), 7.15 (3H, m), 6.90 (1H, m), 6.77 (2H, dd, J=9, 3), 6.71 (2H, d, J=9), 6.56 (1H, m), 4.80 (1H, m), 4.53 (2H, t, J=9), 3.92 (1H, m), 3.79 (3H, s), 3.60 (1H, m), 3.45 (1H, m), 3.19 (2H, t, J=9), 3.18 (1H, m), 3.03 (1H, dd, J=15, 6), 2.85 (1H, m), 2.55 (1H, m), 2.18 (3H, m), 1.40–1.05 (4H, m), 1.00–0.80 (6H, m). MS (DCl/NH$_3$) m/e 575 (M+H$^+$). Anal calcd for C$_{34}$H$_{39}$FN$_2$O$_5$.0.35 H$_2$O: C, 70.29; H, 6.89; N, 4.82. Found: C, 70.37; H, 6.92; N, 4.30.

EXAMPLE 421 trans,trans-4-(1,2-Dihydrobenzofuran-5-yl)-2-(4-methoxyphenyl)-1-(((N-butyl-N-(3-chlorophenyl) amino)carbonyl)methyl)pyrrolidine-3-carboxylic Acid Using the procedures described in Example 1, the title compound was prepared. $^1$H NMR (300 MHz, CDCl$_3$) δ 7.29 (1H, d, J=3), 7.25–7.05 (5H, m), 6.98 (1H, bs), 6.80 (2H, m), 6.72 (2H, d, J=9), 4.53 (2H, t, J=9), 3.85 (1H, d, J=10), 3.79 (3H, s), 3.58 (3H, m), 3.42 (1H, dd, J=10, 6), 3.18 (4H, m), 2.87 (1H, m), 2.66 (1H, m), 1.40 (2H, m), 1.25 (2H, m), 0.86 (3H, t, J=9). MS (DCl/NH$_3$) m/e 563 (M+H$^+$). Anal calcd for C$_{32}$H$_{35}$ClN$_2$O$_5$.0.25 H$_2$O: C, 67.72; H, 6.30; N, 4.94. Found: C, 67.72; H, 6.21; N, 4.55.

EXAMPLE 422 trans,trans-4-(1,3-Benzodioxol-5-yl)-2-(5-ethylfuran-2-yl)-1-(N,N-di(n-butyl) aminocarbonylmethyl)-pyrrolidine-3-carboxylic Acid Using the procedures described in Example 1, the title compound was prepared. $^1$H NMR (300 MHz, CDCl$_3$) δ 7.77 (1H, bs), 7.11 (1H, d, J=3), 7.02 (1H, dd, J=9, 3), 6.82 (1H, d, J=9), 6.52 (1H, d, J=4), 6.08 (1H, d, J=4), 5.98 (2H, s), 5.80 (1H, d, J=6), 4.70 (1H, bd, J=15), 4.37 (2H, m), 3.70 (2H, m), 3.39 (2H, m), 3.20 (1H, m), 3.10–2.82 (2H, m), 2.76 (2H, q, J=8), 1.45 (2H, m), 1.32 (3H, t, J=9), 1.30–1.10 (6H, m), 0.87 (3H, t, J=9), 0.85 (3H, t, J=9). MS (DCl/NH$_3$) m/e 499 (M+H$^+$). Anal calcd for C$_{28}$H$_{38}$N$_2$O$_6$.1.75 HCl: C, 59.80; H, 7.12; N, 4.98. Found: C, 59.51; H, 6.96; N, 4.88.

EXAMPLE 423 trans,trans-4-(1,2-Dihydrobenzofuran-5-yl)-2-(4-fluorophenyl)-1-(((N-(2-pentyl)-N-(4-fluoro-3-methylphenyl)amino)carbonyl)methyl)pyrrolidine-3-carboxylic Acid Using the procedures described in Example 1, the title compound was prepared. $^1$H NMR (300 MHz, CDCl$_3$) δ 7.30–7.10 (4H, m), 6.92 (3H, m), 6.73 (2H, d, J=9), 6.59 (1H, m), 4.80 (1H, m), 4.53 (2H, t, J=9), 4.00 (1H, bd, J=10), 3.62 (1H, m), 3.45 (1H, m), 3.22 (1H, m), 3.21 (2H, t, J=9), 3.02 (1H, dd, J=15, 6), 3.85 (1H, t, J=10), 2.58 (1H, bd, J=18), 2.20 (3H, bs), 1.40–1.30 (3H, m), 1.15 (1H, m), 1.0014 0.80 (6H, m). MS (DCl/NH$_3$) m/e 563 (M+H$^+$). Anal calcd for C$_{33}$H$_{36}$F$_2$N$_2$O$_4$: C, 70.44; H, 6.45; N, 4.98. Found: C, 70.06; H, 6.47; N, 4.71.

EXAMPLE 424 trans,trans-4-(1,2-Dihydrobenzofuran-5-yl)-2-(4-fluorophenyl)-1-(((N-butyl-N-(3-chlorophenyl) amino)carbonyl)methyl)pyrrolidine-3-carboxylic Acid Using the procedures described in Example 1, the title compound was prepared. $^1$H NMR (300 MHz, CDCl$_3$) δ 7.30 (2H, m), 7.25–7.10 (4H, m), 6.95 (3H, m), 6.82 (1H, bd, J=9), 6.73 (1H, d, J=9), 4.55 (2H, t, J=9), 3.92 (1H, bd, J=11), 3.60 (3H, m), 3.43 (1H, dd, J=9, 6), 3.21 (2H, t, J=9), 3.16 (2H, m), 2.87 (1H, m), 2.69 (1H, m), 1.42 (2H, m), 1.26 (2H, m), 0.87 (3H, t, J=9). MS (DCl/NH$_3$) m/e 551 (M+H$^+$). Anal calcd for C$_{31}$H$_{32}$ClFN$_2$O$_4$.0.25 H$_2$O: C, 67.02; H, 5.90; N, 5.04. Found: C, 66.98; H, 5.71; N, 4.76.

EXAMPLE 425 trans,trans-4-(1,2-Dihydrobenzofuran-5-yl)-2-(4-ethylphenyl)-1-(((N-butyl-N-(3-chlorophenyl)amino) carbonyl)methyl)pyrrolidine-3-carboxylic Acid Using the procedures described in Example 1, the title compound was prepared. $^1$H NMR (300 MHz, CDCl$_3$) δ 7.30 (1H, m), 7.21 (1H, d, J=9), 7.15 (2H, m), 7.09 (4H, bs), 6.96 (1H, bs), 6.80 (1H, bd, J=9), 6.73 (1H, d, J=9), 4.54 (2H, t, J=9), 3.89 (1H, bd, J=11), 3.60 (3H, m), 3.43 (1H, m), 3.22 (2H, t, J=9), 3.18 (2H, m), 2.92 (1H, m), 2.72 (1H, m), 2.62 (2H, q, J=8), 1.41 (2H, m), 1.26 (2H, m), 1.23 (3H, t, J=9), 0.87 (3H, t, J=9). MS (DCl/NH$_3$) m/e 561 (M+H$^+$). Anal calcd for C$_{33}$H$_{37}$ClN$_2$O$_4$·0.25 H$_2$O: C, 70.08; H, 6.68; N, 4.95. Found: C, 70.13; H, 6.59; N, 4.65.

EXAMPLE 426 trans,trans-1-(N-Butyl-N-(3-chlorophenyl)carboxamidomethyl)-2-(4-methoxyphenyl)-4-(5-benzofuranyl)pyrrolidine-3-carboxylic Acid Using the procedures described in Example 1, the title compound was prepared. $^1$H NMR (300 MHz, CDCl$_3$) δ 7.67 (1H, bs), 7.60 (1H, d, J=3 Hz), 7.48 (1H, d, J=8 Hz), 7.42 (1H, dd, J=8&3 Hz), 7.29 (1H, dt, J=8&3 Hz), 7.21 (1H, d, J=8 Hz), 7.14 (2H, m), 6.99 (1H, bs), 6.76 (4H, m), 3.88 (1H, d, J=10 Hz), 3.75 (1H, ddd, J=6, 5&3 Hz), 3.59 (2H, m), 3.53 (1H, dd, J=10&3 Hz), 3.22 (1H, t, J=9 Hz), 3.19 (1H, m), 2.96(1H, m), 2.70 (1H, d, J=16 Hz), 1.42 (2H, m), 1.26 (2H, m), 0.87 (3H, t, J=7 Hz). MS (DCl, NH$_3$) m/e 563, 561 (M+H$^+$). Anal. calcd for C$_{32}$H$_{33}$ClN$_2$O$_5$·0.5 H$_2$O: C, 67.42; H, 6.01; N, 4.91. Found: C, 67.45; H, 5.82; N, 4.68.

EXAMPLE 427 trans,trans-4-(1,3-Benzodioxol-5-yl)-2-(4-methoxyphenyl)-1-(((N-cyclohexyl-N-butylamino)carbonyl)methyl)pyrrolidine-3-carboxylic Acid Using the procedures described in Example 1, the title compound was prepared. $^1$H NMR (300 MHz, CDCl$_3$) (rotamer) δ 0.78 (0.86) (t, 3H, J=7 Hz), 0.90–1.90 (envelope, 14H), 2.69 (2.80) (d, 1H, J=12 Hz), 2.9–3.8 (envelope, 10H), 3.78 (3.80) (s, 3H), 5.92 (s, 2H), 6.72 (d, 1H, J=9 Hz) 6.86 (m, 3H) 7.03 (d, 1H, J=6 Hz), 7.34 (m, 2H). MS (DCl/NH$_3$) m/e 537 (M+H)$^+$. Anal. calc'd for C$_{31}$H$_{40}$N$_2$O$_6$·1 H$_2$O: C, 67.13; H, 7.63; N, 5.05. Found: C, 67.09; H, 7.34; N, 4.92.

EXAMPLE 428 trans,trans-4-(1,3-Benzodioxol-5-yl)-2-(4-ethylphenyl)-1-(((N-(3-methylphenyl)-N-butylamino)carbonyl)methyl)pyrrolidine-3-carboxylic Acid Using the procedures described in Example 1, the title compound was prepared. $^1$H NMR (300 MHz, CDCl$_3$) δ 0.86 (t, 3H, J=7 Hz), 1.22 (t, 3H, J=7 Hz), 1.25 (m, 2H), 1.43 (m, 2H), 2.26 (s, 3H), 2.6 (q, 2H, J=7 Hz), 2.68 (d, 1H, J=12 Hz), 2.86 (t, 1H, J=8 Hz), 3.19 (q, 2H, J=7 Hz), 3.44 (dd, 1H, J=3 Hz, 10 Hz), 3.59 (m. 3H), 3.94 (d, 1H, 9 Hz), 5.92 (s, 2H), 6.75 (m, 3H), 6.86 (dd, 1H, J=2 Hz, 8 Hz), 7.08 (m, 6H), 7.17 (t, 1H, J=8 Hz). MS (DCl/NH$_3$) m/e 543 (M+H)$^+$. Anal. calc'd for C$_{33}$H$_{38}$N$_2$O$_5$·0.60 H$_2$O: C, 71.61; H, 7.14; N, 5.06. Found: C, 71.57; H, 6.80; N, 4.87.

EXAMPLE 429 trans,trans-4-(Benzofuran-5-yl)-2-(4-ethylphenyl)-1-(((N-(3-methylphenyl)-N-butylamino)carbonyl)methyl)pyrrolidine-3-carboxylic Acid Using the procedures described in Example 1, the title compound was prepared. $^1$H NMR (300 MHz, CDCl$_3$) δ 0.90 (t, 3H, J=7 Hz), 1.30 (t, 3H, J=7 Hz), 1.31 (m, 2H), 1.43 (m, 2H), 2.27 (s, 3H), 2.73 (q, 2H, J=7 Hz), 3.15 (d, 2H, J=17 Hz), 3.61 (t, 2H, J=8 Hz), 3.82 (m, 2H), 4.00 (t, 1H, 12 Hz), 4.26 (m, 2H), 5.53 (br d, 1H), 6.54 (br s, 2H), 6.76 (d, 1H, J=2 Hz), 7.14 (m, 3H), 7.28 (s, 1H), 7.40 (m, 3H), 7.48 (d, 1H, J=8 Hz), 7.63 (d, 1H, J=2 Hz), 7.73 (s, 1H). HRMS. calc'd for C$_{34}$H$_{39}$N$_2$O$_4$ (M+H)$^+$: 539.2910. Found: 539.2891.

Example 430 trans,trans-4-(1,4-Benzodioxan-6-yl)-2-(4-ethylphenyl)-1-(((N-(3-methylphenyl)-N-butylamino)carbonyl)methyl)pyrrolidine-3-carboxylic Acid Using the procedures described in Example 1, the title compound was prepared. $^1$H NMR (300 MHz, CDCl$_3$) δ 0.87 (t, 3H, J=7 Hz), 1.22 (t, 3H, J=7 Hz), 1.24 (m, 2H), 1.42 (m, 2H), 2.30 (s, 3H), 2.61 (q, 2H, J=7 Hz), 2.67 (d, 1H, J=14 Hz), 2.86 (t, 1H, J=8 Hz), 3.18 (q, 2H, J=7 Hz), 3.41 (dd, 1H, J=4, 10 Hz), 3.59 (m, 3H), 3.93 (d, 1H, J=10 Hz), 4.25 (m, 4H), 6.74 (brs, 2H), 6.80 (d, 1H, J=8 Hz), 6.93 (dd, 1H, J=2 Hz, 8 Hz), 6.99 (d, 1H, J=2 Hz), 7.07 (m, 5H), 7.17 (t, IH, J=8 Hz). MS (DCl/NH$_3$) m/e 557 (M+H)$^+$. Anal. calc'd for C$_{34}$H$_{40}$N$_2$O$_5$·0.40 H$_2$O: C, 72.42; H, 7.29; N, 4.97. Found: C, 72.49; H, 7.16; N, 4.62.

EXAMPLE 431 trans,trans-2-(3-Fluoro-4-methoxyphenyl)-4-(1,3-benzodioxol-5-yl)-1-[2-(N-propyl-N-2-mesitylenesulfonylamino)ethyl]pyrrolidine-3-carboxylic Acid Using the procedures described in Example 66, the title compound was prepared and isolated as a white solid. m.p. 80–82° C. $^1$H NMR (CDCl$_3$, 300 MHz) δ 0.69 (t, J=7 Hz, 3H), 1.37 (sextet, J=7 Hz, 2H), 2.09–2.17 (m, 1H), 2.24 (s, 3H), 2.53 (s, 6H), 2.54–2.64 (m, 1H), 2.73–2.86 (m, 2H), 3.02 (sextet, J=7 Hz, 2H), 3.13–3.28 (m, 3H)), 3.44–3.53 (m, 2H), 3.57 (d, J=9 Hz, 1H), 3.89 (s, 3H), 5.94 (s, 2H), 6.74 (d, J=28 Hz, 1H), 6.78 (dd, J=2 Hz, J=8 Hz, 1H), 6.85 (s, 2H), 6.92 (d, J=8 Hz, 1H), 1H), 9.94 (d, J=2 Hz, 1H), 7.06 (d, J=8 Hz, 1H), 7.13 (dd, J=2 Hz, J=12 Hz, 1H). MS (DCl/NH$_3$) m/e 627 (M+H)$^+$.

EXAMPLE 432 trans,trans-2-(4-Methoxyphenyl)-4-(3,4-difluorophenyl)-1-[(N-butyl-N-(3-chlorophenyl)amino)carbonylmethyl]pyrrolidine-3-carboxylic Acid Using the procedures described in Example 1, the title compound was prepared. $^1$NMR (300 MHz, CDCl$_3$) δ 0.86 (t, J=7 Hz, 3H), 1.18–1.32 (m, 2H), 1.35–1.48 (m, 2H), 2.64 (d, J=13 Hz, 1H), 2.71 (t, J=7 Hz, 1H), 3.08–3.18 (m, 2H), 3.42–3.48 (m, 1H), 3.53–3.64 (m, 3H), 3.77 (s, 3H), 3.80 (d, J=9 Hz, 1H), 6.73–6.85 (m, 3H), 6.94 (s, H), 7.04–7.40 (m, 7H).

EXAMPLE 433 trans,trans-2-(3-Fluoro-4-methoxyphenyl)-4-(1,3-benzodioxol-5-yl)-1-(2-(N-propyl-N-(3-chloropropanesulfonyl)amino)ethyl)pyrrolidine-3-carboxylic Acid Using the procedures described in Example 1, the title compound was prepared. $^1$H NMR (CD$_3$OD, 300 MHz), δ

0.80 (t, 3H, J=7), 1.47 (bd hex, 2H, J=8), 2.15 (pen, 2H, J=7), 2.32 (m, 1H), 2.7–3.2 (m, 9H), 3.46 (dd, 1H, J=4, 10), 3.57 (m, 1H), 3.64 (t, 2H, J=6), 3.67 (d, 1H, J=9), 3.86 (s, 3H), 5.92 (s, 2H), 6.74 (d, 1H, J=8), 6.84 (dd, 1H, J=2, 8), 6.96 (d, 1H, J=2), 7.06 (t, 1H, J=9), 7.18 (m, 2H). MS (DCl/NH$_3$) m/e 585 (M+H; $^{35}$Cl)$^+$; 587 (M+H; $^{37}$Cl)$^+$. Anal calcd for C$_{27}$H$_{34}$N$_2$O$_7$ClFS: C, 55.43; H, 5.86; N, 4.79. Found: C, 55.65; H, 5.81; N, 4.70.

EXAMPLE 434 trans,trans-2-(3-Fluoro-4-methoxyphenyl)-4-(1,3-benzodioxol-5-yl)-1-(2-(N-isobutyl-N-(3-chloropropanesulfonyl)amino)ethyl)pyrrolidine-3-carboxylic Acid Using the procedures described in Example 66, the title compound was prepared. $^1$H NMR (CD$_3$OD, 300 MHz) δ 0.79 (d, 3H, J=7), 0.84 (d, 3H, J=7),1.68 (hept, 1H, J=7), 2.18 (pen, 2H, J=7), 2.8–3.4 (m, 10H), 3.5–3.8 (m, 3H), 3.65 (t, 2H, J=6), 3.90 (s, 3H), 5.94 (s, 2H), 6.77 (d, 1H, J=8), 6.87 (dd, 1H, J=2, 8), 6.99 (d, 1H, J=2), 7.13 (t, 1H, J=9), 7.27 (m, 2H). MS (DCl/NH$_3$) m/e 599 (M+H)$^+$. Anal calcd for C$_{28}$H$_{36}$N$_2$O$_7$ClFS.0.3 TFA: C, 54.24; H, 5.78; N, 4.42. Found: C, 54.19; H, 5.71; N, 4.01.

EXAMPLE 435 trans,trans-2-Propoxymethyl-4-(1,3-benzodioxol-5-yl)-1-(N,N-di(n-butyl)aminocarbonylmethyl)-pyrrolidine-3-carboxylic Acid Using the procedures described in Example 1, the title compound was prepared. $^1$H NMR (CDCl$_3$, 300 MHz) δ 0.87–0.98 (m, 9H), 1.21–1.39 (m, 4H), 1.43–1.57 (m, 4H), 1.58–1.70 (m, 2H), 3.13–3.29 (m, 4H), 3.34–3.43 (m, 3H), 3.45–3.55 (m, 3H), 3.69 (dd, J=10.2, 4.5 Hz, 1H), 3.80–4.20 (m, 4H), 5.93 (s, 2H), 6.73 (d, J=7.8 Hz, 1H), 6.84 (dd, J=8.2, 1.7 Hz, 1H), 6.93 (d, J=1.7 Hz, 1H). MS(DCl/NH$_3$) m/e 477 (M+H)$^+$. Anal calcd for C$_{26}$H$_{40}$N$_2$O$_6$.0.50 TFA: C, 60.77; H, 7.65; N, 5.25. Found: C, 60.73; H, 7.74; N, 5.22.

EXAMPLE 436 trans,trans-2-(3-Fluoro-4-methoxyphenyl)-4-(1,3-benzodioxol-5-yl)-1-[2-(N-propyl-N-(4-methylbutanesulfonyl)amino)ethyl]pyrrolidine-3-carboxylic Acid Using the procedures described in Example 66, the title compound was prepared and isolated as a white solid. m.p. 65–67° C. $^1$H NMR (CDCl$_3$, 300 MHz) δ 0.82 (t, J=7 Hz, 3H), 0.88 (d, J=5 Hz, 6H), 1.46 (sextet, J=7 Hz, 2H), 1.56–1.64 (m, 3H), 2.24–2.33 (m, 1H), 2.68–2.93 (m, 5H), 2.98–3.12 (m, 2H), 3.15–3.35 (m, 2H), 3.43 (dd, J=3 Hz, J=9 Hz, 1H), 3.52–3.58 (1H), 3.65 (d, J=12 Hz, 1H), 3.87 (s, 3H), 5.95 (s, 2H), 6.73 (d, J=8 Hz, 1H), 6.82 (dd, J=2 Hz, J=8 Hz, 1H), 6.92 (t, J=8 Hz, 1H), 6.97 (d, J=2 Hz, 1H), 7.10 (d, J=9 Hz, 1 Hz), 7.16 (dd, J=2 Hz, J=12 Hz, 1H). MS (DCl/NH$_3$) m/e 579 (M+H)$^+$.

EXAMPLE 437 trans,trans-2-(4-Methoxy-3-fluorophenyl)-4-(7-methoxy-1,3-benzodioxol-5-yl)-1-[2-(N-propyl-N-(n-pentanesulfonyl)amino)ethyl]pyrrolidine-3-carboxylic Acid Using the procedures described in Example 66, the title compound was prepared. $^1$H NMR (300 MHz, CDCl$_3$) δ 0.81 (t, J=7 Hz, 3H), 0.90 (t, J=9 Hz, 3H), 1.25–1.35 (m, 4H), 1.44 (sextet, J=7 Hz, 2H), 1.67–1.78 (m, 2H), 2.22–2.34 (m, 1H), 2.30–2.95 (m, 5H), 2.95–3.10 (m, 2H), 3.15–3.33 (m, 2H), 3.45 (dd, J=3 Hz, 9 Hz, 1H), 3.47–3.56 (m, 1H), 3.65 (d, J=9 Hz, 1H), 3.88 (s, 3H), 3.94 (s, 3H), 5.95 (s, 2H), 6.55 (s, 1H), 6.65 (s, 1H), 6.92 (t, J=7H, 1H), 7.11 (d, J=9 Hz, 1H), 7.17 (d, J=12 Hz, 1H).

EXAMPLE 438 trans,trans-2-(3-Fluoro-4-methoxyphenyl)-4-(1,3-benzodioxol-5-yl)-1-[2-(N-Propyl-N-(2,2,3,3,3-pentafluoropropoxyethanesulfonyl)amino)ethyl]pyrrolidine-3-carboxylic acid Using the procedures described in Example 66, the title compound was prepared and isolated as a white solid. m.p. 63–64° C. $^1$H NMR (CDCl$_3$, 300 MHz) δ 0.82 (t, J=7 Hz, 3H), 1.45 (sextet, J=7 Hz, 2H), 2.24–2.33 (m, 1H), 2.70–2.82 (m, 1H), 2.85–3.09 (m, 5H), 3.14–3.28 (m, 4H), 3.43 (dd, J=3 Hz, J=9 Hz, 1H), 3.52–3.58 (m, 1H), 3.65 (d, J=9 Hz, 1H), 3.87 (s, 3H), 3.92–3.98 (m, 3H), 5.94 (s, 2H), 6.74 (d, J=8 Hz, 1H), 6.82 (dd, J=2 Hz, J=8 Hz, 1H), 6.92 (t, J=8 Hz, 1H), 6.97 (d, J=2 Hz, 1H), 7.10 (d, J=9 Hz, 1H), 7.17 (dd, J=2 Hz, J=12 Hz, 1H). MS (DCl/NH$_3$) m/e 685 (M+H)$^+$.

EXAMPLE 439 trans,trans-2-(1,4-Benzodioxan-6-yl)-4-(7-methoxy-1,3-benzodioxol-5-yl)-1-[2-(N-propyl-N-(n-pentanesulfonyl)amino)ethyl]pyrrolidine-3-carboxylic Acid Using the procedures described in Example 66, the title compound was prepared. $^1$H NMR (CDCl$_3$) δ 0.81 (t, J=7 Hz, 3H), 0.90 (t, J=7 Hz, 3H), 1.23–1.36 (m, 4H), 1.45 (sextet, J=7 Hz, 2H), 1.65–1.78 (m, 2H), 2.20–2.30 (m, 1H), 2.30–2.95 (m, 5H), 2.95–3.10 (m, 2H), 3.15–3.35 (m, 2H), 3.42 (dd, J=3 Hz, 9 Hz, 1H), 3.46–3.56 (m, H), 3.59 (d, J=9 Hz, 1H), 3.91 (s, 3H), 4.24 (s, 4H), 5.95 (s, 2H), 6.57 (s, 1H), 6.68 (s, 1H), 6.82 (d, J=8 Hz, 1H), 6.88 (dd, J=2 Hz, 8 Hz, 1H), 6.95 (d, J=2 Hz, 1H).

EXAMPLE 440 trans,trans-4-(1,3-Benzodioxol-5-yl)-2-(4-methoxyphenyl)-1-(((N-butyl-N-(4-methoxybenzyl)amino)carbonyl)methyl)pyrrolidine-3-carboxylic Acid Using the procedures described in Example 1, the title compound was prepared. $^1$H NMR (300 MHz, CDCl$_3$) δ (rotamer) 7.32 (1H, d, J=10), 7.22 (1H, m), 7.10 (1H, d, J=9), 7.03 (6.98) (1H, d, J=3), 6.90–6.80 (4H, m), 6.79 (2H, d, J=9), 6.77 (1H, t, J=8), 5.85 (2H, s), 4.92 (4.10) (1H, d, J=15), 4.42 (4.22) (1H, d, J=15), 3.81 (1H, m), 3.79 (3.78) (3H, s), 3.76 (3H, s), 3.62 (1H, m), 3.43 (2H, m), 3.30–2.70 (5H, m), 1.42 (1H, m), 1.23 (2H, m), 1.01 (1H, m), 0.83 (0.75) (3H, t, J=8). MS (DCl/NH$_3$) m/e 575 (M+H$^+$). Anal calcd for C$_{33}$H$_{38}$N$_2$O$_7$.0.5 H$_2$O: C, 67.91; H, 6.73; N, 4.80. Found: C, 67.78; H, 6.44; N, 4.55.

EXAMPLE 441 trans,trans-2-(3-Fluoro-4-methoxyphenyl)-4-(1,3-benzodioxol-5-yl)-1-(2-(N-isobutyl-N-(pentanesulfonylamino)ethyl)pyrrolidine-3-carboxylic Acid Using the procedures described in Example 66, the title compound was prepared. $^1$H NMR (CD$_3$OD, 300 MHz) δ

0.76 (d, 3H, J=7), 0.84 (d, 3H, J=7), 0.92 (t, 3H, J=7), 1.36 (m, 4H), 1.70 (m, 3H), 2.90 (m, 2H), 3.02 (m, 2H), 3.1–3.8 (m, 7H), 3.84 (d, 2H, J=8), 3.91 (s, 3H), 5.96 (s, 2H), 6.80 (d, 1H, J=8), 6.88 (dd, 1H, J=2, 8), 7.00 (d, 1H, J=2), 7.19 (t, 1H, J=9), 7.35 (m, 2H). MS (DCl/NH$_3$) m/e 593 (M+H)$^+$. Anal calcd for C$_{30}$H$_{41}$N$_2$O$_7$F.0.5 TFA: C, 57.31; H, 6.44; N, 4.31. Found: C, 57.08; H, 6.15; N, 3.95.

EXAMPLE 442 trans,trans-4-(1,3-Benzodioxol-5-yl)-2-(4-methoxyphenyl)-1-(N-butyl-N-(3-fluorophenylamino)carbonylmethyl)pyrrolidine-3-carboxylic Acid Using the procedures described in Example 1, the title compound was prepared. $^1$H NMR (300 MHz, CD$_3$OD) δ 0.87 (t, J=7 Hz, 3H), 1.10–1.30 (m, 4H), 2.70–2.90 (m, 2H), 3.13 (t, J=8 Hz, 1H), 3.40–3.90 (m, 6H), 3.79 (s, 3H), 5.93 (s, 2H), 6.75 (d, J=8 Hz, 1H), 6.80–7.20 (m, 9H), 7.40 (m, 1H). MS (DCl) m/e 549 (M+H)$^+$. Anal calcd for C$_{31}$H$_{33}$N$_2$O$_6$F.0.8 H$_2$O: C, 66.13; H, 6.19; N, 4.98. Found: C, 66.21; H, 5.83; N, 4.84.

EXAMPLE 443 trans,trans-4-(1,3-Benzodioxol-5-yl)-2-(4-fluorophenyl)-1-(N-butyl-N-(3-chlorophenylamino)carbonylmethyl)pyrrolidine-3-carboxylic Acid Using the procedures described in Example 1, the title compound was prepared. $^1$H NMR (300 MHz, CD$_3$OD) δ 0.87 (t, J=7 Hz, 3H), 1.20–1.50 (m, 4H), 2.65–2.85 (m, 2H), 3.05–3.85 (m, 7H), 5.93 (s, 2H), 6.75 (d, J=8 Hz, 1H), 6.85 (dd, J=8 Hz, 1H), 6.90–7.10 (m, 4H), 7.10–7.25 (m, 3H), 7.33–7.45 (m, 2H). MS (DCl) m/e 553 (M+H)$^+$. Anal calcd for C$_{30}$H$_{30}$N$_2$O$_5$FCl: C, 65.16; H, 5.47; N, 5.07. Found: C, 65.37; H, 5.41; N, 4.98.

EXAMPLE 444 trans,trans-4-(1,3-Benzodioxol-5-yl)-2-(4-methoxyphenyl)-1-(((N-butyl-N-(3,4-dimethoxybenzyl)amino)carbonyl)methyl)pyrrolidine-3-carboxylic Acid Using the procedures described in Example 1, the title compound was prepared. $^1$H NMR (300 MHz, CDCl$_3$) δ (rotamer) 7.33 (1H, d, J=10), 7.23 (1H, m), 7.03 (6.97) (1H, d, J=3), 6.90–6.60 (6H, m), 6.47 (1H, m), 5.93 (2H, m), 4.83 (4.09) (1H, d, J=15), 4.45 (4.22) (1H, d, J=15), 3.83 (3.86) (3H, s), 3.79 (1H, m), 3.77 (3.76) (3H, s), 3.75 (3.65) (3H, s), 3.60 (1H, m), 3.43 (2H, m), 3.28 (1H, m), 3.20–2.70 (4H, m), 1.43 (1H, m), 1.23 (2H, m), 1.02 (1H, m), 0.84 (0.77) (3H, t, J=8), MS (DCl/NH$_3$) m/e 605 (M+H$^+$). Anal calcd for C$_{34}$H$_{40}$N$_2$O$_8$: C, 67.53; H, 6.67; N, 4.63. Found: C, 67.28; H, 6.63; N, 4.38.

EXAMPLE 445 trans,trans-4-(1,3-Benzodioxol-5-yl)-2-(4-methoxyphenyl)-1-(((N-butyl-N-(2-methoxybenzyl)amino)carbonyl)methyl)pyrrolidine-3-carboxylic Acid Using the procedures described in Example 1, the title compound was prepared. $^1$H NMR (300 MHz, CDCl$_3$) δ (rotamer) 7.33 (1H, d, J=10), 7.11 (2H, m), 7.03 (1H, dd, J=8, 3), 6.90–6.60 (7H, m), 5.93 (2H, m), 4.83 (4.15) (1H, d, J=15), 4.47 (4.30) (1H, d, J=15), 3.81 (1H, m), 3.78 (3.73) (3H, s), 3.72 (3H, s), 3.59 (1H, m), 3.43 (2H, m), 3.30 (1H, m), 3.20–2.70 (4H, m), 1.42 (1H, m), 1.23 (2H, m), 1.01 (1H, m), 0.83 (0.77) (3H, t, J=8). MS (DCl/NH$_3$) m/e 575 (M+H$^+$). Anal calcd for C$_{33}$H$_{38}$N$_2$O$_7$: C, 68.97; H, 6.66; N, 4.87. Found: C, 68.70; H, 6.56; N, 4.61.

EXAMPLE 446 trans,trans-4-(1,3-Benzodioxol-5-yl)-2-(4-methoxyphenyl)-1-(((N-butyl-N-(3-methoxybenzyl)amino)carbonyl)methyl)pyrrolidine-3-carboxylic Acid Using the procedures described in Example 1, the title compound was prepared. $^1$H NMR (300 MHz, CDCl$_3$) δ (rotamer) 7.31 (1H, d, J=10), 7.13 (1H, d, J=9), 7.16 (1H, dt, J=8, 3), 7.03 (1H, dd, J=10, 2), 6.90–6.60 (6H, m), 6.50 (1H, m), 5.94 (2H, m), 4.82 (4.19) (1H, d, J=15), 4.50 (4.23) (1H, d, J=15), 3.78 (3.76) (3H, s), 3.77 (1H, m), 3.75 (3.67) (3H, s), 3.59 (1H, m), 3.57–3.35 (2H, m), 3.25 (1H, m), 3.20–2.70 (4H, m), 1.43 (1H, m), 1.23 (2H, m), 1.02 (1H, m), 0.84 (0.77) (3H, t, J=8). MS (DCl/NH$_3$) m/e 575 (M+H$^+$). Anal calcd for C$_{33}$H$_{38}$N$_2$O$_7$: C, 68.97; H, 6.66; N, 4.87. Found: C, 68.72; H, 6.55; N, 4.60.

EXAMPLE 447 trans,trans-2-(3-Fluoro-4-methoxyphenyl)-4-(1,3-benzodioxol-5-yl)-1-(2-(N-(2-methoxyethyl)-N-(3-chloropropanesulfonyl)amino)ethyl)pyrrolidine-3-carboxylic Acid Using the procedures described in Example 66, the title compound was prepared. $^1$H NMR (CD$_3$OD, 300 MHz) δ 2.15 (pen, 2H, J=7), 2.33 (m, 1H), 2.81 (m, 2H); 2.93 (t, 1H, J=9); 3.1–3.6 (m, 10H), 3.24 (s, 3H); 3.65 (t, 2H, J=6), 3.70 (d, 1H, J=9), 3.87 (s, 3H), 5.92 (s, 2H), 6.74 (d, 1H, J=8), 6.84 (dd, 1H, J=2, 8), 6.97 (d, 1H, J=2), 7.07 (t, 1H, J=9), 7.17 (m, 2H). MS (DCl/NH$_3$) m/e 601 (M+H)$^+$. Anal calcd for C$_{27}$H$_{34}$N$_2$O$_8$ClFS: C, 53.95; H, 5.70; N, 4.66. Found: C, 53.65; H, 5.49; N, 4.26.

EXAMPLE 448 trans,trans-2-(3-Fluoro-4-methoxyphenyl)-4-(1,3-benzodioxol-5-yl)-1-(2-(N-(2-methoxyethyl)-N-(pentanesulfonyl)amino)ethyl)pyrrolidine-3-carboxylic Acid Using the procedures described in Example 66, the title compound was prepared. $^1$H NMR (CD$_3$OD, 300 MHz) δ 0.93 (m, 3H), 1.34 (m, 4H), 1.69 (m, 2H), 2.33 (m, 1H), 2.75–3.1 (m, 7H), 3.23 (s, 3H), 3.3–3.6 (m, 6H), 3.70 (d, 1H, J=9), 3.86 (s, 3H), 5.92 (s, 2H), 6.74 (d, 1H, J=8), 6.84 (dd, 1H, J=2, 8), 6.97 (d, 1H, J=2), 7.07 (t, 1H, J=9), 7.18 (m, 2H). MS (DCl/NH$_3$) m/e 595 (M+H)$^+$. Anal calcd for C$_{29}$H$_{39}$N$_2$O$_8$FS: C, 58.57; H, 6.61; N, 4.71. Found: C, 58.21; H, 6.29; N, 4.29.

EXAMPLE 449 trans,trans-4-(1,3-Benzodioxol-5-yl)-2-(4-methoxyphenyl)-1-(((N-4-heptyl)-N-(4-fluoro-3-methylphenylamino)carbonyl)methyl)pyrrolidine-3-carboxylic Acid Using the procedures described in Example 1, the title compound was prepared. $^1$H NMR (300 MHz, CD$_3$OD) δ 0.89 (m, 6H), 1.18–1.36 (m, 8H), 2.15 (bs, 1.5 (CH$_3$ rotamer)), 2.28 (bs, 1.5 (CH$_3$ rotamer)), 2.64 (t, J=14.9 Hz, 1H), 2.82 (m, 1H), 3.07–3.29 (m, 2H), 3.32–3.41 (m, 1H), 3.53–3.60 (m, 1H), 3.70–3.79 (m, 1H), 3.79 (s, 3H), 4.68 (m, 1H), 5.92 (m, 2H), 6.69–6.90 (m, 6H), 6.93–7.07 (m, 4H), MS (DCl) m/e 605 (M+H$^+$). Anal calcd for $C_{35}H_{41}FN_2O_6$: C, 69.52; H, 6.83; N, 4.63. Found: C, 69.31; H, 6.78; N, 4.35.

EXAMPLE 450 trans,trans-4-(1,3-Benzodioxol-5-yl)-2-(4-methoxyphenyl)-1-(((N-(5-nonyl)-N-(4-fluoro-3-methylphenyl)amino)carbonyl)methyl)pyrrolidine-3-carboxylic Acid Using the procedures described in Example 1, the title compound was prepared. $^1$H NMR (300 MHz, CD$_3$OD) δ 0.81–0.90 (m, 6H), 1.30 (m, 12H), 2.14 (s, 1.5 (CH$_3$ rotamer)), 2.30 (s, 1.5 (CH$_3$ rotamer)), 2.60 (t, J=14.8 Hz, 1H), 2.80 (m, 1H), 3.09–3.24 (m, 2H), 3.33–3.42 (m, 1H), 3.50–3.55 (m, 1H), 3.65–3.77 (m, 1H), 3.79 (s, 3H), 4.64 (m, 1H), 5.93 (m, 2H), 6.70–6.84 (m, 5H), 6.91–7.13 (m, 5H). MS (DCl) m/e 633 (M+H$^+$). Anal calcd for $C_{37}H_{45}FN_2O_6$: C, 70.23; H, 7.17; N, 4.43. Found: C, 70.14; H, 7.13; N, 4.19.

EXAMPLE 451 trans,trans-4-(1,3-Benzodioxol-5-yl)-2-(4-methoxyphenyl)-1-((N-(5-nonylamino)carbonyl)methyl)pyrrolidine-3-carboxylic Acid Using the procedures described in Example 1, the title compound was prepared. $^1$H NMR (300 MHz, CD$_3$OD) δ 0.80 (t, J=7.0 Hz, 3H), 0.84 (t, J=7.1 Hz, 3H), 1.15–1.55 (m, 12H), 2.88 (d, J=15.9 Hz, 1H), 3.07 (m, 2H), 3.26 (d, J=16.3 Hz, 1H), 3.36 (dd, J=4.4, 9.8 Hz, 1H), 3.64 (m, 1H), 3.76 (m, 1H), 3.79 (s, 3H), 3.98 (d, J=9.5 Hz, 1H), 5.93 (m, 2H), 6.77 (d, J=7.8 Hz, 1H), 6.85 (dd, J=1.7, 8.1 Hz, 1H), 6.93 (m, 2H), 6.99 (d, J=1.7 Hz, 1H), 7.39 (m, 2H). MS (DCl) m/e 525 (M+H$^+$). Anal calcd for $C_{30}H_{46}N_2O_6$·0.35 H$_2$O: C, 67.86; H, 7.73; N, 5.28. Found: C, 67.87; H, 7.63; N, 5.11.

EXAMPLE 452 trans,trans-4-(1,3-Benzodioxol-5-yl)-2-(4-methoxyphenyl)-1-((N-butyl-N-(2-fluorophenyl)amino)carbonylmethyl)pyrrolidine-3-carboxylic Acid Using the procedures described in Example 1, the title compound was prepared. $^1$H NMR (300 MHz, CD$_3$OD) δ0.87 (dt, J=7 Hz, 3H), 1.15–1.32 (m, 4H), 3.77 (d, J=2 Hz, 3H), 2.65–5.92 (m, 9H), 5.93 (d, J=4 Hz, 2H), 6.70–6.90 (m, 4H), 7.00–7.45 (m, 7H). MS (DCl) m/e 549 (M+H)$^+$. Anal calcd for $C_{31}H_{33}N_2O_6$·0.4 H$_2$O: C, 66.99; H, 6.13; N, 5.04. Found: C, 67.01; H, 6.23; N, 4.68.

EXAMPLE 453 trans,trans-2-(4-Methoxphenyl)-4-(1,3-benzodioxol-5-yl)-1-[2-(N-propyl-N-(2-benzothiazolyl)amino)ethyl]pyrrolidine-3-carboxylic Acid The title compound was prepared by the method of Example 418, substituting 2-chlorobenzothiazole for 2-bromopyrimidine. $^1$H NMR (300 MHz, CDCl$_3$) δ 0.88 (t, J=7 Hz, 3H), 1.59 (sextet, J=7 Hz, 2H), 2.25–2.37 (m, 1H), 2.85–2.97 (m 3H), 3.28–3.36 (m, 2H), 3.50–3.58 (m, 3H), 3.60–3.65 (m, 1H), 3.67 (d, J=9 Hz, 1H), 3.71 (s, 3H), 5.87 (d, J=2 Hz, 1H), 5.91 (d, J=2 Hz, 1H), 6.57 (d, J=8 Hz, 1H), 6.73 (dd, J=2 Hz, 9 Hz, 1H), 6.76 (d, J=8 Hz, 2H), 6.91 (d, J=2 Hz, 1H), 7.01 (t, J=8 Hz, 1H), 7.22 (t, J=8 Hz, 1H), 7.29 (d, J=8 Hz, 2H), 7.40 (d, J=7 Hz, 1H), 7.55 (d, J=7 Hz, 1H).

EXAMPLE 454 trans,trans-2-(2-Ethoxyethyl)-4-(1,3-benzodioxol-5-yl)-1-(N,N-di(n-butyl)aminocarbonylmethyl)-pyrrolidine-3-carboxylic Acid Using the procedures described in Example 1, the title compound was prepared. $^1$H NMR (CDCl$_3$, 300 MHz) δ 0.91 (t, J=7.4 Hz, 3H), 0.94 (t, J=7.4 Hz, 3H), 1.19 (t, J=7.0 Hz, 3H), 1.24–1.38 (m, 5H), 1.46–1.60 (m, 4H), 2.03–2.12 (m, 2H), 3.07 (t, J=8.0 Hz, 1H), 3.07–3.34 (m, 6H), 3.43–3.52 (m, 3H), 3.59–3.74 (m, 3H), 3.80–4.01 (m, 2H), 5.93 (s, 2H), 6.72 (d, J=8.1 Hz, 1H), 6.79 (dd, J=8.2 Hz, J=1.7 Hz, 1H), 6.87 (d, J=1.7 Hz, 1H). MS(DCl/NH$_3$) m/e 477 (M+H)$^+$. Anal calcd for $C_{26}H_{40}N_2O_6$·0.4 TFA: C, 61.64; H, 7.80; N, 5.36. Found: C, 61.63; H, 7.84; N, 5.29.

EXAMPLE 455 trans,trans-2-(4-Methoxy-3-fluorophenyl)-4-(1,3-benzodioxol-5-yl)-1-[2-(N-propyl-N-(2-(morpholin-4-ylethyl)sulfonylamino)ethyl]pyrrolidine-3-carboxylic Acid Ethyl 2-(4-methoxy-3-fluorophenyl)-4-(1,3-benzodioxol-5-yl)-1-[2-(N-propyl-N-[2-vinylsulfonyl]amino)ethyl]pyrrolidine-3-carboxylic Acid, prepared by the procedures of Example 125, was reacted with excess morpholine for 4 hours at room temperature. Chromatography on silica gel eluting with EtOAc gave a 65% yield of an intermediate ethyl ester which was hydrolyzed to the title compound with NaOH in ethanol/water. $^1$H NMR (300 MHz, CDCl$_3$) δ 0.81 (t, J=7 Hz, 3H), 1.46 (sextet, J=7 Hz, 2H), 2.43–2.52 (m, 4H), 2.70–2.92 (m, 5H), 2.97–3.33 (m, 6H), 3.60 (dd, J=3 Hz, 9 Hz, 1H), 3.51–3.59 (m, 1H), 3.62–3.70 (m, 5H), 3.88 (s, 3H), 5.95 (s, 2H), 6.72 (d, J=8 Hz, 1H), 6.70 (dd, J=2 Hz, 8 Hz, 1H), 6.90 (t, J=9 Hz, 1H), 6.96 (d, J=2 Hz, 1H), 7.10 (d, J=8 Hz, 1H), 7.18 (dd, J=2 Hz, 12 Hz, 1H).

EXAMPLE 456 trans,trans-2-(3-Fluoro-4-methoxyphenyl)-4-(1,3-benzodioxol-5-yl)-1-[2-(N-propyl-N-((2,2,2-trifluoroethoxyethane)sulfonyl)amino)ethyl]pyrrolidine-3-carboxylic Acid Using the procedures described in Example 66, the title compound was prepared and isolated as a white solid. m.p. 95–96° C. $^1$H NMR (CD$_3$OD, 300 MHz) δ 0.80 (t, J=7 Hz, 3H), 1.35–1.48 (m, 2H), 3.07 (sextet, J=7 Hz, 2H), 3.23–3.55 (m, 8H), 3.80–3.87 (m, 2H), 3.93 (s, 3H), 3.94–4.02 (m, 4H), 4.66 (d, J=12 Hz, 1H), 5.96 (s, 2H), 6.83 (d, J=8 Hz, 1H), 6.94 (d, J=8 Hz, 1H), 7.06 (d, J=2 Hz, 1H), 7.23 (t, J=9 Hz, 1H), 7.43 (d, J=9 Hz, 1H), 7.49 (dd, J=2 Hz, J=12 Hz, 1H). MS (DCl/NH$_3$) m/e 635 (M+H)$^+$.

EXAMPLE 457 trans,trans-4-(1,3-Benzodioxol-5-yl)-2-(4-fluorophenyl)-1-(N-butyl-N-(3-methylphenyl)aminocarbonylmethyl)pyrrolidine-3-carboxylic acid Using the procedures described in Example 1, the title compound was prepared. $^1$H NMR (300 MHz, CD$_3$OD) δ 0.87 (t, J=7 Hz, 3H), 1.20–1.50 (m, 4H), 2.31 (s, 3H), 2.65–2.80 (m, 2H), 3.19 (t, J=7 Hz, 1H), 3.25 (d, J=10 Hz, 1H), 3.35–3.65 (m, 4H), 3.79 (d, J=10 Hz, 1H), 5.93 (s, 2H), 6.74 (d, J=7 Hz, 1H), 6.80–6.90 (m, 3H), 6.91–7.09 (m, 3H), 7.10–7.35 (m, 4H). MS (DCl) m/e 533 (M+H)⁺. Anal calcd for C₃₁H₃₃N₂O₅F: C, 69.91; H, 6.25; N, 5.26. Found: C, 69.56; H, 6.26; N, 5.23.

EXAMPLE 458 trans,trans-2-(3-Fluoro-4-methoxyphenyl)-4-(1,3-benzodioxol-5-yl)-1-(2-(N-(2-methoxyethyl)-N-(butanesulfonylamino)ethyl)pyrrolidine-3-carboxylic acid Using the procedures described in Example 66, the title compound was prepared. ¹H NMR (CD₃OD, 300 MHz) δ 0.94 (m, 3H), 1.23 (hex, 2H, J=8), 1.69 (m, 2H), 3.08 (m, 2H), 3.20 (s, 3H), 3.3–3.5 (m, 10H), 3.77 (m, 2H), 3.92 (s, 3H), 4.60 (m, 1H), 5.96 (s, 2H), 6.81 (d, 1H, J=8), 6.88 (dd, 1H, J=2, 8), 6.99 (d, 1H, J=2), 7.22 (t, 1H, J=9), 7.38 (m, 2H). MS (APCl) m/e 581 (M+H)⁺. Anal calcd for C₂₈H₃₇N₂O₈FS.1.1 TFA: C, 51.37; H, 5.44; N, 3.97. Found: C, 51.27; H, 5.35; N, 4.11.

EXAMPLE 459 trans,trans-2-(3-Fluoro-4-methoxyphenyl)-4-(1,3-benzodioxol-5-yl)-1-[2-(N-propyl-N-(2-methylpropanesulfonyl)amino)ethyl]pyrrolidine-3-carboxylic acid Using the procedures described in Example 66, the title compound was prepared and isolated as a white solid. m.p. 77–78° C. ¹H NMR (CDCl₃, 300MHz) δ 0.83 (t, J=7 Hz, 3H), 1.06 (d, J=6 Hz, 6H), 1.45 (q, J=7 Hz, 2H), 2.20 (septet, J=6 Hz, 1H), 2.26–2.36 (m, 1H), 2.62–2.78 (m, 3H), 2.85–2.95 (m, 2H), 2.97–3.10 (m, 2H), 3.15–3.35 (m, 2H), 3.43 (dd, J=3 Hz, J=9 Hz, 1H), 3.53–3.62 (m, 1H), 3.66 (d, J=9 Hz, 1H), 3.88 (s, 3H), 5.95 (s, 2H), 6.74 (d, J=8 Hz, 1H), 6.82 (dd, J=2 Hz, J=8 Hz, 1H), 6.92 (t, J=8Hz, 1H), 6.97 (d, J=2 Hz, 1H), 7.12 (d, J=9 Hz, 1H), 7.18 (dd, J=2 Hz, J=12 Hz, 1H). MS (DCl/NH₃) m/e 565 (M+H)⁺.

EXAMPLE 460 trans,trans-4-(1,3-Benzodioxol-5-yl)-2-(4-methoxyphenyl)-1-(((N-butyl-N-(4-nitrobenzyl)amino)carbonyl)methyl)pyrrolidine-3-carboxylic Acid Using the procedures described in Example 1, the title compound was prepared. ¹H NMR (300 MHz, CDCl₃) δ(rotamer) 8.11 (2H, m), 7.32 (3H, dd, J=9, 2), 7.16 (7.07) (1H, bd, J=10), 6.98 (6.94) (1H, d, J=2), 6.85 (2H, d, J=9), 6.83–6.70 (2H, m), 5.99 (5.97) (2H, d, J=2), 5.02 (4.18) (1H, d, J=15), 4.63 (4.38)(1H, d, J=15), 3.79 (3.77) (3H, s), 3.72 (1H, d, J=10), 3.61 (1H, m), 3.48 (1H, bd, J=15), 3.43–3.20 (2H, m), 3.06 (2H, m), 2.90 (1H, m), 3.79 (1H, bd, J=14), 1.43 (1H, m), 1.23 (2H, m), 1.02 (1H, m), 0.84 (0.78) (3H, t, J=8). MS (DCl/NH₃) m/e 590 (M+H⁺). Anal calcd for C₃₂H₃₅N₃O₈: C, 65.18; H, 5.98; N, 7.13. Found: C, 65.89; H, 5.85; N, 6.85.

EXAMPLE 461 trans,trans-2-(4-Ethylphenyl)-4-(3,4-difluorophenyl)-1-(N,N-di(n-butyl)aminocarbonylmethyl)-pyrrolidine-3-carboxylic Acid Using the procedures described in Example 1, the title compound was prepared. ¹H NMR (CD₃OD, 300 MHz) δ 0.78 (t, 3H, J=7), 0.87 (t, 3H, J=7), 1.02 (hex, 2H, J=7), 1.22 (t, 3H, J=7), 1.27 (m, 2H), 1.45 (m, 2H, J=7), 2.63 (q, 2H, J=7), 2.77 (d, 1H, J=14), 2.94 (dd, 1H, J=7, 9), 3.05 (m, 3H), 3.3–3.5 m, 3H), 3.44 (d, 1H, J=14), 3.66 (m, 1H), 3.75 (d, 1H, J=10), 7.20 (td, 2H, J=1,8), 7.22 (m, 2H), 7.32 (td, 2H, J=1,8), 7.43 (ddd, 1H, J=2,8,12). MS (DCl/NH₃) m/e 501 (M+H)₊. Anal calcd for C₂₉H₃₈N₂O₃F₂.0.6 H₂O: C, 68.11; H, 7.73; N, 5.48. Found: C, 68.03; H, 7.53; N, 5.37.

EXAMPLE 462 trans,trans-4-(1,3-Benzodioxol-5-yl)-2-(4-methoxyphenyl)-1-(N-butyl-N-(4-fluoro-3-methylphenyl)aminocarbonylmethyl)pyrrolidine-3-carboxylic Acid Using the procedures described in Example 1, the title compound was prepared. ¹H NMR (300 MHz, CD₃OD) δ 0.87 (t, J=7 Hz, 3H), 1.20–1.50 (m, 4H), 2.21 (d, J=2 Hz, 3H), 2.64 (d, J=14 Hz, 1H), 2.75 (dd, J=10 Hz, 1H), 3.05 (t, J=7 Hz, 1H), 3.25 (d, J=15 Hz, 1H), 3.35–3.70 (m, 5H), 3.77 (s, 3H), 5.92 (s, 2H), 6,70–6.92 (m, 6H), 6.96–7.10 (m, 4H). MS (DCl) m/e 563 (M+H)⁺. Anal calcd for C₃₂H₃₅N₂O₆F.0.5 H₂O: C, 67.24; H, 6.35; N, 4.90. Found: C, 67.16; H, 6.06; N, 4.81.

EXAMPLE 463 trans,trans-4-(1,3-Benzodioxol-5-yl)-2-(4-methoxyphenyl)-1-(N-butyl-N-((3-isopropyl)phenyl)amino)carbonylmethyl)-pyrrolidine-3-carboxylic Acid Using the procedures described in Example 1, the title compound was prepared. ¹H NMR (300 MHz, CD₃OD) δ 0.87 (t, 3H), 1.17 (d, J=7 Hz, 6H), 1.20–1.50 (m, 4H), 2.63 (d, J=15 Hz, 1H), 2.75 (t, J=7 Hz, 1H), 2.85 (m, 1H), 3.00 (t, J=7 Hz, 1H), 3.25 (d, J=15 Hz, 1H), 3.40–3.70 (m, 5H), 3.75 (s, 3H), 5.90 (s, 2H), 6.65–6.80 (m, 3H), 6.71 (dt, J=7 Hz, 3H), 7.07 (m, 3H), 7.20–7.35 (m, 2H). MS (DCl) m/e 573 (M+H)⁺. Anal calcd for C₃₄H₄₀N₂O₆.0.15 H₃PO₄: C, 69.52; H, 6.94; N, 4.77. Found: C, 63.31; H, 6.72; N, 4.43.

EXAMPLE 464 trans,trans-4-(1,3-Benzodioxol-5-yl)-2-(4-methoxyphenyl)-1-(N-butyl-N-(3-ethylphenyl)aminocarbonylmethyl)pyrrolidine-3-carboxylic Acid Using the procedures described in Example 1, the title compound was prepared. ¹H NMR (300 MHz, CD₃OD) δ 0.87 (m, J=7 Hz, 3H), 1.16 (t, J=7 Hz, 3H), 1.20–1.47 (m, 4H), 2.50 (q, J=7 Hz, 2H), 2.70–2.85 (m, 2H), 3.13 (t, J=7 Hz, 1H), 3.20–4.5 (m, 6H), 3.78 (s, 3H), 3.83 (d, J=8 Hz, 1H), 5.92 (s, 2H), 6.72 (d, J=8 Hz, 1H), 6.80–6.90 (m, 5H), 7.02–7.13 (m, 3H), 7.15–7.25 (m, 2H). MS (DCl) m/e 559 (M+H)⁺. Anal calcd for C₃₃H₃₈N₂O₆.0.3 H₂O: C, 70.27; H, 6.90; N, 4.97. Found: C, 70.31; H, 6.63; N, 4.60.

EXAMPLE 465 trans,trans-4-(1,3-Benzodioxol-5-yl)-2-(4-ethylphenyl)-1-(((N-(3-chlorophenyl)-N-butylamino)carbonyl)methyl)pyrrolidine-3-carboxylic Acid Using the procedures described in Example 1, the title compound was prepared. ¹H NMR (300 MHz, CDCl₃) δ 0.87 (t, 3H, J=7 Hz), 1.23 (t, 3H, J=7 Hz), 1.28 (m, 2H), 1.41 (m, 2H), 2.63 (q, 2H, J=7 Hz), 2.67 (m, 1H), 2.92 (m, 1H), 3.20 (m, 2H), 3.42 (m, 1H), 3.60 (q, 2H, J=7 Hz), 3.93 (m, 1H), 5.92 (s, 2H), 6.75 (d, 1H, J=8 Hz), 6.84 (m, 3H), 6.95 (br s, 1H), 7.02 (s, 1H), 7.10 (br s, 3H), 7.25 (m, 2H). MS (APCl) m/e 563 (M+H)$^+$. Anal. calc'd for $C_{32}H_{35}N_2O_5Cl.0.80$ $H_3PO_4$: C, 59.92; H, 5.88; N, 4.37. Found: C, 59.90; H, 5.83; N, 4.07.

EXAMPLE 466 trans,trans-4-(1,4-Benzodioxan-6-yl)-2-(4-ethylphenyl)-1-(((N-(3-chlorophenyl)-N-butylamino)carbonyl)methyl)pyrrolidine-3-carboxylic Acid Using the procedures described in Example 1, the title compound was prepared. $^1$H NMR (300 MHz, CDCl$_3$) δ 0.86 (t, 3H, J=7 Hz), 1.23 (t, 3H, J=7 Hz), 1.25 (m, 2H), 1.40 (m, 2H), 2.64 (q, 2H, J=7 Hz), 2.70 (m, 1H), 2.95 (m, 1H), 3.20 (m, 2H), 3.40 (m, 1H), 3.57 (m, 3H), 3.90 (m, 1H), 4.25 (s, 4H), 6.80 (d, 1H, J=8 Hz), 6.95 (d, 1H, J=2 Hz), 6.95 (m, 2H), 7.07 (br s, 3H), 7.22 (m, 3H). MS (APCl) m/e 577. (M+H)$^+$. Anal. calc'd for $C_{33}H_{37}N_2O_5Cl.0.85$ $H_2O$: C, 66.90; H, 6.58; N, 4.73. Found: C, 66.92; H, 6.25; N, 4.36.

EXAMPLE 467 trans,trans-4-(Benzofuran-5-yl)-2-(4-ethylphenyl)-1-(((N-(3-chlorophenyl)-N-butylamino)carbonyl)methyl)pyrrolidine-3-carboxylic Acid Using the procedures described in Example 1, the title compound was prepared. $^1$H NMR (300 MHz, CDCl$_3$) δ 0.85 (t, 3H, J=7 Hz), 1.26 (t, 3H, J=7 Hz), 1.30 (m, 2H), 1.40 (m, 2H), 2.60 (q, 2H, J=7 Hz), 2.72 (m, 1H), 2.93 (m, 1H), 3.22 (m, 2H), 3.50 (m, 1H), 3.55 (m, 2H), 3.75 (m, 1H), 3.90 (br d, 1H), 6.75 (d, 1H, J=1 Hz), 6.80 (br d, 1H), 6.95 (br s, 1H), 7.08 (m, 4H), 7.20 (t, 1H, J=8 Hz), 7.28 (t, 1H, J=8 Hz), 7.42 (m, 2H), 7.58 (d, 1H, J=1 Hz), 7.63 (s, 1H). MS (APCl) m/e 559 (M+H)$^+$. Anal. calc'd for $C_{33}H_{35}N_2O_4Cl.0.45$ $H_2O$: C, 69.88; H, 6.38; N, 4.94. Found: C, 69.83; H, 6.04; N, 4.87.

EXAMPLE 468 trans,trans-2-(4-Methoxy-3-fluorophenyl)-4-(7-methoxy-1,3-benzodioxol-5-yl)-1-[2-(N-butyl-N-phenylamino)ethyl]pyrrolidine-3-carboxylic Acid Ethyl 2-(4-methoxy-3-fluorophenyl)-4-(7-methoxy-1,3-benzodioxol-5-yl)-1-[2-(bromoethyl]-pyrrolidine-3-carboxylate, prepared using the procedures of Example 61A (300 mg), was reacted with N-butyl aniline (190 mg) in 1 mL of dioxane containing 130 mg of diisopropylethylamine to give the ethyl ester. The ester was hydroyzed with sodium hydroxide to give 148 mg of the title compound as a white powder. $^1$H NMR (300 MHz, CDCl$_3$) δ 0.90 (t, J=9 Hz, 3H), 1.28 (sextet, J=7 Hz, 2H), 1.46 (quintet, J=7 Hz, 2H), 2.20–2.32 (m, 1H), 2.68–2.77 (m, 1H), 2.82–2.95 (m, 2H), 3.12–3.22 (m, 2H), 3.30–3.44 (m, 3H), 3.45–3.55 (m, 1H), 3.62 (d, J=9 Hz, 1H), 3.83 (s, 3H), 3.90 (s, 3H), 5.95 (s, 2H), 6.51 (d, J=7 Hz, 2H), 6.55–6.62 (m, 2H), 6.69 (d, J=2 Hz, 1H), 6.84 (t, J=8 Hz, 1H), 7.02–7.15 (m, 3H), 7.19 (dd, J=2 Hz, 12 Hz, 1H).

EXAMPLE 469 trans,trans-4-(1,4-Benzodioxan-6-yl)-2-(4-ethylphenyl)-1-(((N,N-di(n-butyl)aminocarbonylmethyl)-pyrrolidine-3-carboxylic Acid Using the procedures described in Example 1, the title compound was prepared. $^1$H NMR (300 MHz, CDCl$_3$) δ 0.78 (t, 3H, J=7 Hz), 0.88 (t, 3H, J=7 Hz), 1.05 (q, 2H, J=7 Hz), 1.23 (t, 3H, J=7 Hz), 1.28 (m, 2H), 1.45 (m, 2H), 2.64 (q, 2H, J=7 Hz), 2.78 (m, 1H), 2.9–3.2 (envelope, 4H), 3.30 (m, 1H), 3.40 (m, 3H), 3.60 (m, 1H), 3.80 (m, 1H), 4.25 (s, 4H), 6.80 (d, 1H, J=8 Hz), 6.90 (m, 1H), 6.98 (d, 1H, J=2 Hz), 7.17 (d, 2H, J=8 Hz), 7.30 (m, 2H). MS (APCl) m/e 523 (M+H)$^+$. Anal. calc'd for $C_{31}H_{42}N_2O_5.1.1HOAc$: C, 67.73; H, 7.94; N, 4.76. Found: C, 67.81; H, 7.55; N, 4.48.

EXAMPLE 470 trans,trans-4-(1,4-Benzodioxan-6-yl)-2-(4-methoxyphenyl)-1-((N-butyl-N-(3-methylphenylamino)carbonyl)methyl)pyrrolidine-3-carboxylic Acid Using the procedures described in Example 1, the title compound was prepared. $^1$H NMR (300 MHz, CD$_3$OD) δ 0.87 (t, J=7.1 Hz, 3H), 1.30 (m, 2H), 1.44 (m, 2H), 2.30 (s, 3H), 2.80 (d, J=15.2 Hz, 1H), 2.85 (t, J=9.3 Hz, 1H), 3.19 (t, J=9.3 Hz, 1H), 3.33 (d, J=10.2 Hz, 1H), 3.42–3.61 (m, 3H), 3.79 (s, 3H), 3.91 (d, J=9.8 Hz, 1H), 4.22 (m, 4H), 6.75–6.86 (m, 6H), 6.95 (d, J=2.0 Hz, 1H), 7.09 (d, J=8.8 Hz, 2H), 7.22 (d, J=10.2 Hz, 1H), 7.26 (t, J=7.6 Hz, 1H). MS (DCl) m/e 559 (M+H$^+$). Anal calcd for $C_{33}H_{38}N_2O_6.0.4$ $CH_3CO_2C_2H_5$: C, 69.97; H, 6.99; N, 4.72. Found: C, 0.06; H, 6.66; N, 4.48.

EXAMPLE 471 trans,trans-4-(1,4-Benzodioxan-6-yl)-2-(4-methoxyphenyl)-1-((N-butyl-N-(3-chlorophenylamino)carbonyl)methyl)pyrrolidine-3-carboxylic Acid Using the procedures described in Example 1, the title compound was prepared. $^1$H NMR (300 MHz, CD$_3$OD) δ 0.87 (t, J=7.0 Hz, 3H), 1.25 (m, 2H), 1.40 (m, 2H), 2.78 (d, J=14.6 Hz, 1H), 2.86 (t, J=9.0 Hz, 1H), 3.16 (t, J=9.5 Hz, 1H), 3.34–3.43 (m, 2H), 3.48–3.62 (m, 3H), 3.79 (s, 3H), 3.85 (d, J=9.5 Hz, 1H), 4.22 (m, 4H), 6.78 (d, J=8.5 Hz, 1H), 6.81–6.86 (m, 3H), 6.93–7.09 (m, 5H), 7.33–7.38 (m, 2H). MS (DCl) m/e 579 (M+H$^+$). Anal calcd for $C_{32}H_{35}ClN_2O_6.1.1$ $CH_3CO_2C_2H_5.0.15$ $H_3PO_4$: C, 63.30; H, 6.46; N, 4.06. Found: C, 63.54; H, 6.09; N, 3.98.

EXAMPLE 472 trans,trans-4-(1,3-Benzodioxol-5-yl)-2-(4-methoxyphenyl)-1-(4-pyridylmethyl)pyrrolidine-3-carboxylic Acid Using the procedures described in Example 1, the title compound was prepared. $^1$H NMR (300 MHz, CD$_3$OD) δ 2.84 (t, J=9.6 Hz, 1H), 2.88 (dd, J=9.6, 7.3 Hz, 1H), 3.09 (dd, J=3.3, 9.6 Hz, 1H), 3.21 (d, J=14.3 Hz, 1H), 3.53 (m, 1H), 3.78 (s, 3H), 3.81 (m, 2H), 5.92 (m, 2H), 6.73 (d, J=8.1 Hz, 1H), 6.82 (dd, J=1.8, 8.1 Hz, 1H), 6.93 (m, 2H), 6.95 (d, J=1.5 Hz, 1H), 7.43 (m, 4H), 8.44 (d, J=5.2 Hz, 2H). MS (DCl) m/e 433 (M+H$^+$). Anal calcd for $C_{25}H_{24}N_2O_5.0.3$ $CH_3CO_2C_2H_5$: C, 68.57; H, 5.80; N, 6.10. Found: C, 68.68; H, 5.60; N, 5.81.

EXAMPLE 473 trans,trans-4-(1,3-Benzodioxol-5-yl)-2-(4-methoxyphenyl)-1-((N-butyl-N-(3-tert-butylphenylamino)carbonyl)methyl)pyrrolidine-3-carboxylic Acid Using the procedures described in Example 1, the title compound was prepared. $^1$H NMR (300 MHz, CD$_3$OD) δ

0.88 (t, J=7.2 Hz, 3H), 1.23 (s, 9H), 1.26–1.45 (m, 4H), 2.74 (dd, J=15.1 Hz, 1H), 2.84 (m, 1H), 3.13 (t, J=9.0 Hz, 1H), 3.29 (d, J=15.1 Hz, 1H), 3.50–3.66 (m, 4H), 3.77 (s, 3H), 3.84 (d, J=9.6 Hz, 1H), 5.92 (s, 2H), 6.74 (d, J=7.7 Hz, 1H), 6.79–6.85 (m, 4H), 6.86–6.90 (m, 1H), 6.99 (t, J=1.8 Hz, 1H), 7.06 (d, J=1.8 Hz, 1H), 7.13 (m, 2H), 7.33 (t, J=7.7 Hz, 1H), 7.42 (m, 1H). MS (DCl) m/e 587 (M+H$^+$). Anal calcd for $C_{35}H_{42}N_2O_6$: C, 71.65; H, 7.22; N, 4.77. Found: C, 71.56; H, 7.33; N, 4.69.

EXAMPLE 474 trans,trans-4-(1,3-Benzodioxol-5-yl)-2-(4-methoxyphenyl)-1-((N-butyl-N-(3-n-butylphenylamino)carbonyl)methyl)pyrrolidine-3-carboxylic Acid Using the procedures described in Example 1, the title compound was prepared. $^1$H NMR (300 MHz, CD$_3$OD) δ 0.88 (t, J=7.3 Hz, 3H), 0.92 (t, J=7.3 Hz, 3H), 1.23–1.59 (m, 8H), 2.58 (t, J=7.6 Hz, 2H), 2.75 (d, J=15.3 Hz, 1H), 2.80 (dd, J=8.5, 9.5 Hz, 1H), 3.12 (t, J=9.3 Hz, 1H), 3.29 (d, J=15.6 Hz, 1H), 3.46 (dd, J=4.9, 9.7 Hz, 1H), 3.52–3.64 (m, 3H), 3.78 (s, 3H), 3.83 (d, J=9.8 Hz, 1H), 5.92 (s, 2H), 6.74 (d, J=8.1 Hz, 1H), 6.79–6.87 (m, 4H), 7.05 (d, J=1.7 Hz, 1H), 7.10 (d, J=8.8 Hz, 2H), 7.20 (d, 7.8H), 7.29 (t, J=7.6 Hz, 1H). MS (DCl) m/e 587 (M+H$^+$). Anal calcd for $C_{35}H_{42}N_2O_6$: C, 71.65; H, 7.22; N, 4.77. Found: C, 71.33; H, 7.28; N, 4.74.

EXAMPLE 475 trans,trans-4-(3,4-Difluorophenyl)-2-(4-ethylphenyl)-1-(N-(n-butyl)-N-(3-methylphenyl)aminocarbonylmethyl)pyrrolidine-3-carboxylic Acid Using the procedures described in Example 1, the title compound was prepared. $^1$H NMR (CD$_3$OD, 300 MHz) δ 0.87 (t, 3H, J=7), 1.19 (t, 3H, J=7), 1.28 (m, 2H), 1.43 (m, 2H), 2.28 (s, 3H), 2.60 (q, 2H, J=7), 2.66 (m, 2H), 3.06 (m, 1H), 3.21 (d, 1H, J=15), 3.42 (dd, 1H, J=4,9), 3.58 (m, 3H), 3.71 (d, 1H, J=9), 6.80 (s, 2H), 7.06 (s, 4H), 7.18 (m, 4H), 7.45 (m, 1H). MS (APCl) m/e 535 (M+H$^+$). Anal calcd for $C_{32}H_{36}N_2O_3F_2$.1.3 HOAc: C, 67.83; H, 6.78; N, 4.57. Found: C, 67.83; H, 6.46; N, 4.70.

EXAMPLE 476 trans,trans-2-(4-Ethylphenyl)-4-(3,4-difluorophenyl)-1-(N-(n-butyl)-N-(3-chlorophenyl)aminocarbonylmethyl)pyrrolidine-3-carboxylic Acid Using the procedures described in Example 1, the title compound was prepared. $^1$H NMR (CD$_3$OD, 300 MHz) δ 0.82 (t, 3H, J=7), 1.16 (t, 3H, J=7), 1.23 (m, 2H), 1.35 (m, 2H), 2.55 (q, 2H, J=7), 2.66 (m, 2H), 3.01 (t, 1H, J=9), 3.16 (d, 1H, J=15), 3.32 (dd, 1H, J=4,9), 3.56 (m, 3H), 3.67 (d, 1H, J=9), 6.94 (d, 1H, J=7), 7.02 (m, 5H), 7.14 (m, 2H), 7.32 (m, 3H). MS (APCl) m/e 555 (M+H$^+$). Anal calcd for $C_{31}H_{33}N_2O_3ClF_2$.0.6 TFA: C, 61.88; H, 5.42; N, 4.48. Found: C, 61.90; H, 5.62; N, 3.98.

EXAMPLE 477 trans,trans-4-(1,4-Benzodioxan-6-yl)-2-(4-fluorophenyl)-1-(N-butyl-N-(3-chlorophenyl)aminocarbonylmethyl)pyrrolidine-3-carboxylic Acid Using the procedures described in Example 1, the title compound was prepared. $^1$H NMR (300 MHz, CD$_3$OD) δ 0.87 (t, J=7 Hz, 3H), 1.10–1.30 (m, 4H), 2.60–2.75 (m, 2H), 3.03 (t, J=7 Hz, 1H), 3.15–3.75 (m, 6H), 4.02 (m, 4H), 6.75 (d, J=6 Hz, 1H), 6.85 (dd, J=7 Hz, 1H), 6.90 (7.19, J=m Hz, 6H), 7.32–7.43 (m, 3H). MS (DCl) m/e 567 (M+H)$^+$. Anal calcd for $C_{31}H_{32}N_2O_5FCl$.1.6 H$_2$O: C, 62.49; H, 5.95; N, 4.70. Found: C, 62.20; H, 5.54; N, 4.42.

EXAMPLE 478 trans,trans-4-(Benzofuran-5-yl)-2-(4-ethylphenyl)-1-(N,N-di(n-butyl)aminocarbonylmethyl)-pyrrolidine-3-carboxylic Acid Using the procedures described in Example 1, the title compound was prepared. $^1$H NMR (300 MHz, CDCl$_3$) δ 0.78 (t, 3H, J=7 Hz), 0.84 (t, 3H, J=7 Hz), 1.05 (q, 2H, J=7 Hz), 1.21 (t, 3H, J=7 Hz), 1.25 (m, 2H), 1.45 (m, 2H), 2.62 (q, 2H, J=7 Hz), 2.80 (d, 1H, J=13 Hz), 3.0 (m, 2H), 3.15 (m, 2H), 3.35 (m, 1H), 3.43 (m, 2H), 3.52 (m, 1H), 4.40 (m, 2H), 6.73 (d, 1H, J=1 Hz), 7.14 (d, 2H, J=8 Hz), 7.26 (s, 1H), 7.31 (d, 2H, J=8 Hz), 7.44 (s, 2H), 7.60 (d, 1H, J=1 Hz), 7.65 (s, 1H). MS (APCl) m/e 505 (M+H)$^+$. Anal. calc'd for $C_{31}H_{40}N_2O_4$: C, 73.78; H, 7.99; N, 5.55. Found: C, 73.69; H, 7.97; N, 5.21.

EXAMPLE 479 trans,trans-2-(4-Methoxy-3-fluorophenyl)-4-(7-methoxy-1,3-benzodioxol-5-yl)-1-[2-(N-propyl-N-(pyrrolidine-1-carbonylmethyl)amino)ethyl] pyrrolidine-3-carboxylic Acid Ethyl 2-(4-methoxy-3-fluorophenyl)-4-(7-methoxy-1,3-benzodioxol-5-yl)-1-[2-(N-propyl-aminoethyl]-pyrrolidine-3-carboxylate, prepared according to the procedures of Example 61B (300 mg), N-bromoacetyl pyrrrolidine (132 mg) and diisopropylethylamine (154 mg) were heated for 1 hour at 50° C. in 1 mL of acetonitrile to give the intermediate ethyl ester. The ester was hydrolyzed to the title compound by the method of Example 1D. $^1$H NMR (300 MHz, CDCl$_3$) δ 0.88 (t, J=7 Hz, 3H), 1.30–1.45 (m, 2H), 1.75–1.92 (m, 4H), 2.30–2.40 (m, 1H), 2.47–2.58 (m, 2H), 2.70–3.00 (m, 5H), 3.24–3.45 (m, 6H), 3.50–3.70 (m, 2H), 3.83 (s, 3H), 3.86 (d, J=9 Hz, 1H), 3.88 (s, 3H), 5.93 (s, 2H), 6.58 (d, J=2 Hz, 1H), 6.70 (d, J=2 Hz, 1H), 6.87 (t, J=8 Hz, 1H), 7.10 (d, J=9 Hz, 1H), 7.21 (dd, J=2 Hz, 12 Hz, 1H).

EXAMPLE 480 trans,trans-2-(4-Methoxyphenyl)-4-(1,3-benzodioxol-5-yl)-1-(2-((N-(perhydroazepinylcarbonyl)-(D)-leucyl)amino)ethyl) pirrolidine-3-carboxylic Acid

EXAMPLE 480A

D-Leucine O-benzyl Ester Tosylate Salt

To benzyl alcohol (8.2 g) dissolved in benzene (30 mL) was added D-leucine (5.0 g) and p-toluenesulfonic acid monohydrate (8.0 g). The reaction was warmed to reflux with removal of water overnight. Once TLC indicated consumption of starting material, the reaction was cooled, and the resulting solid was filtered and washed with EtOAc to give the title compound as a white powder (14.26 g, 99%).

EXAMPLE 480B

N-Perhydroazepinylcarbonyl-D-Leucine O-Benzyl Ester

To the compound resulting from Example 480A (1.0 g) dissolved in chloroform (20 mL) was added triethylamine (0.4 mL). The solution was cooled to 0° C., and carbonyl-diimidazole was added. After 1.5 hours, TLC indicated complete consumption of starting material, so hexamethylene imine (0.327 mL) was added. After 1 hour, an additional amount of hexamethylene imine (0.330 mL) was added, and the reaction was stirred at ambient temperature overnight. The solution was washed with sodium bicarbonate (2×20 mL), 1 N $H_3PO_4$ (2×20 mL), and brine (20 mL), dried over $Na_2SO_4$, decanted and evaporated. The residue was purified by flash chromatography on silica gel eluting with 25–50% EtOAc in hexanes to give the title compound as a crystalline solid (0.835 g, 89%).

EXAMPLE 480C

N-Perhydroazepinylcarbonyl-D-Leucine

To the compound resulting from Example 480B (200 mg) dissolved in dry ethanol (1.0 mL) was added 10% palladium on carbon (10 mg). After flushing the flask with nitrogen, the reaction was stirred vigorously under an atmosphere of hydrogen for 1 hour. The reaction was filtered through infusorial earth and evaporated to give the title compound (140 mg).

EXAMPLE 480D trans,trans-2-(4-Methoxyphenyl)-4-(1,3-benzodioxol-5-yl)-1-(cyanomethyl)-pyrrolidine-3-carboxylic Acid Ethyl Ester To the compound resulting from Example 1C (510 mg of a 50 % wt. solution in toluene) dissolved in acetonitrile (2.0 mL) was added diisopropylethylamine (0.24 mL), followed by bromoacetonitrile (0.072 mL). After 2 hours, TLC indicated complete comsumption of starting material. The solvent was evaporated, and the residue was purified by flash chromatography on silica gel eluting with 20–40% EtOAc in hexanes to give the title compound as a colorless oil (0.28 g, 99%).

EXAMPLE 480E trans,trans-2-(4-Methoxyphenyl)-4-(1,3-benzodioxol-5-yl)-1-(2-aminoethyl)-pyrrolidine-3-carboxylic Acid Ethyl Ester To the compound resulting from Example 480D (275 mg) dissolved in 10 mL each of triethylamine and ethanol was added Raney nickel catalyst (0.2 g), and the reaction was placed under a hydrogen atmosphere (4 atmospheres) for 3 days. The reaction was filtered and evaporated. The residue was dissolved in methylene chloride (10 mL) and extracted with 1 M HCl (5×1 mL). The combined aqueous extracts were basified and then extracted with methylene chloride (5×2 mL). The combined organic extracts were dried with $MgSO_4$, filtered and evaporated to give the title compound as an unstable oil (0.14 g).

EXAMPLE 480F trans,trans-2-(4-Methoxyphenyl)-4-(1,3-benzodioxol-5-yl)-1-(2-((N-(perhydroazepinylcarbonyl)leucyl)amino)ethyl)-pyrrolidine-3-carboxylic Acid, Ethyl Ester The compound resulting from Example 480E (0.10 g) was dissolved in methylene chloride (3.0 mL), and the compound resulting from Example 480C (0.07 g) was added. The solution was cooled to 0° C., and EDCI (0.052 g) was added. After 4 hours, the reaction was evaporated and partitioned between water (1 mL), and EtOAc (10 mL). The organic solution was washed with water (1 mL) and brine (1 mL), dried over $MgSO_4$, filtered and evaporated. The residue was purified by flash chromatography on silica gel eluting with 50–60% EtOAc in hexanes to give the title compound as a colorless oil (0.075 g, 48%).

EXAMPLE 480G trans,trans-2-(4-Methoxyphenyl)-4-(1,3-benzodioxol-5-yl)-1-(2-((N-(perhydroazepinylcarbonyl)leucyl)amino)ethyl) pyrrolidine-3-carboxylic Acid The compound resulting from Example 480F (0.75 g) was dissolved in ethanol (1.0 mL) and 5 M NaOH (0.050 mL) was added. After 2 hours, additional 5 M NaOH (0.090 mL) was added. After an additional 3.5 hours, the reaction was evaporated. The residue was dissolved in water (5 mL) and washed with diethyl ether (2×2 mL). The aqueous solution was acidified with 1 N $H_3PO_4$ to pH 3. The solid which precipitated dissolved when the mixture was extracted with chloroform (3×3 mL). The chloroform extracts were washed with brine (2 mL), dried with $MgSO_4$, filtered and evaporated to give the title compound as a tan solid (0.053 g). Purification by HPLC (Vydac mC18) eluting with a 10–70% gradient of $CH_3CN$ in 0.1% TFA provided suitable material (0.049 g) after lyophilization of the desired fractions. $^1$H NMR ($CDCl_3$, 300 MHz) δ 0.82 (dd, 6.4, 4.4 Hz, 6H), 0.87 (dd, J=5.7, 5.7 Hz, 6H), 1.04–1.28 (m, 3H), 1.34–1.65 (m, 19H), 2.95 (br m, 2H), 3.15–3.40 (m, 14H), 3.40–3.55 (m, 4H), 3.58–3.68 (m, 2H), 3.70–3.76 (br m, 2H), 3.80 (s, 3H), 3.81 (s, 3H), 4.15 (br m, 2H), 5.10 (br m, 2H), 5.93 (s, 3H), 5.95 (s, 3H, 5.95 (s, 3H), 6.70–6.97 (m, 13H), 7.43–7.56 (br m, 3H), 8.2 (br s, 1H), 8.5 (br s, 1H). MS(DCl/$NH_3$) m/e 623 (M+H)$^+$. Anal calcd for $C_{34}H_{46}N_2O_7$.2.00 TFA: C, 53.65; H, 5.69; N, 6.58. Found: C, 53.66; H, 5.66; N, 6.54.

EXAMPLE 481 trans,trans-4-(1,3-Benzodioxol-5-yl)-2-(4-methoxyphenyl)-1-(N,N-di(n-hexyl) aminocarbonylmethyl)pyrrolidine-3-carboxylic Acid Using the procedures described in Example 1, the title compound was prepared. $^1$H NMR (300 MHz, $CD_3OD$) δ 0.80–0.95 (m, 6H), 1.0 (m, 2H), 1.07 (1.55, J=m Hz, 14H), 2.70 (d, J=13 Hz, 1H), 2.85–3.15 (m, 4H), 3.20–3.60 (m, 9H), 3.64 (d, J=10 Hz, 1H), 3.79 (s, 3H), 5.90 (m, 2H), 6.70 (d, 8H), 1, 6.80–6.93 (m, 3H), 7.05 (2, 1H), 7.35 (d, J=10 Hz, 2H). Anal calcd for $C_{33}H_{46}N_2O_6$.1.7 $H_2O$: C, 66.35; H, 8.34; N, 4.69. Found: C, 66.32; H, 8.04; N, 4.52.

EXAMPLE 482 trans,trans-4-(1,4-Benzodioxan-6-yl)-2-(4-fluorophenyl)-1-(N-butyl-N-(3-methylphenyl) aminocarbonylmethyl)pyrrolidine-3-carboxylic Acid Using the procedures described in Example 1, the title compound was prepared. $^1$H NMR (300 MHz, $CD_3OD$) δ 0.87 (t, J=7 Hz, 3H), 1.20–1.35 (m, 2H), 1.35–1.40 (m, 2H), 2.32 (s, 3H), 2.55–2.70 (m, 2H), 2.97 (t, J=7 Hz, 1H), 3.22 (d, J=14 Hz, 1H), 3.25–3.70 (m, 5H), 4.20 (m, 4H), 6.97 (d, J=2 Hz, 1H), 7.09 (m, 2H), 7.15–7.35 (m, 2H). MS (DCl) m/e 547 (M+H)$^+$. Anal calcd for $C_{32}H_{35}N_2O_5F$.1.2 $H_2O$: C, 67.64; H, 6.63; N, 4.93. Found: C, 67.73; H, 6.37; N, 4.70.

EXAMPLE 483 trans,trans-4-(1,3-Benzodioxol-5-yl)-2-(4-methoxyphenyl)-1-(((N-butyl-N-(3-nitrobenzyl) amino)carbonyl)methyl)pyrrolidine-3-carboxylic Acid Using the procedures described in Example 1, the title compound was prepared. $^1$H NMR (300 MHz, $CDCl_3$)

δ(rotamer) 8.14 (2H, m), 8.05 (7.83) (1H, m), 7.60–7.30 (3H, m), 7.13 (1H, m), 7.10–6.70 (5H, m), 5.94 (2H, m), 5.43 (5.33) (1H, d, J=12), 4.75 (1H, bd, J=15), 4.60–4.20 (2H, m), 4.10 (2H, m), 3.80 (3.76)(3H, s), 3.75–3.40 (3H, m), 3.20–2.80 (2H, m), 1.50 (1H, m), 1.30 (1H, m), 1.20–1.00 (2H, m), 0.91 (0.78) (3H, t, J=8). MS (DCl/NH$_3$) m/e 590 (M+H)$^+$. Anal calcd for C$_{32}$H$_{35}$N$_3$O$_8$.2.1 TFA: C, 52.44; H, 4.51; N, 5.07. Found: C, 52.25; H, 4.83; N, 5.71.

EXAMPLE 484 trans,trans-4-(1,2-Dihydrobenzofuran-5-yl)-2-(4-ethylphenyl)-1-(((N-butyl-N-(3,4-dimethoxybenzyl)amino)carbonyl)methyl)pyrrolidine-3-carboxylic Acid Using the procedures described in Example 1, the title compound was prepared. $^1$H (300MHz, CDCl$_3$)δ(rotamer) 7.40 (2H, m), 7.30–7.10 (4H, m), 6.90–6.70 (3H, m), 6.48 (1H, m), 5.45 (1H, m), 4.65 (1H, d, J=15), 4.57 (2H, dt, J=9, 3), 4.40–4.00 (5H, m), 3.87 (3.85) (3H, s), 3.84 (1H, m), 3.83 (3.79) (3H, s), 3.56 (2H, m), 3.20 (2H, t, J=10), 2.90 (1H, m), 2.64 (2H, q, J=8), 1.52 (1H, m), 1.3 (2H, m), 1.22 (3H, dt, J=9, 2), 1.07 (1H, m), 0.92 (0.78) (3H, t, J=8). MS (DCl/NH$_3$) m/e 601 (M+H)$^+$. Anal calcd for C$_{36}$H$_{44}$N$_2$O$_6$.1.35 TFA: C, 61.59; H, 6.06; N, 3.71. Found: C, 61.69; H, 6.04; N, 3.63.

EXAMPLE 485 trans,trans-4-(1,3-Benzodioxol-5-yl)-2-(4-methoxyphenyl)-1-(((N-butyl-N-(4-heptyl)amino)carbonyl)methyl)pyrrolidine-3-carboxylic Acid Using the procedures described in Example 1, the title compound was prepared. $^1$H NMR (300 MHz, CD$_3$OD) δ 0.71–1.04 (m, 11H), 1.07–1.35 (m, 6H), 1.73–1.53 (m, 4H), 2.79–3.25 (m, 5H), 3.35–3.44 (m, 1H), 3.51–3.68 (m, 3H), 3.78–3.89 (m, 1H), 3.79 (s, 3H), 5.92 (m, 2H), 6.74 (dd, J=1.7, 8.1 Hz, 1H), 6.85 (td, J=1.7, 8.1 Hz, 1H), 6.93 (m, 2H), 7.02 (dd, J=1.7, 9.5 Hz, 1H), 7.36 (m, 2H). MS (C.l.) m/e 553 (M+H)$^+$. Anal calcd for C$_{32}$H$_{44}$N$_2$O$_6$: C, 69.54; H, 8.02; N, 5.07. Found: C, 69.31; H, 7.89; N, 5.06.

EXAMPLE 486 trans,trans-2-(4-Methylcyclohexyl)-4-(1,3-benzodioxol-5-yl)-1-(N,N-di(n-butyl)aminocarbonylmethyl)-pyrrolidine-3-carboxylic Acid Using the procedures described in Example 1, the title compound was prepared and isolated as an amorphous solid. $^1$H NMR (CDCl$_3$, 300 MHz) δ 0.88 (3H, d, J=7 Hz), 0.92 (3H, t, J=7 Hz), 0.96 (3H, t, J=7 Hz), 1.05 (1H, m), 1.22–1.40 (7H, m), 1.45–1.65 (6H, m), 1.67–1.84 (4H, m), 3.17–3.45 (6H, m), 3.70 (1H, brm), 3.82 (1H, dd, J=9 Hz, 15 Hz), 3.86 (1H, d, J=15 Hz), 5.93 (2H, s), 6.73 (1H, d, J=8 Hz), 6.78 (1H, dd, J=2 Hz, 8 Hz), 6.88 (1H, d, J=2 Hz). MS (DCl/NH$_3$) m/e 501 (M+H)$^+$. Anal calcd for C$_{29}$H$_{44}$N$_2$O$_5$.0.25 CF$_3$CO$_2$H: C, 66.96; H, 8.43; N, 5.29. Found: C, 66.79; H, 8.60; N, 4.87.

EXAMPLE 487 trans,trans-2-(2-Propylpentyl)-4-(1,3-benzodioxol-5-yl)-1-(N,N-di(n-butyl)aminocarbonylmethyl)-pyrrolidine-3-carboxylic Acid Using the procedures described in Example 1, the title compound was prepared and isolated as an amorphous solid. $^1$H NMR (CDCl$_3$, 300 MHz) δ 0.85 (6H, m), 0.92 (3H, t, J=7 Hz), 0.97 (3H, t, J=7 Hz), 1.12–1.40 (13H, m), 1.42–1.68 (6H, m), 2.90 (1H, m), 3.14–3.30 (2H, m), 3.33 (4H, m), 3.72 (1H, brm), 3.90 (1H, brm), 5.93 (2H, dd, J=2 Hz, 4 Hz), 6.73 (1H, d, J=8 Hz), 6.78 (1H, dd, J=2 Hz, 8 Hz), 6.88 (1H, d, J=2 Hz). MS (DCl/NH$_3$) m/e 517 (M+H)$^+$. Anal calcd for C$_{30}$H$_{48}$N$_2$O$_5$.0.35 CF$_3$CO$_2$H: C, 66.24; H, 8.76; N, 5.03. Found: C, 66.26; H, 8.82; N, 4.98.

EXAMPLE 488 trans,trans-4-(1,4-Benzodioxan-6-yl)-2-(4-fluorophenyl)-1-(N,N-di(n-butyl)aminocarbonylmethyl)-pyrrolidine-3-carboxylic Acid Using the procedures described in Example 1, the title compound was prepared. $^1$H NMR (300 MHz, CD$_3$OD) δ 0.83 (t, J=7 Hz, 3H), 0.89 (t, J=7 Hz, 3H), 0.90–1.17 (m, 4H), 1.20–1.65 (m, 5H), 2.77d (13, 1H), 2.87 (dd, J=8, 2 Hz, 1H), 2.95–3.60 (m, 7H), 3.71 (d, J=9 Hz, 1H), 4.21 (s, 4H), 6.72 (d, 1H), 6.91 (dd, J=8 Hz, 1H), 6.97 (d, J=2 Hz, 1H), 7.05 (t, J=7 Hz, 2H), 7.40–7.50 (m, 2H). MS (DCl) m/e 513 (M+H)$^+$. Anal calcd for C$_{29}$H$_{37}$N$_2$O$_5$F.1.2C F$_3$COOH: C, 58.07; H, 5.93; N, 4.31. Found: C, 57.94; H, 5.81; N, 4.56.

EXAMPLE 489 trans,trans-2-(3-Methylpentyl)-4-(1,3-benzodioxol-5-yl)-1-(N,N-di(n-butyl)aminocarbonylmethyl)-pyrrolidine-3-carboxylic Acid Using the procedures described in Example 1, the title compound was prepared and isolated as an amorphous solid. $^1$H NMR (CDCl$_3$, 300 MHz) δ 0.83 (3H, t, J=7 Hz), 0.85 (3H, d, J=7 Hz), 0.91 (3H, t, J=7 Hz), 0.97 (3H, t, J=7 Hz), 1.05–1.22 (2H, m), 1.22–1.41 (7H, m), 1.43–1.68 (5H, m), 1.89 (1H, m), 2.94 (1H, t, J=6 Hz), 3.15–3.27 (3H, m), 3.29–3.60 (5H, m), 3.72 (1H, brd, J=6 Hz), 3.92 (1H, brd, J=13.5 Hz), 5.93 (2H, dd, J=2 Hz, 4 Hz), 6.73 (1H, d, J=8 Hz), 6.78 (1H, dd, J=2 Hz, 8 Hz), 6.88 (1H, d, J=2 Hz). MS (DCl/NH$_3$) m/e 489 (M+H)$^+$. Anal calcd for C$_{28}$H$_{44}$N$_2$O$_5$.0.30 CF$_3$CO$_2$H: C, 65.70; H, 8.54; N, 5.36. Found: C, 65.93; H, 8.81; N, 4.84.

EXAMPLE 490 trans,trans-2-(2-Ethylbutyl)-4-(1,3-benzodioxol-5-yl)-1-(N,N-di(n-butyl)aminocarbonylmethyl)-pyrrolidine-3-carboxylic Acid Using the procedures described in Example 1, the title compound was prepared and isolated as an amorphous solid. $^1$H NMR (CDCl$_3$, 300 MHz) δ 0.85 (6H, m), 0.92 (3H, t, J=7 Hz), 0.97 (3H, t, J=7 Hz), 1.13–1.41 (13H, m), 1.43–1.72 (6H, m), 2.96 (1H, brm), 3.12–3.52 (6H, m), 3.55–3.70 (1H, m), 3.70–3.86 (2H, m), 3.99 (1H, brm), 5.93 (2H, dd, J=2 Hz, 4 Hz), 6.73 (1H, d, J=8 Hz), 6.78 (1H, dd, J=2 Hz, 8 Hz), 6.88 (1H, d, J=2 Hz). MS (DCl/NH$_3$) m/e 489 (M+H)$^+$. Anal calcd for C$_{28}$H$_{44}$N$_2$O$_5$.0.45 CF$_3$CO$_2$H: C, 64.28; H, 8.30; N, 5.19. Found: C, 64.16; H, 8.38; N, 5.08.

EXAMPLE 491 trans,trans-2-(3-Fluoro-4-methoxyphenyl)-4-(1,3-benzodioxol-5-yl)-1-(2-(N-isobutyl-N-(butanesulfonylamino))ethyl)pyrrolidine-3-carboxylic Acid Using the procedures described in Example 66, the title compound was prepared. $^1$H NMR (CD$_3$OD, 300 MHz) δ

0.74 (d, 3H, J=7), 0.83 (d, 3H, J=7), 0.94 (t, 3H, J=7), 1.44 (hex, 2H), 1.67 (m, 4H), 2.91 (d, 2H, J=8), 3.04 (dd, 2H, J=8, 10), 3.1–3.6 (m, 5H), 3.78 (m, 2H), 3.92 (s, 3H), 4.60 (m, 1H), 5.97 (s, 2H), 6.82 (d, 1H, J=8), 6.89 (dd, 1H, J=2, 8), 7.01 (d, 1H, J=2), 7.22 (t, 1H, J=9), 7.39 (m, 2H). MS (ESl) m/e 579 (M+H)$^+$.

EXAMPLE 492 trans,trans-2-(4-Methoxy-3-fluorophenyl)-4-(1,3-benzodioxol-5-yl)-1-[2-(N-propyl-N-[4-ethylpyrimidin-2-yl]amino)ethyl]pyrrolidine-3-carboxylic Acid 1-Dimethylamino-1-pentene-3-one, prepared by the method described in Syn. Comm. 12 (1), 35 (1982), was converted to 2-amino-4-ethyl-pyrimidine with guanidine by the method of Chem. Ber. 97, 3397 (1964). This material was converted to 2-bromo-4-ethyl-pyrimidine with NaNO$_2$ and HBr, using the method of Helv. Chim. Acta 75, 1629 (1992). This bromopyrimidine was reacted with ethyl 2-(4-methoxphenyl)-4-(1,3-benzodioxol-5-yl)-1-[2-(N-propylamino)propyl]-pyrrolidine-3-carboxylate, prepared using the procedures of Example 61B, using the procedure for Example 418, to give the title compound as a white powder. $^1$H NMR (300 MHz, CDCl$_3$) δ 0.83 (t, J=7 Hz, 3H), 1.11 (t, J=7 Hz, 3H), 1.45 (sextet, J=7 Hz, 2H), 2.18–2.27 (m, 1H), 2.45 (q, J=7 Hz, 2H), 2.80–2.97 (m, 3H), 3.40–3.75 (m, 7H), 3.83 (s, 3H), 5.95 (s, 2H), 6.25 (d, J=4 Hz, 1H), 6.68 (d, J=8 Hz, 1H), 6.79 (dd, J=2 Hz, 8 Hz, 1H), 6.82 (t, J=9 Hz, 1H), 6.92 (d, J=2 Hz, 1H), 7.05 (d, J=9 Hz, 1H), 7.15 (dd, J=2 Hz, 12 Hz, 1H), 8.10 (d, J=4 Hz, 1H).

EXAMPLE 493 trans,trans-4-(1,3-Benzodioxol-5-yl)-2-(4-methoxyphenyl)-1-((N-butyl-N-(3,4-dimethylphenyl)aminocarbonyl)methyl)pyrrolidine-3-carboxylic Acid Using the procedures described in Example 1, the title compound was prepared. $^1$H NMR (300 MHz, CD$_3$OD) δ 0.87 (t, J=7.3 Hz, 3H), 1.23–1.36 (m, 2H), 1.38–1.43 (m, 2H), 2.22 (s, 3H), 2.29 (s, 3H), 2.79 (d, J=14.9 Hz, 1H), 2.84 (dd, J=8.6, 9.7 Hz, 1H), 3.16 (t, J=9.5 Hz, 1H), 3.32 (d, J=15.3 Hz, 1H), 3.43–3.61 (m, 4H), 3.79 (s, 3H), 3.88 (d, J=9.8 Hz, 1H), 5.93 (s, 2H), 6.74 (m, 3H), 6.83 (m, 3H), 7.04 (d, J=1.7 Hz, 1H), 7.11 (m, 3H). MS (C.I.) m/e 559(MH$^+$). Anal calcd for C$_{33}$H$_{38}$N$_2$O$_6$.0.3H$_2$O: C, 70.27; H, 6.90; N, 4.97. Found: C, 70.24; H, 6.62; N, 4.58.

EXAMPLE 494 trans,trans-2-(3-Methylpentyl-3-en-1-yl)-4-(1,3-benzodioxol-5-yl)-1-(N,N-di(n-butyl) aminocarbonylmethyl)-pyrrolidine-3-carboxylic Acid Using the procedure described in Example 1, the title compound was prepared and isolated as an amorphous solid. $^1$H NMR (CDCl$_3$, 300 MHz) δ 0.92 (3H, t, J=7 Hz), 0.97 (3H, t, J=7 Hz), 1.22–1.40 (5H, m), 1.44–1.61 (8H, m), 1.82 (1H, brm), 2.02 (2H, m), 3.05–3.30 (4H, m), 3.3.8 (1H, m), 3.55 (1H, brm), 3.85 (2H, m), 4.12 (1H, brd, J=15 Hz), 5.11 (1H, dd, J=6 Hz, 12 Hz), 5.93 (2H, s), 6.73 (1H, d, J=8 Hz), 6.78 (1H, dd, J=2 Hz, 8 Hz), 6.88 (1H, d, J=2 Hz). MS (DCl/NH$_3$) m/e 487 (M+H)$^+$. Anal calcd for C$_{28}$H$_{42}$N$_2$O$_5$.0.7 CF$_3$CO$_2$H: C, 62.34; H, 7.60; N, 4.95. Found: C, 62.49; H, 7.43; N, 4.73.

EXAMPLE 495

1-(N-Phenylaminocarbonylmethyl)-2-(4-methoxyphenyl)-4-(1,3-benzodioxol-5-yl) pyrrolidine-3-carboxylic Acid

EXAMPLE 495A

N-Phenylbromoacetamide

To a stirred solution of aniline (7.40 mmol) in methylene chloride (25 mL) at −50° C. was added successively N,N-diisopropylethylamine (1.58 mL, 8.14 mmol, 1.1 eq) and bromoacetyl bromide (0.72 mL, 7.40 mmol, 1 eq) such that the temperature did not exceed −40° C. On completion of the addition, the cooling bath was removed, and the reaction mixture was allowed to warm to room temperature. After stirring for a further 30 minutes, the mixture was diluted with ether (70 mL) and poured into 1 N sodium bisulfate solution. The phases were separated, and the upper layer was washed successively with water and brine. The organic phase was dried (Na$_2$SO$_4$) and the solvent evaporated to half volume, at which point the product crystallized. The crystals were removed by vacuum filtration to afford the title compound.

EXAMPLE 495B trans,trans-1-(N-Phenylaminocarbonylmethyl)-2-(4-methoxyphenyl)-4-(1,3-benzodioxol-5-yl) pyrrolidine-3-carboxylic Acid Using the procedures described in Example 1 and the compound resulting from Exampe 495A, the title compound was prepared. $^1$H NMR (300 MHz, CDCl$_3$) δ 8.8 (bs, 1H) 7.49 (2H, d, J=8 Hz), 7.38 (4H, m), 7.11 (1H, tt, J=8&2 Hz), 6.99 (1H, d, J=2 Hz), 6.91 (2H, d, J=8 Hz), 6.86 (1H, d, J=2 Hz), 6.81 (1H, d, J=8 Hz), 5.99 (1H, d, J=2 Hz), 5.98 (1H, d, J=2 Hz), 3.94 (1H, d, J=10 Hz), 3.78 (3H, s), 3.70 (1H, ddd, J=6, 5&3 Hz), 3.42 (1H, dd, J=10&3 Hz), 3.41 (1H, d, J=16 Hz), 3.18 (1H, dd, J=11&9 Hz), 3.01 (1H, t, J=10 Hz), 2.93 (1H, d, J=16 Hz). MS (DCl, NH$_3$) m/e 475 (M+H$^+$). Anal. Calc for C$_{27}$H$_{26}$N$_2$O$_6$.1 H$_2$O: C, 65.85, H, 5.73, N 5.69, Found: C, 65.95, H, 5.52, N, 5.38.

EXAMPLE 496 trans,trans-1-(N-(2,3-Dimethylphenyl) aminocarbonylmethyl)-2-(4-methoxyphenyl)-4-(1,3-benzodioxol-5-yl)pyrrolidine-3-carboxylic Acid Using the procedures described in Example 1, the title compound was prepared. $^1$H NMR (300 MHz, CDCl$_3$) δ 8.68 (1H, bs), 7.64 (d, J=8 Hz), 7.38, (2H, d, J=8 Hz), 7.09 (1H, t, J=8 Hz), 6.97, (1H, d, J=8 Hz), 6.90 (1H, d, J=2 Hz), 6.88 (2H, d, J=8 Hz), 6.82 (1H, dd, J=8&3 Hz), 6.67 (1H, d, J=8 Hz), 5.97 (1H, d, J=2 Hz), 5.96 (1H, d, J=2 Hz), 3.95 (1H, d, J=10 Hz), 3.80 (3H, s), 3.70 (1H, ddd, J=6, 5&3 Hz), 3.48 (1H, dd, J=10&3 Hz), 3.44 (1H, d, J=16 Hz), 3.18 (1H, dd, J=11&9 Hz), 3.06 (1H, t, J=10 Hz), 2.96 (1H, d, J=16 Hz), 2.31 (3H, s), 2.16 (3H, s). MS (DCl, NH$_3$) m/e 503 (M+H$^+$). Anal. Calc for C$_{29}$H$_{30}$N$_2$O$_6$.0.5 H$_2$O: C, 68.09, H, 6.11, N, 5.48. Found: C, 68.13, H, 5.91, N, 5.29.

EXAMPLE 497 trans,trans-1-(N-(2,4-Dimethylphenyl) aminocarbonylmethyl)-2-(4-methoxyphenyl)-4-(1,3-benzodioxol-5-yl)pyrrolidine-3-carboxylic Acid Using the procedures described in Example 1, the title compound was prepared. $^1$H NMR (300 MHz, CDCl$_3$) δ

8.60 (1H, bs), 7.78 (d, J=8 Hz), 7.38, (2H, d, J=8 Hz), 6.99 (1H, m), 6.95, (1H, d, J=8 Hz), 6.94 (1H, d, J=2 Hz), 6.88 (2H, d, J=8 Hz), 6.82 (1H, dd, J=8&3 Hz), 6.77 (1H, d, J=8 Hz), 5.97 (1H, d, J=2 Hz), 5.96 (1H, d, J=2 Hz), 3.92 (1H, d, J=10 Hz), 3.79 (3H, s), 3.68 (1H, ddd, J=6, 5&3 Hz), 3.43 (1H, dd, J=10&3 Hz), 3.42 (1H, d, J=16 Hz), 3.18 (1H, dd, J=11&9 Hz), 3.04 (1H, t, J=10 Hz), 2.95 (1H, d, J=16 Hz), 2.29 (3H, s), 2.24 (3H, s). MS (DCl, NH$_3$) m/e 503 (M+H$^+$). Anal. Calc for C$_{29}$H$_{30}$N$_2$O$_6$·0.75 H$_2$O: C, 67.50, H, 6.15, N, 5.43. Found: C, 67.42; H, 5.95; N, 5.13.

EXAMPLE 498 trans,trans-1-(N-(2,5-Dimethylphenyl) aminocarbonylmethyl)-2-(4-methoxyphenyl)-4-(1,3-benzodioxol-5-yl)pyrrolidine-3-carboxylic Acid Using the procedures described in Example 1, the title compound was prepared. $^1$H NMR (300 MHz, CDCl$_3$) δ 8.62 (1H, bs), 7.79 (1H, bs), 7.38, (2H, d, J=8 Hz), 7.03 (1H, d, J=8 Hz), 6.95, (1H, d, J=8 Hz), 6.94 (1H, d, J=2 Hz), 6.88 (2H, d, J=8 Hz), 6.82 (1H, dd, J=8&3 Hz), 6.77 (1H, d, J=8 Hz), 5.97 (2H, s), 3.92 (1H, d, J=10 Hz), 3.78 (3H, s), 3.70 (1H, ddd, J=6, 5&3 Hz), 3.48 (1H, dd, J=10&3 Hz), 3.42 (1H, d, J=16 Hz), 3.18 (1H, dd, J=11&9 Hz), 3.04 (1H, t, J=10 Hz), 2.95 (1H, d, J=16 Hz), 2.29 (3H, s), 2.24 (3H, s). MS (DCl, NH$_3$) m/e 503 (M+H$^+$). Anal. Calc for C$_{29}$H$_{30}$N$_2$O$_6$·0.5 H$_2$O: C, 68.09; H, 6.11; N, 5.48. Found: C, 67.72; H, 5.89; N, 5.25.

EXAMPLE 499 trans,trans-1-(N-(3,4-Dimethylphenyl) aminocarbonylmethyl)-2-(4-methoxyphenyl)-4-(1,3-benzodioxol-5-yl)pyrrolidine-3-carboxylic Acid Using the procedures described in Example 1, the title compound was prepared. $^1$H NMR (300 MHz, CDCl$_3$) δ 8.73 (1H, bs), 7.38 (2H, bd, J=8 Hz), 7.30, (1H, d, J=3 Hz), 7.20 (1H, bs), 7.08, (1H, d, J=8 Hz), 7.01 (1H, bs), 6.90 (2H, d, J=8 Hz), 6.85 (1H, bs), 6.80 (1H, d, J=8 Hz), 5.99 (1H, d, J=3 Hz), 5.98 (1H, d, J=3 Hz), 3.92 (1H, d, J=10 Hz), 3.78 (3H, s), 3.70 (1H, ddd, J=6, 5&3 Hz), 3.48 (1H, dd, J=10&3 Hz), 3.42 (1H, d, J=16 Hz), 3.18 (1H, dd, J=11&9 Hz), 3.04 (1H, t, J=10 Hz), 2.95 (1H, d, J=16 Hz), 2.25 (3H, s), 2.21 (3H, s). MS (DCl, NH$_3$) m/e 503 (M+H$^+$). Anal. Calc for C$_{29}$H$_{30}$N$_2$O$_6$·0.75 H$_2$O: C, 67.50; H, 6.15; N 5.43. Found: C, 67.24; H, 5.94; N, 5.20.

EXAMPLE 500 trans,trans-1-(N-(3,5-Dimethylphenyl) aminocarbonylmethyl)-2-(4-methoxyphenyl)-4-(1,3-benzodioxol-5-yl)pyrrolidine-3-carboxylic Acid Using the procedures described in Example 1, the title compound was prepared. $^1$H NMR (300 MHz, CDCl$_3$) δ 8.75 (1H, bs), 7.35, (2H, d, J=8 Hz), 7.10 (2H, s), 7.02 (1H, d, J=3 Hz), 6.90 (2H, d, J=8 Hz), 6.84 (1H, d, J=2 Hz), 6.80, (1H, d, J=8 Hz), 6.76 (1H, bs), 5.99 (1H, d, J=3 Hz), 5.98 (1H, d, J=3 Hz), 3.92 (1H, d, J=10 Hz), 3.79 (3H, s), 3.68 (1H, ddd, J=6, 5&3 Hz), 3.40 (2H, m), 3.18 (1H, dd, J=11&9 Hz), 2.98 (1H, t, J=10 Hz), 2.88 (1H, d, J=16 Hz), 2.3 (6H, s). MS (DCl, NH$_3$) m/e 503 (M+H$^+$). Anal. Calc for C$_{29}$H$_{30}$N$_2$O$_6$·0.5 H$_2$O: C, 68.09; H, 6.11; N, 5.48. Found: C, 67.93; H, 6.01; N, 5.19.

EXAMPLE 501

Alternate Preparation of (+)-trans,trans-1-(N,N-Di (n-butyl)aminocarbonylmethyl)-2-(4-methoxyphenyl)-4-(1,3-benzodioxol-5-yl) pyrrolidine-3-carboxylic Acid Hydrochloride Salt

EXAMPLE 501A

N,N-Dibutyl Bromoacetamide

To a solution of bromoacetyl bromide (72.3 mL, 830 mmol) in toluene (500 mL) cooled to 0° C. was added a solution of dibutylamine (280.0 mL, 1.66 mol) in toluene (220 mL) via an addition funnel maintaining the reaction temperature below 10° C. Upon completion of the addition, the reaction mixture was stirred at 0° C. for 15 minutes. A solution of 2.5% aqueous H$_3$PO$_4$ (500 mL) was slowly introduced, and the reaction mixture was allowed to warm to room temperature with vigorous stirring. The solution is 2.5% phosphoric acid by weight. The layers were separated and the organic phase washed with water (500 mL) and concentrated to provide the bromoacetamide as a solution in toluene.

EXAMPLE 501B 5-(2-Nitrovinyl)-1,3-benzodioxole

To piperonal (15.55 kg, 103.5 mol) under mechanical stirring and under nitrogen was added ammonium acetate (13.4 kg, 173.8 mol), acetic acid (45.2 kg), and nitromethane (18.4 kg, 301.4 mol) sequentially. The mixture was warmed to 70° C. After about 30 minutes, the yellow product began to crystallize. The reaction temperature was raised to 80° C. and stirred for about 10 hours until minimal piperonal remains. The somewhat thick reaction mixture was cooled to 10° C. and filtered. The precipitate was washed with acetic acid (2×8 kg) and then water (2×90 kg). The product was dried under a nitrogen purge and then in a vacuum oven at 50° C. for 2 days to afford 15.94 kg (80%) of the title compound as a bright yellow solid.

EXAMPLE 501C

4-Methoxybenzoyl Acetate

To potassium t-amylate (25 wt %, 50.8 kg, 99.26 mol) in toluene (15.2 kg) cooled to 5° C. under mechanical stirring and under nitrogen was added a mixture of 4-methoxyacetophenone (6.755 kg, 44.98 mol) and diethyl carbonate (6.40 kg, 54.18 mol) in toluene over 1 hour maintaining the temperature below 10° C. The reaction mixture was heated to 60° C. for 8 hours until no 4-methoxyacetophenone was detected by HPLC. The mixture was cooled to 20° C. and quenched by adding to a mixture of acetic acid (8 kg) and water (90 kg) over 30 minutes while maintaining the temperature at <20° C. The layers were separated, and the organic layer was washed with 5% sodium bicarbonate solution (41 kg) and concentrated to 14.65 kg. The temperature is maintained below 50° C. during the distillation. The yellow product concentrate was assayed by HPLC against an external standard and the yield was found to be 9.40 kg (94%).

EXAMPLE 501D

Ethyl 2-(4-methoxybenzoyl)-4-nitromethyl-3-(1,3-benzodioxol-5-yl) Butyrate

To the compound resulting from Example 501B (7.5 kg, 37.9 mol) suspended in THF (56 kg) with mechanical stirring under nitrogen was added the compound resulting from Example C (8.4 kg, 37.9 mol). The mixture was cooled to 17° C., sodium ethoxide (6.4 g, 0.095 mol) was added, and the reaction was stirred for 30 minutes. After about 15 minutes, the nitrostyrene was completely dissolved. Sodium ethoxide (6.4 g, 0.095 mol) was added, and the mixture was stirred at 25° C. until HPLC shows less than 1 area % ketoester remaining. The reaction was concentrated to 32.2 kg which was determined by HPLC assay to be ~14.9 kg (95%).

EXAMPLE 501E

Ethyl cis, cis-2-(4-methoxyphenyl)-4-(1,3-benzodioxol-5-yl) pyrrolidine-3-carboxylate Raney nickel (20.0 g), from which the water had been decanted, was charged to a stirred hydrogenator equipped with a thermocouple. THF (20 mL), the crude compound resulting from Example 501D (40.82 g, 0.0482 mol), and acetic acid (2.75 mL, 0.0482 mol) were added sequentially. The mixture was put under a hydrogen atmosphere at 60 psi until the hydrogen uptake slowed dramatically. TFA was added, and the mixture was hydrogenated at 200 psi until HPLC shows no residual imine and <2 area % nitrone. The catalyst was filtered away and washed with 100 mL of methanol. The filtrate was assayed by HPLC and found to contain 13.3 g (75% yield) of the cis, cis-pyrrolidine compound. The filtrate was concentrated and chased with additional THF (200 mL) to give a final volume of 100 mL. The mixture was neutralized with 2 N NaOH solution (50 mL), diluted with water (200 mL), and extracted with ethyl acetate (2×100 mL). The combined nearly colorless ethyl acetate layers were assayed against an external standard by HPLC to be 13.0 g (73%) of the title compound.

EXAMPLE 501F

Ethyl trans, trans-2-(4-methoxyphenyl)-4-(1,3-benzodioxol-5-yl) Pyrrolidine-3-carboxylate The solution of the compound resulting from Example 501E (38.1 g, 0.103 mol) was chased with ethanol (200 mL) to a final volume of 100 mL and sodium ethoxide (3.40 g, 0.050 mol) was added. The mixture was heated to 75° C. When HPLC shows <3% of the cis,cis isomer remaining, the mixture was cooled to room temperature. The product was assayed by HPLC against an external standard and found to contain 34.4 g (90% yield) of the title compound. The crude compound solution was concentrated and the residue taken up in isopropyl acetate (400 mL). The organic layer was washed with water (2×150 mL) and then extracted with 0.25 M phosphoric acid solution (2×400 mL). The combined phosphate layers were stirred with ethyl acetate (200 mL) and neutralized to pH 7 with solid sodium bicarbonate (21 g). The organic layer was separated and found to contain 32.9 g (87%) of the title compound.

EXAMPLE 501G

Ethyl (2R, 3R, 4S)-(+)-2-(4-methoxyphenyl)-4-(1,3-benzodioxol-5-yl) Pyrrolidine-3-carboxylate, (S)-(+) Mandelate Salt The solution resulting from Example 501F was chased with acetonitrile (100 mL) to give a final volume of 50 mL. (S)-(+)-Mandelic acid (2.06 g, 0.0136 mmol) was added and allowed to dissolve. The mixture was seeded with the product and allowed to stir at room temperature for 16 hours. The reaction mixture was cooled to 0° C. and stirred for 5 hours. The product was filtered and dried in a vacuum oven with a nitrogen purge for 1 day at 50° C. to give 5.65 g (40%) of the title compound. The purity of the product can be determined by chiral HPLC using Chiralpak AS, isocratic elution with 95:5:0.05 hexane-ethanol-diethylamine; flow—1 mL/min.; UV detection at 227 nm. Retention times: (+)-enantiomer: 15.5 min.; (−)-enantiomer: 21.0 min.

EXAMPLE 501H (2R, 3R, 4S)-(+)-2-(4-methoxyphenyl)-4-(1,3-benzodioxol-5-yl)-1-(N,N-di(n-butyl) aminocarbonylmethyl)-pyrrolidine-3-carboxylic Acid The compound resulting from Example 501G (20.0 g, 0.0383 mol) was suspended in ethyl acetate (150 mL) and 5% sodium bicarbonate solution (150 mL). The mixture was stirred at room temperature until the salt dissolved and carbon dioxide evolution had ceased. The organic layer was separated and concentrated. The residue was chased with acetonitrile (200 mL) to a final volume of 100 mL and cooled to 10° C. Diisopropylethylamine (11.8 mL, 0.0574 mol) and the compound resulting from Example A (10.5 g, 0.0421 mol) were added, and the mixture was stirred for 12 hours at room temperature. The reaction mixture was concentrated and chased with ethanol (200 mL) to a final volume of 100 mL. Sodium hydroxide solution (40%, 20 mL, 0.200 mol) was added, and the mixture was heated at 60° C. for 4 hours until HPLC showed no starting material remaining. The reaction mixture was poured into water (400 mL) and washed with hexanes (2×50 mL). The aqueous layer was washed with hexane (2×20 mL). A stirred mixture of the aqueous layer and ethyl acetate (400 mL) was neutralized to pH 5 with concentrated HCl (12 mL). The organic layer was separated and found to contain 18.3 g (94% yield) of the title compound.

EXAMPLE 501I (2R, 3R, 4S)-(+)-2-(4-methoxyphenyl)-4-(1,3-benzodioxol-5-yl)-1-(N,N-di(n-butyl) aminocarbonylmethyl)-pyrrolidine-3-carboxylic Acid Hydrochloride Salt To a solution of the compound of Example 501H in ethyl acetate at room temperature in a mechanically stirred vessel equipped with a thermocouple, was added 39.4 mL of 1 N HCl in ethanol (0.0394 mol) The resultant solution was filtered to remove foreign matter, concentrated in vacuo, and chased with ethyl acetate (400 mL). The solution was seeded repeatedly, as the solvent was removed, until crystallization was initiated. The mixture was concentrated to a volume of 100 mL, and the product was filtered and washed with ethyl acetate (25 mL). The resultant white solid was dried in a vacuum oven under a nitrogen purge at 50° C. to afford 17.6 g (90%) of the title compound.

EXAMPLE 502 trans, trans-2-(2-Methylpentyl)-4-(1,3-benzodioxol-5-yl)-1-(N,N-di(n-butyl)aminocarbonylmethyl)-pyrrolidine-3-carboxylic Acid

EXAMPLE 502A (±)-Ethyl 3-methylhexanoate

To a slurry of 60% sodium hydride (2.26 g, 57 mmol) in 10 mL of hexanes and 100 mL of diethyl ether was added triethylphosphonoacetate (10.3 mL, 52 mmol). Once gas evolution ceased, 2-pentanone (6.0 mL, 64 mmol) was added. After 3 hours at room temperature, the reaction was quenched with water, and partitioned into ether. The organic layer was washed with water and brine, dried with anhydrous sodium sulfate, filtered, and the solvent was removed under reduced pressure. The residue was dissolved in 50 mL of ethanol and 10% palladium on carbon (6.0 g) was added. The vessel was pressurized to 4 atmosphere of hydrogen, and was shaken at room temperature for 3 hours. The reaction was filtered and the solvent was removed under reduced pressure to give 3.0 g of the title compound.

EXAMPLE 502B (±)-Ethyl 5-methyl-3-oxooctanoate

To a solution of ethyl 3-methylhexanoate in 150 mL of ethanol was added sodium hydroxide (2.3 g, 57.6 mmol).

After 48 hours at room temperature, solvent was removed under reduced pressure, and the residue was dissolved in 150 mL of water. The solution was washed with ether, then acidified with concentrated hydrochloric acid and washed with methylene chloride. The organic layer was dried with anhydrous magnesium sulfate, filtered, and the solvent was removed under reduced pressure to give 2.7 g of the corresponding acid from which 3.9 g of the title compound was prepared by the method of Bram and Vilkas, *Bul. Chem. Soc. Fr.*, 945 (1964).

EXAMPLE 502C trans, trans-2-(2-Methylpentyl)-4-(1,3-benzodioxol-5-yl)-1-(N,N-di(n-butyl)aminocarbonylmethyl)-pyrrolidine-3-carboxylic Acid Using the procedures described in Example 1 and substituting ethyl 5-methyl-3-oxooctanoate for ethyl (4-methoxybenzoyl)acetate afforded the title compound, which was isolated by lyophilization from dilute aqueous TFA/CH$_3$CN. Note that the multiplicity of the signals in the aryl region of the NMR spectrum reflects a 1:1 mixture of diastereomers on the alkyl chain. $^1$H NMR (CDCl$_3$, 300 MHz) δ 0.8–1.0 (m, 12H), 1.2–1.4 (m, 7H), 1.45–1.6 (m, 6H), 1.6–1.74 (m, 1H), 1.8–2.0 (m, 1H), 3.1–3.4 (m, 5H), 3.67–3.78 (m, 1H), 3.8–3.91 (m, 1H), 4.0–4.2 (m, 2H), 4.3–4.5 (m, 2H), 5.93 (d, J=1.5 Hz, 2H), 6.73 (dd, J=8.1, 1.2 Hz, 1H), 6.79 (ddd, J=7.8, 1.8, 1.8 Hz, 1H), 6.86 (dd, J=3.9, 1.5 Hz, 1H). MS (DCl/NH$_3$) m/e 489 (M+H)$^+$. Anal calcd for C$_{28}$H$_{44}$N$_2$O$_5$.1.0 TFA.0.5 H$_2$O: C, 58.91; H, 7.58; N, 4.58. Found: C, 58.91; H, 7.58; N, 4.45.

EXAMPLE 503 trans, trans-2-(2,2-Dimethylpentyl)-4-(1,3-benzodioxol-5-yl)-1-(N,N-di(n-butyl) aminocarbonylmethyl)-pyrrolidine-3-carboxylic Acid Ethyl 3,3-dimethylhexanoate was prepared using the general procedure of Cahiez et al., Tetrahedron Lett., 31, 7425 (1990). Using the procedures described in Example 502 and substituting ethyl 3,3-dimethylhexanoate for ethyl 3-methylhexanoate afforded the title compound, which was isolated by lyophilization from dilute aqueous TFANCH$_3$CN. $^1$H NMR (CDCl$_3$, 300 MHz) δ 0.80–0.99 (m, 15H), 1.10–1.37 (m, 8H), 1.43–1.58 (m, 4H), 1.77–1.97 (m, 2H), 3.48–3.12 (m, 5H), 3.60–3.69 (m, 1H), 3.75–3.86 (m, 1H), 3.95–4.16 (m, 2H), 4.28–4.4 (m, 2), 5.94 (s, 2H), 6.74 (d, J=7.8 Hz, 1H), 6.8 (dd, J=8.1, 1.5 Hz, 1H), 6.87 (d, J=1.8 Hz, 1H). MS (DCl/NH$_3$) m/e 503 (M+H)$^+$. Anal calcd for C$_{29}$H$_{46}$N$_2$O$_5$.1.05 TFA: C, 60.01; H, 7.62; N, 4.50. Found: C, 60.21; H, 7.37; N, 4.33.

EXAMPLE 504 trans,trans-2-(2-(1,3-Dioxo-2-yl)ethyl)-4-(1,3-benzodioxol-5-yl)-1-(N,N-di(n-butyl) aminocarbonylmethyl)-pyrrolidine-3-carboxylic Acid

EXAMPLE 504A

Ethyl 5-(1,3-dioxolyl)-3-oxopentanoate

The title compound was synthesized from ethyl acetoacetate and 2-bromomethyl-1,3-dioxane, according to the procedure of Huckin and Weiler, Tetrahedron Lett. 3927, (1971).

Sodium hydride 4.97 g (0.124 mol), as a 60% mineral oil dispersion, was weighed into a 250 mL flask, into which 80 ml of tetrahydrofuran was directly added. The flask was capped with septum cap, flushed with nitrogen, and cooled in an ice bath. To above stirred slurry was added dropwise 15.0 mL (0.118 mol) ethyl acetoacetate. After the addition was complete, the resulting mixture was stirred at 0° C. for additional 10 min. To above mixture was then added 48.4 mL (0.121 mol) n-butyl lithium, a 2.50 M solution in hexane, in a dropwise manner. The resulting orange color solution was stirred for 10 min before 13.5 mL (0.130 mol) bromomethyl-1,3-dioxane was added in one portion. The reaction mixture was then allowed to warm to room temperature and stirred for additional 120 min before it was then quenched by slow addition of 9.8 ml (ca. 0.12 mol) concentrated hydrochloric acid. The biphasic mixture was poured to 50 ml of water and extracted with 150 ml of ethyl ether. The aqueous layer was extracted thoroughly with additional ethyl ether. The ethereal extracts were combined, washed with 2×50 ml of saturated brine, dried over anhydrous magnesium sulfate, filtered and evaporated under reduced pressure to give an brown oily residue. The crude product was purified using silica gel flash chromatography eluting with 20% ether/hexane to give 5.40 g (20%) of b-keto ester as a light yellow oil.

EXAMPLE 504C trans,trans-2-(2-(1,3-Dioxo-2-yl)ethyl)-4-(1,3-benzodioxol-5-yl)-1-(N,N-di(n-butyl) aminocarbonylmethyl)-pyrrolidine-3-carboxylic Acid Using the procedures described in Example 502 and substituting ethyl 5-(1,3-dioxolyl)-2-oxopentanoate for ethyl 3-methylhexanoate afforded the title compound. $^1$H NMR (CDCl$_3$, 300 MHz) δ 0.93 (t, J=7.2 Hz, 3H), 0.95 (t, J=7.2 Hz, 3H), 1.23–1.38 (m, 4H), 1.52 (sextet, J=7.9 Hz, 4H), 1.85–1.95 (m, 2H), 2.02–2.17 (m, 2H), 3.18 (dd, J=6.0 Hz, 9.0 Hz, 2H), 3.30 (dd, J=9.0 Hz, 18.0 Hz, 2H), 3.35 (m, 1H), 3.79 (dd, J=3.6 Hz, 6.9 Hz, 1H), 3.83–3.88 (m, 3H), 3.97 (dd, J=4.8 Hz, 6.0 Hz, 1H), 4.05 (q, J=9.6 Hz, 2H), 4.30–4.40 (m, 1H), 4.37 (s, 2H), 4.87 (t, J=3.6 Hz, 1H), 5.94 (s, 2H), 6.73 (d, J=8.1 Hz, 1H), 6.79 (dd, J=1.8 Hz, 8.1 Hz, 1H), 6.87 (d, J=1.8 Hz, 1H). MS (APCl) (M+H)$^+$ at m/e 505. Anal calcd for C$_{27}$H$_{40}$N$_2$O$_7$.1.2 TFA: C, 55.05; H, 6.47; N, 4.37. Found: C, 55.12; H, 6.44; N, 4.27.

EXAMPLE 505 trans,trans-2-(2-(2-Tetrahydro-2H-pyran)ethyl)-4-(1,3-benzodioxol-5-yl)-1-(N,N-di(n-butyl) aminocarbonylmethyl)-pyrrolidine-3-carboxylic Acid

EXAMPLE 505A

Ethyl 5-(2-tetrahydro-2H-pyran)-3-oxopentanoate

Using the procedure of Huckin and Weiler, Tetrahedron Lett. 3927, (1971), the title compound was prepared from ethyl acetoacetate and 2-(bromomethyl)tetrahydro-2H-pyran as a light yellow oil.

EXAMPLE 505B trans,trans-2-(2-(2-Tetrahydro-2H-pyran)ethyl)-4-(1,3-benzodioxol-5-yl)-1-(N,N-di(n-butyl) aminocarbonylmethyl)-pyrrolidine-3-carboxylic Acid Using the procedures described in Example 502 and substituting ethyl 5-(2-tetrahydro-2H-pyran)-2- oxopentanoate for ethyl 3-methylhexanoate afforded the title compound as an amorphous solid. $^1$H NMR (CDCl$_3$, 300 MHz) as a mixture of two diastereoisomers: δ 0.89 (t, J=8.1 Hz, 3H), 0.89 (t, J=8.1 Hz, 3H), 0.91 (t, J=8.1 Hz, 3H), 0.91 (t, J=8.1 Hz, 3H), 1.20–1.40 (m, 10H), 1.42–1.66 (m, 18H), 1.71 (brm, 2H), 1.85 (brm, 2H), 1.96–2.23 (brm, 4H), 3.10–3.29 (m, 8H), 3.29–3.52 (m, 6H), 3.54–3.81 (m, 6H), 4.01 (q, J=9 Hz, 2H), 4.12–4.25 (m, 4H), 4.43 (d, J=9 Hz, 2H), 4.50 (d, J=2.7 Hz, 2H), 5.94 (s, 2H), 5.95 (s, 2H), 6.76 (s, 2H), 6.76 (s, 2H), 6.81 (s, 1H), 6.81 (s, 1H). MS (APCl) (M+H)$^+$ at m/e 517. Anal calcd for C$_{29}$H$_{44}$N$_2$O$_6$.1.4 TFA: C, 56.48; H, 6.77; N, 4.14. Found: C, 56.46; H, 6.99; N, 3.83.

EXAMPLE 506 trans, trans-2-(2,2,4-Trimethyl-3-pentenyl)-4-(1,3-benzodioxol-5-yl)-1-(N,N-di(n-butyl) aminocarbonylmethyl)-pyrrolidine-3-carboxylic Acid

EXAMPLE 506A

Methyl 3,3,5-trimethyl-4-hexenoate

To a slurry of isopropyltripenylphosphonium iodide (20.5 g, 47 mmol) in 200 mL of tetrahydrofuran was added n-butyllithium (27 mL of a 1.6M solution in hexane, 43 mmol), and the solution was briefly warmed to 0° C. After recooling, a solution of methyl 3,3-dimethyl-4-oxobutenoate (5.7 g, 40 mmol), prepared according to the procedure of Hudlicky et al., Synth. Commun., 16 169 (1986) in 10 mL of tetrahydrofuran was added, and the reaction was warmed to 0° C. for 30 min. The reaction was quenched with dilute hydrochloric acid, and partitioned with ethyl acetate. The organic layer was washed with water, and brine, dried with anhydrous magnesium sulfate, filtered, and the solvent was removed under reduced pressure. The residue was purified by flash chromatography on silica gel eluting with 10% ethyl acetate in hexanes to give 2.1 g (30%) of the title compound.

EXAMPLE 506B trans, trans-2-(2,2,4-Trimethyl-3-pentenyl)-4-(1,3-benzodioxol-5-yl)-1-(N,N-di(n-butyl) aminocarbonylmethyl)-pyrrolidine-3-carboxylic Acid Using the procedures described in Example 502 and substituting methyl 3,3,5-trimethyl-4-hexenoate for ethyl 3-methylhexanoate afforded the title compound, which was isolated by lyophilization from dilute aqueous TFA/CH$_3$CN. $^1$H NMR (CDCl$_3$, 300 MHz) δ 0.92 (t, J=7.2 Hz, 3H), 0.94 (t, J=7.2 Hz, 3H), 1.11 (s, 3H), 1.13 (s, 3H), 1.24–1.37 (m, 4H), 1.46–1.59 (m, 4H), 1.61 (d, J=1.2 Hz, 3H), 1.69 (d, J=1.2 Hz, 3H), 2.04–2.11 (m, 2H), 3.10–3.20 (m, 2H), 3.30–3.39 (m, 3H), 3.67–3.82 (m, 2H), 3.95–4.08 (m, 1H), 4.32 (m, 2H), 4.37–4.47 (m, 1H), 4.99 (s, 1H), 5.95 (s, 2H), 6.73 (d, J=7.8 Hz, 1H), 6.78 (dd, J=8.4, 1.2 Hz, 1H), 6.84 (d, J=1.2 Hz, 1H). MS (DCl/NH$_3$) m/e 515 (M+H)$^+$. Anal calcd for C$_{30}$H$_{46}$N$_2$O$_5$.1.05 TFA: C, 60.77; H, 7.48; N, 4.42. Found: C, 60.83; H, 7.20; N, 4.43.

EXAMPLE 507 trans, trans-2-(2,2,-Dimethyl-2-(1,3-dioxolan-2-yl) ethyl)-4-(1,3-benzodioxol-5-yl)-1-(N,N-di(n-butyl) aminocarbonylmethyl)-pyrrolidine-3-carboxylic Acid

EXAMPLE 507A

Methyl 3,3-dimethyl-3-(1,3-dioxolan-2-yl) propanoate

Methyl 3,3-dimethyl-4-oxobutanoate (10 g, 70 mmol), prepared according to the procedure of Hudlicky et al., Synth. Commun., 16 169 (1986), was dissolved in 40 mL of benzene, followed by addition of ethylene glycol (20 mL), and p-toluenesulfonic acid monohydrate (1.3 g). The reaction was refluxed with azeotropic removal of water for 1 hour. The reaction was poured into 200 mL of ether, washed with saturated sodium bicarbonate, water and brine, dried with anhydrous magnesium sulfate, filtered, and the solvent was removed under reduced pressure to give 12.4 g (94%) of the title compound.

EXAMPLE 507B trans, trans-2-(2,2,-Dimethyl-2-(1,3-dioxolan-2-yl) ethyl)-4-(1,3-benzodioxol-5-yl)-1-(N,N-di(n-butyl) aminocarbonylmethyl)-pyrrolidine-3-carboxylic Acid Using the procedures described in Example 502 and substituting methyl 3,3-dimethyl-3-(1,3-dioxolan-2-yl) propanoate for ethyl 3-methylhexanoate afforded the title compound, which was isolated by lyophilization from dilute aqueous TFA/CH$_3$CN. $^1$H NMR (CDCl$_3$, 300MHz) δ 0.82–1.00 (m, 12H), 1.24–1.40 (m, 4H), 1.43–1.64 (m, 5H), 1.76–1.84 (m, 1H), 2.93–3.00 (m, 1H), 3.15–3.47 (m, 6H), 3.60–3.70 (m, 3H), 3.74–3.95 (m, 5H), 4.48 (s, 1H), 5.94 (m, 2H), 6.72 (d, J=8.0 Hz, 1H), 6.83 (dd, J=8.0, 1.2 Hz, 1H), 6.94 (d, J=1.2 Hz, 1H). MS (DCl/NH$_3$) m/e 533 (M+H)$^+$. Anal calcd for C$_{29}$H$_{44}$N$_2$O$_7$.1.1 TFA.0.2 H$_2$O: C, 56.63; H, 6.93; N, 4.23. Found: C, 56.60; H, 6.96; N, 4.25.

EXAMPLE 508 trans,trans-2-(2-(1,3-Dioxo-2-yl)ethyl)-4-(1,3-benzodioxol-5-yl)-1-[[N-4-heptyl-N-(2-methyl-3-fluorophenyl)-]amino carbonylmethyl]-pyrrolidine-3-carboxylic Acid

EXAMPLE 508A

4-Heptanol

To an ice cooled solution of 1.14 g (10.0 mmol) of 4-heptanone in 20 mL of diethyl ether was added 370 mg (10.0 mmol) of LiAlH$_4$, in portions to keep ether reflux at a minimum. After 45 minutes, the reaction was quenched by sequential dropwise addition of 0.4 mL H$_2$O, 0.4 mL 15% (w/v) NaOH$_{(aq)}$, and 1.2 mL H$_2$O. After stirring another 45 minutes, MgSO$_4$ was added until the salts were free flowing, then the reaction was filtered. The salts were washed with diethyl ether (3×5 mL), then the filtrate and washings were concentrated to a colorless oil. Yield 1.16 g (100%).

EXAMPLE 508B

4-Methanesulfonyloxyheptane

To an ice cooled solution of 834 mg (7.19 mmol) of 4-heptanol in 35 mL of CH$_2$Cl$_2$ was added 1.5 mL of triethylamine. Next, 0.7 mL (9 mmol) of methanesulfonyl chloride was added, dropwise, over 1 minute. The mixture was stirred at 0° C. for 30 minutes, then extracted with H$_2$O (1×15 mL), 5% NH$_4$OH (2×15 mL), 1M HCl (2×15 mL), and brine (1×15 mL), dried over MgSO$_4$, filtered, and concentrated to an oil. Yield 1.31 g (94%). $^1$H NMR (300 MHz, CDCl$_3$) d 0.96 (t, 6, J=9), 1.43 (m, 4), 1.64 (m, 4), 3.00 (s, 3), 4.73 (quintet, 1 J=5).

EXAMPLE 508C

4-Fluoro-3-methylaniline

To a solution of 20 g (129 mmol) of 2-fluoro-5-nitrotoluene in 400 mL of ethanol was added 2 g of 10%

Pd—C. The mixture was shaken under 45 P.S.I. $H_2$ until hydrogen uptake ceased. The catalyst was filtered away and washed with ethanol, then the combined filtrate and washings were concentrated to 15.2 g (94%) of a colorless oil.

EXAMPLE 508D

N-Heptyl-4-fluoro-3-methylaniline

To a solution of 4.10 g (3.28 mmol) of 4-fluoro-3-methylaniline in 30 mL of acetonitrile was added 7.64 g (3.93 mmol) of 4-methanesulfonyloxyheptane, and 3.4 g (4.1 mmol) of $NaHCO_3(s)$. The mixture was stirred at reflux for 24 hours, then poured into 150 mL of $H_2O$ and extracted with diethyl ether (2×30 mL). The combined ether layers were back extracted with brine (1×30 mL), dried over $MgSO_4$, filtered, and concentrated to an oil. This was purified via silica gel chromatography, eluting with 97.5: 2.5 hexanes: ethyl acetate, to give 2.56 g (35%) of a pale yellow oil.

EXAMPLE 508E

N,N-(4-Heptyl)-(4-fluoro-3-methyl) phenylbromoacetamide

To an ice cooled solution of 4.88 g (21.9 mmol) of N-(4-heptyl)-4-fluoro-3-methylaniline and 4.9 mL (61 mmol) of pyridine in 100 mL of toluene was added a solution of 4.90 mL (56.2 mmol) of bromoacetyl bromide in 7 mL of toluene. The solution was stirred for 24 hours, gradually warming to 25° C., then extracted with 1M HCl (1×100 mL). The aqueous layer was back extracted with diethyl ether (1×50 mL), then the combined organic layers were washed with $H_2O$ (2×50 mL), saturated $NaHCO_{3(aq)}$ (2×50 mL), and brine (1×50 mL), dried over $MgSO_4$, filtered, and concentrated in vacuo to an oil. This was purified via silica gel chromatography, eluting with 90:10 hexanes: ethyl acetate to give 7.48 g (99%) of a light yellow oil. $^1H$ NMR (300 MHz, $CDCl_3$) d 0.94 (t, 6, J=5), 1.33 (m, 4), 1.43 (m, 4), 2.30 (s, 1.5), 2.31 (s, 1.5), 3.54 (s, 2), 4.72 (quintet, 1, J=5), 6.96–7.04 (m, 2), 7.07(d, 1, J=7).

EXAMPLE 508F trans,trans-2-(2-(1,3-Dioxol-2-yl)ethyl)-4-(1,3-benzodioxol-5-yl)-1-[[N-4-heptyl-N-2-methyl-3-fluorophenyl)-] amino carbonylmethyl]-pyrrolidine-3-carboxylic Acid Using the procedures described in Example 502, substituting ethyl 5-(1,3-dioxolyl)-2-oxopentanoate for ethyl 3-methylhexanoate and N,N-(4-heptyl)-(4-fluoro-3-methyl) phenyl-bromoacetamide for N,N-dibutylbromoacetamide afforded the title compound as an amorphous solid. $^1H$ NMR ($CDCl_3$, 300 MHz) δ 0.93 (brt, 6H), 1.23–1.47 (m, 8H), 1.67–2.10 (m, 4H), 2.32 (s, 3H), 3.16 (t, J=9.0 Hz, 1H), 3.52–3.67 (brm, 2H), 3.73 (t, J=9.0 Hz, 1H), 3.81–4.02 (m, 6H), 4.13 (brm, 1H), 4.72 (quintet, J=6.9 Hz, 1H), 4.86 (t, J=4.0 Hz, 1H), 5.93 (s, 2H), 6.72 (d, J=8.1 Hz, 1H), 6.78 (dd, J=1.8 Hz, 8.1 Hz, 1H), 6.85 (d, J=1.8 Hz, 1H), 6.96 (m, 2H), 7.08 (t, J=9.0 Hz, 1H). MS ($DCl/NH_3$) $(M+H)^+$ at m/e 599. Anal Calcd for $C_{33}H_{43}N_2O_7F.0.8$ TFA: C, 60.24; H, 6.40; N, 4.06. Found: C, 60.21; H, 6.14; N, 3.86.

EXAMPLE 509 trans,trans-2-(2-(1,3-Dioxol-2-yl)ethyl)-4-(1,3-benzodioxol-5-yl)-1-(N,N-di(n-butyl) aminocarbonylmethyl)-pyrrolidine-3-carboxylic Acid Using the procedures described in Example 502, substituting ethyl 5-(1,3-dioxolyl)-2-oxopentanoate for ethyl 3-methylhexanoate and 6-methoxypiperonal for piperonal afforded the title compound as an amorphous solid. $^1H$ NMR ($CDCl_3$, 300 MHz) δ 0.93 (t, J=7.8 Hz, 3H), 0.95 (t, J=7.8 Hz, 3H), 1.31 (m, 4H), 1.53 (m, 4H), 1.90 (m, 2H), 2.09 (m, 2H), 3.19 (dd, J=8.4 Hz, 8.4 Hz, 2H), 3.30 (q, J=9.6 Hz, 2H), 3.25–3.42 (m, 1H), 3.73 (q, J=10.5 Hz, 1H), 3.78–3.94 (m, 4H), 3.88 (s, 3H), 3.96 (dd, J=5.1 Hz, 6.0 Hz, 1H), 4.03 (dd, J=3.0 Hz, 6.3 Hz, 2H), 4.33 (m, 3H), 4.87 (t, J=3.6 Hz, 1H), 5.94 (s, 2H), 6.53 (d, J=1.8 Hz, 1H), 6.63 (d, J=1.8 Hz, 1H). MS ($DCl/NH_3$) $(M+H)^+$ at m/e 535. Anal calcd for $C_{28}H_{42}N_2O_8.1.05$ TFA: C, 55.25; H, 6.63; N, 4.28. Found: C, 55.39; H, 6.66; N, 4.26.

EXAMPLE 510 trans,trans-2-((2-Methoxyphenoxy)-methyl)-4-(1,3-benzodioxol-5-yl)-1-(N,N-di(n-butyl) aminocarbonylmethyl)-pyrrolidine-3-carboxylic Acid Using the procedures described in Example 502, substituting o-methoxyphenoxyacetic acid for 3-methylhexanoic acid, the above compound was prepared as an amorphous solid. $^1H$ NMR ($CDCl_3$, 300 MHz) δ 0.85 (t, J=7 Hz, 3H), 0.90 (t, J=7 Hz, 3H), 1.15–1.35 (m, 4H), 1.40–1.55 (m, 4H), 3.05–3.25 (m, 4H), 3.28–3.55 (m, 4H), 3.58–3.68 (m, 1H), 3.75–3.80 (m, 1H), 3.82 (s, 3H), 3.91 (d, J=14 Hz, 1H), 4.05–4.15 (m, 1H), 4.23–4.33 (m, 1H), 5.91 (s, 2H), 6.70 (d, J=8 Hz, 1H), 6.82–6.95 (m, 5H), 7.03 (s, 1H). MS ($DCl/NH_3$) $(M+H)^+$ at m/e 541. Anal calcd for $C_{30}H_{40}N_2O_7$: C, 66.65; H, 7.46; N, 5.18. Found: C, 66.37; H, 7.61; N, 5.09.

EXAMPLE 511

(2S, 3R, 4S)-2-(2,2-Dimethylpentyl)-4-(1,3-benzodioxol-5-yl)-1-(N-4-heptyl-N-(4-fluoro-3-methylphenyl))aminocarbonylmethyl)-pyrrolidine-3-carboxylic Acid

EXAMPLE 511A trans, trans-N-tert-Butoxycarbonyl-2-(2,2-dimethylpentyl)-4-(1,3-benzodioxol-5-yl)-pyrrolidine-3-carboxylic Acid Ethyl trans, trans-2-(2,2-dimethylpentyl)-4-(1,3-benzodioxol-5-yl)-pyrrolidine-3-carboxylate (2.5 g, 6.9 mmol), prepared according to Example 503, was dissolved in 50 mL of methylene chloride and di-tert-butyldicarbonate (1.5 g) was added. After stirring overnight at room temperature, the solvent was removed under reduced pressure and the residue was purified by flash chromatography on silica gel eluting with 10% ethyl acetate/hexanes to give the ethyl ester of the title compound (2.8 g) as a colorless oil. The ester was dissolved in 50 mL of ethanol followed by addition of sodium hydroxide (10 mL of a 5M aqueous solution). After stirring for 20 hours at room temperature, the solvent was removed under reduced pressure, and the residue was dissolved in 150 mL of water, and acidified with concentrated phosphoric acid. The mixture was extracted with chloroform (3×50 mL), and the organic layers were washed with brine, dried over anhydrous magnesium sulfate, filtered, and the solvent was removed under reduced pressure to give the title compound (2.4 g) as a white foam.

EXAMPLE 511B

Methyl trans, trans-2-(2,2-dimethylpentyl)-4-(1,3-benzodioxol-5-yl)-1-(N-4-heptyl-N-(4-fluoro-3-methylphenyl))aminocarbonylmethyl)-pyrrolidine-3-carboxylate: As a Single Enantiomer The product from Example 510A (1.97 g, 4.5 mmol) was dissolved in 20 mL of THF and cooled to 0° C., followed by addition of DMF (0.017 mL, 5%), and oxalyl chloride (0.437 mL, 5.00 mmol). After 1 hour, solvent was removed at 0° C. under a stream of nitrogen. The residue was dissolved in 5 mL of benzene and evaporated. In a separate flask, (S)-4-benzyl-2-oxazolidinone (1.2 g, 6.8 mmol) was dissolved in 30 mL of THF followed by addition of n-butyllithium (4.0 mL of a 1.6M solution in hexanes) at 0° C., and the slurry was stirred for 15 min. The acid chloride was dissolved in 20 mL of THF and cooled to 0° C., followed by dropwise addition of the lithium oxazolide suspension via cannula. After 30 min, the reaction was partitioned between ether and saturated bicarbonate. The organic phase was washed with water then brine, dried over anhydrous magnesium sulfate, filtered, and the solvent was removed under reduced pressure. The residue was purified by flash chromatography on silica gel eluting with 15% ethyl acetate/hexanes to give the undesired diastereomer (1.17 g, 43%), then elution with 20% ethyl acetate/hexanes gave the desired diastereomer (1.04 g, 38%).

The desired diastereomer of the N-acyloxazolidinone (0.84 g, 1.42 mmol) was dissolved in 2.5 mL of dichloromethane, and 2.5 mL of trifluoroacetic acid was added. After 30 min, the volatiles were removed under a stream of nitrogen, and the residue was twice dissolved in 5 mL of toluene and evaporated under reduced pressure.

The TFA salt was stirred with 4 mL of acetonitrile followed by addition of diisopropylethyl amine (1.0 mL, 5.7 mmol), and N-4-heptyl-N-(4-fluoro-3-methylphenyl) bromoacetamide (589 mg, 1.7 mmol) as a solution in 2 mL of acetonitrile. After 21 hours, the reaction was warmed to 50° C. for 3.5 hours. The reaction was cooled, the solvent removed under reduced pressure, and the residue was purified by flash chromatography on silica gel eluting with 20–30% ethyl acetate/hexanes to give 0.939 g of amide as a colorless oil.

The above amide (200 mg, 0.26 mmol) was dissolved in 2.0 mL of THF and 0.7 mL of water. Solid lithium hydroxide monohydrate (22 mg, 0.53 mmol) was added at 0° C., followed by 30% hydrogen peroxide (0.55 mL, 0.55 mmol). After 1 hour, the reaction was warmed to room temperature. After an additional hour, the reaction was partitioned between 1:1 ethyl acetate:hexanes and water, 0.15 g of sodium thiosulfate was added and the mixture was mixed thoroughly. The organic layer was washed with water and brine, dried over anhydrous magnesium sulfate, filtered, and the solvent was removed under reduced pressure. The crude residue was dissolved in 2 mL of ether, and 1 mL of methanol. A solution of (trimethylsilyl)diazomethane in hexanes was added dropwise until the yellow color remained. The reaction was quenched by addition of 2 drops of glacial acetic acid, and the solvent was removed under reduced pressure. The residue was purified by flash chromatography on 10 g of silica gel eluting with 15–20% ethyl acetate/hexanes to give 70 mg of the title compound as a crystalline solid (mp 137.5° C.).

EXAMPLE 511C (2S, 3R, 4S)-trans, trans-2-(2,2-Dimethylpentyl)-4-(1,3-benzodioxol-5-yl)-1-(N-4-heptyl-N-(4-fluoro-3-methylphenyl))aminocarbonylmethyl)-pyrrolidine-3-carboxylate The product from Example 510B (65 mg, 0.10 mmol) was dissolved in 1.0 mL of methanol and sodium hydroxide (0.1 mL of a 5M aqueous solution) was added. After 2 hours, the reaction was warmed to reflux. After 6 hours, the reaction was cooled, and the solvent was removed under reduced pressure. The residue was dissolved in water and acidified with concentrated phosphoric acid. The aqueous solution was washed with chloroform (3×5 mL), which was then washed with brine, dried with anhydrous magnesium sulfate, filtered and evaporated under reduced pressure. The title compound was isolated by lyophilization from dilute aqueous TFA/CH$_3$CN. $^1$H NMR (CDCl$_3$, 300 MHz) d 0.78–0.95 (m, 15H), 1.04–1.46 (m, 12H), 1.76–2.95 (m, 2H), 2.31 (s, 3H), 3.23–3.33 (m, 1H), 3.47–3.58 (m, 1H), 3.6≧3.75 (m, 2H), 3.80–3.95 (m, 2H), 4.05–4.15 (m, 1H), 4.73 (m, 1H), 5.94 (s, 2H), 6.70–6.80 (m, 2H), 6.82–6.93 (m, 2H), 6.96–7.14 (m, 2H). MS (DCI/NH$_3$) m/e 597 (M+H)$^+$. Anal calcd for C$_{35}$H$_{49}$N$_2$FO$_5$.0.05H$_2$O.0.8TFA: C, 63.81; H, 7.30; N, 4.07. Found: C, 63.84; H, 7.18; N, 3.94. [a]$_D^{21}$=+46° (c 2.7 g/L, CHCl$_3$)

EXAMPLE 512 trans,trans-2-(2-(2-Oxopyrrolidin-1-yl)ethyl)-4-(1,3-benzodioxol-5-yl)-1-(N,N-di(n-butyl) aminocarbonylmethyl)-pyrrolidine-3-carboxylic Acid

EXAMPLE 512A

2-Oxopyrrolidin-1-ylpropionic Acid

To a stirred solution of 5.0 mL (40.5 mmol) 2-oxopyrrolidin-1-ylpropionitrile in 15 mL of dioxane was added 8.1 mL of hydrochloric acid, a 6.0 M aqueous solution. The resulting mixture was then refluxed at 110° C. over night. The reaction mixture was then allowed to cool to room temperature, extracted with methylene chloride three times. The extracts were combined and washed with saturated brine solution once, dried over anhydrous sodium sulfate, filtered and evaporated under reduced pressure to give 1.60 g (25%) of acid as a brown oil.

EXAMPLE 512B

Ethyl 5-(2-oxopyrrolidin-1-yl)-3-oxopentanoate

The title compound was prepared from the above acid by adapting the method of Bram and Vilkas, Bul. Chem. Soc. Fr., 945 (1964).

EXAMPLE 512C trans,trans-2-(2-(2-Oxopyrrolidin-1-yl)ethyl)-4-(1,3-benzodioxol-5-yl)-1-(N,N-di(n-butyl) aminocarbonylmethyl)-pyrrolidine-3-carboxylic Acid Using the procedures described in Example 502, substituting ethyl 5-(2-oxopyrrolidin-1-yl)-3-oxopentanoate for ethyl 3-methylhexanoate afforded the title compound as an amorphous solid. $^1$H NMR (CDCl$_3$, 300 MHz) δ 0.91 (t, J=7.5 Hz, 3H), 0.94 (t, J=7.5 Hz, 3H), 1.23–1.38 (m, 4H), 1.44–1.60 (m, 4H), 2.05 (t, J=6.9 Hz, 2H), 2.12–2.25 (m, 1H), 2.38 (td, J=4.2 Hz, 8.4 Hz, 2H), 2.47–2.61 (m, 1H), 3.17 (dd, J=6.0 Hz, 8.7 Hz, 2H), 3.24 (t, J=9 Hz, 1H), 3.32 (t, J=7.8 Hz, 2H), 3.38–3.48 (m, 3H), 3.52 (t, J=9 Hz, 1H), 3.66 (t, J=6.9 Hz, 1H), 3.96 (m, 2H), 4.14 (m, 1H), 4.38 (brs, 2H), 5.93 (s, 2H), 6.74 (d, J=8.1 Hz, 1H), 6.89 (dd, J=1.8 Hz, 8.1 Hz, 1H), 6.87 (d, J=1.8 Hz, 1H). MS (DCI/NH$_3$) (M+H)$^+$ at m/e 516. Anal calcd for C$_{28}$H$_{41}$ N$_3$O$_6$.1.4 TFA: C, 54.78; H, 6.33; N, 6.22. Found: C, 54.69; H, 6.33; N, 6.14.

EXAMPLE 513 trans,trans-2-(2-(1,3-Dioxol-2-yl)ethyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic Acid Using the procedures described in Example 502, substituting ethyl 5-(1,3-dioxolyl)-2-oxopentanoate for ethyl 3-methylhexanoate, N₄-heptyl-N-(4-fluoro-3-methylphenyl) bromoacetamide for N,N-dibutyl bromoacetamide and 6-methoxypiperonal for piperonal afforded the title compound as an amorphous solid. $^1$H NMR (CDCl$_3$, 300 MHz) δ 0.93 (br t, 6H), 1.23–1.47 (m, 8H), 1.67–2.10 (m, 4H), 2.32 (s, 3H), 3.16 (t, J=9 Hz, 1H), 3.60–4.03 (m, 8H), 3.88 (s, 3H), 4.21 (brs, 1H), 4.72 (quintet, J=6.6 Hz, 1H), 4.86 (t, J=3.6 Hz, 1H), 5.93 (s, 2H), 6.49 (s, 1H), 6.61 (s, 1H), 6.96 (m, 2H), 7.08 (t, J=9 Hz, 1H). MS (DCl/NH$_3$) (M+H)$^+$ at m/e 629. Anal calcd for C$_{34}$H$_{45}$N$_2$O$_8$F·1.0 TFA: C, 58.21; H, 6.24; N, 3.77. Found: C, 58.11; H, 6.11; N, 3.58.

EXAMPLE 514 trans,trans-2-(2,2-Dimethylpentyl)-4-(7-methoxy-1, 3-benzodioxol-5-yl)-1-(N,N-di(n-butyl) aminocarbonylmethyl)-pyrrolidine-3-carboxylic Acid Using the procedures described in Example 502, substituting ethyl 5-methyl-3-oxooctanoate for ethyl 3-methylhexanoate and 6-methoxypiperonal for piperonal afforded the title compound as an amorphous solid. $^1$H NMR (CDCl$_3$, 300 MHz) δ 0.81 (s, 3H), 0.84 (s, 3H), 0.86 (t, J=6.9 Hz, 3H), 0.93 (t, J=6.9 Hz, 3H), 0.96 (t, J=6.9 Hz, 3H), 1.09–1.38 (m, 8H), 1.45–1.59 (m, 4H), 1.84–2.00 (m, 2H), 3.15 (dd, J=6.9 Hz, 10.0 Hz, 2H), 3.30–3.42 (m, 3H), 3.72 (t, J=10.5 Hz, 1H), 3.86 (t, J=10.5 Hz, 1H), 3.88 (s, 3H), 4.02 (q, J=10.0 Hz, 1H), 4.12 (d, J=16.8 Hz, 1H), 4.29 (d, J=16.8 Hz, 1H), 4.41 (brm, 1H), 5.94 (s, 1H), 6.52 (d, J=1.8 Hz, 1H), 6.67 (d, J=1.8 Hz, 1H). MS (DCl/NH$_3$) (M+H)$^+$ at m/e 533. Anal calcd for C$_{30}$H$_{48}$N$_2$O$_6$·0.9 TFA: C, 60.12; H, 7.76; N, 4.41. Found: C, 60.18; H, 7.62; N, 4.33.

EXAMPLE 515 trans,trans-2-(2,2-dimethylpentyl)-4-(2,3-dihydro-benzofuran-5-yl)-1-(N,N-di(n-butyl) aminocarbonylmethyl)-pyrrolidine-3-carboxylic Acid Using the procedures described in Example 502, substituting ethyl 3,3-dimethylhexanoate for ethyl 3-methylhexanoate and 2,3-dihydro-benzofuran-5-carbaldehyde for piperonal afforded the title compound as an amorphous solid by lyophylization with CH$_3$CN/TFA/H$_2$O. $^1$H NMR (300 MHz, CDCl$_3$) δ 0.83 (s, 3H), 0.85 (s, 3H), 0.86 (t, J=7.2 Hz, 3H), 0.92 (t, J=7.2 Hz, 3H), 0.95 (t, J=7.2 Hz, 3H), 1.09–1.39 (m, 8H), 1.44–1.59 (m, 4H), 1.88 (dd, J=15.0, 7.2 Hz, 1H), 2.00 (d, J=15.0 Hz, 1H), 3.09 (m, 2H), 3.18 (t, J=9.0 Hz, 2H), 3.27–3.38 (m, 3H), 3.65–3.95 (m, 2H), 4.05 (q, J=10.0 Hz, 1H), 4.18 (d, J=16.8 Hz, 1H), 4.30–4.45 (m, 2H), 4.55 (t, J=9.0 Hz, 2H), 6.70 (d, J=8.4 Hz, 1H), 7.04 (dd, J=8.4, 2.1 Hz, 1H), 7.23 (brs, 1H). MS (DCl/NH$_3$) at m/e 501 (M+H)$^+$. Anal calc'd for C$_{30}$H$_{48}$N$_2$O$_4$·1.05 TFA: C, 62.14; H, 7.97; N, 4.51. Found: C, 62.19; H, 8.00; N, 4.43.

EXAMPLE 516 trans,trans-2-(2,2,-Dimethyl-2-(1,3-dioxolan-2-yl) ethyl)-4-(1-methoxy-1,3-benzodioxol-5-yl)-1-(N,N-di(n-butyl)aminocarbonylmethyl)-pyrrolidine-3-carboxylic Acid Using the procedures described in Example 502, substituting methyl 3,3-dimethyl-3-(1,3-dioxolan-2-yl)propanoate for ethyl 3-methylhexanoate and 6-methoxypiperonal for piperonal afforded the title compound as an amorphous solid by lyophylization with CH$_3$CN/TFA/H$_2$O. $^1$H NMR (CDCl$_3$, 300 MHz) δ 0.93 (t, J=7.2 Hz, 3H), 0.94 (t, J=7.2 Hz, 3H), 0.95 (s, 3H), 0.96 (s, 3H), 1.31 (sext, J=7.2 Hz, 4H), 1.45 (m, 4H), 1.93 (dd, J=15.9, 6.0 Hz, 1H), 2.13 (d, J=15.9 Hz, 1H), 3.20 (dd, J=7.7, 7.7 Hz, 1H), 3.26–3.40 (m, 3H), 3.60 (m, 1H), 3.75–3.86 (m, 3H), 3.88 (s, 3H), 3.93–4.01 (m, 3H), 4.00–4.11 (m, 1H), 4.23 (d, J=15.9 Hz, 1H), 4.37–4.48 (m, 2H), 4.49 (s, 1H), 5.94 (s, 2H), 6.51 (d, J=2.1 Hz, 1H), 6.64 (d, J=2.1 Hz, 1H). MS (DCl/NH$_3$) at m/e 563 (M+H)$^+$. Anal calcd for C$_{30}$H$_{46}$N$_2$O$_8$·0.9 TFA: C, 57.41; H, 7.11; N, 4.21; found: C, 57.35; H, 6.86; N, 4.05.

EXAMPLE 517 trans,trans-2-(2-(2-Methoxyphenyl)-ethyl)-4-(1,3-benzodioxol-5-yl)-1-(N,N-di(n-butyl) aminocarbonylmethyl)-pyrrolidine-3-carboxylic Acid Using the procedures described in Example 502, substituting o-methoxyphenylpropionic acid for 3-methylhexanoic acid, the above compound was prepared as an amorphous solid. $^1$H NMR (CDCl$_3$, 300 MHz) δ 0.85 (t, J=7 Hz, 3H), 0.91 (t, J=7 Hz, 3H), 1.10–1.27 (m, 4H), 1.42–1.60 (m, 4H), 1.72–1.89 (m, 1H), 1.91–2.02 (m, 1H), 2.55–2.77 (m, 2H), 2.94 (t, J=6 Hz, 1H), 3.05–330 (m, 6H), 3.59–3.82 (m, 3H), 3.73 (d, J=14 Hz, 1H), 3.77 (s, 3H), 5.91 (s, 2H), 6.70 (d, J=8 Hz, 1H), 6.78–6.88 (m, 3H), 6.92 (d, J=2 Hz, 1H), 7.08–7.19 (m, 2H). MS (DCl/NH$_3$) (M+H)$^+$ at m/e 539. Anal calcd for C$_{31}$H$_{42}$N$_2$O$_6$: C, 69.12; H, 7.86; N, 5.20. Found: C, 68.89; H, 7.70; N, 4.99.

EXAMPLE 518 trans, trans-2-(2,2-Dimethyl-3-(E)-pentenyl)-4-(1-methoxy-1,3-benzodioxol-5-yl)-1-(N,N-di(n-butyl) aminocarbonylmethyl)-pyrrolidine-3-carboxylic Acid

EXAMPLE 518A

4-Methyl-3-penten-2-ol

To a stirred solution of 3-methyl-2-butenal (8.7 g, 103 mmol) in 100 mL of tetrahydrofuran under N$_2$ at 0° C. was added methylmagnesium bromide (38 mL of a 3.0M solution in ethyl ether, 114 mmol) dropwise. The resulting mixture was allowed to warm to room temperature slowly and stirred at room temperature for 1 hour before it was quenched with 25 mL of saturated NH$_4$Cl. The resulting biphasic mixture was partitioned between ethyl ether and water. The organic layer was washed with brine, dried with anhydrous magnesium sulfate, filtered, and the solvent was removed under reduced pressure to give 8.4 g (81%) of alcohol as a colorless oil.

EXAMPLE 518B trans-Ethyl 3,3-dimethyl-4-pentenoate

A mixture of 4-methyl-3-penten-2-ol (7.4 g, 74 mmol), triethyl orthoacetate (13.6 mL, 74 mmol) and propionic acid (0.28 mL, 3.7 mmol) was heated at 150° C. for 7 hours. The product was then distilled under normal pressure (200–220° C.) to give 5.0 g of crude ester as a colorless oil.

EXAMPLE 518C trans, trans-2-(2,2-Dimethyl-3-(E)-pentenyl)-4-(1-methoxy-1,3-benzodioxol-5-yl)-1-(N,N-di(n-butyl) aminocarbonylmethyl)-pyrrolidine-3-carboxylic Acid Using the procedures described in Example 502, substituting trans-ethyl 3,3-dimethyl-4-pentenoate for ethyl 3-methylhexanoate and 6-methoxypiperonal for piperonal afforded the title compound as an amorphous solid by lyophilization from dilute aqueous TFA/CH$_3$CN. $^1$H NMR (CDCl$_3$, 300 MHz) δ 0.92 (t, J=7.2 Hz, 3H), 0.95 (t, J=7.2 Hz, 3H), 0.97 (s, 3H), 0.99 (s, 3H), 1.31 (sextet, J=7.2 Hz, 4H), 1.52 (quintet, J=7.2 Hz, 4H), 1.58 (d, J=5.4 Hz, 3H), 1.92 (dd, J=15.0, 6.6 Hz, 1H), 2.04 (d, J=15.0 Hz, 1H), 3.15 (dd, J=7.8, 7.8 Hz, 1H), 3.30–3.40 (m, 3H), 3.75 (m, 2H), 3.87 (s, 3H), 3.99 (q, J=9 Hz, 2H), 4.11–4.30 (m, 3H), 5.29 (d, J=15.6 Hz, 1H), 5.38 (dd, J=15.6, 6 Hz, 1H), 5.94 (s, 2H), 6.50 (d, J=1.8 Hz, 1H), 6.63 (d, J=1.8 Hz, 1H). MS (DCI/NH$_3$) at m/e 531 (M+H)$^+$. Analysis calc'd for C$_{30}$H$_{46}$N$_2$O$_6$·0.95 TFA: C, 59.95; H, 7.41; N, 4.38; found: C, 60.00; H, 7.33; N, 4.35.

EXAMPLE 519 trans, trans-2-(3-(2-pyridyl)ethyl)-4-(1,3-benzodioxol-5-yl)-1-(N,N-di(n-butyl)aminocarbonylmethyl)-pyrrolidine-3-carboxylic Acid

EXAMPLE 519A

3-(2-Pyridyl)-propionic Acid

In a 50 mL round-bottomed flask equipped with a stirring bar was placed 3-(2-pyridyl)-propanol (1 g, 7.6 mmol), water (13 mL) and concentrated sulfuric acid (0.5 g, 5.1 mmol). To this stirred solution was added over a period of 30 min potassium permanganate (1.8 g, 11.3 mmol) while the reaction temperature was maintained at 50° C. After the addition was completed, the mixture was held at 50° C. until the color of the reaction mixture turned brown, then heated at 80° C. for 1 hour and filtered. The filtrate was evaporated to dryness to yield quantitatively the desired acid (1.14 g) suitable for next step without further purification. To prepare a pure acid, the residue thus obtained was boiled in ethanol (10 mL) in the presence of charcoal (0.1 g) for 5 min, filtered and cooled to give crystalline 3-(2-pyridyl)-propionic acid (0.88 g, 78%).

EXAMPLE 519B trans, trans-2-(3-(2-pyridyl)ethyl)-4-(1,3-benzodioxol-5-yl)-1-(N,N-di(n-butyl)aminocarbonylmethyl)-pyrrolidine-3-carboxylic Acid Using the procedure described in Example 502, the title compound was isolated by lyophilization from dilute aqueous TFA/CH$_3$CN as an amorphous solid. 1H NMR (CDCl$_3$, 300 MHz) δ 8.65 (d, J=6.0 Hz, 1H), 8.06 (t, J=6.91 Hz, 1H), 7.70 (d, J=9.0 Hz, 1H), 7.51 (t, J=6.91 Hz, 1H), 6.82–6.66 (m, 3H), 5.91 (s, 2H), 4.45 (s, 2H), 4.29–4.18 (m, 1H), 4.04 (dd, J=20.1, 10.5 Hz, 1H), 3.84 (t, J=12.6 Hz, 1H), 3.62 (dd, J=13.8, 9.6 Hz, 1H), 3.46–3.13 (m, 7H), 2.51 (broad s, 2H), 1.60–1.43 (m, 4H), 1.37–1.22 (m, 4H), 0.91 (t, J=8.4 Hz, 6H). MS (DCl/NH$_3$) m/e 510 (M+H)$^+$. Anal calcd for C$_{29}$H$_{39}$N$_3$O$_5$·1.75 TFA: C, 55.04; H, 5.79; N, 5.92. Found: C, 55.08; H, 5.64; N, 5.81.

EXAMPLE 520

(2S, 3R, 4S)-2-(2-(2-oxopyrrolidin-1-yl)ethyl)-4-(1,3-benzodioxol-5-yl)-1-(N,N-di(butyl)aminocarbonylmethyl)-pyrrolidine-3-carboxylic Acid

EXAMPLE 520A

(2S, 3R, 4S)-Ethyl-2-(2-(2-oxopyrrolidin-1-yl)ethyl)-4-(1,3-benzodioxol-5-yl)pyrrolidine-3-carboxylate-(S)-Mandelate The racemic amino ester from Example 512 (3.45 g, 8.98 mmol) in 10 mL of ethyl acetate was treated with (S)-(+)-mandelic acid (0.75 g, 4.93 mmol). Upon the formation of the clear solution, hexane was dropped in slowly with stirring till the solution became light cloudy. The solution was left stirred at room temperature over night. The crystals was then collected by filtration, recrystalized from ethyl acetate/hexane twice to give a yield of 800 mg (17%) of pure salt.

EXAMPLE 520B

(2S, 3R, 4S)-Ethyl-2-(2-(2-oxopyrrolidin-1-yl)ethyl)-4-(1,3-benzodioxol-5-yl)-1-(N,N-di(n-butyl)aminocarbonylmethyl)-pyrrolidine-3-carboxylate To a stirred solution of pure mandelate (150 mg, 0.28 mmol) in CH$_3$CN was added N,N-dibutylbromoacetamide (84 mg, 0.34 mmol) and diisopropylethylamine (98 uL, 0.56 mmol). The resulting mixture was stirred at room temperature over night. Solvent was then removed under reduced pressure and the crude product was purified by silica gel flash chromatography to give 140 mg (90% yield) of the title compound.

EXAMPLE 520C

(2S, 3R, 4S)-2-(2-(2-oxopyrrolidin-1-yl)ethyl)-4-(1,3-benzodioxol-5-yl)-1-(N,N-di(n-butyl)aminocarbonylmethyl)-pyrrolidine-3-carboxylic Acid Using the procedures described in Example 502, the title compound was prepared as an amorphous solid by lyophylization with CH$_3$CN/TFA/H$_2$O. $^1$H NMR (CDCl$_3$, 300 MHz) δ 0.91 (t, J=7.5 Hz, 3H), 0.94 (t, J=7.5 Hz, 3H), 1.23–1.38 (m, 4H), 1.44–1.60 (m, 4H), 2.05 (t, J=6.9 Hz, 2H), 2.12–2.25 (m, 1H), 2.38 (td, J=4.2 Hz, 8.4 Hz, 2H), 2.47–2.61 (m, 1H), 3.17 (dd, J=6.0 Hz, 8.7 Hz, 2H), 3.24 (t, J=9 Hz, 1H), 3.32 (t, J=7.8 Hz, 2H), 3.38–3.48 (m, 3H), 3.52 (t, J=9 Hz, 1H), 3.66 (t, J=6.9 Hz, 1H), 3.96 (m, 2H), 4.14 (m, 1H), 4.38 (brs, 2H), 5.93 (s, 2H), 6.74 (d, J=8.1 Hz, 1H), 6.89 (dd, J=1.8 Hz, 8.1 Hz, 1H), 6.87 (d, J=1.8 Hz, 1H). MS (DCl/NH$_3$) (M+H)$^+$ at m/e 516. Anal calcd for C$_{28}$H$_{41}$N$_3$O$_6$·0.85 TFA: C, 58.23; H, 6.89; N, 6.86. Found: C, 58.37; H, 6.90; N, 6.84.

EXAMPLE 521

(2S, 3R, 4S)-2-(2-(2-oxopyrrolidin-1-yl)ethyl)-4-(1,3-benzodioxol-5-yl)-1-(N-4-heptyl-N-(4-fluoro-3-methylphenyl))aminocarbonylmethyl)-pyrrolidine-3-carboxylic Acid Using the procedures described in Example 520, substituting N,N-(4-heptyl)-(4-fluoro-3-methyl)phenyl-bromoacetamide for N,N-dibutylbromoacetamide afforded the title compound as an amorphous solid by lyophylization with CH$_3$CN/TFA/H$_2$O. $^1$H NMR (CDCl$_3$, 300 MHz) δ 0.85–0.98 (m, 6H), 1.22–1.55 (m, 8H), 2.04 (quintet, J=7.9 Hz, 4H), 2.32 (s, 3H), 2.36 (t, J=7.9 Hz, 2H), 2.61 (m, 1H), 3.14 (m, 1H), 3.25–3.61 (m, 5H), 3.66–3.77 (m, 1H), 3.79–3.90 (m, 2H), 3.92–4.03 (m, 1H), 4.69 (quintet, J=6.8 Hz, 1H), 5.95 (s, 2H), 6.71 (s, 2H), 6.78 (s, 1H), 6.93–7.13 (m, 3H); MS (DCl/NH$_3$) at m/e 610 (M+H)$^+$. Anal calc'd for C$_{34}$H$_{44}$N$_3$O$_6$F$_1$·1.45 TFA: C, 57.18; H, 5.91; N, 5.42. Found: C, 57.20; H, 5.62; N, 5.52.

EXAMPLE 522 trans, trans-2-(2-(1-pyrazolyl)ethyl)-4-(1,3-benzodioxol-5-yl)-1-(N,N-di(n-butyl)aminocarbonylmethyl)-pyrrolidine-3-carboxylic Acid

EXAMPLE 522A

3-(1-Pyrazolyl)-propionic Acid

In a 10 mL round-bottomed flask equipped with a condenser and a stirring bar was placed pyrazole (0.50 g, 7.3 mmol), acrylic acid (0.50 mL, 7.3 mmol) and triethylamine (3 mL). The reaction mixture was refluxed for 6 hours. After removing triethylamine, the viscous oil was dried on high vacuo during 12 hours to yield quantitatively the desired acid (1.0 g) suitable for the next step without further purification.

EXAMPLE 522B trans, trans-2-(2-(1-pyrazolyl)ethyl)-4-(1,3-benzodioxol-5-yl)-1-(N,N-di(n-butyl) aminocarbonylmethyl)-pyrrolidine-3-carboxylic Acid Using the procedure described in Example 502, the title compound was isolated by lyophilization from dilute aqueous TFA/CH$_3$CN as an amorphous solid $^1$H NMR (CDCl$_3$, 300 MHz) δ 7.56 (d, J=3.0 Hz, 1H), 7.50 (d, J=3 Hz, 1H), 6.83–6.66 (m, 3H), 6.28 (t, J=3 Hz, 1H), 5.91 (s, 2H), 4.55–3.98 (m, 6H), 3.83–3.72 (t, J=10.5 Hz, 1H), 3.61–3.40 (t, J=10.5 Hz, 1H), 3.36–3.12 (m, 5H), 2.69–2.43 (m, 2H), 1.59–1.42 (m, 4H), 1.38–1.21 (m, 4H), 0.91 (t, J=7.5 Hz, 6H). MS (DCl/NH$_3$) at m/e 499 (M+H)$^+$. Anal calcd for C$_{27}$H$_{38}$N$_4$O$_5$.0.75 TFA: C, 58.60; H, 6.69; N, 9.59. Found: C, 58.53; H, 6.45; N, 9.67.

EXAMPLE 523 trans, trans-2-(4-Methoxyphenyl)-4-(1,3-benzodioxol-5-yl)-1-[(N-butyl-N-(3-hydroxypropyl) amino)carbonylmethyl]-pyrrolidine-3-carboxylic Acid

EXAMPLE 523A

N-Butyl-N-(3-hydroxypropyl)-amine

To a solution of 15.9 g (100 mmol) of methyl 3-N-(n-butyl)aminopropionate in 150 mL of diethyl ether at 0° C. was added 50 mL (0.35 mmol) of 1.0M LiAlH$_4$ in diethyl ether, keeping reflux at a minimum. The mixture was stirred at 0° C. for 2.25 hours, the quenched by sequential dropwise addition of 1.9 mL H$_2$O, 1.9 mL 15% w/v NaOH$_{(aq)}$, and 5.7 mL H$_2$O. After stirring for 30 min, the salts were filtered and washed with diethyl ether, then the filtrate was concentrated to 11.3 g (86%) of a light yellow oil.

EXAMPLE 523B

N-Butyl-N-(3-hydroxypropyl)-chloroacetamide

To an ice cooled solution of 1.31 g (10.0 mmol) of N-butyl,N-(3-hydroxypropyl)amine in 20 mL of ethyl acetate was added a solution of 1.71 g (10.0 mmol) of chloroacetic anhydride in 100 mL of ethyl acetate. The mixture was stirred, and gradually warmed to room temperature over 18 hours. The reaction was extracted with H$_2$O (1×50 mL), saturated NaHCO$_3$ (aq) (2×50 mL), and brine (1×50 mL), dried over MgSO$_4$, filtered, and concentrated to an oil. The product was purified via silica gel chromatography, eluting with 80:20 hexanes:ethyl acetate to give 723 mg (35%) of a light yellow oil.

EXAMPLE 523C trans, trans-2-(4-Methoxyphenyl)-4-(1,3-benzodioxol-5-yl)-1-[(N-butyl-N-(3-hydroxypropyl) amino)carbonylmethyl]-pyrrolidine-3-carboxylic Acid Using the procedures described in Example 1D, substituting N-butyl-N-(3-hydroxypropyl)-chloroacetamide for N-propyl bromoacetamide and adding DMSO as cosolvent, afforded the title compound, which was isolated by lyophilization from dilute aqueous TFA/CH$_3$CN. $^1$H NMR (CD$_3$OD, 300 MHz) δ 0.78–0.95 (m, 3H), 1.00–1.80 (m, 4H), 2.80–3.65 (m, 15H), 3.80 (d, J=1.5 Hz, 2H), 5.93 (s, 2H), 6.72–7.05 (m, 5H), 7.33–7.40 (m, 2H). MS (DCl/NH$_3$) at m/e 513 (M+H)$^+$. Anal calc'd for C$_{28}$H$_{36}$N$_2$O$_7$.1.6 H2O: C, 62.12; H, 7.30; N, 5.17. Found: C, 62.04; H, 7.21; N, 4.88.

EXAMPLE 524 trans, trans-2-(4-Methoxyphenyl)-4-(1,3-benzodioxol-5-yl)-1-[(N-propyl-N-propoxyamino) carbonylmethyl]-pyrrolidine-3-carboxylic Acid

EXAMPLE 524A

N-Boc-O-allylhydroxylamine

O-Allylhydroxylamine hydrochloride hydrate (5.0 g) was dissolved in THF (15 mL). The solution was cooled to 0° C. in an ice bath. Diisopropylethylamine (8 mL) and di-t-butyldicarbonate (10.0 g) were added. The mixture was stirred at 0° C. for 1 hour at which point the bath was removed and the reaction allowed to warm to room temperature and stirred overnight. The THF was removed in vacuo and the residue taken up in EtOAc (25 mL), and washed with water (1×50 mL), saturated sodium bicarbonate solution (3×50 mL), 1N phosphoric acid (3×50 mL), and brine (1×50 mL). The organic layer was dried with sodium sulfate and evaporated to give a light yellow oil (6.5 g) which was used without any further purification.

EXAMPLE 524B

N-Boc-N-propyl-O-allylhydroxylamine

N-Boc-O-allylhydroxylamine (6.5 g) from the above procedure was dissolved in dry THF (25 mL) and the solution cooled to 0° C. in an ice bath. Sodium hydride (1.5 g, 60% dispersion in oil) was added portionwise over 5 min. The resulting mixture was stirred for 30 min at 0° C. 1-Iodopropane (3.8 mL) was added dropwise to the mixture. The reaction was stirred at 0° C. for 1 hour, then stirred overnight at room temperature. The THF was removed in vacuo and the residue taken up in EtOAc (50 mL) and washed with water (1×50 mL), saturated sodium bicarbonate solution (3×50 mL), 1N phosphoric acid (3×50 mL), and brine (1×50 mL). The organic layer was dried with sodium sulfate and evaporated to give a light yellow oil, which was purified by flash chromatography on silica gel eluting with 5% EtOAc/hexanes to give the title compound as a colorless oil (6.0 g).

EXAMPLE 524C

N-Boc-N-propyl-N-propoxyamine

N-Boc-N-propyl-O-allylhydroxylamine (6.0 g) was dissolved in EtOAc (100 mL). 10% Palladium-on-carbon (0.5 g) was added, and the mixture was purged with nitrogen. The nitrogen line was exchanged for a balloon of hydrogen, and the mixture was stirred at room temperature for 6 hours. The catalyst was removed by filtration through a pad of Celite and the solvents were removed in vacuo to give a yellow oil which was purified by flash chromatography on silica gel eluting with 5% EtOAc/hexanes to give the title compound as a colorless oil (5.8 g).

EXAMPLE 524D

N-Propyl-N-iropoxyamine Hydrochloride

N-Boc-N-propyl-N-propoxyamine (5.8 g) was dissolved in 4N HCl/dioxane (10 mL) and stirred at room temperature for 7 hours. The solvent was removed in vacuo and the residue triturated with diethyl ether. The resulting yellow solid (2.1 g) was collected by filtration and washed with diethyl ether.

EXAMPLE 524E

N-propyl-N-propoxy-bromoacetamide

N-Propyl-N-propoxyamine hydrochloride (0.30 g) was dissolved in acetonitrile and cooled to −20° C. Pyridine (0.2 mL) was added. Bromoacetyl bromide (0.15 g) was added dropwise over 5 min. The solution was stirred at −20° C. for 30 min. The bath was removed and the solution was stirred for 6 hours at room temperature. The solvent was removed in vacuo and the residue taken up in EtOAc (50 mL) and washed with water (1×25 mL), 1N phosphoric acid (3×25 mL), and brine (1×25 mL). The organic layer was dried with sodium sulfate and evaporated to give a dark orange oil (0.35 g). The product is a mixture of chloro- and bromoacetamides in a ratio of ~3:1.

EXAMPLE 524F trans, trans-2-(4-Methoxyphenyl)-4-(1,3-benzodioxol-5-yl)-1-[(N-butyl-N-(3-hydroxypropyl)amino)carbonylmethyl]-pyrrolidine-3-carboxylic Acid Prepared according to the procedure of Example 523C, employing N-propyl-N-propoxy-bromoacetamide and ethyl 2-(4-methoxyphenyl)-4-(1,3-benzodioxol-5-yl)-pyrrolidine-3-carboxylate. The crude product was purified by preparative HPLC (Vydac mC18) eluting with a 10–70% gradient of $CH_3CN$ in 0.1% TFA. The appropriate fraction was lyophilized to give the product as a white solid. $^1H$ NMR ($CDCl_3$, 300 MHz) δ 0.87 (m, 6H, J=8 Hz), 1.49 (m, 2H, J=8 Hz), 1.61 (m, 2H, J=8 Hz), 3.55 (m, 6H), 3.80 (m, 2H), 3.81 (s, 3H), 4.00 (m, 2H), 4.13 (d, 2H, J=17 Hz), 5.96 (s, 2H), 6.77 (d, 1H, J=9 Hz), 6.90 (m, 3H), 7.05 (d, 1H, J=1 Hz), 7.44 (d, 2H, J=9 Hz). MS ($DCl/NH_3$) m/e 499 $(M+H)^+$. Anal calcd for $C_{27}H_{34}N_2O_7 \cdot 1.20$ TFA: C, 55.57; H, 5.58; N, 4.41. Found: C, 55.59; H, 5.58; N, 4.55.

EXAMPLE 525 trans, trans-2-(4-Methoxyphenyl)-4-(1,3-benzodioxol-5-yl)-1-[(N-butyl-N-propoxyamino)carbonylmethyl]-pyrrolidine-3-carboxylic Acid

EXAMPLE 525A

N-butyl-N-(2-hydroxyethyl)-amine

In a thick walled glass tube 5 ml (100 mmol) of ethylene oxide was condensed at −78° C. To this 12.5 ml (120 mmol) of butylamine was added and the tube was sealed. The resultant solution was allowed to heat in an oil bath at 50° C. for 18 hours. Unreacted reagents were removed by evaporation to give the title compound.

EXAMPLE 525B

N-Butyl-N-(2-azidoethyl)-chloroacetamide

To 500 mg of N-butyl,N-2-hydroxyethylamine was added 2 mL of thionyl chloride, dropwise. After the initial reaction had ceased, the reaction was stirred for 10 min, then concentrated to an oil. Diethyl ether was added and evaporated to aid in removal of the thionyl chloride. The residue was taken up in 10 mL of DMF, and 1.0 g (16 mmol) of sodium azide was added. The reaction was stirred at 75° C. for 2 hours, then poured into 50 mL of 0.6M $NaHCO_{3(aq.)}$ and extracted with diethyl ether (3×15 mL). The combined ether layers were back extracted with brine (1×15 mL), dried over $MgSO_4$, and filtered. To the ether solution was added 850 mg (4.97 mmol) of chloroacetic anhydride. The reaction was stirred for 10 min, then concentrated to an oil. This was taken up in 10 mL of saturated $NaHCO_{3(aq.)}$ and extracted with diethyl ether (3×5 mL). The combined ether layers were back extracted with brine (1×5 mL), dried over $MgSO_4$, filtered, and concentrated to an oil. This was purified via silica gel chromatography, eluting with 30% ethyl acetate: hexanes, to give 161 mg (17%) of an oil.

EXAMPLE 525C trans, trans-2-(4-Methoxyphenyl)-4-(1,3-benzodioxol-5-yl)-1-[(N-butyl-N-(2-aminoethyl)amino)carbonylmethyl]-pyrrolidine-3-carboxylic Acid According to the procedure of Example 523C, N-butyl-N-(2-azidoethyl)-chloroacetamide was coupled with ethyl 2-(4-Methoxyphenyl)-4-(1,3-benzodioxol-5-yl)-pyrrolidine-3-carboxylate. The crude product was chromatographed on silica, using 40% EtOAc in hexanes to elute. The product was dissolved in a solution of ethanol and aqueous 2.5 N sodium hydroxide and stirred for 3 hours at room temperature. The solution was concentrated in vacuo and water added. The mixture was extracted with ether; the aqueous layer was acidified to pH 4 with 1N $H_3PO_4$ and extracted with EtOAc. The latter organic extract was washed with brine and dried over $Na_2SO_4$. To 100 mg (0.10 mmol) of the azide was added 1 mL of 1M $HCl_{(aq.)}$, 0.5 mL of dioxane, and 5 mg of 10% Pd—C. The suspension was stirred under 1 atm. of $H_2$ for 5 hours, then filtered and concentrated to a white solid. The product was purified via HPLC, eluting with a 0 to 70 $CH_3CN$ in 0.1% aqueous TFA gradient to give the title compound as its TFA salt. $^1H$ NMR ($CD_3OD$, 300 MHz) δ 0.92 (t, J=7.0 Hz, 3H), 0.96 (t, rotamer), 1.23 (m, 2H), 1.41 (m, 2H), 3.06 (m, 4H), 3.39 (m, 2H), 3.69 (m, 2H), 3.84 (s, 3H), 3.94 (m, 3H), 4.18 (m, 2H), 5.05 (bd, J=10.7 Hz, 1H), 5.98 (s, 2H), 6.84 (d, J=7.7 Hz, 1H), 6.93 (dd, J=1.8, 8.1 Hz, 1H), 7.05 (m, 3H), 7.56 (m, 2H). MS ($DCl/NH_3$) at m/e 498 $(M+H)^+$. Anal calcd for $C_{27}H_{35}N_3O_6 \cdot 3.15$ TFA: C, 46.68. H, 4.49. N, 4.90. Found: C, 46.61; H, 4.73; N, 4.79.

EXAMPLE 526 trans, trans-2-(4-Methoxyphenyl)-4-(1,3-benzodioxol-5-yl)-1-[(N-butyl-N-(3-aminopropyl)amino)carbonylmethyl]-pyrrolidine-3-carboxylic Acid To and ice-cold solution of the compound of Example 523C (100 mg, 0.19 mmol) in 1 mL of dichloromethane was added 17 mL of methanesulfonyl chloride, and 39 mL of triethylamine. The mixture was stirred for 20 min, then diluted with 1.5 mL of dichloromethane and extracted once with 5 mL of water to which had been added 1 drop of 85% $H_3PO_4$, then 5% ammonium hydroxide (1×2.5 mL), and brine (1×2.5 mL), dried over $MgSO_4$, filtered, and concentrated to an oil. To a solution of 81 mg (0.13 mmol) of the mesylate in 1 mL of DMF was added 65 mg (10 mmol) of sodium azide. The mixture was stirred for 1 hour at 50° C., then poured into 10 mL of water and extracted with diethyl ether (3×5 mL). The combined ether layers were back extracted with brine (1×5 mL), dried over MgSO$_4$, filtered, and concentrated to an oil. This was purified via silica gel chromatography, eluting with 60:40 hexanes: ethyl acetate to give 57 mg of a colorless oil. The product was dissolved in a solution of ethanol and aqueous 2.5 N sodium hydroxide and stirred for 3 hours at room temperature. The solution was concentrated in vacuo and water added. The mixture was extracted with ether; the aqueous layer was acidified to pH 4 with 1N H$_3$PO$_4$ and extracted with EtOAc. The latter organic extract was washed with brine and dried over Na$_2$SO$_4$. To this azide was added 1 mL of 1M HCl$_{(aq.)}$, 0.5 mL of dioxane, and 5 mg of 10% Pd—C. The suspension was stirred under 1 atm. of H$_2$ for 5 hours, then filtered and concentrated to a white solid. The product was purified via HPLC, eluting with a 0 to 70 CH$_3$CN in 0.1% aqueous TFA gradient to give the title compound as its TFA salt. $^1$H NMR (D$_6$-DMSO, 300 MHz) δ 0.85 (apparent q, J=6.8 Hz, 3H), 1.17 (m, 2H), 1.30 (m, 2H), 1.67 (m, 2H), 2.71 (m, 2H), 3.04 (m, 1H), 3.21 (m, 3H), 3.45 (m, 1H), 3.75 (m, 3H), 3.97 (s, 3H), 3.85–4.80 (broad m, 3H), 6.03 (m, 2H), 6.87 (dd, J=1.4, 8.1 Hz, 1H), 6.92 (d, J=7.8 Hz, 1H), 7.01 (m, 2H), 7.16 (m, 1H), 7.55 (m, 2H), 7.72 (m, 2H), 7.85 (m, 1H); MS (DCl/NH$_3$) (M+H)$^+$ at m/e 512. Anal calcd for C$_{28}$H$_{37}$N$_3$O$_6$.3.0 TFA: C, 47.84. H, 4.72. N, 4.92. Found: C, 47.86; H, 4.75; N, 4.97.

EXAMPLE 527 trans, trans-2-(4-Methoxyphenyl)-4-(1,3-benzodioxol-5-yl)-1-[(N-butyl-N-(3-dimethylaminopropyl)amino)carbonylmethyl]-pyrrolidine-3-carboxylic Acid

EXAMPLE 527A

N-butyl-N-(3-bromopropyl)bromoacetamide

To 1.50 g (11.4 mmol) of N-butyl-N-(3-hydroxy) propylamine was added 3 mL of 48% HBr$_{(aq.)}$, and 1.5 mL of conc. H$_2$SO$_4$. The reaction was stirred at reflux for 3 hours, then cooled to room temperature and stirred for 22 hours. The mixture was poured over 50 mL of ice, and the solution was treated with 50 mL of 2M NaOH$_{(aq.)}$. The basic solution was extracted with ethyl acetate (3×25 mL), then the combined ethyl acetate layers were back extracted with brine (1×25 mL), dried, and filtered. To the ice cooled ethyl acetate solution was added 3 mL of triethylamine, then 1.5 mL of bromoacetyl bromide as a solution in 3.5 mL of ethyl acetate. The reaction was stirred at 0° C. for 30 min, then extracted with 1M HCl$_{(aq.)}$ (2×25 mL) saturated NaHCO$_3$ $_{(aq.)}$(1×25 mL) and brine (1×25 mL). The organic layer was dried over MgSO4, filtered, and concentrated to an oil. This was purified via silica gel chromatography, eluting with 30% ethyl acetate in hexanes to give 1.47 g of a colorless oil.

EXAMPLE 527B

Ethyl trans, trans-2-(4-Methoxyphenyl)-4-(1,3-benzodioxol-5-yl)-1-[(N-butyl-N-(3-bromopropyl)amino)carbonylmethyl]-pyrrolidine-3-carboxylate According to the procedure of Example 523C, N-butyl-N-(3-bromopropyl-bromoacetamide was coupled with ethyl 2-(4-Methoxyphenyl)-4-(1,3-benzodioxol-5-yl)-pyrrolidine-3-carboxylate. The crude product was chromatographed on silica, using 40% EtOAc in hexanes to elute.

EXAMPLE 527C trans, trans-2-(4-Methoxyphenyl)-4-(1,3-benzodioxol-5-yl)-1-[(N-butyl-N-(3-dimethylaminopropyl)amino)carbonylmethyl]-pyrrolidine-3-carboxylic Acid To 400 mg (0.663 mmol) of the compound of Example 527B in 4 mL of absolute EtOH was added 1.2 mL of 2.0 M Me$_2$NH in THF. The reaction was heated at 50° C. for 3 h, then stirred at room temperature for 18 hours. The mixture was concentrated, then reconcentrated from CH$_3$CN to remove most of the trimethylamine. The product was purified via silica gel chromatography, eluting with 9:1 CH$_2$Cl$_2$: MeOH over about 20 mL of silica gel to give the ethyl ester. The product was dissolved in a solution of ethanol and aqueous 2.5 N sodium hydroxide and stirred for 3 hours at room temperature. The solution was concentrated in vacuo and water added. The mixture was extracted with ether; the aqueous layer was acidified to pH 4 with 1N H$_3$PO$_4$, and the product was purified by preparative HPLC. $^1$H NMR (CD$_3$OD, 300 MHz) δ 0.92 (t, J=7.0 Hz, 3H), 1.22 (m, 2H), 1.39 (m, 2H), 1.90 (m, 2H), 2.87 (s, 6H), 3.07 (m, 4H), 3.24 (m, 1H), 3.43 (m, 1H), 3.62 (m, 1H), 3.84 (s, 3H), 3.88 (m, 3H), 4.07 (m, 1H), 4.17 (m, 1H), 4.97 (m, 1H), 5.97 (s, 2H), 6.83 (d, J=8.1 Hz, 1H), 6.93 (dd, J=1.7, 8.1 Hz, 1H), 7.05 (m, 3H), 7.53 (m, 2H). MS (DCl/NH$_3$) at m/e 540 (M+H)$^+$. Anal calcd for C$_{30}$H$_{41}$N$_3$O$_6$.2.95 TFA: C, 49.22. H, 5.06. N, 4.80. Found: C, 49.16; H, 5.11; N, 4.62.

EXAMPLE 528 trans, trans-2-(4-Methoxyphenyl)-4-(1,3-benzodioxol-5-yl)-1-[(N-butyl-N-(3-trimethylammoniopropyl)amino)carbonylmethyl]-pyrrolidine-3-carboxylic Acid Prepared according to the procedures of Example 527C, substituting aqueous Me$_3$N for Me$_2$NH. $^1$H NMR (CD$_3$OD, 300 MHz) δ 0.91 (m, 3H), 1.24 (m, 2H), 1.40 (m, 2H), 1.99 (m, 2H), 3.13 (s, 9H), 3.18 (s, rotamer), 3.20 (m, 3H), 3.39 (m, 4H), 3.72 (m, 1H), 3.84 (s, 3H), 4.03 (m, 3H), 4.35 (m, 1H), 5.19 (m, 1H), 5.97 (s, 2H), 6.84 (d, J=8.1 Hz, 1H), 6.96 (dd, J=1.7, 7.9 Hz, 1H), 7.10 (m, 3H), 7.62 (m, 2H). MS (DCl/NH$_3$) at m/e 554 (M+H)$^+$. Anal calcd for C$_{31}$H$_{44}$N$_3$O$_6$.0.1 H$_2$O.1.65 TFA: C, 47.25. H, 4.96. N, 4.32. Found: C, 47.25; H, 4.74; N, 4.75.

EXAMPLE 529 trans, trans-2-(4-Methoxyphenyl)-4-(1,3-benzodioxol-5-yl)-1-[(N-butyl-N-(4-aminobutyl)amino)carbonylmethyl]-pyrrolidine-3-carboxylic Acid

EXAMPLE 529A

N-butyl-N-(4-hydroxybutyl)-amine

A solution of 8.1 g (110 mmol) of n-butylamine and 8.6 g of butyrolactone in 50 ml toluene was allowed to reflux under nitrogen atmosphere for 50 hours. Volatile solvents were removed in vacuo. To a solution of 3.18 gm (20 mmol) of the resultant N-butyl 4-hydroxybutyramide in 50 ml of toluene were added 120 ml (120 mmol) DIBAL(25% W). The solution was heated with stirring at 70° C. for 18 hours. After cooling to 0° C., the reaction was quenched with methanol (⅓ amount of DIBAL solution was used) followed by addition of saturated solution of Rochelle's salt. The mixture was extracted twice with EtOAc; the organic extracts were washed with brine and dried over $Na_2SO_4$.

EXAMPLE 529B

N-butyl-N-(4-hydroxybutyl)-chloroacetamide

Pyridine (2 ml) was added to an ice cold solution of 0.58 gm (4 mmol) of N-butyl-N-(4-hydroxybutyl)-amine in 10 ml of EtOAc. To this solution 0.769 gm (4.5 mmol) chloroacetic anhydride was added in small portions. The reaction mixture was allowed to stir for 5 hours at 0° C., and then was allowed to warm to room temperature. Bicarbonate was added, and the resultant mixture was extracted with EtOAc. The organic layer was washed with water and brine. The crude material was purified by column chromatography.

EXAMPLE 529C

Ethyl trans, trans-2-(4-Methoxyphenyl)-4-(1,3-benzodioxol-5-yl)-1-[(N-butyl-N-(4-hydroxybutyl)amino)carbonylmethyl]-pyrrolidine-3-carboxylate According to the procedure of Example 523C, N-butyl-N-(4-hydroxybutyl-chloroacetamide was coupled with ethyl 2-(4-Methoxyphenyl)-4-(1,3-benzodioxol-5-yl)-pyrrolidine-3-carboxylate. The crude product was chromatographed on silica gel.

EXAMPLE 529D

Ethyl trans, trans-2-(4-Methoxyphenyl)-4-(1,3-benzodioxol-5-yl)-1-[(N-butyl-N-(4-bromobutyl)amino)carbonylmethyl]-pyrrolidine-3-carboxylate To the solution of 0.180 gm (0.33 mmol) of the compound of Example 529C in 2 ml DMF 0.086 gm (1 mmol) of lithium bromide and 0.120 ml (0.66 mmol) of $PBr_3$ was added. The reaction mixture was allowed to stir at 0° C. for 2 hours and was slowly warmed to room temperature. Bicarbonate was added, and the resultant mixture was extracted with EtOAc. The organic layer was washed with water and brine. The crude material was purified by column chromatography.

EXAMPLE 529E trans, trans-2-(4-Methoxyphenyl)-4-(1,3-benzodioxol-5-yl)-1-[(N-butyl-N-(4-aminobutyl)amino)carbonylmethyl]-pyrrolidine-3-carboxylic Acid To a solution of 0.135 gm (0.21 mmol) of the compound of Example 529D in 2 ml DMF was added 0.1 gm of sodium azide. Reaction was allowed to stir at room temperature for 18 hours under nitrogen atmosphere. After addition of water, the product was extracted into EtOAc. The crude product (117 mg) was dissolved in 10 ml ethanol under nitrogen atmosphere. To this 45 mgs of 10% Pd/C catalyst was added, the nitrogen from the reaction flask was evacuated and was flushed with hydrogen by placing a balloon filled with hydrogen.

The reaction was allowed to stir for 4 hours under hydrogen atmosphere, and was worked up by filtering through a Celite pad. The product was dissolved in a solution of ethanol and aqueous 2.5 N sodium hydroxide and stirred for 8 hours at room temperature. The solution was concentrated in vacuo and water added. The mixture was extracted with ether; the aqueous layer was acidified to pH 4 with 1N $H_3PO_4$, and the product was purified by preparative HPLC. $^1$H NMR ($CD_3OD$, 300 MHz) δ 0.90 (t, J=7 Hz, 3H), 1.10–1.65 (m, 6H), 2.85–2.95 (m, 2H), 3.00–4.10 (m, 14H), 5.50 (d, J=3 Hz, 2H), 5.97 (s, 2H), 6.82 (d, J=8 Hz, 1H), 6.91 (dd, J=7 Hz, 1H), 7.00–7.06 (m, 3H), 7.45–7.55 (m, 2H). MS ($DCl/NH_3$) at m/e 526 (M+H)$^+$. Anal calc'd for $C_{29}H_{39}N_3O_6$.2.2 TFA: C, 51.75; H, 5.35; N, 5.41. Found: C, 51.75; H, 5.31; N, 5.30.

EXAMPLE 530 trans, trans-2-(4-Methoxyphenyl)-4-(1,3-benzodioxol-5-yl)-1-[(N-butyl-N-(4-dimethylaminobutyl)amino)carbonylmethyl]-pyrrolidine-3-carboxylic Acid The title compound was prepared from the compound of Example 529D, employing the procedures of Example 527C. $^1$H NMR ($CD_3OD$, 300 MHz) δ 0.90 (dt, J=7 Hz, 3H), 1.1–1.75 (m, 8H), 2.75 (d, J=7 Hz, 6H), 3.0–4.25 (m, 16H), 5.97 (s, 2H), 6.83 (d, J=8 Hz, 1H), 6.93 (dd, J=8 Hz, 1H), 7.02–7.08 (m, 3H), 7.49–7.56 (m, 2H). MS ($DCl/NH_3$) at m/e 554 (M+H)$^+$. Anal calc'd for $C_{31}H_{43}N_3O_6$.2.1 TFA: C, 53.31; H, 5.73; N, 5.30. Found: C, 53.50; H, 5.38; N, 5.34.

EXAMPLE 531 trans, trans-2-(4-Methoxyphenyl)-4-(1,3-benzodioxol-5-yl)-1-[(N-butyl-N-(3-pyridyl)amino)carbonylmethyl]-pyrrolidine-3-carboxylic Acid

EXAMPLE 531A

N-butyl-N-(3-pyridyl)-amine

To a solution of 941 mg (10 mmol) of 3-aminopyridine and 0.9 mL of butyraldehyde in 30 mL of $CH_3OH$ was added 10 mL of glacial acetic acid. The mixture was stirred at room temperature for 1 hour, then the reaction was cooled with an ice bath, and 650 mg (10.3 mmol) of sodium cyanoborohydride was added. The ice bath was removed, and the reaction was stirred for 4.5 hours at room temperature. The mixture was poured into 300 mL of 0.67M $NaOH_{(aq.)}$, and extracted with ethyl acetate (3×50 mL). The combined organic layers were back extracted with brine (1×50 mL), dried over MgSO4, filtered, and concentrated to an oil. The product was isolated via silica gel chromatography, eluting with 3:1 ethyl acetate: hexanes to give 1.18 g (79%) of a colorless solid.

EXAMPLE 531B trans, trans-2-(4-Methoxyphenyl)-4-(1,3-benzodioxol-5-yl)-1-[(N-butyl-N-(3-pyridyl)amino)carbonylmethyl]-pyrrolidine-3-carboxylic Acid The compound of Example 531A was reacted according to the procedures of Example 523, to give the title compound. $^1$H NMR ($D_6$-DMSO, 300 MHz) δ 0.80 (t, J=6.4 Hz, 3H), 1.15–1.99 (m, 4H), 2.59 (m, 1H), 3.05 (m, 2H), 3.26 (m, 2H), 3.49 (m, 2H), 3.56 (t, J=7.1 Hz, 2H), 3.73 (s, 3H), 6.00 (s, 2H), 6.80 (m, 3H), 6.85 (d, J=8.1 Hz, 1H), 6.98 (m, 2H), 7.04 (m, 1H), 7.41 (dd, J=1, 4.7 Hz, 8.1H), 7.58 (m, 1H), 8.36 (bs, 1H), 8.54 (bs, 1H), 12.24 (bs, 1H). MS ($DCl/NH_3$) at m/e 532 (M+H)$^+$. Anal calcd for $C_{30}H_{33}N_3O_6$.0.1 $H_3PO_4$: C, 66.55. H, 6.20. N, 7.76. Found: C, 66.59; H, 6.06; N, 7.60.

EXAMPLE 532 trans, trans-2-(4-Methoxyphenyl)-4-(1,3-benzodioxol-5-yl)-1-[(N-butyl-N-(3-aminomethylphenyl)amino)carbonylmethyl]-pyrrolidine-3-carboxylic Acid

EXAMPLE 532A

N-butyl-N-(3-hydroxymethylphenyl)-amine

To a solution of 3.69 g (30 mmol) of 3-amino benzyl alcohol in 20 ml DMSO was added 3.78 g (45 mmol) solid NaHCO$_3$ and 2.91 ml (27 mmol) 1-bromobutane. The reaction was allowed to stir at 50° C. for 18 hours (overnight). Reaction was worked up by adding 250 ml water and product was extracted in ethyl acetate. Water was added, and the resultant mixture was extracted with EtOAc. The organic layer was washed with water and brine.

EXAMPLE 532B

N-butyl-N-(3-hydroxymethylphenyl)-bromoacetamide

To a solution of 3.42 g (19.2 mmol) of the compound of Example 532A in 20 ml toluene, was added 2.42 ml (30 mmol) pyridine. The mixture was cooled to 0° C.; 4.025 gm (20.0 mmol) of bromoacetyl bromide (diluted with 5 ml toluene) was added in a dropwise fashion.

The reaction mixture was allowed to stir for 5 hours at 0° C. and then was allowed to warm to room temperature. Saturated potassium carbonate solution was added, and the mixture was stirred vigorously for 2 hours. The mixture was extracted with EtOAc; the organic layer was washed with 1N H$_3$PO$_4$, water, and brine.

EXAMPLE 532C

Ethyl trans, trans-2-(4-Methoxyphenyl)-4-(1,3-benzodioxol-5-yl)-1-[(N-butyl-N-(3-chloromethylphenyl)amino)carbonylmethyl]-pyrrolidine-3-carboxylate According to the procedure of Example 523C, N-butyl-N-(3-hydroxymethylphenyl)-bromoacetamide was coupled with ethyl 2-(4-Methoxyphenyl)-4-(1,3-benzodioxol-5-yl)-pyrrolidine-3-carboxylate. The crude product (129 mg) was dissolved in 0.5 ml of DMF and cooled to 0° C.; 19 mg of LiCl was added, followed by 85 μl of thionyl chloride. The mixture was allowed to stir for 30 min; water was added, and the mixture was extracted with EtOAc. The organic extracts were washed with water and brine, and dried over Na$_2$SO$_4$.

EXAMPLE 532D trans, trans-2-(4-Methoxyphenyl)-4-(1,3-benzodioxol-5-yl)-1-[(N-butyl-N-(3-aminomethylphenyl)amino)carbonylmethyl]-pyrrolidine-3-carboxylic Acid The compound of Example 532C (182 mg) was dissolved in 1 mL of DMF. Two drops of water were added, followed by 126 mg (2.0 mmol, 6.5 eq) of sodium azide. The resultant solution was heated at 115° C. for 3 hours. Water was added, and the mixture was extracted with EtOAc. The organic extracts were washed with water and brine, and dried over Na$_2$SO$_4$.

EXAMPLE 532E trans, trans-2-(4-Methoxyphenyl)-4-(1,3-benzodioxol-5-yl)-1-[(N-butyl-N-(3-aminomethylphenyl)amino)carbonylmethyl]-pyrrolidine-3-carboxylic Acid In a 50 ml round bottom flask 0.090 gm Tin (II) chloride was suspended in 1 ml acetonitrile. Triethylamine (0.2 mL) was added, followed by 0.19 ml of thiophenol the reaction mixture turned yellow. Reaction flask was cooled to 0° C. in ice bath; a solution of 0.185 gm of the compound of Example 532D in 2 ml acetonitrile was added. The mixture was allowed to stir for 30 min. Ether (10 ml) was added, followed by addition of 10 ml 2N HCl. The aqueous extract was basified with 4N NaOH and extracted with dichloromethane. The organic layer was washed with water and brine. The crude product was dissolved in a solution of ethanol and aqueous 2.5 N sodium hydroxide and stirred for 8 hours at room temperature. The solution was concentrated in vacuo and water added. The mixture was extracted with ether; the aqueous layer was acidified to pH 4 with 1N H$_3$PO$_4$, and the product was purified by preparative HPLC. $^1$H NMR (CD$_3$OD, 300 MHz) δ 0.88 (t, J=7 Hz, 3H), 1.15–1.45 (m, 4H), 3.40–4.20 (m, 14H), 5.97 (s, 2H), 6.82 (d, J=8 Hz, 1H), 6.88 (dd, J=8 Hz, 1H), 6.97–7.20 (m, 5H), 7.40 (d, J=9 Hz, 2H), 7.56 (d, J=5 Hz, 2H). MS (DCl/NH$_3$) at m/e 560 (M+H)$^+$. Anal calcd for C$_{32}$H$_{37}$N$_3$O$_6$.4.2 TFA: C, 46.72; H, 4.00; N, 4.05. Found: C, 46.66; H, 4.06; N, 4.00.

EXAMPLE 533 trans, trans-2-(4-Methoxyphenyl)-4-(1,3-benzodioxol-5-yl)-1-[(N-butyl-N-(3-trimethylammoniomethylphenyl)amino)carbonylmethyl]-pyrrolidine-3-carboxylic Acid To a stirred solution of 0.128 gm of the compound of Example 532C in 0.5 ml methanol, 0.25 ml of an aqueous solution of trimethylamine was added. The mixture was allowed to stir at room temperature under nitrogen atmosphere for 4 hours. 1N HCl was added; the aqueous was washed with ether to extract organic impurities. The aqueous layer was dried azeotropically with toluene, and the residue was dried under high vacuum. Yield 0.115 gm. $^1$H NMR (300 MHz, D6-DMSO) δ 0.83 (t, J=7 Hz, 3H), 1.15–1.40 (m, 4H), 2.62 (s, 2H), 3.35 (s, 9H), 3.40–3.80 (m, 10H), 4.47 (s, 2H), 6.00 (s, J=3 Hz, 2H), 6.75–6.90 (m, 3H), 7.25–7.37 (m, 2H), 7.45–7.60 (m, 3H). MS (DCl/NH$_3$) at m/e 602 (M+H)$^+$.

EXAMPLE 534

(2R,3R,4S)-2-(3-Fluoro-4-methoxyphenyl)-4-(1,3-benzodioxol-5-yl)1-(2-(N-propyl-N-pentanesulfonylamino)ethyl)-pyrrolidine-3-carboxylic Acid

EXAMPLE 534A

Ethyl (3-fluoro-4-methoxy)benzoylacetate

Sodium hydride (17 g of a 60% suspension in mineral oil) is washed three times with toluene. The powder is suspended in 138 mL of toluene, and 35 mL of diethyl carbonate is added. The mixture is heated to 90° C., and a solution of 25 g of 3-fluoro-4-methoxyacetophenone and 50 ml of diethyl carbonate in 50 ml of toluene was added portionwise. Heating is continued for 30 min, then the reaction is cooled to room temperature. A solution of 50 ml of concentrated HCl in 75 ml of ice water is added slowly, and the mixture is stirred. The mixture is extracted with toluene; the combined organic extracts are washed with brine and bicarbonate solutions. The product is dried over Na$_2$SO$_4$ and decolorized with charcoal to give 34.5 g (97%) of the title compound.

EXAMPLE 534B

Ethyl 2-(3-Fluoro-4-methoxyphenyl)-4-(1,3-benzodioxol-5-yl)-pyrrolidine-3-carboxylate The compound of Example 534A (12.5 g) and 5-(nitrovinyl)-1,3-benzodioxole (13.1 g, 20% excess) were suspended in a mixture of 75 ml of THF and 13 ml of iPrOH. DBU (0.25 g) was added, and the mixture was stirred at room temperature for 30 min. An additional 0.1 g of DBU was added, and the solution was stirred for 1 hour. The solvents were removed in vacuo; toluene was added, along with brine containing 3 ml of concentrated HCl. The mixture was extracted twice with toluene; the organics were dried over $MgSO_4$. The residue was flashed on silica, using $CH_2Cl_2$ to elute. Yield 75%. This material (17.4 g) is combined with 35 g of Raney Nickel (washed) in 250 mL of EtOAc. The mixture is shaken under 4 atm of hydrogen for 18 hours. The solution is concentrated in vacuo; the residue is chromatographed on silica, eluting with 4% EtOAc in $CH_2Cl_2$. Yield 10.13 g=66%. The product is combined with 26 ml of THF and 50 ml of EtOH; 2.18 g of $NaBH_3CN$ are added, along with a trace of bromcresol green as indicator. A solution of 1:2 concentrated HCl/EtOH is added dropwise to maintain pH at green-yellow; after color persists, the reaction mixture is stirred for an additional 20 min. The solvents are removed in vacuo; the residue is stirred with mixture of toluene and $KHCO_3$ solution. The organic phase is washed with water and brine, and dried over $MgSO_4$. The crude product is purified by flash chromatography on silica, eluting with 2:1 EtOAc/hexanes. Yield 5.92 g (58%) of a 2:1 mixture of trans-trans and cis-trans isomers.

EXAMPLE 534C

Ethyl (2R,3R,4S)-2-(3-Fluoro-4-methoxyphenyl)4-(1,3-benzodioxol-5-yl)-Pyrrolidine-3-carboxylate To the racemic amino ester above (15.0 g, 38.8 mmol), dissolved in 75 ml methylene chloride and cooled in an ice bath, was added Boc anhydride (9.30 g, 42.7 mmol). After stirring 2 hours at room temperature, the solution was concentrated in vacuo; the residue was dissolved in 50 ml ethanol and treated with a solution of 3.75 g sodium hyroxide in 19 ml water. The solution was warmed until all was soluble. After stirring for 2 hours at room temperature, the solution was concentrated and redissolved in 200 ml of water. This was extracted with 75 ml of diethyl ether. The ether layer was extracted with 40 ml of water. The combined aqueous phases were acidified with 7.5 g acetic acid; the mixture was stirred until a solid formed. The solid was filtered, washed with water and dissolved in methylene chloride. After drying with sodium sulfate, the solution was concentrated and the residue crystallized from 1:1 ether-:hexane to get 15.99 g of product, m.p. 200–203 (90% yield). The crude acid was suspended in 80 ml ethyl acetate and treated with 4.00 g (33.1 mmol) of (S)-(−)-a-methylbenzylamine. After heating to dissolve the acid, 80 ml of ether was added. Scratching with a glass rod caused the product to crystallize. The solids were filtered and washed with ether-ethyl acetate solution to give 8.22 g (81% yield based on 50% maximum recovery) of salt, m.p. 165–168° C. After one recrystallization, chiral HPLC analysis, using a Regis Whelk-O column, indicated >99.5% e.e. The salt was dissolved in 500 ml of 36% HCl in ethanol; a white solid forms. The resultant suspension was heated for 16 hours at 52° C. After concentrating in vacuo, the residue was combined with toluene and stirred with potassium bicarbonate in water for 30 minutes. The toluene was separated, dried ($Na_2SO_4$) and concentrated. The residue was chromatographed on silica gel, eluting with 33% hexane-67% ethyl acetate to get 6.9 g (99%) of the resolved amino ester.

EXAMPLE 534D

Ethyl (2R,3R,4S)-2-(3-Fluoro-4-methoxyphenyl)-4-(1,3-benzodioxol-5-yl)1-(2-(N-propylamino)ethyl)-pyrrolidine-3-carboxylate The compound of Example 534C was dissolved in 1,2-dibromoethane (10 mL per 1 g of starting material); diisopropylethylamine (1 mL per 1 g of starting material) and NaI (100 mg per 1 g of starting material) were added, and the mixture was stirred at 100° C. for 1 hour. Toluene was added, and the mixture was washed with bicarbonate. The solvents were concentrated, and the resultant black residue was chromatographed on silica gel, eluting with 4:1 hexane-EtOAc to give the N-(2-bromoethyl)pyrrolidine (85–92%). This compound was combined with n-propylamine (3.5 eq.) and NaI (10% by weight of bromide) in ethanol (5 mL per 1 g of bromide), and was heated at 80° C. for 2 hours. Toluene was added, and the mixture was washed with bicarbonate, dried ($Na_2SO_4$), and concentrated. More toluene was added, and removed in vacuo, to get rid of the primary amine. The residue was dissolved in heptane and filtered to remove a small amount of insoluble material. Evaporation of the solvent gave the desired product (86–93% yield), which was used for the next step without further purification.

EXAMPLE 534E

1-Pentanesulfonyl Chloride

1-Pentanesulfonic acid, sodium salt (10 g, 57.5 mmol) was charged into a 250 ml round bottom flask (allow headroom). Thionyl chloride (20 mL) is added; gas evolves, and a while solid forms. The mixture is heated at 60° C. for 3 hours. The solvents are removed in vacuo; toluene is added and removed in vacuo to remove residue of $SOCl_2$. The residue is partitioned between $CH_2Cl_2$ and ice water; the organic layer is dried over $Na_2SO_4$. The crude product is purified by distillation (bp 54–56° C. @ 0.5 mm Hg) to give a clear oil, 61% yield.

EXAMPLE 534F (2R,3R,4S)-2-(3-Fluoro-4-methoxyphenyl)-4-(1,3-benzodioxol-5-yl)1-(2-(N-propyl-N-pentanesulfonylamino)ethyl)-pyrrolidine-3-carboxylic Acid The compound of Example 534D (200 mg, 0.43 mmol) was dissolved in 5 mL of $CH_3CN$; 110 mg (2 eq) of N,N-diisopropylethylamine and 72.8 mg (1.2 eq) of 1-pentanesulfonyl chloride were added sequentially, the resultant solution was allowed to stir at room temperature for 30 min. The solvent was evaporated under reduced pressure and the residue was dissolved in EtOAc. The solution was washed with saturated $NaHCO_3$ solution, 1N $H_3PO_4$, and brine, dried over $Na_2SO_4$ and evaporated to give a yellowish oil which was purified by flash chromatography on silica gel eluting with 40% EtOAc/hexane to give 220 mg of product (85%). This ester was dissolved in 5 mL of EtOH, to which was added NaOH (46 mg, 3 eq) solution in 2 mL of $H_2O$. This mixture was stirred for 3 hours at room temperature. The solution was concentrated in vacuo using low (<40° C.) heat. Water (10 mL) and ether (50 mL) were added; the ether layer was extracted with 5 mL of water. The combined aqueous mixture was back-extracted with ether and then neutralized with acetic acid. This solution was extracted twice with ether. The ether was dried ($Na_2SO_4$) and concentrated in vacuo. EtOAc (1 mL) and ether (1 mL) were added to dissolve the product, and hexane was added dropwise to produce a white solid. The solid was collected and dried in vacuo to give 125 mg of the title compound.

EXAMPLE 534H (2R,3R,4S)-2-(3-Fluoro-4-methoxyphenyl)4-(1,3-benzodioxol-5-yl)1-(2-(N-propyl-N-pentanesulfonylamino)ethyl)-pyrrolidine-3-carboxylic Acid, Hydrochloride Salt The free amine is dissolved in iPrOH; a slight excess of HCl in iPrOH is added, and the solution is concentrated in vacuo. More IPA is added, and the solution is reconcentrated. The resultant sticky material is stirred with ether overnight to give a white powder, which is collected by filtration and dried overnight in vacuo at 60° C. Yield 95%.
EXAMPLE 535
The compounds in Table 3C may be prepared using methods presented in the above Examples.
TABLE 3C
1
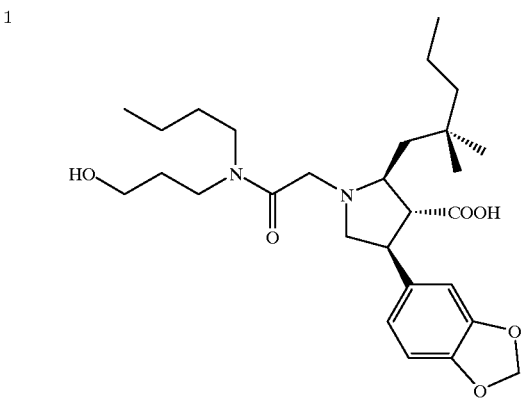
2
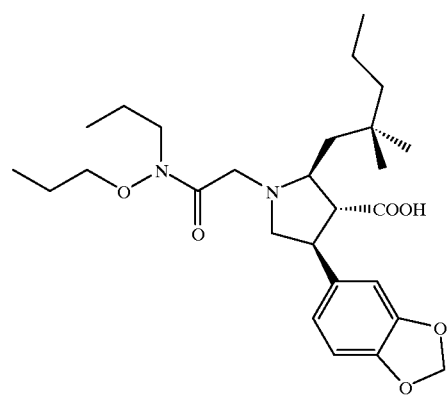
3
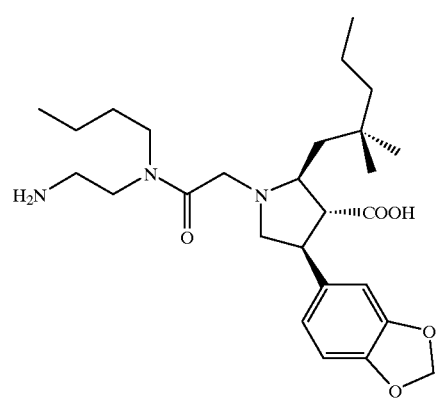

TABLE 3C-continued
4
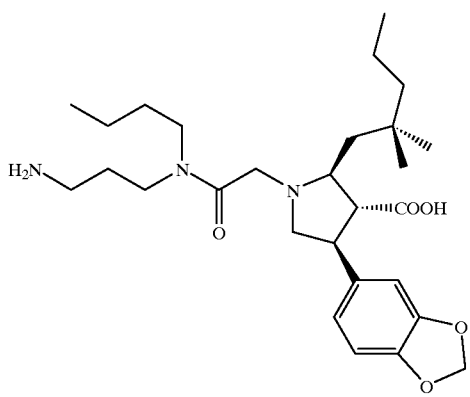
5
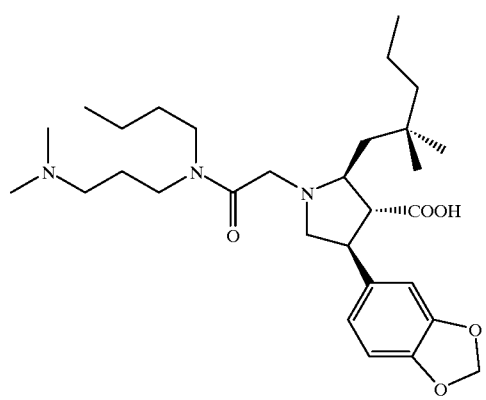
6
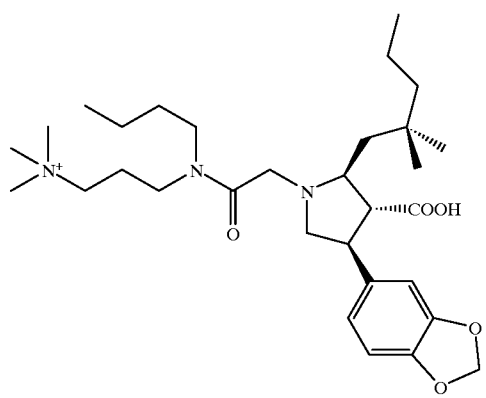
7
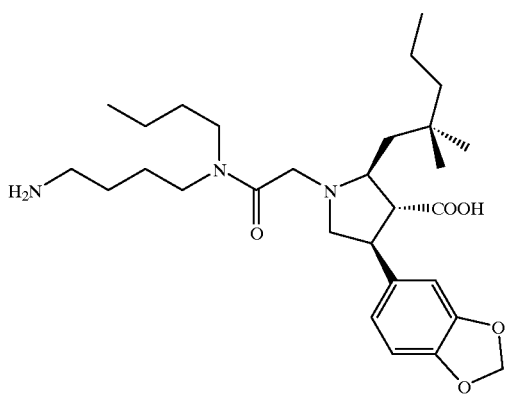

TABLE 3C-continued
8
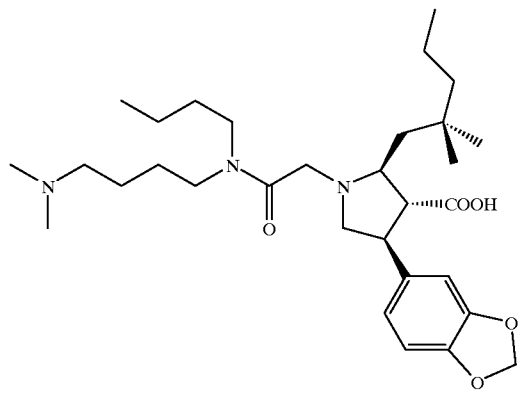
9
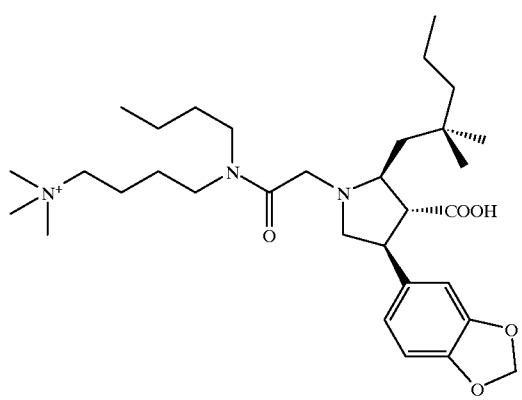
10
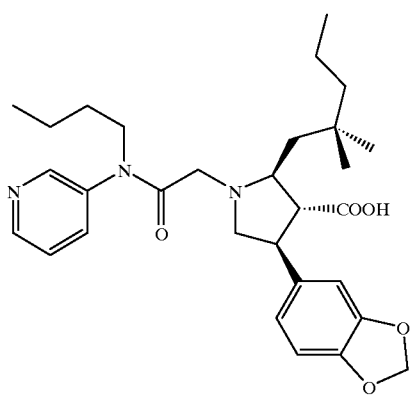
11
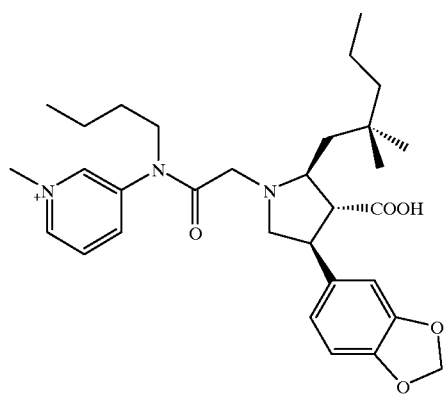

TABLE 3C-continued
| 12 | 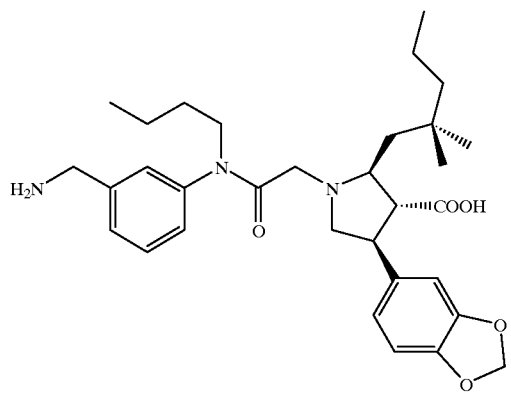 |
| 13 | 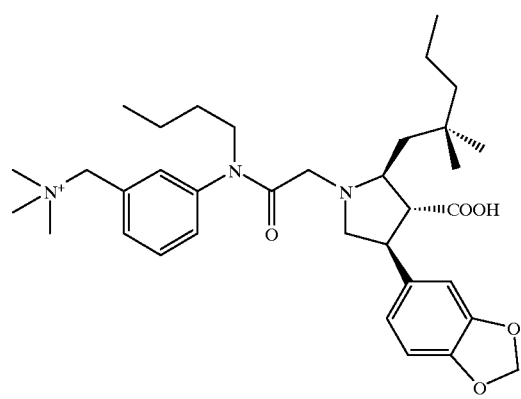 |
| 14 | 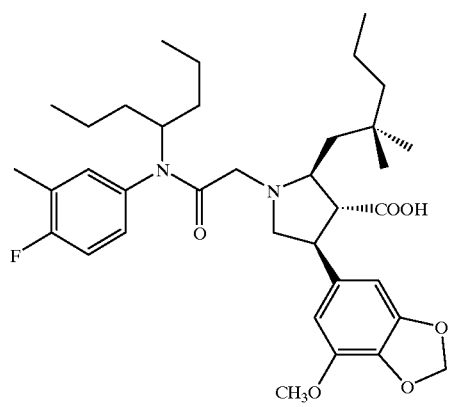 |
| 15 | 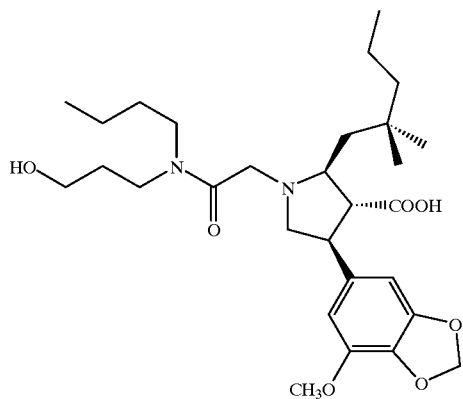 |

TABLE 3C-continued
16
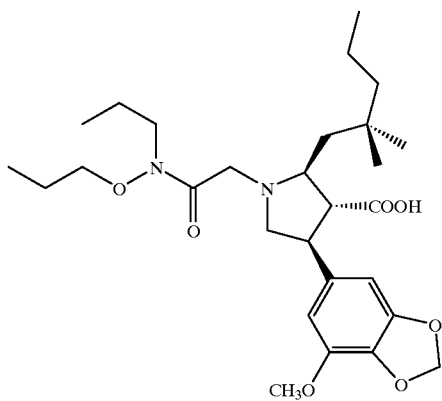
17
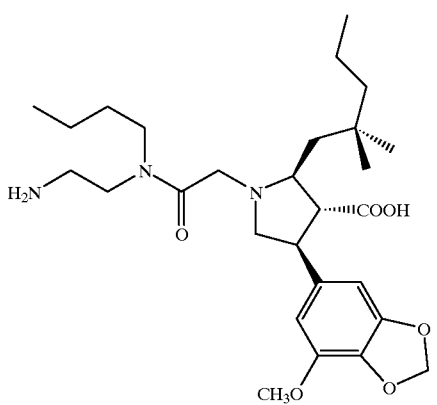
18
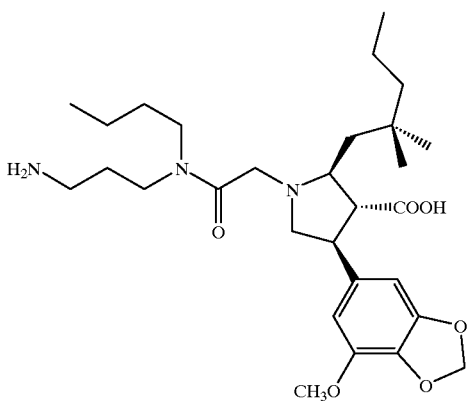

TABLE 3C-continued
19
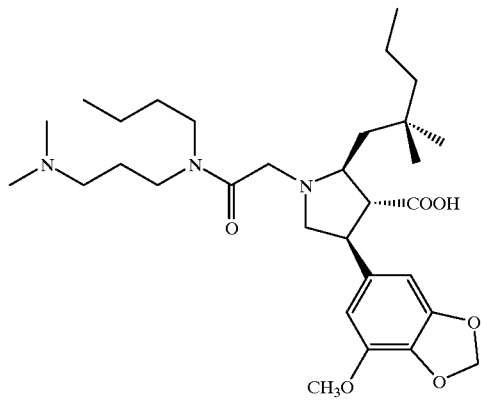
20
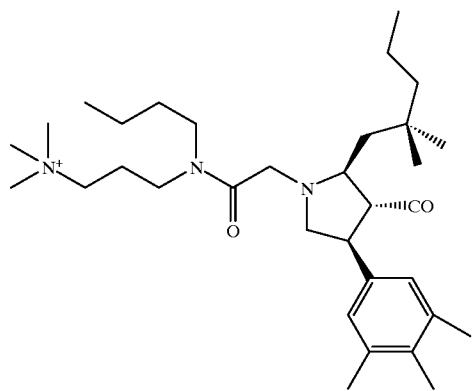
21
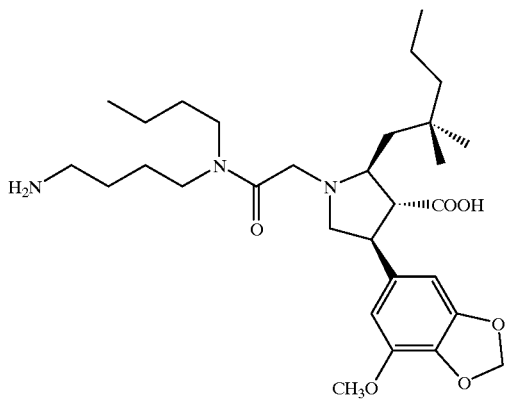

TABLE 3C-continued
22
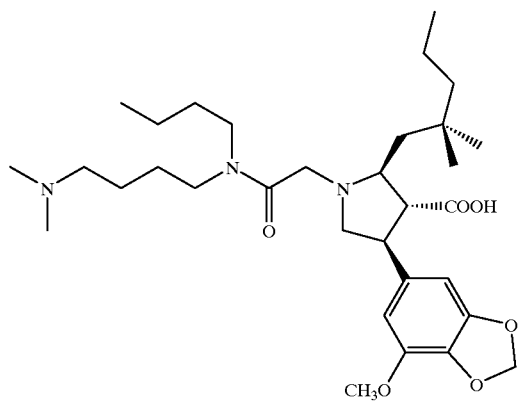
23
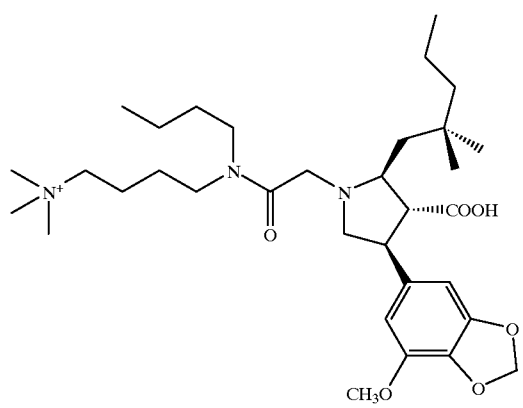
24
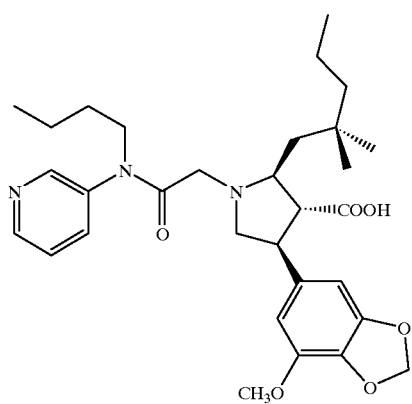

TABLE 3C-continued
25 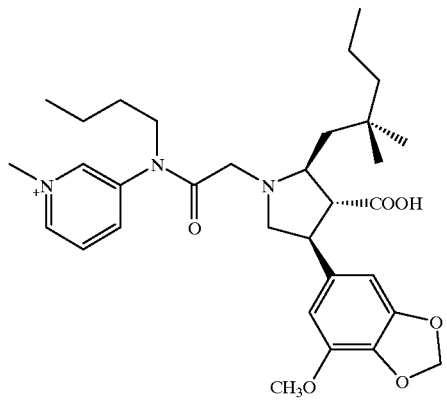
26 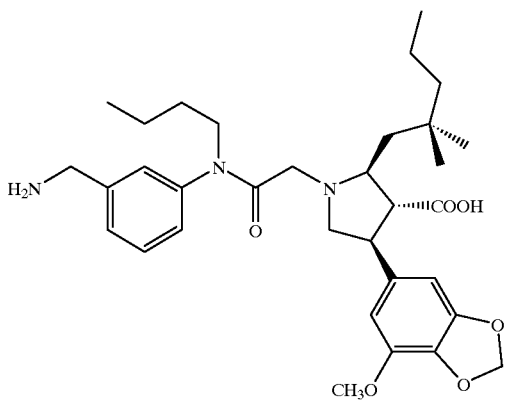
27 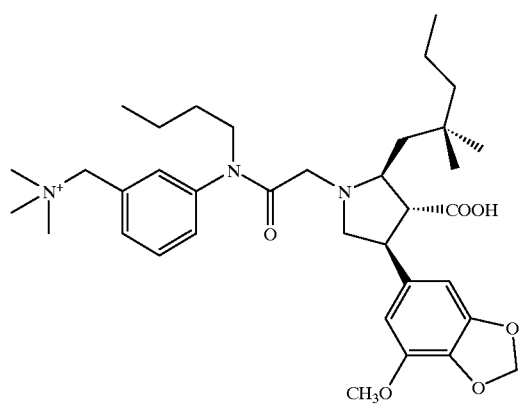

TABLE 3C-continued
28 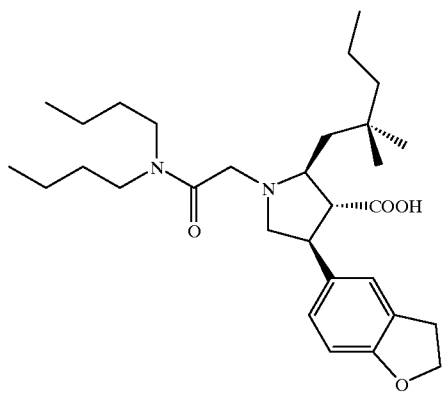
29 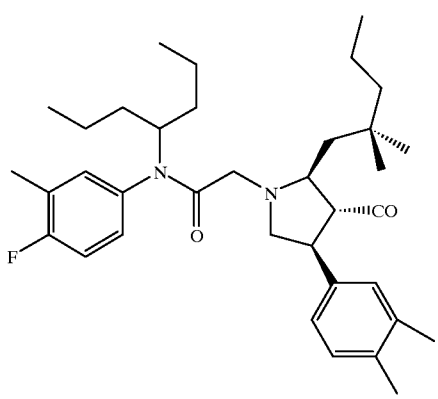
30 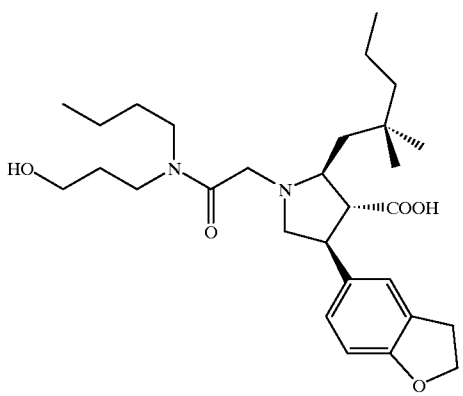
31 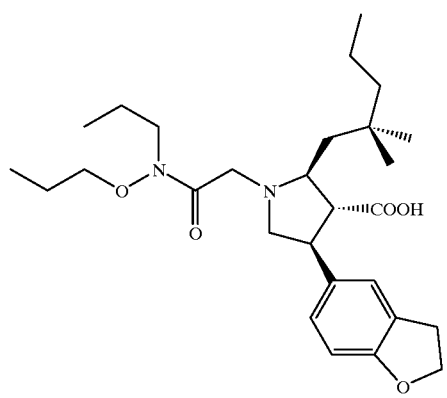

TABLE 3C-continued
| 32 | 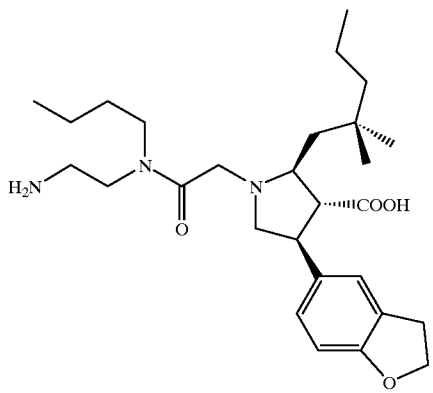 |
|---|---|
| 33 | 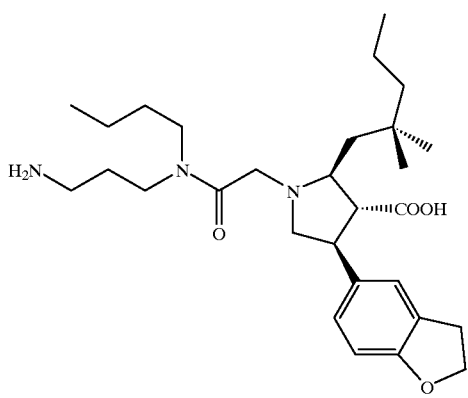 |
| 34 | 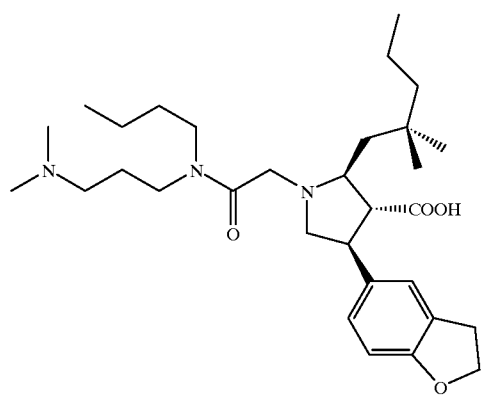 |
| 35 | 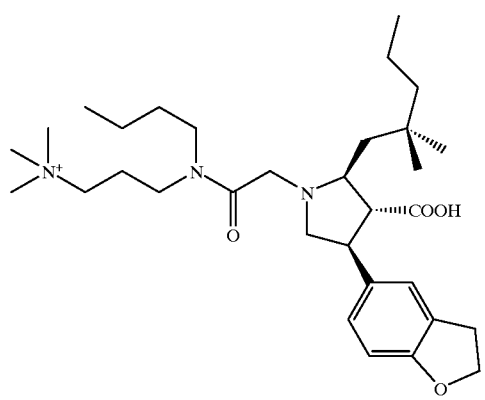 |

TABLE 3C-continued
| 36 | 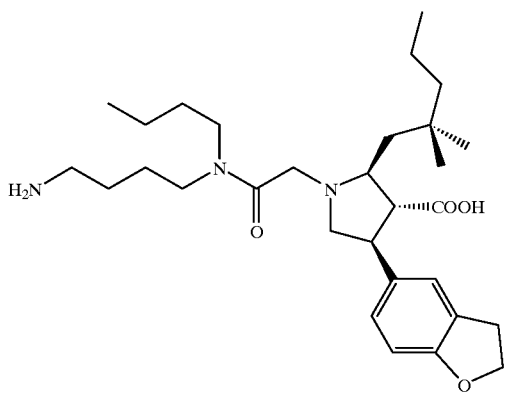 |
| --- | --- |
| 37 | 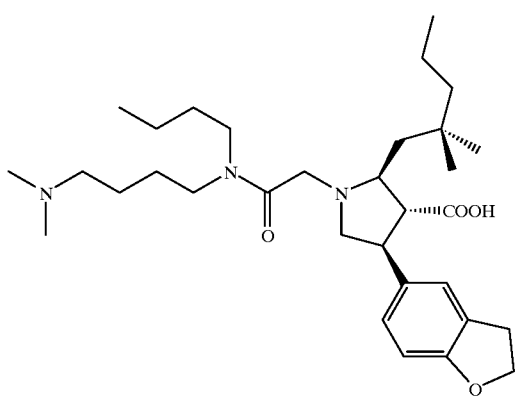 |
| 38 | 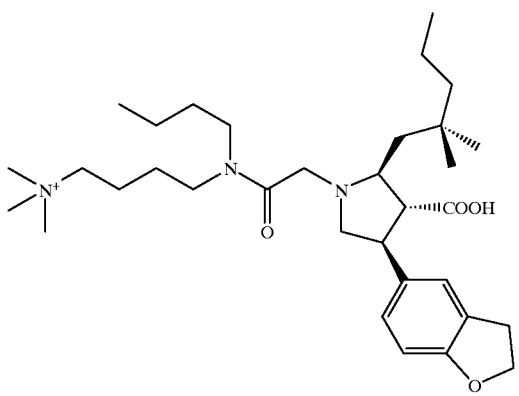 |
| 39 | 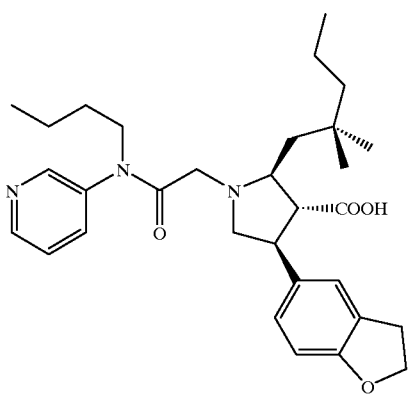 |

TABLE 3C-continued
40 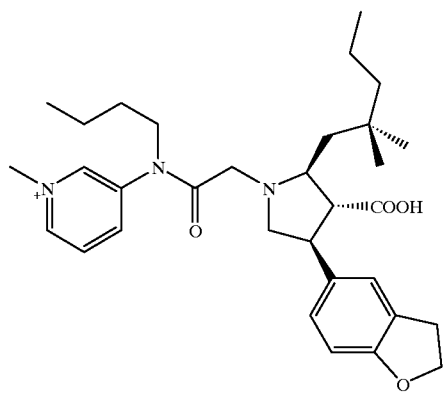
41 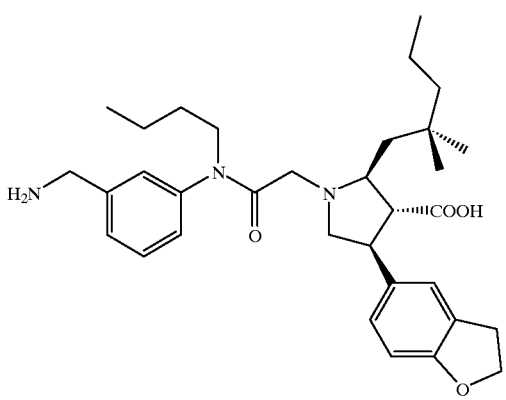
42 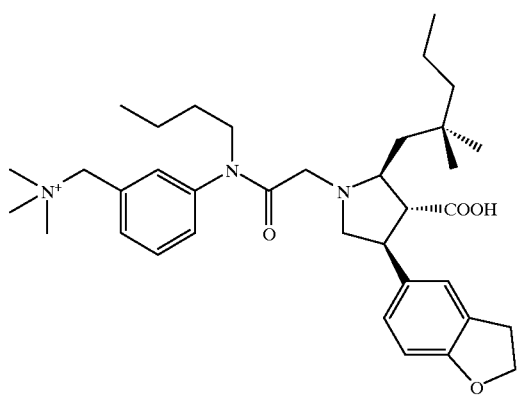
43 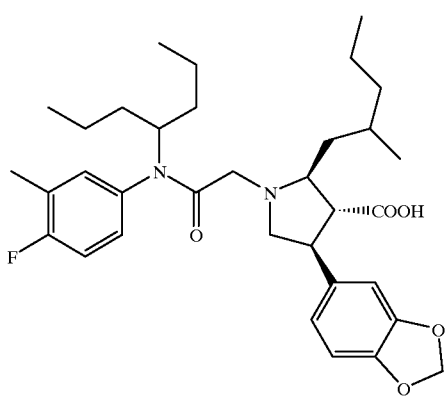

TABLE 3C-continued
| 44 | 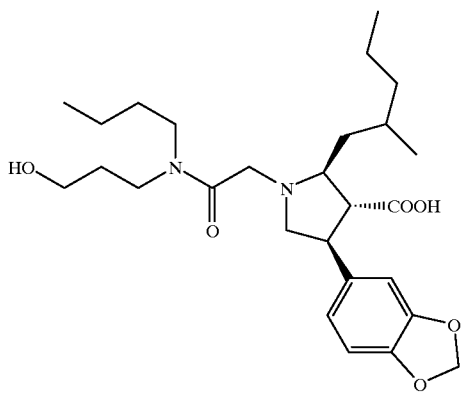 |
| 45 | 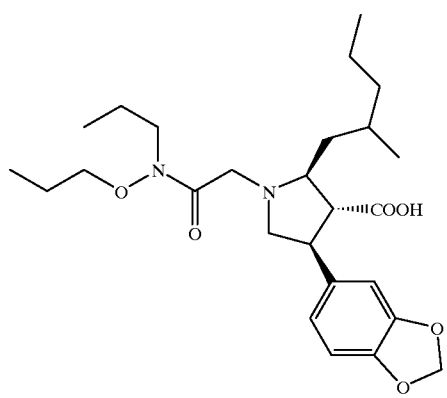 |
| 46 | 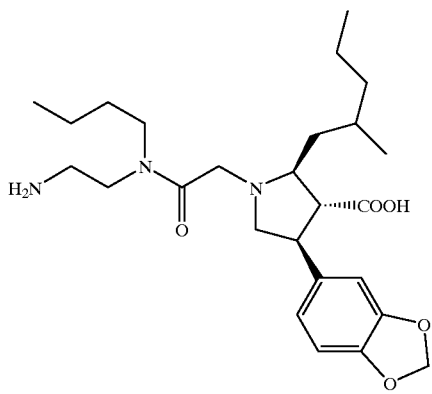 |
| 47 | 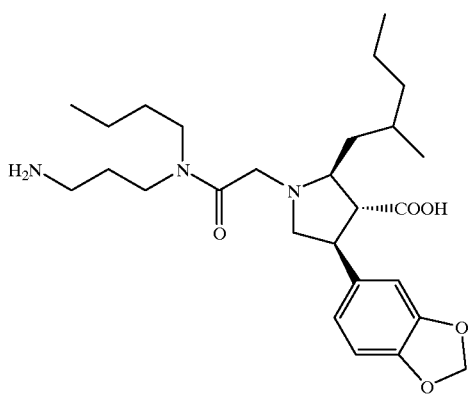 |

TABLE 3C-continued
| 48 | 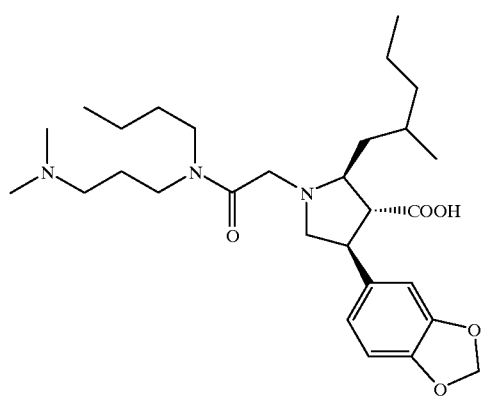 |
| --- | --- |
| 49 | 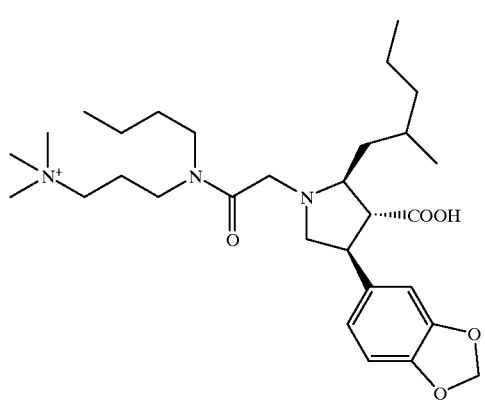 |
| 50 | 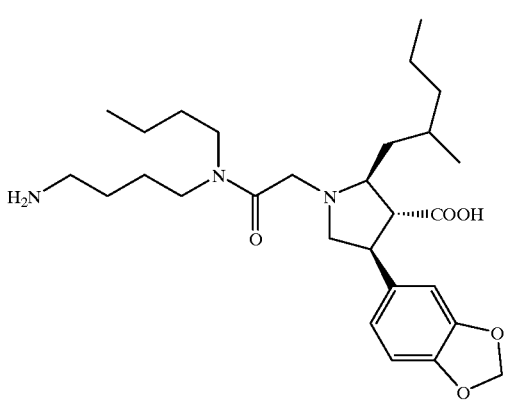 |
| 51 | 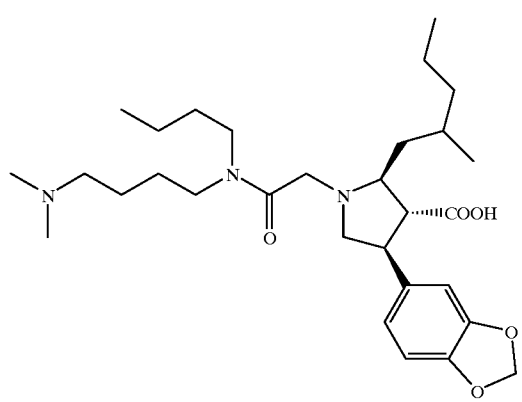 |

TABLE 3C-continued
52 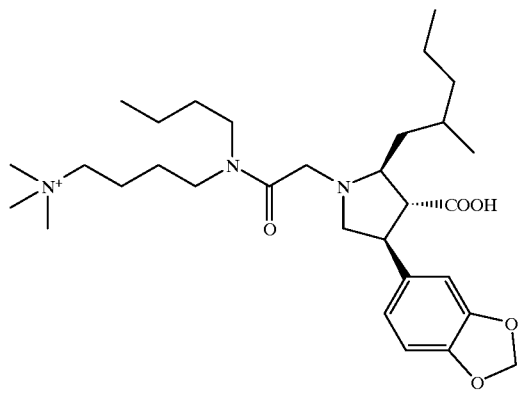
53 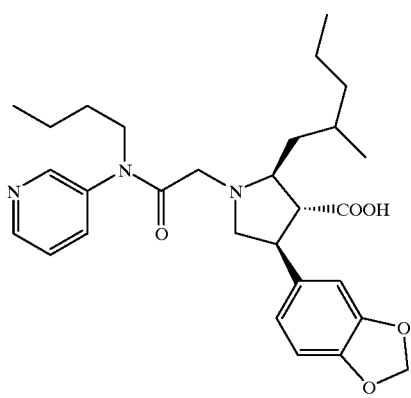
54 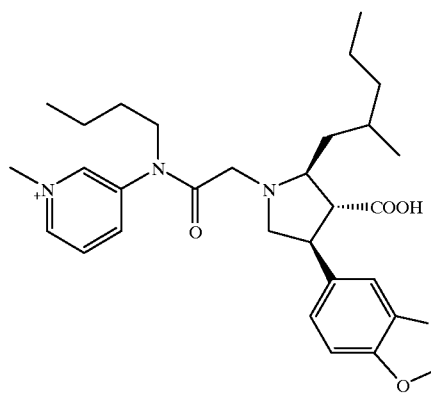
55 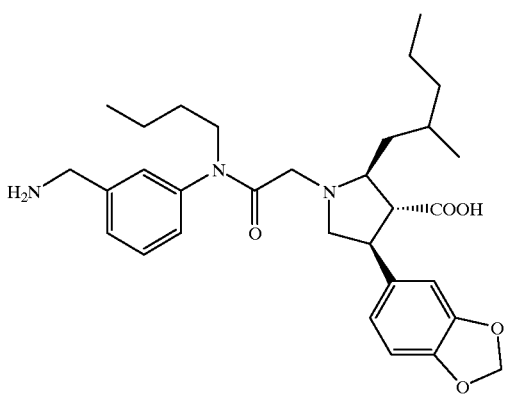

TABLE 3C-continued
56
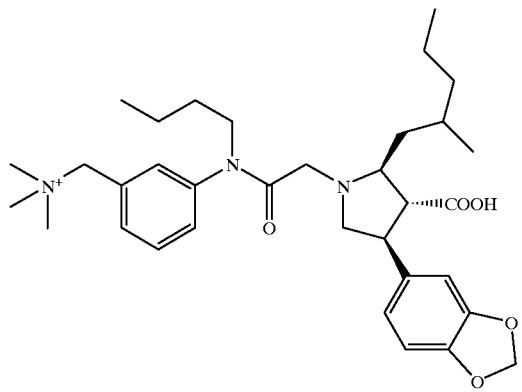
57
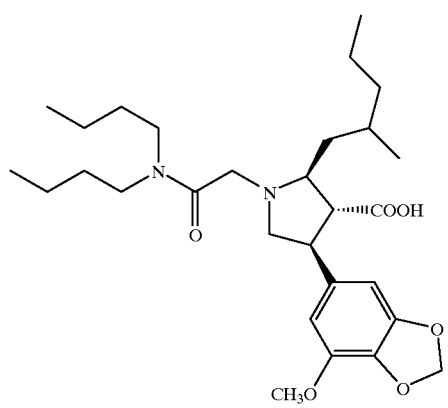
58
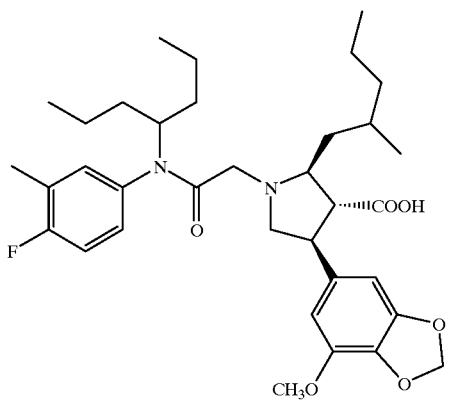

TABLE 3C-continued
59
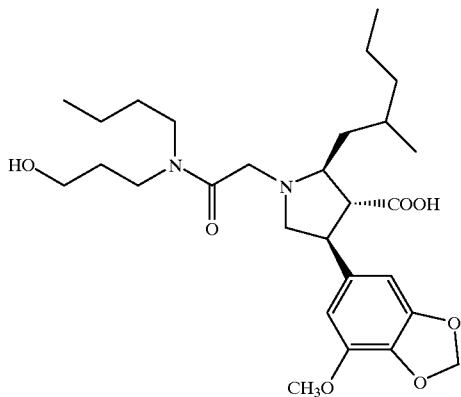
60
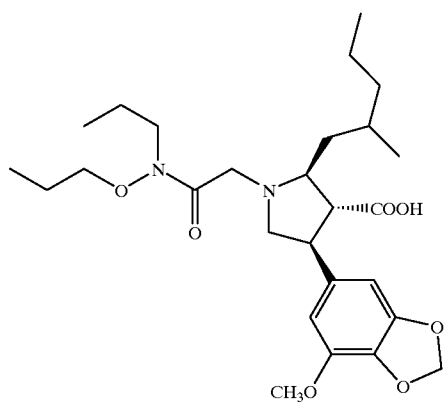
61
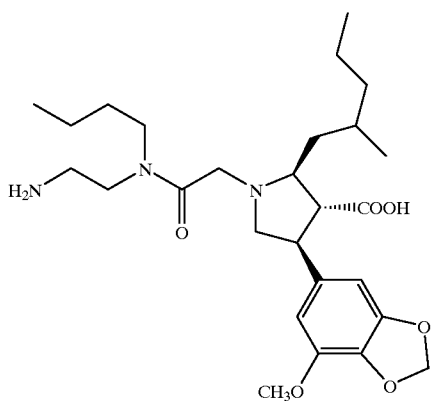

TABLE 3C-continued
62 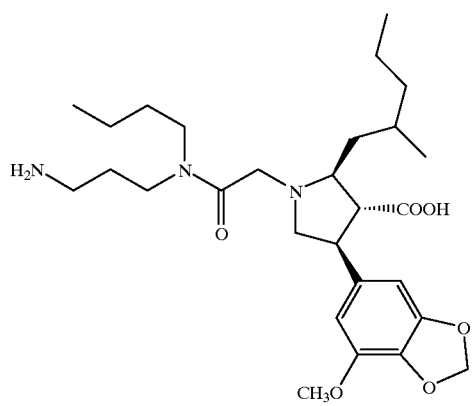
63 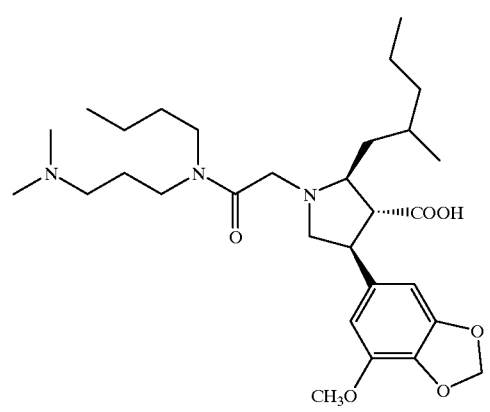
64 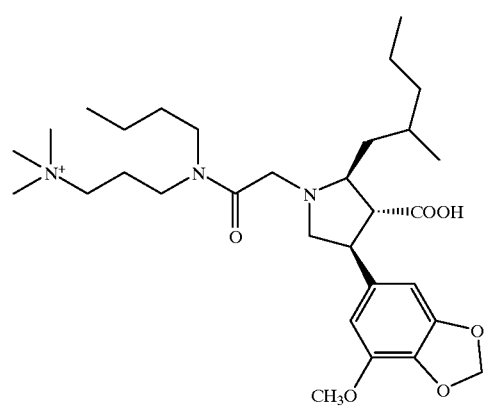

TABLE 3C-continued
65
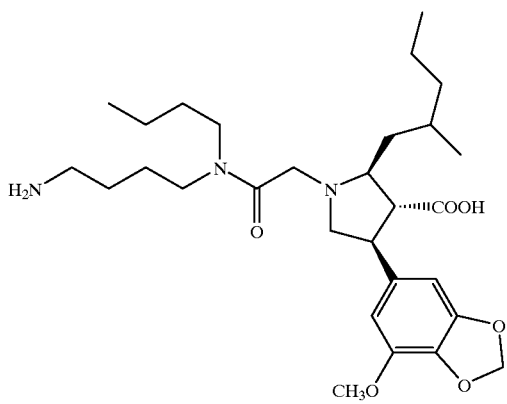
66
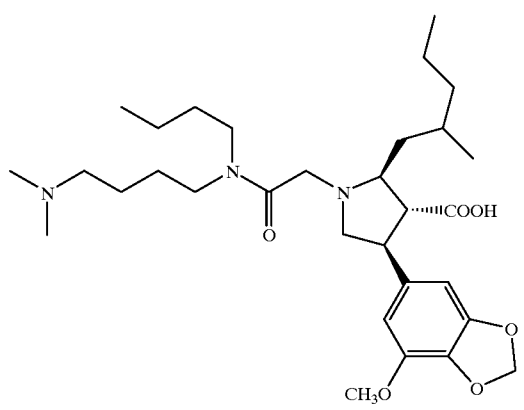
67
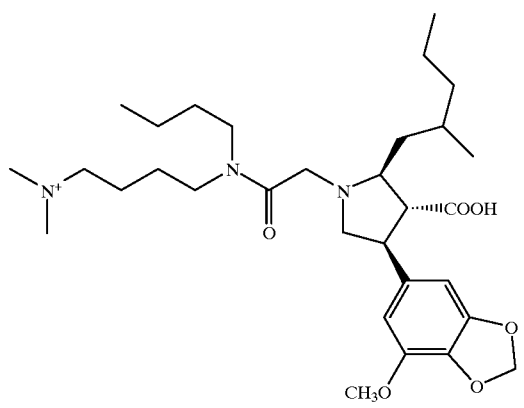

TABLE 3C-continued
68
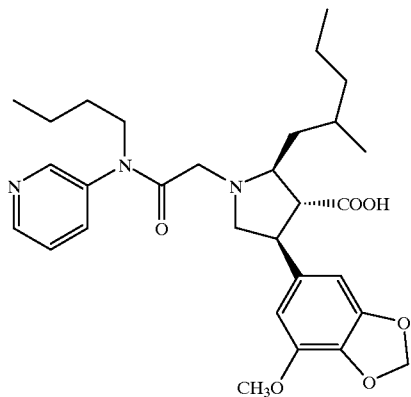
69
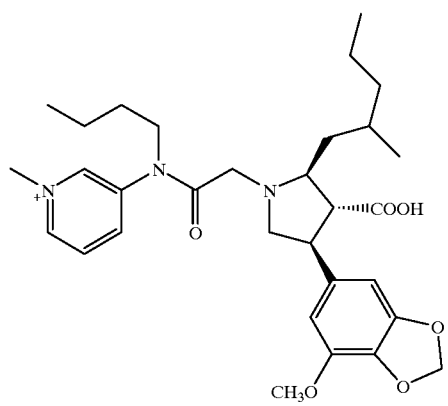
70
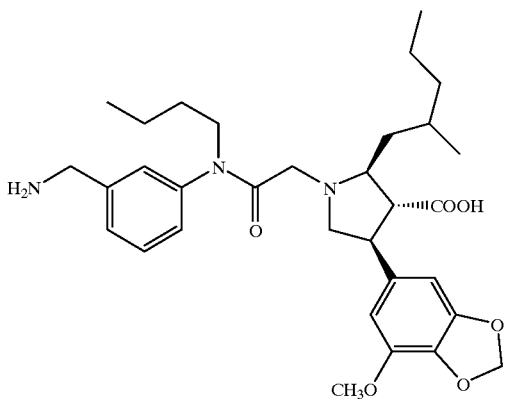

TABLE 3C-continued
| 71 | 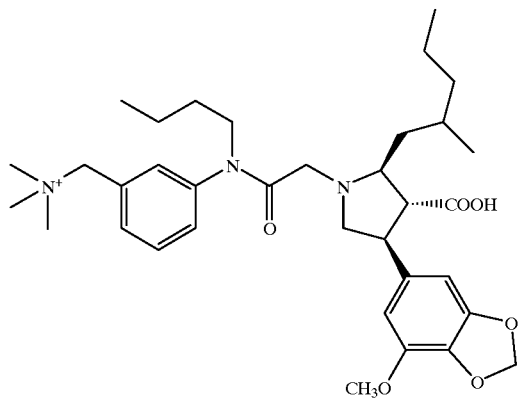 |
| --- | --- |
| 72 | 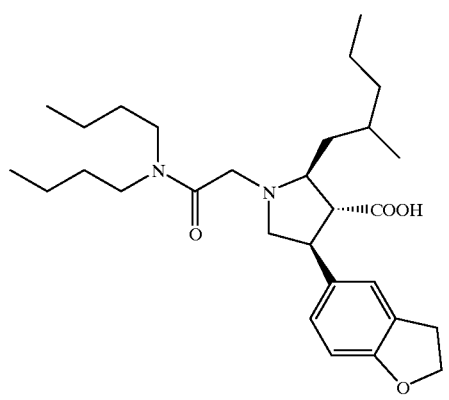 |
| 73 | 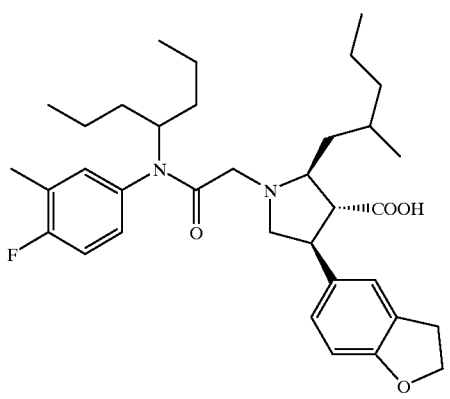 |
| 74 | 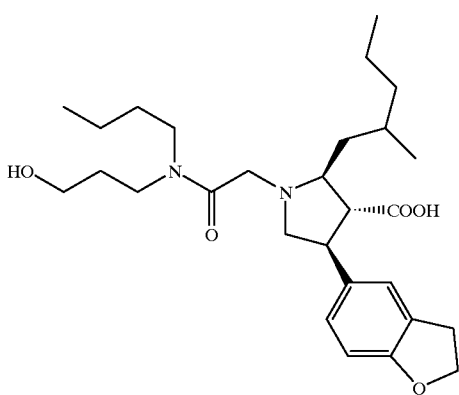 |

TABLE 3C-continued
75 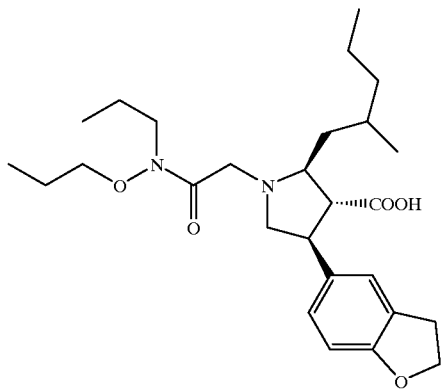
76 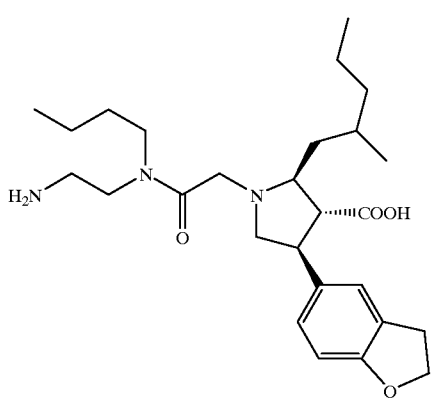
77 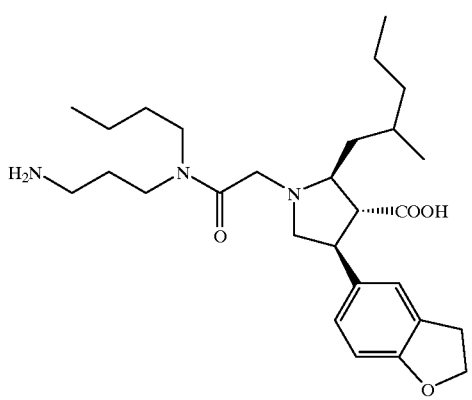
78 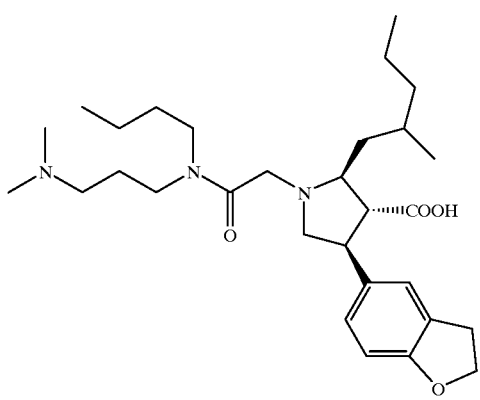

TABLE 3C-continued
79 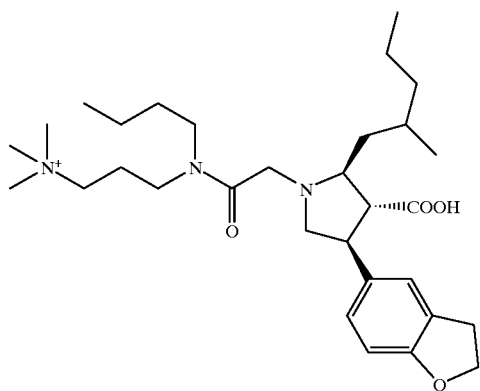
80 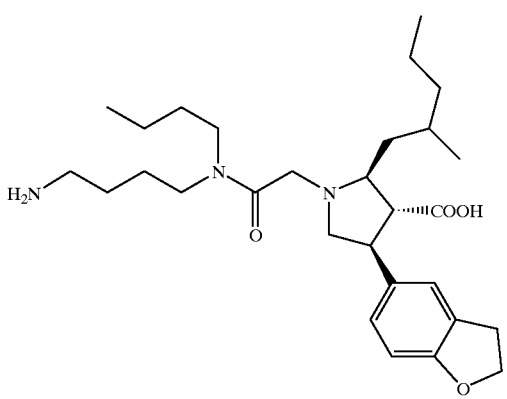
81 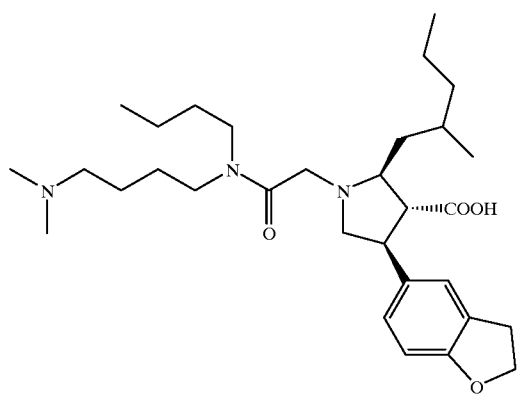
82 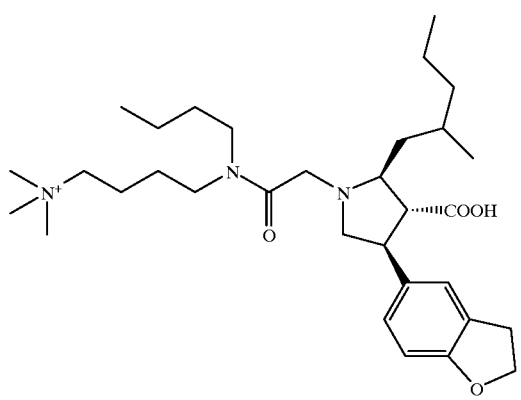

TABLE 3C-continued
83 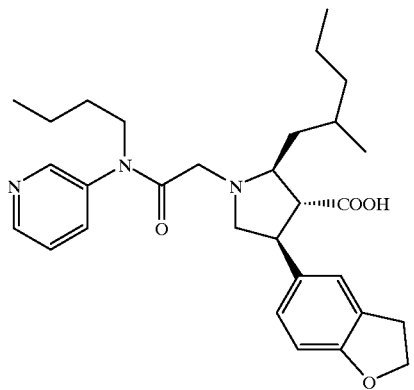
84 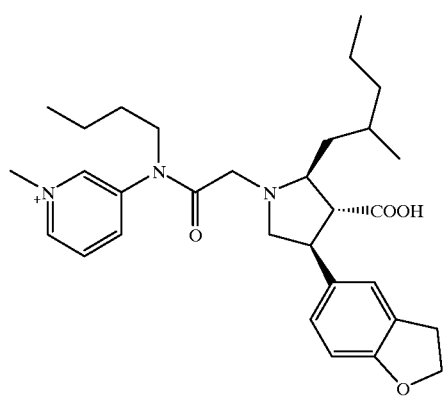
85 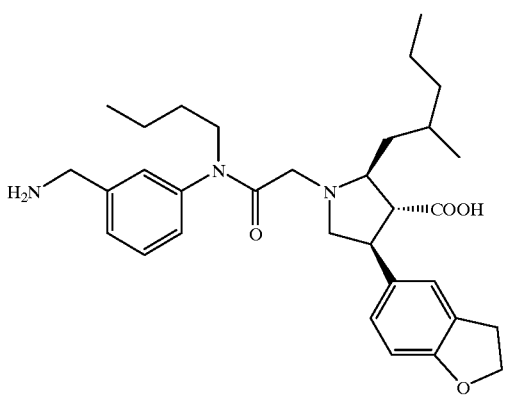
86 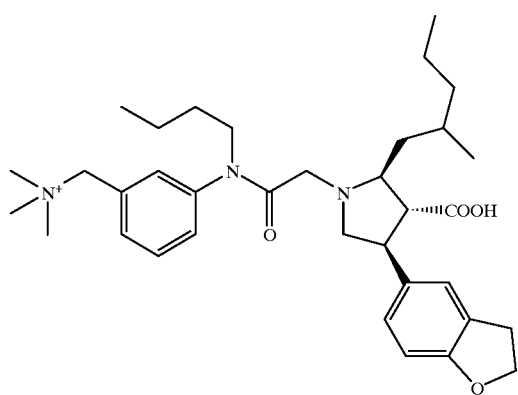

TABLE 3C-continued
87 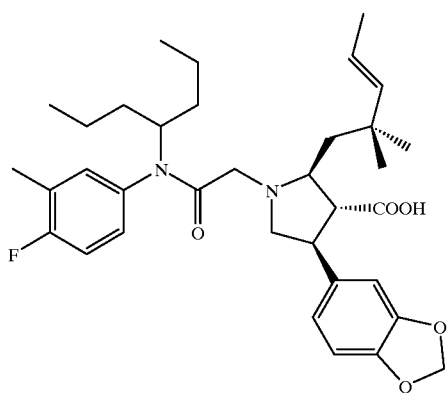
88 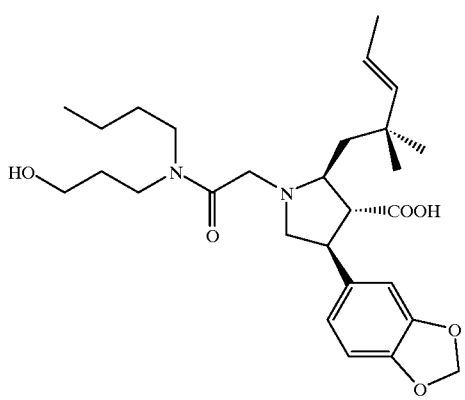
89 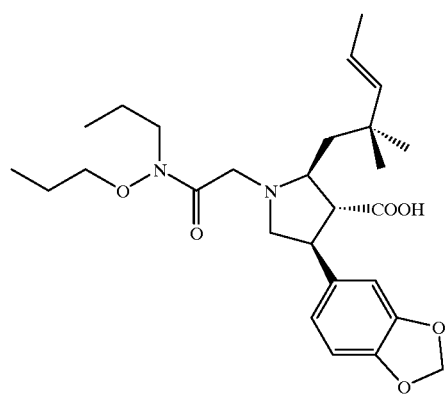
90 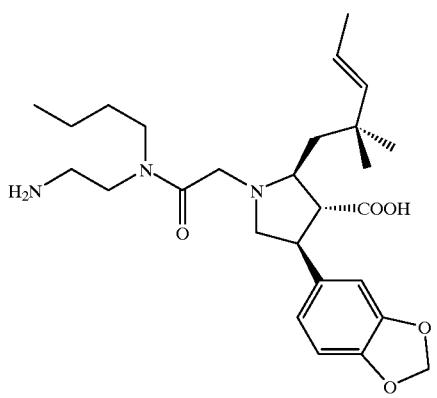

TABLE 3C-continued
91 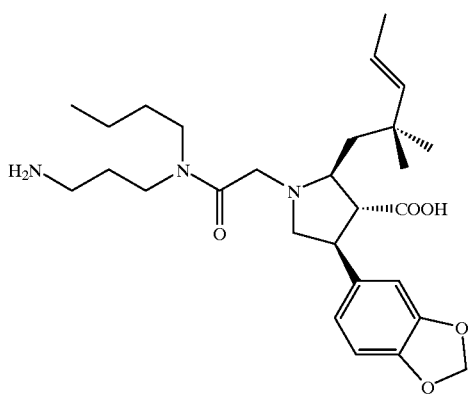
92 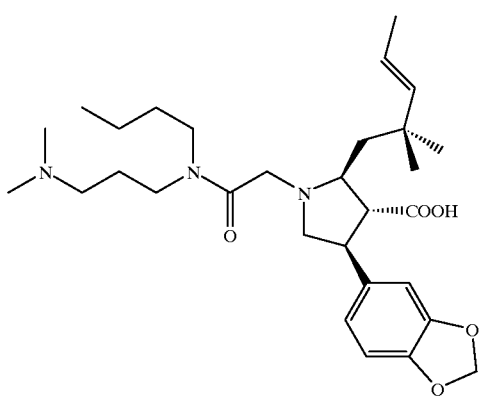
93 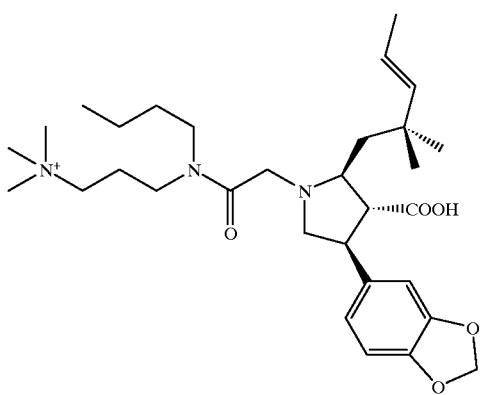
94 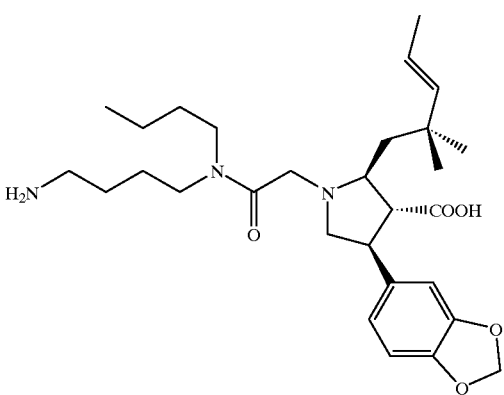

TABLE 3C-continued
95
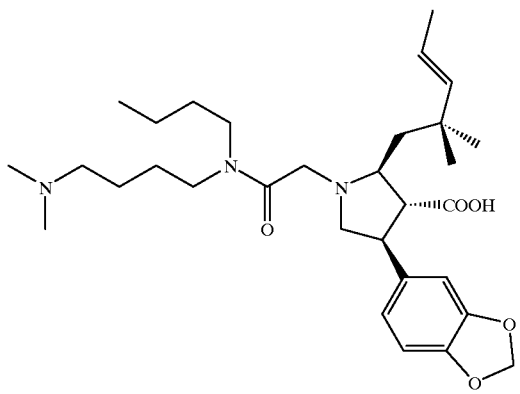
96
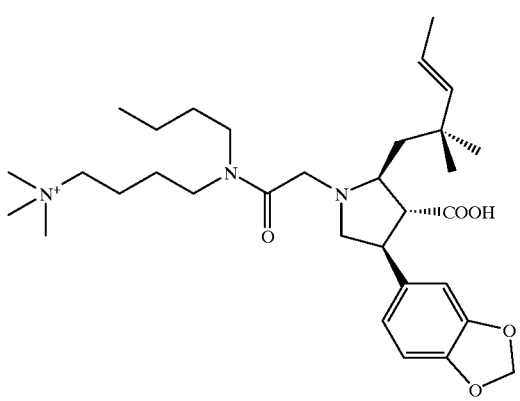
97
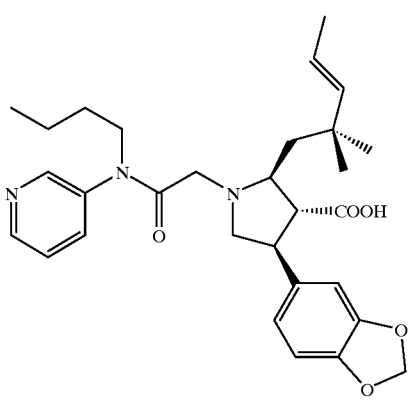
98
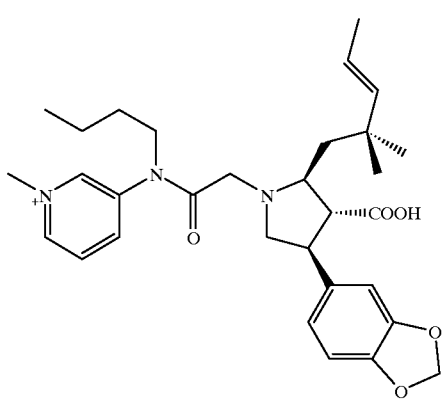

TABLE 3C-continued
99
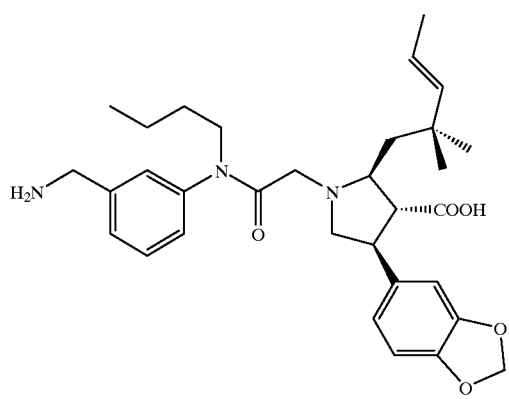
100
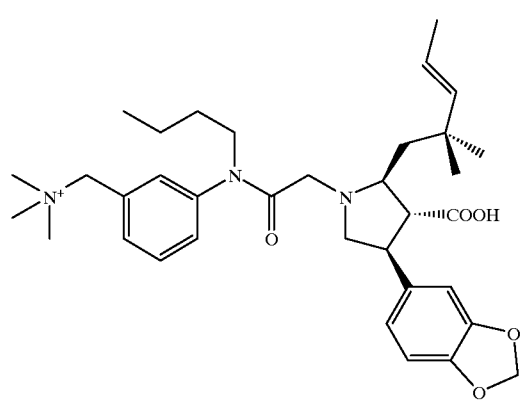
101
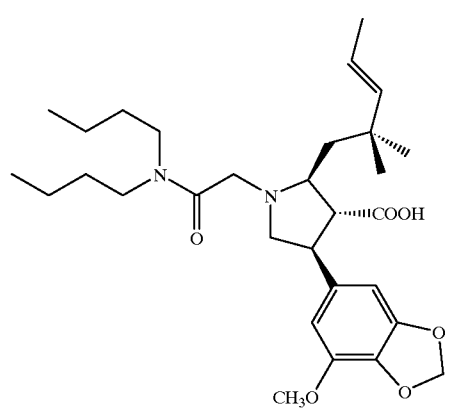

TABLE 3C-continued
102
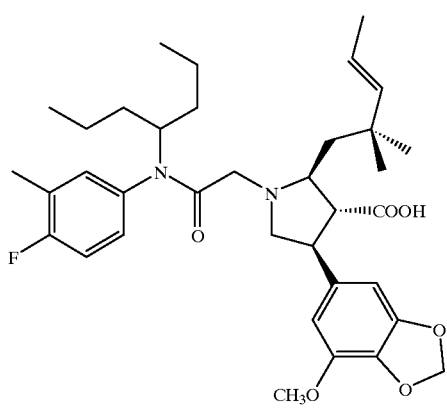
103
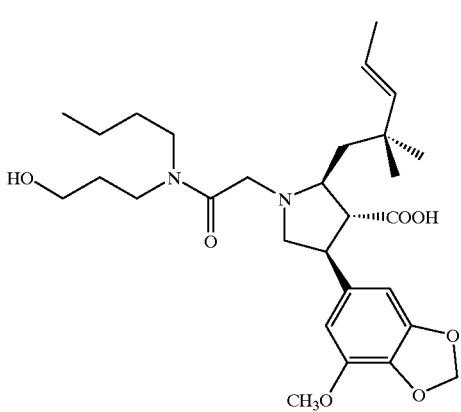
104
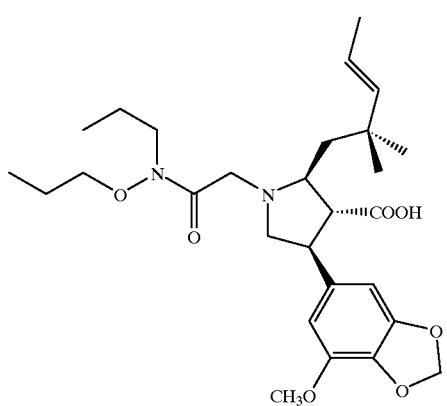

TABLE 3C-continued
105
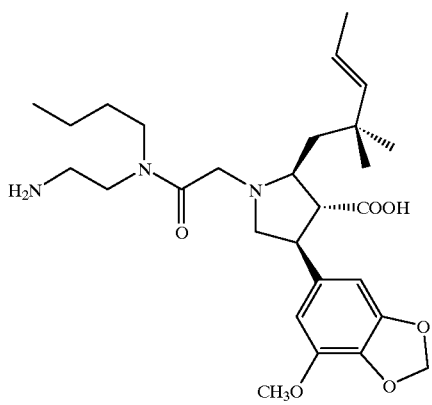
106
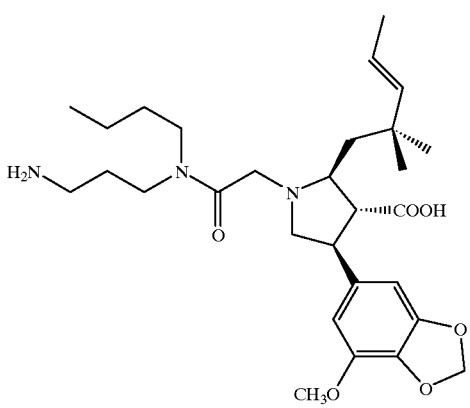
107
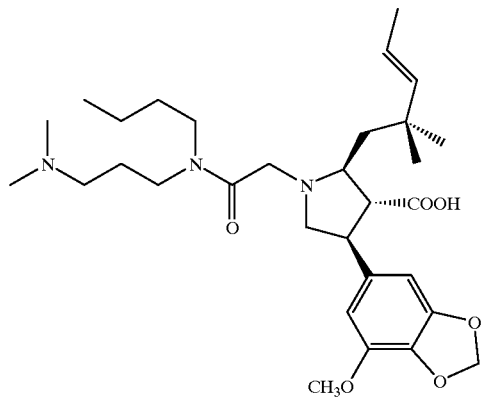

TABLE 3C-continued
108
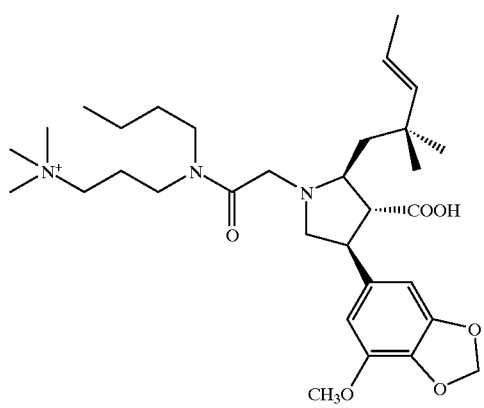
109
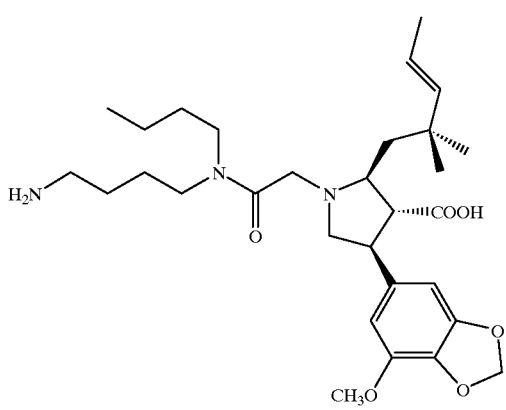
110
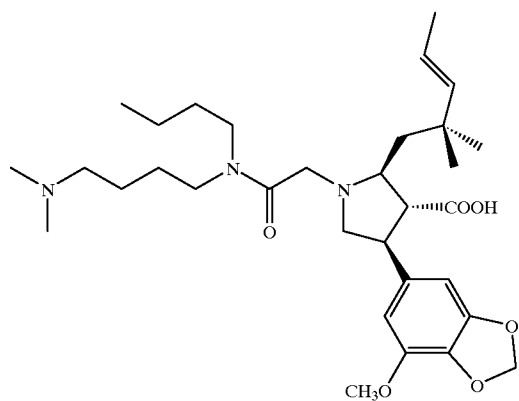

TABLE 3C-continued
111
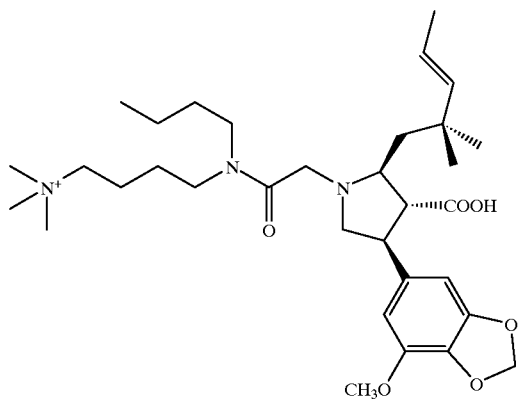
112
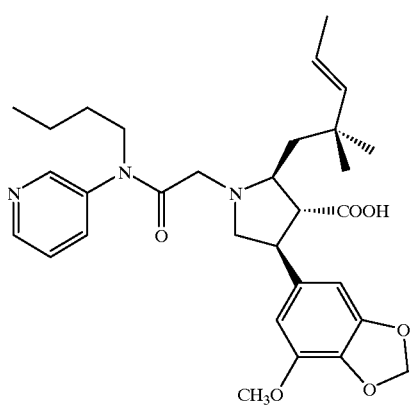
113
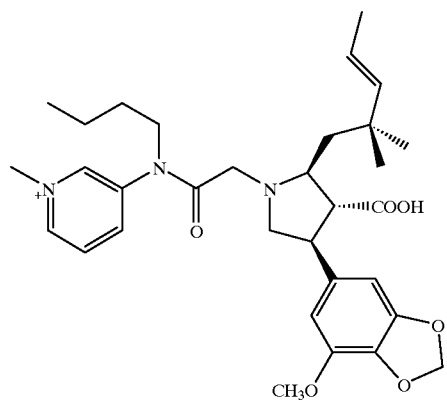

TABLE 3C-continued
114 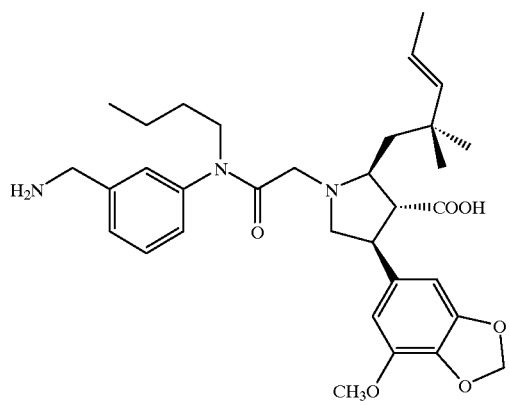
115 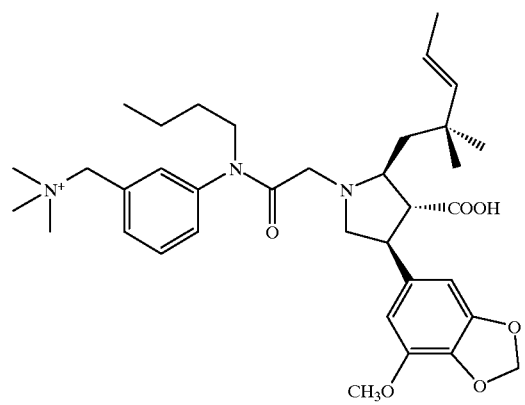
116 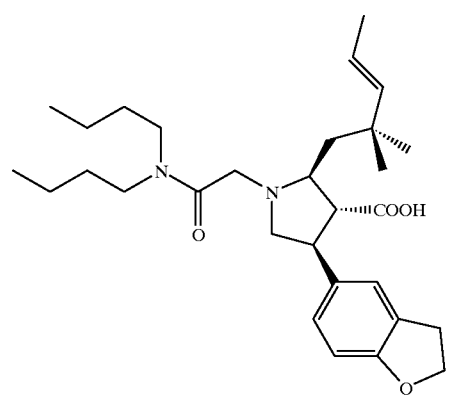
117 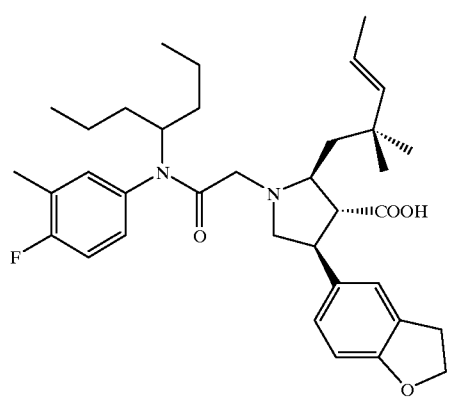

TABLE 3C-continued
118
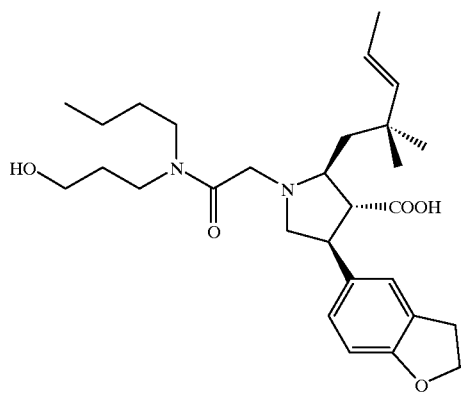
119
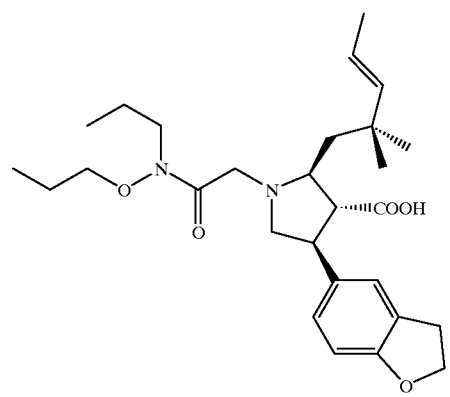
120
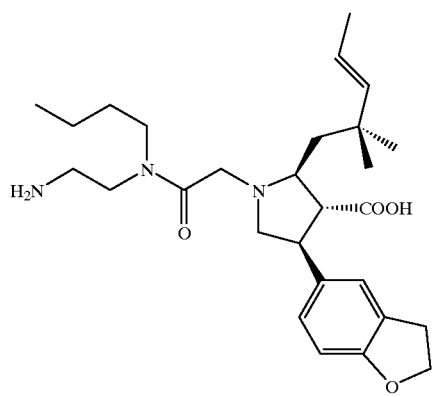

TABLE 3C-continued
| 121 | 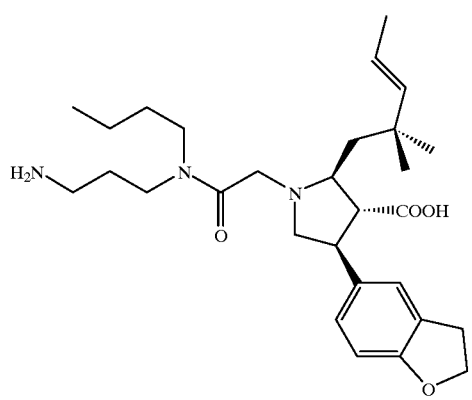 |
| 122 | 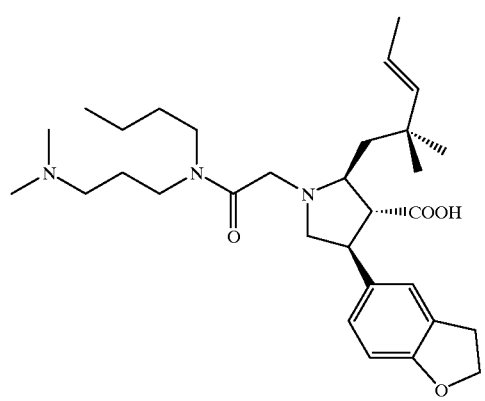 |
| 123 | 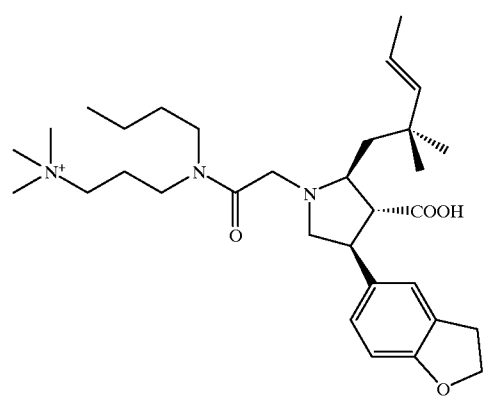 |
| 124 | 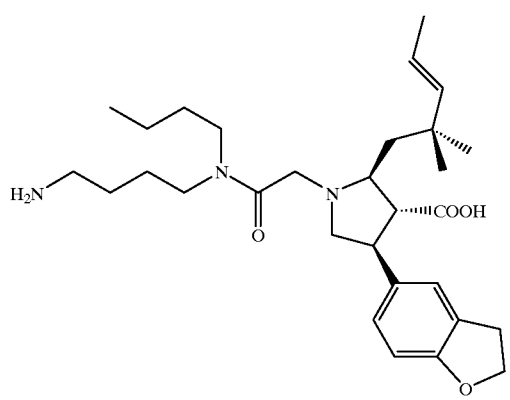 |

TABLE 3C-continued
125 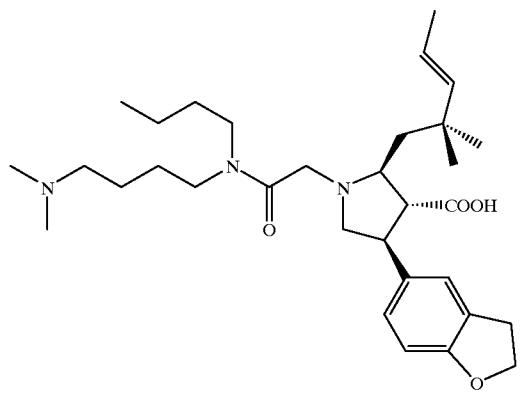
126 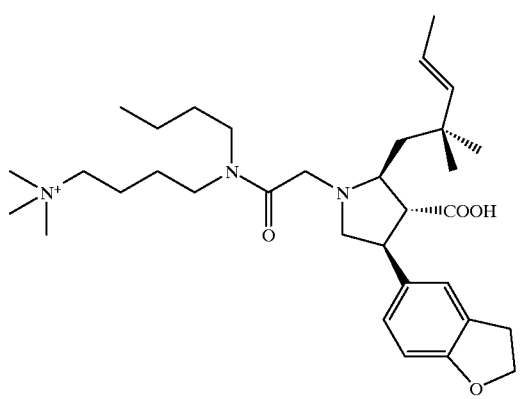
127 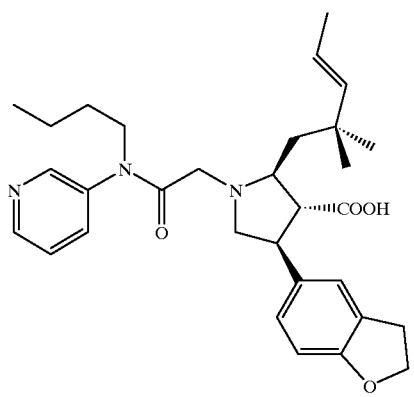
128 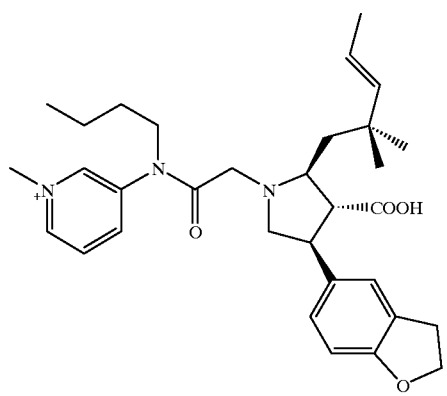

TABLE 3C-continued
| 129 | 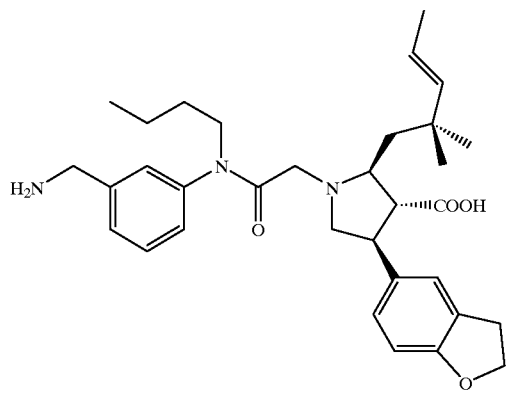 |
| --- | --- |
| 130 | 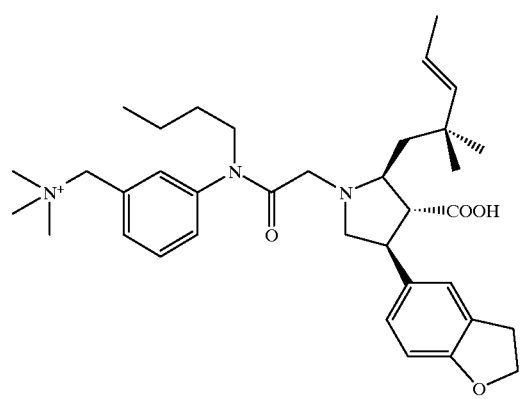 |
| 131 | 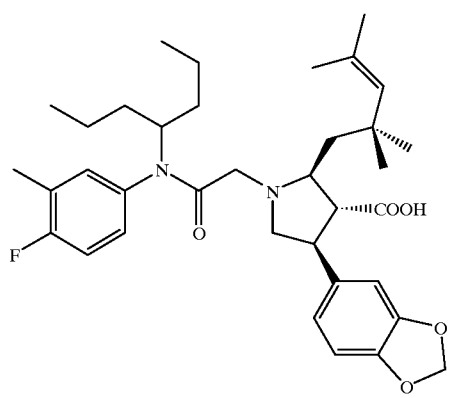 |
| 132 | 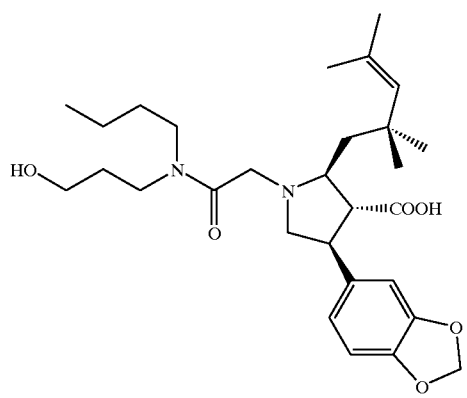 |

TABLE 3C-continued
133
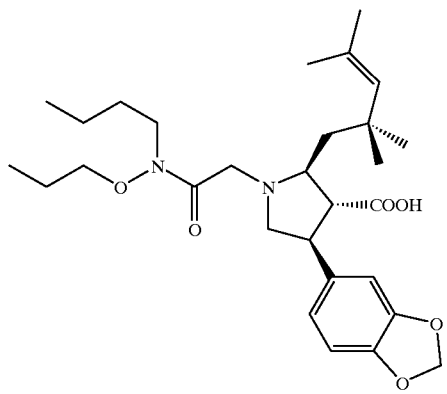
134
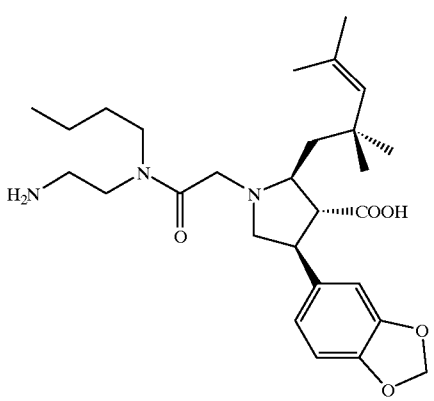
135
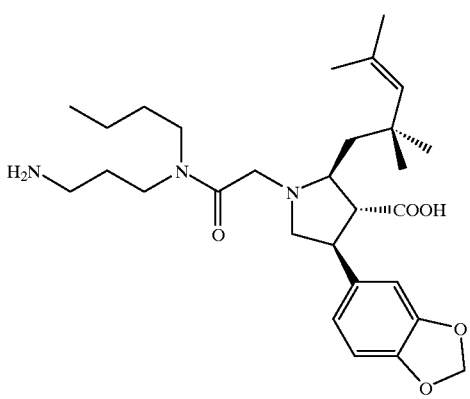
136
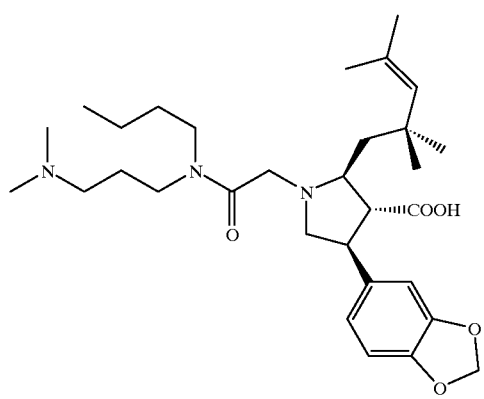

TABLE 3C-continued
137 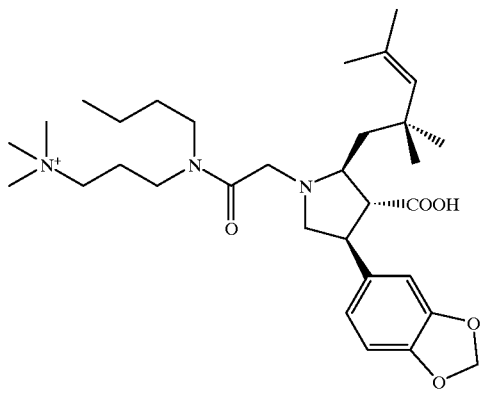
138 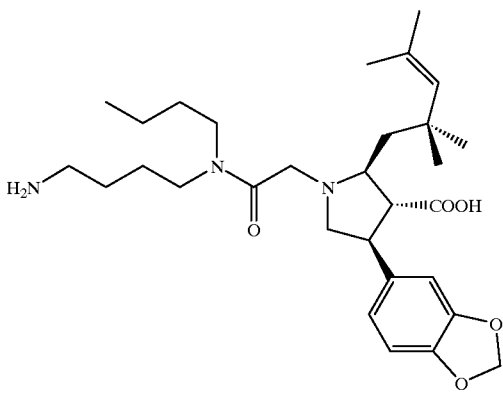
139 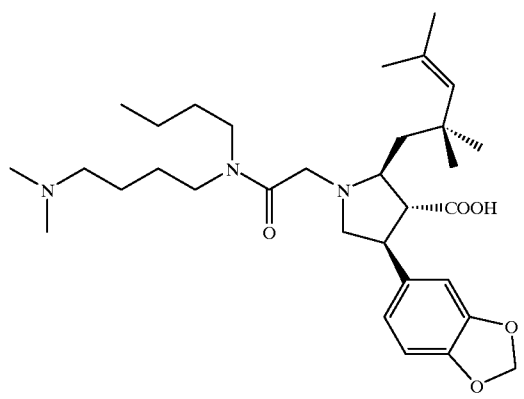
140 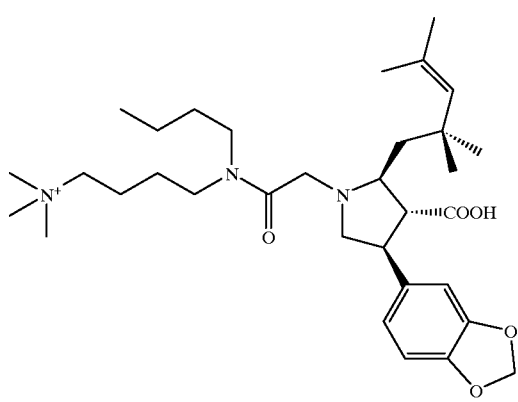

TABLE 3C-continued
141
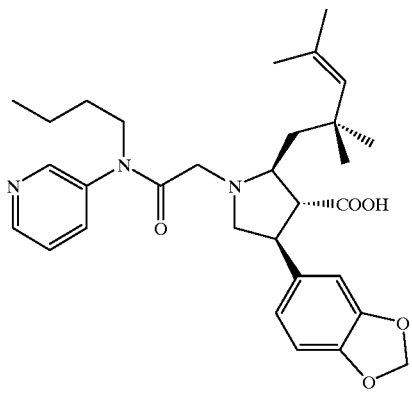
142
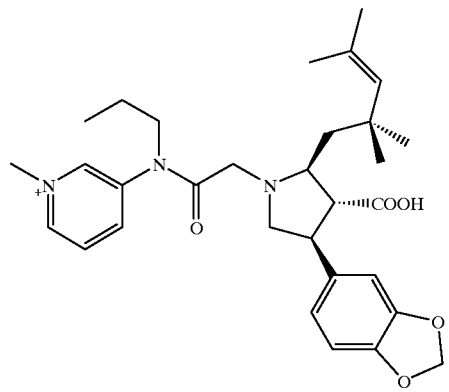
143
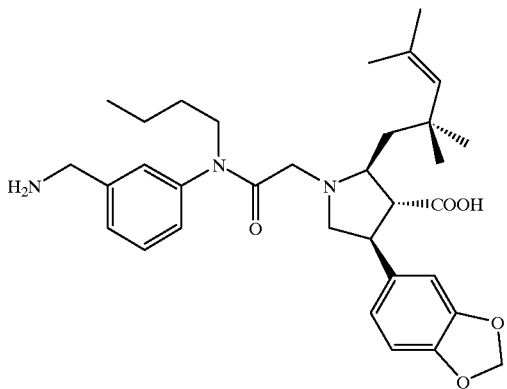
144
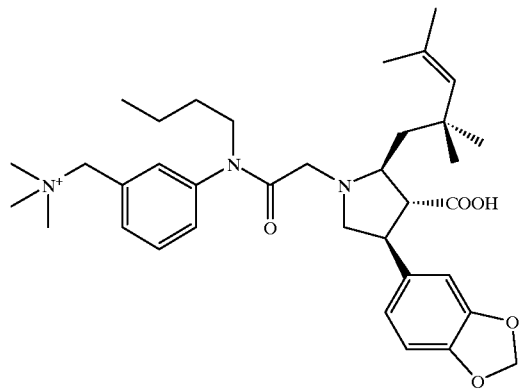

TABLE 3C-continued
145
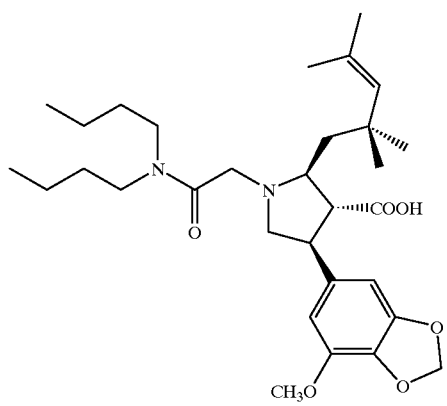
146
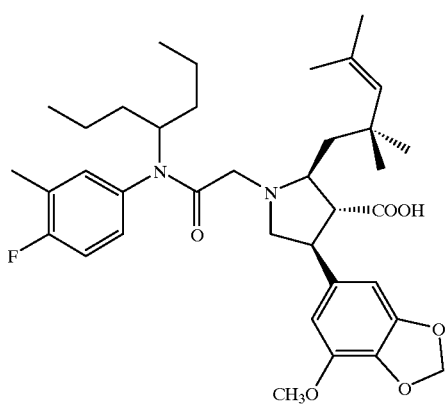
147
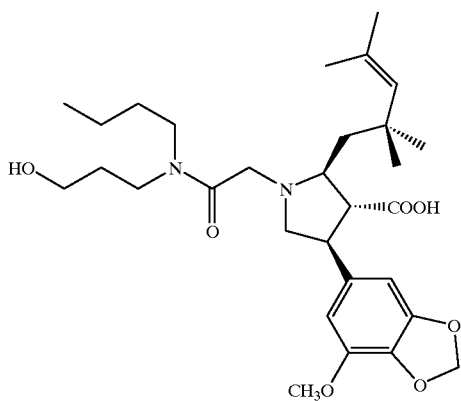

TABLE 3C-continued
148
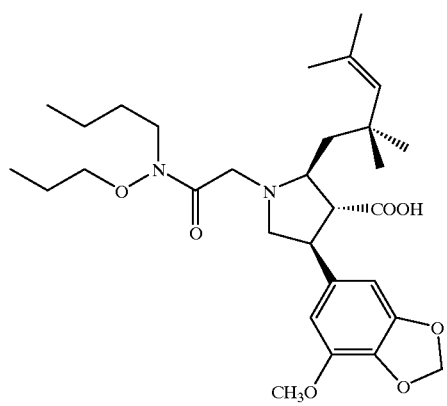
149
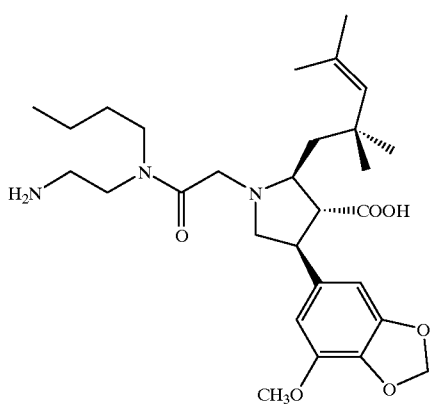
150
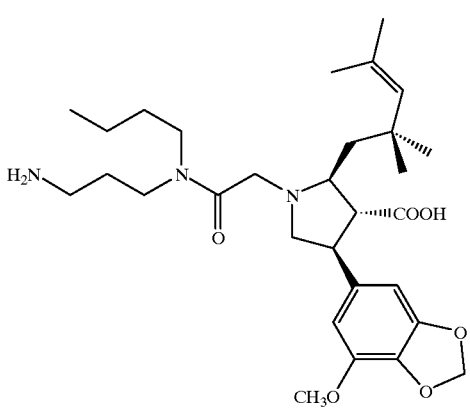

TABLE 3C-continued
151
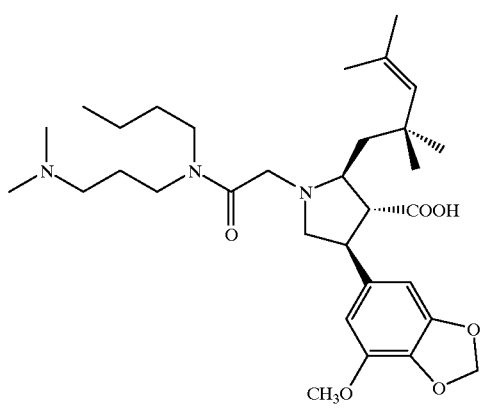
152
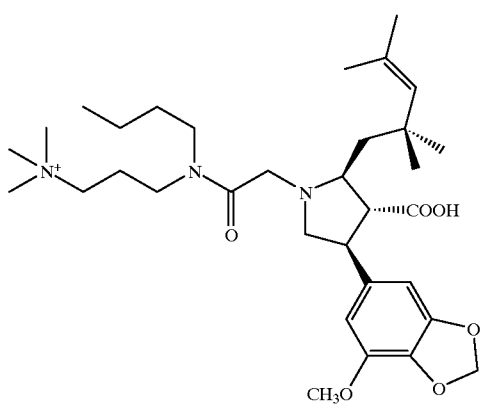
153
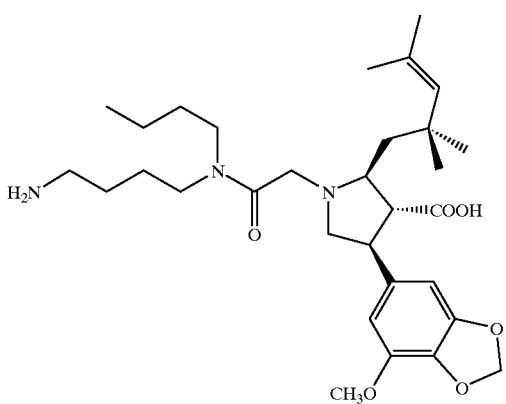

TABLE 3C-continued
154
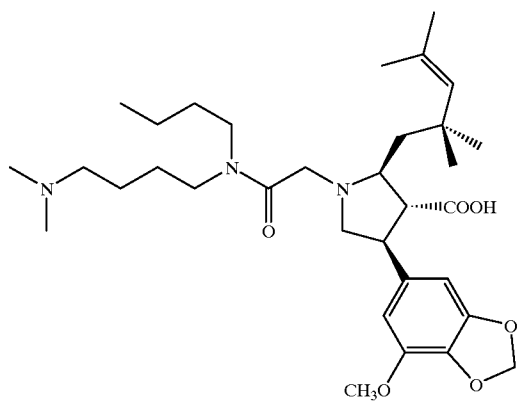
155
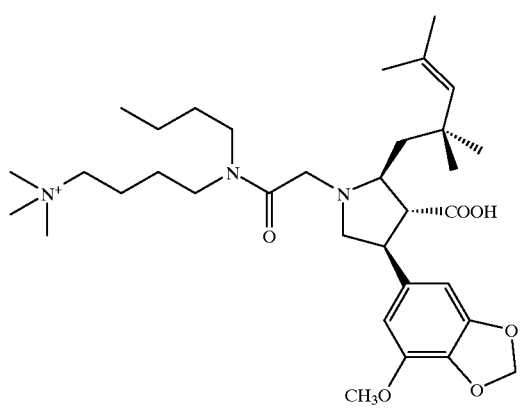
156
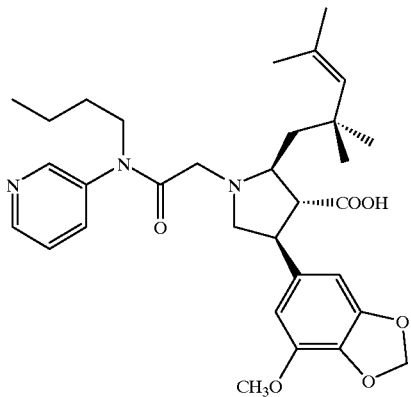

TABLE 3C-continued
157 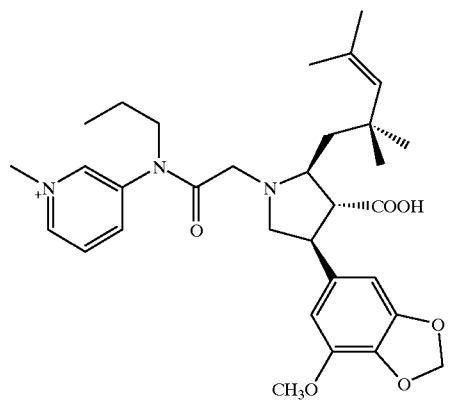
158 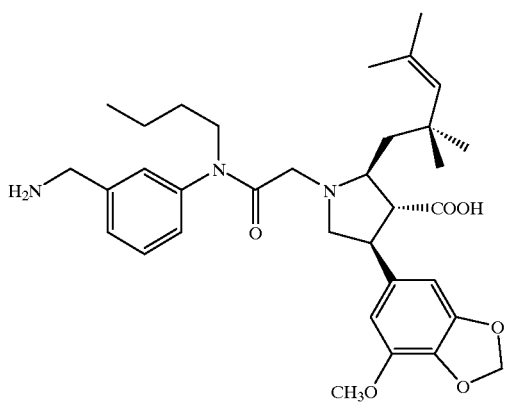
159 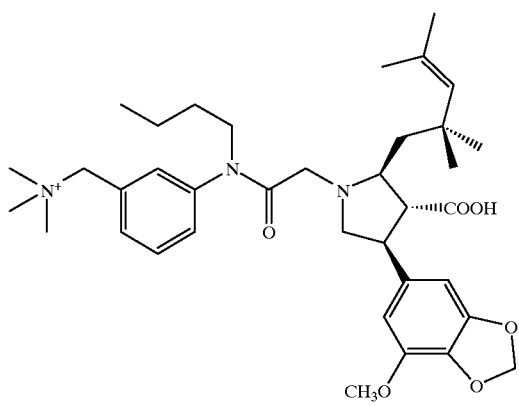
160 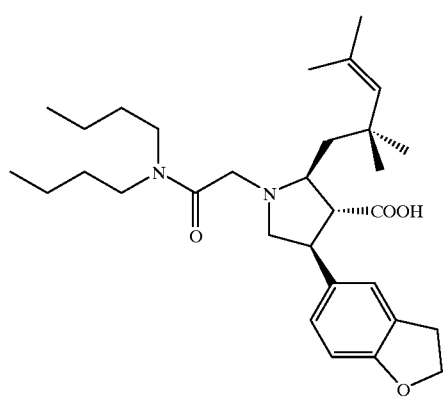

TABLE 3C-continued
| 161 | 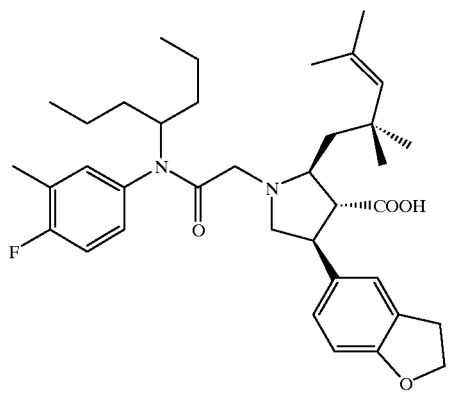 |
| --- | --- |
| 162 | 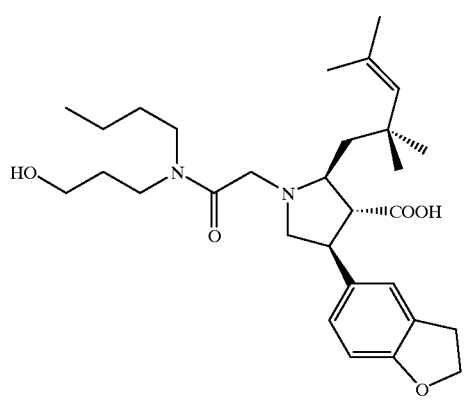 |
| 163 | 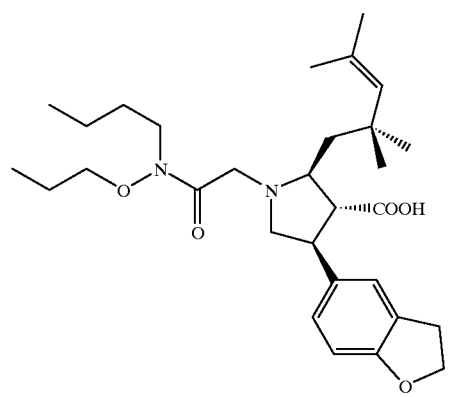 |
| 164 | 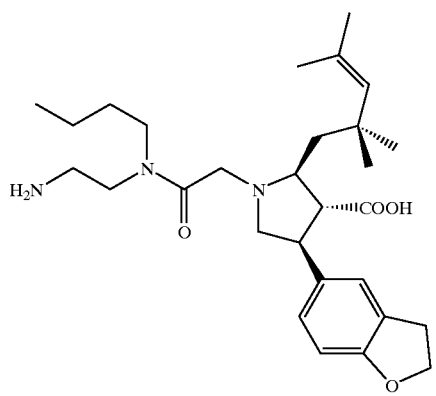 |

TABLE 3C-continued
165 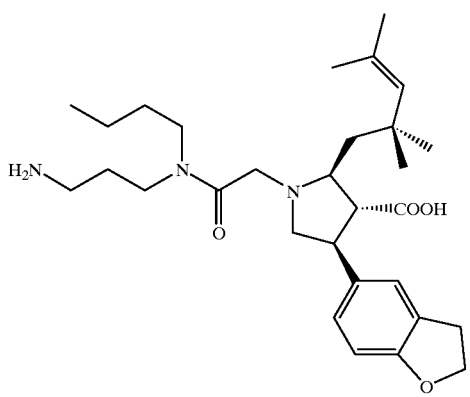
166 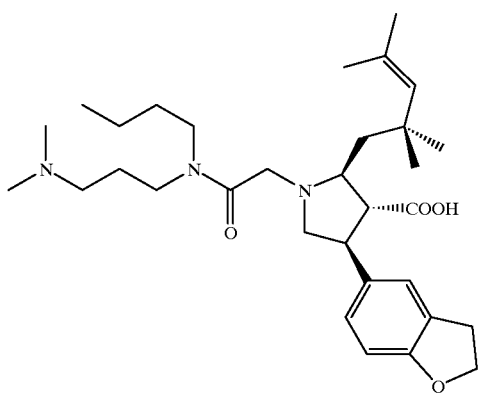
167 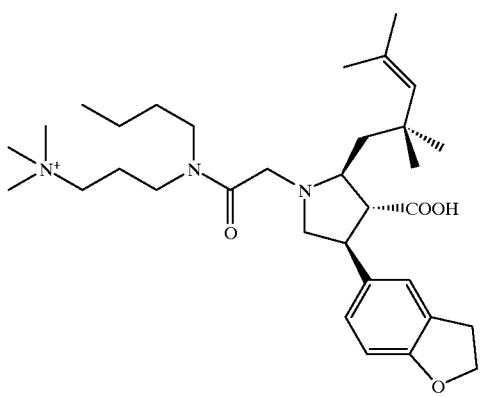
168 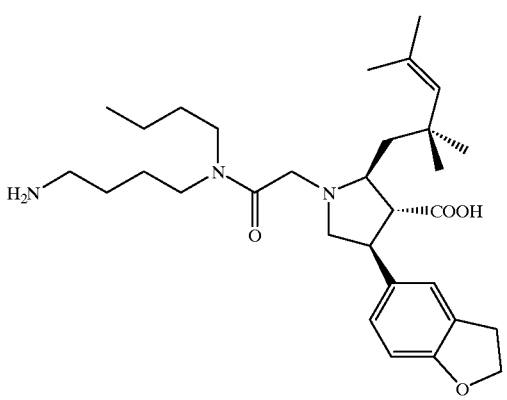

TABLE 3C-continued
169 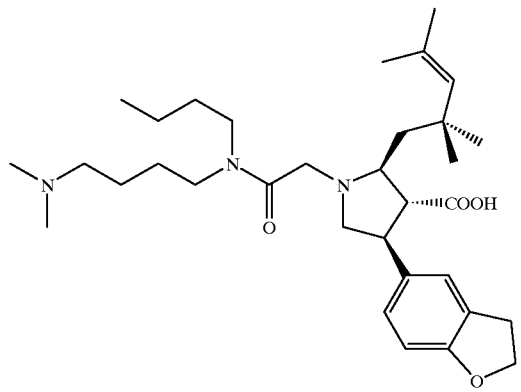
170 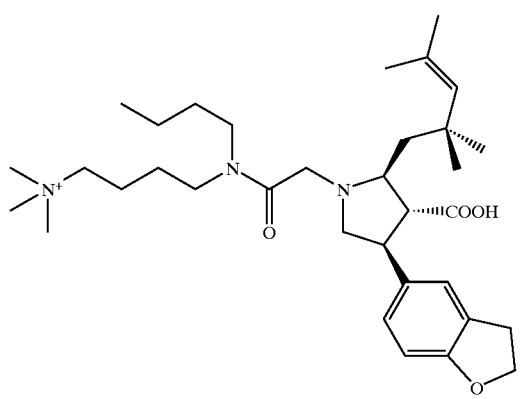
171 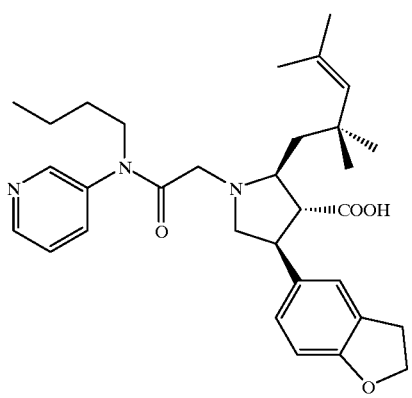
172 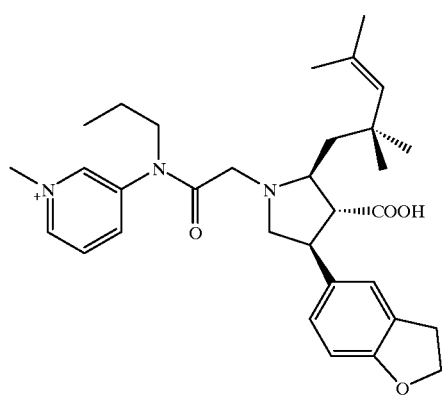

TABLE 3C-continued
173 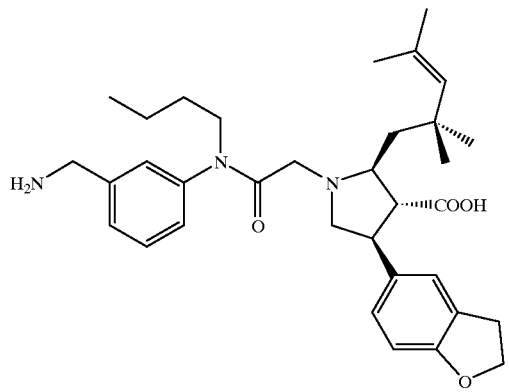
174 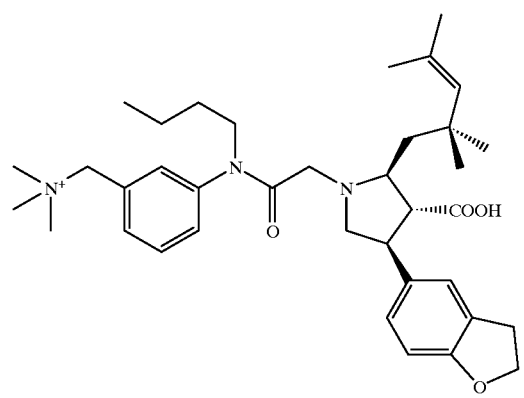
175 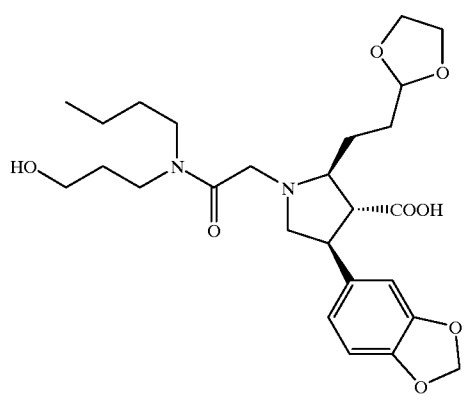
176 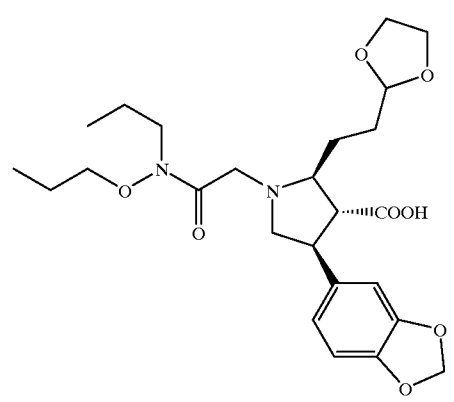

TABLE 3C-continued
177 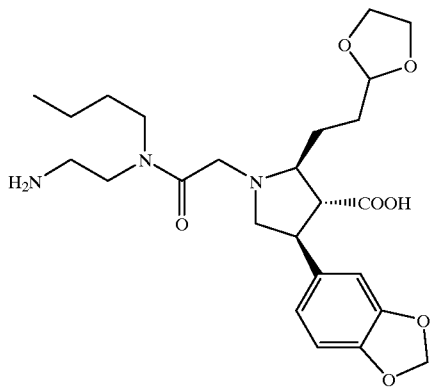
178 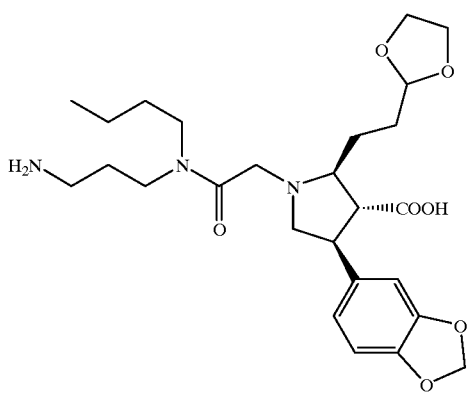
179 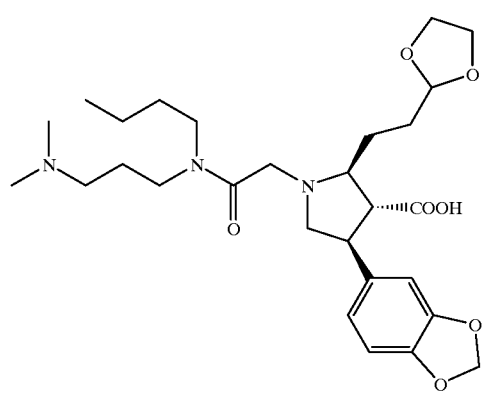
180 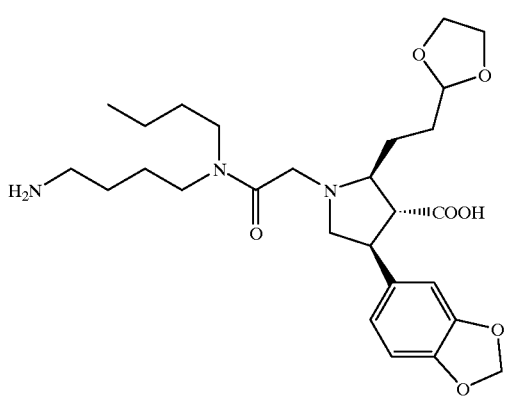

TABLE 3C-continued
181 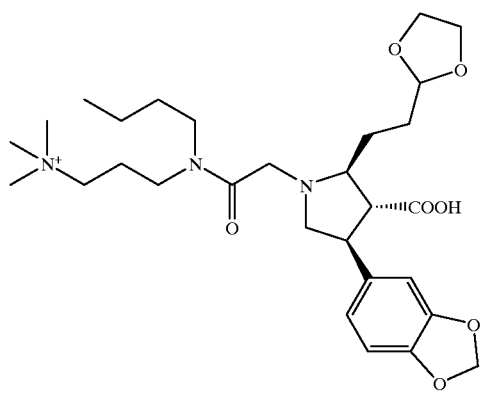
182 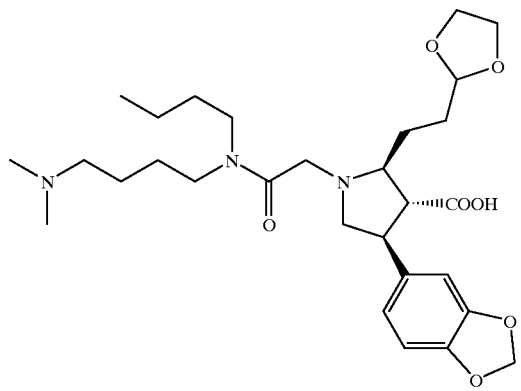
183 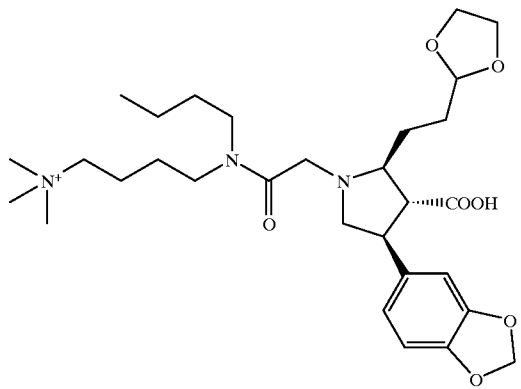
184 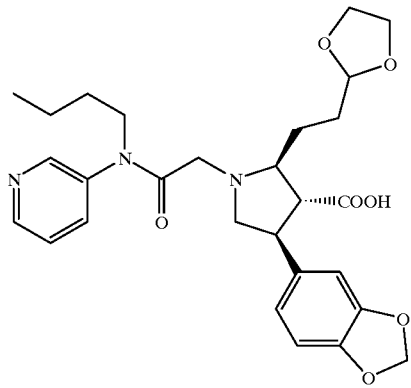

TABLE 3C-continued
185 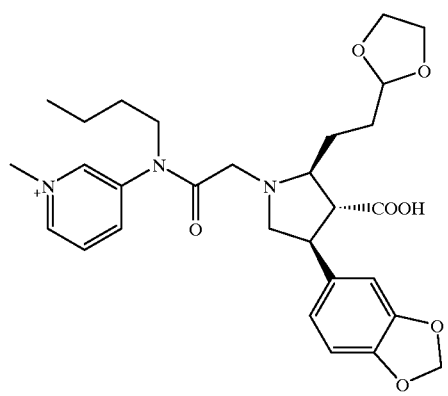
186 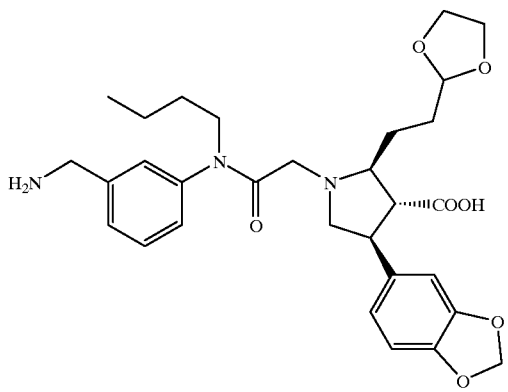
187 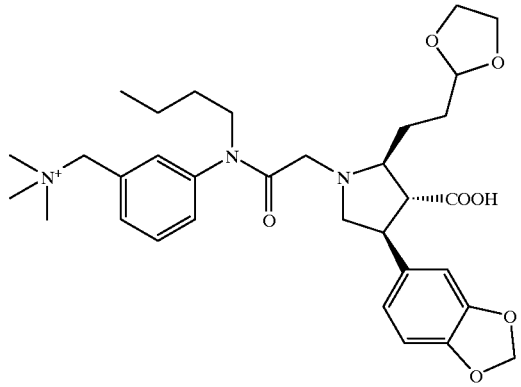
188 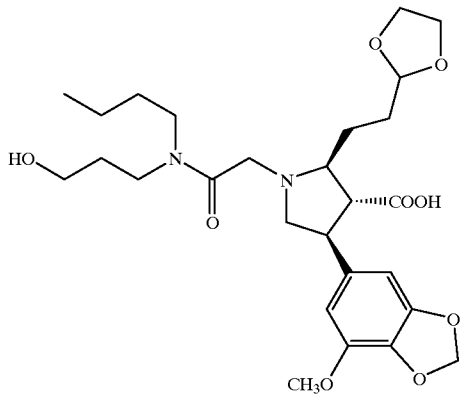

TABLE 3C-continued
189
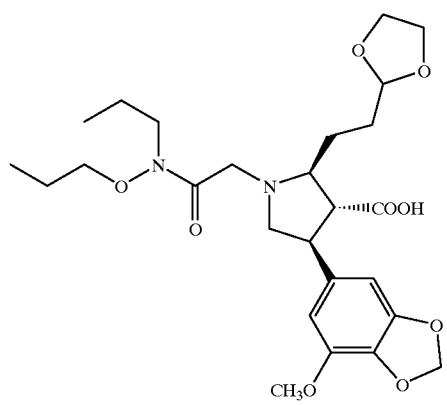
190
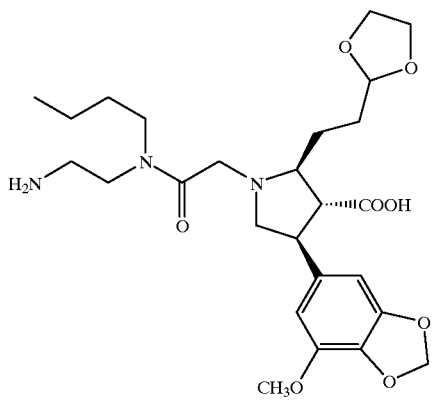
191
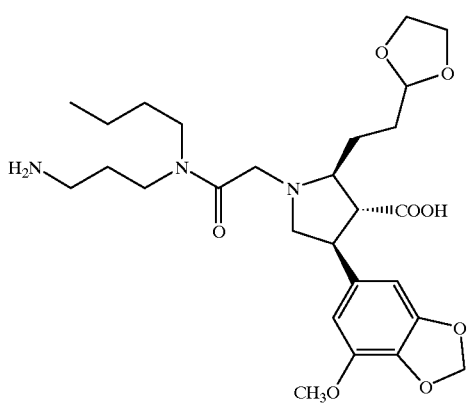

TABLE 3C-continued
192
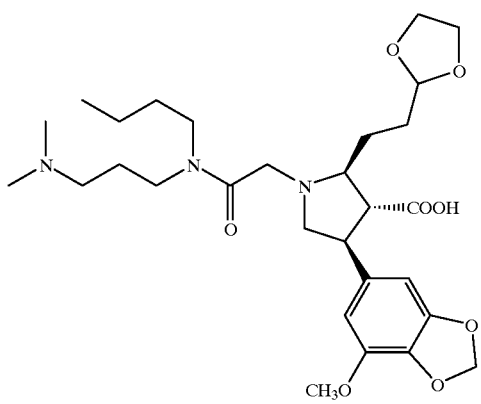
193
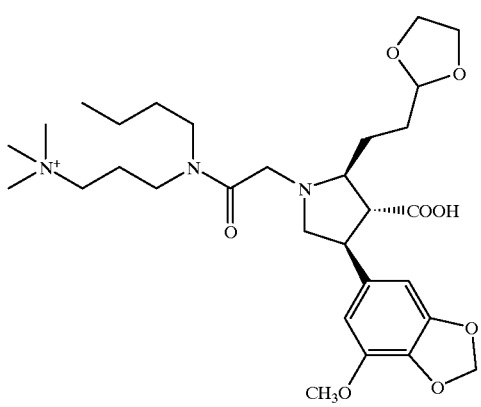
194
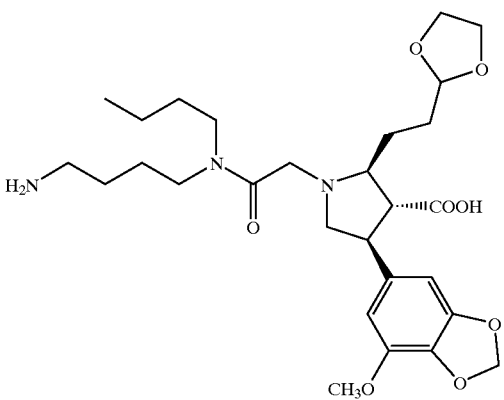

TABLE 3C-continued
195
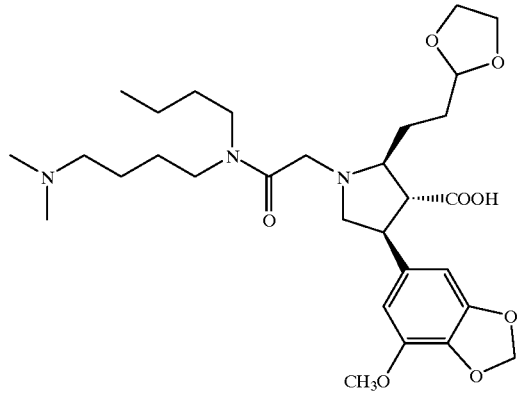
196
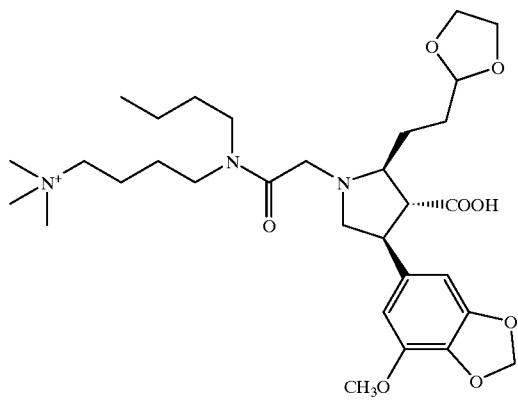
197
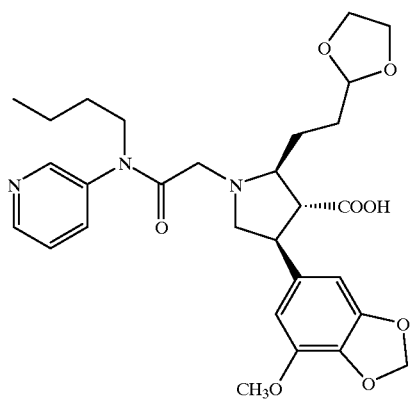

TABLE 3C-continued
| 198 | 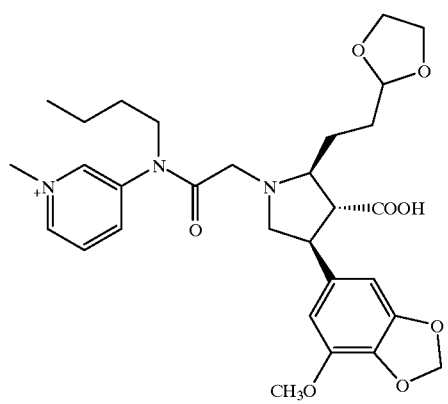 |
| --- | --- |
| 199 | 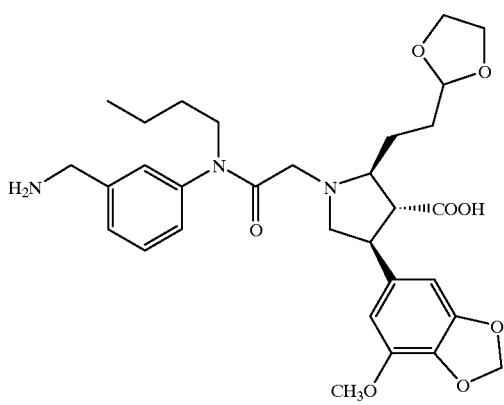 |
| 200 | 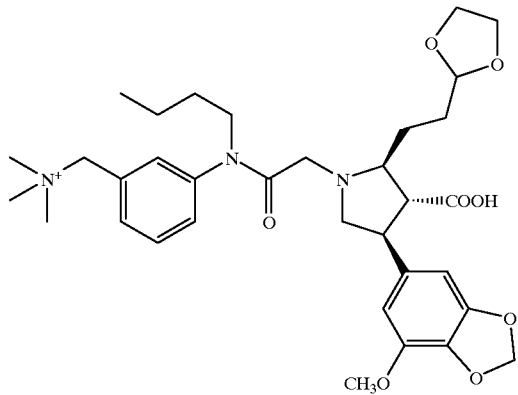 |
| 201 | 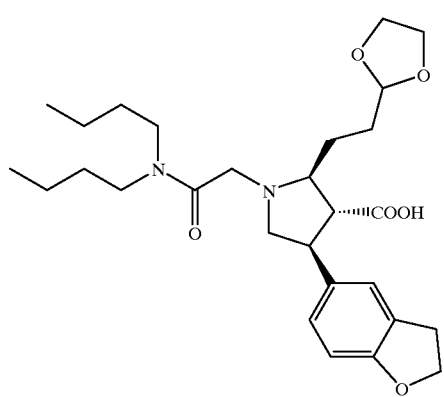 |

TABLE 3C-continued
202
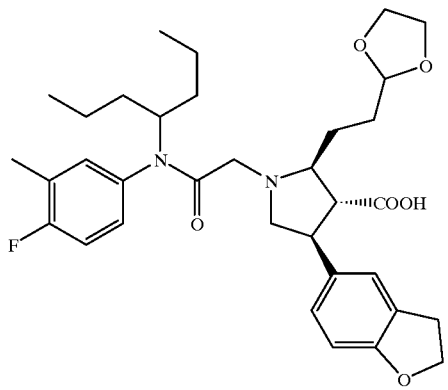
203
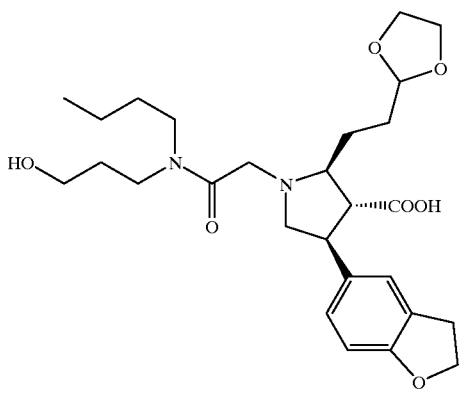
204
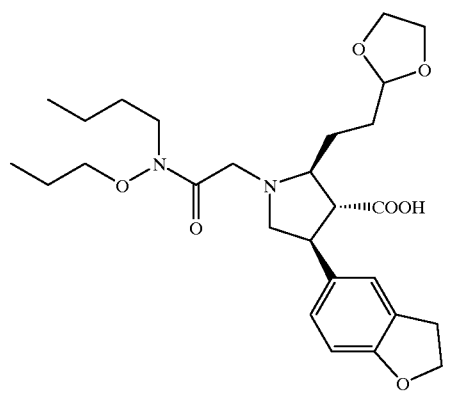
205
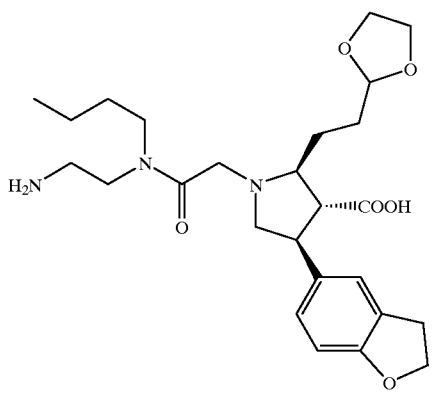

TABLE 3C-continued
| 206 | 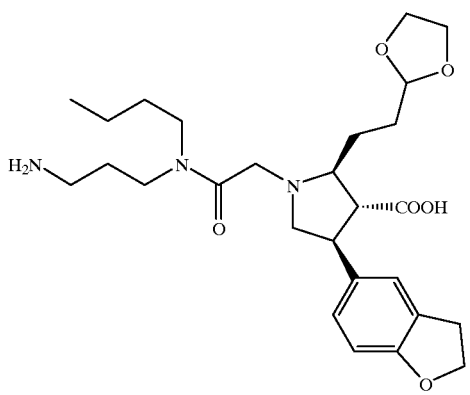 |
| 207 | 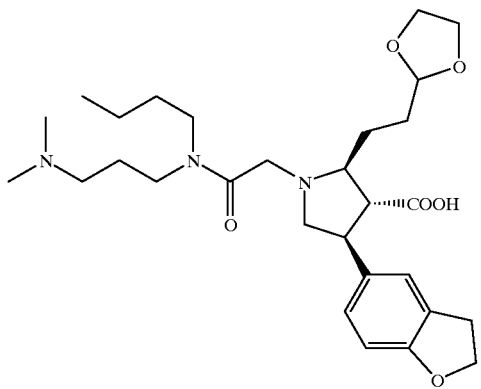 |
| 208 | 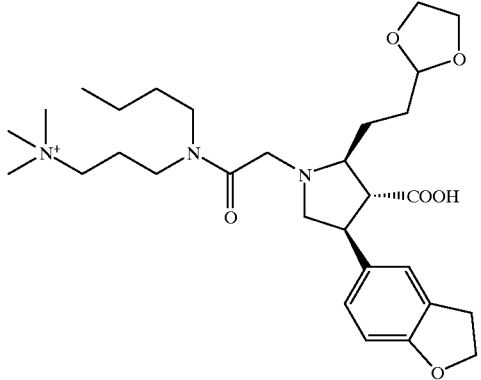 |
| 209 | 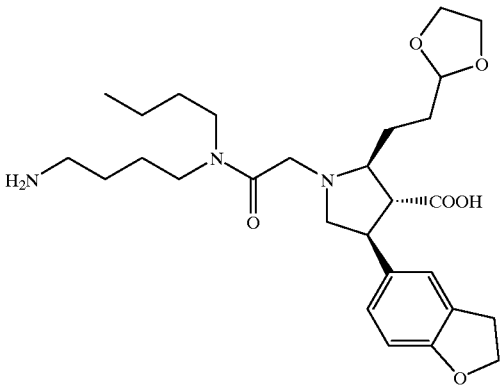 |

TABLE 3C-continued
210
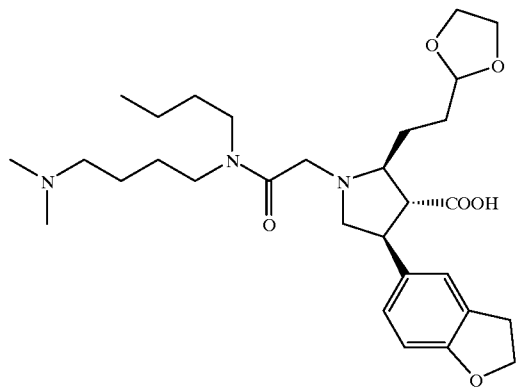
211
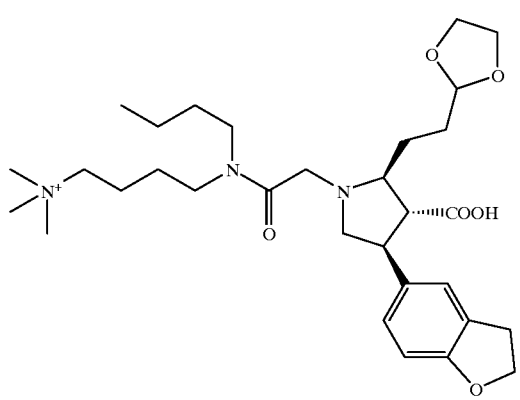
212
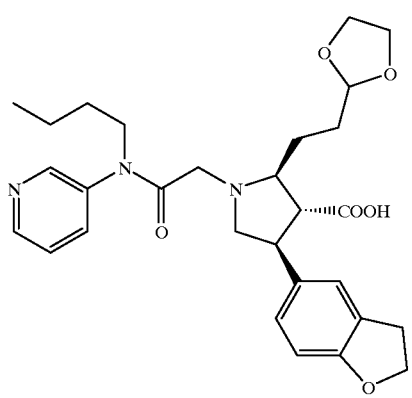
213
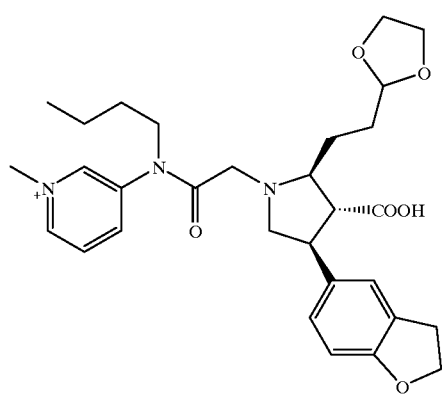

TABLE 3C-continued
214
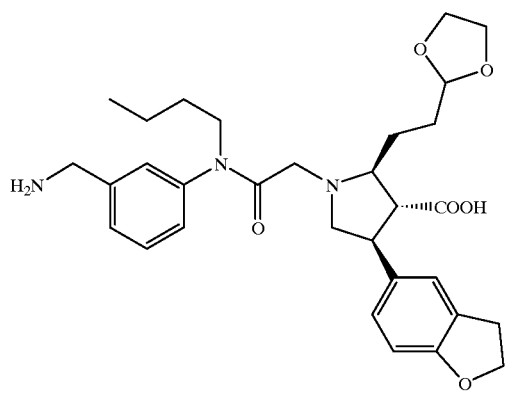
215
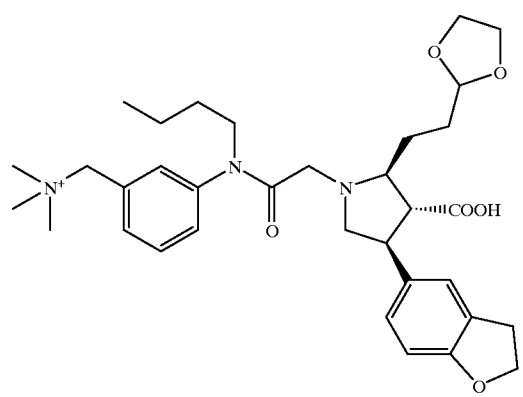
216
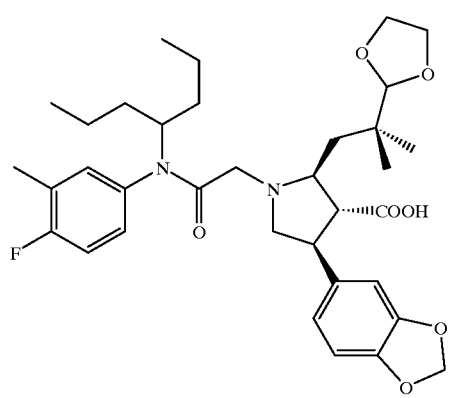
217
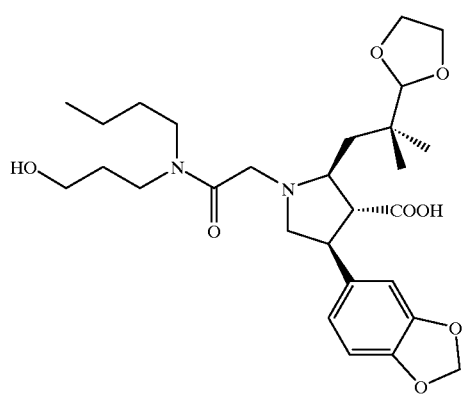

TABLE 3C-continued
| 218 | 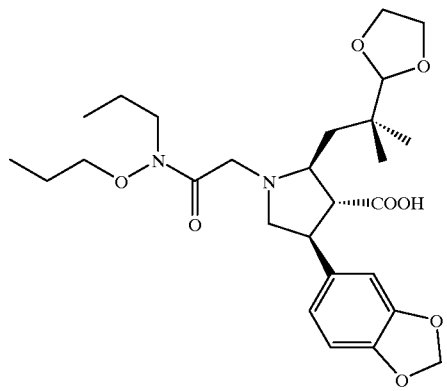 |
| --- | --- |
| 219 | 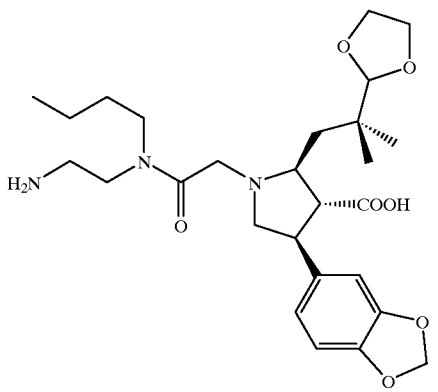 |
| 220 | 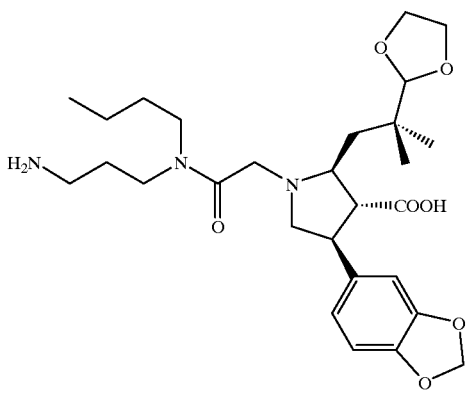 |
| 221 | 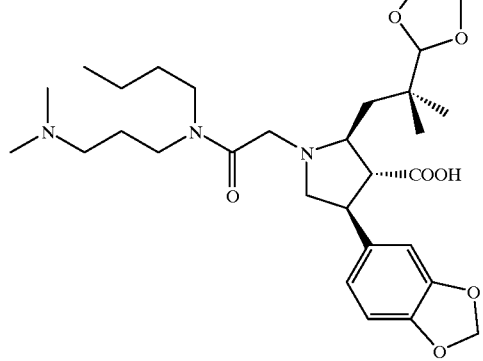 |

TABLE 3C-continued
222 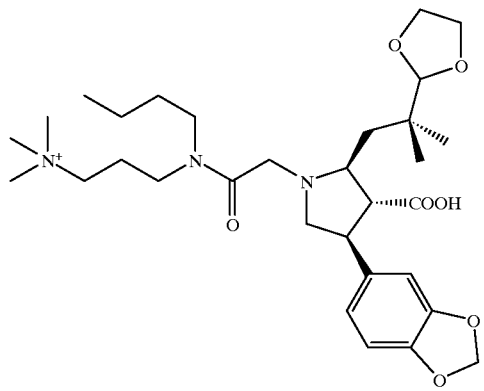
223 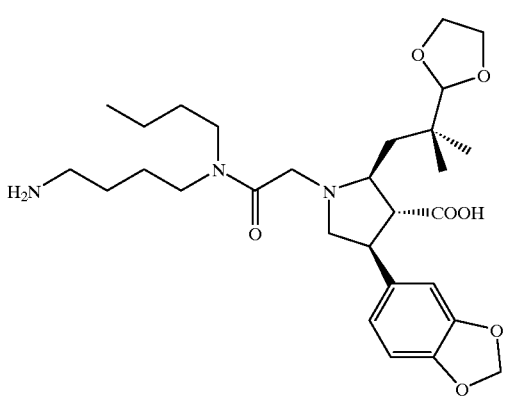
224 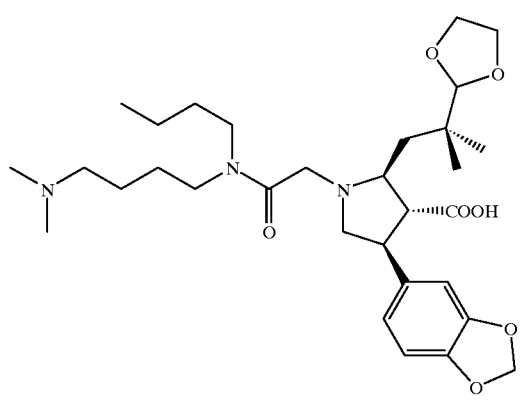
225 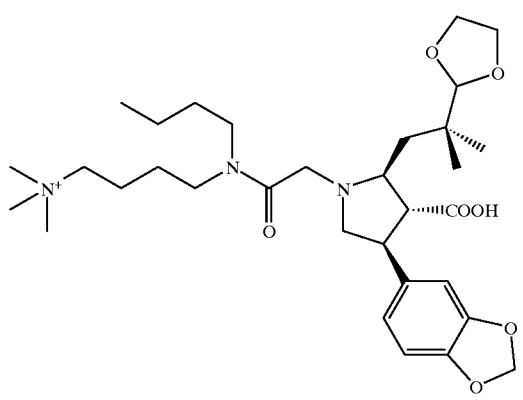

TABLE 3C-continued
226 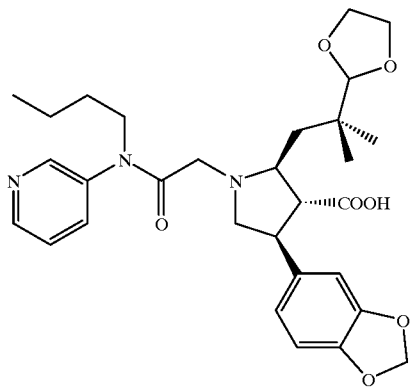
227 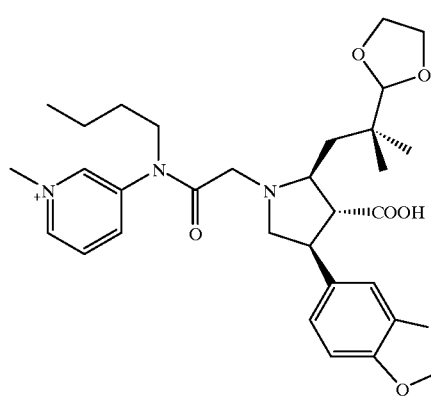
228 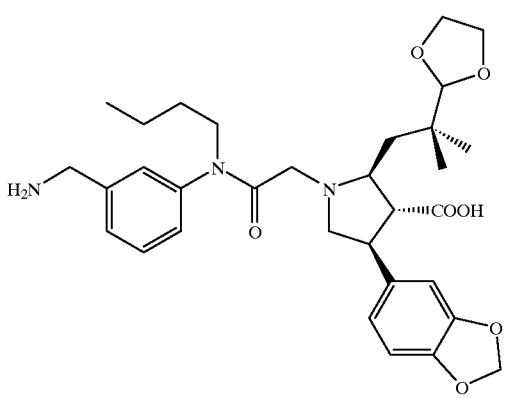
229 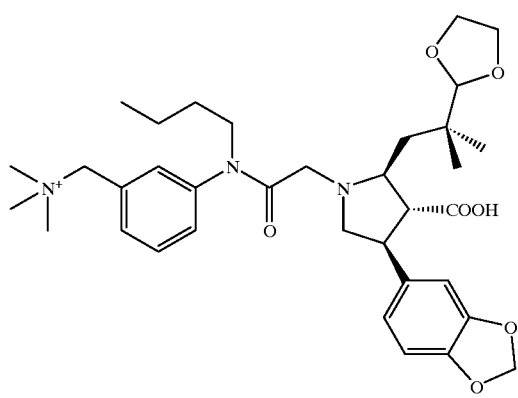

TABLE 3C-continued
230
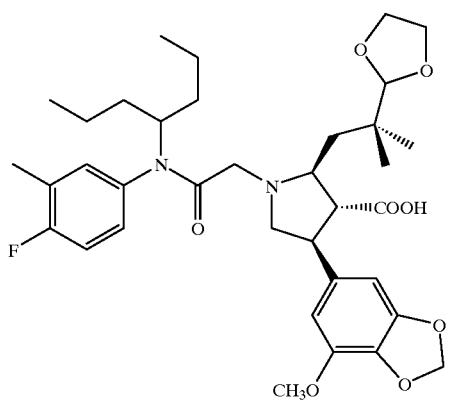
231
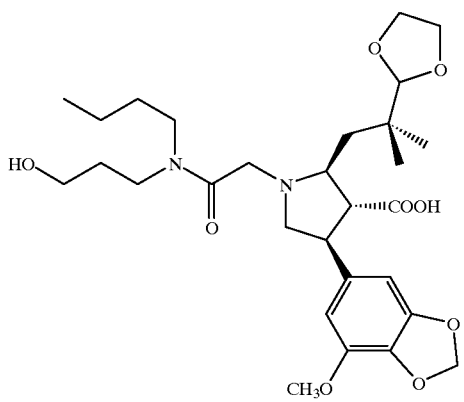
232
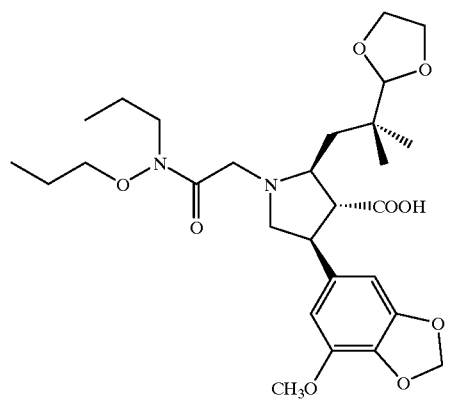

TABLE 3C-continued
233
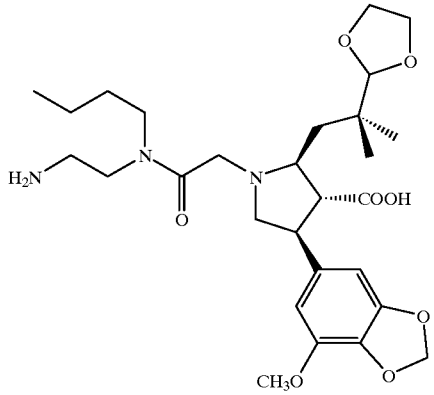
234
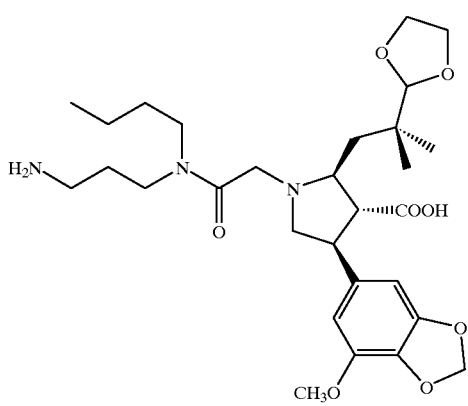
235
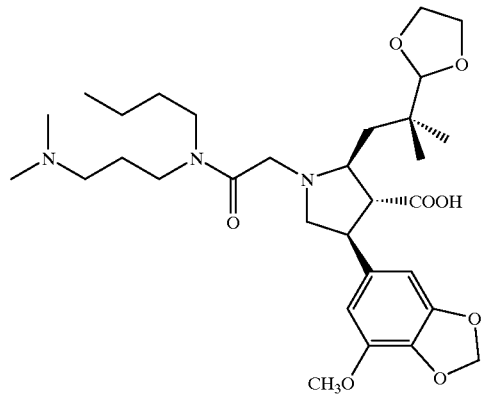

TABLE 3C-continued
236
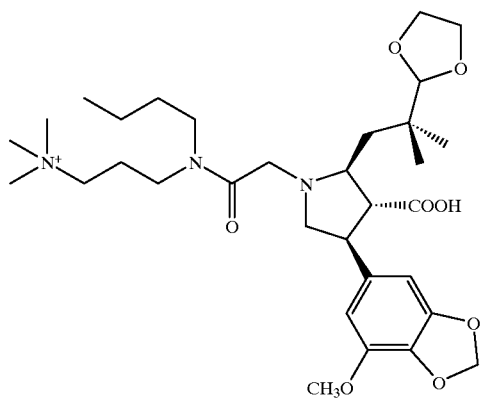
237
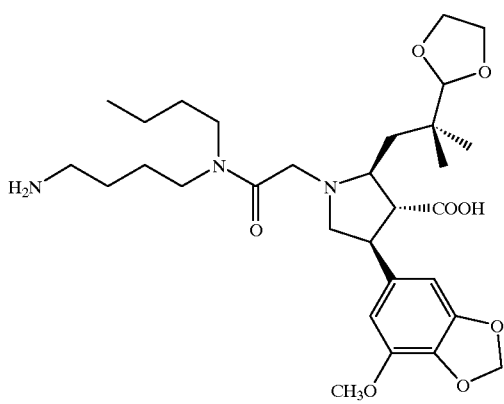
238
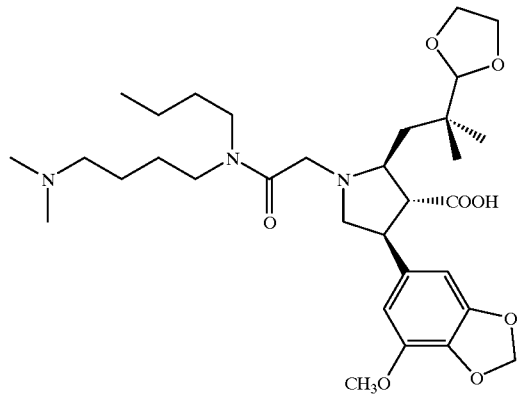

TABLE 3C-continued
239
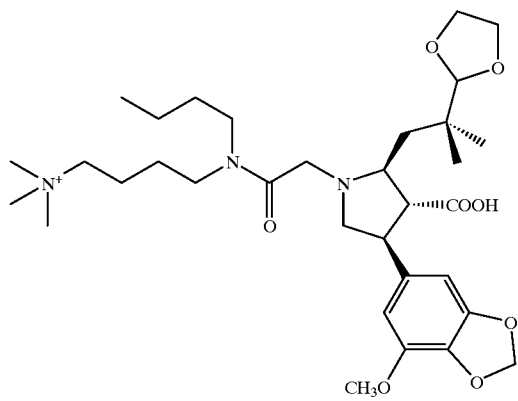
240
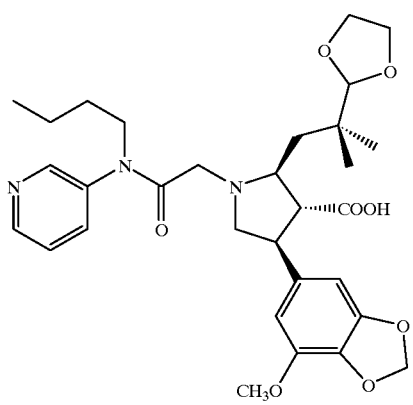
241
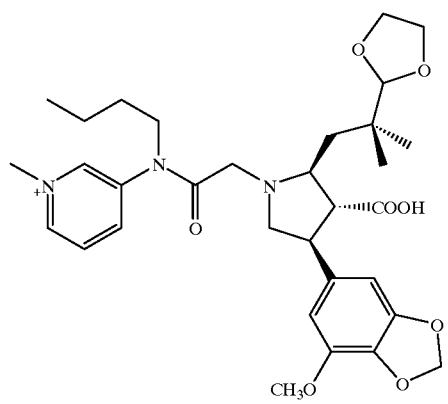

TABLE 3C-continued
242 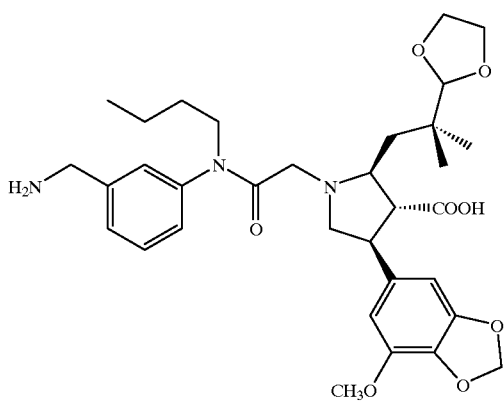
243 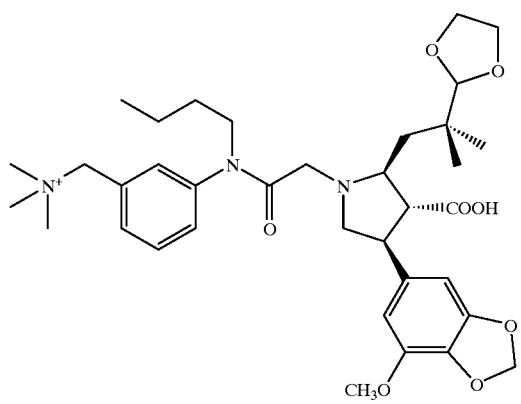
244 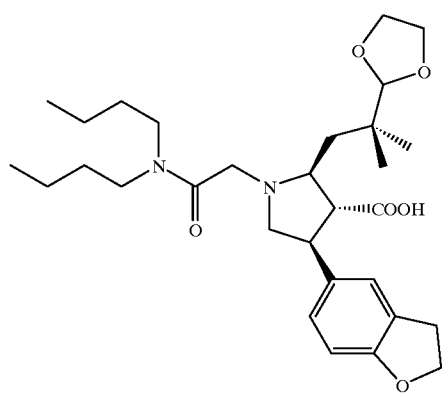
245 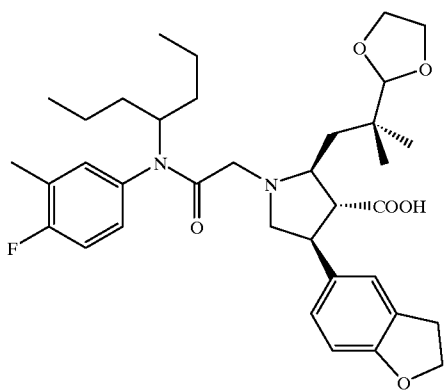

TABLE 3C-continued
246
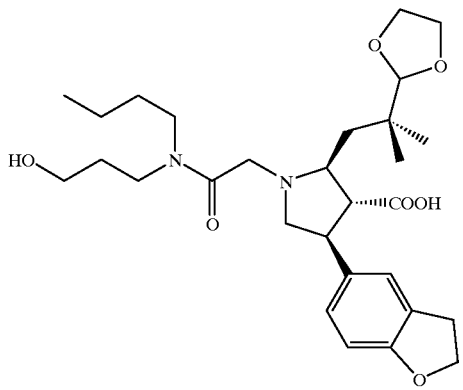
247
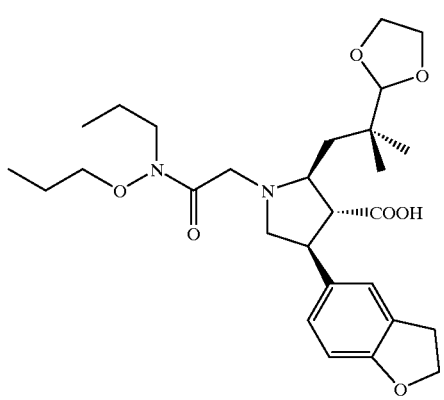
248
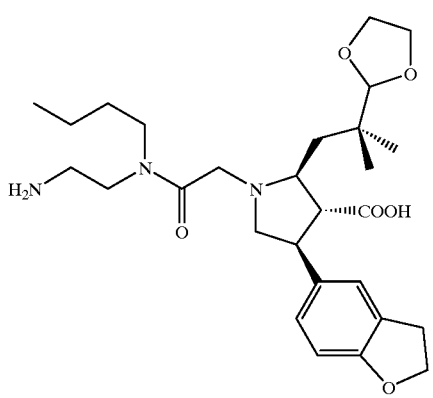
249
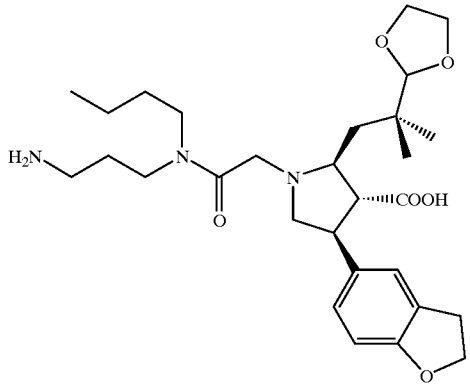

TABLE 3C-continued
| 250 | 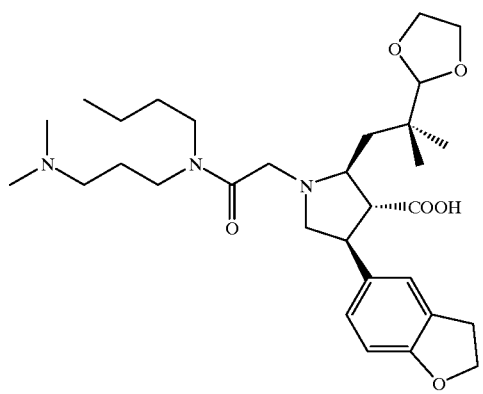 |
| --- | --- |
| 251 | 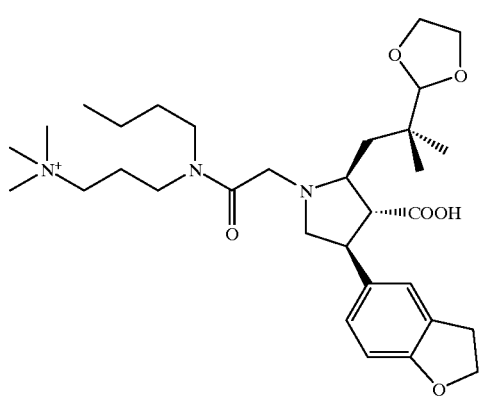 |
| 252 | 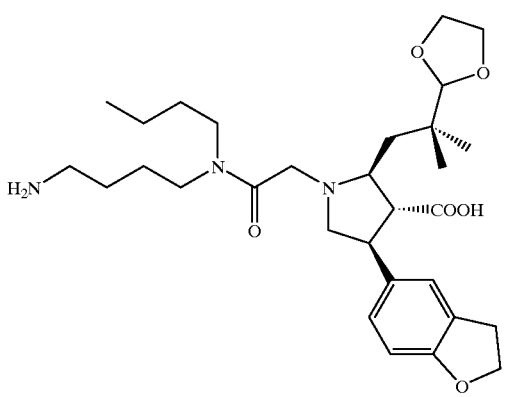 |
| 253 | 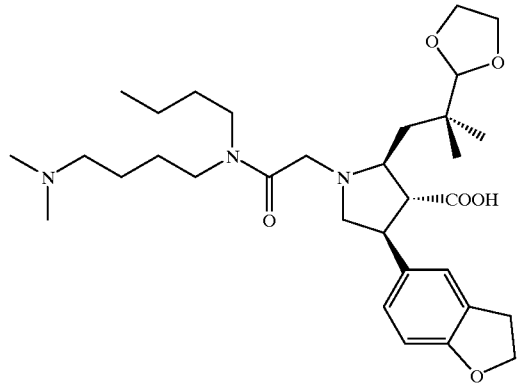 |

TABLE 3C-continued
254
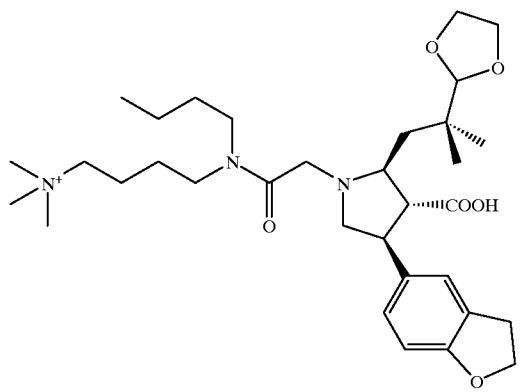
255
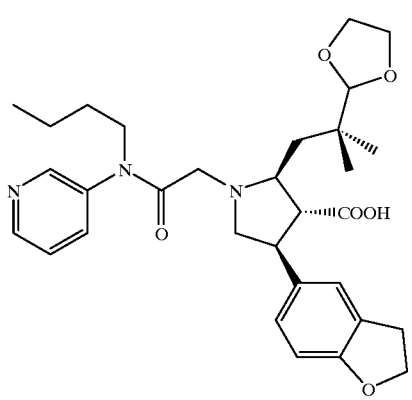
256
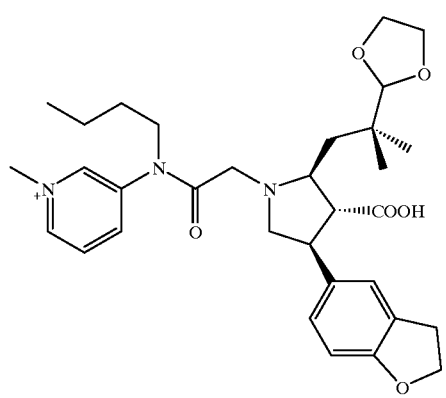
257
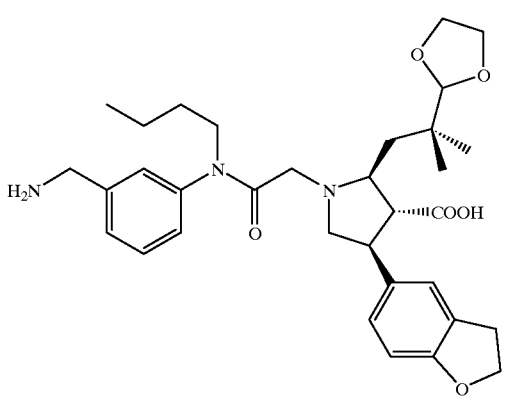

TABLE 3C-continued
258
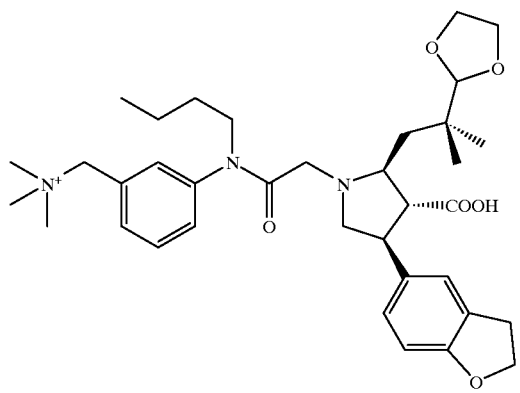
259
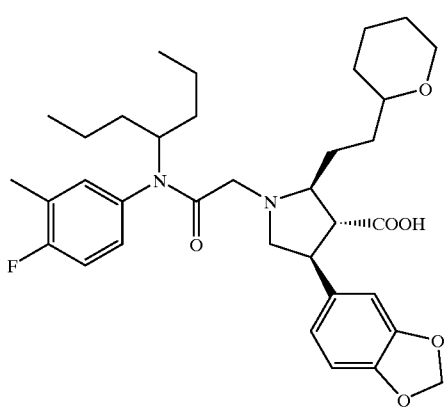
260
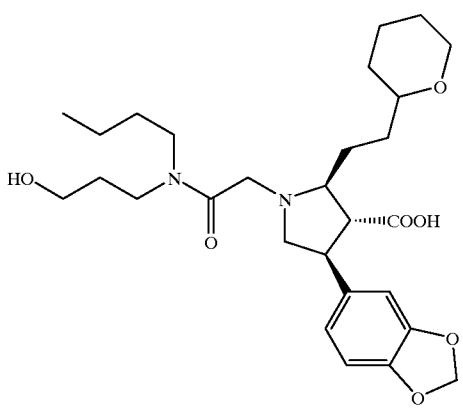

TABLE 3C-continued
261
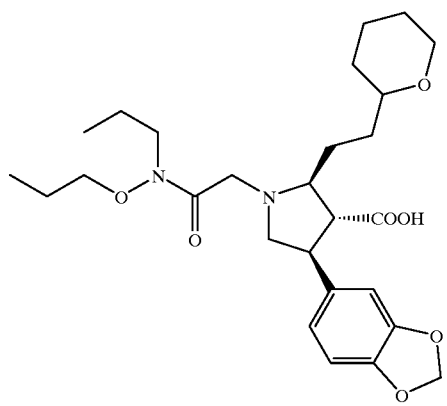
262
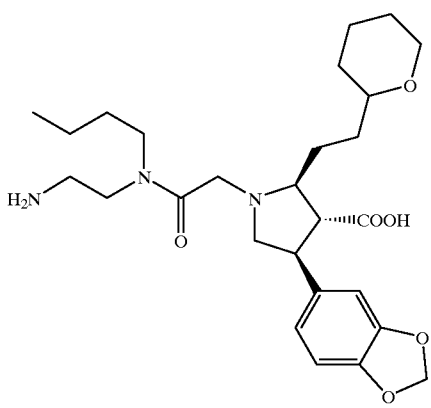
263
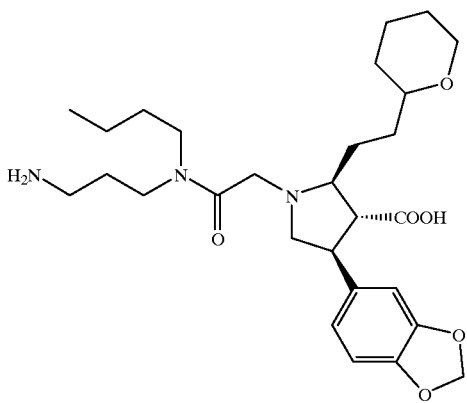

TABLE 3C-continued
264
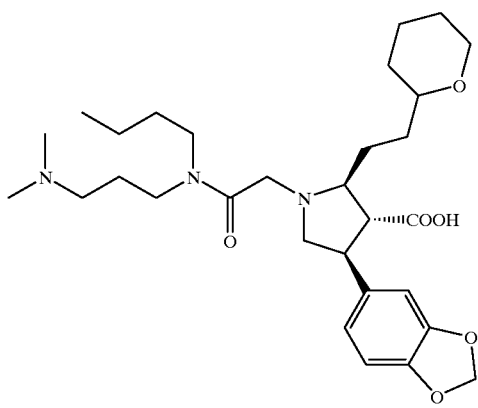
265
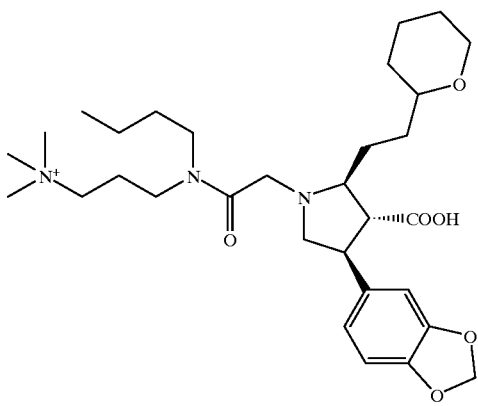
266
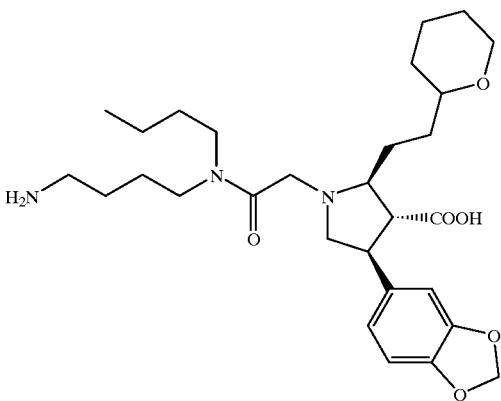

TABLE 3C-continued
267
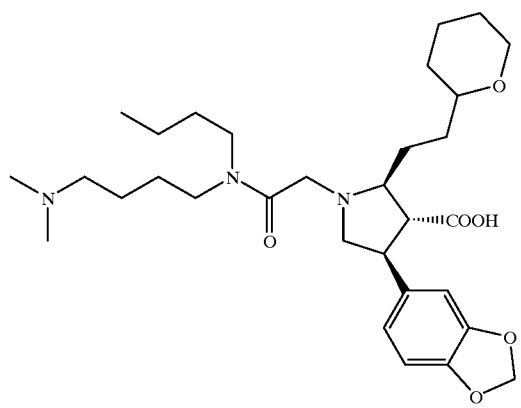
268
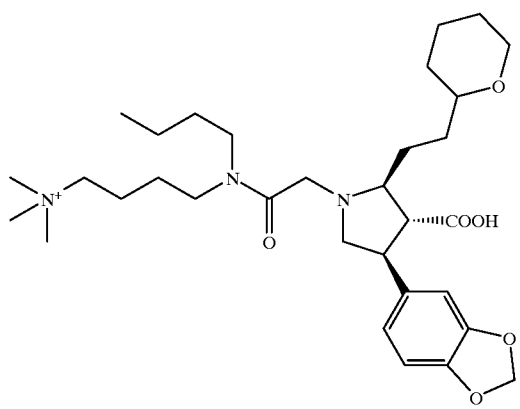
269
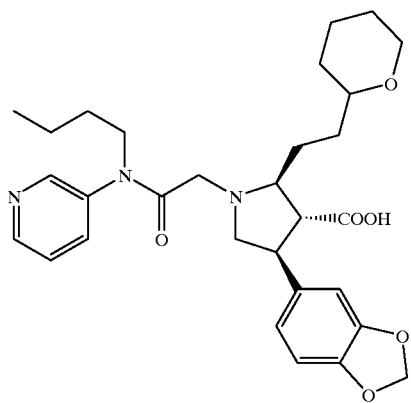

TABLE 3C-continued
270
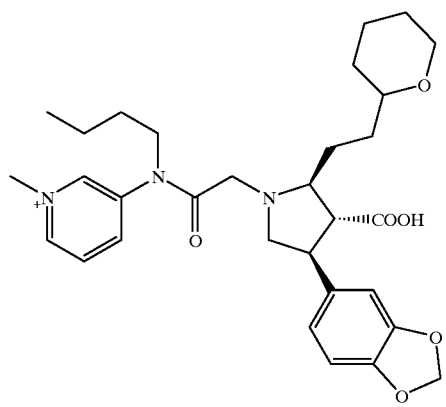
271
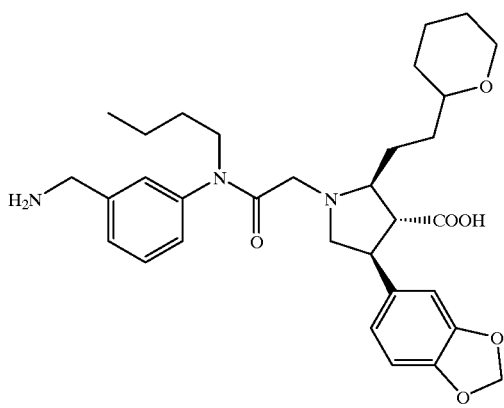
272
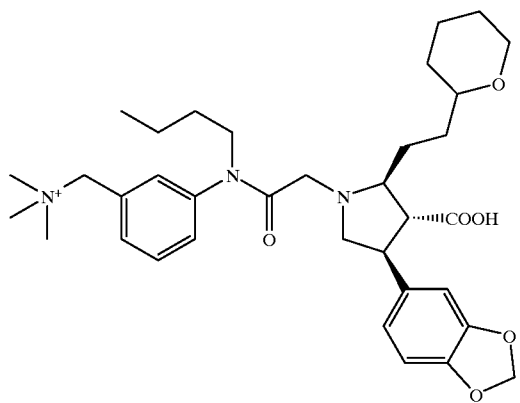

TABLE 3C-continued
273
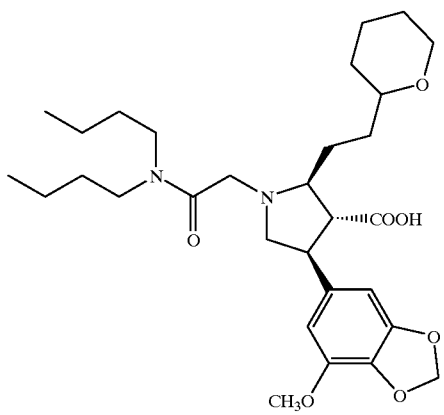
274
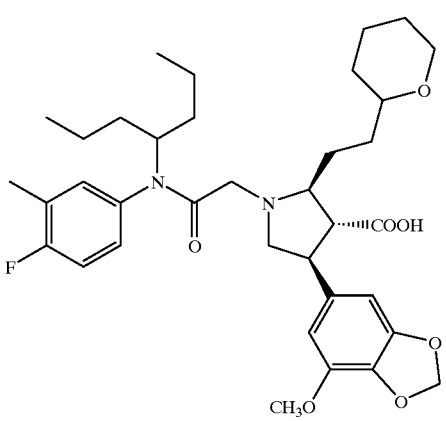
275
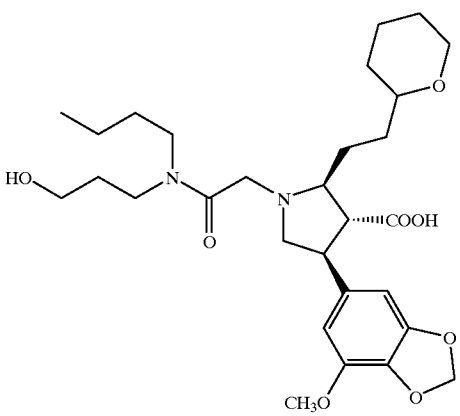

TABLE 3C-continued
276
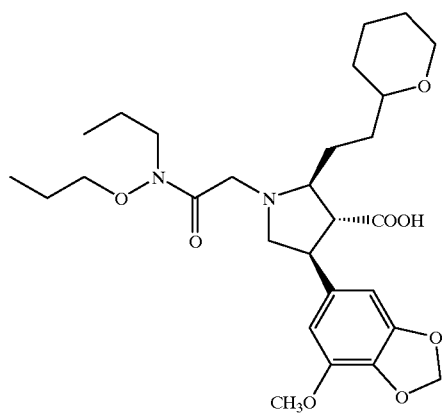
277
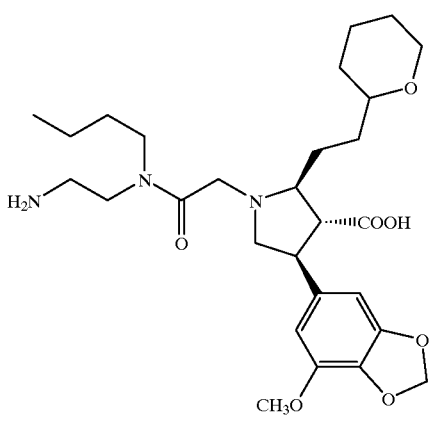
278
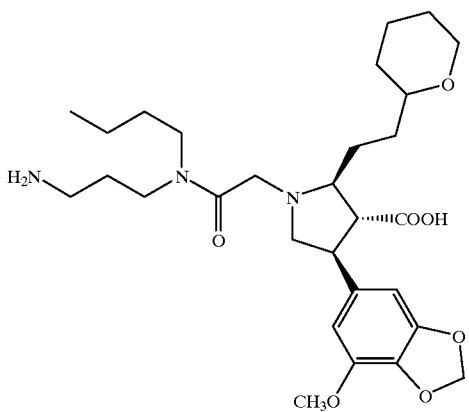

TABLE 3C-continued
279
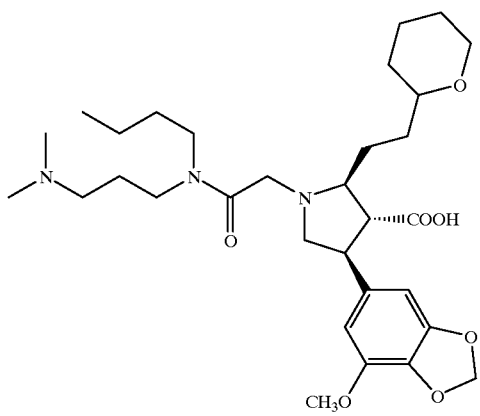
280
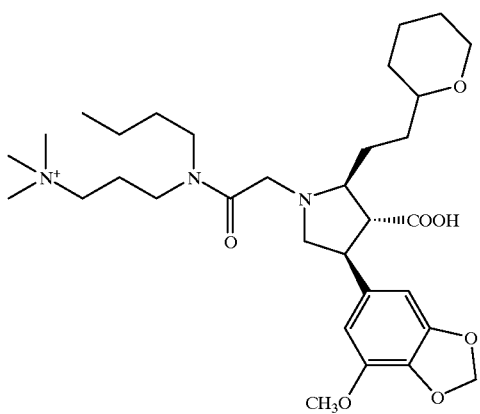
281
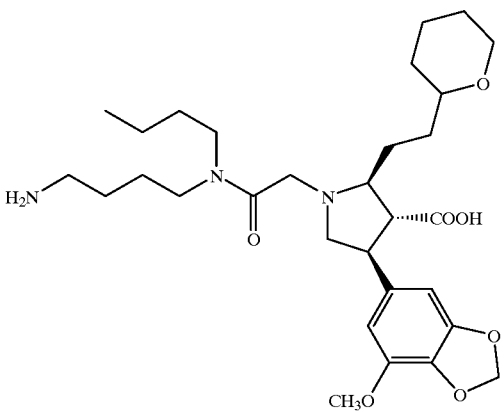

TABLE 3C-continued
282
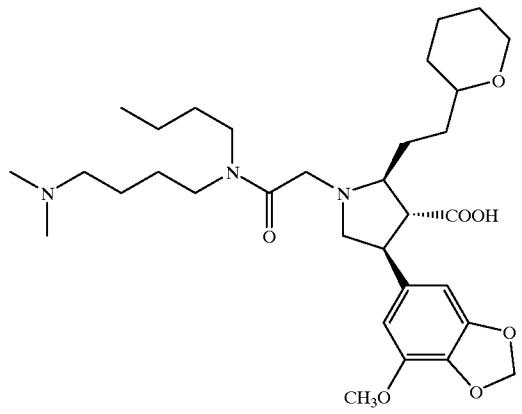
283
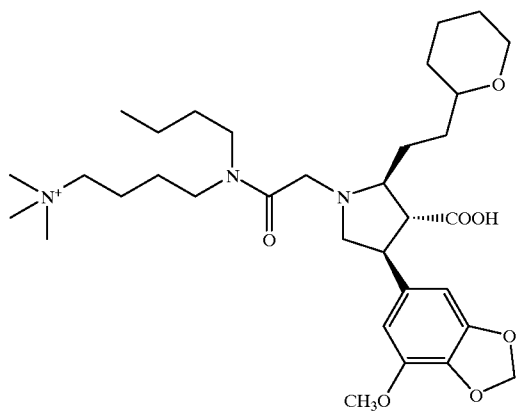
284
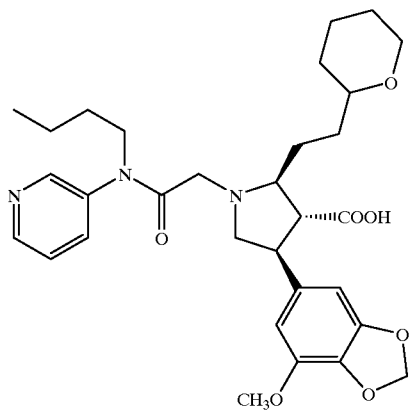

TABLE 3C-continued
285
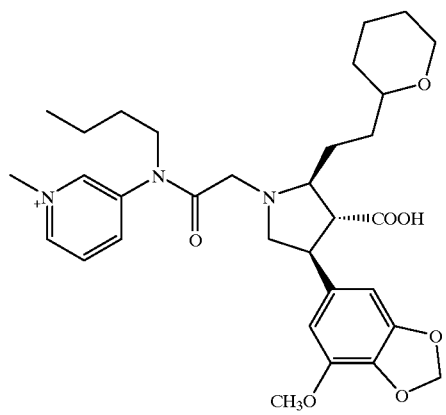
286
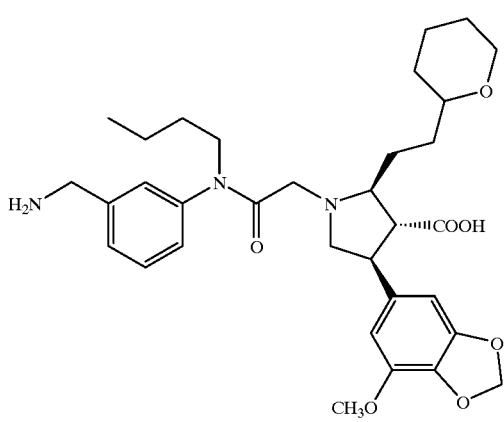
287
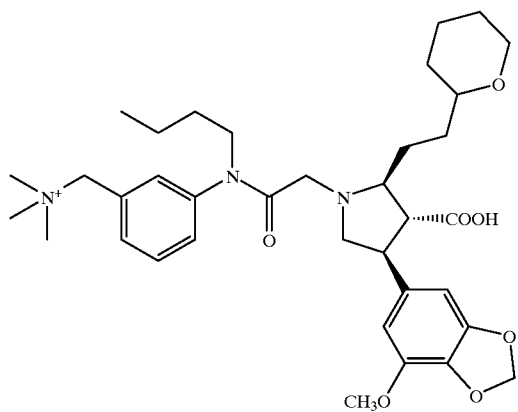

TABLE 3C-continued
288
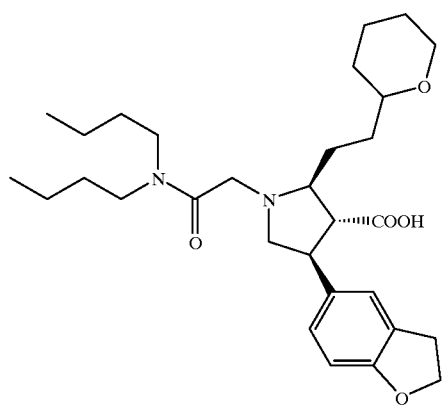
289
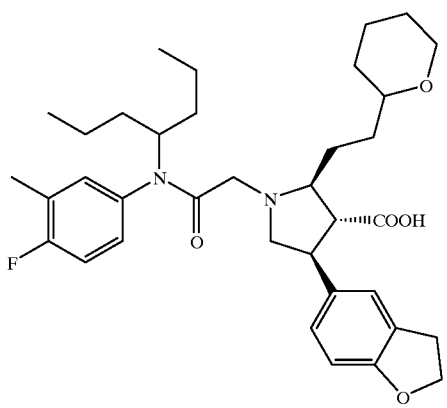
290
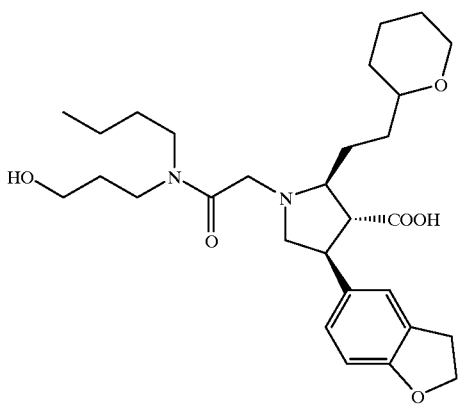

TABLE 3C-continued
291
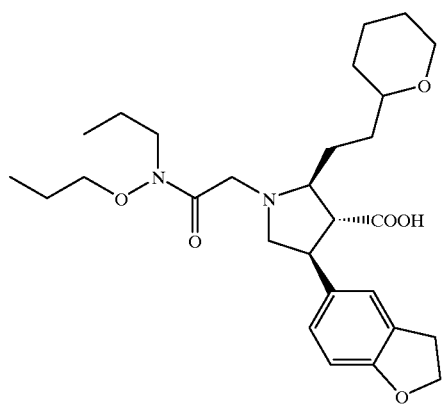
292
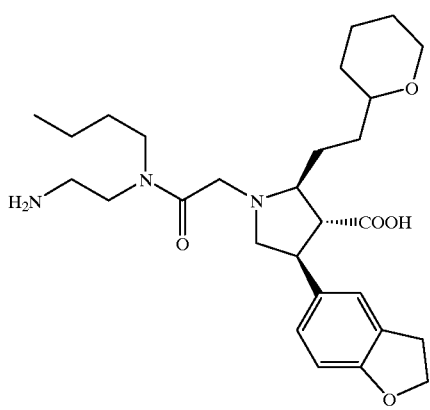
293
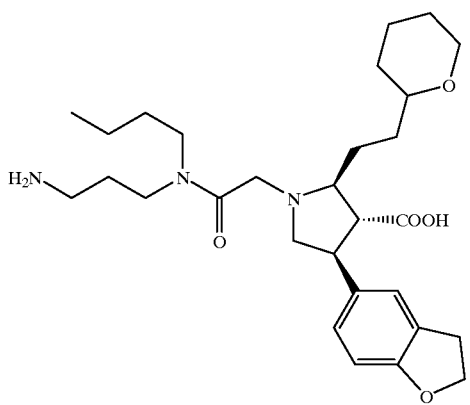

TABLE 3C-continued
294
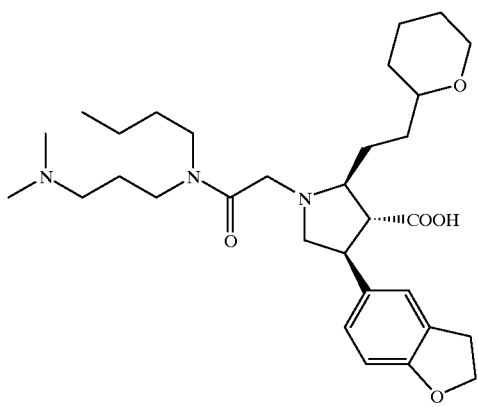
295
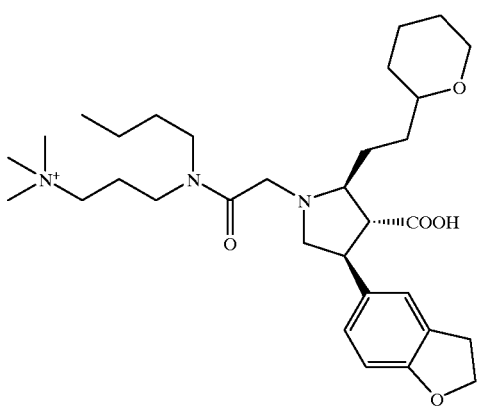
296
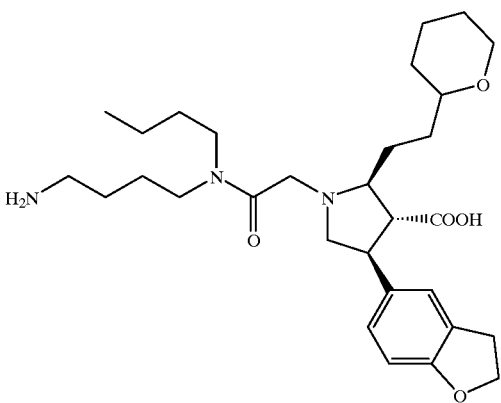

TABLE 3C-continued
297
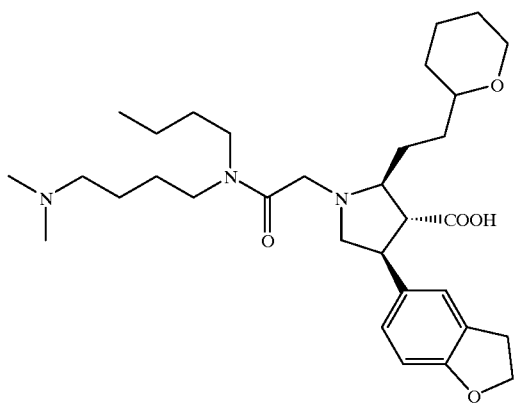
298
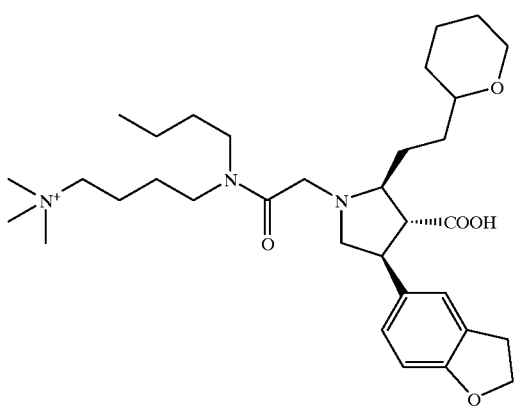
299
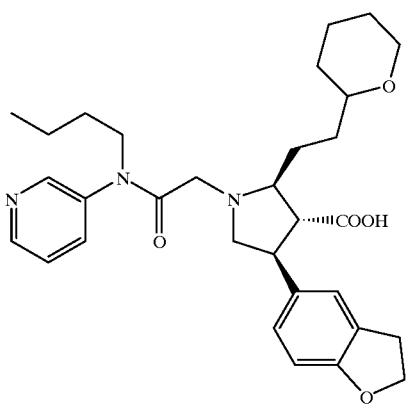

TABLE 3C-continued
300
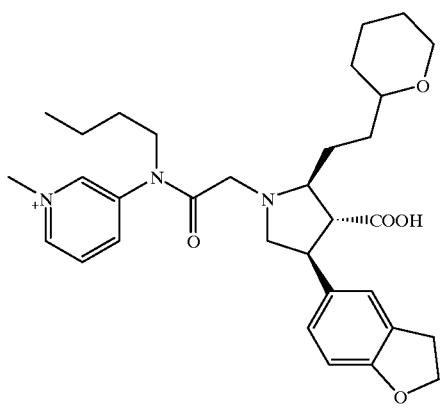
301
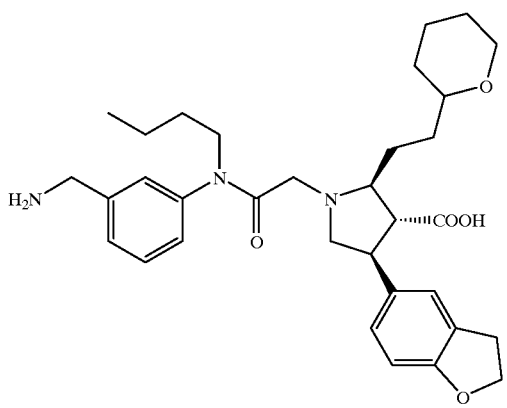
302
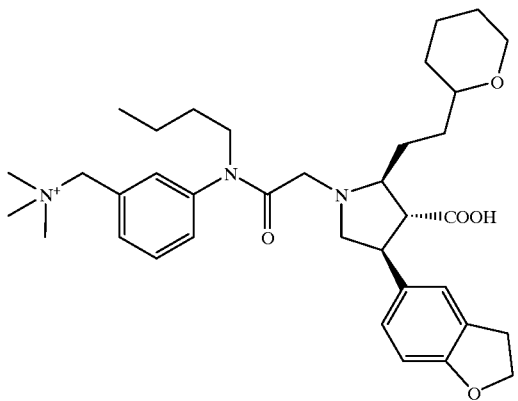

TABLE 3C-continued
303
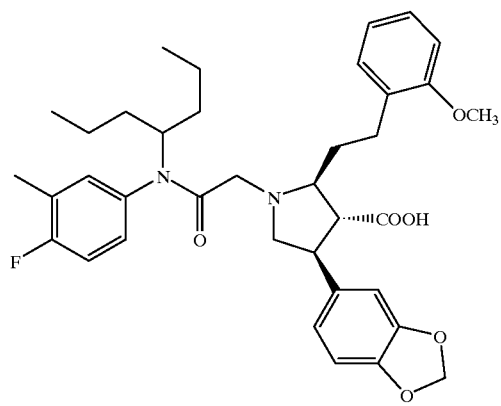
304
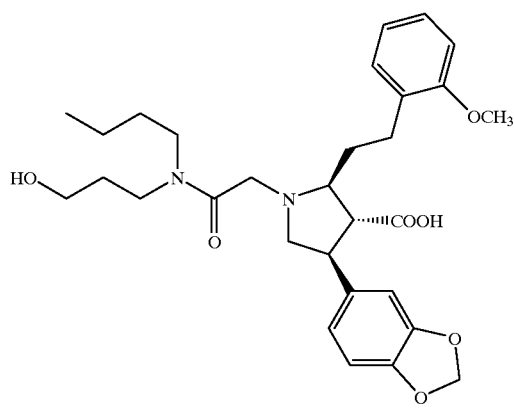
305
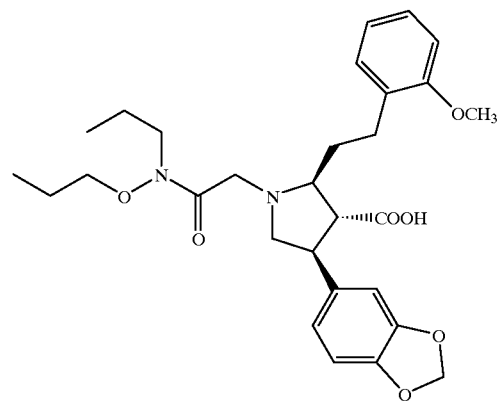

TABLE 3C-continued
306 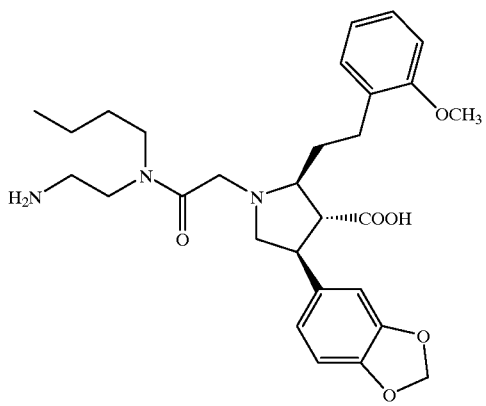
307 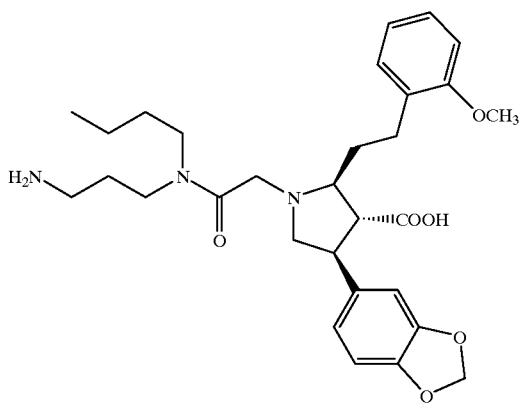
308 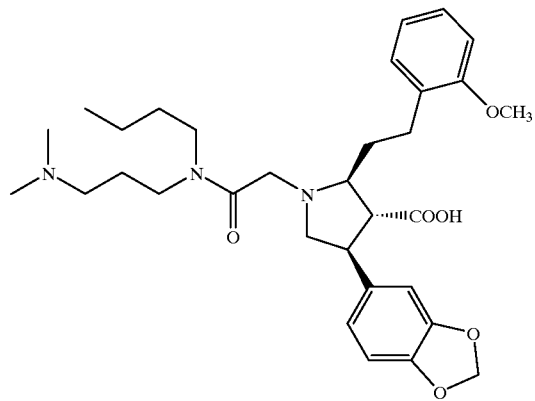

TABLE 3C-continued
309
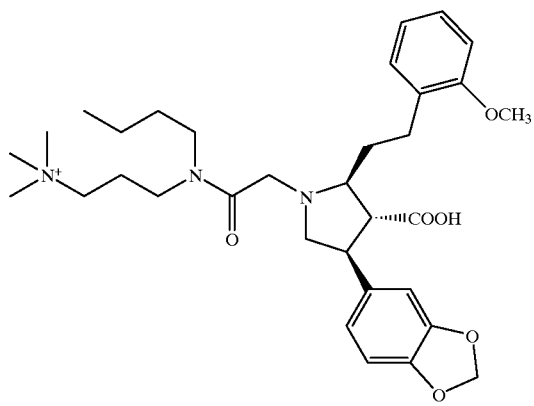
310
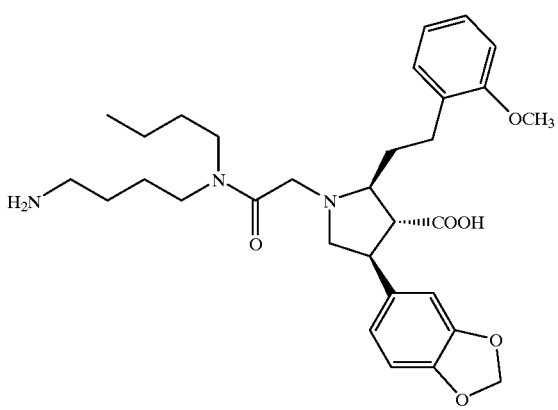
311
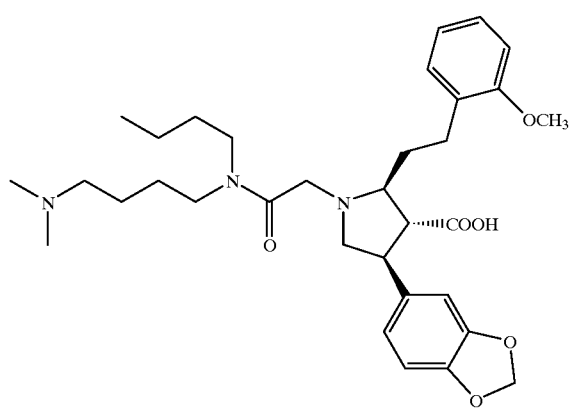

TABLE 3C-continued
312
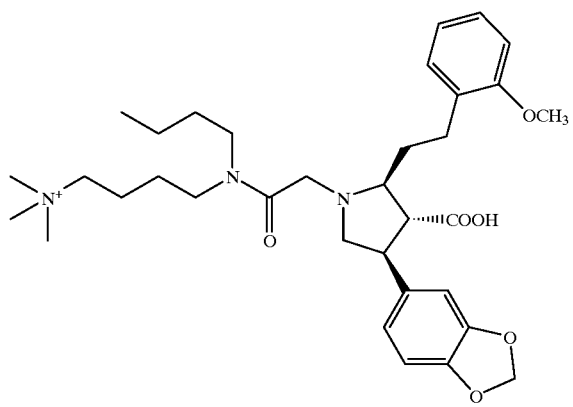
313
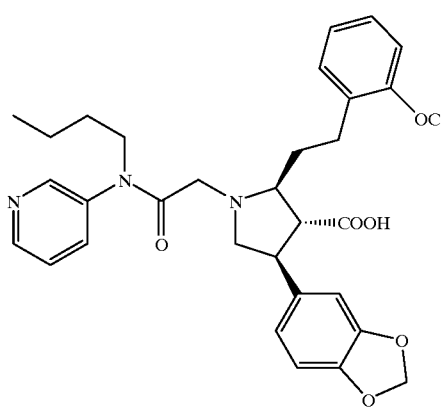
314
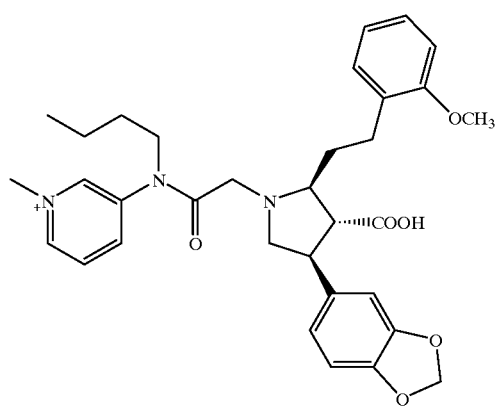

TABLE 3C-continued
315
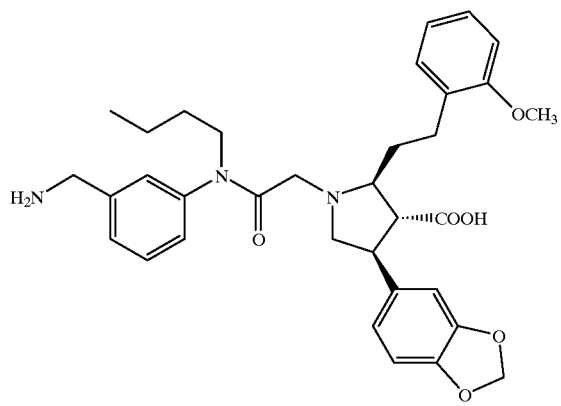
316
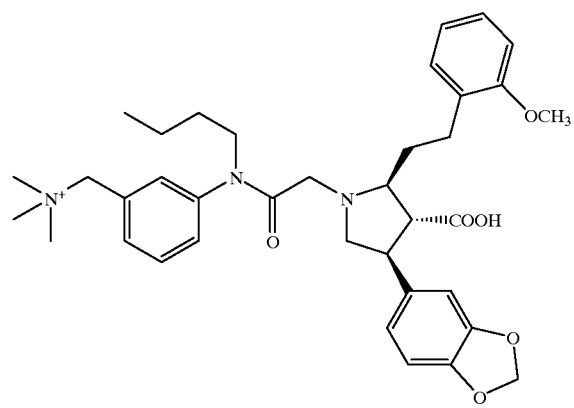
317
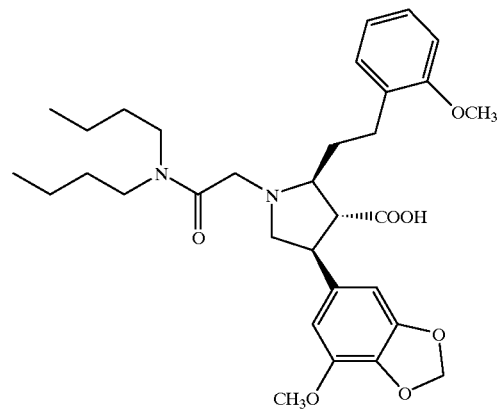

TABLE 3C-continued
318
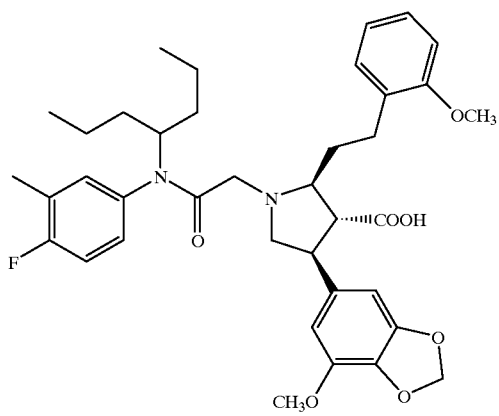
319
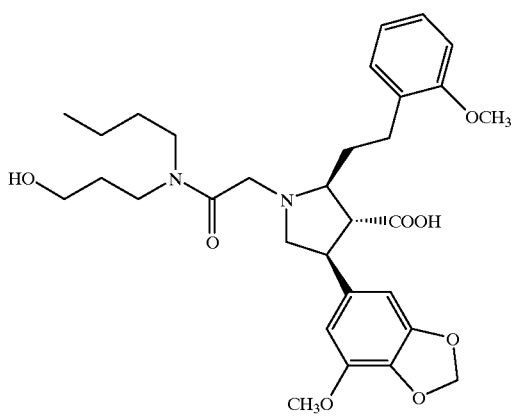
320
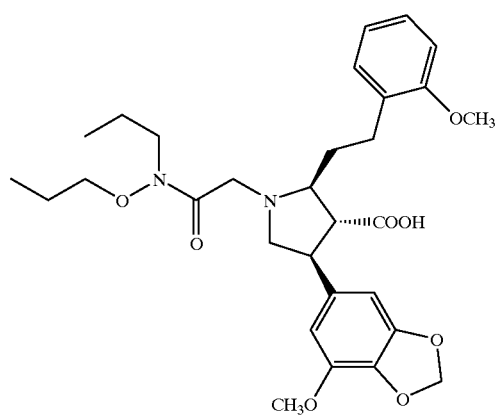

TABLE 3C-continued
321
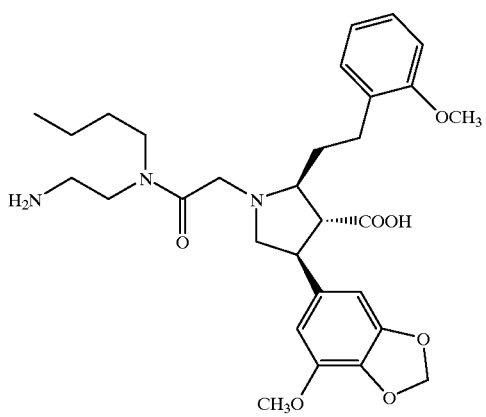
322
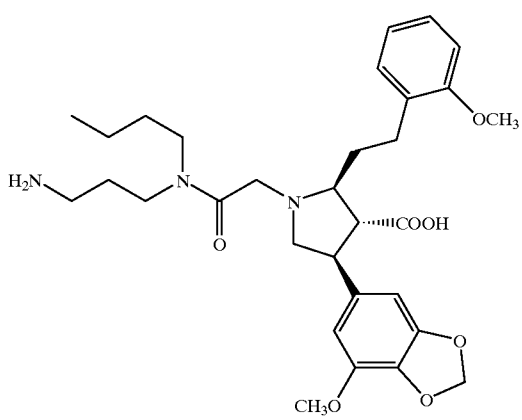
323
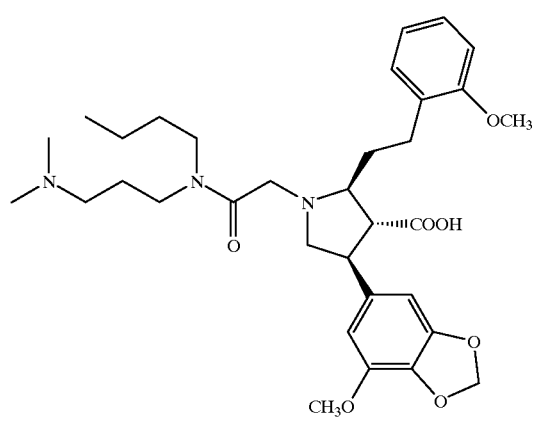

TABLE 3C-continued
324
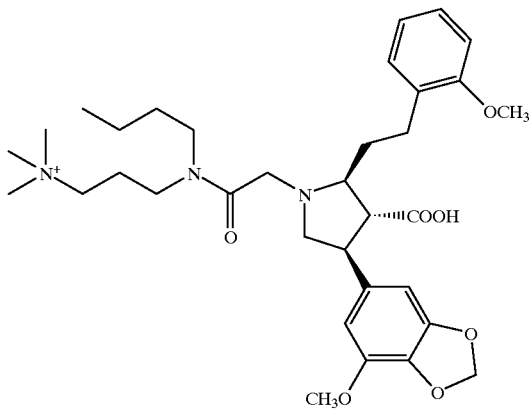
325
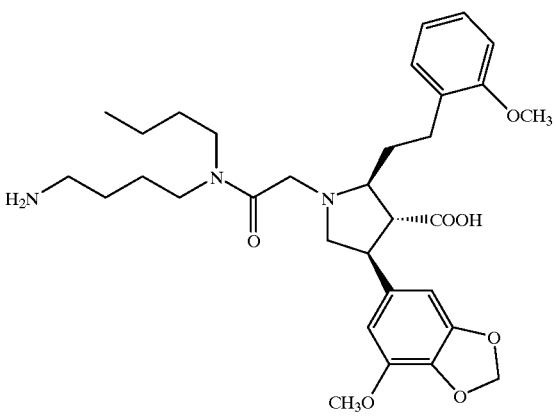
326
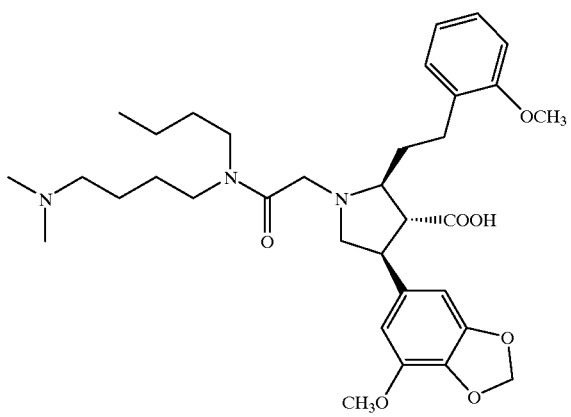

TABLE 3C-continued
327
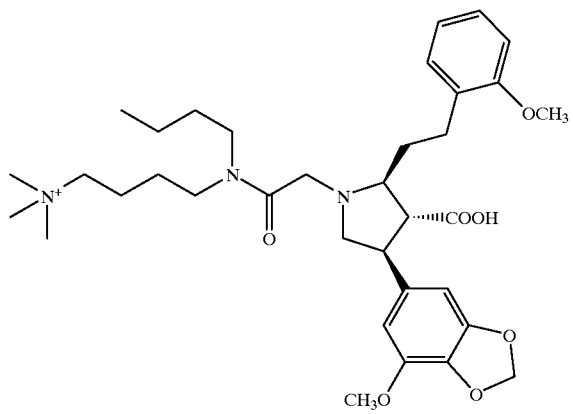
328
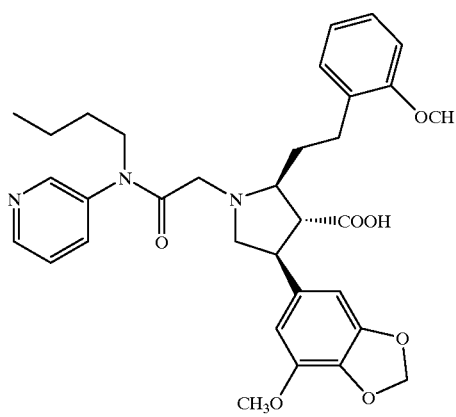
329
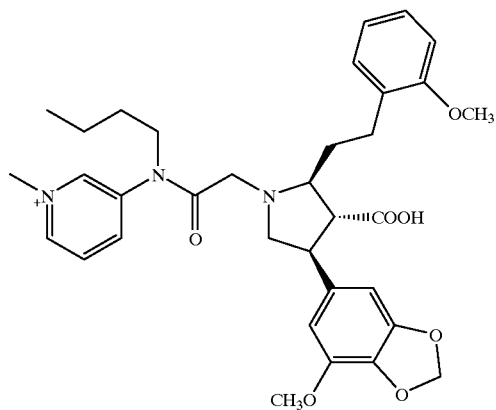

TABLE 3C-continued
330
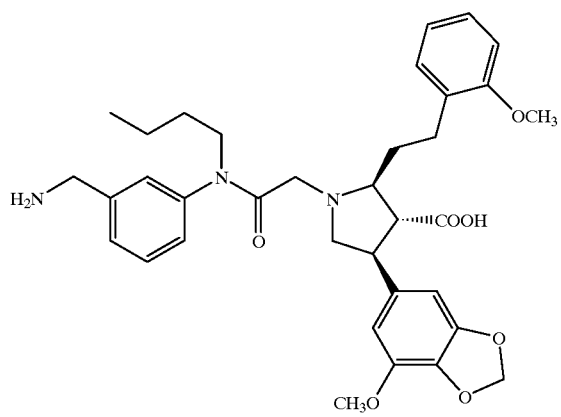
331
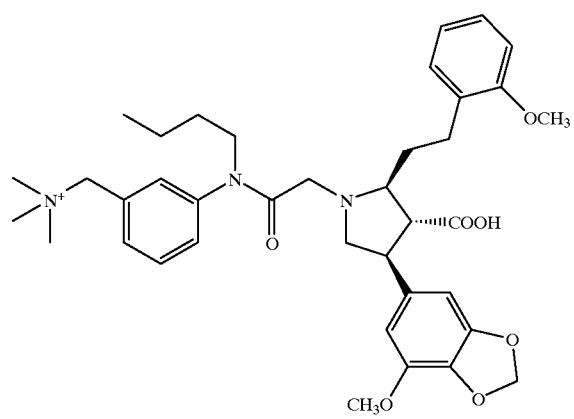
332
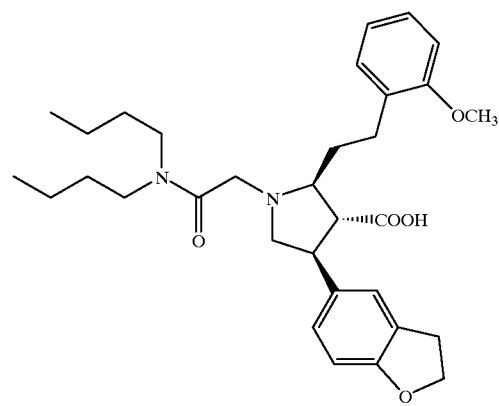

TABLE 3C-continued
333
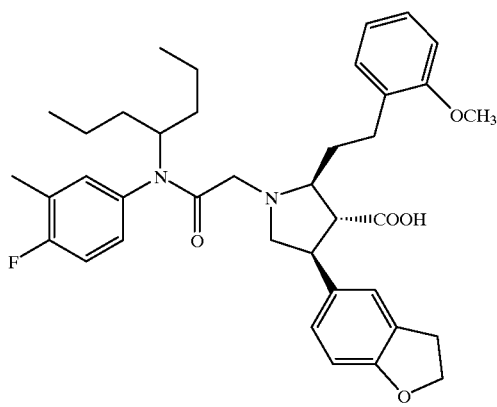
334
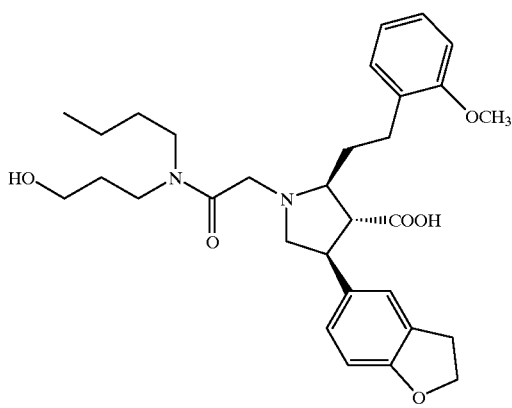
335
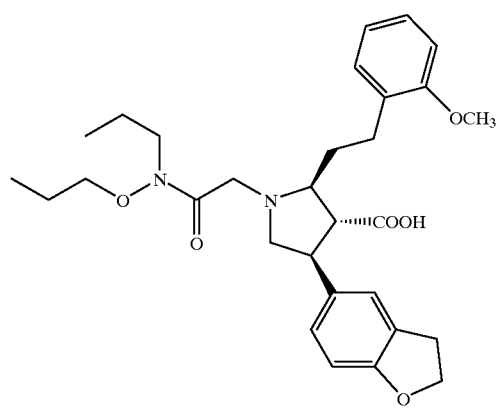

TABLE 3C-continued
336
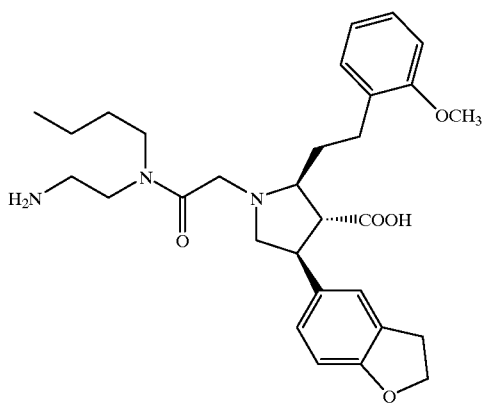
337
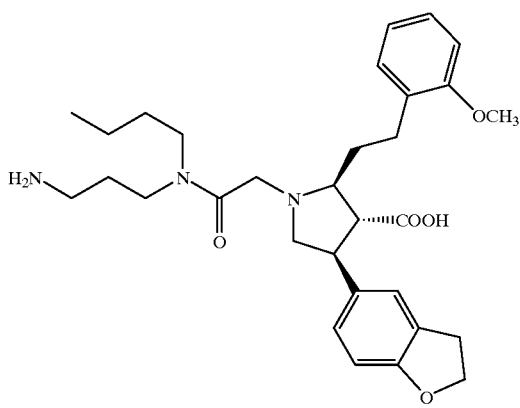
338
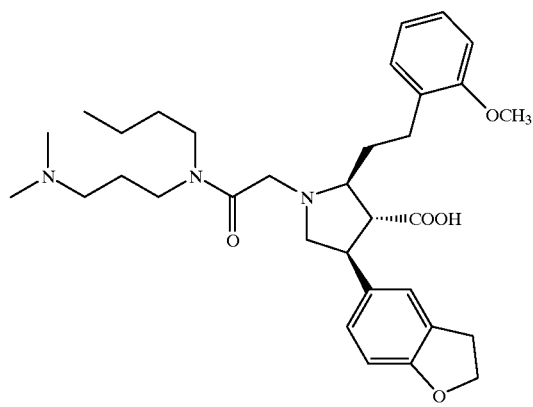

TABLE 3C-continued
339
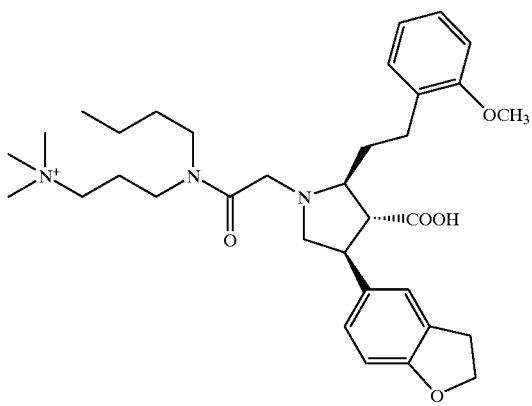
340
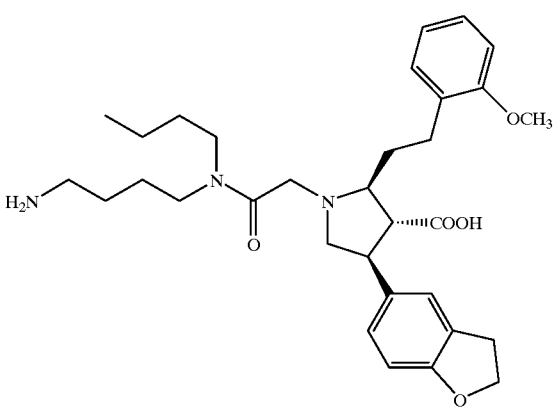
341
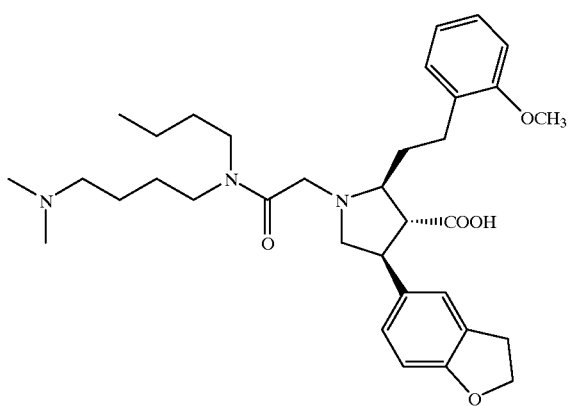

TABLE 3C-continued
342
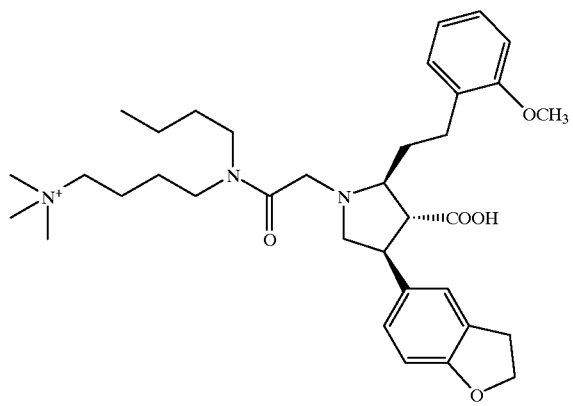
343
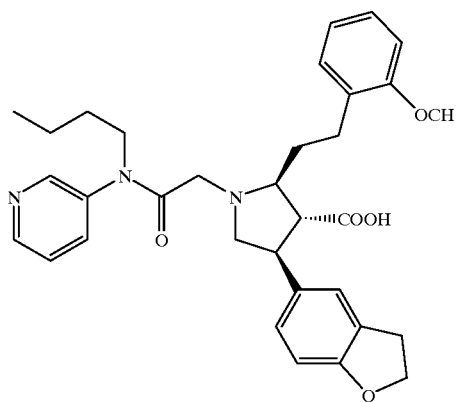
344
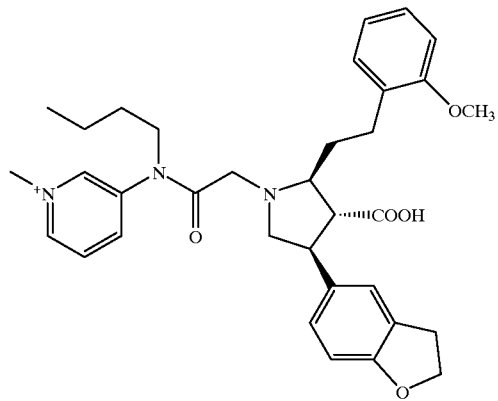

TABLE 3C-continued
345
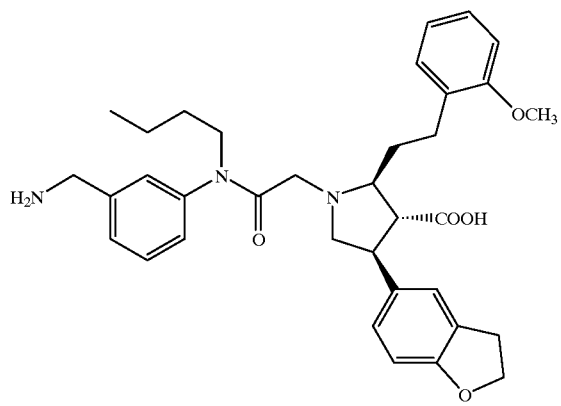
346
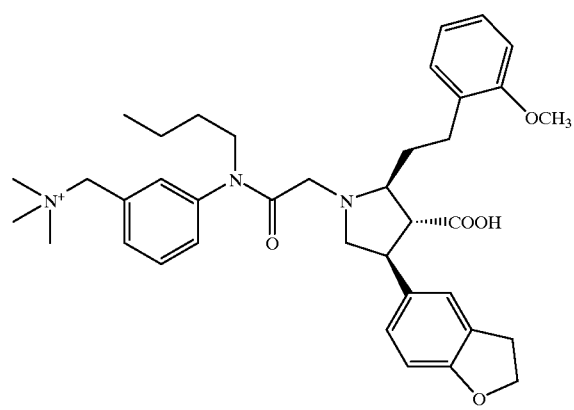
347
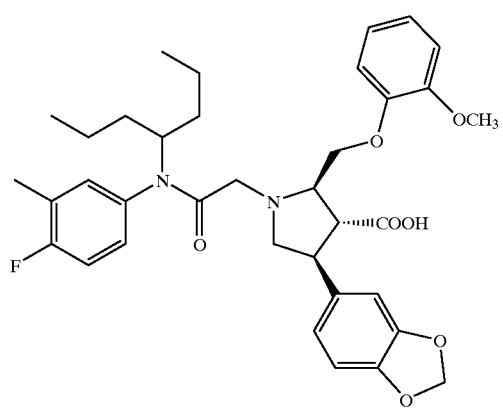

TABLE 3C-continued
348
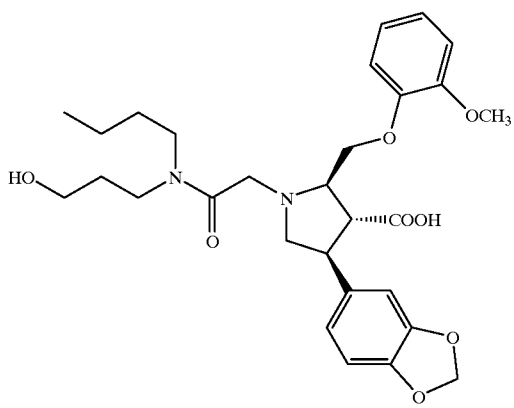
349
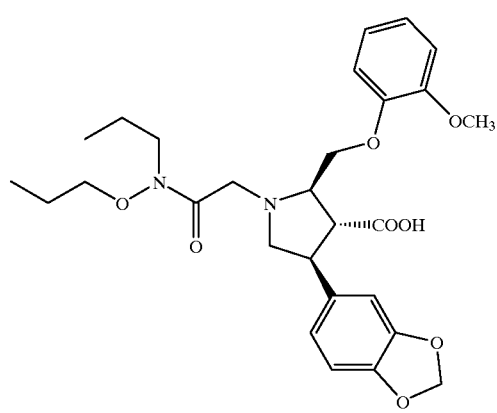
350
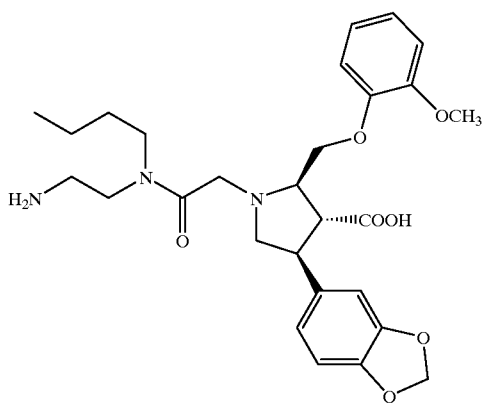

TABLE 3C-continued
351
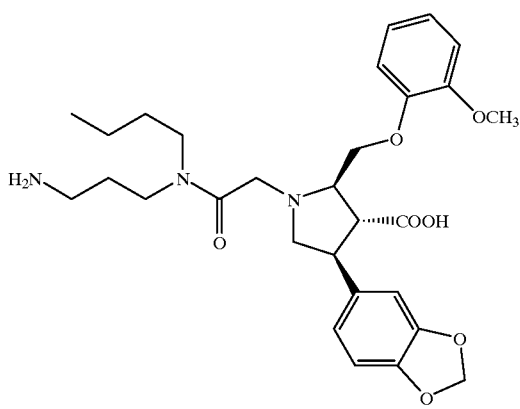
352
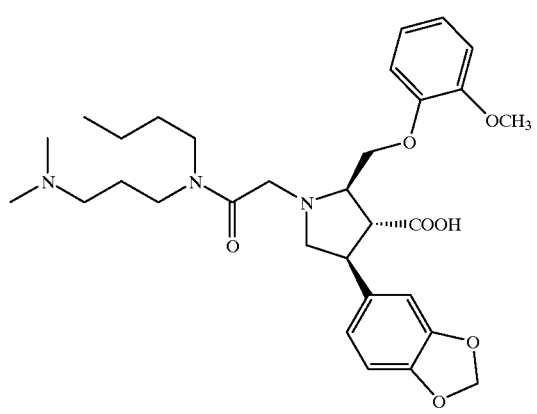
353
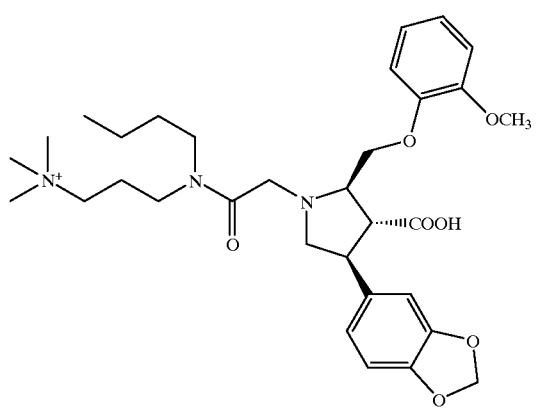

TABLE 3C-continued
354
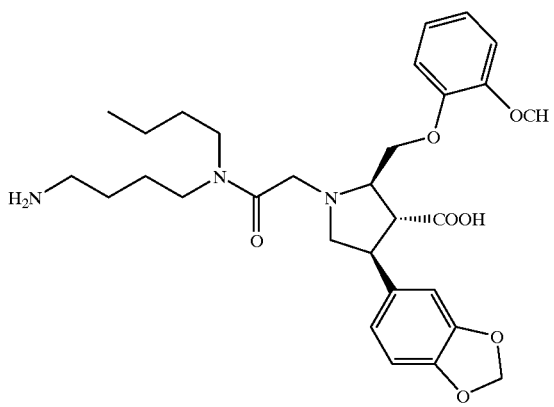
355
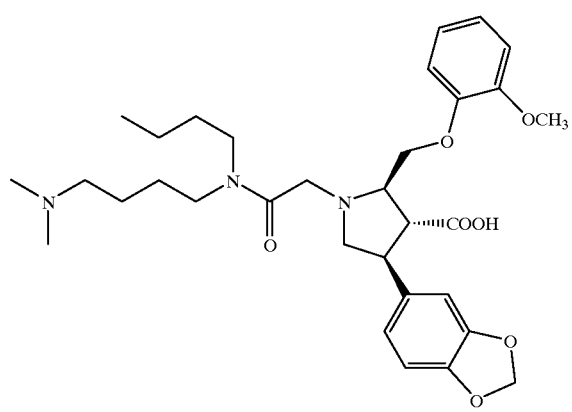
356
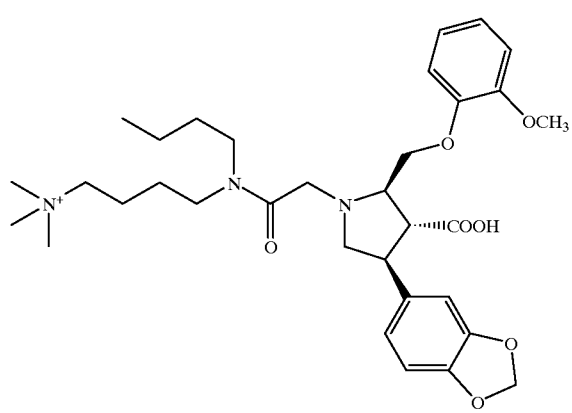

TABLE 3C-continued
357
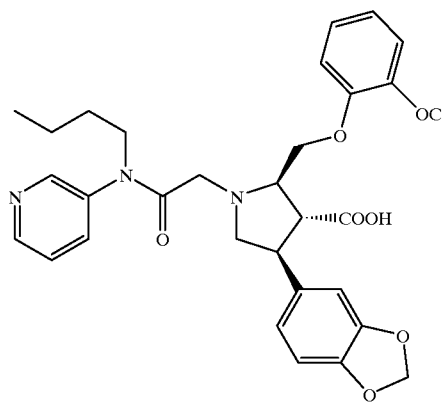
358
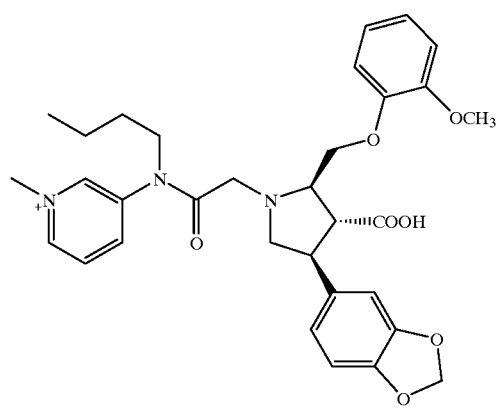
359
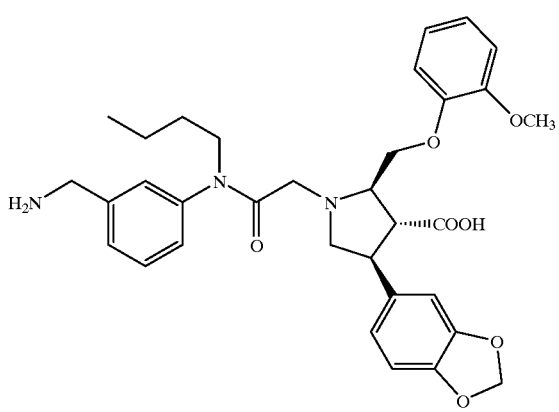

TABLE 3C-continued
360
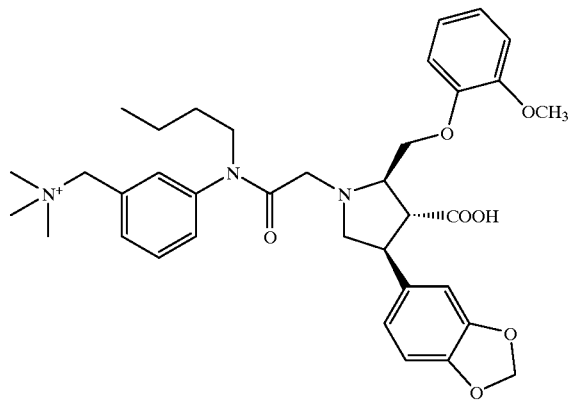
361
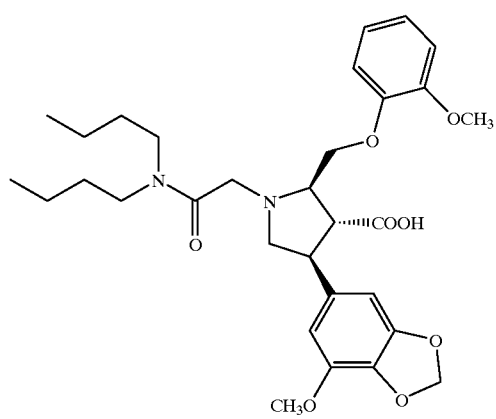
362
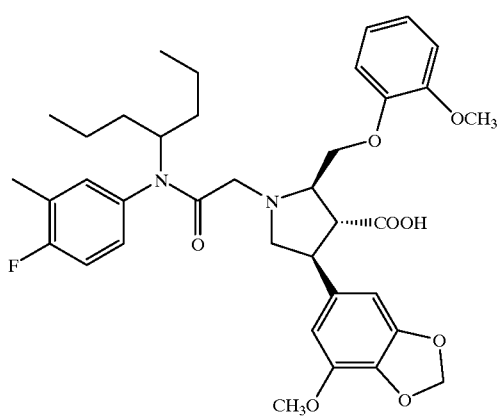

TABLE 3C-continued
363
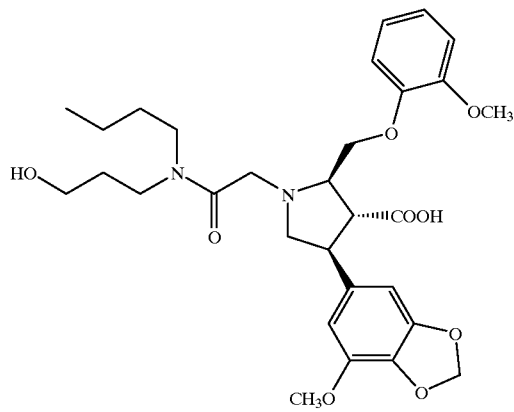
364
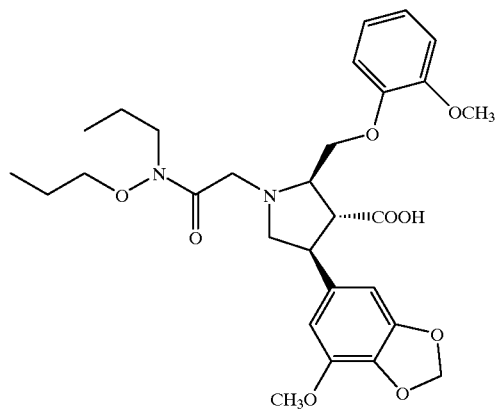
365
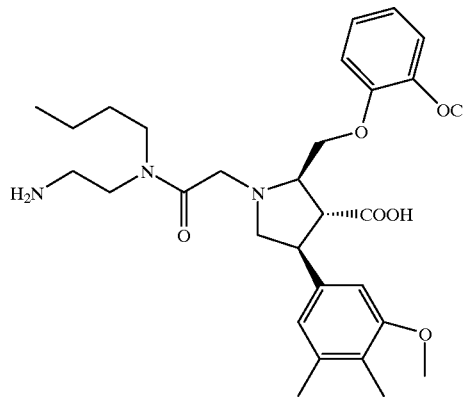

TABLE 3C-continued
366 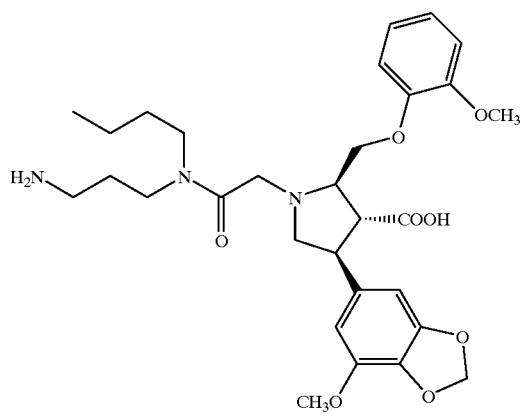
367 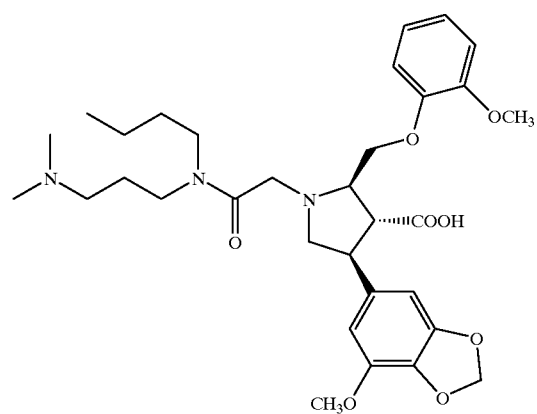
368 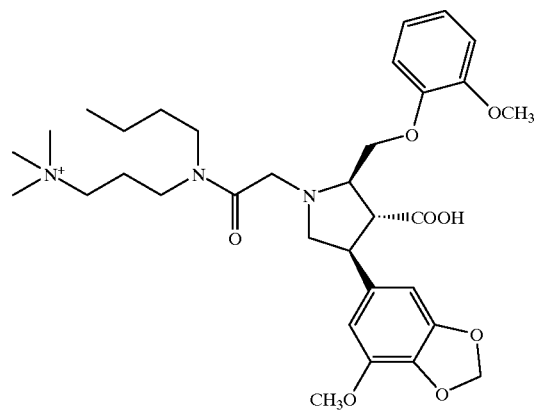

TABLE 3C-continued
369
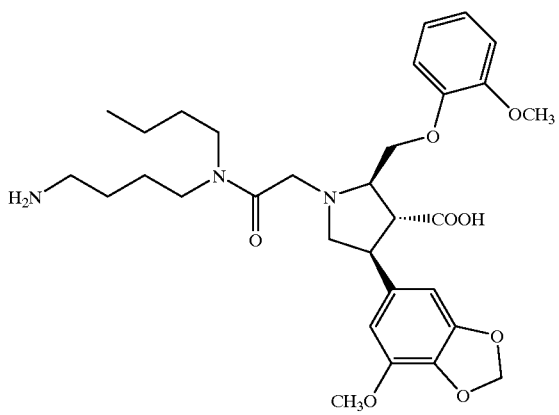
370
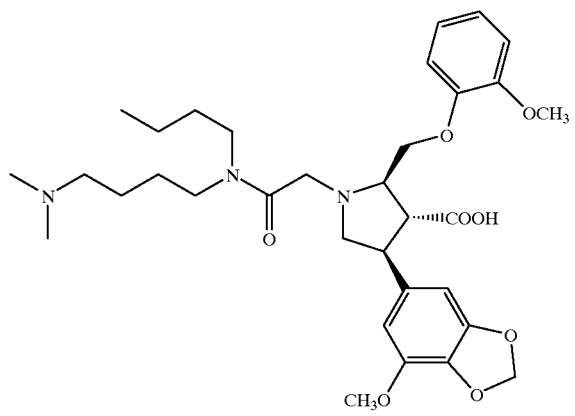
371
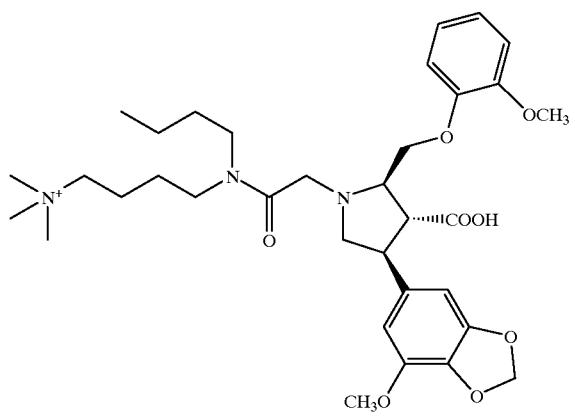

TABLE 3C-continued
372
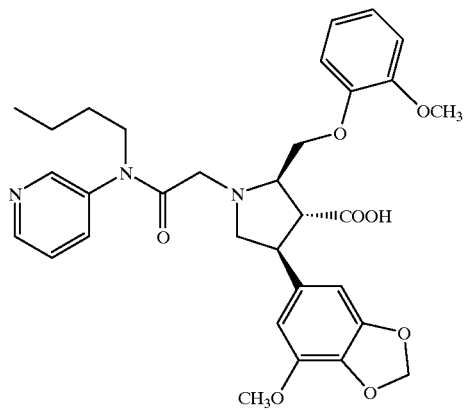
373
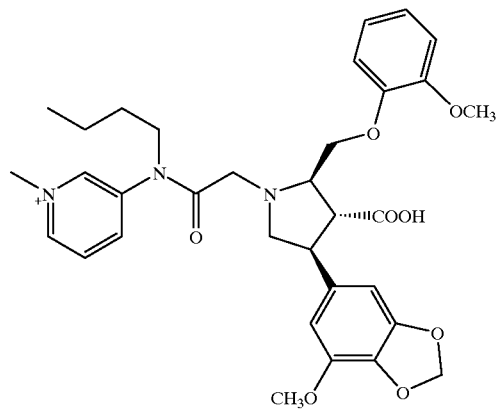
374
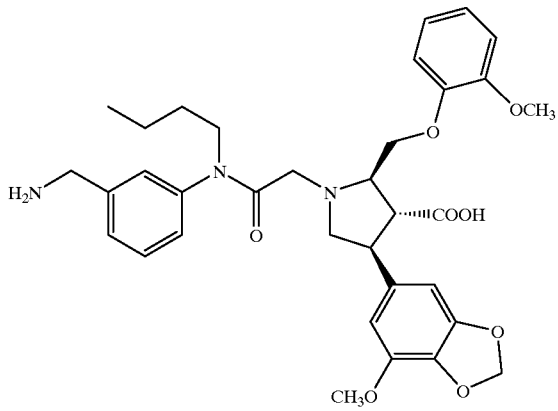

TABLE 3C-continued
375
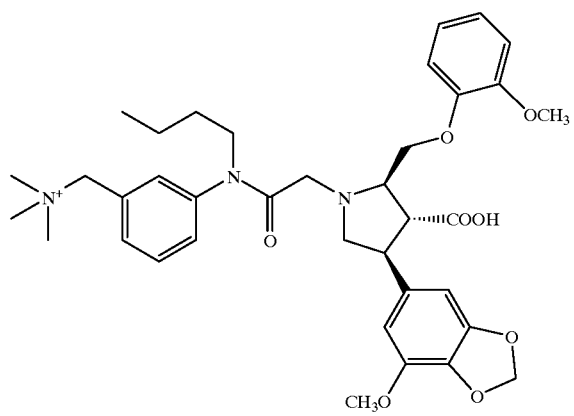
376
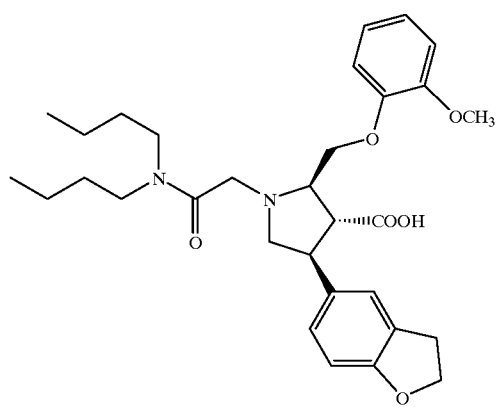
377
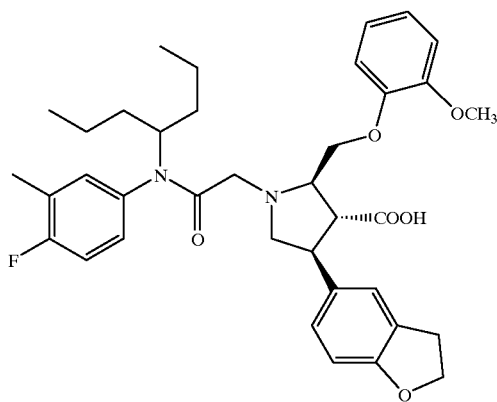

TABLE 3C-continued
378
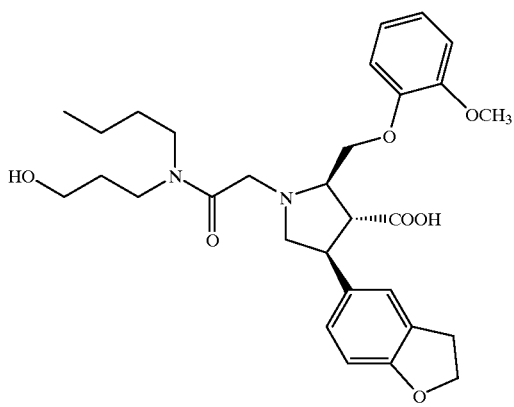
379
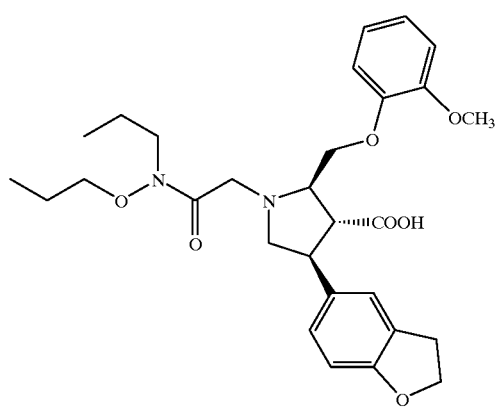
380
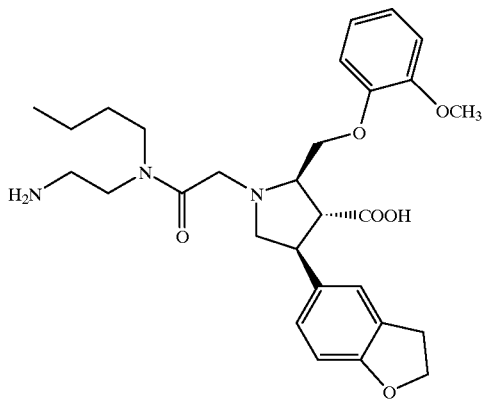

TABLE 3C-continued
381
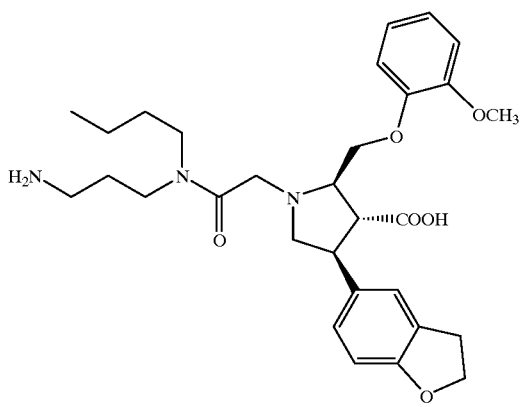
382
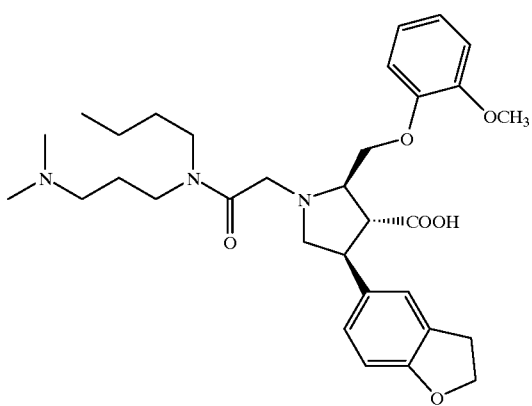
383
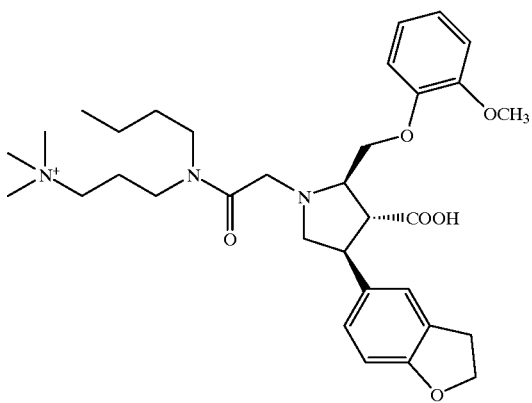

TABLE 3C-continued
384
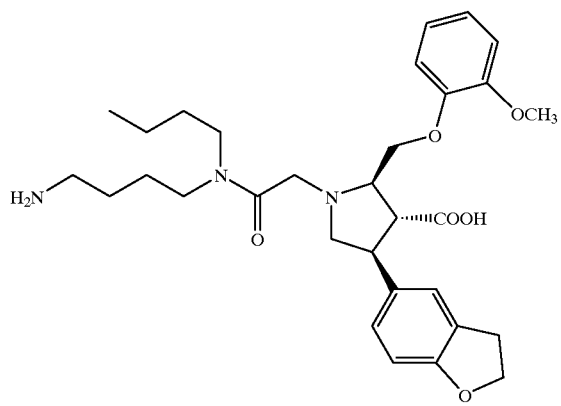
385
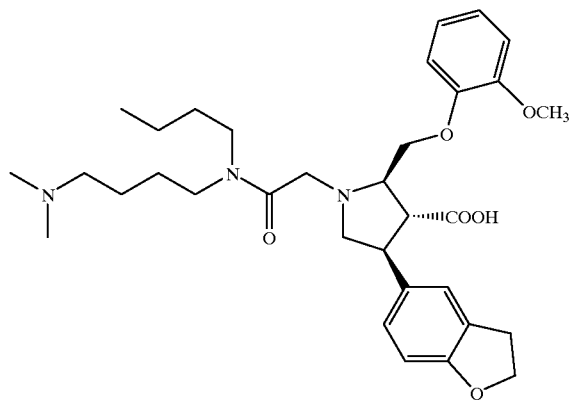
386
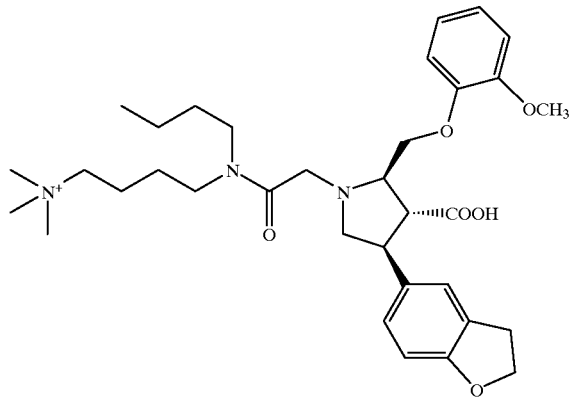

TABLE 3C-continued
387
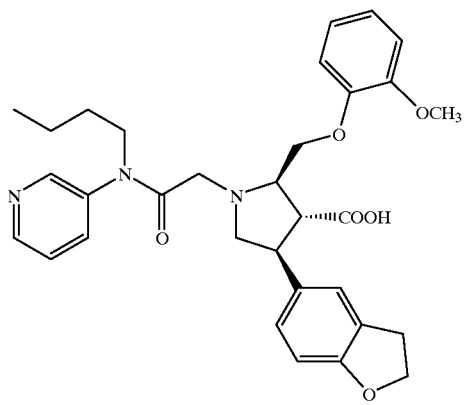
388
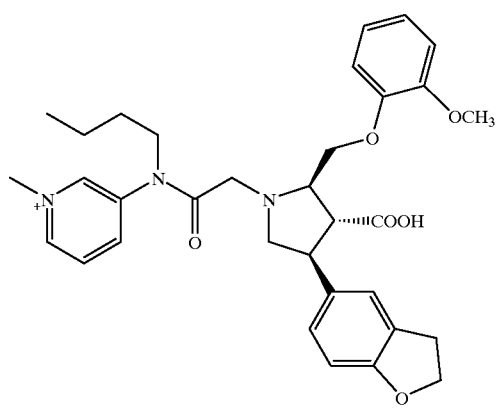
389
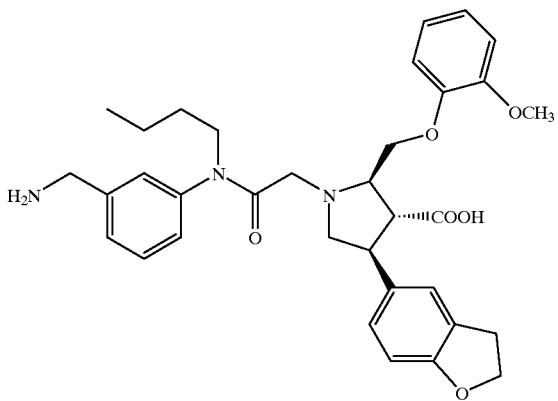

TABLE 3C-continued
390
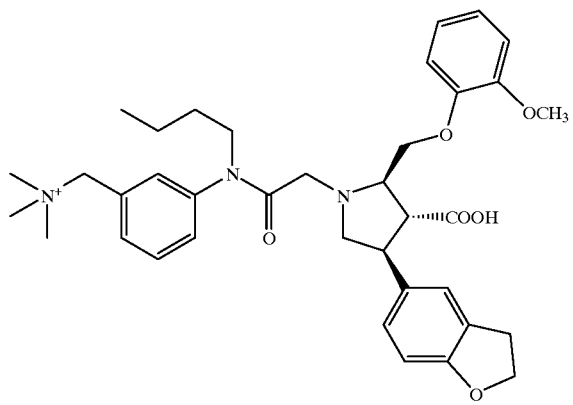
391
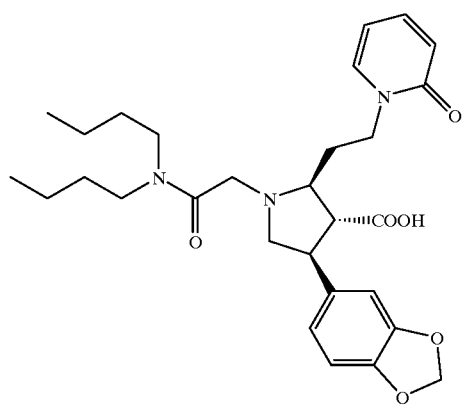
392
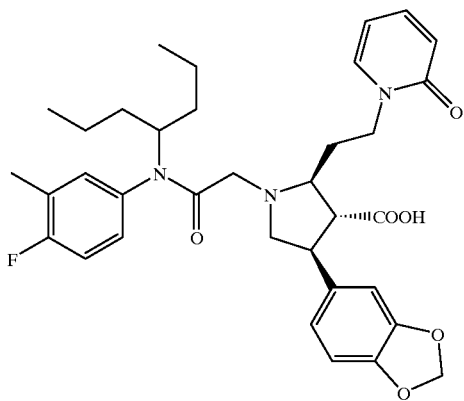

TABLE 3C-continued
393
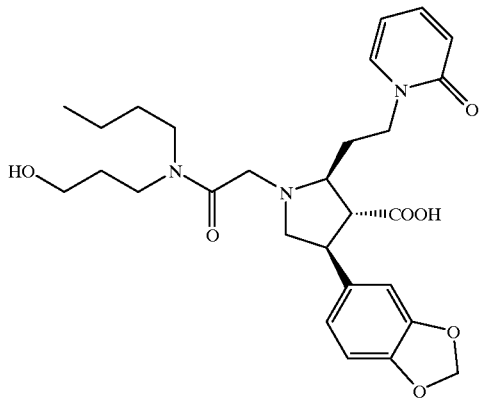
394
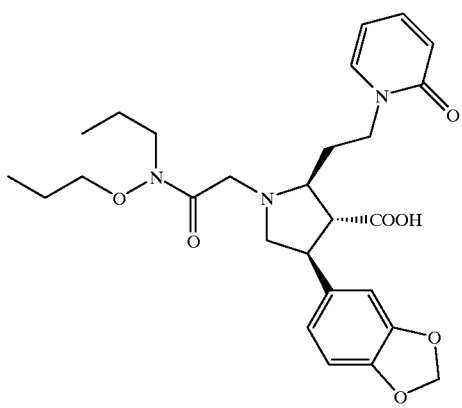
395
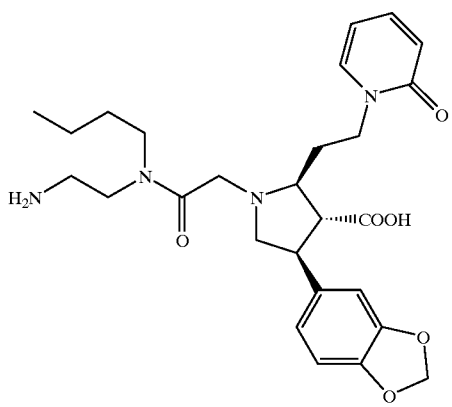

TABLE 3C-continued
396
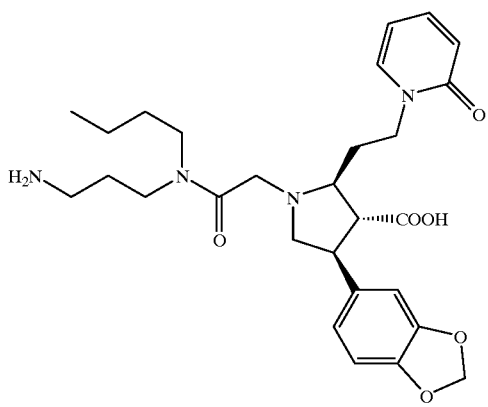
397
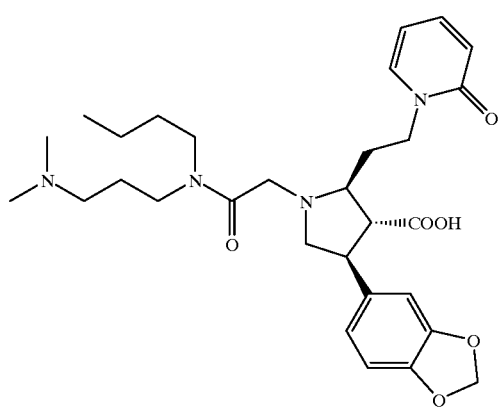
398
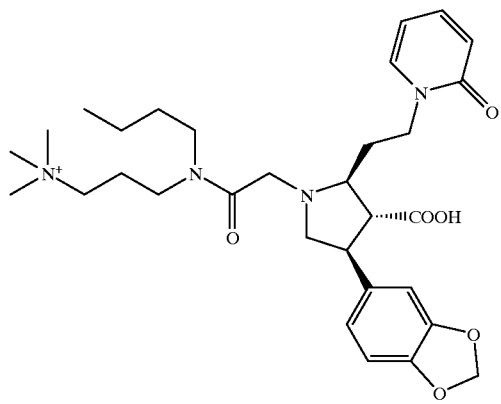

TABLE 3C-continued
399
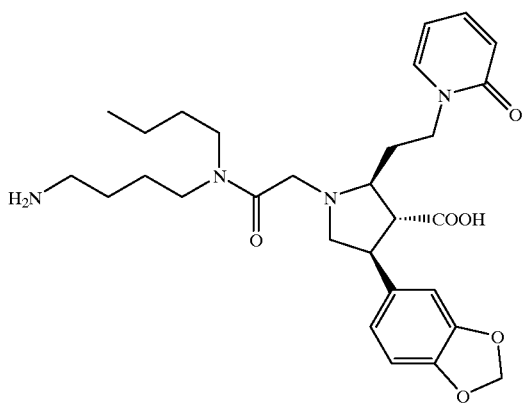
400
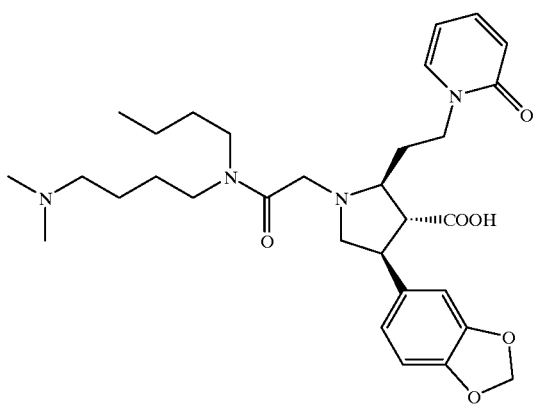
401
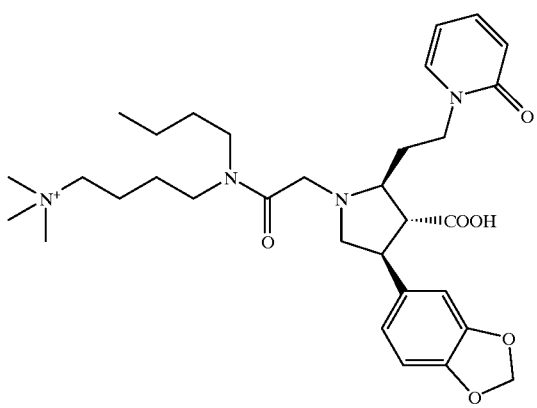

TABLE 3C-continued
402
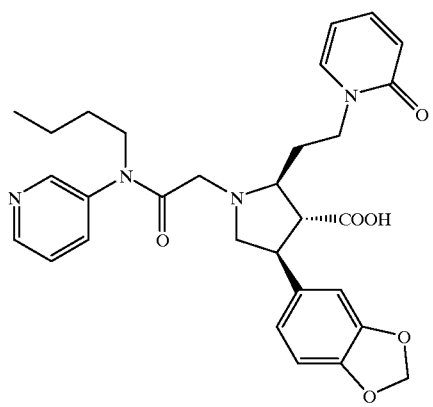
403
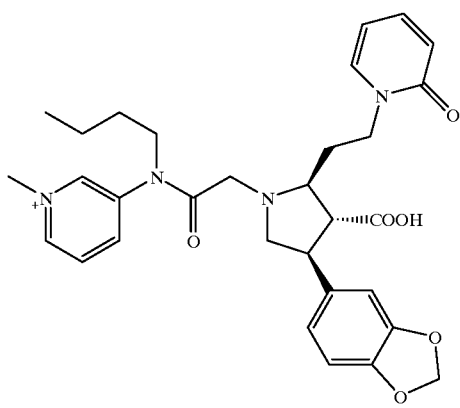
404
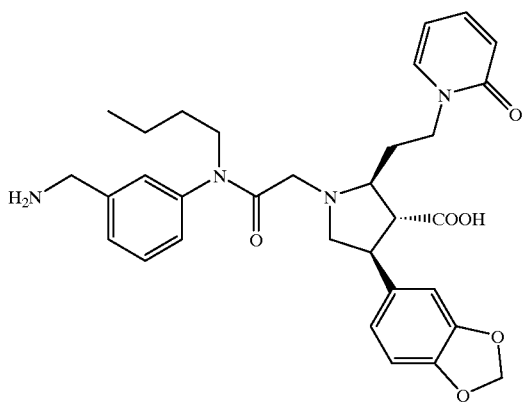

TABLE 3C-continued
405
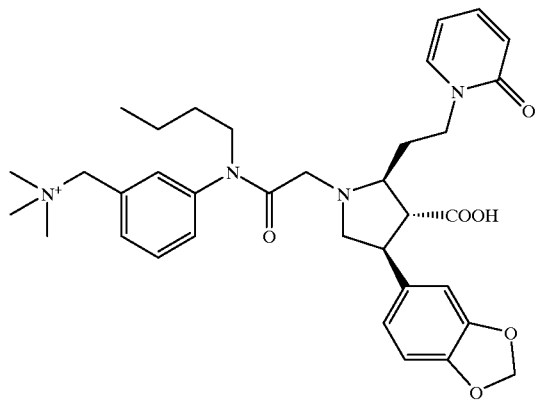
406
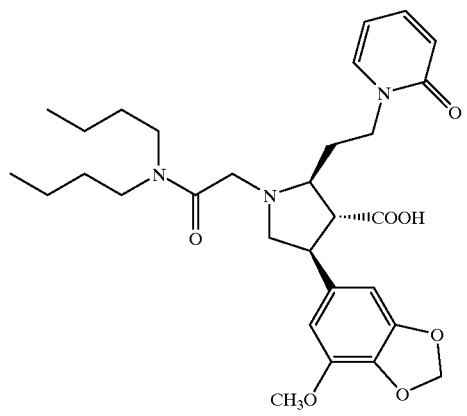
407
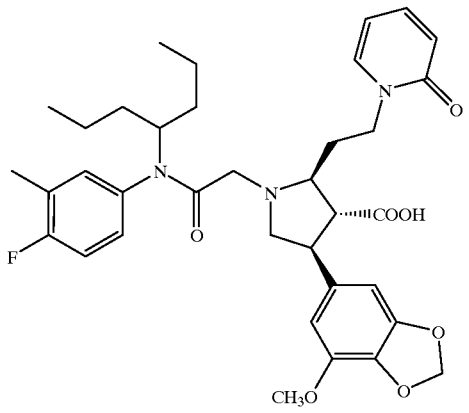

TABLE 3C-continued
408
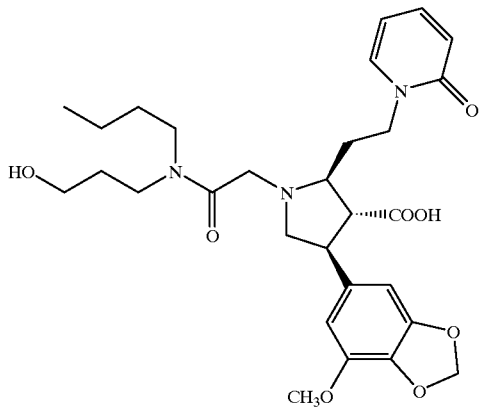
409
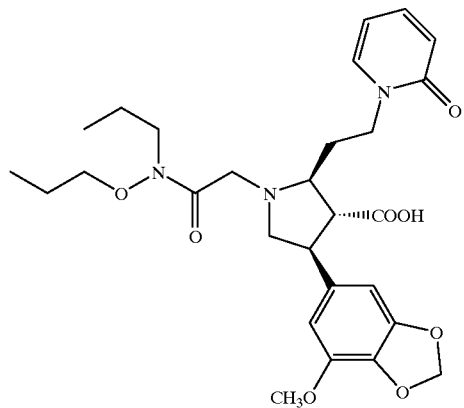
410
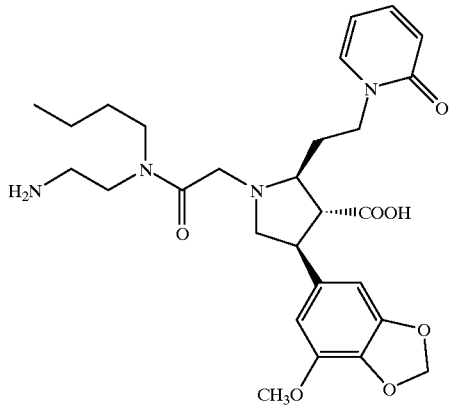

TABLE 3C-continued
411
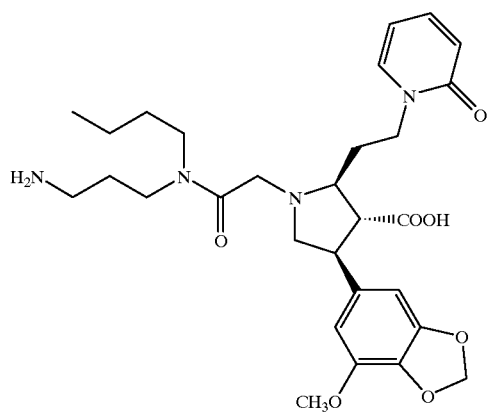
412
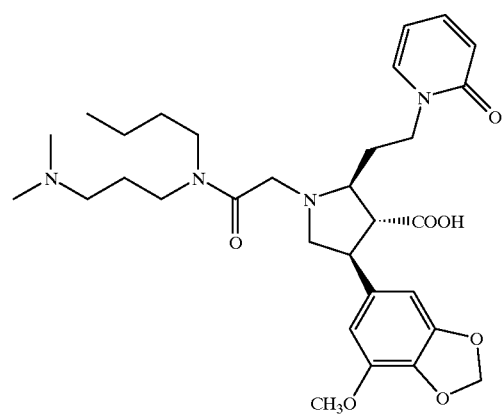
413
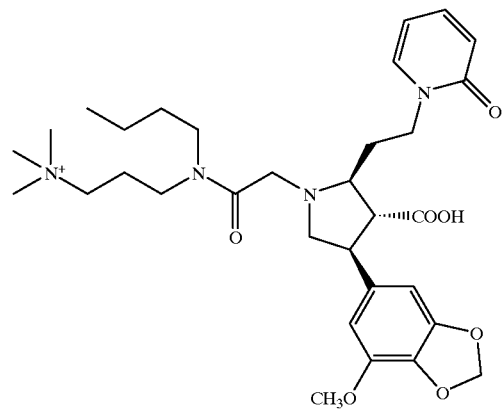

TABLE 3C-continued
414
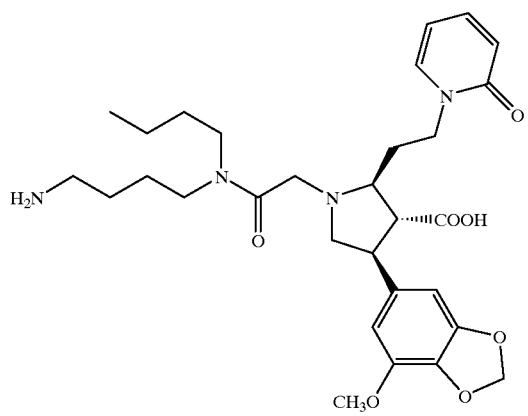
415
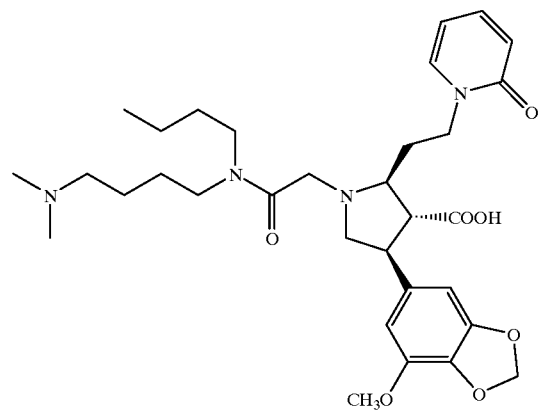
416
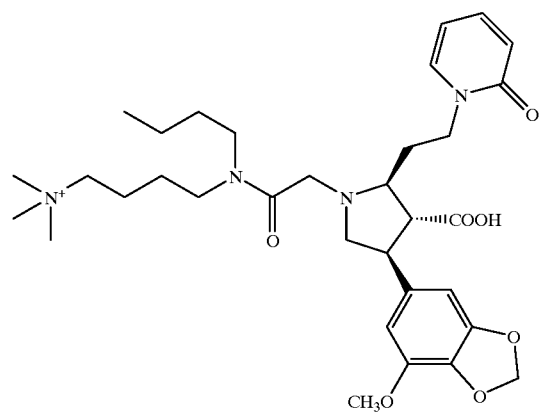

TABLE 3C-continued
417 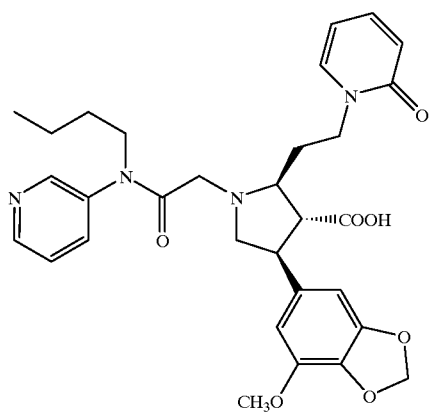
418 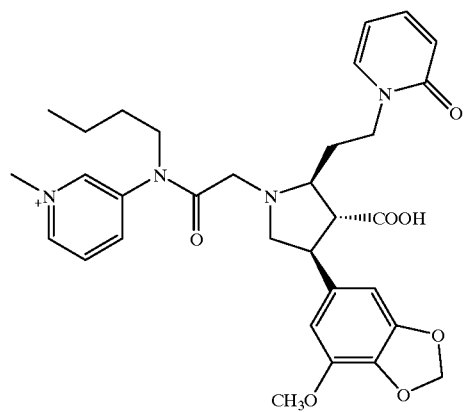
419 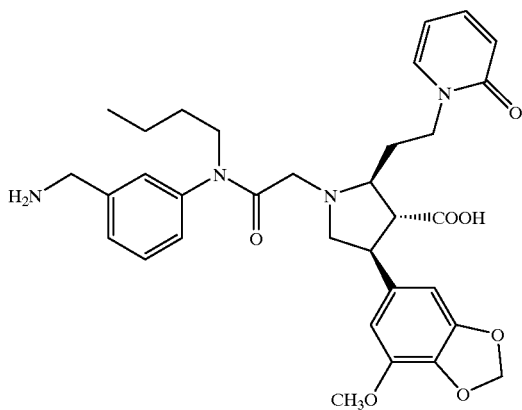

TABLE 3C-continued
420
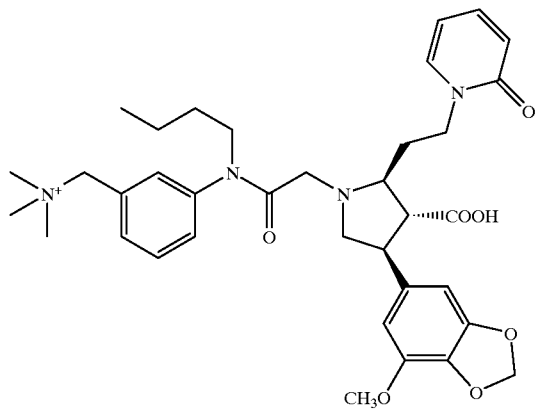
421
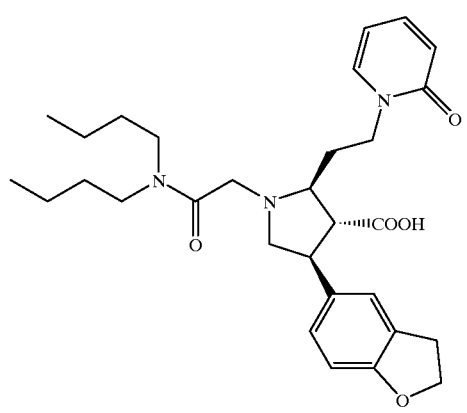
422
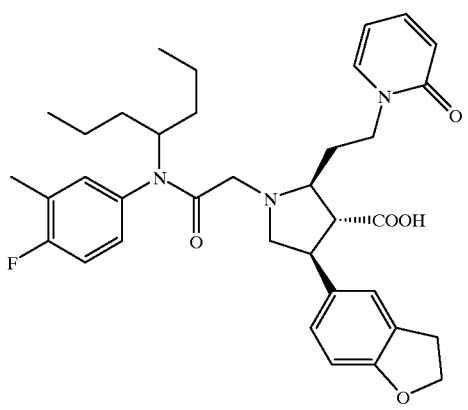

TABLE 3C-continued
423
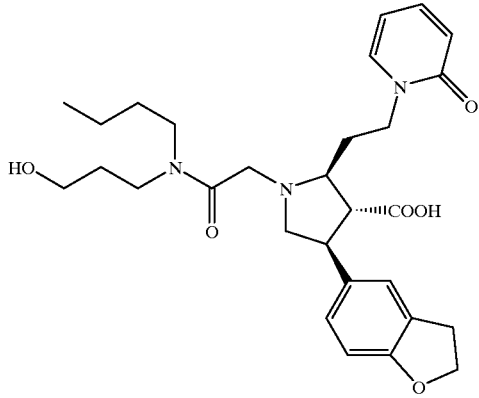
424
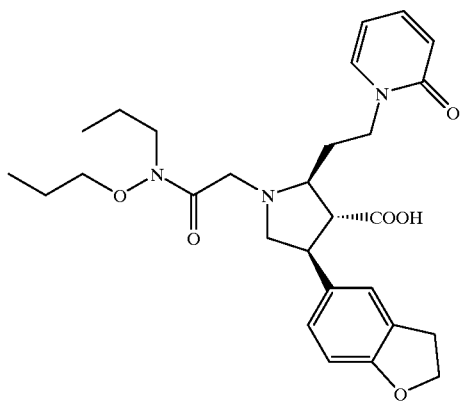
425
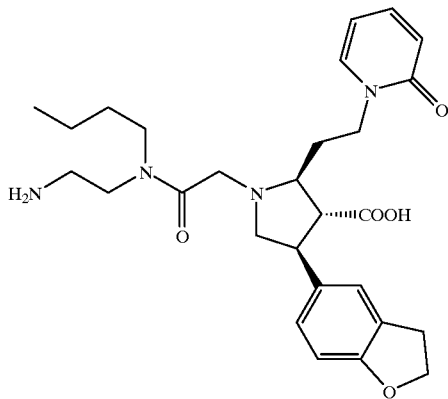

TABLE 3C-continued
426
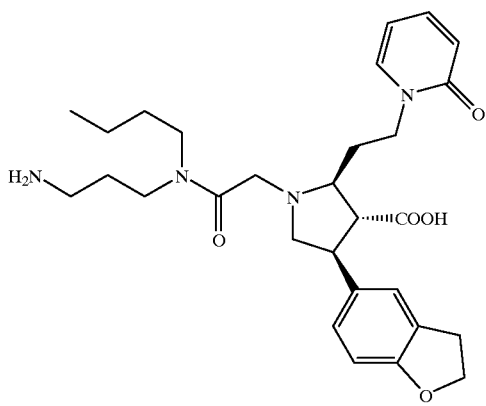
427
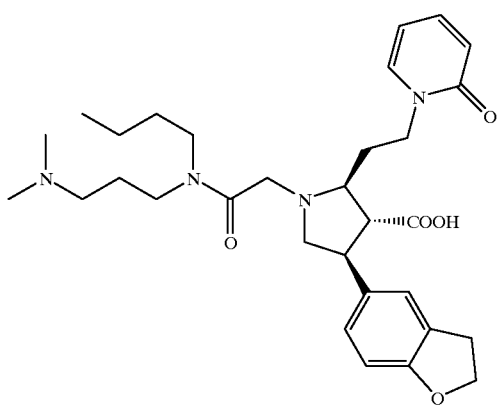
428
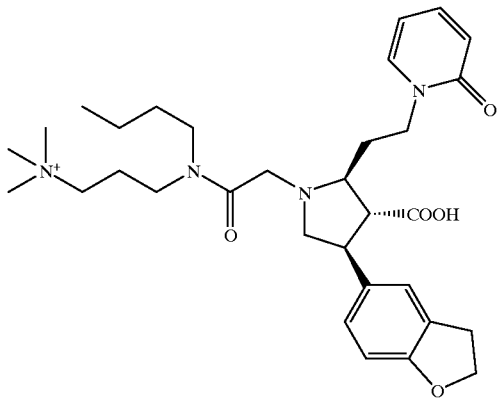

TABLE 3C-continued
429
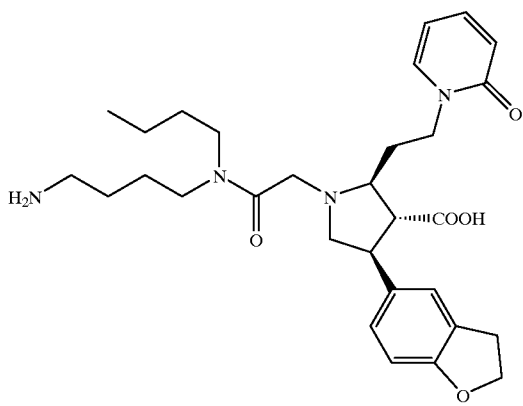
430
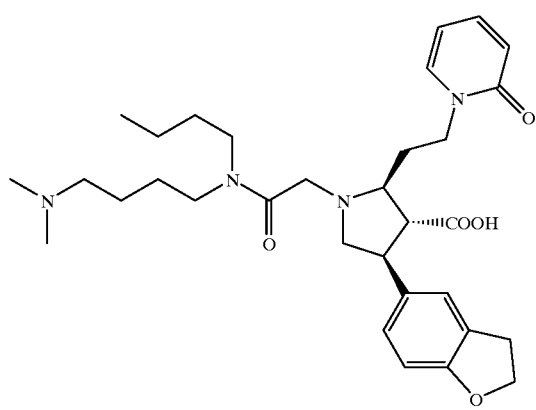
431
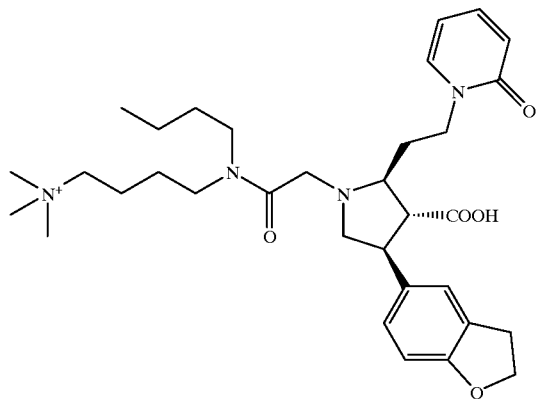

TABLE 3C-continued
432
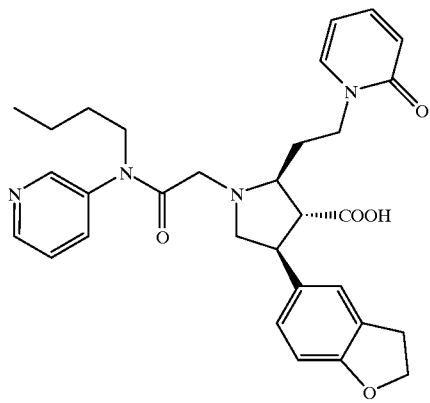
433
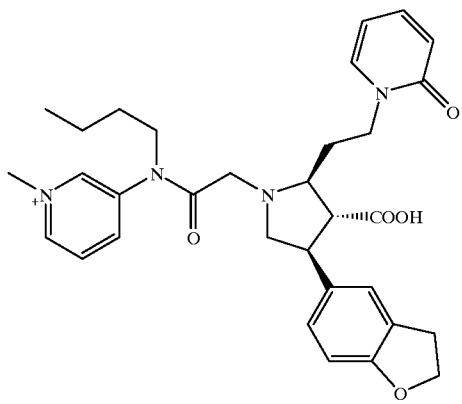
434
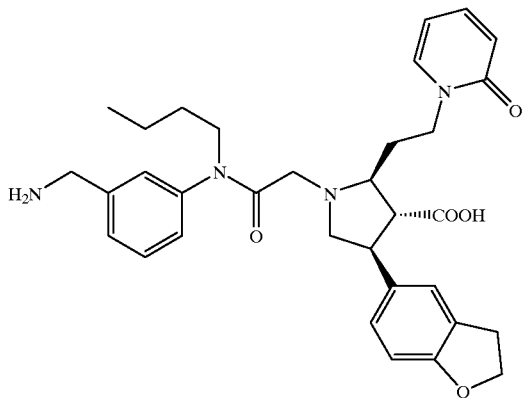

TABLE 3C-continued
435
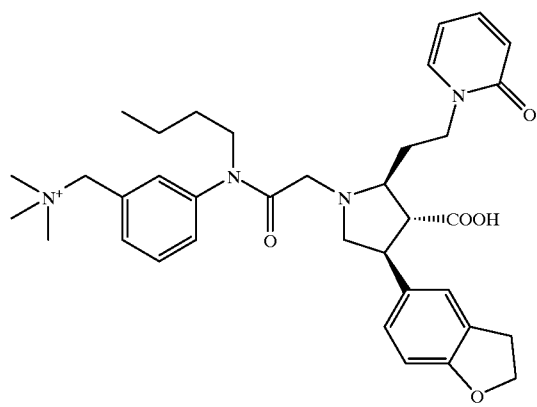
436
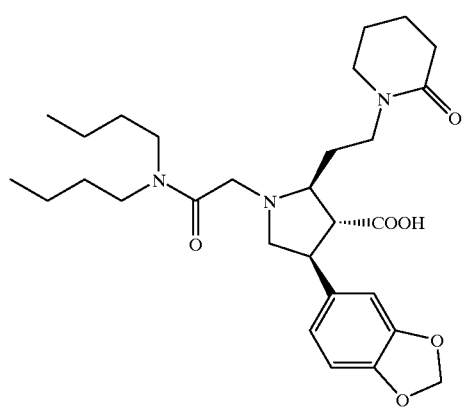
437
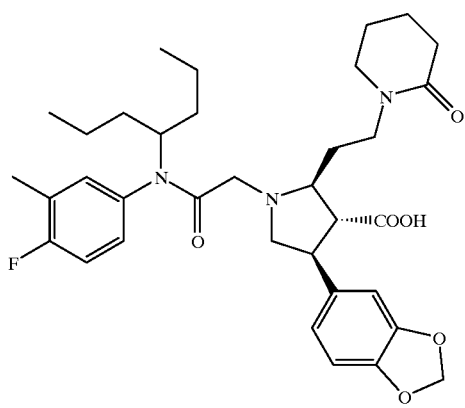

TABLE 3C-continued
438
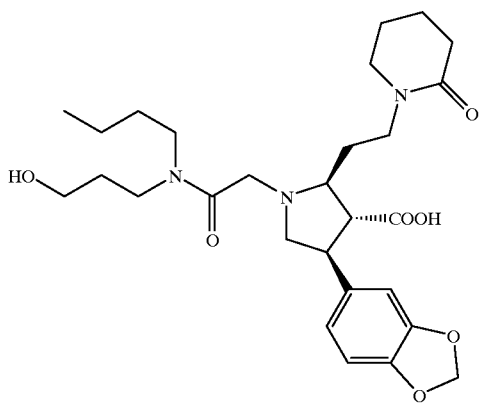
439
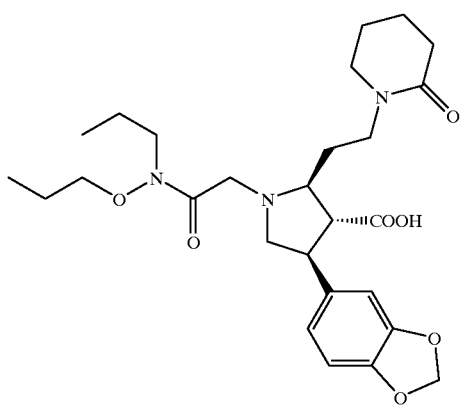
440
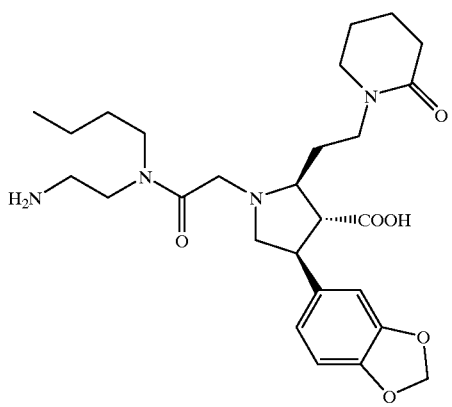

TABLE 3C-continued
441
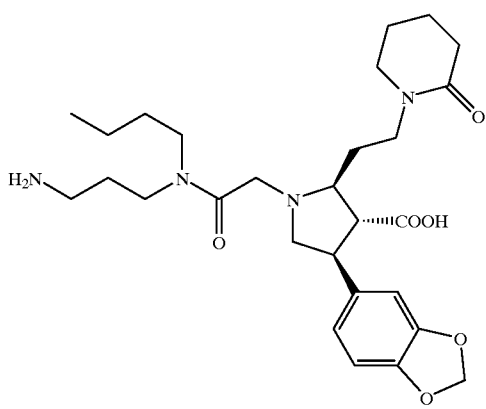
442
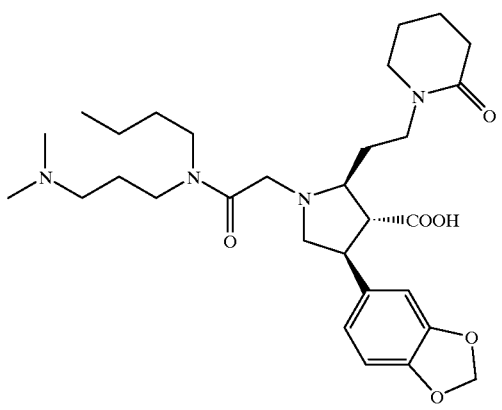
443
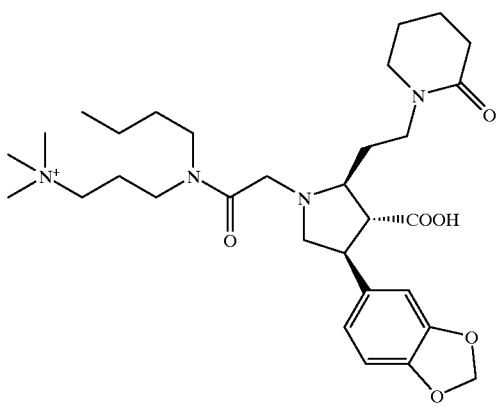

TABLE 3C-continued
444
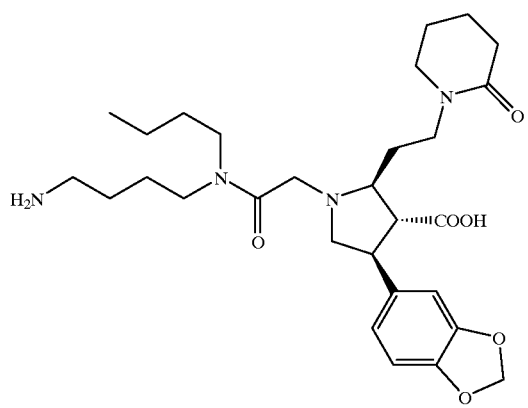
445
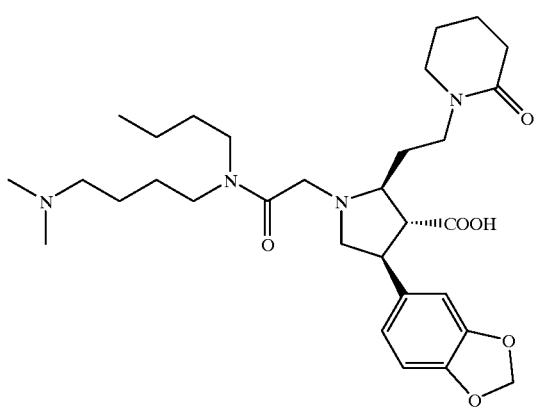
446
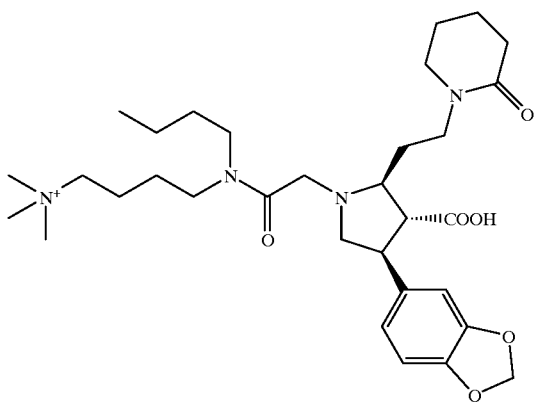

TABLE 3C-continued
447
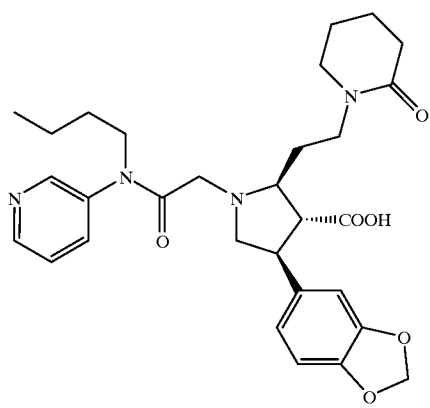
448
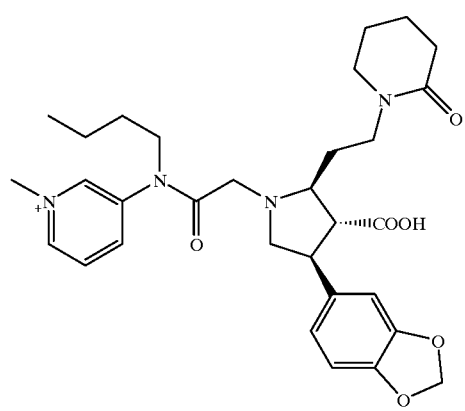
449
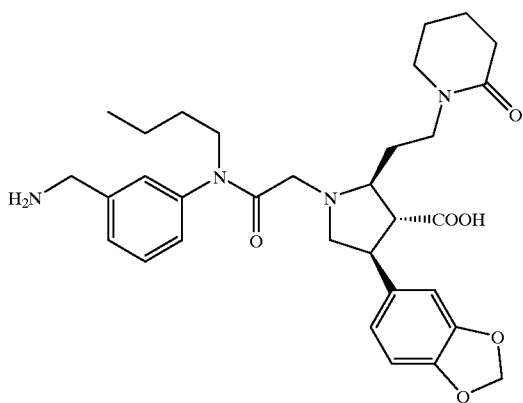

TABLE 3C-continued
450
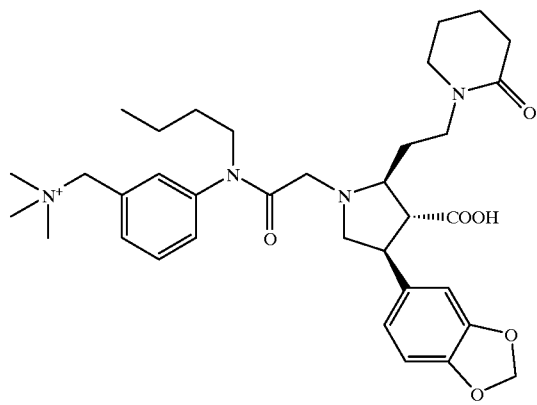
451
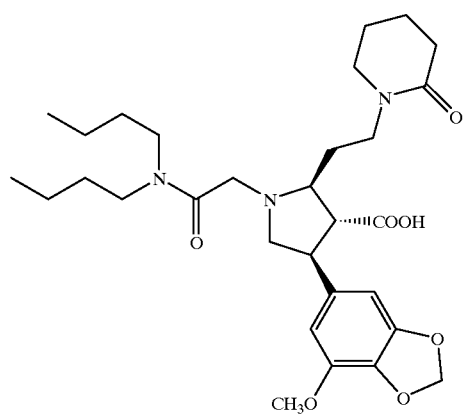
452
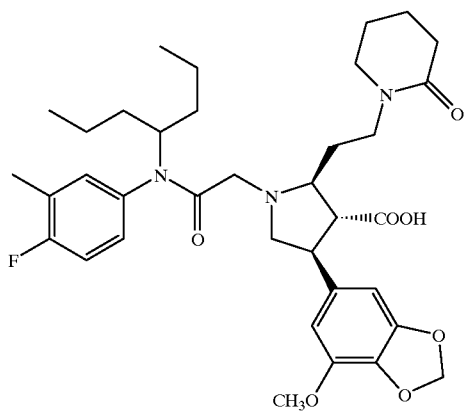

TABLE 3C-continued
453
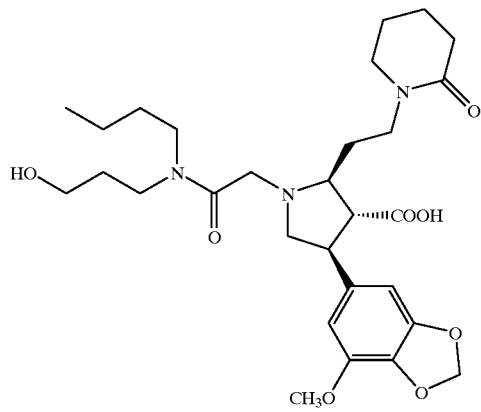
454
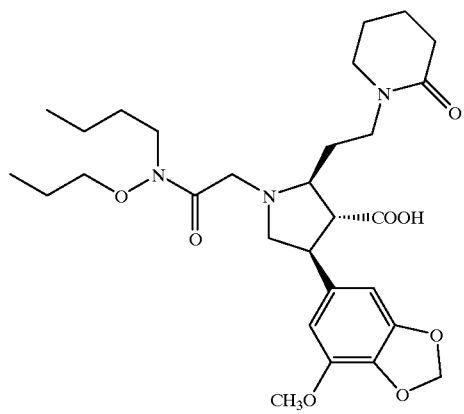
455
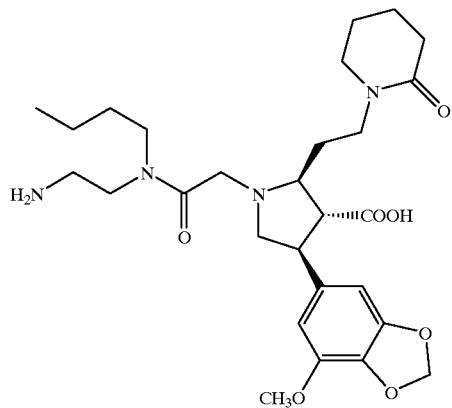

TABLE 3C-continued
456
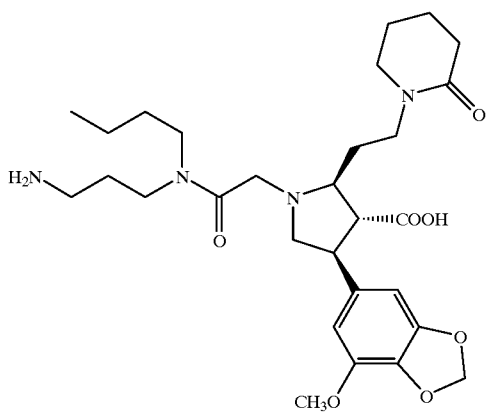
457
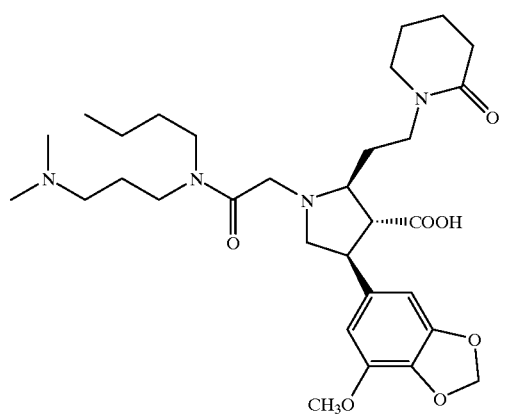
458
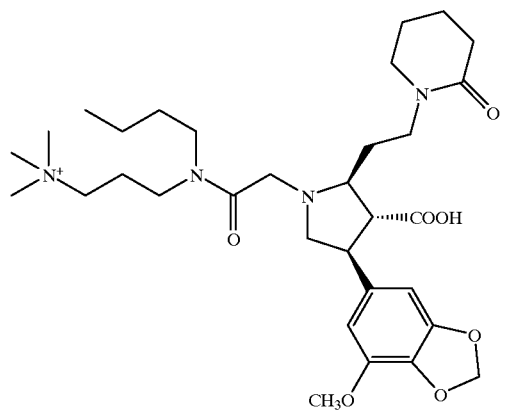

TABLE 3C-continued
459
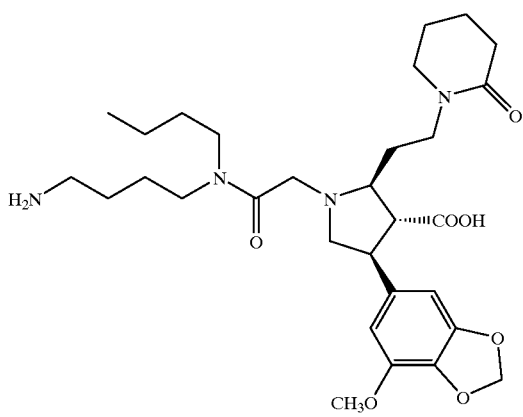
460
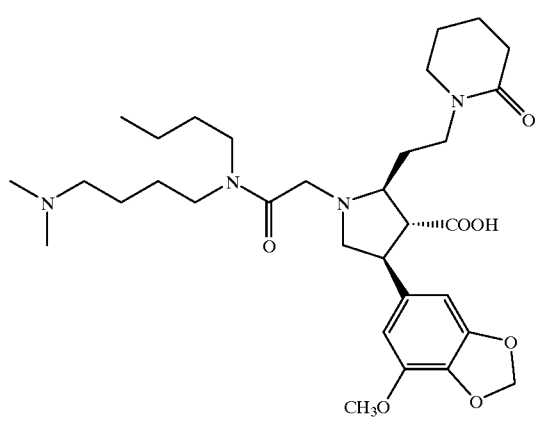
461
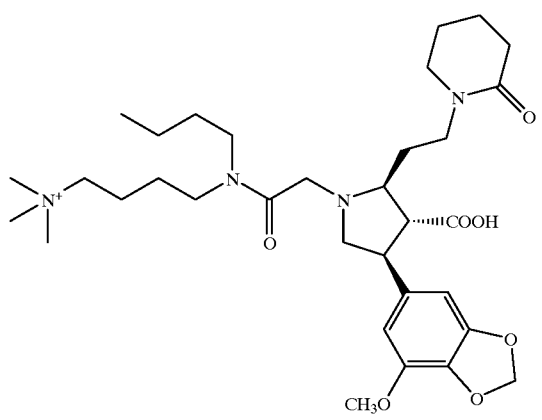

TABLE 3C-continued
462
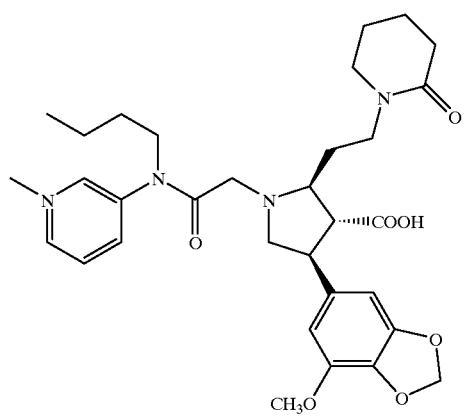
463
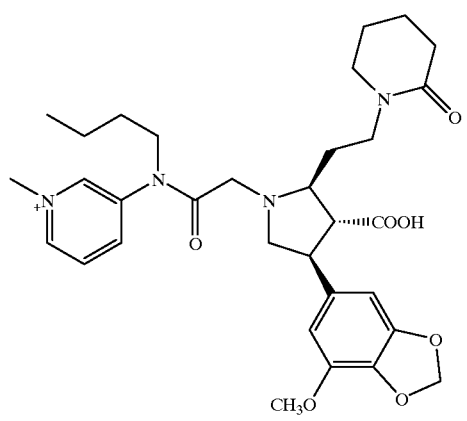
464
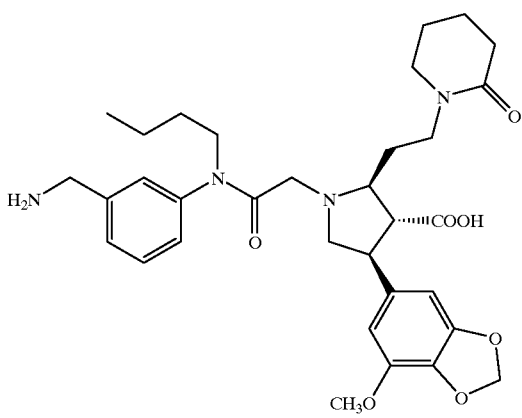

TABLE 3C-continued
465
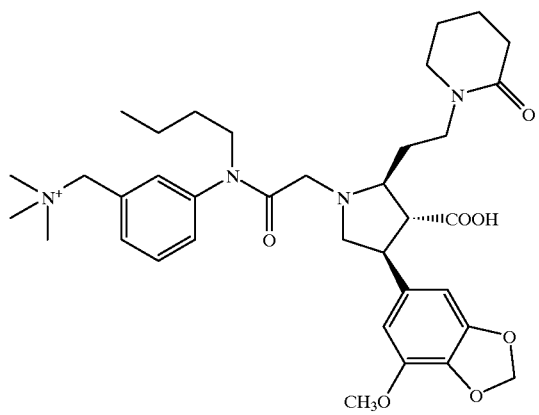
466
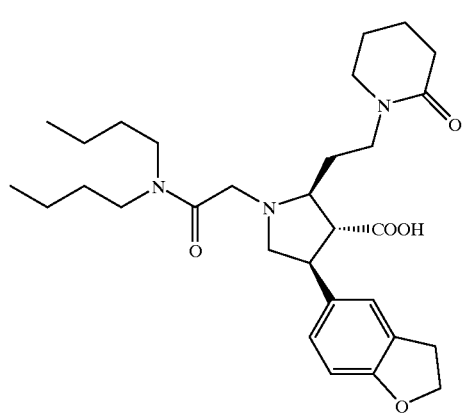
467
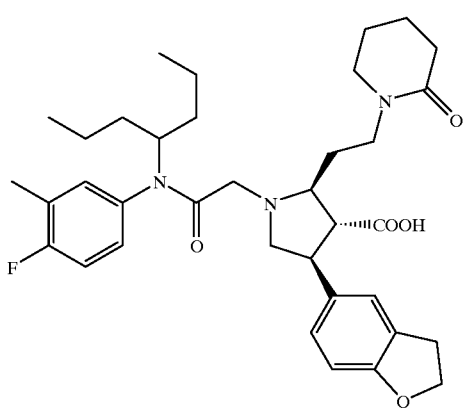

TABLE 3C-continued
468
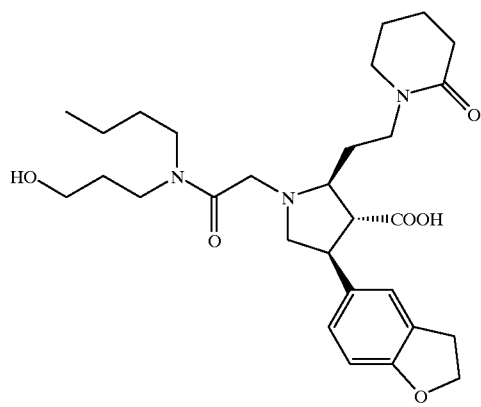
469
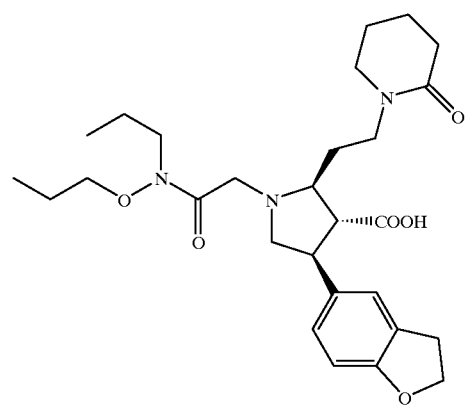
470
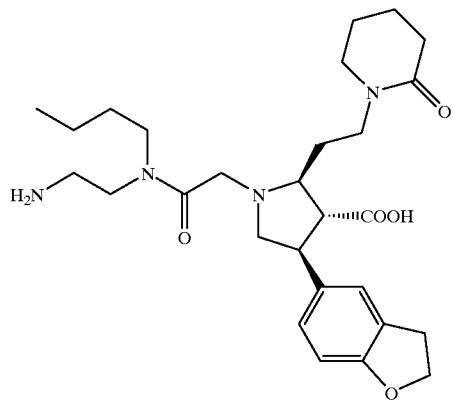

TABLE 3C-continued
471
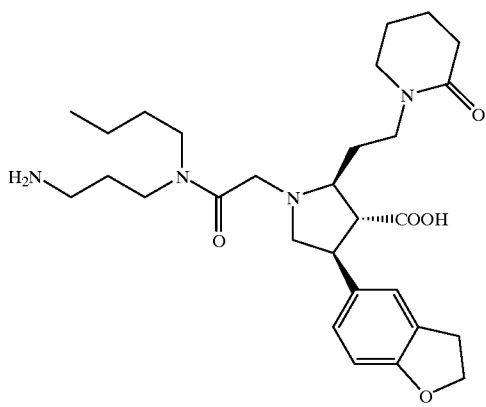
472
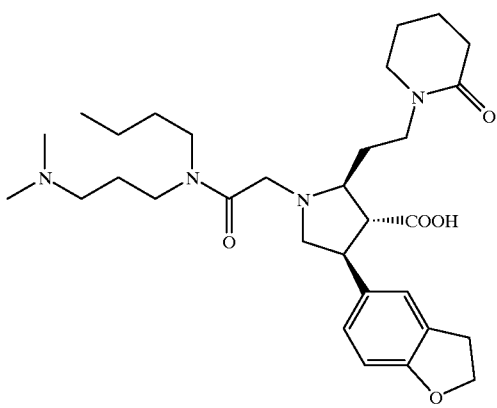
473
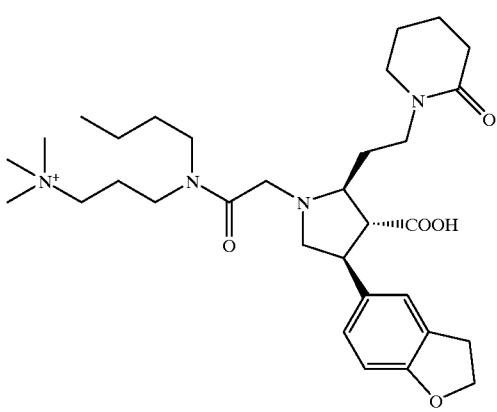

TABLE 3C-continued
474
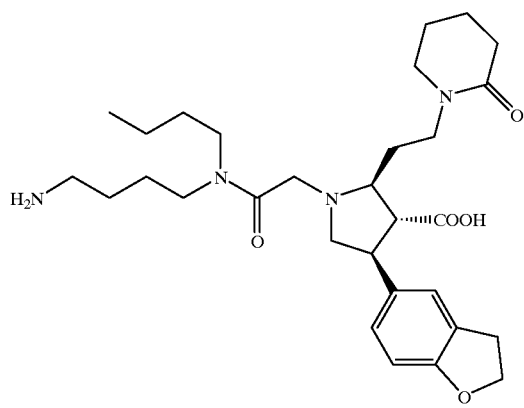
475
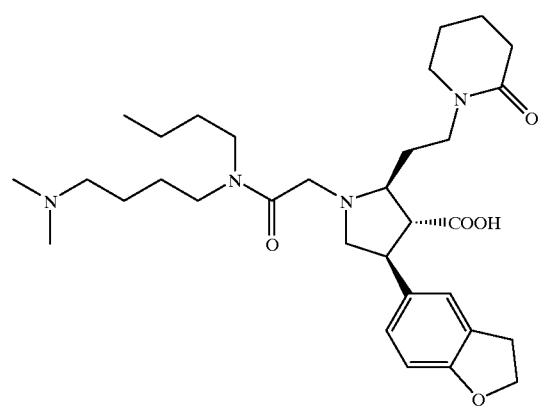
476
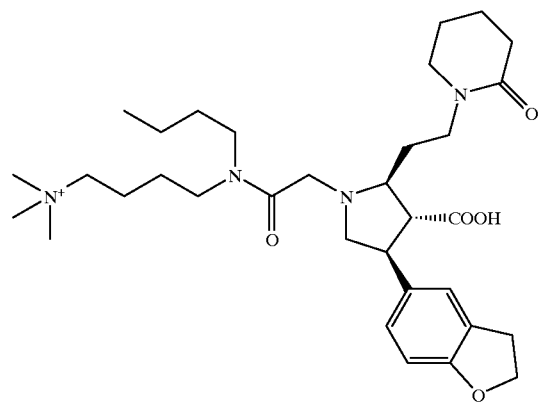

TABLE 3C-continued
477
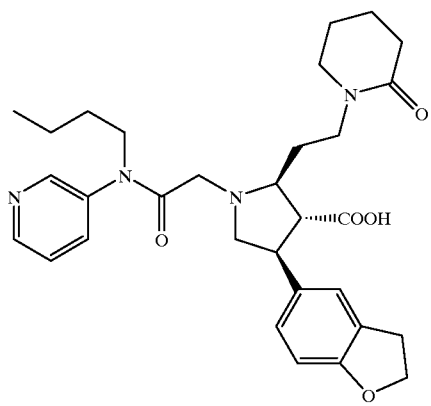
478
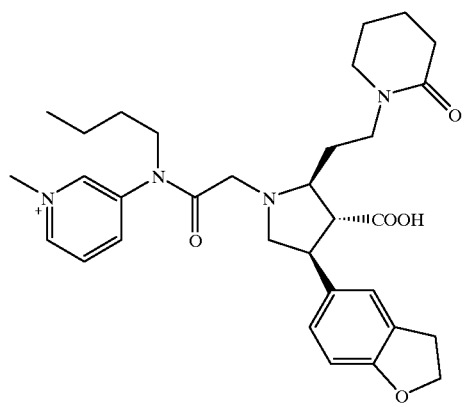
479
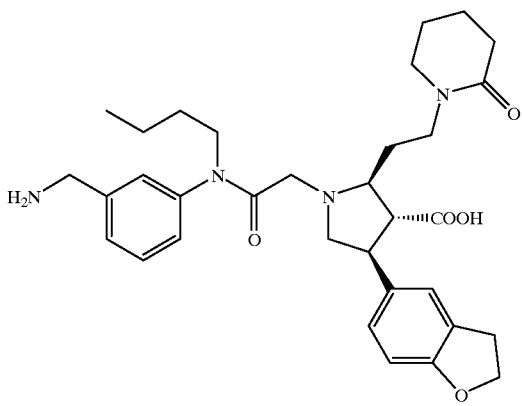

TABLE 3C-continued
480
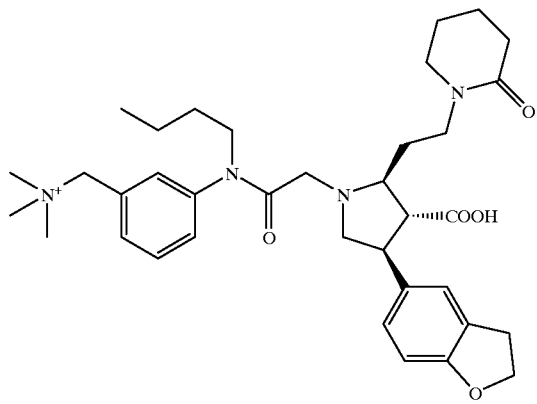
481
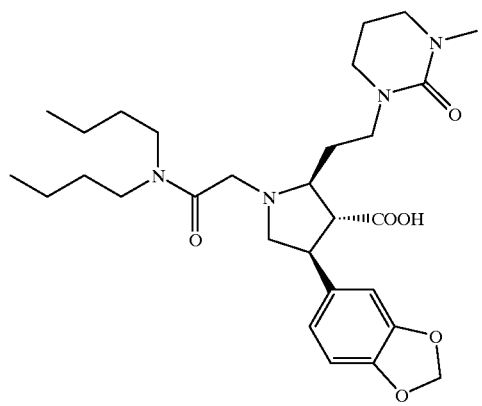
482
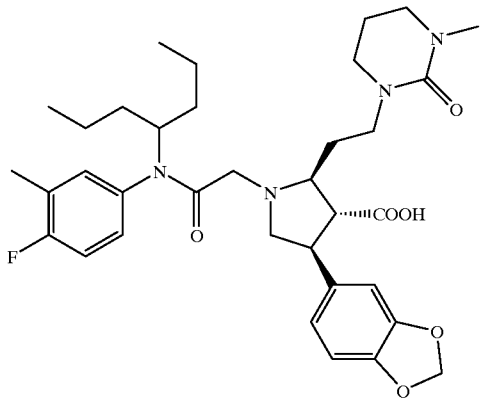

TABLE 3C-continued
483
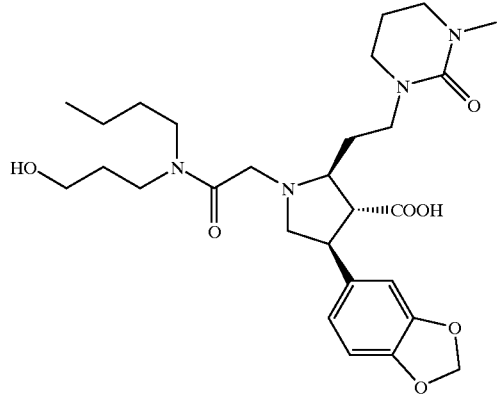
484
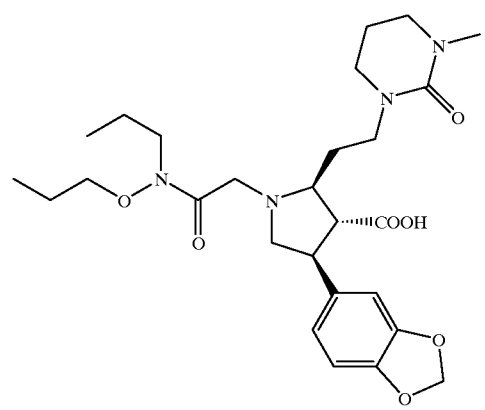
485
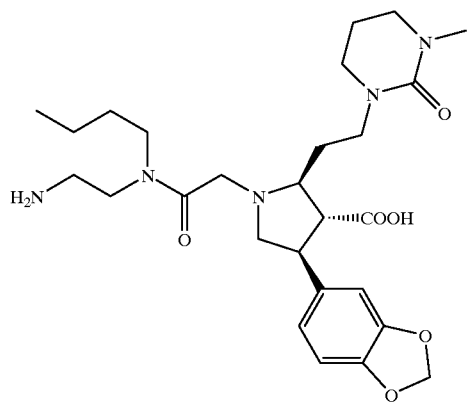

TABLE 3C-continued
486
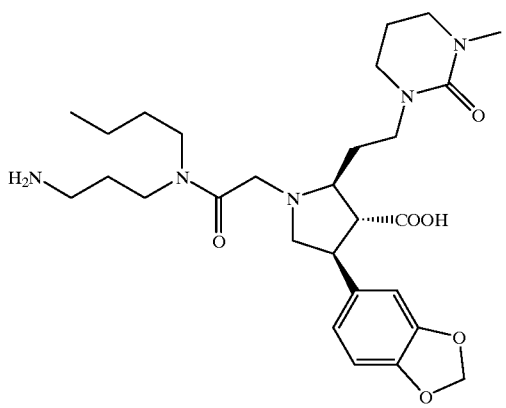
487
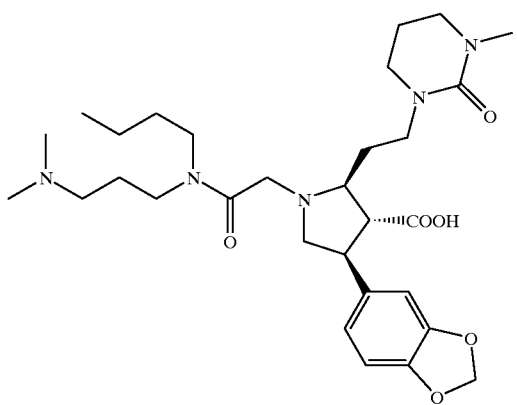
488
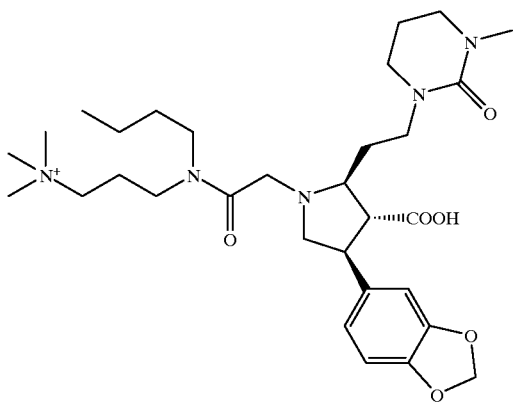

TABLE 3C-continued
489
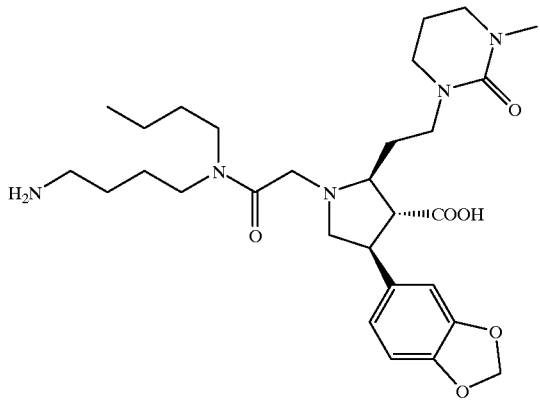
490
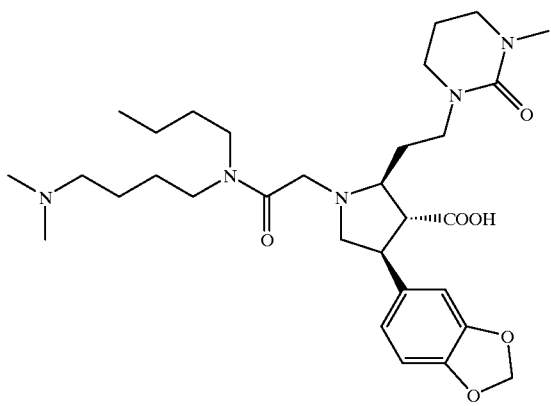
491
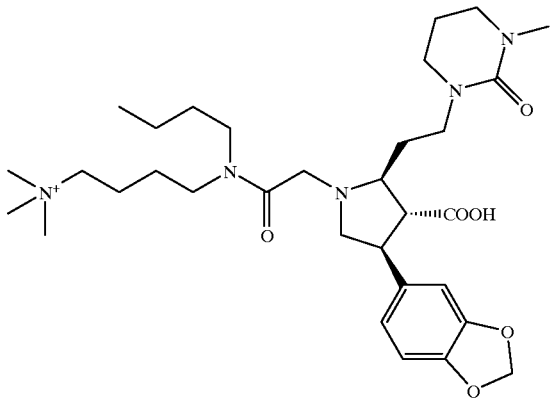

TABLE 3C-continued
492
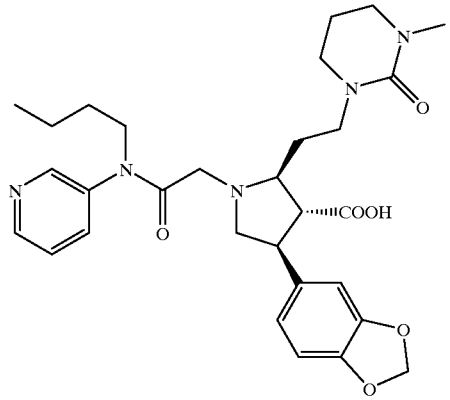
493
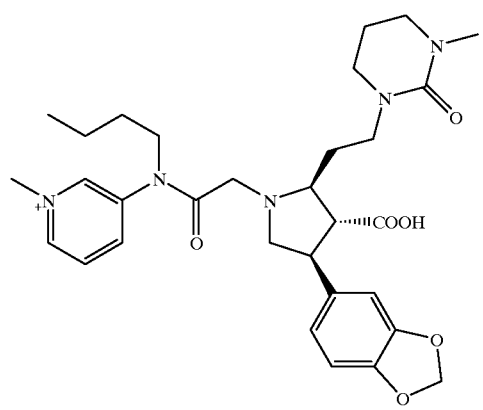
494
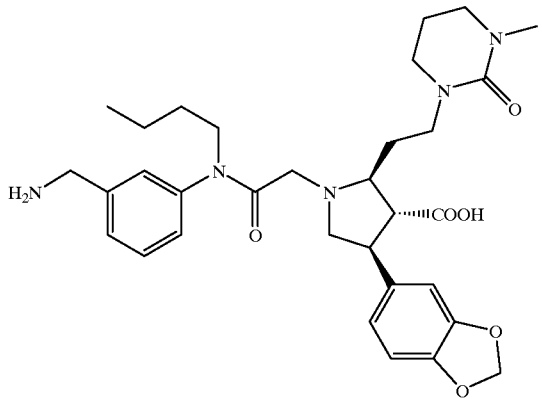

TABLE 3C-continued
495
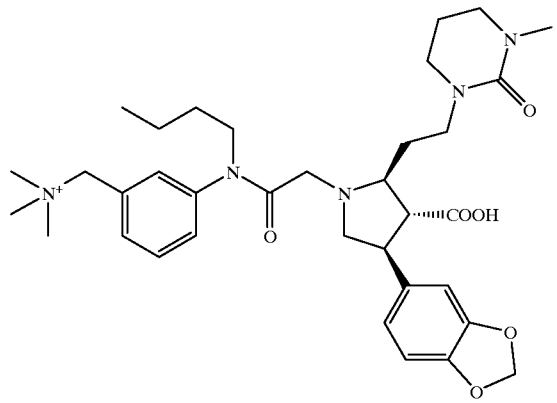
496
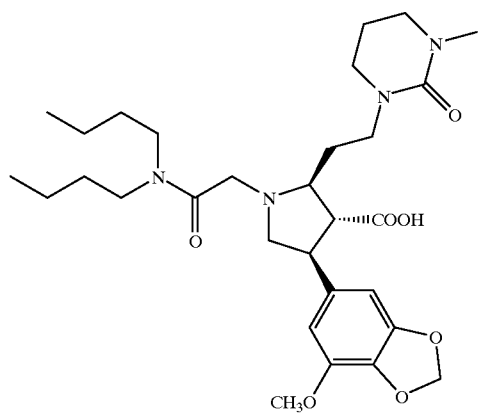
497
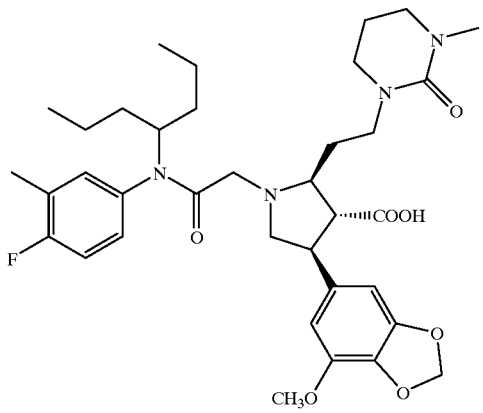

TABLE 3C-continued
498
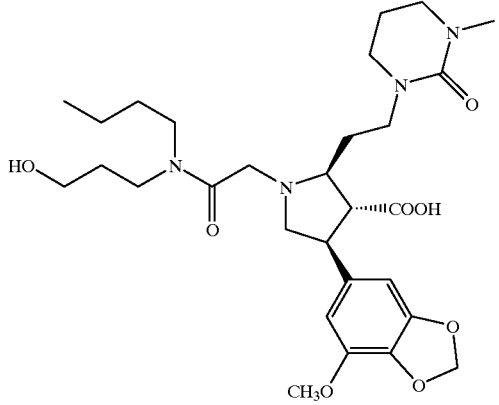
499
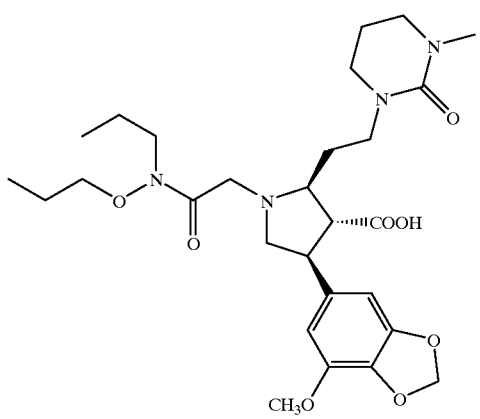
500
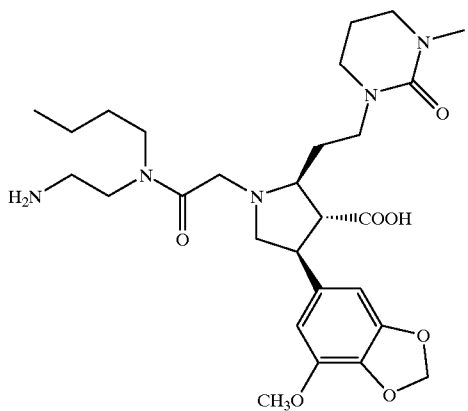

TABLE 3C-continued
501
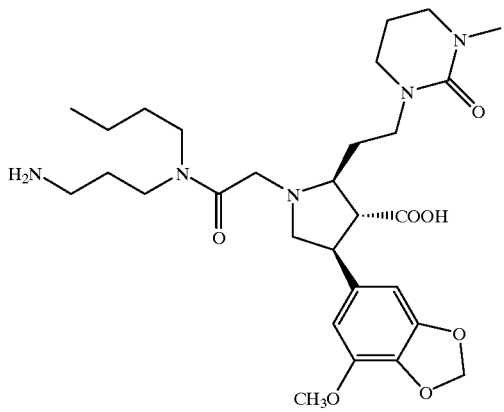
502
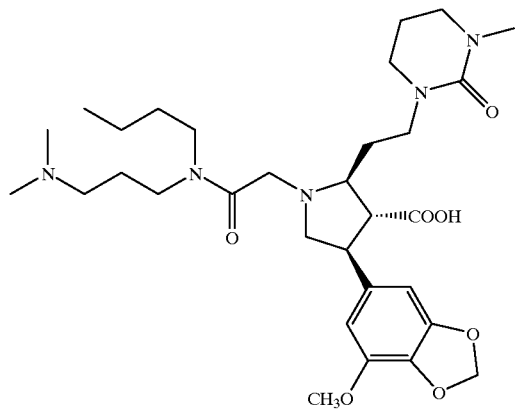
503
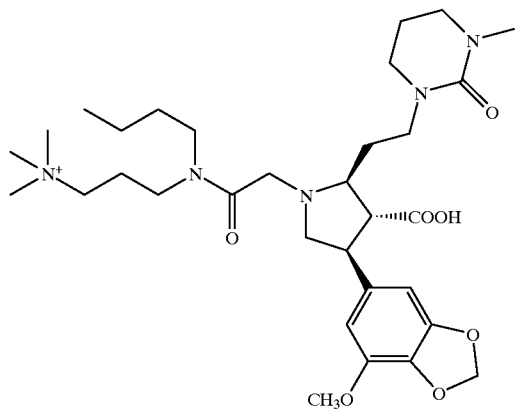

TABLE 3C-continued
504
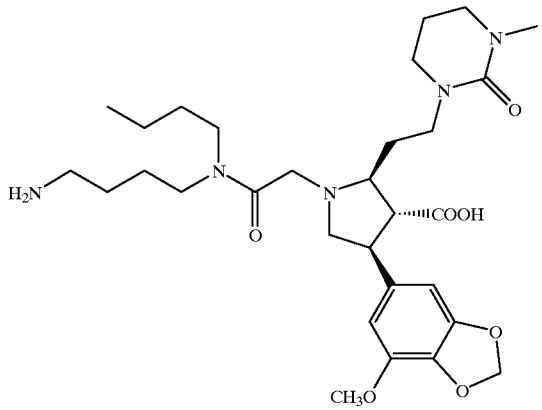
505
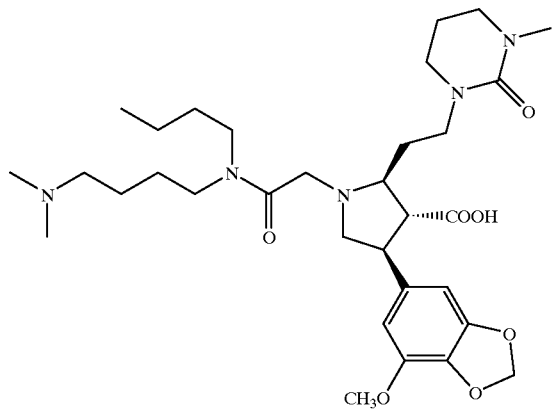
506
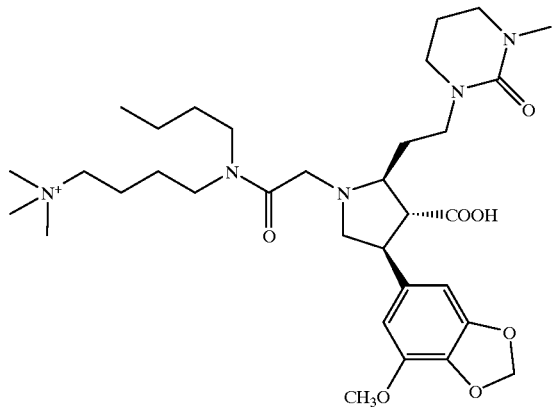

TABLE 3C-continued
507
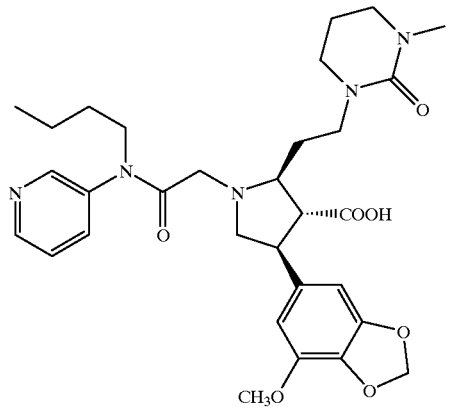
508
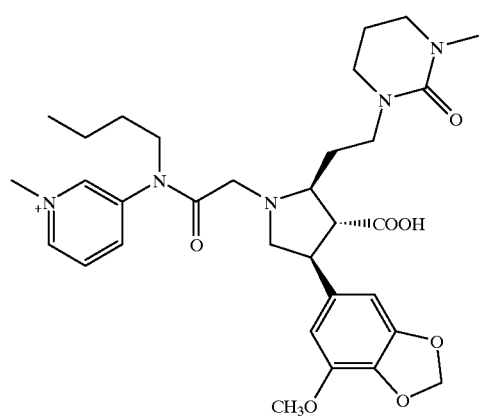
509
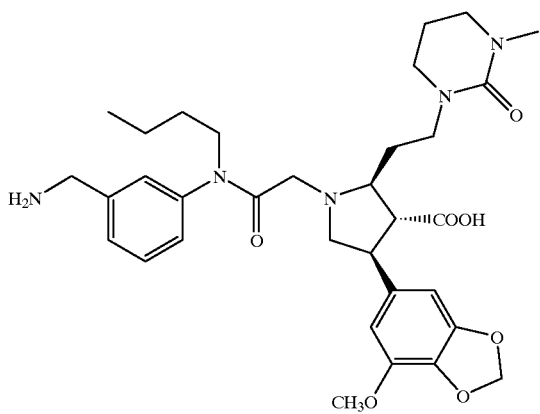

TABLE 3C-continued
510
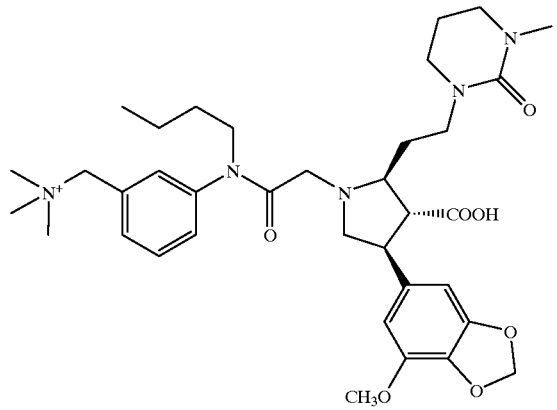
511
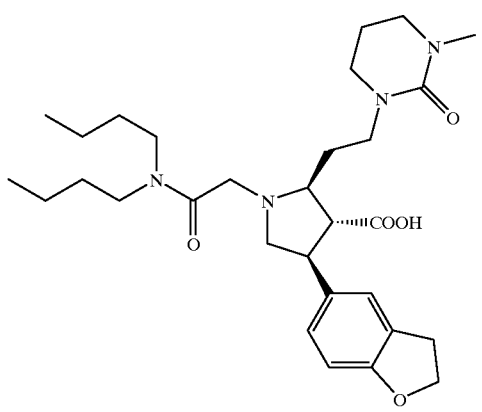
512
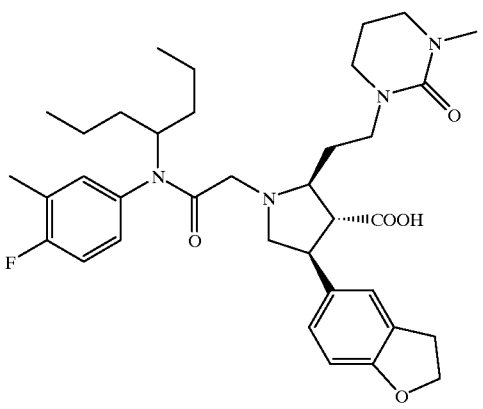

TABLE 3C-continued
513
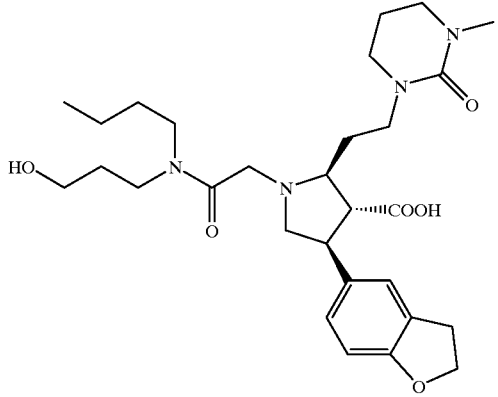
514
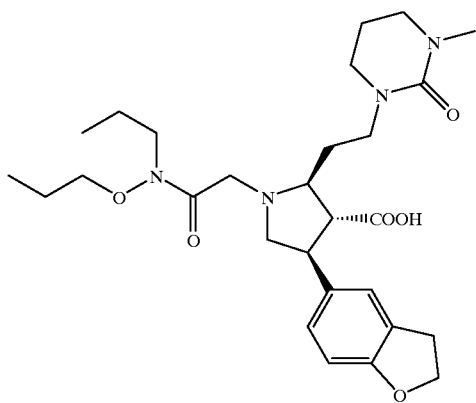
515
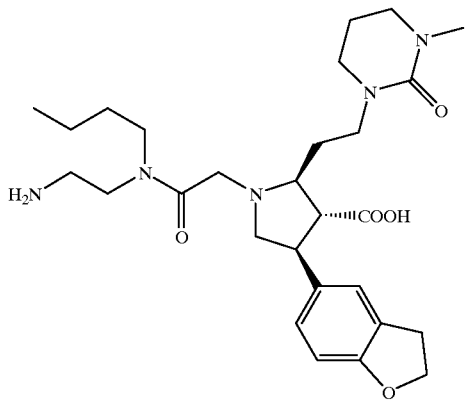

TABLE 3C-continued
516
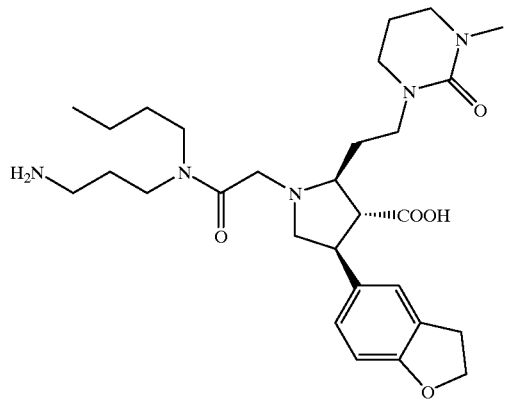
517
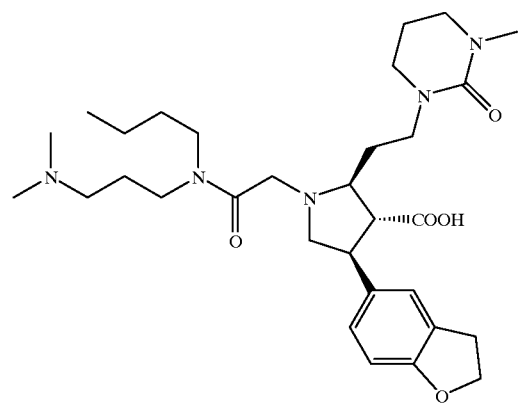
518
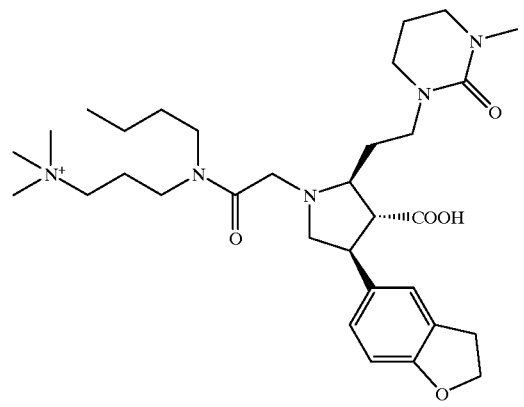

TABLE 3C-continued
519
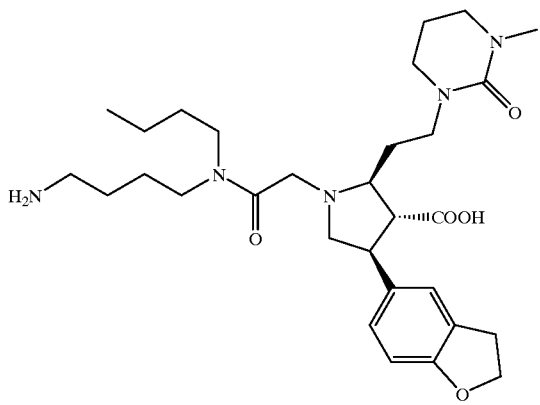
520
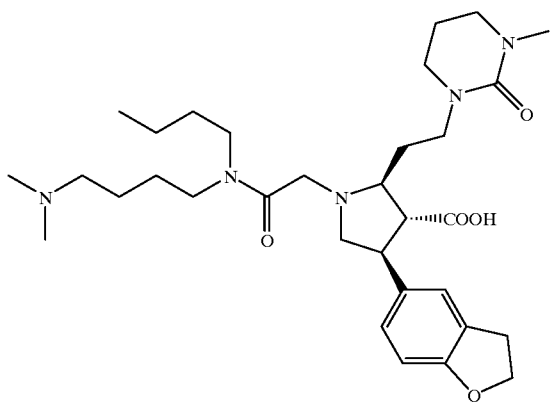
521
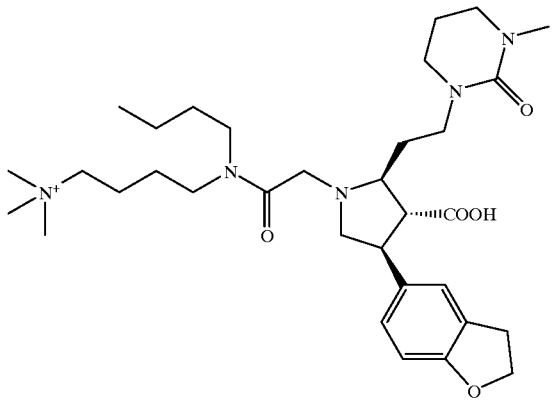

TABLE 3C-continued
522
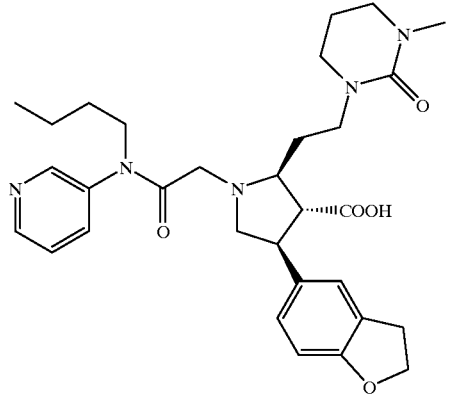
523
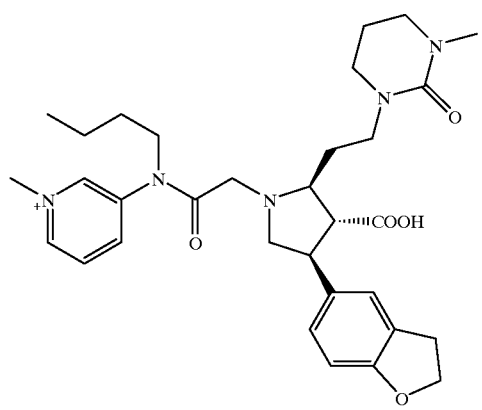
524
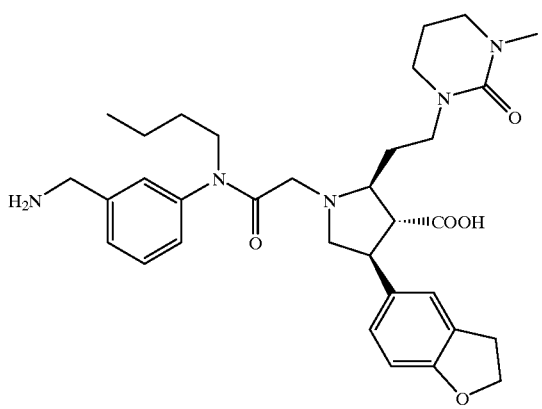

TABLE 3C-continued
525
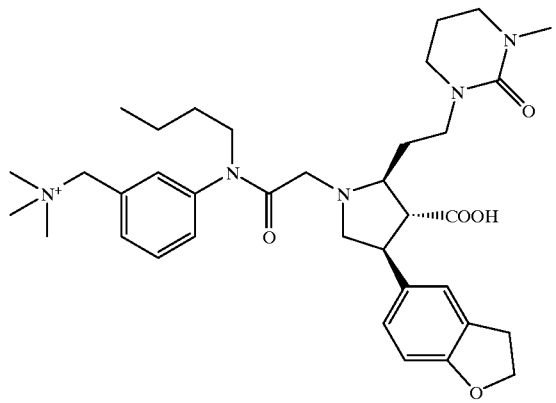
526
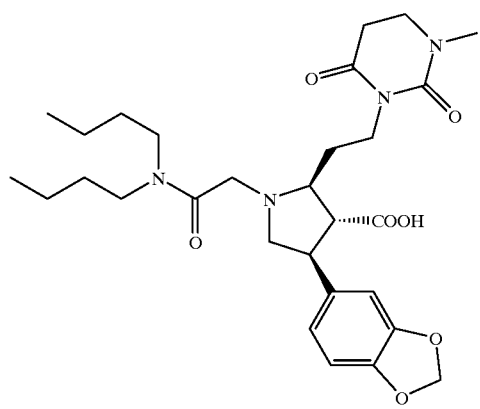
527
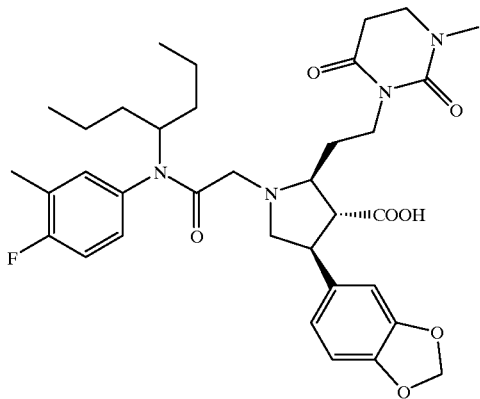

TABLE 3C-continued
528
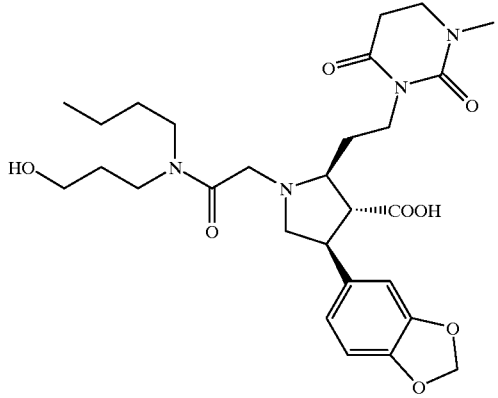
529
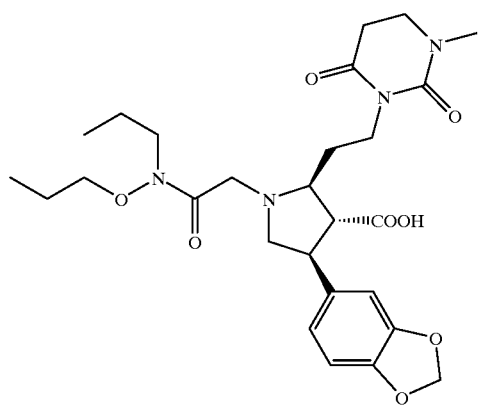
530
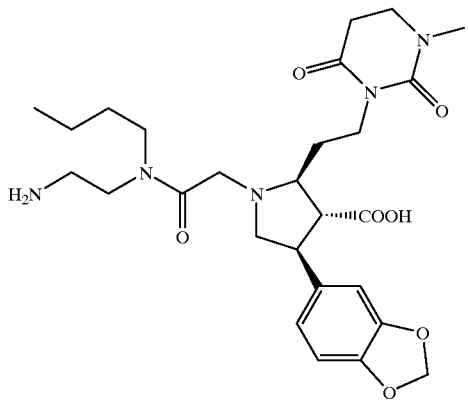

TABLE 3C-continued
531 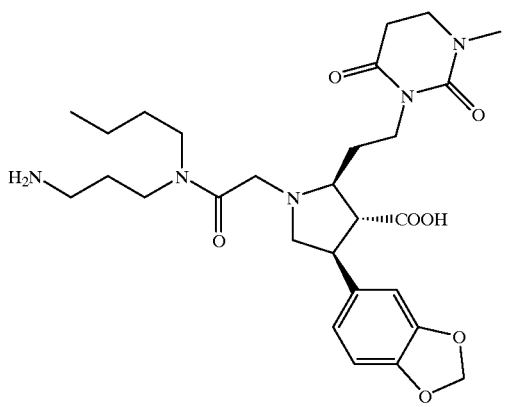
532 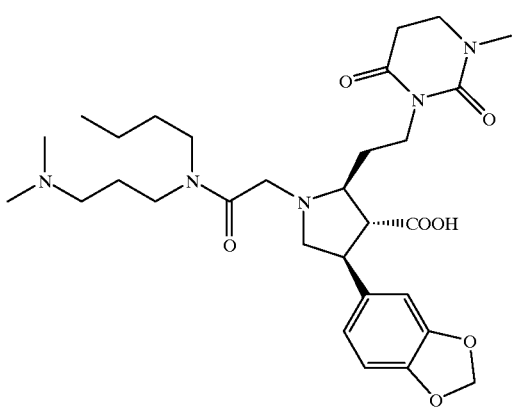
533 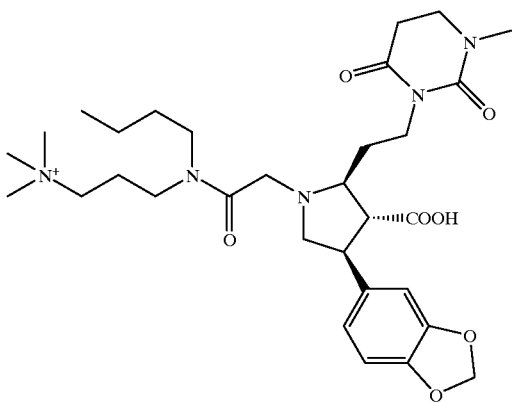

TABLE 3C-continued
534
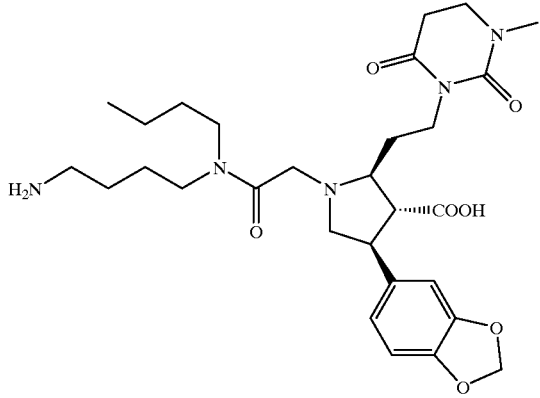
535
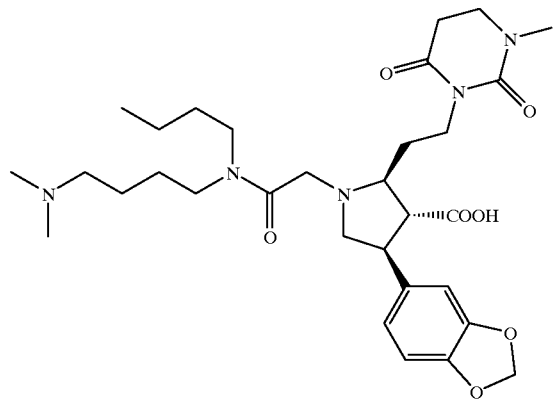
536
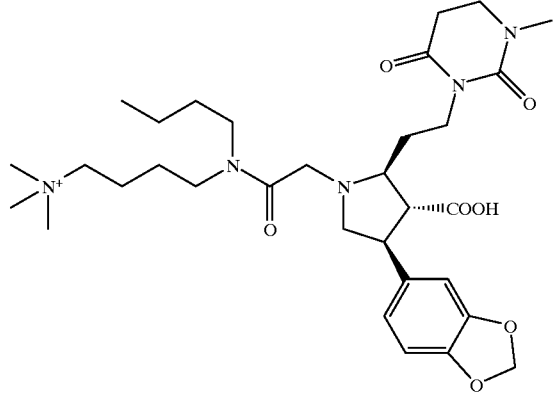

TABLE 3C-continued
537
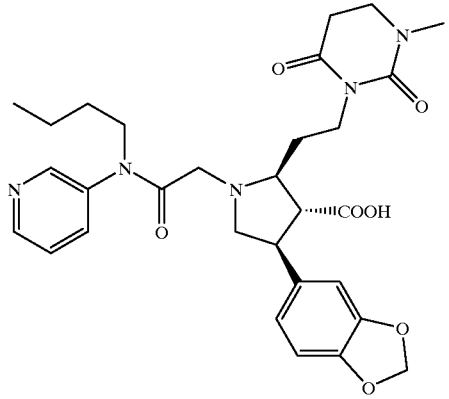
538
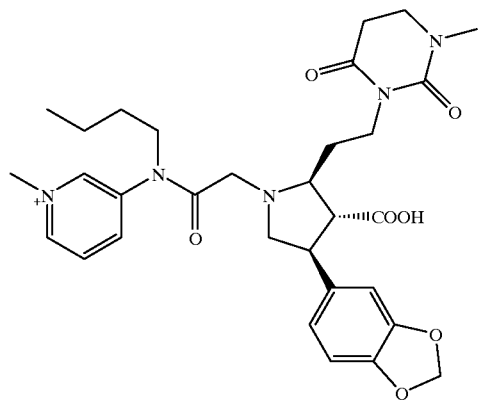
539
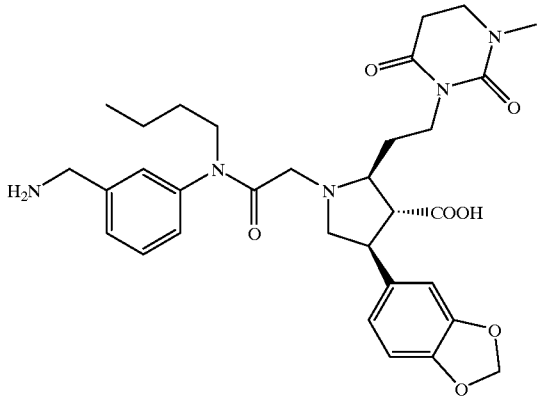

TABLE 3C-continued
540
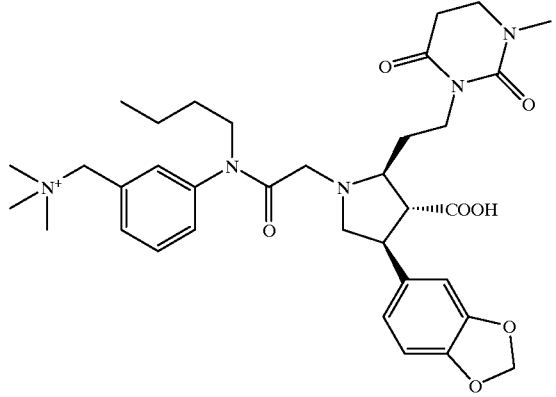
541
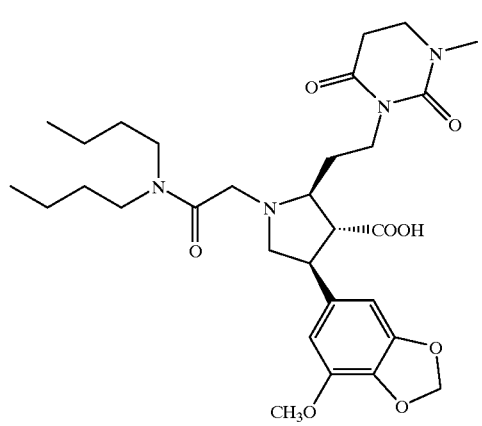
542
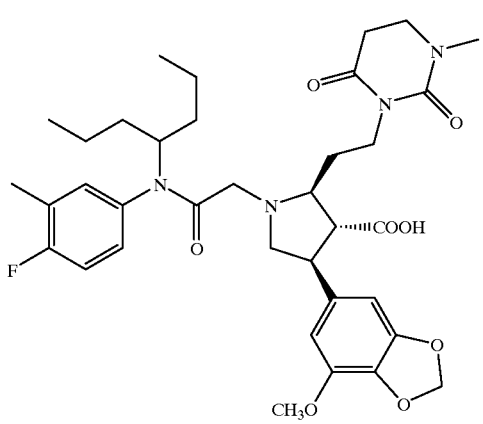

TABLE 3C-continued
543
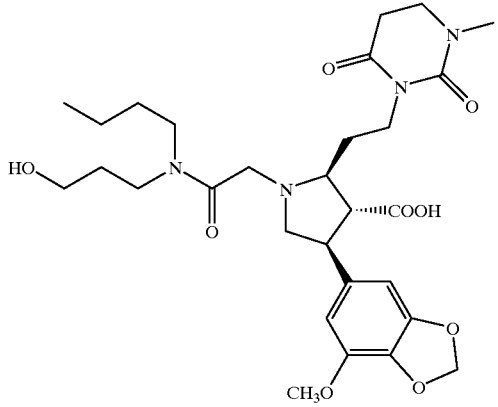
544
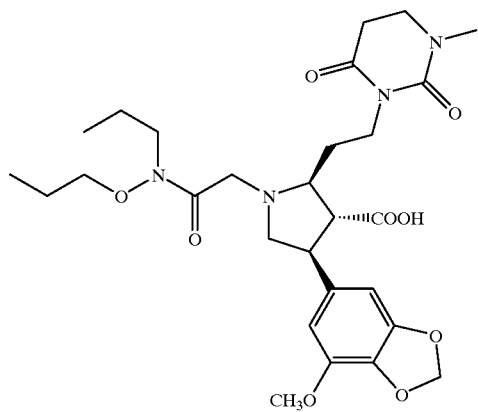
545
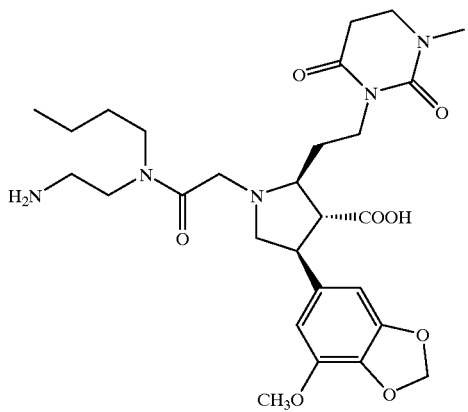

TABLE 3C-continued
546
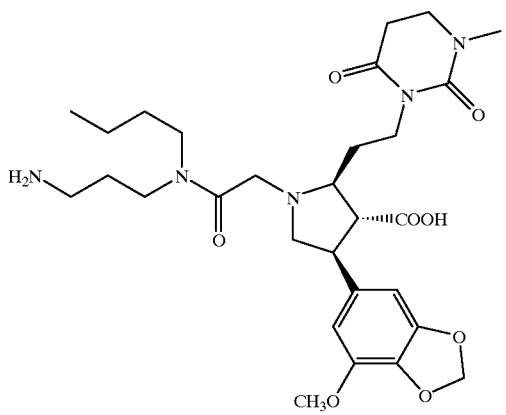
547
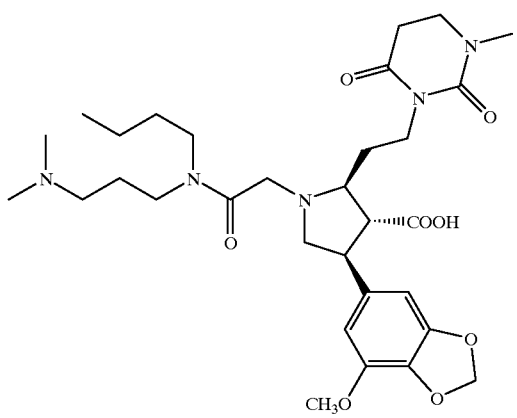
548
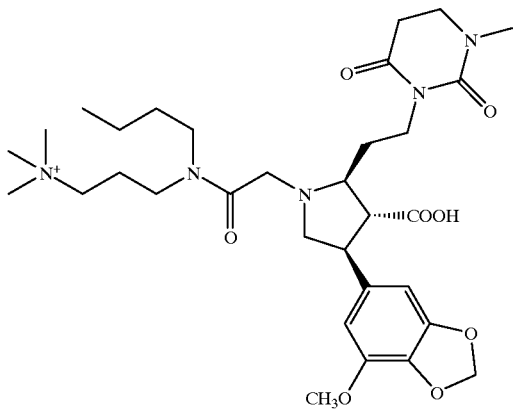

TABLE 3C-continued
549
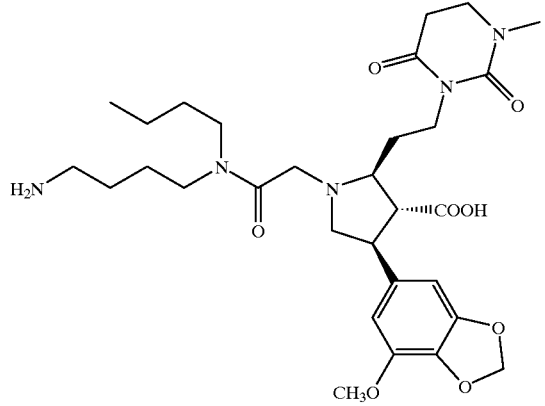
550
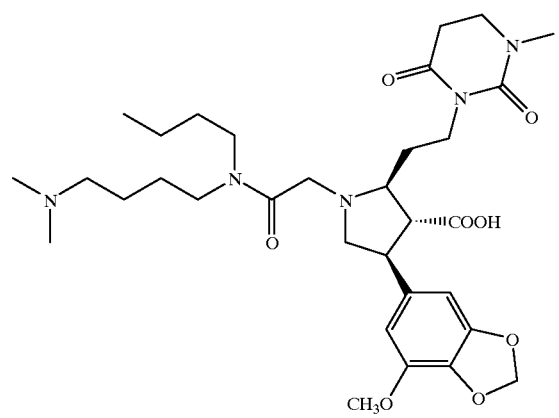
551
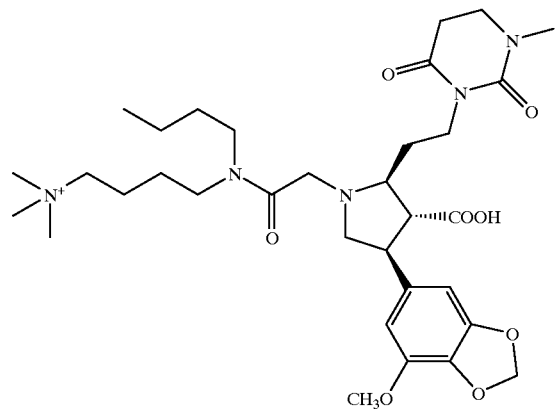

TABLE 3C-continued
552
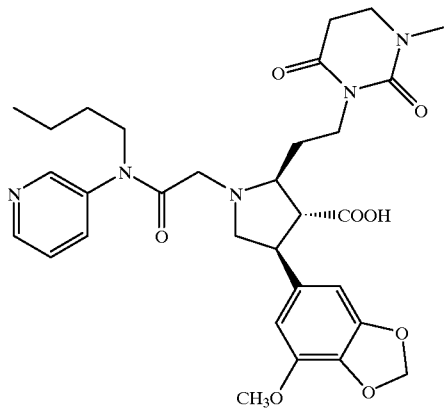
553
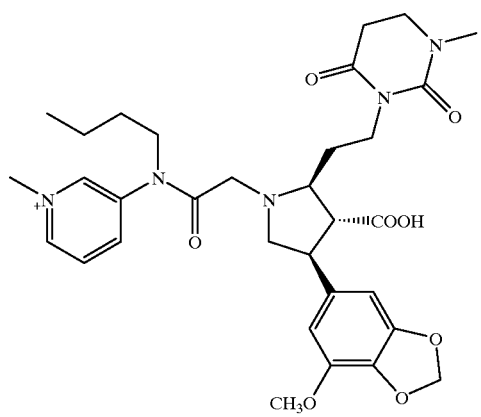
554
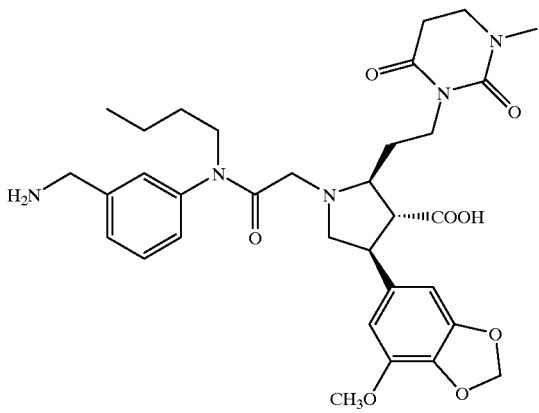

TABLE 3C-continued
555
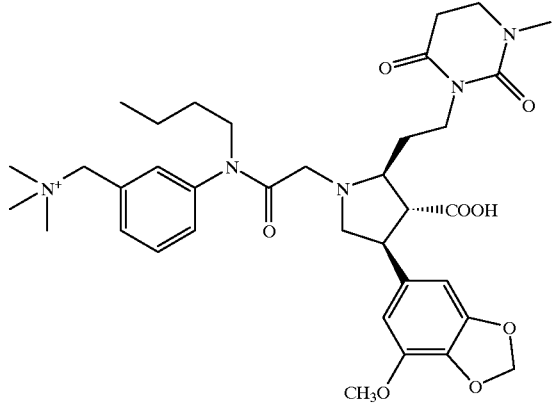
556
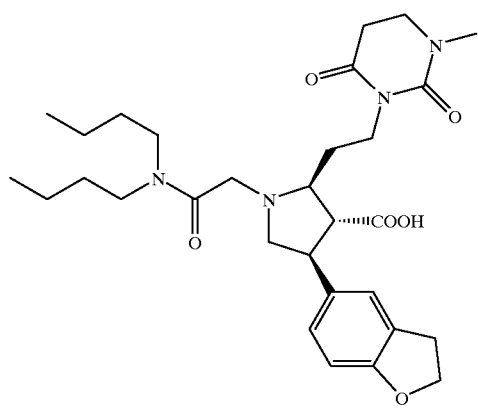
557
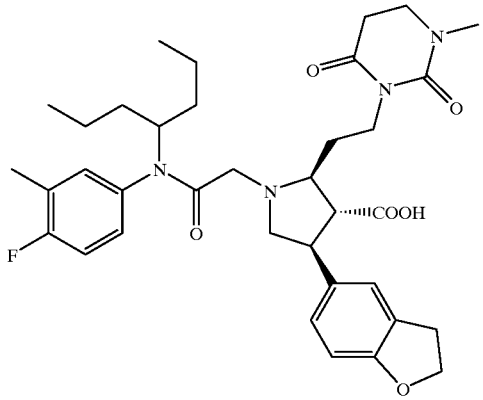

TABLE 3C-continued
558
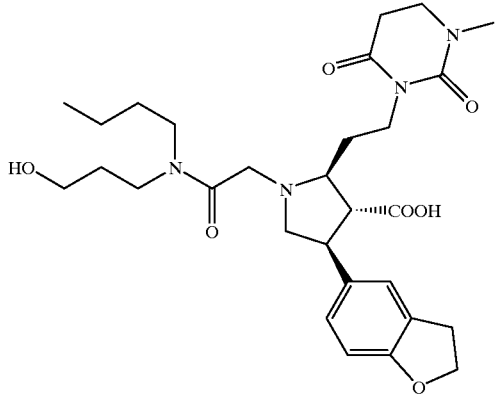
559
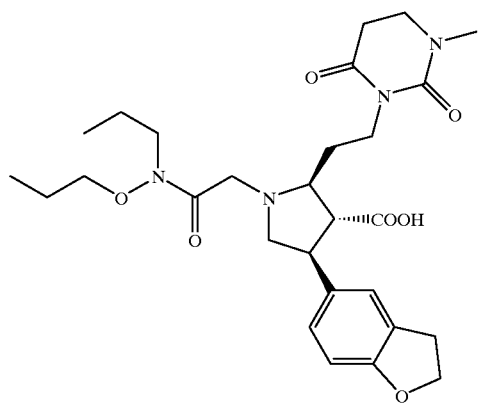
560
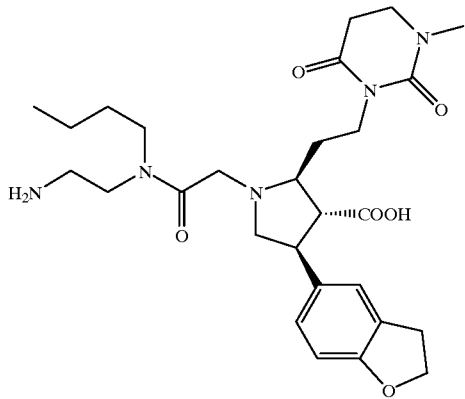

TABLE 3C-continued
561
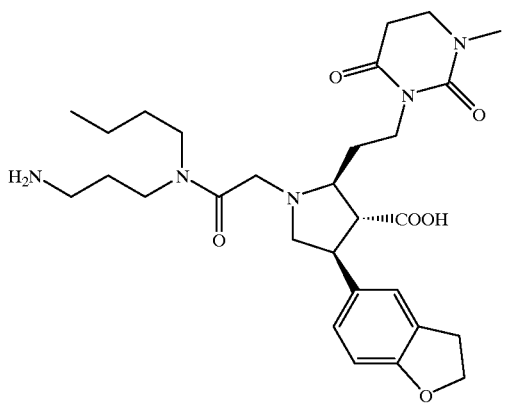
562
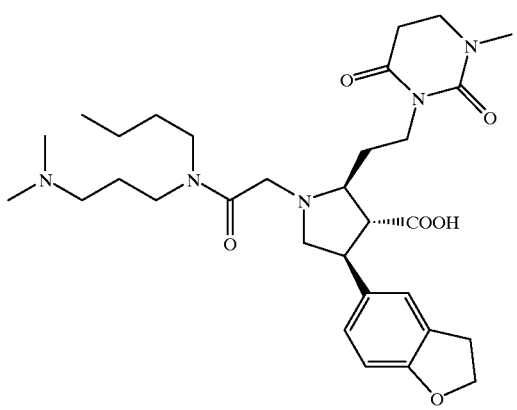
563
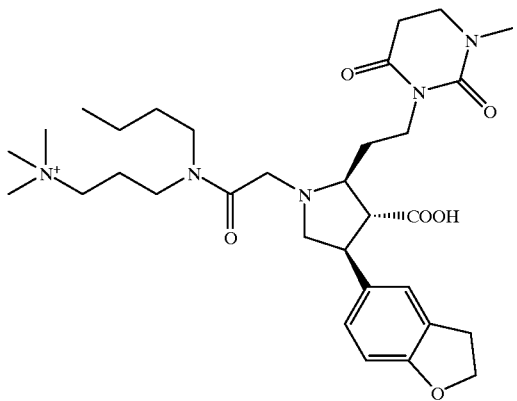

TABLE 3C-continued
564
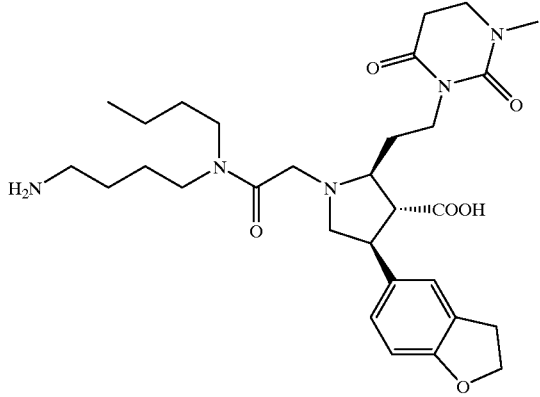
565
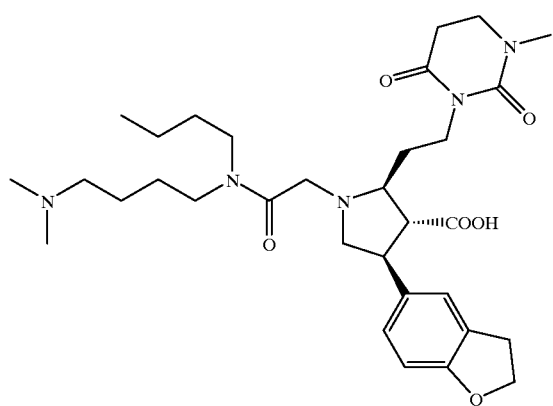
566
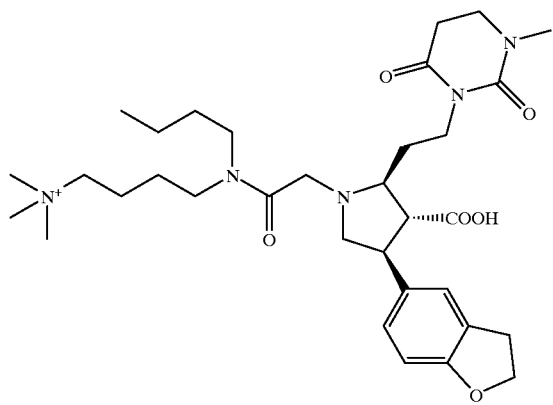

TABLE 3C-continued
567
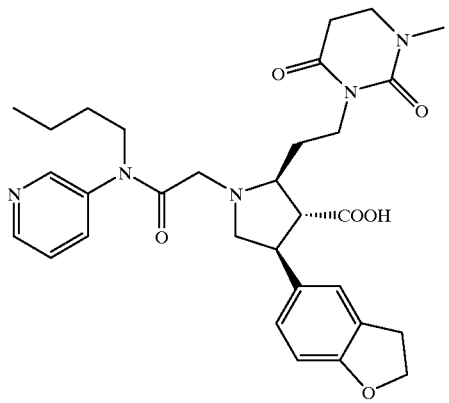
568
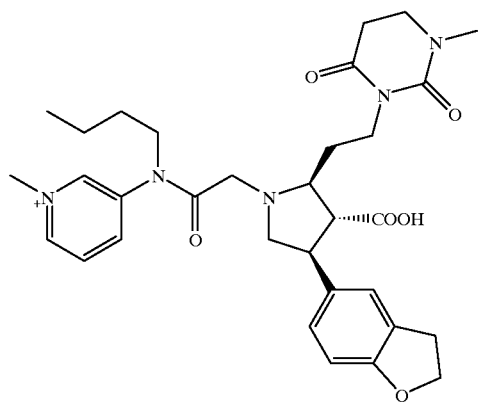
569
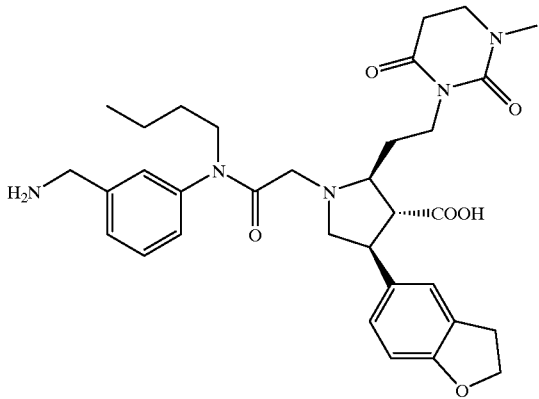

TABLE 3C-continued
570
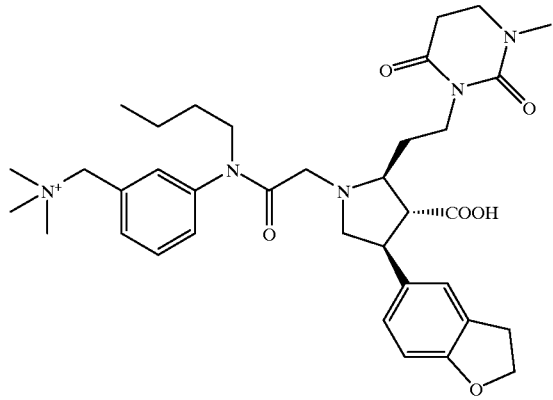
571
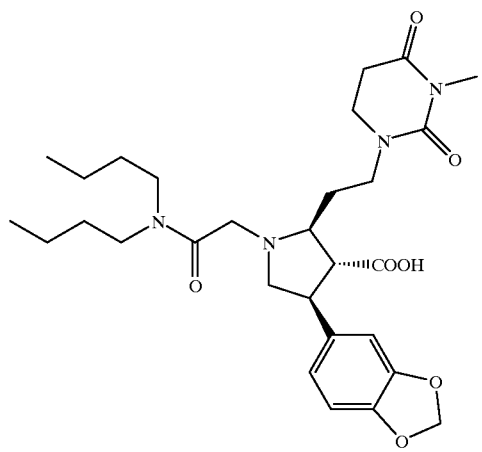
572
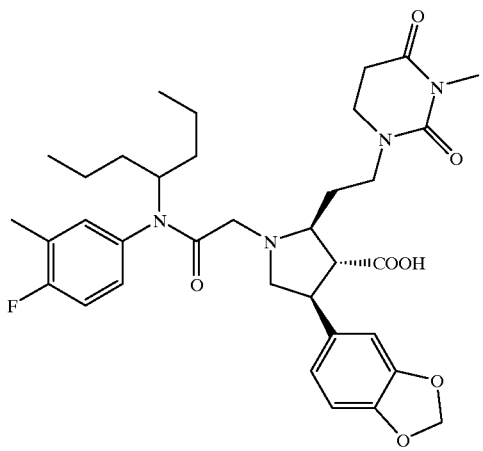

TABLE 3C-continued
573
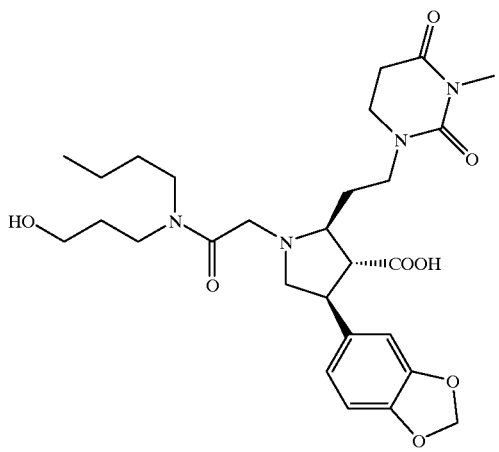
574
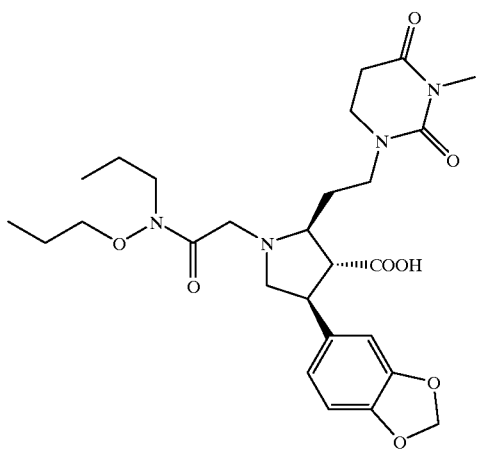
575
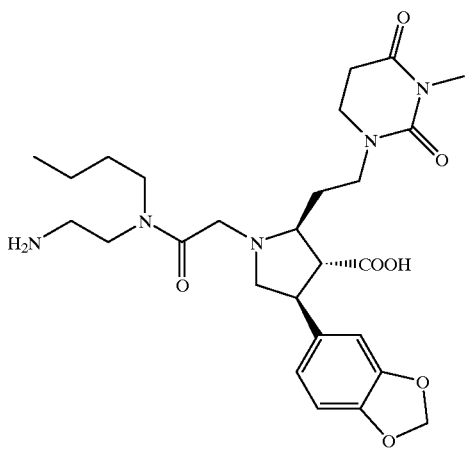

TABLE 3C-continued
576
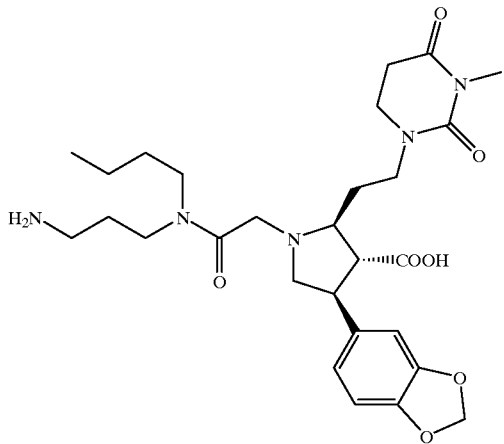
577
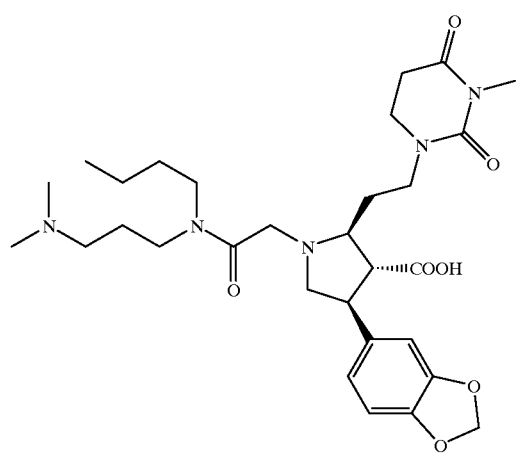
578
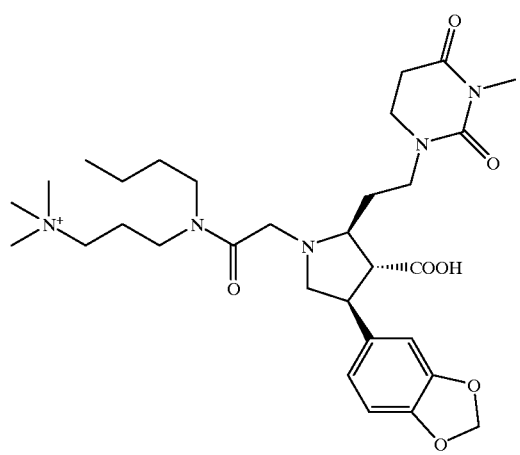

TABLE 3C-continued
579
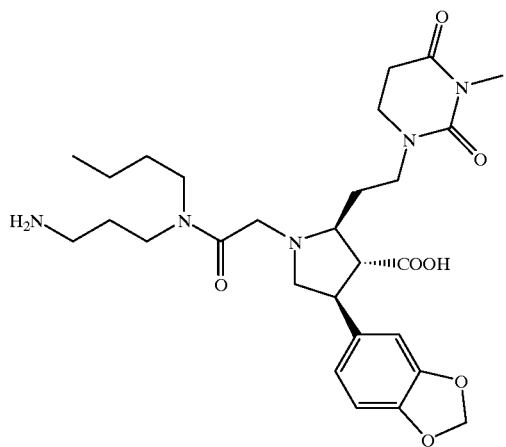
580
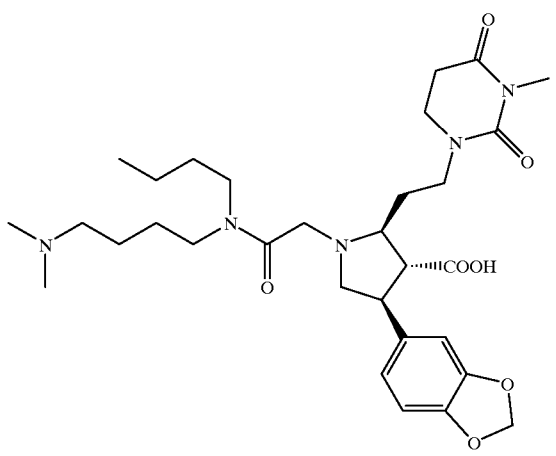
581
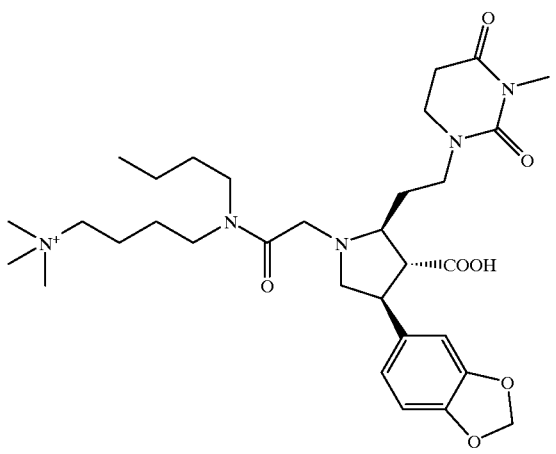

TABLE 3C-continued
582
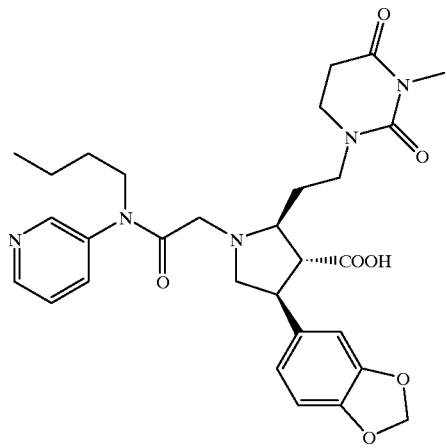
583
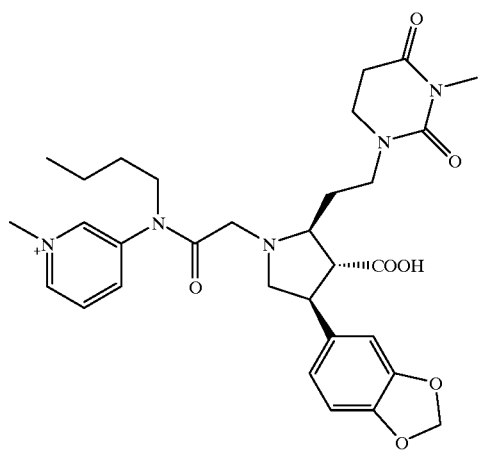
584
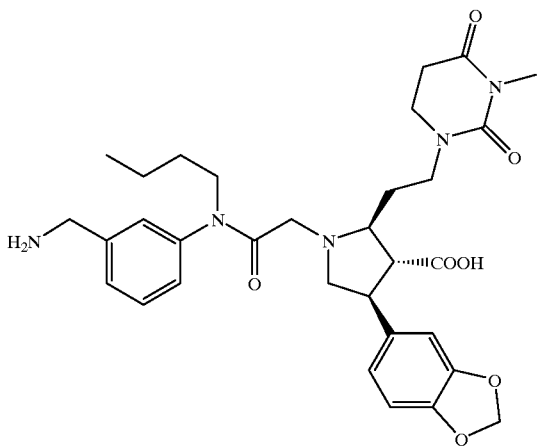

TABLE 3C-continued
585
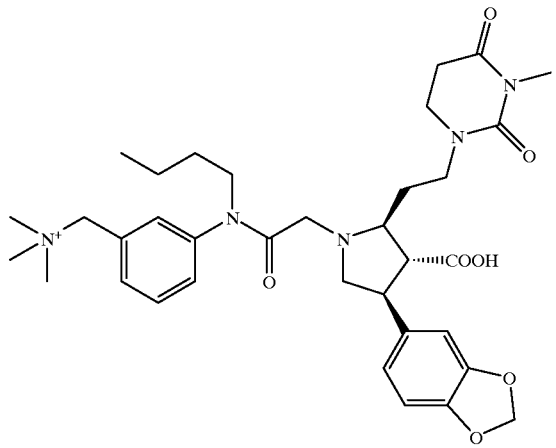
586
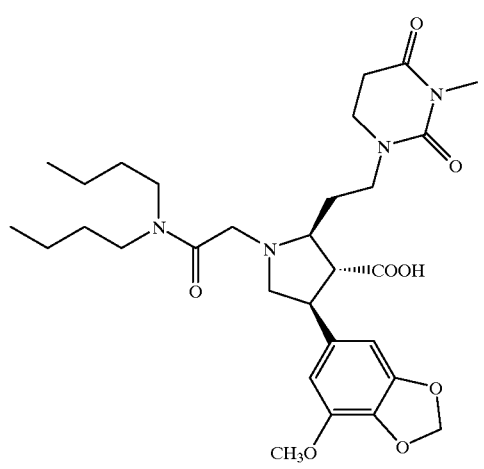
587
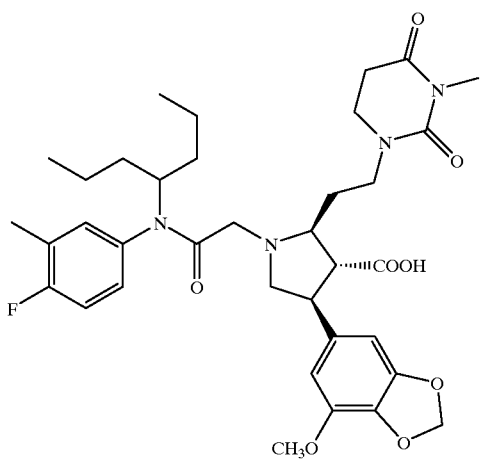

TABLE 3C-continued
588
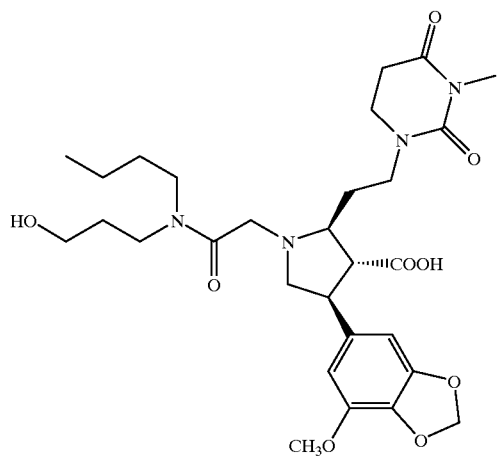
589
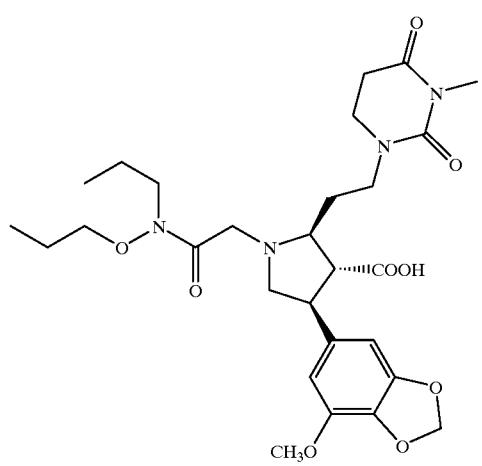
590
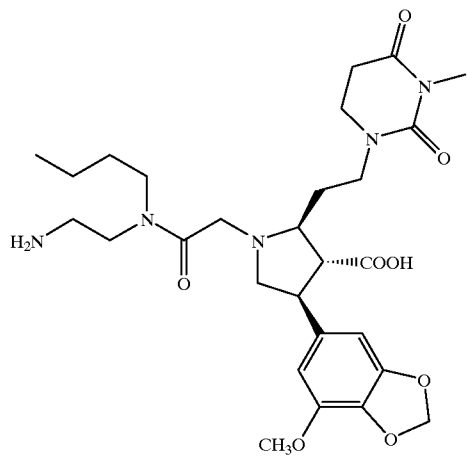

TABLE 3C-continued
591
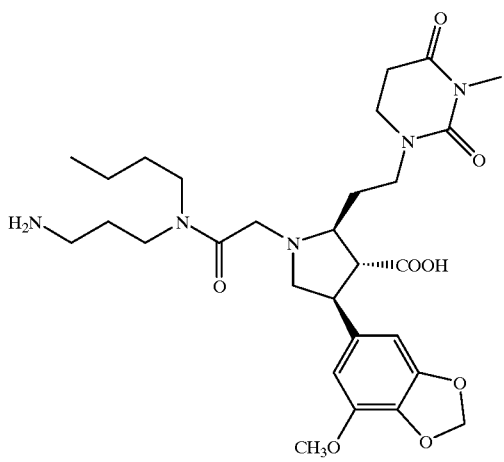
592
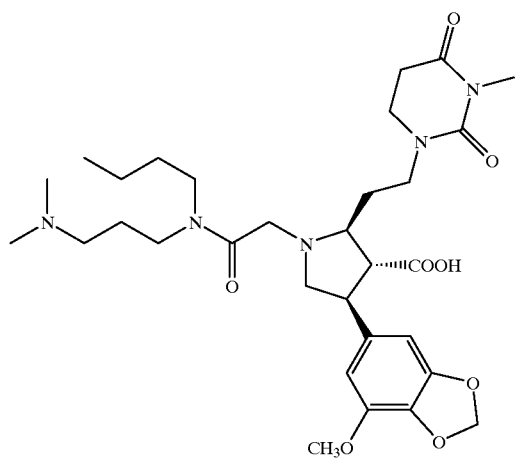
593
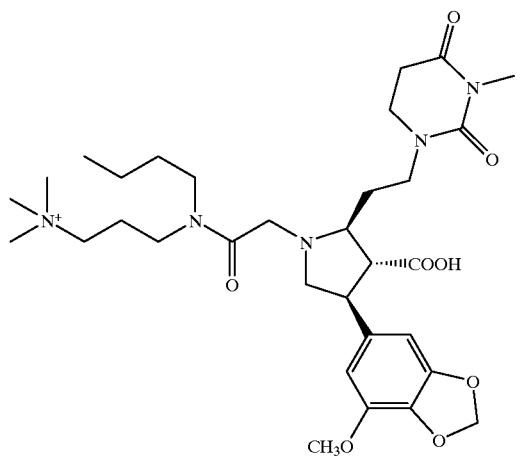

TABLE 3C-continued
594
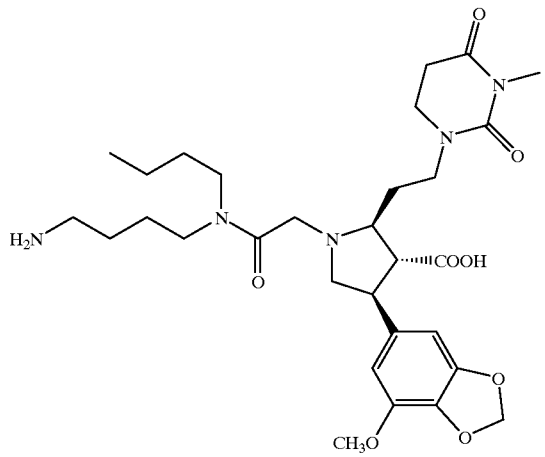
595
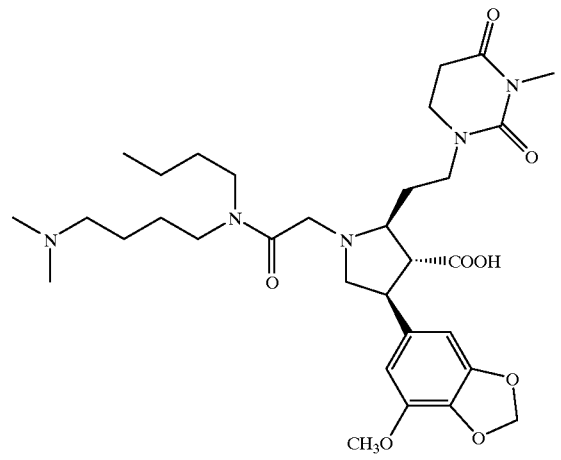
596
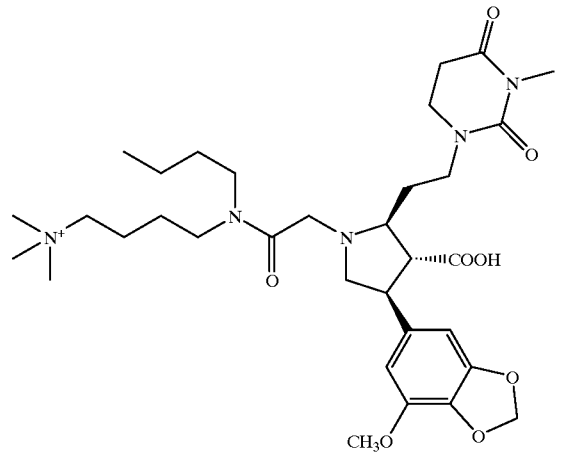

TABLE 3C-continued
597
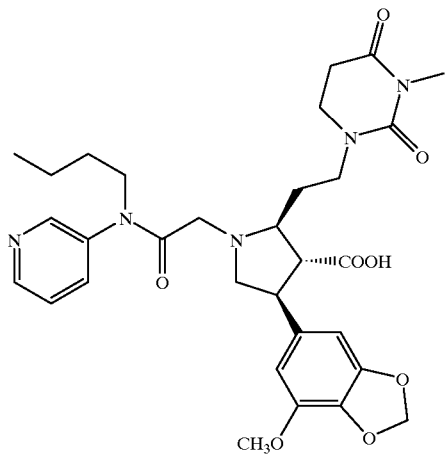
598
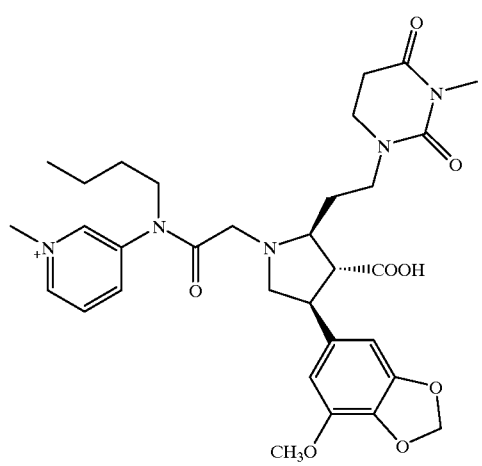
599
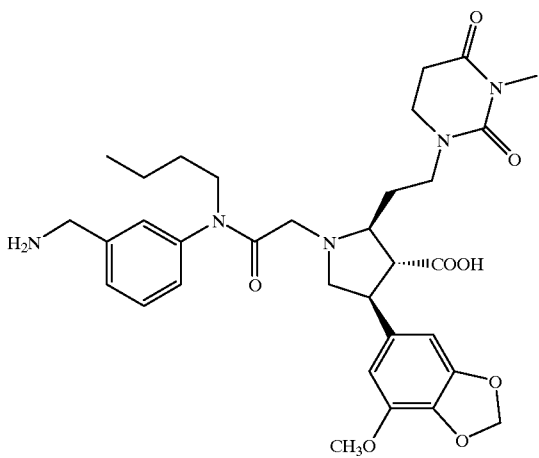

TABLE 3C-continued
600
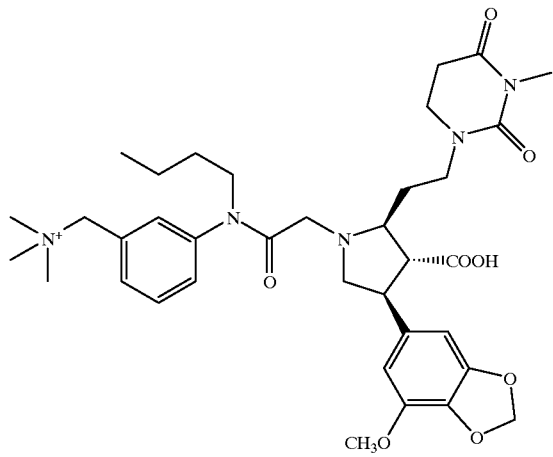
601
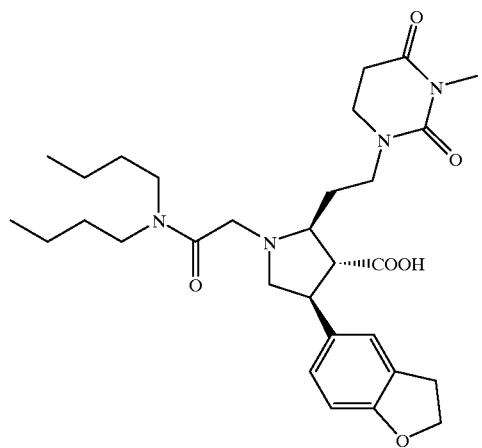
602
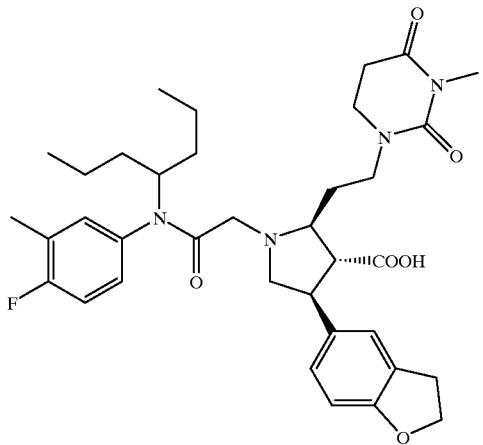

TABLE 3C-continued
603
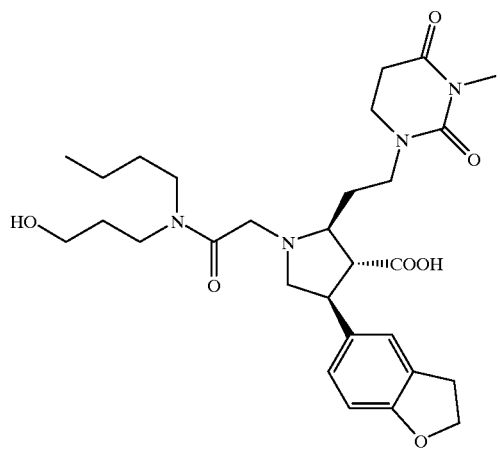
604
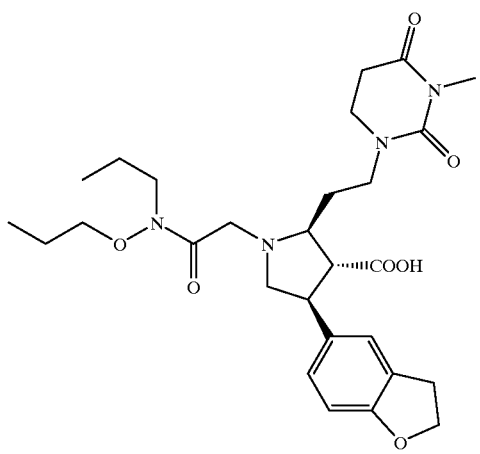
605
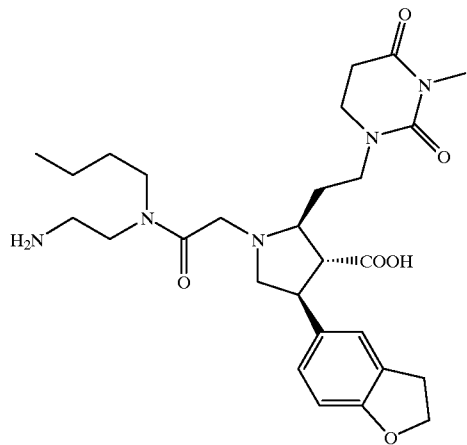

TABLE 3C-continued
606
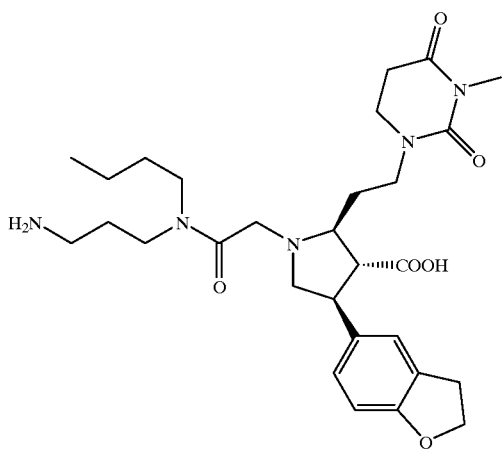
607
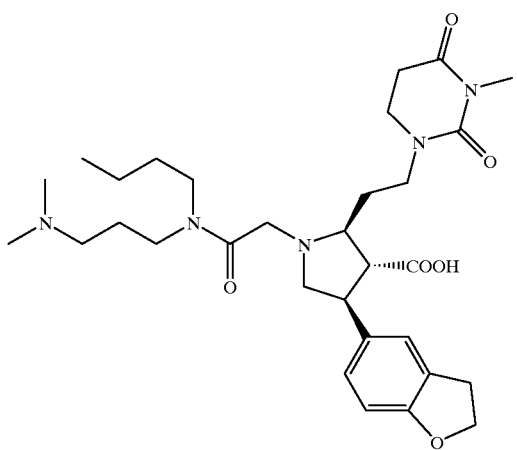
608
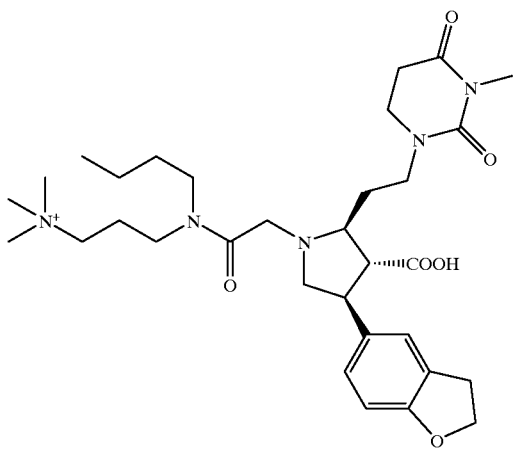

TABLE 3C-continued
609
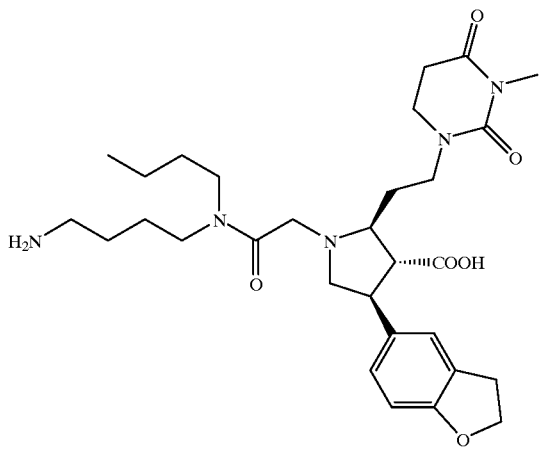
610
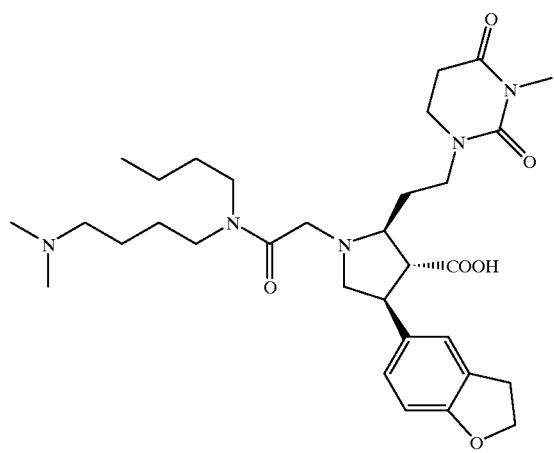
611
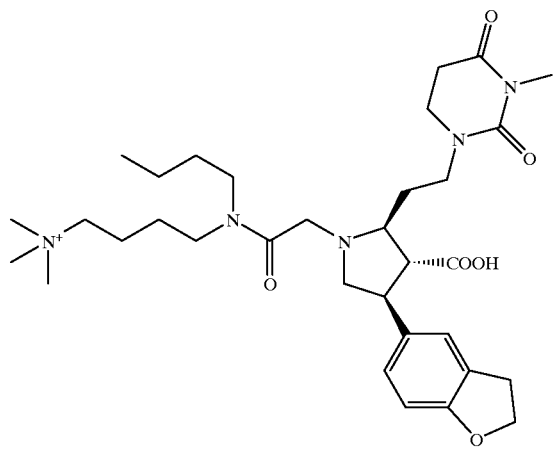

TABLE 3C-continued
612
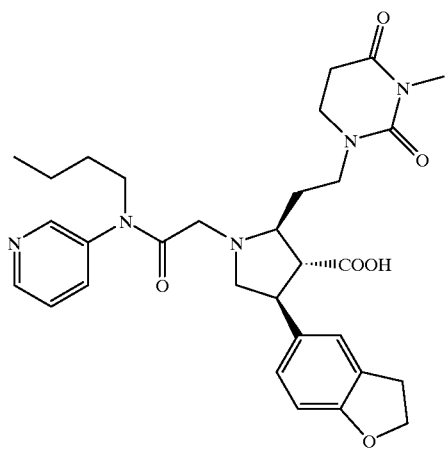
613
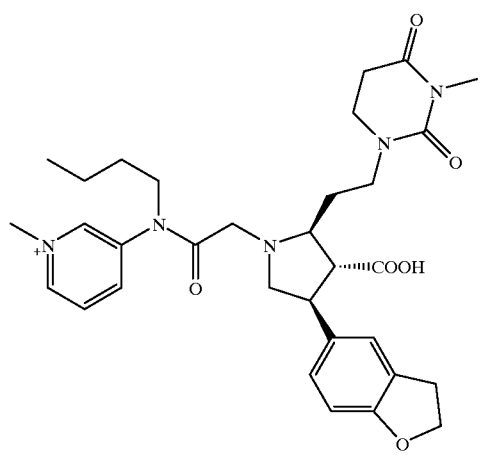
614
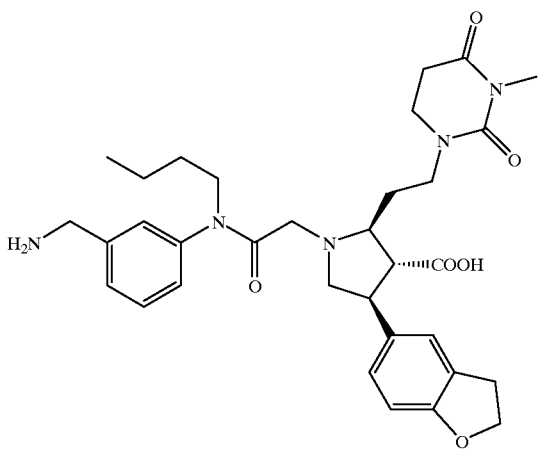

TABLE 3C-continued
615
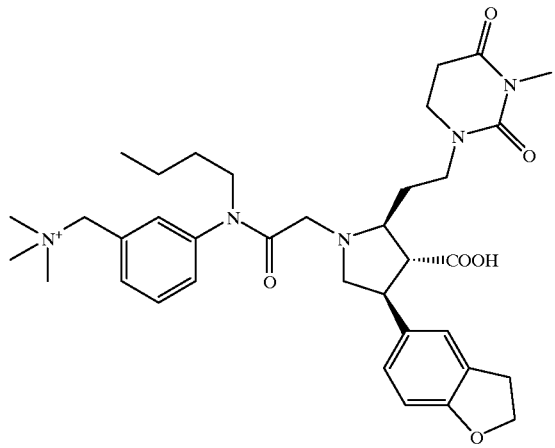
616
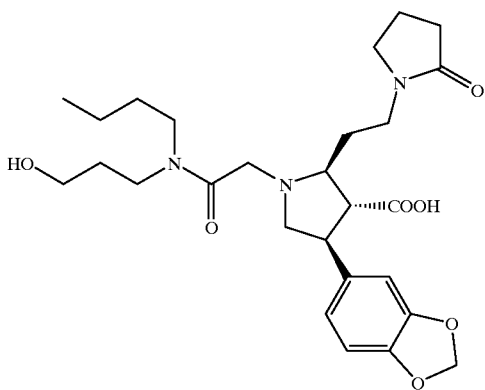
617
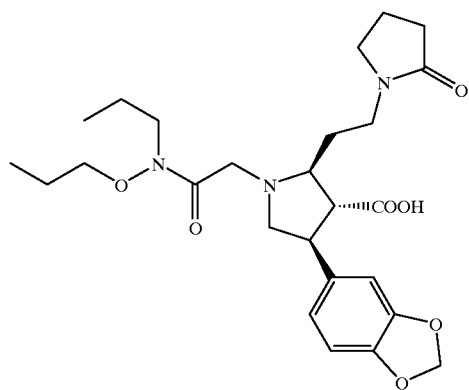

TABLE 3C-continued
618
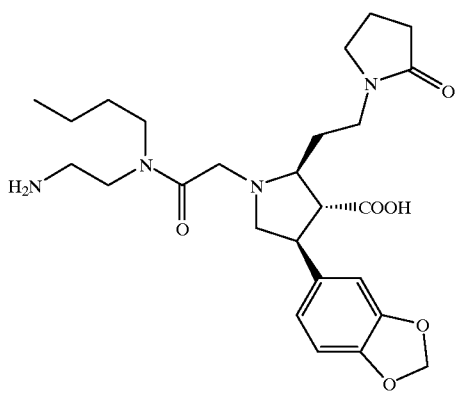
619
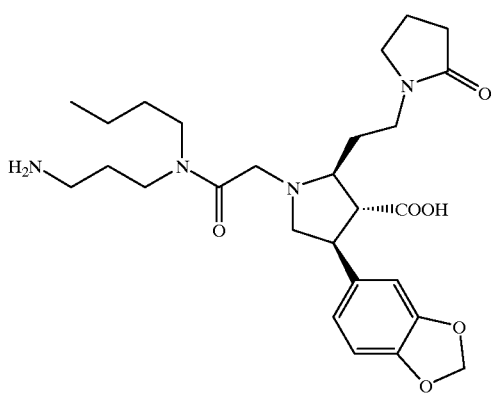
620
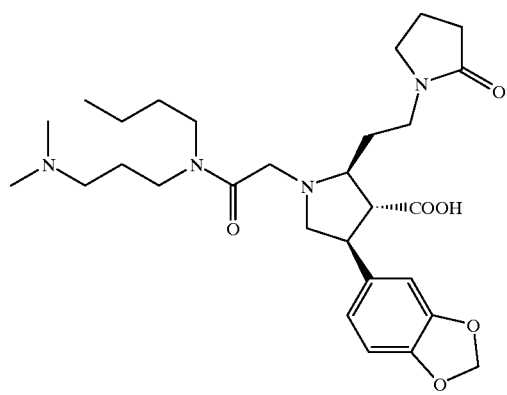
621
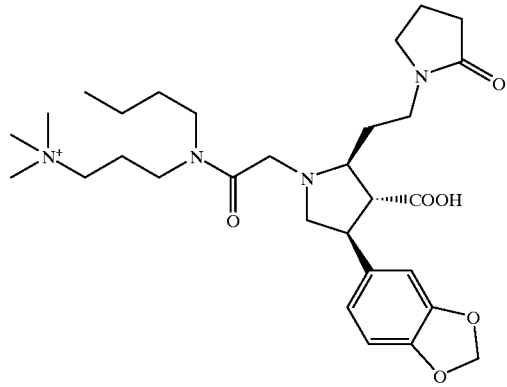

TABLE 3C-continued
622
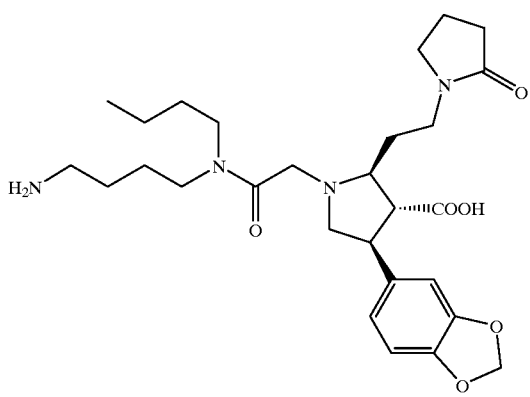
623
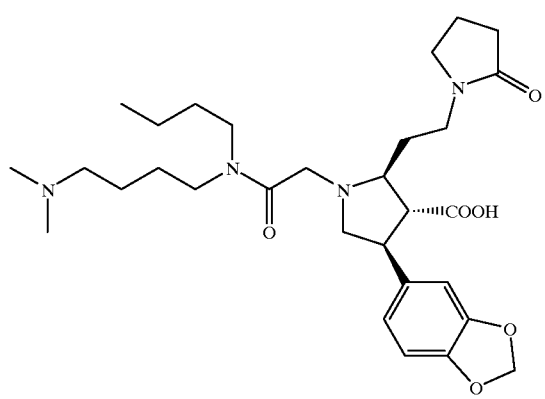
624
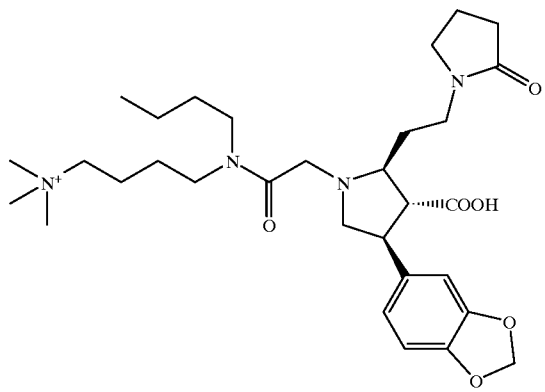
625
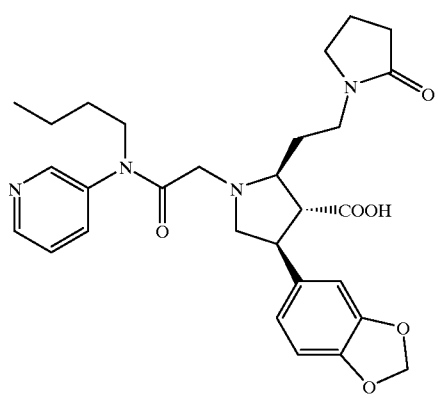

TABLE 3C-continued
626
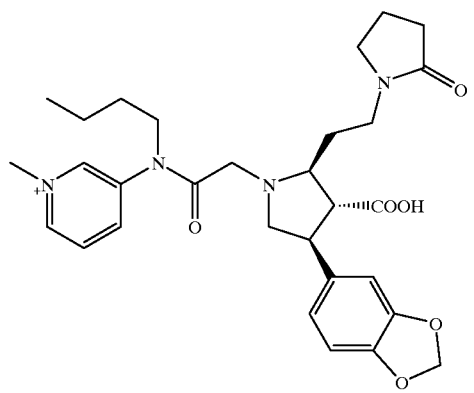
627
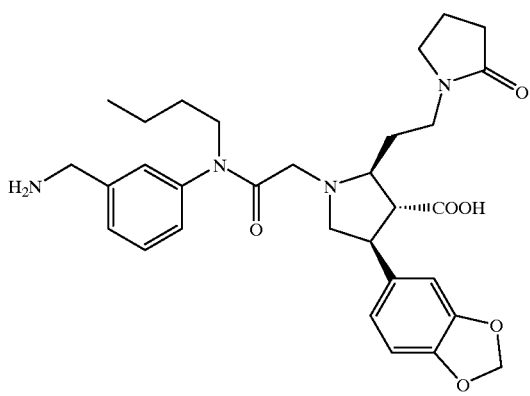
628
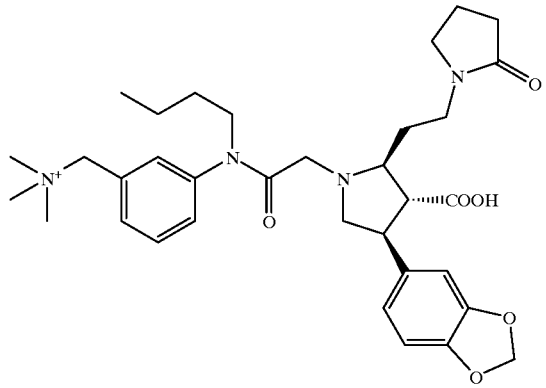
629
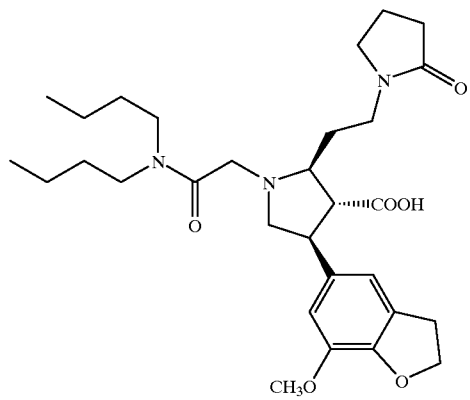

TABLE 3C-continued
630
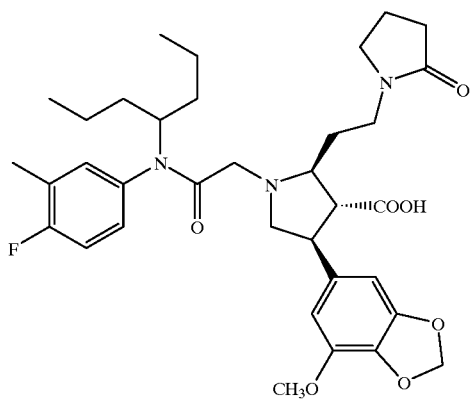
631
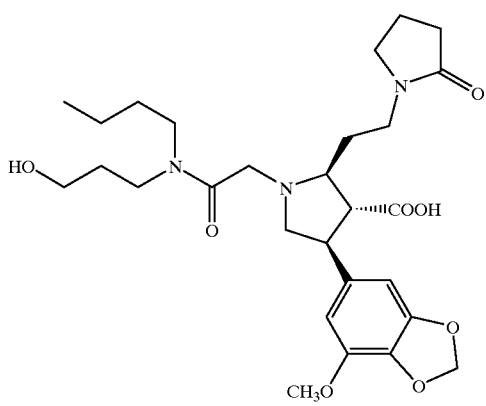
632
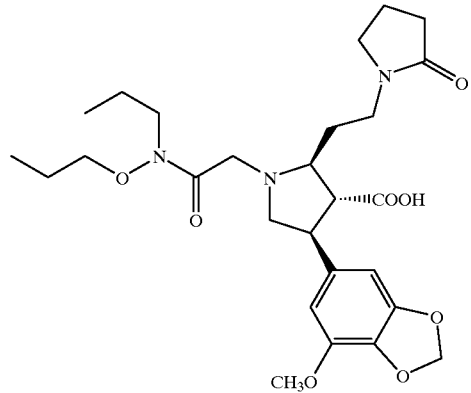

TABLE 3C-continued
633
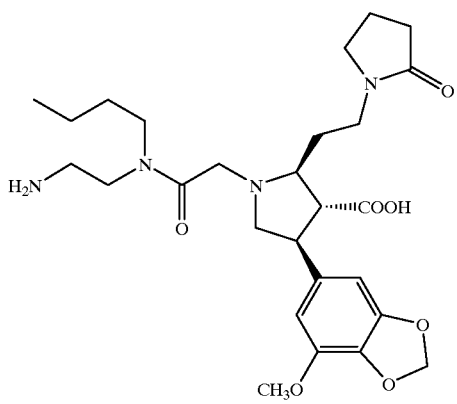
634
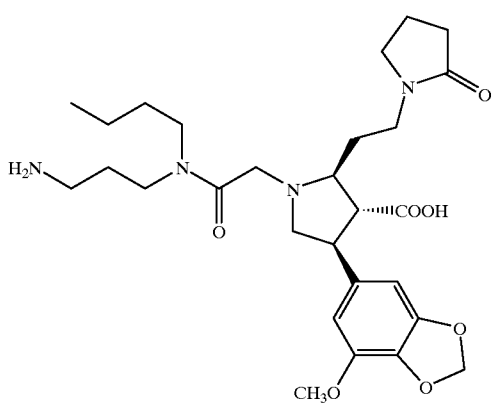
635
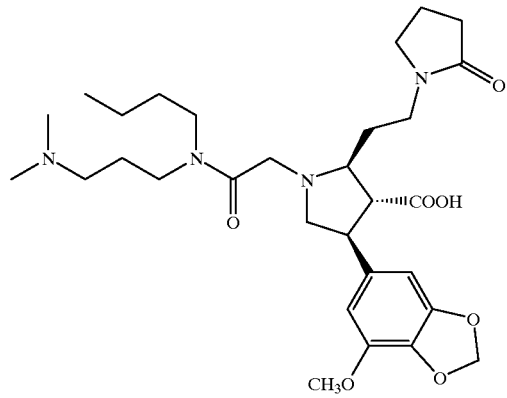

TABLE 3C-continued
636
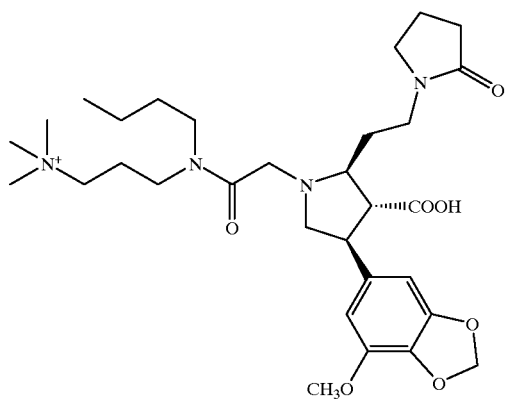
637
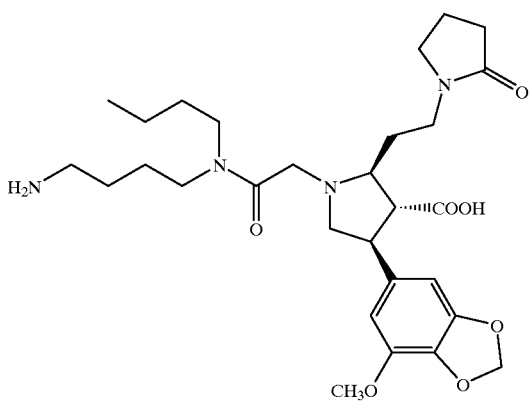
638
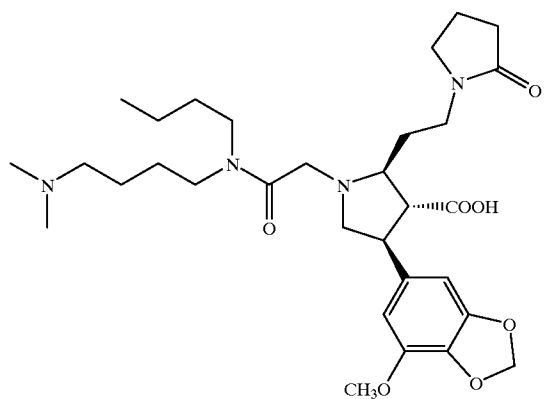

TABLE 3C-continued
639
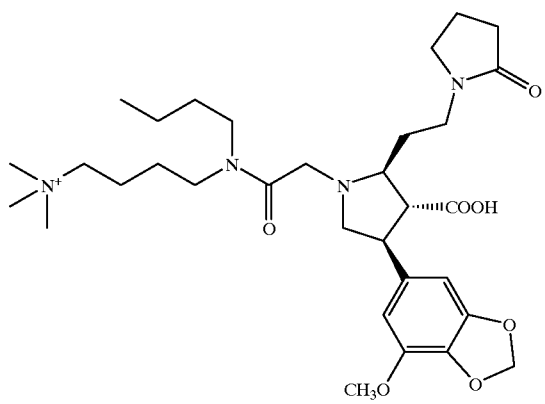
640
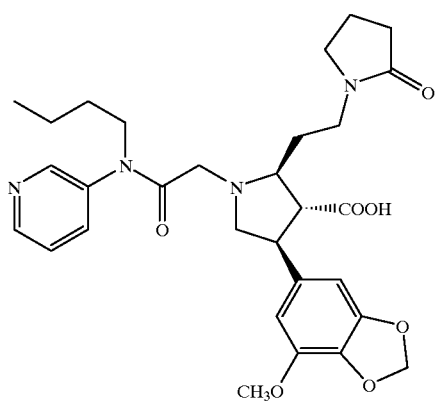
641
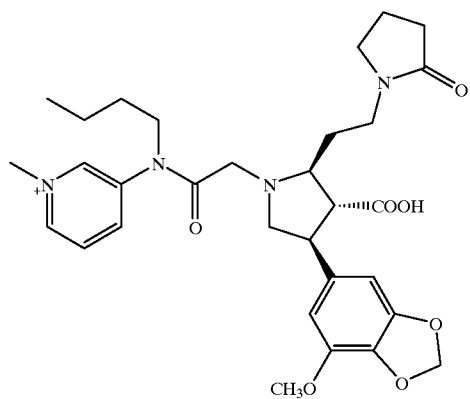

TABLE 3C-continued
642
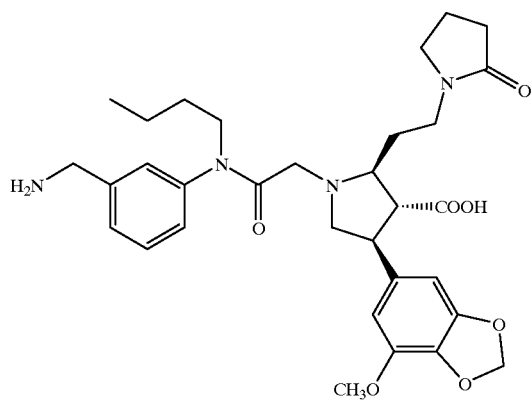
643
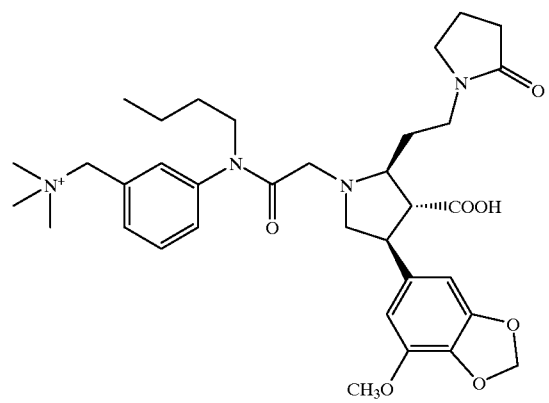
644
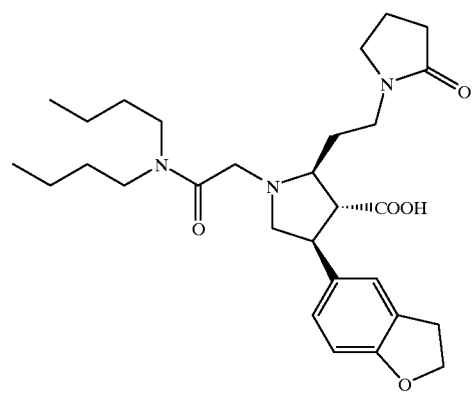
645
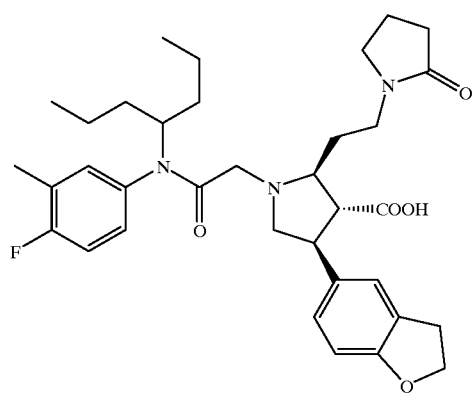

TABLE 3C-continued
646
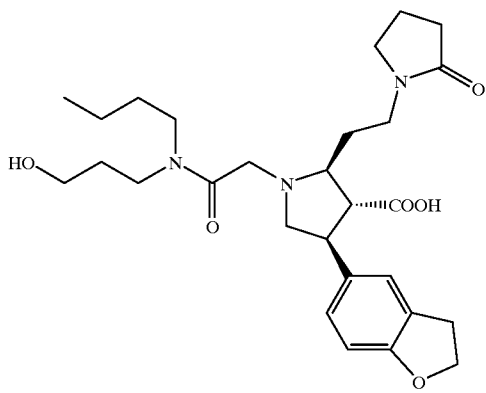
647
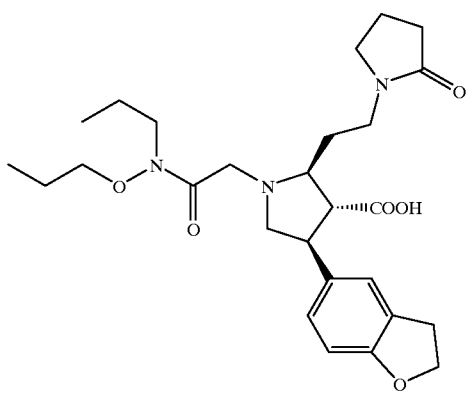
648
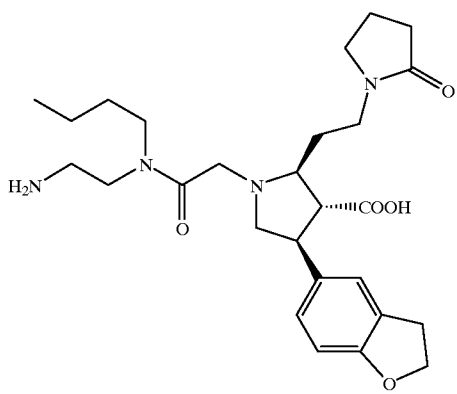
649
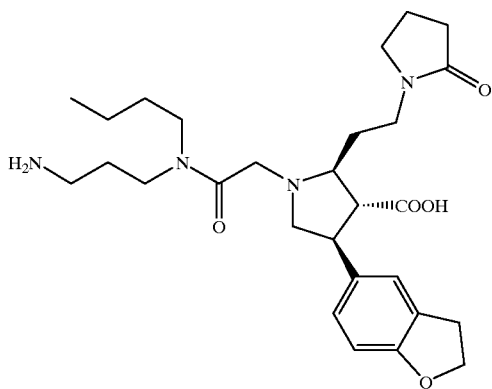

TABLE 3C-continued
650
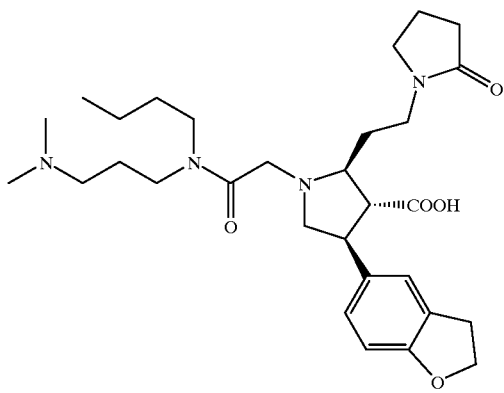
651
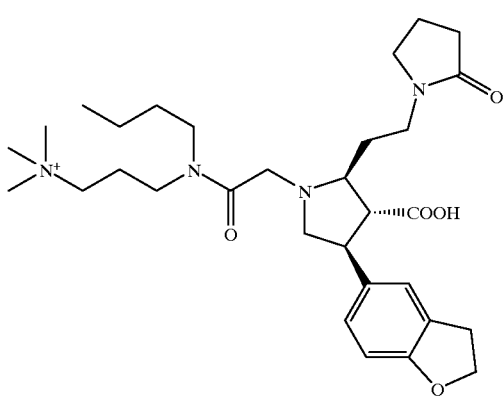
652
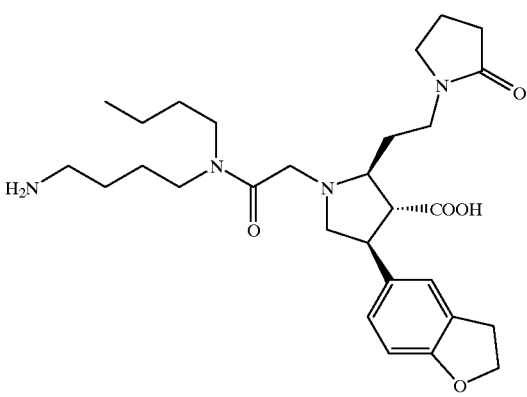
653
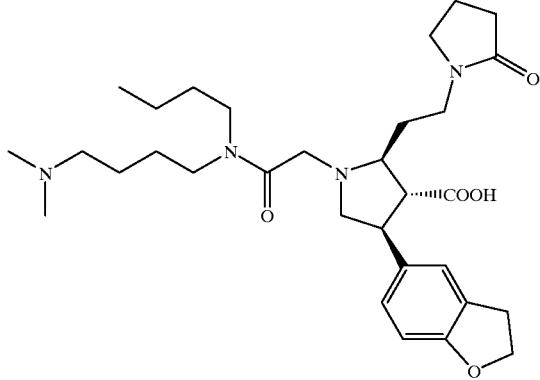

TABLE 3C-continued
654
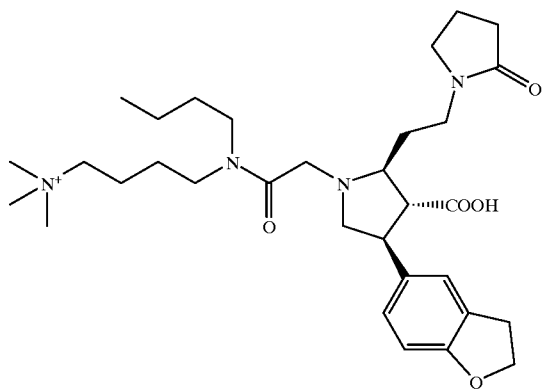
655
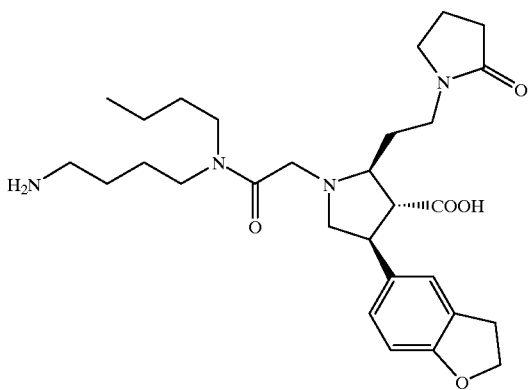
656
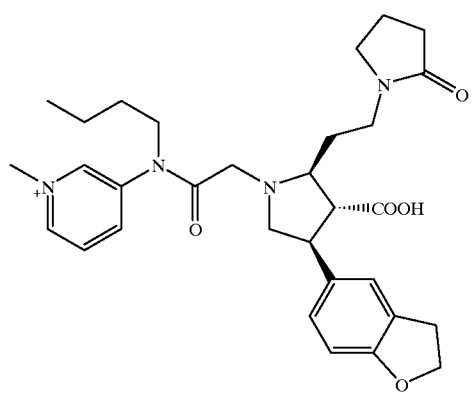
657
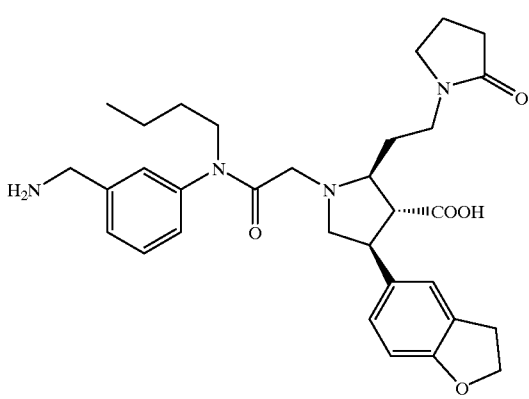

TABLE 3C-continued
658
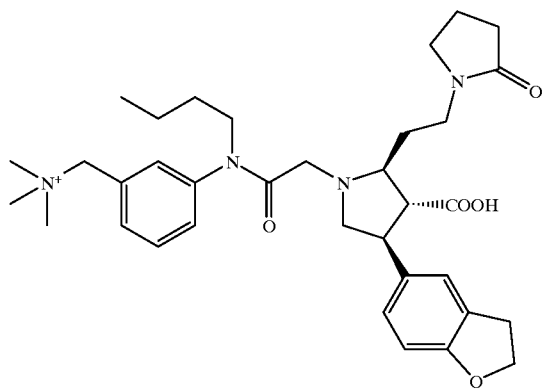
659
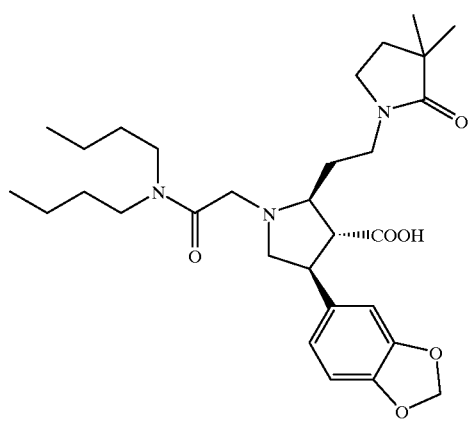
660
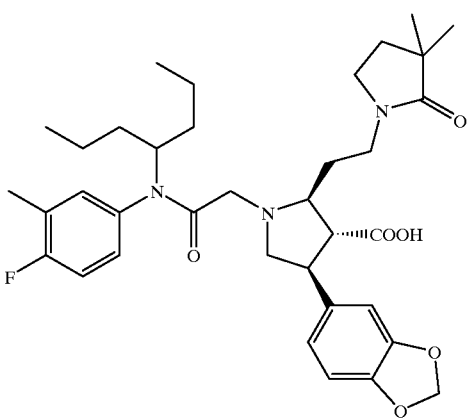

TABLE 3C-continued
661
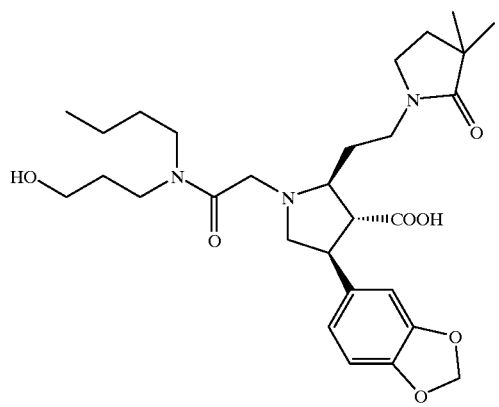
662
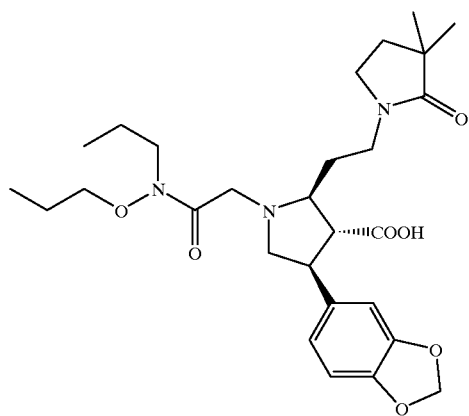
663
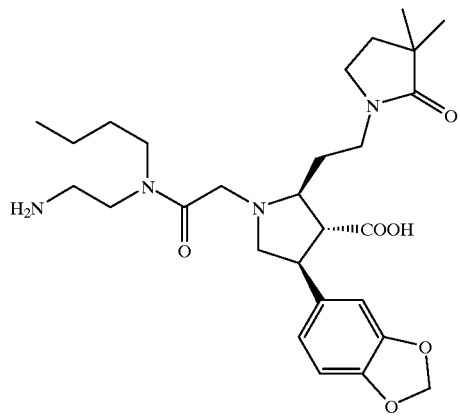

TABLE 3C-continued
664
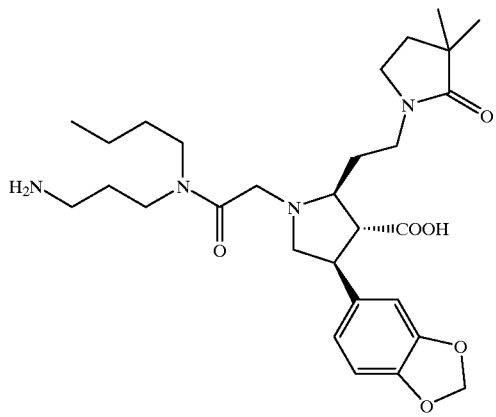
665
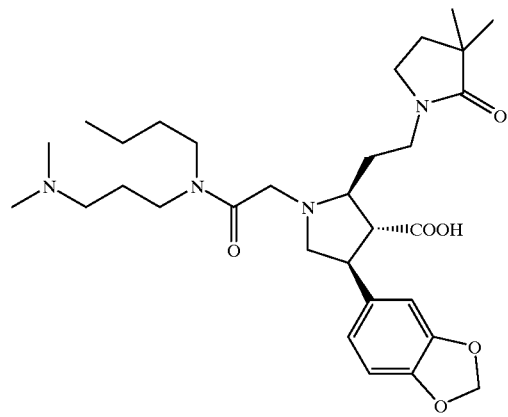
666
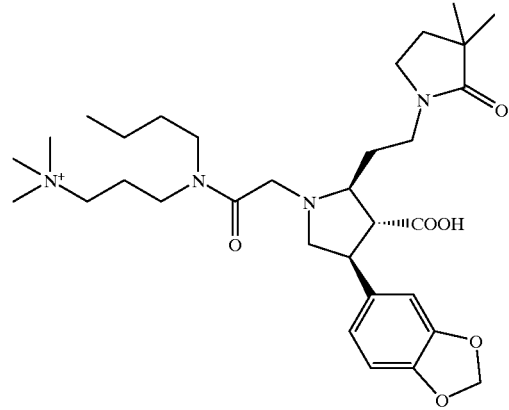

TABLE 3C-continued
667
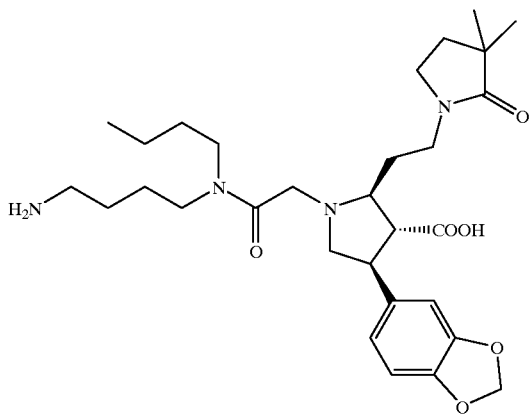
668
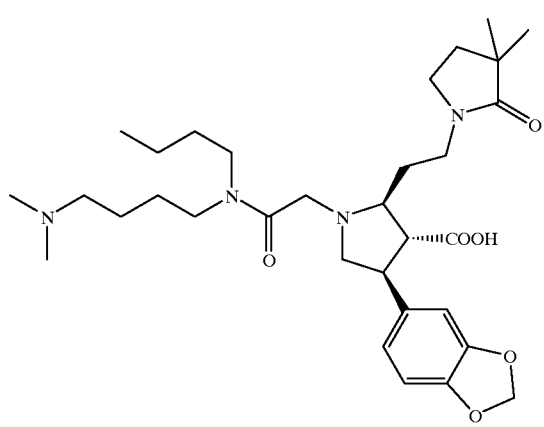
669
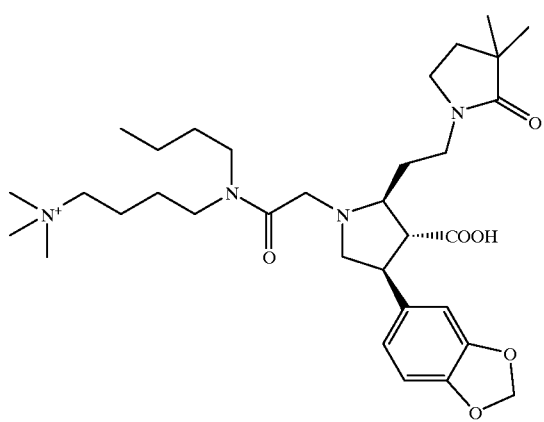

TABLE 3C-continued
670
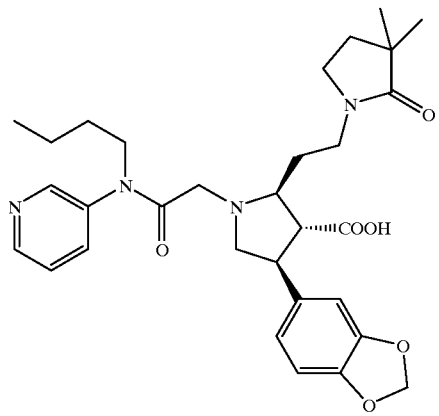
671
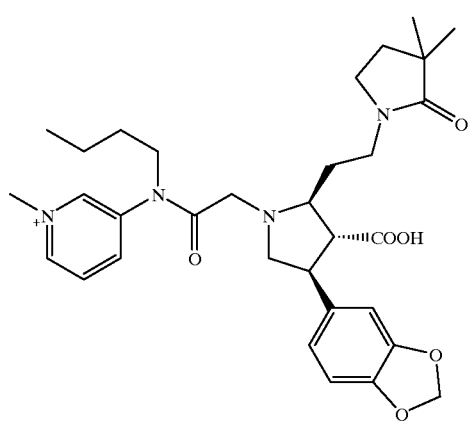
672
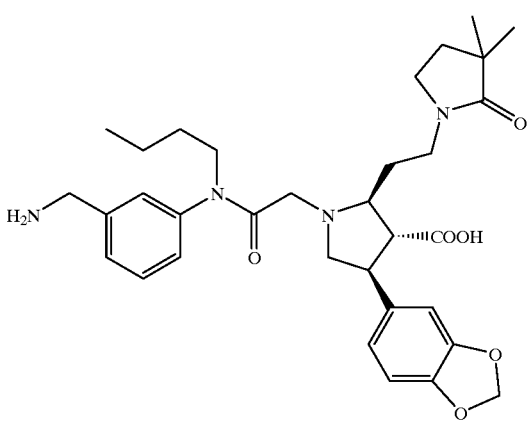

TABLE 3C-continued
673
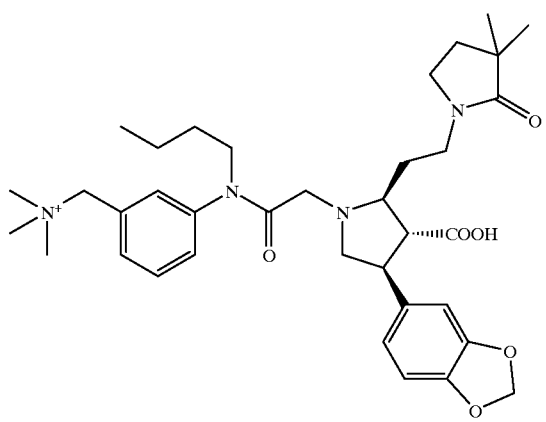
674
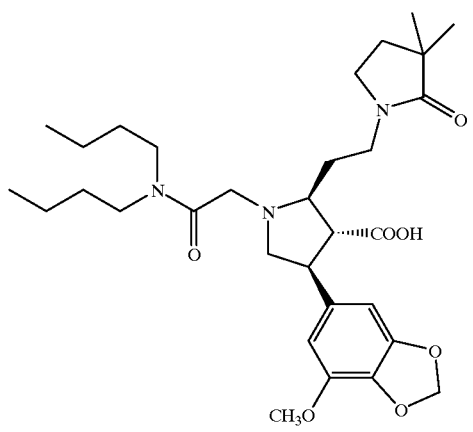
675
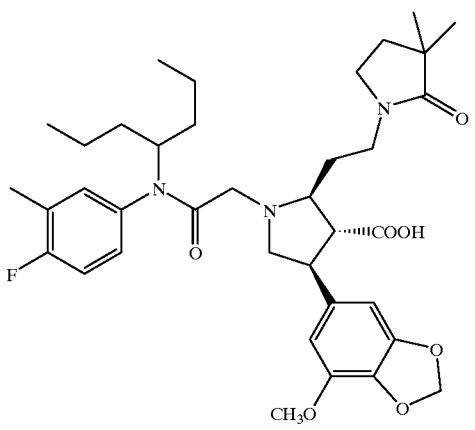

TABLE 3C-continued
676
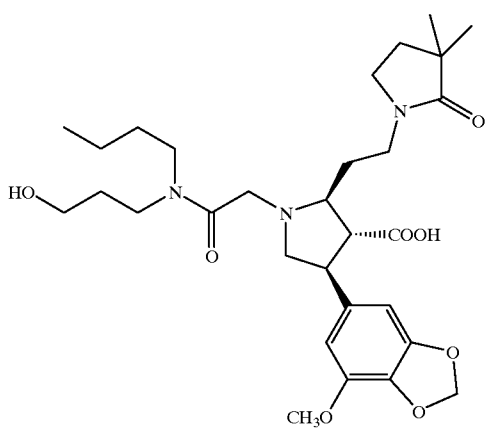
677
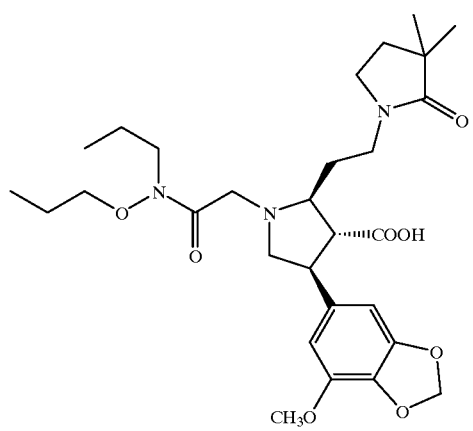
678
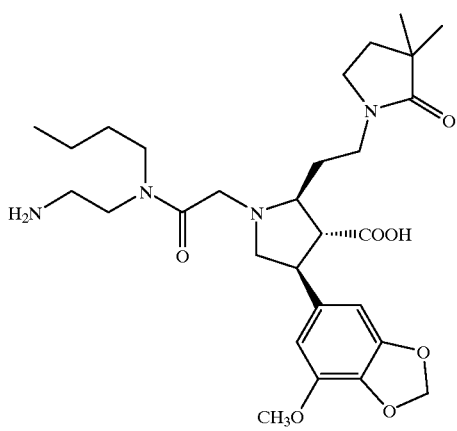

TABLE 3C-continued
679
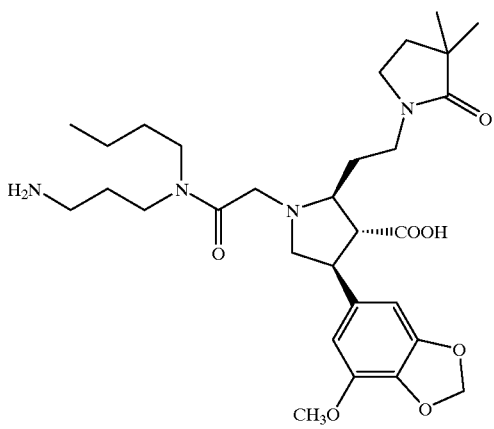
680
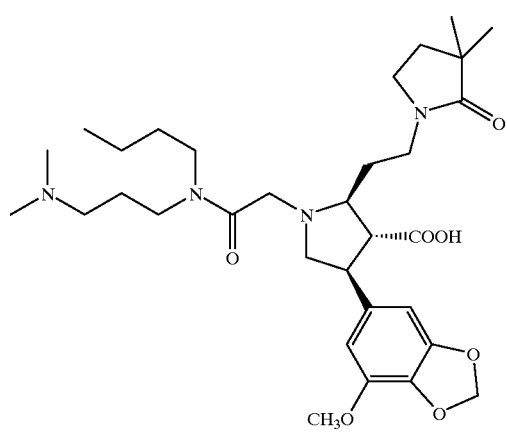
681
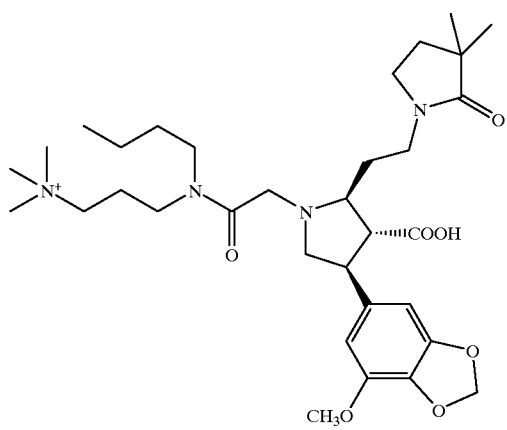

TABLE 3C-continued
682
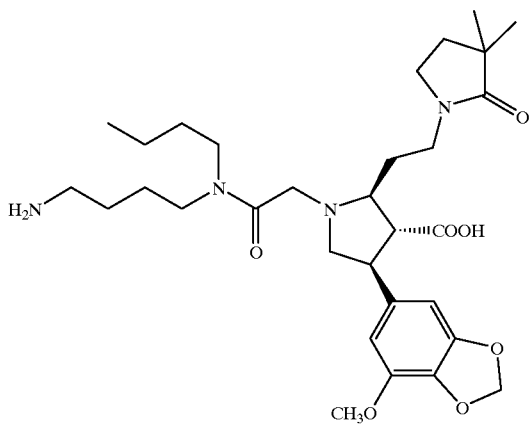
683
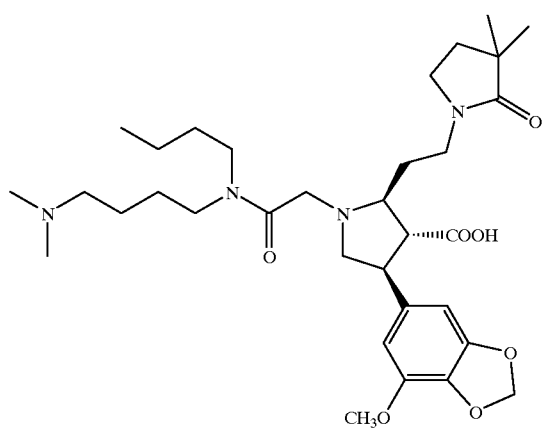
684
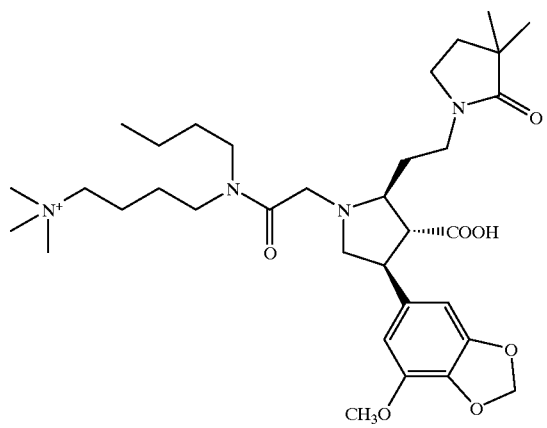

TABLE 3C-continued
685
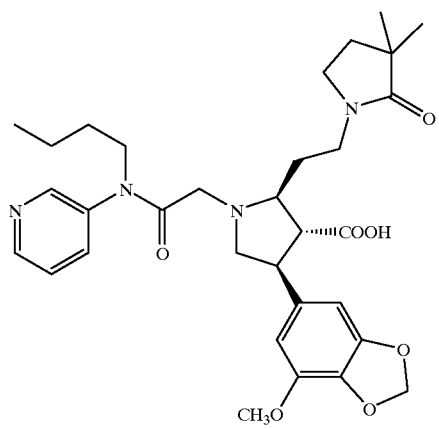
686
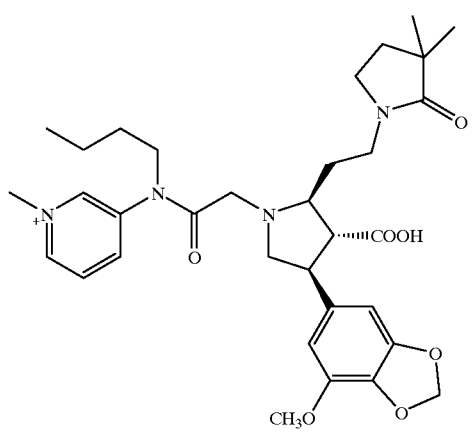
687
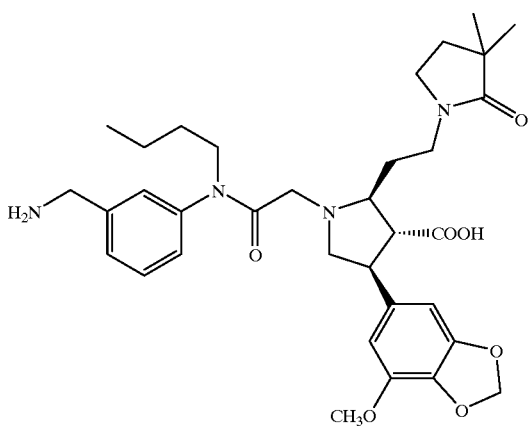

TABLE 3C-continued
688
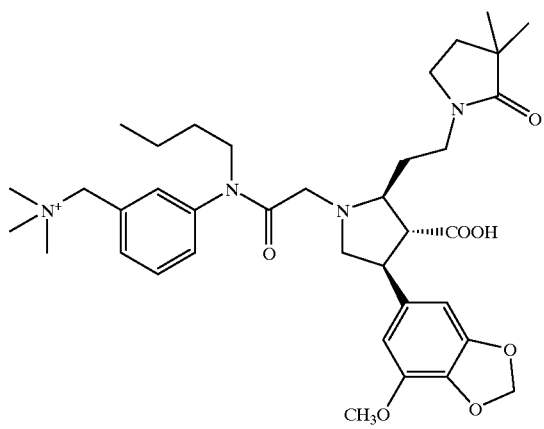
689
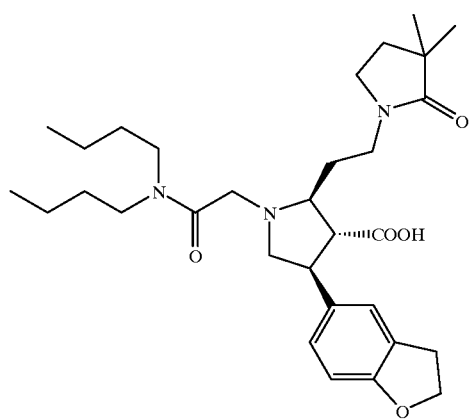
690
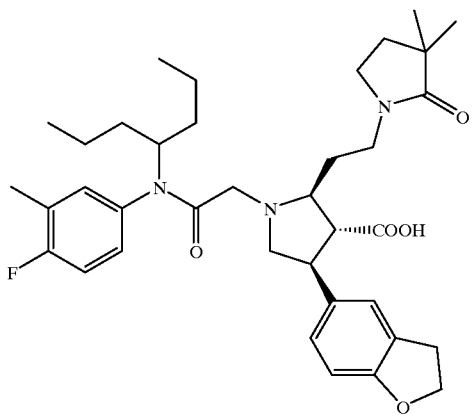

TABLE 3C-continued
691
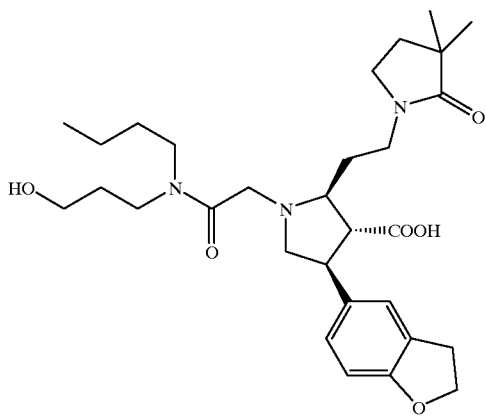
692
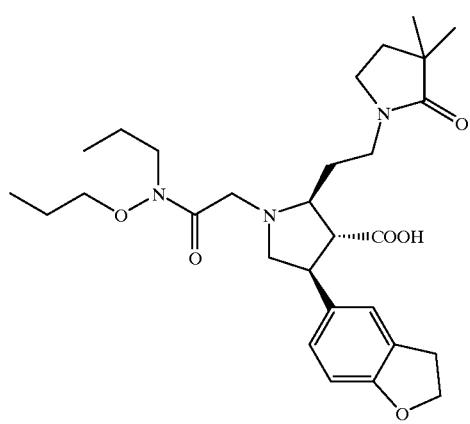
693
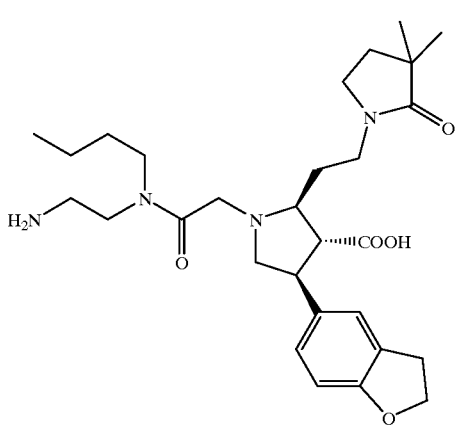

TABLE 3C-continued
694
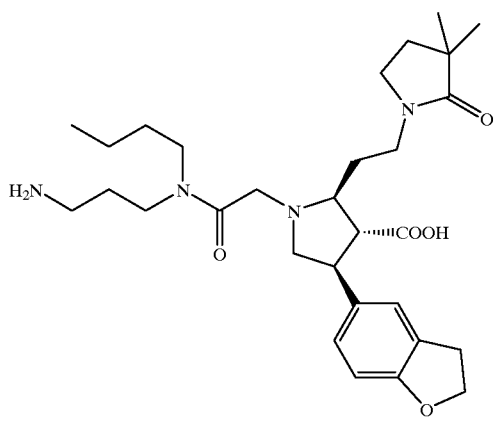
695
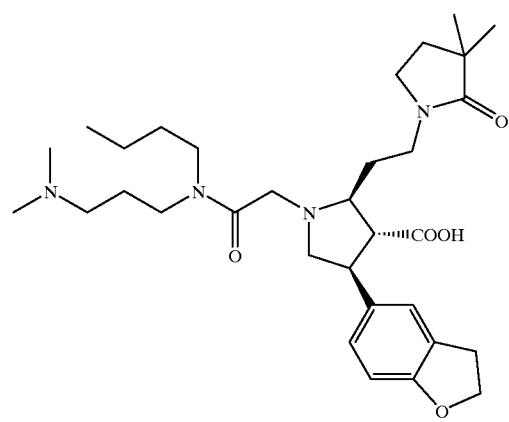
696
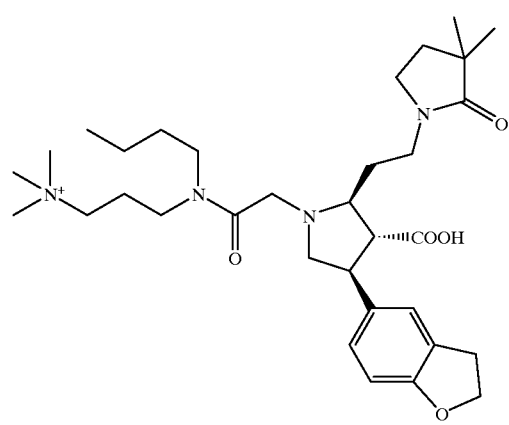

TABLE 3C-continued
697
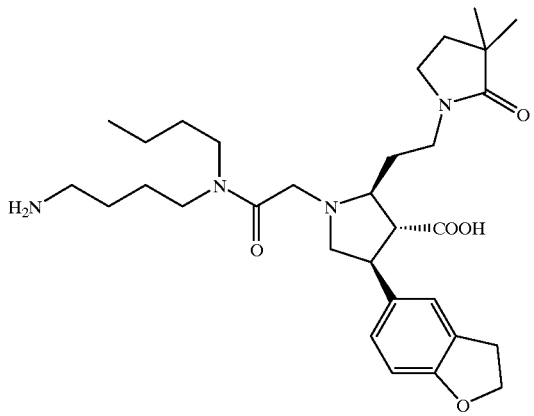
698
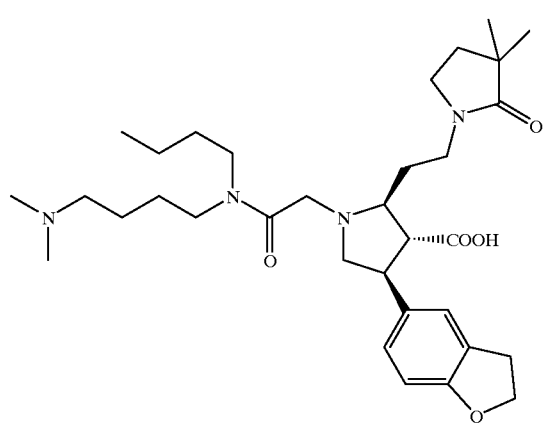
699
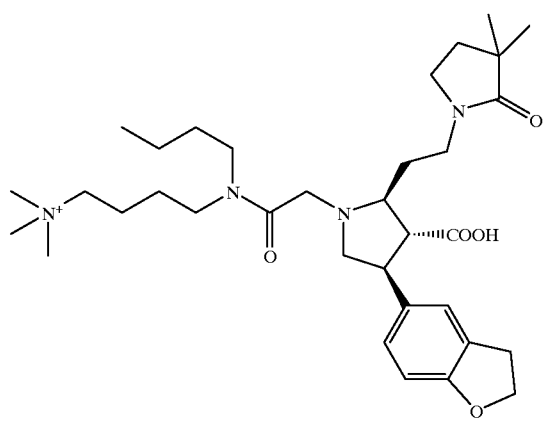

TABLE 3C-continued
700
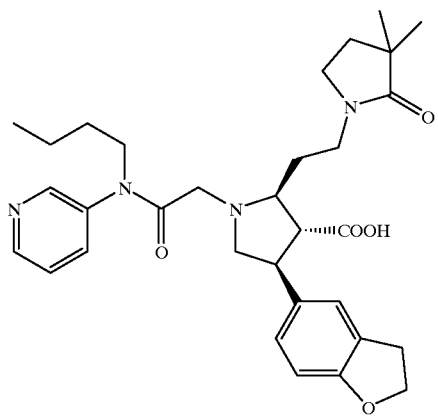
701
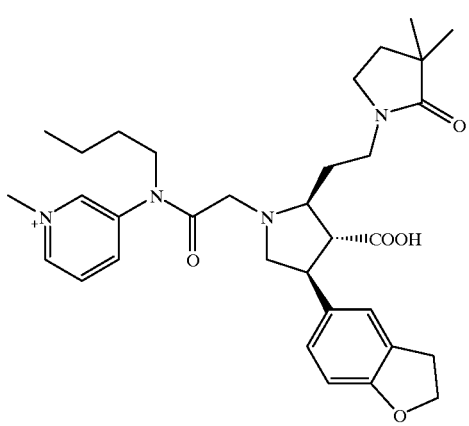
702
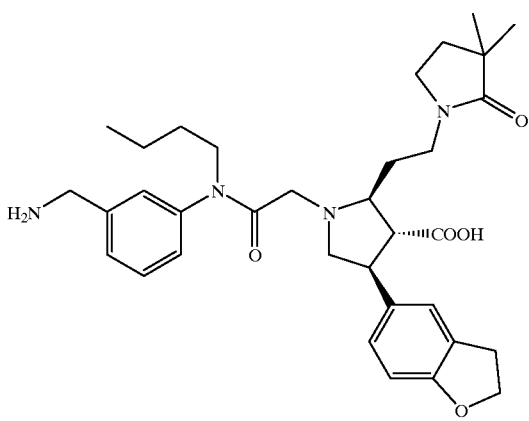

TABLE 3C-continued
703
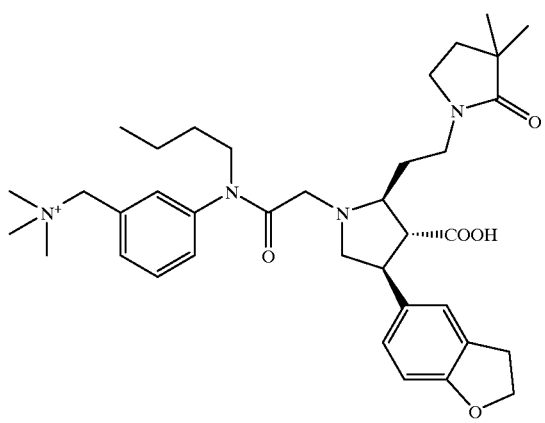
704
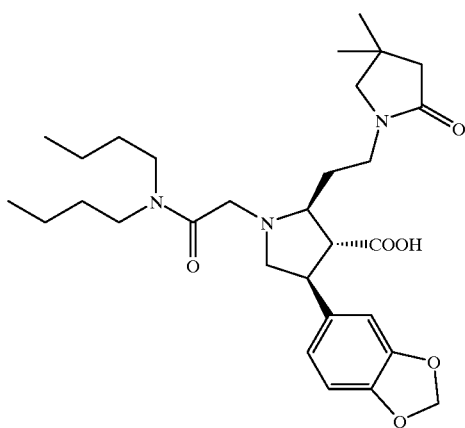
705
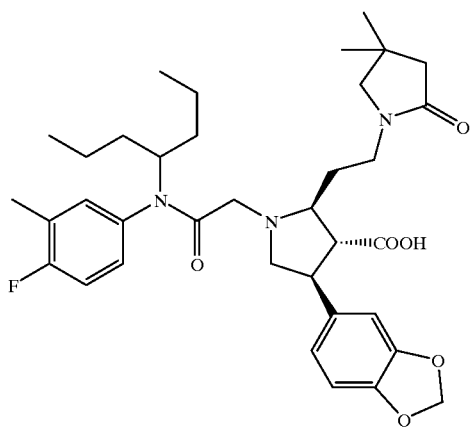

TABLE 3C-continued
706
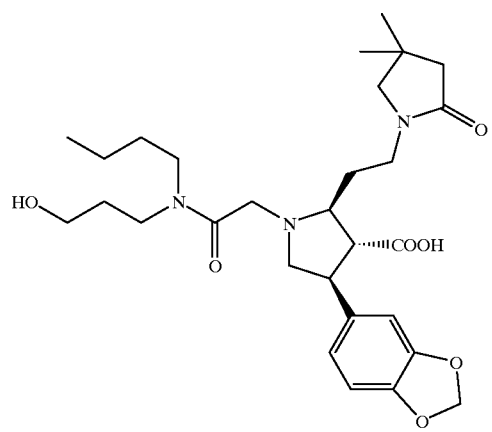
707
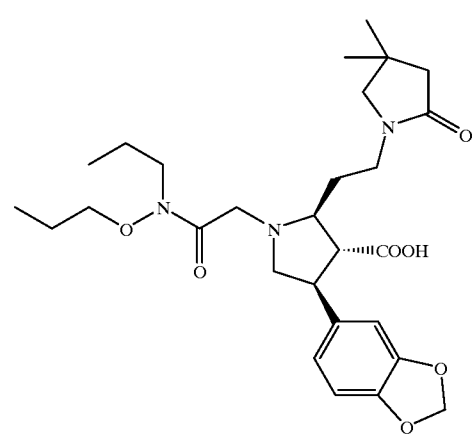
708
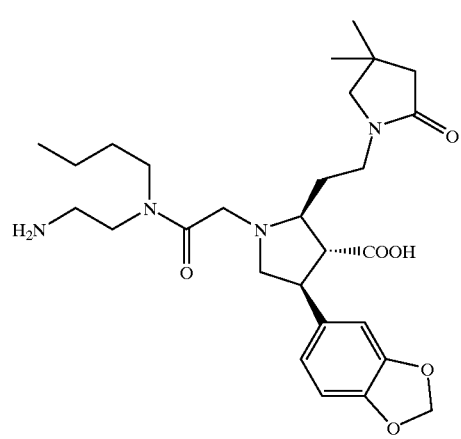

TABLE 3C-continued
709
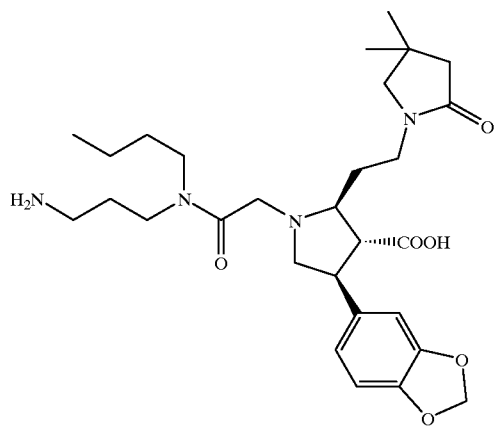
710
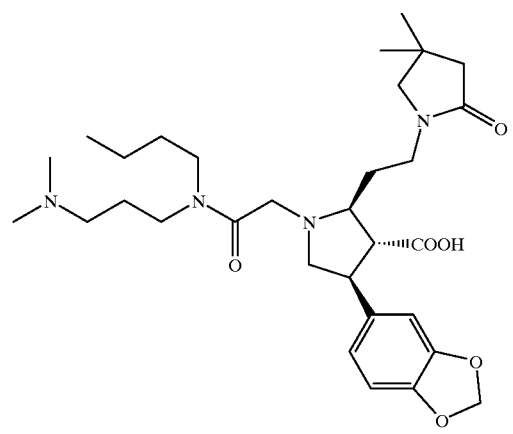
711
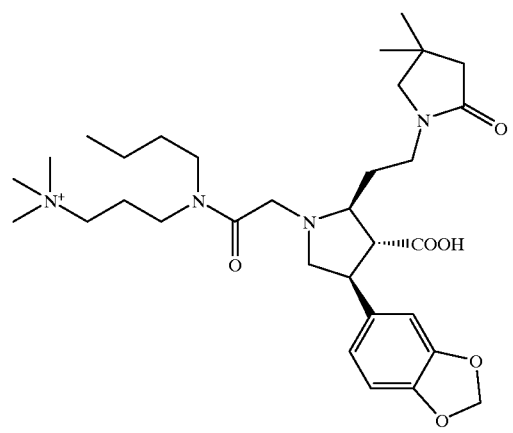

TABLE 3C-continued
712
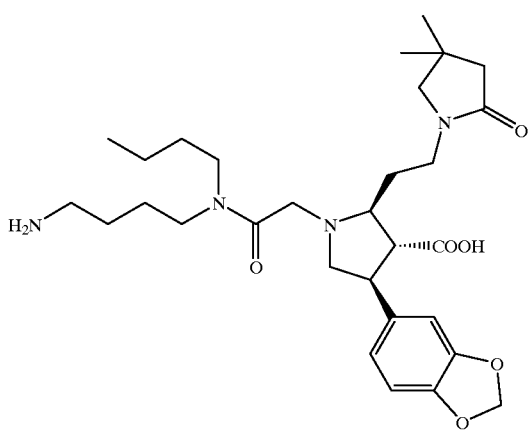
713
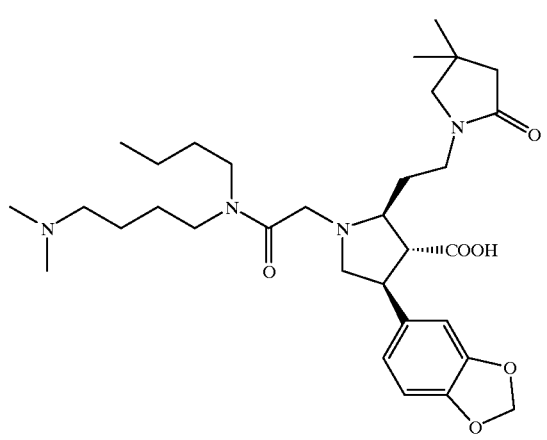
714
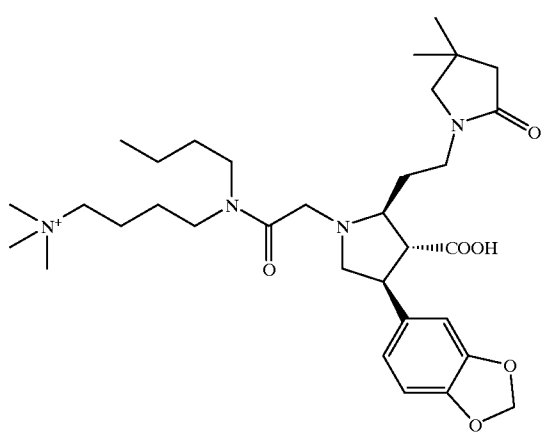

TABLE 3C-continued
715 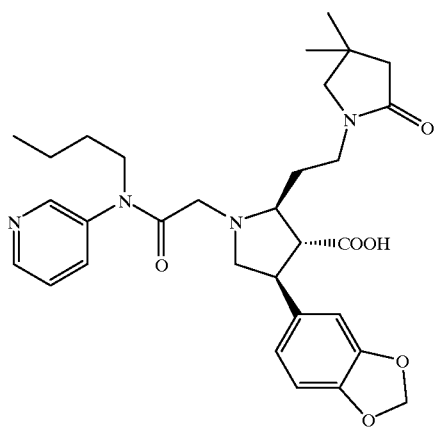
716 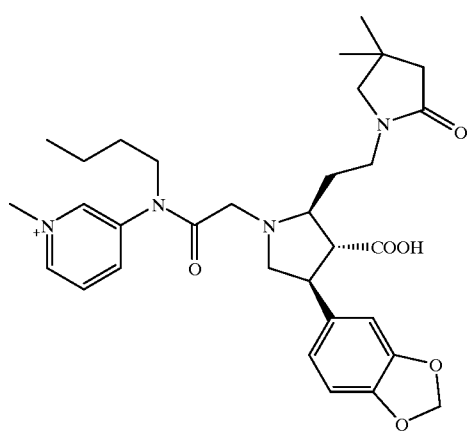
717 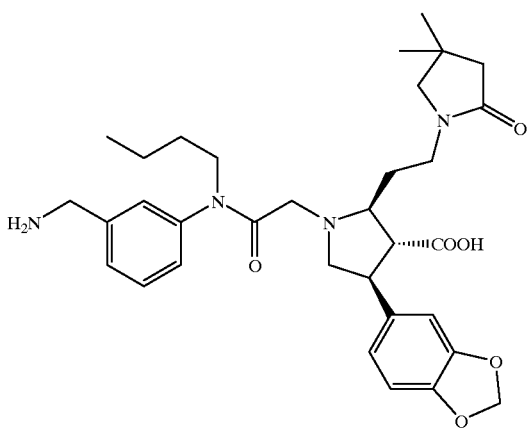

TABLE 3C-continued
| 718 | 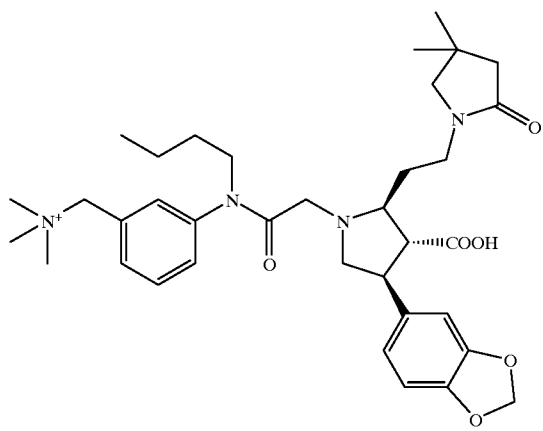 |
| --- | --- |
| 719 | 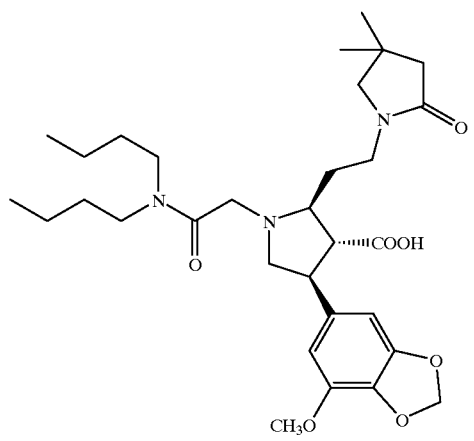 |
| 720 | 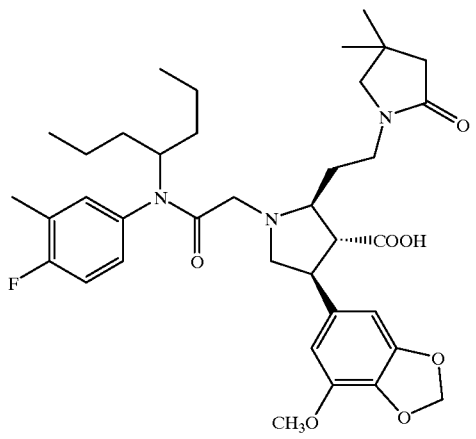 |

TABLE 3C-continued
721
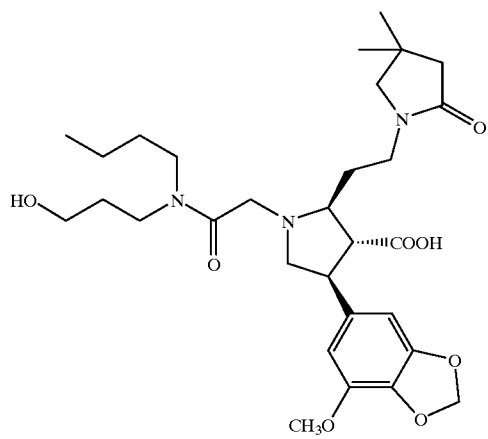
722
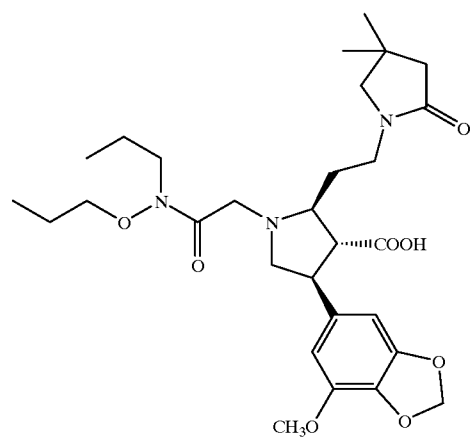
723
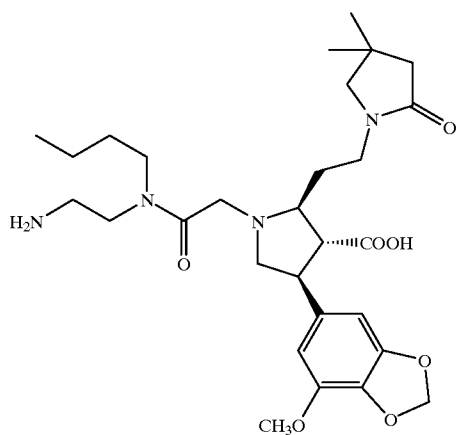

TABLE 3C-continued
724
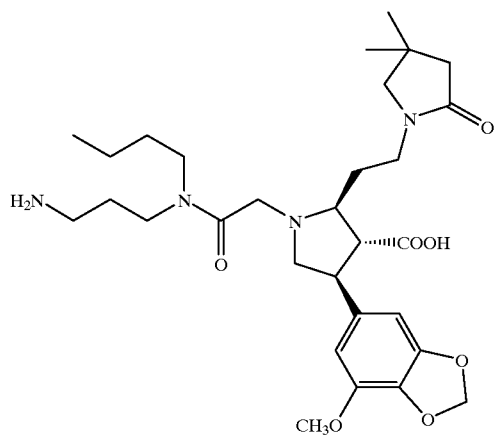
725
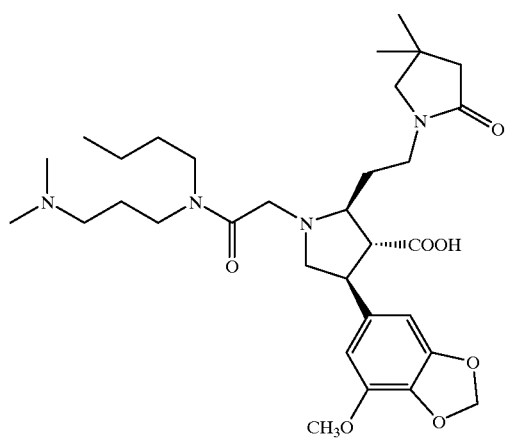
726
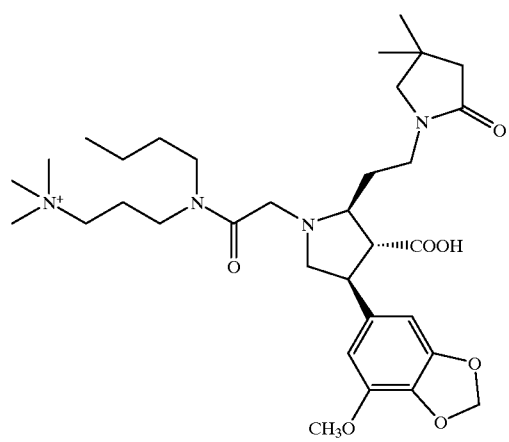

TABLE 3C-continued
727
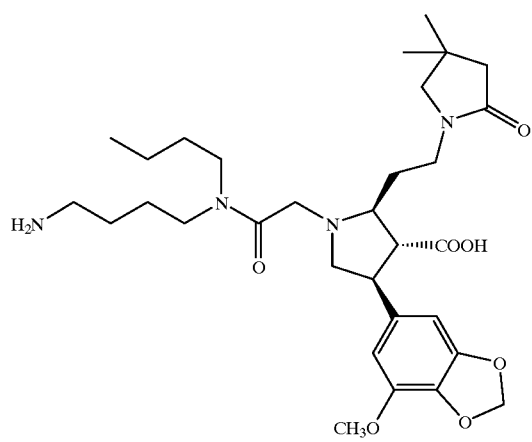
728
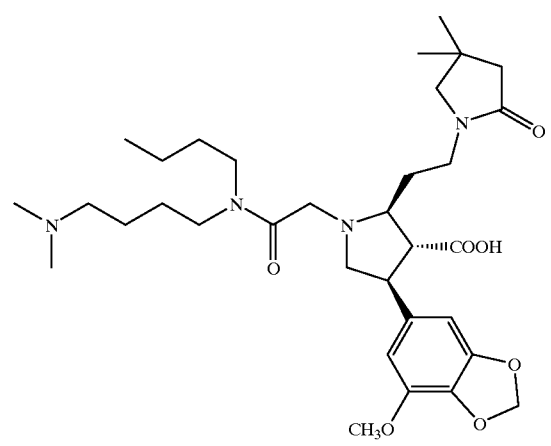
729
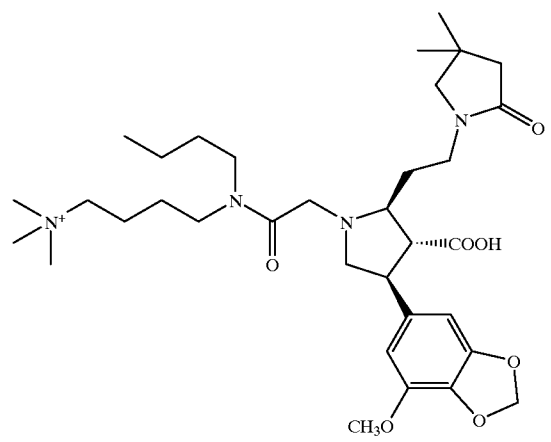

TABLE 3C-continued
730
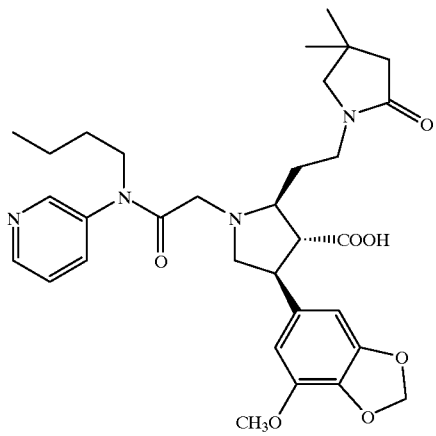
731
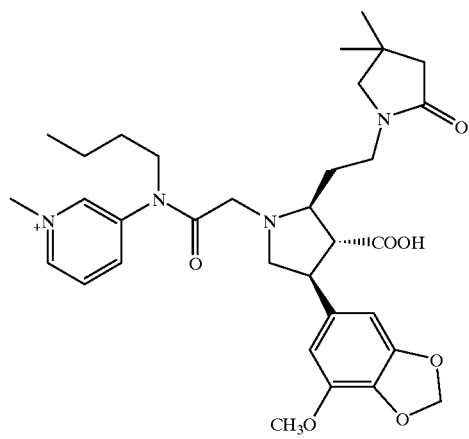
732
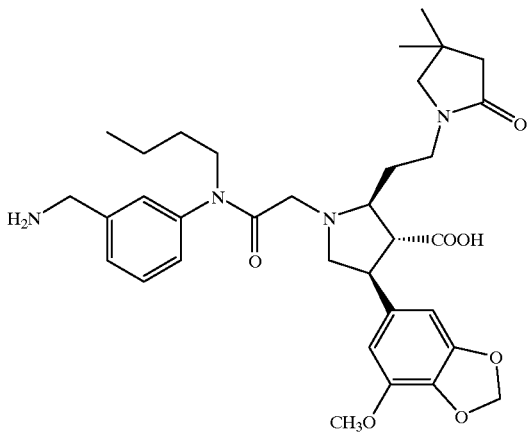

TABLE 3C-continued
733
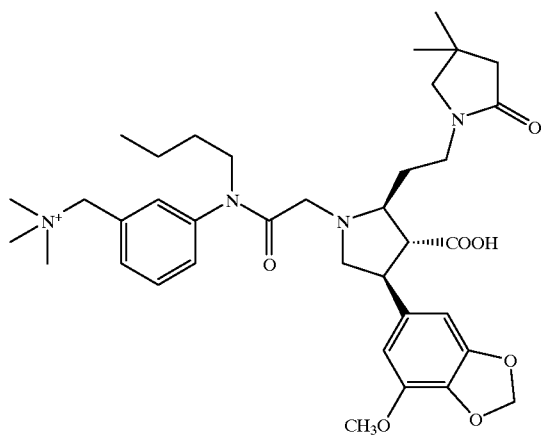
734
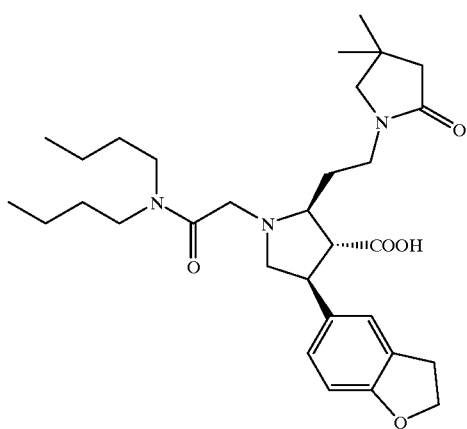
735
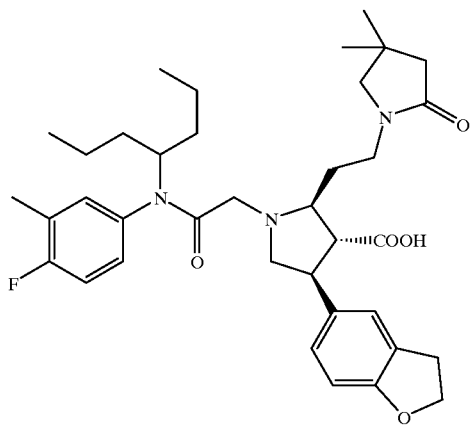

TABLE 3C-continued
736
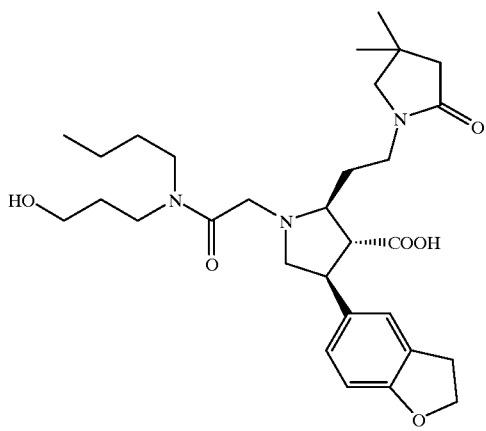
737
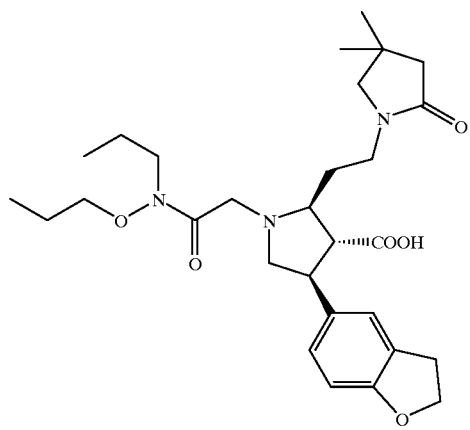
738
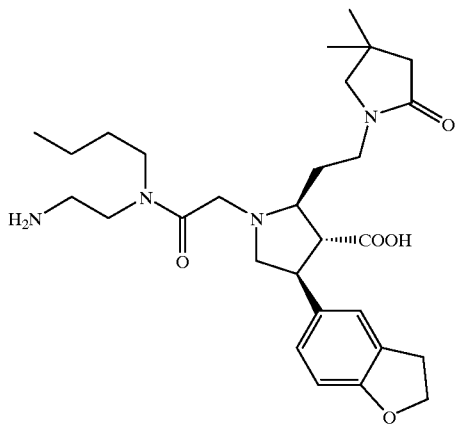

TABLE 3C-continued
739
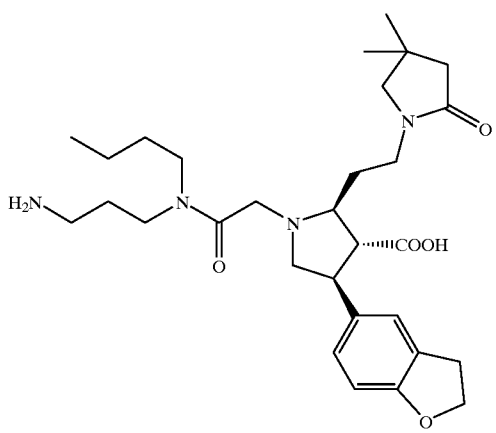
740
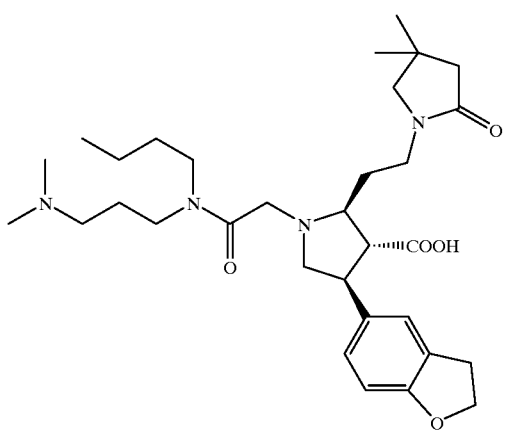
741
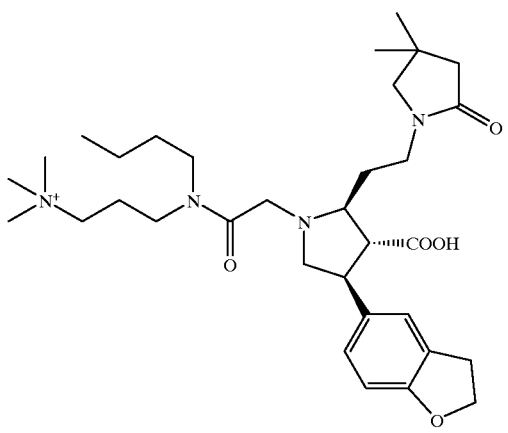

TABLE 3C-continued
742
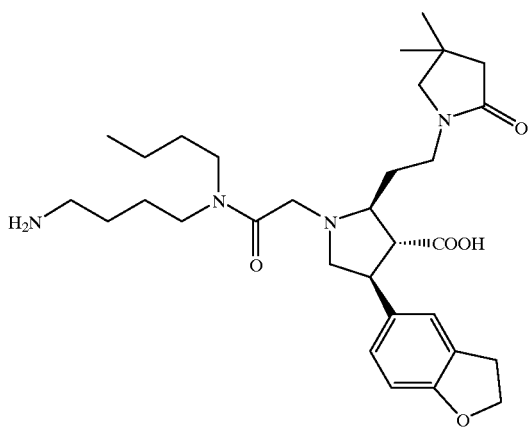
743
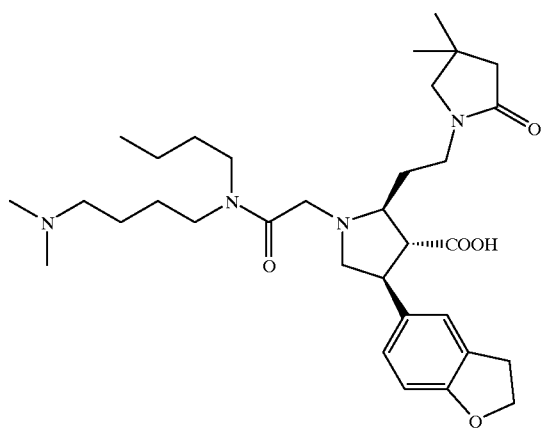
744
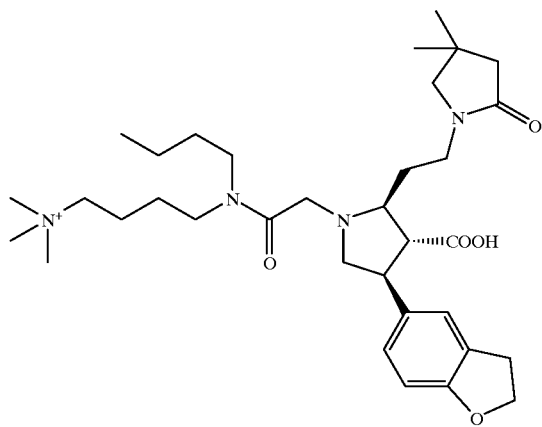

TABLE 3C-continued
745
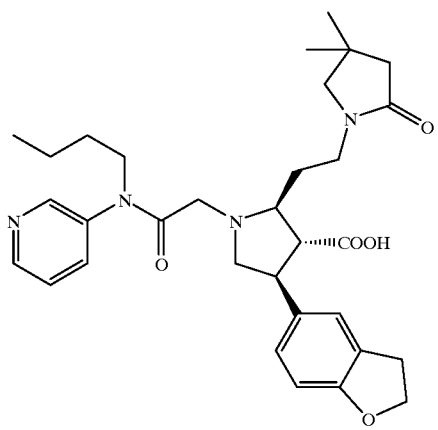
746
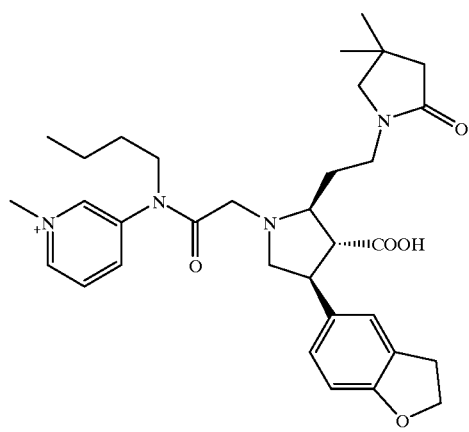
747
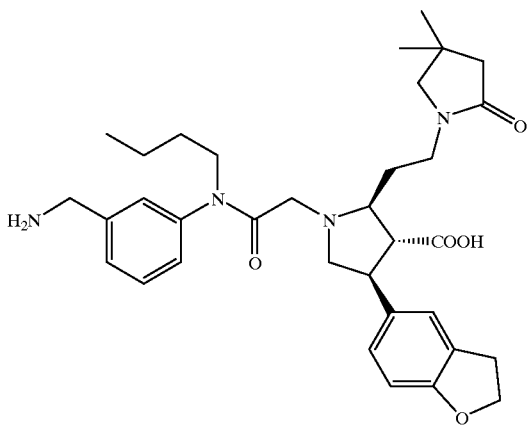

TABLE 3C-continued
748
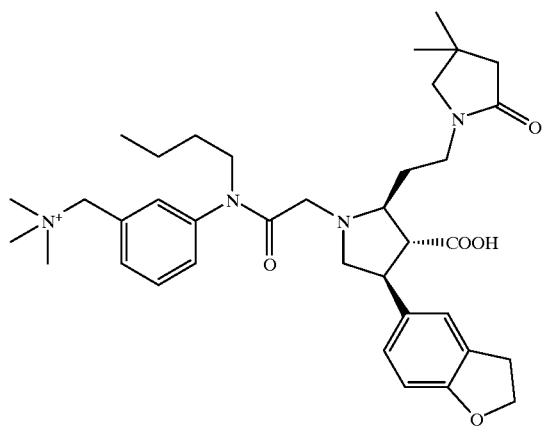
749
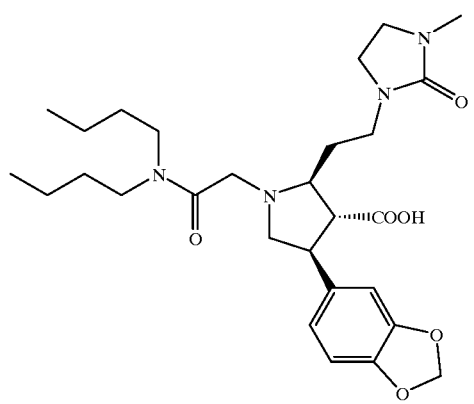
750
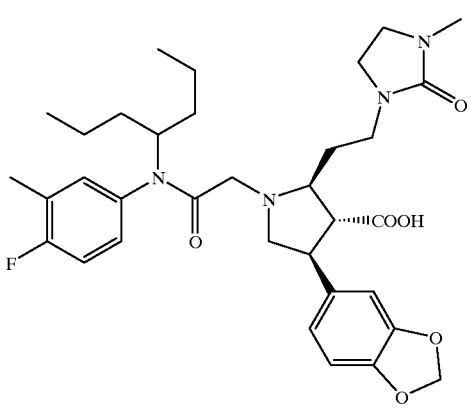

TABLE 3C-continued
751 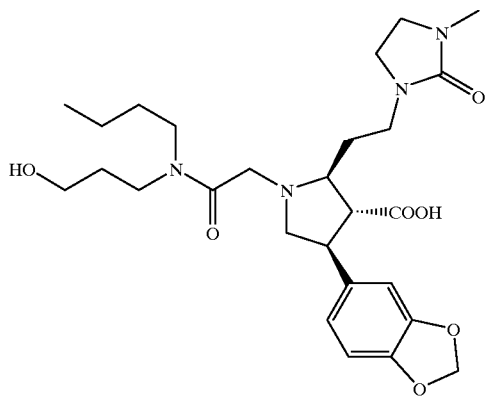
752 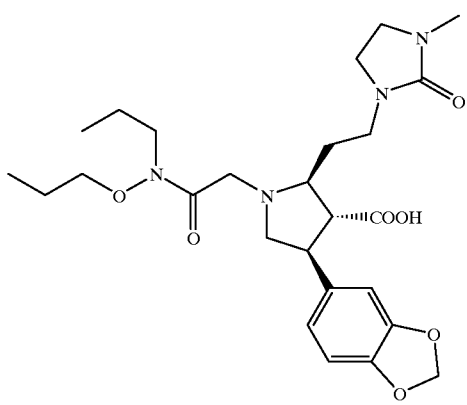
753 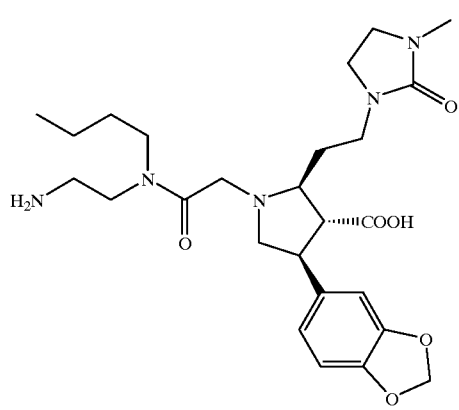
754 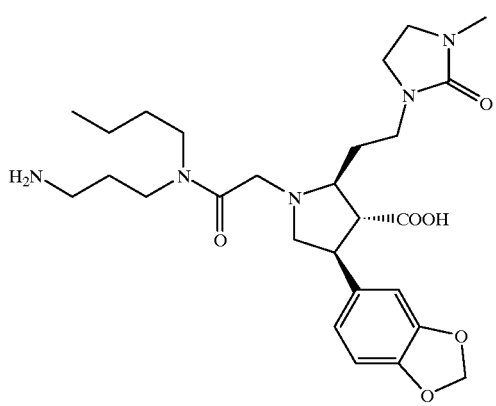

TABLE 3C-continued
755
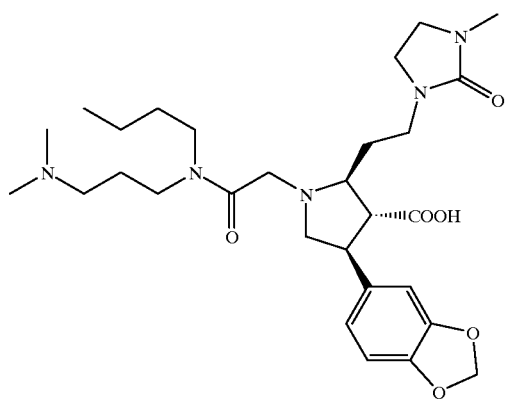
756
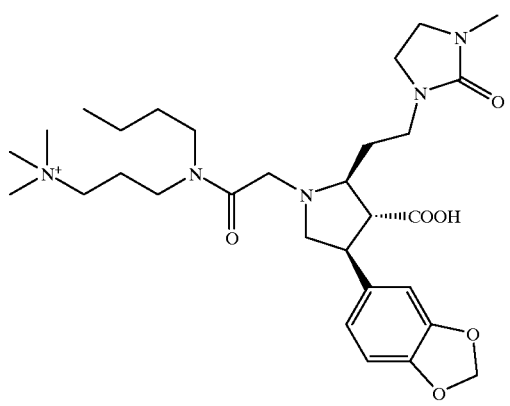
757
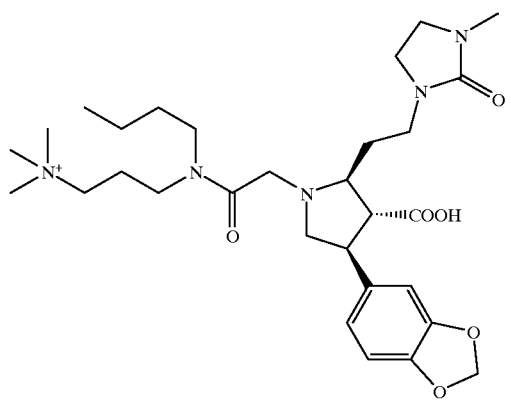

TABLE 3C-continued
758
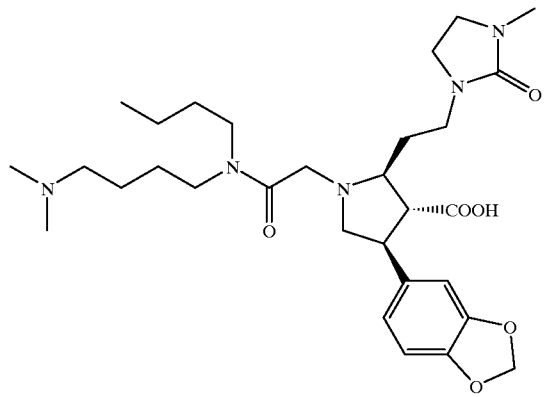
759
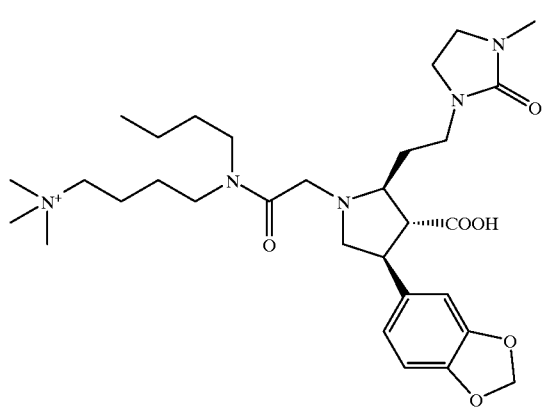
760
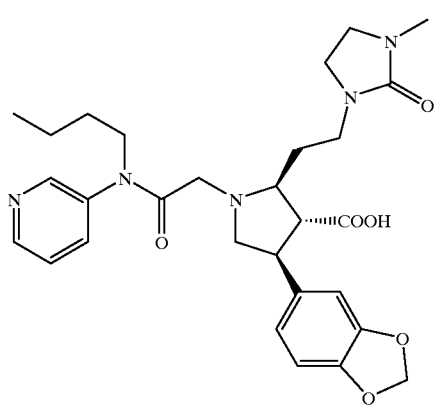
761
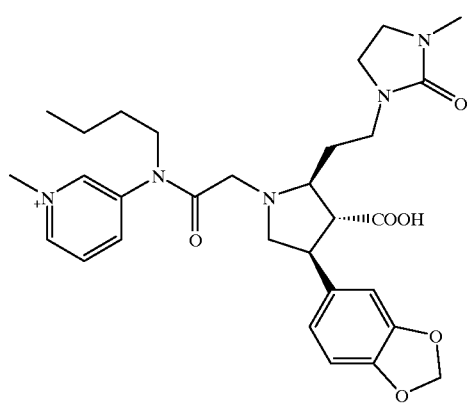

TABLE 3C-continued
762
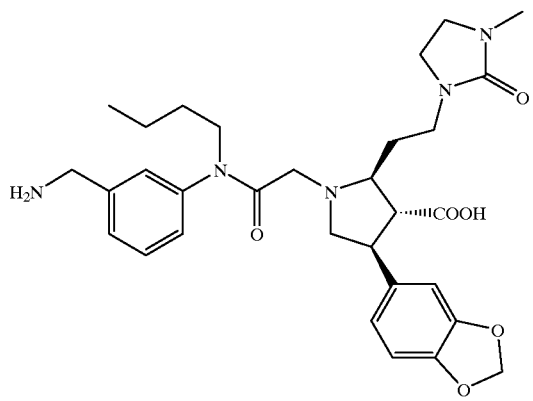
763
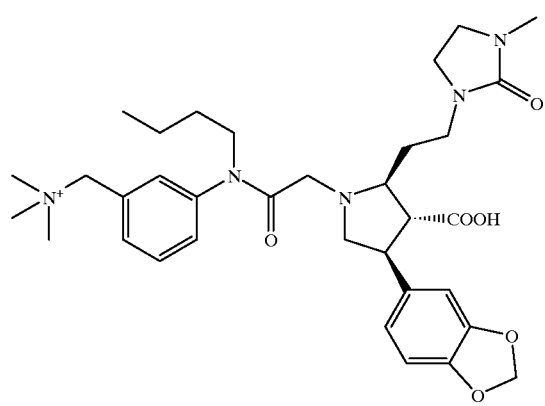
764
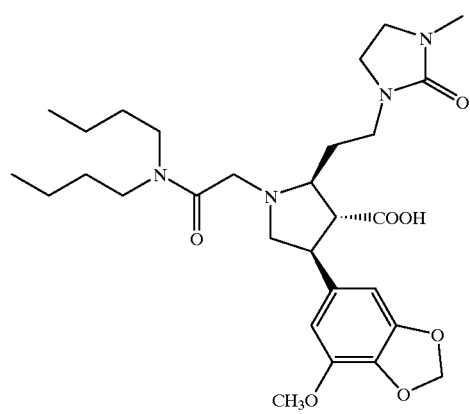

TABLE 3C-continued
765
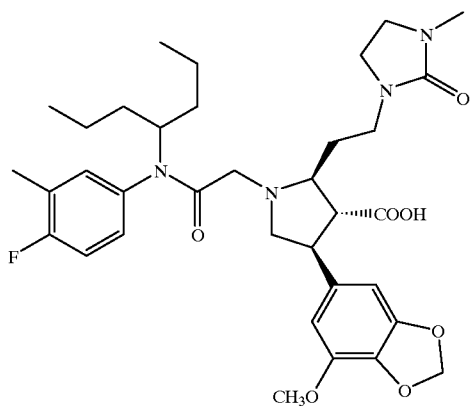
766
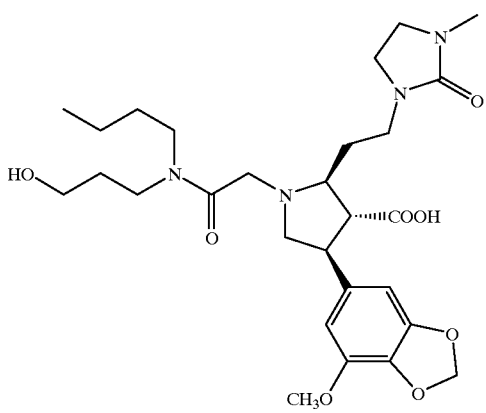
767
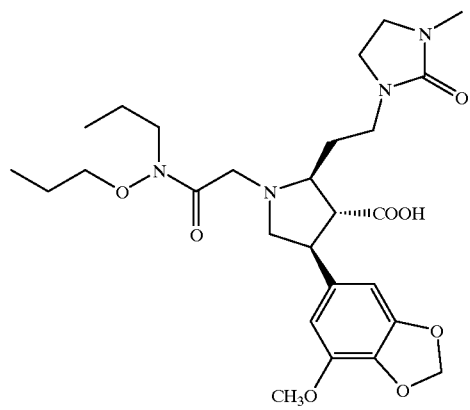

TABLE 3C-continued
768
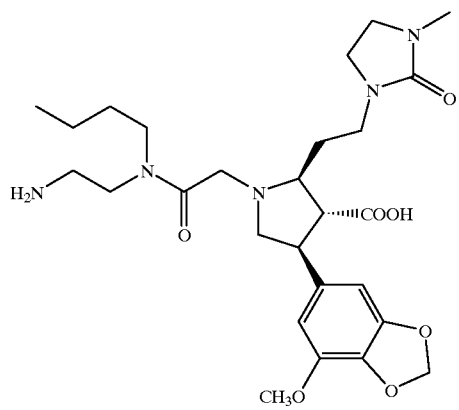
769
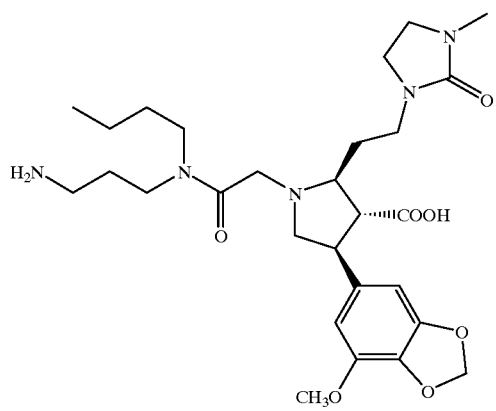
770
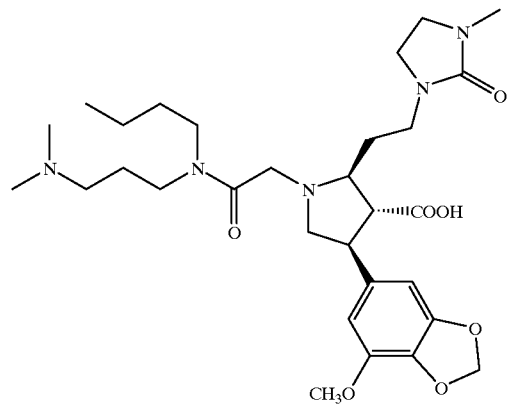

TABLE 3C-continued
771
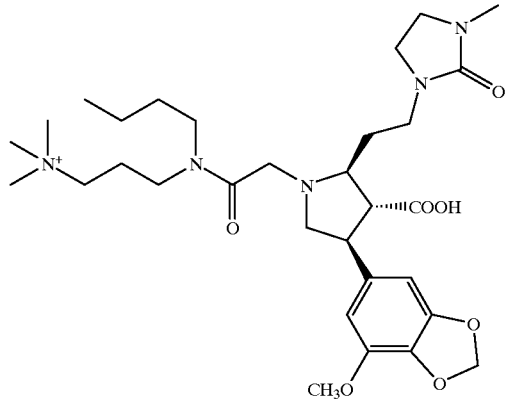
772
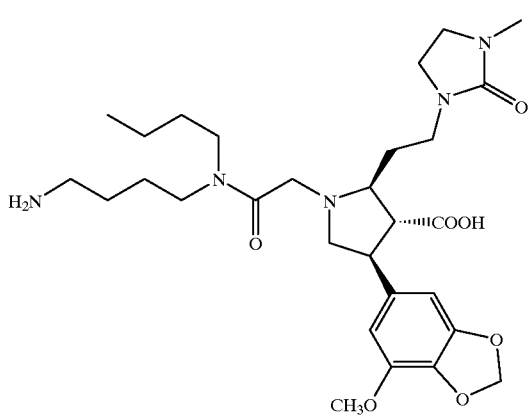
773
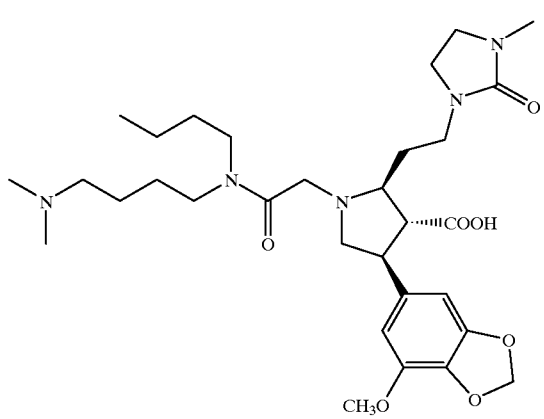

TABLE 3C-continued
774
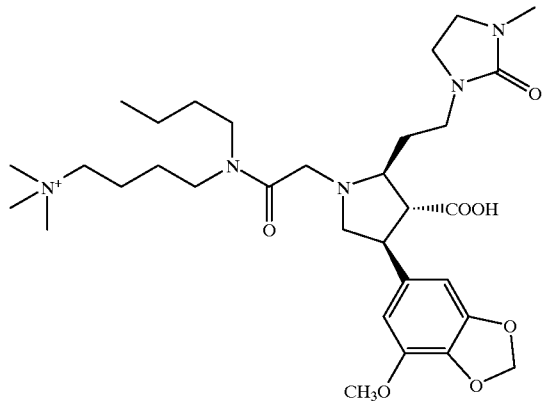
775
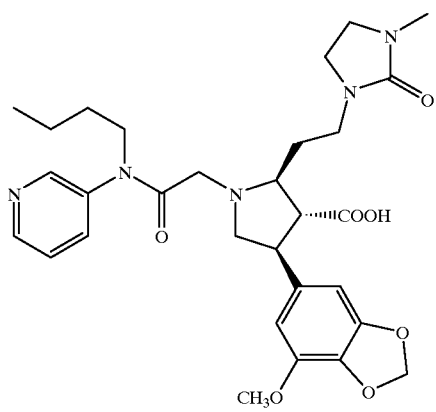
776
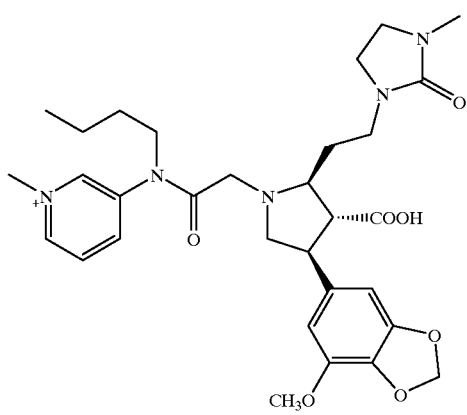

TABLE 3C-continued
777
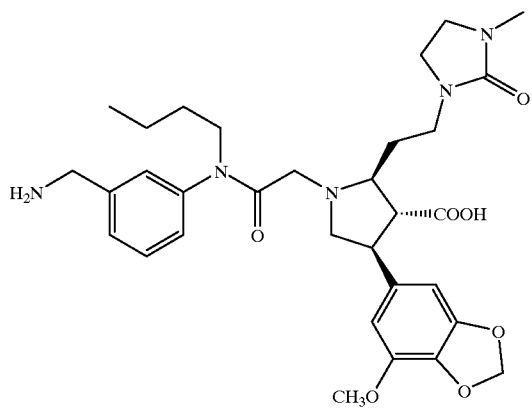
778
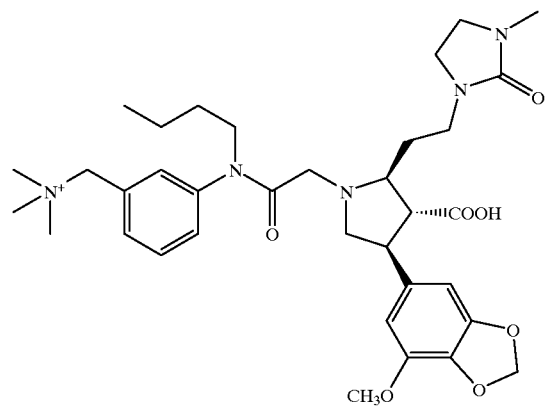
779
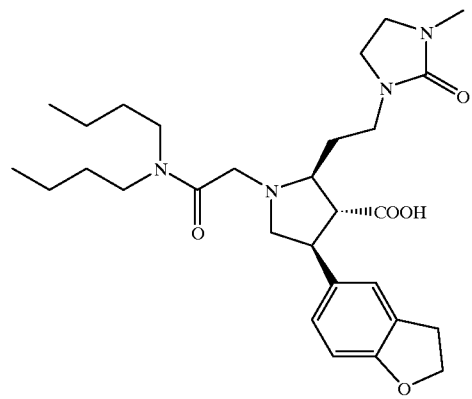

TABLE 3C-continued
780
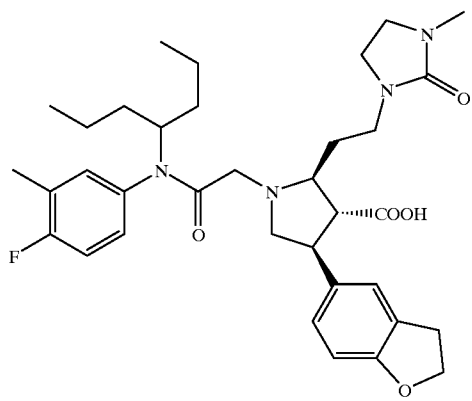
781
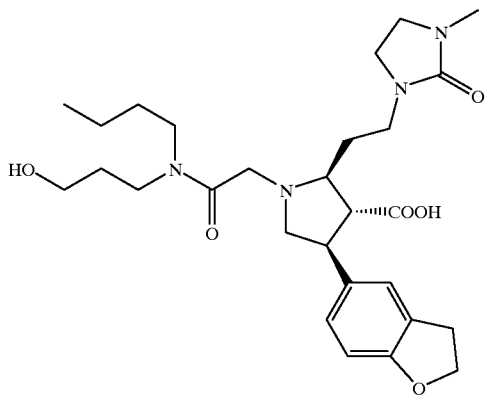
782
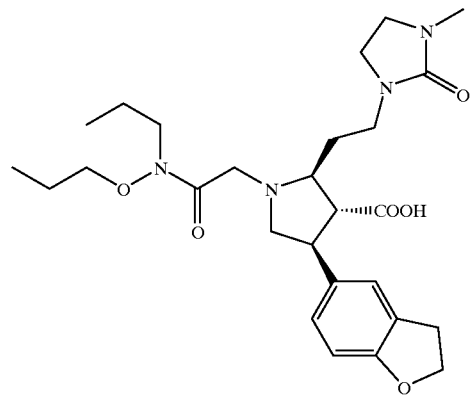
783
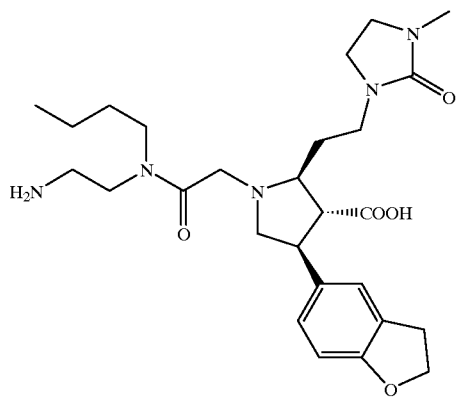

TABLE 3C-continued
784
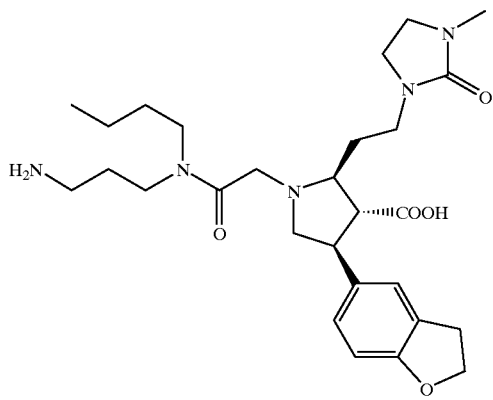
785
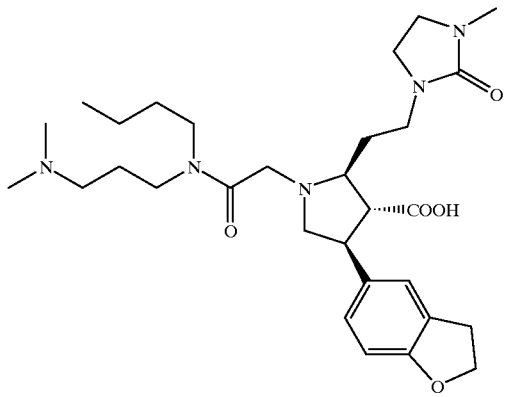
786
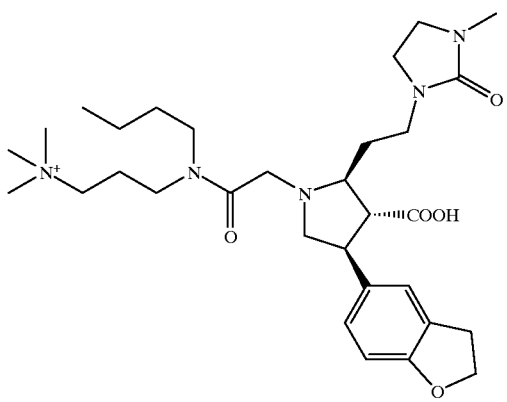

TABLE 3C-continued
787
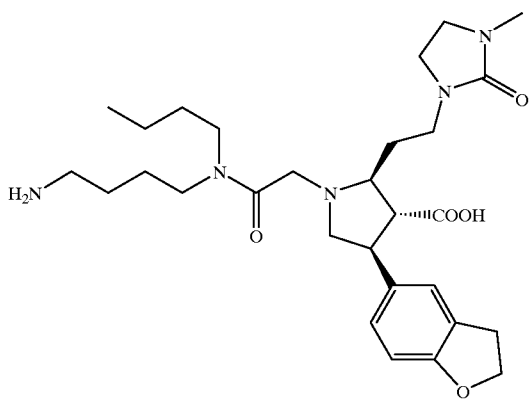
788
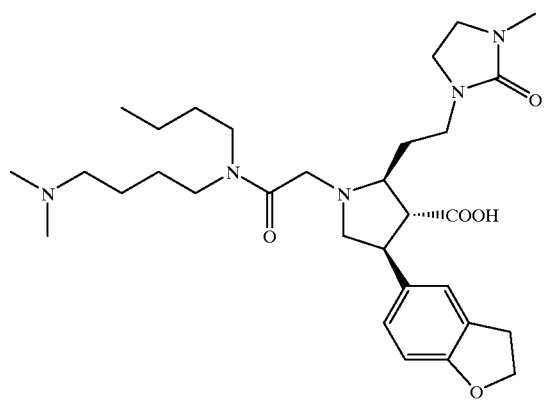
789
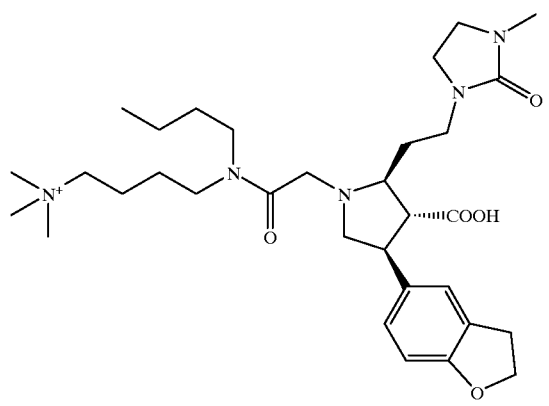
790
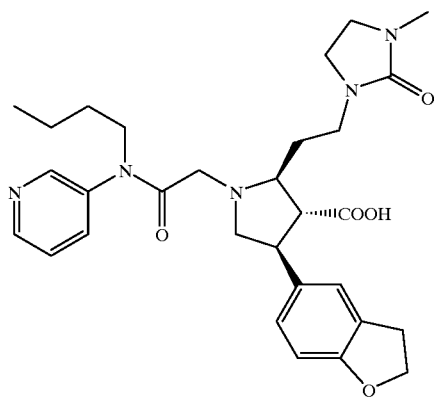

TABLE 3C-continued
791
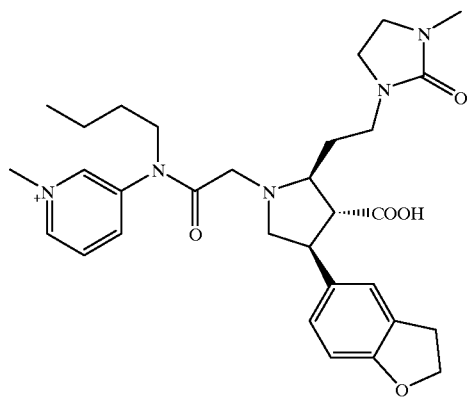
792
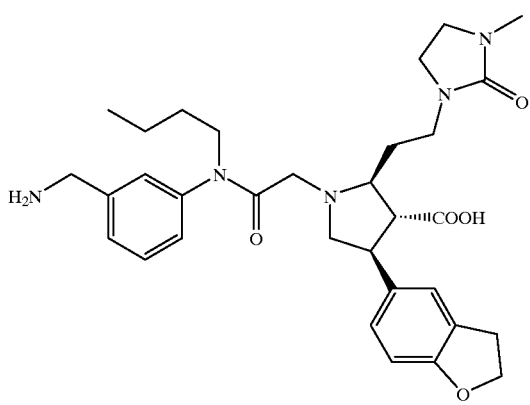
793
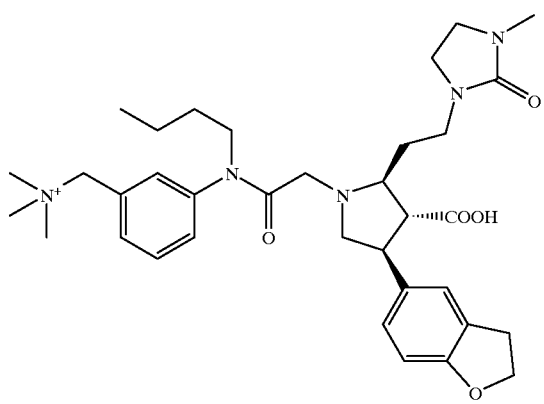

TABLE 3C-continued
794
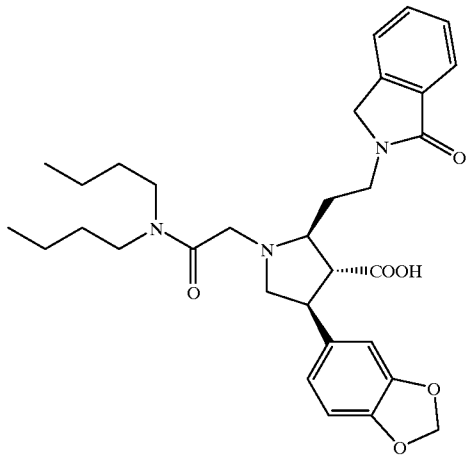
795
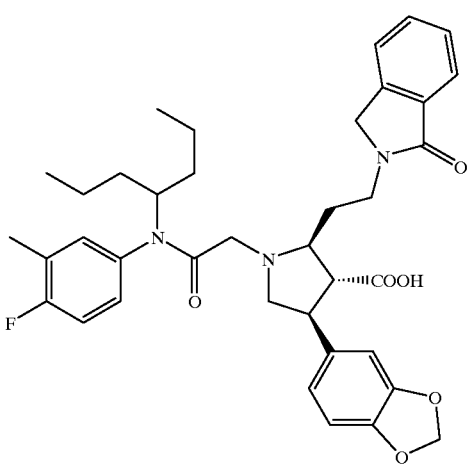
796
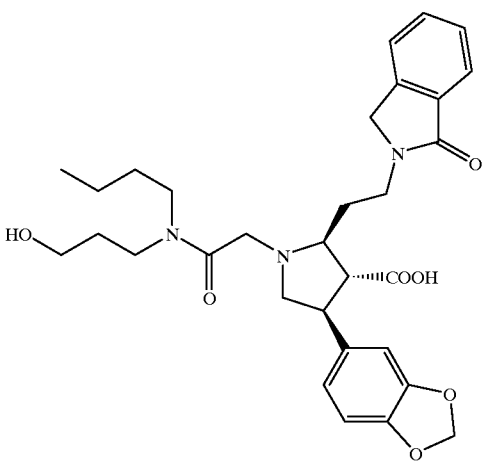

TABLE 3C-continued
797
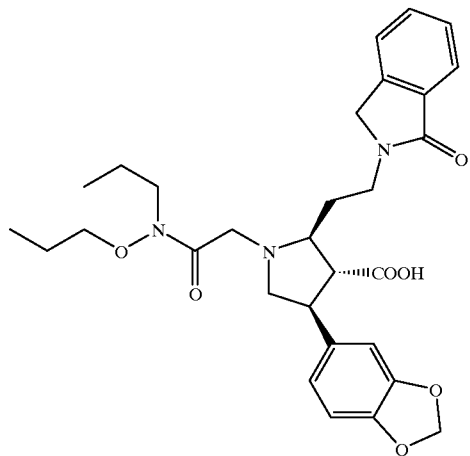
798
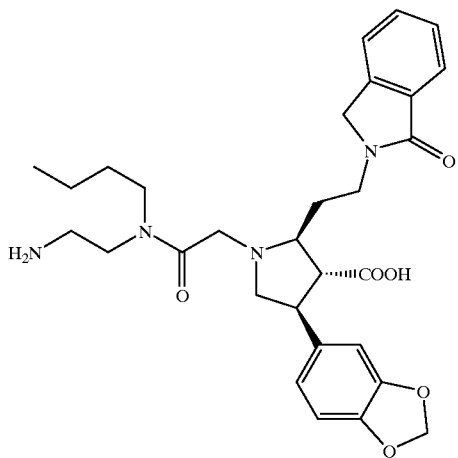
799
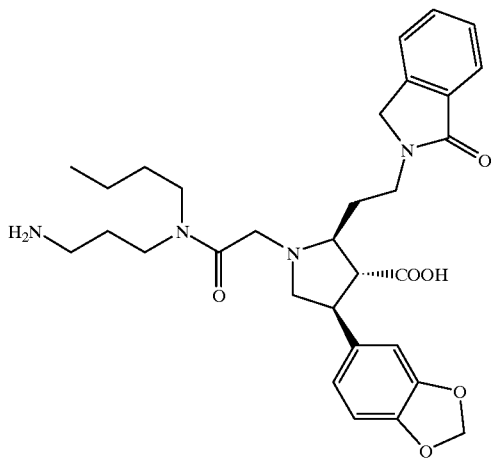

TABLE 3C-continued
800
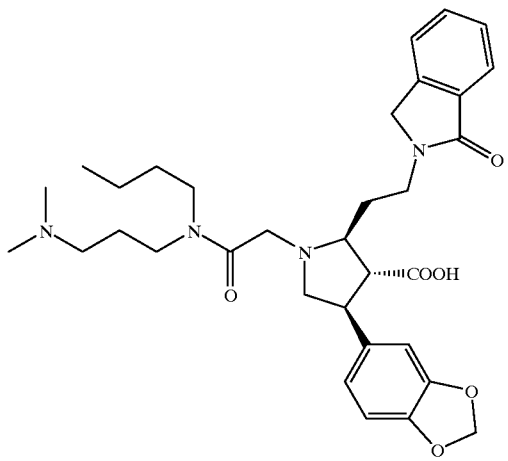
801
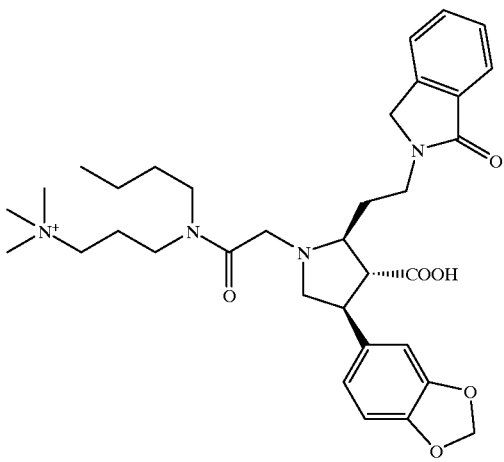
802
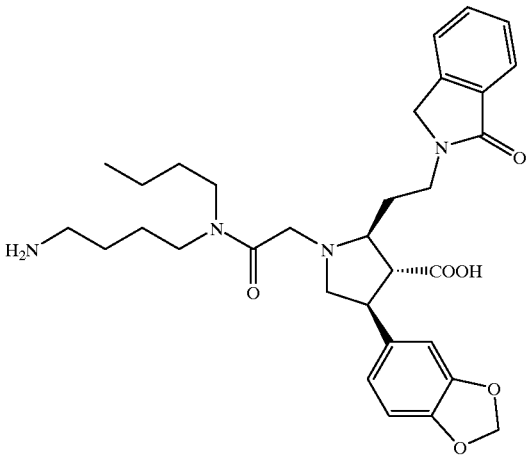

TABLE 3C-continued
803
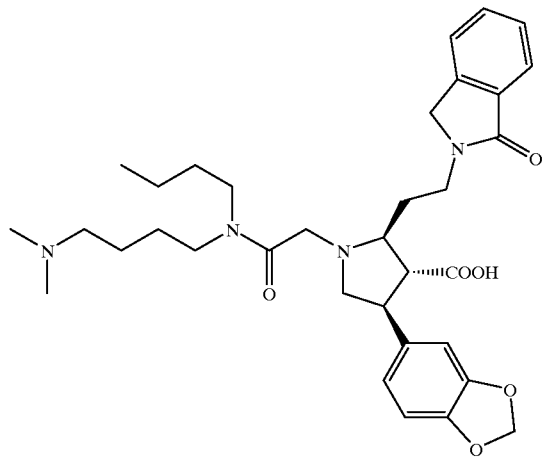
804
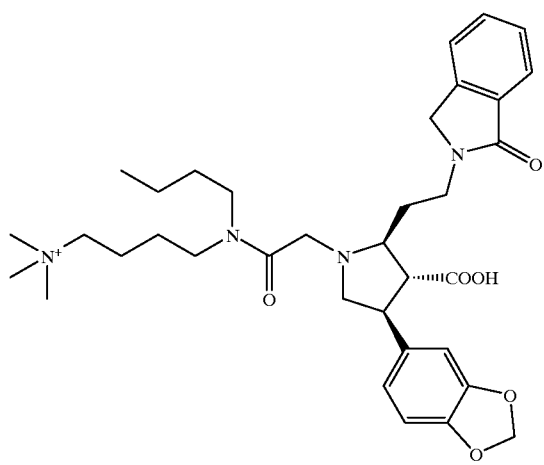
805
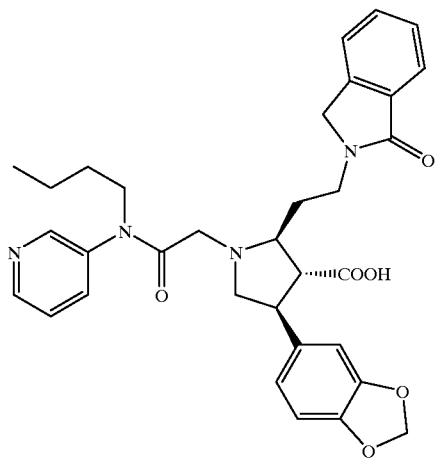

TABLE 3C-continued
806
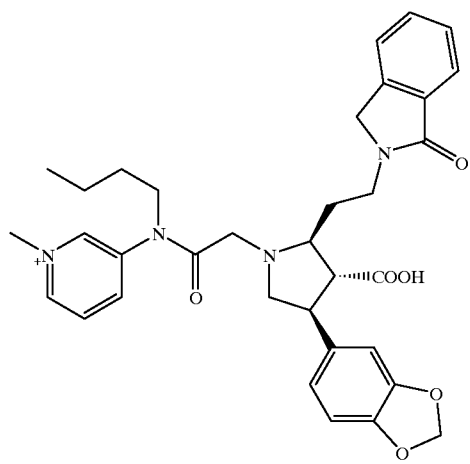
807
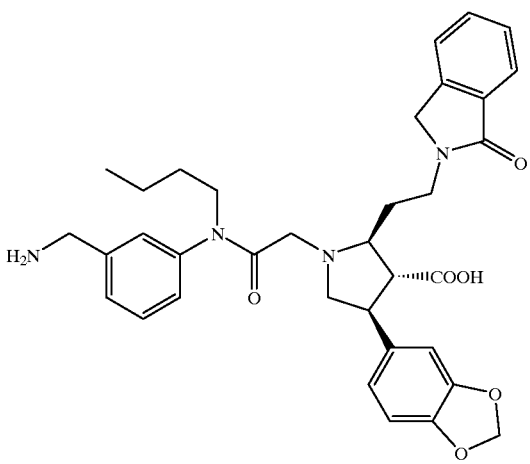
808
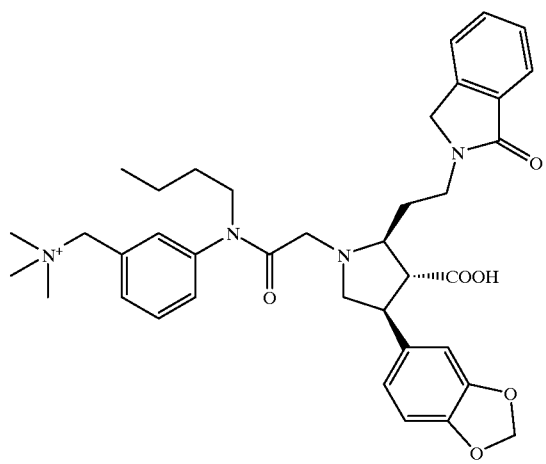

TABLE 3C-continued
809
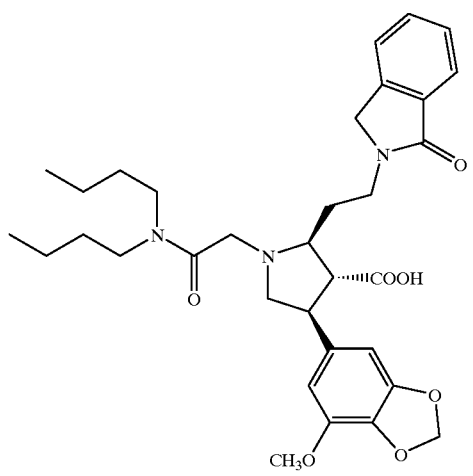
810
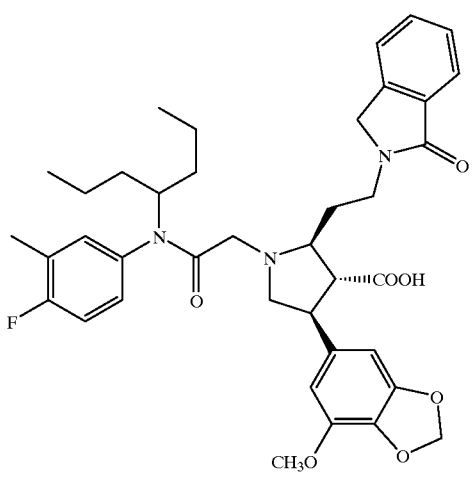
811
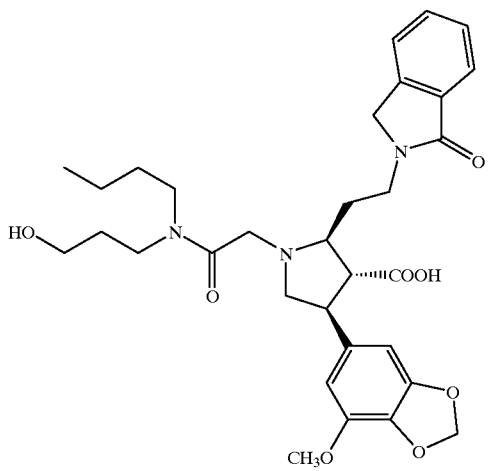

TABLE 3C-continued
812
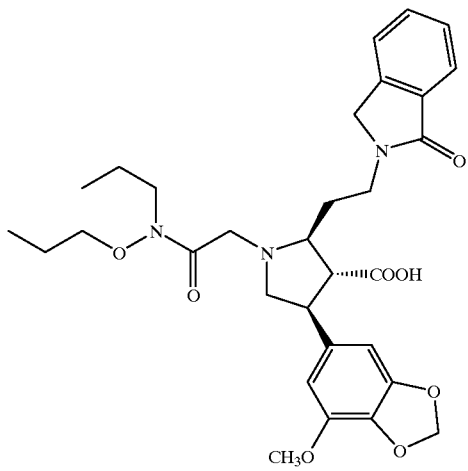
813
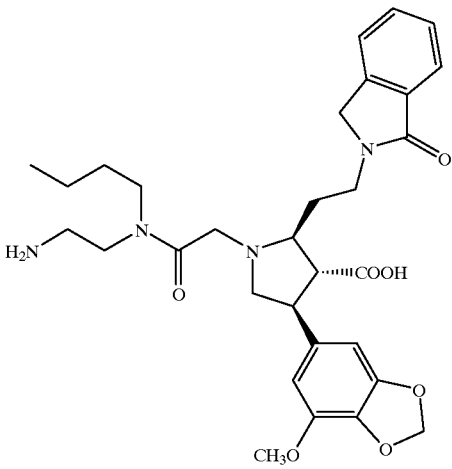
814
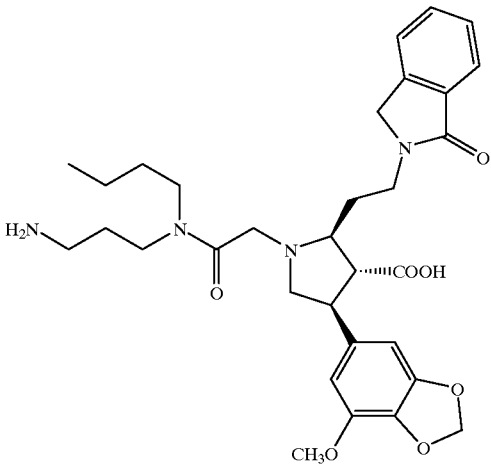

TABLE 3C-continued
815
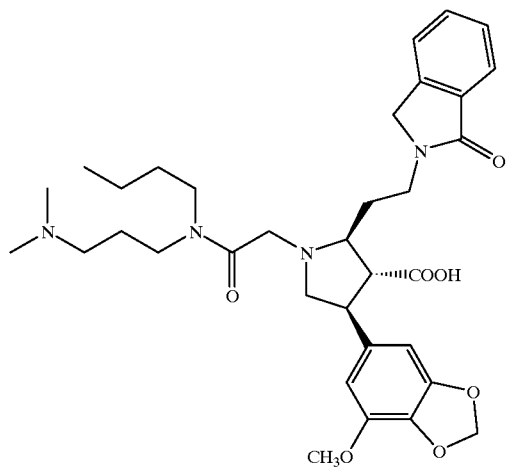
816
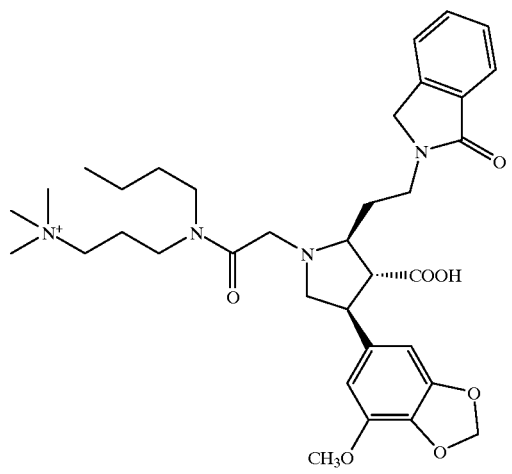
817
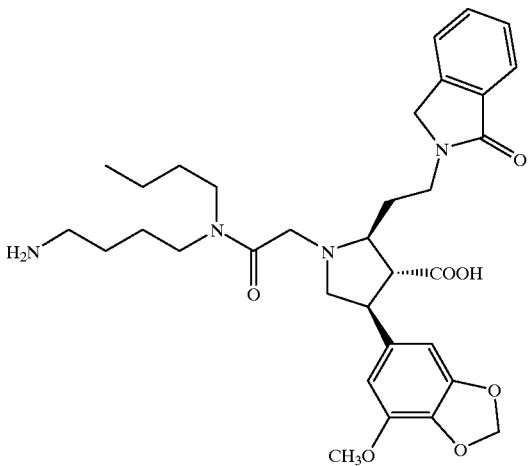

TABLE 3C-continued
818
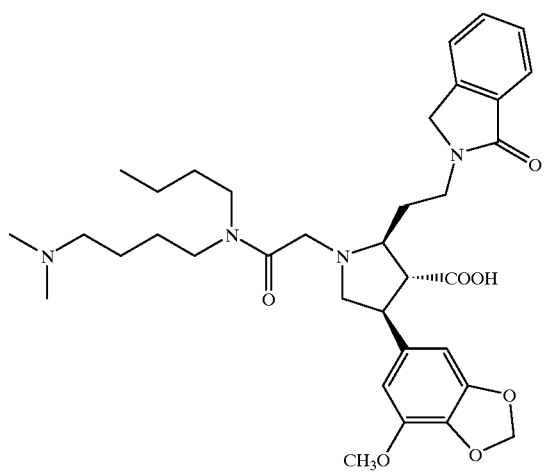
819
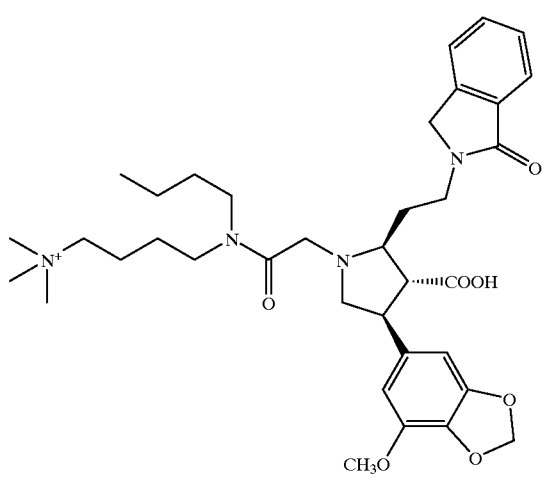
820
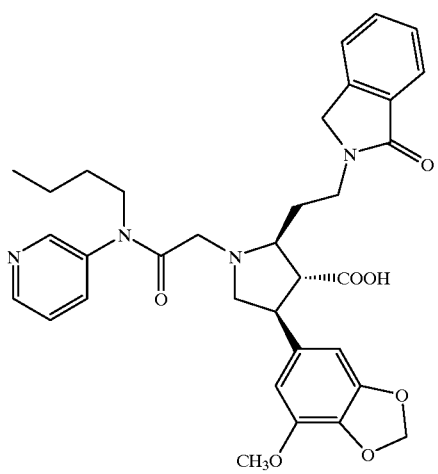

TABLE 3C-continued
821
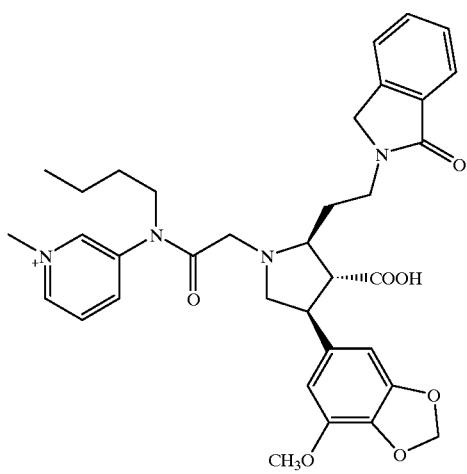
822
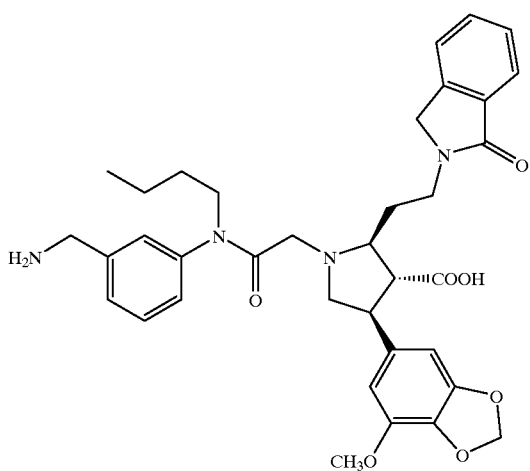
823
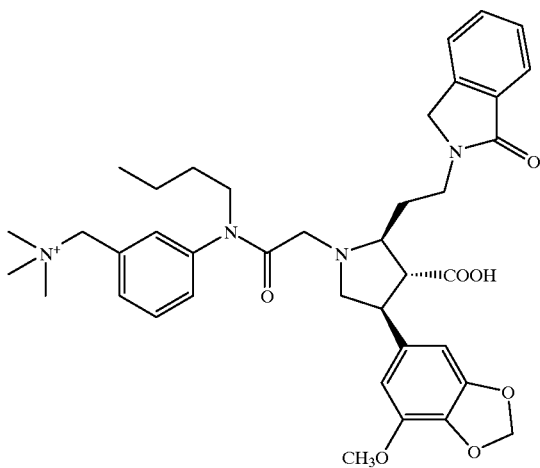

TABLE 3C-continued
824
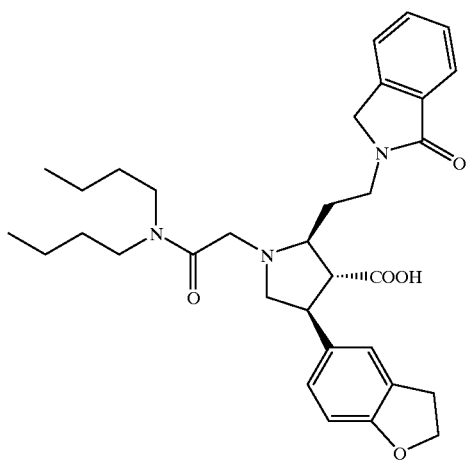
825
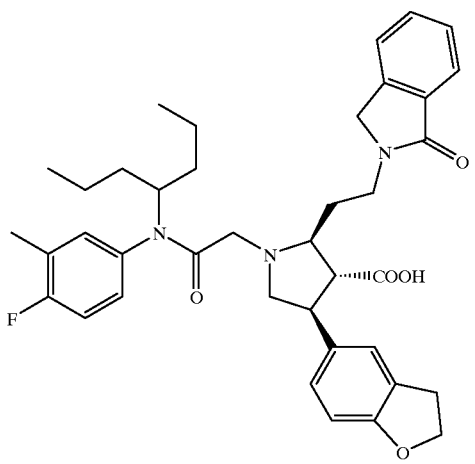
826
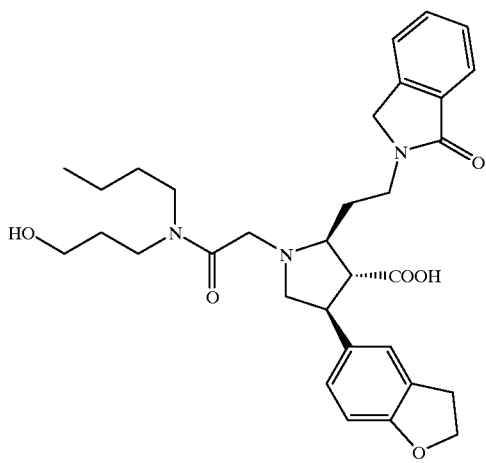

TABLE 3C-continued
827 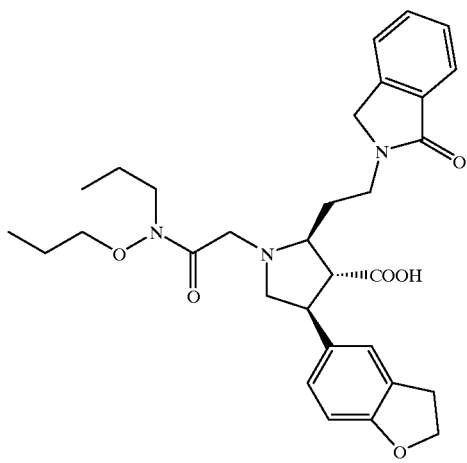
828 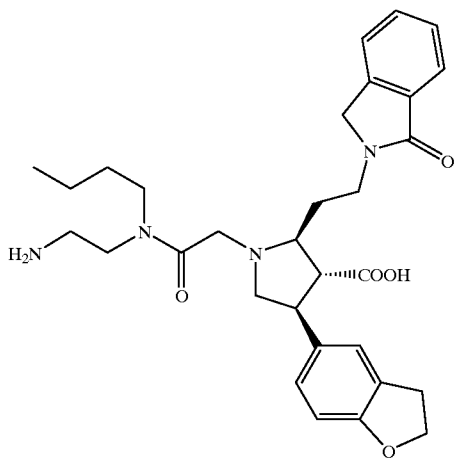
829 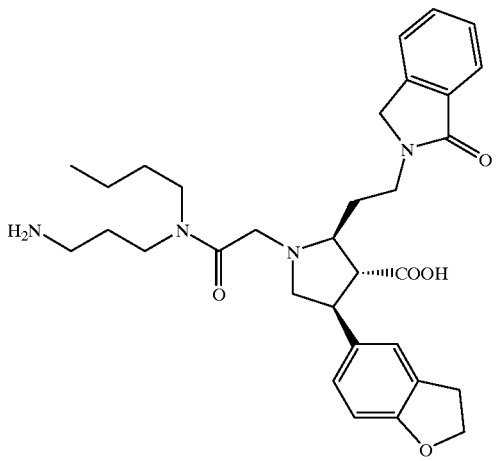

TABLE 3C-continued
830
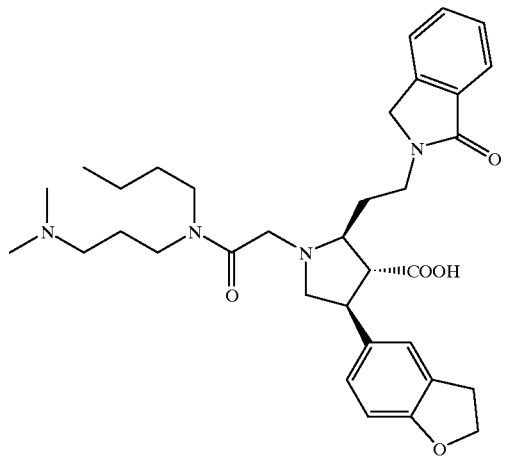
831
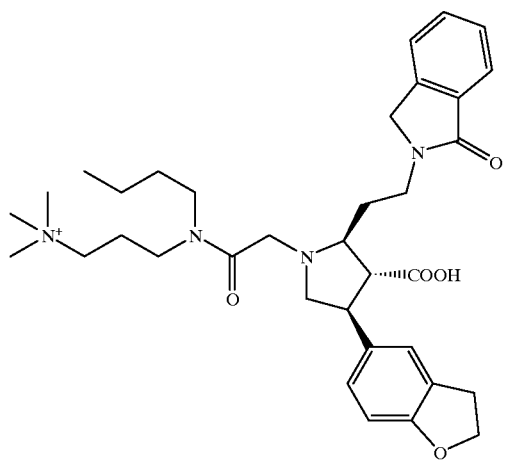
832
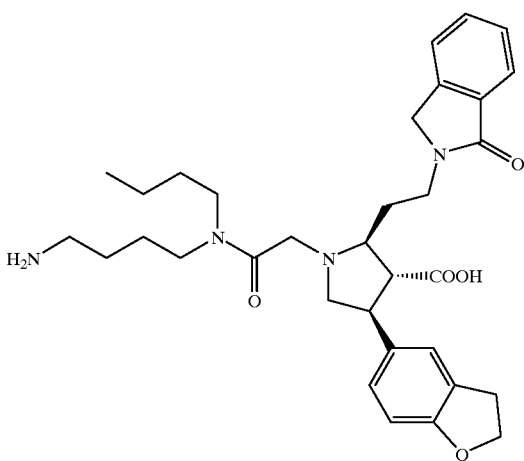

TABLE 3C-continued
833
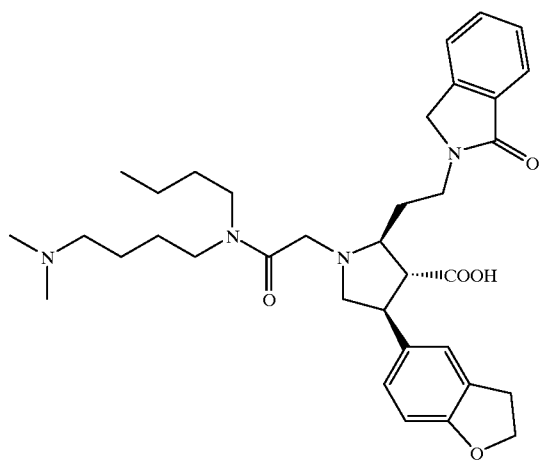
834
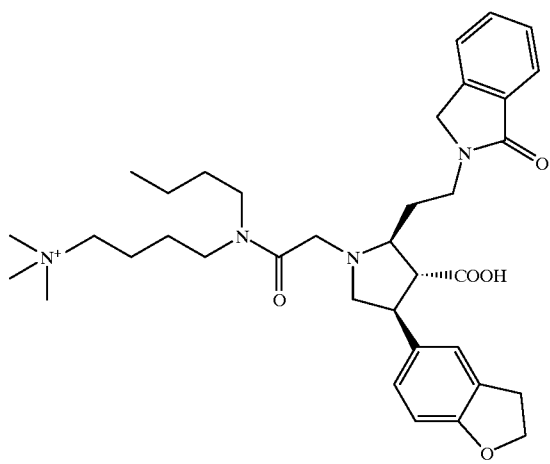
835
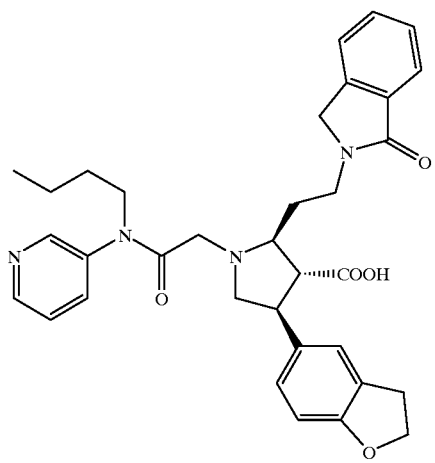

TABLE 3C-continued
836
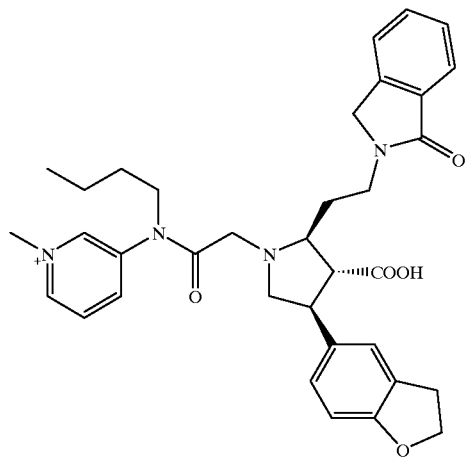
837
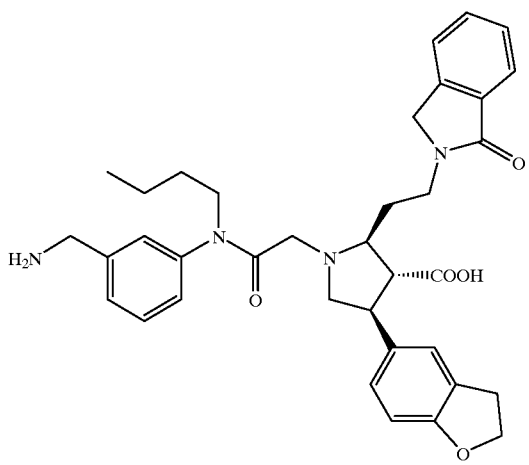
838
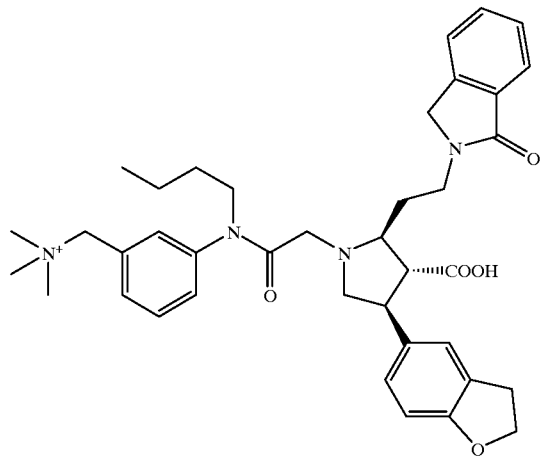

TABLE 3C-continued
839
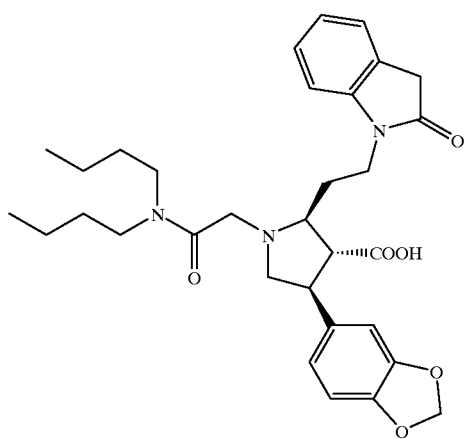
840
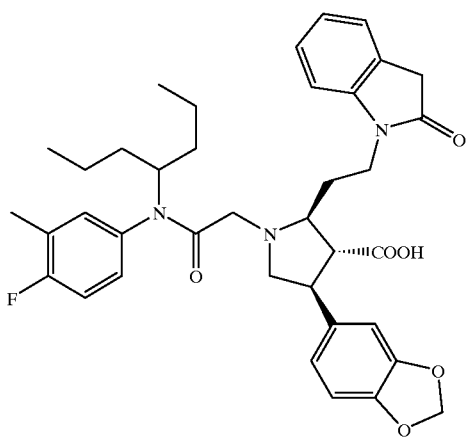
841
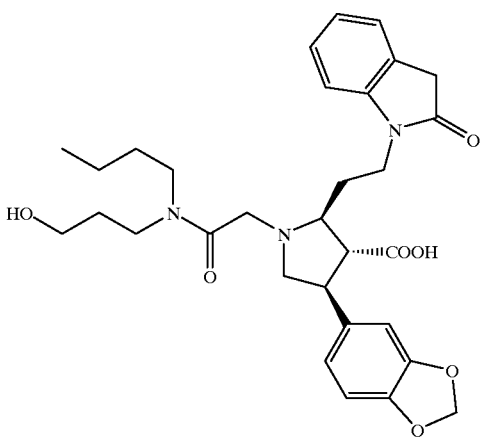

TABLE 3C-continued
842
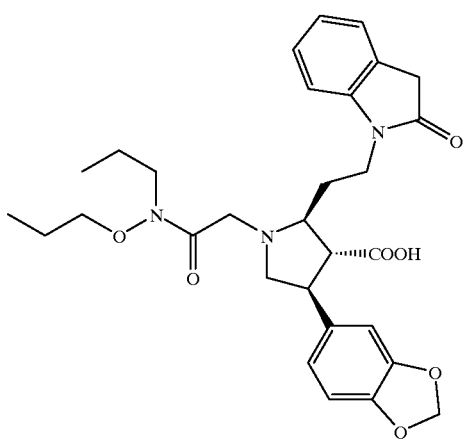
843
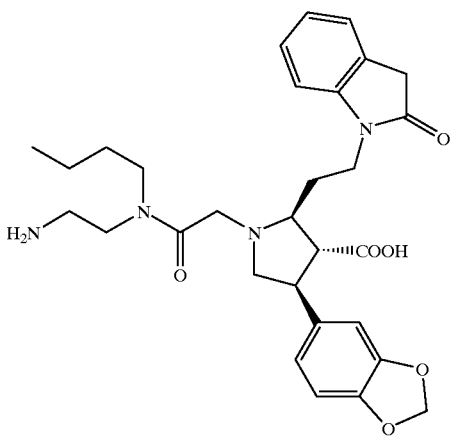
844
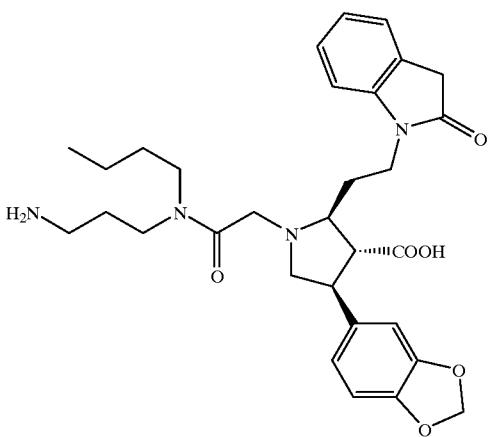

TABLE 3C-continued
845
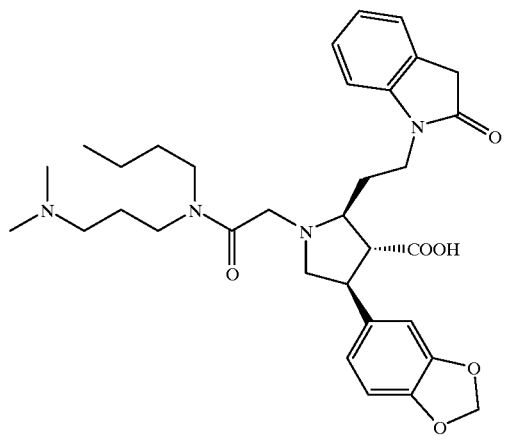
846
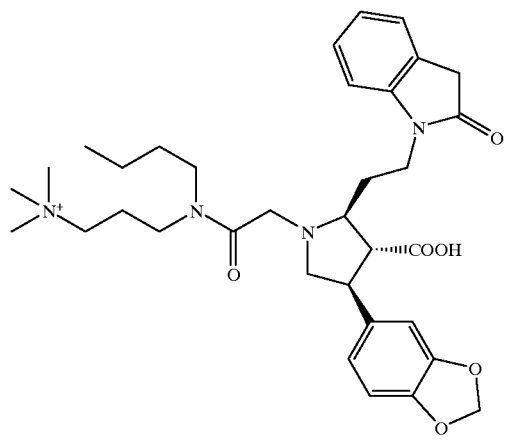
847
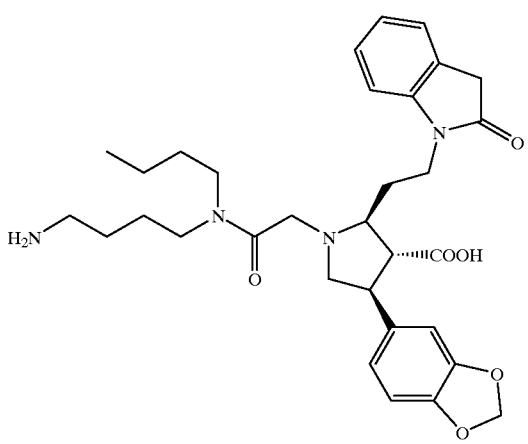

TABLE 3C-continued
848
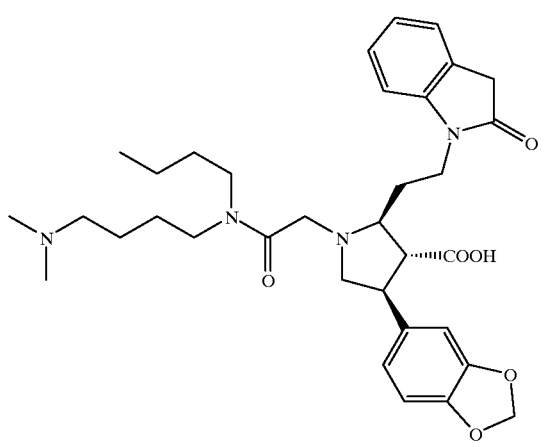
849
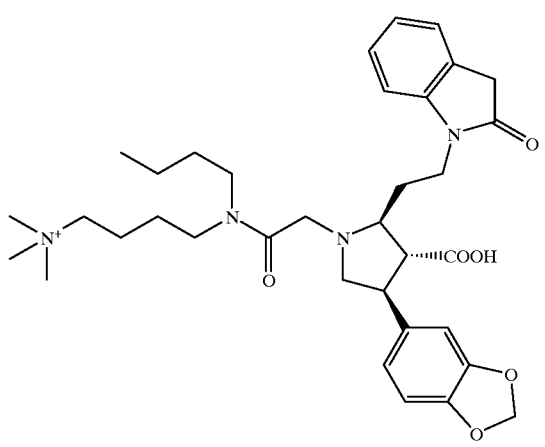
850
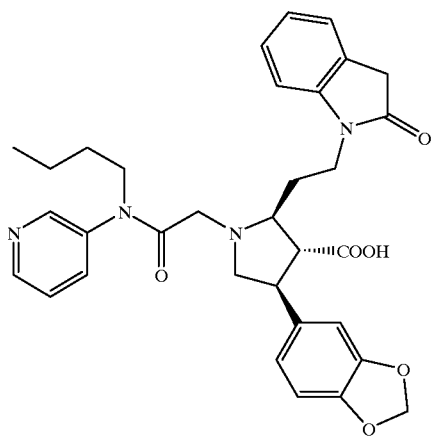

TABLE 3C-continued
851 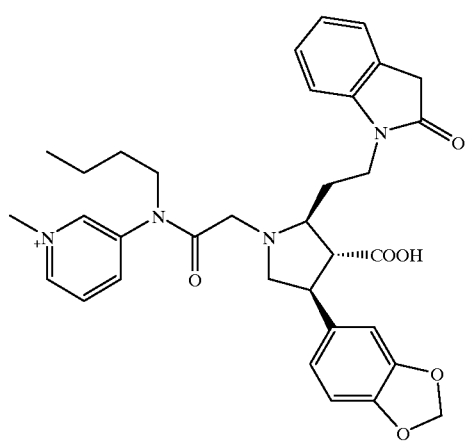
852 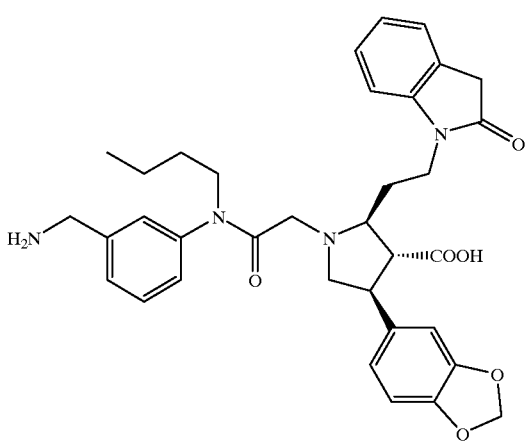
853 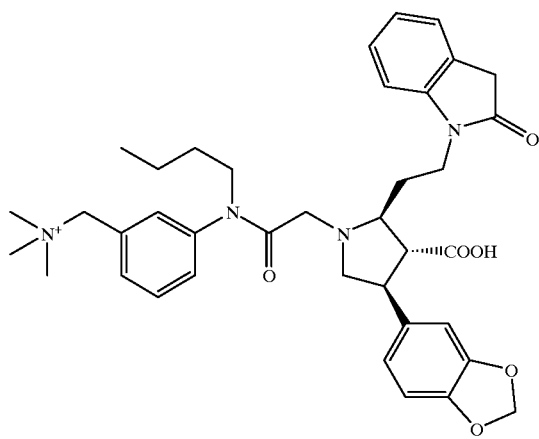

TABLE 3C-continued
854
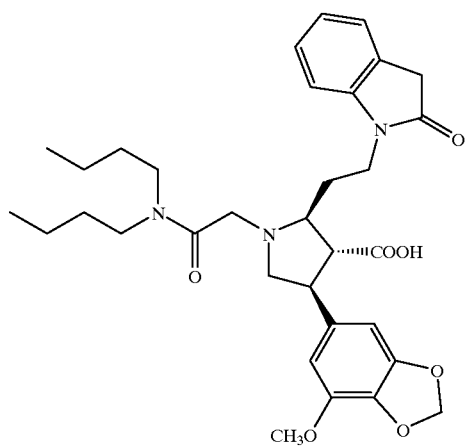
855
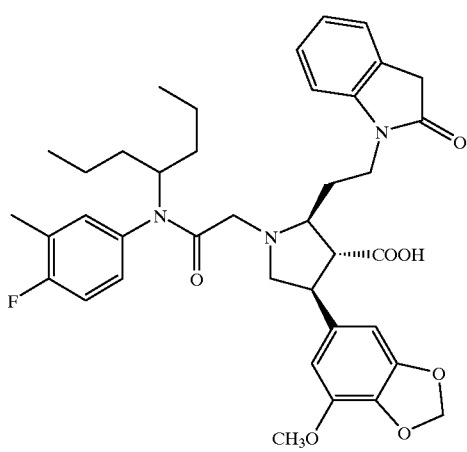
856
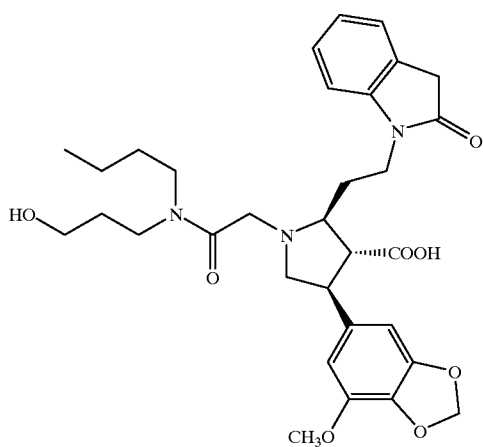

TABLE 3C-continued
857
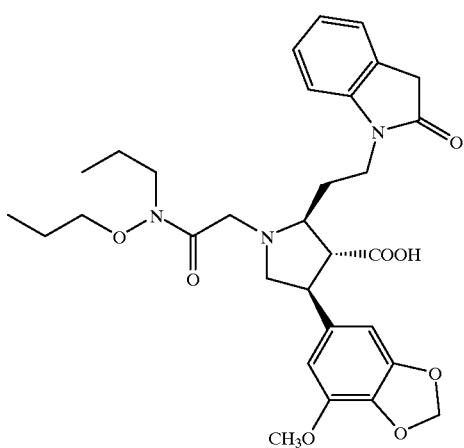
858
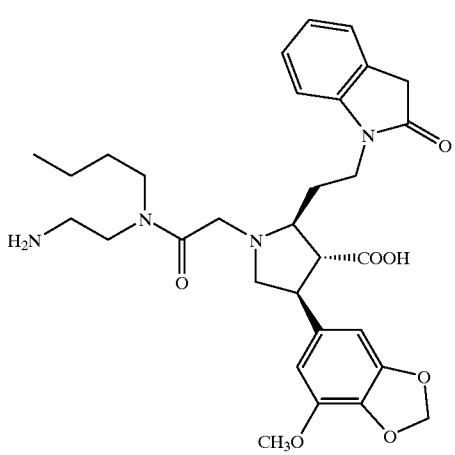
859
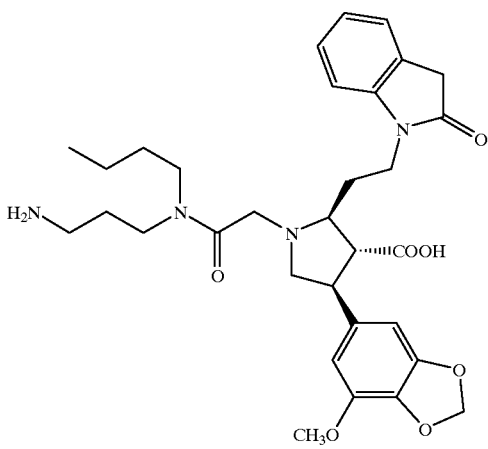

TABLE 3C-continued
860
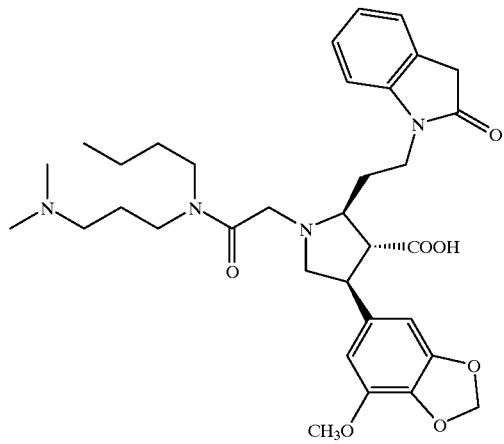
861
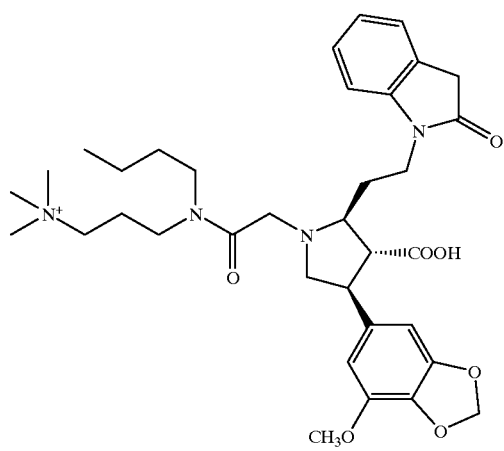
862
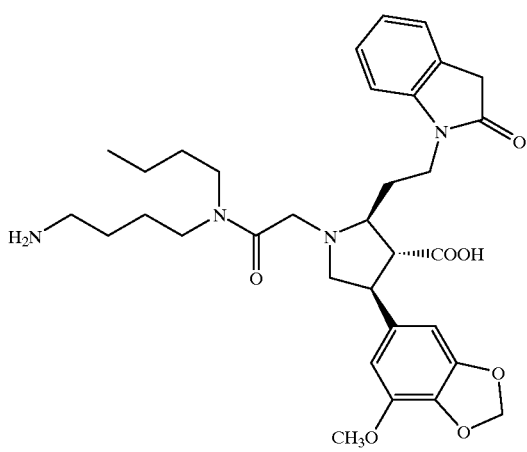

TABLE 3C-continued
863
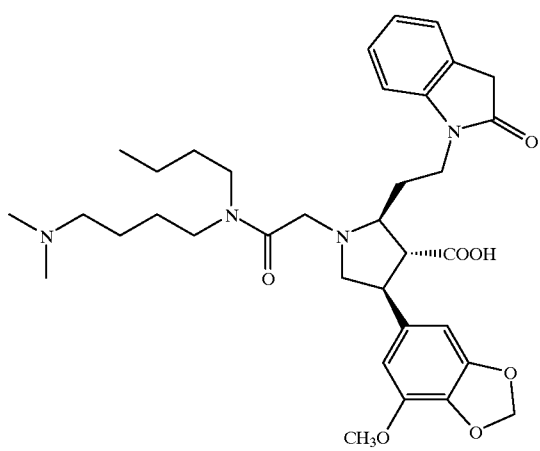
864
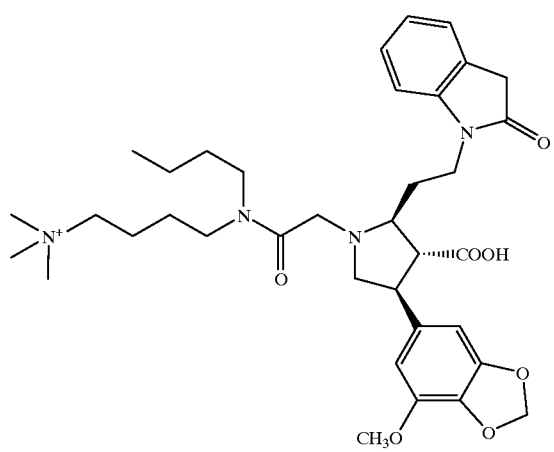
865
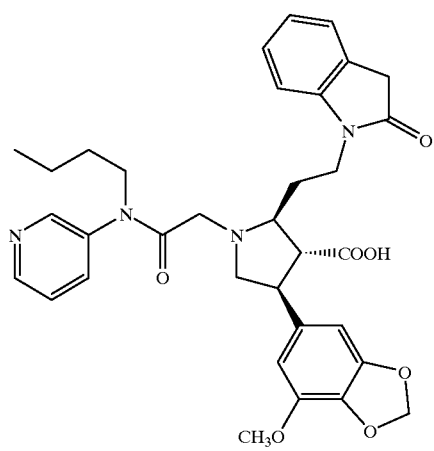

TABLE 3C-continued
866
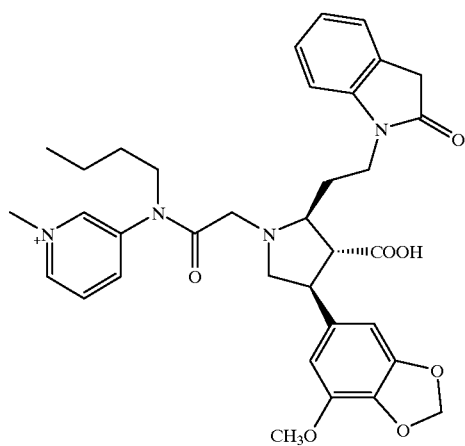
867
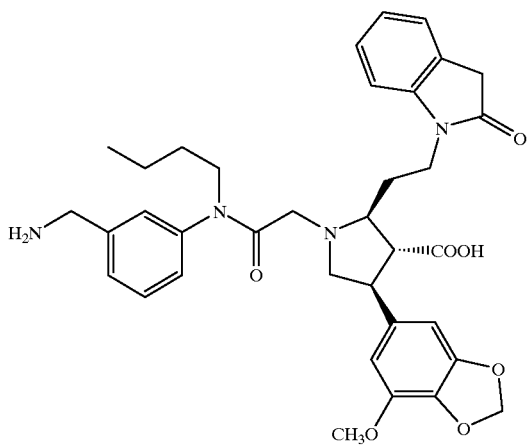
868
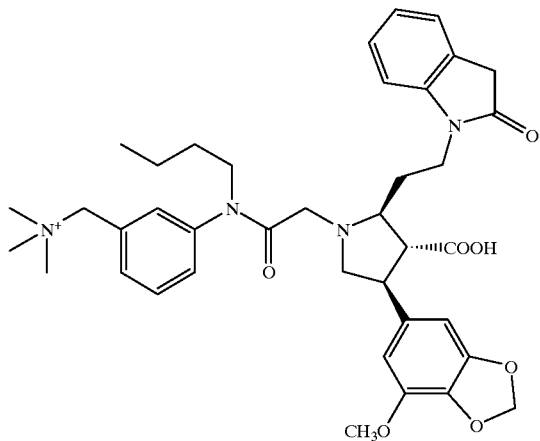

TABLE 3C-continued
869
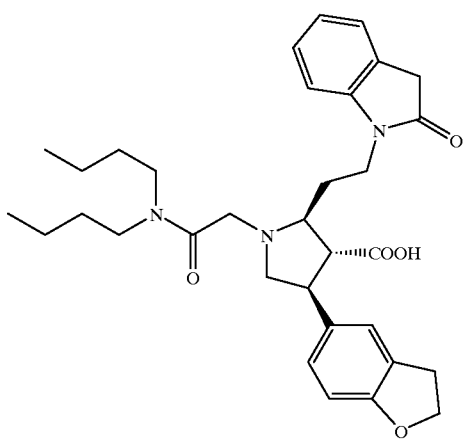
870
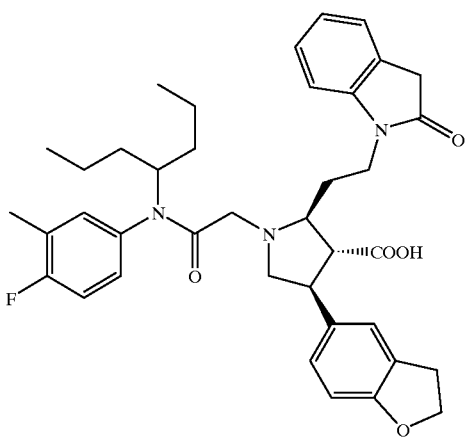
871
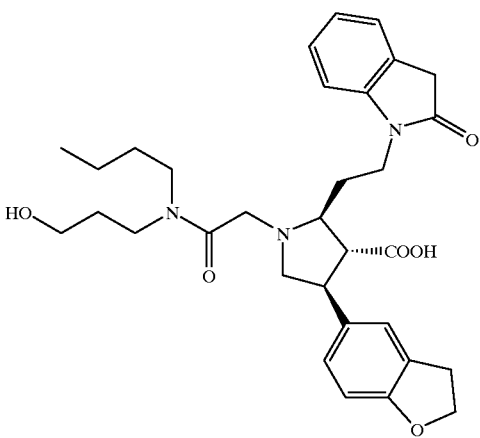

TABLE 3C-continued
872
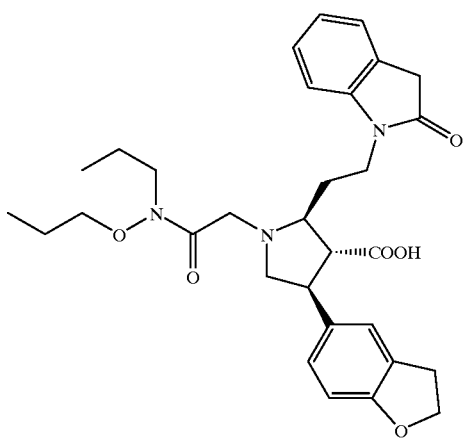
873
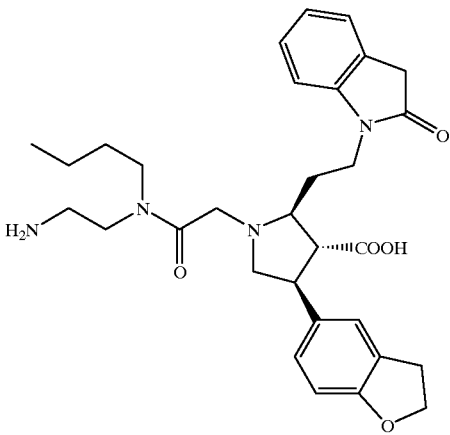
874
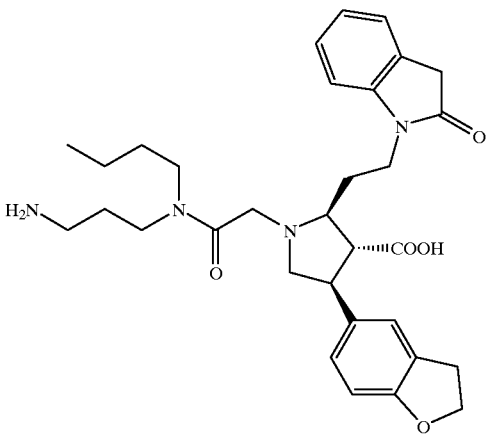

TABLE 3C-continued
875
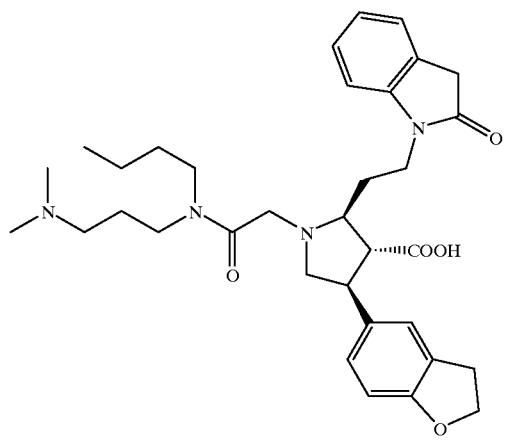
876
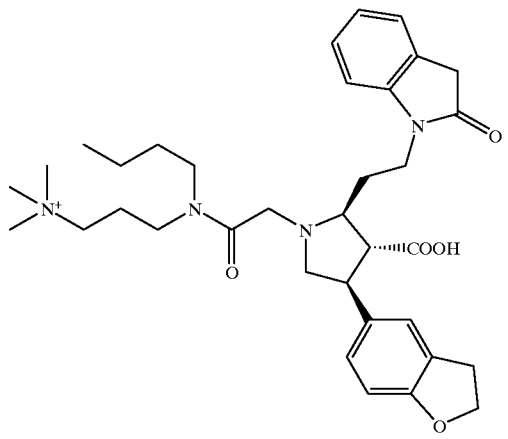
877
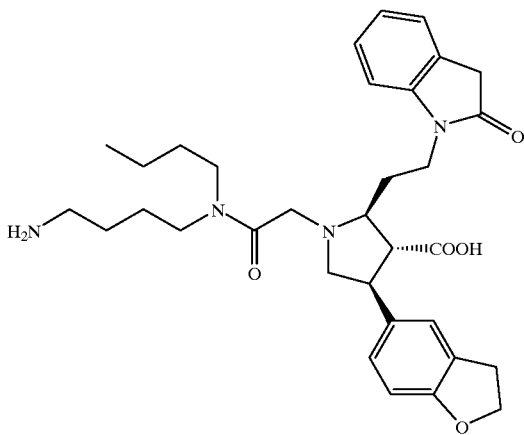

TABLE 3C-continued
878
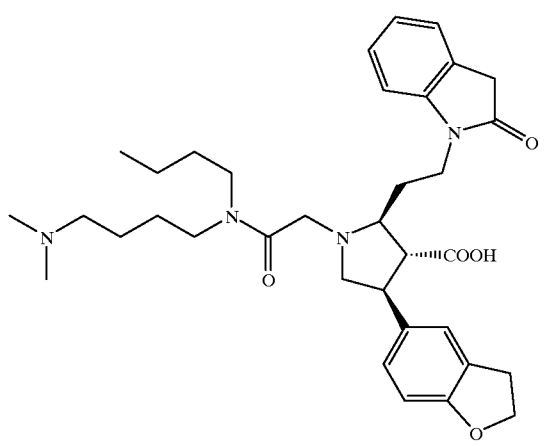
879
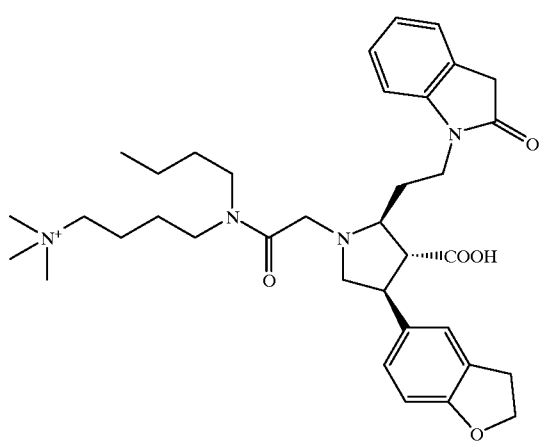
880
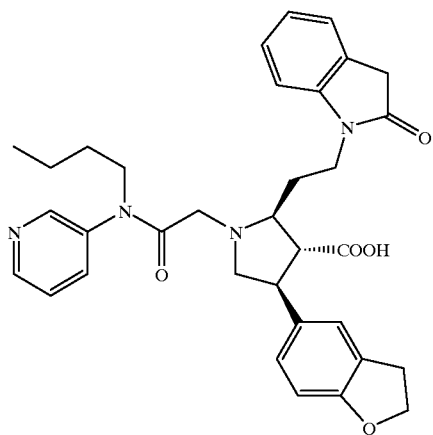

TABLE 3C-continued
881
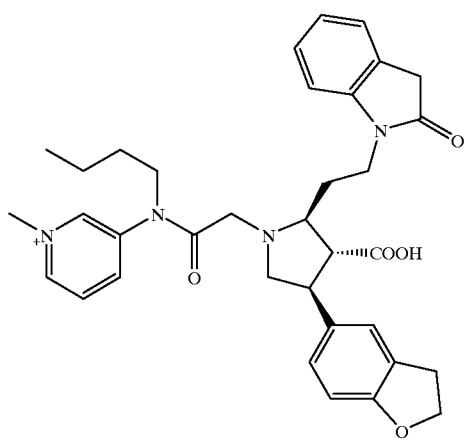
882
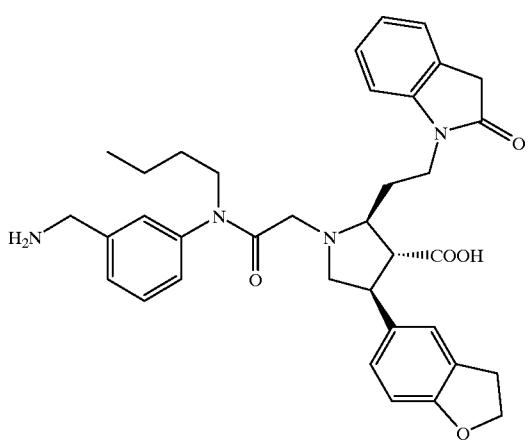
883
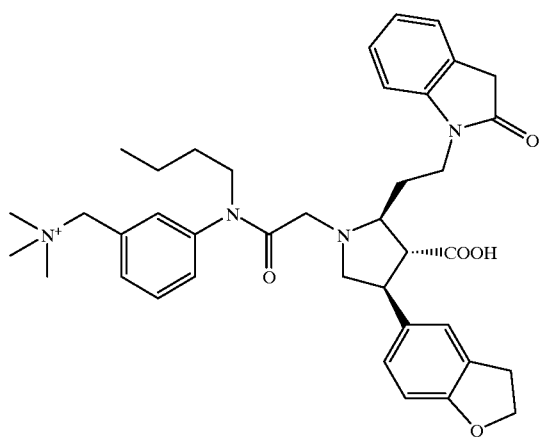

TABLE 3C-continued
884
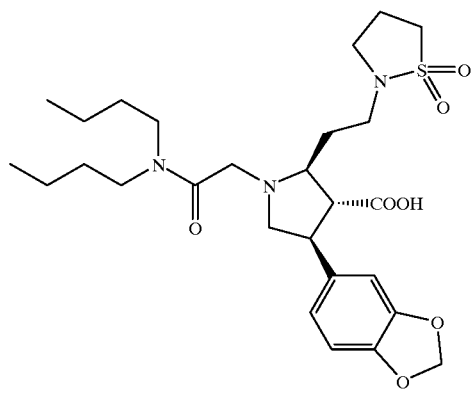
885
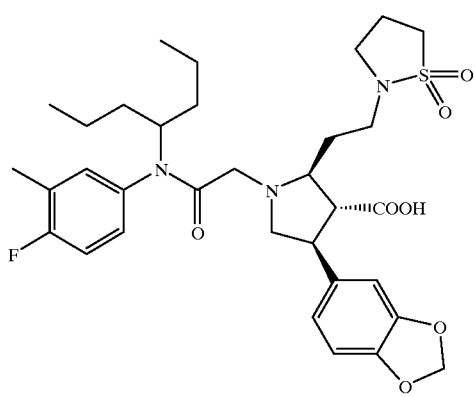
886
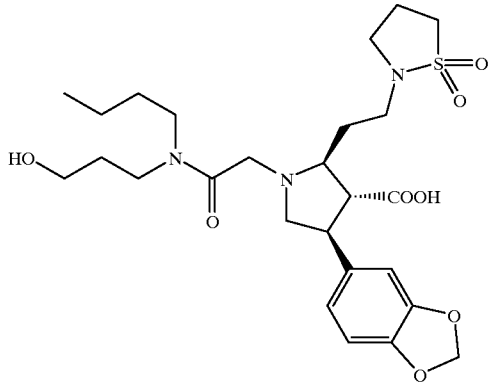
887
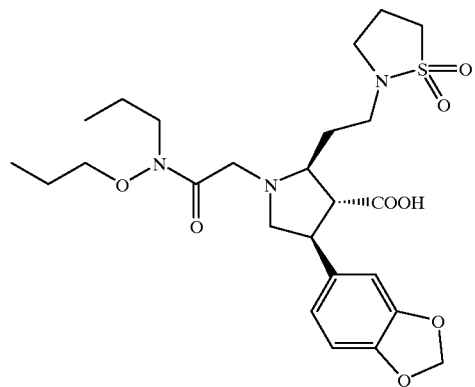

TABLE 3C-continued
888
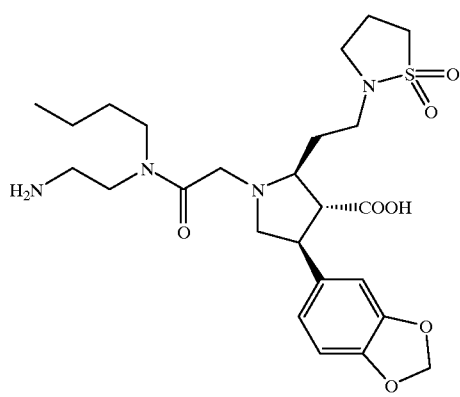
889
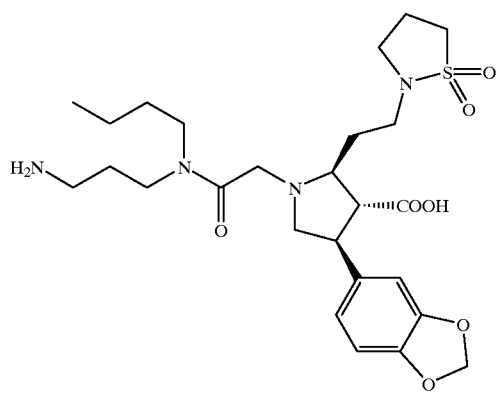
890
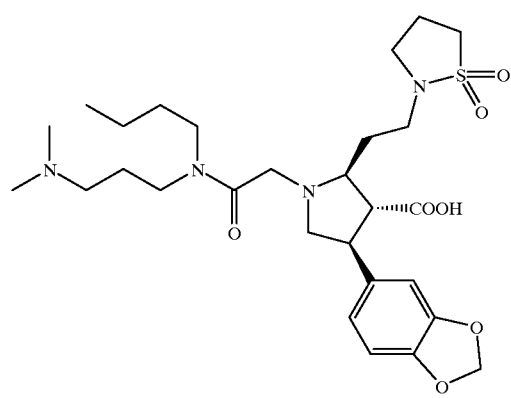
891
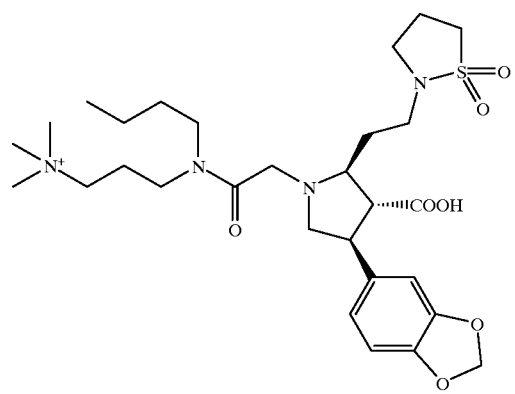

TABLE 3C-continued
892 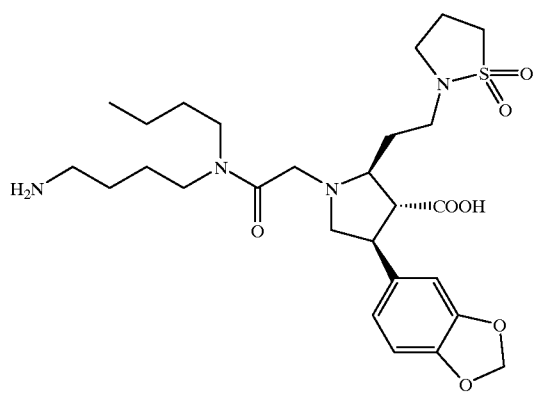
893 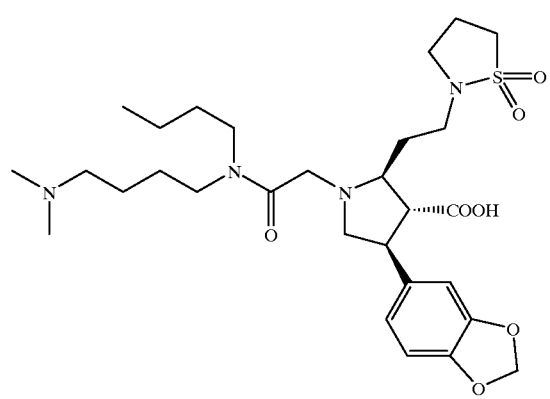
894 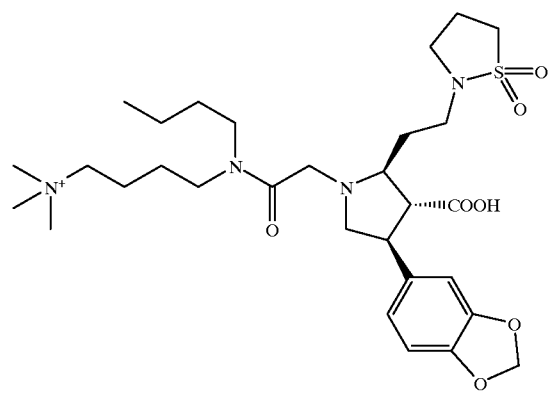
895 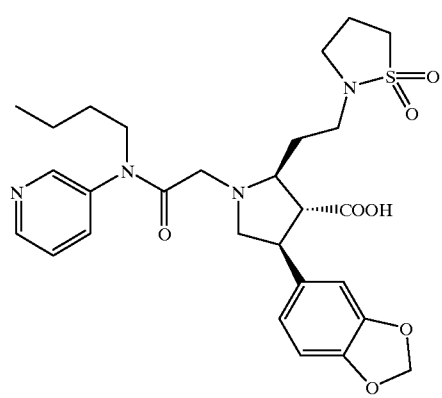

TABLE 3C-continued
896
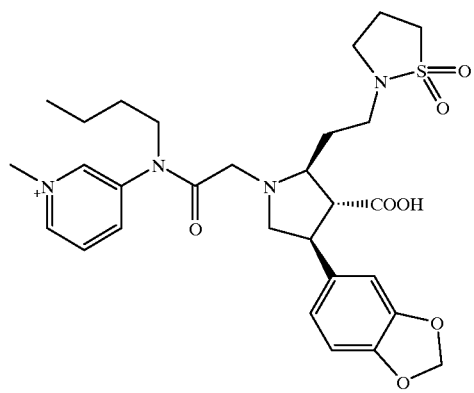
897
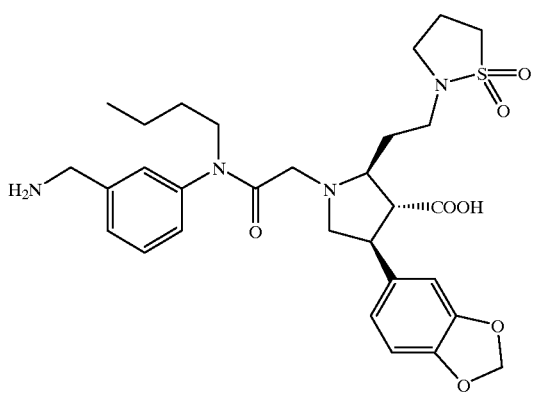
898
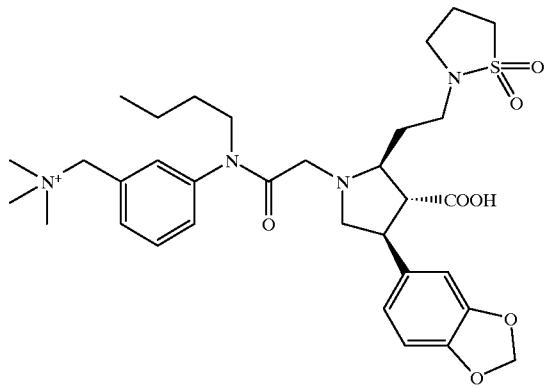
899
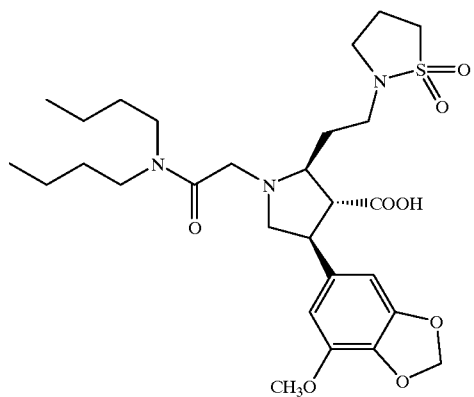

TABLE 3C-continued
900
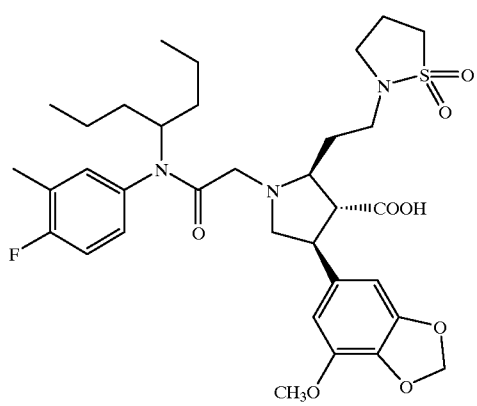
901
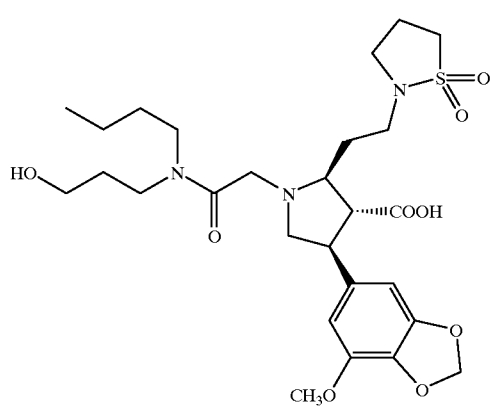
902
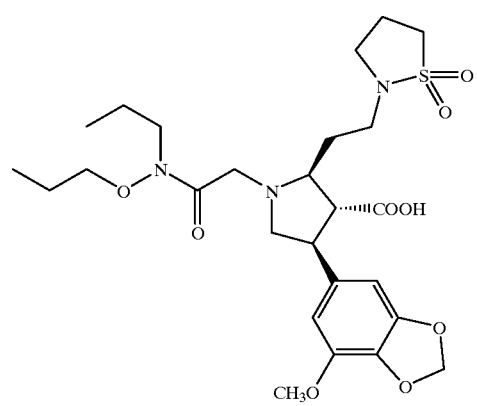
903
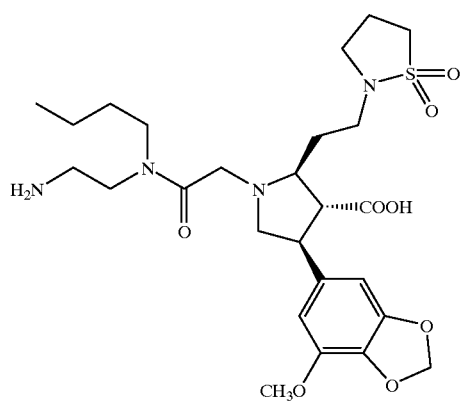

TABLE 3C-continued
904
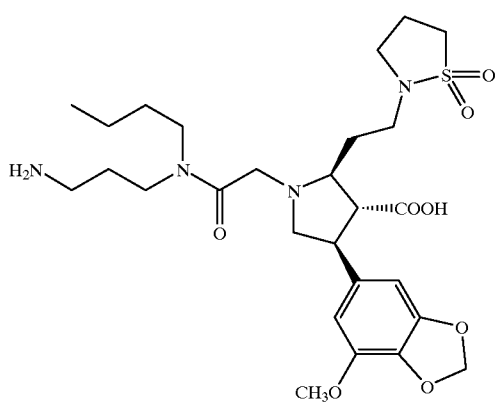
905
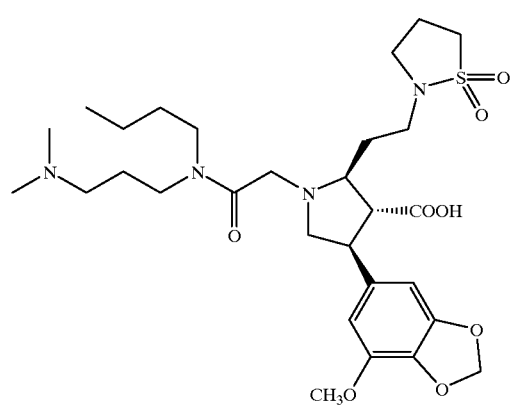
906
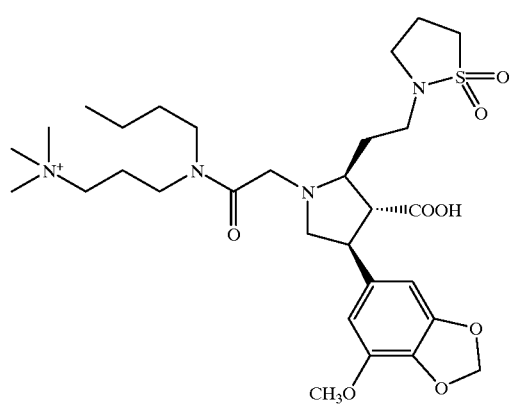

TABLE 3C-continued
907
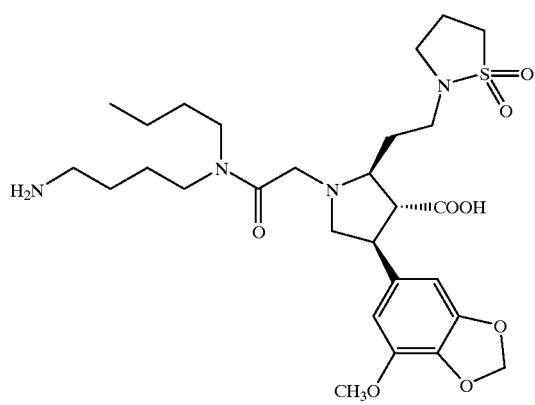
908
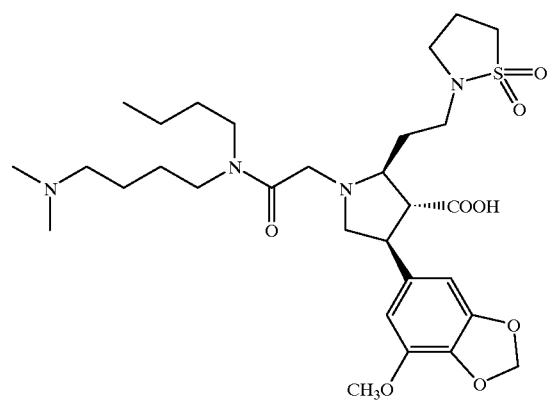
909
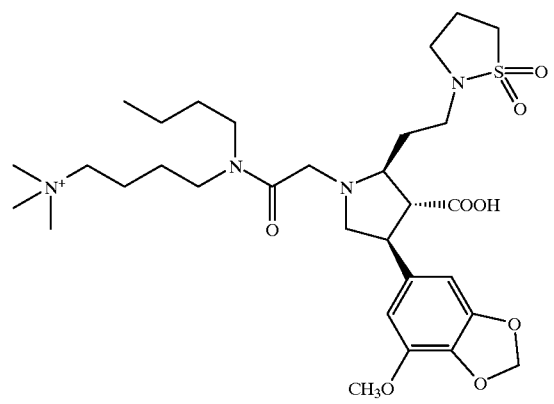

TABLE 3C-continued
910 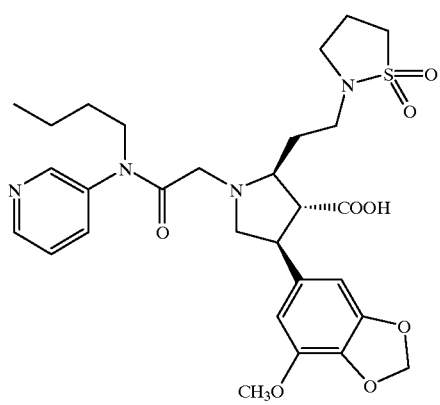
911 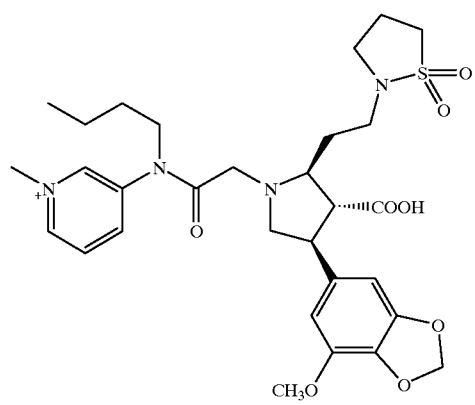
912 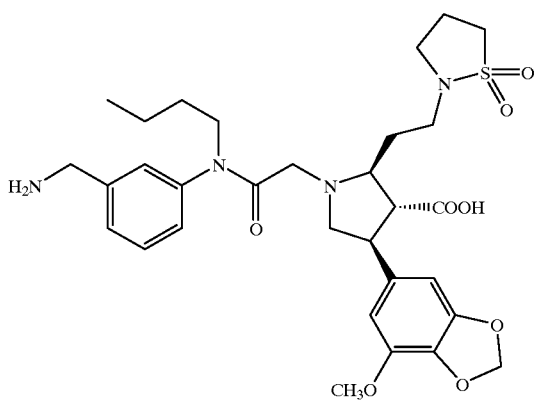
913 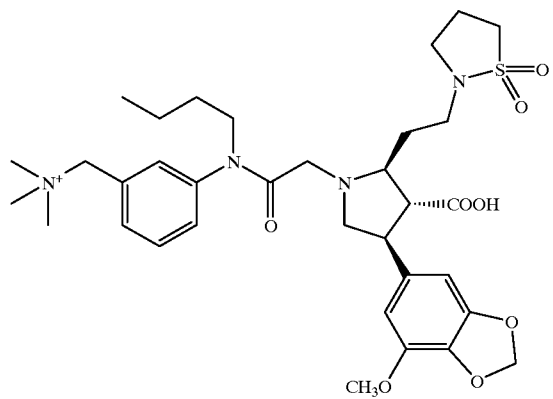

TABLE 3C-continued
914 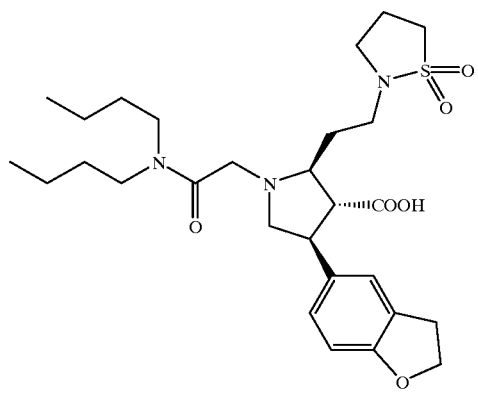
915 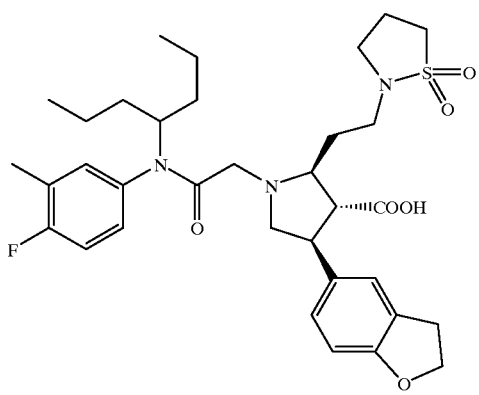
916 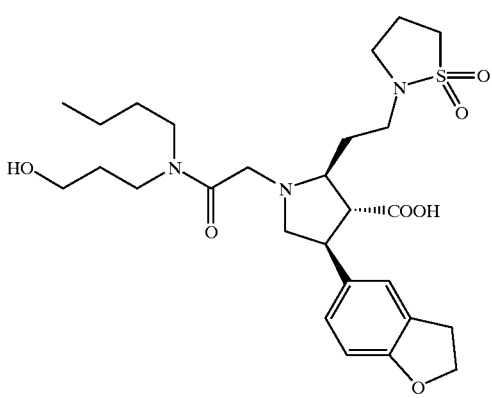
917 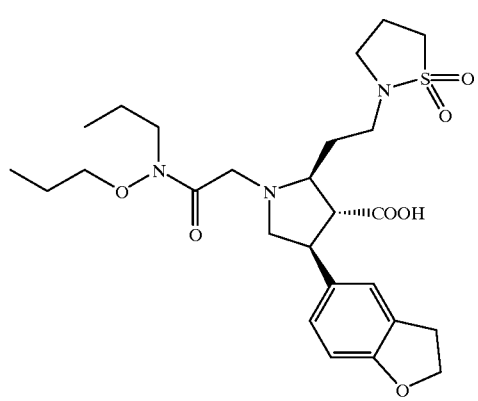

TABLE 3C-continued
918
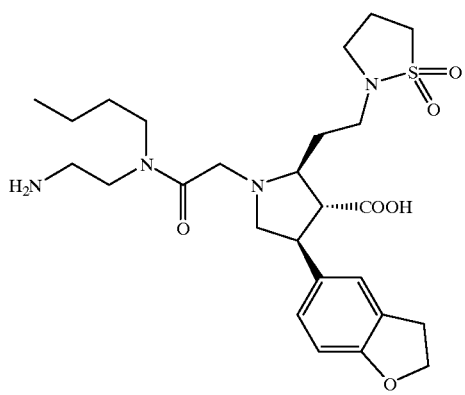
919
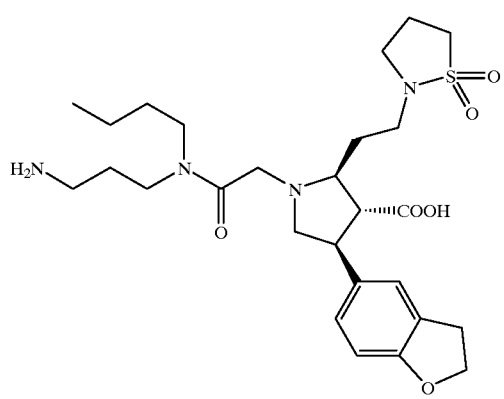
920
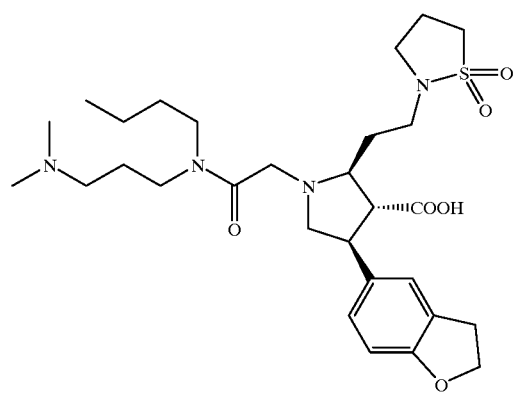
921
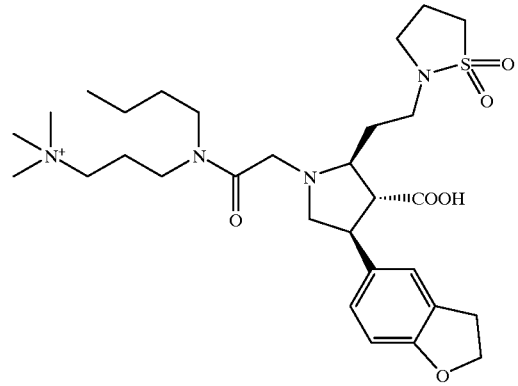

TABLE 3C-continued
922
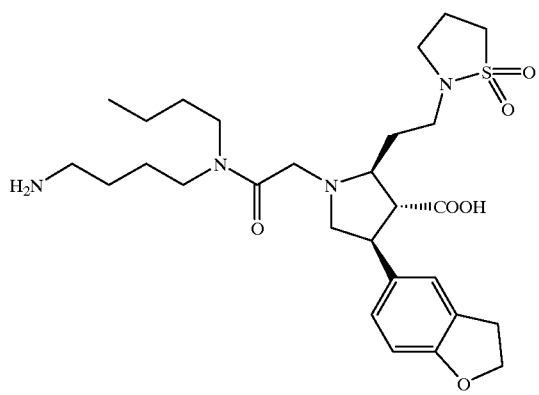
923
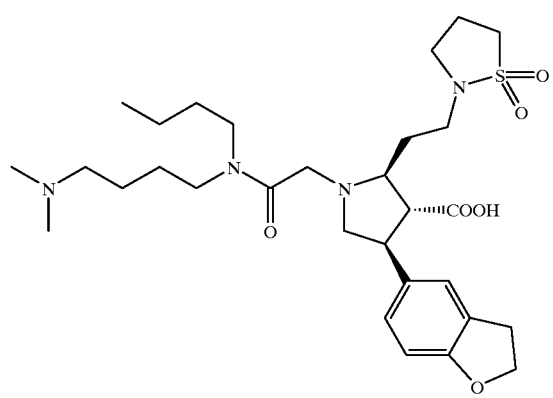
924
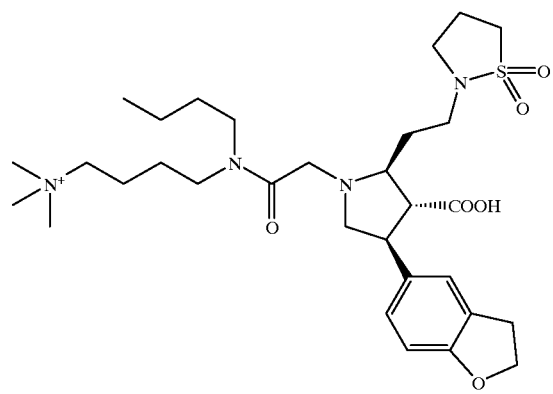
925
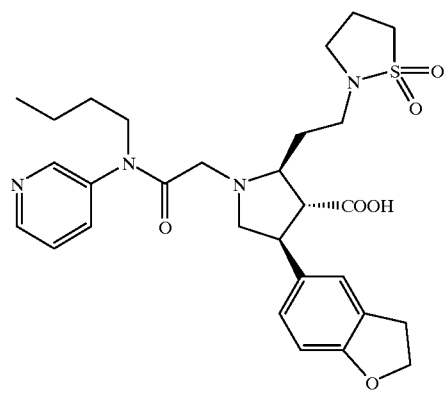

TABLE 3C-continued
926
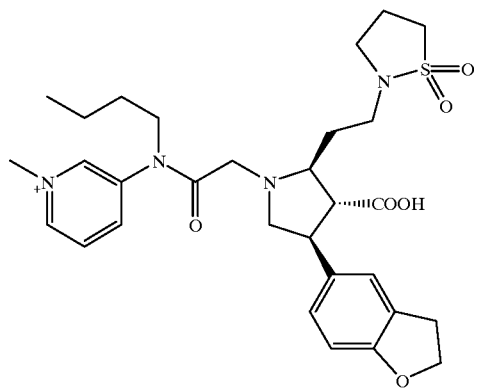
927
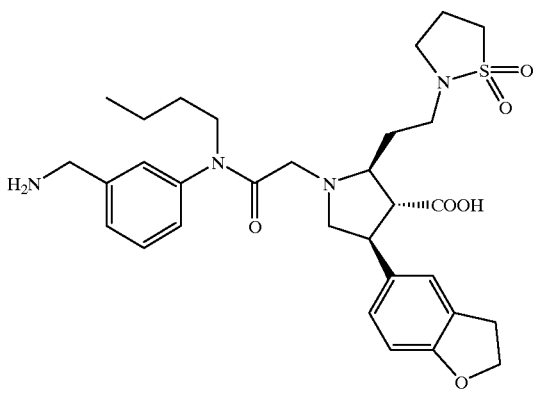
928
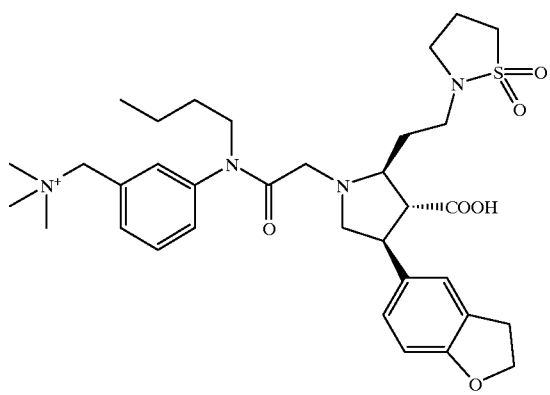
929
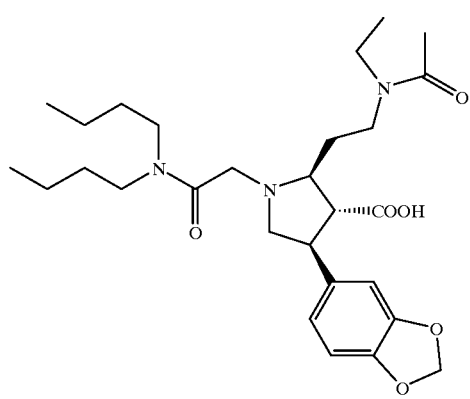

TABLE 3C-continued
930
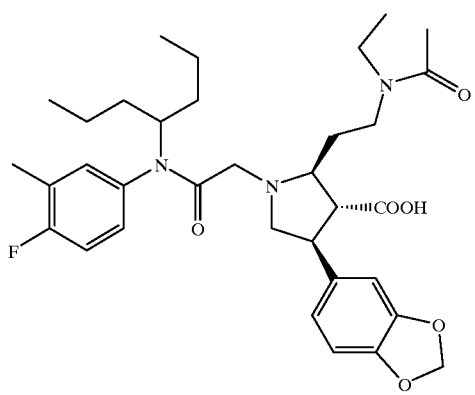
931
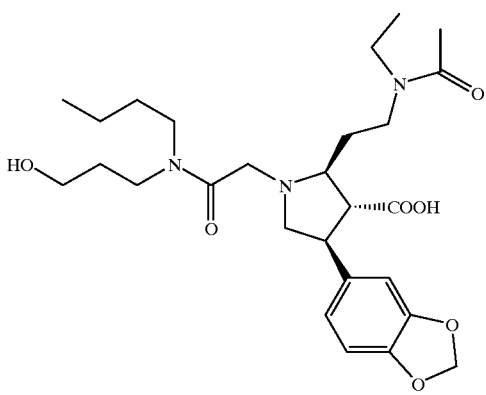
932
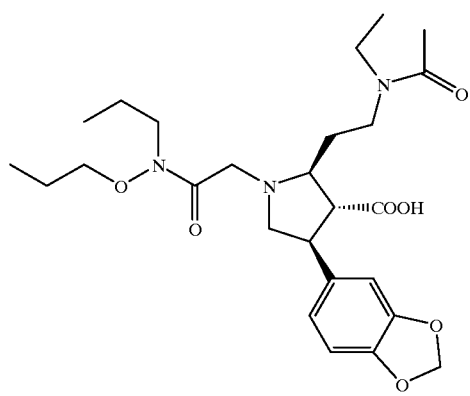
933
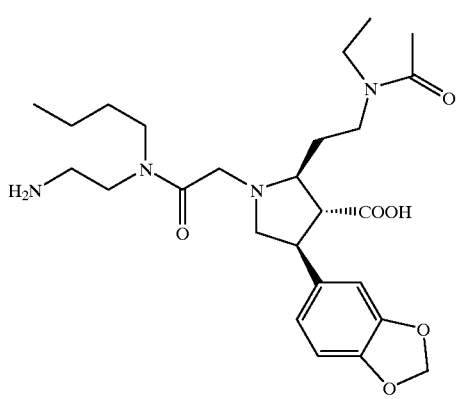

TABLE 3C-continued
934
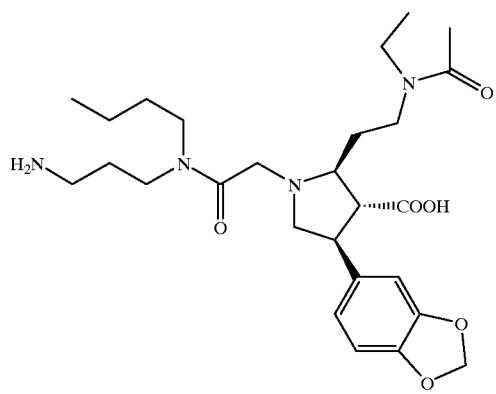
935
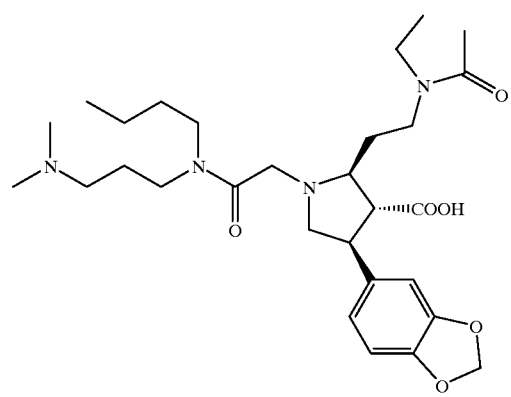
936
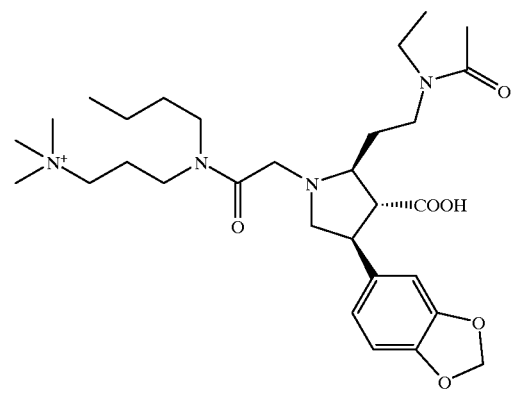
937
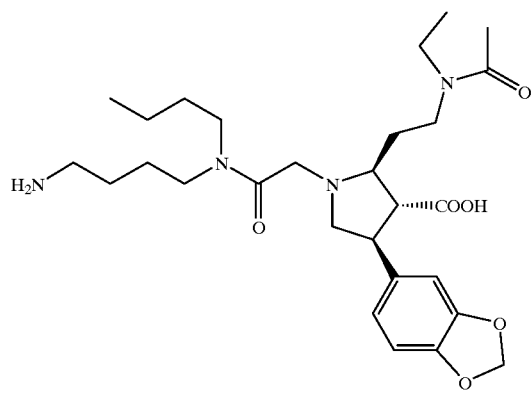

TABLE 3C-continued
938
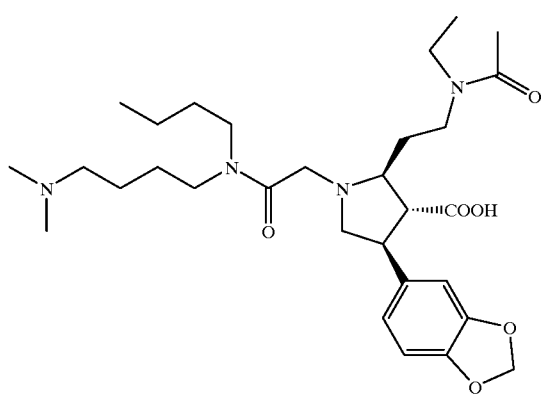
939
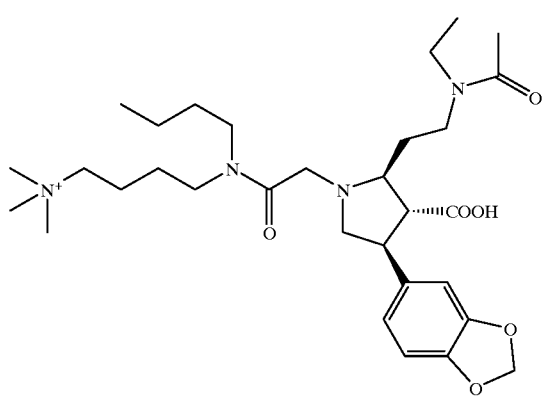
940
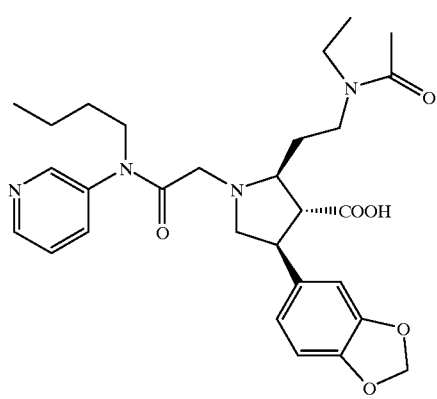
941
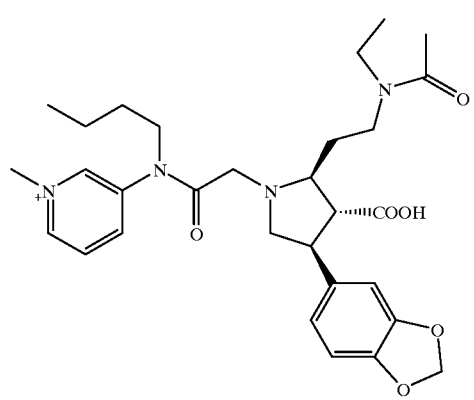

TABLE 3C-continued
942
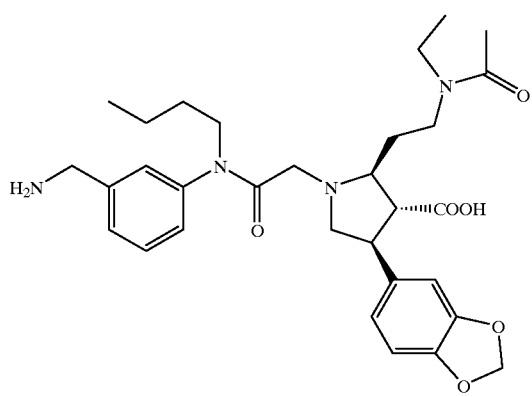
943
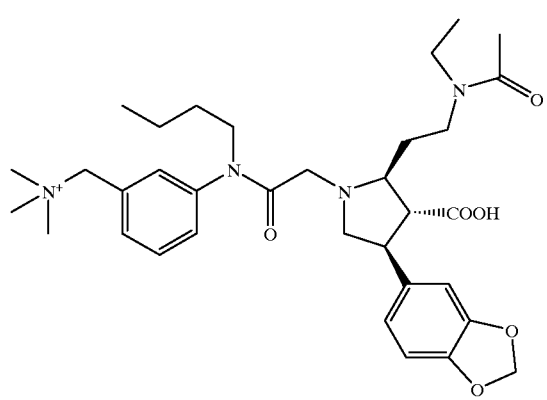
944
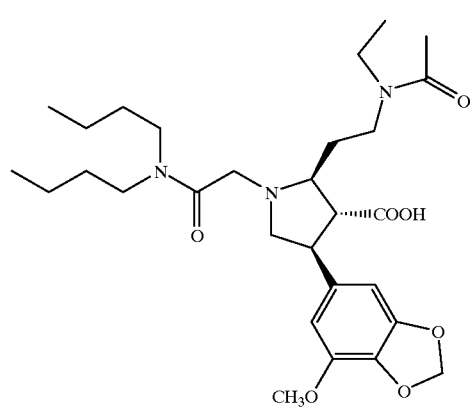
945
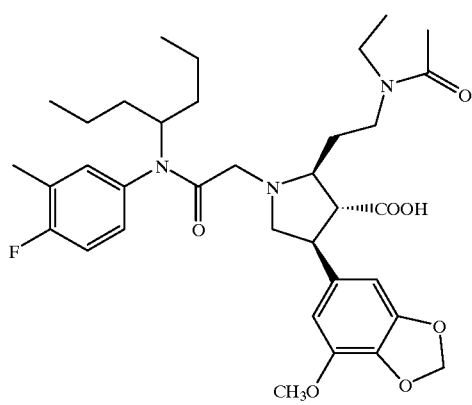

TABLE 3C-continued
946
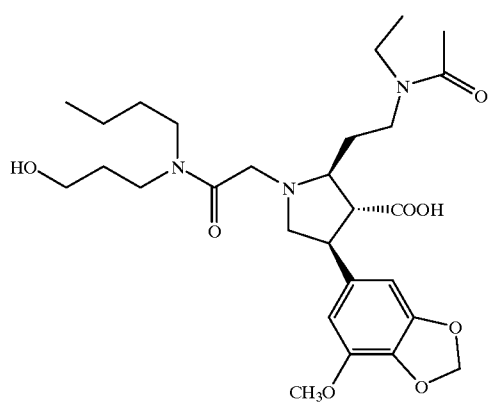
947
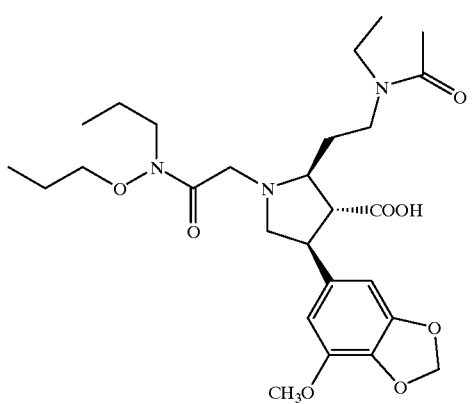
948
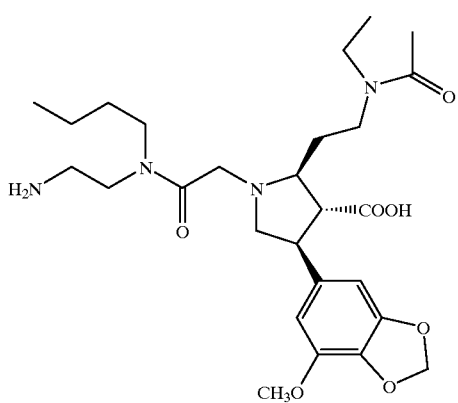
949
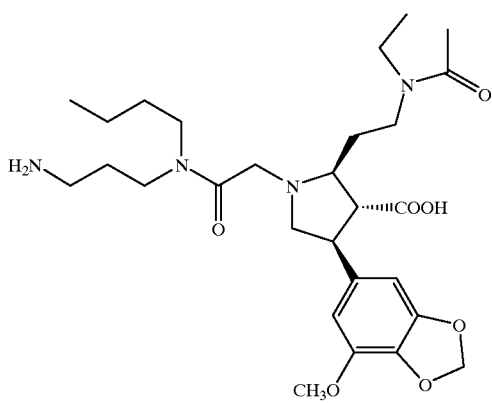

TABLE 3C-continued
950
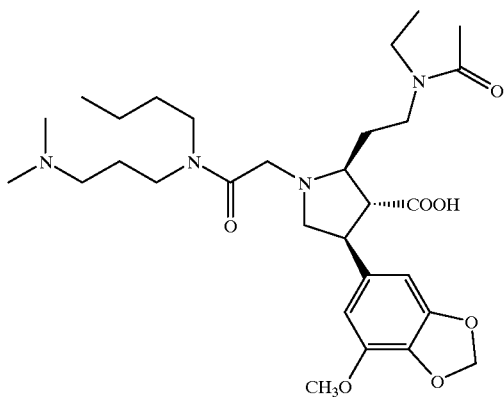
951
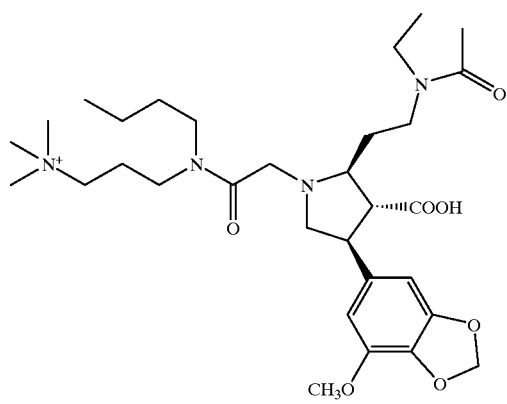
952
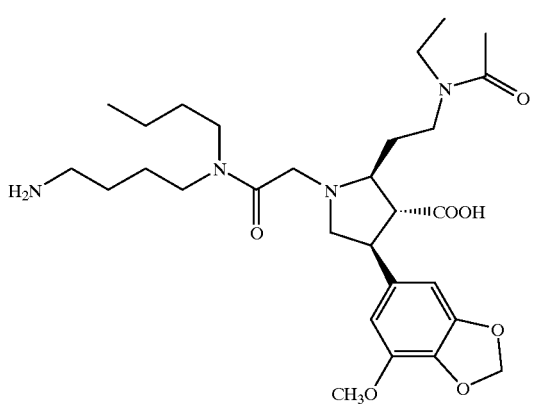

TABLE 3C-continued
953
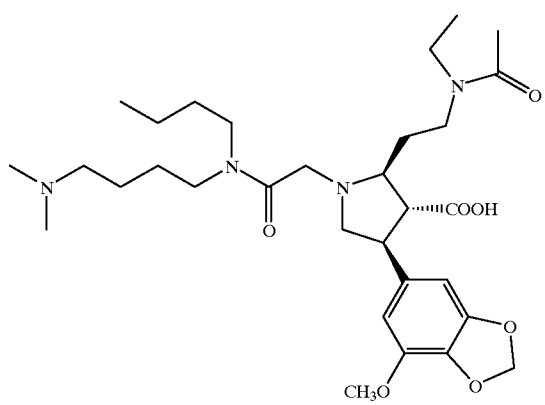
954
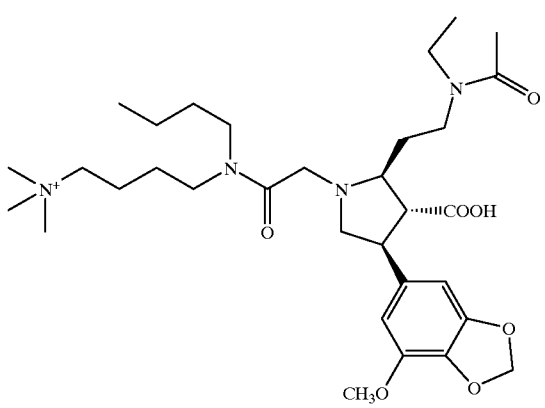
955
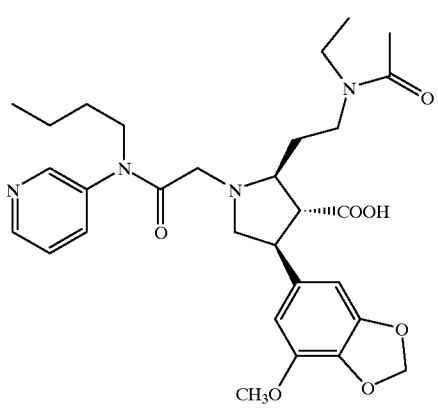
956
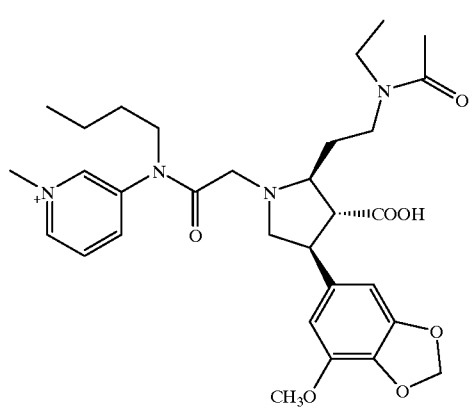

TABLE 3C-continued
957 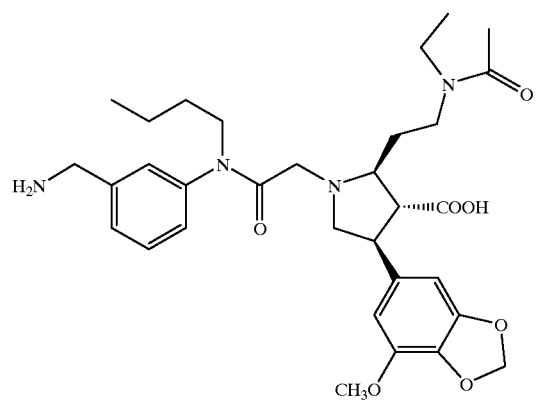
958 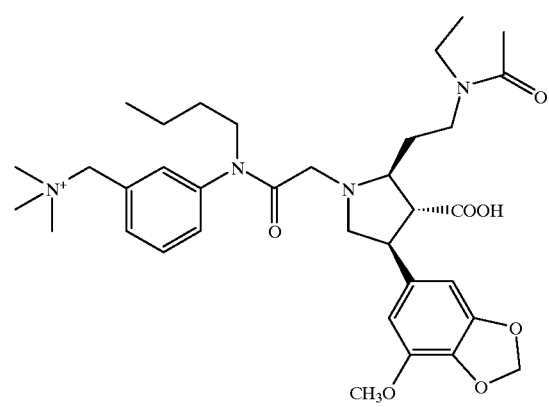
959 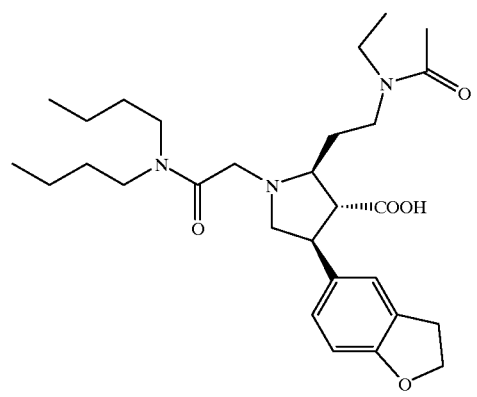
960 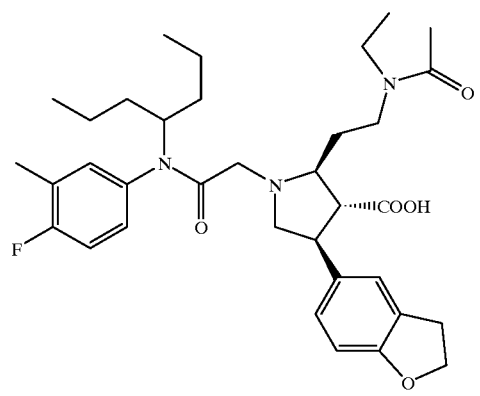

TABLE 3C-continued
961
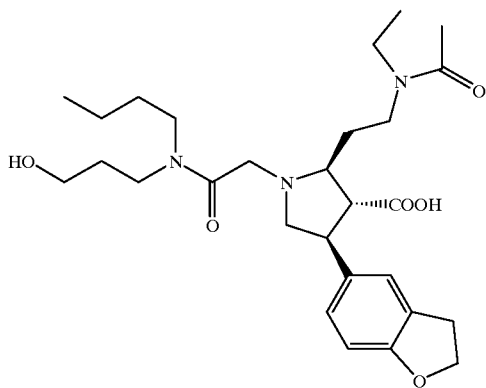
962
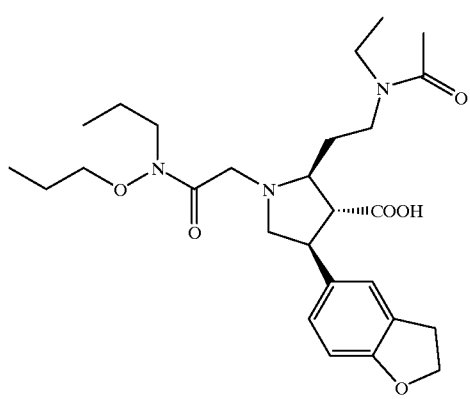
963
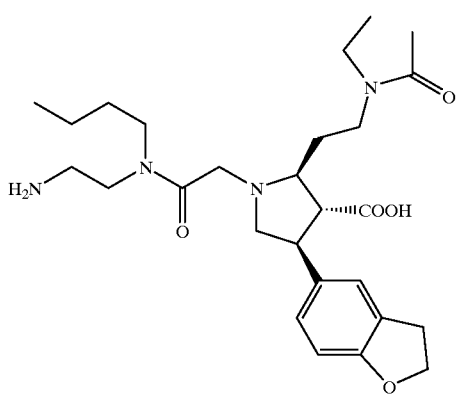
964
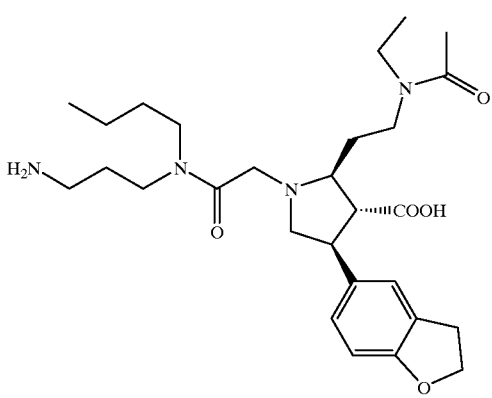

TABLE 3C-continued
965 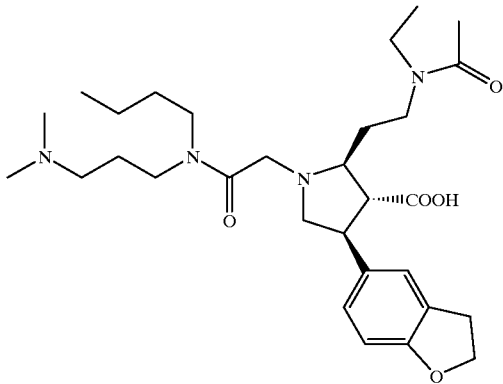
966 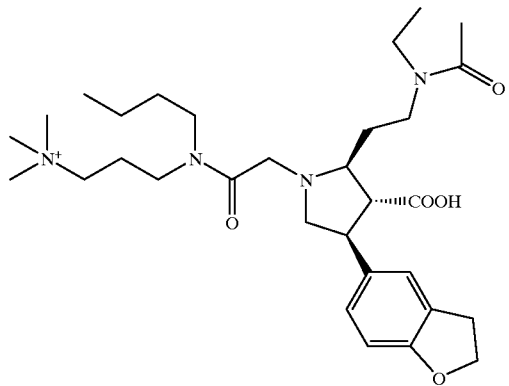
967 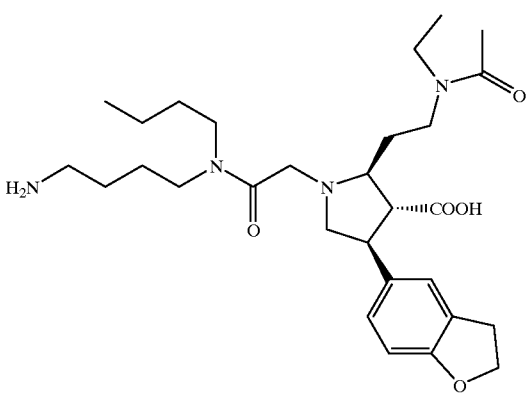
968 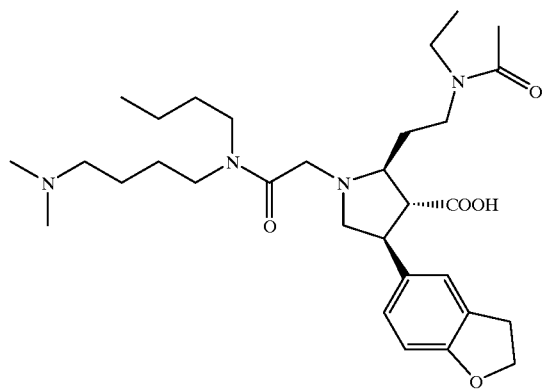

TABLE 3C-continued
969 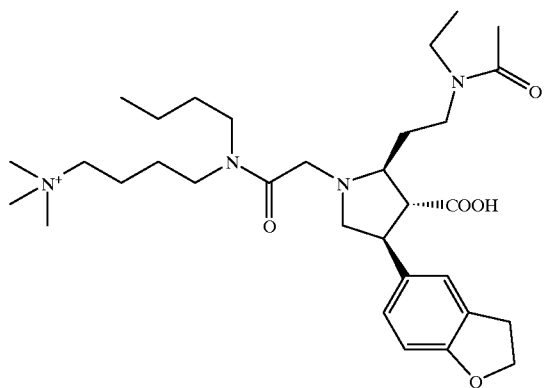
970 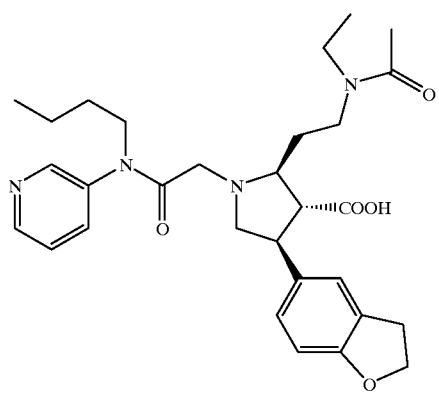
971 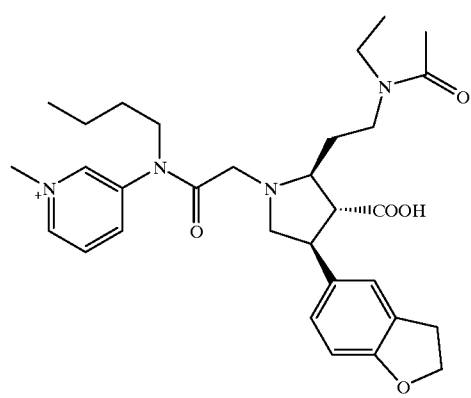
972 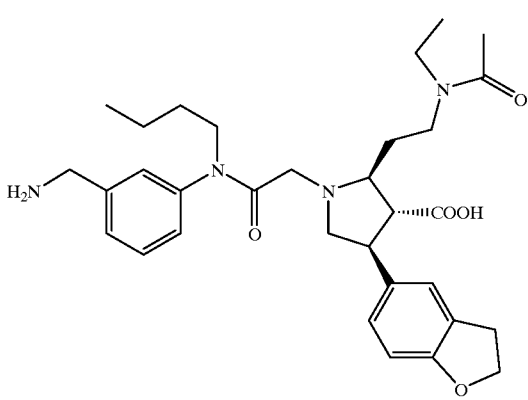

TABLE 3C-continued
973
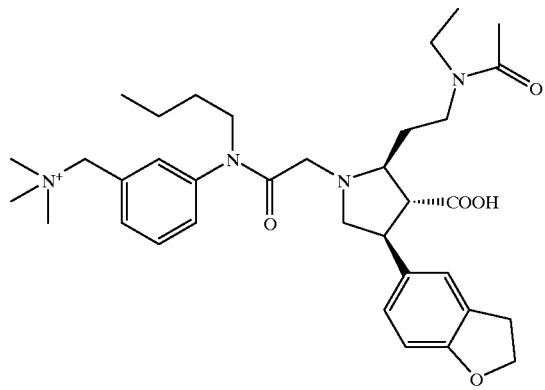
974
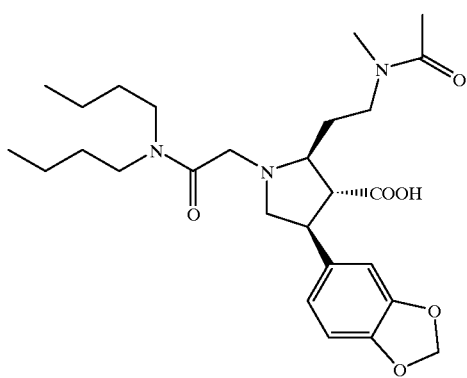
975
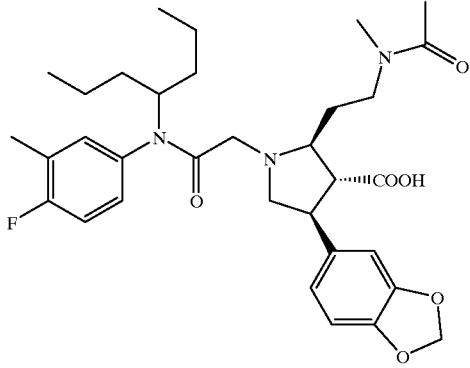
976
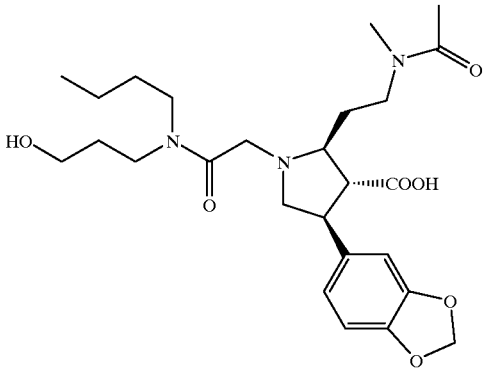

TABLE 3C-continued
977
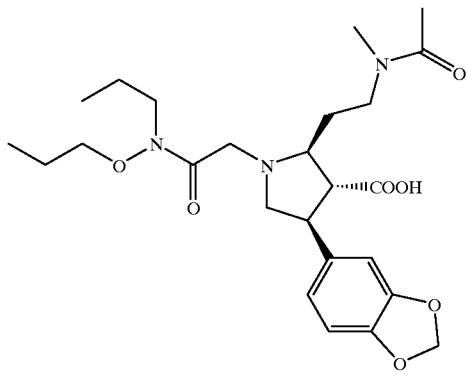
978
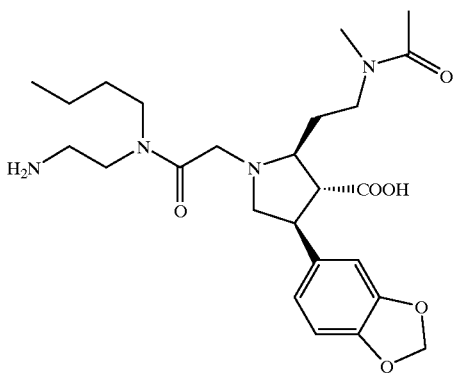
979
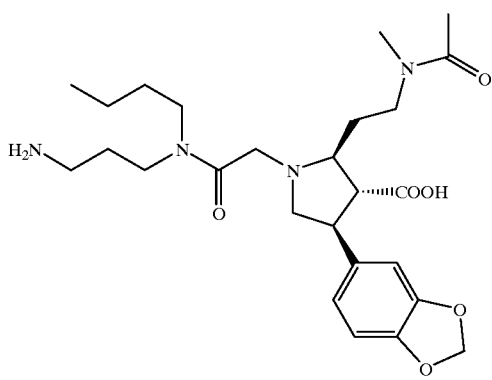
980
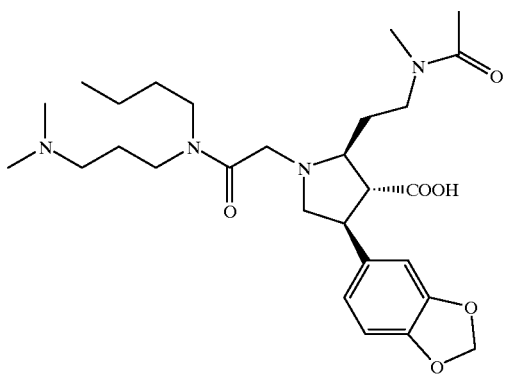

TABLE 3C-continued
981
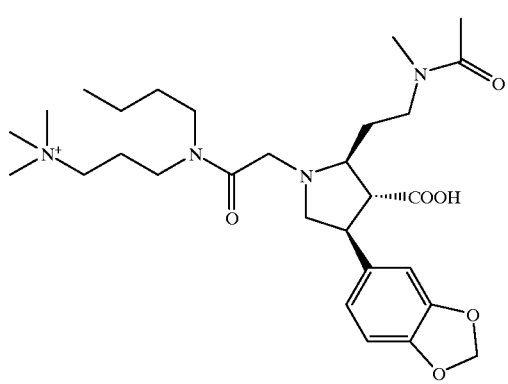
982
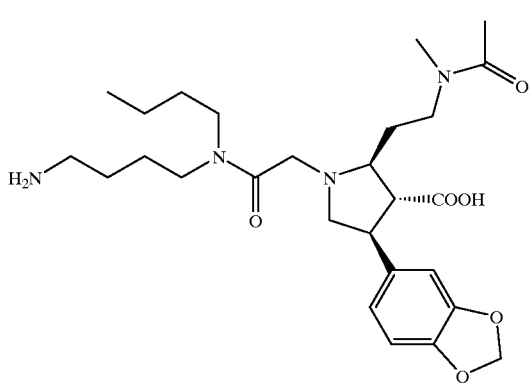
983
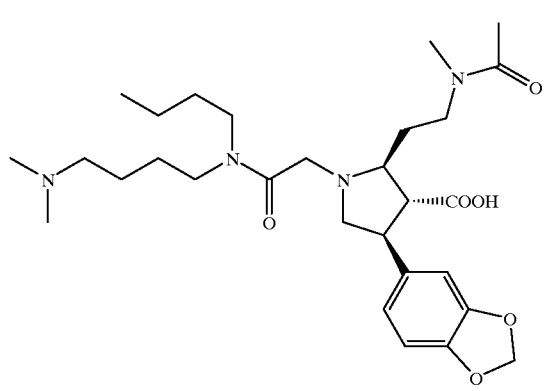
984
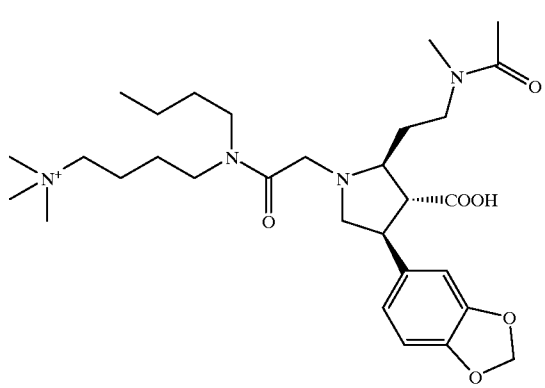

TABLE 3C-continued
985
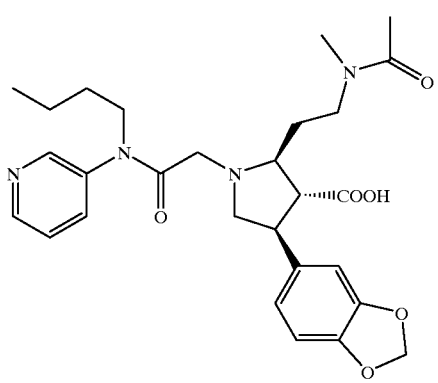
986
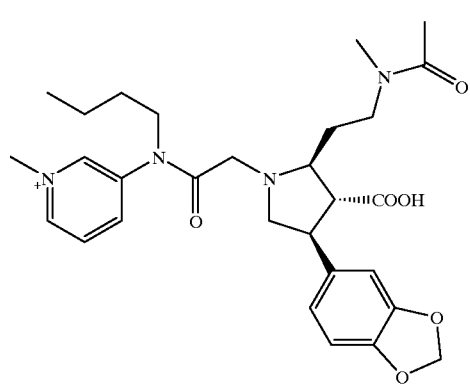
987
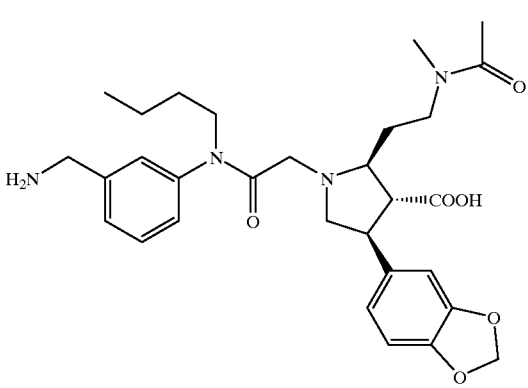
988
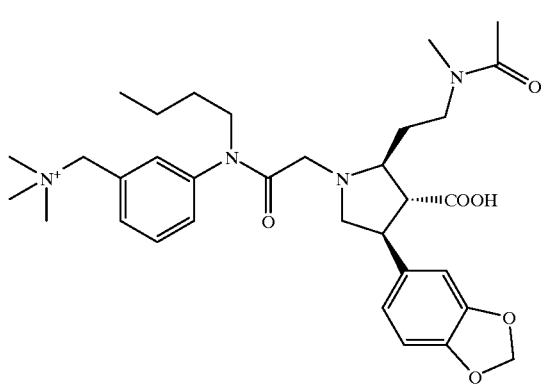

TABLE 3C-continued
| 989 | 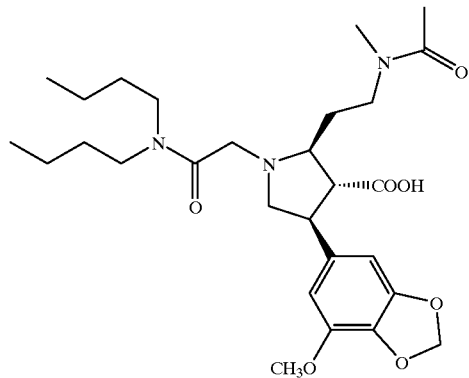 |
| --- | --- |
| 990 | 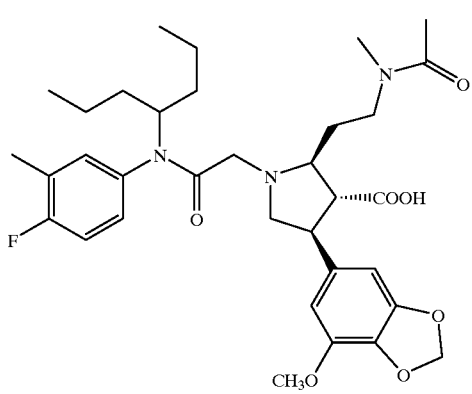 |
| 991 | 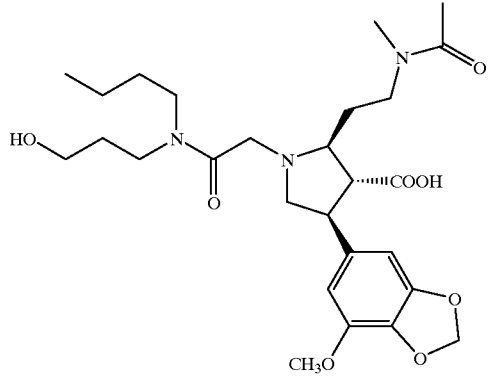 |
| 992 | 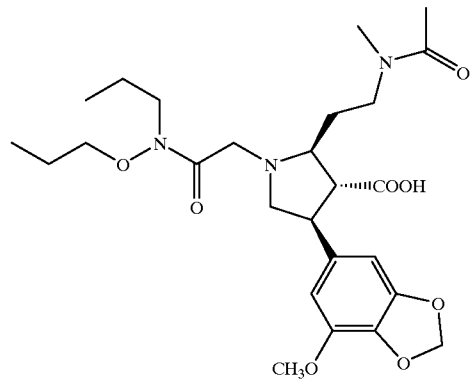 |

TABLE 3C-continued
993
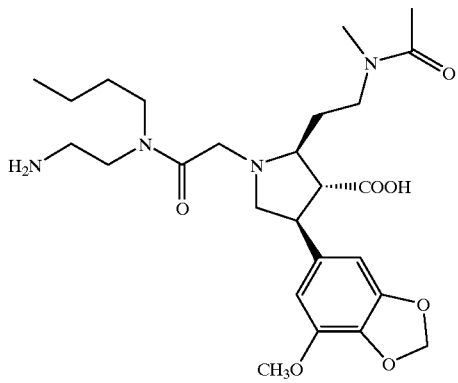
994
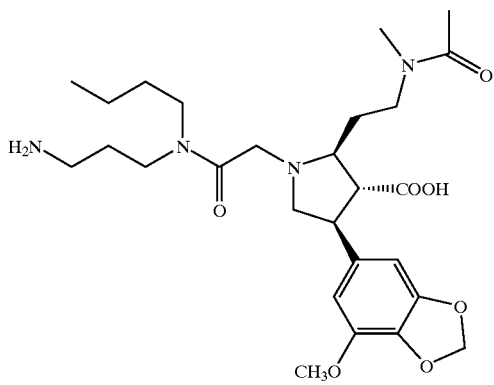
995
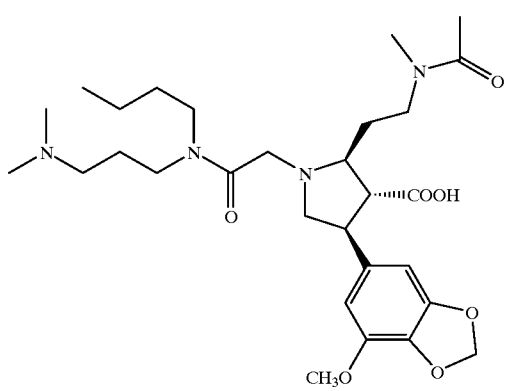
996
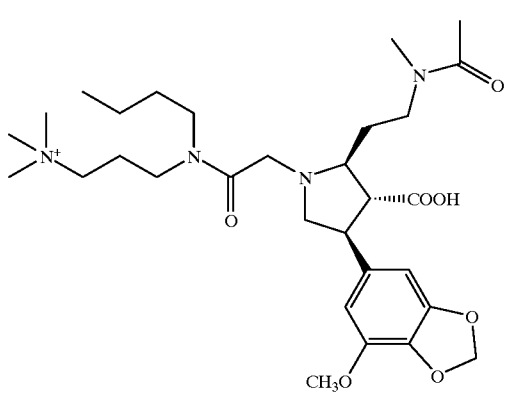

TABLE 3C-continued
997
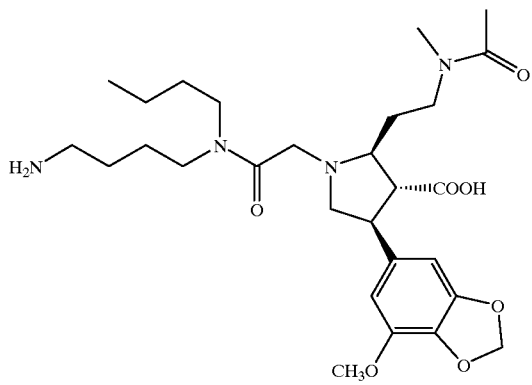
998
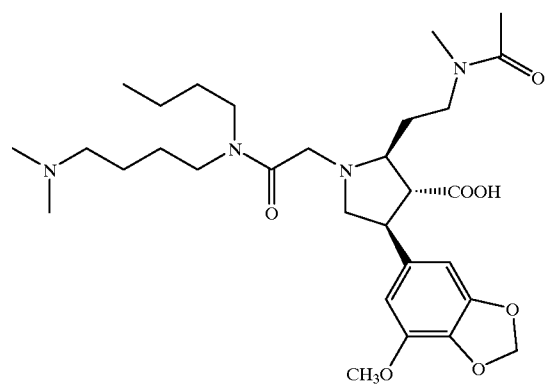
999
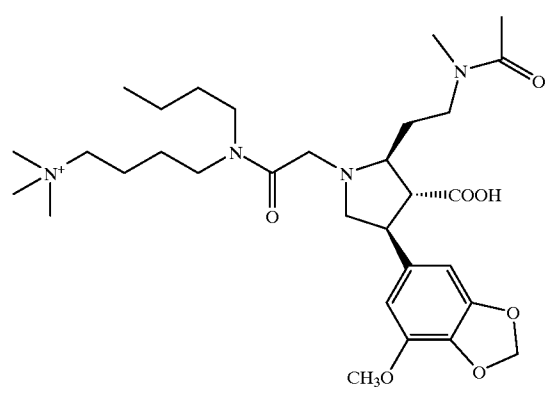
1000
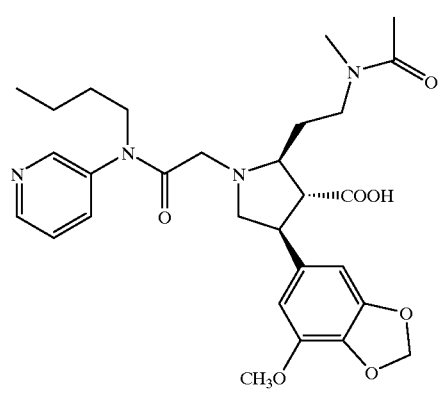

TABLE 3C-continued
1001
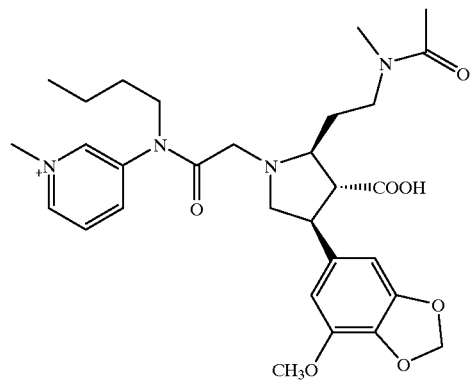
1002
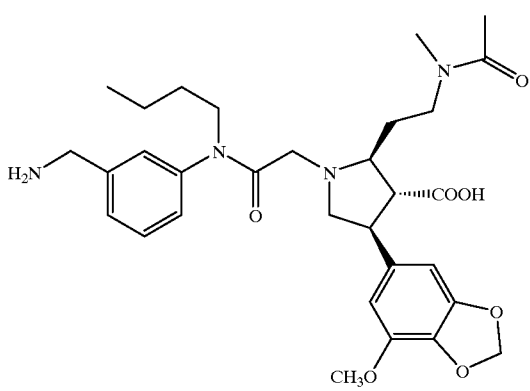
1003
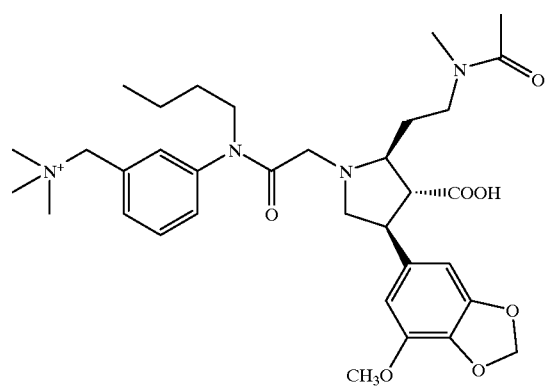
1004
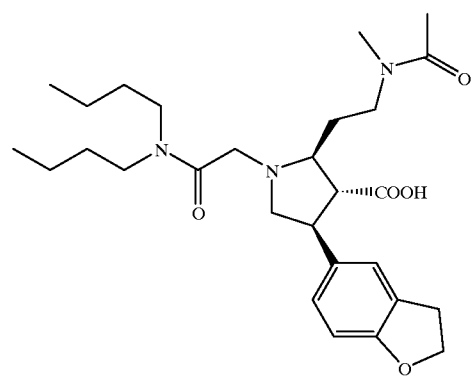

TABLE 3C-continued
1005
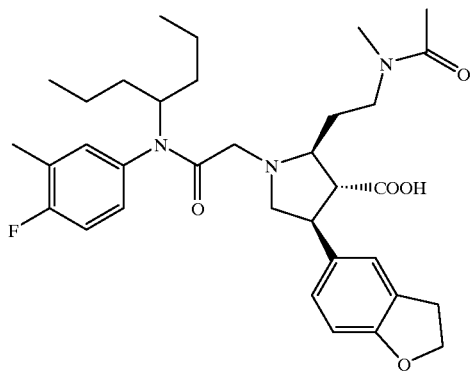
1006
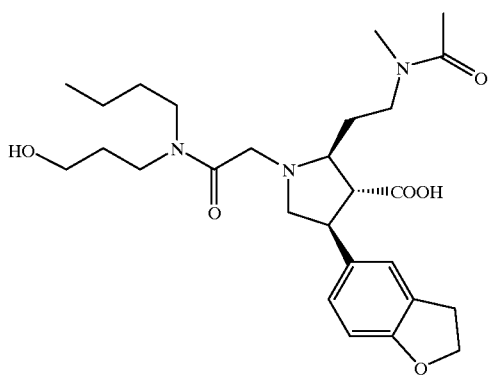
1007
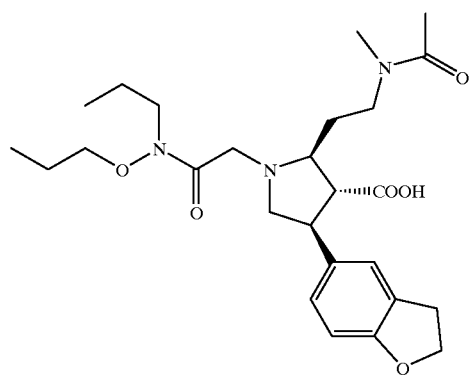
1008
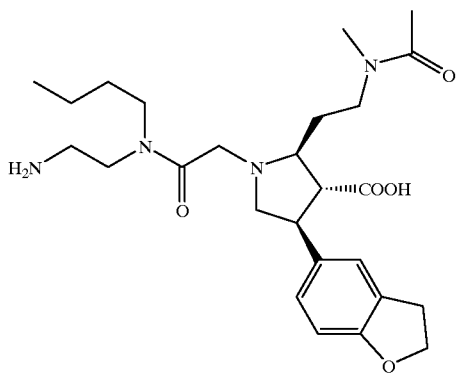

TABLE 3C-continued
1009
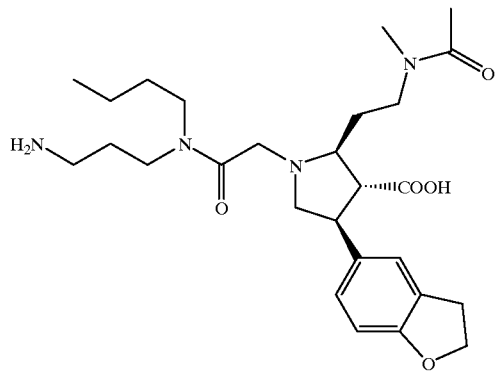
1010
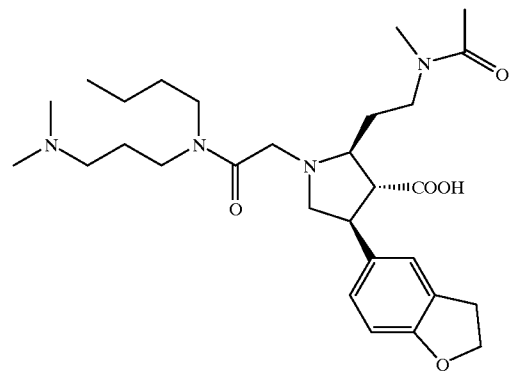
1011
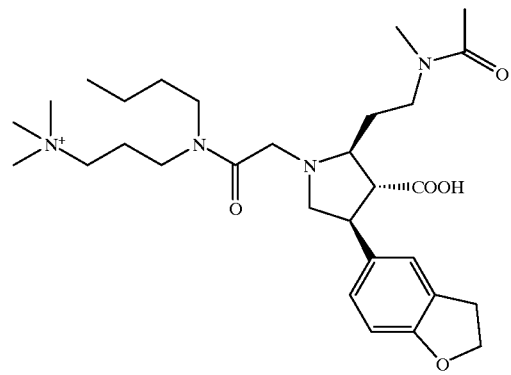
1012
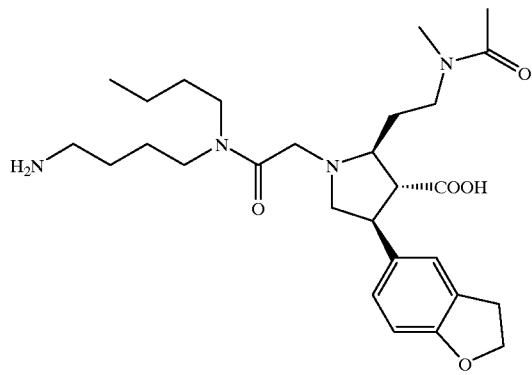

TABLE 3C-continued
1013
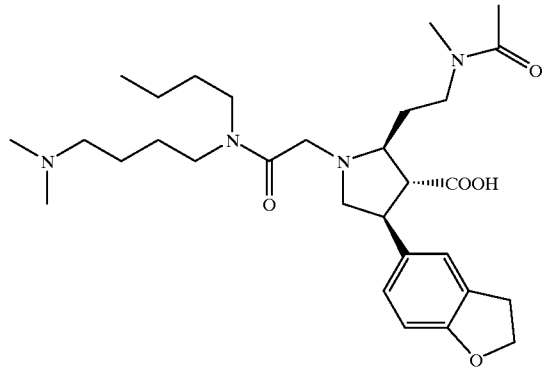
1014
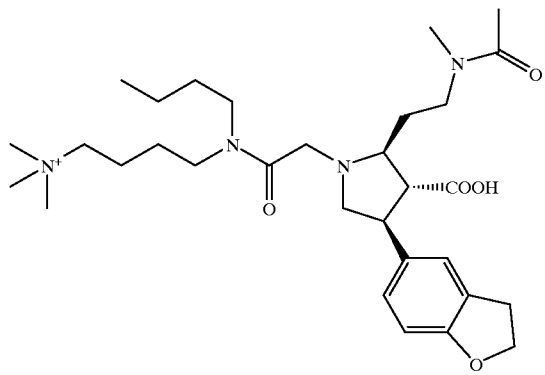
1015
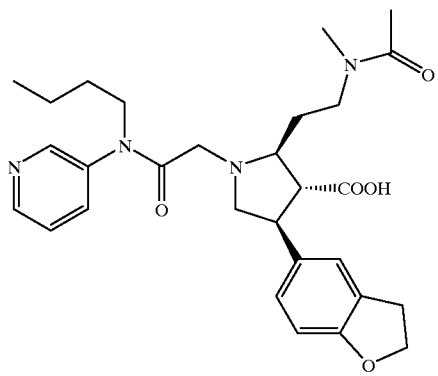
1016
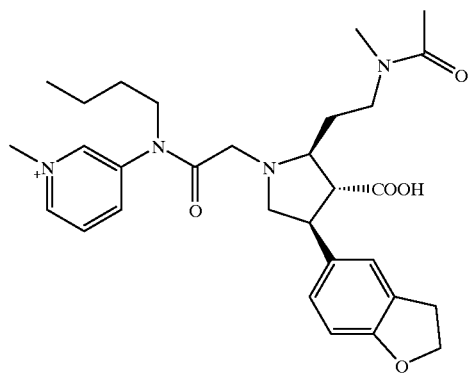

TABLE 3C-continued
1017
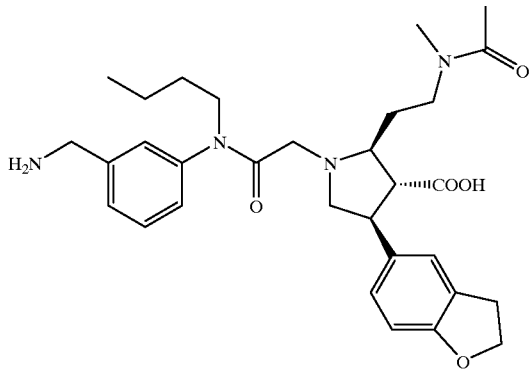
1018
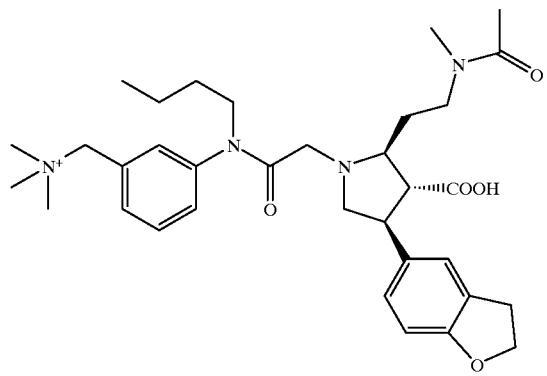
1019
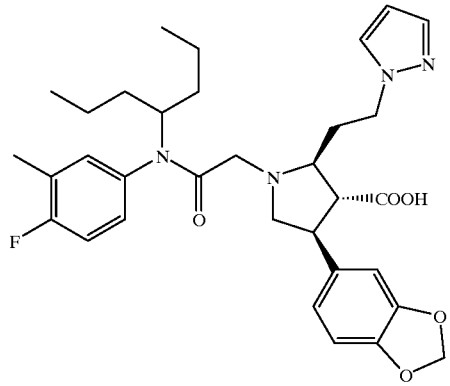
1020
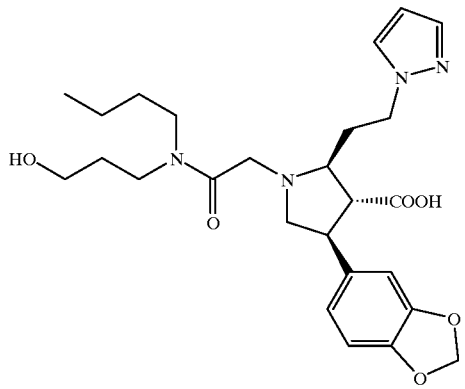

TABLE 3C-continued
1021
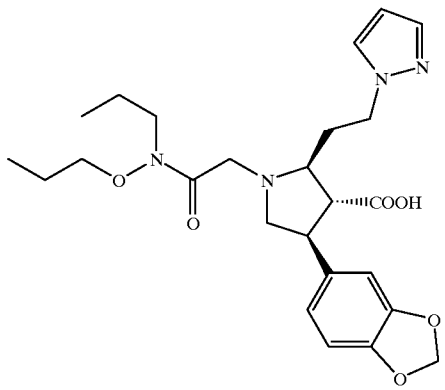
1022
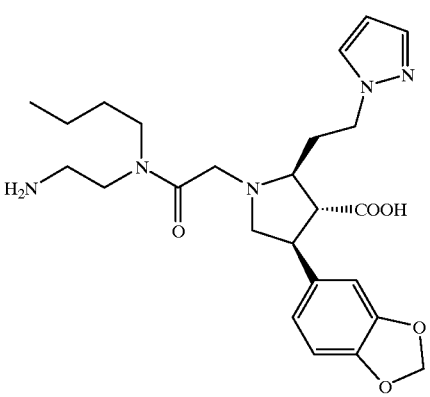
1023
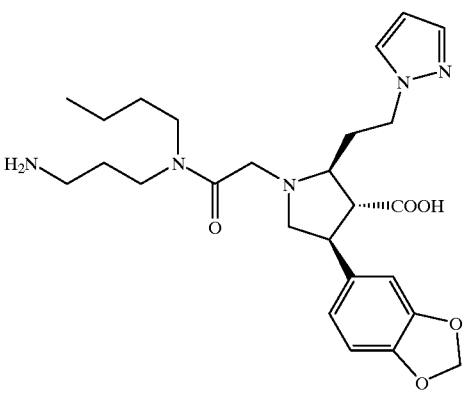
1024
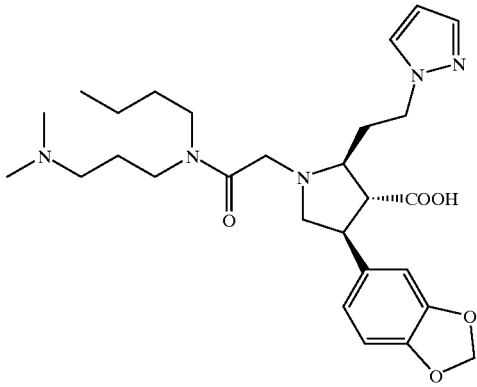

TABLE 3C-continued
1025 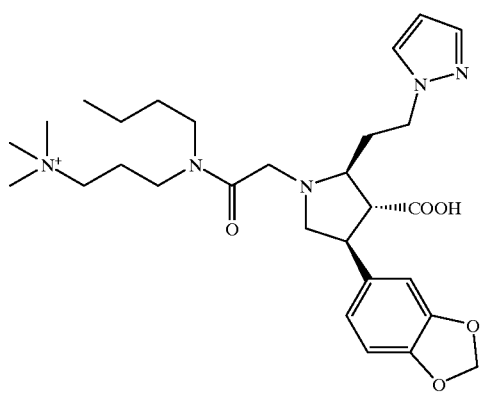
1026 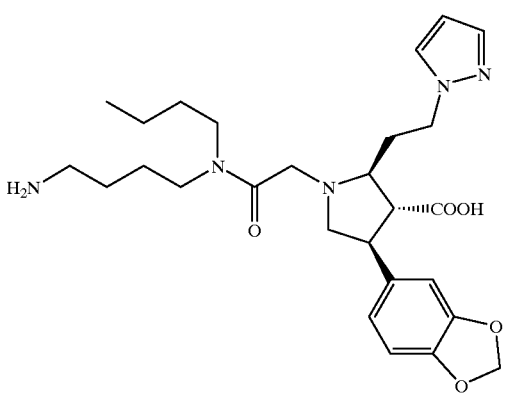
1027 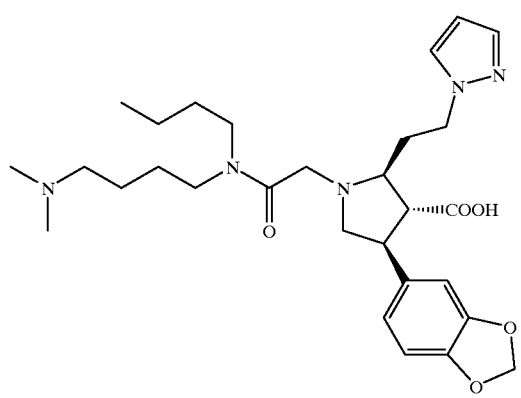
1028 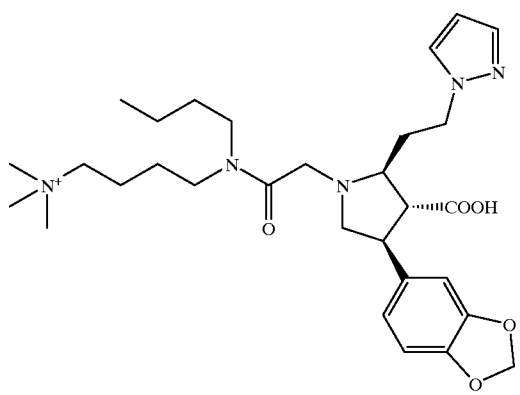

TABLE 3C-continued
1029
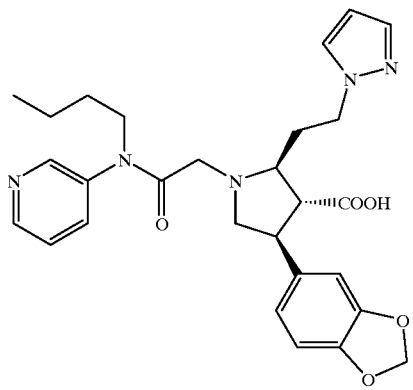
1030
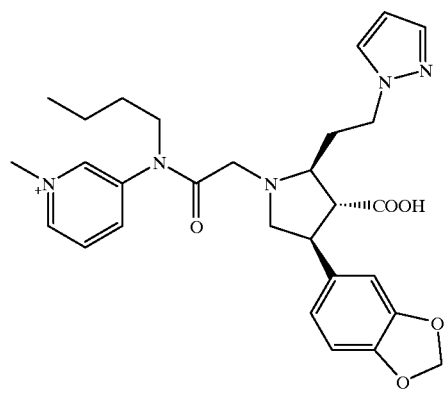
1031
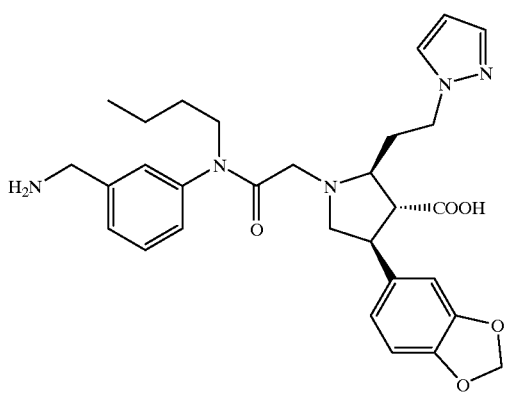
1032
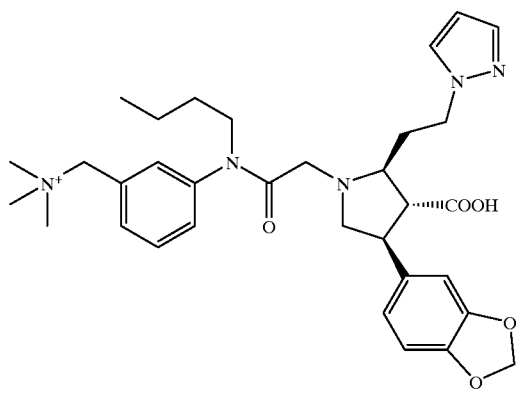

TABLE 3C-continued
1033
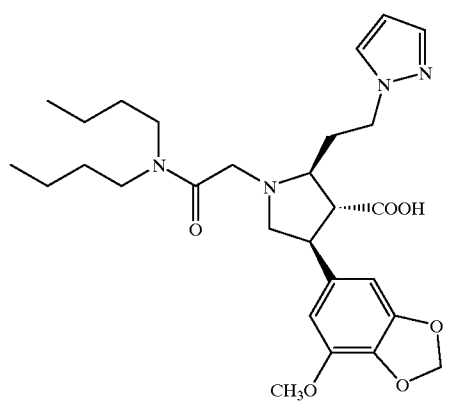
1034
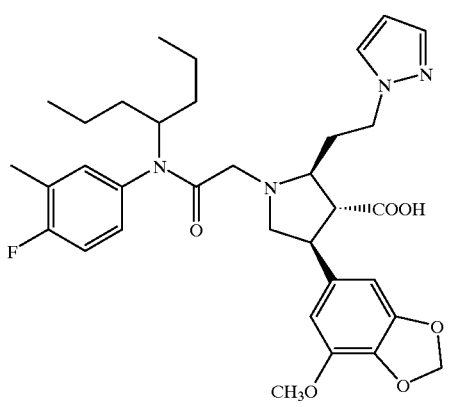
1035
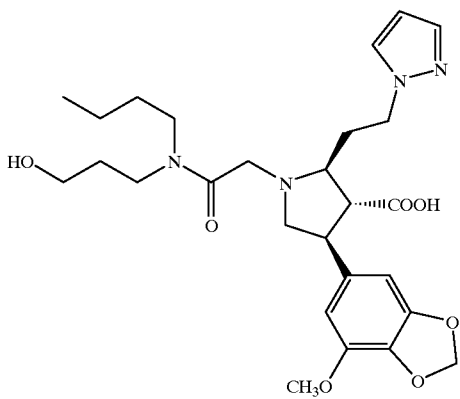

TABLE 3C-continued
1036
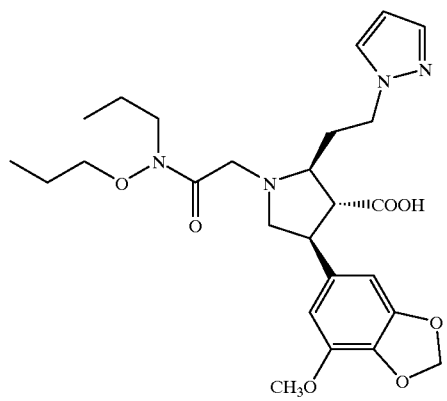
1037
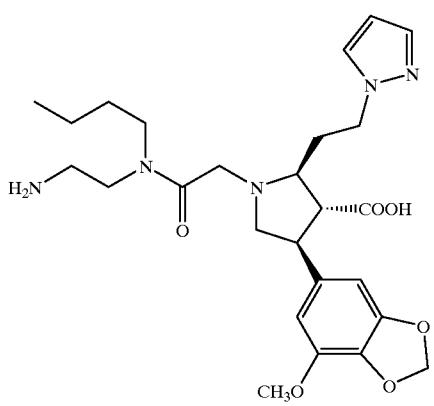
1038
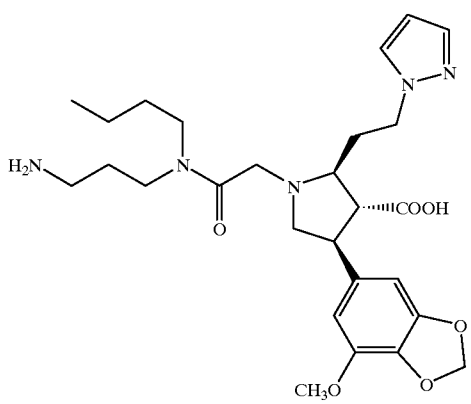
1039
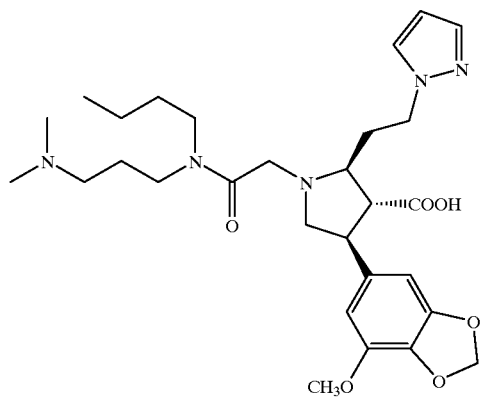

TABLE 3C-continued
1040
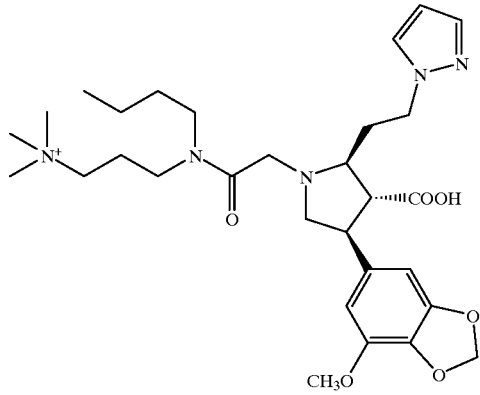
1041
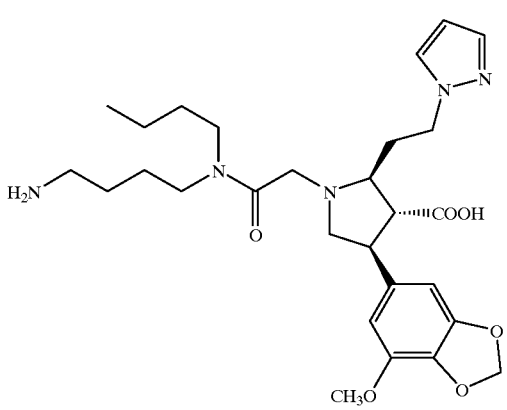
1042
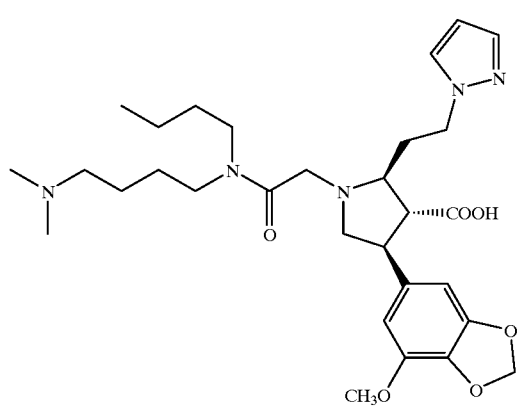

TABLE 3C-continued
1043
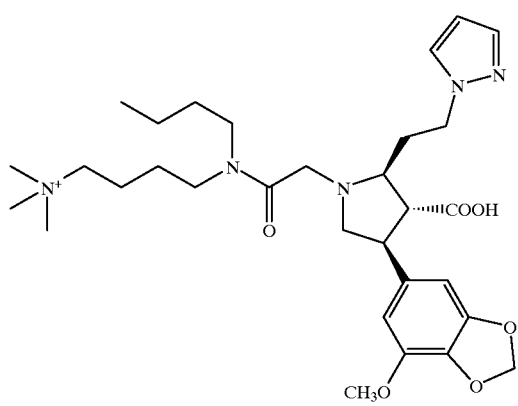
1044
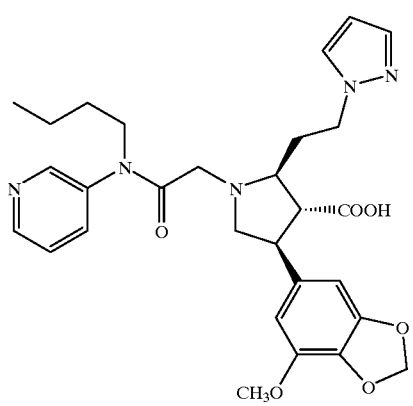
1045
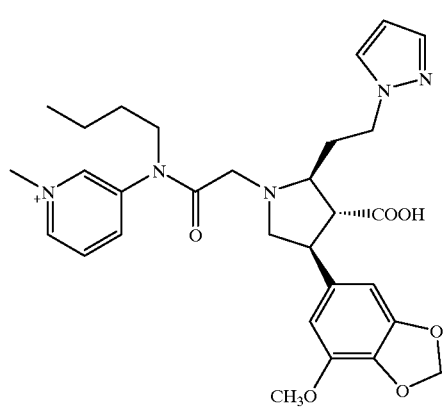
1046
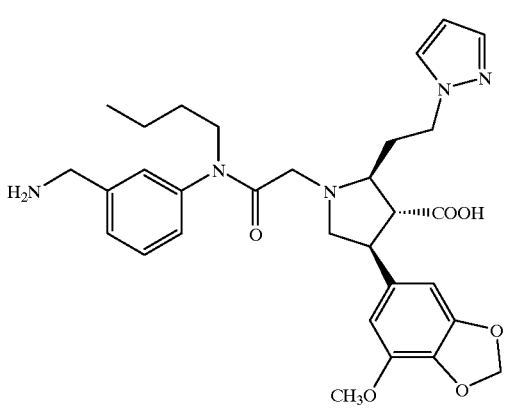

TABLE 3C-continued
1047 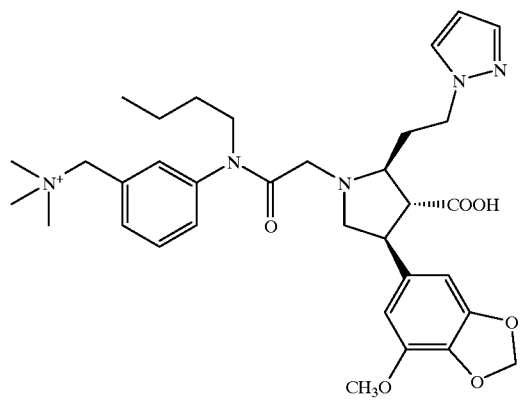
1048 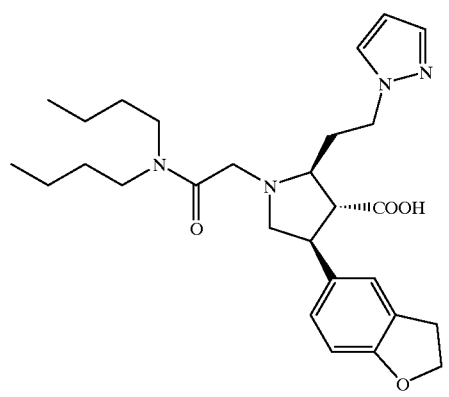
1049 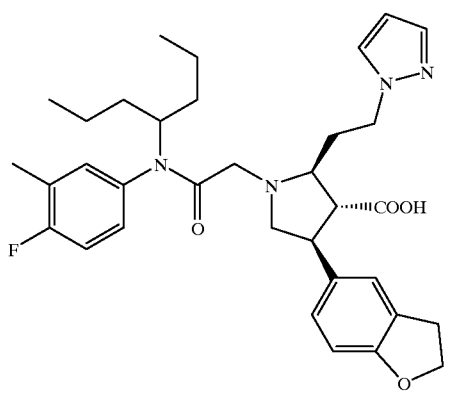
1050 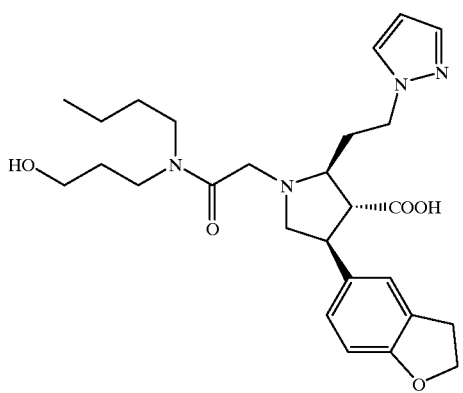

TABLE 3C-continued
1051 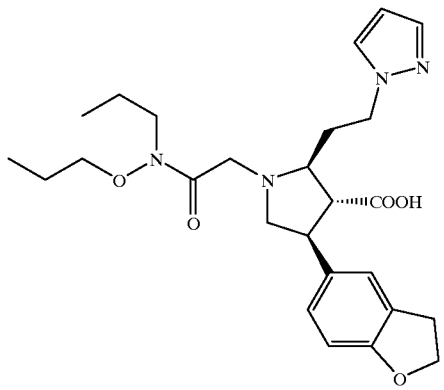
1052 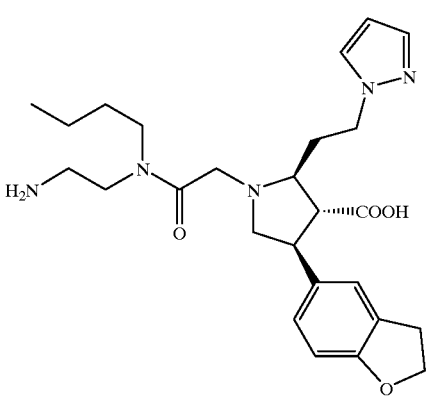
1053 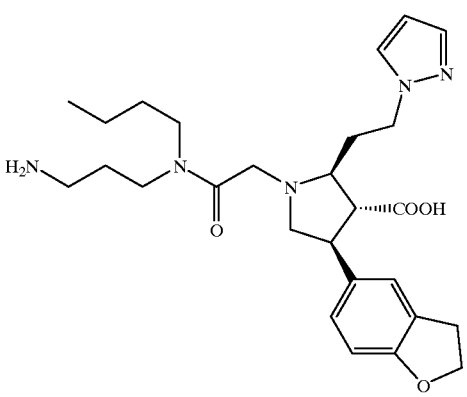
1054 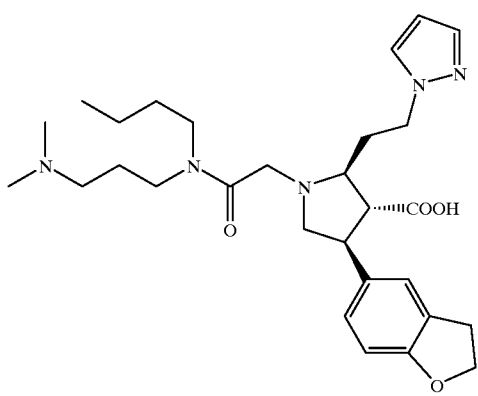

TABLE 3C-continued
1055
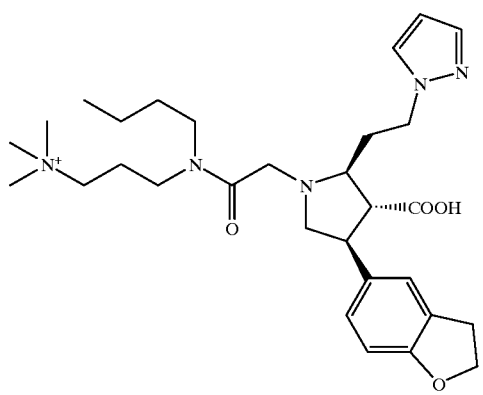
1056
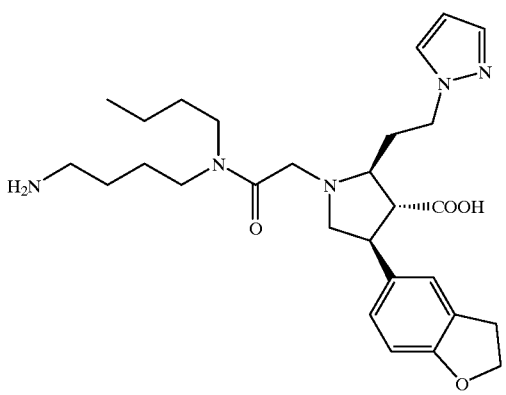
1057
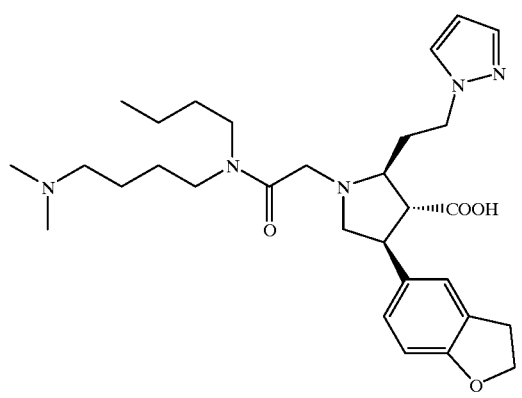
1058
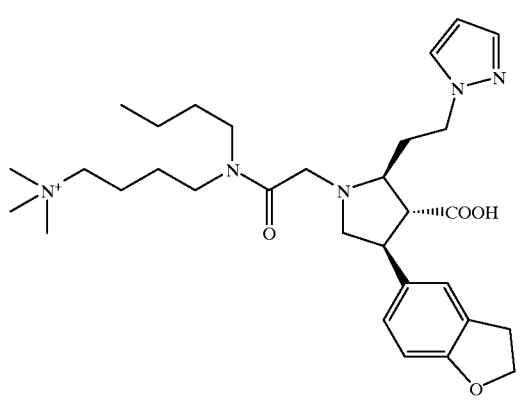

TABLE 3C-continued
1059
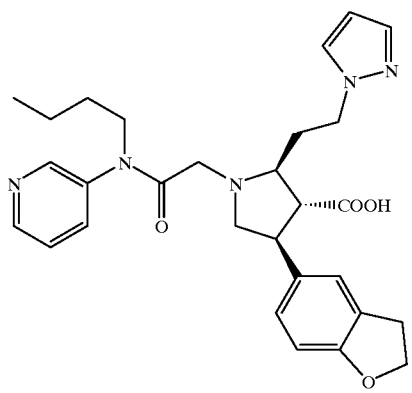
1060
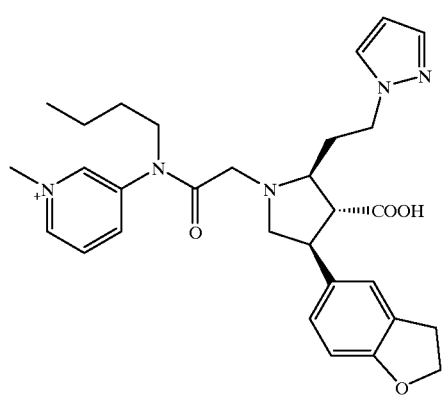
1061
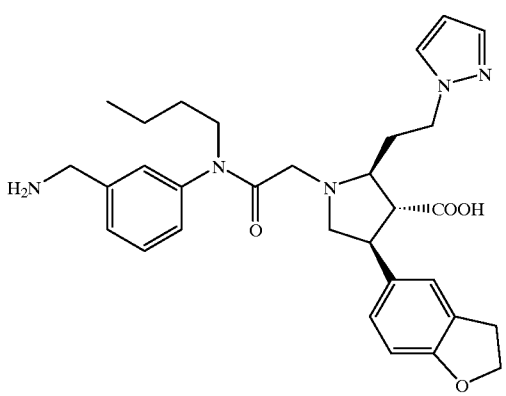
1062
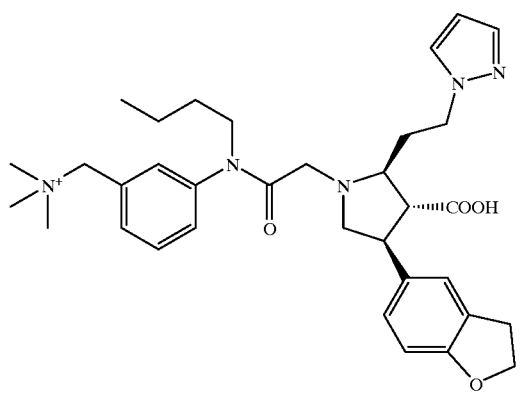

TABLE 3C-continued
1063 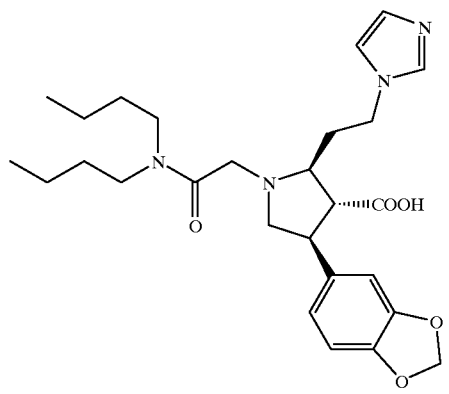
1064 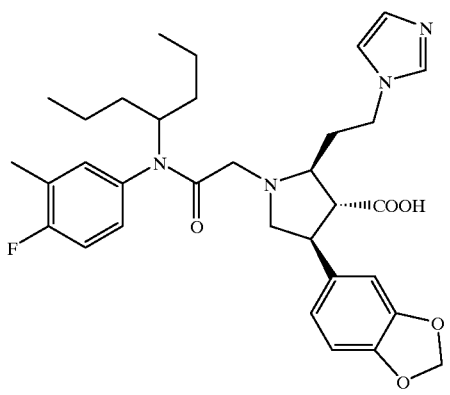
1065 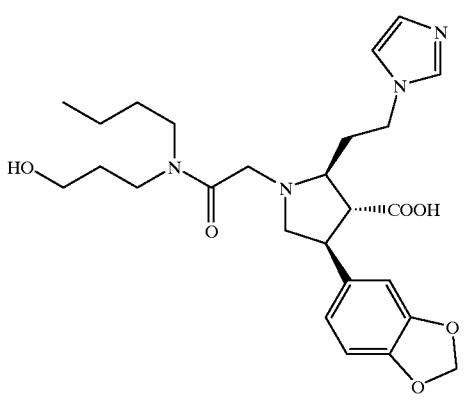
1066 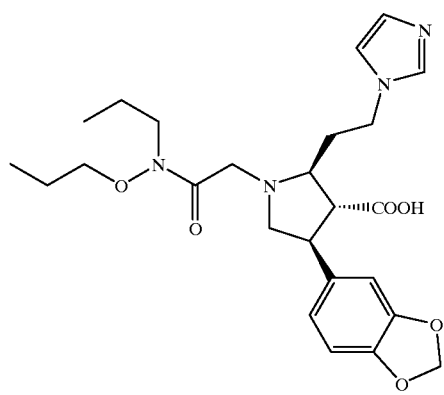

TABLE 3C-continued
1067
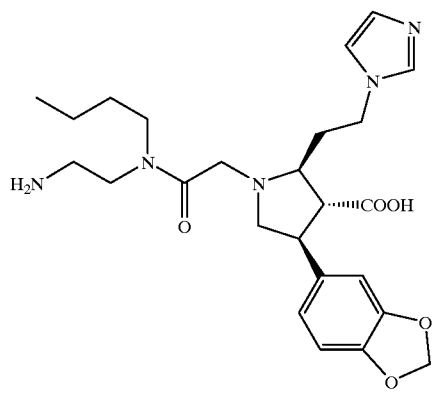
1068
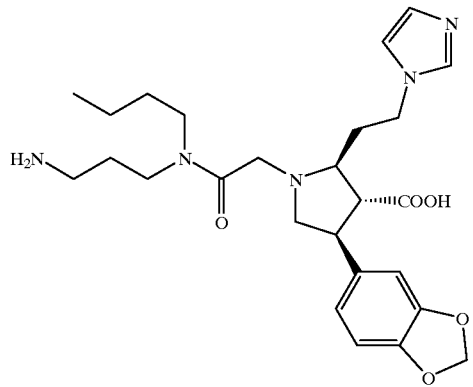
1069
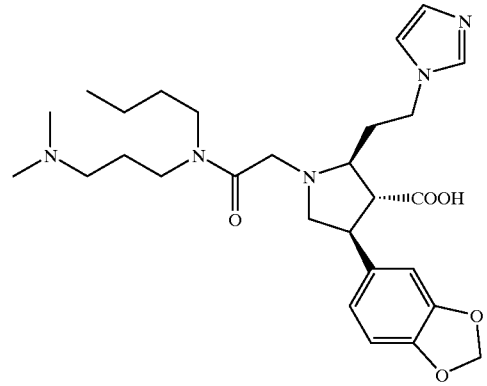
1070
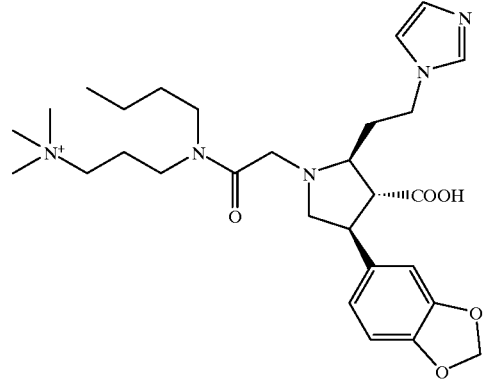

TABLE 3C-continued
1071 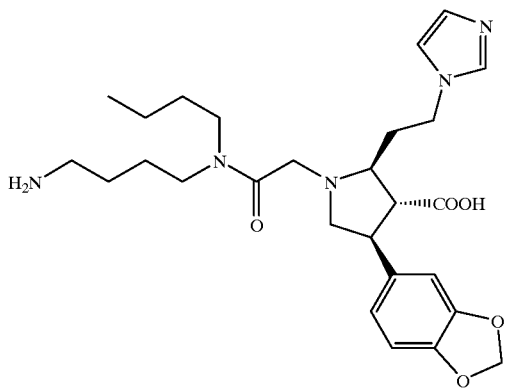
1072 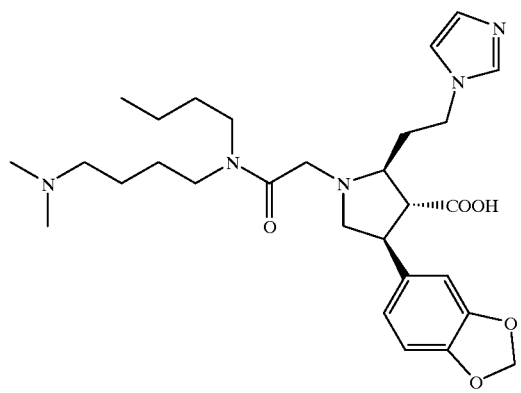
1073 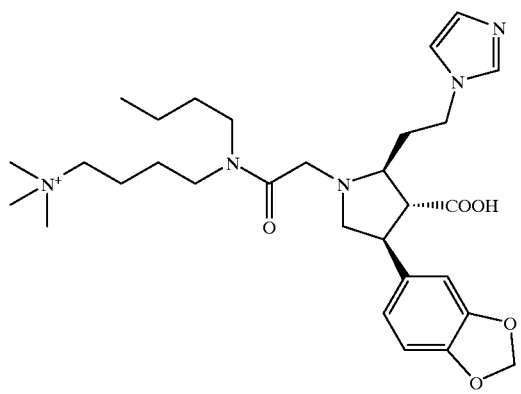
1074 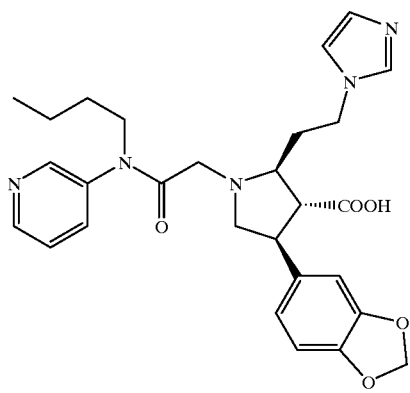

TABLE 3C-continued
1075 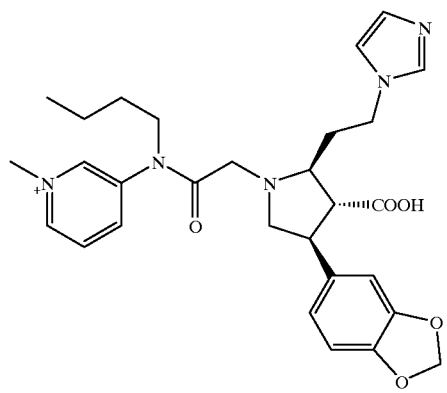
1076 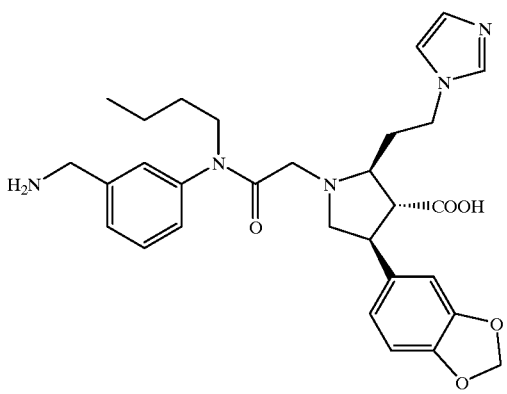
1077 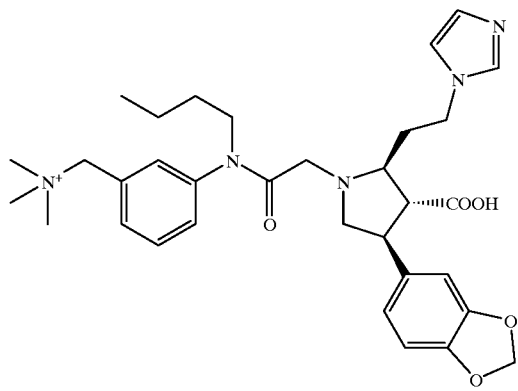
1078 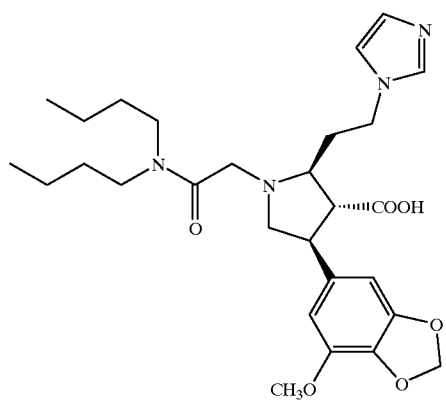

TABLE 3C-continued
1079
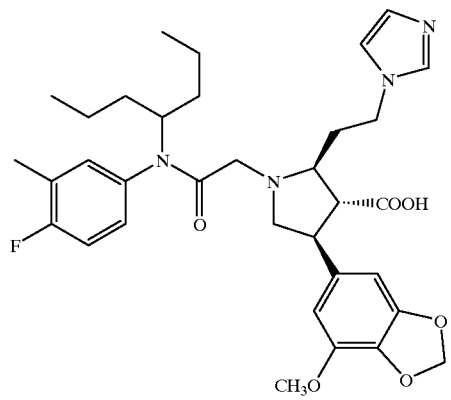
1080
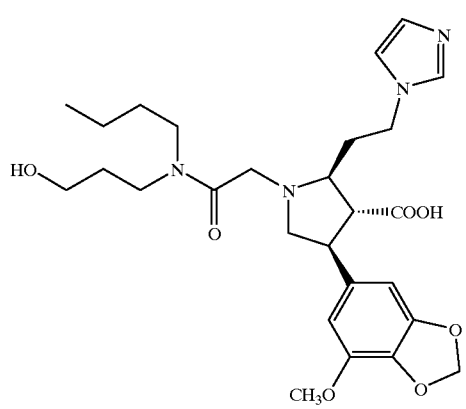
1081
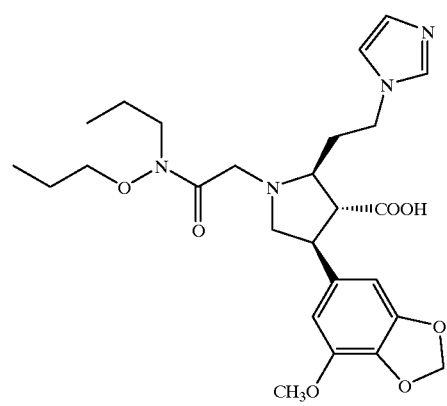
1082
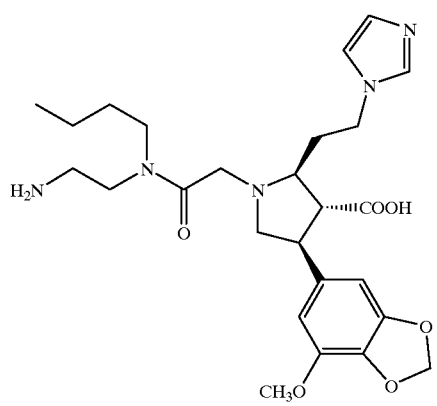

TABLE 3C-continued
1083
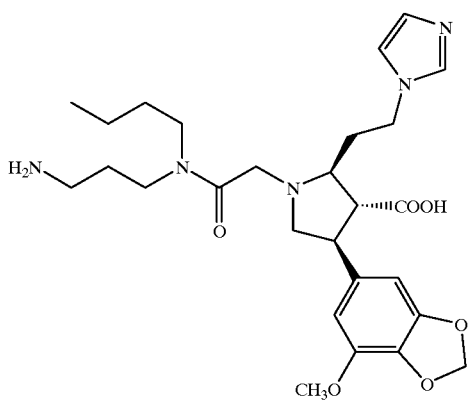
1084
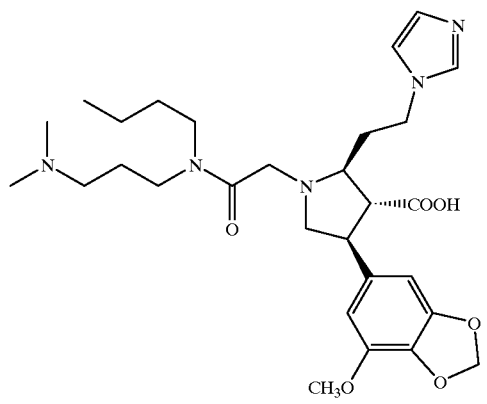
1085
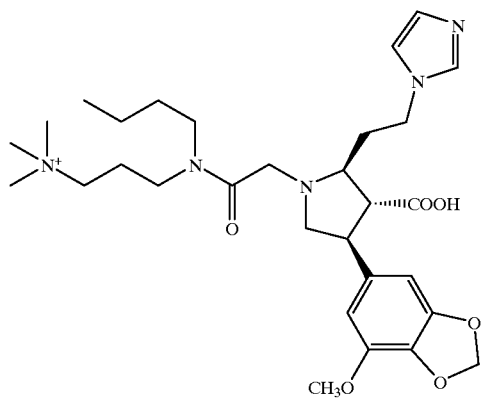

TABLE 3C-continued
1086
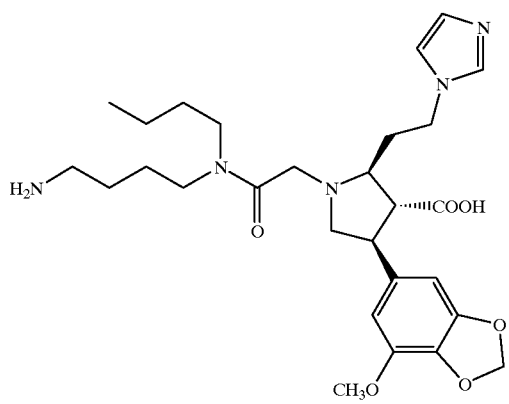
1087
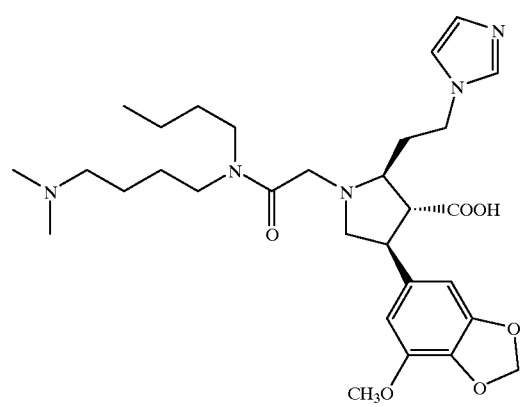
1088
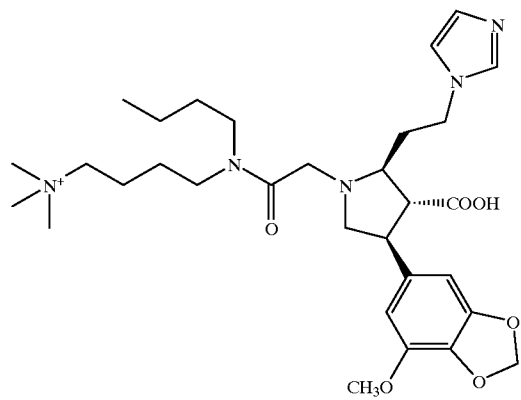

TABLE 3C-continued
1089
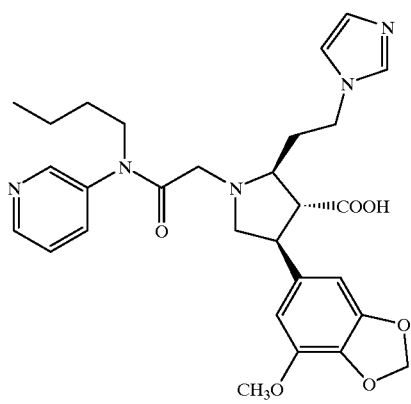
1090
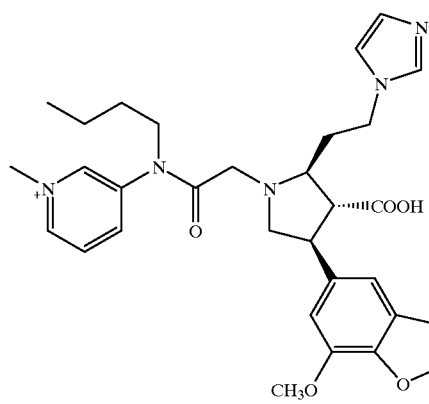
1091
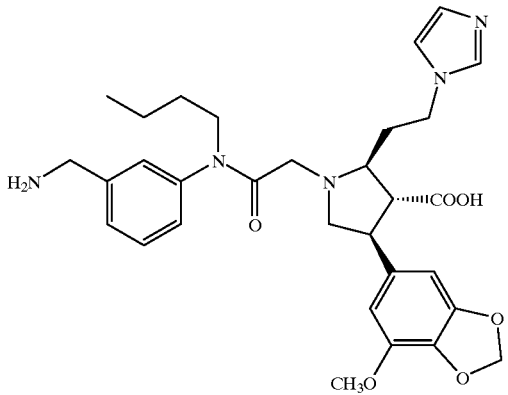

TABLE 3C-continued
1092
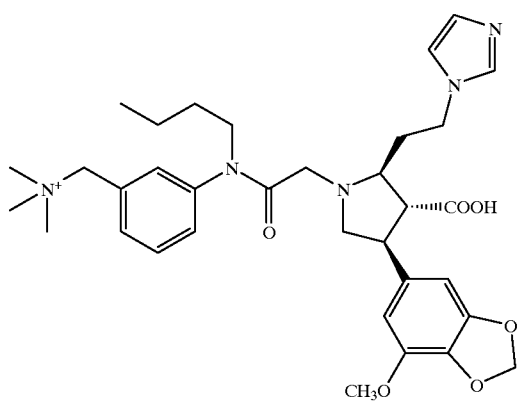
1093
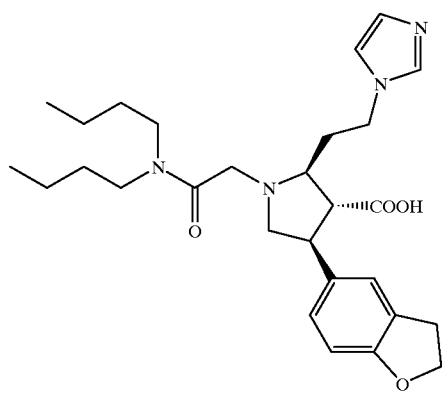
1094
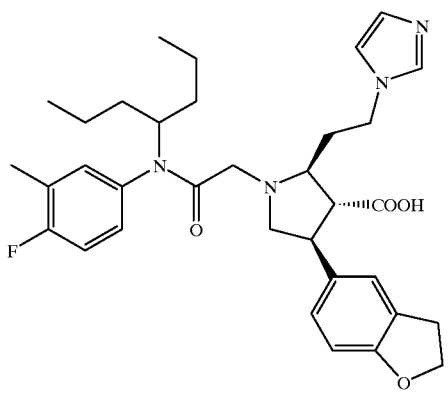
1095
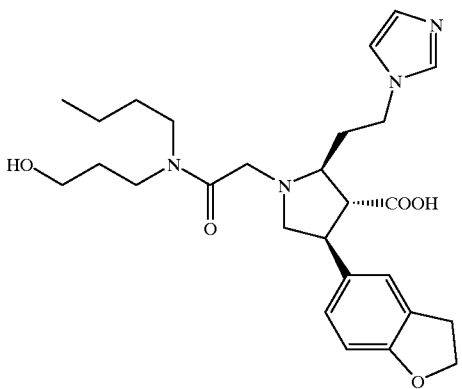

TABLE 3C-continued
1096
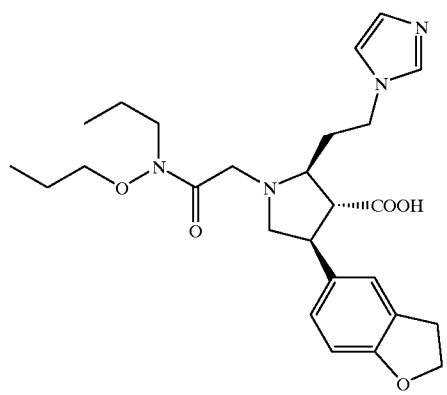
1097
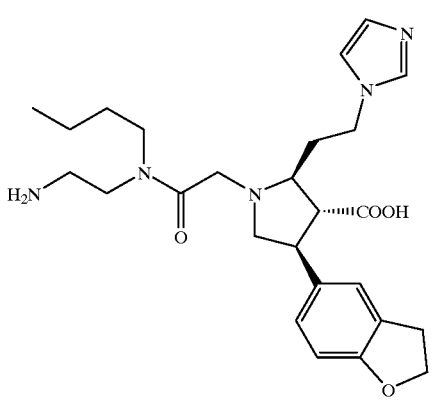
1098
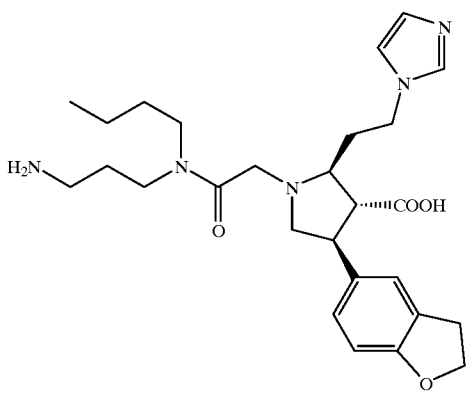
1099
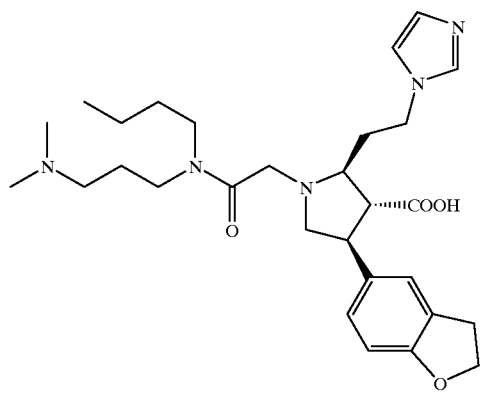

TABLE 3C-continued
1100
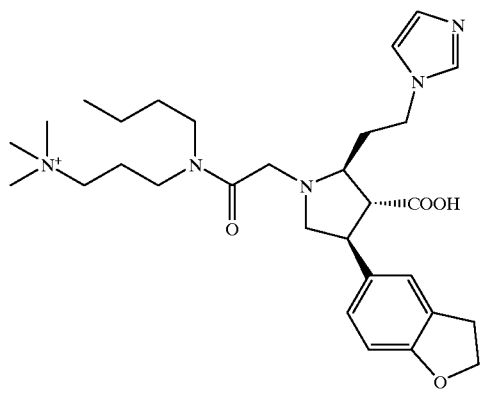
1101
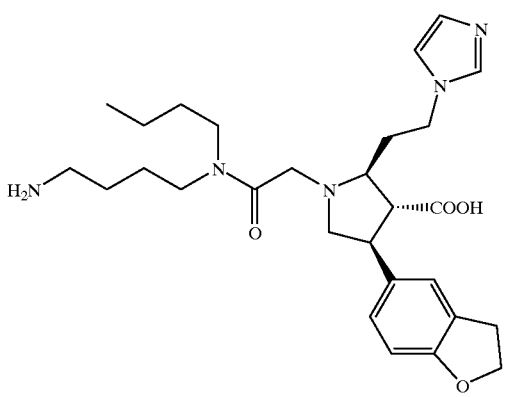
1102
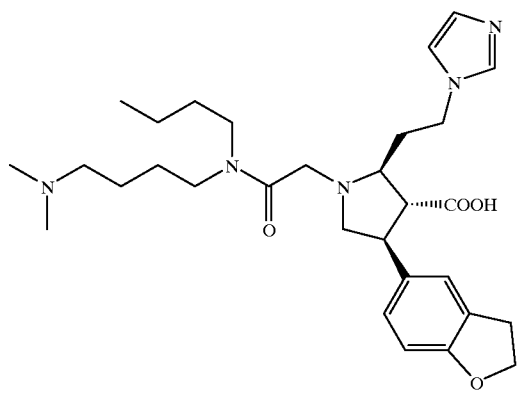
1103
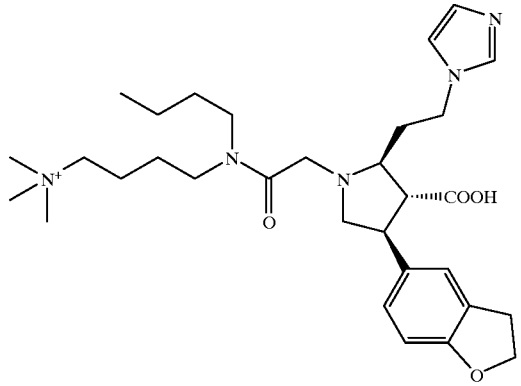

TABLE 3C-continued
1104
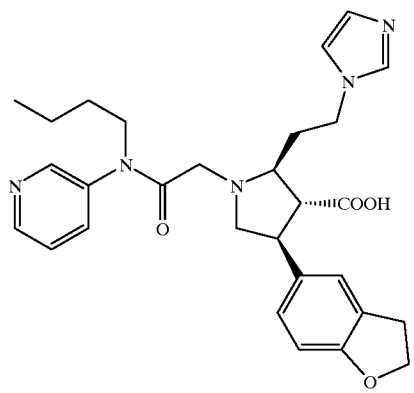
1105
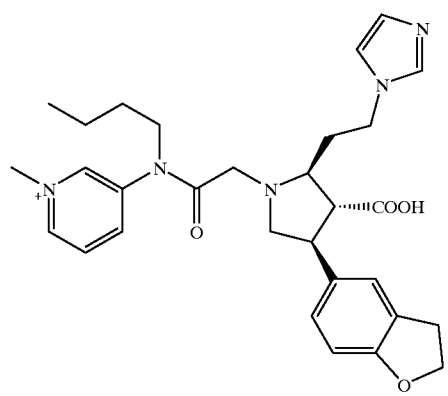
1106
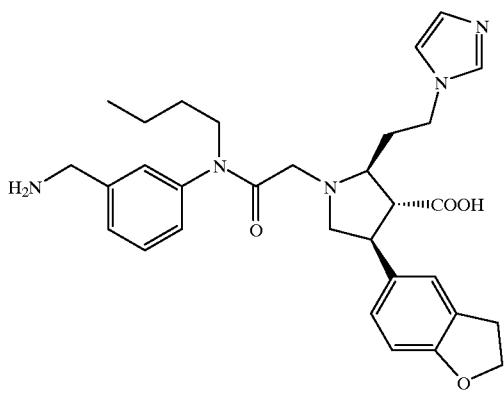
1107
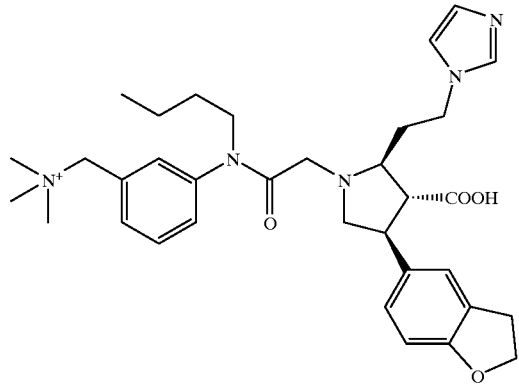

TABLE 3C-continued
1108 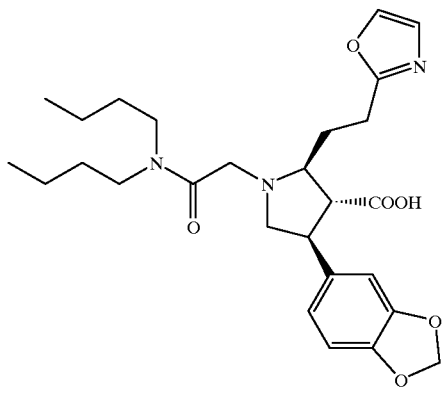
1109 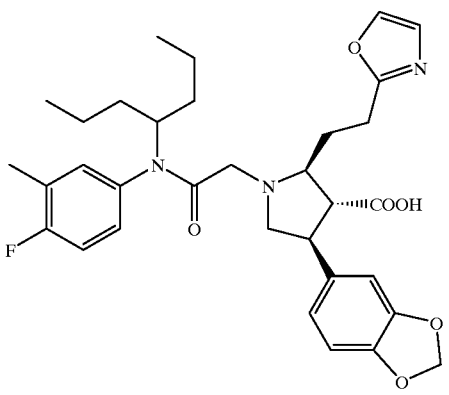
1110 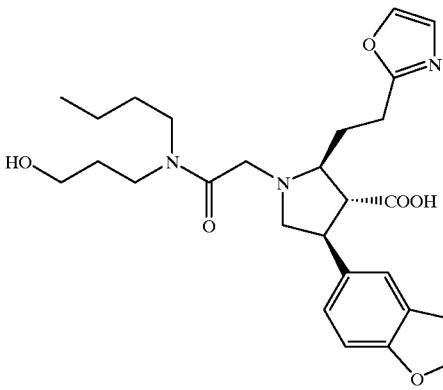
1111 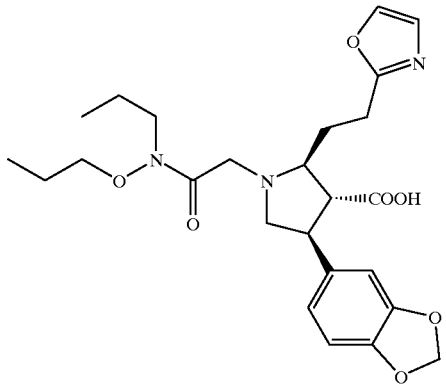

TABLE 3C-continued
1112 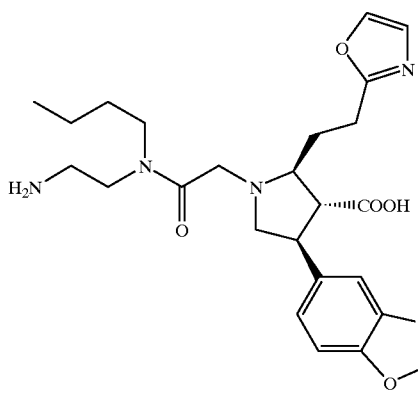
1113 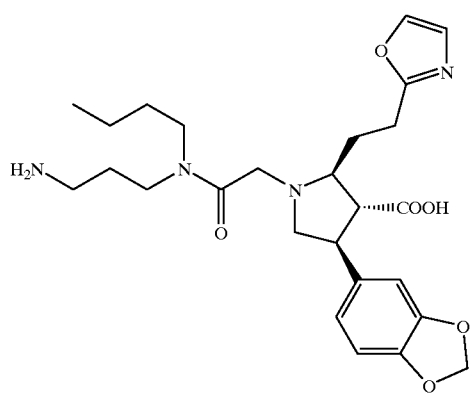
1114 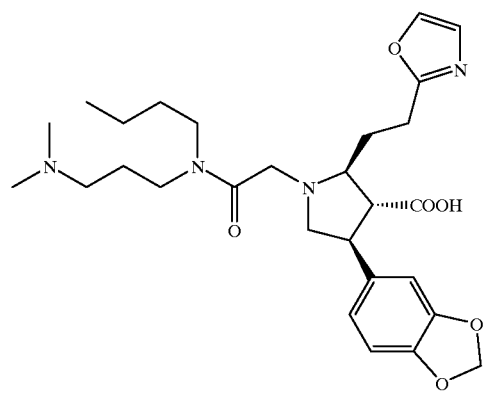
1115 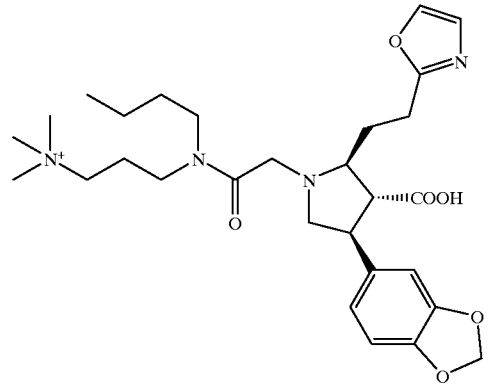

TABLE 3C-continued
1116
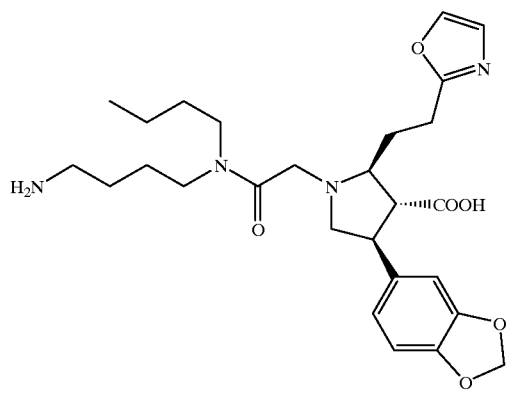
1117
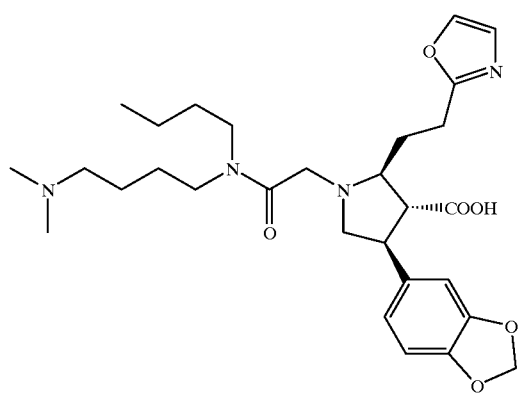
1118
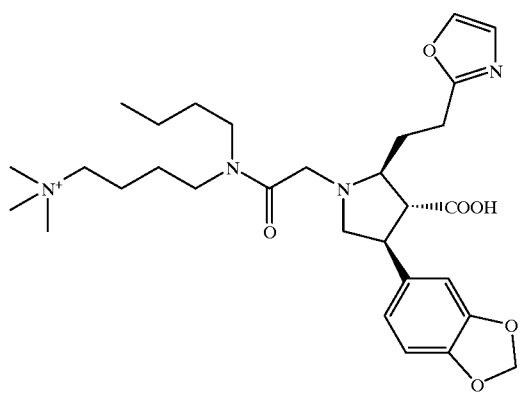
1119
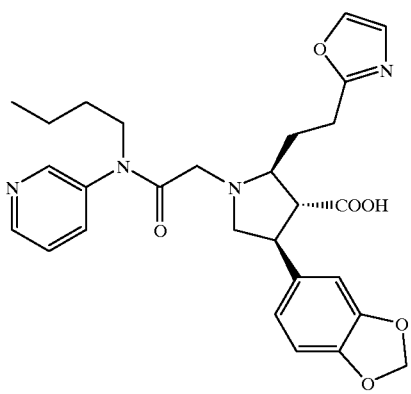

TABLE 3C-continued
1120 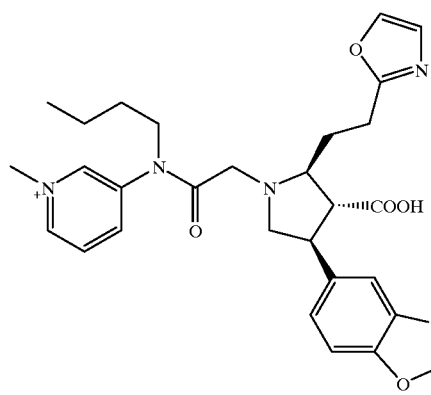
1121 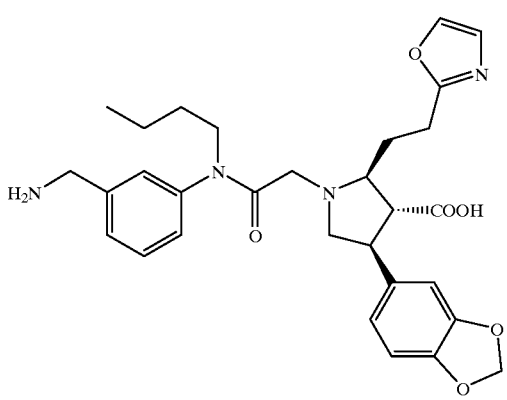
1122 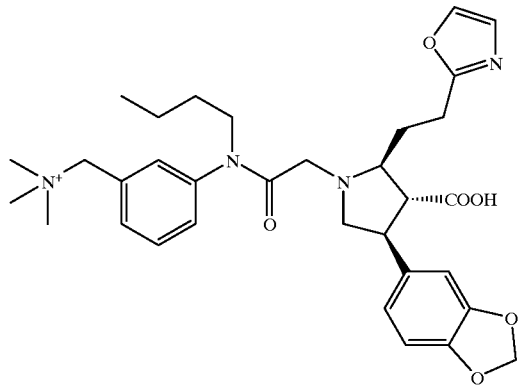
1123 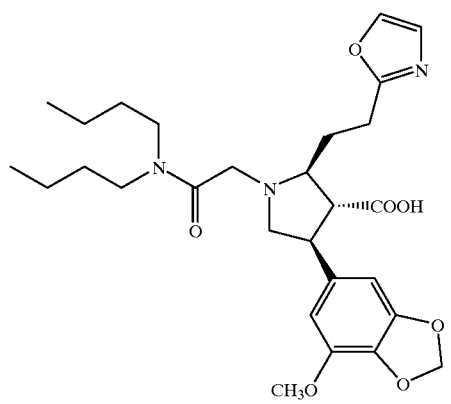

TABLE 3C-continued
1124
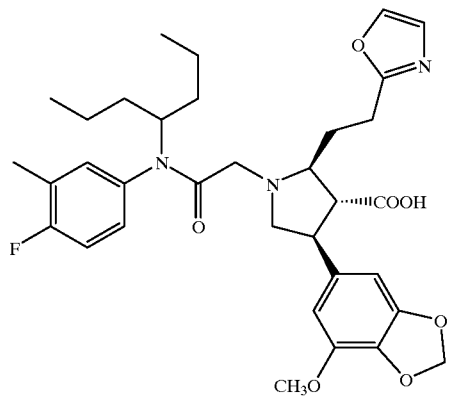
1125
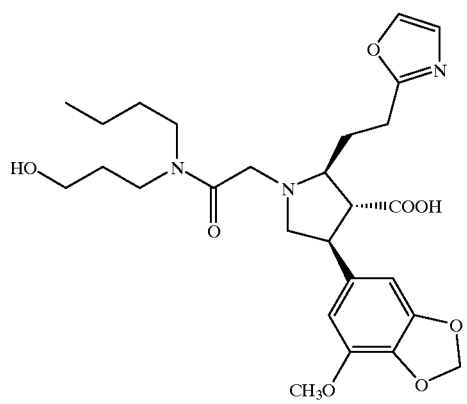
1126
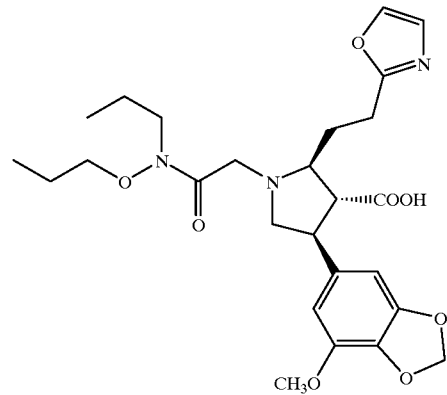

TABLE 3C-continued
1127
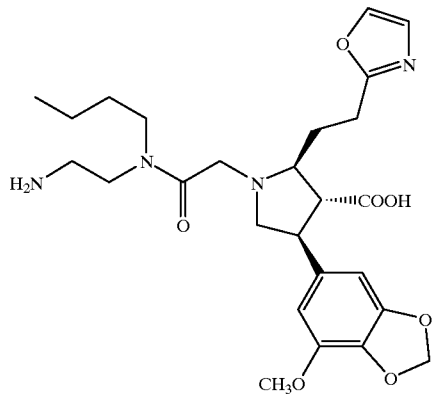
1128
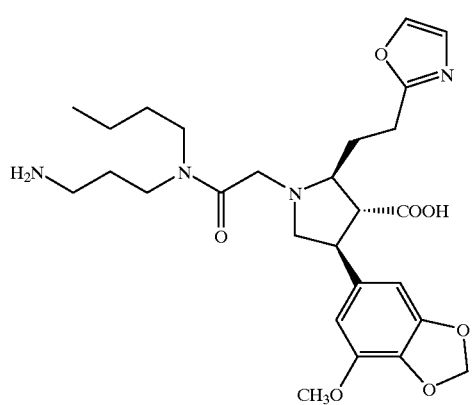
1129
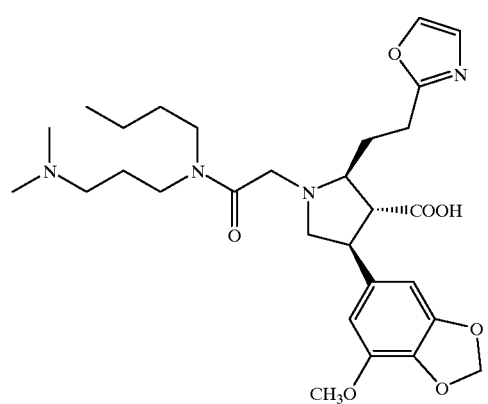

TABLE 3C-continued
1130
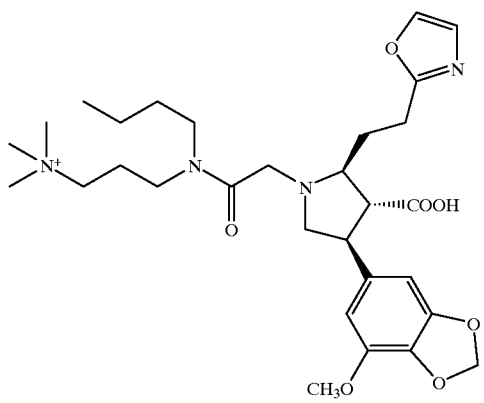
1131
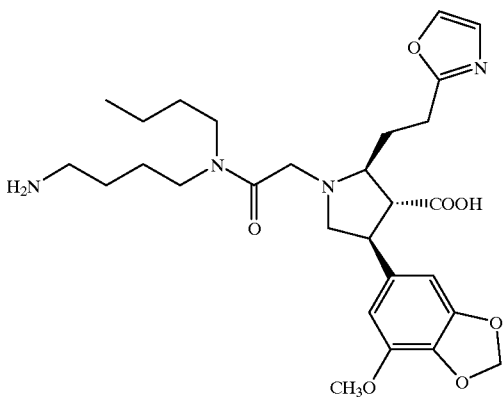
1132
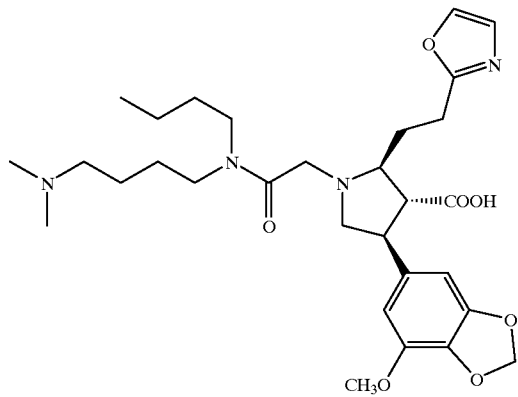

TABLE 3C-continued
1133
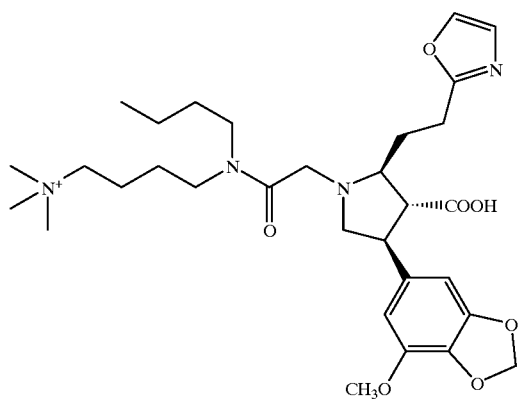
1134
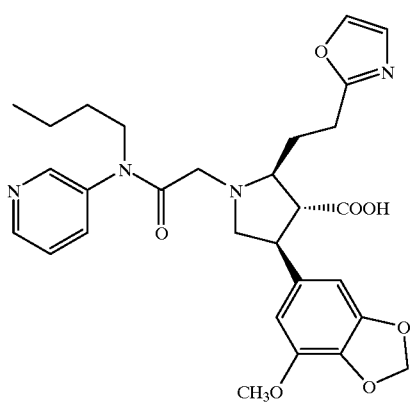
1135
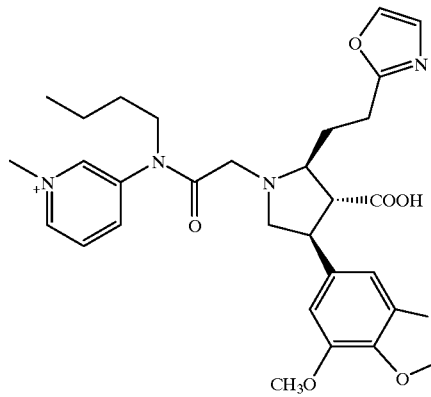

TABLE 3C-continued
1136
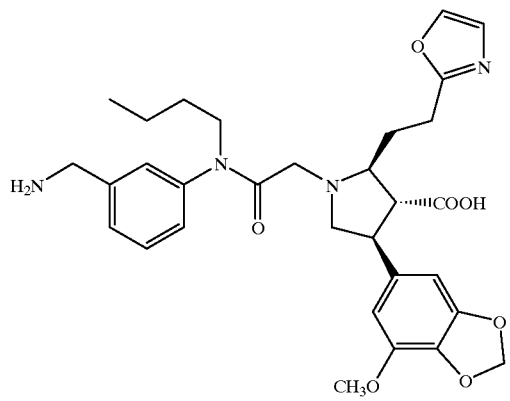
1137
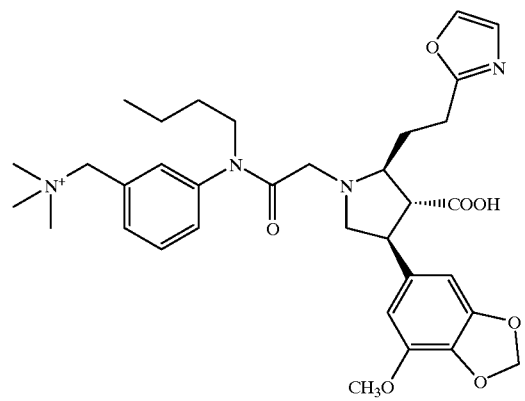
1138
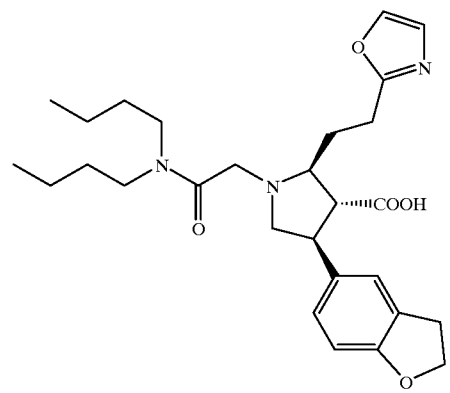
1139
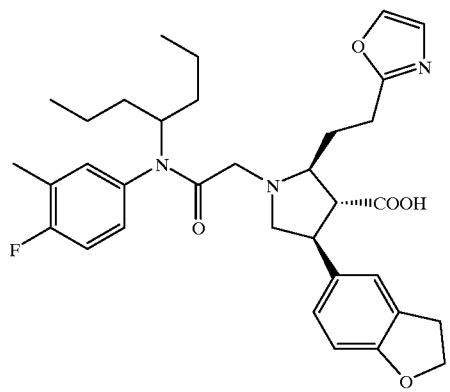

TABLE 3C-continued
1140
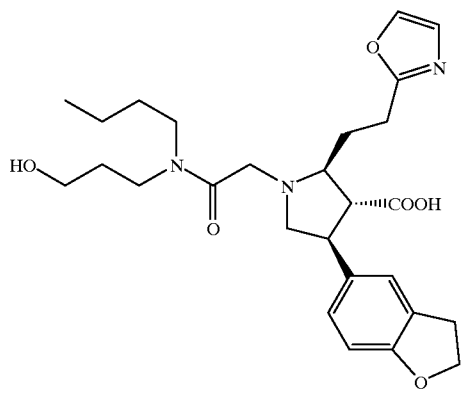
1141
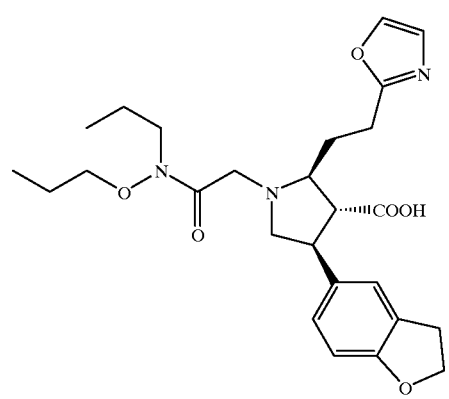
1142
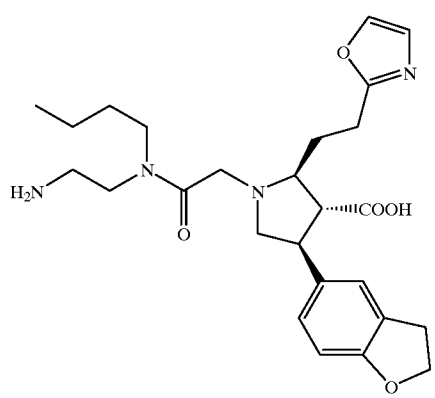
1143
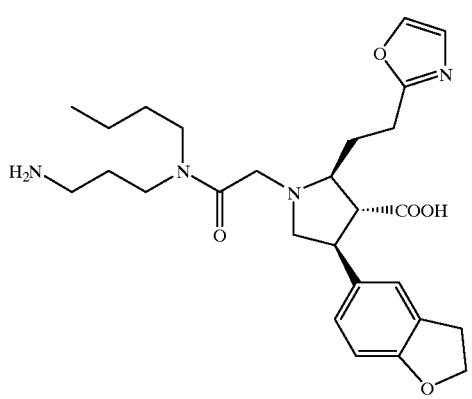

TABLE 3C-continued
1144
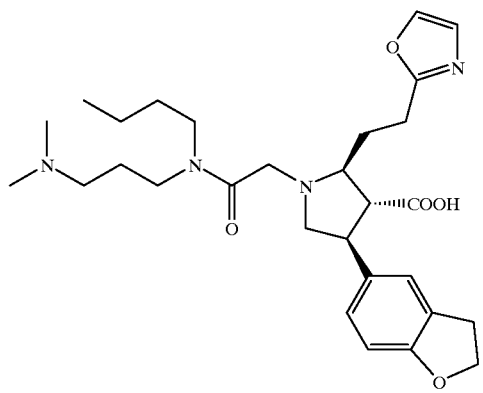
1145
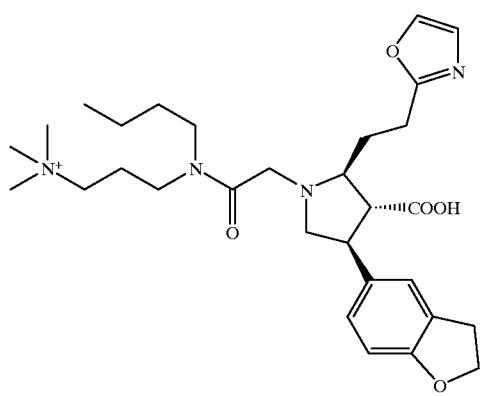
1146
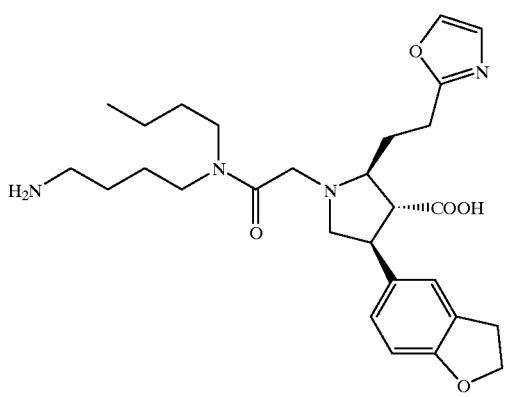
1147
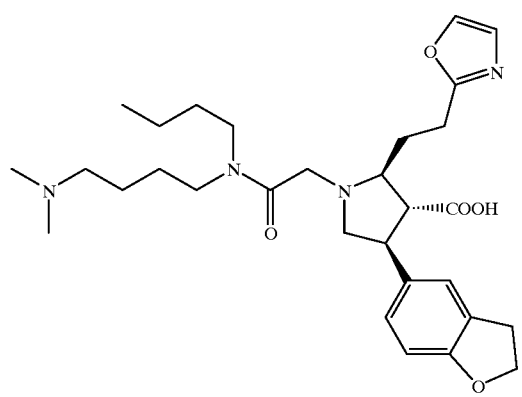

TABLE 3C-continued
1148
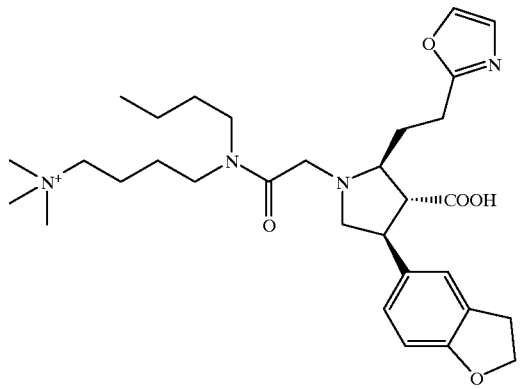
1149
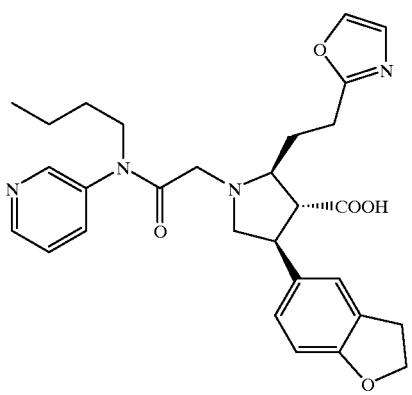
1150
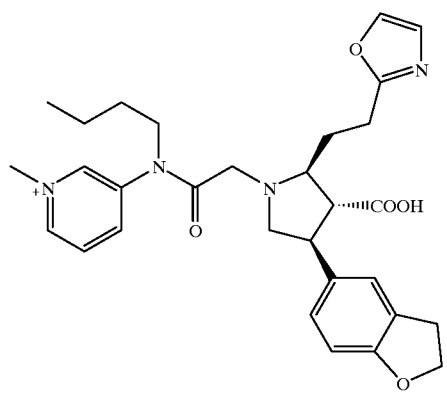
1151
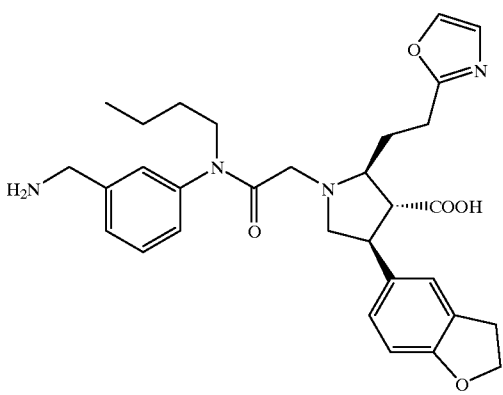

TABLE 3C-continued
1152
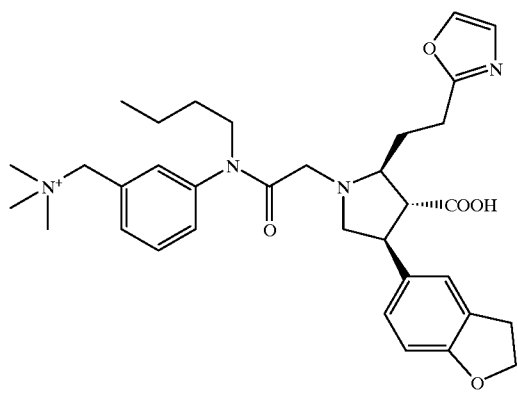
1153
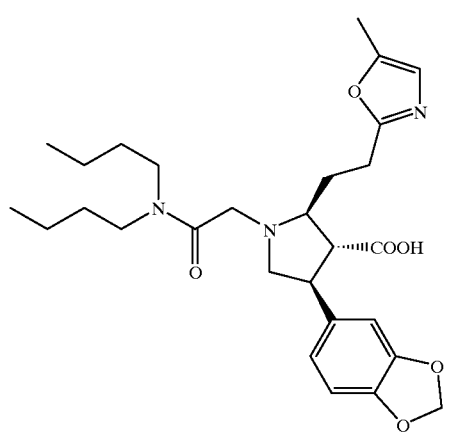
1154
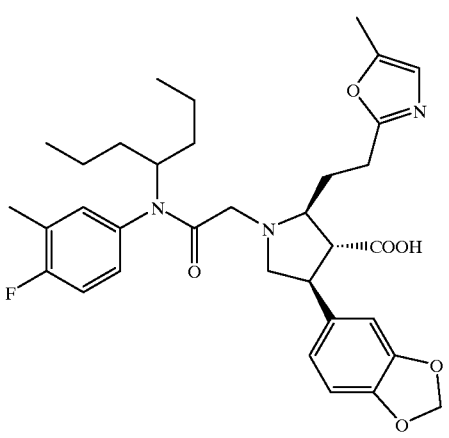

TABLE 3C-continued
1155
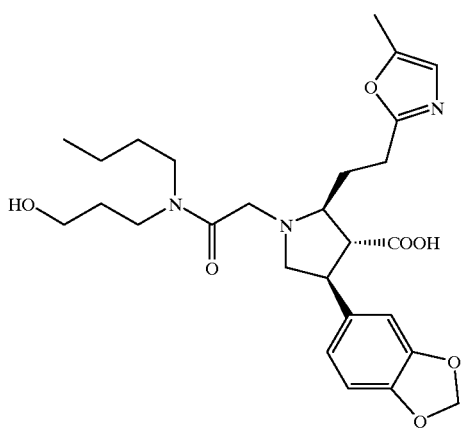
1156
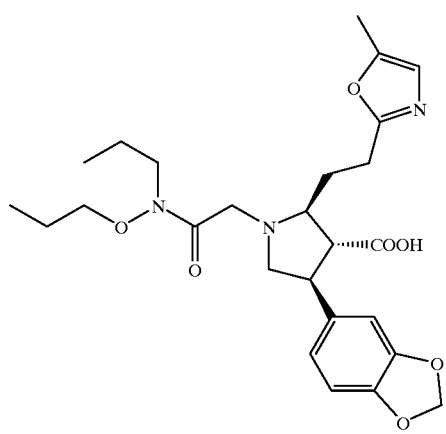
1157
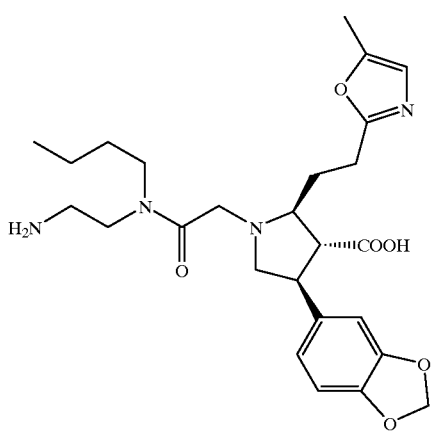

TABLE 3C-continued
1158
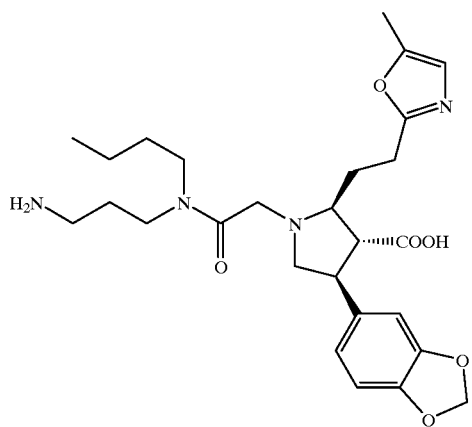
1159
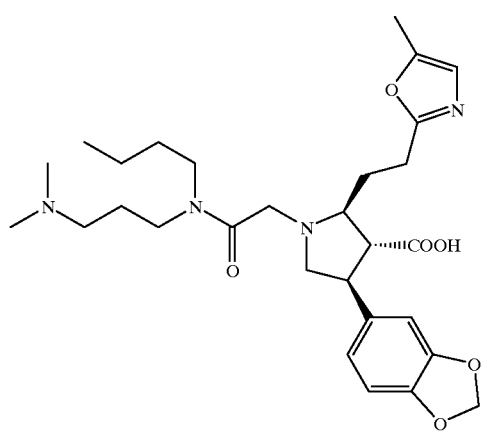
1160
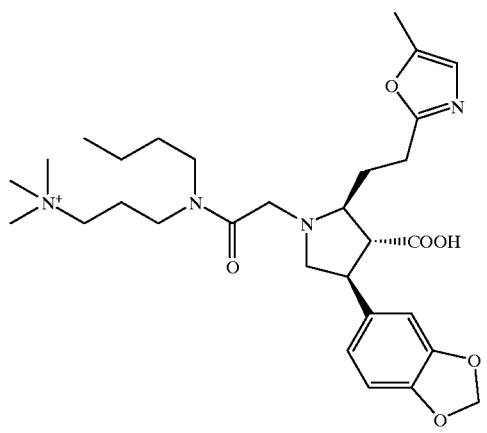

TABLE 3C-continued
1161
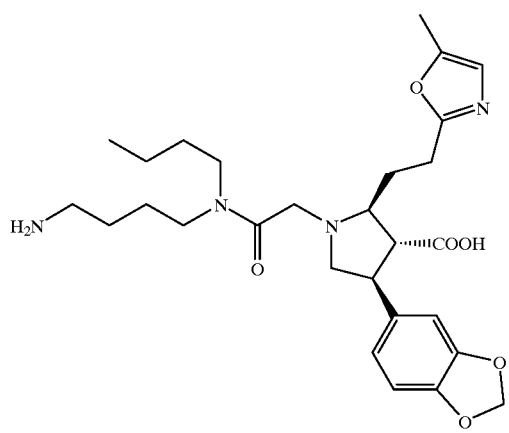
1162
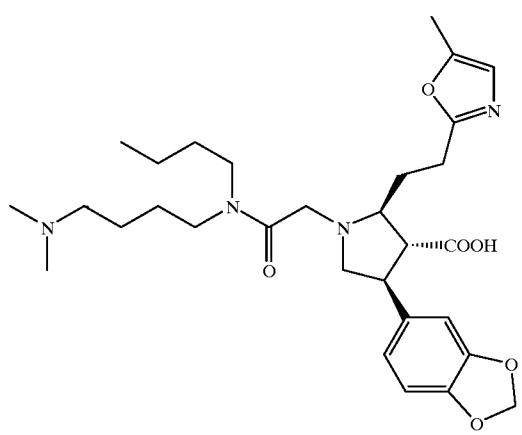
1163
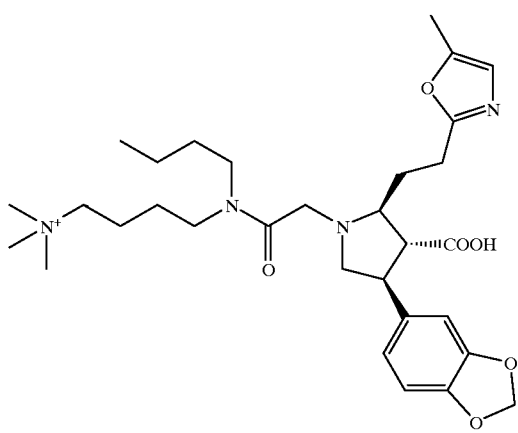

TABLE 3C-continued
1164
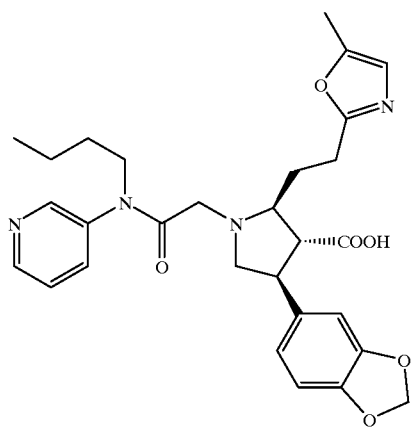
1165
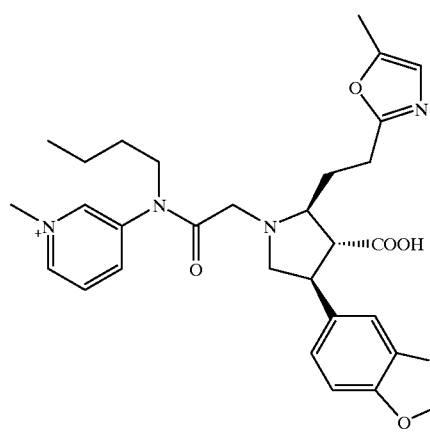
1166
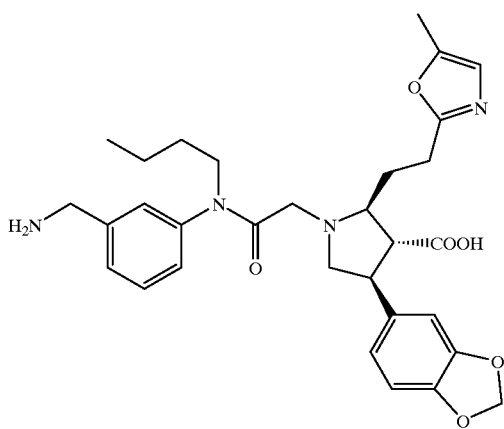

TABLE 3C-continued
1167
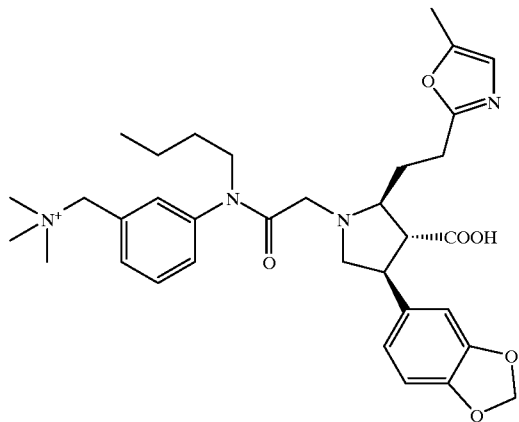
1168
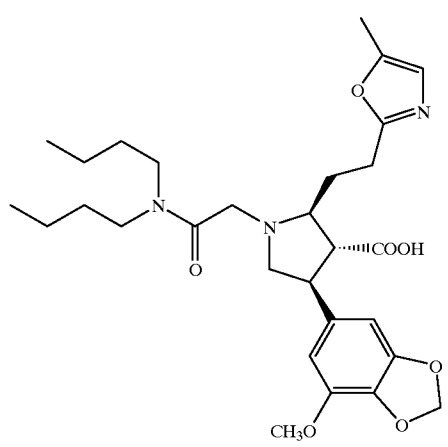
1169
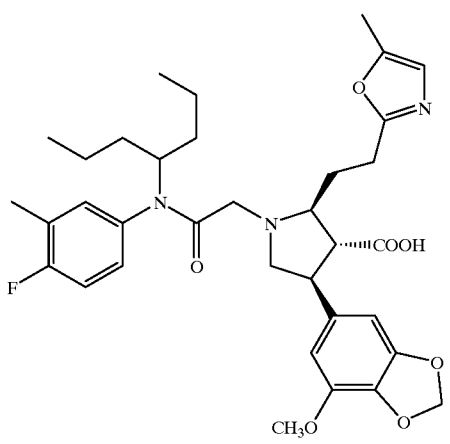

TABLE 3C-continued
1170
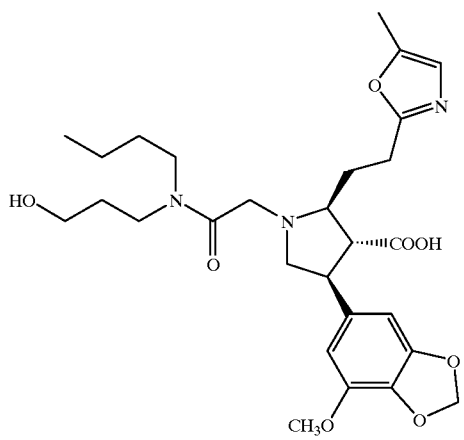
1171
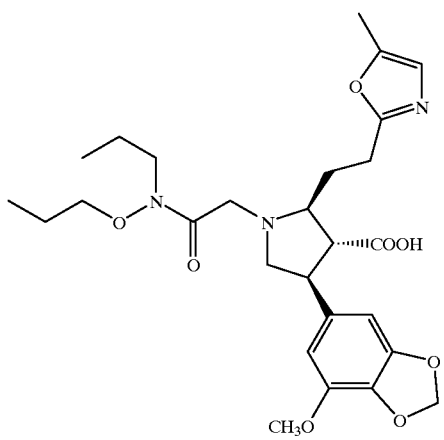
1172
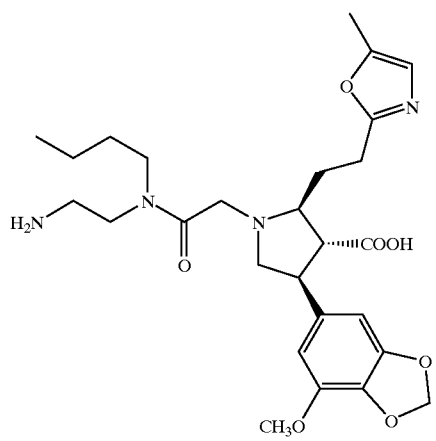

TABLE 3C-continued
1173
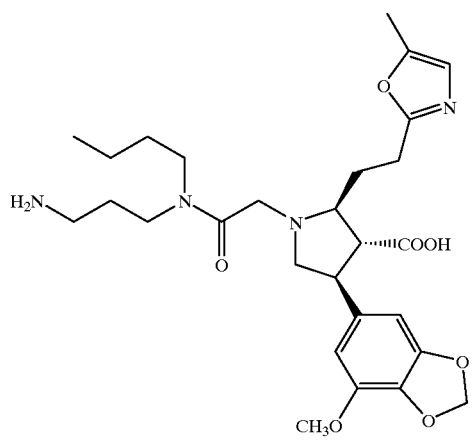
1174
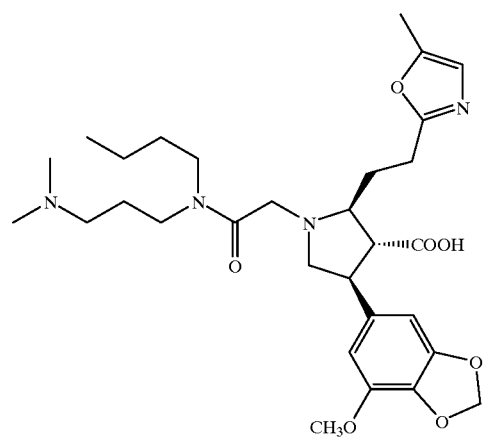
1175
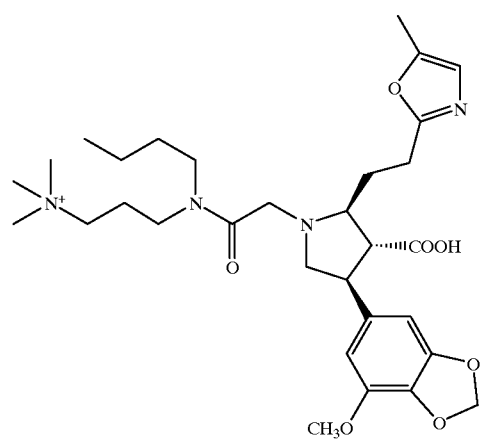

TABLE 3C-continued
1176
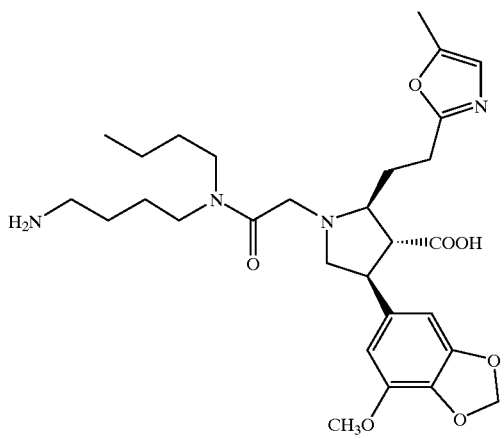
1177
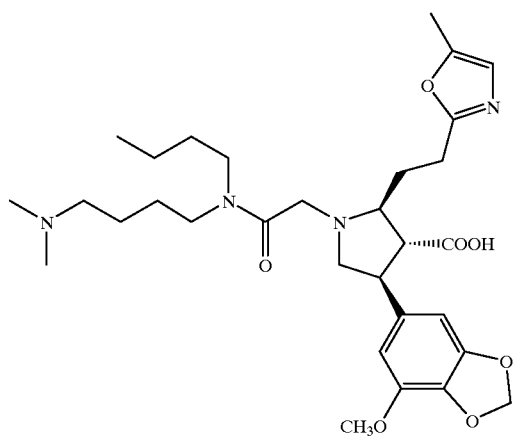
1178
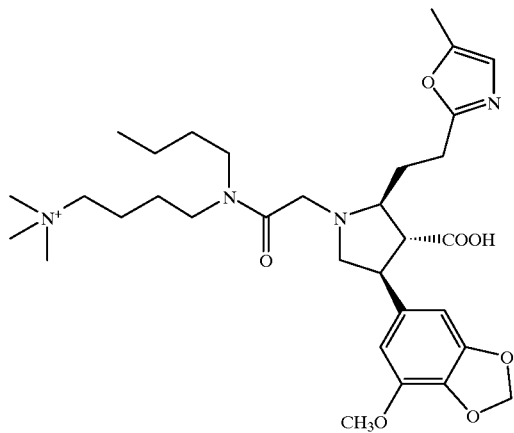

TABLE 3C-continued
1179
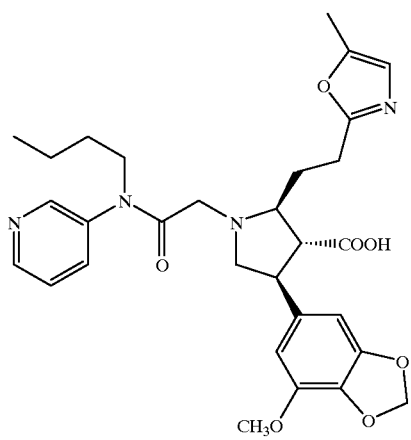
1180
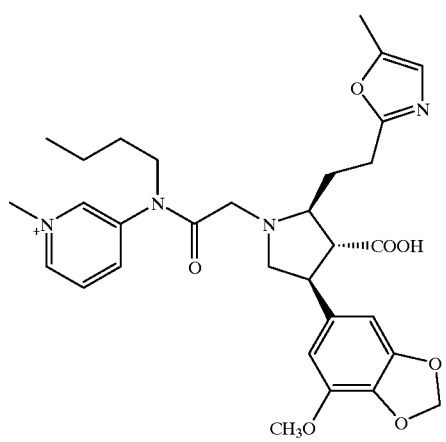
1181
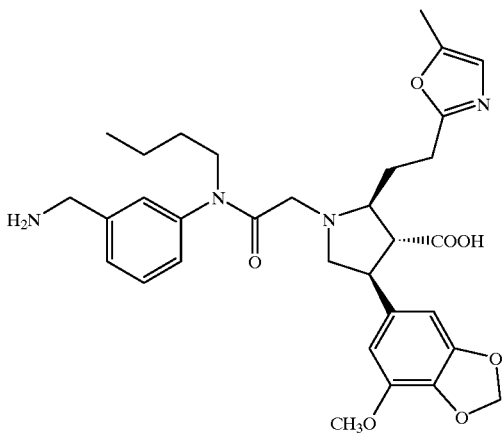

TABLE 3C-continued
1182
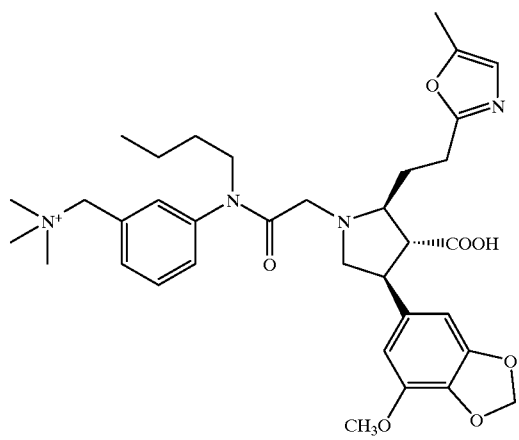
1183
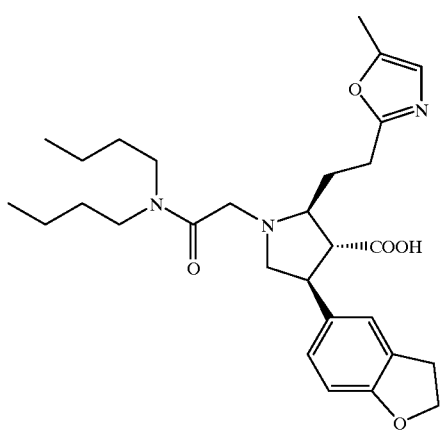
1184
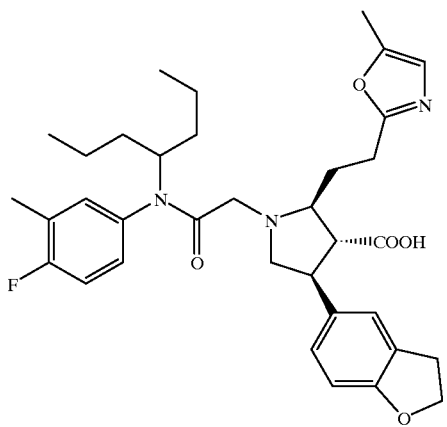

TABLE 3C-continued
1185
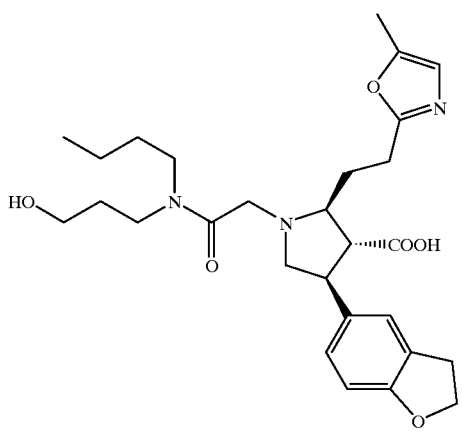
1186
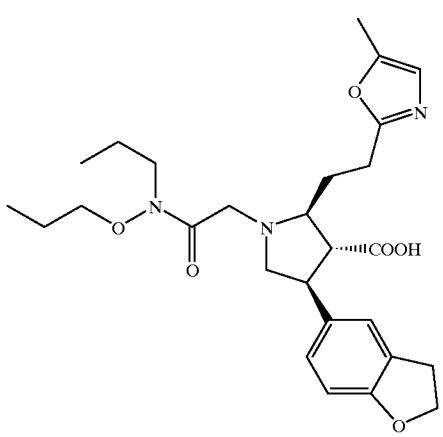
1187
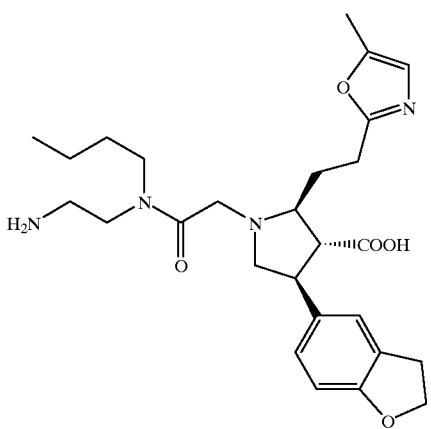

TABLE 3C-continued
1188
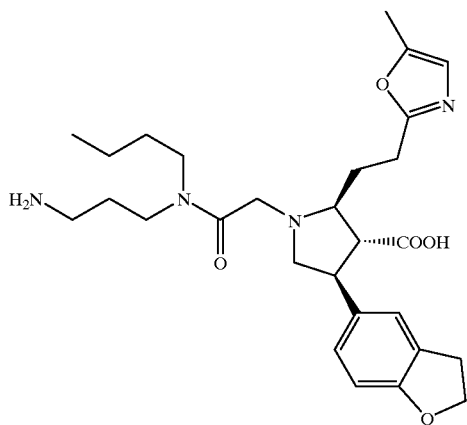
1189
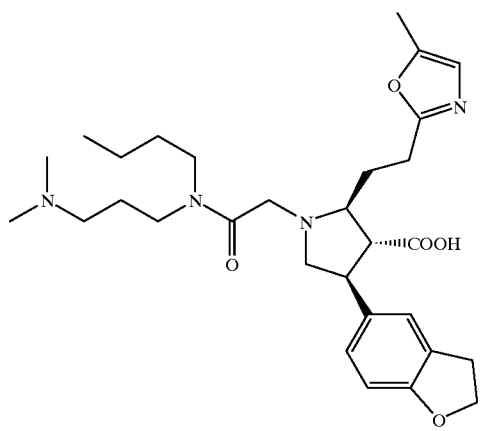
1190
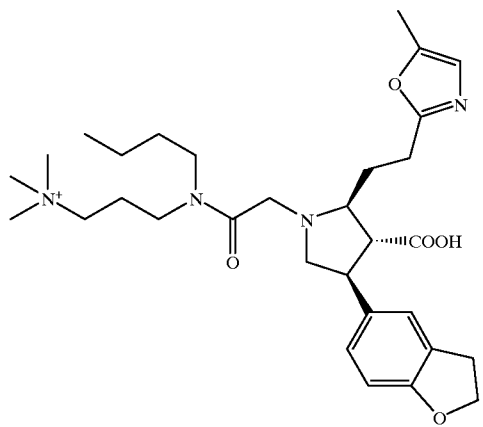

TABLE 3C-continued
1191
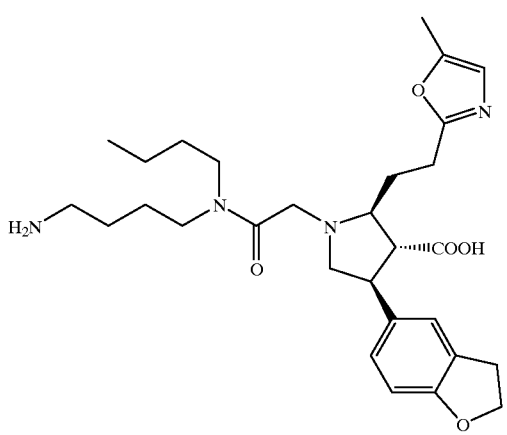
1192
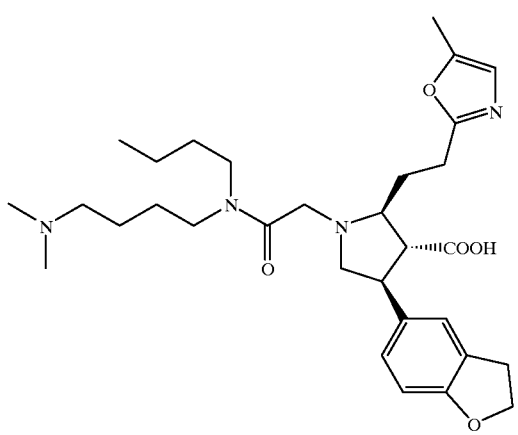
1193
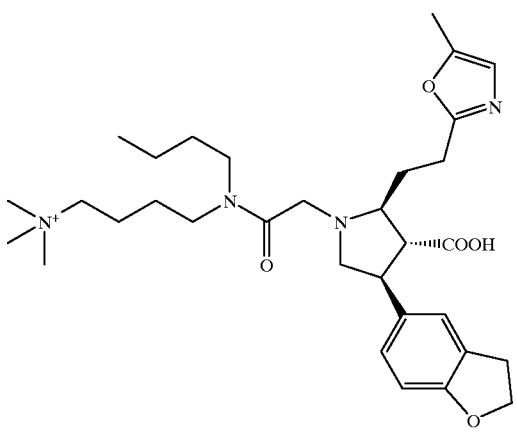

TABLE 3C-continued
1194
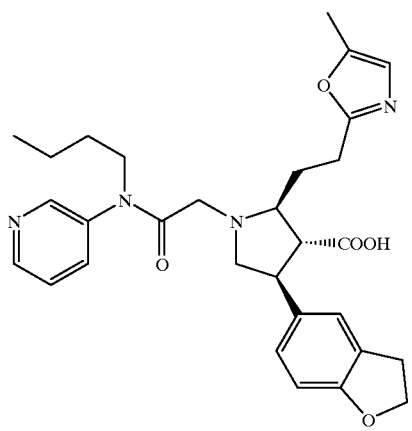
1195
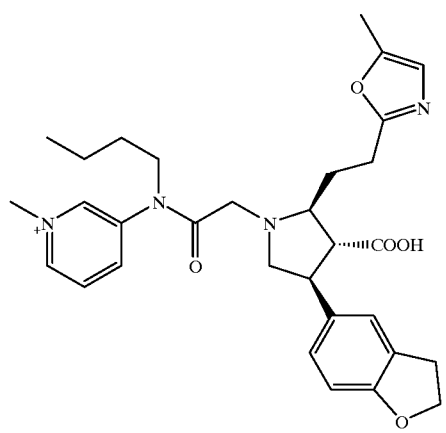
1196
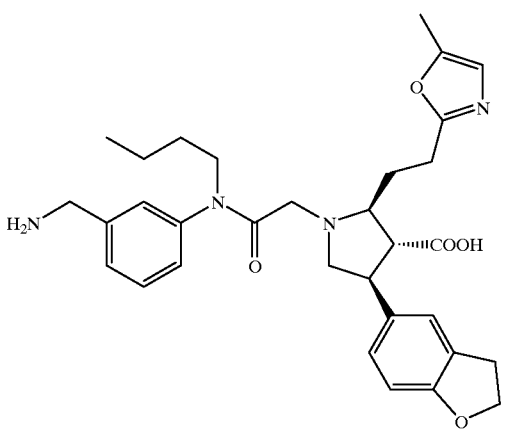

TABLE 3C-continued
1197
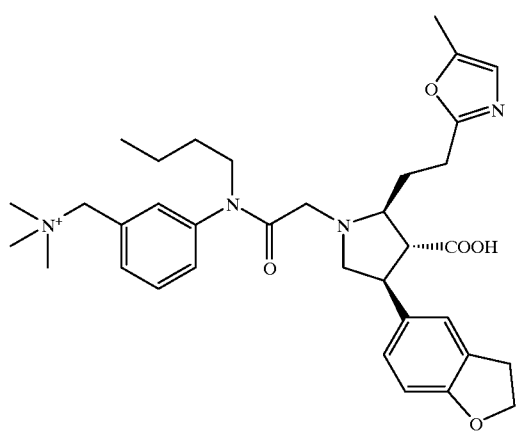
1198
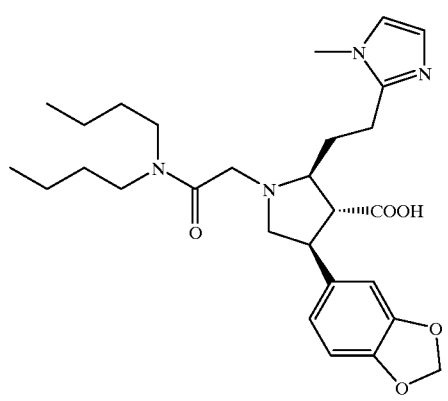
1199
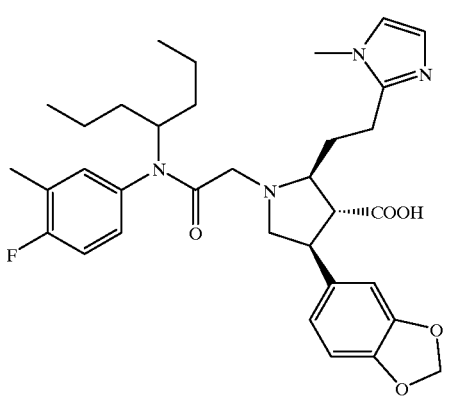
1200
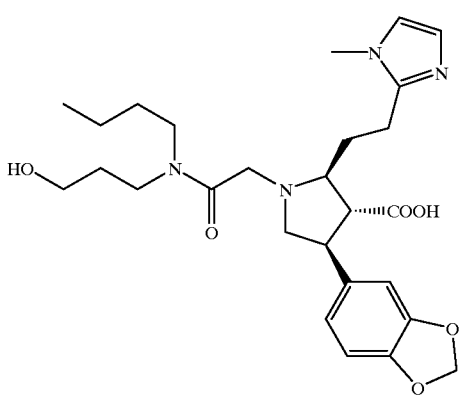

TABLE 3C-continued
1201 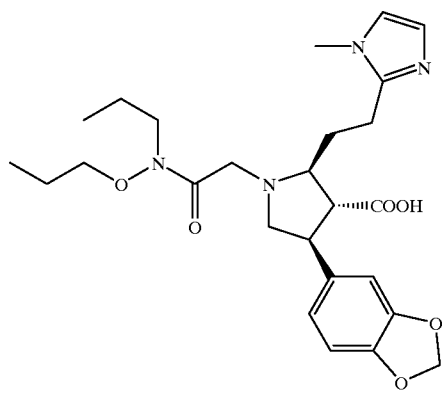
1202 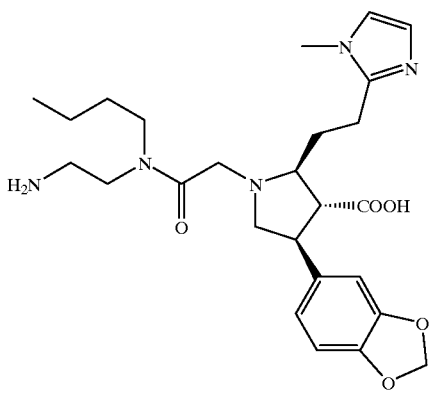
1203 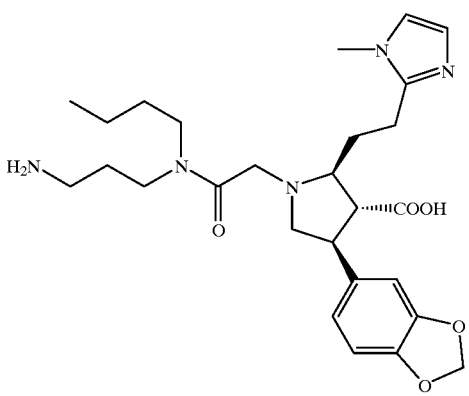
1204 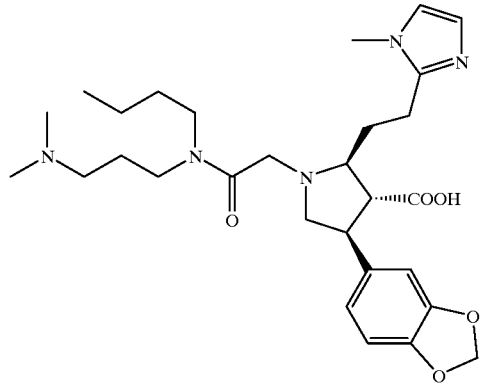

TABLE 3C-continued
1205 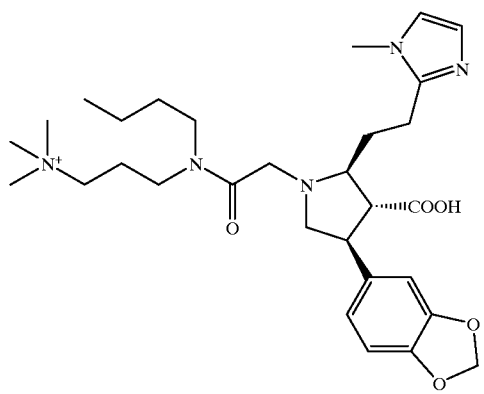
1206 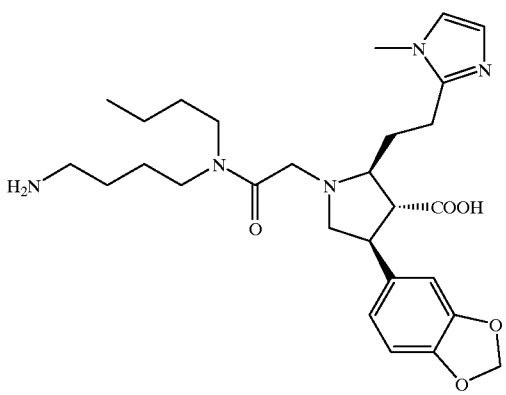
1207 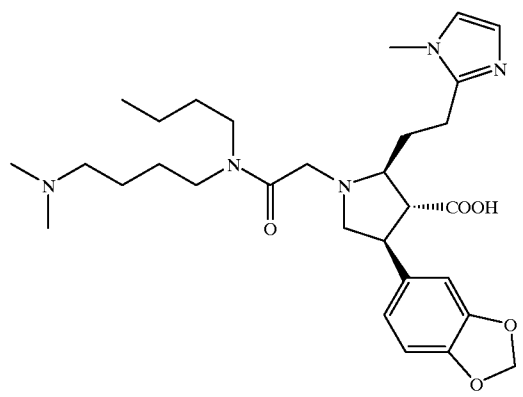
1208 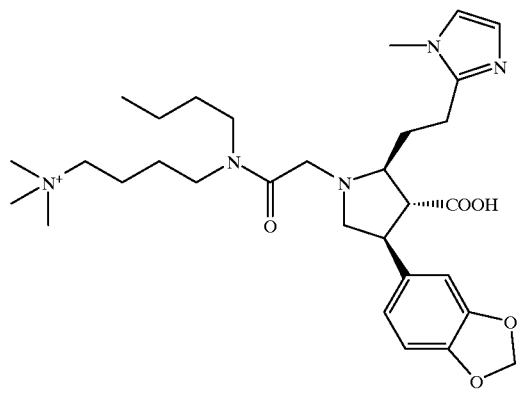

TABLE 3C-continued
1209
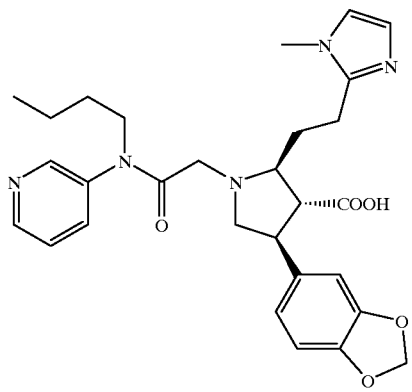
1210
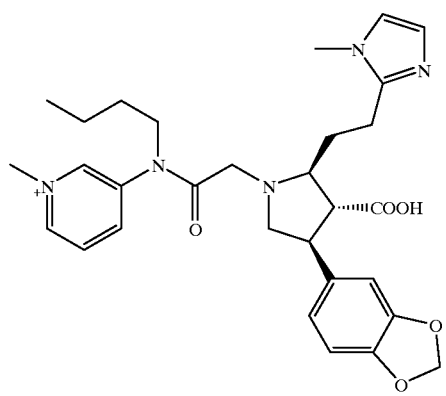
1211
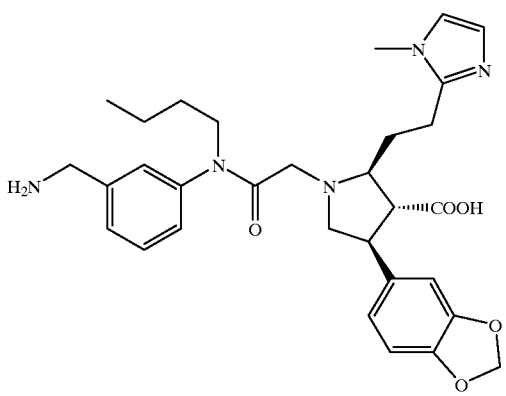
1212
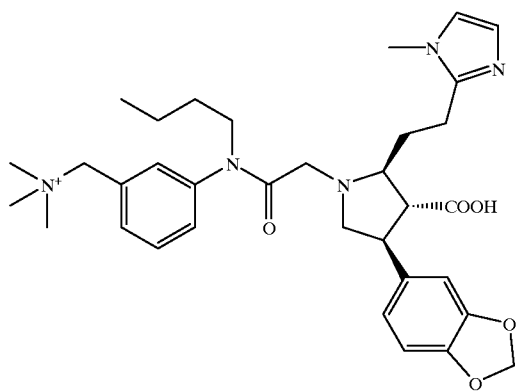

TABLE 3C-continued
1213
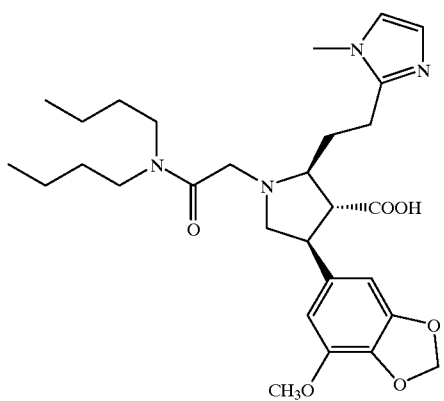
1214
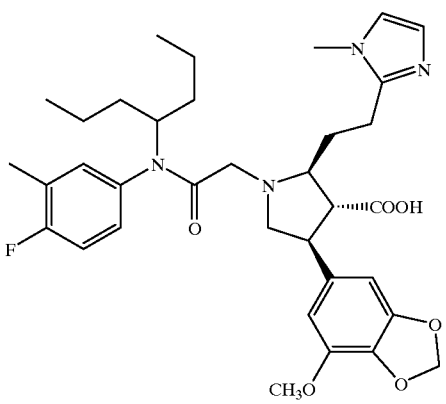
1215
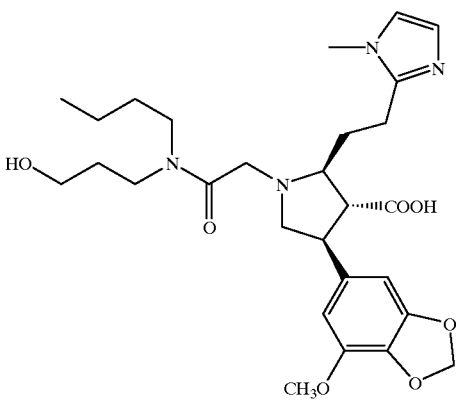

TABLE 3C-continued
1216
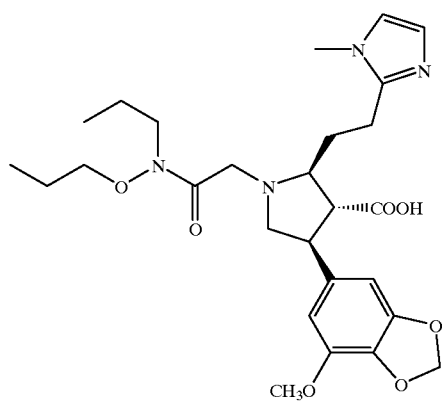
1217
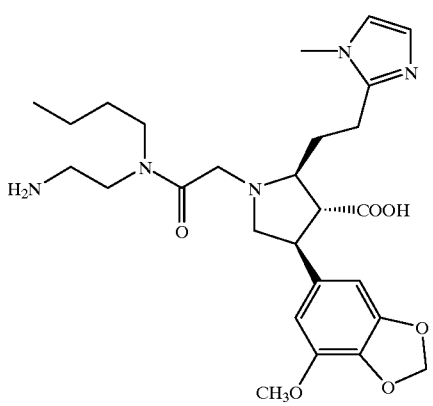
1218
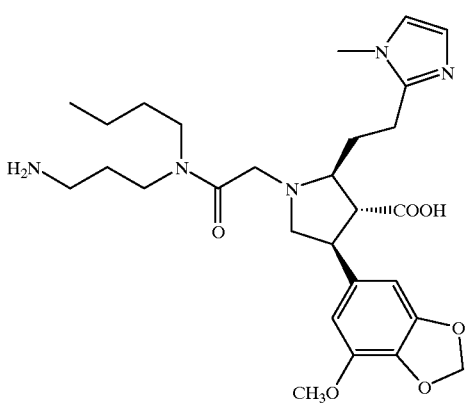
1219
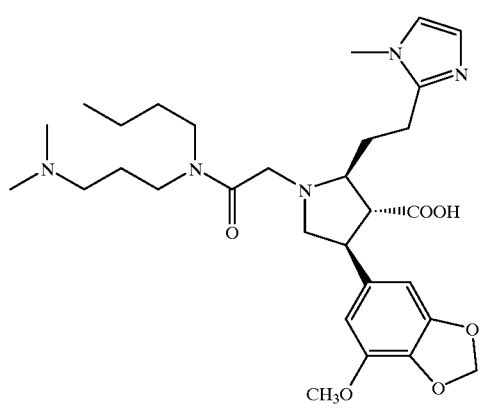

TABLE 3C-continued
1220
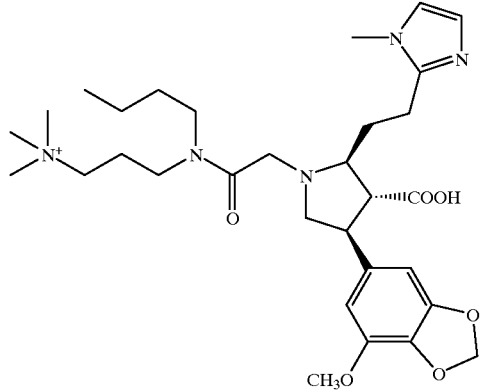
1221
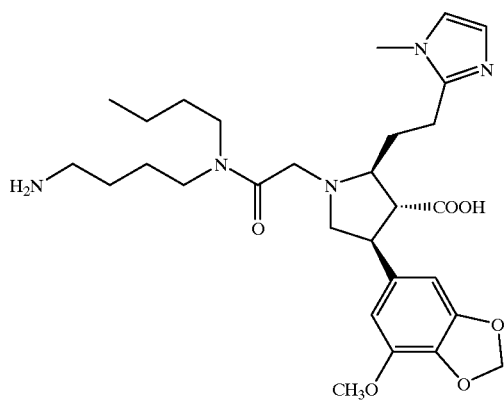
1222
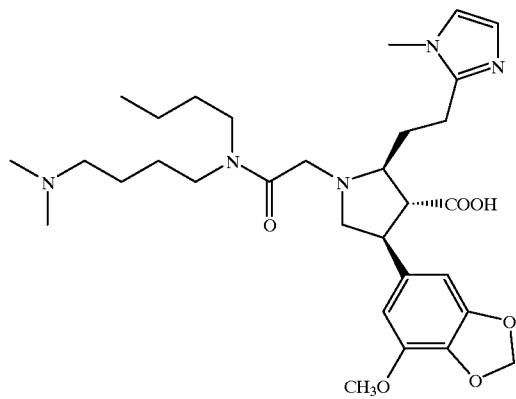

TABLE 3C-continued
1223
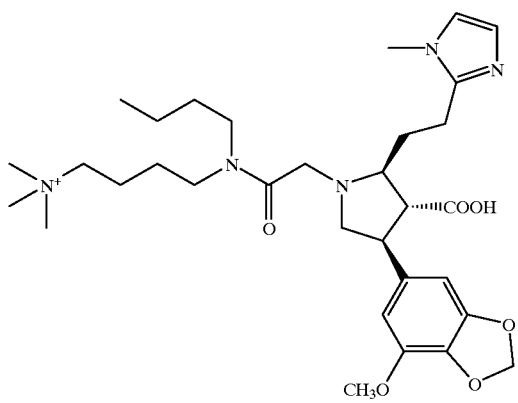
1224
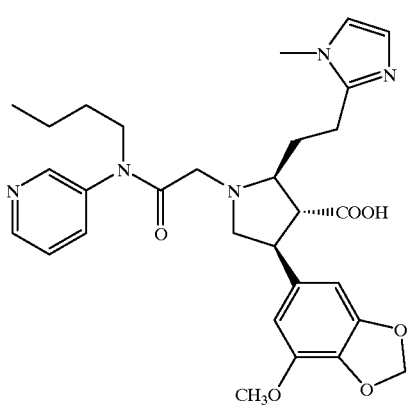
1225
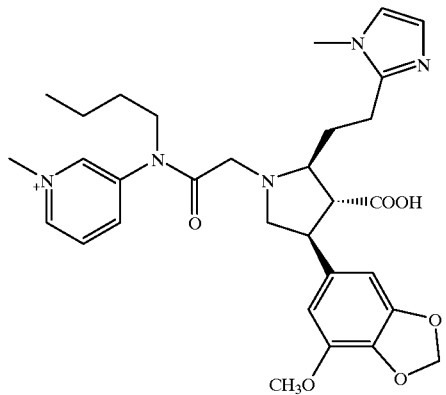

TABLE 3C-continued
1226
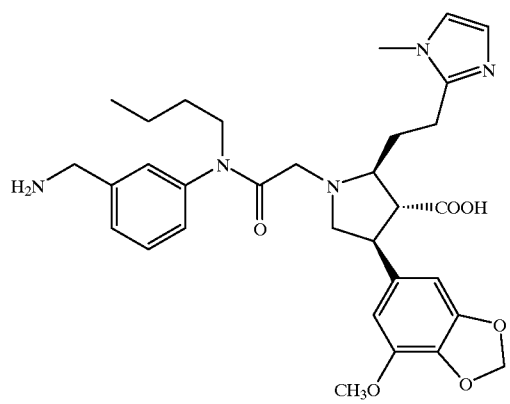
1227
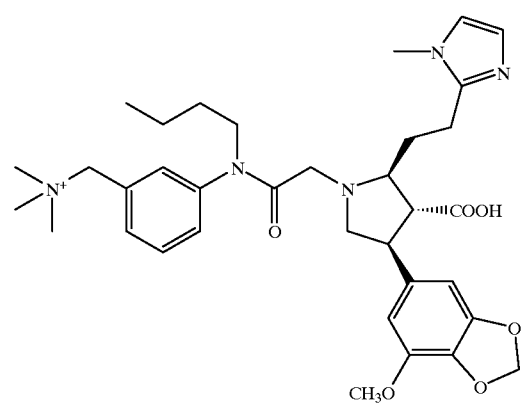
1228
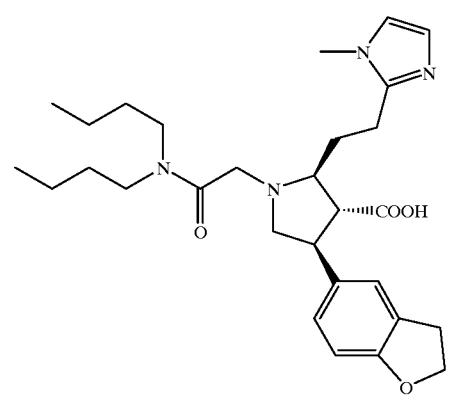
1229
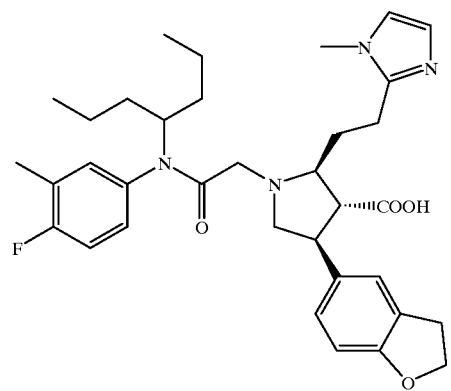

TABLE 3C-continued
1230 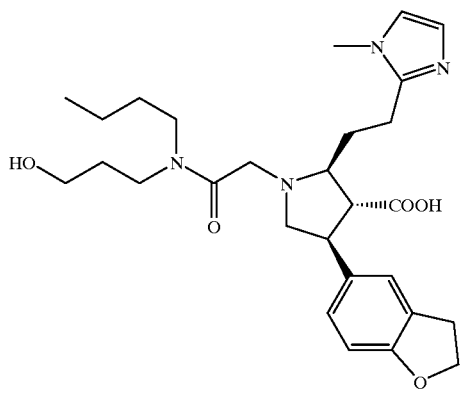
1231 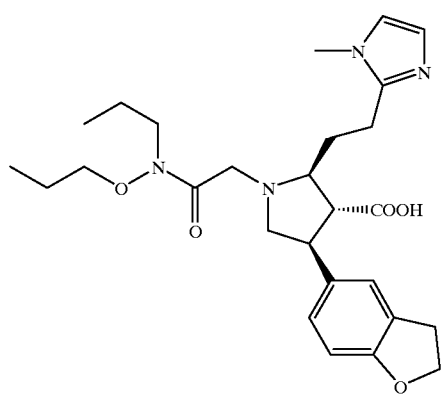
1232 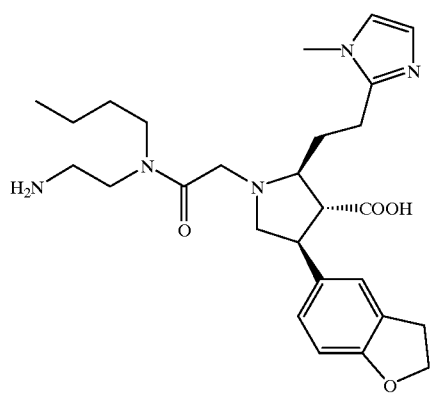
1233 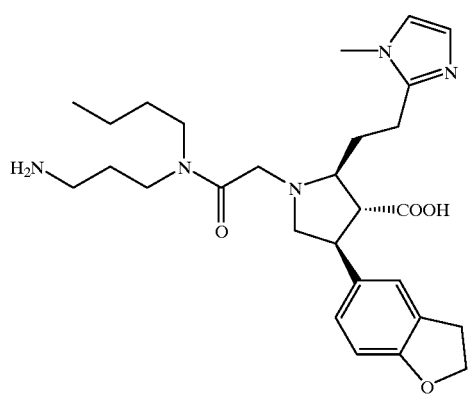

TABLE 3C-continued
1234
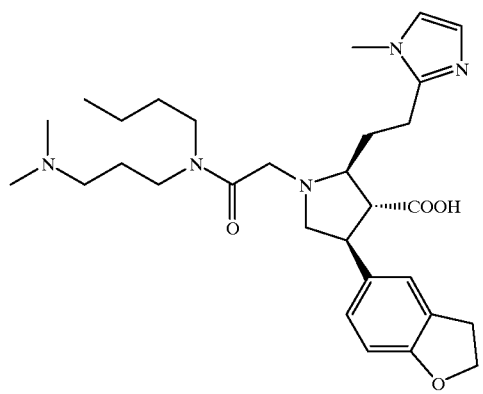
1235
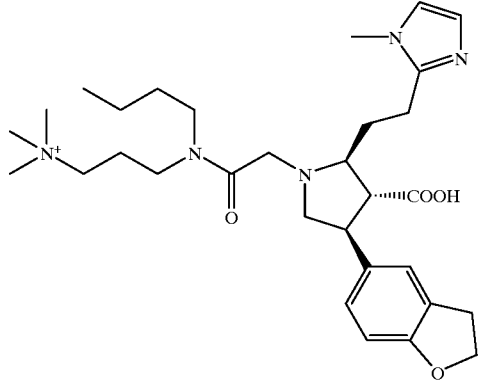
1236
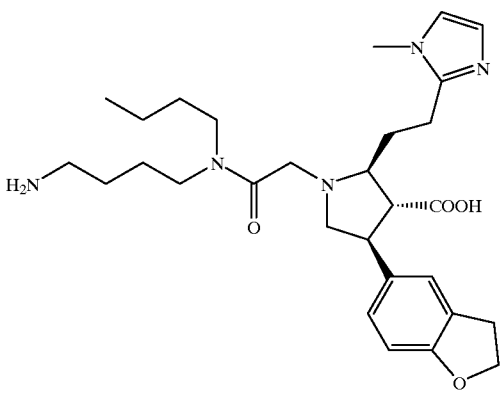
1237
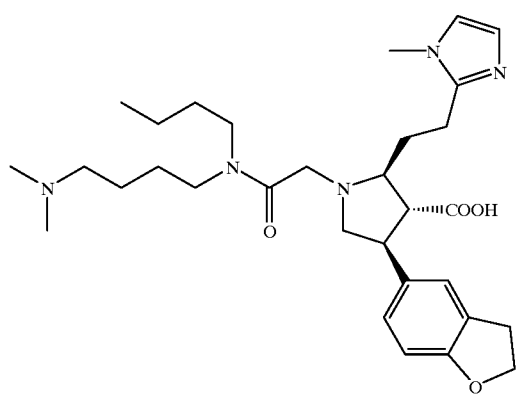

TABLE 3C-continued
1238
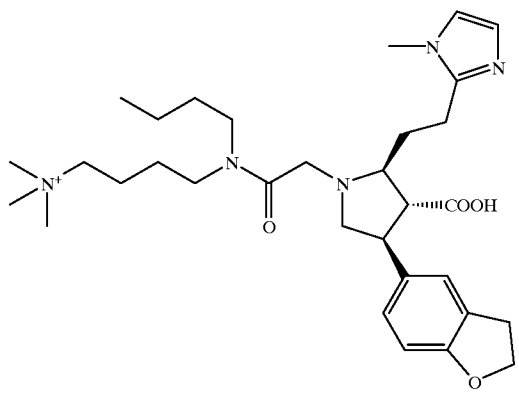
1239
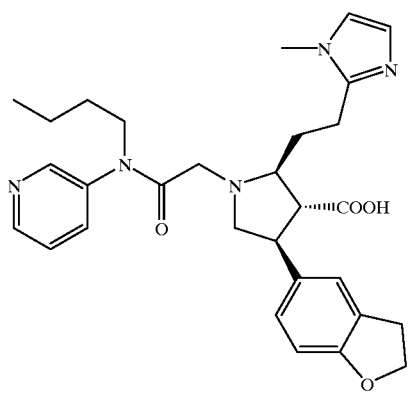
1240
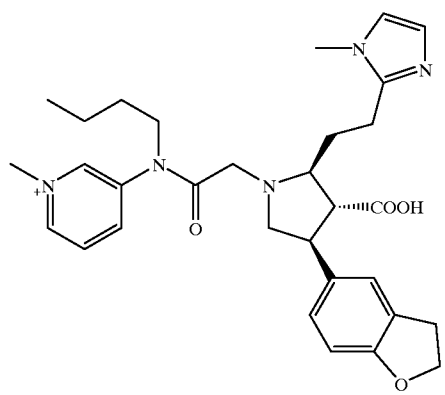
1241
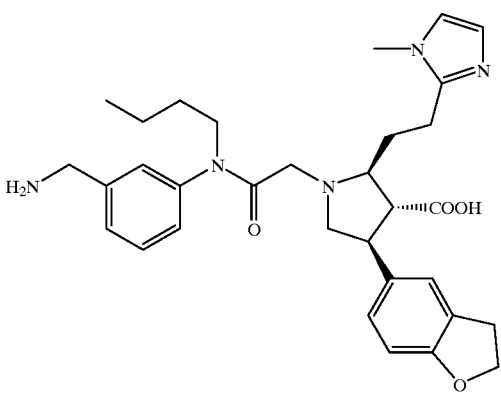

TABLE 3C-continued
1242 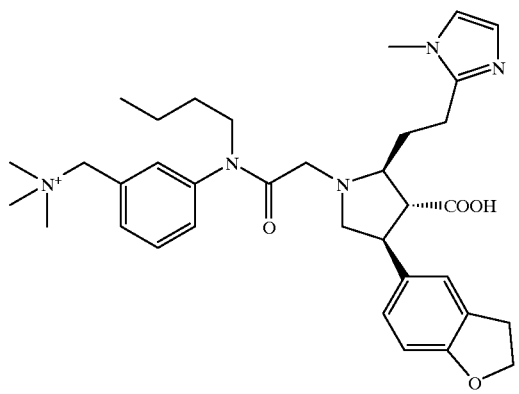
1243 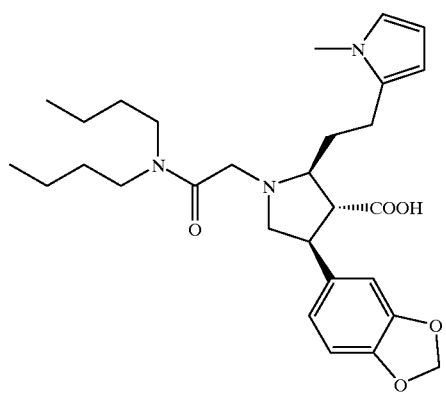
1244 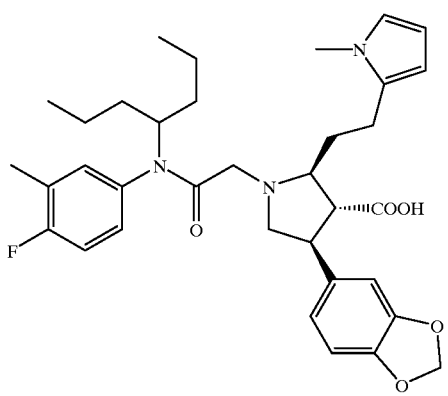
1245 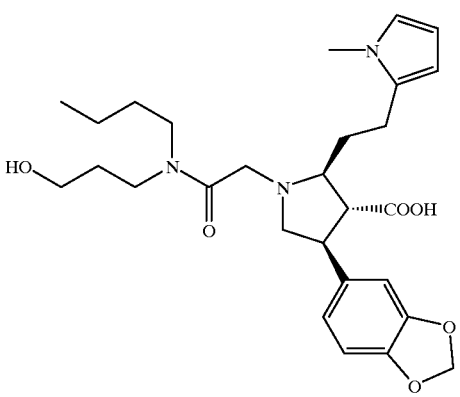

TABLE 3C-continued
1246
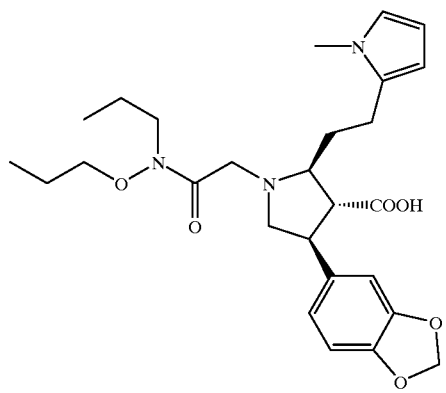
1247
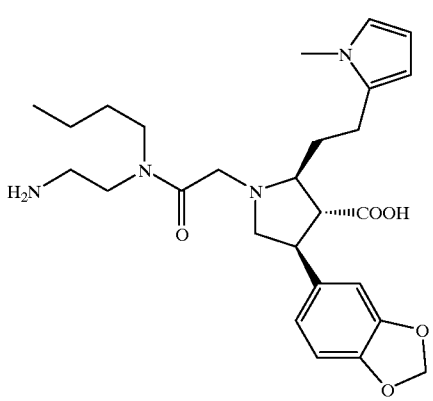
1248
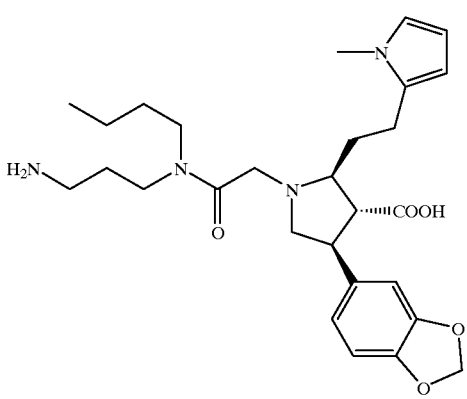
1249
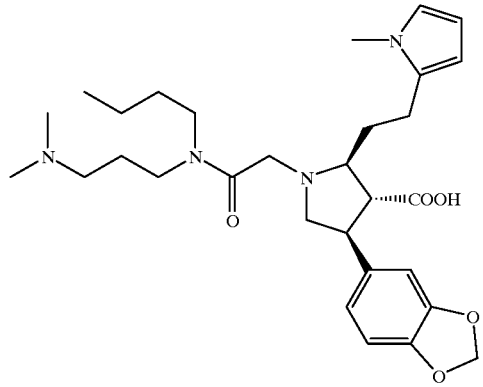

TABLE 3C-continued
1250 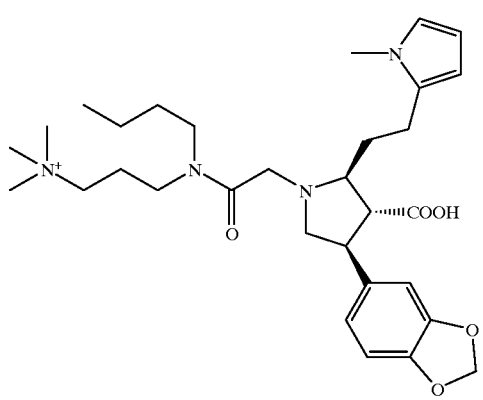
1251 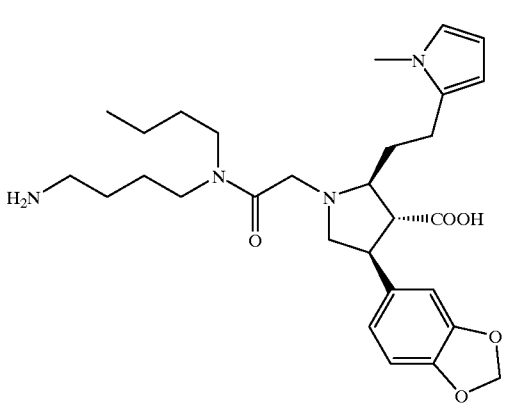
1252 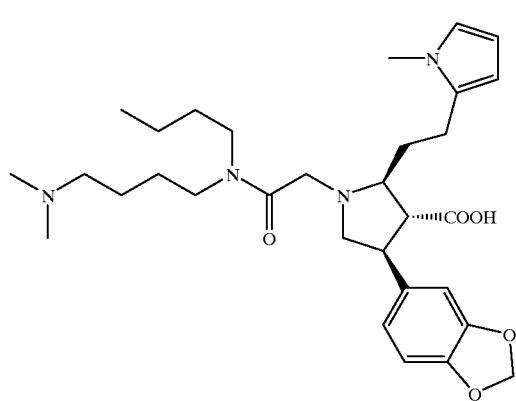
1253 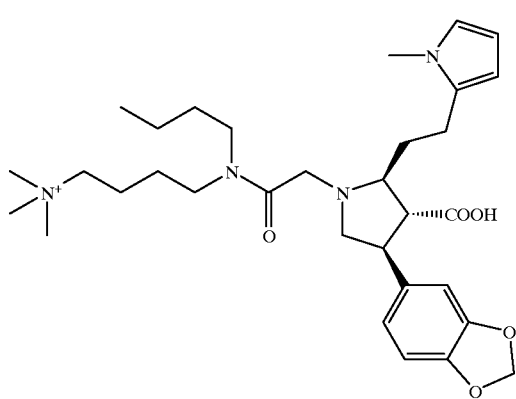

TABLE 3C-continued
1254
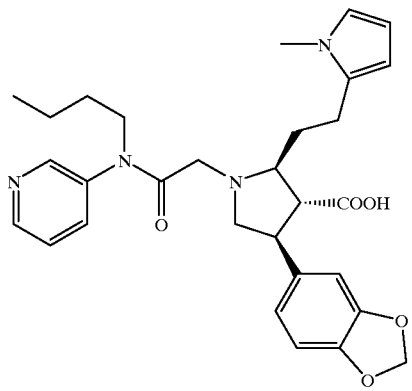
1255
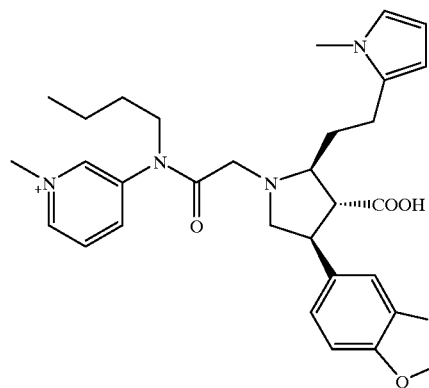
1256
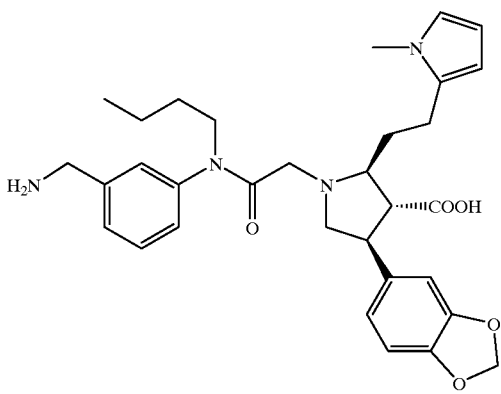
1257
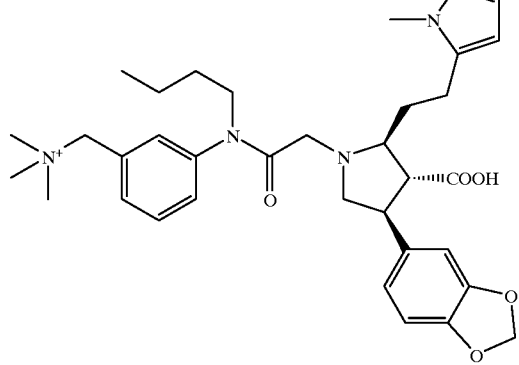

TABLE 3C-continued
1258
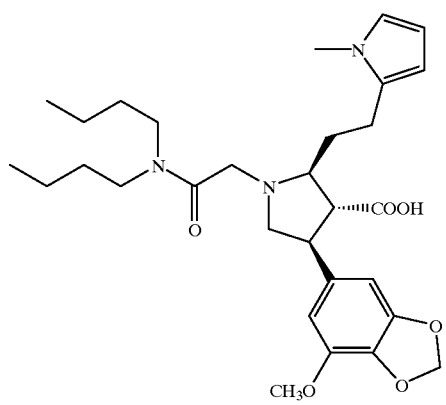
1259
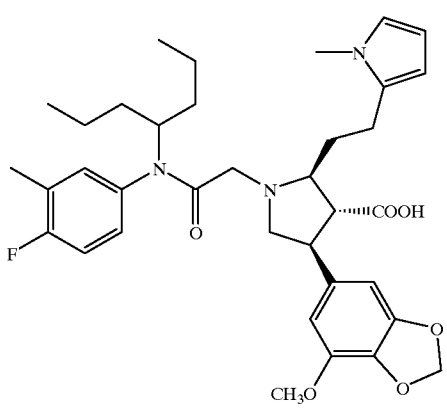
1260
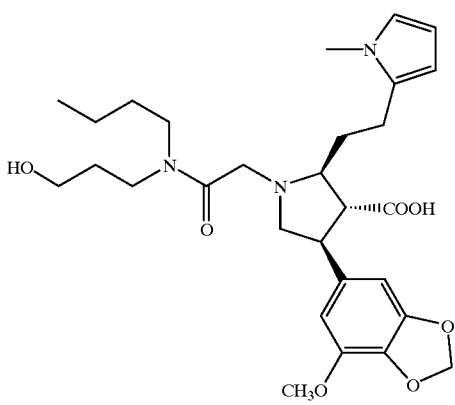

TABLE 3C-continued
1261
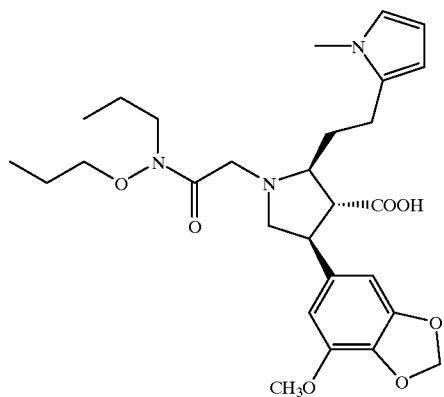
1262
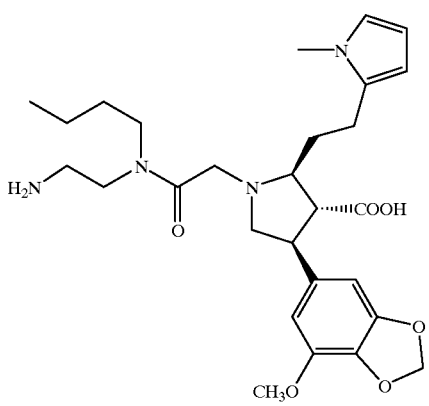
1263
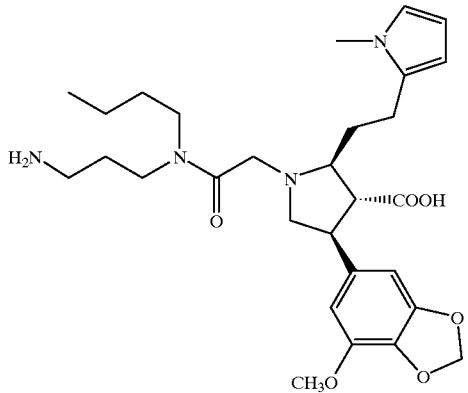

TABLE 3C-continued
1264
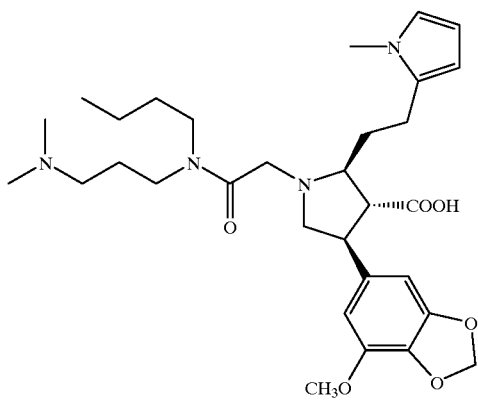
1265
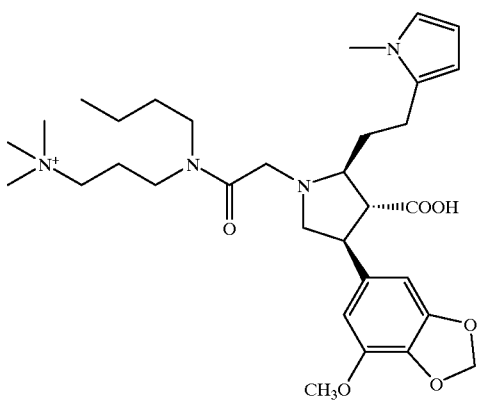
1266
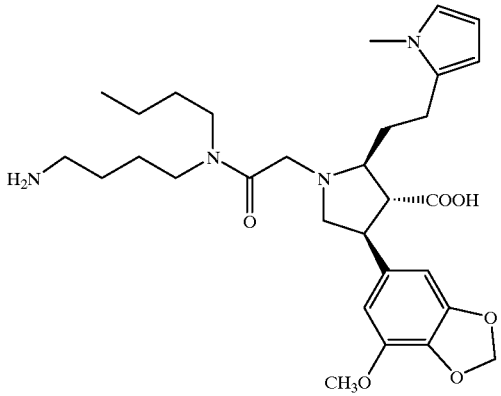

TABLE 3C-continued
1267
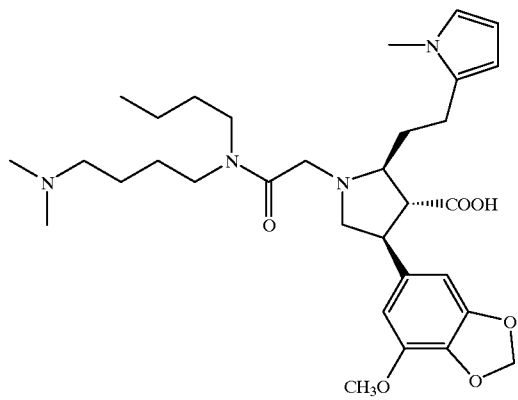
1268
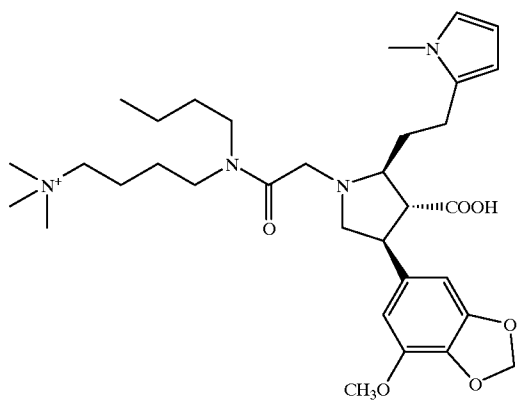
1269
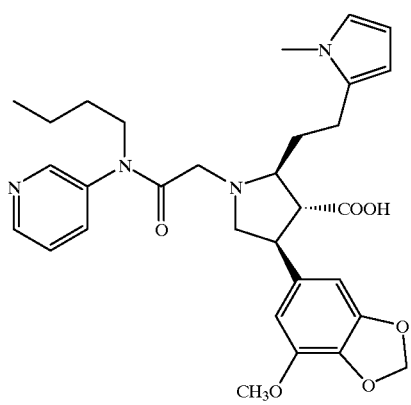
1270
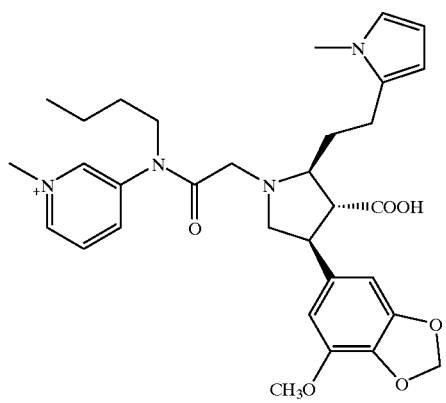

TABLE 3C-continued
1271
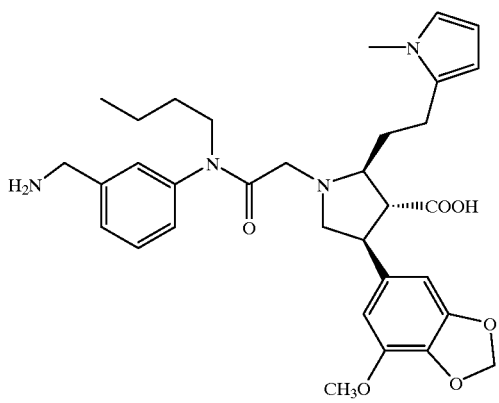
1272
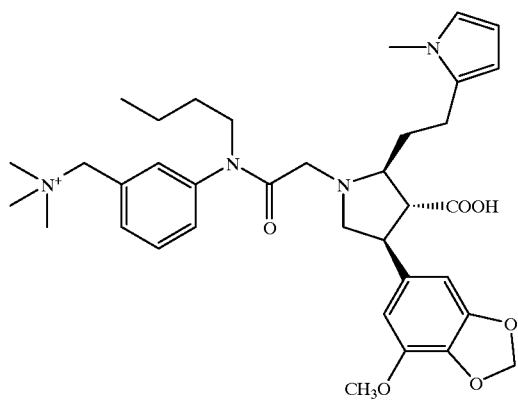
1273
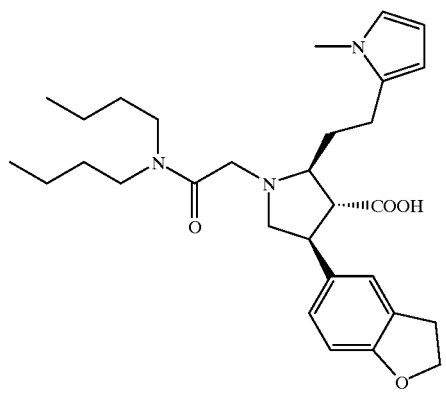

TABLE 3C-continued
1274
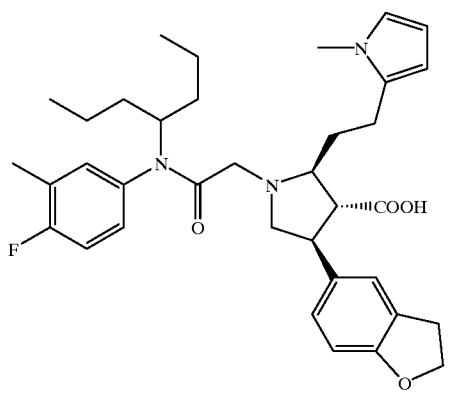
1275
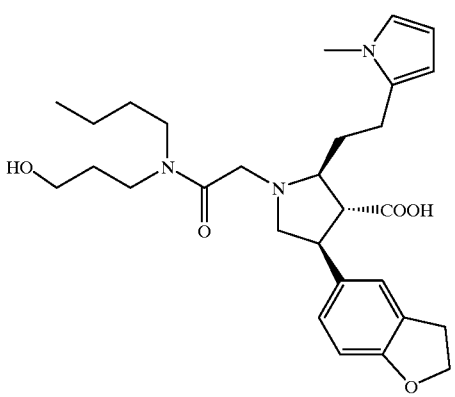
1276
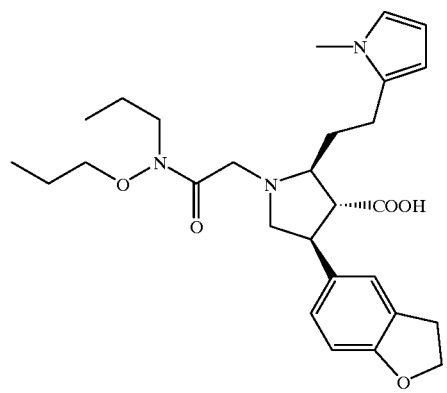
1277
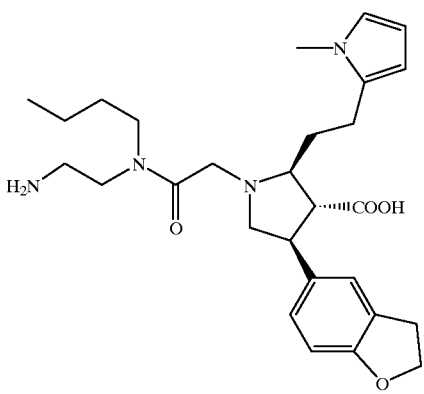

TABLE 3C-continued
1278
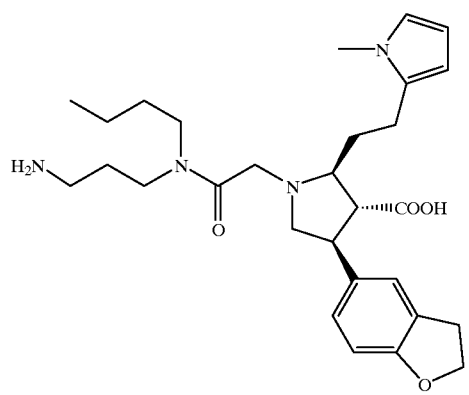
1279
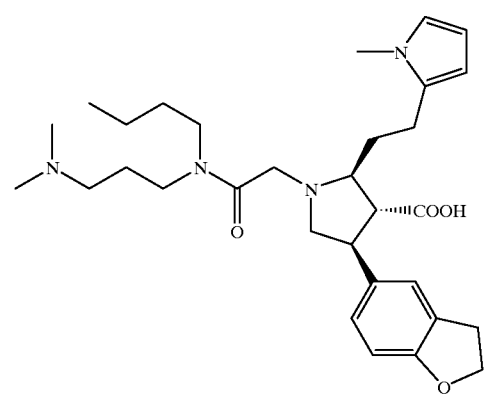
1280
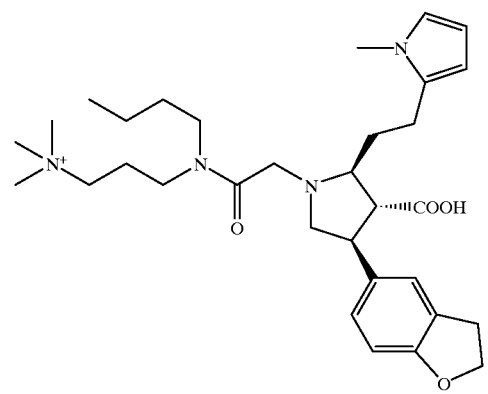
1281
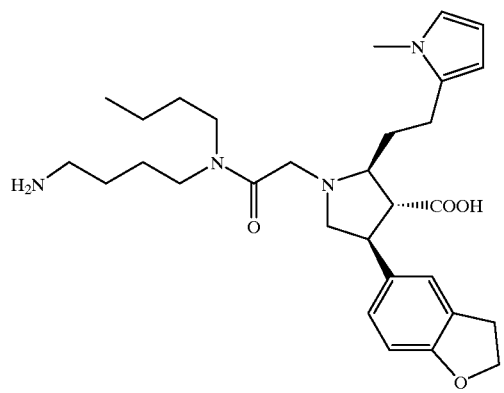

TABLE 3C-continued
1282
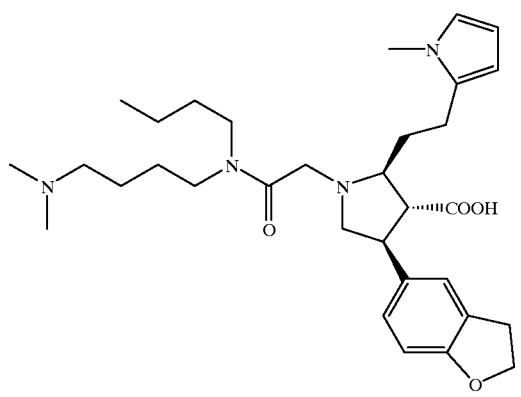
1283
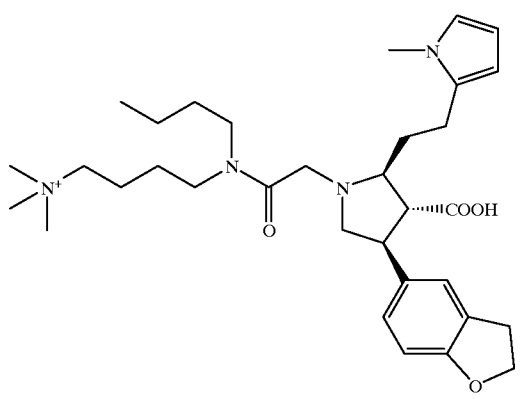
1284
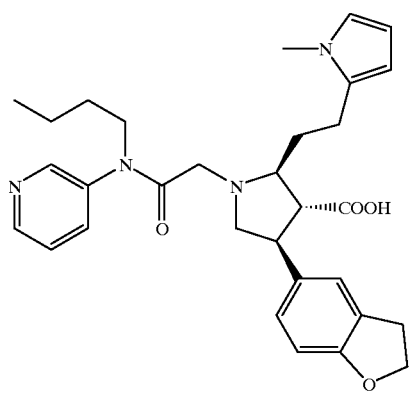
1285
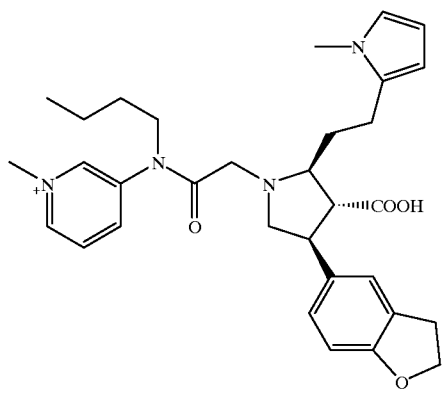

TABLE 3C-continued
1286
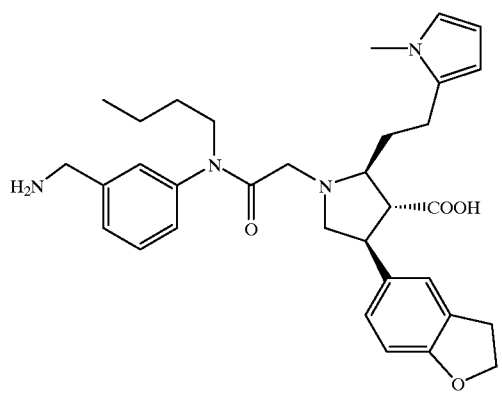
1287
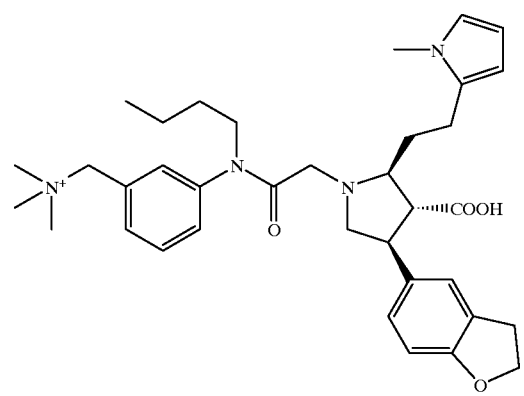
1288
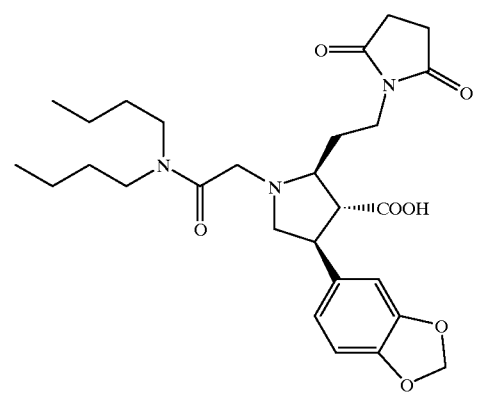
1289
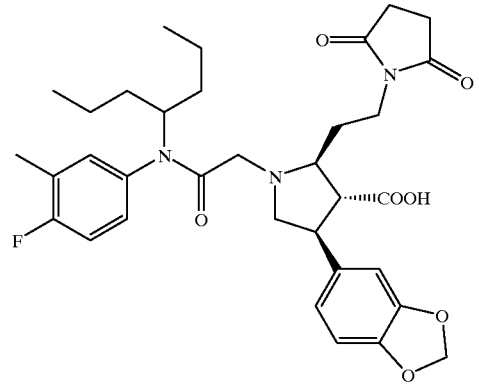

TABLE 3C-continued
1290
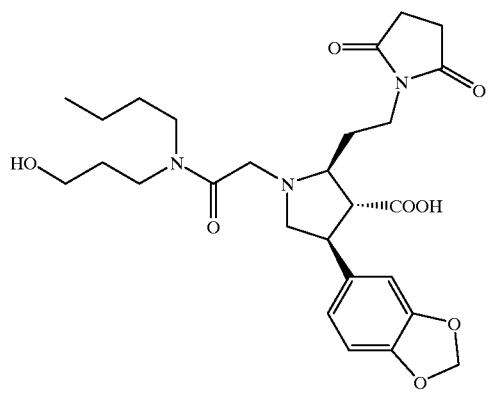
1291
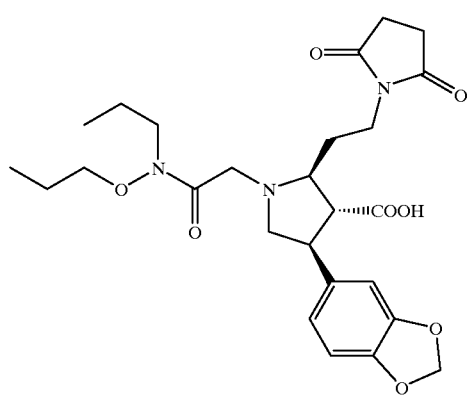
1292
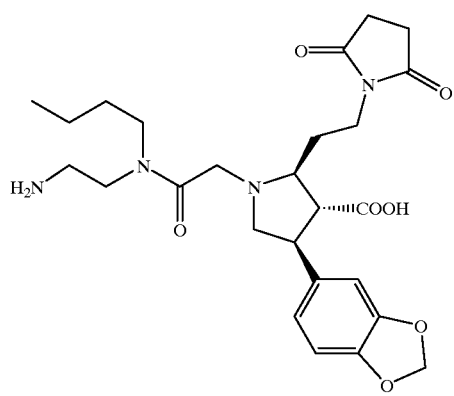
1293
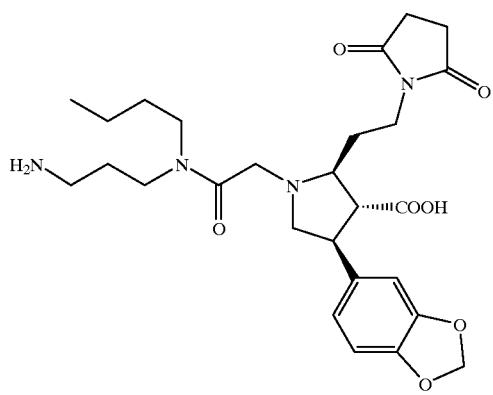

TABLE 3C-continued
1294
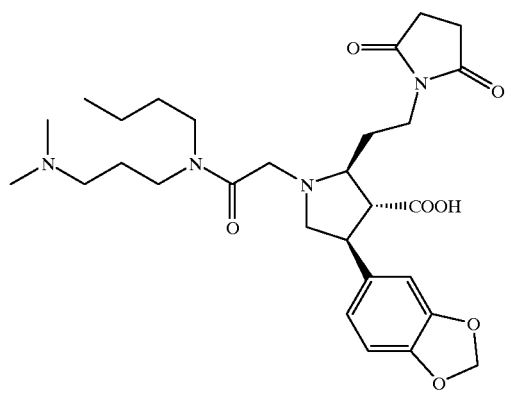
1295
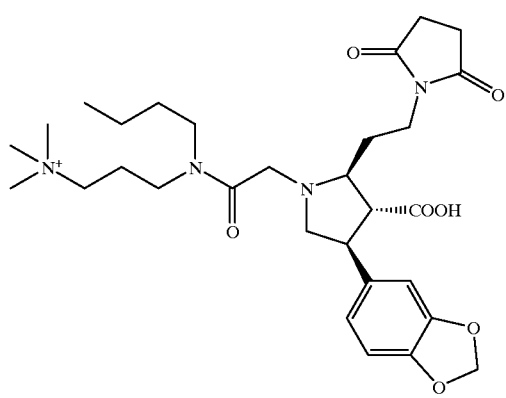
1296
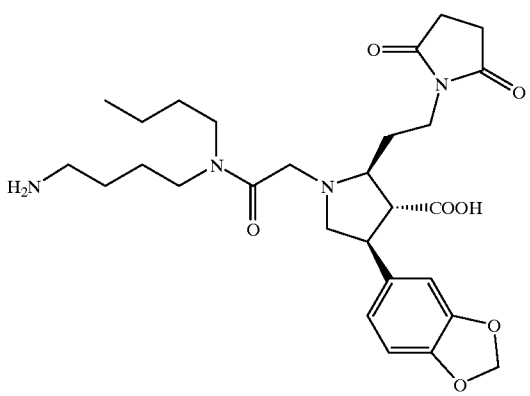
1297
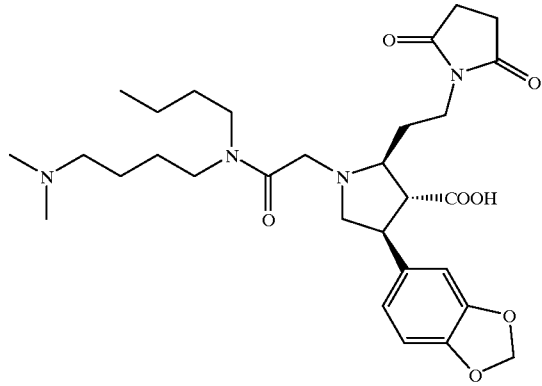

TABLE 3C-continued
1298
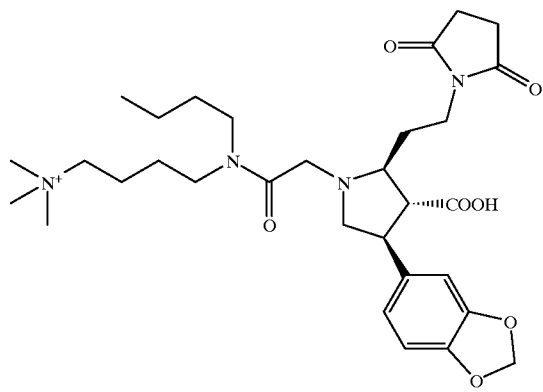
1299
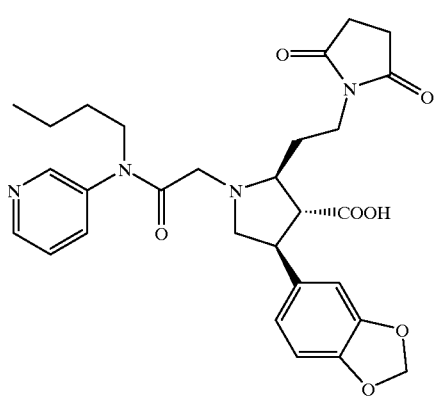
1300
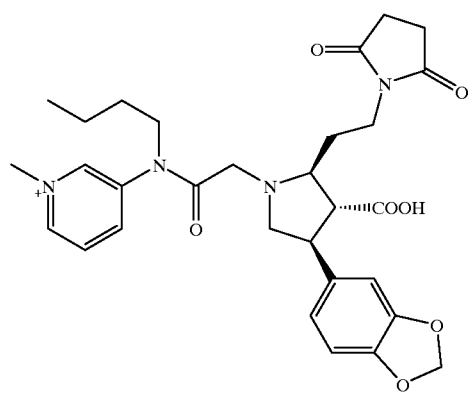
1301
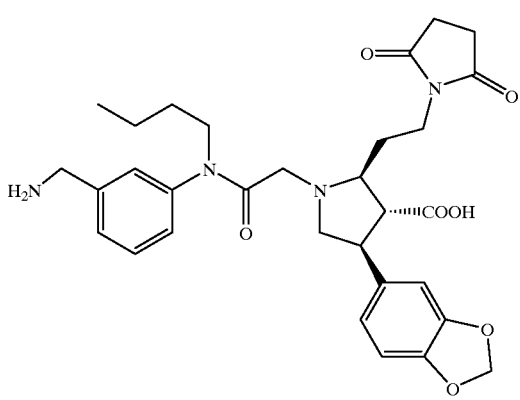

TABLE 3C-continued
1302
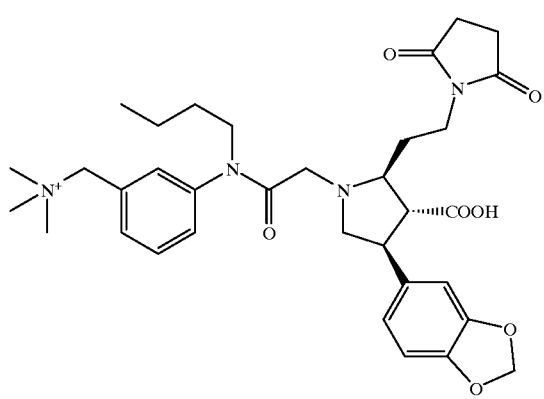
1303
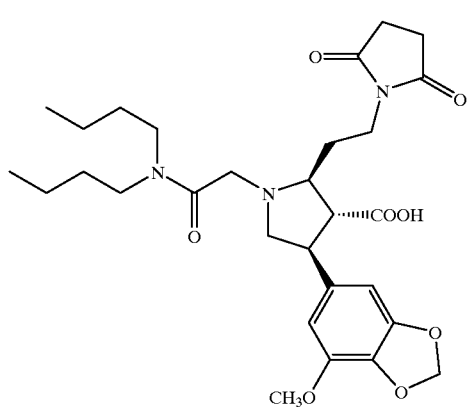
1304
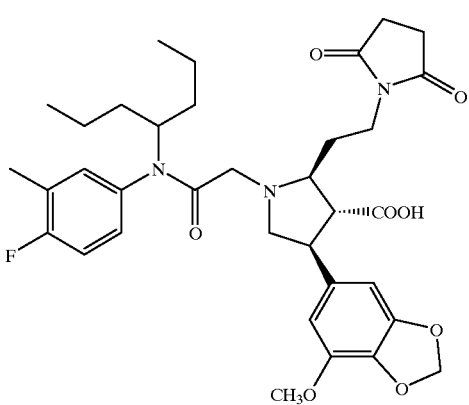
1305
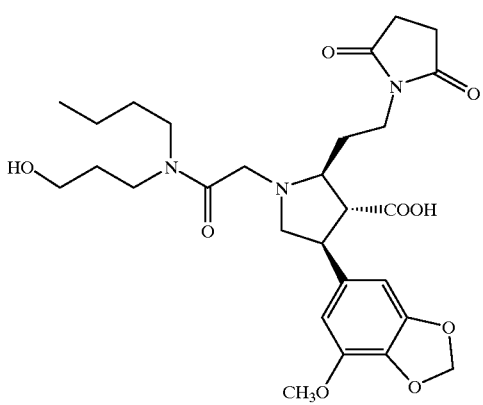

TABLE 3C-continued
1306
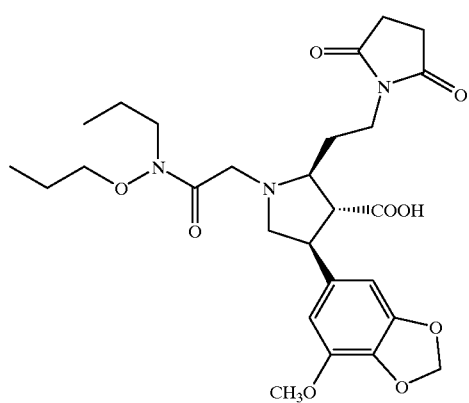
1307
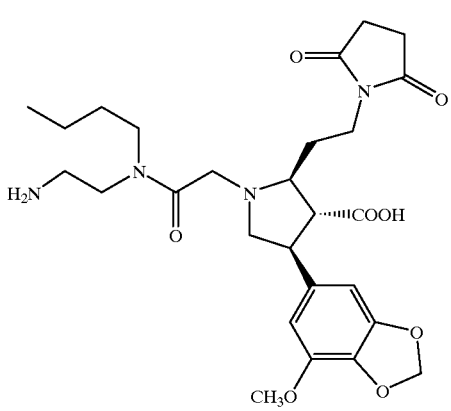
1308
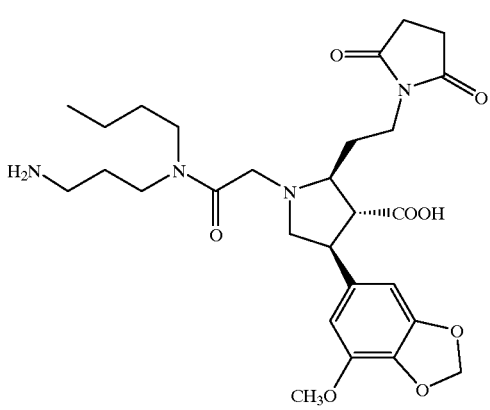

TABLE 3C-continued
1309
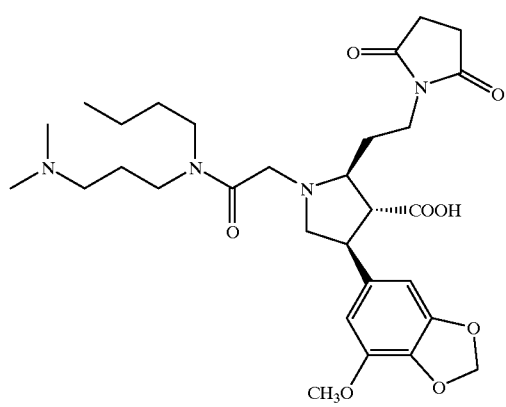
1310
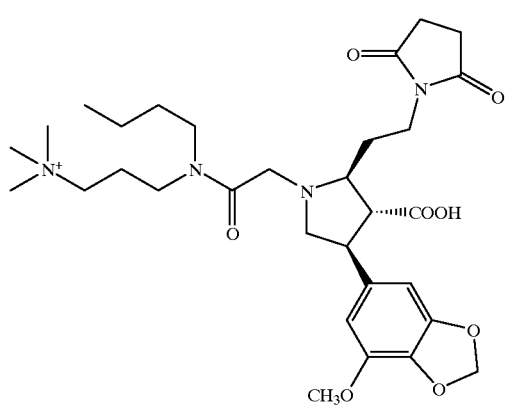
1311
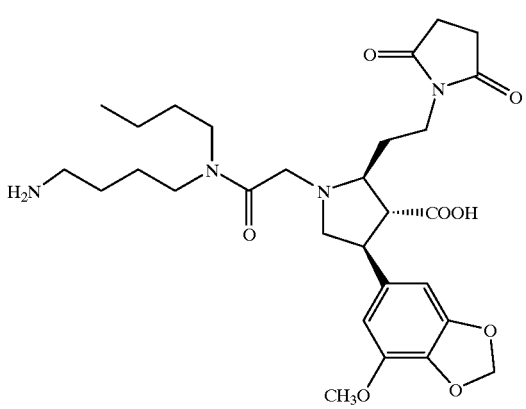
1312
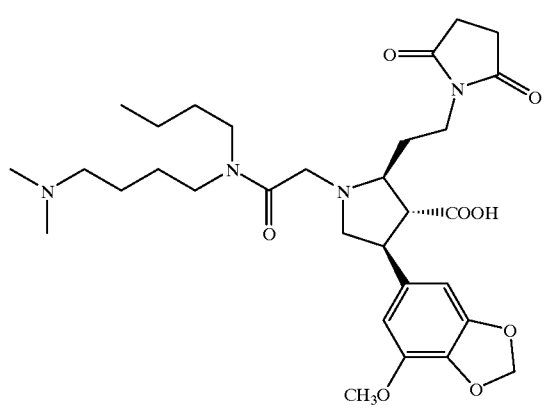

TABLE 3C-continued
1313
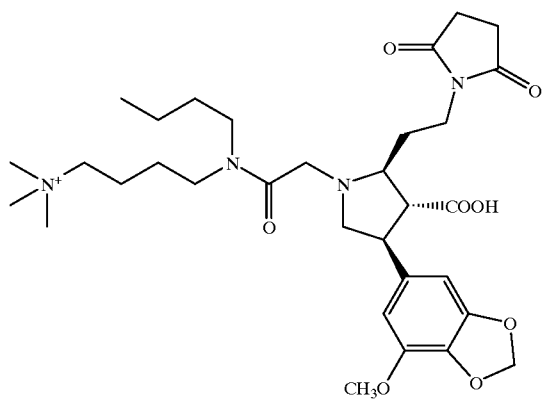
1314
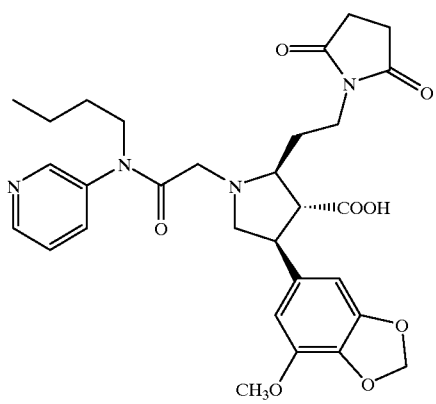
1315
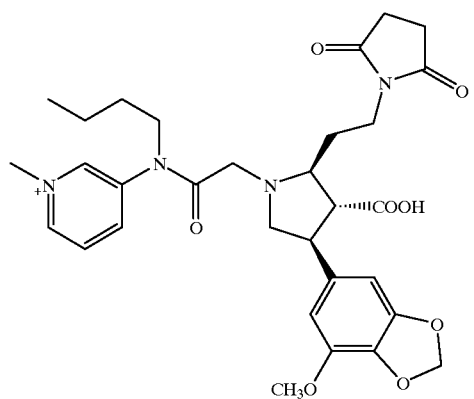

TABLE 3C-continued
1316
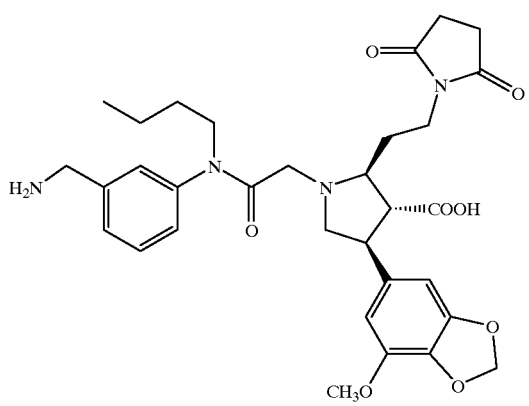
1317
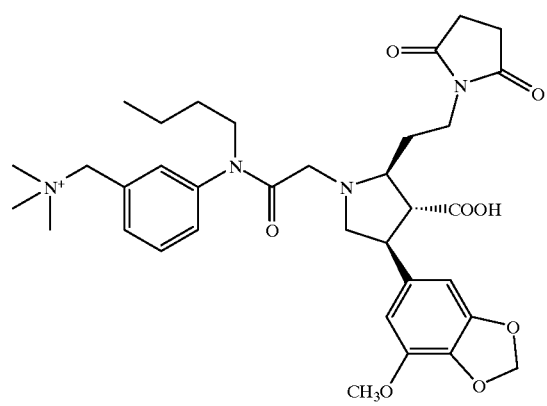
1318
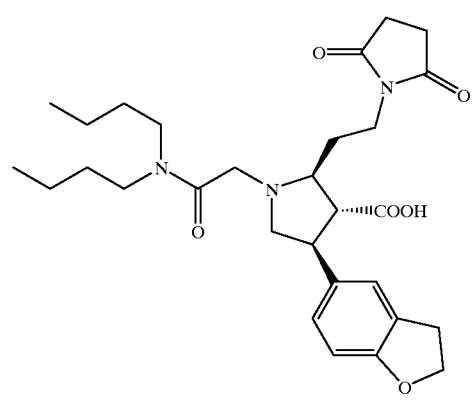
1319
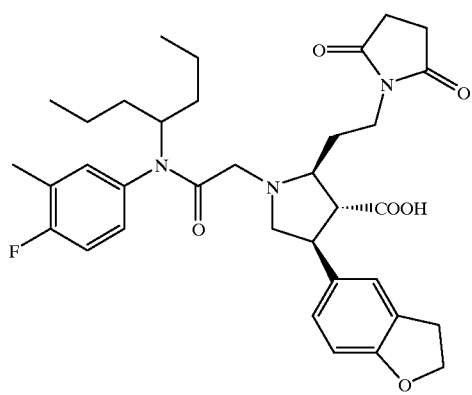

TABLE 3C-continued
| 1320 | 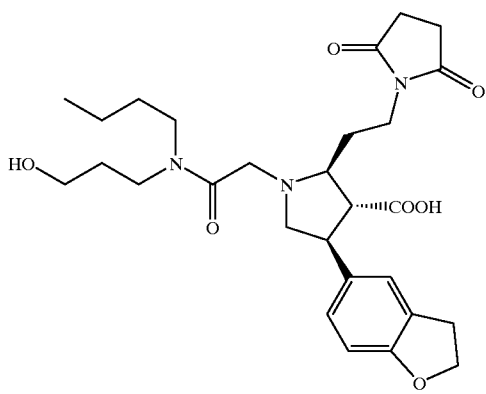 |
| --- | --- |
| 1321 | 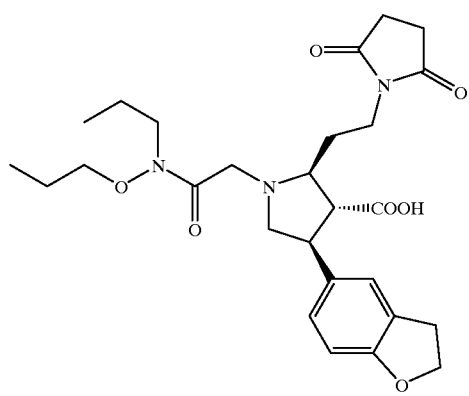 |
| 1322 | 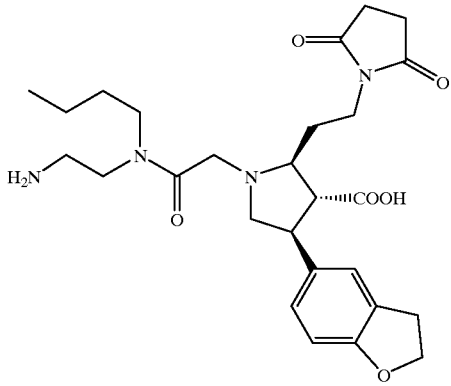 |
| 1323 | 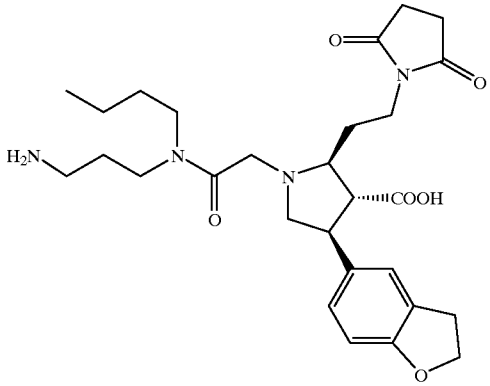 |

TABLE 3C-continued
1324
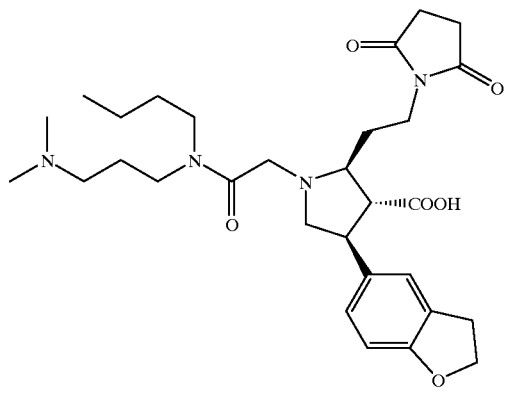
1325
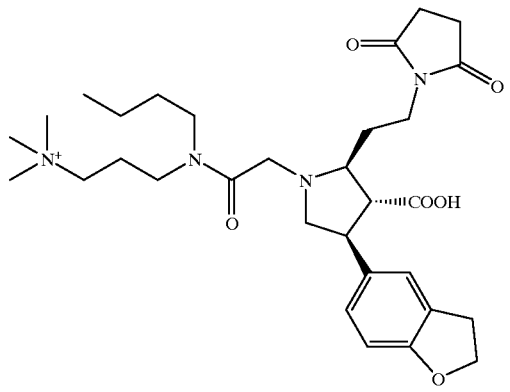
1326
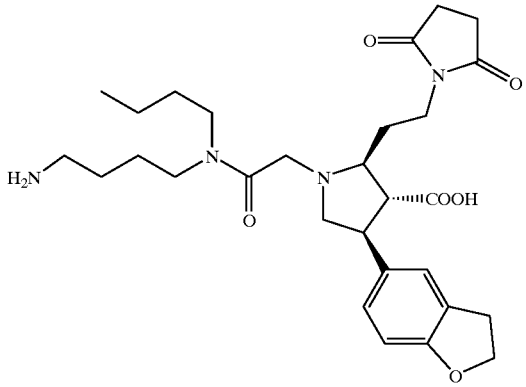
1327
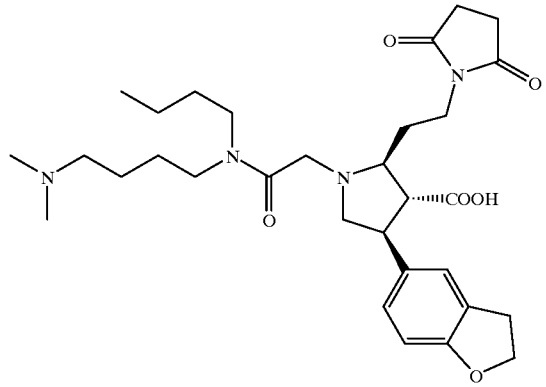

TABLE 3C-continued
1328 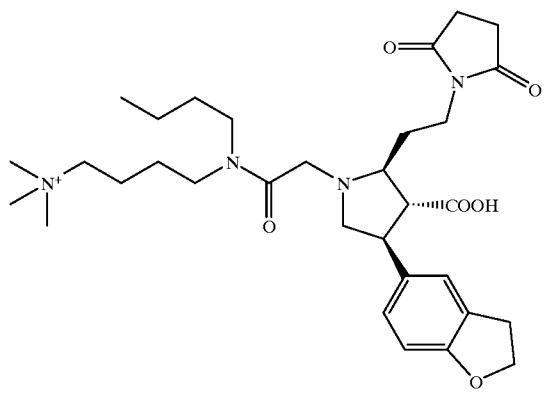
1329 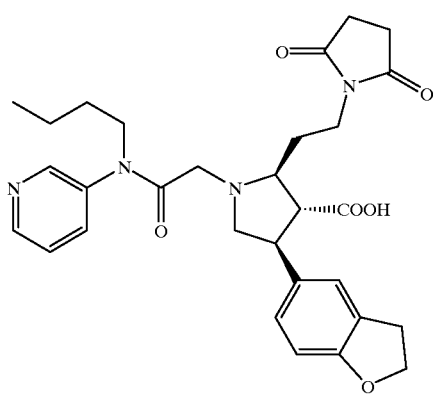
1330 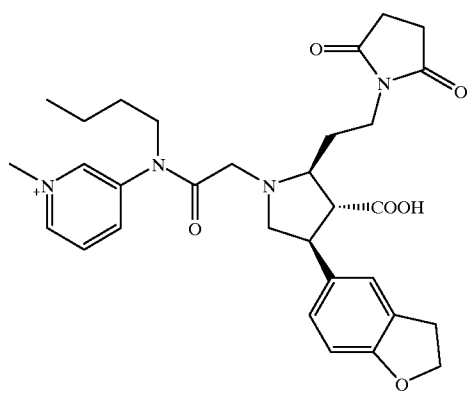
1331 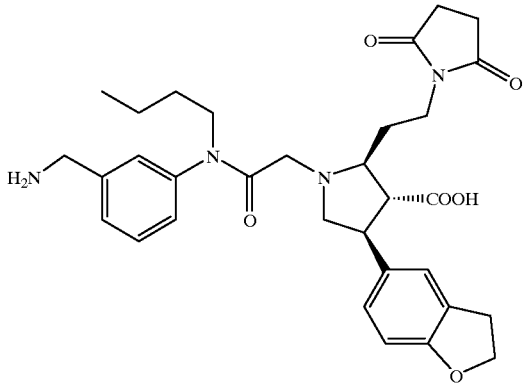

TABLE 3C-continued
1332
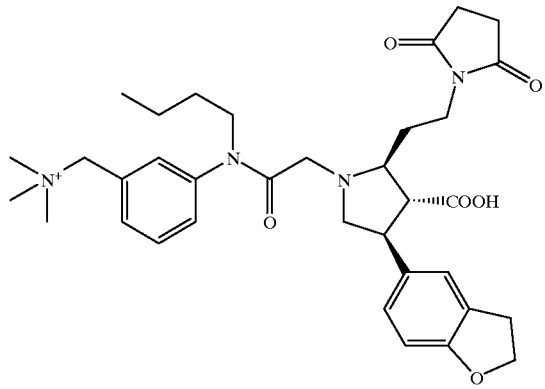
1333
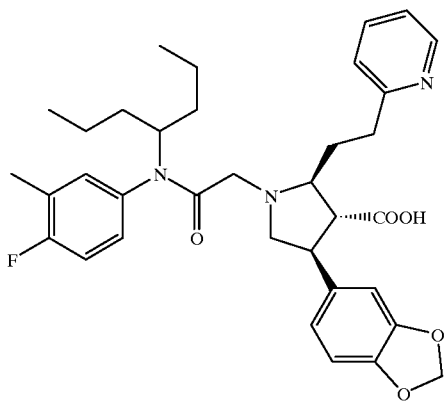
1334
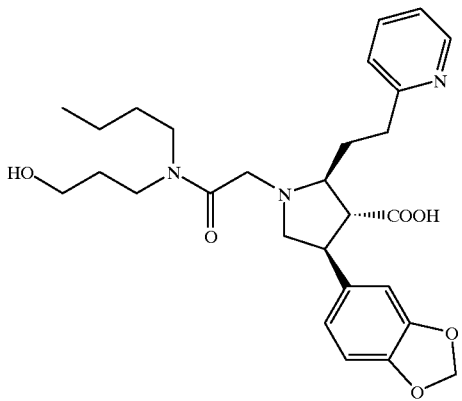

TABLE 3C-continued
1335
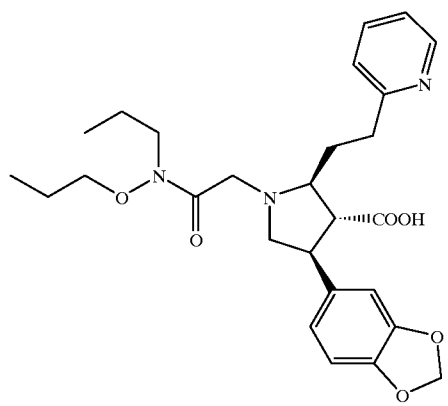
1336
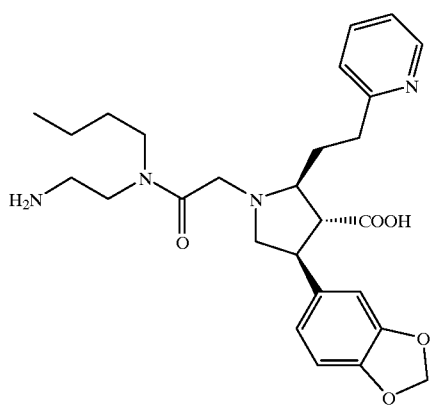
1337
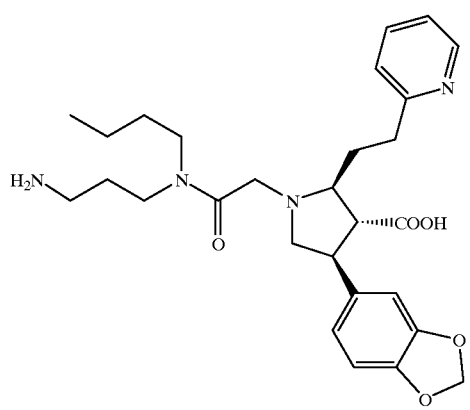

TABLE 3C-continued
1338
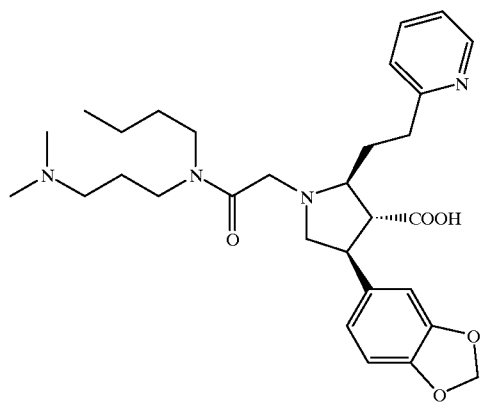
1339
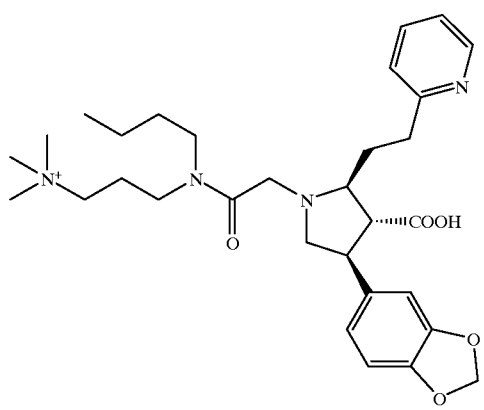
1340
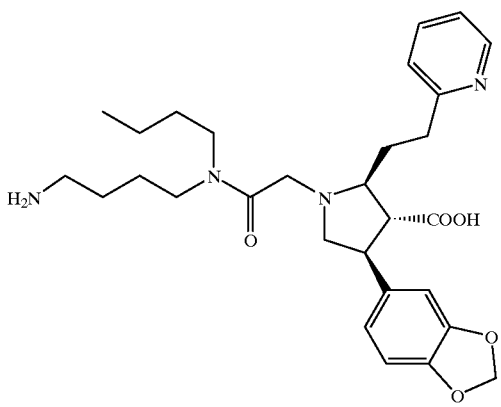

TABLE 3C-continued
1341
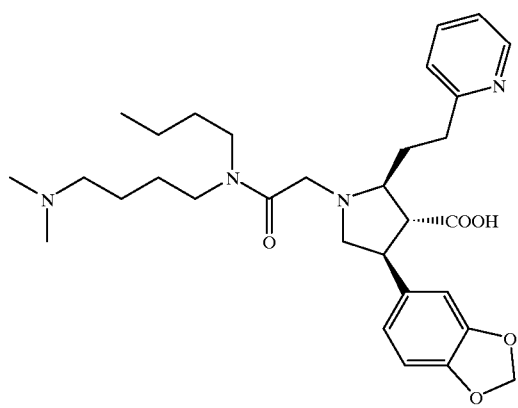
1342
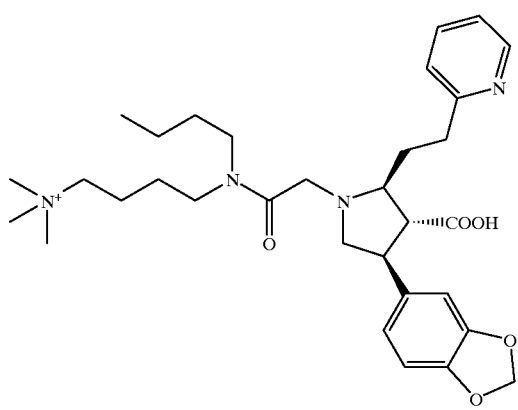
1343
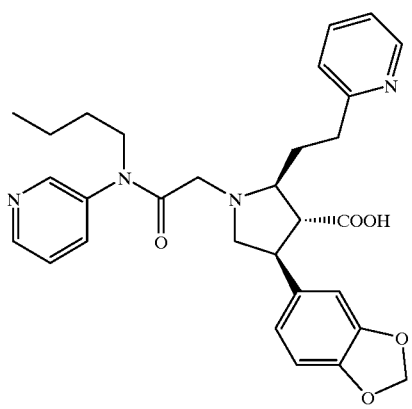

TABLE 3C-continued
1344
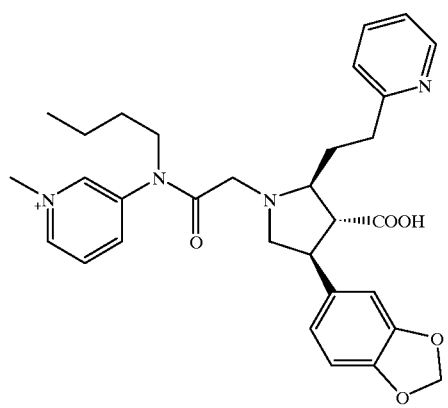
1345
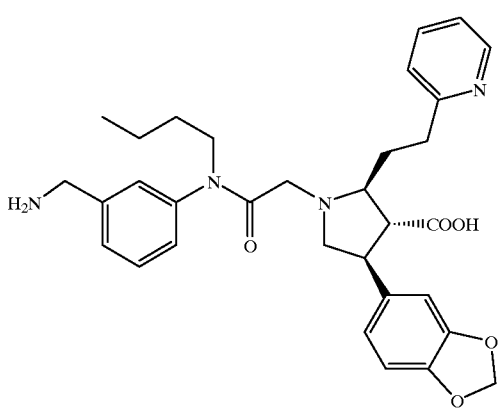
1346
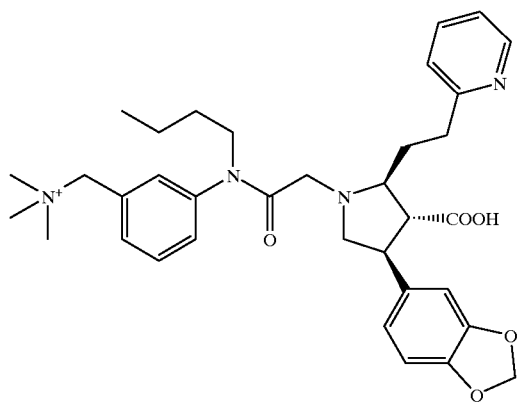

TABLE 3C-continued
1347
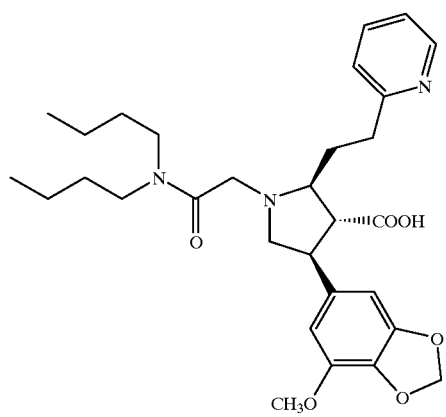
1348
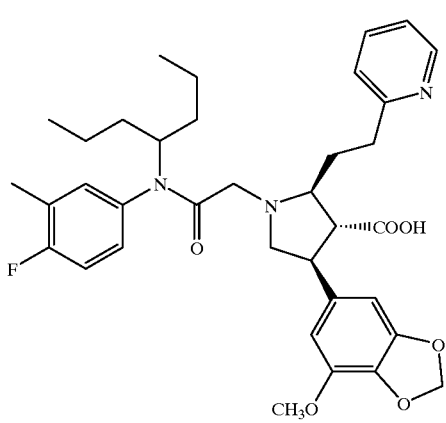
1349
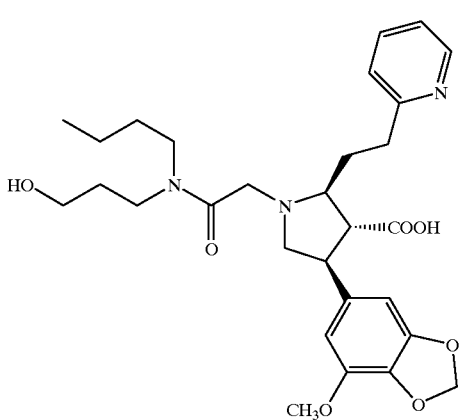

TABLE 3C-continued
1350
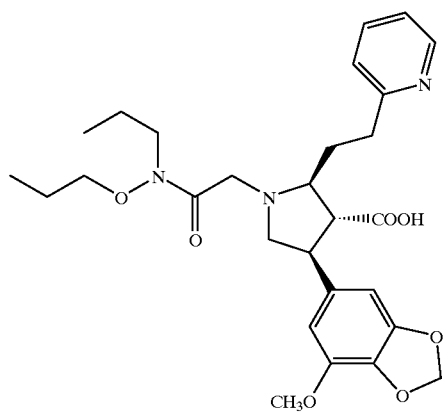
1351
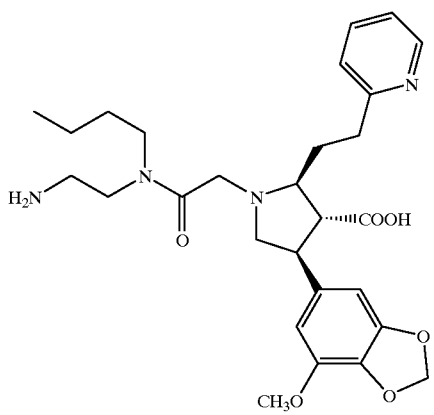
1352
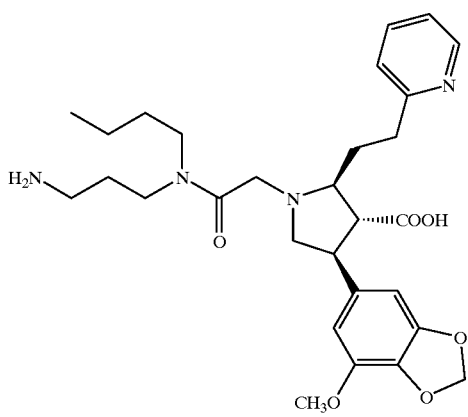

TABLE 3C-continued
1353
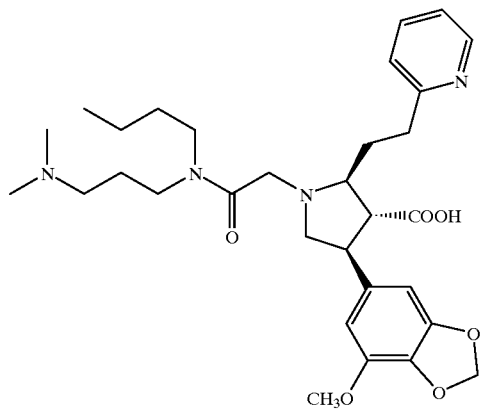
1354
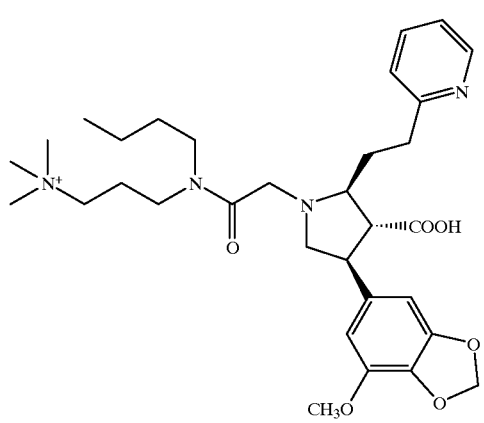
1355
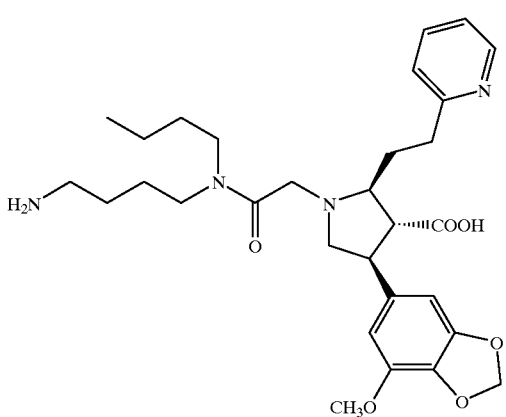

TABLE 3C-continued
1356
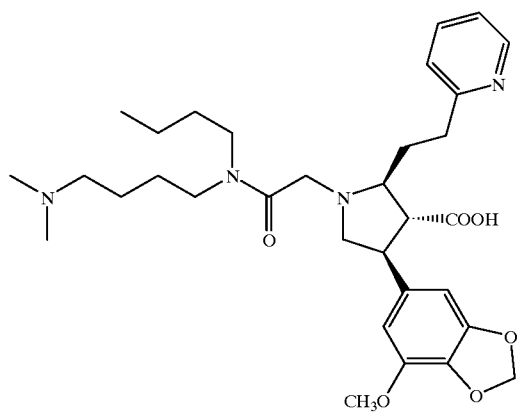
1357
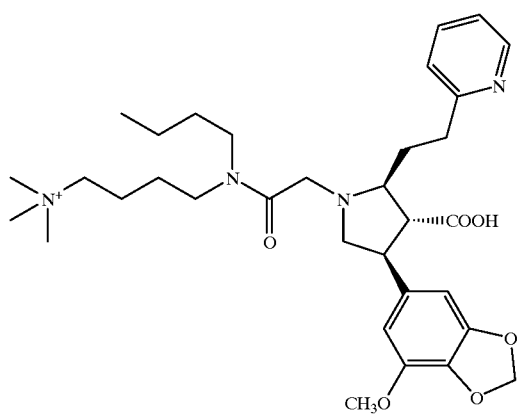
1358
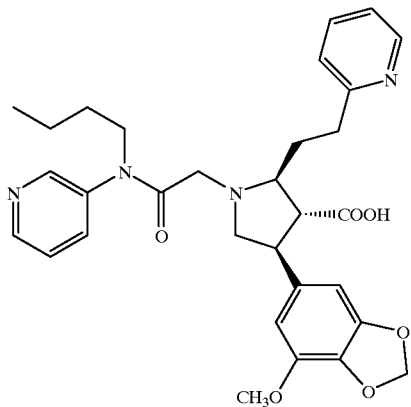

TABLE 3C-continued
1359
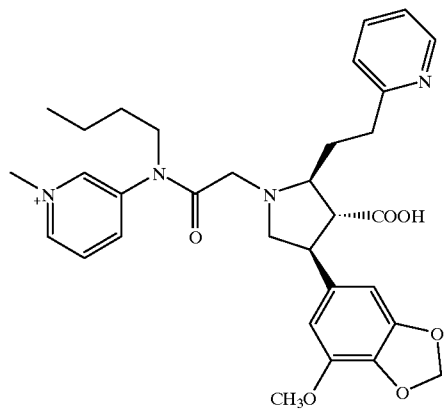
1360
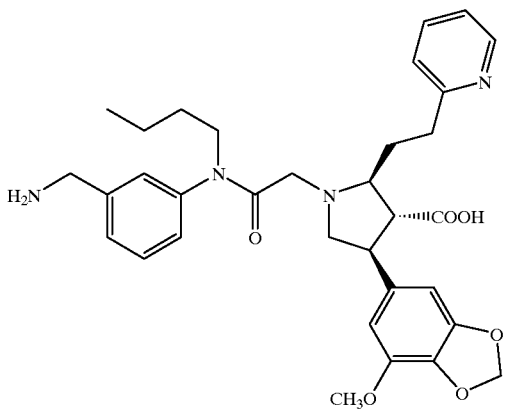
1361
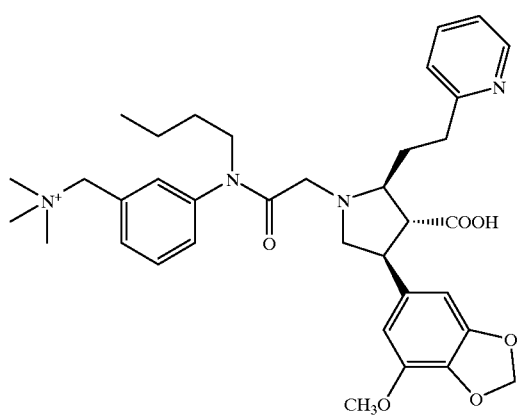

TABLE 3C-continued
1362
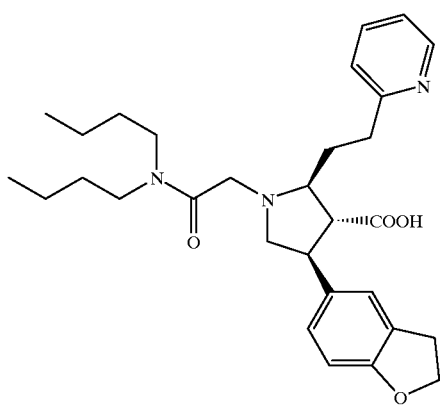
1363
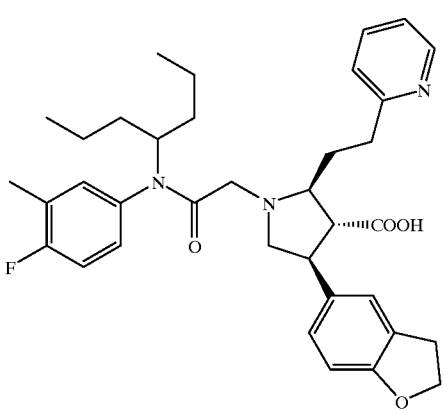
1364
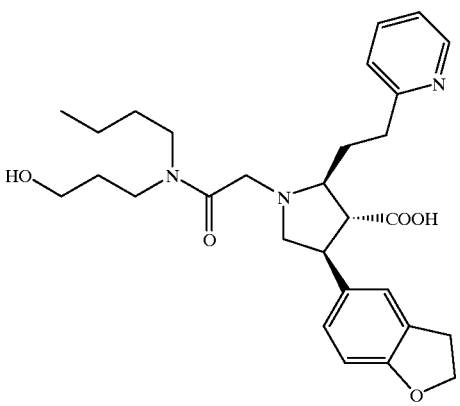

TABLE 3C-continued
1365
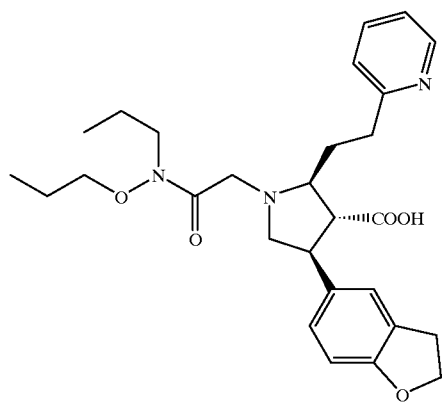
1366
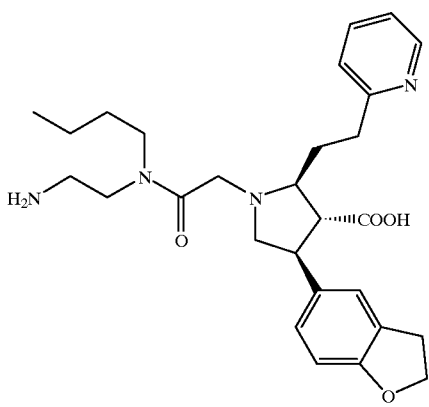
1367
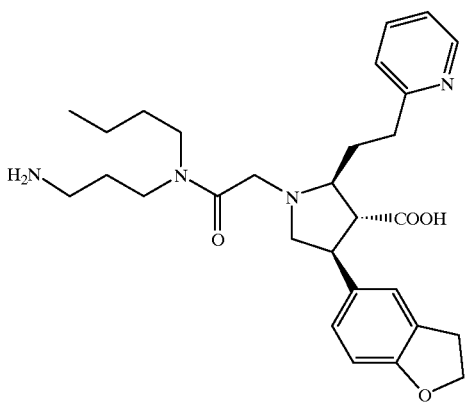

TABLE 3C-continued
1368
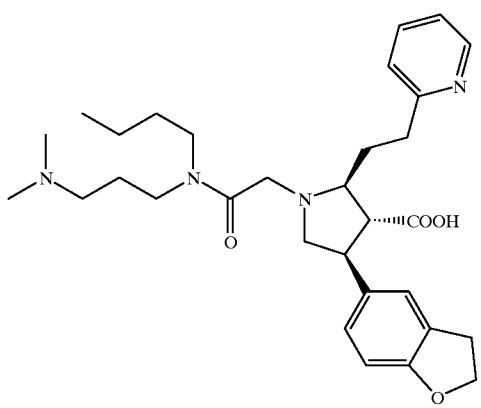
1369
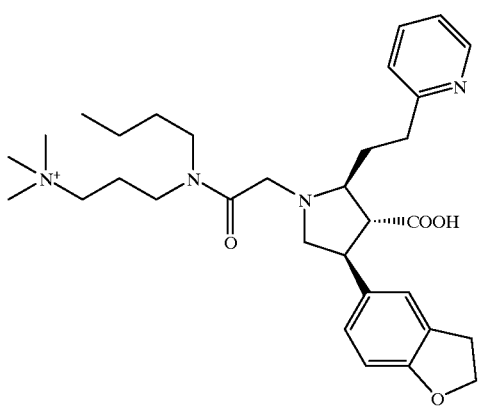
1370
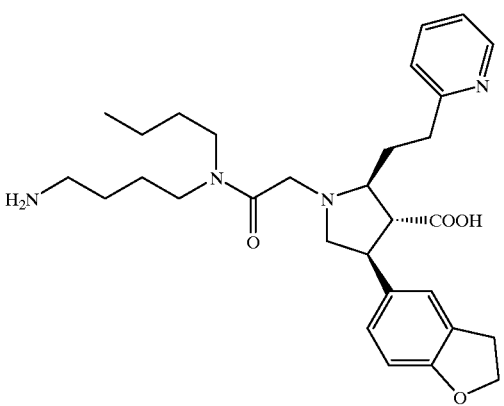

TABLE 3C-continued
1371
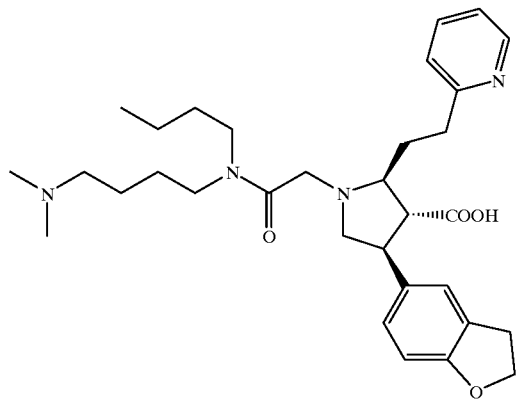
1372
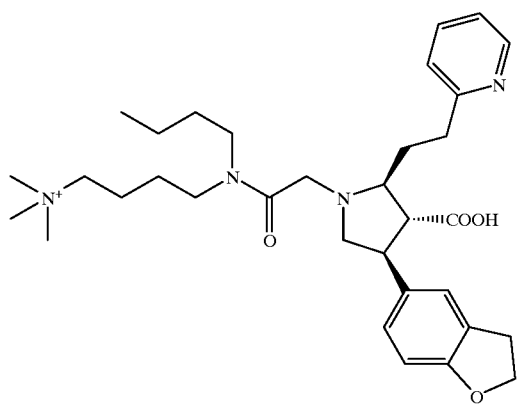
1373
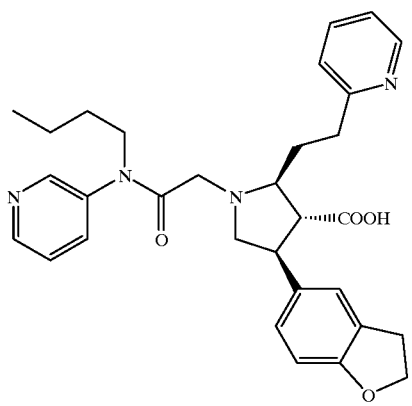

TABLE 3C-continued
1374
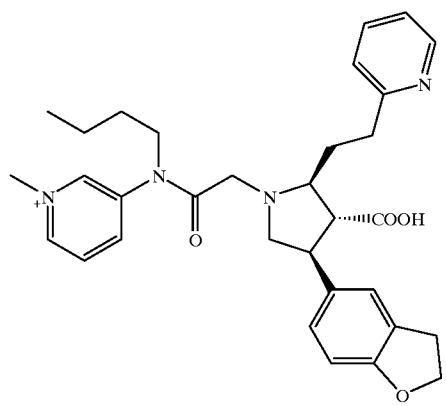
1375
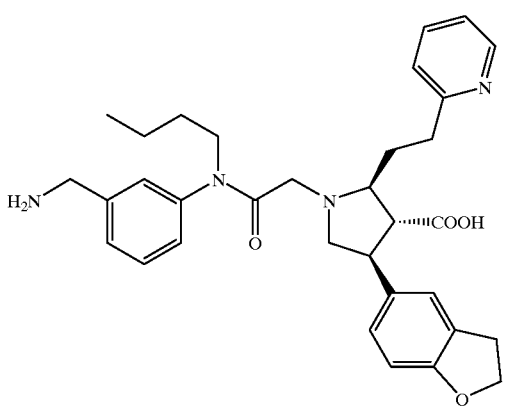
1376
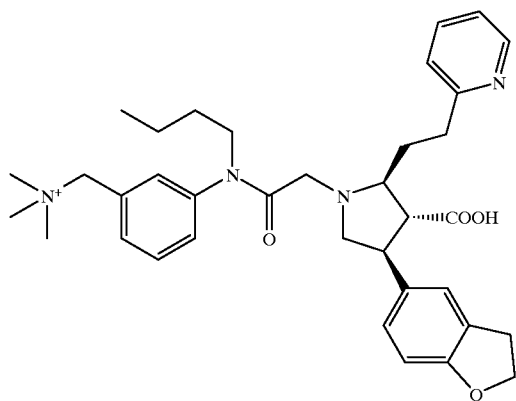

TABLE 3C-continued
1377
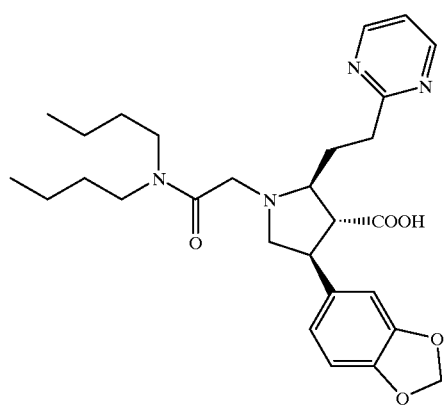
1378
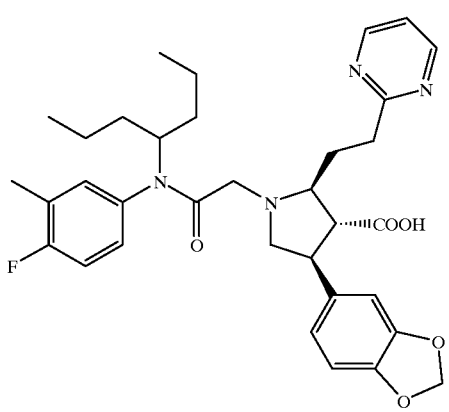
1379
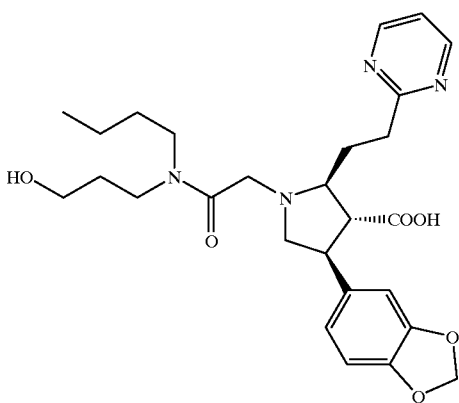

TABLE 3C-continued
1380
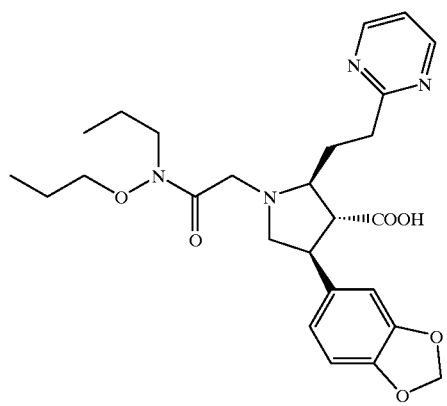
1381
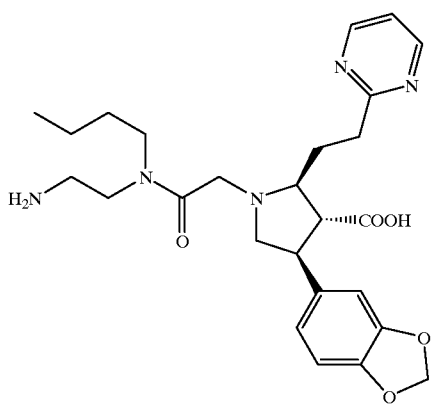
1382
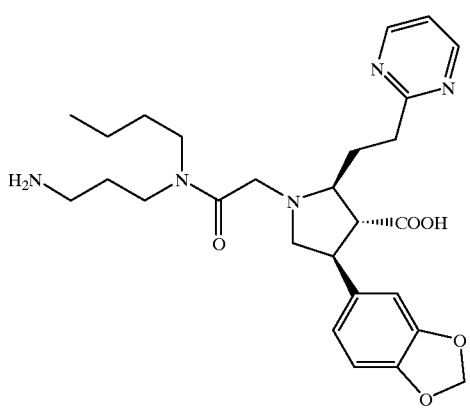

TABLE 3C-continued
1383
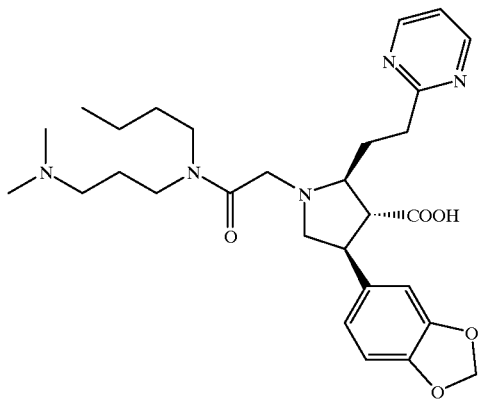
1384
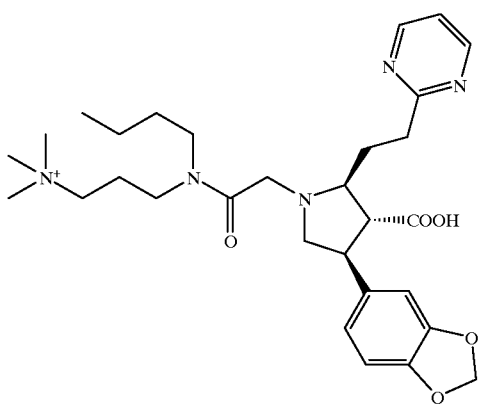
1385
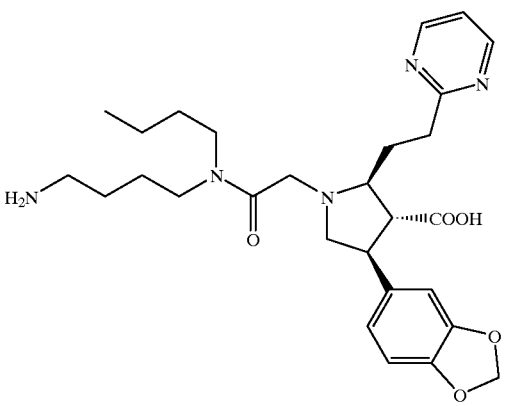

TABLE 3C-continued
1386
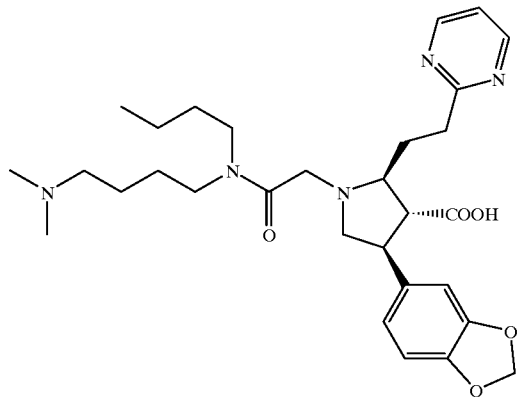
1387
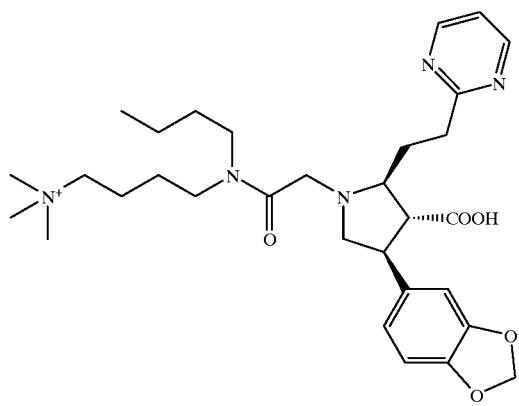
1388
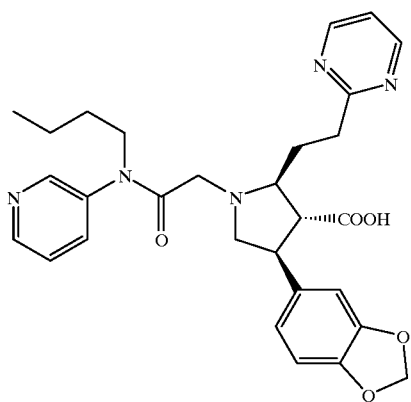

TABLE 3C-continued
1389
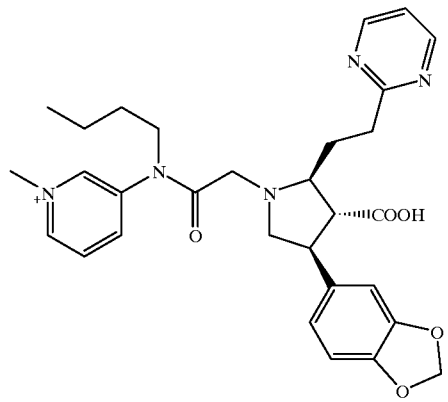
1390
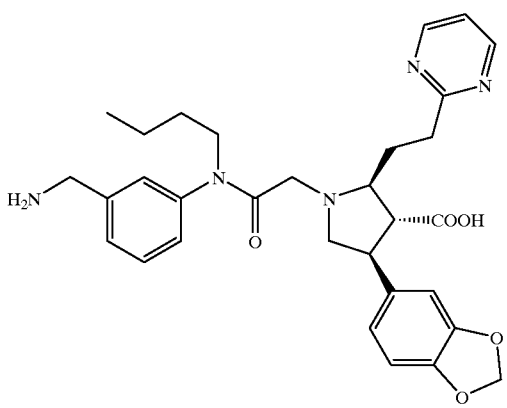
1391
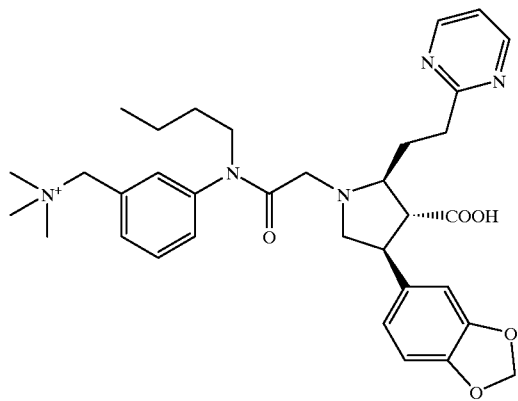

TABLE 3C-continued
1392
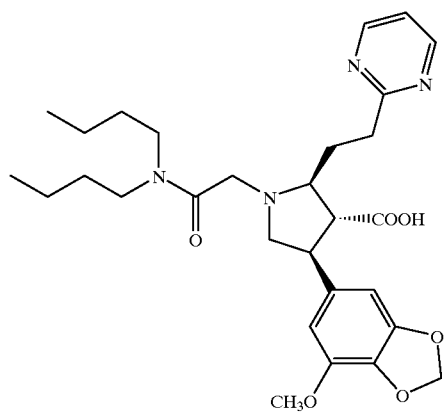
1393
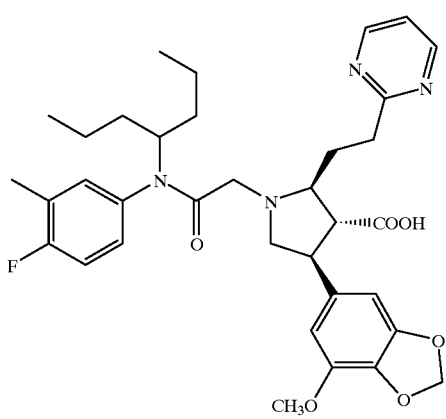
1394
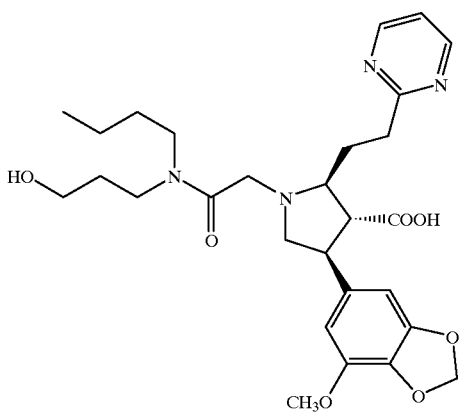

TABLE 3C-continued
1395
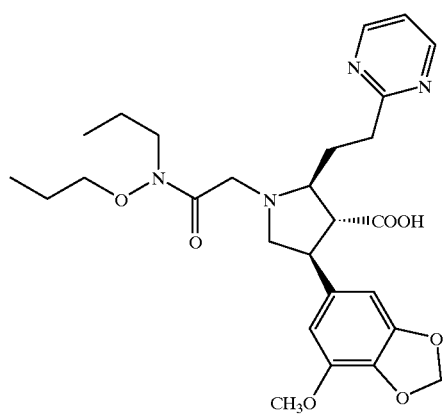
1396
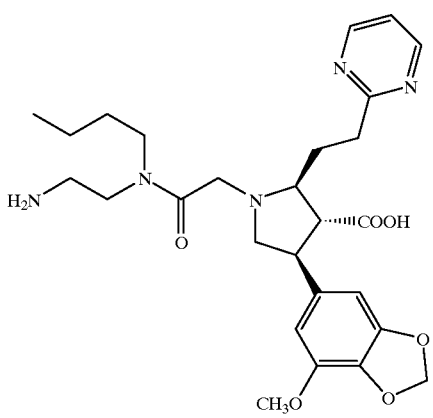
1397
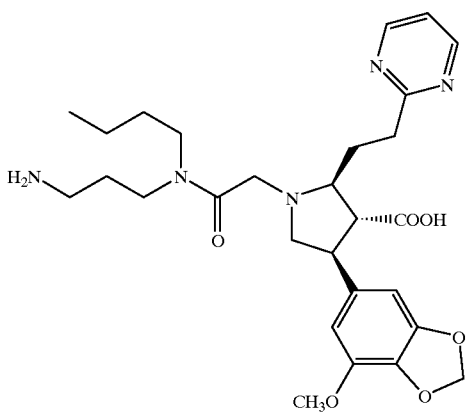

TABLE 3C-continued
1398
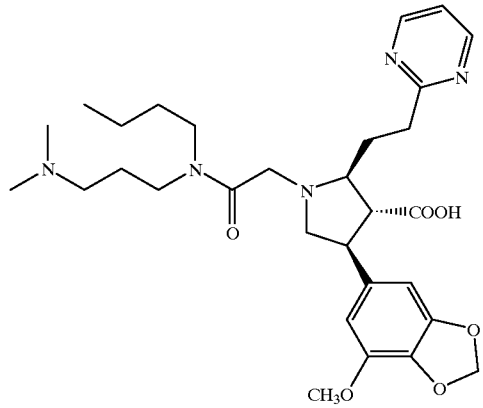
1399
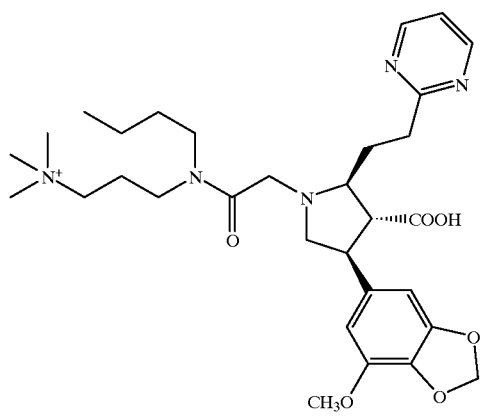
1400
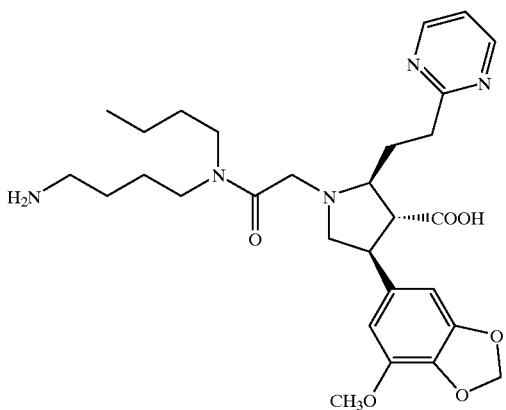

TABLE 3C-continued
1401
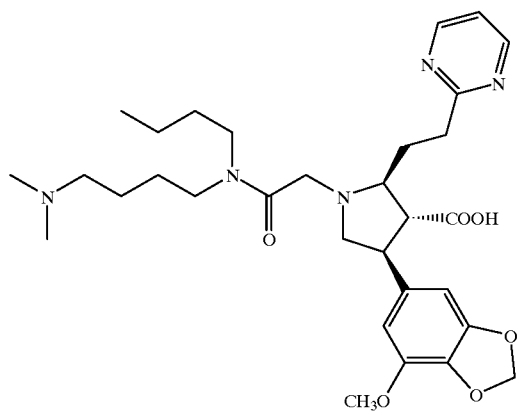
1402
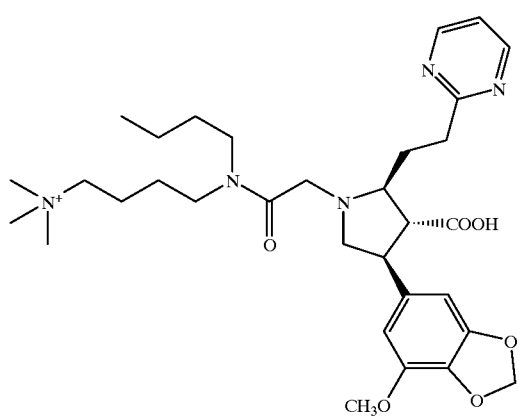
1403
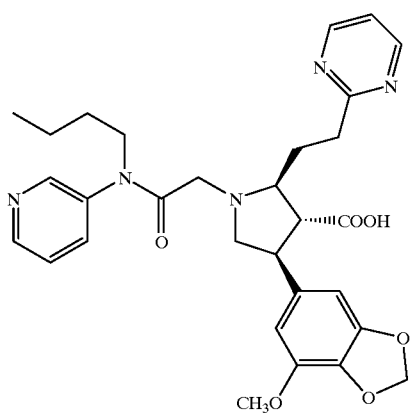

TABLE 3C-continued
1404
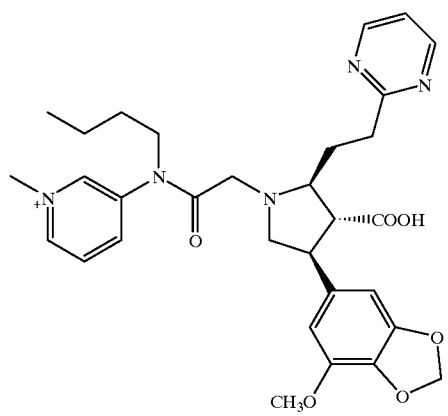
1405
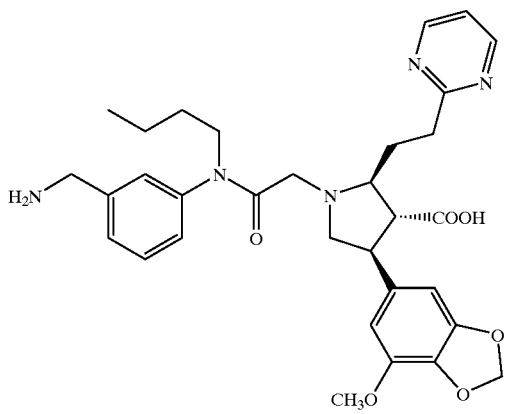
1406
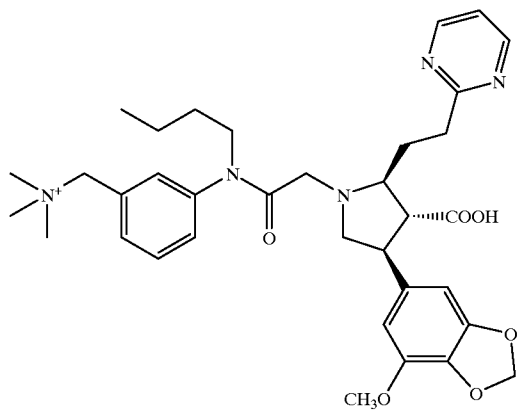

TABLE 3C-continued
1407
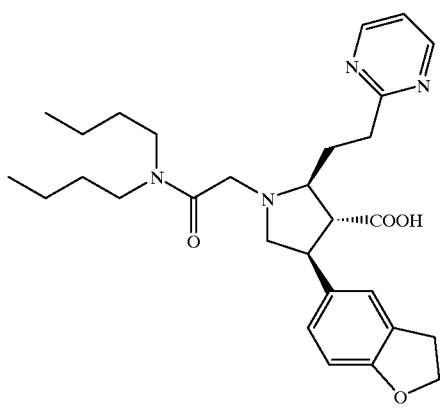
1408
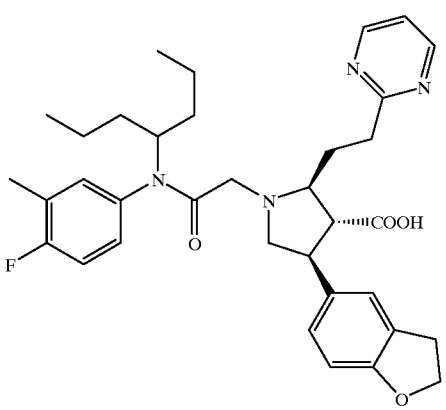
1409
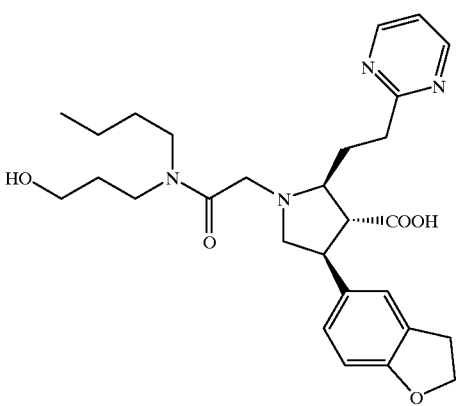

TABLE 3C-continued
1410
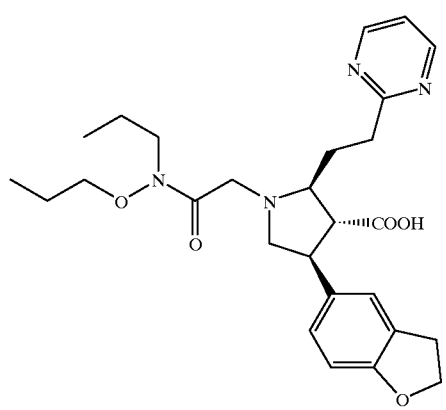
1411
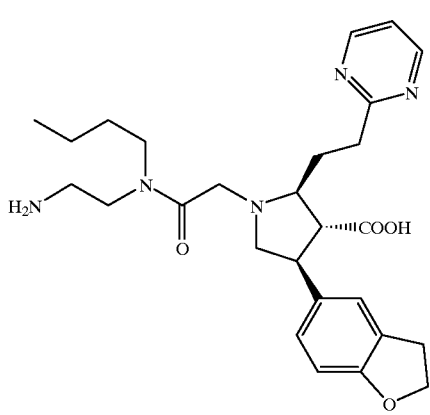
1412
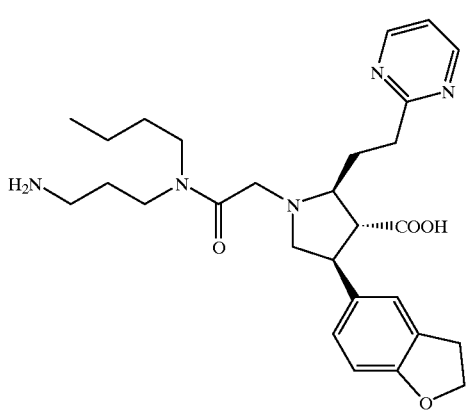

TABLE 3C-continued
1413
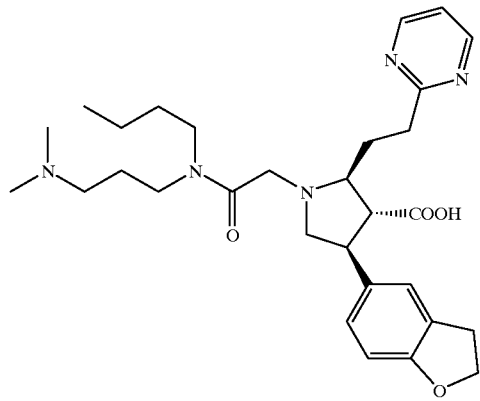
1414
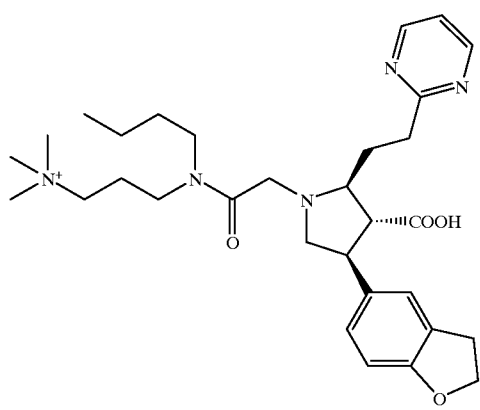
1415
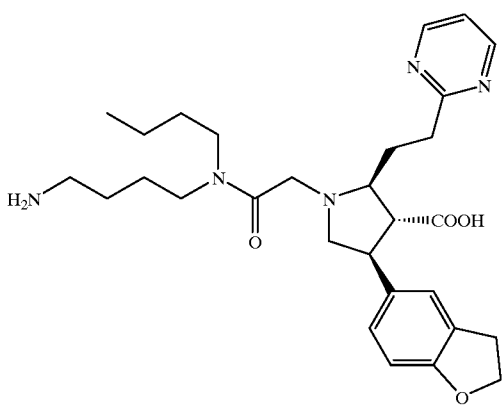

TABLE 3C-continued
1416
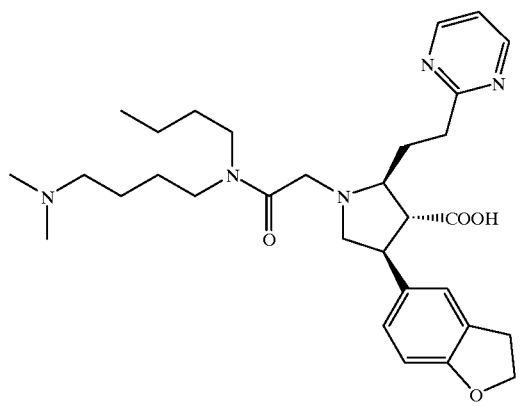
1417
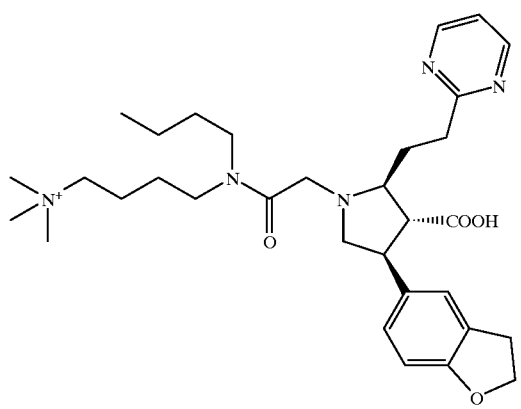
1418
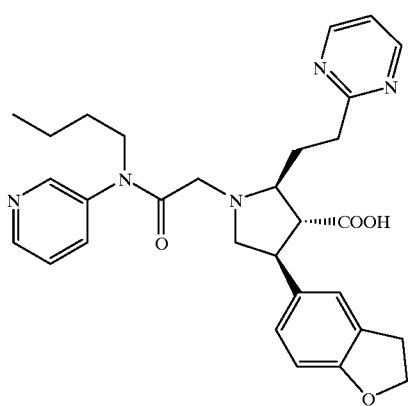

TABLE 3C-continued
1419
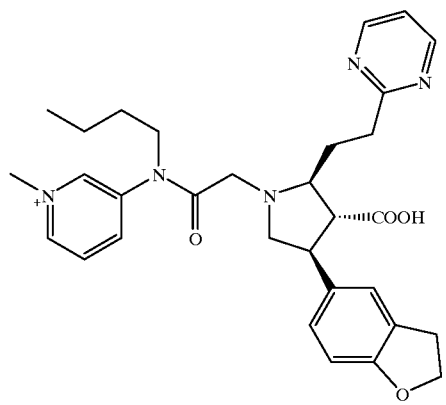
1420
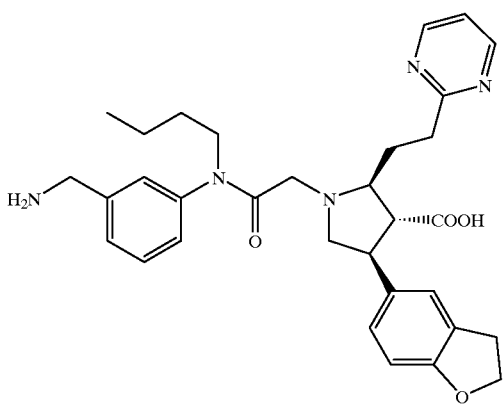
1421
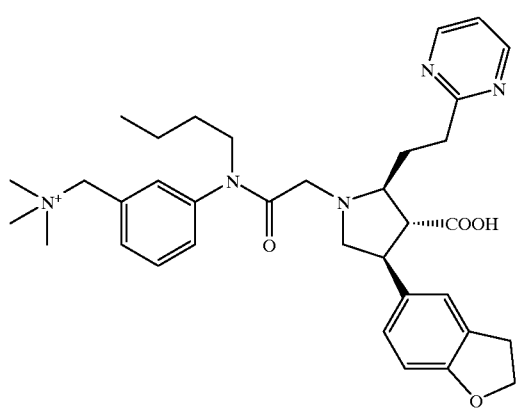

TABLE 3C-continued
1422
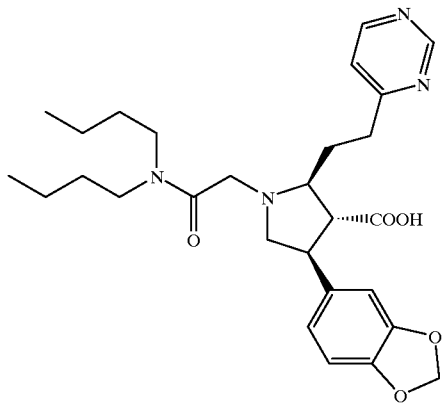
1423
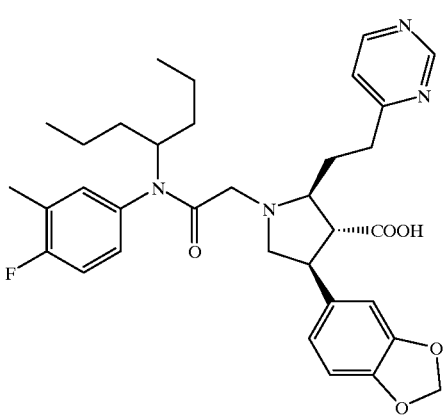
1424
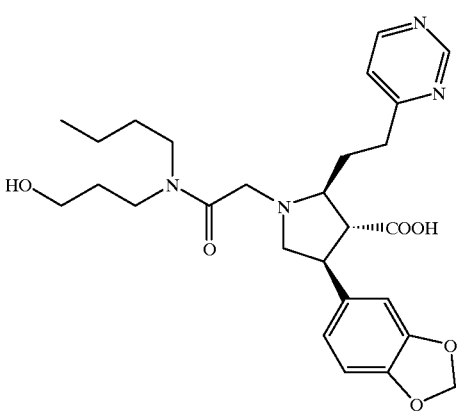

TABLE 3C-continued
1425
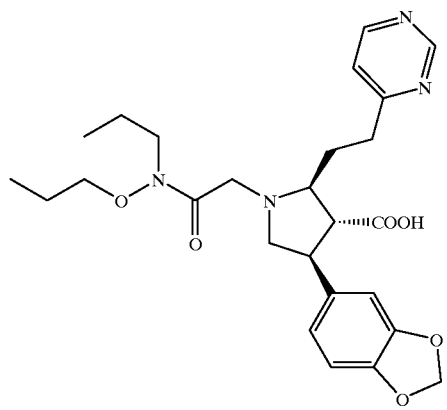
1426
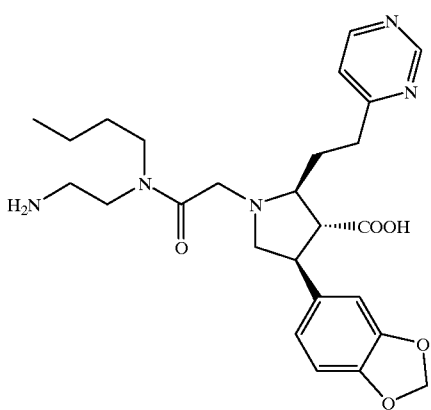
1427
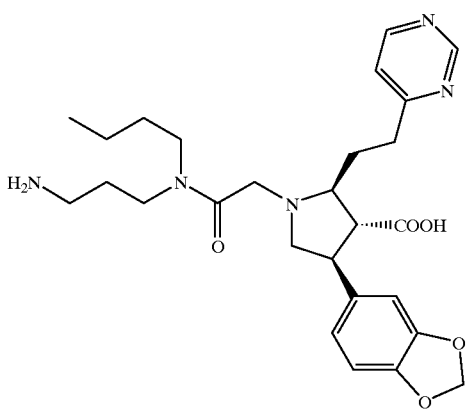

TABLE 3C-continued
1428
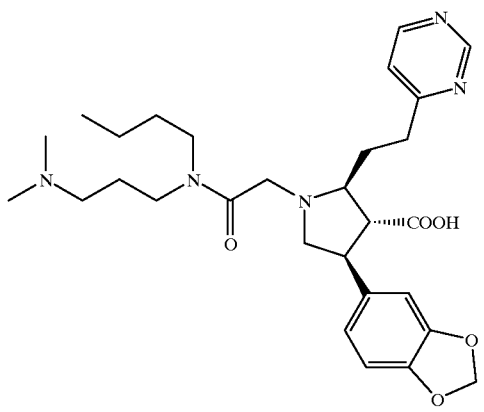
1429
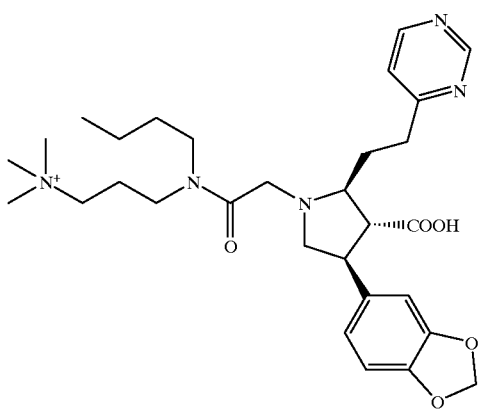
1430
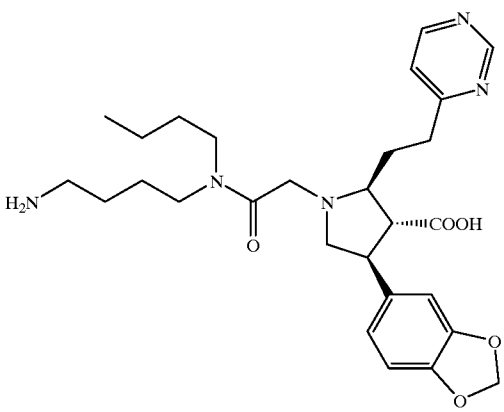

TABLE 3C-continued
1431
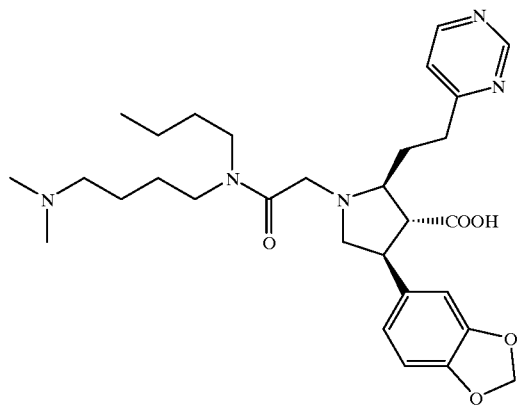
1432
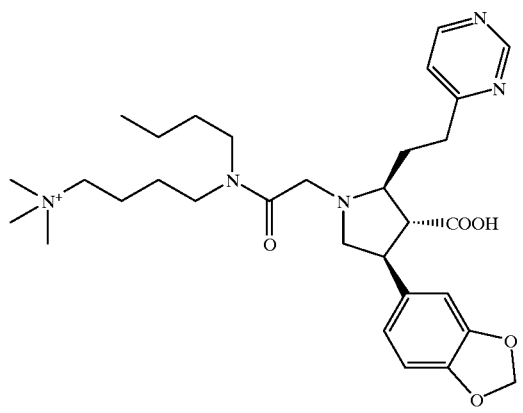
1433
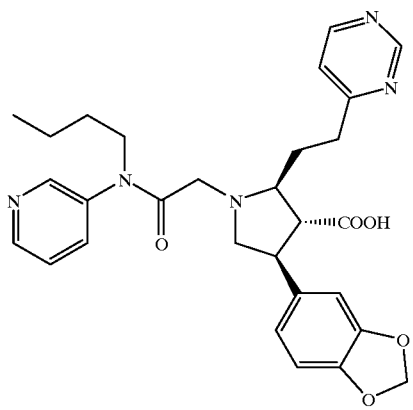

TABLE 3C-continued
1434
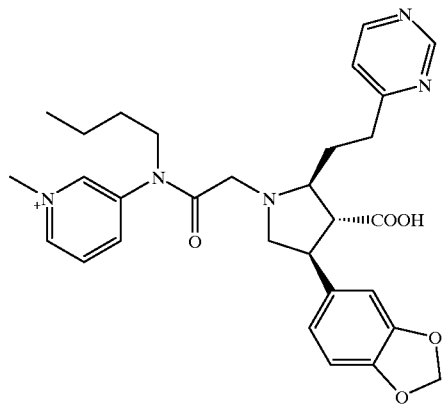
1435
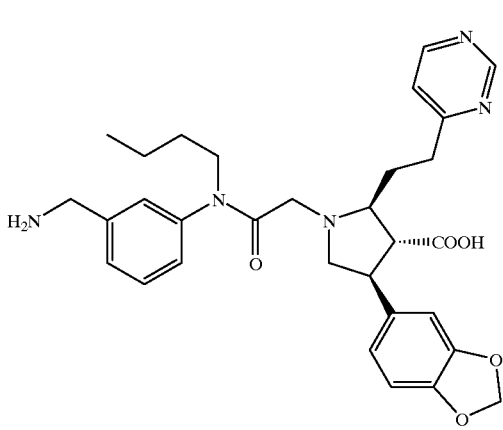
1436
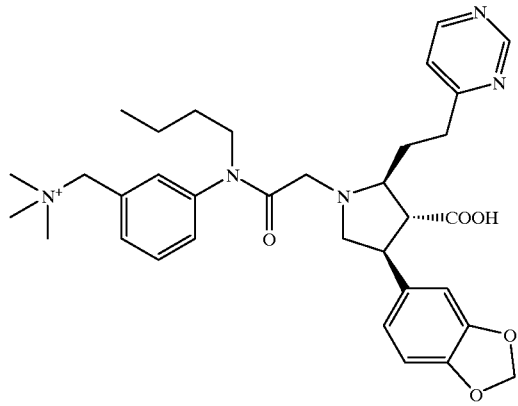

TABLE 3C-continued
1437
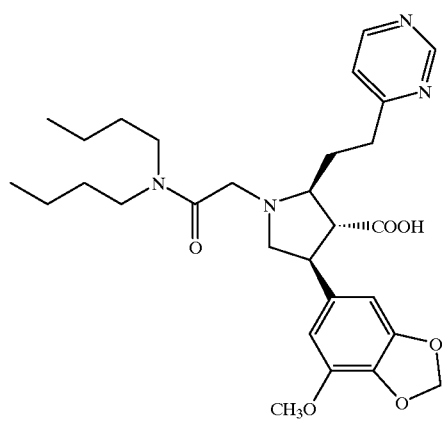
1438
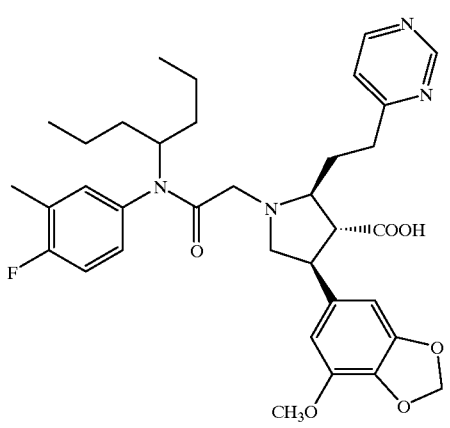
1439
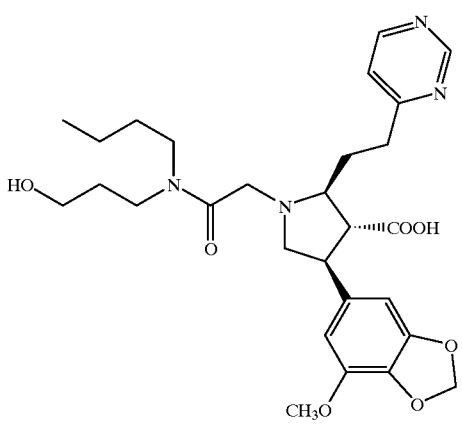

TABLE 3C-continued
1440
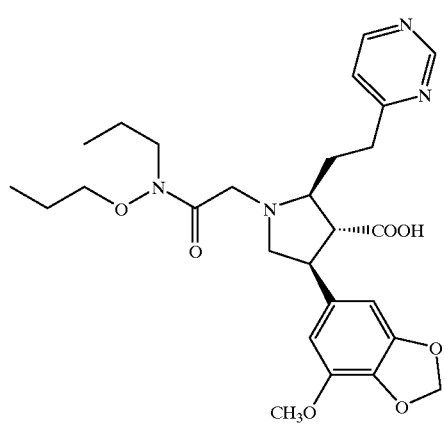
1441
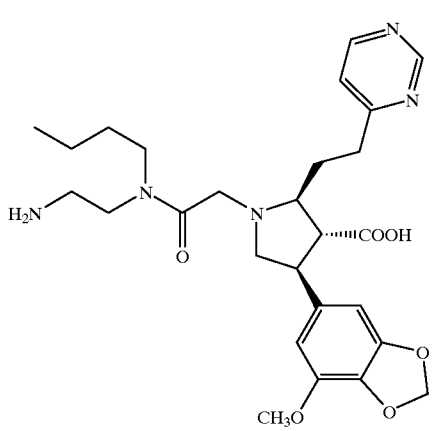
1442
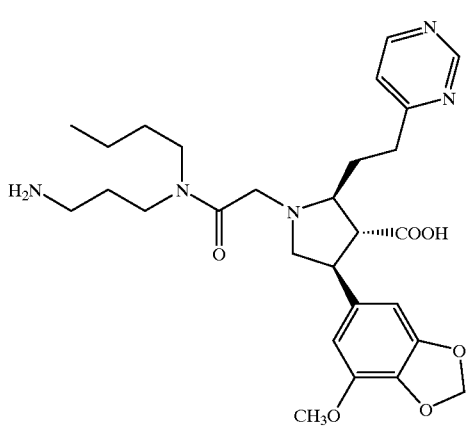

TABLE 3C-continued
1443
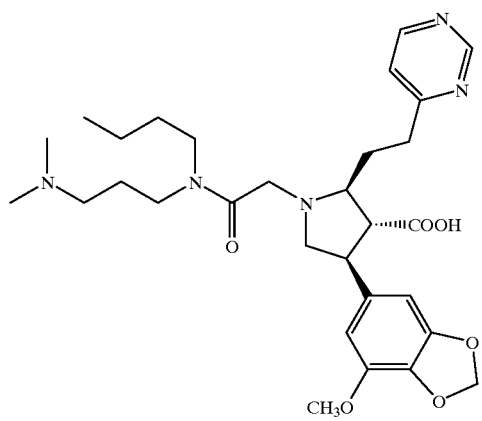
1444
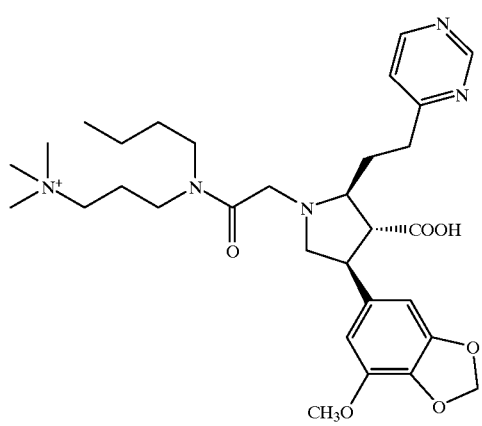
1445
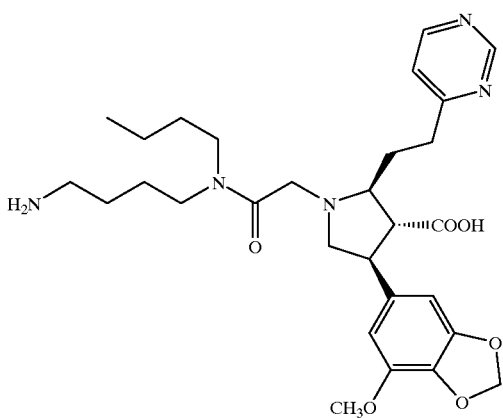

TABLE 3C-continued
1446
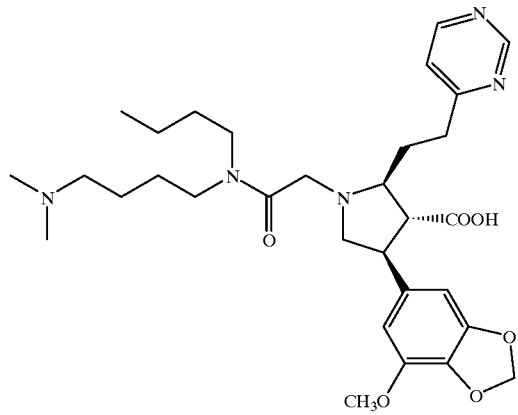
1447
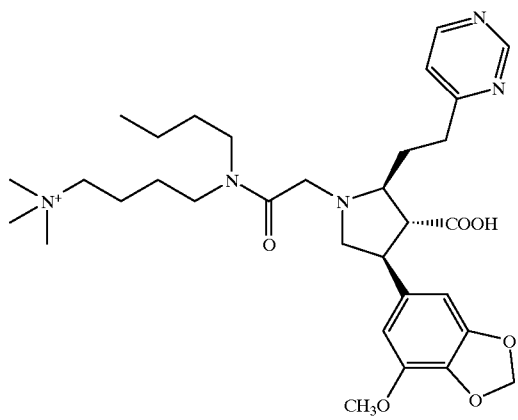
1448
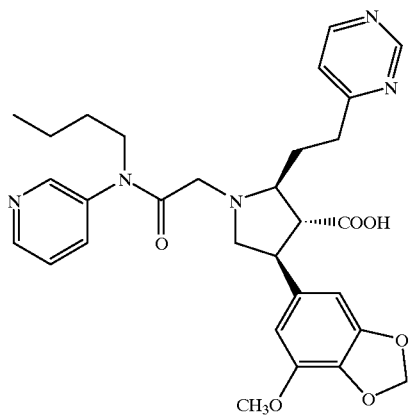

TABLE 3C-continued
1449
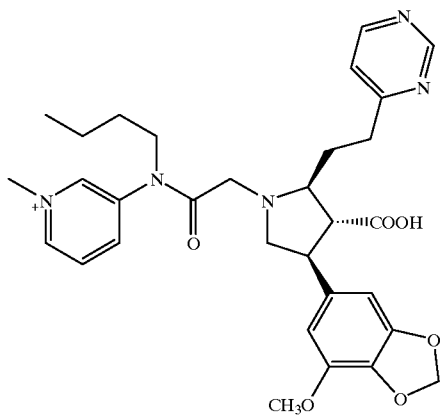
1450
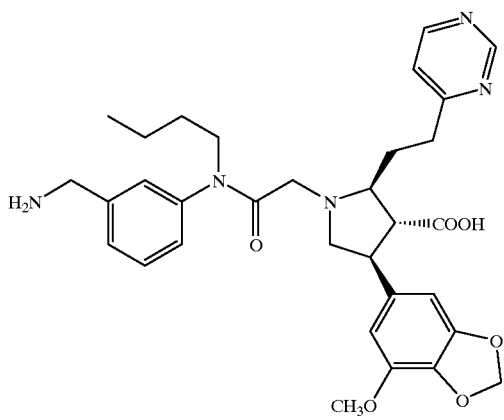
1451
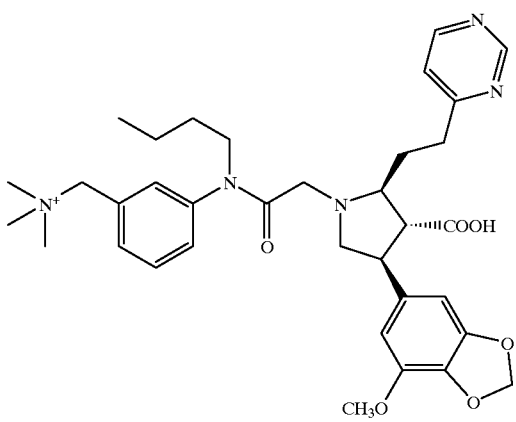

TABLE 3C-continued
1452
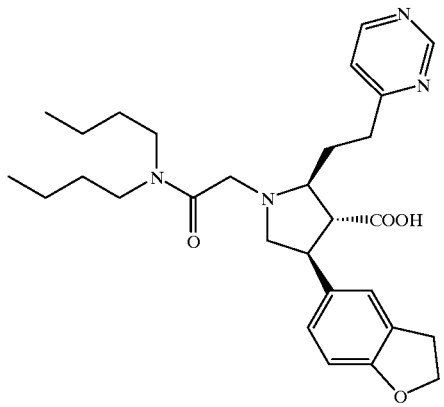
1453
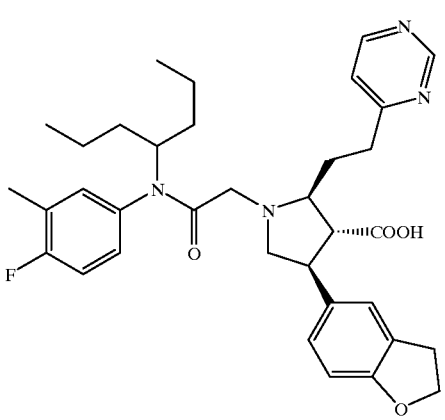
1454
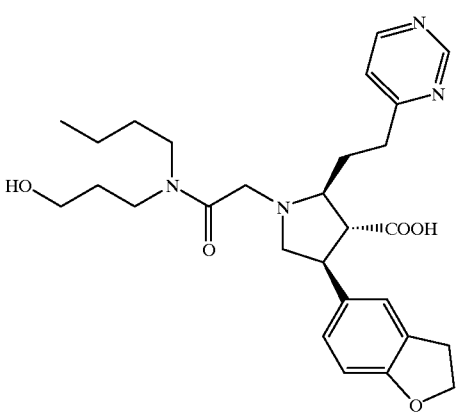

TABLE 3C-continued
1455
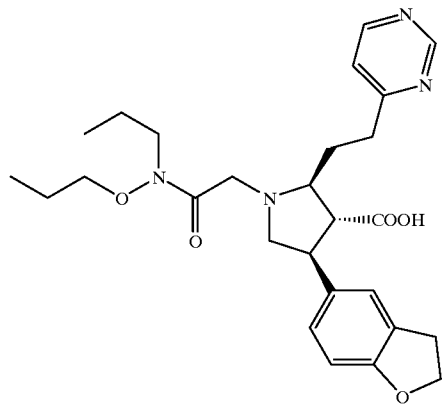
1456
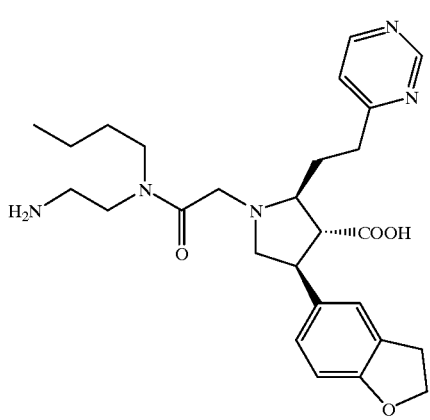
1457
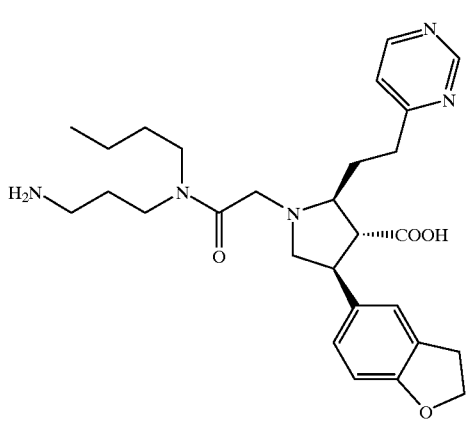

TABLE 3C-continued
1458
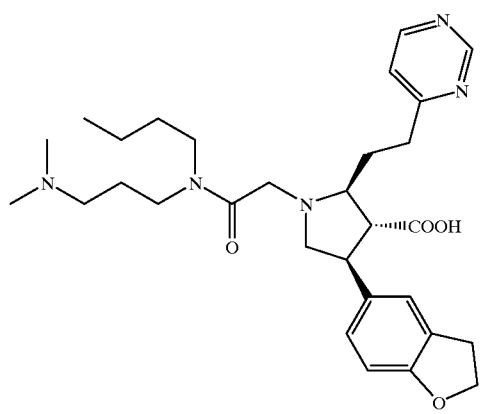
1459
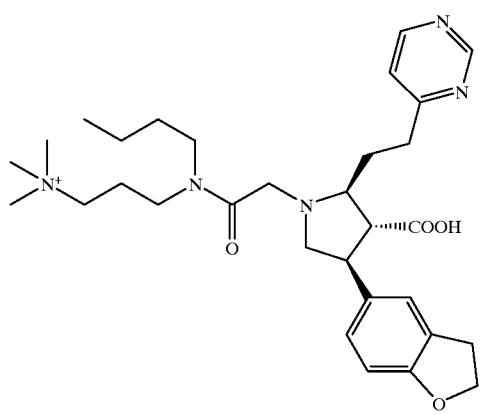
1460
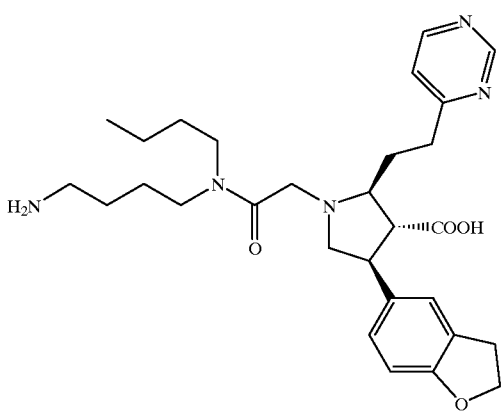

TABLE 3C-continued
1461
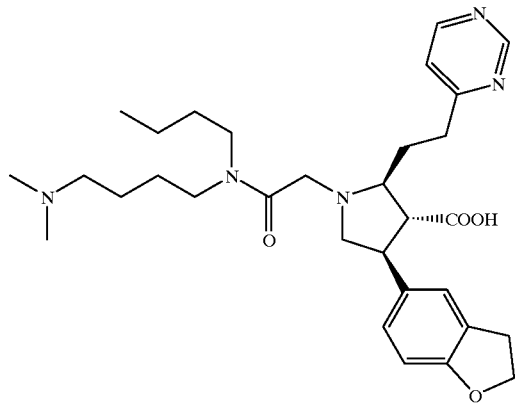
1462
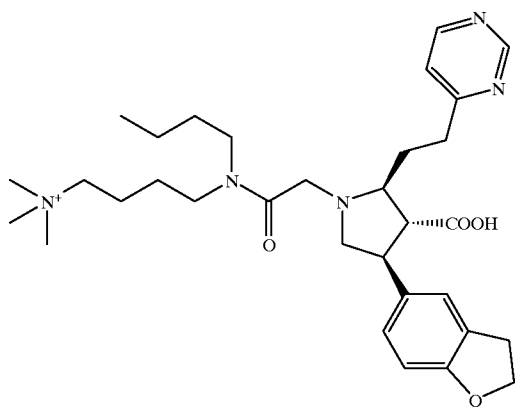
1463
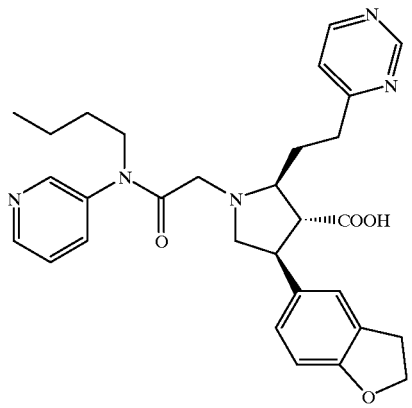

TABLE 3C-continued
1464
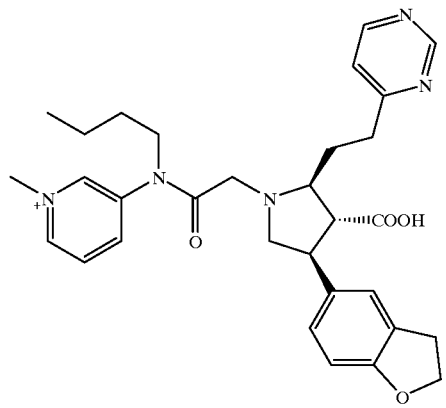
1465
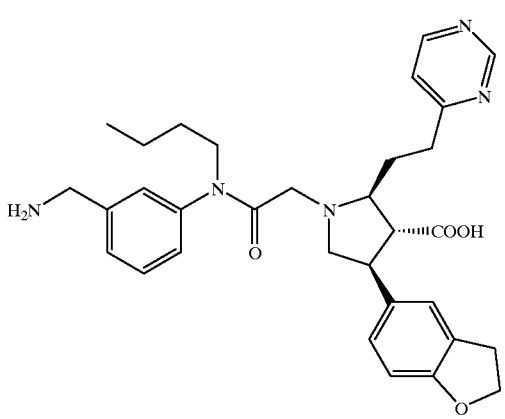
1466
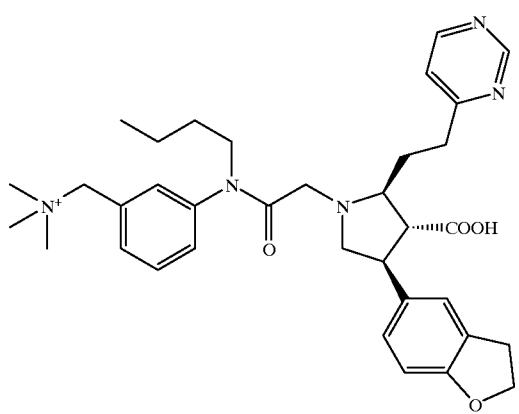
1467
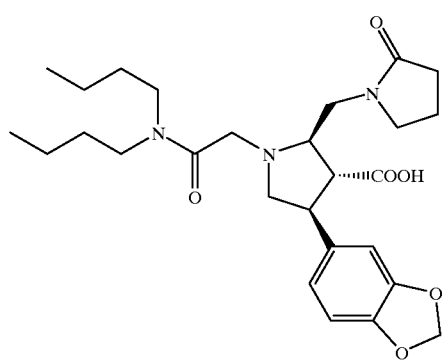

TABLE 3C-continued
1468
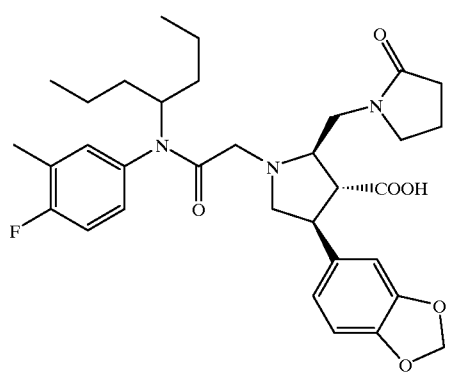
1469
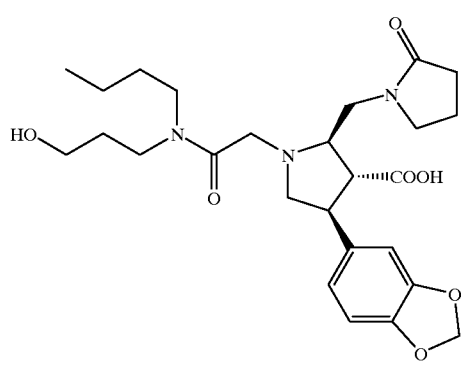
1470
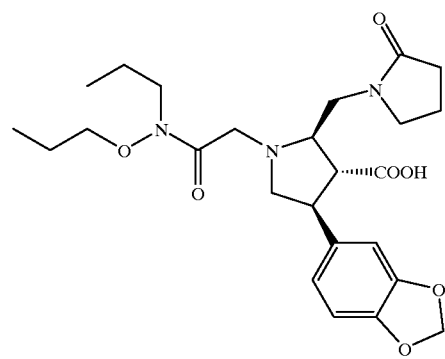
1471
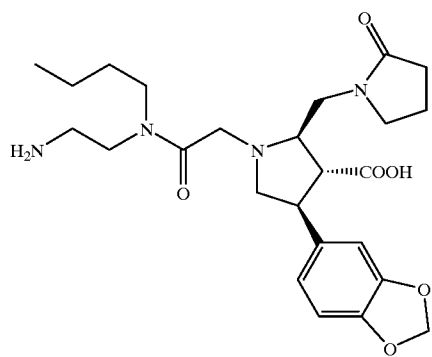

TABLE 3C-continued
1472
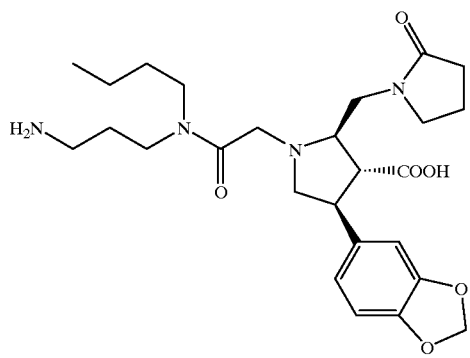
1473
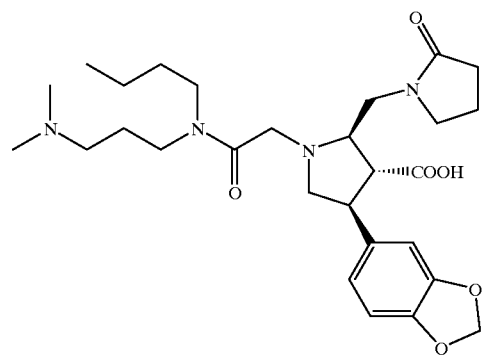
1474
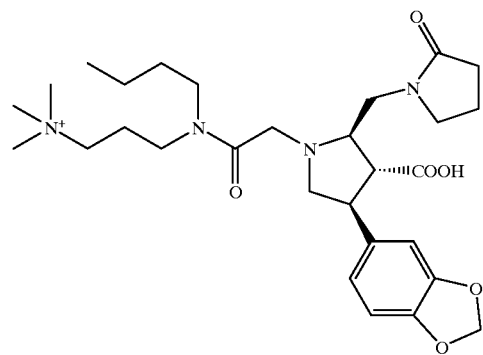
1475
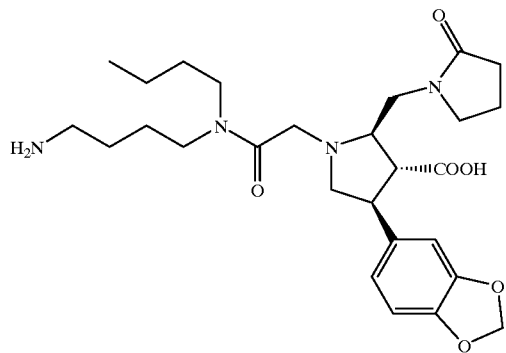

TABLE 3C-continued
1476 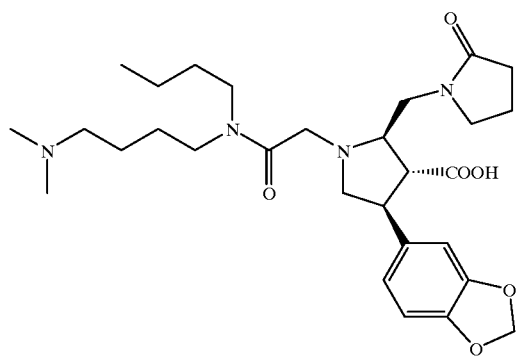
1477 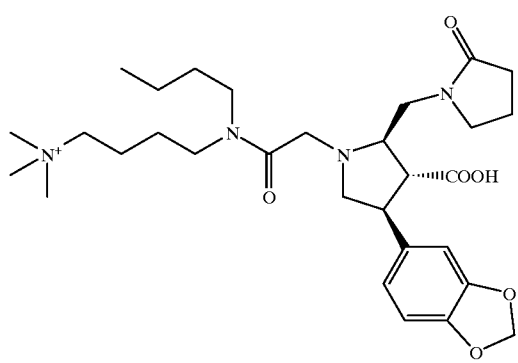
1478 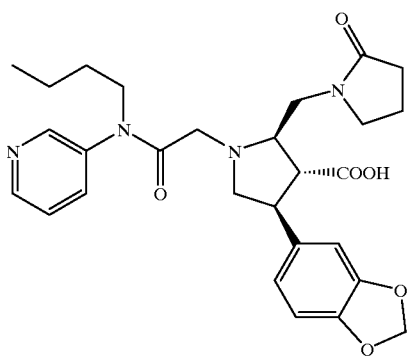
1479 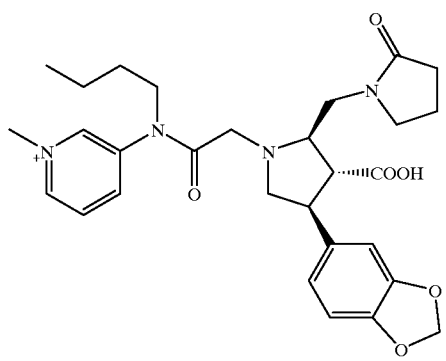

TABLE 3C-continued
1480
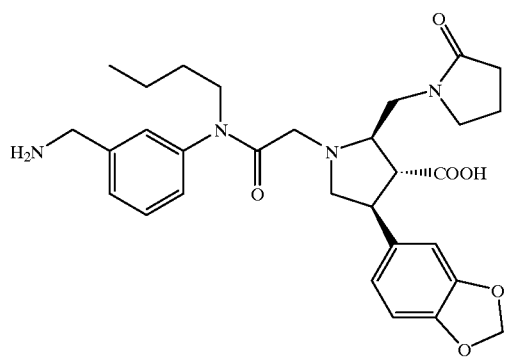
1481
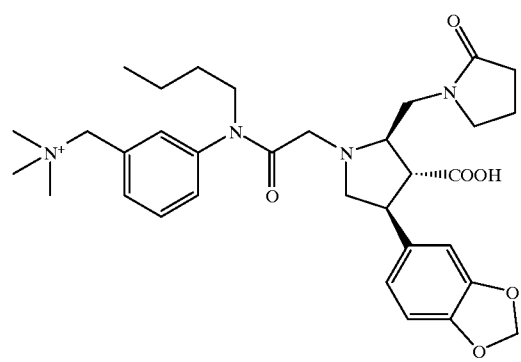
1482
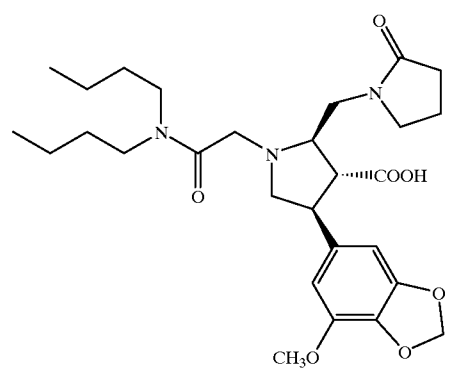
1483
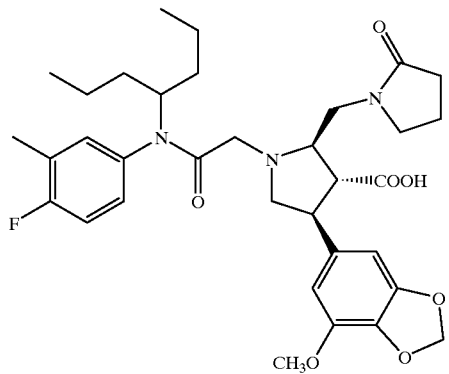

TABLE 3C-continued
1484
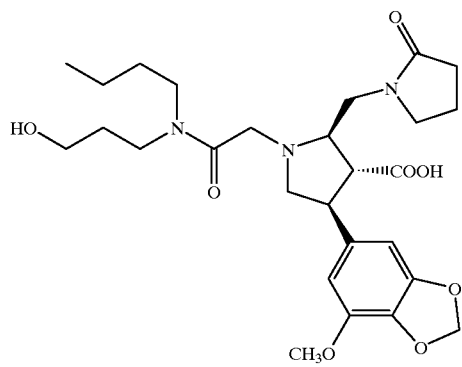
1485
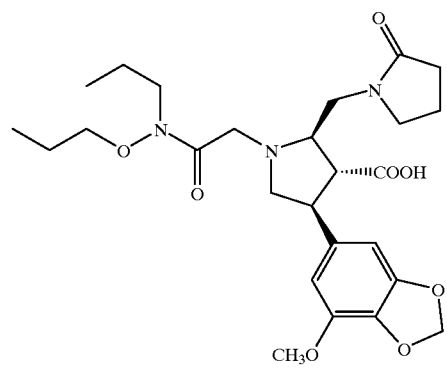
1486
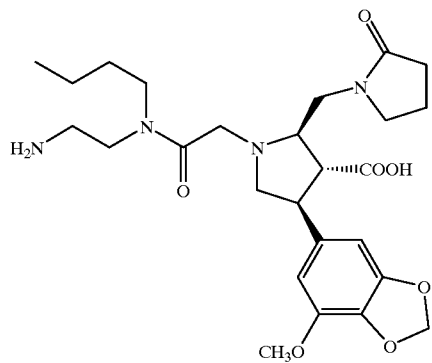
1487
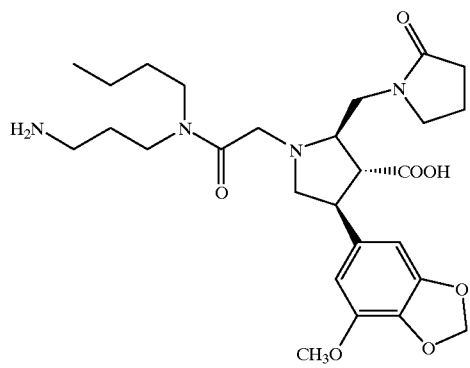

TABLE 3C-continued
1488
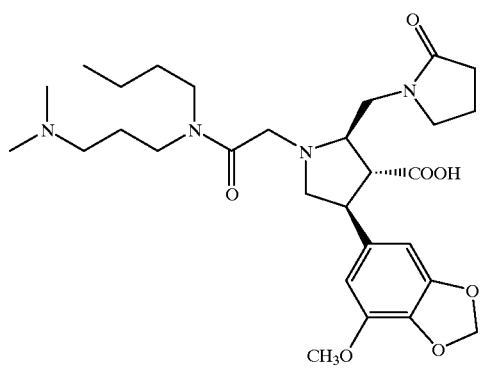
1489
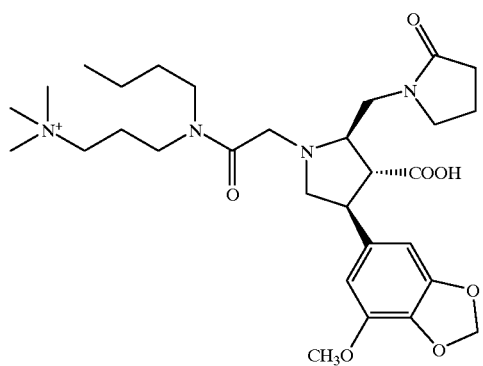
1490
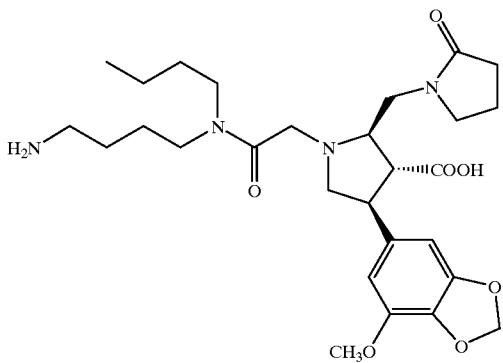
1491
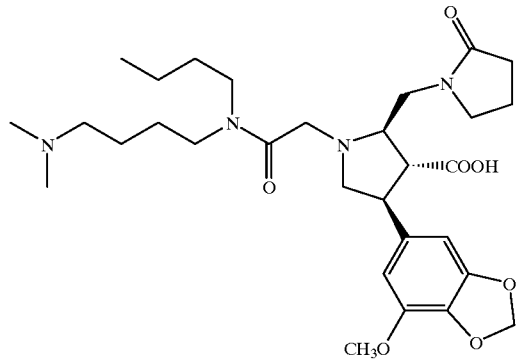

TABLE 3C-continued
1492
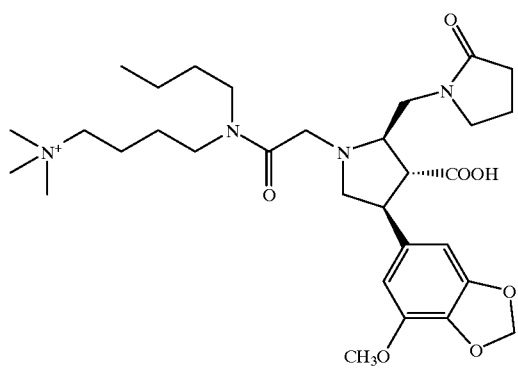
1493
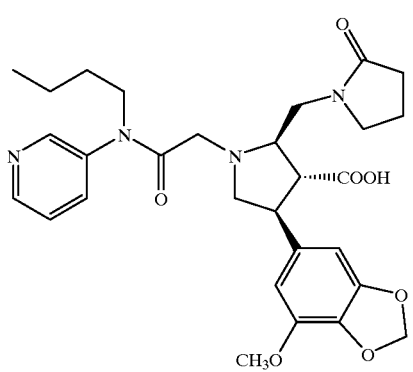
1494
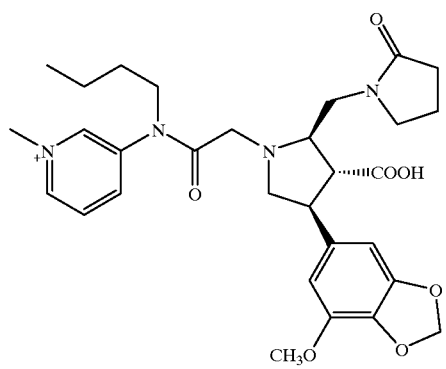
1495
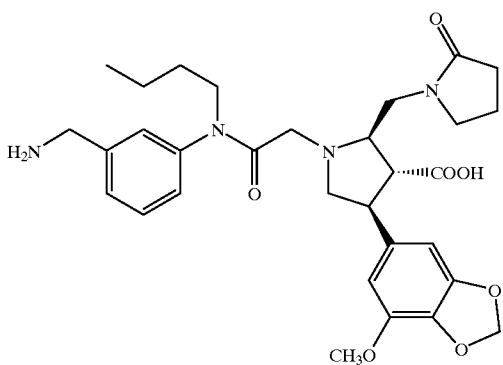

TABLE 3C-continued
1496
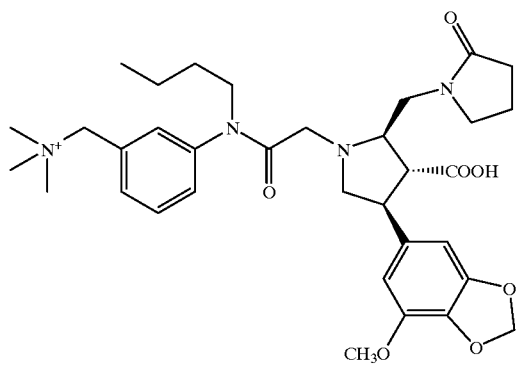
1497
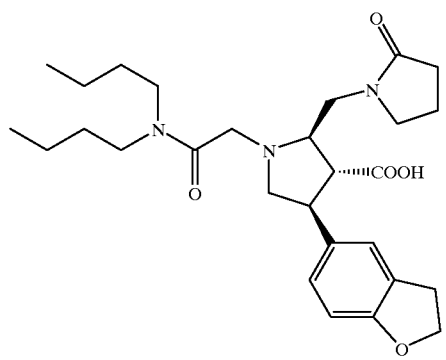
1498
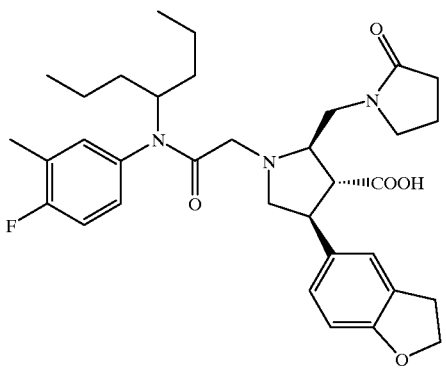
1499
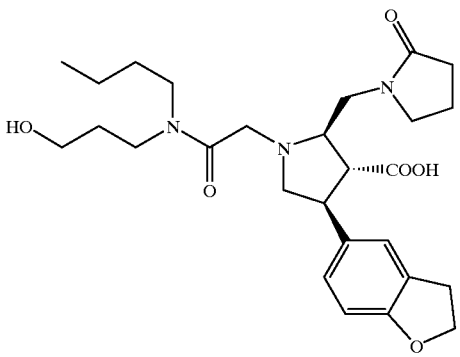

TABLE 3C-continued
1500 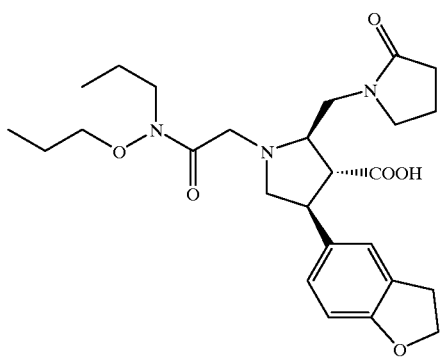
1501 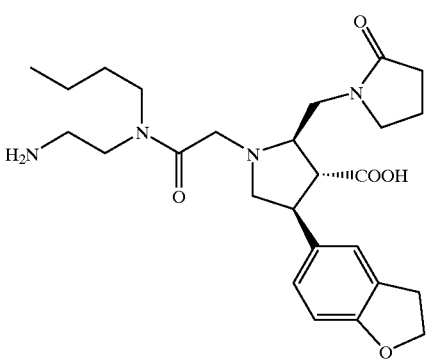
1502 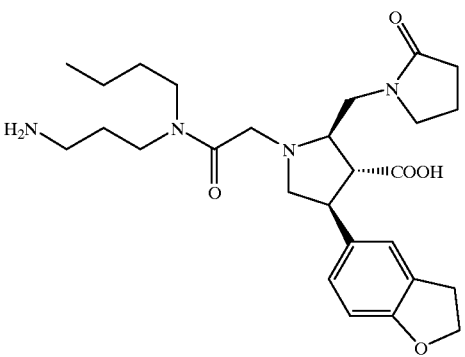
1503 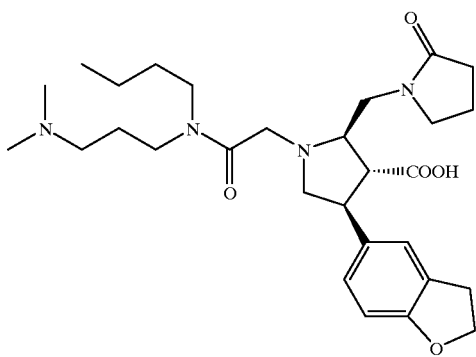

TABLE 3C-continued
1504
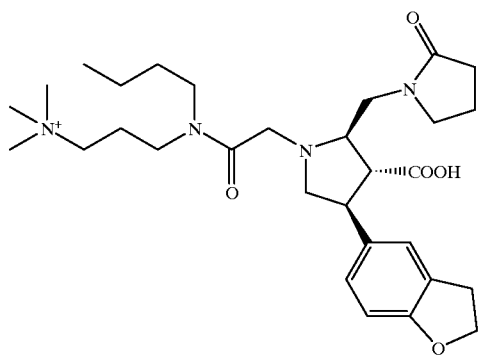
1505
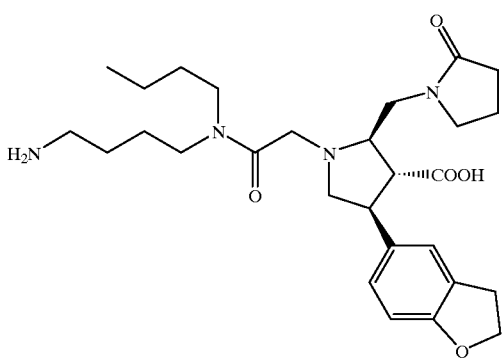
1506
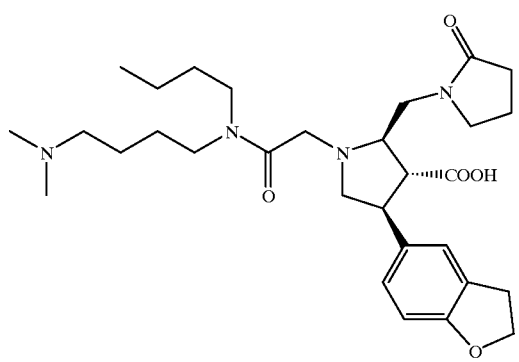
1507
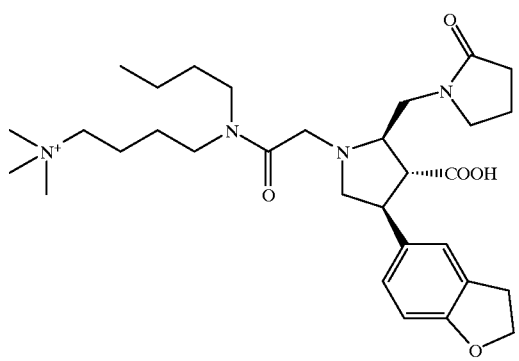

TABLE 3C-continued
1508 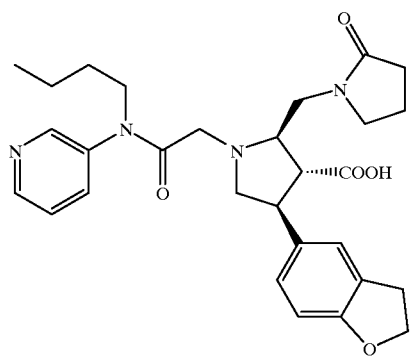
1509 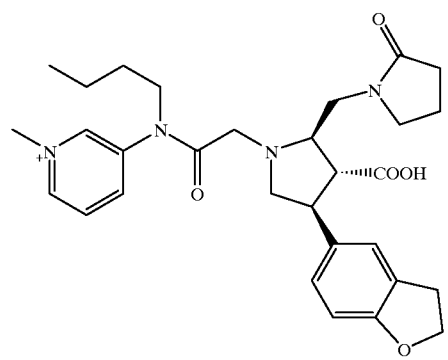
1510 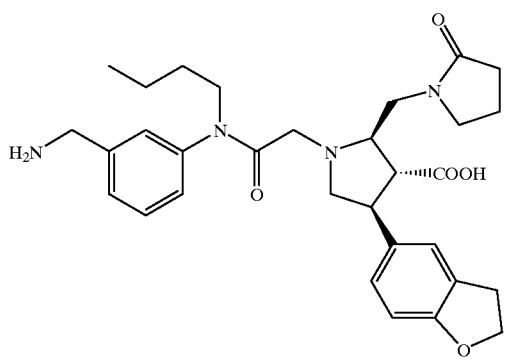
1511 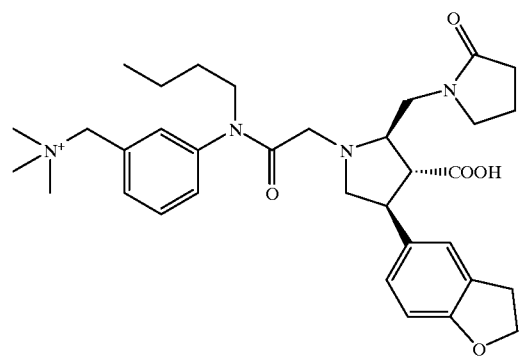

TABLE 3C-continued
1512 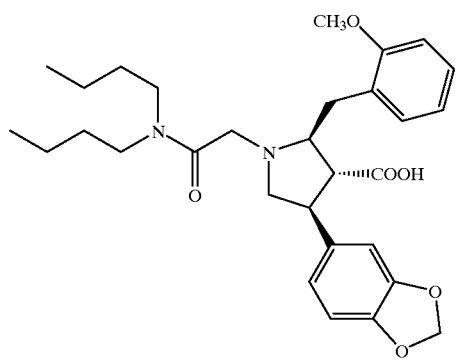
1513 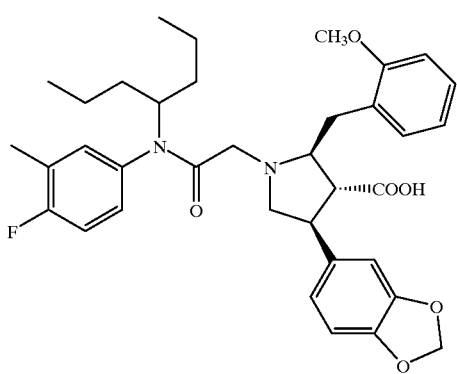
1514 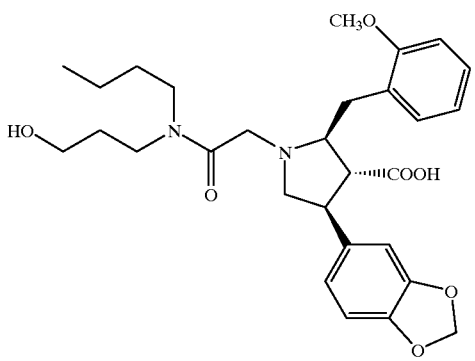
1515 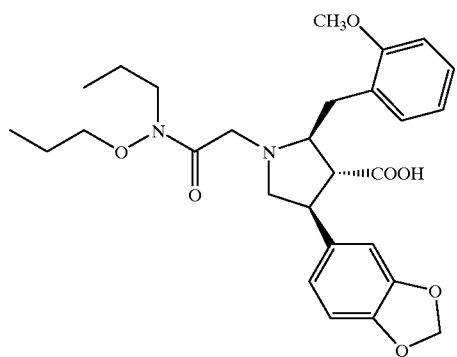

TABLE 3C-continued
1516
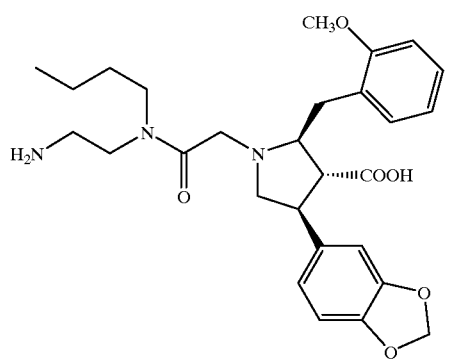
1517
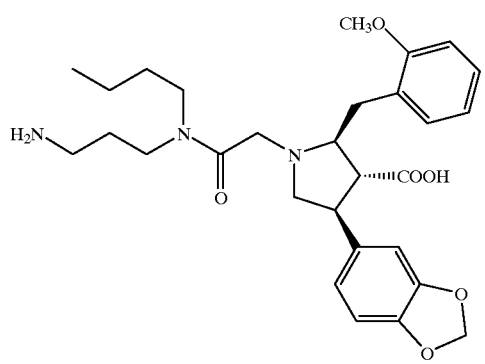
1518
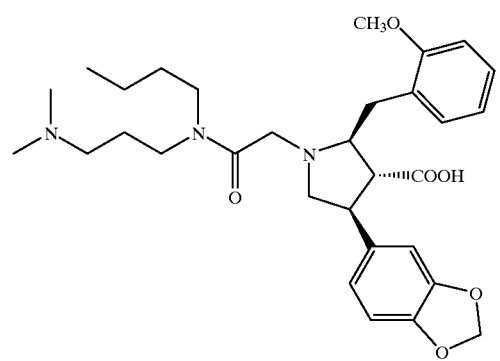
1519
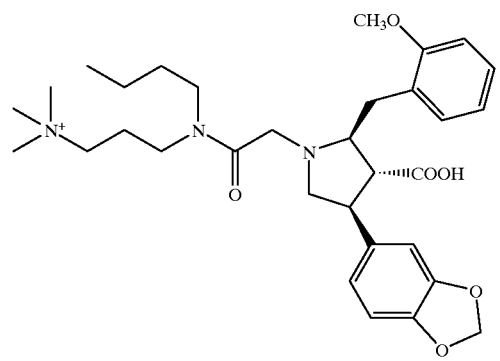

TABLE 3C-continued
1520 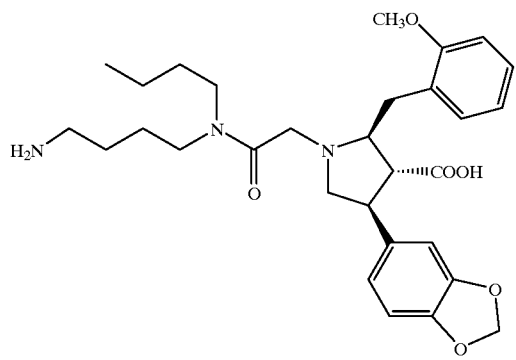
1521 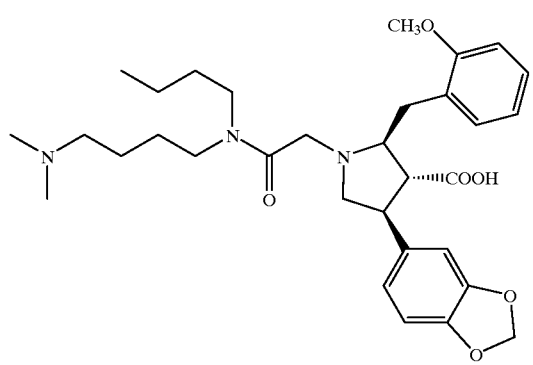
1522 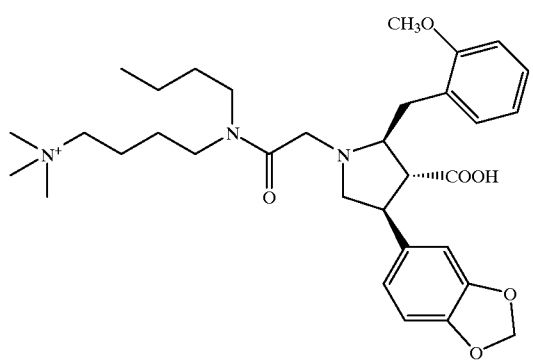
1523 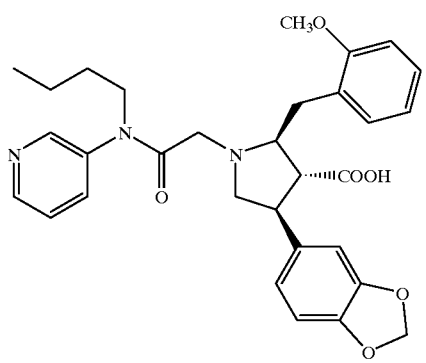

TABLE 3C-continued
1524 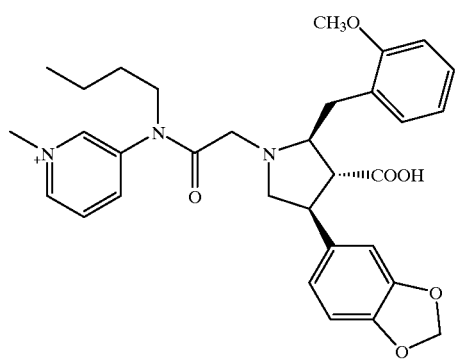
1525 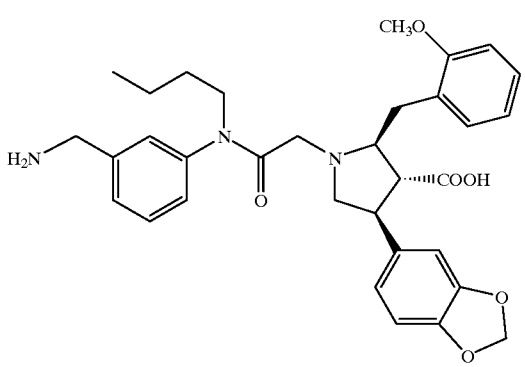
1526 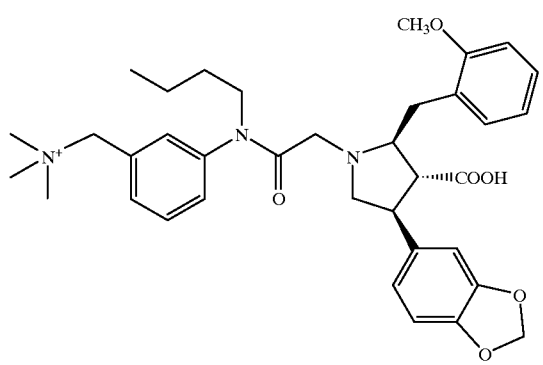
1527 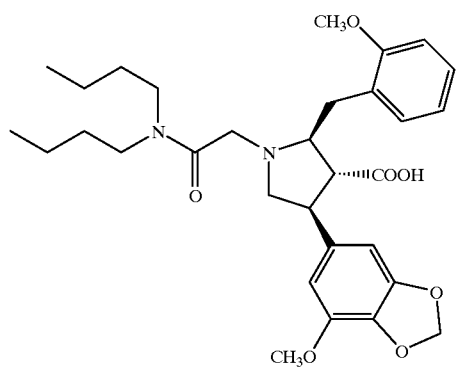

TABLE 3C-continued
1528
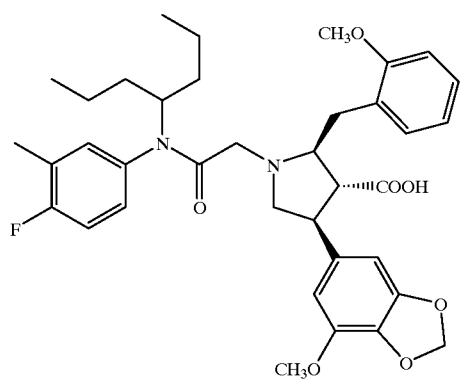
1529
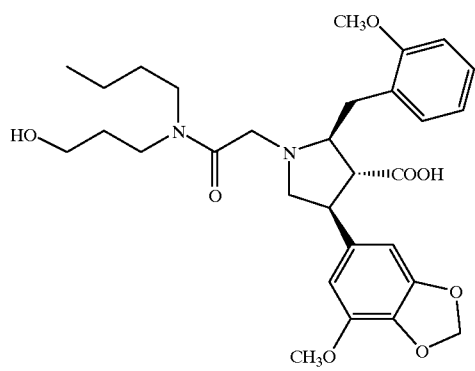
1530
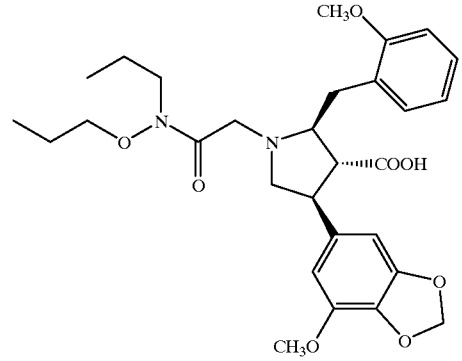
1531
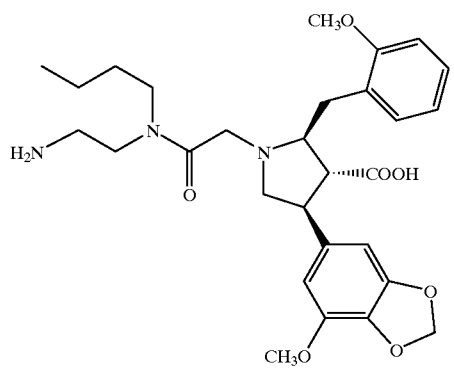

TABLE 3C-continued
| 1532 | 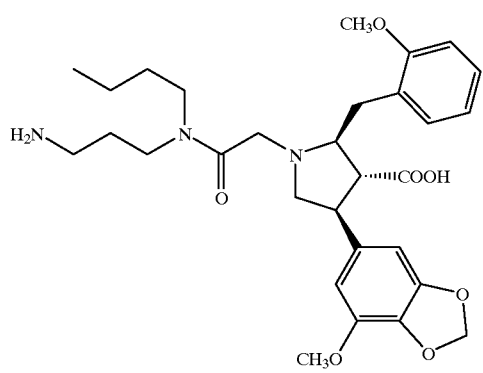 |
| 1533 | 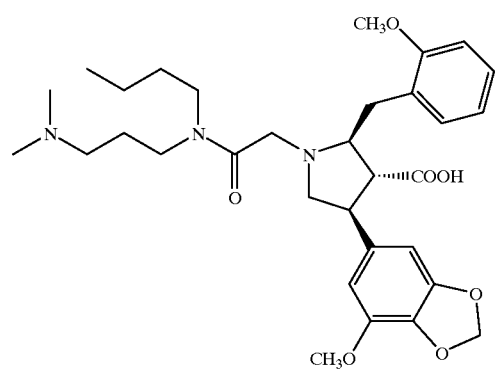 |
| 1534 | 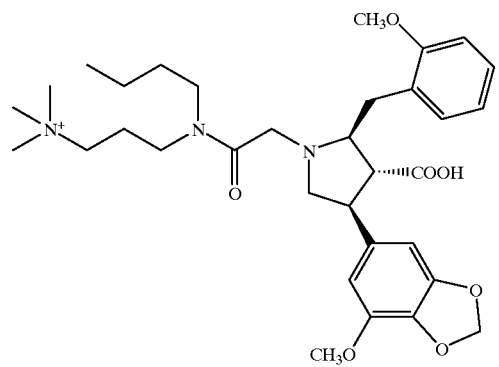 |
| 1535 | 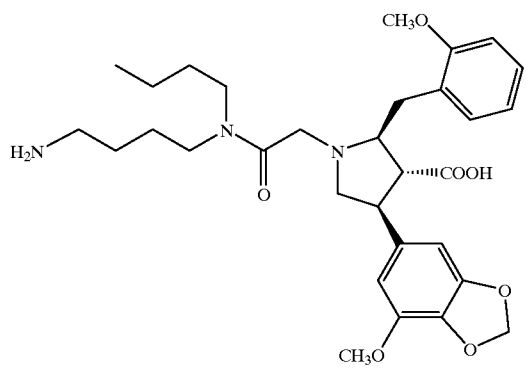 |

TABLE 3C-continued
1536
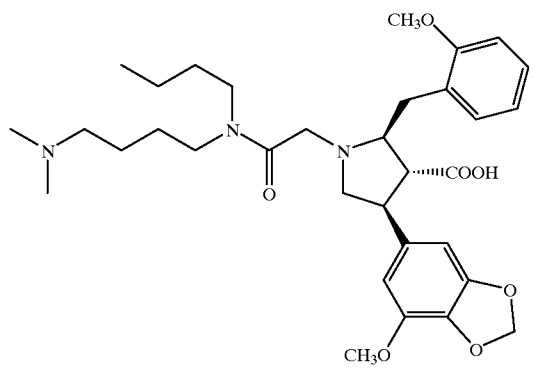
1537
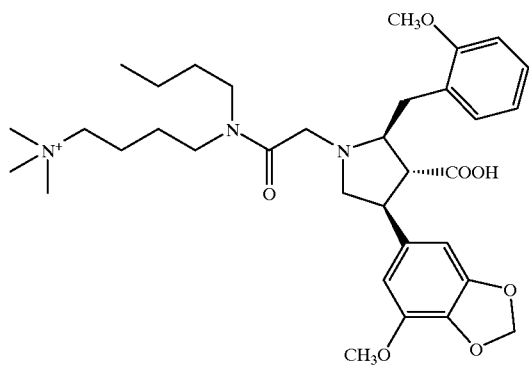
1538
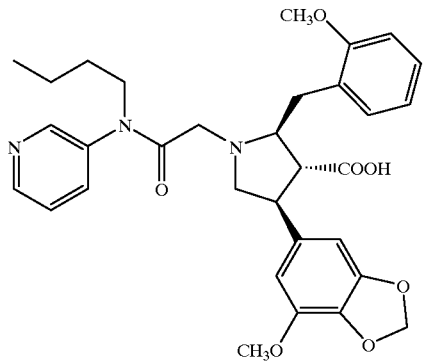
1539
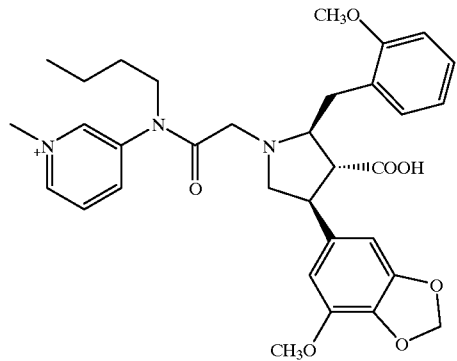

TABLE 3C-continued
1540
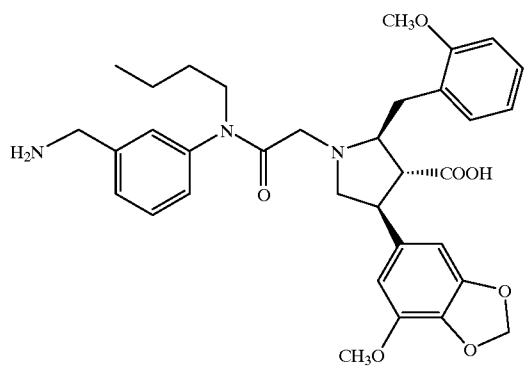
1541
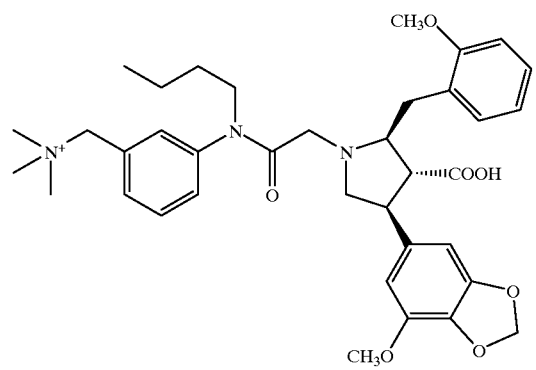
1542
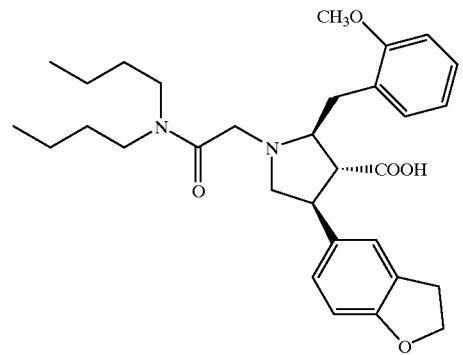
1543
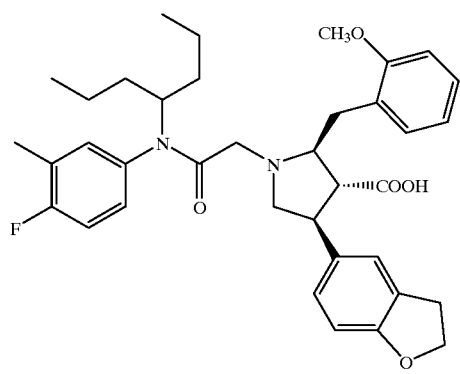

TABLE 3C-continued
1544
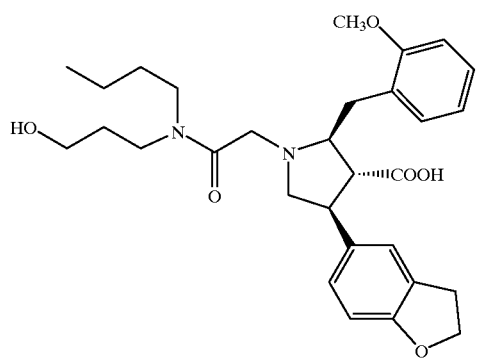
1545
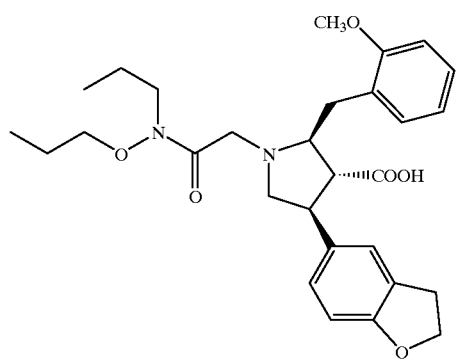
1546
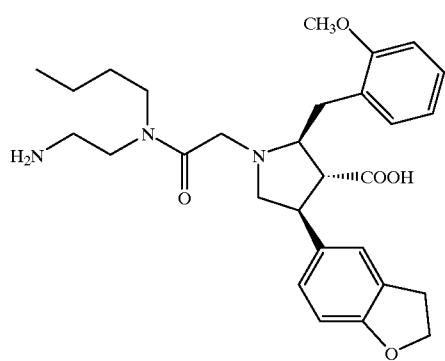
1547
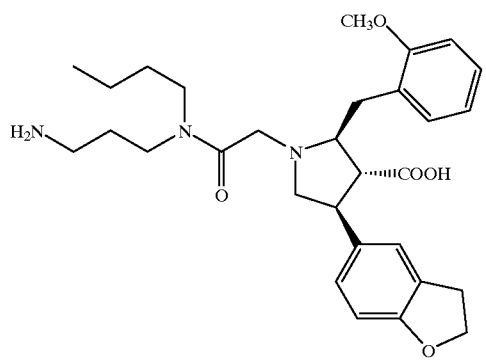

TABLE 3C-continued
1548
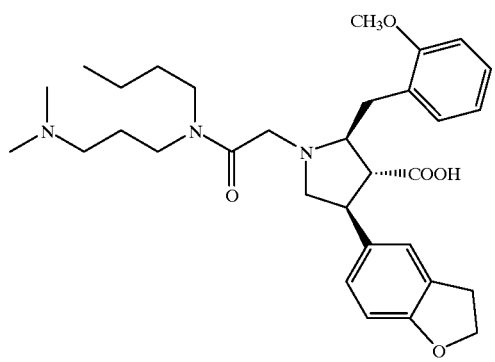
1549
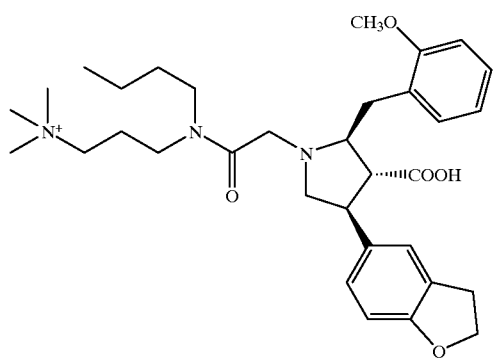
1550
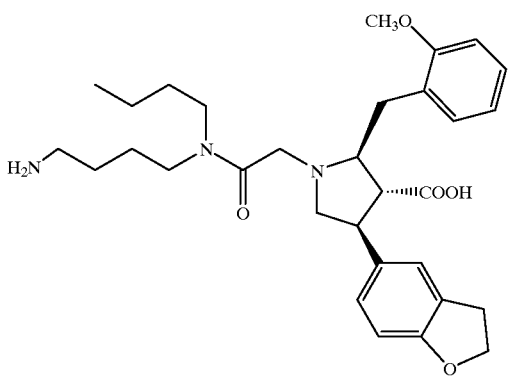
1551
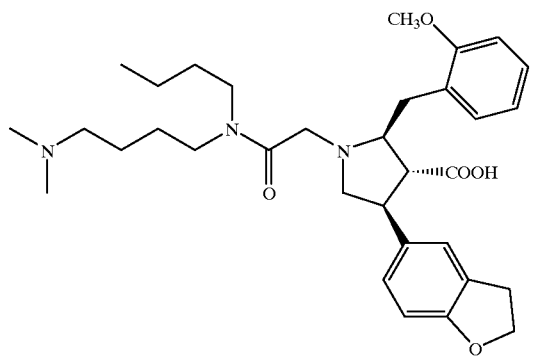

TABLE 3C-continued
1552
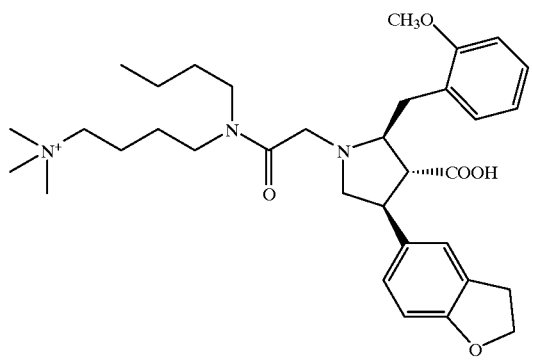
1553
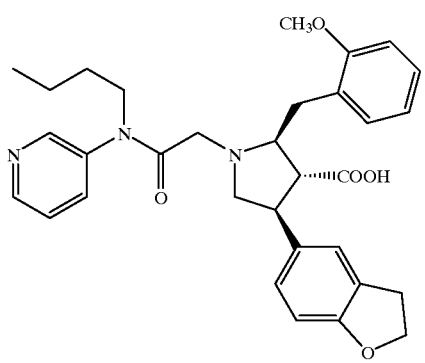
1554
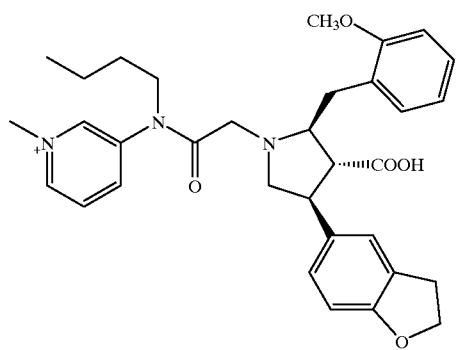
1555
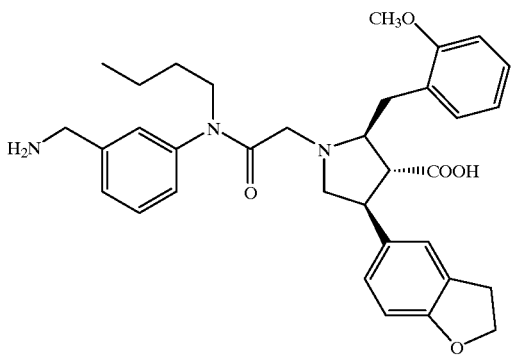

TABLE 3C-continued
1556
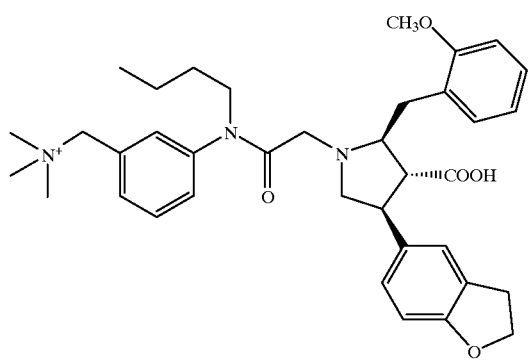
1557
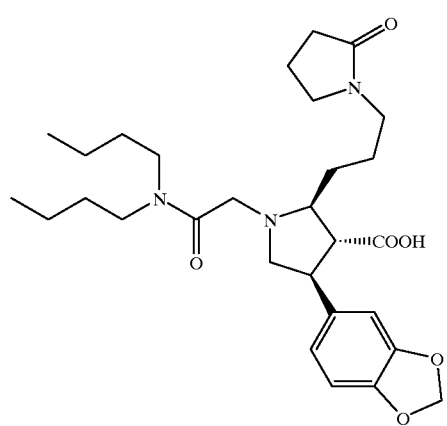
1558
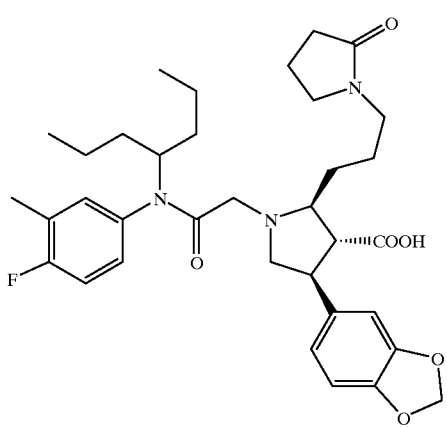

TABLE 3C-continued
1559
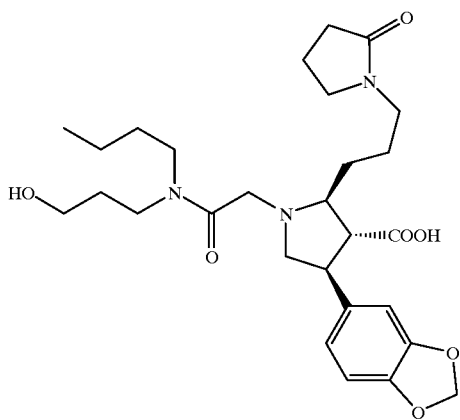
1560
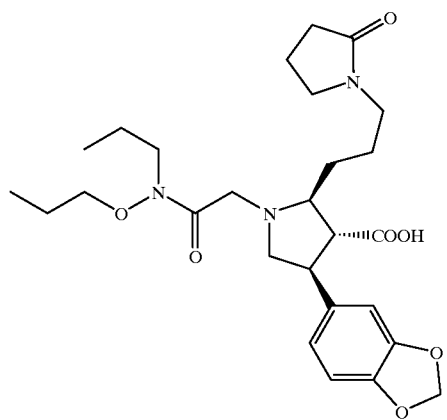
1561
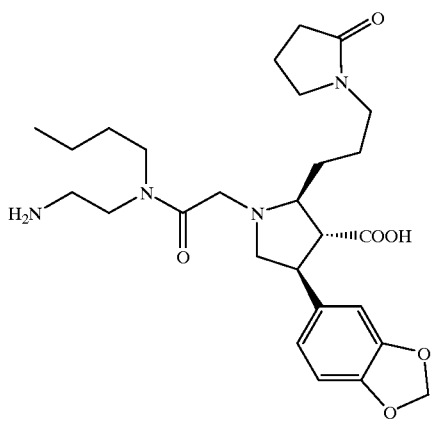

TABLE 3C-continued
1562
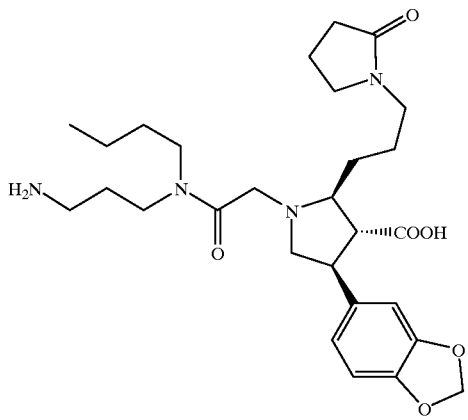
1563
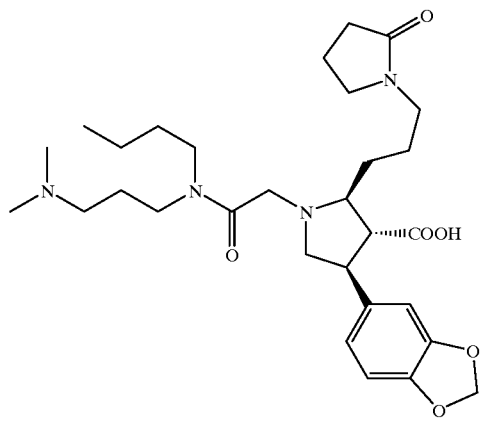
1564
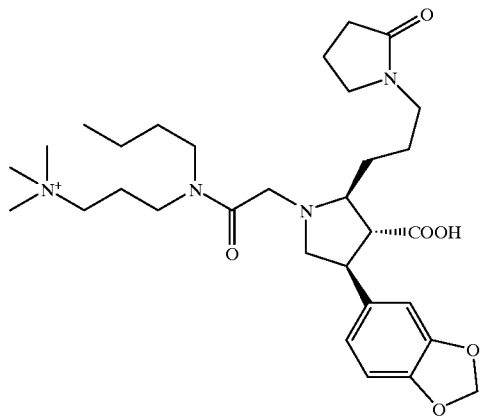

TABLE 3C-continued
1565
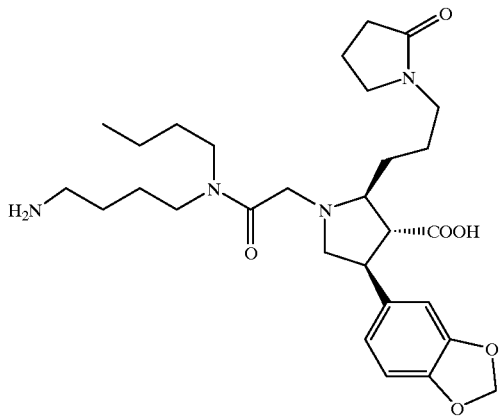
1566
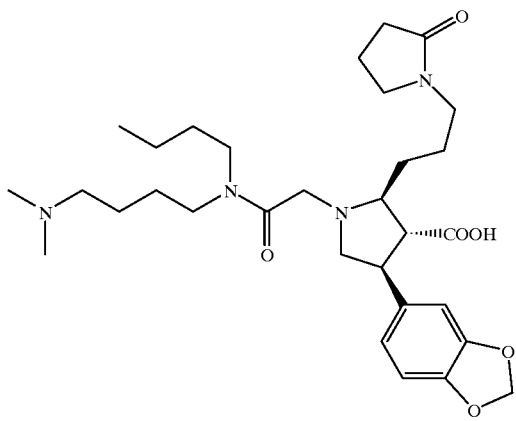
1567
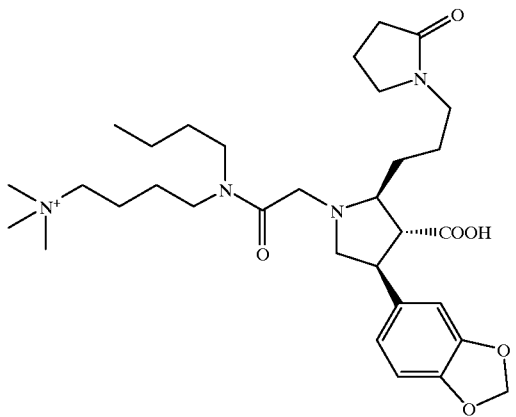

TABLE 3C-continued
1568
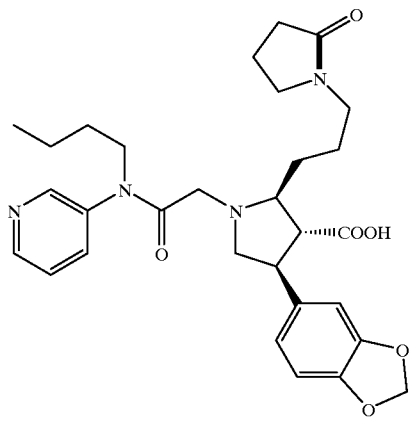
1569
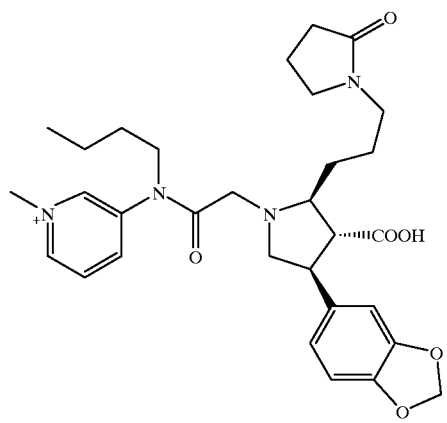
1570
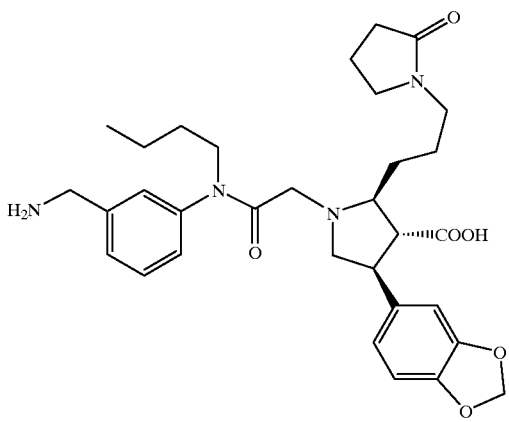

TABLE 3C-continued
1571
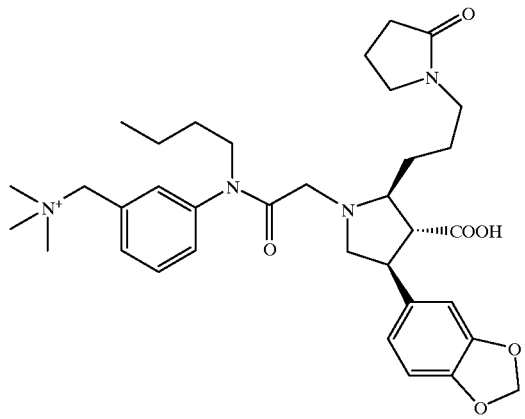
1572
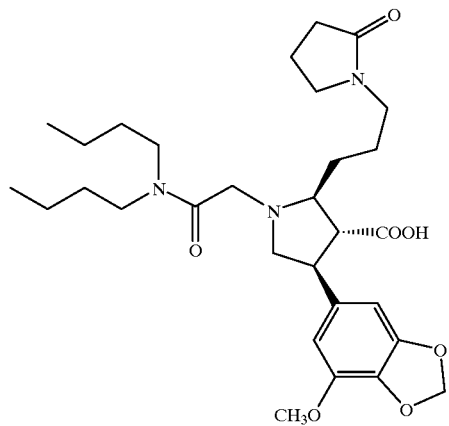
1573
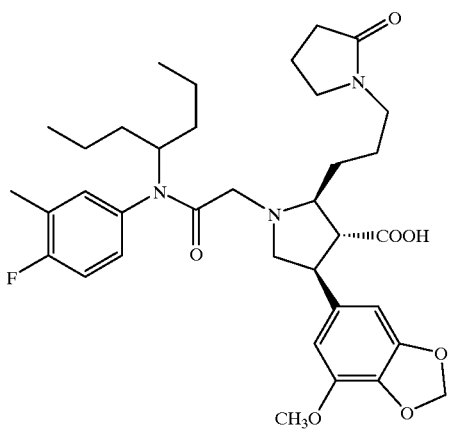

TABLE 3C-continued
1574
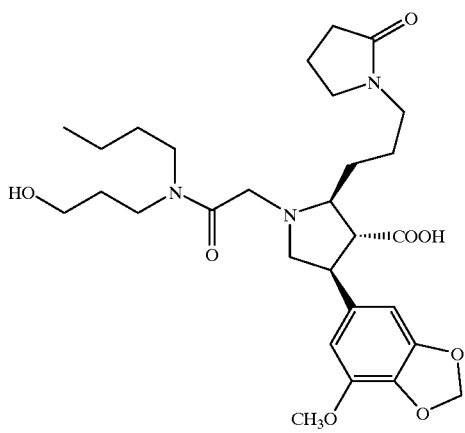
1575
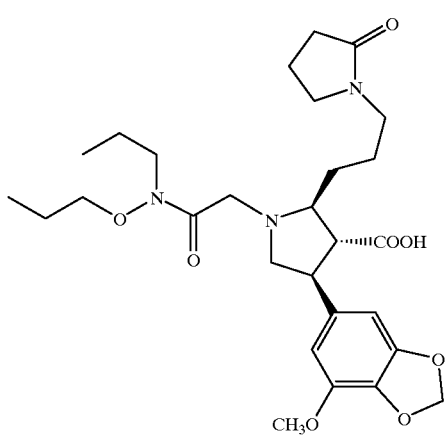
1576
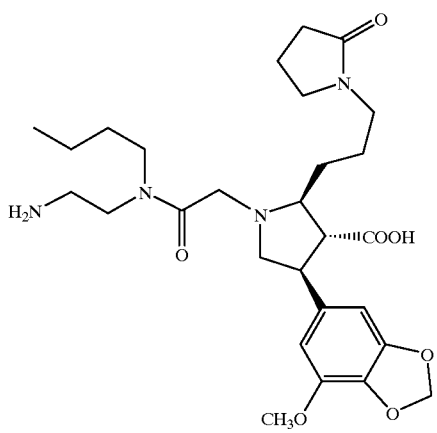

TABLE 3C-continued
1577
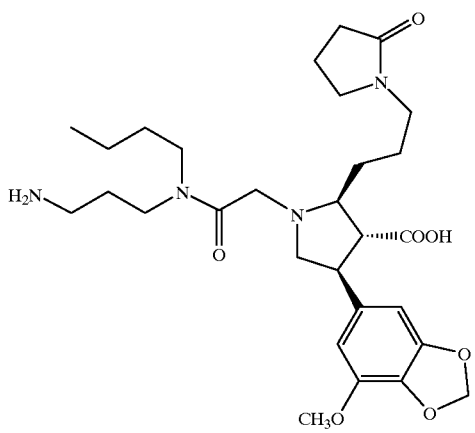
1578
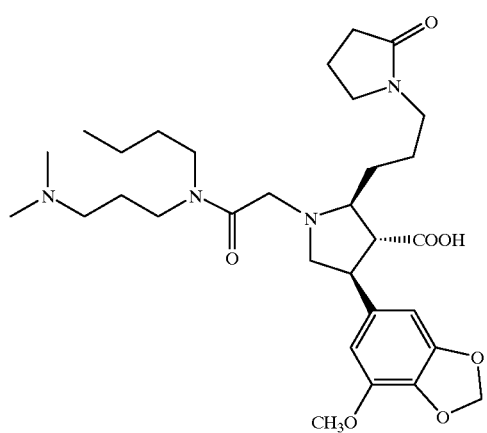
1579
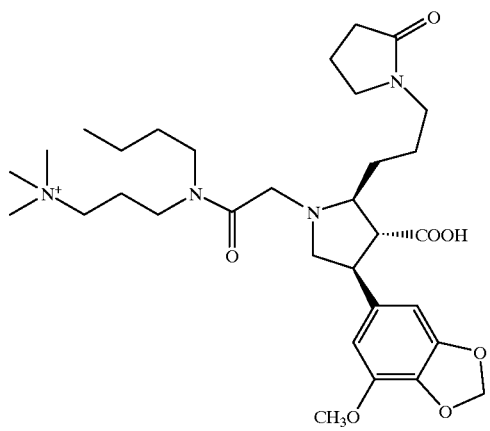

TABLE 3C-continued
1580
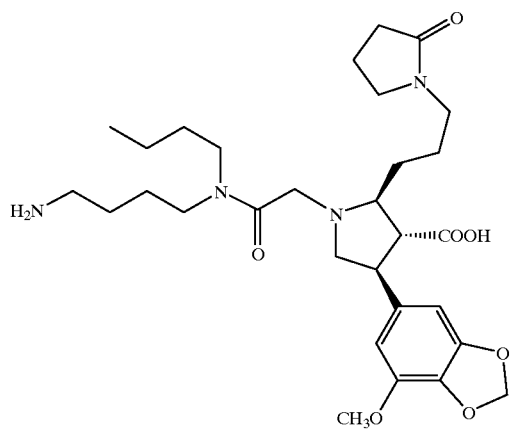
1581
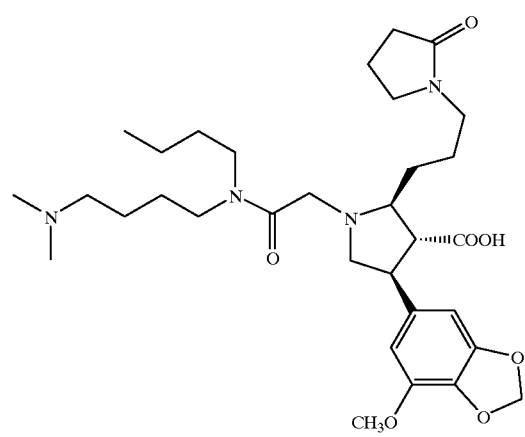
1582
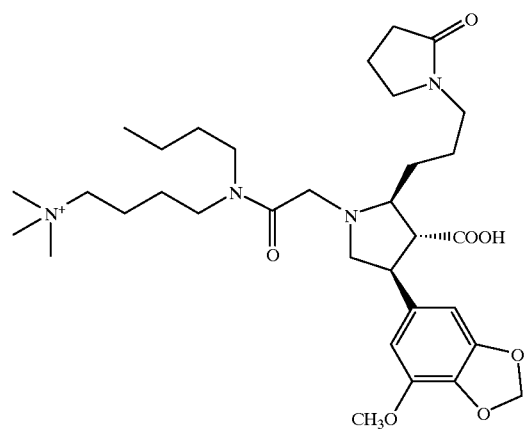

TABLE 3C-continued
1583
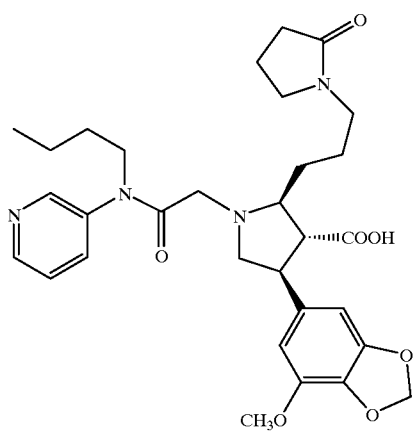
1584
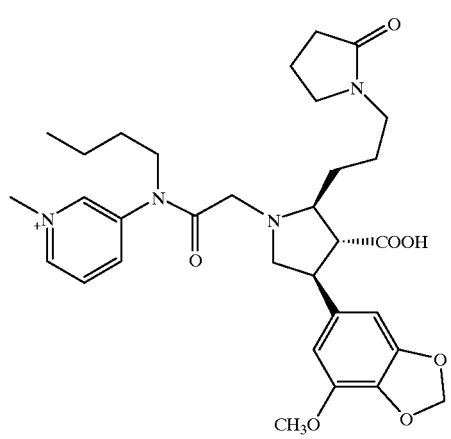
1585
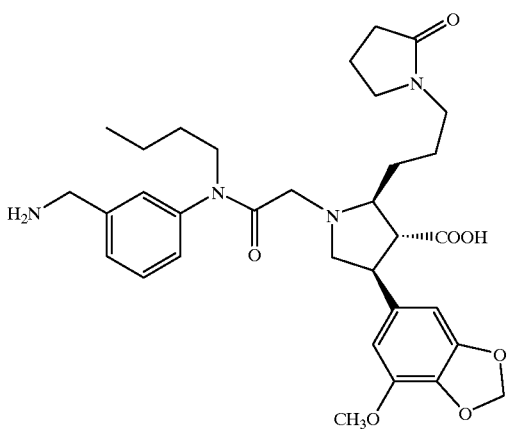

TABLE 3C-continued
1586
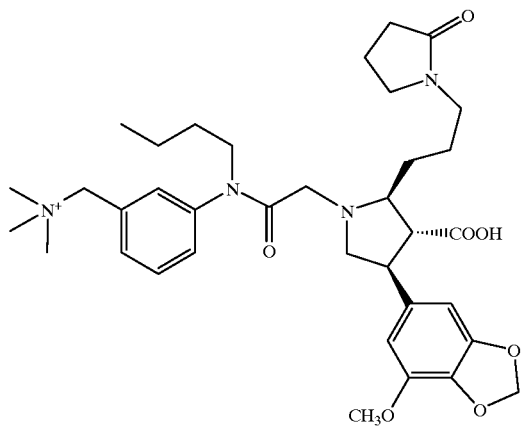
1587
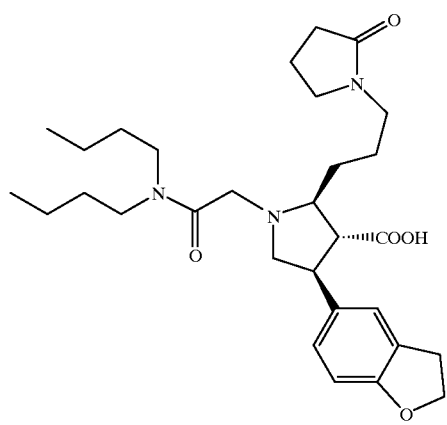
1588
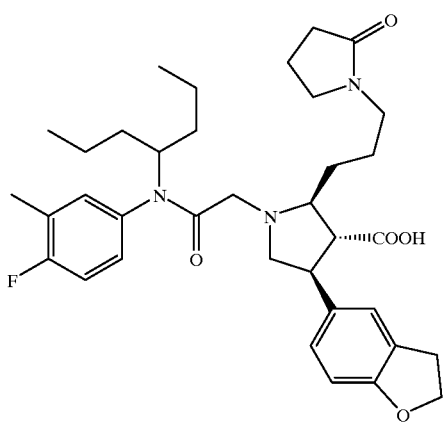

TABLE 3C-continued
1589
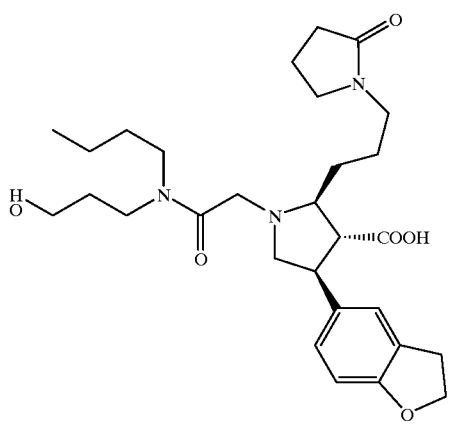
1590
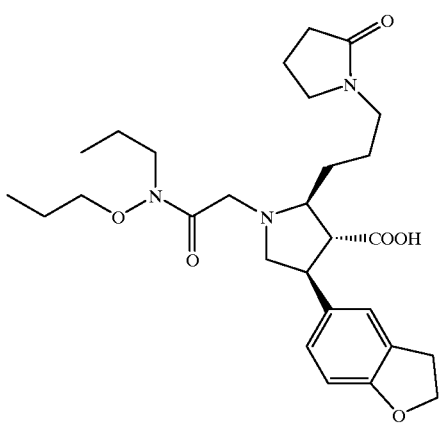
1591
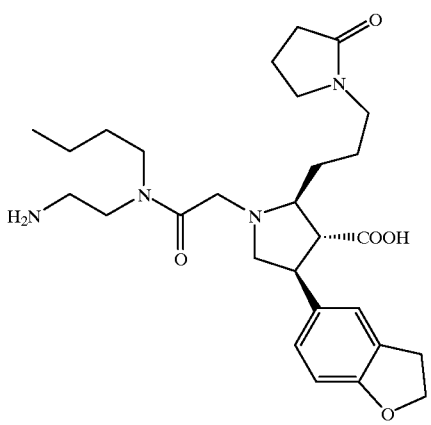

TABLE 3C-continued
1592
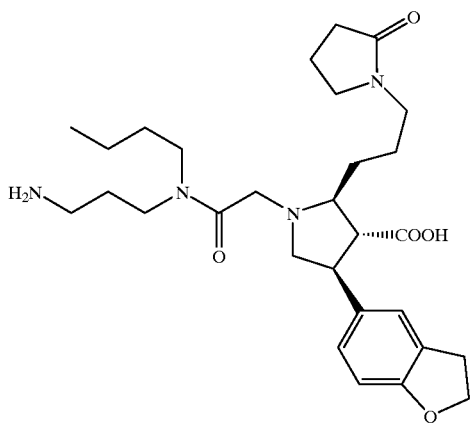
1593
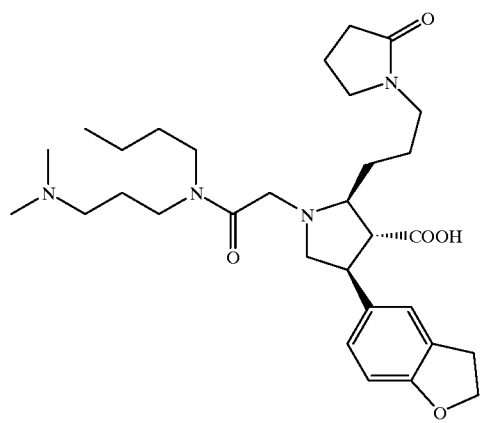
1594
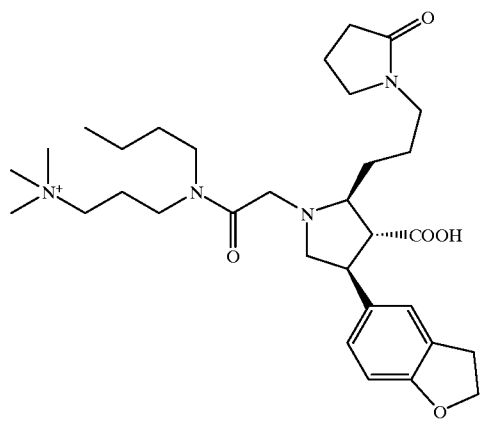

TABLE 3C-continued
1595
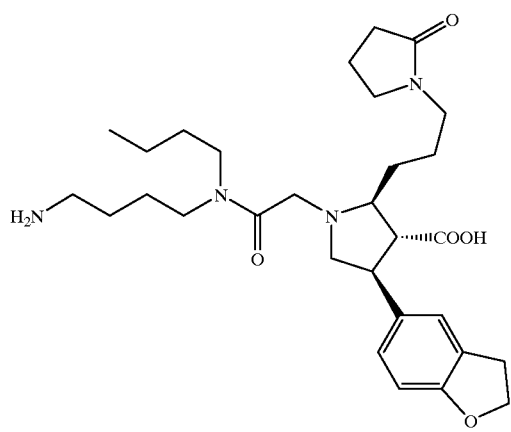
1596
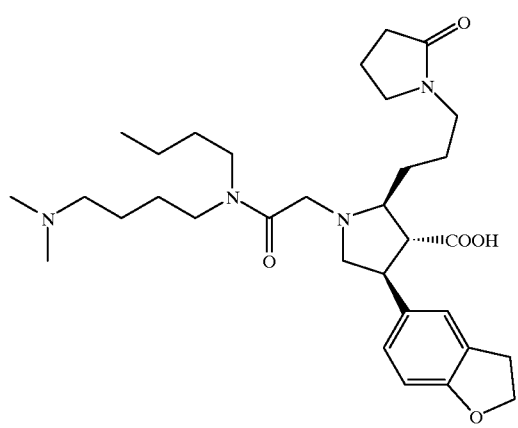
1597
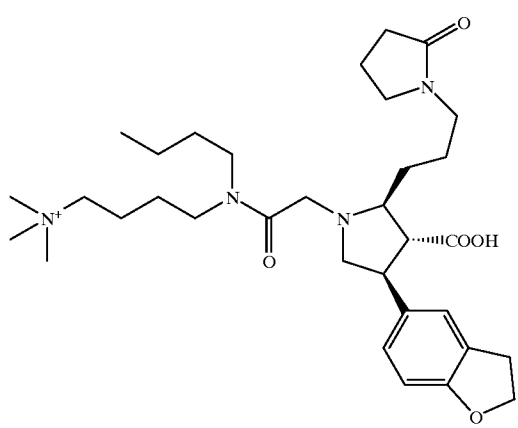

TABLE 3C-continued
1598
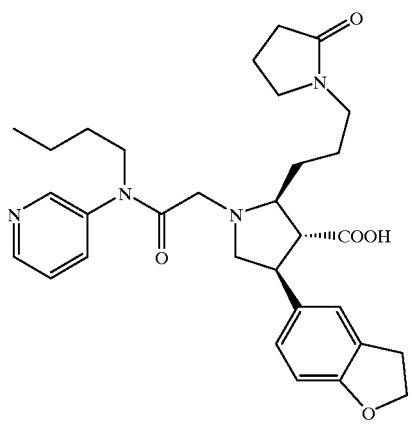
1599
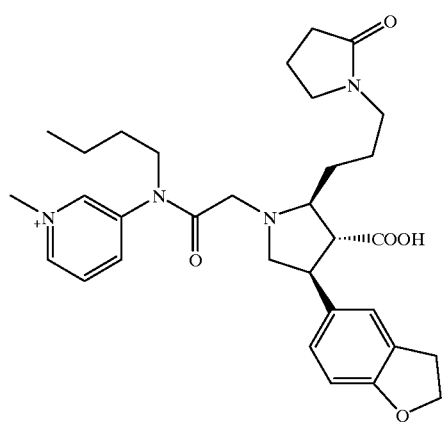
1600
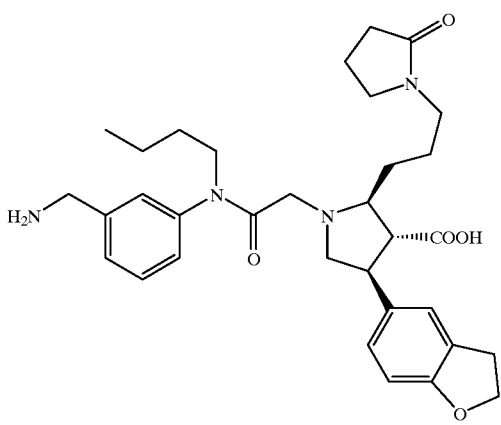

TABLE 3C-continued
1601
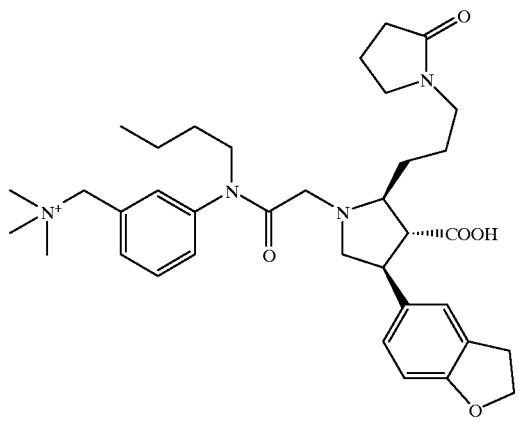
1602
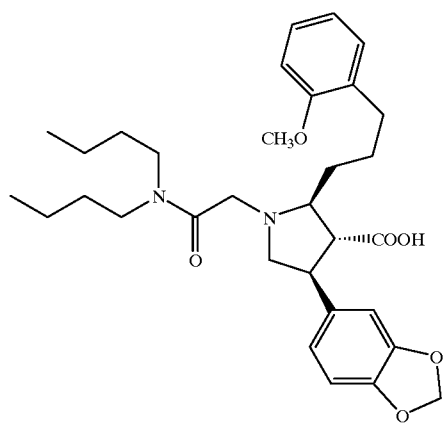
1603
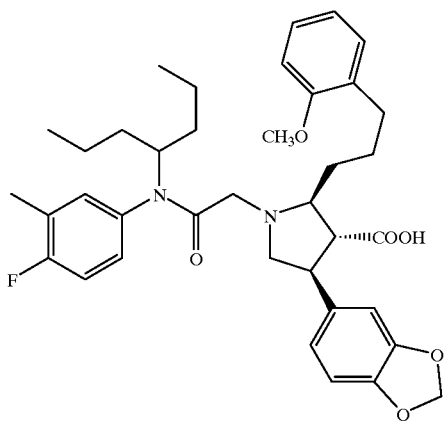

TABLE 3C-continued
1604
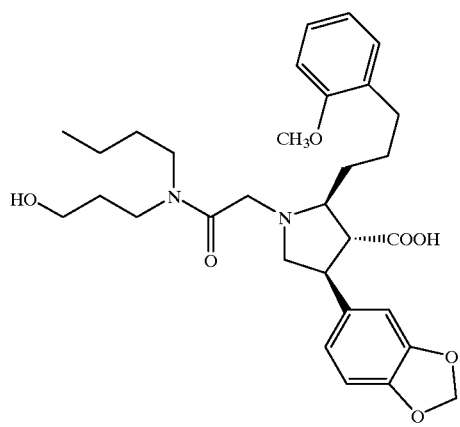
1605
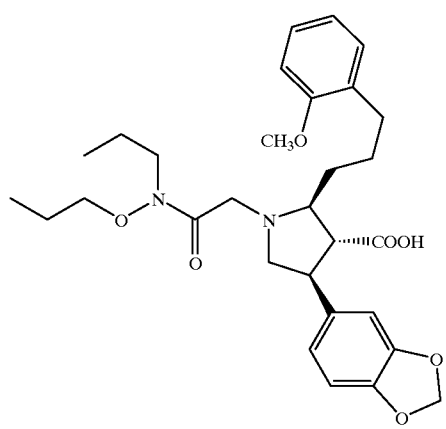
1606
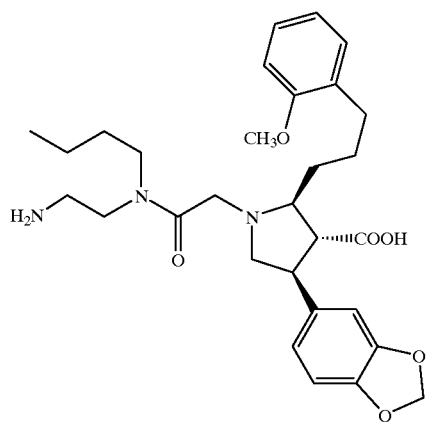

TABLE 3C-continued
1607
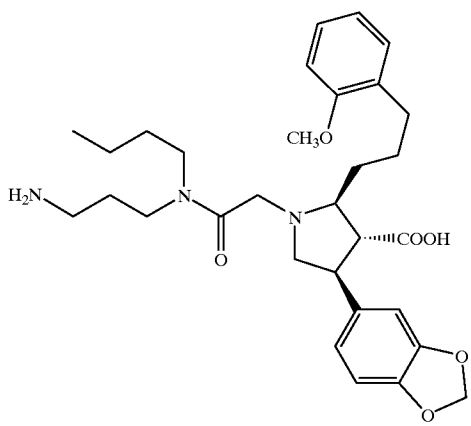
1608
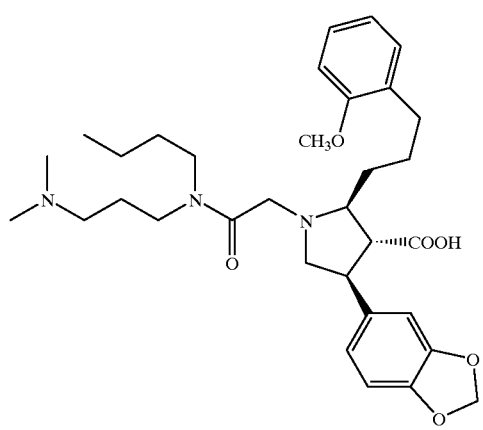
1609
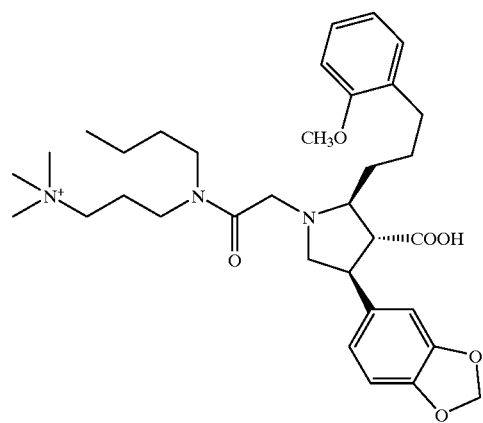

TABLE 3C-continued
1610
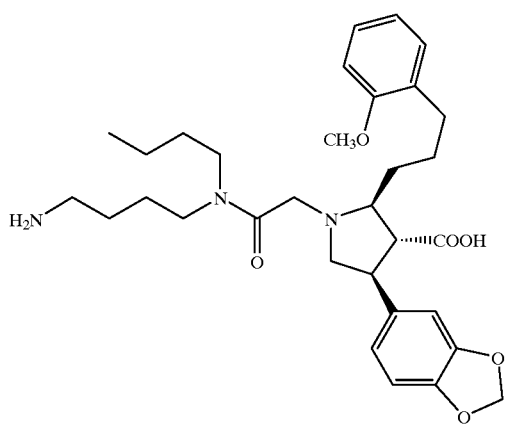
1611
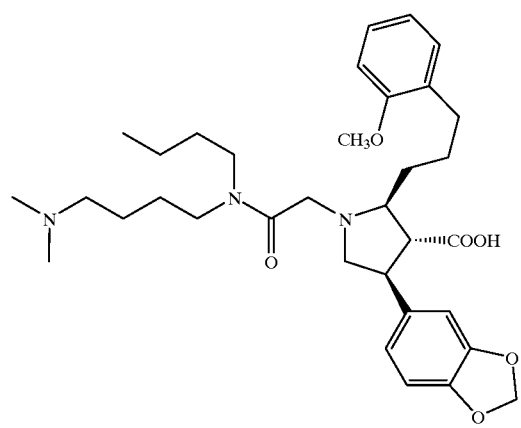
1612
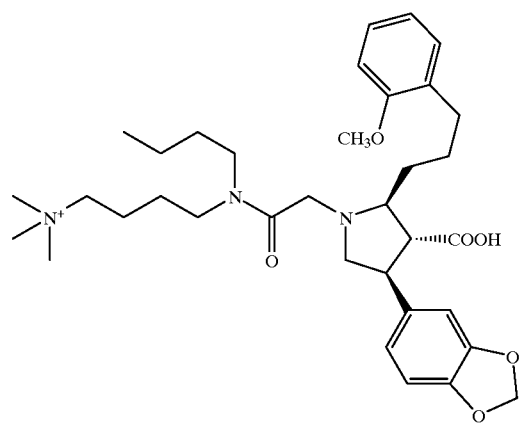

TABLE 3C-continued
1613
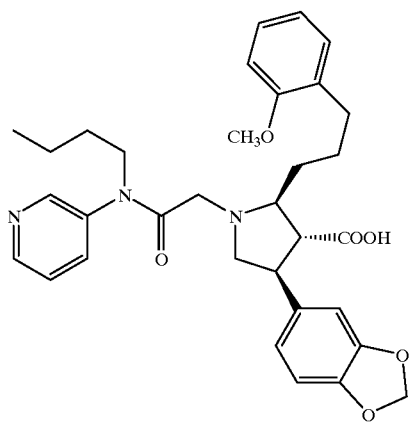
1614
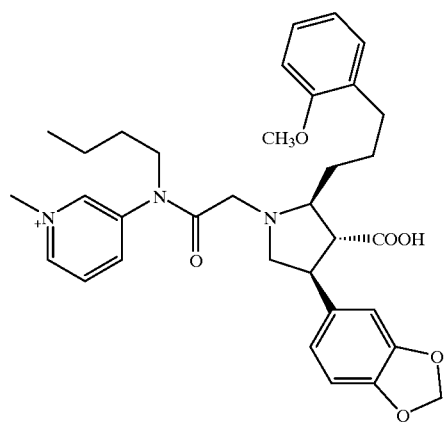
1615
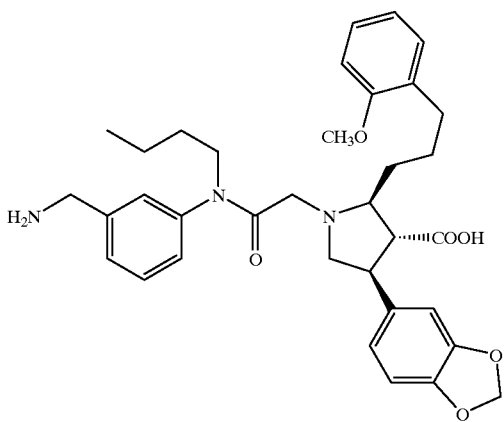

TABLE 3C-continued
1616
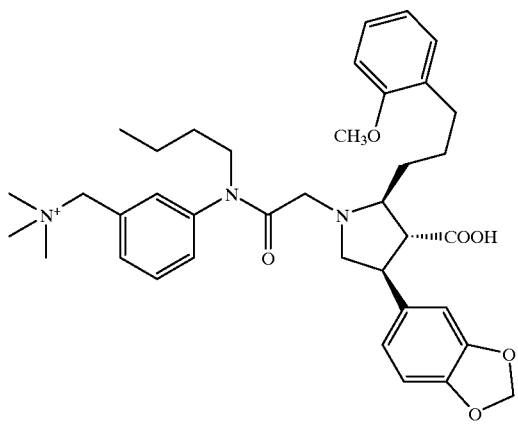
1617
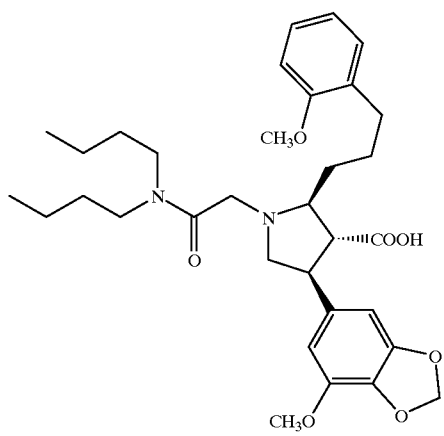
1618
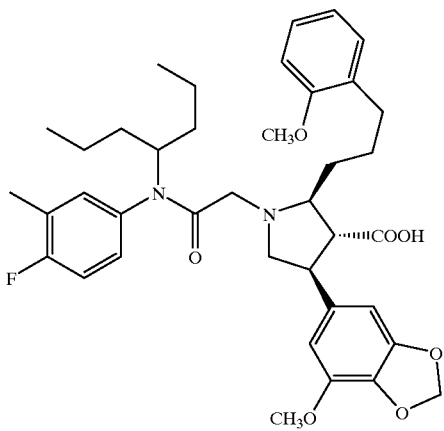

TABLE 3C-continued
1619
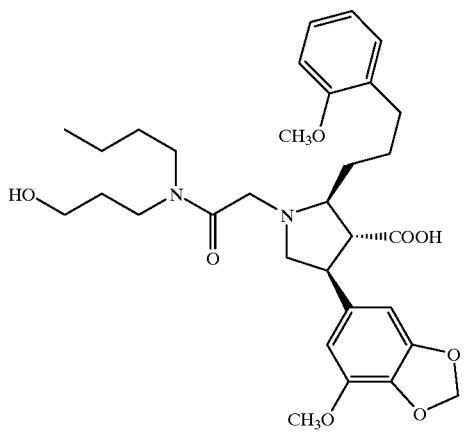
1620
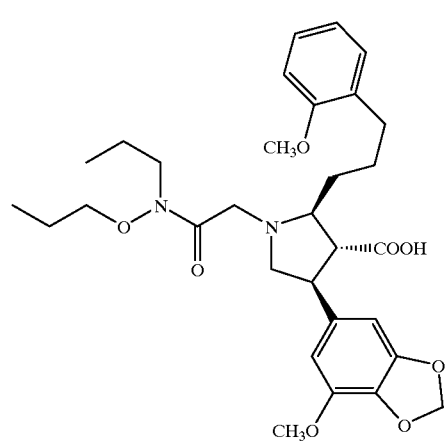
1621
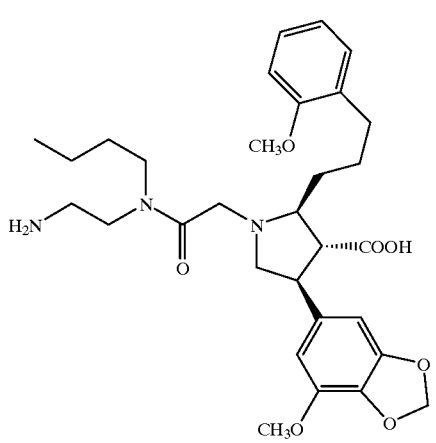

TABLE 3C-continued
1622
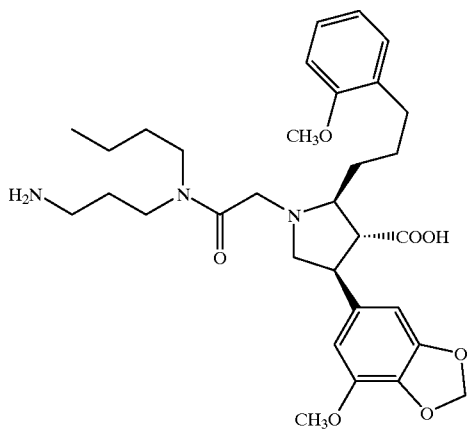
1623
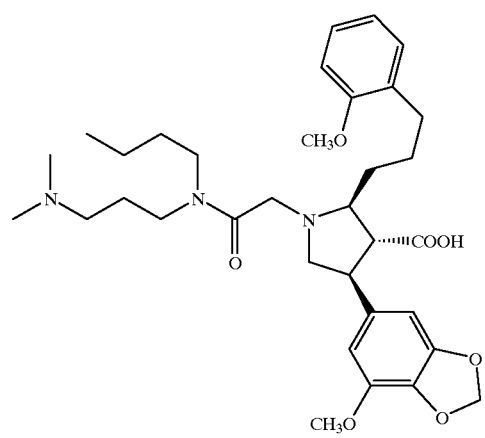
1624
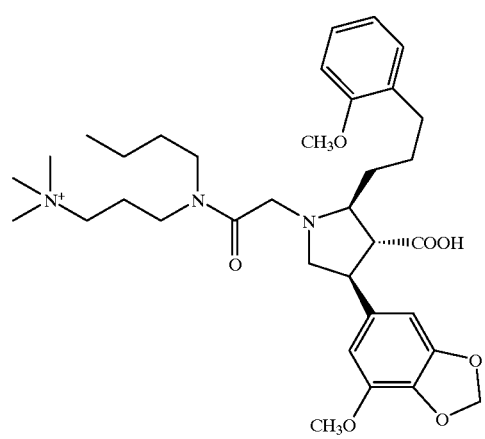

TABLE 3C-continued
1625
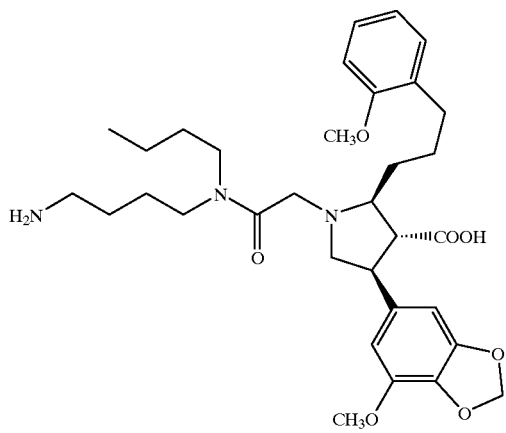
1626
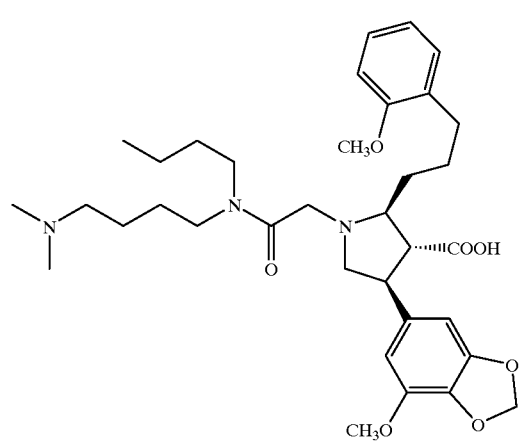
1627
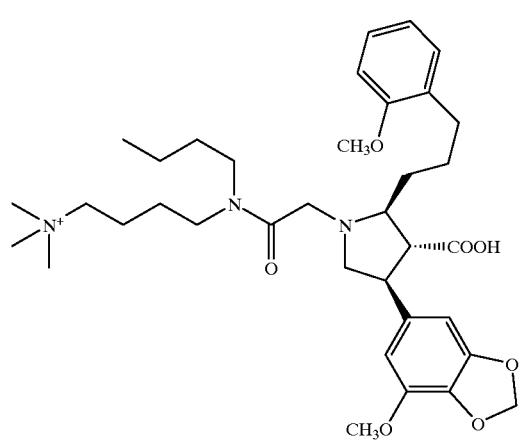

TABLE 3C-continued
1628
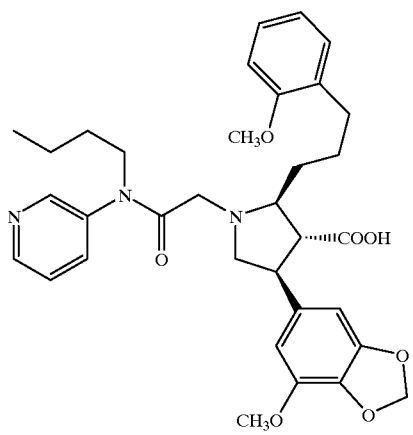
1629
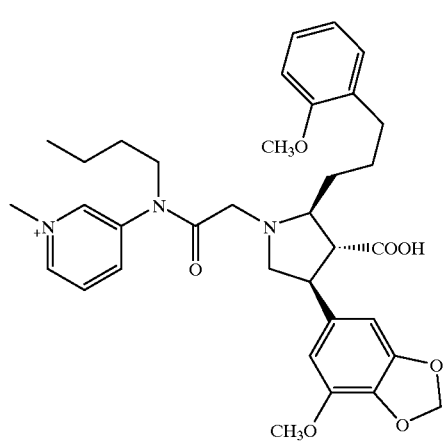
1630
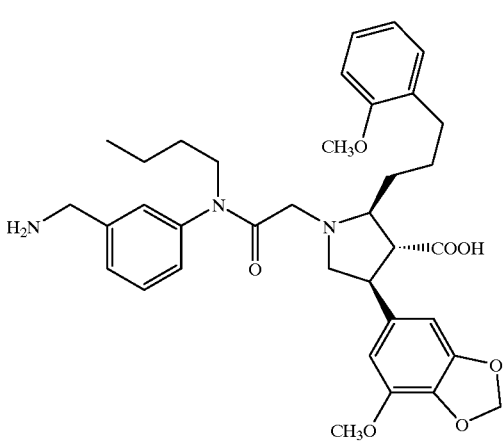

TABLE 3C-continued
1631
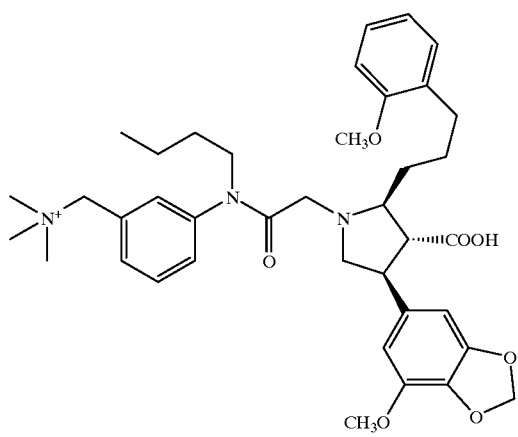
1632
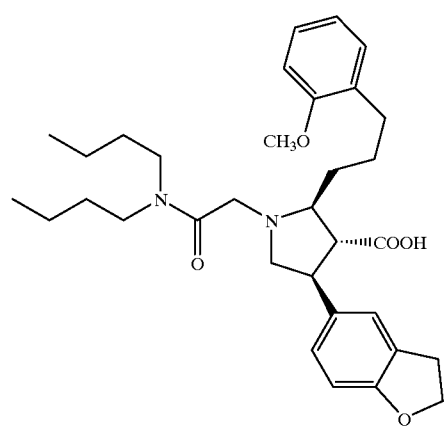
1633
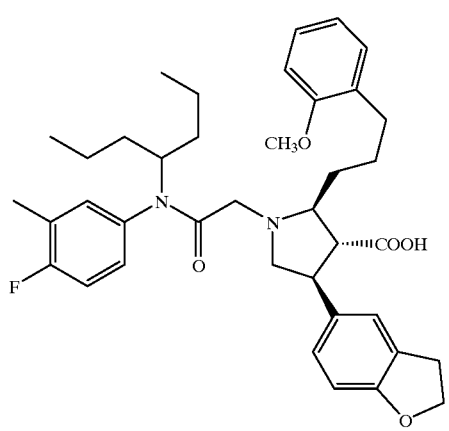

TABLE 3C-continued
1634
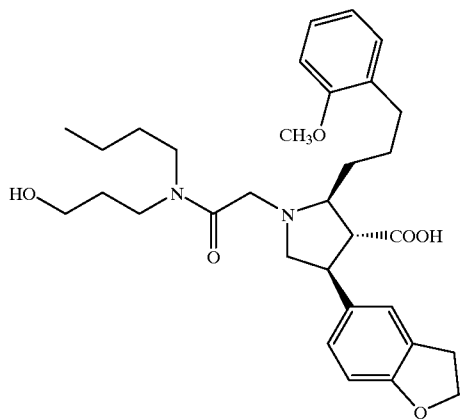
1635
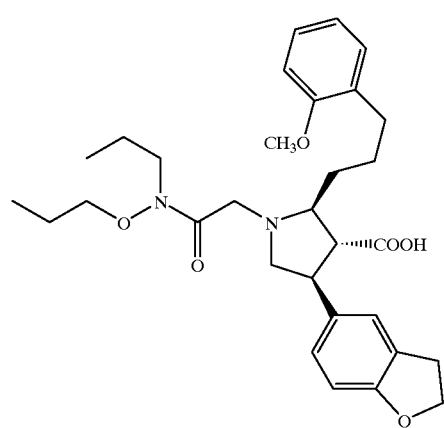
1636
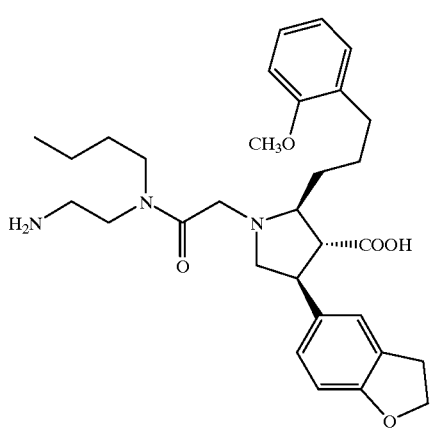

TABLE 3C-continued
1637
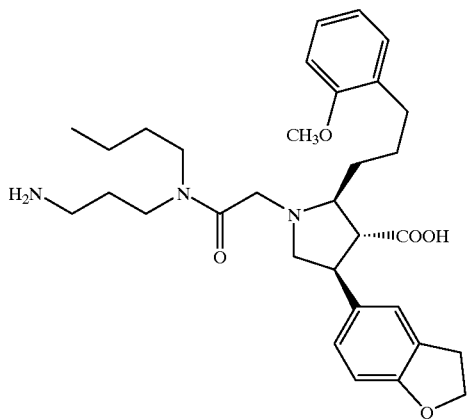
1638
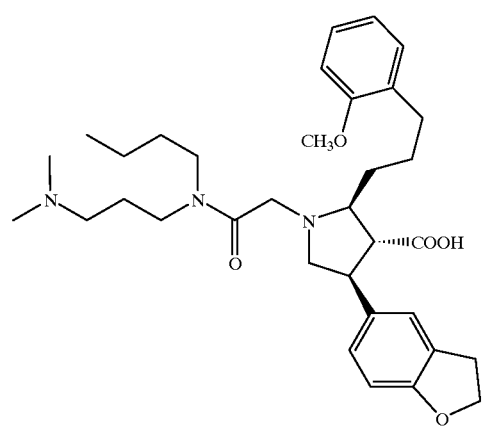
1639
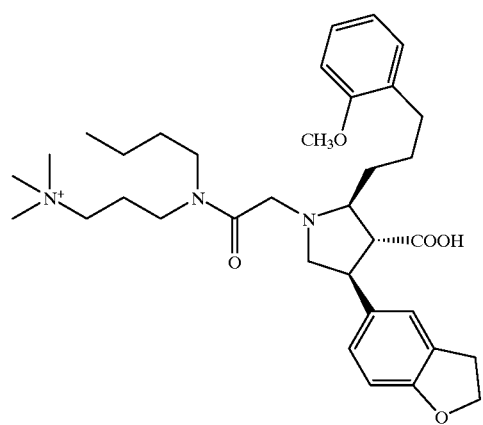

TABLE 3C-continued
1640
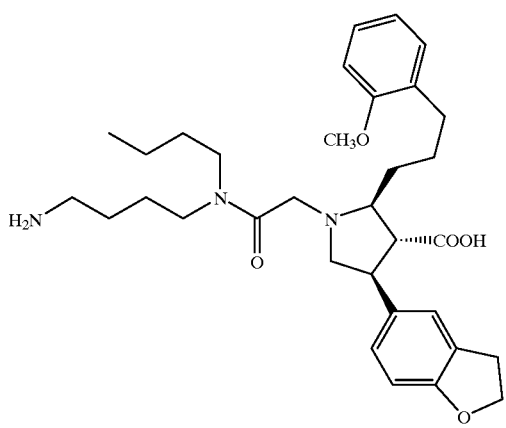
1641
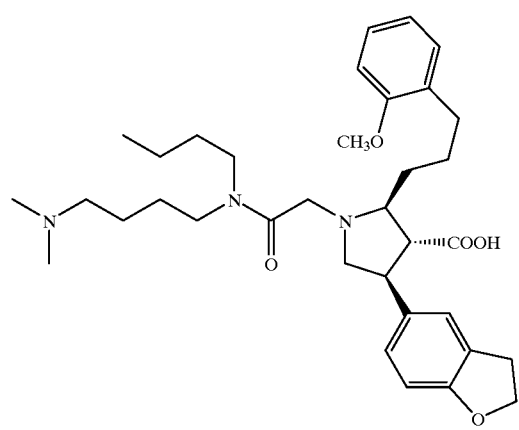
1642
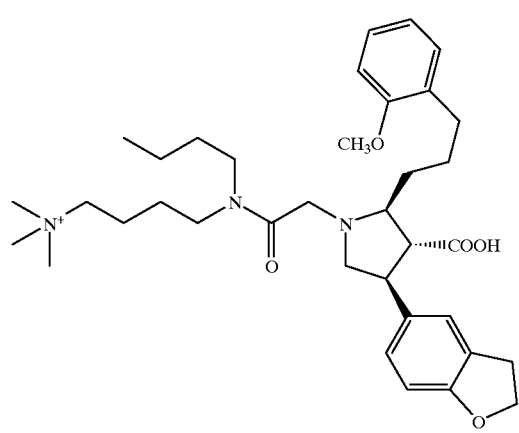

TABLE 3C-continued
1643
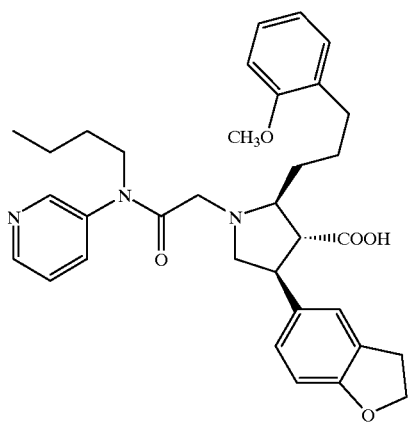
1644
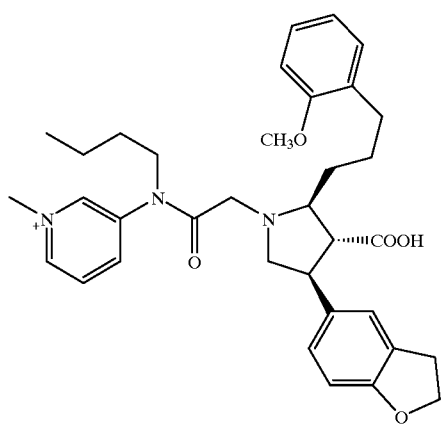
1645
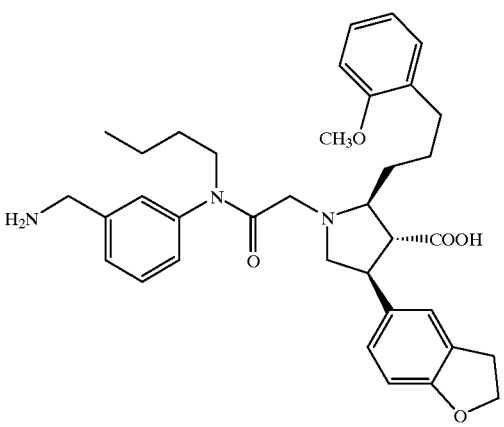

TABLE 3C-continued
1646
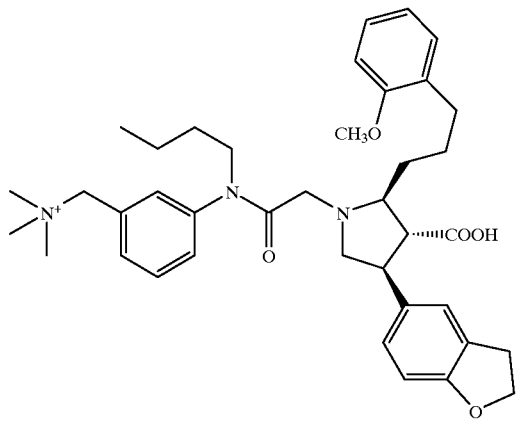
1647
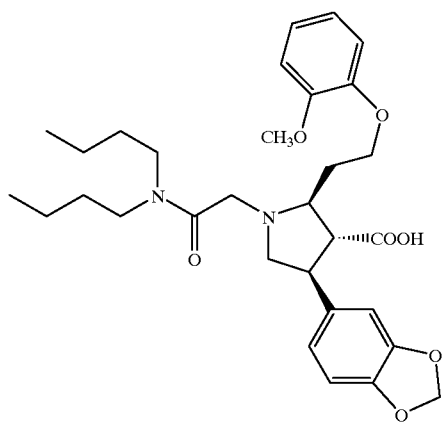
1648
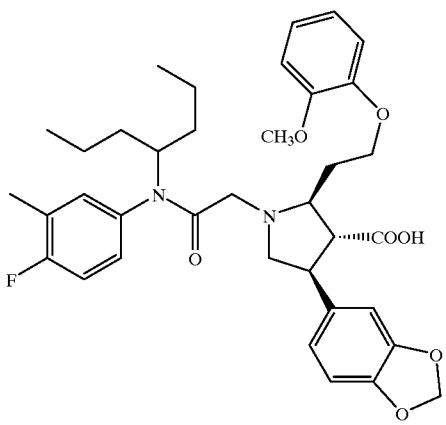

TABLE 3C-continued
1649
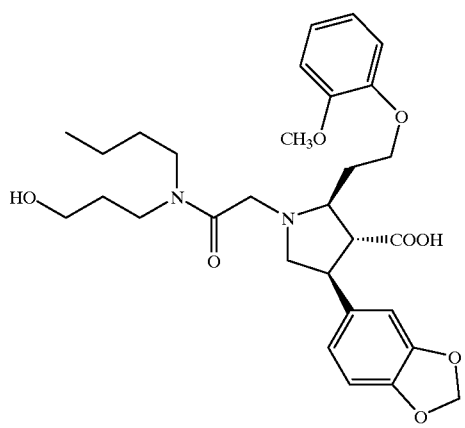
1650
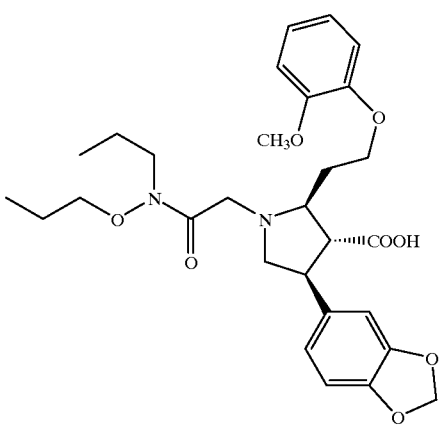
1651
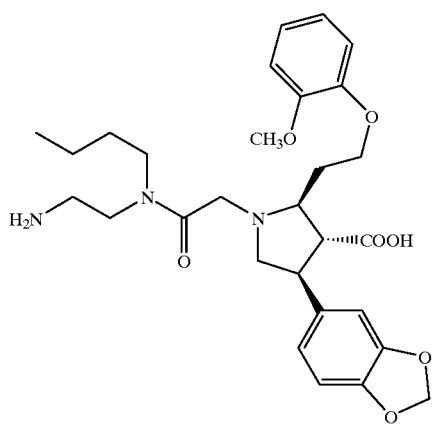

TABLE 3C-continued
1652
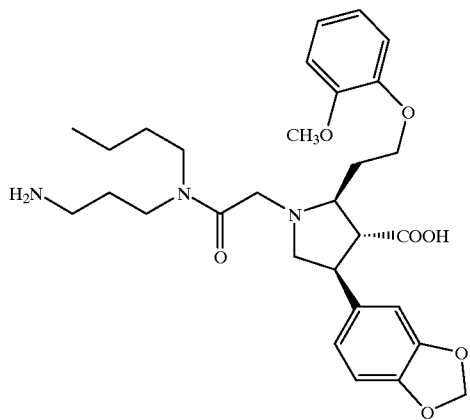
1653
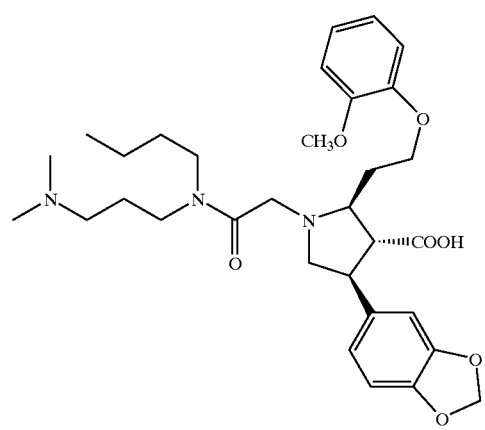
1654
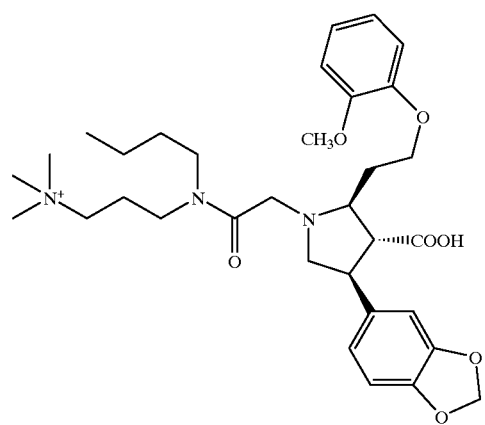

TABLE 3C-continued
1655
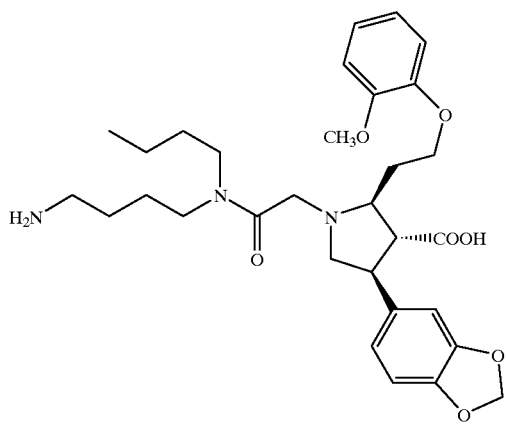
1656
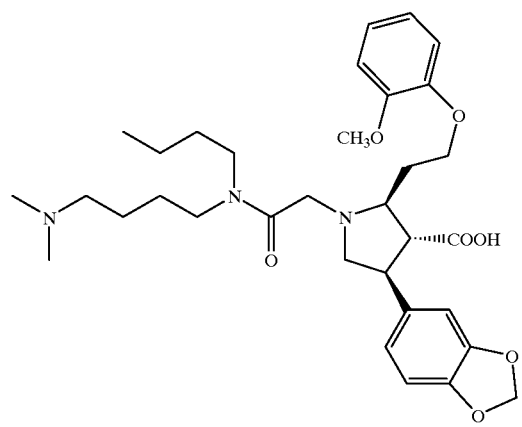
1657
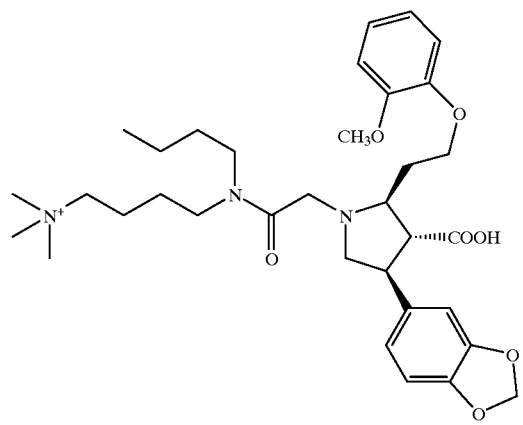

TABLE 3C-continued
1658
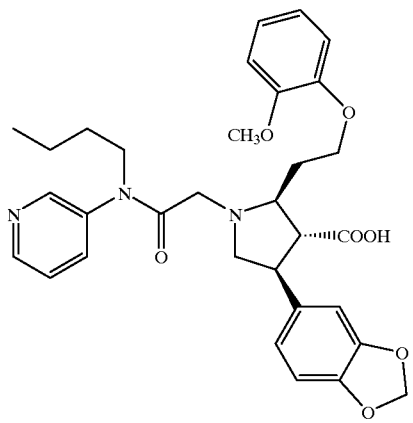
1659
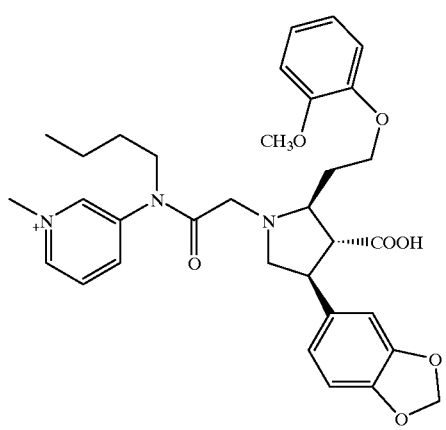
1660
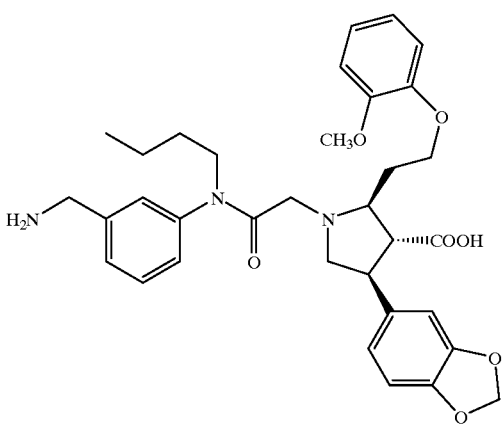

TABLE 3C-continued
1661
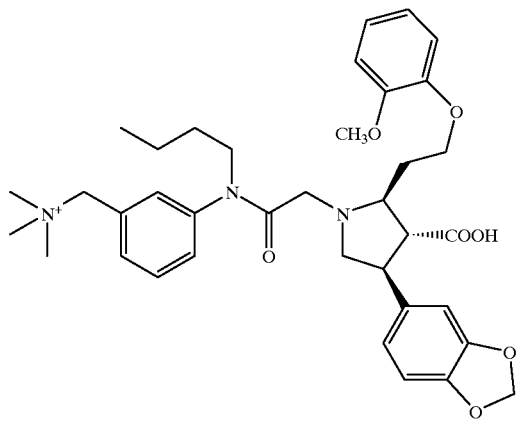
1662
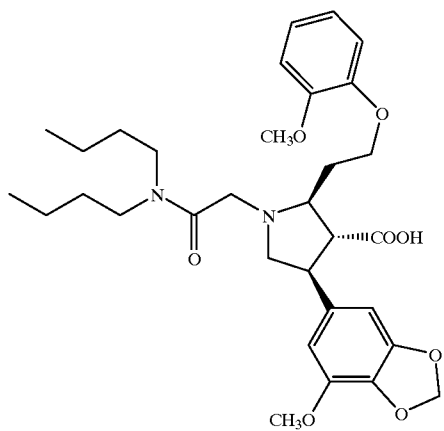
1663
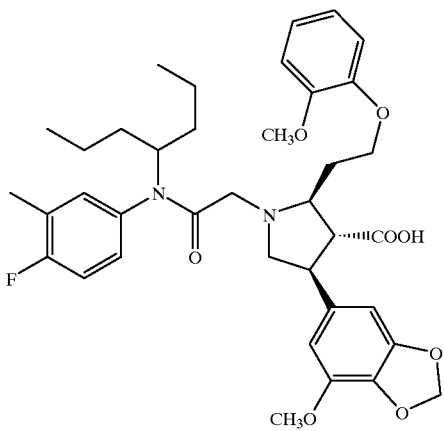

TABLE 3C-continued
1664
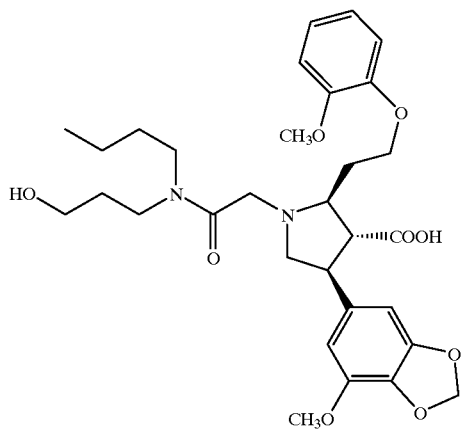
1665
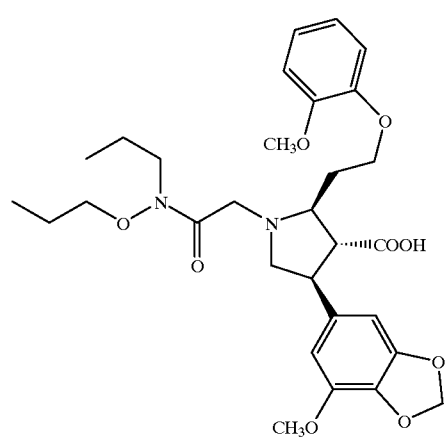
1666
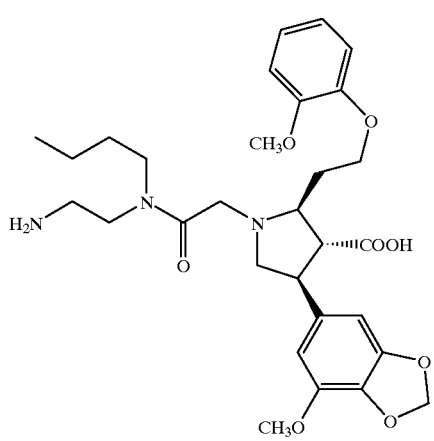

TABLE 3C-continued
1667
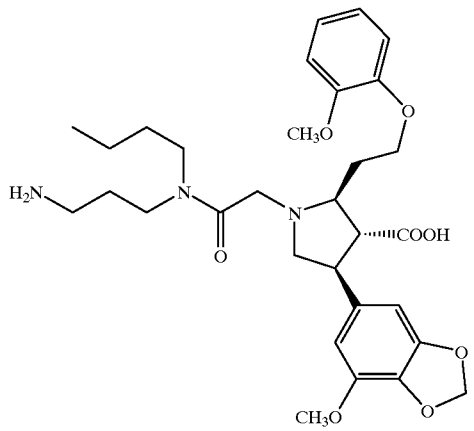
1668
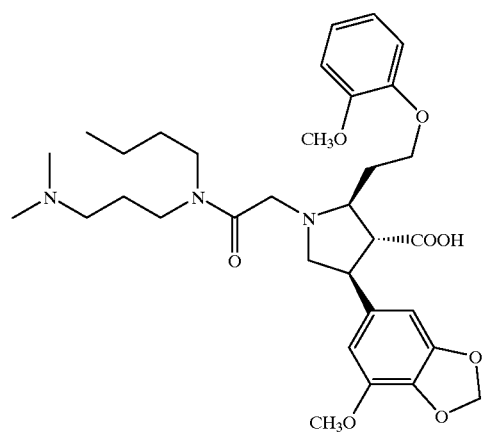
1669
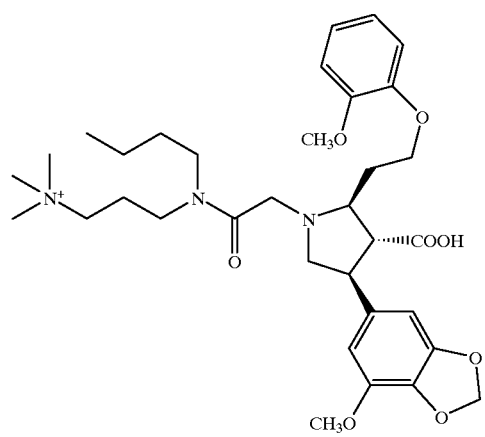

TABLE 3C-continued
1670
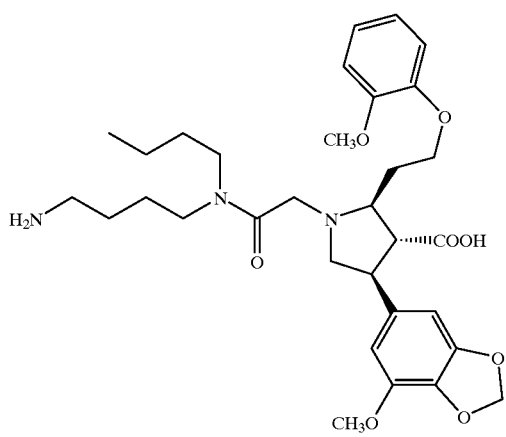
1671
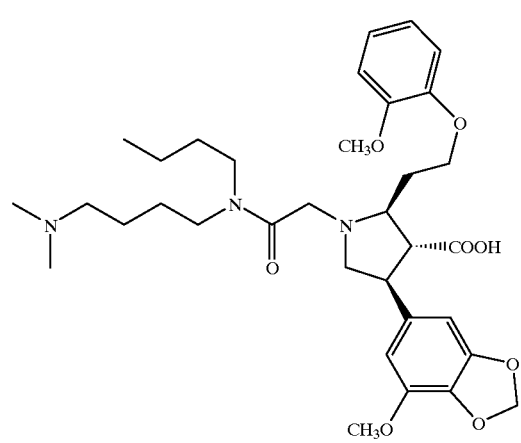
1672
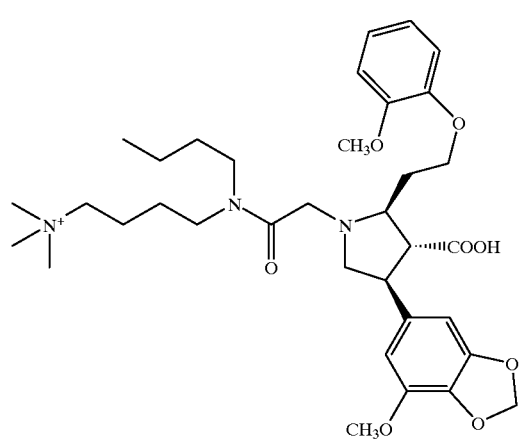

TABLE 3C-continued
1673
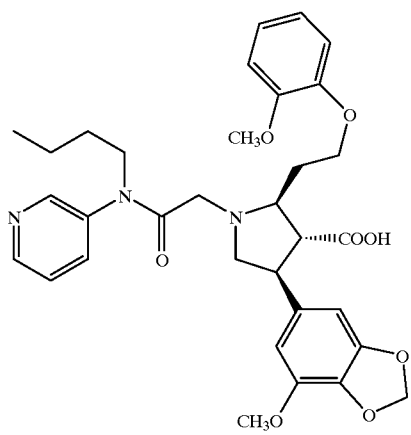
1674
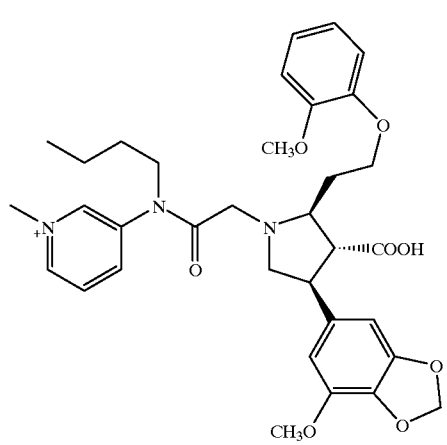
1675
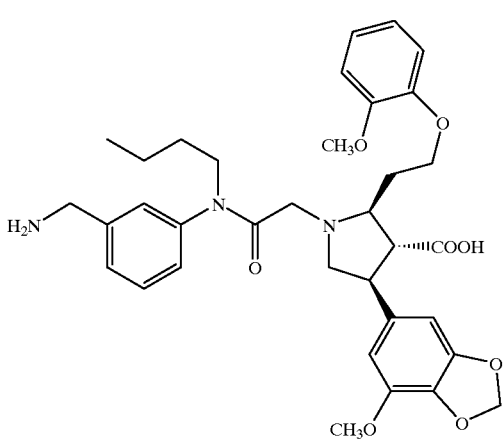

TABLE 3C-continued
1676
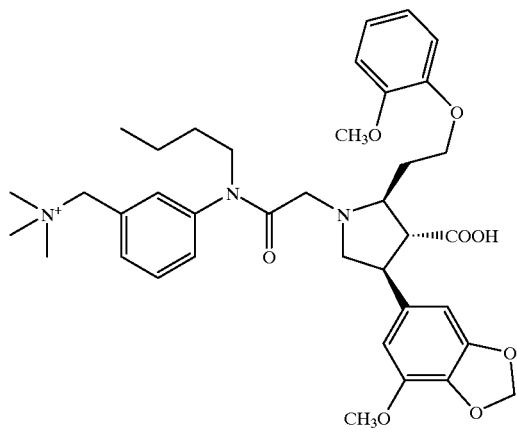
1677
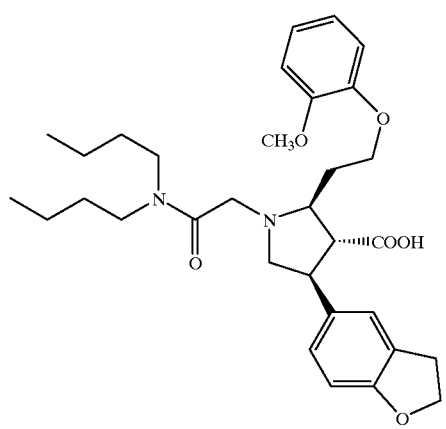
1678
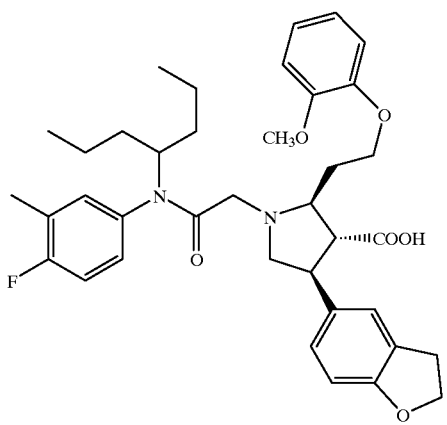

TABLE 3C-continued
1679
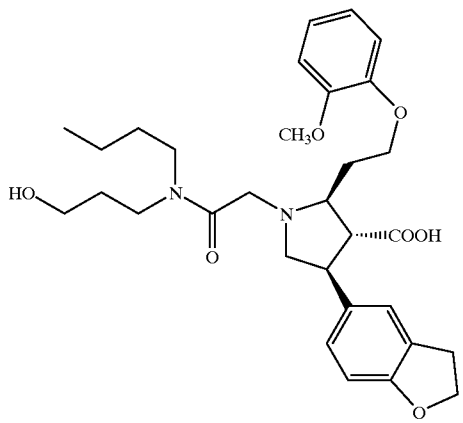
1680
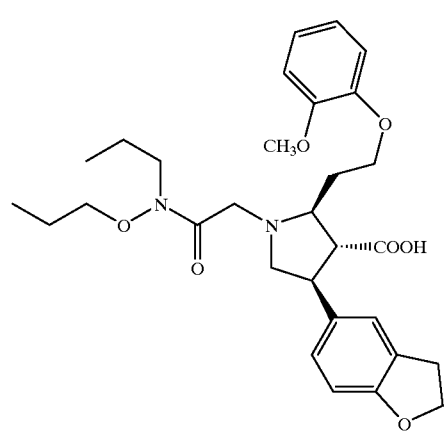
1681
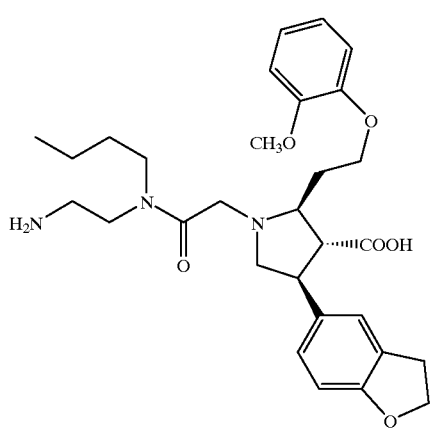

TABLE 3C-continued
1682
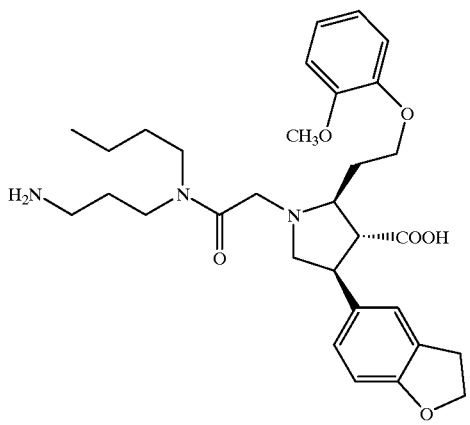
1683
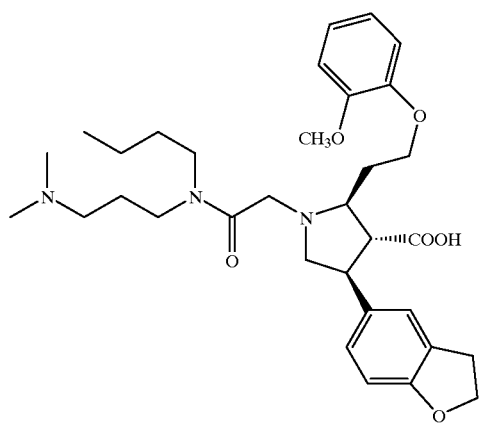
1684
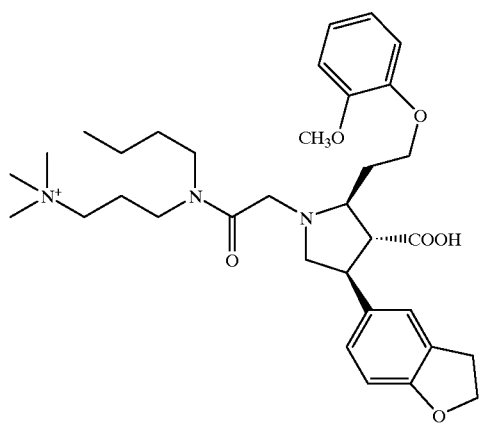

TABLE 3C-continued
1685
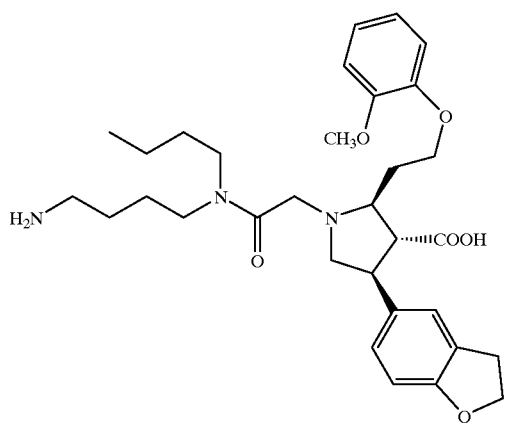
1686
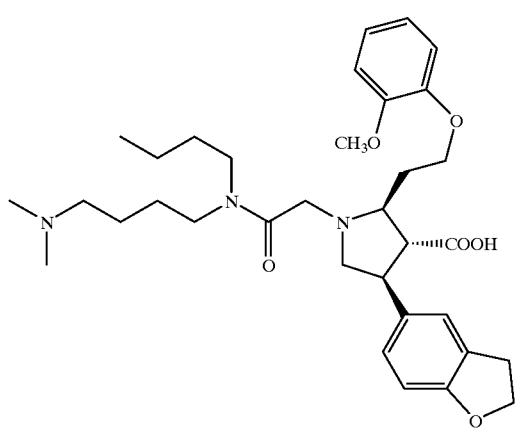
1687
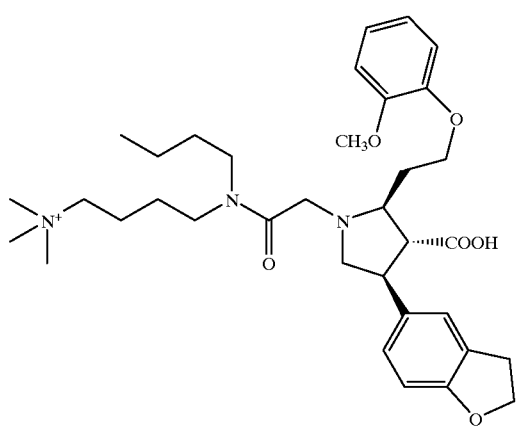

TABLE 3C-continued
1688
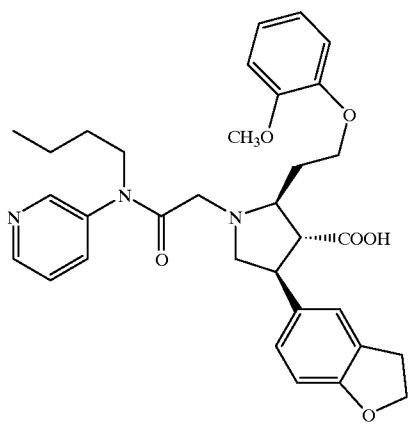
1689
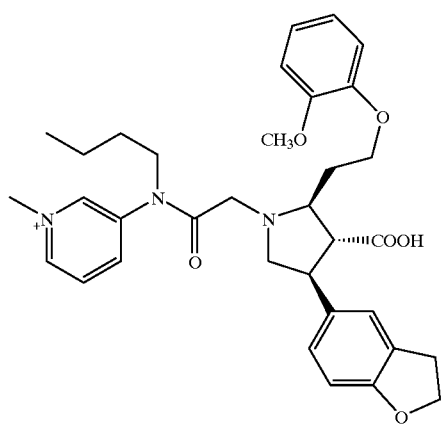
1690
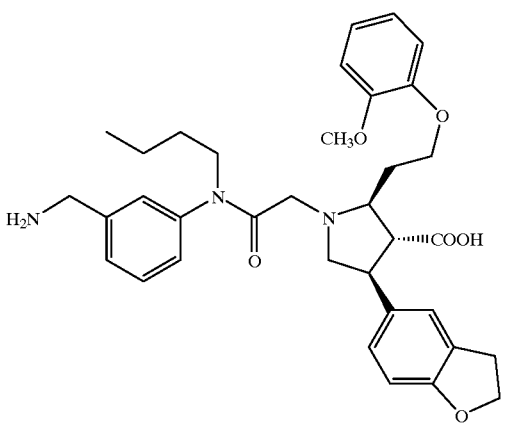

TABLE 3C-continued
1691
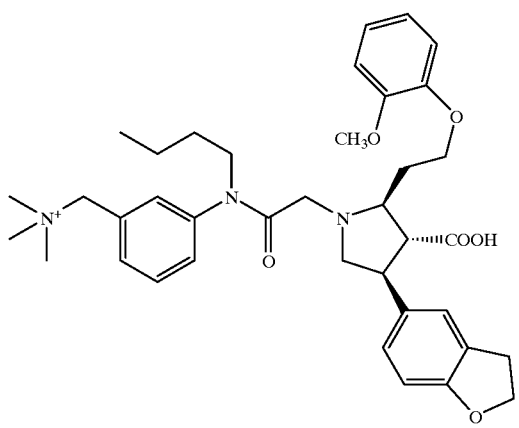
1692
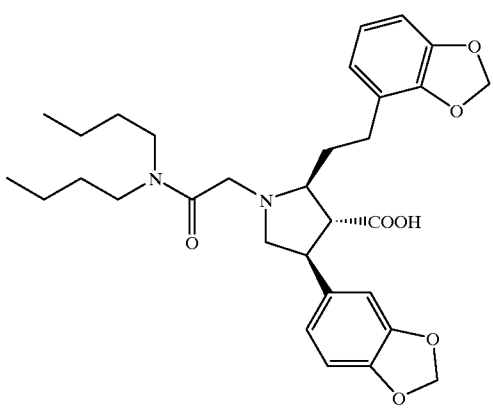
1693
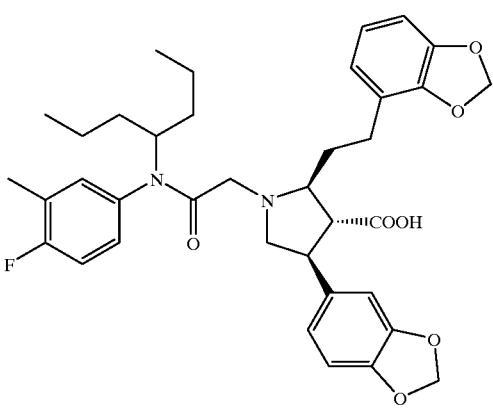

TABLE 3C-continued
1694
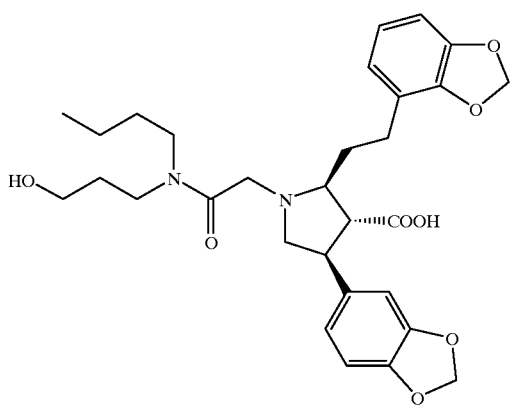
1695
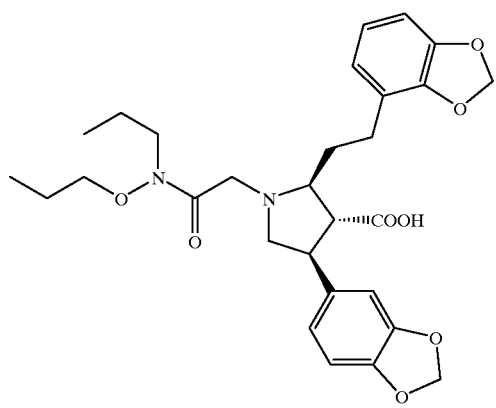
1696
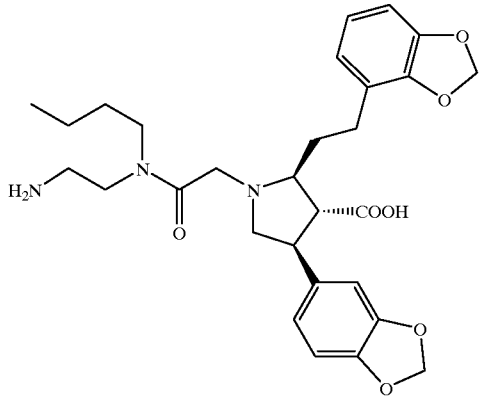

TABLE 3C-continued
1697
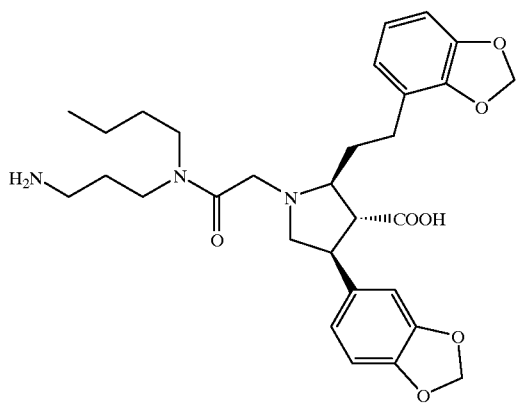
1698
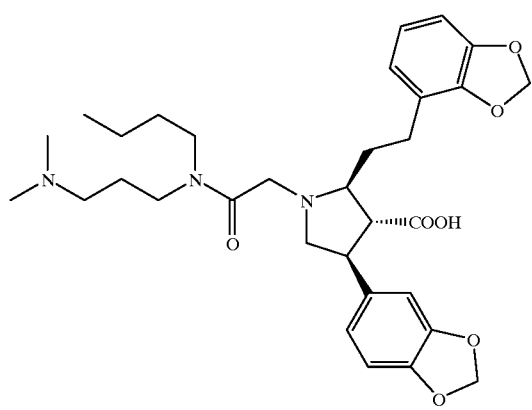
1699
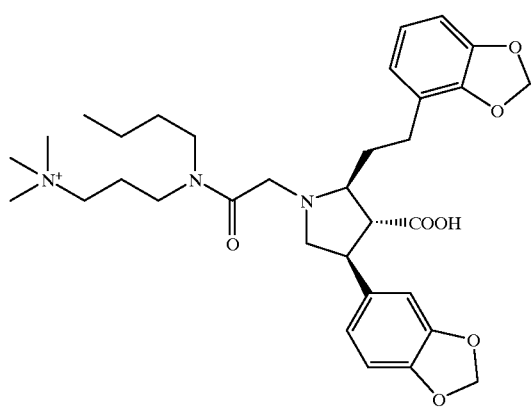

TABLE 3C-continued
1700
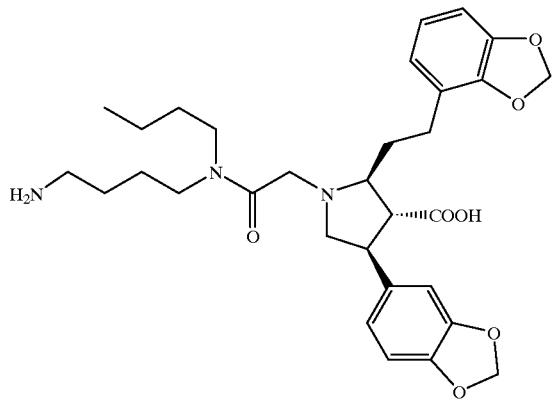
1701
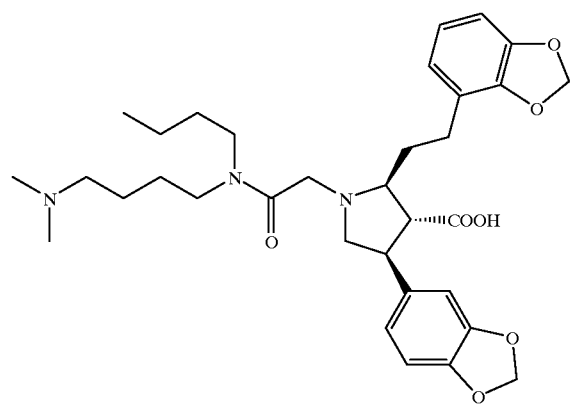
1702
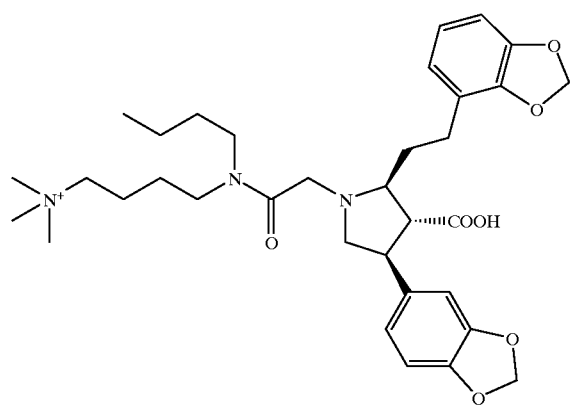

TABLE 3C-continued
1703
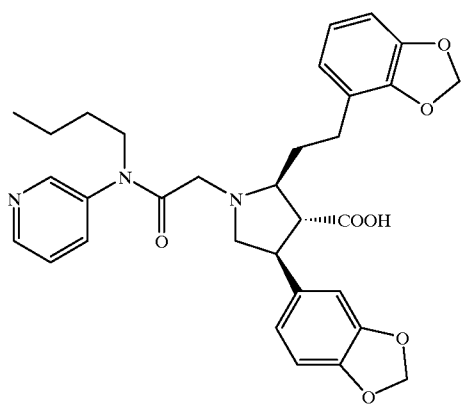
1704
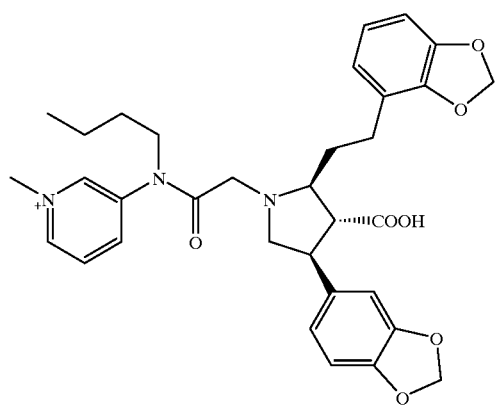
1705
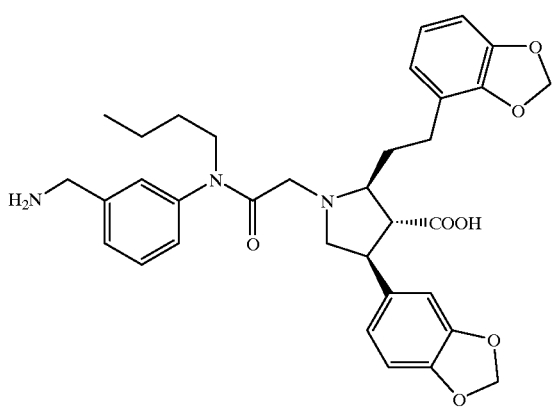

TABLE 3C-continued
1706
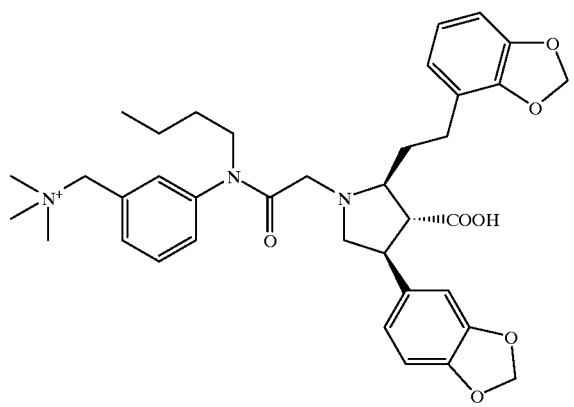
1707
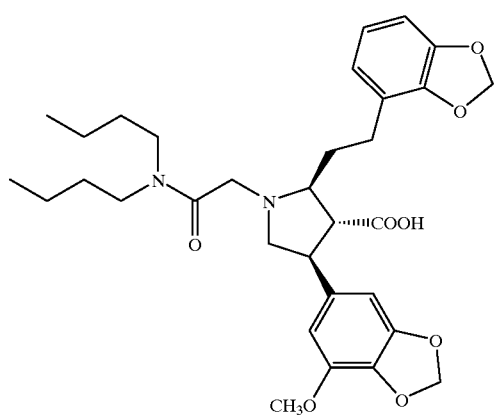
1708
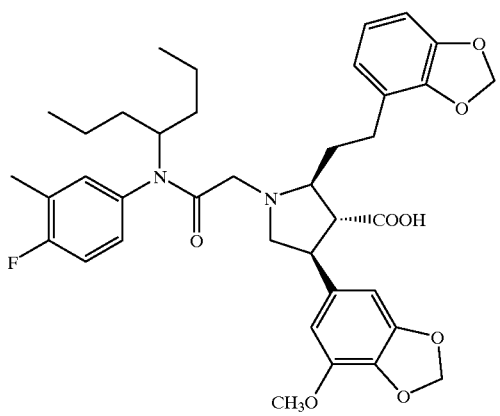

TABLE 3C-continued
1709
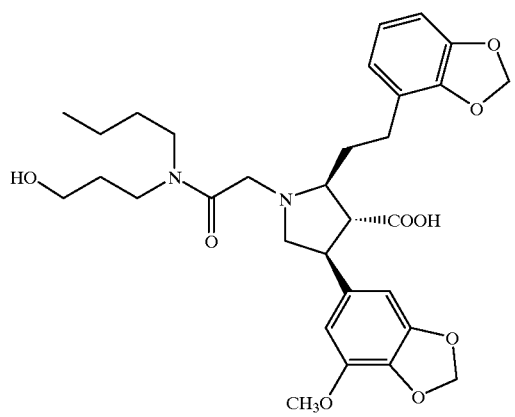
1710
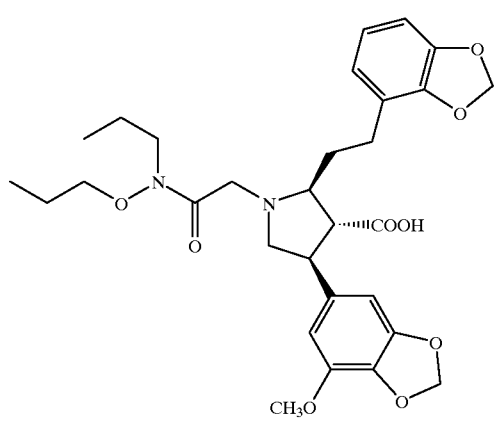
1711
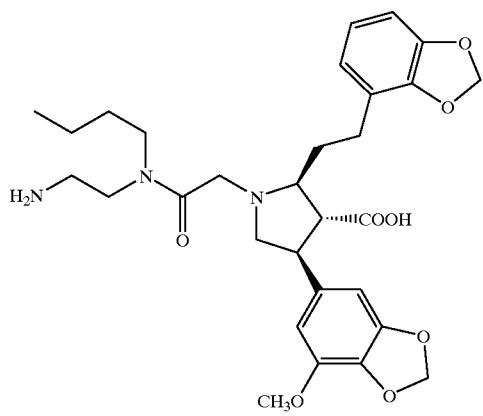

TABLE 3C-continued
1712
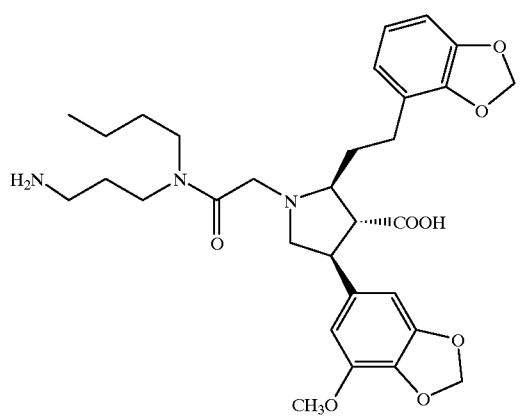
1713
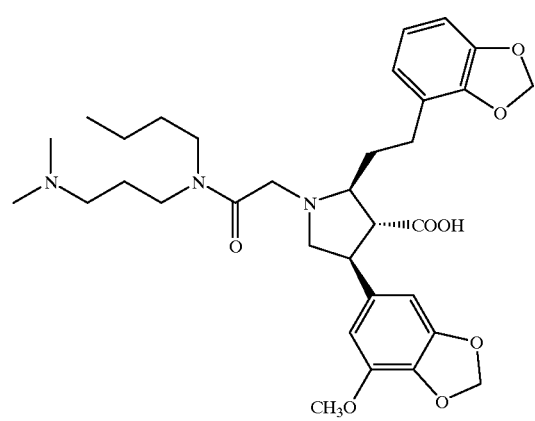
1714
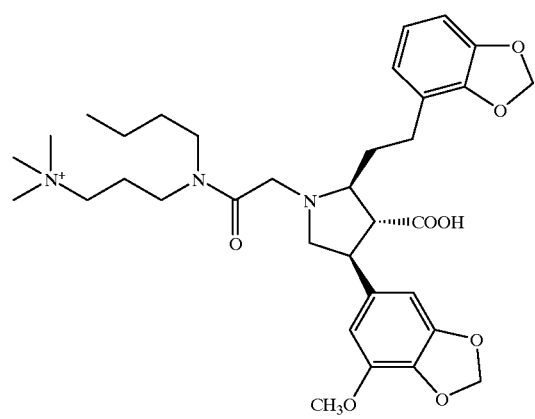

TABLE 3C-continued
1715
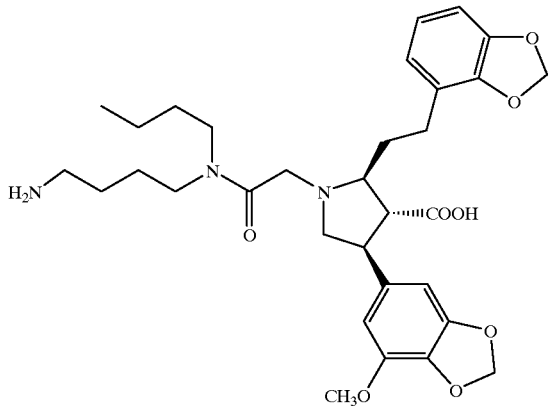
1716
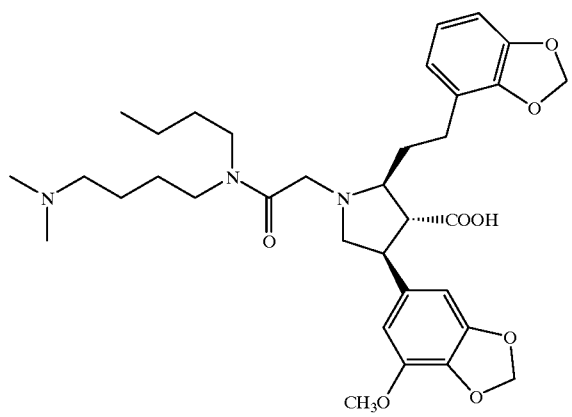
1717
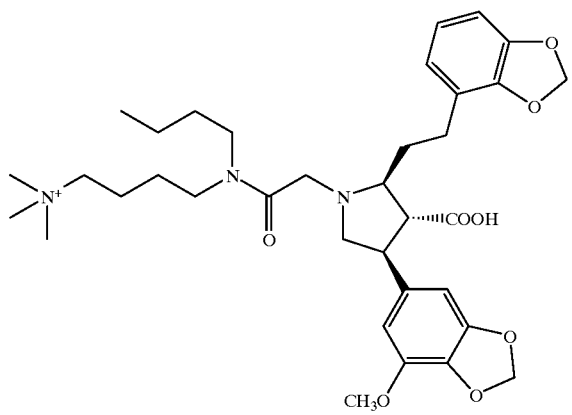

TABLE 3C-continued
1718
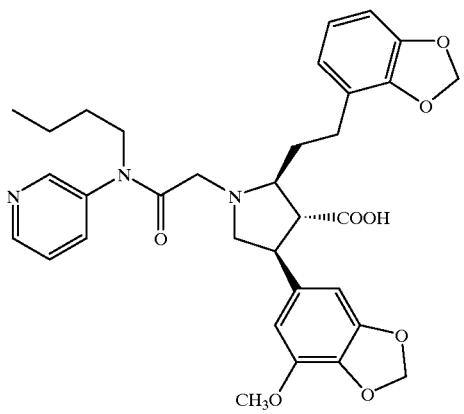
1719
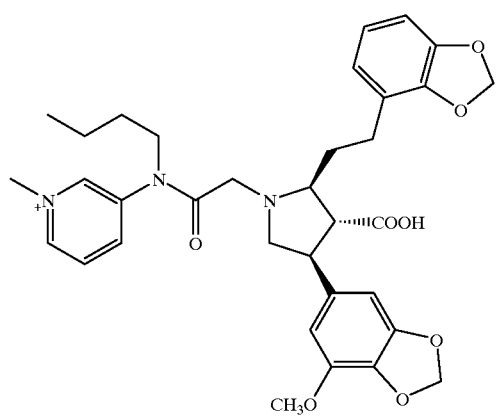
1720
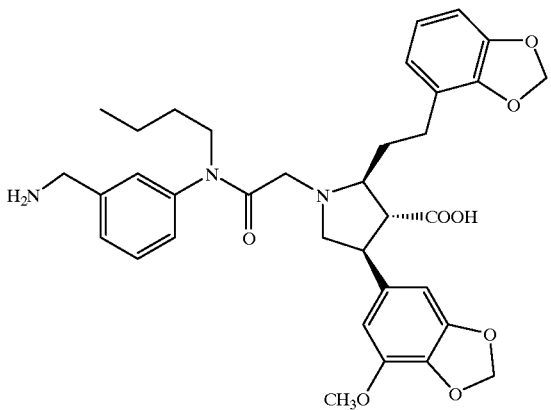

TABLE 3C-continued
1721
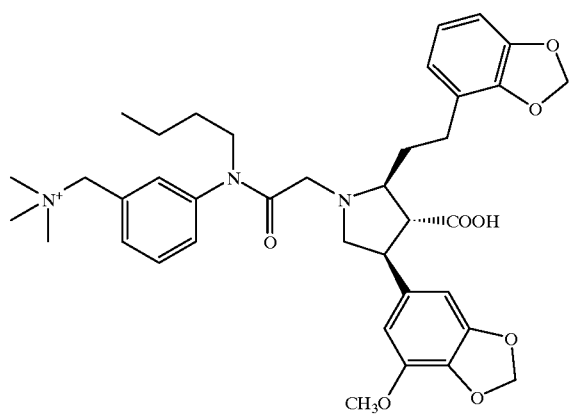
1722
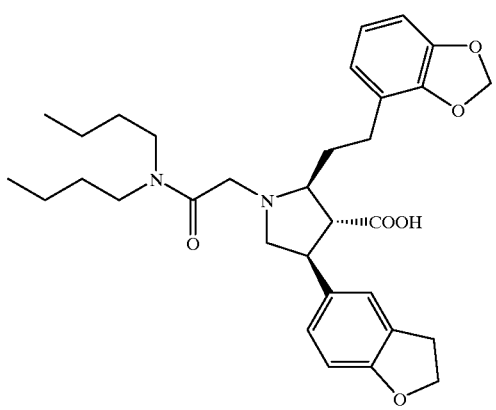
1723
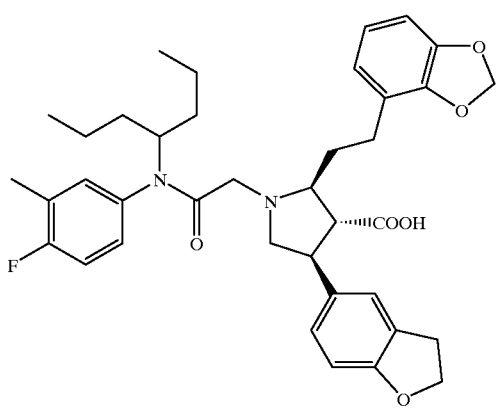

TABLE 3C-continued
1724
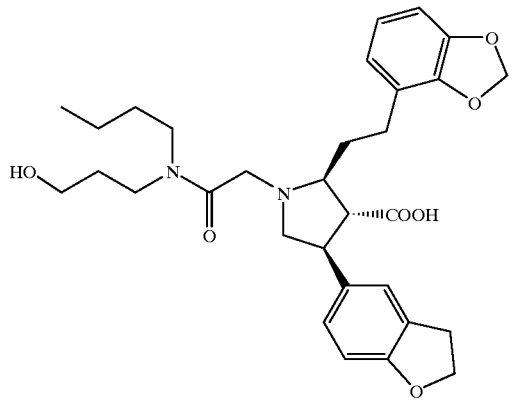
1725
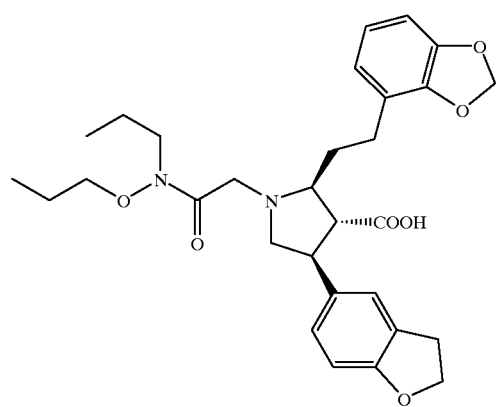
1726
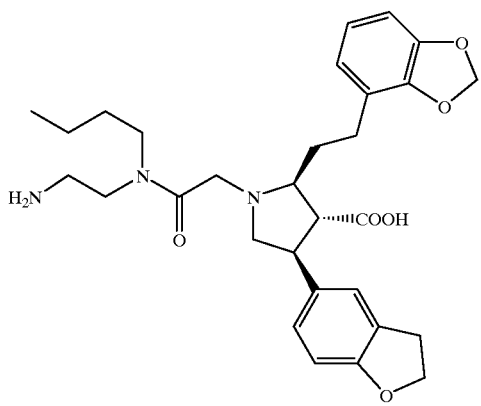

TABLE 3C-continued
1727
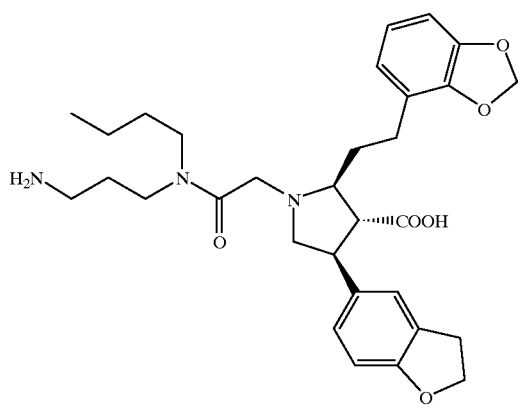
1728
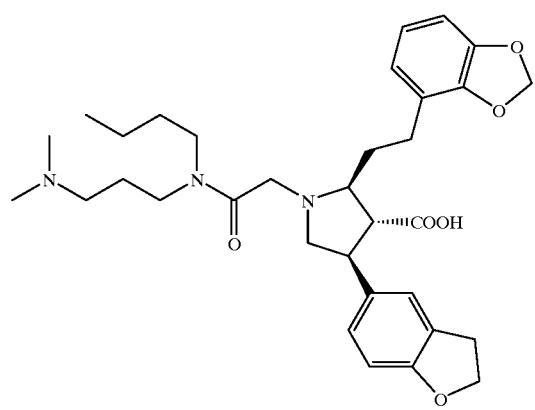
1729
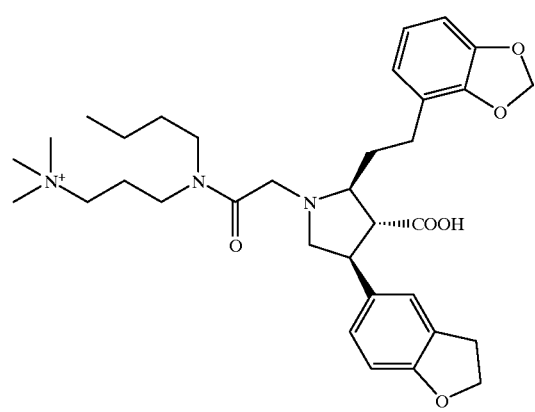

TABLE 3C-continued
1730
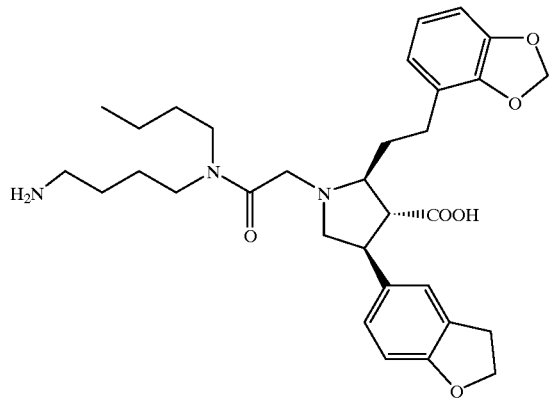
1731
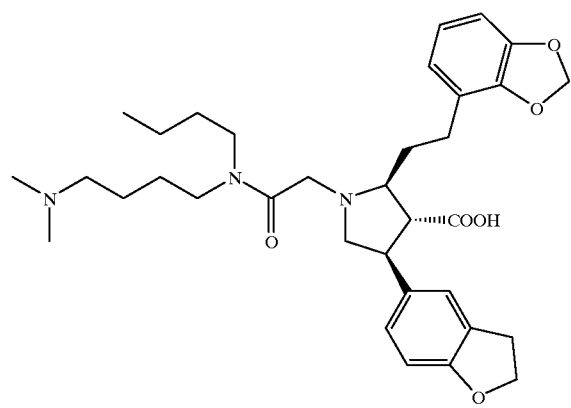
1732
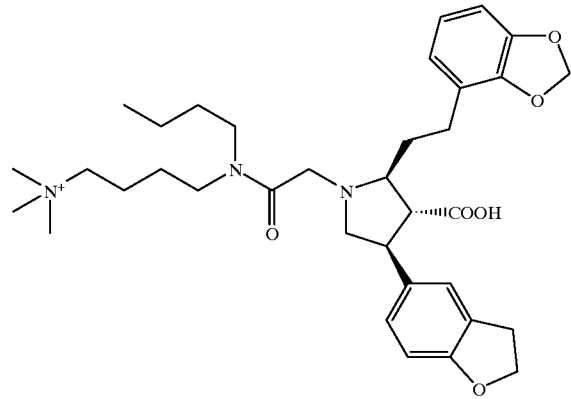

TABLE 3C-continued
1733
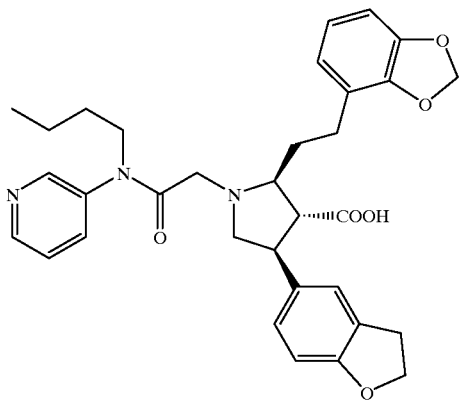
1734
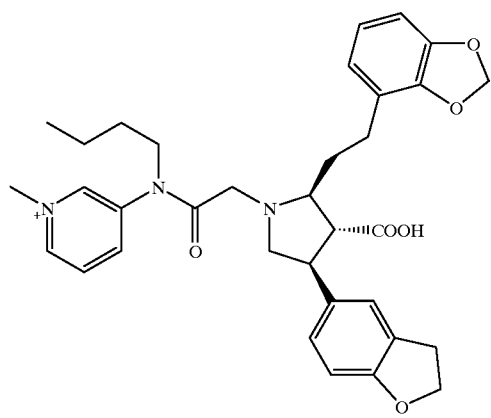
1735
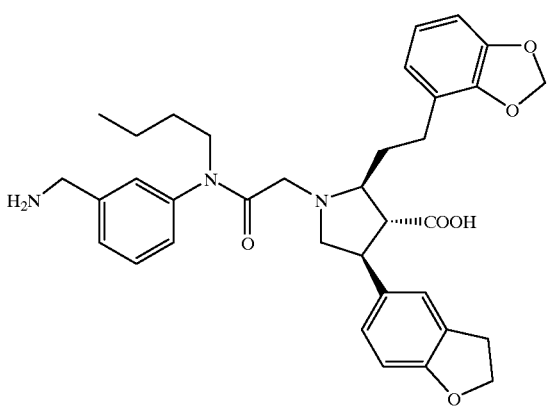

TABLE 3C-continued
1736
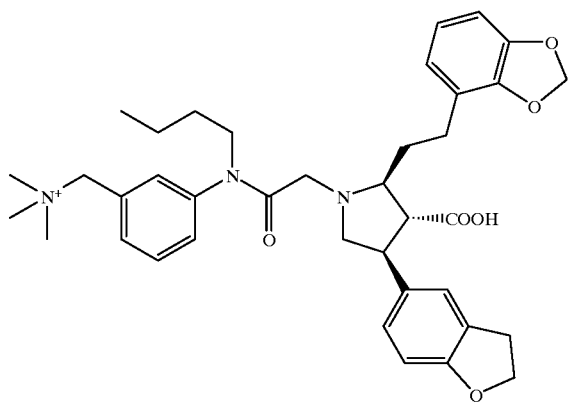
1737
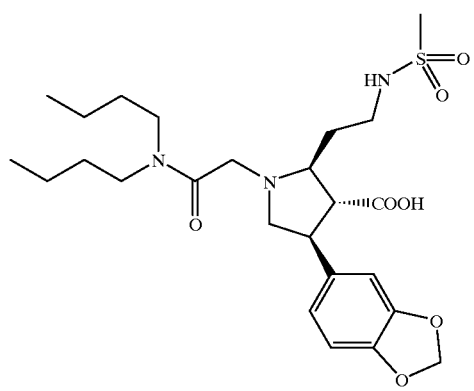
1738
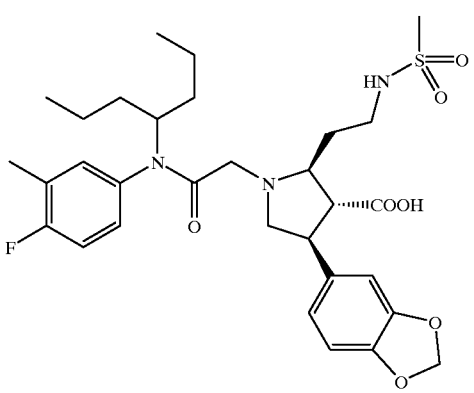
1739
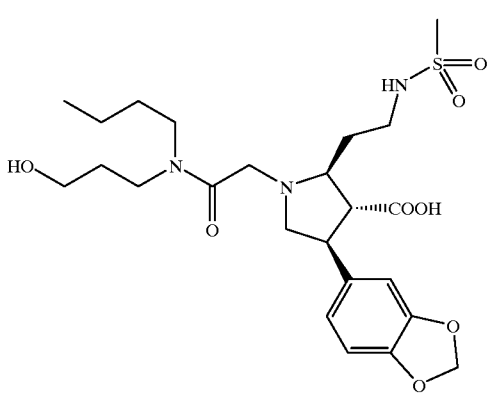

TABLE 3C-continued
1740
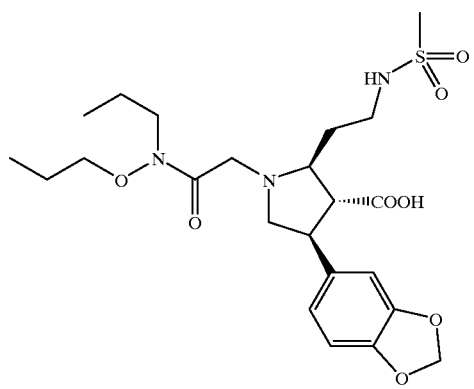
1741
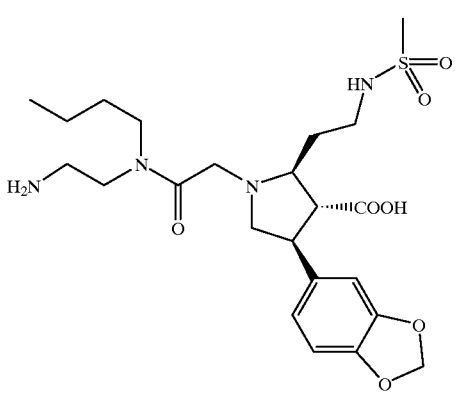
1742
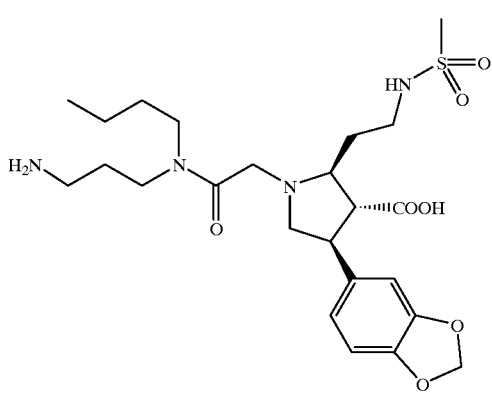
1743
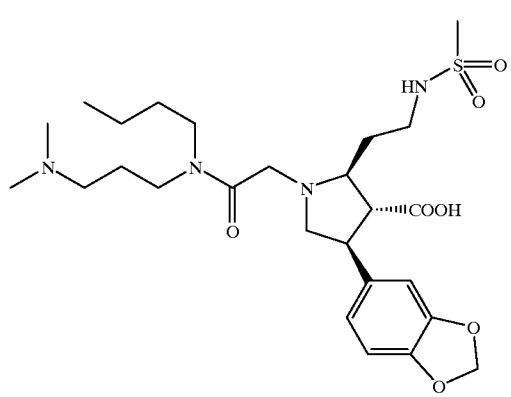

TABLE 3C-continued
1744
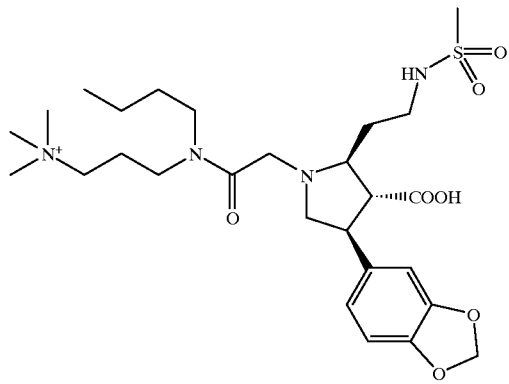
1745
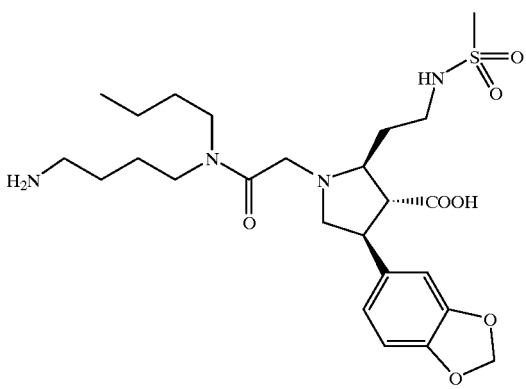
1746
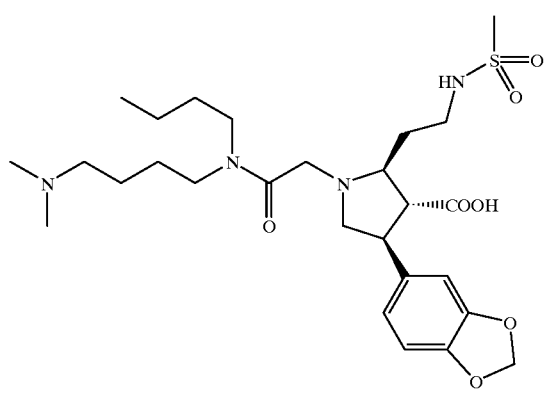
1747
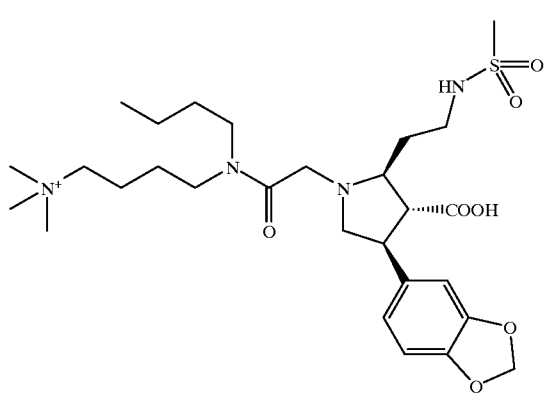

TABLE 3C-continued
1748
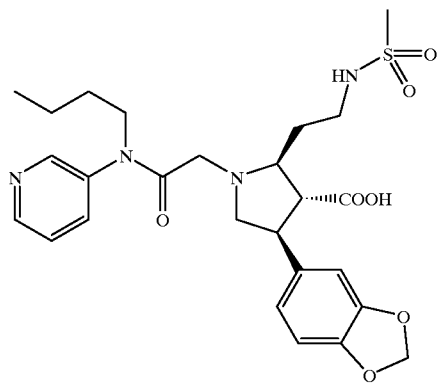
1749
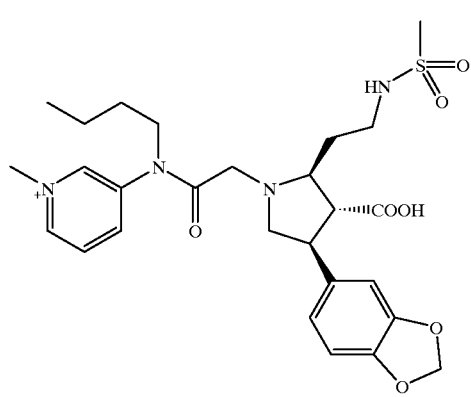
1750
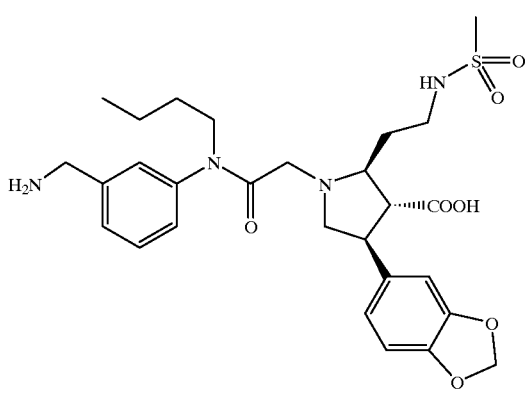
1751
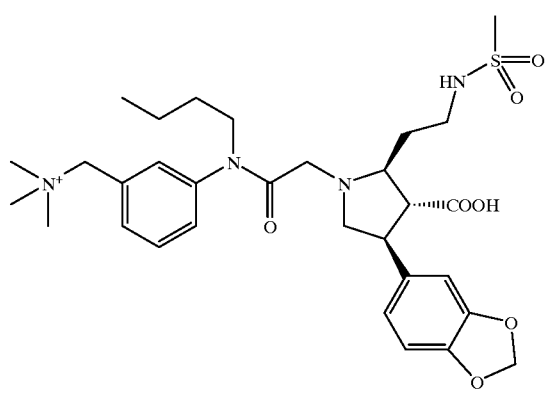

TABLE 3C-continued
1752 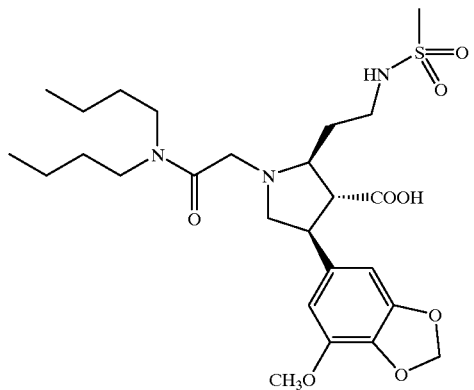
1753 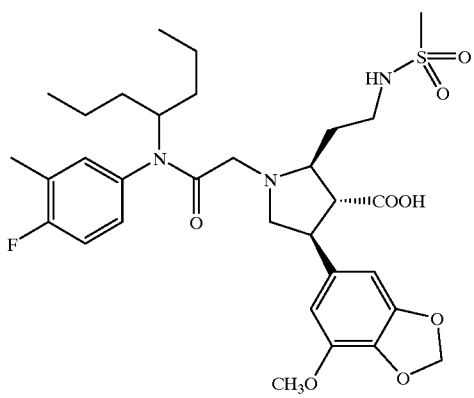
1754 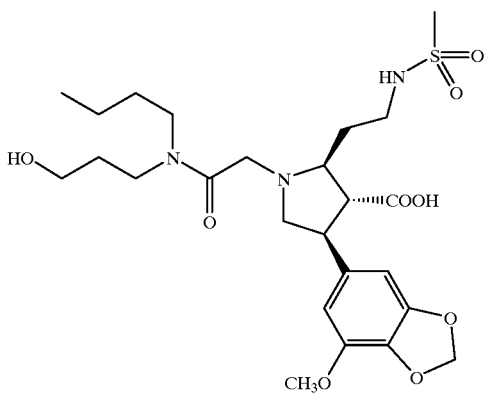
1755 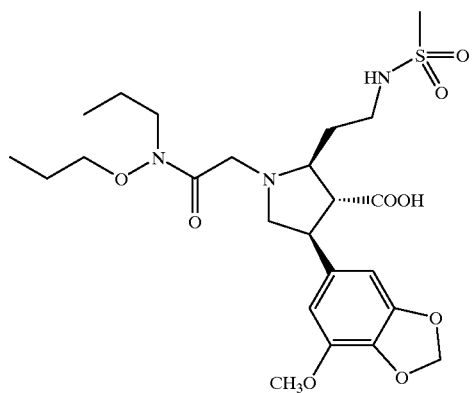

TABLE 3C-continued
1756 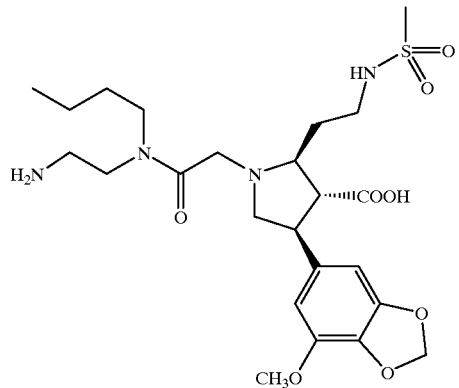
1757 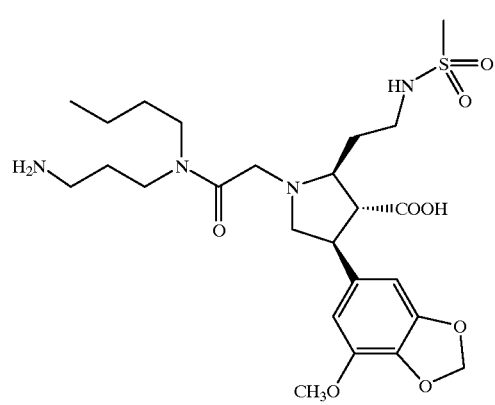
1758 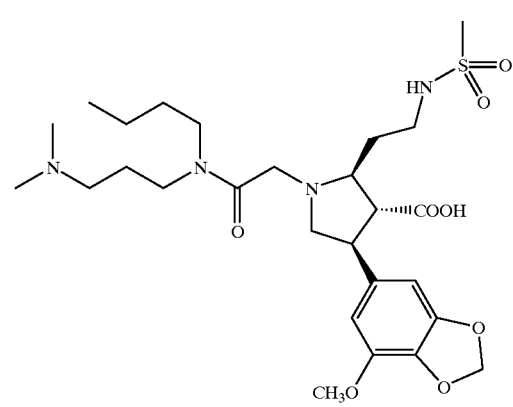
1759 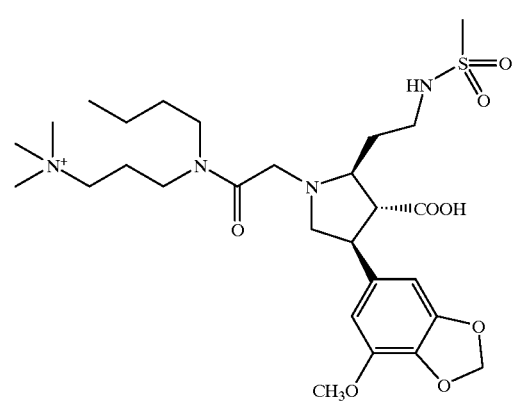

TABLE 3C-continued
1760
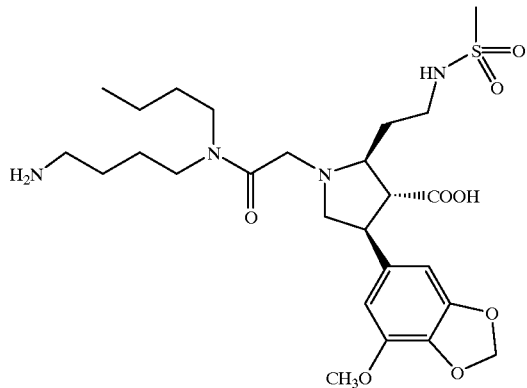
1761
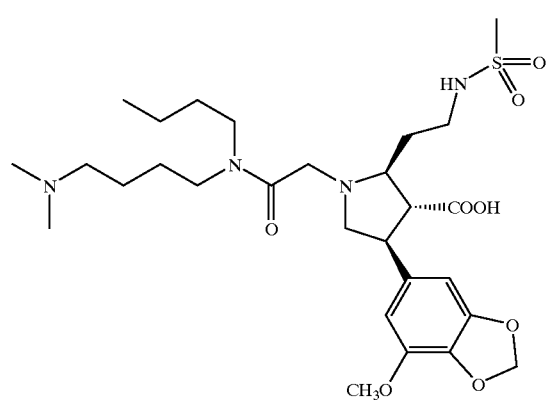
1762
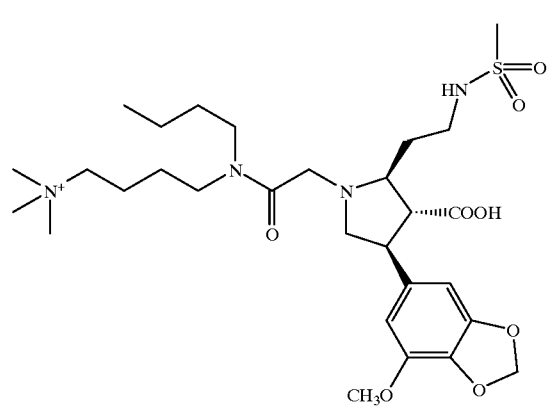
1763
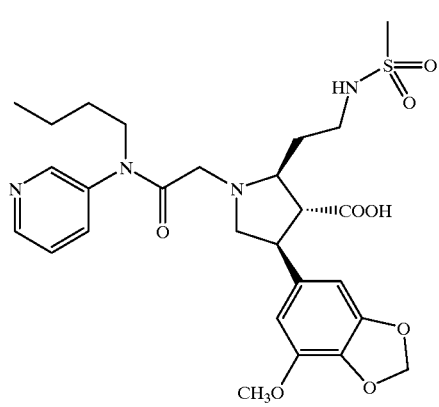

TABLE 3C-continued
1764
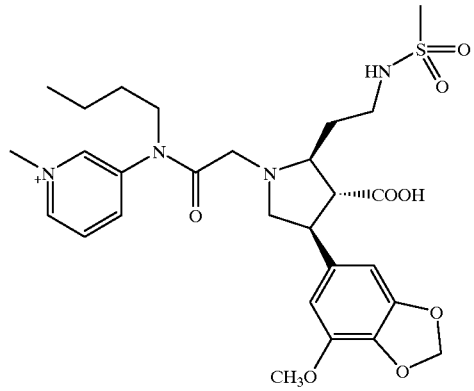
1765
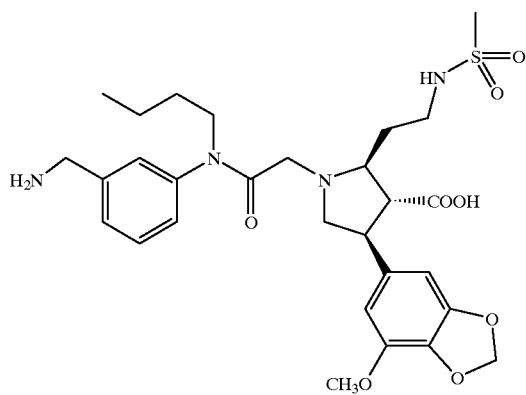
1766
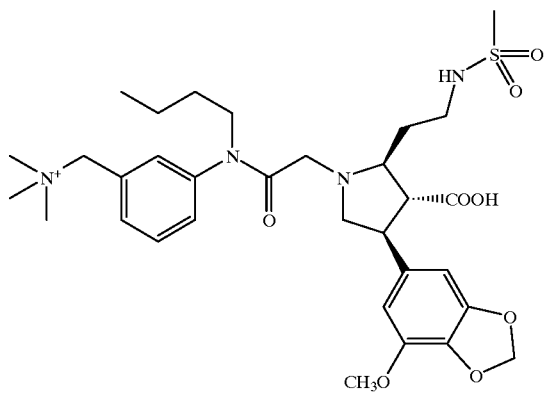
1767
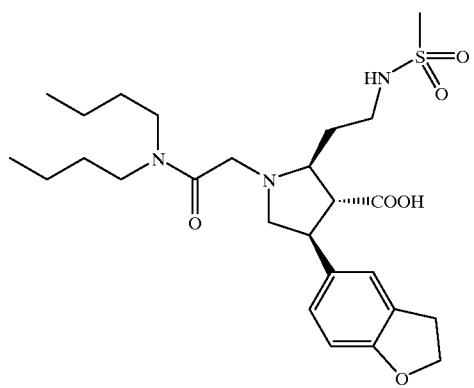

TABLE 3C-continued
1768
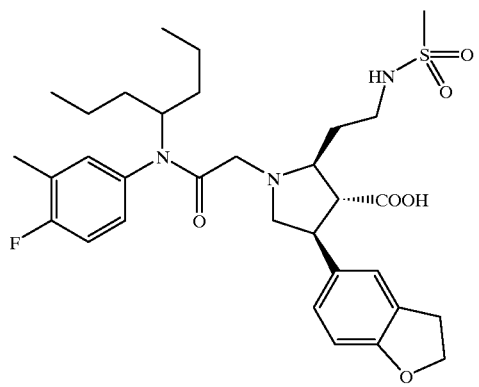
1769
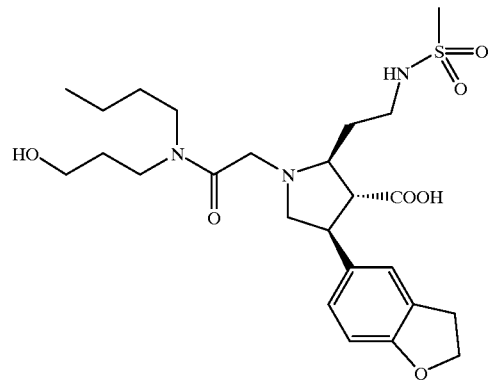
1770
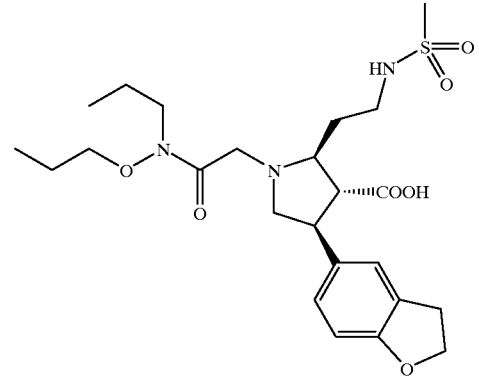
1771
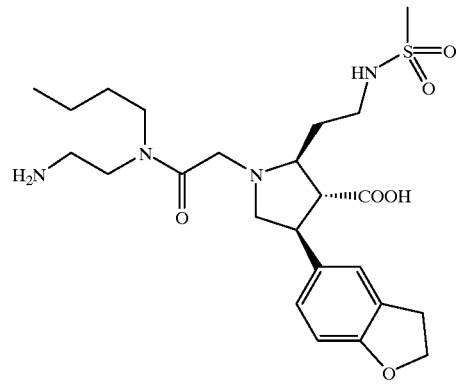

TABLE 3C-continued
1772
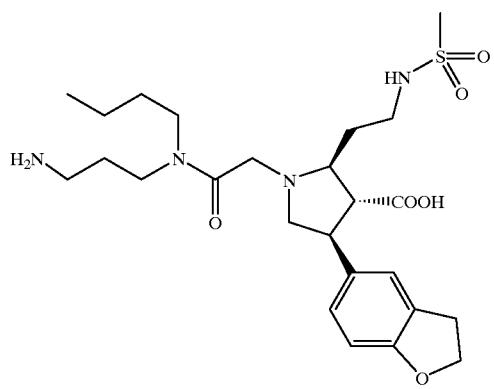
1773
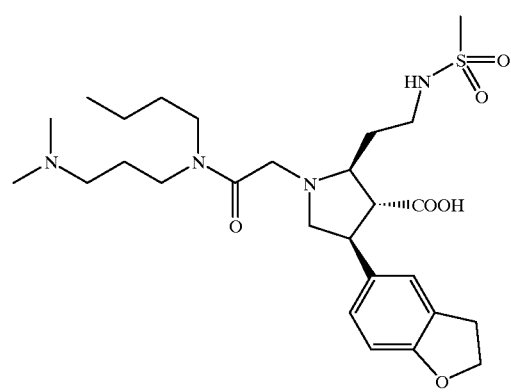
1774
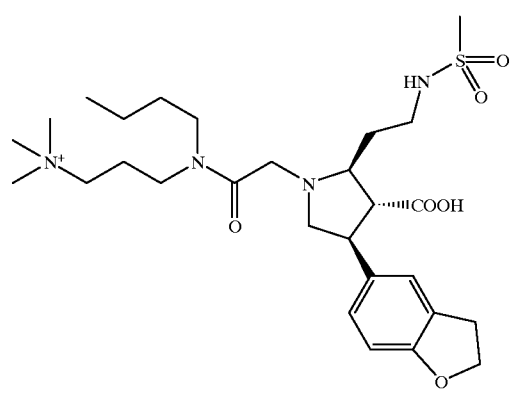
1775
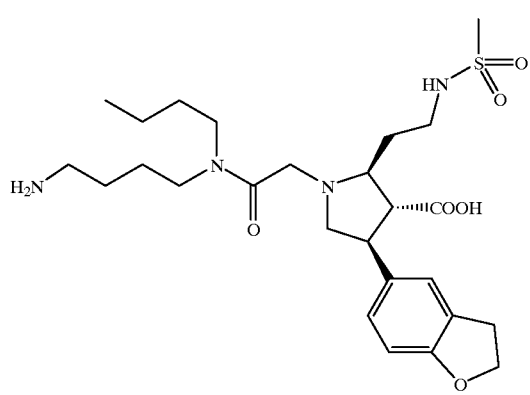

TABLE 3C-continued
1776
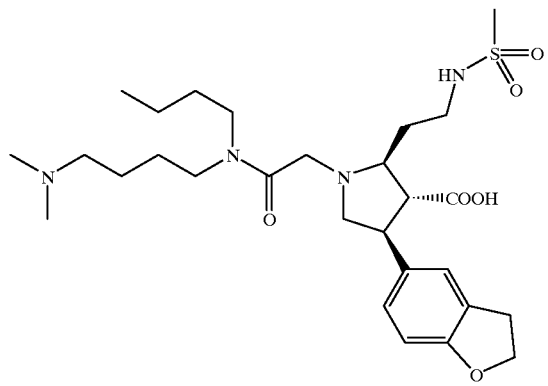
1777
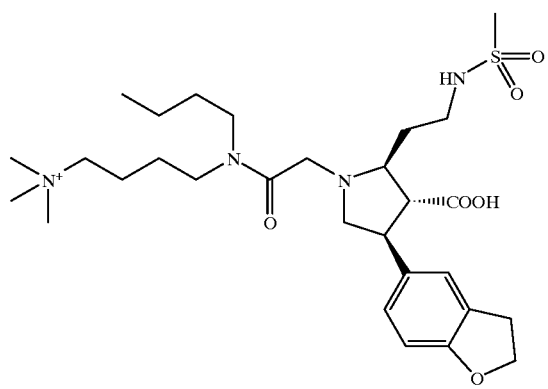
1778
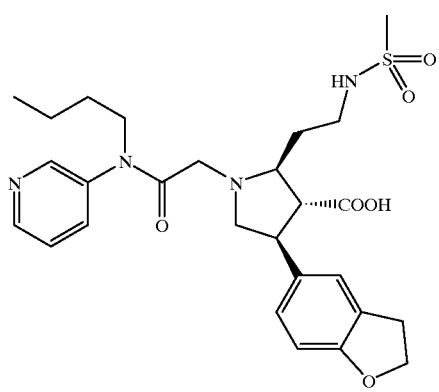
1779
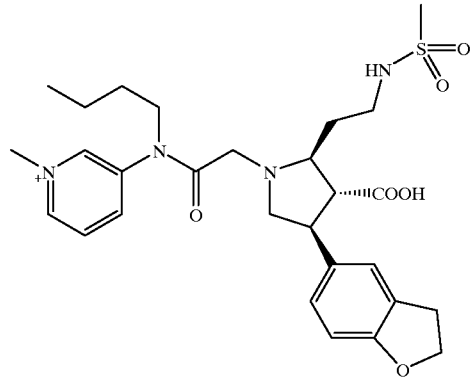

TABLE 3C-continued

1780

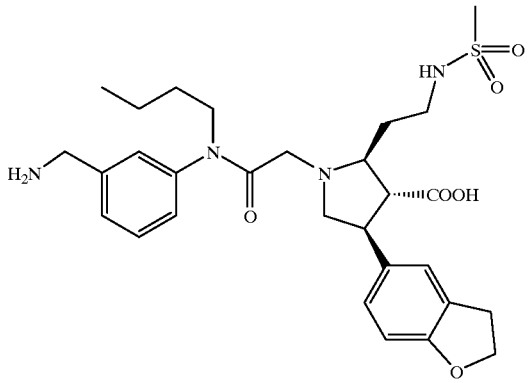

1781

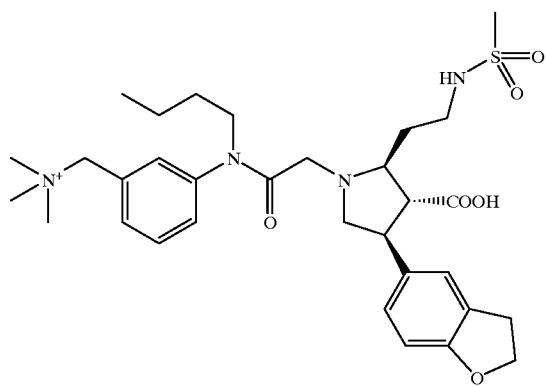

EXAMPLE 536

[2S,3R,4S]-2-(2,2-Dimethylpentyl)-4-(7-methoxy-1,3-benzodioxol-5-yl)-1-(N,N-di(n-butyl)aminocarbonylmethyl)-pyrrolidine-3-carboxylic Acid

EXAMPLE 536A

Ethyl 5,5-dimethyl-3-oxooctanoate

Ethyl 3,3-dimethylhexanoate was prepared using the general procedure of Cahiez et al., Tetrahedron Lett., 31, 7425 (1990). To a solution of 63.8 g (370 mmol) of this compound in 400 mL of ethanol, cooled to 0° C., was added a solution of 30 g of NaOH in 150 mL of water. The resultant solution was warmed to ambient temperature and stirred overnight. Solvents were removed in vacuo; the residue was taken up in 700 mL of water, and extracted twice with 1:1 ether/hexanes. The aqueous layer was acidified to pH3 with 1N HCl and extracted twice with hexanes. The combined hexane extracts were washed with brine, dried over sodium sulfate, filtered and concentrated. A 20.2 g (150 mmol) sample of the crude product is dissolved in 150 mL of THF; 27.3 g of 1,1'-carbonyldiimidazole is added portionwise, to control gas evolution. In meantime, 33.4 g of potassium ethylmalonate and 13.4 g of magnesium chloride are combined in 350 mL of THF (overhead mechanical stirring) and warmed to 50° C. for 3 hrs. This mixture is cooled to ambient temperature, and the above acid imidazolide solution is added. The resultant slurry is stirred overnight. Ether (600 mL), hexanes (600 mL) and aqueous 1N phosphoric acid (500 mL) are added, and the mixture is stirred for 30 min. The aqueous layer is separated; the organics are washed sequentially with bicarb (2×), water and brine. The organics are dried over sodium sulfate, filtered and concentrated to give 30.2 g (95% yield) of a colorless liquid.

EXAMPLE 536B

4-Methoxy-6-(2-nitrovinyl)-1,3-benzodioxole

3-Methoxypiperonal (50.0 g) is combined with 71.9 mL of nitromethane in 250 mL of acetic acid; 36 g of ammonium acetate is added, and the mixture is heated to 50° C. for 4 hrs. Solvents are removed in vacuo; the residue is taken up in water and stirred for 20 min. The solution is filtered; the filtrate is washed with water, then ether, to give 51.8 g of a yellow solid.

EXAMPLE 536C

Ethyl trans, trans-2-(2,2-Dimethylpentyl)-4-(7-methoxy-1,3-benzodioxol-5-yl)-pyrrolidine-3-carboxylate The compound of Example 536A (6.42 g, 30 mmol) was combined with 5.79 g of the compound of Example 536B in 40 mL of THF. DBU (0.5 mL) was added, and the mixture was stirred at ambient temperature for 6 hrs, during which time it turns reddish brown, and homogeneous. The solvents were removed in vacuo; the residue was taken up in EtOAc and washed sequentially with aqueous 1N phosphoric acid and brine. The organic phase was dried over sodium sulfate, filtered and concentrated. The residue was dissolved in 50 mL of THF; 12 g of Raney Nickel catalyst (washed sequentially with water and ethanol) was added, followed by 10 mL of acetic acid. The resultant mixture was hydrogenated under 4 atmospheres of hydrogen until hydrogen uptake ceased (~3 hrs). The catalyst was removed by filtration; solvents were removed in vacuo. The residue was dissolved in 90 mL of 2:1 ethanol/THF; 30 mg of bromcresol green indicator was added, followed by 30 mL of 1N sodium cyanoborohydride in THF. Concentrated HCl was added dropwise to maintain pH at the indicator point, over 1 hr. The resultant solution was stirred overnight at ambient temperature. Bicarb was added, and the solvents were removed in vacuo; the residue was partitioned between water and EtOAc. The organic material was washed with water (2x) and brine. The organic phase was dried over sodium sulfate, filtered and concentrated. The crude product was dissolved in 100 mL of acetonitrile; 10 mL of Hunig's base was added, and the solution was warmed to 40° C. overnight. Removal of solvents in vacuo provided 5.0 g of a yellowish oil.

EXAMPLE 536D

Ethyl [2S,3R,4S]-2-(2,2-Dimethylpentyl)-4-(7-methoxy-1,3-benzodioxol-5-yl)-pyrrolidine-3-carboxylate The crude compound of Example 536C (2.0 g) was combined with 4 mL of triethylamine in 40 mL of THF; 2.0 g of di-tert-butyldicarbonate was added, and the mixture was stirred at ambient temperature for 5 hrs. Solvents were removed in vacuo, and the residue was taken up in 60 mL of ethanol. Aqueous sodium hydroxide (10 mL of 2.5 N solution) was added, and the resultant solution was stirred overnight. Solvents were removed in vacuo; the residue was taken up in water and extracted with ether. The aqueous phase was acidified with aqueous 1N phosphoric acid and extracted with EtOAc. The organic extracts were washed with brine, dried over sodium sulfate, filtered, and concentrated to give 1.0 g of a colorless oil. A sample of this material (0.734 g, 1.58 mmol) was combined with 0.35 g of pentafluorophenol and 0.364 g of EDAC in 5 mL of DMF. The resultant solution was stirred at ambient temperature for 1 hr, then was poured onto 50 mL of 0.6M sodium bicarbonate solution and extracted (3x15 mL) with ether. The combined ether extracts were washed with brine, dried over magnesium sulfate, filtered, and concentrated in vacuo to give a foam, which was dissolved in 5 mL of THF and cooled to 0° C. Simultaneously, 0.418 g (2.37 mmol) of R-4-benzyl-2-oxazolidinone was combined with ~0.1 mg of pyreneacetic acid in 5 mL of THF and cooled to 0° C. N-butyllithium (1.6M in hexanes) was added to a red endpoint (persists ~10 sec), and the solution was stirred for 10 min. The solution was transferred into the solution of the pentafluorophenyl ester, and the resultant solution was stirred at 0° C. for 40 min. Solvents were removed in vacuo; the residue was taken up in bicarb and extracted with ether (3x10 mL). The combined ether extracts were washed with brine, dried over magnesium sulfate, filtered, and concentrated in vacuo. The crude mixture of diasteromeric products was separated by flash chromatography on silica gel, eluting with a gradient from 4:1->3:1->2:1 hexanes/EtOAc, giving 423 mg of the faster-moving and 389 mg of the slower-moving diastereomer, respectively. The faster-moving diastereomer was dissolved in 2 mL of a 2.0 M solution of sodium methoxide in methanol (freshly prepared, containing 5% methyl formate by volume) and stirred at ambient temperature for 16 hrs. Solvents were removed in vacuo, and the residue was partitioned between ether and aqueous 1N sodium hydroxide. The ether layer was washed with brine, dried over magnesium sulfate, filtered, and concentrated in vacuo. The residue was purified by flash chromatography on silica gel, eluting with 4:1 hexanes/EtOAc. The resultant material was dissolved in 5 mL of TFA and stirred at ambient temperature for 1 hr. Solvents were removed in vacuo; the residue was suspended in bicarb and extracted with EtOAc. The organic phase was washed with brine, dried over magnesium sulfate, filtered, and concentrated in vacuo to give 98 mg of product.

EXAMPLE 536E

[2S,3R,4S]2-(2,2-Dimethylpentyl)-4-(7-methoxy-1,3-benzodioxol-5-yl)-1-(N,N-di(n-butyl)aminocarbonylmethyl)-pyrrolidine-3-carboxylic Acid The compound of Example 536D (48 mg) was combined with 35 mg of the compound of Example 501A in 3 mL of acetonitrile; 0.5 mL of Hünig's base was added, and the solution was allowed to stir overnight at ambient temperature. Solvents were removed in vacuo; the residue was partitioned between EtOAc and aqueous 1N phosphoric acid. The organic layer was washed with bicarb and brine, then dried over sodium sulfate, filtered and concentrated. The residue was purified by flash chromatography on silica gel, eluting with 2:1 hexanes/EtOAc. The product was dissolved in 4 mL of ethanol; 1 mL of 2.5N aqueous sodium hydroxide was added, and the resultant solution was stirred overnight at ambient temperature. Solvents were removed in vacuo; the residue was taken up in water and extracted with ether. The aqueous phase was acidified to pH 3 with aqueous 1N phosphoric acid and extracted with EtOAc. The organic extracts were washed with brine, dried over sodium sulfate, filtered and concentrated to give a colorless oil. Lyophilization from acetonitrile/0.1% aqueous TFA gave 56 mg of a white solid.

$^1$H NMR (CDCl$_3$, 300 MHz) d 0.81 (s, 3H), 0.84 (s, 3H), 0.86 (t, J=6.9 Hz, 3H), 0.93 (t, J=6.9 Hz, 3H), 0.96 (t, J=6.9 Hz, 3H), 1.09–1.38 (m, 8H), 1.45–1.59 (m, 4H), 1.84–2.00 (m, 2H), 3.15 (dd, J=6.9 Hz, 10.0 Hz, 2H), 3.30–3.42 (m, 3H), 3.72 (t, J=10.5 Hz, 1H), 3.86 (t, J=10.5 Hz, 1H), 3.88 (s, 3H), 4.02 (q, J=10.0 Hz, 1H), 4.12 (d, J=16.8 Hz, 1H), 4.29 (d, J=16.8 Hz, 1H), 4.41 (brm, 1H), 5.94 (s, 1H), 6.52 (d, J=1.8 Hz, 1H), 6.67 (d, J=1.8 Hz, 1H). MS (ESI)(M+H)$^+$ at m/e 533. Anal calcd for C$_{30}$H$_{48}$N$_2$O$_6$.0.7 TFA: C, 61.57; H, 8.01; N, 4.57. Found: C, 61.59; H, 8.20; N, 4.63.

EXAMPLE 537

[2S,3R,4S]-2-(2,2-Dimethylpentyl)-4-(1,3-benzodioxol-5-yl)-1-(N,N-di(n-butyl)aminocarbonylmethyl)-pyrrolidine-3-carboxylic Acid

EXAMPLE 537A

Ethyl trans, trans-2-(2,2-Dimethylpentyl)-4-(1,3-benzodioxol-5-yl)-pyrrolidine-3-carboxylate Prepared according to the procedures of Example 536C above, substituting the compound of Example 501B (5-(2-nitrovinyl)-1,3-benzodioxole) for 4-methoxy-6-(2-nitrovinyl)-1,3-benzodioxole.

Example 537B

Ethyl [2S,3R,4S]-2-(2,2-Dimethylpentyl)4-(1,3-benzodioxol-5-yl)-pyrrolidine-3-carboxylate The compound of Example 537A (6.8 g) was dissolved in 100 mL of ether; a solution of 1.6 g of (S)-(+)-mandelic acid

EXAMPLE 537C

[2S,3R,4S]-2-(2,2-Dimethylpentyl)-4-(1,3-benzodioxol-5-yl)-1-(N,N-di(n-butyl) aminocarbonylmethyl)-pyrrolidine-3-carboxylic Acid Prepared from the compound of Example 537B according to the procedures of Example 536E. $^1$H NMR (CDCl$_3$, 300 MHz) d 0.80–0.99 (m, 15H), 1.10–1.37 (m, 8H), 1.43–1.58 (m, 4H), 1.77–1.97 (m, 2H), 3.48–3.12 (m, 5H), 3.60–3.69 (m, 1H), 3.75–3.86 (m, 1H), 3.95–4.16 (m, 2H), 4.28–4.4 (m, 2H), 5.94 (s, 2H), 6.74 (d, J=7.8 Hz, 1H), 6.8 (dd, J=8.1, 1.5 Hz, 1H), 6.87 (d, J=1.8 Hz, 1H). MS (APCl+) m/e 503 (M+H)$^+$.

EXAMPLE 538

[2S,3R,4S]-2-(2,2-Dimethylpentyl)-4-(1,3-benzodioxol-5-yl)-1-((N-propoxy, N-(n-butyl)) aminocarbonylmethyl)-pyrrolidine-3-carboxylic Acid

EXAMPLE 538A

N-Boc-N-butyl-O-allylhydroxylamine

O-Allylhydroxylamine hydrochloride hydrate (5.0 g) was dissolved in THF (15 mL). The solution was cooled to 0° C. in an ice bath. Diisopropylethylamine (8 mL) and di-t-butyldicarbonate (10.0 g) were added. The mixture was stirred at 0° C. for one hour at which point the bath was removed and the reaction allowed to warm to room temperature and stirred overnight. The THF was removed in vacuo and the residue taken up in EtOAc (25 mL), and washed with water (1×50 mL), saturated sodium bicarbonate solution (3×50 mL), 1N phosphoric acid (3×50 mL), and brine (1×50 mL). The organic layer was dried with sodium sulfate and evaporated to give a light yellow oil (6.5 g). This crude product was dissolved in dry THF (25 mL) and the solution cooled to 0° C. in an ice bath. Sodium hydride (1.5 g, 60% dispersion in oil) was added portionwise over five minutes. The resulting mixture was stirred for 30 minutes at 0° C. 1-Iodobutane (4.1 mL) was added dropwise to the mixture. The reaction was stirred at 0° C. for one hour, then stirred overnight at room temperature. The THF was removed in vacuo and the residue taken up in EtOAc (50 mL) and washed with water (1×50 mL), saturated sodium bicarbonate solution (3×50 mL), 1N phosphoric acid (3×50 mL), and brine (1×50 mL). The organic layer was dried with sodium sulfate and evaporated to give a light yellow oil, which was purified by flash chromatography on silica gel eluting with 5% EtOAc/hexanes to give the title compound as a colorless oil (6.0 g).

EXAMPLE 538B

N-butyl-N-propoxyamine trifluoroacetate

The compound of Example 538A (6.0 g) was dissolved in EtOAc (100 mL). 10% Palladium-on-carbon (0.5 g) was added, and the mixture was purged with nitrogen. The nitrogen line was exchanged for a balloon of hydrogen, and the mixture was stirred at room temperature for 6 hours. The catalyst was removed by filtration through a pad of Celite and the solvents were removed in vacuo to give a yellow oil which was purified by flash chromatography on silica gel eluting with 5% EtOAc/hexanes to give a colorless oil (5.8 g). A sample of the resultant material (1.15 g) was dissolved in CH$_2$Cl$_2$ (5 mL) and cooled in an ice bath. Trifluoroacetic acid (3mL) was added and the solution stirred cold for two hours. The solvent was removed in vacuo, care being taken not to allow the solution to warm above room temperature. The residue contained considerable TFA and was used without further purification.

EXAMPLE 538C

N-butyl-N-propoxy-bromoacetamide

The salt of Example 538B (0.60 g) was dissolved in acetonitrile (5 mL) and cooled to –20° C. Hünig's base (5.5 mL) was added slowly. Bromoacetyl bromide (0.5 mL) was added dropwise over five minutes. The solution was stirred at –20° C. for 30 minutes. The bath was removed and the solution was stirred for six hours at room temperature. The solvent was removed in vacuo and the residue taken up in EtOAc (50 mL) and washed with water (1×25 mL), 1N phosphoric acid (3×25 mL), and brine (1×25 mL). The organic layer was dried with sodium sulfate and evaporated to give a dark orange oil (0.65 g) which was used without further purification.

EXAMPLE 538D

[2S,3R,4S]-2-(2,2-Dimethylpentyl)-4-(1,3-benzodioxol-5-yl)-1-((N-propoxy, N-(n-butyl)) aminocarbonylmethyl)-pyrrolidine-3-carboxylic Acid The compound of Example 537B was reacted with the compound of Example 538C according to the procedures of Example 536E.

EXAMPLE 539

[2S,3R,4S]-2-(2,2-Dimethylpentyl)-4-(1,3-benzodioxol-5-yl)-1-((N-propoxy, N-(n-propyl)) aminocarbonylmethyl)-pyrrolidine-3-carboxylic Acid

EXAMPLE 539A

N-propyl-N-propoxy bromoacetamide

Prepared according to the procedures of Example 538A–C, substituting iodopropane for iodobutane in Example 538A.

EXAMPLE 539B

[2S,3R,4S]-2-(2,2-Dimethylpentyl)-4-(1,3-benzodioxol-5-yl)-1-((N-propoxy, N-(n-propyl)) aminocarbonylmethyl)-pyrrolidine-3-carboxylic Acid The compound of Example 537B was reacted with the compound of Example 539A according to the procedures of Example 536E.

EXAMPLE 540

[2S,3R,4S]-2-(2,2-Dimethylpentyl)-4-(7-methoxy-1,3-benzodioxol-5-yl)-1-((N-propoxy, N-(n-butyl)) aminocarbonylmethyl)-pyrrolidine-3-carboxylic Acid The compound of Example 536D was reacted with the compound of Example 538C according to the procedures of Example 536E.

EXAMPLE 541

2S,3R,4S]-2-(2,2-Dimethylpentyl)4-(7-methoxy-1,3-benzodioxol-5-yl)-1-((N-propoxy, N-(n-propyl)) aminocarbonylmethyl)-pyrrolidine-3-carboxylic Acid The compound of Example 536D was reacted with the compound of Example 539A according to the procedures of Example 536E.

EXAMPLE 542

[2S,3R,4S]-2-(2,2-Dimethylpent-3-enyl)-4-(1,3-benzodioxol-5-yl)-1-((N-propoxy, N-(n-butyl)) aminocarbonylmethyl)-pyrrolidine-3-carboxylic Acid

EXAMPLE 542A trans-Ethyl 3,3-dimethyl-4-hexenoate

A mixture of 4-methyl-3-penten-2-ol (7.4 g, 74 mmol), triethyl orthoacetate (13.6 mL, 74 mmol) and propionic acid (0.28 mL, 3.7 mmol) was heated at 150° C. for 7 hr. The product was then distilled under normal pressure (200–220° C.) to give 5.0 g of crude ester as a colorless oil.

EXAMPLE 542B

Ethyl trans,trans-2-(2,2-Dimethylpent-3-enyl)-4-(1,3-benzodioxol-5-yl)-pyrrolidine-3-carboxylate The title compound is prepared according to the procedures of Examples 536A and 536C, substituting the compound of Example 542A for ethyl 3,3-dimethylhexanoate in Example 536A and the compound of Example 501B (5-(2-nitrovinyl)- 1,3-benxodioxole) for 4-methoxy-6-(2-nitrovinyl)-1,3-benzodioxole in Example 536C.

EXAMPLE 542C

Ethyl [2S,3R,4S]-2-(2,2-Dimethylpent-3-enyl)-4-(1,3-benzodioxol-5-yl)-pyrrolidine-3-carboxylate The compound of Example 542B was resolved according to the procedure described in Example 537B.

EXAMPLE 542D

[2S,3R,4S]-2-(2,2-Dimethylpent-3-enyl)-4-(1,3-benzodioxol-5-yl)-1-((N-propoxy, N-(n-butyl)) aminocarbonylmethyl)-pyrrolidine-3-carboxylic Acid The compound of Example 542C was reacted with the compound of Example 538C according to the procedures of Example 536E.

EXAMPLE 543

[2S,3R,4S2-(2,2-Dimethylpent-3-enyl)-4-(1,3-benzodioxol-5-yl)-1-((N-propoxy, N-(n-propyl)) aminocarbonylmethyl)-pyrrolidine-3-carboxylic Acid The compound of Example 542C was reacted with the compound of Example 539A according to the procedures of Example 536E.

EXAMPLE 544

[2S,3R,4S]-2-(2,2-Dimethylpent-3-enyl)-4-(7-methoxy-1,3-benzodioxol-5-yl)-1-((N-propoxy, N-(n-butyl))aminocarbonylmethyl)-pyrrolidine-3-carboxylic Acid

EXAMPLE 544A

Ethyl trans,trans-2-(2,2-Dimethylpent-3-enyl)-4-(7-methoxy-1,3-benzodioxol-5-yl)-pyrrolidine-3-carboxylate The title compound is prepared according to the procedures of Examples 536A and 536C, substituting the compound of Example 542A for ethyl 3,3-dimethylhexanoate in Example 536A.

EXAMPLE 544B

Ethyl [2S,3R,4S]-2-(2,2-Dimethylpent-3-enyl)-4-(7-methoxy-1,3-benzodioxol-5-yl)-pyrrolidine-3-carboxylate The compound of Example 544A was reached with the compound of Example 538C according to the procedures of Example 536E.

EXAMPLE 544C

[2S,3R,4S]-2-(2,2-Dimethylpent-3-enyl)-4-(7-methoxy-1,3-benzodioxol-5-yl)-1-((N-propoxy, N-(n-butyl))aminocarbonylmethyl)-pyrrolidine-3-carboxylic acid The compound of Example 544B was reacted with the compound of Example 538C according to the procedures of Example 536E.

EXAMPLE 545

[2S,3R,4S]-2-(2,2-Dimethylpent-3-enyl)-4-(7-methoxy-1,3-benzodioxol-5-yl)-1-((N-propoxy, N-(n-propyl))aminocarbonylmethyl)-pyrrolidine-3-carboxylic Acid The compound of Example 544B was reacted with the compound of Example 539A according to the procedures of Example 536E.

EXAMPLE 546

[2S,3R,4S]-2-(2-(2-pyridyl)ethyl)-4-(1,3-benzodioxol-5-yl)-1-[[N-4-heptyl-N-(2-methyl-3-fluorophenyl)] amino carbonylmethyl]-pyrrolidine-3-carboxylic Acid

EXAMPLE 546A

Ethyl trans,trans-2-(2-(2-pyridyl)ethyl)-4-(1,3-benzodioxol-5-yl)-pyrrolidine-3-carboxylate The title compound is prepared according to the procedures of Examples 536A and 536C, substituting the compound of Example 519A for 3,3-dimethylhexanoic acid in Example 536A.

EXAMPLE 546B

Ethyl [2S,3R,4S]-2-(2-(2-pyridyl)ethyl)-4-(1,3-benzodioxol-5-yl)-pyrrolidine-3-carboxylate The compound of Example 546A (1.5 g) was dissolved in $CH_2Cl_2$ (25 mL). Di-t-butyldicarbonate (0.9 g) was added and the solution stirred overnight at room temperature. The solvent was evaporated in vacuo and the residue taken up in EtOAc (50 mL), washed with water (1×50 mL), saturated sodium bicarbonate solution (3×50 mL), and brine (1×5mL). The organic layer was dried with sodium sulfate and evaporated in vacuo to give an oil with was purified by flash chromatography on silica gel eluting with 1/10/10 EtOH/EtOAc/hexanes to give a colorless oil (1.5 g). The oil was dissolved in EtOH (10 mL) and 50% NaOH solution (0.5 mL) and water (5 mL) were added. The mixture was stirred overnight at room temperature. The solvents were evaporated in vacuo and the residue taken up in EtOAc (25 mL)

and acidified with 1 N H₃PO₄ (10 mL). The layers were separated and the organic layer dried with sodium sulfate and evaporated to give a white semi-solid (1.3 g). A sample of the resultant Boc-protected amino acid (0.9 g) was dissolved in DMF (5 mL). (S)-Phenylalaninol (0.32 g), HOOBt (0.33 g), and EDCl (0.40 g) were added and the solution stirred overnight at room temperature. Water (50 mL) was added and the mixture extracted with EtOAc (3×25 mL). The organic layers were combined, washed with water (2×50 mL), saturated sodium bicarbonate solution (3×50 mL), and brine (1×50 mL), and evaporated to give a yellow oil; tlc indicated the presence of two diastereomeric products. The diastereomeric amides were separated by flash chromatography on silica gel eluting with 1/12/12 EtOH/EtOAc/hexanes to give faster-(450 mg) and slower-moving isomers (400 mg). The faster-moving diastereomer (400 mg) was taken up in 6N HCl and heated at reflux overnight. The solvent was evaporated and the residue was taken up in toluene (75 mL) and evaporated. This was repeated two additional times to give a brown solid, which was dissolved in EtOH (50mL). 4N HCl/dioxane (10 mL) was added and the solution heated at reflux overnight. The EtOH was evaporated and the residue taken up in EtOAc which was treated with saturated sodium bicarbonate solution (3×50 mL), and brine (1×50 mL), and evaporated to give a brown solid. Flash chromatography on silica gel eluting with 30% EtOH/EtOAc gave a mixture of products (130 mg) which was approximately 70% desired material. This product was carried forward without additional purification.

EXAMPLE 546C

[2S,3R,4S]-2-(2-(2-pyridyl)ethyl)-4-(1,3-benzodioxol-5-yl)-1-[[N-4-heptyl-N-(2-methyl-3-fluorophenyl)] amino carbonylmethyl]-pyrrolidine-3-carboxylic Acid The compound of Example 546B was reacted with the compound of Example 508E according to the procedures of Example 536E.

EXAMPLE 547

[2S,3R,4S]-2-(4-Methoxyphenyl)-4-(1,3-benzodioxol-5-yl)-1-[(N-butyl-N-(4-dimethylaminobutyl)amino)carbonylmethyl]-pyrrolidine-3-carboxylic Acid

EXAMPLE 547A

N-butyl-4-hydroxybutyramide

To 30 mL (390 mmol) of g-butyrolactone was added 45 ml (455 mmol) of n-butylamine. The solution was heated at 85° C. for 1.5 hr, then the excess n-butylamine was removed in vacuo. The product crystallized on standing to give about 62 g of a colorless, low melting solid.

EXAMPLE 547B

N-butyl-4-hydroxybutyl chloroacetamide

To an ice cooled solution of 3.40 g (91.9 mmol) of LiAlH₄ in 90 mL of THF was added 2.4 mL of 98% H₂SO₄, dropwise, with stirring. After bubbling had ceased, a solution of 4.7 g of the compound of Example 547A in 10 mL of THF was added. The mixture was stirred at reflux for 24 hr, then cooled with an ice bath and quenched by sequential dropwise addition of 1.7 mL H₂O, and 17 mL of 25% w/v aqueous NaOH. The white precipitate was filtered, and washed with about 50 mL of THF. The combined filtrate and washings were concentrated to 3.85 g of an oil. To an ice cooled solution of this material in 35 mL of ethyl acetate was added a solution of 5.0 g (29.2 mmol) of chloroacetic anhydride in 10 mL of ethyl acetate. The solution was stirred at 0° C. for 30 min, then extracted with saturated aqueous NaHCO₃ solution (1×25 mL), 2M NaOH (1×25 mL), 5% NH₄OH (1×25 mL), 1M HCl (1×25 mL), and brine (1×25 mL), dried over MgSO₄, filtered, and concentrated in vacuo to an oil. The product was purified via silica gel chromatography, eluting with 98:2 diethyl ether: methanol, to give 1.52 g (31%) of a colorless oil.

EXAMPLE 547C

Ethyl [2S,3R,4S]-2-(4-Methoxyphenyl)-4-(1,3-benzodioxol-5-yl)-1-[(N-butyl-N-(4-hydroxybutyl)amino)carbonylmethyl]-pyrrolidine-3-carboxylate To 1.52 g (6.85 mmol) of the compound of Example 547B was added 2.75 g (7.44 mmol) of the ethyl [2S,3R,4S]-2-(4-Methoxyphenyl)-4-(1,3-benzodioxol-5-yl)-pyrrolidine-3-carboxylate (prepared by neutralization of the compound of Example 501G), 10 mL of DMSO, and 2 mL of N,N-diisopropylethylamine. The solution was stirred at ambient temperature for 22 h, then poured into 100 mL of water and extracted with diethyl ether (3×25 mL). The combined ether layers were washed with water (1×25 mL), 4% (v/v) H₃PO₄ (1×25 mL), saturated aqueous NaHC₃ solution (1×25 mL), and brine (1×25 mL), dried over MgSO₄, filtered, and concentrated to an oil. This was purified via silica gel chromatography, eluting with 98:2 diethyl ether: methanol to give 3.0 g (79%) of a colorless oil.

EXAMPLE 547D

Ethyl [2S,3R,4S]-2-(4-Methoxyphenyl)-4-(1,3-benzodioxol-5-yl)1-[(N-butyl-N-(4-bromobutyl)amino)carbonylmethyl]-pyrrolidine-3-carboxylate To an ice cooled solution of 2.80 g (5.05 mmol) of the compound of Example 547C in 27 mL of diethyl ether was added 1.4 mL (10 mmol) of triethylamine, then 0.58 mL of methanesulfonyl chloride. A white precipitate formed, and the suspension was stirred at 0° C. for 20 min. The reaction was diluted with 75 mL of diethyl ether, then extracted with saturated aqueous NaHCO₃ solution (2×25 mL), 5% NH₄OH (2×25 mL), and brine (1×25 mL), dried over MgSO₄, filtered, and concentrated to 3.0 g of a colorless oil. To this material in 45 mL of DMF was added 6.0 g (69 mmol) of LiBr. The reaction warmed to about 50° C., then gradually cooled. The solution was stirred at ambient temperature for 4 h, then poured into 450 mL of water, and extracted with diethyl ether (3×100 mL). The combined ether layers were back extracted with water (1×100 mL), and brine (1×100 mL), dried over MgSO₄, filtered, and concentrated in vacuo to an oil. The product was purified via silica gel chromatography, eluting with 3:1 diethyl ether: petroleum ether, to give 2.65 g (90%) of a colorless oil.

EXAMPLE 547E

[2S,3R,4S]-2-(4-Methoxyphenyl)-4-(1,3-benzodioxol-5-yl)-1-[(N-butyl-N-(4-dimethylaminobutyl)amino)carbonylmethyl]-pyrrolidine-3-carboxylic acid To a solution of the compound of Example 547D (0.825 g, 1.34 mmol) in 3 mL of ethanol was added 5 mL of 4.07M dimethylamine in ethanol; the resultant solution was heated at reflux for 75 min. Solvents were removed in vacuo. The residue was purified by flash chromatography on silica gel, eluting with 9:1 dichloromethane/methanol. The resultant material was taken up in 5 mL of 1.4N NaOH in 5:1 ethanol/water and stirred at ambient temperature for 14 hrs. Solvents were removed in vacuo; the residue was taken up in water, then adjusted to pH 6–7 with 1M HCl (~7 mL required). The mixture was extracted with EtOAc (3×); the aqueous layer was concentrated in vacuo. The residue was washed 3× with acetonitrile; the combined washes were filtered through Celite and concentrated to give 596 mg of a white foam.

EXAMPLE 548

[2S,3R,4S]-2-(2,2-Dimethylpentyl)-4-(1,3-benzodioxol-5-yl)-1-[(N-butyl-N-(4-dimethylaminobutyl)amino)carbonylmethyl]-pyrrolidine-3-carboxylic acid Prepared according to the procedures of Example 547, substituting the compound of Example 537B (ethyl [2S,3R,4S]-2-(2,2-Dimethylpentyl)-4-(1,3-benzodioxol-5-yl)-pyrrolidine-3-carboxylate) in Example 547C.

EXAMPLE 549

[2S,3R,4S]-2-(2,2-Dimethylpentyl)-4-(7-methoxy-1,3-benzodioxol-5-yl)-1-[(N-butyl-N-(4-dimethylaminobutyl)amino)carbonylmethyl]-pyrrolidine-3-carboxylic Acid Prepared according to the procedures of Example 547, substituting the compound of Example 536D (ethyl [2S,3R,4S]-2-(2,2-Dimethylpentyl)-4-(7-methoxy-1,3-benzodioxol-5-yl)-pyrrolidine-3-carboxylate) in Example 547C.

EXAMPLE 550

[2S,3R,4S]-2-(2,2-Dimethylpent-3-enyl)-4-(1,3-benzodioxol-5-yl)-1-[(N-butyl-N-(4-dimethylaminobutyl)amino)carbonylmethyl]-pyrrolidine-3-carboxylic acid Prepared according to the procedures of Example 547, substituting the compound of Example 542C (ethyl [2S,3R,4S]-2-(2,2-Dimethylpent-3-enyl)-4-(1,3-benzodioxol-5-yl)-pyrrolidine-3-carboxylate) in Example 547C.

EXAMPLE 551

[2S,3R,4S]-2-(2,2-Dimethylpent-3-enyl)-4-(7-methoxy-1,3-benzodioxol-5-yl)-1-[(N-butyl-N-(4-dimethylaminobutyl)amino)carbonylmethyl]-pyrrolidine-3-carboxylic acid Prepared according to the procedures of Example 547, substituting the compound of Example 544A (ethyl [2S,3R,4S]-2-(2,2-Dimethylpent-3-enyl)-4-(7-methoxy-1,3-benzodioxol-5-yl)-pyrrolidine-3-carboxylate) in Example 547C.

EXAMPLE 552

[2S,3R,4S]-2-(2,2-Dimethylpent-3-enyl)-4-(1,3-benzodioxol-5-yl)-1-[(N,N-di(nbutyl)amino)carbonylmethyl]-pyrrolidine-3-carboxylic Acid Prepared according to the procedures of Example 1, substituting the compound of Example 541C (ethyl[2S,3R,4S]-2-(2,2-Dimethylpent-3-enyl)-4-(1,3-benzodioxol-5-yl)-pyrrolidine-3-carboxylate).

EXAMPLE 553

[2S,3R4S]-2-(2,2-Dimethylpent-3-enyl)-4-(7-methoxy-1,3-benzodioxol-5-yl)-1-[(N,N-di(n-butyl)amino)carbonylmethyl]-pyrrolidine-3-carboxylic Acid Prepared according to the procesures of Example 1, substituting the compound of Example 544B (ethyl [2S,3R,4S]-2-(2,2-Dimethylpent-3-enyl)-4-(7-methoxy-1,3-benzodioxol-5-yl)-pyrrolidine-3-carboxylate).

As an indication that the compounds described herein act through binding to endothelin receptors, the compounds have been evaluated for their ability to displace endothelin from its receptor.

Binding Assay $ET_A$ Receptor
Preparation of membranes from MMQ cells:

MMQ [MacLeod/MacQueen/Login cell line (prolactin secreting rat pituitary cells)] cells from 150 mL culture flasks were collected by centrifugation (1,000×g for 10 min) and then homogenized in 25 mL of 10 mM Hepes (pH 7.4) containing 0.25M sucrose and protease inhibitors [3 mM EDTA, 0.1 mM PMSF, and 5 µg/mL Pepstatin A] by a micro ultrasonic cell disruptor (Kontes). The mixture was centrifuged at 1000×g for 10 min. The supernatant was collected and centrifuged at 60,000×g for 60 min. The precipitate was resuspended in 20 mM Tris, pH 7.4 containing the above protease inhibitors and centrifuged again. The final pellet was resuspended in 20 mM Tris, pH 7.4 containing protease inhibitors and stored at −80° C. until used. Protein content was determined by the Bio-Rad dye-binding protein assay.
[$^{125}$I]ET-1 binding to membranes:

Binding assays were performed in 96-well microtiter plates pretreated with 0.1% BSA. Membranes prepared from cells were diluted ~100 fold in Buffer B (20 mM Tris, 100 mM NaCl, 10 mM MgCl$_2$, pH 7.4, with 0.2% BSA, 0.1 mM PMSF, 5 µg/mL Pepstatin A, 0.025% bacitracin, and 3 mM EDTA) to a final concentration of 0.2 mg/mL of protein. In competition studies, membranes (0.02 mg) were incubated with 0.1 nM of [$^{125}$I]ET-1 in Buffer B (final volume: 0.2 mL) in the presence of increasing concentrations of unlabeled ET-1 or a test compound for 4 hours at 25° C. After incubation, unbound ligands were separated from bound ligands by a vacuum filtration method using glass-fiber filter strips in PHD cell harvesters (Cambridge Technology, Inc., MA), followed by washing the filter strips with saline (1 mL) for three times. Nonspecific binding was determined in the presence of 1 µM ET-1. The data are shown in Table 4. The per cent inhibition at a concentration of 1 mM is shown. The data show that the compounds of the invention bind to the endothelin receptor.

TABLE 4

Binding Data

| Example | % Inhibition $ET_A$ at 1 µM |
|---------|------------------------------|
| 1D | 96.4 |
| 2 | 58.4 |
| 3 | 42.2 |
| 4 | 78.2 |

TABLE 4-continued

Binding Data

| Example | % Inhibition $ET_A$ at 1 $\mu M$ |
|---|---|
| 5 | 95.1 |
| 6B | 34.9 |
| 7 | 63.4 |
| 8 | 53.7 |
| 9 | 69.2 |
| 10 | 66.1 |
| 14 | 86.6 |
| 15 | 84.8 |
| 16 | 96.0 |
| 17 | 73.9 |
| 18 | 97.3 |
| 19 | 90.3 |
| 20 | 80.9 |
| 21 | 56.3 |
| 22 | 86.3 |
| 23 | 85.9 |
| 26 | 83.0 |
| 27 | 61.2 |
| 28 | 63.8 |
| 29 | 85.3 |
| 30 | 80.0 |
| 31B | 93.6 |
| 34 | 95.5 |
| 35 | 91.8 |
| 36 | 94.5 |
| 37 | 47.9 |
| 38 | 100.0 |
| 39 | 83.6 |
| 40 | 94.8 |
| 41 | 89.9 |
| 42 | 95.2 |
| 43 | 99.2 |
| 44 | 91.3 |
| 45 | 85.4 |
| 46 | 90.4 |
| 47 | 95.1 |
| 48 | 96.3 |
| 52 | 84.0 |
| 54 | 64.6 |
| 55 | 50.5 |
| 56 | 34.3 |
| 57 | 93.2 |
| 58 | 81.9 |
| 59 | 70.8 |
| 60 | 42.8 |
| 61C | 90.6 |
| 62 | 94.1 |
| 63 | 92.0 |
| 64 | 95.0 |
| 65 | 82.8 |
| 66 | 87.7 |
| 67 | 96.3 |
| 68 | 84.6 |
| 69D | 37.4 |
| 70 | 62.7 |
| 71 | 81.4 |
| 72C | 80.7 |
| 73C | 96.3 |
| 74 | 95.6 |
| 75C | 95.3 |
| 76 | 93.1 |
| 79 | 100.4 |
| 80 | 89.4 |
| 82 | 90.3 |
| 83 | 85.0 |
| 84 | 65.3 |
| 86 | 52.6 |
| 87 | 62.4 |
| 88 | 84.3 |
| 89 | 84.6 |
| 91C | 91.6 |
| 92C | 107.4 |
| 93C | 59.2 |
| 95D | 82.1 |
| 96 | 86.1 |
| 97 | 89.0 |
| 98 | 86.8 |
| 99 | 92.1 |
| 100 | 76.8 |
| 101 | 89.2 |
| 102 | 75.2 |
| 103 | 69.0 |
| 104 | 98.0 |
| 105 | 98.6 |
| 106 | 90.0 |
| 107 | 97.2 |
| 109 | 96.8 |
| 110 | 94.4 |
| 111 | 101.8 |
| 112 | 94.9 |
| 113 | 94.3 |
| 114 | 86.2 |
| 115 | 88.4 |
| 116 | 79.3 |
| 117 | 95.4 |
| 118 | 93.2 |
| 119 | 86.6 |
| 120 | 99.5 |
| 121 | 98.6 |
| 122 | 95.3 |
| 125 | 97.2 |
| 126 | 91.7 |
| 127 | 91.4 |
| 128 | 95.4 |
| 123 | 89.7 |
| 124 | 91.0 |
| 129 | 100.1 |
| 130 | 91.0 |
| 131 | 89.5 |
| 132 | 90.0 |
| 133 | 88.6 |
| 134 | 92.2 |
| 135B | 77.7 |
| 136 | 79.4 |
| 138 | 83.0 |
| 139 | 98.6 |
| 140 | 106.3 |
| 141 | 92.8 |
| 142B | 78.7 |
| 143 | 20.6 |
| 144 | 78.2 |
| 145 | 32.4 |
| 146 | 25.0 |
| 147 | 73.0 |
| 148 | 94.7 |
| 149 | 84.6 |
| 150 | 93.6 |
| 151 | 80.5 |
| 152 | 86.9 |
| 153 | 97.1 |
| 154 | 80.2 |
| 155 | 92.7 |
| 156 | 92.6 |
| 157 | 83.8 |
| 158 | 91.8 |
| 159 | 36.2 |
| 160B | 80.3 |
| 161 | 93.6 |
| 162B | 91.5 |
| 163 | 90.6 |
| 164 | 98.6 |
| 165 | 54.1 |
| 166 | 91.6 |
| 167 | 94.4 |
| 291 | 100.0 |
| 293 | 89.8 |
| 294 | 77.7 |
| 295 | 93.0 |
| 296 | 87.1 |
| 297 | 84.4 |

TABLE 4-continued

Binding Data

| Example | % Inhibition ET$_A$ at 1 μM |
|---|---|
| 298 | 93.3 |
| 299 | 90.4 |
| 300 | 96.1 |
| 301 | 96.7 |
| 302 | 86.6 |
| 303 | 87.2 |
| 304 | 89.7 |
| 305 | 87.4 |
| 306 | 93.3 |
| 307 | 92.2 |
| 308 | 93.0 |
| 309 | 80.7 |
| 310 | 87.1 |
| 311 | 92.3 |
| 312 | 88.2 |
| 313 | 96.3 |
| 314 | 86.0 |
| 315 | 82.7 |
| 316 | 74.0 |
| 317 | 68.5 |
| 318 | 79.0 |
| 319 | 79.0 |
| 320 | 82.2 |
| 322 | 95.6 |
| 323 | 91.3 |
| 324 | 95.0 |
| 334 | 88.0 |
| 335 | 84.1 |
| 340 | 94.0 |
| 341 | 87.4 |
| 342 | 89.9 |
| 343 | 98.7 |
| 344 | 95.6 |
| 345 | 86.6 |
| 346 | 88.9 |
| 348 | 91.3 |
| 349 | 73.0 |
| 350 | 92.1 |
| 351 | 99.0 |
| 352 | 96.2 |
| 353 | 73.7 |
| 354 | 79.3 |
| 355 | 100 |
| 356 | 93.5 |
| 357 | 96.3 |
| 358 | 62.7 |
| 359 | 94.7 |
| 360 | 93.7 |
| 361 | 92.8 |
| 362 | 94.1 |
| 363 | 92.3 |
| 365 | 59.2 |
| 366 | 91.5 |
| 367 | 71.0 |
| 368 | 94.6 |
| 370 | 84.3 |
| 371 | 97.2 |
| 373 | 91.6 |
| 373 | 92.9 |
| 374 | 91.4 |
| 375 | 97.8 |
| 376 | 90.2 |
| 377 | 85.6 |
| 378 | 91.1 |
| 379 | 90.7 |
| 380 | 99.0 |
| 381 | 95.7 |
| 382 | 96.8 |
| 383 | 91.4 |
| 384 | 79.4 |
| 385 | 86.2 |
| 386 | 47.8 |
| 387 | 98.7 |
| 388 | 69.2 |
| 389 | 100 |
| 390 | 98.2 |
| 391 | 45.6 |
| 392 | 93.7 |
| 393 | 100 |
| 394 | 97.8 |
| 395 | 79.8 |
| 396 | 98.7 |
| 397 | 100 |
| 398 | 90.0 |
| 399 | 59.9 |
| 400 | 93.0 |
| 401 | 96.5 |
| 402 | 80.5 |
| 403 | 96.1 |
| 404 | 95.4 |
| 405 | 86.4 |
| 406 | 94.5 |
| 407 | 100 |
| 408 | 100 |
| 409 | 89.4 |
| 410 | 91.4 |
| 411 | 93.5 |
| 412 | 86.4 |
| 413 | 99.5 |
| 414 | 91.4 |
| 415 | 87.3 |
| 416 | 86.4 |
| 417 | 98.7 |
| 418 | 100 |
| 420 | 100 |
| 421 | 100 |
| 422 | 96.6 |
| 423 | 89.1 |
| 424 | 85.8 |
| 425 | 90.8 |
| 426 | 97.2 |
| 427 | 100 |
| 428 | 100 |
| 429 | 100 |
| 430 | 94.1 |
| 431 | 99.1 |
| 432 | 95.5 |
| 433 | 99.6 |
| 434 | 100 |
| 435 | 97.8 |
| 436 | 100 |
| 437 | 100 |
| 438 | 94.3 |
| 439 | 94.3 |
| 440 | 100 |
| 441 | 98.3 |
| 442 | 100 |
| 443 | 100 |
| 444 | 100 |
| 445 | 98.1 |
| 446 | 97.8 |
| 447 | 96.9 |
| 448 | 97.4 |
| 449 | 100.0 |
| 450 | 99.7 |
| 451 | 100 |
| 452 | 100 |
| 453 | 94.4 |
| 454 | 96.8 |
| 455 | 99.1 |
| 456 | 95.3 |
| 457 | 88.9 |
| 458 | 93.4 |
| 459 | 97.4 |
| 460 | 91.6 |
| 461 | 99.6 |
| 462 | 98.3 |
| 463 | 96.1 |
| 464 | 97.1 |
| 465 | 95.1 |

TABLE 4-continued

Binding Data

| Example | % Inhibition ET$_A$ at 1 μM |
|---|---|
| 466 | 94.2 |
| 467 | 93.6 |
| 468 | 88.7 |
| 469 | 98.7 |
| 470 | 100 |
| 471 | 100 |
| 475 | 91.6 |
| 476 | 82.3 |
| 477 | 80.1 |
| 479 | 96.5 |
| 495 | 95.9 |
| 496 | 92.7 |
| 497 | 83.7 |
| 498 | 81.6 |
| 499 | 68.5 |
| 500 | 55.7 |
| 502 | 95.7 |
| 503 | 97.0 |
| 504 | 97.1 |
| 505 | 95.8 |
| 506 | 99.7 |
| 507 | 99.3 |
| 508 | 97.6 |
| 509 | 100 |
| 510 | 100 |
| 511 | 99.2 |
| 512 | 98.9 |
| 513 | 98.0 |
| 514 | 100 |
| 515 | 99.1 |
| 516 | 99.7 |
| 517 | 94.1 |
| 518 | 96.3 |
| 519 | 99.1 |
| 520 | 97.4 |
| 521 | 100 |
| 523 | 99.0 |
| 524 | 99.2 |
| 525 | 100 |
| 526 | 100 |
| 527 | 96.6 |
| 528 | 98.3 |
| 529 | 98.1 |
| 531 | 99.8 |
| 532 | 100 |
| 533 | 97.9 |
| 536 | 100 |
| 537 | 97.2 |

As further demonstration of the efficacy of the described compounds as functional antagonists of endothelin, the ability of the described compounds to inhibit ET-1-induced phosphatidylinositol hydrolysis was measured.

Determination of Phosphatidylinositol (PI) Hydrolysis

MMQ cells (0.4×106 cells/mL) were labeled with 10 μCi/mL of [$^3$H]myo-inositol in RPMI for 16 hours. The cells were washed with PBS, then incubated with Buffer A containing protease inhibitors and 10 mM LiCl for 60 minutes. The cells were then incubated with test compounds for 5 minutes, and then challenged with 1 nM ET-1. ET-1 challenge was terminated by the addition of 1.5 mL of 1:2 (v/v) chloroform-methanol. Total inositol phosphates were extracted after adding chloroform and water to give final proportions of 1:1:0.9 (v/v/v) chloroform-methanol-water as described by Berridge (Biochem. J. 206 587–595 (1982)). The upper aqueous phase (1 mL) was retained and a small portion (100 μL) was counted. The rest of the aqueous sample was analyzed by batch chromatography using anion-exchange resin AG1-X8 (Bio-Rad). The IC$_{50}$ is the concentration of test compound required to inhibit the ET-induced increase in PI turnover by 50%. The results of the above study clearly indicate that the compounds act as functional ET antagonists.

TABLE 5

Phosphatidylinositol Hydrolysis

| Example | IC$_{50}$ μM |
|---|---|
| 1D | 0.025 |
| 14 | 0.017 |
| 15 | 0.010 |
| 16 | 0.009 |
| 18 | 0.009 |
| 19 | 0.024 |
| 30 | 0.001 |
| 31B | 0.002 |
| 43 | 0.0001 |
| 46 | 0.002 |
| 47 | 0.0005 |
| 48 | 0.0004 |
| 291 | 0.0098 |
| 300 | 0.0012 |
| 534 | 0.05 |
| 553 | 0.0004 |

Table 6

ET$_A$/ET$_B$ Selectivity

MMQ cells, porcine cerebellar tissues (known to contain ET$_B$ receptors) and chinese hamster ovary cells (CHO) permanently transfected with the human ETA or ETB receptor were homogenized in 25 ml of 10 mM Hepes (pH 7.4) containing 0.25 M sucrose and a protease inhibitor [50 mM EDTA, 0.1 mM PMSF, 5 μg/ml Pepstatin A, and 0.025% Bacitracin] using a micro ultrasonic cell disruptor. The mixture was centrifuged at 1000×g for 10 min. The supernatant was collected and centrifuged at 60,000×g for 60 min. The precipitate was resuspended in 20 mM Tris, pH 7.4 containing protease inhibitor and centrifuged again. The final membrane pellet was resuspended in 20 mM Tris, pH 7.4 containing protease inhibitors and stored at –80° C. until used. Protein content was determined by the Bio-Rad dye-binding protein assay.

Binding assays were performed in 96-well microtiter plates pretreated with 0.1% SA. Membranes prepared from cells were diluted 100 fold in Buffer B (20 mM Tris, 100 mM NaCl, 10 mM MgCl2, pH 7.4, with 0.2% BSA, 0.1 mM PMSF, 5 Pepstatin A, 0.025% bacitracin, and 50 mM EDTA) to a final concentration of 0.2 mg/mL of protein. In competition binding studies, membranes (0.02 mg) were incubated with 0.1 nM of [125I]ET-1 (for ETA assay in MMQ or CHO cells transfected with human ETA receptor) or [125I] ET-3 (for ETB assay in porcine cerebellum or CHO cells transfected with human ETB receptor) in Buffer B (final volume: 0.2 mL) in the presence of increasing concentrations of the test compound for 3 hours at 25° C. After incubation, unbound ligands were separated from bound ligands by a vacuum filtration method using glass-fiber filter strips in PHD cell harvesters (Cambridge Technology, Inc., MA), washing the filter strips three times with saline (1 mL). Nonspecific binding was determined in the presence of 1 pM ET-1. IC50 values are calculated using an average of at least two separate determinations. The data shows the selectivity of the compounds of the invention in binding to the endothelin receptors.

TABLE 6

| EXAMPLE NO. | rET-A (% I @ 1 μM) | rET-A IC$_{50}$ (nM) | pET-B IC$_{50}$ (nM) | Selectivity (rA/pB ratio) | hET-A IC$_{50}$ (nM) | hET-B IC$_{50}$ (nM) | Selectivity (hA/hB ratio) |
|---|---|---|---|---|---|---|---|
| 502 | 95.7 | 3.0 | 71,000 | 23,000 | | | |
| 503 | 97.0 | 1.4 | 50,000 | 35,000 | 0.92 | 52,000 | 56,000 |
| 504 | 97.1 | 3.1 | >100,000 | >32,000 | 4.6 | >100,000 | >21,000 |
| 505 | 95.8 | 2.0 | 60,000 | 30,000 | 5.7 | 68,000 | 12,000 |
| 506 | 99.7 | 3.2 | >100,000 | >31,000 | 3.0 | 61,000 | 20,000 |
| 507 | 99.3 | 3.0 | >100,000 | >33,000 | 1.63 | >100,000 | >60,000 |
| 508 | 97.6 | 1.9 | 45,000 | 23,000 | 2.1 | 51,000 | 24,000 |
| 509 | 100 | 0.56 | 30,000 | 53,000 | 0.51 | 23,000 | 45,000 |
| 510 | 100 | 0.50 | 35,000 | 68,000 | 1.0 | 11,000 | 11,000 |
| 511 | 99.2 | 0.81 | N. D. | — | 0.60 | 15,000 | 25,000 |
| 512 | 98.9 | 0.42 | >80,000 | >190,000 | 0.58 | 60,000 | >102,000 |
| 513 | 98.0 | 0.30 | 8,800 | 29,000 | 0.36 | 14,000 | 37,000 |
| 514 | 100 | 1.0 | 26,000 | 26,000 | 0.36 | 9,800 | 29,000 |
| 515 | 99.1 | 1.6 | >62,000 | >37,000 | 6.7 | >100,000 | >15,000 |
| 516 | 99.7 | 0.71 | 29,000 | 40,000 | 1.8 | 37,000 | 21,000 |
| 517 | 94.1 | 1.0 | 30,000 | 30,000 | 0.43 | 12,000 | 29,000 |
| 518 | 96.3 | 1.3 | 85,000 | 63,000 | 0.31 | 38,000 | 124,000 |
| 519 | 99.1 | 0.38 | 14,000 | 36,000 | 0.23 | 19,000 | 83,000 |
| 520 | 97.4 | 0.20 | 28,000 | 130,000 | | | |
| 521 | 100 | 0.67 | 37,000 | 54,000 | | | |
| 523 | 99.0 | 0.42 | 360 | 880 | 0.33 | 290 | 880 |
| 524 | 99.2 | 0.79 | 1,700 | 2,100 | 0.82 | 890 | 1,100 |
| 525 | 100 | 8.2 | 560 | 70 | | | |
| 526 | 100 | 42 | — | — | 17 | 7,400 | 440 |
| 527 | 96.6 | 7.9 | 10,000 | 1,300 | | | |
| 528 | 98.3 | 11 | 43,000 | 3,800 | | | |
| 529 | 98.1 | 3.6 | 6,300 | 1,700 | | | |
| 531 | 99.8 | 1.2 | — | — | 0.71 | 870 | 1,200 |
| 532 | 100 | 5.1 | 3,200 | 630 | | | |
| 533 | 97.9 | 76 | 7,900 | 100 | 40 | 22,000 | 560 |
| 534 | | 0.12 | 0.36 | 3.0 | 0.08 | 0.28 | 3.5 |
| 536 | 100 | 0.52 | 17,000 | 33,000 | 0.92 | 52,000 | 56,000 |
| 537 | 97.2 | 0.96 | 5,900 | 6,200 | 0.23 | 1,900 | 8,200 |
| 552 | 97.3 | 0.78 | 7100,000 | 7125,000 | 1.0 | >96,000 | >96,000 |
| 553 | 100 | 0.26 | 42,400 | 160,000 | 0.29 | 39,500 | 136,000 |

Determination of Plasma Protein Binding

A stock solution of the test compound in 50% ethanol (2 mg/mL) was diluted 10× into PBS. A 0.4 mL sample of this secondary stock solution was added to 3.6 mL of fresh plasma, and incubated at room temperature for 1 hour. A 1 mL sample of this incubation mixture was transferred to a Centrifree ultrafiltration tube. The sample was centrifuged in a fixed-bucket rotor for approximately 2 min and the filtrate was discarded. The sample was centrifuged for another 15–30 min. A 100 μL sample of the ultrafiltrate was transfered to a micro HPLC sample vial containing 150 ML of HPLC mobile phase and mixed thoroughly. A 50 μL sample was injected and the concentration of drug in the ultrafiltrate was determined by HPLC analysis compared against a standard sample prepared identically in the absence of plasma. Ultrafiltrate concentrations are calculated from a calibration curve. Protein binding is calculated according to the equation:

$$\%PB = [1 - (Cu/Ci)] * 100\%$$

where Cu is the ultrafiltrate concentration and Ci is the initial plasma concentration.
Data:

| Example #43 | >99.5% |
| Example #532 | 96.8% |
| Example #533 | 82.6% |

The ability of the compounds of the invention to lower blood pressure can be demonstrated according to the methods described in Matsumura, et al., Eur. J. Pharmacol. 185 103 (1990) and Takata, et al., Clin. Exp. Pharmacol. Physiol. 10 131 (1983).

The ability of the compounds of the invention to treat congestive heart failure can be demonstrated according to the method described in Margulies, et al., Circulation 82 2226 (1990).

The ability of the compounds of the invention to treat myocardial ischemia can be demonstrated according to the method described in Watanabe, et al., Nature 344 114 (1990).

The ability of the compounds of the invention to treat coronary angina can be demonstrated according to the method described in Heistad, et al., Circ. Res. 54 711 (1984).

The ability of the compounds of the invention to treat cerebral vasospasm can be demonstrated according to the methods described in Nakagomi, et al., J. Neurosurg. 66 915 (1987) or Matsumura, et al., Life Sci. 49 841–848 (1991).

The ability of the compounds of the invention to treat cerebral ischemia can be demonstrated according to the method described in Hara et al., European. J. Pharmacol. 197: 75–82, (1991).

The ability of the compounds of the invention to treat acute renal failure can be demonstrated according to the method described in Kon, et al., J. Clin. Invest. 83 1762 (1989).

The ability of the compounds of the invention to treat chronic renal failure can be demonstrated according to the method described in Benigni, et al., Kidney Int. 44 440–444 (1993).

The ability of the compounds of the invention to treat gastric ulceration can be demonstrated according to the method described in Wallace, et al., Am. J. Physiol. 256 G661 (1989).

The ability of the compounds of the invention to treat cyclosporin-induced nephrotoxicity can be demonstrated according to the method described in Kon, et al., Kidney Int. 37 1487 (1990).

The ability of the compounds of the invention to treat endotoxin-induced toxicity (shock) can be demonstrated according to the method described in Takahashi, et al., Clinical Sci. 79 619 (1990).

The ability of the compounds of the invention to treat asthma can be demonstrated according to the method described in Potvin and Varma, Can. J. Physiol. and Pharmacol. 67 1213 (1989).

The ability of the compounds of the invention to treat transplant-induced atherosclerosis can be demonstrated according to the method described in Foegh, et al., Atherosclerosis 78 229–236 (1989).

The ability of the compounds of the invention to treat atherosclerosis can be demonstrated according to the methods described in Bobik, et al., Am. J. Physiol. 258 C408 (1990) and Chobanian, et al., Hypertension 15 327 (1990).

The ability of the compounds of the invention to treat LPL-related lipoprotein disorders can be demonstrated according to the method described in Ishida, et al., Biochem. Pharmacol. 44 1431–1436 (1992).

The ability of the compounds of the invention to treat proliferative diseases can be demonstrated according to the methods described in Bunchman ET and CA Brookshire, Transplantation Proceed. 23 967–968 (1991); Yamagishi, et al., Biochem. Biophys. Res. Comm. 191 840–846 (1993); and Shichiri, et al., J. Clin. Invest. 87 1867–1871 (1991). Proliferative diseases include smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scleroderma, prostatic hyperplasia, cardiac hyperplasia, restenosis following arterial injury or other pathologic stenosis of blood vessels.

The ability of the compounds of the invention to treat acute or chronic pulmonary hypertension can be demonstrated according to the method described in Bonvallet et al., Am. J. Physiol. 266 H1327 (1994). Pulmonary hypertension can be associated with congestive heart failure, mitral valve stenosis, emphysema, lung fibrosis, chronic obstructive pulmonary disease (COPD), acute repiratory distress syndrome (ARDS), altitude sickness, chemical exposure, or may be idiopathic.

The ability of the compounds of the invention to treat plaletet aggregation, and thrombosis, can be demonstrated according to the method described in McMurdo et al. Eu. J. Pharmacol. 259 51 (1994).

The ability of the compounds of the invention to treat cancers can be demonstrated according to the method described in Shichiri, et al., J. Clin. Invest. 87 1867 (1991).

The ability of the compounds of the invention to treat IL-2 (and other cytokine) mediated cardiotoxicity and vascular permeability disorders can be demonstrated according to the method described in Klemm et al., Proc. Nat. Acad. Sci. 92 2691 (1995).

The ability of the compounds of the invention to treat nociception can be demonstrated according to the method described in Yamamoto et al., J. Pharmacol. Exp. Therap. 271 156 (1994).

The ability of the compounds of the invention to treat colitis can be demonstrated according to the method described in Hogaboam et al (EUR. J. Pharmacol. 1996, 309, 261–269).

The ability of the compounds of the invention to treat ischemia-repurfusion injury in kidney transplantation can be demonstrated according to the method described in Aktan et al (Transplant Int 1996, 9, 201–207).

The ability of the compounds of the invention to treat angina, pulmonary hypertension, raynaud's disease, and migraine can be demonstrated according to the method described in Ferro and Webb (Drugs 1996, 51,12–27).

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formula (1), or separately by reacting the carboxylic acid function with a suitable base such as the hydroxide, carbonate or bicarbonate of a pharmaceutically acceptable metal cation or with ammonia, or an organic primary, secondary or tertiary amine. Such pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful for antagonizing endothelin in a human or other mammal. In addition, the compounds of the present invention are useful (in a human or other mammal) for the treatment of hypertension, acute or chronic pulmonary hypertension, Raynaud's disease, congestive heart failure, myocardial ischemia, reperfusion injury, coronary angina, cerebral ischemia, cerebral vasospasm, chronic or acute renal failure, non-steroidal antiinflammatory drug induced gastric ulceration, cyclosporin induced nephrotoxicity, endotoxin-induced toxicity, asthma, fibrotic or proliferative diseases, including smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scleroderma, prostatic hyperplasia, cardiac hyperplasia, restenosis following arterial injury or other pathologic stenosis of blood vessels, LPL-related lipoprotein disorders, transplantation-induced atherosclerosis or atherosclerosis in general, platelet aggregation, thrombosis, cancers, prostate cancer, IL-2 and other cytokine mediated cardiotoxicity and permeability disorders, and nociception, especially treatment of bone pain associated with bone cancer.

Total daily dose administered to a host in single or divided doses may be in amounts, for example, from 0.001 to 1000 mg/kg body weight daily and more usually 0.1 to 100 mg/kg for oral administration or 0.01 to 10 mg/kg for parenteral administration. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

A representative solid dosage form, for example, a tablet or a capsule, comprises:

| | |
|---|---|
| Compound of the invention | 35% w/w |
| Starch, Pregelatinized, NF | 50% w/w |
| Microcrystalline Cellulose, NF | 10% w/w |
| Talc, Powder, USP | 5% w/w |

While the compounds of the invention can be administered as the sole active pharmaceutical agent, they can also be used in combination with one or more cardiovascular agents independently selected from diuretics, adrenergic blocking agents, vasodilators, calcium channel blockers, renin inhibitors, angiotensin converting enzyme (ACE) inhibitors, angiotensin 11 antagonists, potassium channel activators and other cardiovascular agents.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative renin inhibitors include enalkiren, zankiren, RO 42-5892, PD-134672 and the like or a pharmaceutically acceptable salt thereof.

Representative angiotensin 11 antagonists include DUP 753, A-81988 and the like.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

The compounds of the invention and the cardiovascular agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds, processes, compositions and methods. Variations and changes which are obvious to one skilled in the art are intended to be within the scope and nature of the invention which are defined in the appended claims.

What is claimed is:

1. The compound trans,trans-2-(3-fluoro-4-methoxyphenyl)-4-(1,3-benzodioxol-5-yl)-1-(2-N-propyl-N-pentanesulfonylamino)ethyl)-pyrrolidine-3-carboxylic acid; or a salt or ester thereof.

2. The compound [2S,3R,4S]-2-(4-methoxyphenyl)-4-(1,3-benzodioxol-5-yl)-1-[(N-butyl-N-(4-dimethylaminobutyl)amino)carbonylmethyl]-pyrrolidine-3-carboxylic acid; or a salt or ester thereof.

3. A pharmaceutical composition for antagonizing the action of endothelin comprising a therapeutically effective amount of [2S,3R,4S]-2-(4-methoxyphenyl)-4-(1,3-benzodioxol-5-yl)-1-[(N-butyl-N-(4-dimethylaminobutyl)amino)carbonylmethyl]-pyrrolidine-3-carboxylic acid and a pharmaceutically acceptable carrier.

4. A method for antagonizing the action of endothelin comprising adminstering to a mammal in need of such treatment a therapeutically effective amount of [2S,3R,4S]-2-(4-methoxyphenyl)-4-(1,3-benzodioxol-5-yl)-1-[(N-butyl-N-(4-dimethylaminobutyl)-amino)carbonylmethyl]-pyrrolidine-3-carboxylic acid; or a salt or ester thereof.

5. A method for treating hypertension, congestive heart failure, restenosis following arterial injury, renal failure, cancer, colitis, reperfusion injury, angina, pulmonary hypertension, migraine, cerebral or myocardial ischemia or atherosclerosis comprising adminstering to a mammal in need of such treatment a therapeutically effective amount of [2S,3R,4S]-2-(4-methoxyphenyl)-4-(1,3-benzodioxol-5-yl)-1-[(N-butyl-N-(4-dimethylaminobutyl)amino)carbonylmethyl]-pyrrolidine-3-carboxylic acid or a salt or ester thereof.

6. A method for treating coronary angina, cerebral vasospasm, acute and chronic renal failure, gastric ulceration, cyclosporin-induced nephrotoxicity, endotoxin-induced toxicity, asthma, LPL-related lipoprotein disorders, proliferative diseases, acute or chronic pulmonary hypertension, platlet aggregation, thrombosis, IL-2 mediated cardiotoxicity, nociception, colitis, vascular permeability disorders, ischemia-repurfusion injury, raynaud's disease, and migraine comprising adminstering to a mammal in need of such treatment a therapeutically effective amount of [2S,3R,4S]-2-(4-methoxyphenyl)-4-(1,3-benzodioxol-5-yl)-1-[(N-butyl-N-(4-dimethylaminobutyl)amino)carbonylmethyl]-pyrrolidine-3-carboxylic acid or a salt or ester thereof.

* * * * *